US011840737B2

(12) United States Patent
Akoulitchev et al.

(10) Patent No.: US 11,840,737 B2
(45) Date of Patent: Dec. 12, 2023

(54) GENETIC REGULATION OF IMMUNORESPONSE BY CHROMOSOME INTERACTIONS

(71) Applicant: OXFORD BIODYNAMICS PLC, Oxford (GB)

(72) Inventors: Alexandre Akoulitchev, Oxford (GB); Aroul Selvam Ramadass, Oxford (GB); Ewan Hunter, Oxford (GB)

(73) Assignee: OXFORD BIODYNAMICS PLC, Oxford (GB)

( * ) Notice: Subject to any disclaimer, the term of this patent is extended or adjusted under 35 U.S.C. 154(b) by 0 days.

(21) Appl. No.: 16/760,541

(22) PCT Filed: Nov. 2, 2018

(86) PCT No.: PCT/GB2018/053196
§ 371 (c)(1),
(2) Date: Apr. 30, 2020

(87) PCT Pub. No.: WO2019/086898
PCT Pub. Date: May 9, 2019

(65) Prior Publication Data
US 2021/0230702 A1    Jul. 29, 2021

Related U.S. Application Data

(60) Provisional application No. 62/581,287, filed on Nov. 3, 2017.

(30) Foreign Application Priority Data

Oct. 3, 2018  (WO) ................ PCT/GB2018/052818

(51) Int. Cl.
*C12Q 1/6886* (2018.01)
*C12Q 1/686* (2018.01)

(52) U.S. Cl.
CPC ........... *C12Q 1/6886* (2013.01); *C12Q 1/686* (2013.01); *C12Q 2600/106* (2013.01)

(58) Field of Classification Search
None
See application file for complete search history.

(56) References Cited

U.S. PATENT DOCUMENTS

2006/0034826 A1*  2/2006  Carreno ................ A61P 37/06
                                                                    424/130.1
2016/0122829 A1*  5/2016  Hammerman ....... C12Q 1/6886
                                                                    514/44 A

FOREIGN PATENT DOCUMENTS

| JP | 2010-515449 A | 5/2010 |
|---|---|---|
| JP | 2011-502108 A | 1/2011 |
| JP | 2017-184729 A | 10/2017 |
| WO | 2007/093819 A2 | 8/2007 |
| WO | 2008084405 A2 | 7/2008 |
| WO | 2009051268 A2 | 4/2009 |
| WO | 2009/147386 A1 | 12/2009 |
| WO | 2010131195 A1 | 11/2010 |
| WO | 2015/077414 A1 | 5/2015 |
| WO | 2016/207653 A1 | 12/2016 |
| WO | 2016/207661 A1 | 12/2016 |

OTHER PUBLICATIONS

Juppner (Bone 1995 vol. 17 No. 2 Supplement 39S-42S) (Year: 1995).*
Evans (Science 1999 vol. 286 pp. 487-491) (Year: 1999).*
Bastonini et al., "Chromatin barcodes as biomarkers for melanoma", Pigment Cell and Melanoma Research, 2014, vol. 27, Issue 5, pp. 788-800.
Crutchley et al., "Chromatin conformation signatures: ideal human disease biomarkers?", Biomarkers in Medicine, 2010, vol. 4, pp. 611-629.
Jakub et al., "A pilot study of chromosomal aberrations and epigenetic changes in peripheral blood samples to identify patients with melanoma", Melanoma Research, 2015, vol. 25, No. 5, pp. 2-7.
Oxford Biodynamics Announcement, Nov. 15, 2017, 3 pages.
Oxford Biodynamics Announcement, Jul. 17, 2018, 2 pages.
Poesen, "The Chromosomal Conformation Signature: A New Kid on the Block in the ALS Biomarker Research?", EBioMedicine, 2018, vol. 33, pp. 6-7.
Presentation at the Foundation for National Institute for Health (FNIH) Biomarker Consortium Cancer Steering Committee, held in Washington, DC on Nov. 6-7, 2017, 24 pages.
Presentation at the American Society of Hematology (ASH) Summit on Emerging Immunotherapies for Hematologic Diseases, Jul. 12-13, 2018, Washington DC, 27 pages.
Westera et al., "EpiSwitch Biomarker Discovery", Oxford Biodynamics, May 2018.
Akoulitchev et al., "Pharmacogenetic 3C interaction associated with the PDGFRA gene as a chromatin conformation marker for treatment with tyrosine kinase inhibitors", Journal of Clinical Oncology, vol. 35, Issue 15, May 30, 2017, Meeting Abstract | 2017 ASCO Annual Meeting I, DOI: 10.1200/JCO.2017.35.15_suppl.e23054.

* cited by examiner

*Primary Examiner* — Katherine D Salmon
(74) *Attorney, Agent, or Firm* — Seed IP Law Group LLP

(57) ABSTRACT

A process for analysing chromosome regions and interactions relating to immunoresponsiveness.

4 Claims, 30 Drawing Sheets
Specification includes a Sequence Listing.

Patient Annotations For Study

| Used For | Sample ID | Response/ Progression | 12 weeks sample ID | 12 weeks PDL1 | Age | Gender | LDH high Y/N | Nr therapies | BRAF Y/N | Chemo | Targeted | immuno IPI=1; others=2 |
|---|---|---|---|---|---|---|---|---|---|---|---|---|
| D | 1378 | R | 1432 | 0.157 | 62 | F | N | 6 | Y | 1 | 1 | 2 |
| D | 1379 | R | 1430 | 5.172 | 57 | F | Y | 1 | | 0 | 0 | 1 |
| D | 1380 | R | 1434 | 6.411 | 73 | M | N | 3 | N | 1 | 0 | 2 |
| D | 1386 | P | 1438 | 0.174 | 70 | F | Y | 1 | N | 0 | 0 | 1 |
| D | 1390 | P | 1443 | 12.21 | 62 | M | Y | 3 | Y | 0 | 1 | 1 |
| D | 1392 | R | 1439 | 0.308 | 62 | F | N | 2 | | 0 | 0 | 2 |
| D | 1399 | P | 1436 | 0.213 | 63 | F | Y | 3 | Y | 0 | 1 | 1 |
| D | 1416 | R | 1459 | 0.569 | 49 | F | Y | 2 | Y | 1 | 1 | 1 |
| V | 1370 | R | 1431 | 0.324 | 74 | M | N | 2 | N | 1 | 0 | 1 |
| V | 1372 | R | 1483 | 0.607 | 39 | F | Y | 2 | | 1 | | 1 |
| V | 1393 | P | 1447 | 0.222 | 66 | F | Y | 3 | | 0 | 0 | 1 |
| V | 1414 | R | 1457 | 0.389 | 46 | M | Y | 3 | Y | 0 | 1 | 1 |
| V | 1482 | P | | | 55 | F | Y | 2 | N | 1 | 0 | 1 |
| V | 1426 | P | 1469 | | 63 | M | Y | 1 | | 0 | 0 | 1 |
| V | 1458 | P | 1481 | | 52 | F | N | 4 | N | 1 | 0 | 2 |
| V | 1440 | P | 1508 | | 74 | M | N | 4 | N | 1 | 0 | 2 |
| | | Response was defined based on RECIST 1.1 criteria | | | | | | | | | | |

D: indicates the Samples were used in the discovery stage of the study, identifying which EpiSwitch to move to the PCR platform from the array platform
V: indicates samples used to verify the identified EpiSwitch markers on the PCR platform

| PCR Probe | GeneLocus |
|---|---|
| 69/71 | IL15 |
| 73/75 | STAT5B |
| 85/87 | HLA-DQB1 |
| 9/11 | MYD88 |
| 29/31 | IL12B |
| 13/15 | PVRL1 |

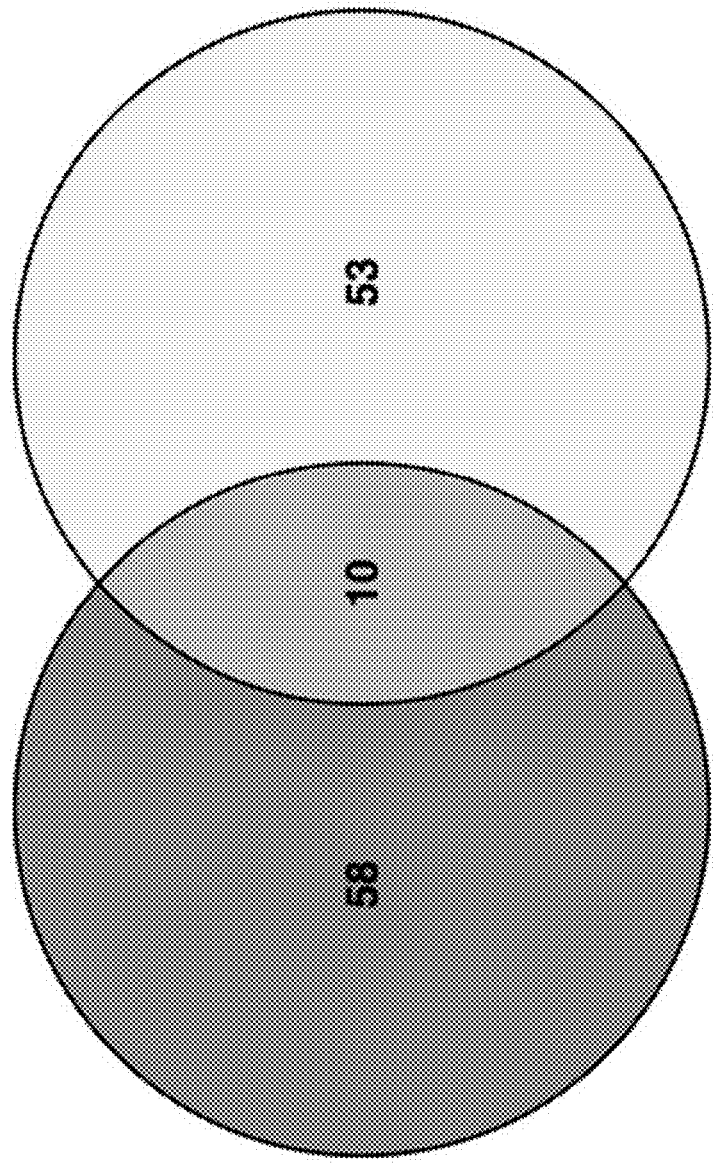

Analytical Pipeline for anti-PD-1 Array Analysis. 68 EpiSwitch™ Markers identified by statistical processing as strong candidates for predictive biomarkers at baseline for anti-PD-1 therapy. (PD1-R vs NR BL). 63 EpiSwitch™ Markers identified by statistical processing as strong candidates for response biomarkers for anti-PD-1 therapy. (PD1 R-BL v R-12W). 10 Markers are both good candidates for predictive and response markers.

Anti-PD-1 Markers for R-BL v NR-BL:
EpiSwitch™ PCR Data

| PCR Probe | GeneLocus | Responder | | | | Non-Responder | | | |
|---|---|---|---|---|---|---|---|---|---|
| | | 1370 (BL) | 1372 (BL) | 1393 (BL) | 1414 (BL) | 1482 (BL) | 1426 (BL) | 1458 (BL) | 1440 (BL) |
| 69/71 | IL15 | 1 | 1 | 1 | 1 | 0 | 0 | 1 | 0 |
| 73/75 | STAT5B | 1 | 1 | 1 | 1 | 0 | 0 | 0 | 1 |
| 85/87 | HLA-DQB1 | 1 | 1 | 0 | 1 | 0 | 0 | 0 | 0 |
| 9/11 | MYD88 | 1 | 1 | 1 | 1 | 1 | 0 | 0 | 0 |
| 29/31 | IL12B | 1 | 0 | 0 | 0 | 1 | 1 | 1 | 1 |
| 13/15 | PVRL1 | 0 | 0 | 1 | 0 | 1 | 1 | 1 | 1 |

| Array Probe | Array |
|---|---|
| IL15_4_142530356_142539177_142656375_142659066_RF | R |
| STAT5B_17_40403935_40406459_40464294_40468456_FR | R |
| HLA-DQB1_6_32607972_32614493_32630138_32632737_RR | R |
| MYD88_3_38139864_38141788_38192489_38194027_RR | NR |
| IL12B_5_158737480_158738689_158781589_158783887_FF | NR |
| PVRL1_11_119599998_119609544_119620830_119624585_FR | NR |

Patients for aPD-L1 verification of aPD-1 identified markers

Aim: To determine if 30 EpiSwitch™ markers identified in Melanoma aPD-1 study translate to aPD-L1 therapy in NSCLC 16 Non-small cell lung carcinoma (NSCLC) Patients treated with anti PD-L1

2 time points:
Baseline (BL)
2 Weeks (2W)
PBMCs were used in the Study

| | A | B | C |
|---|---|---|---|
| 1 | Patient | Class | Time |
| 2 | Patient 1_A | R | BL |
| 3 | Patient 1_B | R | 2W |
| 4 | Patient 2_A | R | BL |
| 5 | Patient 2_B | R | 2W |
| 6 | Patient 3_A | R | BL |
| 7 | Patient 3_B | R | 2W |
| 8 | Patient 4_A | R | BL |
| 9 | Patient 4_B | R | 2W |
| 10 | Patient 5_A | NR | BL |
| 11 | Patient 5_B | NR | 2W |
| 12 | Patient 6_A | NR | BL |
| 13 | Patient 6_B | NR | 2W |
| 14 | Patient 7_A | NR | BL |
| 15 | Patient 7_B | NR | 2W |
| 16 | Patient 8_A | NR | BL |
| 17 | Patient 8_B | NR | 2W |

Figure 5

Compiled Statistics for Top discerning EpiSwitch™

| Gene | Column | Chi.Square | FT_p_value | sd | LD_p_value | Marker_Class |
|---|---|---|---|---|---|---|
| PDCD1LG2 | OBD117_029.OBD117_031_1 | 4.286 | 0.079 | -0.4 | 0.0455002 | NR |
| PDCD1 | OBD117_057.OBD117_059_1 | 4.286 | 0.08 | -0.4 | 0.04550026 | NR |
| ITK | OBD117_089.OBD117_091_0.25 | 2.637 | 0.194 | -0.3399346 | 0.11666446 | NR |
| IFNA1 | OBD117_033.OBD117_035_0.125 | 3.281 | 0.201 | -0.4 | 0.08011831 | NR |
| IRF1 | OBD117_045.OBD117_047_0.25 | 2.143 | 0.274 | -0.4714045 | 0.15729921 | NR |
| XIAP | OBD117_073.OBD117_075_0.25 | 2.143 | 0.278 | -0.4714045 | 0.15729921 | NR |
| IFNA2 | OBD117_109.OBD117_111_0.03125 | 4.286 | 0.079 | 0.4 | 0.04550026 | R |
| STAT5B | OBD117_009.OBD117_011_0.25 | 3.348 | 0.115 | 0.4714045 | 0.07709987 | R |
| BBC3 | OBD117_085.OBD117_087_0.25 | 3.616 | 0.122 | 0.4898979 | 0.06619258 | R |
| KLRK1 | OBD117_053.OBD117_055_0.125 | 3.233 | 0.124 | 0.4988877 | 0.08235222 | R |
| PIK3CA | OBD117_117.OBD117_119_0.0625 | 2.637 | 0.2 | 0.3399346 | 0.11666446 | R |
| BIRC2 | OBD117_101.OBD117_103_0.25 | 2.637 | 0.204 | 0.3399346 | 0.11666446 | R |
| CD14 | OBD117_105.OBD117_107_0.5 | 1.759 | 0.271 | 0.4422166 | 0.20004505 | R |

The table above shows the top 13 out of the 30 aPD-1 markers examined in the aPD-L1 patients 6 NR Markers 7 R Markers Same R marker STAT5B marker was identified in the aPD-L1 patients as in the aPD-1 patients and a strong NR marker associated to PD-L2 was identified

Figure 6

PCA plot of the patients with top 13 EpiSwitch™ markers

These are 3D PCA plots and show that the spread between the 2 time points (BL and 2 weeks) in Responders and non-Responders is the similar. This emphasizes that the markers are capturing the difference in response at baseline

PCA plot of the patients with top 13 EpiSwitch™ markers

These are 3D PCA plots and show that the spread between the 2 time points (BL and 2 weeks) in Responders and non-Responders is the similar. This emphasizes that the markers are capturing the difference in response at baseline

EpiSwitch™ markers generated from 2 IO studies and used to classify a 3rd IO cohort

| Marker | Assoicated_ORF |
|---|---|
| OBD117_009/OBD117_011 | STAT5A-STAT5B |
| OBD117_045/OBD117_047 | IRF1 |
| OBD117_089/OBD117_091 | ITK |
| OBD117_105/OBD117_107 | CD14 |
| OBD117_029/OBD117_031 | CD274-PDCD1LG2 |

5 marker model used to classify un-known response NSCLC patients

These were baseline patients for aPD-L1 therapy

Markers were developed from 2 cohorts
8 baseline Melanoma patients (4 R and 4 NR to aPD-1, Pembrolizumab)
24 baseline NSCLC patients (12 R and 12 NR to aPD-L1. This is a different aPD-L1 therapy than the blinded samples)
The ORF's associated to the markers are shown in the table above, the last marker forms a loop between PD-L1 (CD274) and PD-L2 (PCD1LG2)

Figure 8

5 EpiSwitch™ Classifier Call for 3rd IO cohort using Random Forest

| Marker | Assoicated_ORF |
|---|---|
| OBD117_009/OBD117_011 | STAT5A-STAT5B |
| OBD117_045/OBD117_047 | IRF1 |
| OBD117_089/OBD117_091 | ITK |
| OBD117_105/OBD117_107 | CD14 |
| OBD117_029/OBD117_031 | CD274-PDCD1LG2 |

5 marker model used to classify un-known response NSCLC patients

These were baseline patients for aPD-L1 therapy, which is different from the discovery aPD-L1 therapy

| inst#, | actual, | predicted, | error, | probabi | lity distribution |
|---|---|---|---|---|---|
| 1 | ? | 1:R | + | 0.621 | 0.379 |
| 2 | ? | 1:R | + | 0.699 | 0.301 |
| 3 | ? | 1:R | + | 0.621 | 0.379 |
| 4 | ? | 1:R | + | 0.621 | 0.379 |
| 5 | ? | 2:NR | + | 0.461 | 0.539 |
| 6 | ? | 2:NR | + | 0.311 | 0.689 |
| 7 | ? | 1:R | + | 0.551 | 0.449 |
| 8 | ? | 1:R | + | 0.621 | 0.379 |
| 9 | ? | 2:NR | + | 0.461 | 0.539 |
| 10 | ? | 2:NR | + | 0.311 | 0.689 |
| 11 | ? | 2:NR | + | 0.461 | 0.539 |
| 12 | ? | 2:NR | + | 0.311 | 0.689 |
| 13 | ? | 2:NR | + | 0.311 | 0.689 |
| 14 | ? | 2:NR | + | 0.461 | 0.539 |
| 15 | ? | 2:NR | + | 0.461 | 0.539 |

Class call for the 15 unknown samples Random Forest Classifier model was based on the 32 IO samples with known response call

Figure 9

EpiSwitch™ Classifier Call for 3rd IO cohort using Random Forest

| inst#, | actual, | predicted, | error, | probability | distribution | Statistic | Formula | Value | 95% CI |
|---|---|---|---|---|---|---|---|---|---|
| 1 | R | 1:R | + | 0.621 | 0.379 | Sensitivity | $\frac{a}{a+b}$ | 71.43% | 29.04% to 96.33% |
| 2 | R | 1:R | + | 0.699 | 0.301 | | | | |
| 3 | R | 1:R | + | 0.621 | 0.379 | Specificity | $\frac{d}{c+d}$ | 87.50 % | 47.35% to 99.68% |
| 4 | R | 1:R | + | 0.621 | 0.379 | | | | |
| 5 | R | 2:NR | + | 0.461 | 0.539 | Positive Likelihood Ratio | $\frac{Sensitivity}{1-Specificity}$ | 5.71 | 0.86 to 37.91 |
| 6 | R | 2:NR | + | 0.311 | 0.689 | | | | |
| 7 | R | 1:R | + | 0.551 | 0.449 | Negative Likelihood Ratio | $\frac{1-Sensitivity}{Specificity}$ | 0.33 | 0.10 to 1.08 |
| 8 | NR | 1:R | + | 0.621 | 0.379 | | | | |
| 9 | NR | 2:NR | + | 0.461 | 0.539 | Disease prevalence | $\frac{a+b}{a+b+c+d}$ | 46.67% (*) | 21.27% to 73.41% |
| 10 | NR | 2:NR | + | 0.311 | 0.689 | | | | |
| 11 | NR | 2:NR | + | 0.461 | 0.539 | Positive Predictive Value | $\frac{a}{a+c}$ | 83.33% (*) | 42.97% to 97.07% |
| 12 | NR | 2:NR | + | 0.311 | 0.689 | | | | |
| 13 | NR | 2:NR | + | 0.311 | 0.689 | Negative Predictive Value | $\frac{d}{b+d}$ | 77.78 % (*) | 51.31% to 92.08% |
| 14 | NR | 2:NR | + | 0.461 | 0.539 | | | | |
| 15 | NR | 2:NR | + | 0.461 | 0.539 | | | | |

After un-blinding, the 5 marker model generated 3 miss calls which are highlighted.
The test statistics are shown above for the 5 marker model on the 15 blinded samples

Figure 10

ROC Curve of the 15 baseline aPD-L1 patients

The AUC for the blinded samples was 0.786

PCA of the 47 baseline IO patients using the 5 EpiSwitch™ marker

PCA of the 47 IO baseline Patients, using the EpiSwitch™ binary values 37 (R called NR) and 40 (NR called R are 2 of the miss called samples The VENN Diagram shows the overlap between the significant conformations for the Responders at baseline for aPD-1 (melanoma) and aPD-L1 (NSCLC). The 2 responder groups share 276 EpiSwitch CCSs, this equates to 11% of the total number of markers shared on the 2 screening arrays.

The VENN Diagram shows the overlap between the significant conformations for the Non-Responders at baseline for aPD-1 (melanoma) and aPD-L1 (NSCLC). Only 1 marker is shared between the 2 Non-responder groups.

Figure 16

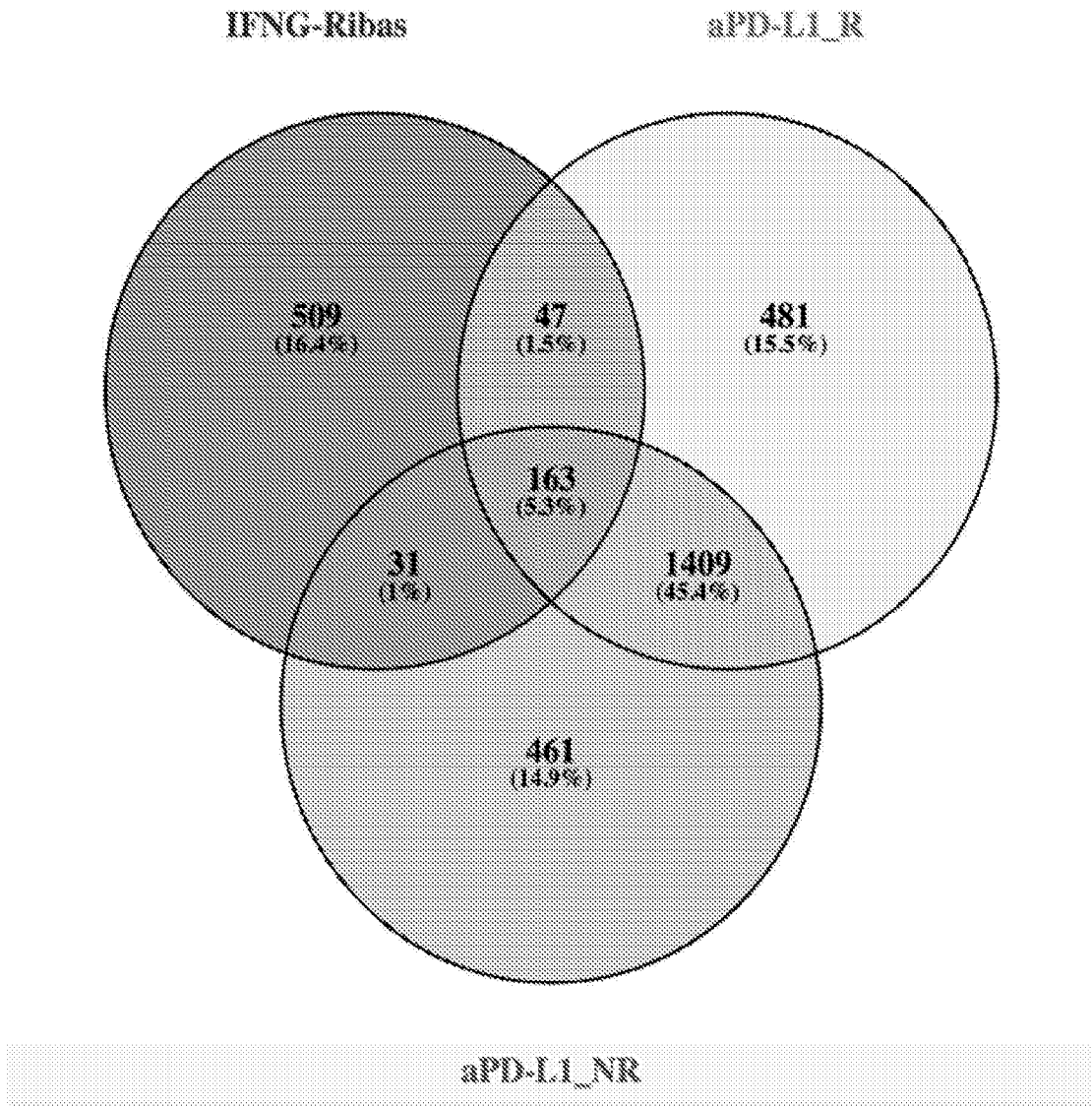

Comparison of ORFs with significant EpiSwitch™ CCSs for R-aPD-L1 and NR-aPD-L1 against the IFNG-Response ORFs. The significant EpiSwitch™ CCSs were compared to Gencode Hg38 annotation using Bedtools window option. All the protein coding regions within 50Kb of significant EpiSwitch™ CCSs were then compared between responders and non-responders for the aPD-L1 study. These 2 list were further compared to a list of IFNG activated ORFs (750), the majority of which are known interferon response genes. The adjacent VENN diagram show the comparison of these 3 lists. 210 IFNG activated ORFs have significant *Responder CCSs* associated to them. 194 IFNG activated ORFs have significant *Non-Responder CCSs* associated to them

Figure 17

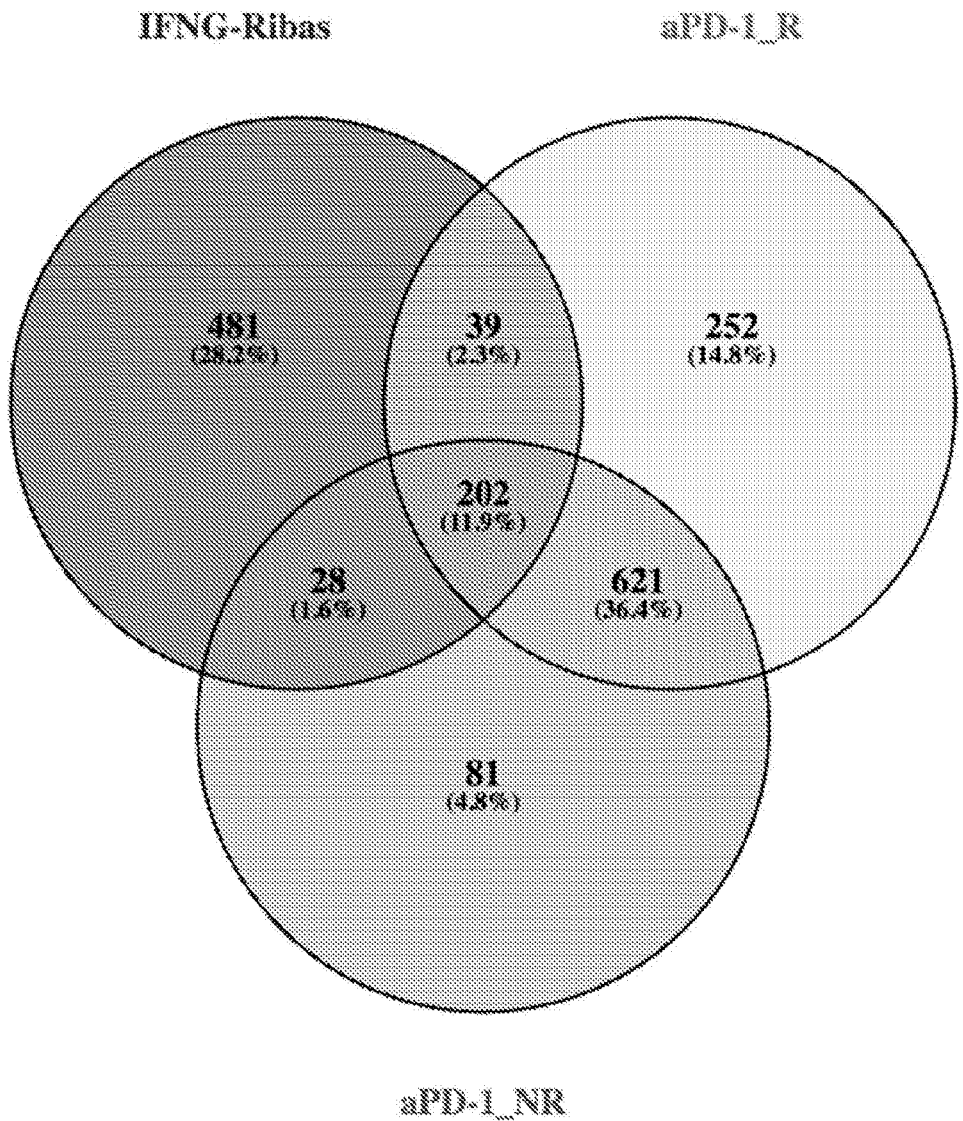

Comparison of ORFs with significant EpiSwitch™ CCSs for R-aPD-1 and NR-aPD-1 against the IFNG-Response ORFs. The same mapping analysis was done using the aPD-1 data. These 2 list were further compared to a list of IFNG activated ORFs (750), the majority of which are known interferon response genes. The adjacent VENN diagram show the comparison of these 3 lists. 241 IFNG activated ORFs have significant Responder CCSs associated to them. 231 IFNG activated ORFs have significant Non-Responder CCSs associated to them.

Figure 18

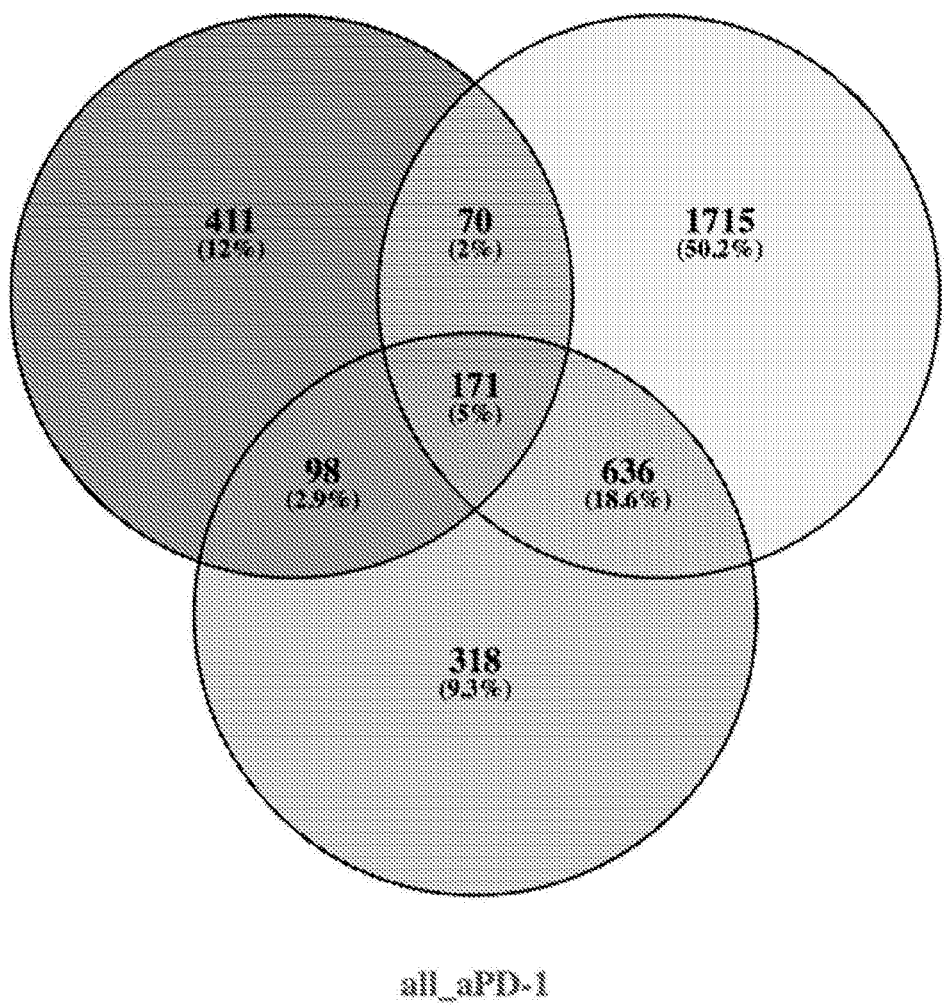

Comparison of ORFs with significant EpiSwitch™ CCSs for all aPD-1 and all aPD-L1 against the IFNG-Response ORFs. The significant CCSs associated ORFs were combined for each study (R and NR as 1 list) and then compared to the IFNG activated ORFs. The adjacent VENN diagram show the comparison of these 3 lists. On the aPD-L1 array there was 260 of the 750 IFNG activated ORFs. On the aPD-1 array there was 274 of the 750 IFNG activated ORFs. 241 of the 260 aPD-L1 IFNG activated ORFs contain significant EpiSwitch™ CCSs. 269 of the 274 aPD-L1 IFNG activated ORFs contain significant EpiSwitch™ CCSs.

Comparison of ORFs with significant EpiSwitch™ CCSs for aPD-L1 against the aPD-1 and IFNG-Response ORFs. The ORF's containing significant EpiSwitch™ CCSs broken down for the Responders and Non-Responders for aPD-L1 compared to IFNG activated ORFs and the combined significant EpiSwitch™ CCSs ORF's for the aPD-1.

Comparison of ORFs with significant EpiSwitch™ CCSs for aPD-1 against the aPD-L1 and IFNG-Response ORFs. The ORF's containing significant EpiSwitch™ CCSs broken down for the Responders and Non-Responders for aPD-1 compared to IFNG activated ORFs and the combined significant EpiSwitch™ CCSs ORF's for the aPD-L1.

Comparison of ORFs with shared Response EpiSwitch™ CCSs for aPD-L1 and aPD-1 with the IFNG-Response ORFs. The adjacent VENN diagram show the comparison of the ORF's with shared significant Responders EpiSwitch™ CCSs between the aPD-L1 and aPD-1 studies. 95 of the ORFs overlap with the IFNG activated ORFs.

Comparison of ORFs with shared Response EpiSwitch™ CCSs for aPD-L1 and aPD-1 with the IFNG-Response ORFs.

Figure 22B

The list of the 95 of the ORFs overlap with the IFNG activated ORFs

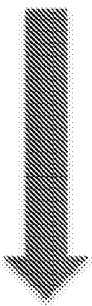

| | | | |
|---|---|---|---|
| AIRE | IFNG | CD4 | PRF1 |
| AKT1 | IGF1R | CD47 | PTPRC |
| BAX | IKBKB | CD6 | PVR |
| BID | IL12RB1 | CD79A | PYCARD |
| BLNK | IL17B | CD79B | RAC1 |
| C1S | IL25 | CD86 | RAG1 |
| C5 | IL26 | CFI | RELA |
| C8A | IL3 | CSF2 | SMAD3 |
| C8B | IL5 | CXCL13 | SPA17 |
| C8G | IRF1 | CYFIP2 | SPN |
| CASP10 | IRF2 | FAS | STAT3 |
| CASP8 | IRF3 | FN1 | STAT4 |
| CCL14 | IRF4 | HAVCR2 | STAT5A |
| CCL15 | ITGAM | HLA-DMA | STAT5B |
| CCL16 | ITGAX | HLA-DMB | SYK |
| CCL18 | ITK | HLA-DQA1 | TNFRSF11A |
| CCL23 | LAG3 | HLA-DQB1 | TNFRSF1A |
| CCL3 | LCK | ICAM1 | TNFSF8 |
| CCL4 | LTBR | ICAM2 | TRAF2 |
| CCR6 | LYN | ICAM3 | TRAF6 |
| CD14 | MAPK3 | ICAM4 | TYK2 |
| CD180 | MCAM | ICOSLG | UBC |
| CD19 | NFKB1 | | MTOR |
| CD2 | PDCD1 | | |
| CD33 | PIK3R1 | | |

Figure 23A

IFNG activated ORFs compared to significant shared Response EpiSwitch™

| Gene | Probe_Count_Sig | Probe_Count_Total |
|---|---|---|
| IGF1R | 16 | 104 |
| CD6 | 14 | 56 |
| CXCL13 | 14 | 108 |
| IKBKB | 12 | 46 |
| PIK3R1 | 12 | 148 |
| ITK | 10 | 26 |
| PTPRC | 10 | 214 |
| C8B | 9 | 151 |
| C8A | 8 | 166 |
| CCL18 | 8 | 42 |
| CYFIP2 | 8 | 40 |
| FAS | 8 | 50 |
| ICOSLG | 8 | 40 |
| IRF1 | 8 | 42 |
| ITGAM | 8 | 50 |
| ITGAX | 8 | 41 |
| CCL3 | 7 | 33 |
| CCL4 | 7 | 32 |
| CD14 | 6 | 62 |
| CD4 | 6 | 42 |
| NFKB1 | 6 | 64 |
| SYK | 6 | 78 |
| LAG3 | 5 | 29 |
| AKT1 | 4 | 60 |
| BLNK | 4 | 66 |

Figure 23B

| | | |
|---|---|---|
| C5 | 4 | 41 |
| CASP8 | 4 | 41 |
| CCR6 | 4 | 46 |
| CD180 | 4 | 38 |
| CD19 | 4 | 56 |
| CD33 | 4 | 32 |
| FN1 | 4 | 42 |
| HLA-DQA1 | 4 | 28 |
| HLA-DQB1 | 4 | 22 |
| IL17B | 4 | 44 |
| IL5 | 4 | 20 |
| LCK | 4 | 46 |
| MAPK3 | 4 | 44 |
| MTOR | 4 | 60 |
| PRF1 | 4 | 28 |
| SPN | 4 | 56 |
| TNFRSF11A | 4 | 58 |
| TNFSF8 | 4 | 50 |
| TYK2 | 4 | 75 |
| AIRE | 3 | 17 |
| ICAM3 | 3 | 70 |
| STAT3 | 3 | 100 |
| STAT5A | 3 | 99 |
| STAT5B | 3 | 106 |
| BAX | 2 | 52 |
| BID | 2 | 42 |
| C15 | 2 | 29 |
| C8G | 2 | 35 |
| CASP10 | 2 | 53 |

Figure 23C

| CCL15 | 2 | 12 |
|---|---|---|
| CCL23 | 2 | 16 |
| CD2 | 2 | 34 |
| CD47 | 2 | 46 |
| CD79A | 2 | 44 |
| CD79B | 2 | 20 |
| CD89 | 2 | 46 |
| CFI | 2 | 16 |
| CSF2 | 2 | 36 |
| HAVCR2 | 2 | 10 |
| HLA-DMA | 2 | 16 |
| HLA-DMB | 2 | 26 |
| ICAM1 | 2 | 63 |
| IFNG | 2 | 10 |
| IL25 | 2 | 74 |
| IL26 | 2 | 20 |
| IL3 | 2 | 42 |
| IRF2 | 2 | 38 |
| IRF3 | 2 | 30 |
| IRF4 | 2 | 40 |
| LTBR | 2 | 33 |
| LYN | 2 | 48 |
| PDCD1 | 2 | 36 |
| PVR | 2 | 65 |
| RAC1 | 2 | 64 |
| RAG1 | 2 | 51 |
| RELA | 2 | 56 |
| SMAD3 | 2 | 34 |
| STAT4 | 2 | 58 |

Figure 23D

| | | |
|---|---|---|
| TNFRSF1A | 2 | 46 |
| TRAF2 | 2 | 46 |
| TRAF6 | 2 | 60 |
| UBC | 2 | 64 |
| CCL14 | 1 | 9 |
| CCL16 | 1 | 9 |
| ICAM2 | 1 | 24 |
| ICAM4 | 1 | 53 |
| IL12RB1 | 1 | 51 |
| MCAM | 1 | 33 |
| PYCARD | 1 | 6 |
| SPA17 | 1 | 17 |

95 of the ORFs overlap with the IFNG activated ORFs

The table shows the number of significant EpiSwitch™ in each of the 95 ORFs with the number of total EpiSwitch™ screened at these ORF's on the aPD-L1 array

The most enriched ORF for the shared Responder EpiSwitch™ CCSs is IGF1R followed by CD6

US 11,840,737 B2

GENETIC REGULATION OF IMMUNORESPONSE BY CHROMOSOME INTERACTIONS

FIELD OF THE INVENTION

The invention relates to detecting chromosome interactions.

STATEMENT REGARDING THE SEQUENCE LISTING

The Sequence Listing associated with this application is provided in text format in lieu of a paper copy, and is hereby incorporated by reference into the specification. The name of the text file containing the Sequence Listing is Sequence_Listing.TXT. The text file is 293 KB, was created on Mar. 25, 2022, and is being submitted electronically via EFS-Web.

BACKGROUND OF THE INVENTION

Disease processes are complex and outcomes cannot be predicted using available methods. In particular it is difficult to predict how patients will react to specific therapies.

SUMMARY OF THE INVENTION

Specific Chromosome Conformation Signatures (CCSs) at loci either exist or are absent due to the regulatory epigenetic control settings associated with pathology or treatment. CCSs have mild off-rates and when representing a particular phenotype or pathology, they will only change with a physiologically signalled transition to a new phenotype, or as a result of external intervention. In addition, the measurement of these events is binary, and so this read-out is in stark contrast to the continuum readout of varying levels of DNA methylation, histone modifications and most of the non-coding RNAs. The continuum read-out used for most molecular biomarkers to date offers a challenge to data analysis, in that the magnitude of change for particular biomarkers varies greatly from patient to patient, which causes problems for classification statistics when they are used to stratify cohorts of patients. These classification statistics are better-suited to using biomarkers that are absent of magnitude and offer just a "yes or no" binary score of phenotypic differences—signifying that chromosome conformation (EpiSwitch™) biomarkers are an excellent resource for potential diagnostic, prognostic and predictive biomarkers.

The inventors have identified regions of the genome with chromosomal interactions relevant to immunoresponsiveness using an approach which allows identification of subgroups in a population. The identified regions, genes and specific chromosome interactions from two separate studies using different therapies to treat two different conditions have been found to determine general immunoresponsiveness in a patient, including through the immune response regulating cell surface signalling pathway and regulation of T cell activation. The inventors' work allows changes in immunoresponsiveness to be followed, for example during the course of disease or therapy.

Accordingly, the invention provides a process for detecting a chromosome state which represents a subgroup in a population comprising determining whether a chromosome interaction relating to that chromosome state is present or absent within a defined region of the genome, wherein said subgroup relates to how immunoresponsive individuals are; and
wherein said chromosome interaction has optionally been identified by a method of determining which chromosomal interactions are relevant to a chromosome state corresponding to an immunoresponsive subgroup of the population, comprising contacting a first set of nucleic acids from subgroups with different states of the chromosome with a second set of index nucleic acids, and allowing complementary sequences to hybridise, wherein the nucleic acids in the first and second sets of nucleic acids represent a ligated product comprising sequences from both the chromosome regions that have come together in chromosomal interactions, and wherein the pattern of hybridisation between the first and second set of nucleic acids allows a determination of which chromosomal interactions are specific to an immunoresponsive subgroup; and
wherein the chromosome interaction:
(i) is present in any one of the regions or genes listed in Table 1; and/or
(ii) corresponds to any one of the chromosome interactions represent by any probe shown in Table 1, and/or
(iii) is present in a 4,000 base region which comprises or which flanks (i) or (ii).

The invention also provides a process for detecting a chromosome state which represents a subgroup in a population comprising determining whether a chromosome interaction relating to that chromosome state is present or absent within a defined region of the genome, wherein said subgroup relates to how immunoresponsive individuals are; and
wherein said chromosome interaction has optionally been identified by a method of determining which chromosomal interactions are relevant to a chromosome state corresponding to an immunoresponsive subgroup of the population, comprising contacting a first set of nucleic acids from subgroups with different states of the chromosome with a second set of index nucleic acids, and allowing complementary sequences to hybridise, wherein the nucleic acids in the first and second sets of nucleic acids represent a ligated product comprising sequences from both the chromosome regions that have come together in chromosomal interactions, and wherein the pattern of hybridisation between the first and second set of nucleic acids allows a determination of which chromosomal interactions are specific to an immunoresponsive subgroup; and
wherein the chromosome interaction:
a) is present in any one of the regions or genes listed in Table 13; and/or
b) corresponds to any one of the chromosome interactions represented by any probe shown in Table 13, and/or
c) is present in a 4,000 base region which comprises or which flanks (a) or (b).

The invention further provides a process for detecting a chromosome state which represents a subgroup in a population comprising determining whether a chromosome interaction relating to that chromosome state is present or absent within a defined region of the genome, wherein said subgroup relates to how immunoresponsive individuals are; and
wherein said chromosome interaction has optionally been identified by a method of determining which chromosomal interactions are relevant to a chromosome state corresponding to an immunoresponsive subgroup of the population, comprising contacting a first set of nucleic acids from subgroups with different states of the chromosome with a second set of index nucleic acids, and allowing complementary sequences to hybridise, wherein the nucleic acids in the first and second sets of nucleic acids represent a ligated product comprising sequences from both the chromosome regions that have come together in chromosomal interactions, and wherein the pattern of hybridisation between the first and second set of nucleic acids allows a determination of which chromosomal interactions are specific to an immunoresponsive subgroup; and wherein the chromosome interaction:

($\alpha$) is present in any one of the regions or genes listed in Table 16; and/or ($\beta$) corresponds to any one of the chromosome interactions represented by any probe shown in Table 16, and/or ($\gamma$) is present in a 4,000 base region which comprises or which flanks ($\alpha$) or ($\beta$).

DETAILED DESCRIPTION OF THE INVENTION

Aspects of the Invention

The inventions concerns a panel of epigenetic markers which relate to the regulation of the immune system, in particular via cell surface signalling pathways and T cell activation.

The invention also includes monitoring the state of the immune system to determine its responsiveness to particular therapies. That means appropriate therapies can be given to a patient, and whether or not the patient is retaining or losing 'responder' status can be determined. The invention therefore provides in one embodiment a 'live' ongoing readout of 'responder' status allowing a personalised therapy to be given to the patient which accurately reflects the patient's needs.

Immunoresponsiveness

The invention relates to determining immunoresponsiveness. This is preferably responsiveness to a therapy which comprises a molecule or cell that is relevant to the immune system, such as administration of a composition that comprises an antibody or immune cell (for example a T cell or dendritic cell) or administration of any therapeutic substance mentioned herein. It may be responsiveness to a substance that modulates or stimulates the immune system, such as a vaccine therapy. The immunoresponsiveness is thus preferably the responsiveness to an immunotherapy. The immunotherapy may modulate, block or stimulate an immune checkpoint, and thus may target or modulate PD-L1, PD-L2 or CTLA4 or any other immune checkpoint molecule disclosed herein, and thus may be an immunocheckpoint therapy. Preferably the immunoresponsiveness is responsiveness to an antibody therapy, or to any specific therapy disclosed herein (see specific drugs in later sections). The therapy may be a combination therapy.

In one embodiment immunoresponsiveness to responsiveness to a PD-1 inhibitor or PD-L1 inhibitor, including an antibody specific for PD-1 or PD-L1. PD-1 is 'programmed cell death protein' and PD-L1 is 'programmed death-ligand 1'.

The immunoresponsiveness is preferably to a cancer therapy, and so typically is relevant to whether a specific individual is responsive to the therapy, where the individual may or may not have cancer, or may be at risk of cancer. The cancer is typically any cancer mentioned herein, and for example is melanoma, lung cancer, non-small cell lung carcinoma (NSCLC), diffuse large B-cell lymphoma, liver cancer, hepatocellular carcinoma, prostate cancer, breast cancer, leukaemia, acute myeloid leukaemia, pancreatic cancer, thyroid cancer, nasal cancer, brain cancer, bladder cancer, cervical cancer, non-Hodgkin lymphoma, ovarian cancer, colorectal cancer or kidney cancer.

The term 'antibody' includes all fragments and derivatives of an antibody that retain the ability to bind the antigen target, for example single chain scFV's or Fab's.

As will be discussed later immunoresponsiveness can be determined for any therapy, cell or drug which is mentioned herein. In some embodiments any therapy, cell or drug that is mentioned herein may be administered to individuals whose immunoresponsiveness has been determined.

The Process of the Invention

The process of the invention comprises a typing system for detecting chromosome interactions relevant to immunoresponsiveness. This typing may be performed using the EpiSwitch™ system mentioned herein which is based on cross-linking regions of chromosome which have come together in the chromosome interaction, subjecting the chromosomal DNA to cleavage and then ligating the nucleic acids present in the cross-linked entity to derive a ligated nucleic acid with sequence from both the regions which formed the chromosomal interaction. Detection of this ligated nucleic acid allows determination of the presence or absence of a particular chromosome interaction.

The chromosomal interactions may be identified using the above described method in which populations of first and second nucleic acids are used. These nucleic acids can also be generated using EpiSwitch™ technology.

The Epigenetic Interactions Relevant to the Invention

As used herein, the term 'epigenetic' and 'chromosome' interactions typically refers to interactions between distal regions of a chromosome, said interactions being dynamic and altering, forming or breaking depending upon the status of the region of the chromosome.

In particular processes of the invention chromosome interactions are typically detected by first generating a ligated nucleic acid that comprises sequence from both regions of the chromosomes that are part of the interactions. In such processes the regions can be cross-linked by any suitable means. In a preferred embodiment, the interactions are cross-linked using formaldehyde, but may also be cross-linked by any aldehyde, or D-Biotinoyl-e-aminocaproic acid-N-hydroxysuccinimide ester or Digoxigenin-3-O-methylcarbonyl-e-aminocaproic acid-N-hydroxysuccinimide ester. Para-formaldehyde can cross link DNA chains which are 4 Angstroms apart. Preferably the chromosome interactions are on the same chromosome and optionally 2 to 10 Angstroms apart.

The chromosome interaction may reflect the status of the region of the chromosome, for example, if it is being transcribed or repressed in response to change of the physiological conditions. Chromosome interactions which are specific to subgroups as defined herein have been found to be stable, thus providing a reliable means of measuring the differences between the two subgroups.

In addition, chromosome interactions specific to a characteristic (such as immunoresponsiveness) will normally occur early in a biological process, for example compared to other epigenetic markers such as methylation or changes to binding of histone proteins. Thus the process of the invention is able to detect early stages of a biological process. This allows early intervention (for example treatment) which may as a consequence be more effective. Chromosome interactions also reflect the current state of the individual and therefore can be used to assess changes to immunoresponsiveness. Furthermore there is little variation in the relevant chromosome interactions between individuals within the same subgroup. Detecting chromosome interactions is highly informative with up to 50 different possible interactions per gene, and so processes of the invention can interrogate 500,000 different interactions.

Preferred Marker Sets

Herein the term 'marker' or 'biomarker' refers to a specific chromosome interaction which can be detected (typed) in the invention. Specific markers are disclosed herein, any of which may be used in the invention. Further sets of markers may be used, for example in the combinations or numbers disclosed herein. The specific markers disclosed in the tables herein are preferred as well as markers presents in genes and regions mentioned in the tables herein are preferred. These may be typed by any suitable method, for example the PCR or probe based methods disclosed herein, including a qPCR method. The markers are defined herein by location or by probe and/or primer sequences.

Location and Causes of Epigenetic Interactions

Epigenetic chromosomal interactions may overlap and include the regions of chromosomes shown to encode relevant or undescribed genes, but equally may be in intergenic regions. It should further be noted that the inventors have discovered that epigenetic interactions in all regions are equally important in determining the status of the chromosomal locus. These interactions are not necessarily in the coding region of a particular gene located at the locus and may be in intergenic regions.

The chromosome interactions which are detected in the invention could be caused by changes to the underlying DNA sequence, by environmental factors, DNA methylation, non-coding antisense RNA transcripts, non-mutagenic carcinogens, histone modifications, chromatin remodelling and specific local DNA interactions. The changes which lead to the chromosome interactions may be caused by changes to the underlying nucleic acid sequence, which themselves do not directly affect a gene product or the mode of gene expression. Such changes may be for example, SNPs within and/or outside of the genes, gene fusions and/or deletions of intergenic DNA, microRNA, and non-coding RNA. For example, it is known that roughly 20% of SNPs are in non-coding regions, and therefore the process as described is also informative in non-coding situation. In one embodiment the regions of the chromosome which come together to form the interaction are less than 5 kb, 3 kb, 1 kb, 500 base pairs or 200 base pairs apart on the same chromosome.

The chromosome interaction which is detected is preferably within any of the genes mentioned in Table 1. However it may also be upstream or downstream of the gene, for example up to 50,000, up to 30,000, up to 20,000, up to 10,000 or up to 5000 bases upstream or downstream from the gene or from the coding sequence.

The chromosome interaction which is detected is preferably within any of the genes mentioned in Table 13. However it may also be upstream or downstream of the gene, for example up to 50,000, up to 30,000, up to 20,000, up to 10,000 or up to 5000 bases upstream or downstream from the gene or from the coding sequence.

The chromosome interaction which is detected is preferably within any of the genes mentioned in Table 16. However it may also be upstream or downstream of the gene, for example up to 50,000, up to 30,000, up to 20,000, up to 10,000 or up to 5000 bases upstream or downstream from the gene or from the coding sequence.

Subgroups, Time Points and Personalised Treatment

The aim of the present invention is to determine the level of immunoresponsiveness. This may be at one or more defined time points, for example at at least 1, 2, 5, 8 or 10 different time points. The durations between at least 1, 2, 5 or 8 of the time points may be at least 5, 10, 20, 50, 80 or 100 days. Typically at least 1, 2 or 5 time points are before therapy begins and/or at least 1, 2 or 5 time points are after the beginning of therapy.

As used herein, a "subgroup" preferably refers to a population subgroup (a subgroup in a population), more preferably a subgroup in the population of a particular animal such as a particular eukaryote, or mammal (e.g. human, non-human, non-human primate, or rodent e.g. mouse or rat). Most preferably, a "subgroup" refers to a subgroup in the human population.

The invention includes detecting and treating particular subgroups in a population. The inventors have discovered that chromosome interactions differ between subsets (for example at least two subsets) in a given population. Identifying these differences will allow physicians to categorize their patients as a part of one subset of the population as described in the process. The invention therefore provides physicians with a process of personalizing medicine for the patient based on their epigenetic chromosome interactions.

In one embodiment the invention relates to testing whether an individual is a 'responder'. Once a person is found to be a 'responder' they can be given the relevant therapy which is typically a therapy that targets an immune checkpoint molecule such as PD-1, PD-L1 or CTLA4. In one embodiment if an individual is found to be a non-responder then they will be given a combination therapy, such as any combination therapy listed herein. Typically a combination therapy comprises an antibody and a small molecule.

Generating Ligated Nucleic Acids

Certain embodiments of the invention utilise ligated nucleic acids, in particular ligated DNA. These comprise sequences from both of the regions that come together in a chromosome interaction and therefore provide information about the interaction. The EpiSwitch™ method described herein uses generation of such ligated nucleic acids to detect chromosome interactions.

Thus a process of the invention may comprise a step of generating ligated nucleic acids (e.g. DNA) by the following steps (including a method comprising these steps):
 (i) cross-linking of epigenetic chromosomal interactions present at the chromosomal locus, preferably in vitro;
 (ii) optionally isolating the cross-linked DNA from said chromosomal locus;
 (iii) subjecting said cross-linked DNA to cutting, for example by restriction digestion with an enzyme that cuts it at least once (in particular an enzyme that cuts at least once within said chromosomal locus);
 (iv) ligating said cross-linked cleaved DNA ends (in particular to form DNA loops); and
 (v) optionally identifying the presence of said ligated DNA and/or said DNA loops, in particular using techniques such as PCR (polymerase chain reaction), to identify the presence of a specific chromosomal interaction.

These steps may be carried out to detect the chromosome interactions for any embodiment mentioned herein. The steps may also be carried out to generate the first and/or second set of nucleic acids mentioned herein.

PCR (polymerase chain reaction) may be used to detect or identify the ligated nucleic acid, for example the size of the PCR product produced may be indicative of the specific chromosome interaction which is present, and may therefore be used to identify the status of the locus. In preferred embodiments at least 1, 2 or 3 primers or primer pairs as shown in Table 4 are used in the PCR reaction. In other embodiments at least 1, 2 or 3 primers or primer pairs as shown in Table 13 are used in the PCR reaction. In other embodiments at least 1, 2 or 3 primers or primer pairs as shown in Table 17 are used in the PCR reaction. The skilled person will be aware of numerous restriction enzymes which can be used to cut the DNA within the chromosomal locus of interest. It will be apparent that the particular enzyme used will depend upon the locus studied and the sequence of the DNA located therein. A non-limiting example of a restriction enzyme which can be used to cut the DNA as described in the present invention is Taql.

Embodiments Such as EpiSwitch™ Technology

The EpiSwitch™ Technology also relates to the use of microarray EpiSwitch™ marker data in the detection of epigenetic chromosome conformation signatures specific for phenotypes. Embodiments such as EpiSwitch™ which utilise ligated nucleic acids in the manner described herein have several advantages. They have a low level of stochastic noise, for example because the nucleic acid sequences from the first set of nucleic acids of the present invention either hybridise or fail to hybridise with the second set of nucleic acids. This provides a binary result permitting a relatively simple way to measure a complex mechanism at the epigenetic level. EpiSwitch™ technology also has fast processing time and low cost. In one embodiment the processing time is 3 hours to 6 hours.

Samples and Sample Treatment

The process of the invention will normally be carried out on a sample. The sample may be obtained at a defined time point, for example at any time point defined herein. The sample will normally contain DNA from the individual. It will normally contain cells. In one embodiment a sample is obtained by minimally invasive means, and may for example be a blood sample. DNA may be extracted and cut up with a standard restriction enzyme. This can pre-determine which chromosome conformations are retained and will be detected with the EpiSwitch™ platforms. Due to the synchronisation of chromosome interactions between tissues and blood, including horizontal transfer, a blood sample can be used to detect the chromosome interactions in tissues, such as tissues relevant to disease. For certain conditions, such as cancer, genetic noise due to mutations can affect the chromosome interaction 'signal' in the relevant tissues and therefore using blood is advantageous.

Properties of Nucleic Acids of the Invention

The invention relates to certain nucleic acids, such as the ligated nucleic acids which are described herein as being used or generated in the process of the invention. These may be the same as, or have any of the properties of, the first and second nucleic acids mentioned herein. The nucleic acids of the invention typically comprise two portions each comprising sequence from one of the two regions of the chromosome which come together in the chromosome interaction. Typically each portion is at least 8, 10, 15, 20, 30 or 40 nucleotides in length, for example 10 to 40 nucleotides in length. Preferred nucleic acids comprise sequence from any of the genes mentioned in any of the tables. Typically preferred nucleic acids comprise the specific probe sequences mentioned in Table 1; or fragments and/or homologues of such sequences. The preferred nucleic acids may comprise the specific probe sequences mentioned in Table 13; or fragments and/or homologues of such sequences. The preferred nucleic acids may comprise the specific probe sequences mentioned in Table 16; or fragments and/or homologues of such sequences.

Preferably the nucleic acids are DNA. It is understood that where a specific sequence is provided the invention may use the complementary sequence as required in the particular embodiment. Preferably the nucleic acids are DNA. It is understood that where a specific sequence is provided the invention may use the complementary sequence as required in the particular embodiment.

The primers shown in Table 4 may also be used in the invention as mentioned herein. In one embodiment primers are used which comprise any of: the sequences shown in Table 4; or fragments and/or homologues of any sequence shown in Table 4. The primers shown in Table 13 may also be used in the invention as mentioned herein. In one embodiment primers are used which comprise any of: the sequences shown in Table 13; or fragments and/or homologues of any sequence shown in Table 13. The primers shown in Table 17 may also be used in the invention as mentioned herein. In one embodiment primers are used which comprise any of: the sequences shown in Table 17; or fragments and/or homologues of any sequence shown in Table 17.

The Second Set of Nucleic Acids—the 'Index' Sequences

The second set of nucleic acid sequences has the function of being a set of index sequences, and is essentially a set of nucleic acid sequences which are suitable for identifying subgroup specific sequence. They can represents the 'background' chromosomal interactions and might be selected in some way or be unselected. They are in general a subset of all possible chromosomal interactions.

The second set of nucleic acids may be derived by any suitable process. They can be derived computationally or they may be based on chromosome interaction in individuals. They typically represent a larger population group than the first set of nucleic acids. In one particular embodiment, the second set of nucleic acids represents all possible epigenetic chromosomal interactions in a specific set of genes. In another particular embodiment, the second set of nucleic acids represents a large proportion of all possible epigenetic chromosomal interactions present in a population described herein. In one particular embodiment, the second set of nucleic acids represents at least 50% or at least 80% of epigenetic chromosomal interactions in at least 20, 50, 100 or 500 genes, for example in 20 to 100 or 50 to 500 genes.

The second set of nucleic acids typically represents at least 100 possible epigenetic chromosome interactions which modify, regulate or in any way mediate a phenotype in population. The second set of nucleic acids may represent chromosome interactions that affect a disease state (typically relevant to diagnosis or prognosis) in a species. The second set of nucleic acids typically comprises sequences representing epigenetic interactions both relevant and not relevant to an immunoresponsiveness subgroup.

In one particular embodiment the second set of nucleic acids derive at least partially from naturally occurring sequences in a population, and are typically obtained by in silico processes. Said nucleic acids may further comprise single or multiple mutations in comparison to a corresponding portion of nucleic acids present in the naturally occurring nucleic acids. Mutations include deletions, substitutions and/or additions of one or more nucleotide base pairs. In one particular embodiment, the second set of nucleic acids may comprise sequence representing a homologue and/or orthologue with at least 70% sequence identity to the corresponding portion of nucleic acids present in the naturally occurring species. In another particular embodiment, at least 80% sequence identity or at least 90% sequence identity to the corresponding portion of nucleic acids present in the naturally occurring species is provided.

Properties of the Second Set of Nucleic Acids

In one particular embodiment, there are at least 100 different nucleic acid sequences in the second set of nucleic acids, preferably at least 1000, 2000 or 5000 different nucleic acids sequences, with up to 100,000, 1,000,000 or 10,000,000 different nucleic acid sequences. A typical number would be 100 to 1,000,000, such as 1,000 to 100,000 different nucleic acids sequences. All or at least 90% or at least 50% or these would correspond to different chromosomal interactions.

In one particular embodiment, the second set of nucleic acids represent chromosome interactions in at least 20 different loci or genes, preferably at least 40 different loci or genes, and more preferably at least 100, at least 500, at least 1000 or at least 5000 different loci or genes, such as 100 to 10,000 different loci or genes. The lengths of the second set of nucleic acids are suitable for them to specifically hybridise according to Watson Crick base pairing to the first set of nucleic acids to allow identification of chromosome interactions specific to subgroups. Typically the second set of nucleic acids will comprise two portions corresponding in sequence to the two chromosome regions which come together in the chromosome interaction. The second set of nucleic acids typically comprise nucleic acid sequences which are at least 10, preferably 20, and preferably still 30 bases (nucleotides) in length. In another embodiment, the nucleic acid sequences may be at the most 500, preferably at most 100, and preferably still at most 50 base pairs in length. In a preferred embodiment, the second set of nucleic acids comprises nucleic acid sequences of between 17 and 25 base pairs. In one embodiment at least 100, 80% or 50% of the second set of nucleic acid sequences have lengths as described above. Preferably the different nucleic acids do not have any overlapping sequences, for example at least 100%, 90%, 80% or 50% of the nucleic acids do not have the same sequence over at least 5 contiguous nucleotides.

Given that the second set of nucleic acids acts as an 'index' then the same set of second nucleic acids may be used with different sets of first nucleic acids which represent subgroups for different characteristics, i.e. the second set of nucleic acids may represent a 'universal' collection of nucleic acids which can be used to identify chromosome interactions relevant to different characteristics.

The First Set of Nucleic Acids

The first set of nucleic acids are typically from subgroups relevant to immunoresponsiveness. The first nucleic acids may have any of the characteristics and properties of the second set of nucleic acids mentioned herein. The first set of nucleic acids is normally derived from samples from the individuals which have undergone treatment and processing as described herein, particularly the EpiSwitch™ cross-linking and cleaving steps. Typically the first set of nucleic acids represents all or at least 80% or 50% of the chromosome interactions present in the samples taken from the individuals.

Typically, the first set of nucleic acids represents a smaller population of chromosome interactions across the loci or genes represented by the second set of nucleic acids in comparison to the chromosome interactions represented by second set of nucleic acids, i.e. the second set of nucleic acids is representing a background or index set of interactions in a defined set of loci or genes.

Library of Nucleic Acids

Any of the types of nucleic acid populations mentioned herein may be present in the form of a library comprising at least 200, at least 500, at least 1000, at least 5000 or at least 10000 different nucleic acids of that type, such as 'first' or 'second' nucleic acids. Such a library may be in the form of being bound to an array.

Hybridisation

The invention requires a means for allowing wholly or partially complementary nucleic acid sequences from the first set of nucleic acids and the second set of nucleic acids to hybridise. In one embodiment all of the first set of nucleic acids is contacted with all of the second set of nucleic acids in a single assay, i.e. in a single hybridisation step. However any suitable assay can be used.

Labelled Nucleic Acids and Pattern of Hybridisation

The nucleic acids mentioned herein may be labelled, preferably using an independent label such as a fluorophore (fluorescent molecule) or radioactive label which assists detection of successful hybridisation. Certain labels can be detected under UV light. The pattern of hybridisation, for example on an array described herein, represents differences in epigenetic chromosome interactions between the two subgroups, and thus provides a process of comparing epigenetic chromosome interactions and determination of which epigenetic chromosome interactions are specific to a subgroup in the population of the present invention.

The term 'pattern of hybridisation' broadly covers the presence and absence of hybridisation between the first and second set of nucleic acids, i.e. which specific nucleic acids from the first set hybridise to which specific nucleic acids from the second set, and so it not limited to any particular assay or technique, or the need to have a surface or array on which a 'pattern' can be detected.

Selecting a Subgroup with Particular Characteristics

The invention provides a process which comprises detecting the presence or absence of chromosome interactions, typically 5 to 20 or 5 to 500 such interactions, preferably 20 to 300 or 50 to 100 interactions, in order to determine the presence or absence of a characteristic relating to immunoresponsiveness in an individual. Preferably the chromosome interactions are those in any of the genes mentioned herein. In one embodiment the chromosome interactions which are typed are those represented by the nucleic acids in Table 1. In another embodiment the chromosome interactions are those represented in Table 13. In another embodiment the chromosome interactions are those represented in Table 16. The column titled 'Loop Detected' in the tables shows which subgroup is detected (i.e. responder or non-responder) by each probe.

The Individual that is Tested

Examples of the species that the individual who is tested is from are mentioned herein. In addition the individual that is tested in the process of the invention may have been selected in some way. The individual may be susceptible to any condition mentioned herein and/or may be in need of any therapy mentioned in. The individual may be receiving any therapy mentioned herein.

In one embodiment the individual that is tested has shown a lack of response to therapy, and the purpose of testing them is to discover whether they are a 'pseudo-progressor' that will respond to therapy in the second stage of disease, though they have not responded at an earlier stage.

Preferred Gene Regions, Loci, Genes and Chromosome Interactions

For all aspects of the invention preferred gene regions, loci, genes and chromosome interactions are mentioned in the tables, for example in Table 1. Typically in the processes of the invention chromosome interactions are detected from at least 1, 2, 10, 50, 100, 150, 200 or 300 of the relevant genes listed in Table 1. Preferably the presence or absence of at least 1, 2, 10, 50, 100, 150, 200 or 300 of the relevant specific chromosome interactions represented by the probe sequences in Table 1 are detected. The chromosome interaction may be upstream or downstream of any of the genes mentioned herein, for example 50 kb upstream or 20 kb downstream, for example from the coding sequence.

In one embodiment at least 5, 10, 15, 20 or all of the chromosome interactions in Table 1.a are typed. In one embodiment at least 5, 10, 15, 20 or all of the chromosome interactions in Table 1.b are typed. In one embodiment at least 5, 10, 15, 20 or all of the chromosome interactions in Table 1.c are typed. In one embodiment at least 5, 10, 15, 20 or all of the chromosome interactions in Table 1.d are typed. In one embodiment at least 5, 10, 15, 20 or all of the chromosome interactions in Table 1.e are typed. In one embodiment at least 5, 10, 15, 20 or all of the chromosome interactions in Table 1.f are typed. In one embodiment at least 5, 10, 15, 20 or all of the chromosome interactions in Table 1.g are typed.

Typically at least 5, 10, 15, 20, 30, 40 or 70 chromosome interactions are typed from any of genes or regions disclosed the tables herein, or parts of tables disclosed herein. Typically the chromosome interactions which are typed are present in at least 20, 50, 100, 200, 300 or all of the genes mentioned in Table 2. Typically the chromosome interactions which are typed are present in at least 10, 20, 50, 70 or all of the genes mentioned in Table 3.

For all aspects of the invention preferred gene regions, loci, genes and chromosome interactions are mentioned in Table 13. Typically in the processes of the invention chromosome interactions are detected from at least 1, 2, 10, 50, 100, 150, 200 or 300 of the relevant genes listed in Table 13. Preferably the presence or absence of at least 1, 2, 10, 50, 100, 150, 200 or 300 of the relevant specific chromosome interactions represented by the probe sequences in Table 13 are detected. The chromosome interaction may be upstream or downstream of any of the genes mentioned herein, for example 50 kb upstream or 20 kb downstream, for example from the coding sequence.

In one embodiment at least 5, 10, 15, 20 or all of the chromosome interactions in Table 13.a are typed. In one embodiment at least 5, 10, 15, 20 or all of the chromosome interactions in Table 13.b are typed. In one embodiment at least 5, 10, 15, 20 or all of the chromosome interactions in Table 13.c are typed. In one embodiment at least 5, 10, 15, 20 or all of the chromosome interactions in Table 13.d are typed. In one embodiment at least 5, 10, 15, 20 or all of the chromosome interactions in Table 13.e are typed. In one embodiment at least 5, 10, 15, 20 or all of the chromosome interactions in Table 13.f are typed. In one embodiment at least 5, 10, 15, 20 or all of the chromosome interactions in Table 13.g are typed. In one embodiment at least 5, 10, 15, 20 or all of the chromosome interactions in Table 13.h are typed. In one embodiment at least 5, 10, 15, 20 or all of the chromosome interactions in Table 13.i are typed.

Typically at least 5, 10, 15, 20, 30, 40 or 70 chromosome interactions are typed from any of genes or regions disclosed the tables herein, or parts of tables disclosed herein. Typically the chromosome interactions which are typed are present in at least 20, 50, 100, 200, 300 or all of the genes mentioned in Table 13. Typically the chromosome interactions which are typed are present in at least 10, 20, 50, 70 or all of the genes mentioned in Table 13.

For all aspects of the invention preferred gene regions, loci, genes and chromosome interactions are mentioned in Table 16. Typically in the processes of the invention chromosome interactions are detected from at least 1, 2, 10, 20. 30 or 40 of the relevant genes listed in Table 16. Preferably the presence or absence of at least 1, 2, 10, 20, 30 or 40 of the relevant specific chromosome interactions represented by the probe sequences in Table 16 are detected. The chromosome interaction may be upstream or downstream of any of the genes mentioned herein, for example 50 kb upstream or 20 kb downstream, for example from the coding sequence.

In one embodiment at least 5, 10 or 15 or all of the chromosome interactions in Table 18 are typed.

Typically at least 5, 10, 15, 20, 30, 40 or 70 chromosome interactions are typed from any of genes or regions disclosed the tables herein, or parts of tables disclosed herein. Typically the chromosome interactions which are typed are present in at least 20, 50, 100, 200, 300 or all of the genes mentioned in Table 13. Typically the chromosome interactions which are typed are present in at least 10, 20, 50, 70 or all of the genes mentioned in Table 13.

In one embodiment at least 5, 10, 15, 20, 30, 40 or 70 different chromosome interactions are typed from those defined in any of Tables 1, 13 and 16. In another embodiment at least 50%, 80% or all of the chromosome interactions which are typed are from Tables 1, 13 and 16.

In one embodiment the locus (including the gene and/or place where the chromosome interaction is detected) may comprise a CTCF binding site. This is any sequence capable of binding transcription repressor CTCF. That sequence may consist of or comprise the sequence CCCTC which may be present in 1, 2 or 3 copies at the locus. The CTCF binding site sequence may comprise the sequence CCGCGNGG-NGGCAG (in IUPAC notation). The CTCF binding site may be within at least 100, 500, 1000 or 4000 bases of the chromosome interaction or within any of the chromosome regions shown Table 1. The CTCF binding site may be within at least 100, 500, 1000 or 4000 bases of the chromosome interaction or within any of the chromosome regions shown Table 13.

In one embodiment the chromosome interactions which are detected are present at any of the gene regions shown Table 13. In the case where a ligated nucleic acid is detected in the process then sequence shown in any of the probe sequences in Table 13 may be detected.

Thus typically sequence from both regions of the probe (i.e. from both sites of the chromosome interaction) could be detected. In preferred embodiments probes are used in the process which comprise or consist of the same or complementary sequence to a probe shown in any table. In some embodiments probes are used which comprise sequence which is homologous to any of the probe sequences shown in the tables.

Tables Provided Herein

Table 1 shows probe (Episwitch™ marker) data and gene data representing chromosome interactions relevant to immunoresponsiveness. The probe sequences show sequence which can be used to detect a ligated product generated from both sites of gene regions that have come together in chromosome interactions, i.e. the probe will comprise sequence which is complementary to sequence in the ligated product. The first two sets of Start-End positions show probe positions, and the second two sets of Start-End positions show the relevant 4 kb region. The following information is provided in the probe data table:

HyperG_Stats: p-value for the probability of finding that number of significant EpiSwitch™ markers in the locus based on the parameters of hypergeometric enrichment Probe Count Total: Total number of EpiSwitch™ Conformations tested at the locus Probe Count Sig: Number of EpiSwitch™ Conformations found to be statistically significant at the locus FDR HyperG: Multi-test (Fimmunoresposivenesse Discovery Rate) corrected hypergeometric p-value Percent Sig: Percentage of significant EpiSwitch™ markers relative the number of markers tested at the locus log FC: logarithm base 2 of Epigenetic Ratio (FC)

AveExpr: average log 2-expression for the probe over all arrays and channels

T: moderated t-statistic p-value: raw p-value adj. p-value: adjusted p-value or q-value B—B-statistic (lods or B) is the log-odds that that gene is differentially expressed.

FC—non-log Fold Change

FC_1—non-log Fold Change centred around zero

LS—Binary value this relates to FC_1 values. FC_1 value below −1.1 it is set to −1 and if the FC_1 value is above 1.1 it is set to 1. Between those values the value is 0

Table 1 shows genes where a relevant chromosome interaction has been found to occur. Other tables show similar data. The p-value in the loci table is the same as the HyperG_Stats (p-value for the probability of finding that number of significant EpiSwitch™ markers in the locus based on the parameters of hypergeometric enrichment). The LS column shows presence or absence of the relevant interaction with that particular responder status.

The probes are designed to be 30 bp away from the Taq1 site. In case of PCR, PCR primers are typically designed to detect ligated product but their locations from the Taq1 site vary.

Probe Locations:
  Start 1-30 bases upstream of Taq1 site on fragment 1
  End 1—Taq1 restriction site on fragment 1
  Start 2—Taq1 restriction site on fragment 2
  End 2-30 bases downstream of Taq1 site on fragment 2
  4 kb Sequence Location:
  Start 1-4000 bases upstream of Taq1 site on fragment 1
  End 1—Taq1 restriction site on fragment 1
  Start 2—Taq1 restriction site on fragment 2
  End 2-4000 bases downstream of Taq1 site on fragment 2

GLMNET values related to procedures for fitting the entire lasso or elastic-net regularization (Lambda set to 0.5 (elastic-net)).

Tables 1 and 4 relates to detection of immunoresponsiveness. Table 2 shows the overlap between the two studies that were done, and Table 3 shows the overlap with markers relating to interferon gamma. The invention can be carried out using markers as disclosed/represented in any of the tables. Other tables, including Tables 13 and 1, can be interpreted in a similar manner as set out for Table 1 above.

Preferred Embodiments for Sample Preparation and Chromosome Interaction Detection Methods of preparing samples and detecting chromosome conformations are described herein. Optimised (non-conventional) versions of these methods can be used, for example as described in this section.

Typically the sample will contain at least $2 \times 10^5$ cells. The sample may contain up to $5 \times 10^5$ cells. In one embodiment, the sample will contain $2 \times 10^5$ to $5.5 \times 10^5$ cells Crosslinking of epigenetic chromosomal interactions present at the chromosomal locus is described herein. This may be performed before cell lysis takes place. Cell lysis may be performed for 3 to 7 minutes, such as 4 to 6 or about 5 minutes. In some embodiments, cell lysis is performed for at least 5 minutes and for less than 10 minutes.

Digesting DNA with a restriction enzyme is described herein. Typically, DNA restriction is performed at about 55° C. to about 70° C., such as for about 65° C., for a period of about 10 to 30 minutes, such as about 20 minutes.

Preferably a frequent cutter restriction enzyme is used which results in fragments of ligated DNA with an average fragment size up to 4000 base pair. Optionally the restriction enzyme results in fragments of ligated DNA have an average fragment size of about 200 to 300 base pairs, such as about 256 base pairs. In one embodiment, the typical fragment size is from 200 base pairs to 4,000 base pairs, such as 400 to 2,000 or 500 to 1,000 base pairs.

In one embodiment of the EpiSwitch method a DNA precipitation step is not performed between the DNA restriction digest step and the DNA ligation step.

DNA ligation is described herein. Typically the DNA ligation is performed for 5 to 30 minutes, such as about 10 minutes.

The protein in the sample may be digested enzymatically, for example using a proteinase, optionally Proteinase K. The protein may be enzymatically digested for a period of about 30 minutes to 1 hour, for example for about 45 minutes. In one embodiment after digestion of the protein, for example Proteinase K digestion, there is no cross-link reversal or phenol DNA extraction step.

In one embodiment PCR detection is capable of detecting a single copy of the ligated nucleic acid, preferably with a binary read-out for presence/absence of the ligated nucleic acid.

FIG. 25 shows a preferred method of detecting chromosome interactions.

Processes and Uses of the Invention

The process of the invention can be described in different ways. It can be described as a method of making a ligated nucleic acid comprising (i) in vitro cross-linking of chromosome regions which have come together in a chromosome interaction; (ii) subjecting said cross-linked DNA to cutting or restriction digestion cleavage; and (iii) ligating said cross-linked cleaved DNA ends to form a ligated nucleic acid, wherein detection of the ligated nucleic acid may be used to determine the chromosome state at a locus, and wherein preferably:
  the locus may be any of the loci, regions or genes mentioned in Table 1, and/or
  wherein the chromosomal interaction may be any of the chromosome interactions mentioned herein or corresponding to any of the probes disclosed in Table 1, and/or
  wherein the ligated product may have or comprise (i) sequence which is the same as or homologous to any of the probe sequences disclosed in Table 1; or (ii) sequence which is complementary to (ii).

The process of the invention can be described as a process for detecting chromosome states which represent different subgroups in a population comprising determining whether a chromosome interaction is present or absent within a defined epigenetically active region of the genome, wherein preferably:
  the subgroup is defined by presence or absence of immunoresponsiveness, and/or
  the chromosome state may be at any locus, region or gene mentioned in Table 1; and/or the chromosome interaction may be any of those mentioned in Table 1 or corresponding to any of the probes disclosed in that table.

The process of the invention can be described as a method of making a ligated nucleic acid comprising (i) in vitro cross-linking of chromosome regions which have come together in a chromosome interaction; (ii) subjecting said cross-linked DNA to cutting or restriction digestion cleavage; and (iii) ligating said cross-linked cleaved DNA ends to form a ligated nucleic acid, wherein detection of the ligated nucleic acid may be used to determine the chromosome state at a locus, and wherein preferably:
  the locus may be any of the loci, regions or genes mentioned in Table 13, and/or
  wherein the chromosomal interaction may be any of the chromosome interactions mentioned herein or corresponding to any of the probes disclosed in Table 13, and/or
  wherein the ligated product may have or comprise (i) sequence which is the same as or homologous to any of the probe sequences disclosed in Table 13; or (ii) sequence which is complementary to (ii).

The process of the invention can be described as a process for detecting chromosome states which represent different subgroups in a population comprising determining whether a chromosome interaction is present or absent within a defined epigenetically active region of the genome, wherein preferably:
  the subgroup is defined by presence or absence of immunoresponsiveness, and/or
  the chromosome state may be at any locus, region or gene mentioned in Table 13; and/or
  the chromosome interaction may be any of those mentioned in Table 13 or corresponding to any of the probes disclosed in that table.

The process of the invention can be described as a method of making a ligated nucleic acid comprising (i) in vitro cross-linking of chromosome regions which have come together in a chromosome interaction; (ii) subjecting said cross-linked DNA to cutting or restriction digestion cleavage; and (iii) ligating said cross-linked cleaved DNA ends to form a ligated nucleic acid, wherein detection of the ligated nucleic acid may be used to determine the chromosome state at a locus, and wherein preferably:
  the locus may be any of the loci, regions or genes mentioned in Table 16, and/or
  wherein the chromosomal interaction may be any of the chromosome interactions mentioned herein or corresponding to any of the probes disclosed in Table 16, and/or
  wherein the ligated product may have or comprise (i) sequence which is the same as or homologous to any of the probe sequences disclosed in Table 16; or (ii) sequence which is complementary to (ii).

The process of the invention can be described as a process for detecting chromosome states which represent different subgroups in a population comprising determining whether a chromosome interaction is present or absent within a defined epigenetically active region of the genome, wherein preferably:
  the subgroup is defined by presence or absence of immunoresponsiveness, and/or
  the chromosome state may be at any locus, region or gene mentioned in Table 16; and/or
  the chromosome interaction may be any of those mentioned in Table 16 or corresponding to any of the probes disclosed in that table.

The invention includes detecting chromosome interactions at any locus, gene or regions mentioned Table 1. The invention includes use of the nucleic acids and probes mentioned herein to detect chromosome interactions, for example use of at least 1, 5, 10, 50, 100, 200, 250, 300 such nucleic acids or probes to detect chromosome interactions, preferably in at least 1, 5, 10, 50, 100, 200, 250, 300 different loci or genes. The invention includes detection of chromosome interactions using any of the primers or primer pairs listed in Table 4 or using variants of these primers as described herein (sequences comprising the primer sequences or comprising fragments and/or homologues of the primer sequences).

The invention includes detecting chromosome interactions at any locus, gene or regions mentioned Table 13. The invention includes use of the nucleic acids and probes mentioned herein to detect chromosome interactions, for example use of at least 1, 5, 10, 50, 100, 200, 250, 300 such nucleic acids or probes to detect chromosome interactions, preferably in at least 1, 5, 10, 50, 100, 200, 250, 300 different loci or genes. The invention includes detection of chromosome interactions using any of the primers or primer pairs listed in Table 13 or using variants of these primers as described herein (sequences comprising the primer sequences or comprising fragments and/or homologues of the primer sequences).

The invention includes detecting chromosome interactions at any locus, gene or regions mentioned Table 16. The invention includes use of the nucleic acids and probes mentioned herein to detect chromosome interactions, for example use of at least 1, 5, 10, 50, 100, 200, 250, 300 such nucleic acids or probes to detect chromosome interactions, preferably in at least 1, 5, 10, 50, 100, 200, 250, 300 different loci or genes. The invention includes detection of chromosome interactions using any of the primers or primer pairs listed in Table 17 or using variants of these primers as described herein (sequences comprising the primer sequences or comprising fragments and/or homologues of the primer sequences).

When analysing whether a chromosome interaction occurs 'within' a defined gene, region or location, either both the parts of the chromosome which have together in the interaction are within the defined gene, region or location or in some embodiments only one part of the chromosome is within the defined, gene, region or location.

Use of the Method of the Invention to Identify New Treatments

Knowledge of chromosome interactions can be used to identify new treatments for conditions. The invention provides methods and uses of chromosomes interactions defined herein to identify or design new therapeutic agents, for example relating to immunotherapy.

Homologues

Homologues of polynucleotide/nucleic acid (e.g. DNA) sequences are referred to herein. Such homologues typically have at least 70% homology, preferably at least 80%, at least 85%, at least 90%, at least 95%, at least 97%, at least 98% or at least 99% homology, for example over a region of at least 10, 15, 20, 30, 100 or more contiguous nucleotides, or across the portion of the nucleic acid which is from the region of the chromosome involved in the chromosome interaction. The homology may be calculated on the basis of nucleotide identity (sometimes referred to as "hard homology").

Therefore, in a particular embodiment, homologues of polynucleotide/nucleic acid (e.g. DNA) sequences are referred to herein by reference to percentage sequence identity. Typically such homologues have at least 70% sequence identity, preferably at least 80%, at least 85%, at least 90%, at least 95%, at least 97%, at least 98% or at least 99% sequence identity, for example over a region of at least 10, 15, 20, 30, 100 or more contiguous nucleotides, or across the portion of the nucleic acid which is from the region of the chromosome involved in the chromosome interaction.

For example the UWGCG Package provides the BEST-FIT program which can be used to calculate homology and/or % sequence identity (for example used on its default settings) (Devereux et al (1984) Nucleic Acids Research 12, p 387-395). The PILEUP and BLAST algorithms can be used to calculate homology and/or % sequence identity and/or line up sequences (such as identifying equivalent or corresponding sequences (typically on their default settings)), for example as described in Altschul S. F. (1993) J Mol Evol 36:290-300; Altschul, S, F et al (1990) J Mol Biol 215:403-10.

Software for performing BLAST analyses is publicly available through the National Center for Biotechnology Information. This algorithm involves first identifying high scoring sequence pair (HSPs) by identifying short words of length W in the query sequence that either match or satisfy some positive-valued threshold score T when aligned with a word of the same length in a database sequence. T is referred to as the neighbourhood word score threshold (Altschul et al, supra). These initial neighbourhood word hits act as seeds for initiating searches to find HSPs containing them. The word hits are extended in both directions along each sequence for as far as the cumulative alignment score can be increased. Extensions for the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W5 T and X determine the sensitivity and speed of the alignment. The BLAST program uses as defaults a word length (W) of 11, the BLOSUM62 scoring matrix (see Henikoff and Henikoff (1992) Proc. Natl. Acad. Sci. USA 89: 10915-10919) alignments (B) of 50, expectation (E) of 10, M=5, N=4, and a comparison of both strands.

The BLAST algorithm performs a statistical analysis of the similarity between two sequences; see e.g., Karlin and Altschul (1993) Proc. Natl. Acad. Sci. USA 90: 5873-5787. One measure of similarity provided by the BLAST algorithm is the smallest sum probability (P(N)), which provides an indication of the probability by which a match between two polynucleotide sequences would occur by chance. For example, a sequence is considered similar to another sequence if the smallest sum probability in comparison of the first sequence to the second sequence is less than about 1, preferably less than about 0.1, more preferably less than about 0.01, and most preferably less than about 0.001.

The homologous sequence typically differs by 1, 2, 3, 4 or more bases, such as less than 10, 15 or 20 bases (which may be substitutions, deletions or insertions of nucleotides). These changes may be measured across any of the regions mentioned above in relation to calculating homology and/or % sequence identity.

Homology of a 'pair of primers' can be calculated, for example, by considering the two sequences as a single sequence (as if the two sequences are joined together) for the purpose of then comparing against the another primer pair which again is considered as a single sequence.

Arrays

The second set of nucleic acids may be bound to an array, and in one embodiment there are at least 15,000, 45,000, 100,000 or 250,000 different second nucleic acids bound to the array, which preferably represent at least 300, 900, 2000 or 5000 loci. In one embodiment one, or more, or all of the different populations of second nucleic acids are bound to more than one distinct region of the array, in effect repeated on the array allowing for error detection. The array may be based on an Agilent SurePrint G3 Custom CGH microarray platform. Detection of binding of first nucleic acids to the array may be performed by a dual colour system.

Therapeutic Agents (for which Responsiveness is Determined or which are Selected Based on Testing According to the Invention)

Therapeutic agents are mentioned herein. The invention provides such agents for use in preventing or treating a disease condition in certain individuals, for example those identified by a process of the invention. This may comprise administering to an individual in need a therapeutically effective amount of the agent. The invention provides use of the agent in the manufacture of a medicament to prevent or treat a condition in certain individuals.

The formulation of the agent will depend upon the nature of the agent. The agent will be provided in the form of a pharmaceutical composition containing the agent and a pharmaceutically acceptable carrier or diluent. Suitable carriers and diluents include isotonic saline solutions, for example phosphate-buffered saline. Typical oral dosage compositions include tablets, capsules, liquid solutions and liquid suspensions. The agent may be formulated for parenteral, intravenous, intramuscular, subcutaneous, transdermal or oral administration.

The dose of an agent may be determined according to various parameters, especially according to the substance used; the age, weight and condition of the individual to be treated; the route of administration; and the required regimen. A physician will be able to determine the required route of administration and dosage for any particular agent. A suitable dose may however be from 0.1 to 100 mg/kg body weight such as 1 to 40 mg/kg body weight, for example, to be taken from 1 to 3 times daily.

In one embodiment the invention comprises detecting responsiveness to a therapeutic agent, for example any therapeutic agent mentioned herein. This may be before treatment has started and/or during the course of therapy.

The therapy may be mono or combination therapy, for example with immunocheckpoint modulators (inhibitors) for PD-1 and or its ligand, PD-L1. The therapy could be a combination of an anti-PD-1 or anti-PD-L1 combined with another drug that targets a checkpoint like CTLA4 (Ipilimumab/Yervoy) or small molecules. The PD-1 inhibitors could be pembrolizumab (Keytruda) or nivolumab (Opdivo). The modulator of PD-L1 or therapeutic agent could be Atezolizumab (Tecentriq), Avelumab (Bavencio), Durvalumab (Imfinzi), CA-170, Ipilimumab, Tremelimumab, Nivolumab, Pembrolizumab, Pidilizumab, BMS935559, GVAXMPDL3280A, MEDI4736, MSB0010718C, MDX-1105/BMS-936559, AMP-224, MEDI0680.

The therapy may comprise administering agents that target and/or modulate interferon gamma or the JAK-START pathway.

The therapeutic agent may be any such agent disclosed in any table herein (for example in Table 9, 10 or 11), or may target any 'target' disclosed herein, including any protein disclosed herein in any table (including Table 1, 13 or 16).

It is understood that any agent that is disclosed in a combination should be seen as also disclosed for administration individually.

Forms of the Substance Mentioned Herein

Any of the substances, such as nucleic acids or therapeutic agents, mentioned herein may be in purified or isolated form. They may be in a form which is different from that found in nature, for example they may be present in combination with other substance with which they do not occur in nature. The nucleic acids (including portions of sequences defined herein) may have sequences which are different to those found in nature, for example having at least 1, 2, 3, 4 or more nucleotide changes in the sequence as described in the section on homology. The nucleic acids may have heterologous sequence at the 5' or 3' end. The nucleic acids may be chemically different from those found in nature, for example they may be modified in some way, but preferably are still capable of Watson-Crick base pairing. Where appropriate the nucleic acids will be provided in double stranded or single stranded form. The invention provides all of the specific nucleic acid sequences mentioned herein in single or double stranded form, and thus includes the complementary strand to any sequence which is disclosed.

The invention provides a kit for carrying out any process of the invention, including detection of a chromosomal interaction relating to immunoresponsiveness. Such a kit can include a specific binding agent capable of detecting the relevant chromosomal interaction, such as agents capable of detecting a ligated nucleic acid generated by processes of the invention. Preferred agents present in the kit include probes capable of hybridising to the ligated nucleic acid or primer pairs, for example as described herein, capable of amplifying the ligated nucleic acid in a PCR reaction.

The invention provides a device that is capable of detecting the relevant chromosome interactions. The device preferably comprises any specific binding agents, probe or primer pair capable of detecting the chromosome interaction, such as any such agent, probe or primer pair described herein.

Detection Methods

In one embodiment quantitative detection of the ligated sequence which is relevant to a chromosome interaction is carried out using a probe which is detectable upon activation during a PCR reaction, wherein said ligated sequence comprises sequences from two chromosome regions that come together in an epigenetic chromosome interaction, wherein said method comprises contacting the ligated sequence with the probe during a PCR reaction, and detecting the extent of activation of the probe, and wherein said probe binds the ligation site. The method typically allows particular interactions to be detected in a MIQE compliant manner using a dual labelled fluorescent hydrolysis probe.

The probe is generally labelled with a detectable label which has an inactive and active state, so that it is only detected when activated. The extent of activation will be related to the extent of template (ligation product) present in the PCR reaction. Detection may be carried out during all or some of the PCR, for example for at least 50% or 80% of the cycles of the PCR.

The probe can comprise a fluorophore covalently attached to one end of the oligonucleotide, and a quencher attached to the other end of the nucleotide, so that the fluorescence of the fluorophore is quenched by the quencher. In one embodiment the fluorophore is attached to the 5'end of the oligonucleotide, and the quencher is covalently attached to the 3' end of the oligonucleotide. Fluorophores that can be used in the methods of the invention include FAM, TET, JOE, Yakima Yellow, HEX, Cyanine3, ATTO 550, TAMRA, ROX, Texas Red, Cyanine 3.5, LC610, LC 640, ATTO 647N, Cyanine 5, Cyanine 5.5 and ATTO 680. Quenchers that can be used with the appropriate fluorophore include TAM, BHQ1, DAB, Eclip, BHQ2 and BBQ650, optionally wherein said fluorophore is selected from HEX, Texas Red and FAM. Preferred combinations of fluorophore and quencher include FAM with BHQ1 and Texas Red with BHQ2.

Use of the Probe in a qPCR Assay

Hydrolysis probes of the invention are typically temperature gradient optimised with concentration matched negative controls. Preferably single-step PCR reactions are optimized. More preferably a standard curve is calculated. An advantage of using a specific probe that binds across the junction of the ligated sequence is that specificity for the ligated sequence can be achieved without using a nested PCR approach. The methods described herein allow accurate and precise quantification of low copy number targets. The target ligated sequence can be purified, for example gel-purified, prior to temperature gradient optimization. The target ligated sequence can be sequenced. Preferably PCR reactions are performed using about 10 ng, or 5 to 15 ng, or 10 to 20 ng, or 10 to 50 ng, or 10 to 200 ng template DNA.

Forward and reverse primers are designed such that one primer binds to the sequence of one of the chromosome regions represented in the ligated DNA sequence, and the other primer binds to other chromosome region represented in the ligated DNA sequence, for example, by being complementary to the sequence.

Choice of Ligated DNA Target

The invention includes selecting primers and a probe for use in a PCR method as defined herein comprising selecting primers based on their ability to bind and amplify the ligated sequence and selecting the probe sequence based properties of the target sequence to which it will bind, in particular the curvature of the target sequence.

Probes are typically designed/chosen to bind to ligated sequences which are juxtaposed restriction fragments spanning the restriction site. In one embodiment of the invention, the predicted curvature of possible ligated sequences relevant to a particular chromosome interaction is calculated, for example using a specific algorithm referenced herein. The curvature can be expressed as degrees per helical turn, e.g. 10.5° per helical turn. Ligated sequences are selected for targeting where the ligated sequence has a curvature propensity peak score of at least 5° per helical turn, typically at least 10°, 15° or 20° per helical turn, for example 5° to 20° per helical turn. Preferably the curvature propensity score per helical turn is calculated for at least 20, 50, 100, 200 or 400 bases, such as for 20 to 400 bases upstream and/or downstream of the ligation site. Thus in one embodiment the target sequence in the ligated product has any of these levels of curvature. Target sequences can also be chosen based on lowest thermodynamic structure free energy.

PARTICULAR EMBODIMENTS

In one embodiment only intrachromosomal interactions are typed/detected, and no extrachromosomal interactions (between different chromosomes) are typed/detected.

In particular embodiments certain chromosome interactions are not typed, for example any specific interaction mentioned herein (for example as defined by any probe or primer pair mentioned herein). In some embodiments chromosome interactions are not typed in any of the genes mentioned here, for example in any gene mentioned in the Figures, including any or all genes mentioned in FIGS. 2 and 4.

In one embodiment none of the chromosome interactions represented by the probes or primers of any or all of Tables 5 to 7 are typed. In another embodiment no chromosome interactions present in any of the genes listed in any or all of Tables 5 to 7 are typed. In a further embodiment no chromosome interactions present in any of the regions listed in any or all of Tables 5 to 7 are typed.

In one embodiment the immunoresponsiveness does not relate to antibody therapy. In another embodiment the immunoresponsiveness does not relate to anti-PD-1 therapy, for example anti-PD-1 therapy of melanoma. In another embodiment the immunoresponsiveness does not relate to therapy one or more of the following: a blood cancer, leukaemia, prostate cancer, breast cancer, diffuse large B cell lymphoma.

Screening Method

The invention provides a method of determining which chromosomal interactions are relevant to a chromosome state corresponding to an immunoresponsive subgroup of the population, comprising contacting a first set of nucleic acids from subgroups with different states of the chromosome with a second set of index nucleic acids, and allowing complementary sequences to hybridise, wherein the nucleic acids in the first and second sets of nucleic acids represent a ligated product comprising sequences from both the chromosome regions that have come together in chromosomal interactions, and wherein the pattern of hybridisation between the first and second set of nucleic acids allows a determination of which chromosomal interactions are specific to an immunoresponsive subgroup. The subgroup may be any of the specific subgroups defined herein, for example with reference to particular conditions or therapies.

Publications

The contents of all publications mentioned herein are incorporated by reference into the present specification and may be used to further define the features relevant to the invention.

Tables

Table 1 shows the final set of markers for testing immunoresponsiveness.

Table 2 shows the shared markers between the anti-PD-1 and anti-PD-L1 studies.

Table 3 shows markers which overlap with interferon gamma activated ORF's.

Table 4 shows primer pairs that can be used to detect markers relating to immunoresponsiveness.

Tables 5 to 7 show markers, genes and regions which are not included in certain embodiments.

Table 8 shows immune checkpoint molecules.

Table 9 provides example of cancer therapies.

Tables 10 and 11 show combination and mono therapies for certain embodiments of the invention. In some embodiments these are the therapies for which responsiveness is tested. In other embodiments these therapies are given to the patient depending on the outcome of testing according to the invention.

Table 12 provides a description of genes relevant to the invention.

Table 13 shows a further set of markers for testing immunoresponsiveness.

Tables 14 and 15 describe genes that relate to embodiments of the invention.

Tables 16 to 18 shows markers for testing immunoresponsiveness.

EMBODIMENTS OF THE INVENTION

Paragraph A. A process for detecting a chromosome state which represents a subgroup in a population comprising determining whether a chromosome interaction relating to that chromosome state is present or absent within a defined region of the genome, wherein said subgroup relates to how immunoresponsive individuals are; and wherein said chromosome interaction has optionally been identified by a method of determining which chromosomal interactions are relevant to a chromosome state corresponding to an immunoresponsive subgroup of the population, comprising contacting a first set of nucleic acids from subgroups with different states of the chromosome with a second set of index nucleic acids, and allowing complementary sequences to hybridise, wherein the nucleic acids in the first and second sets of nucleic acids represent a ligated product comprising sequences from both the chromosome regions that have come together in chromosomal interactions, and wherein the pattern of hybridisation between the first and second set of nucleic acids allows a determination of which chromosomal interactions are specific to an immunoresponsive subgroup; and wherein the chromosome interaction either:

(i) is present in any one of the regions or genes listed in Table 1; and/or
(ii) corresponds to any one of the chromosome interactions represented by any probe shown in Table 1, and/or
(iii) is present in a 4,000 base region which comprises or which flanks (i) or (ii);

or a) is present in any one of the regions or genes listed in Table 13; and/or
b) corresponds to any one of the chromosome interactions represented by any probe shown in Table 13, and/or
c) is present in a 4,000 base region which comprises or which flanks (a) or (b).

Paragraph B. A process according to paragraph A wherein a specific combination of chromosome interactions are typed:

(i) comprising all of the chromosome interactions represented by the probes in Table 1; and/or
(ii) comprising at least 10, 50, 100, 150, 200 or 300 of the chromosome interactions represented by the probes in Table 1; and/or
(iii) which together are present in at least 10, 50, 100, 150 or 200 of the regions or genes listed in Table 1; and/or
(iv) wherein at least 10, 50, 100, 150, 200 or 300 chromosome interactions are typed which are present in a 4,000 base region which comprises or which flanks the chromosome interactions represented by the probes in Table 1.

Paragraph C. A process according to paragraph A wherein a specific combination of chromosome interactions are typed:

(i) comprising all of the chromosome interactions represented by the probes in Table 13; and/or
(ii) comprising at least 10, 50, 100, 150, 200 or 300 of the chromosome interactions represented by the probes in Table 13; and/or
(iii) which together are present in at least 10, 50, 100, 150 or 200 of the regions or genes listed in Table 13; and/or
(iv) wherein at least 10, 50, 100, 150, 200 or 300 chromosome interactions are typed which are present in a 4,000 base region which comprises or which flanks the chromosome interactions represented by the probes in Table 13.

D. A process according to any one of the preceding paragraphs in which the chromosome interactions are typed:
in a sample from an individual, and/or
by detecting the presence or absence of a DNA loop at the site of the chromosome interactions, and/or
detecting the presence or absence of distal regions of a chromosome being brought together in a chromosome conformation, and/or
by detecting the presence of a ligated nucleic acid which is generated during said typing and whose sequence comprises two regions each corresponding to the regions of the chromosome which come together in the chromosome interaction, wherein detection of the ligated nucleic acid is preferably by using either:
(i) a probe that has at least 70% identity to any of the specific probe sequences mentioned in Table 1, and/or
(ii) by a primer pair which has at least 70% identity to any primer pair in Table 4; or
(a) a probe that has at least 70% identity to any of the specific probe sequences mentioned in Table 13, and/or
(b) by a primer pair which has at least 70% identity to any primer pair in Table 13.

E. A process according to any one of the preceding paragraphs, wherein:
the second set of nucleic acids is from a larger group of individuals than the first set of nucleic acids; and/or
the first set of nucleic acids is from at least 8 individuals; and/or
the first set of nucleic acids is from at least 4 individuals from a first subgroup and at least 4 individuals from a second subgroup which is preferably non-overlapping with the first subgroup; and/or
the process is carried out to select an individual for a medical treatment; and/or
the immunoresponsiveness is responsiveness to immunotherapy or an immunocheckpoint therapy; and/or
the immunoresponsiveness is responsiveness to cancer immunotherapy, and/or
the process is carried out to determine immunoresponsiveness at one or more defined time points, wherein optionally at least one of the time points is during the course of therapy.

F. A process according to any one of the preceding paragraphs wherein:
the second set of nucleic acids represents an unselected group; and/or
wherein the second set of nucleic acids is bound to an array at defined locations; and/or
wherein the second set of nucleic acids represents chromosome interactions in least 100 different genes; and/or
wherein the second set of nucleic acids comprises at least 1,000 different nucleic acids representing at least 1,000 different chromosome interactions; and/or
wherein the first set of nucleic acids and the second set of nucleic acids comprise at least 100 nucleic acids with length 10 to 100 nucleotide bases.

G. A process according to any one of the preceding paragraphs, wherein the first set of nucleic acids is obtainable in a process comprising the steps of:—

(i) cross-linking of chromosome regions which have come together in a chromosome interaction;
(ii) subjecting said cross-linked regions to cleavage, optionally by restriction digestion cleavage with an enzyme; and
(iii) ligating said cross-linked cleaved DNA ends to form the first set of nucleic acids (in particular comprising ligated DNA).

H. A process according to any one of the preceding paragraphs:
wherein at least 10 to 200 different chromosome interactions are typed, preferably in 10 to 200 different regions or genes; and optionally (a) 50 to 100 different chromosome interactions are typed each of which is in a different gene and/or a different region as defined in Table 1; or (b) 50 to 100 different chromosome interactions are typed each of which is in a different gene and/or a different region as defined in Table 13;
and/or
which is carried out to select whether or not an individual will receive an immunotherapy, wherein the immunotherapy preferably comprises a small molecule immunotherapy, antibody immunotherapy or cell immunotherapy.

I. A process according to any one of the preceding paragraphs wherein said defined region of the genome:
(i) comprises a single nucleotide polymorphism (SNP); and/or
(ii) expresses a microRNA (miRNA); and/or
(iii) expresses a non-coding RNA (ncRNA); and/or
(iv) expresses a nucleic acid sequence encoding at least 10 contiguous amino acid residues; and/or
(v) expresses a regulating element; and/or
(vii) comprises a CTCF binding site.

J. A process according to any one of the preceding paragraphs which is carried out to identify or design a therapeutic agent for immunotherapy;
wherein preferably said process is used to detect whether a candidate agent is able to cause a change to a chromosome state which is associated with a different level of immunoresponsiveness;
wherein the chromosomal interaction is represented by any probe in Table 1; and/or
the chromosomal interaction is present in any region or gene listed in Table 1;
and wherein optionally:
the chromosomal interaction has been identified by the method of determining which chromosomal interactions are relevant to a chromosome state as defined in claim 1, and/or
the change in chromosomal interaction is monitored using (i) a probe that has at least 70% identity to any of the probe sequences mentioned in Table 1, and/or (ii) by a primer pair which has at least 70% identity to any primer pair in Table 4.

K. A process according to any one of the preceding paragraphs which is carried out to identify or design a therapeutic agent for immunotherapy;
wherein preferably said process is used to detect whether a candidate agent is able to cause a change to a chromosome state which is associated with a different level of immunoresponsiveness;
wherein the chromosomal interaction is represented by any probe in Table 13; and/or
the chromosomal interaction is present in any region or gene listed in Table 13;

and wherein optionally:
the chromosomal interaction has been identified by the method of determining which chromosomal interactions are relevant to a chromosome state as defined in claim 1, and/or
the change in chromosomal interaction is monitored using (i) a probe that has at least 70% identity to any of the probe sequences mentioned in Table 13, and/or (ii) by a primer pair which has at least 70% identity to any primer pair in Table 13.

L. A process according to paragraph J or K which comprises selecting a target based on detection of chromosome interactions, and preferably screening for a modulator of the target to identify a therapeutic agent for immunotherapy, wherein said target is optionally a protein.

M. A therapeutic agent for use in a method of immunotherapy in an individual that has been identified as being in need of the therapeutic agent by a process according to any one of paragraphs A to I.

N. A process according to any one of paragraphs A to K or a therapeutic agent for use according to paragraph M, wherein the typing or detecting comprises specific detection of the ligated product by quantitative PCR (qPCR) which uses primers capable of amplifying the ligated product and a probe which binds the ligation site during the PCR reaction, wherein said probe comprises sequence which is complementary to sequence from each of the chromosome regions that have come together in the chromosome interaction, wherein preferably said probe comprises:

an oligonucleotide which specifically binds to said ligated product, and/or
a fluorophore covalently attached to the 5' end of the oligonucleotide, and/or
a quencher covalently attached to the 3' end of the oligonucleotide, and
optionally
said fluorophore is selected from HEX, Texas Red and FAM; and/or
said probe comprises a nucleic acid sequence of length 10 to 40 nucleotide bases, preferably a length of 20 to 30 nucleotide bases.

SPECIFIC EMBODIMENTS

The EpiSwitch™ platform technology detects epigenetic regulatory signatures of regulatory changes between normal and abnormal conditions at loci. The EpiSwitch™ platform identifies and monitors the fundamental epigenetic level of gene regulation associated with regulatory high order structures of human chromosomes also known as chromosome conformation signatures. Chromosome signatures are a distinct primary step in a cascade of gene deregulation. They are high order biomarkers with a unique set of advantages against biomarker platforms that utilize late epigenetic and gene expression biomarkers, such as DNA methylation and RNA profiling.

EpiSwitch™ Array Assay

The custom EpiSwitch™ array-screening platforms come in 4 densities of, 15K, 45K, 100K, and 250K unique chromosome conformations, each chimeric fragment is repeated on the arrays 4 times, making the effective densities 60K, 180K, 400K and 1 Million respectively.

Custom Designed EpiSwitch™ Arrays

The 15K EpiSwitch™ array can screen the whole genome including around 300 loci interrogated with the EpiSwitch™ Biomarker discovery technology. The EpiSwitch™ array is built on the Agilent SurePrint G3 Custom CGH microarray platform; this technology offers 4 densities, 60K, 180K, 400K and 1 Million probes. The density per array is reduced to 15K, 45K, 100K and 250K as each EpiSwitch™ probe is presented as a quadruplicate, thus allowing for statistical evaluation of the reproducibility. The average number of potential EpiSwitch™ markers interrogated per genetic loci is 50; as such the numbers of loci that can be investigated are 300, 900, 2000, and 5000.

EpiSwitch™ Custom Array Pipeline

The EpiSwitch™ array is a dual colour system with one set of samples, after EpiSwitch™ library generation, labelled in Cy5 and the other of sample (controls) to be compared/analyzed labelled in Cy3. The arrays are scanned using the Agilent SureScan Scanner and the resultant features extracted using the Agilent Feature Extraction software. The data is then processed using the EpiSwitch™ array processing scripts in R. The arrays are processed using standard dual colour packages in Bioconductor in R: Limma*. The normalisation of the arrays is done using the normalisedWithinArrays function in Limma* and this is done to the on chip Agilent positive controls and EpiSwitch™ positive controls. The data is filtered based on the Agilent Flag calls, the Agilent control probes are removed and the technical replicate probes are averaged, in order for them to be analysed using Limma*. The probes are modelled based on their difference between the 2 scenarios being compared and then corrected by using False Discovery Rate. Probes with Coefficient of Variation (CV)<=30% that are <=−1.1 or =>1.1 and pass the p<=0.1 FDR p-value are used for further screening. To reduce the probe set further Multiple Factor Analysis is performed using the FactorMineR package in R.

* Note: LIMMA is Linear Models and Empirical Bayes Processes for Assessing Differential Expression in Microarray Experiments. Limma is an R package for the analysis of gene expression data arising from microarray or RNA-Seq.

The pool of probes is initially selected based on adjusted p-value, FC and CV<30% (arbitrary cut off point) parameters for final picking. Further analyses and the final list are drawn based only on the first two parameters (adj. p-value; FC).

Statistical Pipeline

EpiSwitch™ screening arrays are processed using the EpiSwitch™ Analytical Package in R in order to select high value EpiSwitch™ markers for translation on to the EpiSwitch™ PCR platform.

Step 1

Probes are selected based on their corrected p-value (False Discovery Rate, FDR), which is the product of a modified linear regression model. Probes below p-value<=0.1 are selected and then further reduced by their Epigenetic ratio (ER), probes ER have to be <=−1.1 or =>1.1 in order to be selected for further analysis. The last filter is a coefficient of variation (CV), probes have to be below <=0.3.

Step 2

The top 40 markers from the statistical lists are selected based on their ER for selection as markers for PCR translation. The top 20 markers with the highest negative ER load and the top 20 markers with the highest positive ER load form the list.

Step 3

The resultant markers from step 1, the statistically significant probes form the bases of enrichment analysis using hypergeometric enrichment (HE). This analysis enables marker reduction from the significant probe list, and along with the markers from step 2 forms the list of probes translated on to the EpiSwitch™ PCR platform.

The statistical probes are processed by HE to determine which genetic locations have an enrichment of statistically significant probes, indicating which genetic locations are hubs of epigenetic difference.

The most significant enriched loci based on a corrected p-value are selected for probe list generation. Genetic locations below p-value of 0.3 or 0.2 are selected. The statistical probes mapping to these genetic locations, with the markers from step 2, form the high value markers for EpiSwitch™ PCR translation.

Array Design and Processing

Array Design

1. Genetic loci are processed using the SII software (currently v3.2) to:
   a. Pull out the sequence of the genome at these specific genetic loci (gene sequence with 50 kb upstream and 20 kb downstream)
   b. Define the probability that a sequence within this region is involved in CCs
   c. Cut the sequence using a specific RE
   d. Determine which restriction fragments are likely to interact in a certain orientation
   e. Rank the likelihood of different CCs interacting together.
2. Determine array size and therefore number of probe positions available (x)
3. Pull out x/4 interactions.
4. For each interaction define sequence of 30 bp to restriction site from part 1 and 30 bp to restriction site of part 2. Check those regions aren't repeats, if so exclude and take next interaction down on the list. Join both 30 bp to define probe.
5. Create list of x/4 probes plus defined control probes and replicate 4 times to create list to be created on array
6. Upload list of probes onto Agilent Sure design website for custom CGH array.
7. Use probe group to design Agilent custom CGH array.

Array Processing

1. Process samples using EpiSwitch™ Standard Operating Procedure (SOP) for template production.
2. Clean up with ethanol precipitation by array processing laboratory.
3. Process samples as per Agilent SureTag complete DNA labelling kit—Agilent Oligonucleotide Array-based CGH for Genomic DNA Analysis Enzymatic labelling for Blood, Cells or Tissues
4. Scan using Agilent C Scanner using Agilent feature extraction software.

EpiSwitch™

EpiSwitch™ biomarker signatures demonstrate high robustness, sensitivity and specificity in the stratification of complex disease phenotypes. This technology takes advantage of the latest breakthroughs in the science of epigenetics, monitoring and evaluation of chromosome conformation signatures as a highly informative class of epigenetic biomarkers. Current research methodologies deployed in academic environment require from 3 to 7 days for biochemical processing of cellular material in order to detect CCSs. Those procedures have limited sensitivity, and reproducibility; and furthermore, do not have the benefit of the targeted insight provided by the EpiSwitch™ Analytical Package at the design stage.

EpiSwitch™ Array in Silico Marker Identification

CCS sites across the genome are directly evaluated by the EpiSwitch™ Array on clinical samples from testing cohorts for identification of all relevant stratifying lead biomarkers. The EpiSwitch™ Array platform is used for marker identification due to its high-throughput capacity, and its ability to screen large numbers of loci rapidly. The array used was the Agilent custom-CGH array, which allows markers identified through the in silico software to be interrogated.

EpiSwitch™ PCR

Potential markers identified by EpiSwitch™ Array are then validated either by EpiSwitch™ PCR or DNA sequencers (i.e. Roche 454, Nanopore MinION, etc.). The top PCR markers which are statistically significant and display the best reproducibility are selected for further reduction into the final EpiSwitch™ Signature Set, and validated on an independent cohort of samples. EpiSwitch™ PCR can be performed by a trained technician following a standardised operating procedure protocol established. All protocols and manufacture of reagents are performed under ISO 13485 and 9001 accreditation to ensure the quality of the work and the ability to transfer the protocols. EpiSwitch™ PCR and EpiSwitch™ Array biomarker platforms are compatible with analysis of both whole blood and cell lines. The tests are sensitive enough to detect abnormalities in very low copy numbers using small volumes of blood.

EXAMPLES

In the first study patients with melanoma were treated with anti-PD-1 (Pembrolizumab) for 12 weeks. Their epigenetic status, measured by EpiSwitch was assessed first at baseline prior to treatment and then at 12 weeks, along with clinical readout of response or no-response. We then screened, evaluated and validated parts of 3D genome architecture profiles, chromosome conformation signatures, at base line to identify profiles conducive to response or no-response to treatment at over 332 genetic locations across the genome. These were evaluate on an EpiSwitch array looking at local multiple 3C interactions at those genetic locations in technical and biological repeats, comparing samples from responders and non-responders at base line. Over 14,000 EpiSwitch markers were directly evaluated on the array. The best markers were translated into PCR and evaluated on the independent patient cohort.

FIG. 1 shows an example of clinical annotations of patients used in the study. Colour coded markings: patients listed in red were used in array screening. Patients in blue were used as part of independent cohort for validation—those patient were not used for marker selection, which is important in development of robust biomarkers. Clinical assessment of response or no-response was defined by the standard RESIST 1.1 criteria.

Stage 1 consist of the initial array screening and evaluation for the 14,000 marker leads (all predicted by pattern recognition). Stage 2 is the translation of statistically significant marker leads from array into PCR. Further evaluation by PCR of the markers by regression analysis for reduction of the final marker number in the final signature. Stage 3 is validation of the final signature of 6 best biomarkers (shown in FIG. 2). The table in FIG. 2 shows the names for the best biomarkers and the genetic loci in which they are positioned, i.e. in this loci they contribute in a particular way to the overall regulation.

FIG. 3 shows the Venn diagram for the best predictive biomarkers from array analysis (comparing baseline for responders and non-responders) and best response biomarkers (comparing responders at baseline and at 12 weeks). The overlap gives not only good response biomarkers that are present at the start for response, but also could be monitored over 12 weeks.

FIG. 4 is an example of a binary PCR readout on individual patients for some of the final signature biomarkers: 1 CCs is present, 0 CCS is absent. One can see visually the difference in profiles for responders and non-responders. R is a responder. NR is a non-responder.

FIG. 5 shows two groups of patients with lung cancer who were treated with anti-PD-L1 monoclonal antibody. Blood was collected at baseline prior to treatment (BL) and at two weeks after the start of treatment (2W). The identity of the two groups for response was established but in the original study had been blinded into group I and group II. The top best 30 PCR-based marker leads predictive for response from anti-PD-1 from the first study (see above) were evaluated on all the patients listed.

FIG. 6 show statistical analysis of the best top 13 statistically significant markers discriminating between groups I and II. PDCD1LG2 and STAT5 are also the top discriminating markers in the original anti-PD-1 study: PDCD1LG2 for non-responders, STAT5B for responders. This helps to identify the groups I and II as responder and non-responder groups correctly. The biomarkers monitor deregulation in the same immunotherapies checkpoint cellular network, triggered either by PD-1 in the first study or by its ligand PD-L1 in the second study, and thus have shared features with overlap on the same markers—6 non-response markers, 7 response markers from the first study on PD-1 still being valid in the second study with PD-L1.

FIG. 7 shows a principle component analysis (PCA) of the top 13 markers selected from the PD-L1 cohort. This is a 3D PCA that shows on the three first components of stratification a good separation of responders and non-responders. Noticeably, non-responders (dark triangles) also separate between for the same patients for baseline (A) and 2 weeks (B) of treatment. This is a separate feature related to how tight the epigenetic profiles are controlled in responders and non-responders.

FIG. 8 show how in a separate, third study, conducted on lung cancer patients with a different anti-PD-L1 monoclonal, 15 patient baseline samples were provided as blinded on annotation for response/no-response to treatment. Combining the first and the second study, using 8 patients from the first (PD-1 treatment in melanoma) and 24 from the second (a different PD-L1 in lung cancer) a pool of markers was evaluated and the top 5 markers on statistical significance (listed in the table) were then used for classification of 15 blinded samples.

FIG. 9 shows how a Random Forest Classifier built on the listed 5 markers produces predicted calls for each of the 15 samples (column predicted).

FIG. 10 shows predicted calls for each sample compared against unblinded validations (column actual). The stratification efficiency is listed in the table. Sensitivity 71%, Specificity 87.5%, Positive predictive value 83% (important in this context of patient selection), negative predictive value 77%.

FIG. 11 shows the standard rOC curve for the classifier. AUC=0.786

FIG. 12 shows a principle component analysis for all the samples used in this analysis: 8 from the first study, 24 from the second, 15 from the validation. On the first principle components the separation for responders and non-responders is already obvious. There are only two miscalled samples in the open classifier for all 47 samples.

The third study relates to anti-PD-L1 treatment in lung cancer. At the array stage of screening 12 responders and 12 non-responders were compared at base line on the array for a total of 180,000 readouts (in technical and biological repeats). There was then PCR translation for the top 100 marker leads from the array followed by validation.

There was a comparison of marker leads from the arrays for the PD-1 (study I), PD-L1 (study II) with the PD-L1 study III. FIG. 13 shows the overlap of a common 2522 leads for responders. FIG. 14 shows the same, but now looking at the most statistically significant—276 common significant leads for both studies for responders (study I on the left, study II on the right). FIG. 15 shows the same, but for non-responders of which there is only one (study I on the left, study II on the right).

FIG. 16 shows how the genetic loci for array reads for response and non-response markers (Studies I and III) overlap with genes involved in interferon gamma pathway. Interferon gamma treatment can increase PD-L1 expression, which is a clinical observation for predisposition for response to treatment. FIG. 17 shows the same, but for statistical significant data only. FIG. 18 shows the same, but for all studies I-III.

Figure 7A:
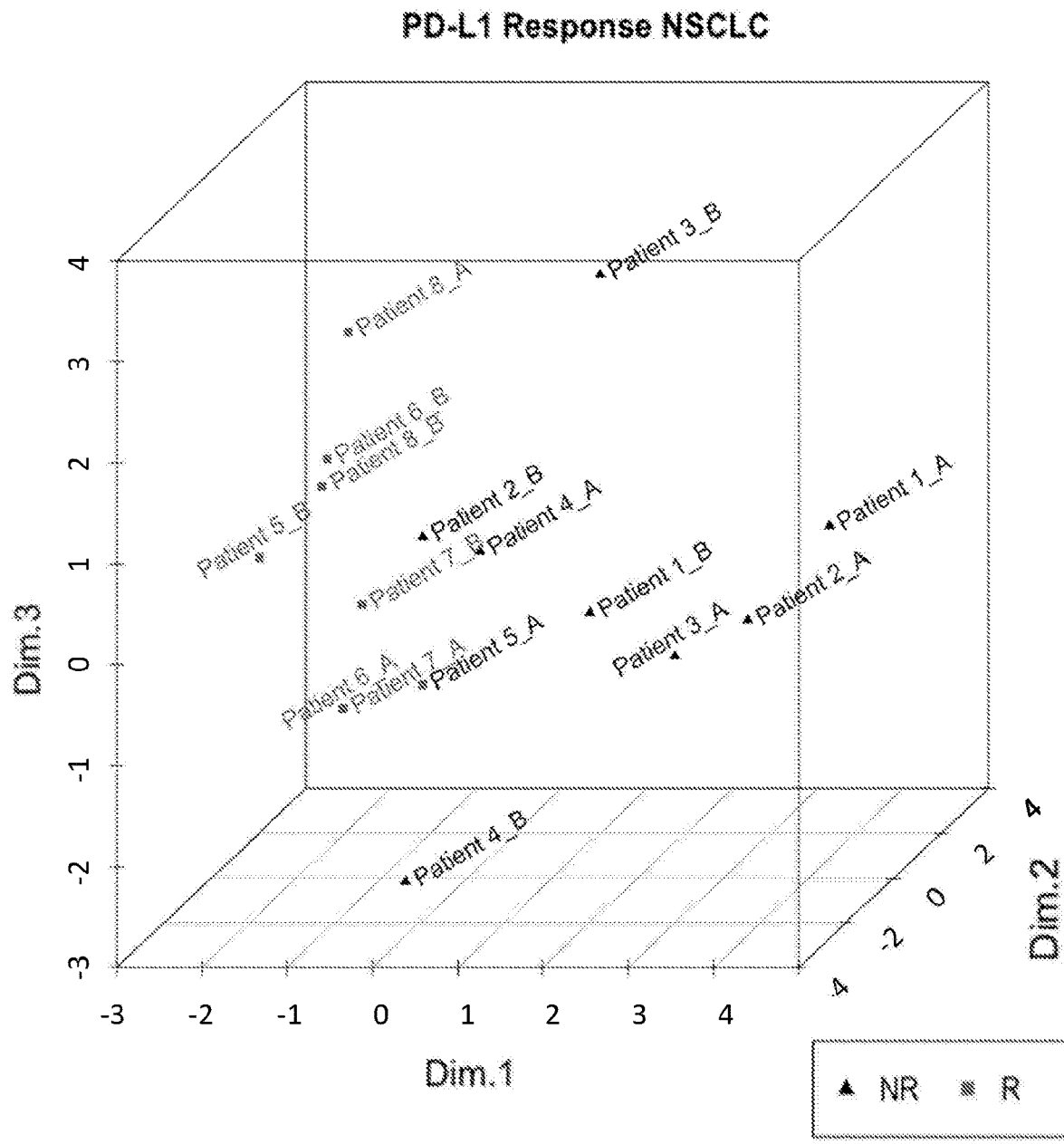
Figure 7B:
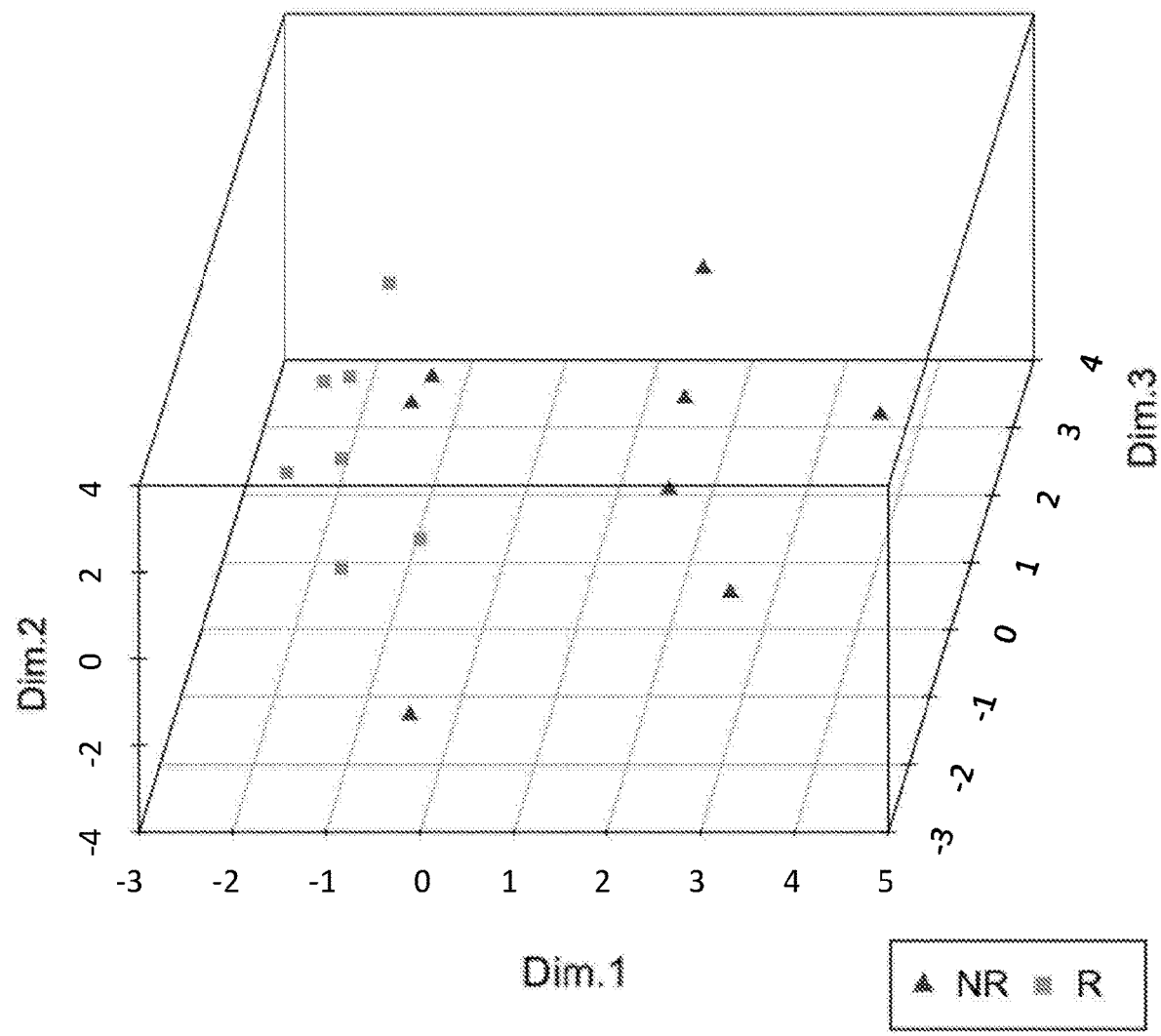
Figure 11:
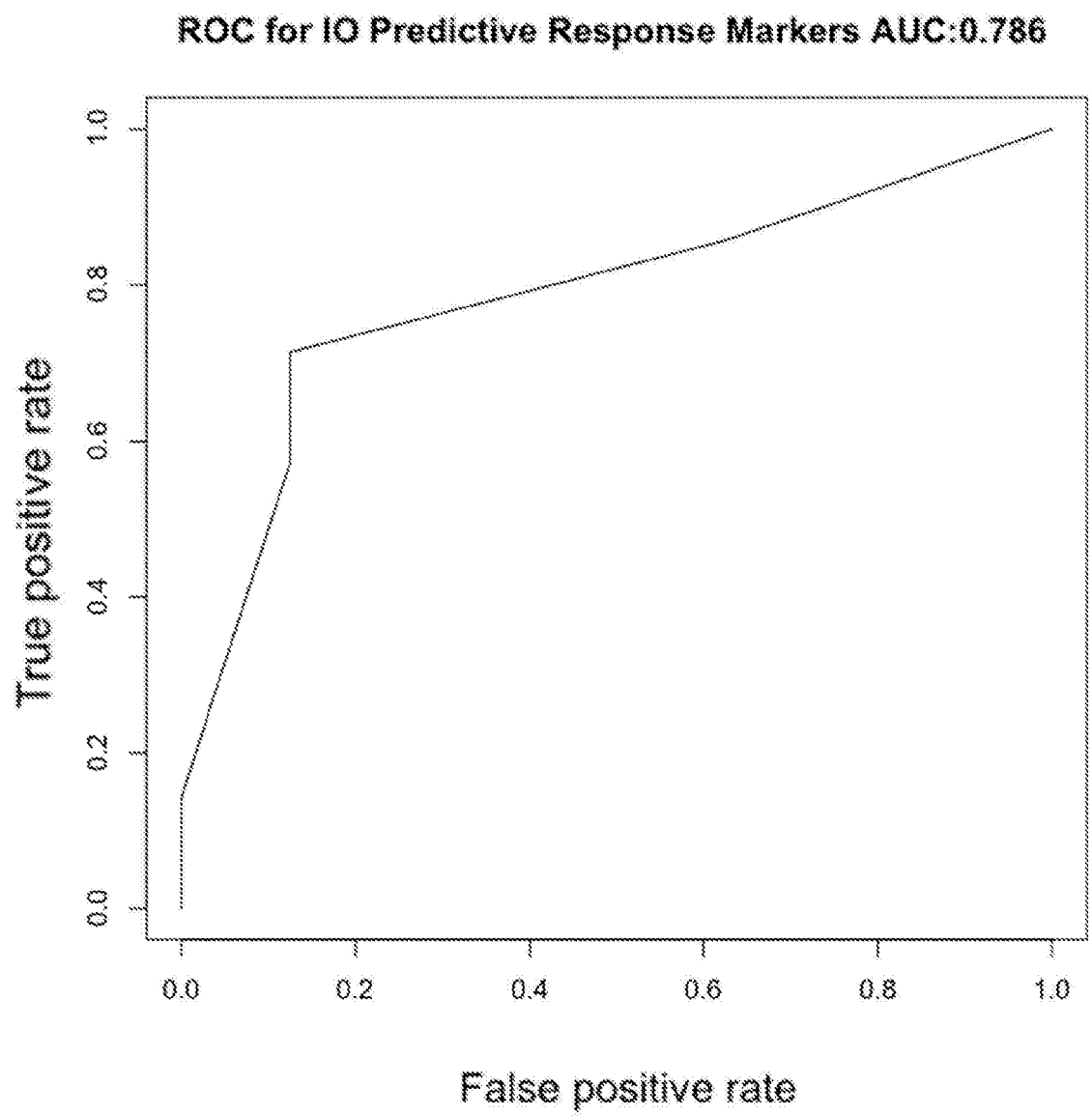
Figure 12:
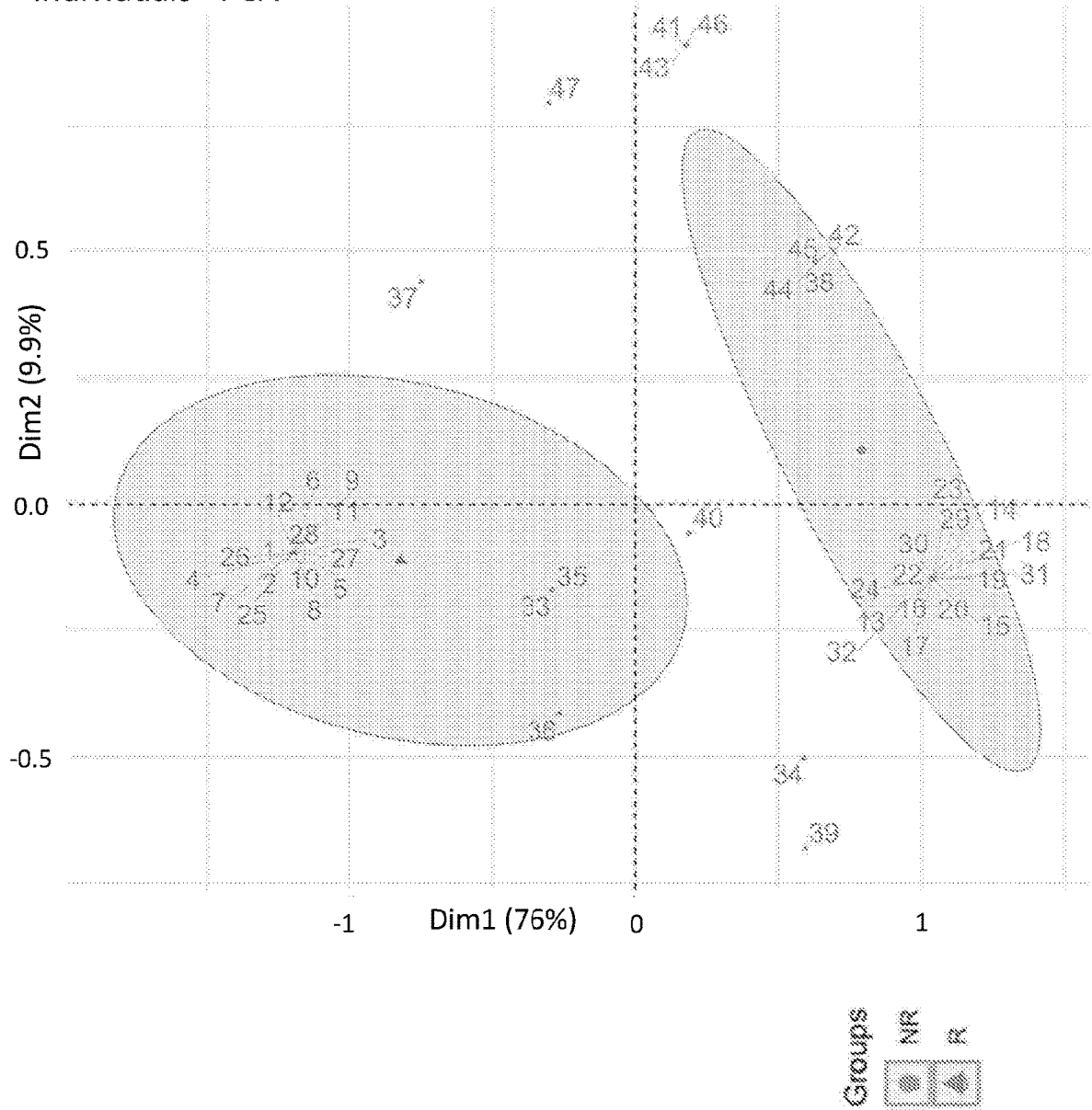
Figure 13:
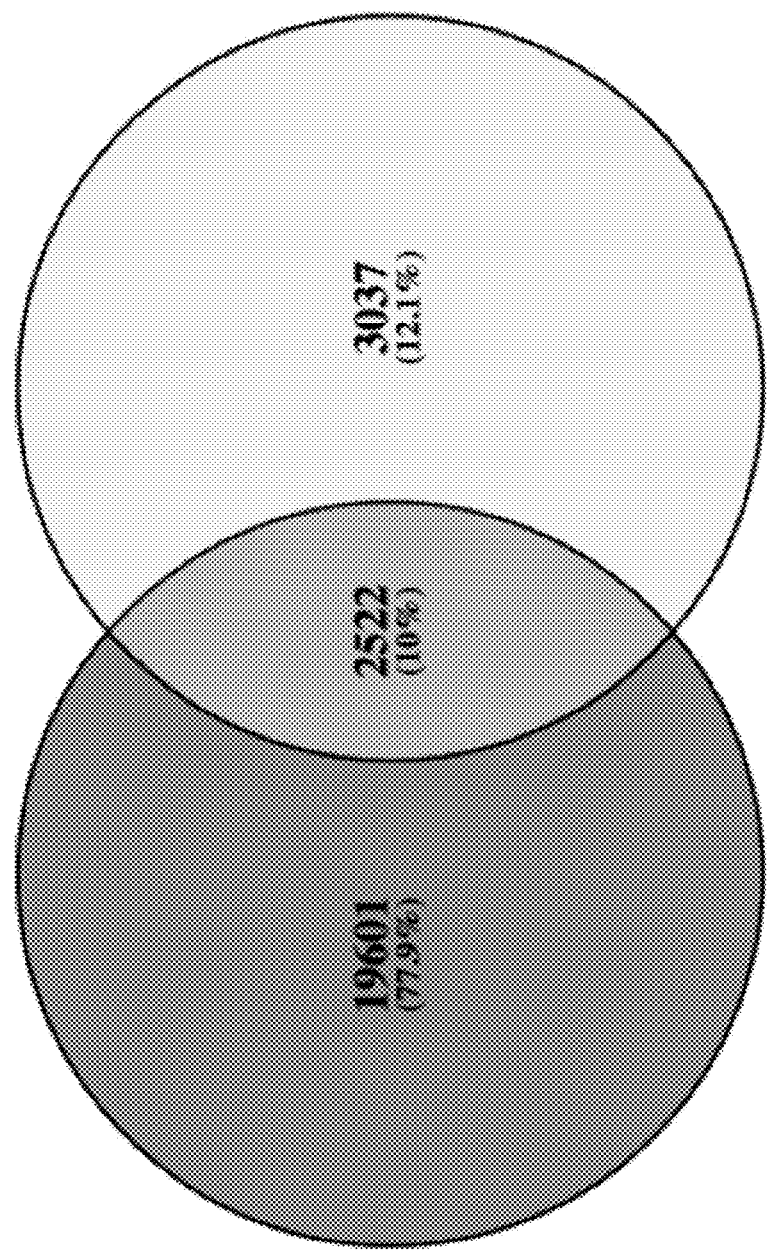
Figure 14:
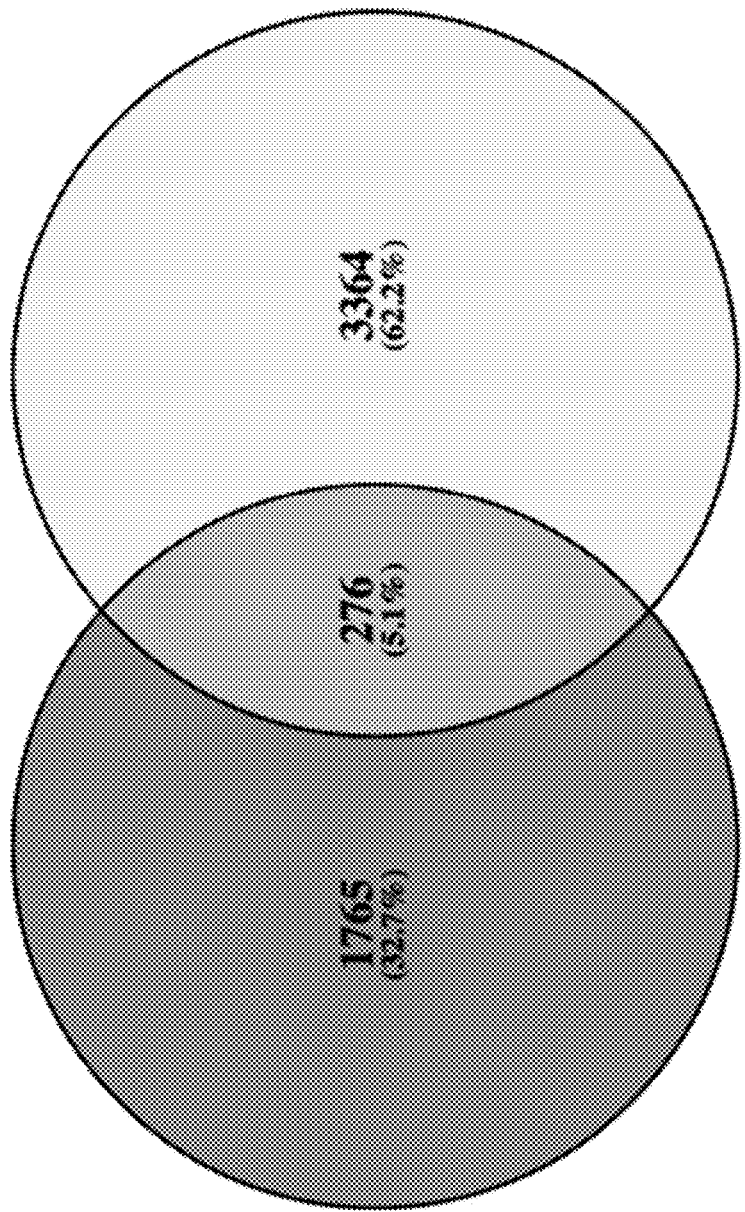
Figure 15:
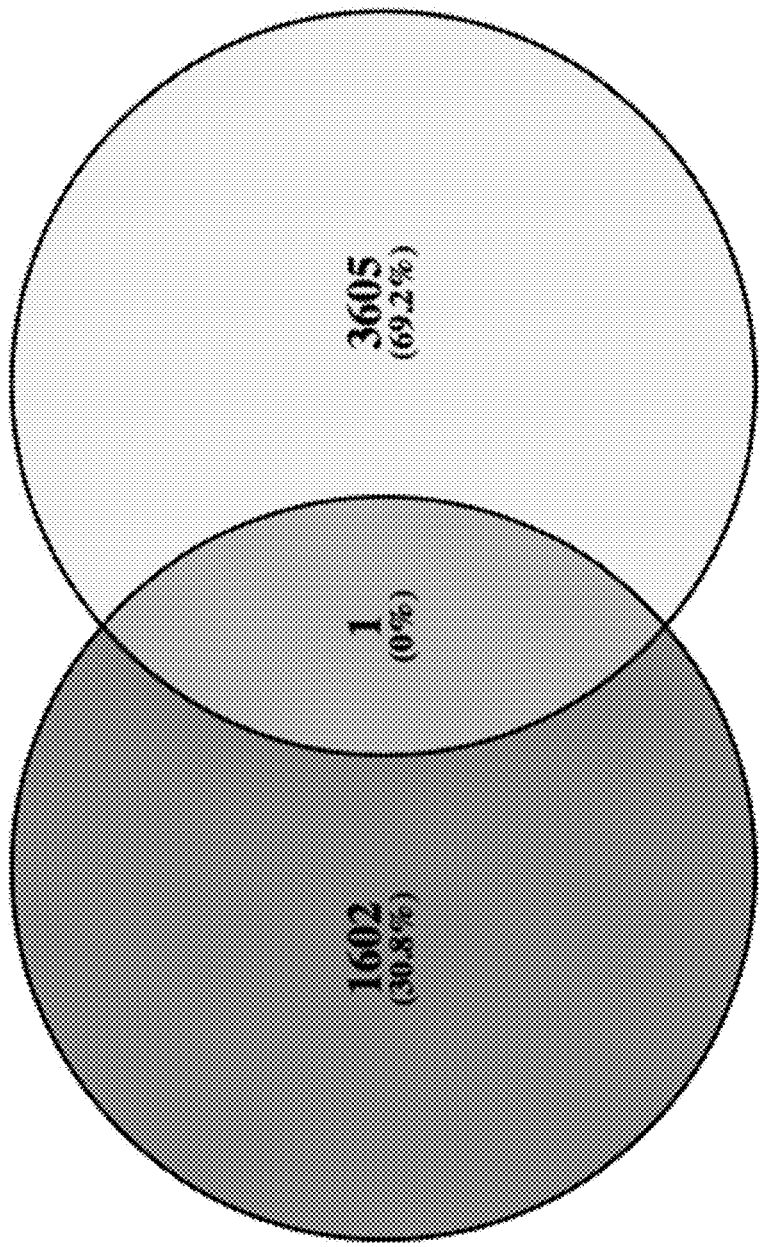
Figure 19:
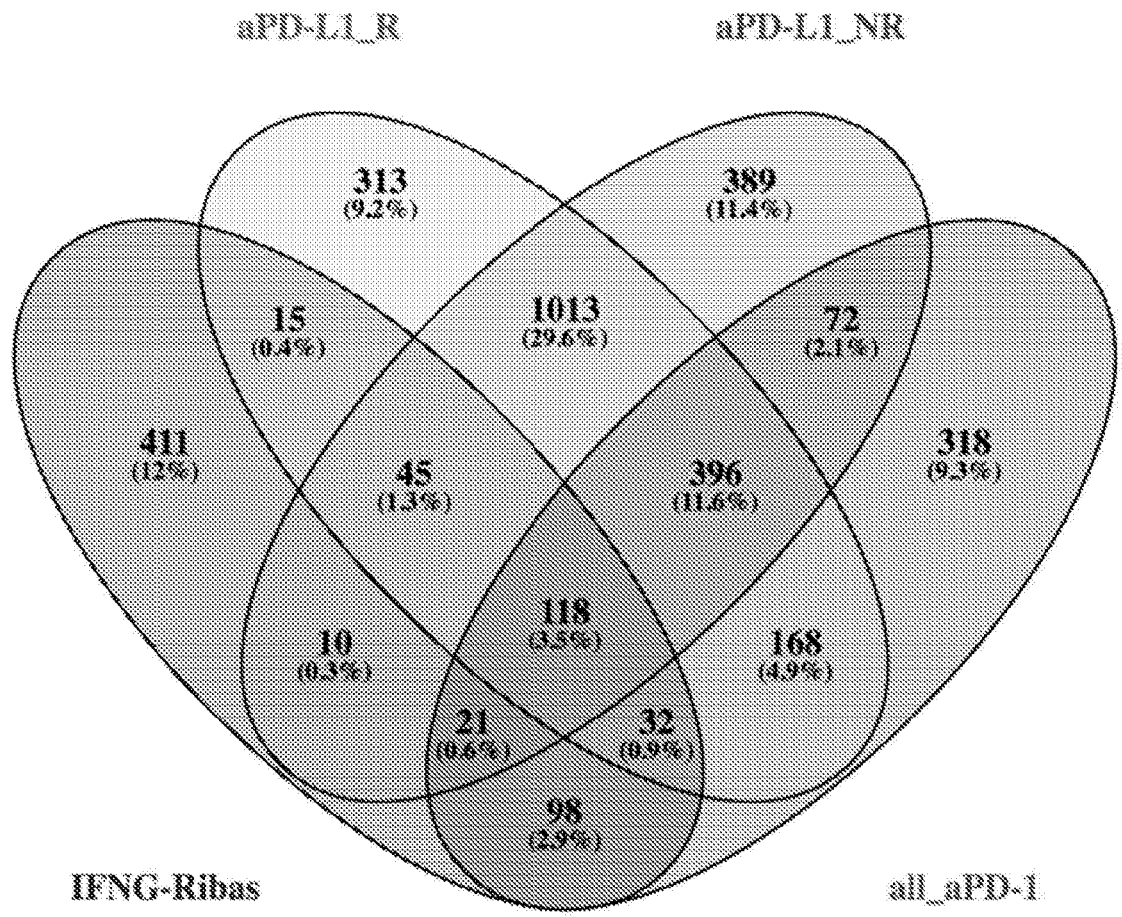
FIG. 19 shows Venn diagrams across four cohorts: gene loci (ORFs) for INFG pathway, anti-PD-L1 responders and non-responders, all anti-PD-1.
Figure 20:
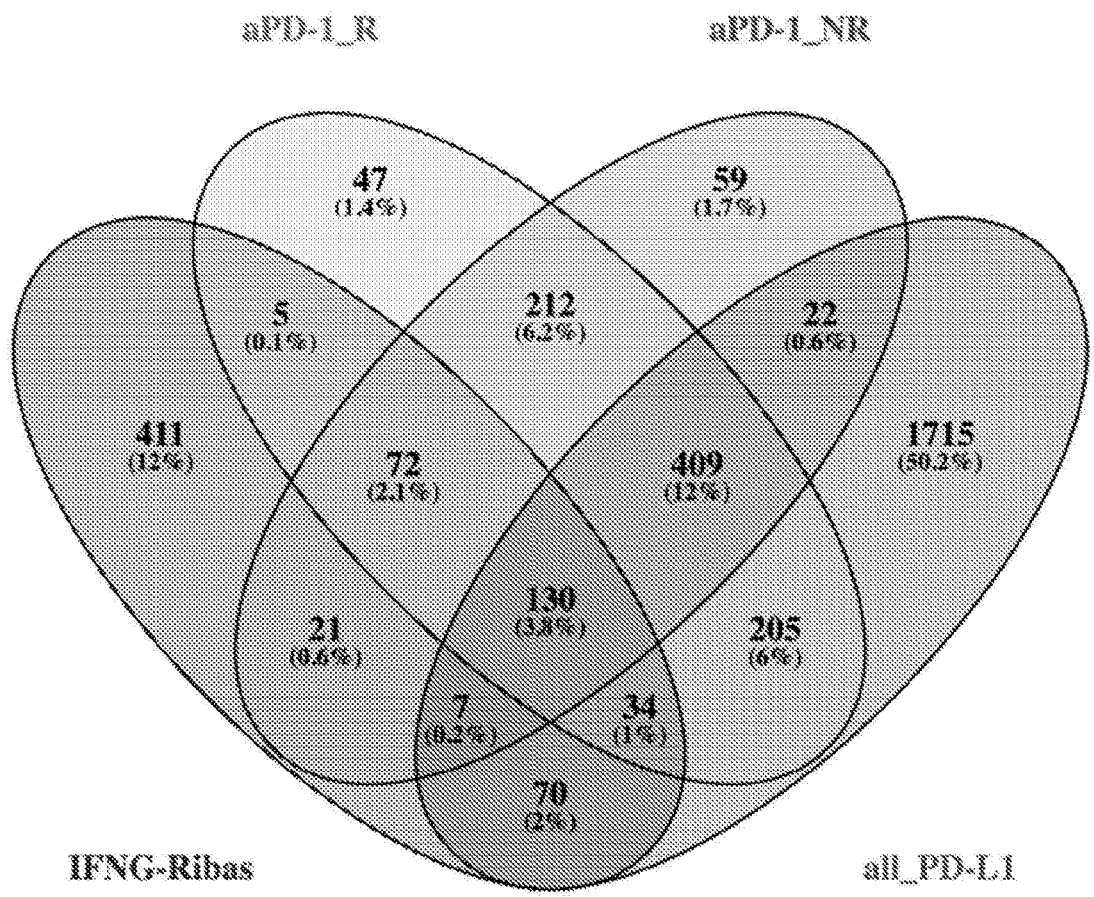
FIG. 20 shows Venn diagrams across four cohorts: gene loci (ORFs) for INFG pathway, anti-PD-1 responders and non-responders, all anti-PD-L1
Figure 21:
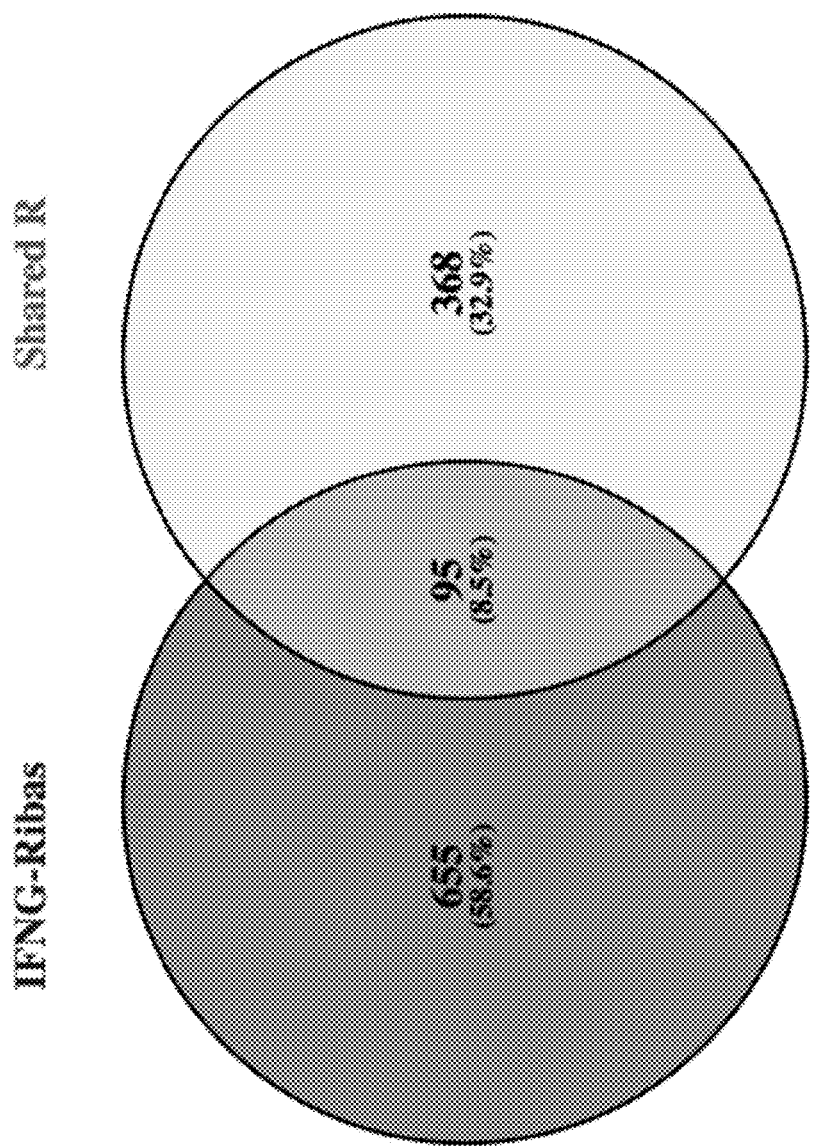
Figure 22A:
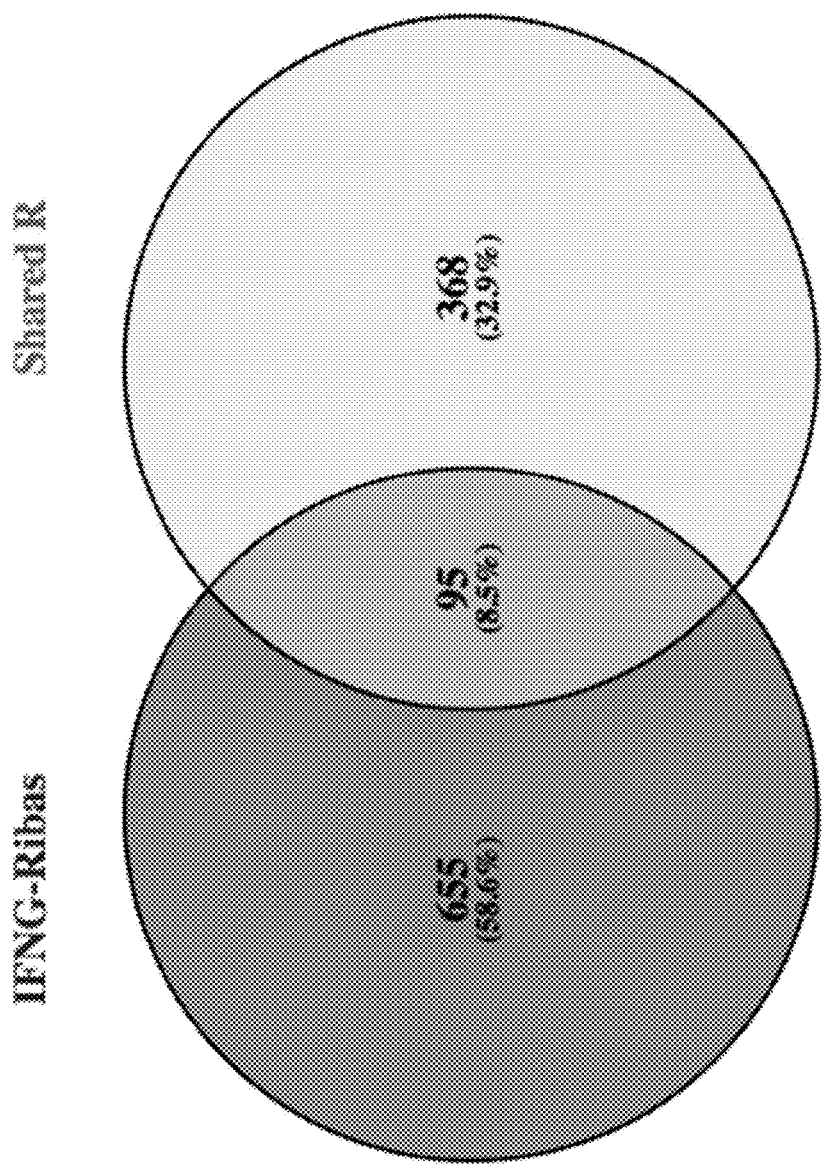
Figure 24:
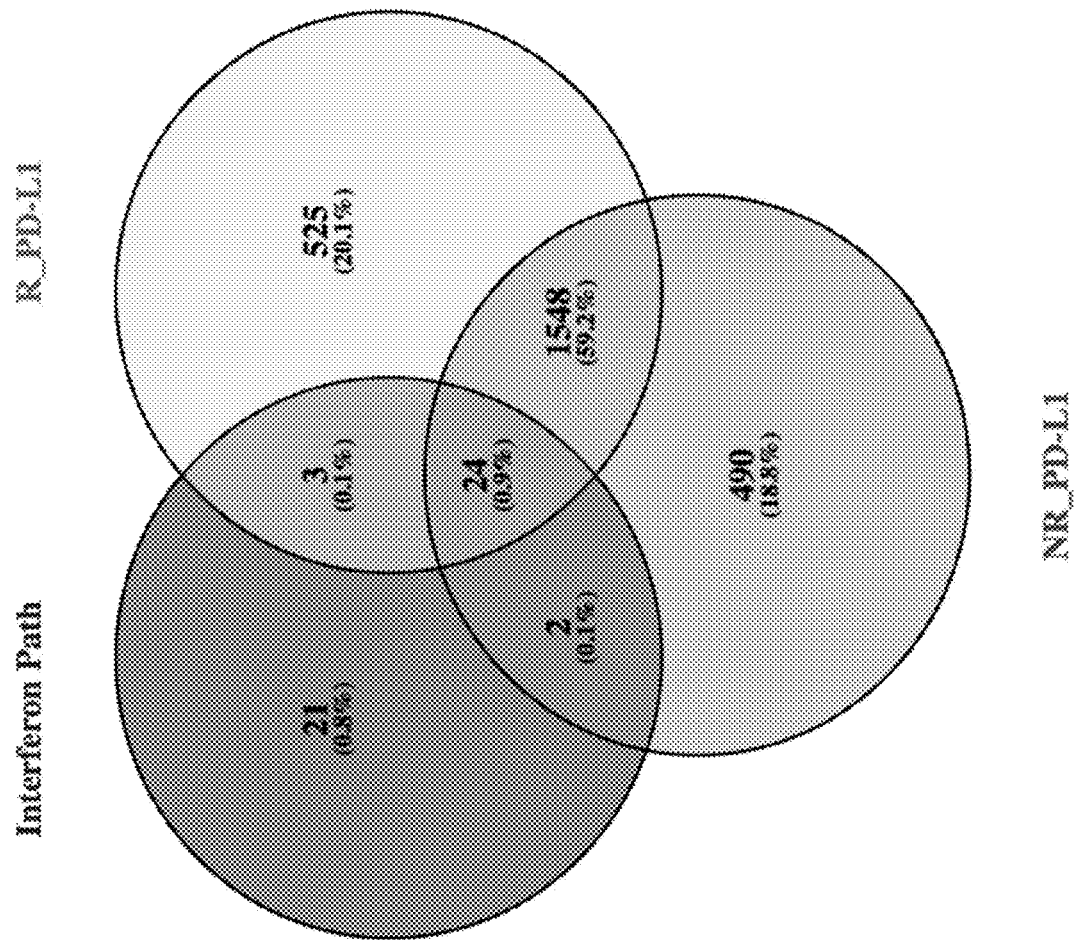
Figure 25:
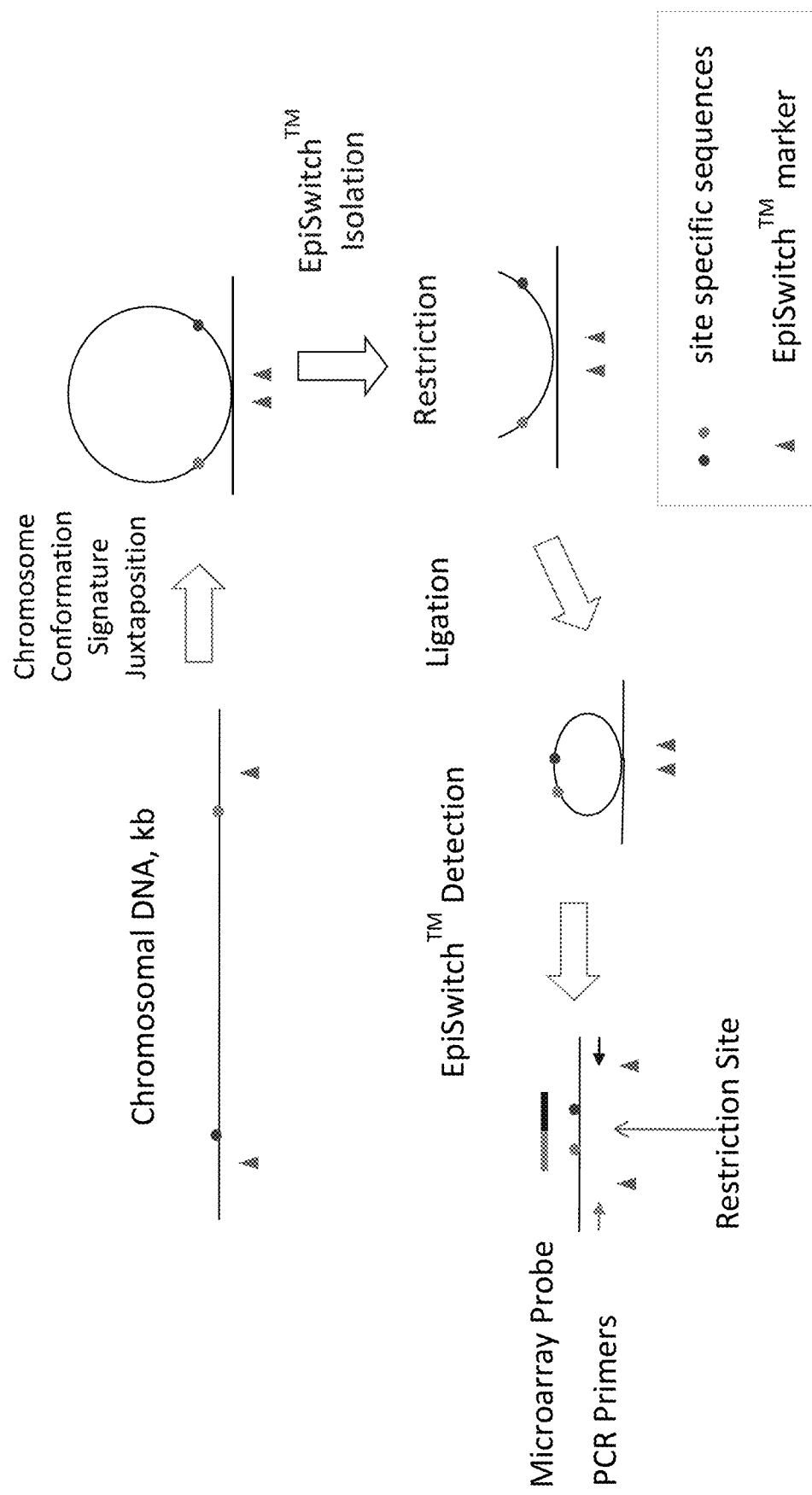

FIG. 21 shows all gene loci for responders markers shared between studies I-Ill and INFG genes. FIG. 22 shows the same, but with the list of 95 loci that contain some of the significant response EpiSwitch markers shared between all three studies I-III. FIG. 23 shows the loci list from FIG. 22 showing the number of significant marker leads and total number of marker leads when these loci were evaluated on array. FIG. 24 shows Interferon Signaling Pathway Matched to aPD-L1 significant EpiSwitch™ CCSs associated ORFs.

Having established common epigenetic settings as markers for responders in PD-1 and PD-L1 treatments, we followed the genetic locations observed under control of epigenetic settings to their protein products and investigated the network relationship for those proteins in the context of known protein-protein networks and their functional roles. Over-imposing the genetic loci affected by EpiSwitch markers of response onto the String database network shows that epigenetically controlled proteins in responders are involved in the close network associated with the two functions: Immune response-regulating cell surface receptor singling pathway and regulation of T-cell activation.

SPECIFIC CONCLUSIONS

Markers have been identified that have statistically significant disseminating powers to identify in baseline patients those who are set up for good response to immunotherapies (including immunocheckpoint therapies), i.e. responders, and those who are not, i.e. non-responders, or progressors. The markers of Table 1 represent a common universal profile of responders across three independent cohorts with either melanoma or lung cancer (NSCLC). Melanoma patients were treated with PD-1 (pembrolizumab), NSCLC with two different PD-L1. These are agnostic makers predictive of treatment and present across different types of cancers. There is also one important agnostic and universal predictive marker for non-response, located between PD-L1 and PD-L2 loci.

The list of markers in Table 1 reflects a common network regulation in responders. These can be used as agnostic markers to monitor response/non-response across various treatments and conditions, including in response to treatments targeting standard immunocheckpoint molecules controlling the immunological network response.

Further Work

Continuing the goal of identifying epigenetic changes based on chromosome conformation signatures (CCSs) that will be able to select a priori patients who will respond to anti PD-1 therapy, either alone or in combination, for the treatment of non-small cell lung cancer (NSCLC). The discovered EpiSwitch™ markers from this array screen were then screened and validated using the EpiSwitch™ PCR platform using three immunotherapies cohorts, two anti-PD-L1 therapies and one anti-PD-1 therapy (Pembrolizumab) in baseline patients' samples. The two anti-PD-L1 response CCSs were developed on NSCLC patients and the Pembrolizumab response CCSs on melanoma patients and further validated on NSCLC patients. Tables 13, 16 and 18 provide the results of further work, and shows a further set of markers that can be used to determine immunoresponsiveness.

Study Designs

In the metastatic melanoma study, a total number of 32 peripheral blood mononuclear cells (PBMC) samples from 16 patients with metastatic melanoma were studied. These patients had received anti-PD1 therapy. The patients were assessed at 2 time-points, baseline and 12-week tumour assessment. A total number of 16 samples were used for the discovery stage using the EpiSwitch Array. The top 100 EpiSwitch Markers identified from the array screening were verified in the baseline and 12 week samples to identify response to anti-PD1 therapy and pharmacodynamics effects. The top EpiSwitch markers were classified into two group of responders and non-responders to anti-PD-1 therapy.

In the NSCLC study a total number of 16 baseline PBMCs from non-small-cell lung carcinoma (NSCLC) patients treated with an anti-PD-L1 therapy were studied. 30 EpiSwitch™ predictive markers were evaluated. The aim of this project was to confirm predictive capability of EpiSwitch markers common for an anti-PD-1 and anti-PD-L1 predictive profile in baseline NSCLC patients who have been treated with anti-PD-L1 therapy.

TABLE 1.a1

| | probe | GeneLocus | Probe_Count_Total |
|---|---|---|---|
| 1 | ORF293_6_32634077_32639503_32662361_32664960_FR | HLA-DQA1 | 28 |
| 2 | ORF241_10_88946200_88948398_88998943_89014190_FF | FAS | 50 |
| 3 | ORF293_6_32626930_32634077_32662361_32664960_RR | HLA-DQA1 | 28 |
| 4 | ORF38_13_111255999_111262146_111317973_111320769_FF | ARHGEF7 | 122 |
| 5 | ORF226_1_94522204_94526809_94565070_94571537_RR | F3 | 36 |
| 6 | ORF553_7_6325447_6327369_6392091_6396545_RR | RAC1 | 64 |
| 7 | ORF705_9_114882931_114894596_114957908_114962933_FR | TNFSF8 | 50 |
| 8 | ORF441_5_68187850_68194388_68215410_68221074_FR | PIK3R1 | 148 |
| 9 | IKBKB_8_42264241_42271203_42302441_42304680_FF | IKBKB | 46 |
| 10 | ORF703_1_6461604_6466207_6481328_6484248_FF | TNFRSF25 | 68 |
| 11 | ORF38_13_111170222_111182176_111317973_111320769_FF | ARHGEF7 | 122 |
| 12 | PRR5_22_44662780_44666500_44696835_44701888_FF | PRR5 | 64 |
| 13 | ORF531_22_44662780_44666500_44696835_44701888_FF | PRR5 | 64 |
| 14 | ORF501_5_68215410_68221074_68272048_68277769_RF | PIK3R1 | 148 |
| 15 | TNFRSF25_1_6461604_6466207_6481328_6484248_FF | TNFRSF25 | 68 |
| 16 | C8A_1_56824227_56829583_56902220_56908104_FR | C8A | 166 |
| 17 | ORF76_2_241559192_241566423_241577996_241581000_RR | BOK | 44 |
| 18 | IKBKB_8_42264241_42271203_42331044_42332799_FR | IKBKB | 46 |
| 19 | BOK_2_241559192_241566423_241577996_241581000_RR | BOK | 44 |
| 20 | ORF464_6_44270723_44274914_44307667_44312139_RF | NFKBIE | 44 |
| 21 | TNFRSF25_1_6461604_6466207_6514024_6515315_FR | TNFRSF25 | 68 |
| 22 | PIK3R1_5_68195469_68198352_68215410_68221074_RR | PIK3R1 | 148 |
| 23 | ORF698_18_62330039_62332469_62356961_62362521_FR | TNFRSF11A | 58 |
| 24 | ORF307_8_42264241_42271203_42331044_42332799_FR | IKBKB | 46 |
| 25 | CD82_11_44526701_44529279_44592038_44600902_RF | CD82 | 50 |
| 26 | ORF703_1_6461604_6466207_6494588_6498048_FF | TNFRSF25 | 68 |
| 27 | ORF307_8_42264241_42271203_42302441_42304680_FF | IKBKB | 46 |
| 28 | TNFRSF25_1_6461604_6466207_6494588_6498048_FF | TNFRSF25 | 68 |
| 29 | CASP6_4_109703339_109705583_109735036_109741090_RF | CASP6 | 28 |

TABLE 1.a2

| | Probe_Count_Sig | HyperG_Stats | FDR_HyperG | Percent_Sig | logFC | AveExpr |
|---|---|---|---|---|---|---|
| 1 | 4 | 0.178427395 | 0.954389149 | 14.29 | −0.64455528 | −0.64455528 |
| 2 | 8 | 0.041957105 | 0.555032562 | 16 | −0.625760222 | −0.625760222 |
| 3 | 4 | 0.178427395 | 0.954389149 | 14.29 | −0.491099473 | −0.491099473 |
| 4 | 6 | 0.928958915 | 0.99999793 | 4.92 | −0.47329526 | −0.47329526 |
| 5 | 2 | 0.791365183 | 0.99999793 | 5.56 | −0.436454288 | −0.436454288 |
| 6 | 2 | 0.967461559 | 0.99999793 | 3.12 | −0.432758998 | −0.432758998 |
| 7 | 4 | 0.568728839 | 0.99999793 | 8 | −0.415876997 | −0.415876997 |
| 8 | 12 | 0.513477047 | 0.99999793 | 8.11 | −0.396269087 | −0.396269087 |
| 9 | 12 | 0.00018363 | 0.010627608 | 26.09 | −0.393553534 | −0.393553534 |
| 10 | 16 | 6.44E−05 | 0.004967399 | 23.53 | −0.391557328 | −0.391557328 |
| 11 | 6 | 0.928958915 | 0.99999793 | 4.92 | −0.390398405 | −0.390398405 |
| 12 | 4 | 0.7582782 | 0.99999793 | 6.25 | −0.385982839 | −0.385982839 |

TABLE 1.a2-continued

|   | Probe_Count_Sig | HyperG_Stats | FDR_HyperG | Percent_Sig | logFC | AveExpr |
|---|---|---|---|---|---|---|
| 13 | 4 | 0.7582782 | 0.99999793 | 6.25 | −0.38593493 | −0.38593493 |
| 14 | 12 | 0.513477047 | 0.99999793 | 8.11 | −0.384094729 | −0.384094729 |
| 15 | 16 | 6.44E−05 | 0.004967399 | 23.53 | −0.375198131 | −0.375198131 |
| 16 | 8 | 0.957766442 | 0.99999793 | 4.82 | −0.374033997 | −0.374033997 |
| 17 | 10 | 0.001969408 | 0.075986326 | 22.73 | −0.367707426 | −0.367707426 |
| 18 | 12 | 0.00018363 | 0.010627608 | 26.09 | −0.363126662 | −0.363126662 |
| 19 | 10 | 0.001969408 | 0.075986326 | 22.73 | −0.362483584 | −0.362483584 |
| 20 | 4 | 0.466402982 | 0.99999793 | 9.09 | −0.361055592 | −0.361055592 |
| 21 | 16 | 6.44E−05 | 0.004967399 | 23.53 | −0.358891419 | −0.358891419 |
| 22 | 12 | 0.513477047 | 0.99999793 | 8.11 | −0.356573442 | −0.356573442 |
| 23 | 4 | 0.686266831 | 0.99999793 | 6.9 | −0.351747423 | −0.351747423 |
| 24 | 12 | 0.00018363 | 0.010627608 | 26.09 | −0.348439424 | −0.348439424 |
| 25 | 6 | 0.203083688 | 0.988148592 | 12 | −0.348220668 | −0.348220668 |
| 26 | 16 | 6.44E−05 | 0.004967399 | 23.53 | −0.347052896 | −0.347052896 |
| 27 | 12 | 0.00018363 | 0.010627608 | 26.09 | −0.346675126 | −0.346675126 |
| 28 | 16 | 6.44E−05 | 0.004967399 | 23.53 | −0.342250575 | −0.342250575 |
| 29 | 2 | 0.663352621 | 0.99999793 | 7.14 | −0.339412631 | −0.339412631 |

TABLE 1.a3

|   | t | P.Value | adj.P.Val | B | FC | FC_1 |
|---|---|---|---|---|---|---|
| 1 | −2.980618242 | 0.01344665400 | 0.040517443 | −3.620544416 | 0.639689949 | −1.563257327 |
| 2 | −6.24344027 | 0.00008620000 | 0.001125209 | 1.58573085 | 0.648078185 | −1.543023701 |
| 3 | −3.580221478 | 0.00482085800 | 0.018832070 | −2.583272553 | 0.711482673 | −1.405515606 |
| 4 | −22.94378205 | 0.00000000038 | 0.000001590 | 13.50068753 | 0.72031744 | −1.388276813 |
| 5 | −6.068793285 | 0.00010890800 | 0.001320738 | 1.342264192 | 0.738948493 | −1.353274294 |
| 6 | −5.571884831 | 0.00021663700 | 0.002075220 | 0.625787741 | 0.740843647 | −1.34981248 |
| 7 | −6.927544857 | 0.00003590000 | 0.000632929 | 2.498799383 | 0.749563705 | −1.33410942 |
| 8 | −16.24057806 | 0.00000001200 | 0.000010700 | 10.48782055 | 0.759820695 | −1.316099977 |
| 9 | −17.46788221 | 0.00000000585 | 0.000010100 | 11.15054812 | 0.761252236 | −1.313625041 |
| 10 | −9.736436082 | 0.00000168000 | 0.000107198 | 5.651749271 | 0.762306283 | −1.311808681 |
| 11 | −17.0031469 | 0.00000000765 | 0.000010700 | 10.90661915 | 0.762918893 | −1.310755324 |
| 12 | −17.18527923 | 0.00000000688 | 0.000010600 | 11.00320387 | 0.765257487 | −1.30674971 |
| 13 | −15.39183699 | 0.00000002050 | 0.000013100 | 9.992593359 | 0.765282901 | −1.306706316 |
| 14 | −16.16361934 | 0.00000001260 | 0.000010700 | 10.44421723 | 0.766259665 | −1.305040636 |
| 15 | −11.77686613 | 0.00000027700 | 0.000044500 | 7.465604014 | 0.770999521 | −1.297017667 |
| 16 | −10.68867959 | 0.00000070000 | 0.000068900 | 6.540229405 | 0.771621904 | −1.295971504 |
| 17 | −11.11416276 | 0.00000048300 | 0.000057900 | 6.912800589 | 0.775013085 | −1.290300795 |
| 18 | −16.40706083 | 0.00000001090 | 0.000010700 | 10.58128991 | 0.777477774 | −1.286210402 |
| 19 | −10.9324899 | 0.00000056500 | 0.000062000 | 6.755470255 | 0.77782441 | −1.285637205 |
| 20 | −19.65763701 | 0.00000000180 | 0.000005770 | 12.19684795 | 0.778594689 | −1.284365299 |
| 21 | −10.66682351 | 0.00000071300 | 0.000069500 | 6.520700487 | 0.779763527 | −1.282440079 |
| 22 | −14.85687535 | 0.00000002900 | 0.000015300 | 9.663464141 | 0.78101738 | −1.280381239 |
| 23 | −2.587519517 | 0.02657975500 | 0.067536623 | −4.295830899 | 0.783634368 | −1.276105338 |
| 24 | −16.6498587 | 0.00000000942 | 0.000010700 | 10.71553998 | 0.785433249 | −1.273182669 |
| 25 | −12.64682486 | 0.00000014000 | 0.000033200 | 8.144494866 | 0.785552353 | −1.272989631 |
| 26 | −12.44559121 | 0.00000016300 | 0.000035700 | 7.991924175 | 0.786188466 | −1.271959642 |
| 27 | −16.03607714 | 0.00000001370 | 0.000010900 | 10.37139589 | 0.786394357 | −1.271626622 |
| 28 | −12.06306132 | 0.00000022000 | 0.000039400 | 7.6945755 | 0.788809824 | −1.26773269 |
| 29 | −13.55417084 | 0.00000007120 | 0.000022100 | 8.801357166 | 0.790363029 | −1.265241367 |

TABLE 1.a4

|   | LS | Loop detected | Probe sequence 60 mer |
|---|---|---|---|
| 1 | −1 | PD-L1 responder | CCCGTCTTCCCCAAAATCTATGTGGTCCTCGAAGTCTTGGATTAAGGTTCATTCAACAAA (SEQ ID NO: 2) |
| 2 | −1 | PD-L1 responder | GTAATATTATGTAAAATTGCATTTGGTATCGAACAAAGCCTTTAACTTGACTTAGTGTCA (SEQ ID NO: 3) |
| 3 | −1 | PD-L1 responder | GTTTATCAGCCAGGCTGGTAAGAAAATGTCGAAGTCTTGGATTAAGGTTCATTCAACAAA (SEQ ID NO: 4) |
| 4 | −1 | PD-L1 responder | GTAAATGAATTTGAAATATTACAAAAGATCGACTCACCTGCGCCTCACATCCCAGGCGGG (SEQ ID NO: 5) |
| 5 | −1 | PD-L1 responder | TTAGCATCACTTGAAAGCTAGTTAAAAATCGATTGCAAATGATATGACAGAATTGCTTTG (SEQ ID NO: 6) |

TABLE 1.a4-continued

| | LS | Loop detected | Probe sequence 60 mer |
|---|---|---|---|
| 6 | -1 | PD-L1 responder | GGATGTATATATATATACTATTTTTATATCGAGCGCTTAATTAGTGCATGTTACCTATGG (SEQ ID NO: 7) |
| 7 | -1 | PD-L1 responder | TGAAACTTAGACATACTTAAGCATTTCTTCGAAAGCTAATGAGGTATGAGGGGAGAATAC (SEQ ID NO: 8) |
| 8 | -1 | PD-L1 responder | CTGAGTCTTCATTACCAAAAAAAAAAGTTCGACCTCCCCGAACCCCTCCGCCTCTGCGCT (SEQ ID NO: 9) |
| 9 | -1 | PD-L1 responder | CCACCCCCGCCCCGGGGGAGTCGCCCGGTCGACAGTCCCAAGAGGTCAGAACTGGCTTCC (SEQ ID NO: 10) |
| 10 | -1 | PD-L1 responder | CCGCGCCCGCAGGGCCCGCCCCGCGCCGTCGAGGCTTTCAAGGGATCCAGGGTGGGGTGC (SEQ ID NO: 11) |
| 11 | -1 | PD-L1 responder | CGCAGCAGTCTCGTTGATCTTCACGGTGTCGACTCACCTGCGCCTCACATCCCAGGCGGG (SEQ ID NO: 12) |
| 12 | -1 | PD-L1 responder | CCAAACTGGCAATCAACCCAGATAGTCTTCGACCCCGGCCCCGGAGGTCTCCCTCCACAG (SEQ ID NO: 13) |
| 13 | -1 | PD-L1 responder | CCAAACTGGCAATCAACCCAGATAGTCTTCGACCCCGGCCCCGGAGGTCTCCCTCCACAG (SEQ ID NO: 14) |
| 14 | -1 | PD-L1 responder | GCAGTCAATCACCGAGTTATATGAGGTCTCGACCTCCCCGAACCCCTCCGCCTCTGCGCT (SEQ ID NO: 15) |
| 15 | -1 | PD-L1 responder | CCGCGCCCGCAGGGCCCGCCCCGCGCCGTCGAGGCTTTCAAGGGATCCAGGGTGGGGTGC (SEQ ID NO: 16) |
| 16 | -1 | PD-L1 responder | GGTGACTGCTCAGAAGAGCAGTACTCATTCGACCTTATGCTAAGCCTAAACTTGCCTTCC (SEQ ID NO: 17) |
| 17 | -1 | PD-L1 responder | GTTTGCTCCGGGGCCGCCGGGCCCGCCCTCGATTTTAACACCACCATGGTTTGAATGAAT (SEQ ID NO: 18) |
| 18 | -1 | PD-L1 responder | CCACCCCCGCCCCGGGGGAGTCGCCCGGTCGACCCCCTGACATGGGGCTGCCTGGAGCAG (SEQ ID NO: 19) |
| 19 | -1 | PD-L1 responder | GTTTGCTCCGGGGCCGCCGGGCCCGCCCTCGATTTTAACACCACCATGGTTTGAATGAAT (SEQ ID NO: 20) |
| 20 | -1 | PD-L1 responder | TTTCAAAGAAGGTATGATGGGAAAGGTCTCGACGCGCCCCCTCTACGCCATGTCCCCCCC (SEQ ID NO: 21) |
| 21 | -1 | PD-L1 responder | CCGCGCCCGCAGGGCCCGCCCCGCGCCGTCGAGAAGCATAAAGCAGGGACAGGTATGGAG (SEQ ID NO: 22) |
| 22 | -1 | PD-L1 responder | AAATCATAATTGTGCAGATGATTTGCCTTCGACCTCCCCGAACCCCTCCGCCTCTGCGCT (SEQ ID NO: 23) |
| 23 | -1 | PD-L1 responder | GAGAATCAATTCCATTTTTAAAGCTTAGTCGATTTTGAGGGCTTCTCACAACTCTAGATT (SEQI D NO: 24) |
| 24 | -1 | PD-L1 responder | CCACCCCCGCCCCGGGGGAGTCGCCCGGTCGACCCCCTGACATGGGGCTGCCTGGAGCAG (SEQ ID NO: 25) |
| 25 | -1 | PD-L1 responder | CACAGCTTCTAAATGGTAGGTGTGGGACTCGACCCGCTTTCCTCCCCGCCCCCTCATCCG (SEQ ID NO: 26) |
| 26 | -1 | PD-L1 responder | CCGCGCCCGCAGGGCCCGCCCCGCGCCGTCGATGTGTTGGAAGTCAGGGCGGCGGTGCCC (SEQ ID: 27) |
| 27 | -1 | PD-L1 responder | CCACCCCCGCCCCGGGGGAGTCGCCCGGTCGACAGTCCCAAGAGGTCAGAACTGGCTTCC (SEQ ID NO: 28) |
| 28 | -1 | PD-L1 responder | CCGCGCCCGCAGGGCCCGCCCCGCGCCGTCGATGTGTTGGAAGTCAGGGCGGCGGTGCCC (SEQ ID NO: 29) |
| 29 | -1 | PD-L1 responder | GGGGCCTCCAGAGTCCCCTTTACAGGCATCGACGCCCCCTGCCTACCTGCCGGGTGCCCC (SEQ ID NO: 30) |

TABLE 1.a5

| | | Probe Location | | | | 4 kb Sequence Location | |
|---|---|---|---|---|---|---|---|
| | Chr | Start1 | End1 | Start2 | End2 | Chr | Start1 | End1 |
| 1 | 6 | 32639472 | 32639501 | 32662363 | 32662392 | 6 | 32635502 | 32639501 |
| 2 | 10 | 88948367 | 88948396 | 89014159 | 89014188 | 10 | 88944397 | 88948396 |
| 3 | 6 | 32626932 | 32626961 | 32662363 | 32662392 | 6 | 32626932 | 32630931 |
| 4 | 13 | 111262115 | 111262144 | 111320738 | 111320767 | 13 | 111258145 | 111262144 |
| 5 | 1 | 94522206 | 94522235 | 94565072 | 94565101 | 1 | 94522206 | 94526205 |
| 6 | 7 | 6325449 | 6325478 | 6392093 | 6392122 | 7 | 6325449 | 6329448 |
| 7 | 9 | 114894565 | 114894594 | 114957910 | 114957939 | 9 | 114890595 | 114894594 |
| 8 | 5 | 68194357 | 68194386 | 68215412 | 68215441 | 5 | 68190387 | 68194386 |
| 9 | 8 | 42271172 | 42271201 | 42304649 | 42304678 | 8 | 42267202 | 42271201 |
| 10 | 1 | 6466176 | 6466205 | 6484217 | 6484246 | 1 | 6462206 | 6466205 |
| 11 | 13 | 111182145 | 111182174 | 111320738 | 111320767 | 13 | 111178175 | 111182174 |
| 12 | 22 | 44666469 | 44666498 | 44701857 | 44701886 | 22 | 44662499 | 44666498 |
| 13 | 22 | 44666469 | 44666498 | 44701857 | 44701886 | 22 | 44662499 | 44666498 |
| 14 | 5 | 68215412 | 68215441 | 68277738 | 68277767 | 5 | 68215412 | 68219411 |
| 15 | 1 | 6466176 | 6466205 | 6484217 | 6484246 | 1 | 6462206 | 6466205 |
| 16 | 1 | 56829552 | 56829581 | 56902222 | 56902251 | 1 | 56825582 | 56829581 |
| 17 | 2 | 241559194 | 241559223 | 241577998 | 241578027 | 2 | 241559194 | 241563193 |
| 18 | 8 | 42271172 | 42271201 | 42331046 | 42331075 | 8 | 42267202 | 42271201 |
| 19 | 2 | 241559194 | 241559223 | 241577998 | 241578027 | 2 | 241559194 | 241563193 |
| 20 | 6 | 44270725 | 44270754 | 44312108 | 44312137 | 6 | 44270725 | 44274724 |
| 21 | 1 | 6466176 | 6466205 | 6514026 | 6514055 | 1 | 6462206 | 6466205 |
| 22 | 5 | 68195471 | 68195500 | 68215412 | 68215441 | 5 | 68195471 | 68199470 |
| 23 | 18 | 62332438 | 62332467 | 62356963 | 62356992 | 18 | 62328468 | 62332467 |
| 24 | 8 | 42271172 | 42271201 | 42331046 | 42331075 | 8 | 42267202 | 42271201 |
| 25 | 11 | 44526703 | 44526732 | 44600871 | 44600900 | 11 | 44526703 | 44530702 |
| 26 | 1 | 6466176 | 6466205 | 6498017 | 6498046 | 1 | 6462206 | 6466205 |
| 27 | 8 | 42271172 | 42271201 | 42304649 | 42304678 | 8 | 42267202 | 42271201 |
| 28 | 1 | 6466176 | 6466205 | 6498017 | 6498046 | 1 | 6462206 | 6466205 |
| 29 | 4 | 109703341 | 109703370 | 109741059 | 109741088 | 4 | 109703341 | 109707340 |

TABLE 1.a6

| | 4 kb Sequence Location | |
|---|---|---|
| | Start2 | End2 |
| 1 | 32662363 | 32666362 |
| 2 | 89010189 | 89014188 |
| 3 | 32662363 | 32666362 |
| 4 | 111316768 | 111320767 |
| 5 | 94565072 | 94569071 |
| 6 | 6392093 | 6396092 |
| 7 | 114957910 | 114961909 |
| 8 | 68215412 | 68219411 |
| 9 | 42300679 | 42304678 |
| 10 | 6480247 | 6484246 |
| 11 | 111316768 | 111320767 |
| 12 | 44697887 | 44701886 |
| 13 | 44697887 | 44701886 |
| 14 | 68273768 | 68277767 |
| 15 | 6480247 | 6484246 |
| 16 | 56902222 | 56906221 |
| 17 | 241577998 | 241581997 |
| 18 | 42331046 | 42335045 |
| 19 | 241577998 | 241581997 |
| 20 | 44308138 | 44312137 |
| 21 | 6514026 | 6518025 |
| 22 | 68215412 | 68219411 |
| 23 | 62356963 | 62360962 |
| 24 | 42331046 | 42335045 |
| 25 | 44596901 | 44600900 |
| 26 | 6494047 | 6498046 |
| 27 | 42300679 | 42304678 |
| 28 | 6494047 | 6498046 |
| 29 | 109737089 | 109741088 |

TABLE 1.b1

| | probe | GeneLocus | Probe_Count_Total |
|---|---|---|---|
| 30 | ORF567_11_65634932_65641044_65653258_65654626_RF | RELA | 56 |
| 31 | PIK3R1_5_68187850_68194388_68215410_68221074_FR | PIK3R1 | 148 |
| 32 | TNFRSF25_1_6450603_6452273_6494588_6498048_RF | TNFRSF25 | 68 |
| 33 | IKBKB_8_42264241_42271203_42290979_42292124_FF | IKBKB | 46 |
| 34 | ORF703_1_6461604_6466207_6514024_6515315_FR | TNFRSF25 | 68 |
| 35 | CD6_11_60938640_60941215_60977084_60983727_RF | CD6 | 56 |
| 36 | PIK3R1_5_68215410_68221074_68272048_68277769_RF | PIK3R1 | 148 |
| 37 | ORF703_1_6450603_6452273_6494588_6498048_RF | TNFRSF25 | 68 |
| 38 | ORF703_1_6461604_6466207_6494588_6498048_FR | TNFRSF25 | 68 |
| 39 | ORF454_2_105728227_105741825_105841316_105844511_FF | NCK2 | 66 |
| 40 | IKBKB_8_42264241_42271203_42290979_42292124_FR | IKBKB | 46 |
| 41 | IKBKB_8_42241866_42245619_42264241_42271203_RF | IKBKB | 46 |
| 42 | ORF529_10_6432893_6439235_6460245_6464187_RF | PRKCQ | 106 |
| 43 | ORF114_16_28959098_28963335_28975508_28978445_RF | CD19 | 56 |
| 44 | NFKBIE_6_44270723_44274914_44307667_44312139_RF | NFKBIE | 44 |
| 45 | ORF104_17_36075902_36084513_36095759_36100192_FR | CCL18 | 42 |

TABLE 1.b1-continued

|    | probe | GeneLocus | Probe_Count_Total |
|----|-------|-----------|-------------------|
| 46 | ORF307_8_42264241_42271203_42281222_42285075_FR | IKBKB | 46 |
| 47 | ORF307_8_42241866_42245619_42264241_42271203_RF | IKBKB | 46 |
| 48 | TNFRSF25_1_6494588_6498048_6514024_6515315_FR | TNFRSF25 | 68 |
| 49 | ORF540_12_112418669_112423831_112478543_112482415_RR | PTPN11 | 56 |
| 50 | ORF329_5_132472660_132477912_132495376_132497062_FF | IRF1 | 42 |
| 51 | ORF22_14_104800011_104801022_104839372_104843321_FF | AKT1 | 60 |
| 52 | BOK_2_241514645_241518779_241559192_241566423_RR | BOK | 44 |
| 53 | ORF703_1_6461604_6466207_6494588_6498048_RF | TNFRSF25 | 68 |
| 54 | ORF307_8_42264241_42271203_42290979_42292124_FR | IKBKB | 46 |
| 55 | ORF703_1_6494588_6498048_6514024_6515315_FR | TNFRSF25 | 68 |
| 56 | PTPN11_12_112418669_112423831_112478543_112482415_RR | PTPN11 | 56 |
| 57 | ITGAM_16_31214801_31216194_31318595_31324659_RF | ITGAM | 50 |
| 58 | IKBKB_8_42264241_42271203_42281222_42285075_FR | IKBKB | 46 |
| 59 | ORF130_11_60938640_60941215_60977084_60983727_RF | CD6 | 56 |
| 60 | ORF703_1_6461604_6466207_6481328_6484248_RF | TNFRSF25 | 68 |
| 61 | IKBKB_8_42264241_42271203_42302441_42304680_FR | IKBKB | 46 |
| 62 | ORF368_1_32254316_32257966_32298315_32301756_FR | LCK | 46 |
| 63 | ORF712_9_120913546_120919710_120936524_120940468_RF | TRAF1 | 42 |
| 64 | IRF1_5_132472660_132477912_132495376_132497062_FF | IRF1 | 42 |
| 65 | ORF307_8_42264241_42271203_42302441_42304680_FR | IKBKB | 46 |
| 66 | ORF673_6_149314242_149316764_149361564_149369248_RF | TAB2 | 151 |
| 67 | TNFRSF25_1_6481328_6484248_6494588_6498048_FF | TNFRSF25 | 68 |
| 68 | CRADD_12_93830263_93837995_93848656_93851009_FR | CRADD | 231 |
| 69 | ORF708_1_3611941_3615812_3638742_3642185_RF | TP73 | 32 |
| 70 | ORF130_11_60938640_60941215_61017867_61025585_RF | CD6 | 56 |
| 71 | ORF307_8_42264241_42271203_42290979_42292124_FF | IKBKB | 46 |
| 72 | ORF715_11_36467487_36469166_36503363_36509375_FR | TRAF6 | 60 |
| 73 | TNFRSF25_1_6461604_6466207_6494588_6498048_RF | TNFRSF25 | 68 |
| 74 | ORF501_5_68215410_68221074_68258878_68268897_FF | PIK3R1 | 148 |
| 75 | ORF464_6_44253666_44257911_44307667_44312139_RF | NFKBIE | 44 |
| 76 | ORF657_2_191108390_191117485_191184623_191189153_RR | STAT4 | 58 |
| 77 | LYN_8_55939615_55941582_55961822_55966587_RR | LYN | 48 |
| 78 | ORF76_2_241535460_241542885_241559192_241566423_RR | BOK | 44 |
| 79 | ORF76_2_241514645_241518779_241559192_241566423_RR | BOK | 44 |

TABLE 1.b2

|    | Probe_Count_Sig | HyperG_Stats | FDR_HyperG | Percent_Sig | logFC | AveExpr |
|----|-----------------|--------------|------------|-------------|-------|---------|
| 30 | 2  | 0.94351322  | 0.99999793  | 3.57  | −0.335793252 | −0.335793252 |
| 31 | 12 | 0.513477047 | 0.99999793  | 8.11  | −0.331665721 | −0.331665721 |
| 32 | 16 | 6.44E−05    | 0.004967399 | 23.53 | −0.330748028 | −0.330748028 |
| 33 | 12 | 0.00018363  | 0.010627608 | 26.09 | −0.325741973 | −0.325741973 |
| 34 | 16 | 6.44E−05    | 0.004967399 | 23.53 | −0.324809038 | −0.324809038 |
| 35 | 14 | 9.03E−05    | 0.005970563 | 25    | −0.321565937 | −0.321565937 |
| 36 | 12 | 0.513477047 | 0.99999793  | 8.11  | −0.31812964  | −0.31812964  |
| 37 | 16 | 6.44E−05    | 0.004967399 | 23.53 | −0.316909254 | −0.316909254 |
| 38 | 16 | 6.44E−05    | 0.004967399 | 23.53 | −0.316023276 | −0.316023276 |
| 39 | 4  | 0.779227696 | 0.99999793  | 6.06  | −0.308568317 | −0.308568317 |
| 40 | 12 | 0.00018363  | 0.010627608 | 26.09 | −0.307578042 | −0.307578042 |
| 41 | 12 | 0.00018363  | 0.010627608 | 26.09 | −0.304258892 | −0.304258892 |
| 42 | 2  | 0.998452566 | 0.99999793  | 1.89  | −0.301937872 | −0.301937872 |
| 43 | 4  | 0.659150649 | 0.99999793  | 7.14  | −0.295598703 | −0.295598703 |
| 44 | 4  | 0.466402982 | 0.99999793  | 9.09  | −0.293579626 | −0.293579626 |
| 45 | 8  | 0.016095432 | 0.256971894 | 19.05 | −0.291933406 | −0.291933406 |
| 46 | 12 | 0.00018363  | 0.010627608 | 26.09 | −0.291439389 | −0.291439389 |
| 47 | 12 | 0.00018363  | 0.010627608 | 26.09 | −0.291244548 | −0.291244548 |
| 48 | 16 | 6.44E−05    | 0.004967399 | 23.53 | −0.282267049 | −0.282267049 |
| 49 | 6  | 0.283634013 | 0.99999793  | 10.71 | −0.281116435 | −0.281116435 |
| 50 | 8  | 0.016095432 | 0.256971894 | 19.05 | −0.279967907 | −0.279967907 |
| 51 | 4  | 0.711822793 | 0.99999793  | 6.67  | −0.279823808 | −0.279823808 |
| 52 | 10 | 0.001969408 | 0.075986326 | 22.73 | −0.269875843 | −0.269875843 |
| 53 | 16 | 6.44E−05    | 0.004967399 | 23.53 | −0.269533141 | −0.269533141 |
| 54 | 12 | 0.00018363  | 0.010627608 | 26.09 | −0.269116289 | −0.269116289 |
| 55 | 16 | 6.44E−05    | 0.004967399 | 23.53 | −0.268243062 | −0.268243062 |
| 56 | 6  | 0.283634013 | 0.99999793  | 10.71 | −0.266902081 | −0.266902081 |
| 57 | 8  | 0.041957105 | 0.555032562 | 16    | −0.266411523 | −0.266411523 |
| 58 | 12 | 0.00018363  | 0.010627608 | 26.09 | −0.265642352 | −0.265642352 |
| 59 | 14 | 9.03E−05    | 0.005970563 | 25    | −0.262767321 | −0.262767321 |
| 60 | 16 | 6.44E−05    | 0.004967399 | 23.53 | −0.262221662 | −0.262221662 |
| 61 | 12 | 0.00018363  | 0.010627608 | 26.09 | −0.258543002 | −0.258543002 |
| 62 | 4  | 0.501622356 | 0.99999793  | 8.7   | −0.256759221 | −0.256759221 |
| 63 | 6  | 0.112492545 | 0.789152247 | 14.29 | −0.255423865 | −0.255423865 |
| 64 | 8  | 0.016095432 | 0.256971894 | 19.05 | −0.25495765  | −0.25495765  |
| 65 | 12 | 0.00018363  | 0.010627608 | 26.09 | −0.254863767 | −0.254863767 |

TABLE 1.b2-continued

|    | Probe_Count_Sig | HyperG_Stats | FDR_HyperG | Percent_Sig | logFC | AveExpr |
|----|---|---|---|---|---|---|
| 66 | 4  | 0.998322979 | 0.99999793  | 2.65  | −0.254467168 | −0.254467168 |
| 67 | 16 | 6.44E−05    | 0.004967399 | 23.53 | −0.253550906 | −0.253550906 |
| 68 | 4  | 0.999992975 | 0.99999793  | 1.73  | −0.249667458 | −0.249667458 |
| 69 | 4  | 0.246707931 | 0.99999793  | 12.5  | −0.248090073 | −0.248090073 |
| 70 | 14 | 9.03E−05    | 0.005970563 | 25    | −0.24505568  | −0.24505568  |
| 71 | 12 | 0.00018363  | 0.010627608 | 26.09 | −0.244420225 | −0.244420225 |
| 72 | 2  | 0.957059624 | 0.99999793  | 3.33  | −0.241600331 | −0.241600331 |
| 73 | 16 | 6.44E−05    | 0.004967399 | 23.53 | −0.240482211 | −0.240482211 |
| 74 | 12 | 0.513477047 | 0.99999793  | 8.11  | −0.240064228 | −0.240064228 |
| 75 | 4  | 0.466402982 | 0.99999793  | 9.09  | −0.239598775 | −0.239598775 |
| 76 | 2  | 0.950729209 | 0.99999793  | 3.45  | −0.238303306 | −0.238303306 |
| 77 | 2  | 0.903339407 | 0.99999793  | 4.17  | −0.237388831 | −0.237388831 |
| 78 | 10 | 0.001969408 | 0.075986326 | 22.73 | −0.235455099 | −0.235455099 |
| 79 | 10 | 0.001969408 | 0.075986326 | 22.73 | −0.233288241 | −0.233288241 |

TABLE 1.b3

|    | t | P.Value | adj. P.Val | B | FC | FC_1 |
|----|---|---|---|---|---|---|
| 30 | −14.59846809 | 0.00000003440 | 0.000016100 | 9.499491123 | 0.792348352 | −1.262071156 |
| 31 | −11.91788456 | 0.00000024800 | 0.000042600 | 7.579137577 | 0.794618496 | −1.258465547 |
| 32 | −18.17630665 | 0.00000000394 | 0.000008640 | 11.50694716 | 0.79512411  | −1.257665297 |
| 33 | −15.03154881 | 0.00000002580 | 0.000014100 | 9.772437866 | 0.79788793  | −1.253308845 |
| 34 | −10.99489816 | 0.00000053700 | 0.000060300 | 6.809806578 | 0.79840406  | −1.252498641 |
| 35 | −13.11065547 | 0.00000009840 | 0.000026300 | 8.486465281 | 0.800200848 | −1.249686254 |
| 36 | −14.30149147 | 0.00000004210 | 0.000017200 | 9.306864203 | 0.802109086 | −1.246713219 |
| 37 | −18.81843594 | 0.00000000279 | 0.000006830 | 11.81480874 | 0.802787883 | −1.245659061 |
| 38 | −9.967999414 | 0.00000135000 | 0.000094900 | 5.875116011 | 0.803281037 | −1.24489432  |
| 39 | −13.88505293 | 0.00000005630 | 0.000020400 | 9.028942709 | 0.807442641 | −1.238478065 |
| 40 | −13.22491838 | 0.00000009050 | 0.000025200 | 8.56869633  | 0.807997065 | −1.237628258 |
| 41 | −11.89187759 | 0.00000025300 | 0.000042700 | 7.5583041   | 0.809858131 | −1.234784169 |
| 42 | −16.13705896 | 0.00000001280 | 0.000010700 | 10.42910997 | 0.811162087 | −1.232799235 |
| 43 | −10.15502575 | 0.00000113000 | 0.000085500 | 6.052012506 | 0.814734156 | −1.227394227 |
| 44 | −14.68901883 | 0.00000003240 | 0.000015800 | 9.557329978 | 0.815875189 | −1.225677668 |
| 45 | −10.89682004 | 0.00000058300 | 0.000063200 | 6.724276277 | 0.816806693 | −1.224279879 |
| 46 | −11.64817138 | 0.00000030800 | 0.000046400 | 7.360765169 | 0.817086438 | −1.223860725 |
| 47 | −11.89788921 | 0.00000025200 | 0.000042600 | 7.56312403  | 0.817196796 | −1.223695449 |
| 48 | −15.53979703 | 0.00000001860 | 0.000012900 | 10.08124721 | 0.822297844 | −1.216104368 |
| 49 | −10.51176015 | 0.00000081900 | 0.000072900 | 6.381022079 | 0.822953925 | −1.215134857 |
| 50 | −13.66679402 | 0.00000006570 | 0.000021400 | 8.879509786 | 0.823609338 | −1.214167875 |
| 51 | −6.169801402 | 0.00009510000 | 0.001205431 | 1.483598722 | 0.823691606 | −1.214046607 |
| 52 | −13.95705976 | 0.00000005350 | 0.000019800 | 9.077666225 | 0.829390919 | −1.205704062 |
| 53 | −8.821110144 | 0.00000419000 | 0.000175127 | 4.718854863 | 0.829587958 | −1.205409446 |
| 54 | −12.17892232 | 0.00000020100 | 0.000038100 | 7.78566957  | 0.829827694 | −1.205069446 |
| 55 | −15.17179069 | 0.00000002360 | 0.000013500 | 9.858864135 | 0.83033012  | −1.204340269 |
| 56 | −10.63311125 | 0.00000073500 | 0.000070500 | 6.490501331 | 0.831102269 | −1.203221357 |
| 57 | −9.608582862 | 0.00000190000 | 0.000114103 | 5.526310904 | 0.831384915 | −1.202812298 |
| 58 | −11.56467535 | 0.00000033000 | 0.000048300 | 7.292110963 | 0.831828285 | −1.202171191 |
| 59 | −9.763551812 | 0.00000164000 | 0.000106067 | 5.678158075 | 0.833487622 | −1.199777866 |
| 60 | −7.729993148 | 0.00001380000 | 0.000350395 | 3.491591234 | 0.833802925 | −1.199324169 |
| 61 | −12.34378327 | 0.00000017600 | 0.000037000 | 7.913735609 | 0.835931712 | −1.196269965 |
| 62 | −12.17180037 | 0.00000020200 | 0.000038100 | 7.780096223 | 0.836965917 | −1.194791783 |
| 63 | −10.52329131 | 0.00000081100 | 0.000072800 | 6.391477553 | 0.837740969 | −1.193686398 |
| 64 | −13.36737718 | 0.00000008150 | 0.000024000 | 8.670136499 | 0.838011734 | −1.193300714 |
| 65 | −9.902604635 | 0.00000144000 | 0.000098100 | 5.812528625 | 0.838066269 | −1.193223062 |
| 66 | −8.107409551 | 0.00000900000 | 0.000268320 | 3.931310999 | 0.838296687 | −1.192895088 |
| 67 | −9.140567696 | 0.00000302000 | 0.000145043 | 5.053843186 | 0.838829261 | −1.192137716 |
| 68 | −9.588148198 | 0.00000194000 | 0.000115278 | 5.506120648 | 0.841090265 | −1.188933034 |
| 69 | −8.279478026 | 0.00000745000 | 0.000241272 | 4.126320504 | 0.842010382 | −1.187633812 |
| 70 | −9.532818868 | 0.00000205000 | 0.000117891 | 5.451255469 | 0.84378323  | −1.18513851  |
| 71 | −14.00748875 | 0.00000005160 | 0.000019700 | 9.111620951 | 0.844154968 | −1.184616614 |
| 72 | −14.96153336 | 0.00000002710 | 0.000014500 | 9.728935581 | 0.845806568 | −1.182303422 |
| 73 | −10.36380562 | 0.00000093600 | 0.000078800 | 6.245881241 | 0.846462341 | −1.181387466 |
| 74 | −7.872213087 | 0.00001170000 | 0.000314692 | 3.659255262 | 0.846707616 | −1.18104524  |
| 75 | −11.49610245 | 0.00000035000 | 0.000050100 | 7.235348626 | 0.846980832 | −1.180664264 |
| 76 | −5.423526716 | 0.00026779500 | 0.002394757 | 0.404995163 | 0.84774172  | −1.179604562 |
| 77 | −9.072038739 | 0.00000324000 | 0.000150461 | 4.982857006 | 0.848279245 | −1.178857087 |
| 78 | −9.387573754 | 0.00000236000 | 0.000128993 | 5.305841842 | 0.849417008 | −1.177278052 |
| 79 | −13.63209575 | 0.00000006730 | 0.000021500 | 8.855508119 | 0.85069375  | −1.175511164 |

TABLE 1.b4

| | LS | Loop detected | Probe sequence 60 mer |
|---|---|---|---|
| 30 | -1 | PD-L1 responder | GTTCAGCAGCTGCTGAAACTCGGAGTTGTCGACACCCCTCTCTCCCCTCCCTGTTTTTCC (SEQ ID NO: 31) |
| 31 | -1 | PD-L1 responder | CTGAGTCTTCATTACCAAAAAAAAAGTTCGACCTCCCCGAACCCCTCCGCCTCTGCGCT (SEQ ID NO: 32) |
| 32 | -1 | PD-L1 responder | GGGCACCGCCGCCCTGACTTCCAACACATCGAAGAATGGGTGGGGCCTTGCACCTCATAC (SEQ ID NO: 33) |
| 33 | -1 | PD-L1 responder | CCACCCCCGCCCCGGGGGAGTCGCCCGGTCGAAGTGCTGTTGAGTTCCCCCATCTCTCAT (SEQ ID NO: 34) |
| 34 | -1 | PD-L1 responder | CCGCGCCCGCAGGGCCCGCCCCGCGCCGTCGAGAAGCATAAAGCAGGGACAGGTATGGAG (SEQ ID NO: 35) |
| 35 | -1 | PD-L1 responder | TTAATGCTGATACAATTCTATTGGATAATCGACACTTCGGCTCCCTGCACCTCCCATGCC (SEQ ID NO: 36) |
| 36 | -1 | PD-L1 responder | GCAGTCAATCACCGAGTTATATGAGGTCTCGACCTCCCCGAACCCCTCCGCCTCTGCGCT (SEQ ID NO: 37) |
| 37 | -1 | PD-L1 responder | GGGCACCGCCGCCCTGACTTCCAACACATCGAAGAATGGGTGGGGCCTTGCACCTCATAC (SEQ ID NO: 38) |
| 38 | -1 | PD-L1 responder | CCGCGCCCGCAGGGCCCGCCCCGCGCCGTCGACAATGTTATTCTTTGTTTCTCTTACCAA (SEQ ID NO: 39) |
| 39 | -1 | PD-L1 responder | TCTTTGCAGATGTTGTAAGATAAGGATGTCGACTTCATAATCCGCCCGCCTCAGCCTCCC (SEQ ID NO: 40) |
| 40 | -1 | PD-L1 responder | CCACCCCCGCCCCGGGGGAGTCGCCCGGTCGATTTCCAAAAGCTCACACATGGGTGCACA (SEQ ID NO: 41) |
| 41 | -1 | PD-L1 responder | CCACCCCCGCCCCGGGGGAGTCGCCCGGTCGAACTAATATTAGAGGAGAGAGGTCAGTTA (SEQ ID NO: 42) |
| 42 | -1 | PD-L1 responder | TCACAACCTGGGAAAACTGTCGCCTTGCTCGACTCCTGCTTCCCTCCCCTCATCTTTAAA (SEQ ID NO: 43) |
| 43 | -1 | PD-L1 responder | CCTGCACTTCCTCACGCCTGCTCACCCCTCGAGTGAGTGGGAGAGATGGCTCTCCACGCC (SEQ ID NO: 44) |
| 44 | -1 | PD-L1 responder | TTTCAAAGAAGGTATGATGGGAAAGGTCTCGACGCGCCCCCTCTACGCCATGTCCCCCCC (SEQ ID NO: 45) |
| 45 | -1 | PD-L1 responder | TCCAGCCTTGCCTGGAGCTAGGGCCACCTCGATCTTGGCTCACCGCAACCTTGGCCTCCC (SEQ ID NO: 46) |
| 46 | -1 | PD-L1 responder | CCACCCCCGCCCCGGGGGAGTCGCCCGGTCGAGGGCCTGGCAAGAAGACAGAAGCCGACT (SEQ ID NO: 47) |
| 47 | -1 | PD-L1 responder | CCACCCCCGCCCCGGGGGAGTCGCCCGGTCGAACTAATATTAGAGGAGAGAGGTCAGTTA (SEQ ID NO: 48) |
| 48 | -1 | PD-L1 responder | GGGCACCGCCGCCCTGACTTCCAACACATCGAGAAGCATAAAGCAGGGACAGGTATGGAG (SEQ ID NO: 49) |
| 49 | -1 | PD-L1 responder | CACCGACCCGTCCGGGCCCGCTGCCACATCGAATAGCTTCTTTTGCTATGTCTCCAAGTT (SEQ ID NO: 50) |
| 50 | -1 | PD-L1 responder | GTGTCTCGGCCCCTGGGGCCCCACCCTTCGATTTCCCTGTTGCCGCCGCGTTTGCAAGA (SEQ ID NO: 51) |
| 51 | -1 | PD-L1 responder | CCCGCGGCGGAGCTGCTACTGTTTACTTTCGAAGCTTCTTCCTTTCGGCCCCCAGGCCTA (SEQ ID NO: 52) |
| 52 | -1 | PD-L1 responder | TCTCCTGCCTACCACACTGTGAGAAAGCTCGAGGGCGGGCCCGGCGGCCCCGGAGCAAAC (SEQ ID NO: 53) |
| 53 | -1 | PD-L1 responder | GGGCACCGCCGCCCTGACTTCCAACACATCGATCTCTGCCTCGCGCAGCCCCAGCGTGCG (SEQ ID NO: 54) |
| 54 | -1 | PD-L1 responder | CCACCCCCGCCCCGGGGGAGTCGCCCGGTCGATTTCCAAAAGCTCACACATGGGTGCACA (SEQ ID NO: 55) |
| 55 | -1 | PD-L1 responder | GGGCACCGCCGCCCTGACTTCCAACACATCGAGAAGCATAAAGCAGGGACAGGTATGGAG (SEQ ID NO: 56) |

TABLE 1.b4-continued

| | LS | Loop detected | Probe sequence 60 mer |
|---|---|---|---|
| 56 | -1 | PD-L1 responder | CACCGACCCGTCCGGGCCCGCTGCCACATCGAATAGCTTCTTTTGCTATGTCTCCAAGTT (SEQ ID NO: 57) |
| 57 | -1 | PD-L1 responder | CAAATCCCGGCTATCTCTTAGAATTGCATCGACGCGCCCGTGACAGCCGAGTGCGGCCAC (SEQ ID NO: 58) |
| 58 | -1 | PD-L1 responder | CCACCCCCGCCCCGGGGGAGTCGCCCGGTCGAGGGCCTGGCAAGAAGACAGAAGCCGACT (SEQ ID NO: 59) |
| 59 | -1 | PD-L1 responder | TTAATGCTGATACAATTCTATTGGATAATCGACACTTCGGCTCCCTGCACCTCCCATGCC (SEQ ID NO: 60) |
| 60 | -1 | PD-L1 responder | GCACCCCACCCTGGATCCCTTGAAAGCCTCGATCTCTGCCTCGCGCAGCCCCAGCGTGCG (SEQ ID NO: 61) |
| 61 | -1 | PD-L1 responder | CCACCCCCGCCCGGGGGAGTCGCCCGGTCGAAGGCTGGACTTAAAAGAGCAGATGCAAG (SEQ ID NO: 62) |
| 62 | -1 | PD-L1 responder | TAATGCTTTTTTTTTGTTCTCTCTGTGTCGACCTCAGATGATCGCCTGCCTCGGCCTCC (SEQ ID NO: 63) |
| 63 | -1 | PD-L1 responder | TATGAGTAATAATTACAATTTCCCCCTTTCGACCTCCAGGTCCCCCGCCACTTCCACGGC (SEQ ID NO: 64) |
| 64 | -1 | PD-L1 responder | GTGTCTCGGCCCCCTGGGGCCCCACCCTTCGATTTCCCTGTTGCCGCCGCGTTTGCAAGA (SEQ ID NO: 65) |
| 65 | -1 | PD-L1 responder | CCACCCCCGCCCGGGGGAGTCGCCCGGTCGAAGGCTGGACTTAAAAGAGCAGATGCAAG (SEQ ID NO: 66) |
| 66 | -1 | PD-L1 responder | ATAAAAATAAGGTGGGTAGTTTTCAACTTCGAACCTAATCTATTTCATGTACCTGCTAGA (SEQ ID NO: 67) |
| 67 | -1 | PD-L1 responder | GCACCCCACCCTGGATCCCTTGAAAGCCTCGATGTGTTGGAAGTCAGGGCGGCGGTGCCC (SEQ ID NO: 68) |
| 68 | -1 | PD-L1 responder | ACAGTTTTATTGTTGACCTTCCATGGACTCGAGATGCGCCACGCCCTGTTCCTCCTTCAT (SEQ ID NO: 69) |
| 69 | -1 | PD-L1 responder | GCTTCTCCCCTCTTTATCCCACCTGGCCTCGACTCACCCTGCAGACAAGCTTTCGGGTAT (SEQ ID NO: 70) |
| 70 | -1 | PD-L1 responder | CAATATGACGGTGACATTAATGATAGCTTCGACACTTCGGCTCCCTGCACCTCCCATGCC (SEQ ID NO: 71) |
| 71 | -1 | PD-L1 responder | CCACCCCCGCCCGGGGGAGTCGCCCGGTCGAAGTGCTGTTGAGTTCCCCCATCTCTCAT (SEQ ID NO: 72) |
| 72 | -1 | PD-L1 responder | AGTGTTGGTGAGATATTGTCTCTCAGTTTCGACTCACTGCAACCCCCGCCTCTGGGTTCT (SEQ ID NO: 73) |
| 73 | -1 | PD-L1 responder | GGGCACCGCCGCCCTGACTTCCAACACATCGATCTCTGCCTCGCGCAGCCCCAGCGTGCG (SEQ ID NO: 74) |
| 74 | -1 | PD-L1 responder | CCCACACACCGCTGGTGCCCAAGGACTGTCGACCTCCCCGAACCCCTCCGCCTCTGCGCT (SEQ ID NO: 75) |
| 75 | -1 | PD-L1 responder | TTTCAAAGAAGGTATGATGGGAAAGGTCTCGAGTGCCCTGTCCCACCTGGCTCCCCCTG (SEQ ID NO: 76) |
| 76 | -1 | PD-L1 responder | TCATCTTTAATGAACAAGACTGTCACTATCGAATTTCCACAAGTGGGTGCCAACCACGGT (SEQ ID NO: 77) |
| 77 | -1 | PD-L1 responder | GCGGCCAACCCACAGCGCACCGGGCCGCTCGACCTCTGAGAGGAAACTTGCTAGCCCCAG (SEQ ID NO: 78) |
| 78 | -1 | PD-L1 responder | GACCCCCGGGAATTGGCTCCAGCACATCTCGAGGGCGGGCCCGGCGGCCCCGGAGCAAAC (SEQ ID NO: 79) |
| 79 | -1 | PD-L1 responder | TCTCCTGCCTACCACACTGTGAGAAAGCTCGAGGGCGGGCCCGGCGGCCCCGGAGCAAAC (SEQ ID NO: 80) |

TABLE 1.b5

| | Probe Location | | | | 4 kb Sequence Location | |
|---|---|---|---|---|---|---|
| | Chr | Start1 | End1 | Start2 | End2 | Chr | Start1 |
| 30 | 11 | 65634934 | 65634963 | 65654595 | 65654624 | 11 | 65634934 |
| 31 | 5 | 68194357 | 68194386 | 68215412 | 68215441 | 5 | 68190387 |
| 32 | 1 | 6450605 | 6450634 | 6498017 | 6498046 | 1 | 6450605 |
| 33 | 8 | 42271172 | 42271201 | 42292093 | 42292122 | 8 | 42267202 |
| 34 | 1 | 6466176 | 6466205 | 6514026 | 6514055 | 1 | 6462206 |
| 35 | 11 | 60938642 | 60938671 | 60983696 | 60983725 | 11 | 60938642 |
| 36 | 5 | 68215412 | 68215441 | 68277738 | 68277767 | 5 | 68215412 |
| 37 | 1 | 6450605 | 6450634 | 6498017 | 6498046 | 1 | 6450605 |
| 38 | 1 | 6466176 | 6466205 | 6494590 | 6494619 | 1 | 6462206 |
| 39 | 2 | 105741794 | 105741823 | 105844480 | 105844509 | 2 | 105737824 |
| 40 | 8 | 42271172 | 42271201 | 42290981 | 42291010 | 8 | 42267202 |
| 41 | 8 | 42241868 | 42241897 | 42271172 | 42271201 | 8 | 42241868 |
| 42 | 10 | 6432895 | 6432924 | 6464156 | 6464185 | 10 | 6432895 |
| 43 | 16 | 28959100 | 28959129 | 28978414 | 28978443 | 16 | 28959100 |
| 44 | 6 | 44270725 | 44270754 | 44312108 | 44312137 | 6 | 44270725 |
| 45 | 17 | 36084482 | 36084511 | 36095761 | 36095790 | 17 | 36080512 |
| 46 | 8 | 42271172 | 42271201 | 42281224 | 42281253 | 8 | 42267202 |
| 47 | 8 | 42241868 | 42241897 | 42271172 | 42271201 | 8 | 42241868 |
| 48 | 1 | 6498017 | 6498046 | 6514026 | 6514055 | 1 | 6494047 |
| 49 | 12 | 112418671 | 112418700 | 112478545 | 112478574 | 12 | 112418671 |
| 50 | 5 | 132477881 | 132477910 | 132497031 | 132497060 | 5 | 132473911 |
| 51 | 14 | 104800991 | 104801020 | 104843290 | 104843319 | 14 | 104797021 |
| 52 | 2 | 241514647 | 241514676 | 241559194 | 241559223 | 2 | 241514647 |
| 53 | 1 | 6461606 | 6461635 | 6498017 | 6498046 | 1 | 6461606 |
| 54 | 8 | 42271172 | 42271201 | 42290981 | 42291010 | 8 | 42267202 |
| 55 | 1 | 6498017 | 6498046 | 6514026 | 6514055 | 1 | 6494047 |
| 56 | 12 | 112418671 | 112418700 | 112478545 | 112478574 | 12 | 112418671 |
| 57 | 16 | 31214803 | 31214832 | 31324628 | 31324657 | 16 | 31214803 |
| 58 | 8 | 42271172 | 42271201 | 42281224 | 42281253 | 8 | 42267202 |
| 59 | 11 | 60938642 | 60938671 | 60983696 | 60983725 | 11 | 60938642 |
| 60 | 1 | 6461606 | 6461635 | 6484217 | 6484246 | 1 | 6461606 |
| 61 | 8 | 42271172 | 42271201 | 42302443 | 42302472 | 8 | 42267202 |
| 62 | 1 | 32257935 | 32257964 | 32298317 | 32298346 | 1 | 32253965 |
| 63 | 9 | 120913548 | 120913577 | 120940437 | 120940466 | 9 | 120913548 |
| 64 | 5 | 132477881 | 132477910 | 132497031 | 132497060 | 5 | 132473911 |
| 65 | 8 | 42271172 | 42271201 | 42302443 | 42302472 | 8 | 42267202 |
| 66 | 6 | 149314244 | 149314273 | 149369217 | 149369246 | 6 | 149314244 |
| 67 | 1 | 6484217 | 6484246 | 6498017 | 6498046 | 1 | 6480247 |
| 68 | 12 | 93837964 | 93837993 | 93848658 | 93848687 | 12 | 93833994 |
| 69 | 1 | 3615781 | 3615810 | 3638744 | 3638773 | 1 | 3611811 |
| 70 | 11 | 60938642 | 60938671 | 61025554 | 61025583 | 11 | 60938642 |
| 71 | 8 | 42271172 | 42271201 | 42292093 | 42292122 | 8 | 42267202 |
| 72 | 11 | 36469135 | 36469164 | 36503365 | 36503394 | 11 | 36465165 |
| 73 | 1 | 6461606 | 6461635 | 6498017 | 6498046 | 1 | 6461606 |
| 74 | 5 | 68215412 | 68215441 | 68268866 | 68268895 | 5 | 68215412 |
| 75 | 6 | 44253668 | 44253697 | 44312108 | 44312137 | 6 | 44253668 |
| 76 | 2 | 191108392 | 191108421 | 191184625 | 191184654 | 2 | 191108392 |
| 77 | 8 | 55939617 | 55939646 | 55961824 | 55961853 | 8 | 55939617 |
| 78 | 2 | 241535462 | 241535491 | 241559194 | 241559223 | 2 | 241535462 |
| 79 | 2 | 241514647 | 241514676 | 241559194 | 241559223 | 2 | 241514647 |

TABLE 1.b6

| | 4 kb Sequence Location | | |
|---|---|---|---|
| | End1 | Start2 | End2 |
| 30 | 65638933 | 65650625 | 65654624 |
| 31 | 68194386 | 68215412 | 68219411 |
| 32 | 6454604 | 6494047 | 6498046 |
| 33 | 42271201 | 42288123 | 42292122 |
| 34 | 6466205 | 6514026 | 6518025 |
| 35 | 60942641 | 60979726 | 60983725 |
| 36 | 68219411 | 68273768 | 68277767 |
| 37 | 6454604 | 6494047 | 6498046 |
| 38 | 6466205 | 6494590 | 6498589 |
| 39 | 105741823 | 105840510 | 105844509 |
| 40 | 42271201 | 42290981 | 42294980 |
| 41 | 42245867 | 42267202 | 42271201 |
| 42 | 6436894 | 6460186 | 6464185 |
| 43 | 28963099 | 28974444 | 28978443 |
| 44 | 44274724 | 44308138 | 44312137 |
| 45 | 36084511 | 36095761 | 36099760 |
| 46 | 42271201 | 42281224 | 42285223 |
| 47 | 42245867 | 42267202 | 42271201 |
| 48 | 6498046 | 6514026 | 6518025 |
| 49 | 112422670 | 112478545 | 112482544 |
| 50 | 132477910 | 132493061 | 132497060 |
| 51 | 104801020 | 104839320 | 104843319 |
| 52 | 241518646 | 241559194 | 241563193 |
| 53 | 6465605 | 6494047 | 6498046 |
| 54 | 42271201 | 42290981 | 42294980 |
| 55 | 6498046 | 6514026 | 6518025 |
| 56 | 112422670 | 112478545 | 112482544 |
| 57 | 31218802 | 31320658 | 31324657 |
| 58 | 42271201 | 42281224 | 42285223 |
| 59 | 60942641 | 60979726 | 60983725 |
| 60 | 6465605 | 6480247 | 6484246 |
| 61 | 42271201 | 42302443 | 42306442 |

TABLE 1.b6-continued

| | 4 kb Sequence Location | | |
|---|---|---|---|
| | End1 | Start2 | End2 |
| 62 | 32257964 | 32298317 | 32302316 |
| 63 | 120917547 | 120936467 | 120940466 |
| 64 | 132477910 | 132493061 | 132497060 |
| 65 | 42271201 | 42302443 | 42306442 |
| 66 | 149318243 | 149365247 | 149369246 |
| 67 | 6484246 | 6494047 | 6498046 |
| 68 | 93837993 | 93848658 | 93852657 |
| 69 | 3615810 | 3638744 | 3642743 |
| 70 | 60942641 | 61021584 | 61025583 |
| 71 | 42271201 | 42288123 | 42292122 |

TABLE 1.b6-continued

| | 4 kb Sequence Location | | |
|---|---|---|---|
| | End1 | Start2 | End2 |
| 72 | 36469164 | 36503365 | 36507364 |
| 73 | 6465605 | 6494047 | 6498046 |
| 74 | 68219411 | 68264896 | 68268895 |
| 75 | 44257667 | 44308138 | 44312137 |
| 76 | 191112391 | 191184625 | 191188624 |
| 77 | 55943616 | 55961824 | 55965823 |
| 78 | 241539461 | 241559194 | 241563193 |
| 79 | 241518646 | 241559194 | 241563193 |

TABLE 1.c1

| | probe | GeneLocus | Probe_Count_Total |
|---|---|---|---|
| 80 | TNFRSF25_1_6486023_6490057_6514024_6515315_FR | TNFRSF25 | 68 |
| 81 | ORF544_1_198595771_198598296_198619087_198627361_RF | PTPRC | 214 |
| 82 | TRAF1_9_120913546_120919710_120936524_120940468_RF | TRAF1 | 42 |
| 83 | ORF479_8_81007411_81018107_81053410_81059648_FR | PAG1 | 144 |
| 84 | ORF463_4_102557818_102560252_102627099_102634363_FR | NFKB1 | 64 |
| 85 | ITK_5_157225228_157231430_157263646_157266576_RF | ITK | 26 |
| 86 | ORF479_8_80968986_80975857_81095100_81099880_RR | PAG1 | 144 |
| 87 | ORF335_16_31331188_31333058_31344274_31352361_RF | ITGAM | 50 |
| 88 | ORF57_19_48955700_48958764_48973070_48975293_RR | BAX | 52 |
| 89 | BOK_2_241559192_241566423_241589009_241592694_RF | BOK | 44 |
| 90 | ORF401_4_86098061_86104840_86327055_86336679_RF | MAPK10 | 186 |
| 91 | ORF305_15_98652565_98657862_98893484_98899517_RR | IGF1R | 104 |
| 92 | CD6_11_60922069_60925026_61017867_61025585_RR | CD6 | 56 |
| 93 | AKT1_14_104800011_104801022_104839372_104843321_FF | AKT1 | 60 |
| 94 | ORF479_8_81007411_81018107_81095100_81099880_FR | PAG1 | 144 |
| 95 | PVRL1_11_119705149_119706599_119729288_119738834_FR | PVRL1 | 96 |
| 96 | ITGAM_16_31331188_31333058_31344274_31352361_RF | ITGAM | 50 |
| 97 | ITGAX_16_31331188_31333058_31344274_31352361_RF | ITGAX | 41 |
| 98 | ORF58_19_47214451_47217416_47236830_47241014_RF | BBC3 | 56 |
| 99 | HLA-DQA1_6_32634077_32639503_32662361_32664960_FF | HLA-DQA1 | 28 |
| 100 | ORF703_1_6481328_6484248_6494588_6498048_FF | TNFRSF25 | 68 |
| 101 | ORF209_4_109875299_109879120_110005130_110011368_FF | EGF | 48 |
| 102 | ORF307_8_42231188_42234849_42264241_42271203_RF | IKBKB | 46 |
| 103 | ORF76_2_241559192_241566423_241589009_241592694_RF | BOK | 44 |
| 104 | MAPKAP1_9_125549822_125553339_125631239_125635100_RF | MAPKAP1 | 52 |
| 105 | PTPN11_12_112418669_112423831_112508400_112510869_RR | PTPN11 | 56 |
| 106 | CD6_11_60938640_60941215_61017867_61025585_RF | CD6 | 56 |
| 107 | MTOR_1_11162452_11169997_11281372_11283081_FR | MTOR | 60 |
| 108 | ORF538_8_140725196_140731179_140877455_140883144_RF | PTK2 | 248 |
| 109 | PIK3R1_5_68215410_68221074_68258878_68268897_RF | PIK3R1 | 148 |
| 110 | IRF2_4_184439815_184446749_184518370_184519514_RF | IRF2 | 38 |
| 111 | ORF336_16_31344274_31352361_31385398_31389135_FF | ITGAX | 41 |
| 112 | MYC_8_127691489_127694045_127732337_127733526_FF | MYC | 42 |
| 113 | ITK_5_157178319_157181048_157266725_157271762_RR | ITK | 26 |
| 114 | ORF703_1_6486023_6490057_6514024_6515315_FR | TNFRSF25 | 68 |
| 115 | ORF406_1_150570652_150572543_150615513_150618018_RR | MCL1 | 77 |
| 116 | TNFRSF1A_12_6358656_6362143_6379726_6384063_FF | TNFRSF1A | 46 |
| 117 | ORF76_2_241535460_241542885_241589009_241592694_FR | BOK | 44 |
| 118 | ORF712_9_120888366_120893320_120919710_120922922_FR | TRAF1 | 42 |
| 119 | PTPN6_12_6934234_6935639_6946597_6948368_RR | PTPN6 | 46 |
| 120 | ORF99_3_105803937_105818229_105883590_105884656_RF | CBLB | 182 |
| 121 | ORF712_9_120888366_120893320_120913546_120919710_FR | TRAF1 | 42 |
| 122 | NFKBIE_6_44253666_44257911_44307667_44312139_RF | NFKBIE | 44 |
| 123 | ORF703_1_6461604_6466207_6486023_6490057_RR | TNFRSF25 | 68 |
| 124 | PTPN6_12_6934234_6935639_6965119_6966968_RR | PTPN6 | 46 |
| 125 | FAS_10_88953662_88956472_88985428_88990419_FF | FAS | 50 |
| 126 | ORF401_4_86050968_86053502_86086215_86098061_RF | MAPK10 | 186 |
| 127 | ORF305_15_98886232_98891127_98957432_98962130_FR | IGF1R | 104 |
| 128 | FAS_10_88940885_88944343_88985428_88990419_FF | FAS | 50 |
| 129 | ITK_5_157249288_157254103_157266725_157271762_RR | ITK | 26 |
| 130 | PTPN11_12_112418669_112423831_112499733_112502544_RF | PTPN11 | 56 |
| 131 | ORF293_6_32634077_32639503_32662361_32664960_FF | HLA-DQA1 | 28 |
| 132 | ORF299_19_10230936_10232348_10245172_10246736_FF | ICAM1 | 63 |
| 133 | RPTOR_17_80636056_80643737_80661868_80664436_RR | RPTOR | 86 |
| 134 | ORF336_16_31318595_31324659_31385398_31389135_FF | ITGAX | 41 |
| 135 | TRAF2_9_136904007_136906211_136939587_136941363_RF | TRAF2 | 46 |

TABLE 1.c1-continued

| | probe | GeneLocus | Probe_Count_Total |
|---|---|---|---|
| 136 | MYC_8_127691489_127694045_127738939_127740424_FR | MYC | 42 |
| 137 | ORF670_9_90789107_90793598_90816328_90822228_RF | SYK | 78 |
| 138 | ORF173_4_77503292_77510413_77602626_77605431_RR | CXCL13 | 108 |
| 139 | ORF544_1_198591683_198595771_198619087_198627361_FR | PTPRC | 214 |

TABLE 1.c2

| | Probe_Count_Sig | HyperG_Stats | FDR_HyperG | Percent_Sig | logFC | AveExpr |
|---|---|---|---|---|---|---|
| 80 | 16 | 6.44E−05 | 0.004967399 | 23.53 | −0.23286156 | −0.23286156 |
| 81 | 10 | 0.978491243 | 0.99999793 | 4.67 | −0.230147469 | −0.230147469 |
| 82 | 6 | 0.112492545 | 0.789152247 | 14.29 | −0.22976066 | −0.22976066 |
| 83 | 12 | 0.474481533 | 0.99999793 | 8.33 | −0.229747184 | −0.229747184 |
| 84 | 6 | 0.398773743 | 0.99999793 | 9.38 | −0.229043922 | −0.229043922 |
| 85 | 10 | 1.57E−05 | 0.002607465 | 38.46 | −0.226854713 | −0.226854713 |
| 86 | 12 | 0.474481533 | 0.99999793 | 8.33 | −0.226025291 | −0.226025291 |
| 87 | 8 | 0.041957105 | 0.555032562 | 16 | −0.224585718 | −0.224585718 |
| 88 | 2 | 0.925958703 | 0.99999793 | 3.85 | −0.224267121 | −0.224267121 |
| 89 | 10 | 0.001969408 | 0.075986326 | 22.73 | −0.223699232 | −0.223699232 |
| 90 | 10 | 0.931377207 | 0.99999793 | 5.38 | −0.223280405 | −0.223280405 |
| 91 | 16 | 0.007797893 | 0.171924974 | 15.38 | −0.222320696 | −0.222320696 |
| 92 | 14 | 9.03E−05 | 0.005970563 | 25 | −0.21998431 | −0.21998431 |
| 93 | 4 | 0.711822793 | 0.99999793 | 6.67 | −0.219972658 | −0.219972658 |
| 94 | 12 | 0.474481533 | 0.99999793 | 8.33 | −0.219792116 | −0.219792116 |
| 95 | 8 | 0.497039718 | 0.99999793 | 8.33 | −0.21590346 | −0.21590346 |
| 96 | 8 | 0.041957105 | 0.555032562 | 16 | −0.215030115 | −0.215030115 |
| 97 | 8 | 0.013975308 | 0.239650655 | 19.51 | −0.212953478 | −0.212953478 |
| 98 | 8 | 0.073465475 | 0.710624303 | 14.29 | −0.211934778 | −0.211934778 |
| 99 | 4 | 0.178427395 | 0.954389149 | 14.29 | −0.211239457 | −0.211239457 |
| 100 | 16 | 6.44E−05 | 0.004967399 | 23.53 | −0.210801738 | −0.210801738 |
| 101 | 2 | 0.903339407 | 0.99999793 | 4.17 | −0.210308957 | −0.210308957 |
| 102 | 12 | 0.00018363 | 0.010627608 | 26.09 | −0.209493573 | −0.209493573 |
| 103 | 10 | 0.001969408 | 0.075986326 | 22.73 | −0.209408376 | −0.209408376 |
| 104 | 6 | 0.229017635 | 0.99999793 | 11.54 | −0.208545117 | −0.208545117 |
| 105 | 6 | 0.283634013 | 0.99999793 | 10.71 | −0.207915939 | −0.207915939 |
| 106 | 14 | 9.03E−05 | 0.005970563 | 25 | −0.207569599 | −0.207569599 |
| 107 | 4 | 0.711822793 | 0.99999793 | 6.67 | −0.206498971 | −0.206498971 |
| 108 | 12 | 0.979779286 | 0.99999793 | 4.84 | −0.205518478 | −0.205518478 |
| 109 | 12 | 0.513477047 | 0.99999793 | 8.11 | −0.20551606 | −0.20551606 |
| 110 | 2 | 0.815788109 | 0.99999793 | 5.26 | −0.204963087 | −0.204963087 |
| 111 | 8 | 0.013975308 | 0.239650655 | 19.51 | −0.204949768 | −0.204949768 |
| 112 | 4 | 0.430324418 | 0.99999793 | 9.52 | −0.204707302 | −0.204707302 |
| 113 | 10 | 1.57E−05 | 0.002607465 | 38.46 | −0.204619133 | −0.204619133 |
| 114 | 16 | 6.44E−05 | 0.004967399 | 23.53 | −0.202040567 | −0.202040567 |
| 115 | 2 | 0.987032863 | 0.99999793 | 2.6 | −0.200905599 | −0.200905599 |
| 116 | 2 | 0.889742685 | 0.99999793 | 4.35 | −0.200276865 | −0.200276865 |
| 117 | 10 | 0.001969408 | 0.075986326 | 22.73 | −0.199287717 | −0.199287717 |
| 118 | 6 | 0.112492545 | 0.789152247 | 14.29 | −0.199273043 | −0.199273043 |
| 119 | 4 | 0.501622356 | 0.99999793 | 8.7 | −0.198832502 | −0.198832502 |
| 120 | 2 | 0.999995464 | 0.99999793 | 1.1 | −0.197007746 | −0.197007746 |
| 121 | 6 | 0.112492545 | 0.789152247 | 14.29 | −0.196616458 | −0.196616458 |
| 122 | 4 | 0.466402982 | 0.99999793 | 9.09 | −0.195945166 | −0.195945166 |
| 123 | 16 | 6.44E−05 | 0.004967399 | 23.53 | −0.195455805 | −0.195455805 |
| 124 | 4 | 0.501622356 | 0.99999793 | 8.7 | −0.1942843 | −0.1942843 |
| 125 | 8 | 0.041957105 | 0.555032562 | 16 | −0.194159165 | −0.194159165 |
| 126 | 10 | 0.931377207 | 0.99999793 | 5.38 | −0.193852528 | −0.193852528 |
| 127 | 16 | 0.007797893 | 0.171924974 | 15.38 | −0.193623643 | −0.193623643 |
| 128 | 8 | 0.041957105 | 0.555032562 | 16 | −0.193599779 | −0.193599779 |
| 129 | 10 | 1.57E−05 | 0.002607465 | 38.46 | −0.191450511 | −0.191450511 |
| 130 | 6 | 0.283634013 | 0.99999793 | 10.71 | −0.190144577 | −0.190144577 |
| 131 | 4 | 0.178427395 | 0.954389149 | 14.29 | −0.188169485 | −0.188169485 |
| 132 | 2 | 0.96511521 | 0.99999793 | 3.17 | −0.188079391 | −0.188079391 |
| 133 | 6 | 0.687444338 | 0.99999793 | 6.98 | −0.187583846 | −0.187583846 |
| 134 | 8 | 0.013975308 | 0.239650655 | 19.51 | −0.187127305 | −0.187127305 |
| 135 | 2 | 0.889742685 | 0.99999793 | 4.35 | −0.18670662 | −0.18670662 |
| 136 | 4 | 0.430324418 | 0.99999793 | 9.52 | −0.186601169 | −0.186601169 |
| 137 | 6 | 0.592795697 | 0.99999793 | 7.69 | −0.186508136 | −0.186508136 |
| 138 | 14 | 0.046569042 | 0.598929617 | 12.96 | −0.18577624 | −0.18577624 |
| 139 | 10 | 0.978491243 | 0.99999793 | 4.67 | −0.185177032 | −0.185177032 |

TABLE 1.c3

|     | t | P.Value | adj.P.Val | B | FC | FC_1 |
| --- | --- | --- | --- | --- | --- | --- |
| 80  | −9.606130665 | 0.00000191000 | 0.000114201 | 5.523890109 | 0.850945382 | −1.175163555 |
| 81  | −3.148603455 | 0.01006256300 | −0.032644588 | −3.329509766 | 0.852547742 | −1.17295484 |
| 82  | −9.762488772 | 0.00000164000 | 0.000106067 | 5.677124024 | 0.852776354 | −1.172640394 |
| 83  | −5.910931698 | 0.00013500300 | 0.001520418 | 1.118479259 | 0.85278432 | −1.172629441 |
| 84  | −4.146762666 | 0.00188918300 | 0.009492832 | −1.621910593 | 0.853200123 | −1.172057966 |
| 85  | −7.188770374 | 0.00002600000 | 0.000519842 | 2.830950394 | 0.854495789 | −1.170280782 |
| 86  | −8.99633921 | 0.00000350000 | 0.000158450 | 4.90389231 | 0.854987189 | −1.169608168 |
| 87  | −9.432629187 | 0.00000226000 | 0.000125198 | 5.351165953 | 0.855840752 | −1.168441673 |
| 88  | −9.299564365 | 0.00000258000 | 0.000135935 | 5.216740329 | 0.856029772 | −1.168183669 |
| 89  | −11.48918083 | 0.00000035200 | 0.000050200 | 7.229600039 | 0.856366798 | −1.167723926 |
| 90  | −6.056778408 | 0.00011069000 | 0.001332889 | 1.325356439 | 0.856615445 | −1.167384975 |
| 91  | −9.042592259 | 0.00000334000 | 0.000153695 | 4.952209419 | 0.857185472 | −1.166608666 |
| 92  | −6.891261434 | 0.00003750000 | 0.000650749 | 2.451958669 | 0.858574774 | −1.164720919 |
| 93  | −4.996552469 | 0.00050161400 | 0.003704426 | −0.24806514 | 0.858581708 | −1.164711512 |
| 94  | −8.380946819 | 0.00000667000 | 0.000227068 | 4.239758043 | 0.85868916 | −1.164565767 |
| 95  | −6.141683115 | 0.00009870000 | 0.001232539 | 1.444399249 | 0.861006802 | −1.161431011 |
| 96  | −9.152973735 | 0.00000298000 | 0.000144884 | 5.066643761 | 0.861528176 | −1.160728143 |
| 97  | −9.692570589 | 0.00000175000 | 0.000109375 | 5.608883602 | 0.862769165 | −1.159058576 |
| 98  | −11.61300437 | 0.00000031700 | 0.000047500 | 7.331061098 | 0.86337859 | −1.158240442 |
| 99  | −3.939059704 | 0.00265151700 | 0.012158182 | −1.970945908 | 0.863794804 | −1.157682352 |
| 100 | −9.768060356 | 0.00000163000 | 0.000106067 | 5.682542516 | 0.864056922 | −1.15733116 |
| 101 | −10.40736882 | 0.00000090000 | 0.000077000 | 6.285863051 | 0.864352108 | −1.156935918 |
| 102 | −7.675120855 | 0.00001470000 | 0.000366068 | 3.426840762 | 0.864840762 | −1.156282225 |
| 103 | −11.65447319 | 0.00000030700 | 0.000046400 | 7.3659264 | 0.864891836 | −1.156213943 |
| 104 | −7.711401904 | 0.00001410000 | 0.000355136 | 3.469495184 | 0.865409512 | −1.155522312 |
| 105 | −6.889497379 | 0.00003760000 | 0.000651415 | 2.449676896 | 0.86578701 | −1.155018484 |
| 106 | −8.105335573 | 0.00000902000 | 0.000268394 | 3.928930998 | 0.86599488 | −1.154741238 |
| 107 | −2.697141397 | 0.02197855900 | 0.058573399 | −4.108873892 | 0.866637776 | −1.153884619 |
| 108 | −7.923787367 | 0.00001100000 | 0.000303945 | 3.719464345 | 0.867226966 | −1.153100675 |
| 109 | −8.305090458 | 0.00000725000 | 0.000237593 | 4.155062284 | 0.867228419 | −1.153098743 |
| 110 | −3.763496869 | 0.00354591900 | 0.015017871 | −2.269233273 | 0.867560884 | −1.152656855 |
| 111 | −11.39755162 | 0.00000038000 | 0.000051600 | 7.153167186 | 0.867568894 | −1.152646213 |
| 112 | −8.414783357 | 0.00000643000 | 0.000223311 | 4.277331934 | 0.867714714 | −1.15245251 |
| 113 | −9.041273175 | 0.00000334000 | 0.000153695 | 4.950834477 | 0.867767745 | −1.152382081 |
| 114 | −9.244873048 | 0.00000272000 | 0.000138639 | 5.160429094 | 0.869320116 | −1.150324239 |
| 115 | −4.428242487 | 0.00120416200 | 0.006890615 | −1.156604974 | 0.870004278 | −1.149419635 |
| 116 | −7.487088438 | 0.00001830000 | 0.000418541 | 3.199585235 | 0.870383513 | −1.148918821 |
| 117 | −8.006905671 | 0.00001010000 | 0.000287708 | 3.815843073 | 0.870980475 | −1.148131363 |
| 118 | −6.213719238 | 0.00008970000 | 0.001156677 | 1.544601478 | 0.870989334 | −1.148119685 |
| 119 | −10.70312653 | 0.00000069000 | 0.000068700 | 6.553116754 | 0.87125534 | −1.147769149 |
| 120 | −4.723247929 | 0.00075994900 | 0.004919307 | −0.679565911 | 0.872358022 | −1.14631834 |
| 121 | −6.590704313 | 0.00005480000 | 0.000830816 | 2.057190334 | 0.872594655 | −1.146007478 |
| 122 | −9.511762166 | 0.00000209000 | 0.000119285 | 5.430299258 | 0.873000772 | −1.14547436 |
| 123 | −8.372647173 | 0.00000673000 | 0.000228439 | 4.230322943 | 0.873296943 | −1.145085882 |
| 124 | −10.52136039 | 0.00000081200 | 0.000072800 | 6.389727527 | 0.87400637 | −1.144156421 |
| 125 | −8.590649368 | 0.00000533000 | 0.000200984 | 4.470605821 | 0.874082182 | −1.144057184 |
| 126 | −7.722891129 | 0.00001390000 | 0.000352401 | 3.483155256 | 0.874267983 | −1.143814047 |
| 127 | −4.845372443 | 0.00063036800 | 0.004341248 | −0.485487626 | 0.874406698 | −1.143632594 |
| 128 | −5.573764843 | 0.00021606000 | 0.002072157 | 0.628565303 | 0.874421161 | −1.143613677 |
| 129 | −6.961093779 | 0.00003440000 | 0.000618186 | 2.541955486 | 0.87572481 | −1.141911236 |
| 130 | −9.052077707 | 0.00000330000 | 0.000152860 | 4.962091343 | 0.876517878 | −1.140878041 |
| 131 | −3.287365783 | 0.00792963500 | 0.027297251 | −3.089016199 | 0.877718679 | −1.139317214 |
| 132 | −9.516115389 | 0.00000208000 | 0.000119006 | 5.434635159 | 0.877773493 | −1.139246068 |
| 133 | −5.431560127 | 0.00026471700 | 0.002374878 | 0.417032009 | 0.878075047 | −1.138854821 |
| 134 | −10.29247019 | 0.00000099900 | 0.000081400 | 6.180062011 | 0.878352958 | −1.138494487 |
| 135 | −5.163579985 | 0.00039119800 | 0.003113294 | 0.010501538 | 0.87860912 | −1.138162554 |
| 136 | −8.01397424 | 0.00000998000 | 0.000286168 | 3.824002229 | 0.878673343 | −1.138079365 |
| 137 | −5.46686154 | 0.00025163400 | 0.002300079 | 0.469815665 | 0.878730006 | −1.138005978 |
| 138 | −6.120444196 | 0.00010159100 | 0.001258366 | 1.414716294 | 0.879175909 | −1.1374288 |
| 139 | −3.18372378 | 0.00947264400 | 0.031204399 | −3.26862691 | 0.879541141 | −1.13695648 |

TABLE 1.c4

|     | LS | Loop detected | Probe sequence 60 mer |
| --- | --- | --- | --- |
| 80 | −1 | PD-L1 responder | GCGCAGCCTCTGGCGCCCCCTGCCGGCCTCGAGAAGCATAAAGCAGGGACAGGTATGGAG (SEQ ID NO: 81) |
| 81 | −1 | PD-L1 responder | AGGAAGTATGTTTGATTTAGAATGTTATTCGAAGATCATTGTCTCATTTTTTTACTTGTT (SEQ ID NO: 82) |
| 82 | −1 | PD-L1 responder | TATGAGTAATAATTACAATTTCCCCCTTTTCGACCTCCAGGTCCCCCGCCACTTCCACGGC (SEQ ID NO: 83) |

TABLE 1.c4-continued

| | LS | Loop detected | Probe sequence 60 mer |
|---|---|---|---|
| 83 | -1 | PD-L1 responder | TCAGATAAGTAACTTCCTGATAATTAACTCGAGAAATGGATTCATATTTCCATGGCTTAC (SEQ ID NO: 84) |
| 84 | -1 | PD-L1 responder | GAATTAGCAATAGTGTGTTACTTCTTTCTCGATATTTTACATGGAATCTTTCCCTTTTTA (SEQ ID NO: 85) |
| 85 | -1 | PD-L1 responder | GGCCGCGAGCCCGGCAGCGGCGACATCCTCGAGAAATTCTCCCGCTTTAGCCTCCCAAAG (SEQ ID NO: 86) |
| 86 | -1 | PD-L1 responder | CTTTTTAAAAATTATCTTTTTATTTGCTTCGATGCCAATCCACGTCATTAGATGAGGACC (SEQ ID NO: 87) |
| 87 | -1 | PD-L1 responder | AGTGGTCTCACCATGGCTTTCTTCCAATTCGAGGTCCCCAACCCCCTGCCGCTCATCGTG (SEQ ID NO: 88) |
| 88 | -1 | PD-L1 responder | CGGGTGCCTCCCCCCCCATTCGCCCTGCTCGAGGGAGGGAAATGATTGGATTACGGGGGT (SEQ ID NO: 89) |
| 89 | -1 | PD-L1 responder | CACTTCCCCAACATAAGCCTCGGTCTCTTCGAGGGCGGGCCCGGCGGCCCCGGAGCAAAC (SEQ ID NO: 90) |
| 90 | -1 | PD-L1 responder | TATTCCATATTTCTGCTCAACATTCTCCTCGAGTAATTTAAATCAACAAAGCCATAGACA (SEQ ID NO: 91) |
| 91 | -1 | PD-L1 responder | TCTTAGAGTTGAACTTTTCTAATCTTTTTCGAGTGTAAAAGGGCTTTTACTGGTGCACAC (SEQ ID NO: 92) |
| 92 | -1 | PD-L1 responder | CTGGCGTTCCAGCCCTCGCACCTTGGCCTCGAGCACCTCTTCAGGGGAGGATTACTGCAA (SEQ ID NO: 93) |
| 93 | -1 | PD-L1 responder | CCCGCGGCGGAGCTGCTACTGTTTACTTTCGAAGCTTCTTCCTTTCGGCCCCCAGGCCTA (SEQ ID NO: 94) |
| 94 | -1 | PD-L1 responder | TCAGATAAGTAACTTCCTGATAATTAACTCGATGCCAATCCACGTCATTAGATGAGGACC (SEQ ID NO: 95) |
| 95 | -1 | PD-L1 responder | AGAAAATATAGTATTGATTGCTTTCAAGTCGATGCGCGCCCGCCGGGGCCCGGTCGGAGC (SEQ ID NO: 96) |
| 96 | -1 | PD-L1 responder | AGTGGTCTCACCATGGCTTTCTTCCAATTCGAGGTCCCCAACCCCCTGCCGCTCATCGTG (SEQ ID NO: 97) |
| 97 | -1 | PD-L1 responder | AGTGGTCTCACCATGGCTTTCTTCCAATTCGAGGTCCCCAACCCCCTGCCGCTCATCGTG (SEQ ID NO: 98) |
| 98 | -1 | PD-L1 responder | CGTGGATCCAGACTGGGAGCCCCCAGCCTCGAGCAGTTGCACTCCAGCCTAGGCAACAAG (SEQ ID NO: 99) |
| 99 | -1 | PD-L1 responder | CCCGTCTTCCCCAAAATCTATGTGGTCCTCGACAGCGACGTGGGGGTGTACCGCGCGGTG (SEQ ID NO: 100) |
| 100 | -1 | PD-L1 responder | GCACCCCACCCTGGATCCCTTGAAAGCCTCGATGTGTTGGAAGTCAGGGCGGCGGTGCCC (SEQ ID NO: 101) |
| 101 | -1 | PD-L1 responder | CAGGCTATTGTAGTGCTCTTCCTGGCCCTCGACACCCCCTTCAAGGGTCTGTGTCCCATA (SEQ ID NO: 102) |
| 102 | -1 | PD-L1 responder | CCACCCCGCCCCGGGGGAGTCGCCCGGTCGAGGTGGCTTGGGTCTTAGTCTTCCAGGCA (SEQ ID NO: 103) |
| 103 | -1 | PD-L1 responder | CACTTCCCCAACATAAGCCTCGGTCTCTTCGAGGGCGGGCCCGGCGGCCCCGGAGCAAAC (SEQ ID NO: 104) |
| 104 | -1 | PD-L1 responder | CACTAATCTTTACTCTTTTTCCACTTATTCGACCCTCCCCTTCCAGCTGGGCACAGGTGG (SEQ ID NO: 105) |
| 105 | -1 | PD-L1 responder | CACCGACCCGTCCGGGCCCGCTGCCACATCGAGGTGAAGTTTTAAAAAAAAAGTTGTGGA (SEQ ID NO: 106) |
| 106 | -1 | PD-L1 responder | CAATATGACGGTGACATTAATGATAGCTTCGACACTTCGGCTCCCTGCACCTCCCATGCC (SEQ ID NO: 107) |
| 107 | -1 | PD-L1 responder | ATTCCCAATGTTTCCTGAGTAGAACTGTTCGACTGCGAGCTCCCTCCCTGCAGTCAGGGA (SEQ ID NO: 108) |
| 108 | -1 | PD-L1 responder | CTTTCAAACAAATGACCTTCACCACTGTTCGATCACGGCTCACTGCAGCCTTGGCCTCCT (SEQ ID NO: 109) |

TABLE 1.c4-continued

| LS | Loop detected | Probe sequence 60 mer |
|---|---|---|
| 109 -1 | PD-L1 responder | CCCACACACCGCTGGTGCCCAAGGACTGTCGACCTCCCCGAACCCCTCCGCCTCTGCGCT (SEQ ID NO: 110) |
| 110 -1 | PD-L1 responder | TTATGATATTGTAAATTATTTTTAATATTCGAGCAAACTGACTTGGGGCCCCTATGTGTG (SEQ ID NO: 111) |
| 111 -1 | PD-L1 responder | AGTGGTCTCACCATGGCTTTCTTCCAATTCGATTCACCCTCCTCAGCCTCCCAAAGTGCT (SEQ ID NO: 112) |
| 112 -1 | PD-L1 responder | AGGGAGAACAAAAGAAGTTCCATCCATCTCGATCCCCCCGGGCTCAAAGCAAACCTCCTA (SEQ ID NO: 113) |
| 113 -1 | PD-L1 responder | CAAAATCAAACACAAATCTAATCAAACTTCGATGTTTGGGGCGGAGGGCTTTGATGAGA (SEQ ID NO:114) |
| 114 -1 | PD-L1 responder | GCGCAGCCTCTGGCGCCCCCTGCCGGCCTCGAGAAGCATAAAGCAGGGACAGGTATGGAG (SEQ ID NO: 115) |
| 115 -1 | PD-L1 responder | AATTTATGGATTGTATGTTACTACTGTATCGAGATCTTCCTACCTCACCGTCCCAAGTAG (SEQ ID NO: 116) |
| 116 -1 | PD-L1 responder | TCCAGGGATGGCAGAGTCTCTGGCAGCCTCGATGCGGGGCGGGAGGGGCGGCCGGGAAAG (SEQ ID NO: 117) |
| 117 -1 | PD-L1 responder | GGGTTTCACCCTGTTGGCCAGGCTGGTCTCGAGACCGGCCTGGCCAACATGGTGAAACCC (SEQ ID NO: 118) |
| 118 -1 | PD-L1 responder | ATAAAATGGGGAGGCCTTCCAGAAGCTCTCGACCGCCACCTCCTCCAGGAAGCCCTGCCT (SEQ ID NO: 119) |
| 119 -1 | PD-L1 responder | CTGACCCCTCCAGGGGAGGCCCGGCCCCTCGAGGAGGAAGTGGCTGATTACTGAGCGGTT (SEQ ID NO: 120) |
| 120 -1 | PD-L1 responder | CCTAATATTTCATTATGATAAGAAAGATTCGAGAGTAAGTTTCTTCTGTTCACTCAGGAG (SEQ ID NO: 121) |
| 121 -1 | PD-L1 responder | ATAAAATGGGGAGGCCTTCCAGAAGCTCTCGACCTCCAGGTCCCCCGCCACTTCCACGGC (SEQ ID NO: 122) |
| 122 -1 | PD-L1 responder | TTTCAAAGAAGGTATGATGGGAAAGGTCTCGAGTGCCCCTGTCCCACCTGGCTCCCCCTG (SEQ ID NO: 123) |
| 123 -1 | PD-L1 responder | CGCACGCTGGGGCTGCGCGAGGCAGAGATCGATCCCCGCCCAGCCCTGGGGGTGCCCACT (SEQ ID NO: 124) |
| 124 -1 | PD-L1 responder | CTGACCCCTCCAGGGGAGGCCCGGCCCCTCGAGAACTCAGGGCCAGCCTTCCCAGCTTGG (SEQ ID NO: 125) |
| 125 -1 | PD-L1 responder | CGTGAATATATTGGGCTCTAATGGATAATCGAGAGCCGGCCTCCTGCCCTTTCTAAAGGC (SEQ ID NO: 126) |
| 126 -1 | PD-L1 responder | ATTGACCTGTTAAAGACTTGATTTAGTGTCGAAGGAATTCAGCTTTCAAAATGCACCTAA (SEQ ID NO: 127) |
| 127 -1 | PD-L1 responder | TCCTAGGAGAGACTGAACTTTAAAGATATCGACCTGCTGATCCTTGGATCCTGAATCTGT (SEQ ID NO: 128) |
| 128 -1 | PD-L1 responder | GTCTTTGTGTAAATAAATAAGGTAACCCTCGAGAGCCGGCCTCCTGCCCTTTCTAAAGGC (SEQ ID NO: 129) |
| 129 -1 | PD-L1 responder | TACAGACTTTTTTTCTCTTCTCAGAAAATCGATGTTTGGGGCGGAGGGCTTTGATGAGA (SEQ ID NO: 130) |
| 130 -1 | PD-L1 responder | GTTCATGGATTACTTTGAAGTCAGGAGTTCGATGTGGCAGCGGGCCCGGACGGGTCGGTG (SEQ ID NO: 131) |
| 131 -1 | PD-L1 responder | CCCGTCTTCCCCAAAATCTATGTGGTCCTCGACAGCGACGTGGGGGTGTACCGCGCGGTG (SEQ ID NO: 132) |
| 132 -1 | PD-L1 responder | TGCGGAAATGATGGACACTACACCTTCATCGAGATCTTGGTTCACTGCAACCTCTGTCTC (SEQ ID NO: 133) |
| 133 -1 | PD-L1 responder | AGCTGGAGTCTTGATTAACACAAAAATCTCGAGATTCACTGCGCTGCACACCAGGGCCTC (SEQ ID NO: 134) |

TABLE 1.c4-continued

| | LS | Loop detected | Probe sequence 60 mer |
|---|---|---|---|
| 134 | -1 | PD-L1 responder | CAAATCCCGGCTATCTCTTAGAATTGCATCGATTCACCCTCCTCAGCCTCCCAAAGTGCT (SEQ ID NO: 135) |
| 135 | -1 | PD-L1 responder | CCGCCTCACCTCCCGCATGGTCTTGAGGTCGAGCATGCAGCGCATCTGAGCAGTGAGGCT (SEQ ID NO: 136) |
| 136 | -1 | PD-L1 responder | AGGGAGAACAAAAGAAGTTCCATCCATCTCGACGGAGTCCTCCCCGCAGGGCAGCCCCGA (SEQ ID NO: 137) |
| 137 | -1 | PD-L1 responder | TTTTACTGTTTTTGTAAGAGATATGTTTTCGAAACTCTCTCCAATGAAACAATTCTTTGA (SEQ ID NO: 138) |
| 138 | -1 | PD-L1 responder | GTATTTTGATGATAAAAGCTGAACAACTTCGATTCCAAAGTGAAGCAAAAAAAAAACTTC (SEQ ID NO: 139) |
| 139 | -1 | PD-L1 responder | TGTTTTTTATTGTTTGATGTCCAATGTATCGAGTTTCAGTGTATTTGACATGTTATTCCA (SEQ ID NO: 140) |

TABLE 1.c5

| | Probe Location | | | | | 4 kb Sequence Location | |
|---|---|---|---|---|---|---|---|
| | Chr | Start1 | End1 | Start2 | End2 | Chr | Start1 |
| 80 | 1 | 6490026 | 6490055 | 6514026 | 6514055 | 1 | 6486056 |
| 81 | 1 | 198595773 | 198595802 | 198627330 | 198627359 | 1 | 198595773 |
| 82 | 9 | 120913548 | 120913577 | 120940437 | 120940466 | 9 | 120913548 |
| 83 | 8 | 81018076 | 81018105 | 81053412 | 81053441 | 8 | 81014106 |
| 84 | 4 | 102560221 | 102560250 | 102627101 | 102627130 | 4 | 102556251 |
| 85 | 5 | 157225230 | 157225259 | 157266545 | 157266574 | 5 | 157225230 |
| 86 | 8 | 80968988 | 80969017 | 81095102 | 81095131 | 8 | 80968988 |
| 87 | 16 | 31331190 | 31331219 | 31352330 | 31352359 | 16 | 31331190 |
| 88 | 19 | 48955702 | 48955731 | 48973072 | 48973101 | 19 | 48955702 |
| 89 | 2 | 241559194 | 241559223 | 241592663 | 241592692 | 2 | 241559194 |
| 90 | 4 | 86098063 | 86098092 | 86336648 | 86336677 | 4 | 86098063 |
| 91 | 15 | 98652567 | 98652596 | 98893486 | 98893515 | 15 | 98652567 |
| 92 | 11 | 60922071 | 60922100 | 61017869 | 61017898 | 11 | 60922071 |
| 93 | 14 | 104800991 | 104801020 | 104843290 | 104843319 | 14 | 104797021 |
| 94 | 8 | 81018076 | 81018105 | 81095102 | 81095131 | 8 | 81014106 |
| 95 | 11 | 119706568 | 119706597 | 119729290 | 119729319 | 11 | 119702598 |
| 96 | 16 | 31331190 | 31331219 | 31352330 | 31352359 | 16 | 31331190 |
| 97 | 16 | 31331190 | 31331219 | 31352330 | 31352359 | 16 | 31331190 |
| 98 | 19 | 47214453 | 47214482 | 47240983 | 47241012 | 19 | 47214453 |
| 99 | 6 | 32639472 | 32639501 | 32664929 | 32664958 | 6 | 32635502 |
| 100 | 1 | 6484217 | 6484246 | 6498017 | 6498046 | 1 | 6480247 |
| 101 | 4 | 109879089 | 109879118 | 110011337 | 110011366 | 4 | 109875119 |
| 102 | 8 | 42231190 | 42231219 | 42271172 | 42271201 | 8 | 42231190 |
| 103 | 2 | 241559194 | 241559223 | 241592663 | 241592692 | 2 | 241559194 |
| 104 | 9 | 125549824 | 125549853 | 125635069 | 125635098 | 9 | 125549824 |
| 105 | 12 | 112418671 | 112418700 | 112508402 | 112508431 | 12 | 112418671 |
| 106 | 11 | 60938642 | 60938671 | 61025554 | 61025583 | 11 | 60938642 |
| 107 | 1 | 11169966 | 11169995 | 11281374 | 11281403 | 1 | 11165996 |
| 108 | 8 | 140725198 | 140725227 | 140883113 | 140883142 | 8 | 140725198 |
| 109 | 5 | 68215412 | 68215441 | 68268866 | 68268895 | 5 | 68215412 |
| 110 | 4 | 184439817 | 184439846 | 184519483 | 184519512 | 4 | 184439817 |
| 111 | 16 | 31352330 | 31352359 | 31389104 | 31389133 | 16 | 31348360 |
| 112 | 8 | 127694014 | 127694043 | 127733495 | 127733524 | 8 | 127690044 |
| 113 | 5 | 157178321 | 157178350 | 157266727 | 157266756 | 5 | 157178321 |
| 114 | 1 | 6490026 | 6490055 | 6514026 | 6514055 | 1 | 6486056 |
| 115 | 1 | 150570654 | 150570683 | 150615515 | 150615544 | 1 | 150570654 |
| 116 | 12 | 6362112 | 6362141 | 6384032 | 6384061 | 12 | 6358142 |
| 117 | 2 | 241542854 | 241542883 | 241589011 | 241589040 | 2 | 241538884 |
| 118 | 9 | 120893289 | 120893318 | 120919712 | 120919741 | 9 | 120889319 |
| 119 | 12 | 6934236 | 6934265 | 6946599 | 6946628 | 12 | 6934236 |
| 120 | 3 | 105803939 | 105803968 | 105884625 | 105884654 | 3 | 105803939 |
| 121 | 9 | 120893289 | 120893318 | 120913548 | 120913577 | 9 | 120889319 |
| 122 | 6 | 44253668 | 44253697 | 44312108 | 44312137 | 6 | 44253668 |
| 123 | 1 | 6461606 | 6461635 | 6486025 | 6486054 | 1 | 6461606 |
| 124 | 12 | 6934236 | 6934265 | 6965163 | 6965192 | 12 | 6934236 |
| 125 | 10 | 88956441 | 88956470 | 88990388 | 88990417 | 10 | 88952471 |
| 126 | 4 | 86050970 | 86050999 | 86098030 | 86098059 | 4 | 86050970 |
| 127 | 15 | 98891096 | 98891125 | 98957434 | 98957463 | 15 | 98887126 |
| 128 | 10 | 88944312 | 88944341 | 88990388 | 88990417 | 10 | 88940342 |

TABLE 1.c5-continued

| | Probe Location | | | | 4 kb Sequence Location | |
|---|---|---|---|---|---|---|
| | Chr | Start1 | End1 | Start2 | End2 | Chr | Start1 |
| 129 | 5 | 157249290 | 157249319 | 157266727 | 157266756 | 5 | 157249290 |
| 130 | 12 | 112418671 | 112418700 | 112502513 | 112502542 | 12 | 112418671 |
| 131 | 6 | 32639472 | 32639501 | 32664929 | 32664958 | 6 | 32635502 |
| 132 | 19 | 10232317 | 10232346 | 10246705 | 10246734 | 19 | 10228347 |
| 133 | 17 | 80636058 | 80636087 | 80661870 | 80661899 | 17 | 80636058 |
| 134 | 16 | 31324628 | 31324657 | 31389104 | 31389133 | 16 | 31320658 |
| 135 | 9 | 136904009 | 136904038 | 136941332 | 136941361 | 9 | 136904009 |
| 136 | 8 | 127694014 | 127694043 | 127738941 | 127738970 | 8 | 127690044 |
| 137 | 9 | 90789109 | 90789138 | 90822197 | 90822226 | 9 | 90789109 |
| 138 | 4 | 77503294 | 77503323 | 77602628 | 77602657 | 4 | 77503294 |
| 139 | 1 | 198595740 | 198595769 | 198619089 | 198619118 | 1 | 198591770 |

TABLE 1.c6

| | 4 kb Sequence Location | | |
|---|---|---|---|
| | End1 | Start2 | End2 |
| 80 | 6490055 | 6514026 | 6518025 |
| 81 | 198599772 | 198623360 | 198627359 |
| 82 | 120917547 | 120936467 | 120940466 |
| 83 | 81018105 | 81053412 | 81057411 |
| 84 | 102560250 | 102627101 | 102631100 |
| 85 | 157229229 | 157262575 | 157266574 |
| 86 | 80972987 | 81095102 | 81099101 |
| 87 | 31335189 | 31348360 | 31352359 |
| 88 | 48959701 | 48973072 | 48977071 |
| 89 | 241563193 | 241588693 | 241592692 |
| 90 | 86102062 | 86332678 | 86336677 |
| 91 | 98656566 | 98893486 | 98897485 |
| 92 | 60926070 | 61017869 | 61021868 |
| 93 | 104801020 | 104839320 | 104843319 |
| 94 | 81018105 | 81095102 | 81099101 |
| 95 | 119706597 | 119729290 | 119733289 |
| 96 | 31335189 | 31348360 | 31352359 |
| 97 | 31335189 | 31348360 | 31352359 |
| 98 | 47218452 | 47237013 | 47241012 |
| 99 | 32639501 | 32660959 | 32664958 |
| 100 | 6484246 | 6494047 | 6498046 |
| 101 | 109879118 | 110007367 | 110011366 |
| 102 | 42235189 | 42267202 | 42271201 |
| 103 | 241563193 | 241588693 | 241592692 |
| 104 | 125553823 | 125631099 | 125635098 |
| 105 | 112422670 | 112508402 | 112512401 |
| 106 | 60942641 | 61021584 | 61025583 |
| 107 | 11169995 | 11281374 | 11285373 |
| 108 | 140729197 | 140879143 | 140883142 |
| 109 | 68219411 | 68264896 | 68268895 |
| 110 | 184443816 | 184515513 | 184519512 |

TABLE 1.c6-continued

| | 4 kb Sequence Location | | |
|---|---|---|---|
| | End1 | Start2 | End2 |
| 111 | 31352359 | 31385134 | 31389133 |
| 112 | 127694043 | 127729525 | 127733524 |
| 113 | 157182320 | 157266727 | 157270726 |
| 114 | 6490055 | 6514026 | 6518025 |
| 115 | 150574653 | 150615515 | 150619514 |
| 116 | 6362141 | 6380062 | 6384061 |
| 117 | 241542883 | 241589011 | 241593010 |
| 118 | 120893318 | 120919712 | 120923711 |
| 119 | 6938235 | 6946599 | 6950598 |
| 120 | 105807938 | 105880655 | 105884654 |
| 121 | 120893318 | 120913548 | 120917547 |
| 122 | 44257667 | 44308138 | 44312137 |
| 123 | 6465605 | 6486025 | 6490024 |
| 124 | 6938235 | 6965163 | 6969162 |
| 125 | 88956470 | 88986418 | 88990417 |
| 126 | 86054969 | 86094060 | 86098059 |
| 127 | 98891125 | 98957434 | 98961433 |
| 128 | 88944341 | 88986418 | 88990417 |
| 129 | 157253289 | 157266727 | 157270726 |
| 130 | 112422670 | 112498543 | 112502542 |
| 131 | 32639501 | 32660959 | 32664958 |
| 132 | 10232346 | 10242735 | 10246734 |
| 133 | 80640057 | 80661870 | 80665869 |
| 134 | 31324657 | 31385134 | 31389133 |
| 135 | 136908008 | 136937362 | 136941361 |
| 136 | 127694043 | 127738941 | 127742940 |
| 137 | 90793108 | 90818227 | 90822226 |
| 138 | 77507293 | 77602628 | 77606627 |
| 139 | 198595769 | 198619089 | 198623088 |

TABLE 1.d1

| | probe | GeneLocus | Probe_Count_Total |
|---|---|---|---|
| 140 | CD2_1_116707374_116708774_116735758_116740399_FR | CD2 | 34 |
| 141 | PVRL1_11_119671081_119677815_119729288_119738834_RR | PVRL1 | 96 |
| 142 | ORF401_4_86120725_86131416_86336679_86343485_FF | MAPK10 | 186 |
| 143 | ORF611_20_1891489_1897350_1924633_1930962_RR | SIRPA | 56 |
| 144 | ORF338_5_157249288_157254103_157266725_157271762_RR | ITK | 26 |
| 145 | IGF2_11_2113132_2119465_2180328_2182624_RR | IGF2 | 32 |
| 146 | ORF631_15_67098632_67101498_67199584_67204251_RR | SMAD3 | 34 |
| 147 | ITGAM_16_31278026_31284381_31331188_31333058_RR | ITGAM | 50 |
| 148 | ORF538_8_140715391_140725081_140877455_140883144_FR | PTK2 | 248 |
| 149 | CD14_5_140643798_140647427_140670568_140672728_FF | CD14 | 62 |
| 150 | IGF1R_15_98731539_98737034_98785670_98790114_FF | IGF1R | 104 |
| 151 | ORF113_5_67178844_67182260_67233989_67237362_FR | CD180 | 38 |
| 152 | ORF130_11_60922069_60925026_60977084_60983727_RR | CD6 | 56 |
| 153 | ORF490_16_2500832_2504754_2543954_2548518_RF | PDPK1 | 60 |
| 154 | BID_22_17731946_17735544_17804446_17806939_FF | BID | 42 |
| 155 | ORF642_16_29613904_29616227_29630194_29632081_RF | SPN | 56 |
| 156 | ORF223_11_124746039_124755799_124783109_124787738_RF | ESAM | 32 |
| 157 | ORF456_11_119671081_119677815_119700077_119705149_FF | PVRL1 | 96 |

TABLE 1.d1-continued

| | probe | GeneLocus | Probe_Count_Total |
|---|---|---|---|
| 158 | ORF138_3_122014664_122021863_122097537_122100802_RF | CD86 | 46 |
| 159 | ITK_5_157178319_157181048_157266725_157271762_FR | ITK | 26 |
| 160 | IRF3_19_49654782_49660360_49691432_49693107_RR | IRF3 | 30 |
| 161 | SHH_7_155794440_155798922_155840981_155842935_RF | SHH | 36 |
| 162 | ORF224_6_151870936_151873891_151985888_151997878_FF | ESR1 | 198 |
| 163 | PDPK1_16_2500832_2504754_2543954_2548518_RF | PDPK1 | 60 |
| 164 | ORF305_15_98779700_98784973_98893484_98899517_FR | IGF1R | 104 |
| 165 | ORF22_14_104760238_104764613_104839372_104843321_RF | AKT1 | 60 |
| 166 | ORF542_12_6934234_6935639_6965161_6966968_RR | PTPN6 | 46 |
| 167 | ORF86_1_56934234_56943891_56962729_56967106_FR | C8A | 166 |
| 168 | ORF544_1_198591683_198595771_198735456_198749256_FF | PTPRC | 214 |
| 169 | SPN_16_29613904_29616227_29630194_29632081_RF | SPN | 56 |
| 170 | PTPRA_20_2816709_2821045_2963104_2968013_RF | PTPRA | 82 |
| 171 | CD6_11_60977084_60983727_60996251_60998956_FR | CD6 | 56 |
| 172 | ORF95_2_201261158_201267239_201286114_201291036_FF | CASP8 | 41 |
| 173 | BBC3_19_47236830_47241014_47256212_47257706_FR | BBC3 | 56 |
| 174 | TRAF1_9_120888366_120893320_120913546_120919710_FR | TRAF1 | 42 |
| 175 | ORF538_8_140715391_140725081_140781905_140783960_FF | PTK2 | 248 |
| 176 | IRF1_5_132472660_132477912_132536450_132537922_FR | IRF1 | 42 |
| 177 | ORF642_16_29613904_29616227_29686079_29687229_RF | SPN | 56 |
| 178 | ORF403_9_125608173_125614421_125631239_125635100_RF | MAPKAP1 | 52 |
| 179 | ORF124_12_6767426_6773999_6796695_6798393_FR | CD4 | 42 |
| 180 | CD82_11_44561823_44564856_44624533_44629606_FF | CD82 | 50 |
| 181 | ORF311_5_149378172_149380861_149421073_149426819_RR | IL17B | 44 |
| 182 | C8B_1_56959632_56962729_56991331_56998079_FF | C8B | 151 |
| 183 | ORF538_8_140715391_140725081_140763162_140771406_FF | PTK2 | 248 |
| 184 | ORF73_10_96186298_96190208_96274838_96286475_RF | BLNK | 66 |
| 185 | ORF331_19_49654782_49660360_49691432_49693107_RR | IRF3 | 30 |
| 186 | ORF305_15_98893484_98899517_98957432_98962130_RR | IGF1R | 104 |
| 187 | BAX_19_48955700_48958764_48973070_48975293_RR | BAX | 52 |
| 188 | ORF317_14_23324243_23329232_23356396_23359421_RF | IL25 | 74 |
| 189 | CD6_11_60932387_60933682_61017867_61025585_FR | CD6 | 56 |
| 190 | ORF501_5_68203536_68213336_68272048_68277769_FF | PIK3R1 | 148 |
| 191 | ORF167_5_132051982_132053273_132068115_132074991_FF | CSF2 | 36 |
| 192 | ORF540_12_112418669_112423831_112478543_112482415_RF | PTPN11 | 56 |
| 193 | ORF456_11_119671081_119677815_119729288_119738834_RR | PVRL1 | 96 |
| 194 | ORF306_11_2113132_2119465_2180328_2182624_RR | IGF2 | 32 |
| 195 | ICOSLG_21_44243731_44245588_44267559_44270033_RR | ICOSLG | 40 |
| 196 | ORF55_11_64267793_64269811_64292591_64296924_FF | BAD | 70 |
| 197 | TNFRSF19_13_23627958_23632852_23678002_23680230_RR | TNFRSF19 | 60 |
| 198 | ORF112_5_140643798_140647427_140670568_140672728_FF | CD14 | 62 |
| 199 | ORF479_8_81007411_81018107_81077565_81079322_FR | PAG1 | 144 |

TABLE 1.d2

| | Probe_Count_Sig | HyperG_Stats | FDR_HyperG | Percent_Sig | logFC | AveExpr |
|---|---|---|---|---|---|---|
| 140 | 2 | 0.764125503 | 0.99999793 | 5.88 | −0.18498091 | −0.18498091 |
| 141 | 8 | 0.497039718 | 0.99999793 | 8.33 | −0.184910905 | −0.184910905 |
| 142 | 10 | 0.931377207 | 0.99999793 | 5.38 | −0.18453906 | −0.18453906 |
| 143 | 4 | 0.659150649 | 0.99999793 | 7.14 | −0.183746617 | −0.183746617 |
| 144 | 10 | 1.57E−05 | 0.002607465 | 38.46 | −0.180610127 | −0.180610127 |
| 145 | 6 | 0.037675475 | 0.528598335 | 18.75 | −0.180180699 | −0.180180699 |
| 146 | 2 | 0.764125503 | 0.99999793 | 5.88 | −0.180175335 | −0.180175335 |
| 147 | 8 | 0.041957105 | 0.555032562 | 16 | −0.179650611 | −0.179650611 |
| 148 | 12 | 0.979779286 | 0.99999793 | 4.84 | −0.179032383 | −0.179032383 |
| 149 | 6 | 0.369692981 | 0.99999793 | 9.68 | −0.178209877 | −0.178209877 |
| 150 | 16 | 0.007797893 | 0.171924974 | 15.38 | −0.178097117 | −0.178097117 |
| 151 | 4 | 0.356577228 | 0.99999793 | 10.53 | −0.176986579 | −0.176986579 |
| 152 | 14 | 9.03E−05 | 0.005970563 | 25 | −0.176532216 | −0.176532216 |
| 153 | 6 | 0.340695433 | 0.99999793 | 10 | −0.176282137 | −0.176282137 |
| 154 | 2 | 0.857080857 | 0.99999793 | 4.76 | −0.1760267 | −0.1760267 |
| 155 | 4 | 0.659150649 | 0.99999793 | 7.14 | −0.175972335 | −0.175972335 |
| 156 | 2 | 0.733846963 | 0.99999793 | 6.25 | −0.175898715 | −0.175898715 |
| 157 | 8 | 0.497039718 | 0.99999793 | 8.33 | −0.175584682 | −0.175584682 |
| 158 | 2 | 0.889742685 | 0.99999793 | 4.35 | −0.17550915 | −0.17550915 |
| 159 | 10 | 1.57E−05 | 0.002607465 | 38.46 | −0.17535973 | −0.17535973 |
| 160 | 2 | 0.700318757 | 0.99999793 | 6.67 | −0.175351435 | −0.175351435 |
| 161 | 6 | 0.062022042 | 0.70039526 | 16.67 | −0.174771304 | −0.174771304 |
| 162 | 4 | 0.999928673 | 0.99999793 | 2.02 | −0.174094119 | −0.174094119 |
| 163 | 6 | 0.340695433 | 0.99999793 | 10 | −0.172705626 | −0.172705626 |
| 164 | 16 | 0.007797893 | 0.171924974 | 15.38 | −0.171537182 | −0.171537182 |
| 165 | 4 | 0.711822793 | 0.99999793 | 6.67 | −0.17111407 | −0.17111407 |
| 166 | 4 | 0.501622356 | 0.99999793 | 8.7 | −0.170682414 | −0.170682414 |
| 167 | 8 | 0.957766442 | 0.99999793 | 4.82 | −0.170673324 | −0.170673324 |

TABLE 1.d2-continued

| | Probe_Count_Sig | HyperG_Stats | FDR_HyperG | Percent_Sig | logFC | AveExpr |
|---|---|---|---|---|---|---|
| 168 | 10 | 0.978491243 | 0.99999793 | 4.67 | −0.170660074 | −0.170660074 |
| 169 | 4 | 0.659150649 | 0.99999793 | 7.14 | −0.169924144 | −0.169924144 |
| 170 | 8 | 0.325435728 | 0.99999793 | 9.76 | −0.169491925 | −0.169491925 |
| 171 | 14 | 9.03E−05 | 0.005970563 | 25 | −0.169304269 | −0.169304269 |
| 172 | 4 | 0.412035429 | 0.99999793 | 9.76 | −0.168954906 | −0.168954906 |
| 173 | 8 | 0.073465475 | 0.710624303 | 14.29 | −0.166543413 | −0.166543413 |
| 174 | 6 | 0.112492545 | 0.789152247 | 14.29 | −0.165440732 | −0.165440732 |
| 175 | 12 | 0.979779286 | 0.99999793 | 4.84 | −0.165036217 | −0.165036217 |
| 176 | 8 | 0.016095432 | 0.256971894 | 19.05 | −0.165001138 | −0.165001138 |
| 177 | 4 | 0.659150649 | 0.99999793 | 7.14 | −0.16436617 | −0.16436617 |
| 178 | 6 | 0.229017635 | 0.99999793 | 11.54 | −0.163709607 | −0.163709607 |
| 179 | 6 | 0.112492545 | 0.789152247 | 14.29 | −0.163562981 | −0.163562981 |
| 180 | 6 | 0.203083688 | 0.988148592 | 12 | −0.162924558 | −0.162924558 |
| 181 | 4 | 0.466402982 | 0.99999793 | 9.09 | −0.162260458 | −0.162260458 |
| 182 | 9 | 0.85591599 | 0.99999793 | 5.96 | −0.161358241 | −0.161358241 |
| 183 | 12 | 0.979779286 | 0.99999793 | 4.84 | −0.161243979 | −0.161243979 |
| 184 | 4 | 0.779227696 | 0.99999793 | 6.06 | −0.160877914 | −0.160877914 |
| 185 | 2 | 0.700318757 | 0.99999793 | 6.67 | −0.160722895 | −0.160722895 |
| 186 | 16 | 0.007797893 | 0.171924974 | 15.38 | −0.160584806 | −0.160584806 |
| 187 | 2 | 0.925958703 | 0.99999793 | 3.85 | −0.15962933 | −0.15962933 |
| 188 | 2 | 0.983929844 | 0.99999793 | 2.7 | −0.159277184 | −0.159277184 |
| 189 | 14 | 9.03E−05 | 0.005970563 | 25 | −0.159211463 | −0.159211463 |
| 190 | 12 | 0.513477047 | 0.99999793 | 8.11 | −0.158345461 | −0.158345461 |
| 191 | 2 | 0.791365183 | 0.99999793 | 5.56 | −0.158073637 | −0.158073637 |
| 192 | 6 | 0.283634013 | 0.99999793 | 10.71 | −0.158042348 | −0.158042348 |
| 193 | 8 | 0.497039718 | 0.99999793 | 8.33 | −0.157293527 | −0.157293527 |
| 194 | 6 | 0.037675475 | 0.528598335 | 18.75 | −0.156852321 | −0.156852321 |
| 195 | 8 | 0.012066038 | 0.223463015 | 20 | −0.156295949 | −0.156295949 |
| 196 | 8 | 0.18964104 | 0.954389149 | 11.43 | −0.155897691 | −0.155897691 |
| 197 | 8 | 0.100733588 | 0.781478358 | 13.33 | −0.155472557 | −0.155472557 |
| 198 | 6 | 0.369692981 | 0.99999793 | 9.68 | −0.154642066 | −0.154642066 |
| 199 | 12 | 0.474481533 | 0.99999793 | 8.33 | −0.154283407 | −0.154283407 |

TABLE 1.d3

| | t | P.Value | adj. P.Val | B | FC | FC_1 |
|---|---|---|---|---|---|---|
| 140 | −9.04469975 | 0.00000333000 | 0.000153670 | 4.954405786 | 0.879660716 | −1.13680193 |
| 141 | −5.863852649 | 0.00014402900 | 0.001584971 | 1.05105187 | 0.879703401 | −1.13674677 |
| 142 | −3.956476668 | 0.00257667000 | 0.011877700 | −1.941508536 | 0.879930168 | −1.136453819 |
| 143 | −7.539548325 | 0.00001720000 | 0.000403646 | 3.263611548 | 0.880413629 | −1.135829759 |
| 144 | −7.561434137 | 0.00001670000 | 0.000397765 | 3.289725067 | 0.882329773 | −1.133363092 |
| 145 | −8.22189382 | 0.00000793000 | 0.000252813 | 4.061431872 | 0.882592444 | −1.133025789 |
| 146 | −8.471609217 | 0.00000605000 | 0.000215806 | 4.34015114 | 0.882595726 | −1.133021576 |
| 147 | −8.796652754 | 0.00000430000 | 0.000176706 | 4.692775469 | 0.882916793 | −1.132609559 |
| 148 | −4.998863428 | 0.00049987800 | 0.003693568 | −0.24446078 | 0.883295225 | −1.132124314 |
| 149 | −7.696109127 | 0.00001430000 | 0.000359185 | 3.451288223 | 0.883798951 | −1.131479053 |
| 150 | −7.086728608 | 0.00002950000 | 0.000560642 | 2.702258066 | 0.88386803 | −1.131390622 |
| 151 | −9.75949409 | 0.00000165000 | 0.000106067 | 5.674204544 | 0.884548664 | −1.13052005 |
| 152 | −5.770771019 | 0.00016383700 | 0.001725769 | 0.916804544 | 0.884827288 | −1.13016406 |
| 153 | −6.7528275 | 0.00004460000 | 0.000732249 | 2.271638916 | 0.884980679 | −1.129968172 |
| 154 | −8.001384234 | 0.00001010000 | 0.000288637 | 3.809465717 | 0.885137383 | −1.129768123 |
| 155 | −7.054965999 | 0.00003060000 | 0.000572312 | 2.661925201 | 0.885170738 | −1.129725551 |
| 156 | −8.062849839 | 0.00000946000 | 0.000276188 | 3.880260462 | 0.885215069 | −1.129667903 |
| 157 | −8.22019318 | 0.00000795000 | 0.000252897 | 4.059509833 | 0.885408616 | −1.129422034 |
| 158 | −7.944299089 | 0.00001080000 | 0.000298984 | 3.743323414 | 0.885454973 | −1.129362905 |
| 159 | −7.936893754 | 0.00001090000 | 0.000300885 | 3.734715272 | 0.885546684 | −1.129245942 |
| 160 | −7.320634642 | 0.00002220000 | 0.000473074 | 2.995279965 | 0.885551776 | −1.12923945 |
| 161 | −4.501723442 | 0.00107250100 | 0.006331857 | −1.036726499 | 0.885907942 | −1.128785456 |
| 162 | −5.359979733 | 0.00029353100 | 0.002553248 | 0.309452325 | 0.886323875 | −1.128255741 |
| 163 | −7.348002424 | 0.00002150000 | 0.000464745 | 3.029109603 | 0.887177311 | −1.127170396 |
| 164 | −4.993189956 | 0.00050415200 | 0.003717896 | −0.253310928 | 0.88789513 | −1.126257866 |
| 165 | −3.519797341 | 0.00533871900 | 0.020318036 | −2.68729466 | 0.888156569 | −1.125927607 |
| 166 | −7.967884713 | 0.00001050000 | 0.000294299 | 3.7706972 | 0.888422346 | −1.125590778 |
| 167 | −6.912341375 | 0.00003650000 | 0.000639759 | 2.47919335 | 0.888427944 | −1.125583686 |
| 168 | −4.143646897 | 0.00189873700 | 0.009528203 | −1.627112625 | 0.888436104 | −1.125573349 |
| 169 | −7.327193408 | 0.00002210000 | 0.000471182 | 3.003395936 | 0.888889417 | −1.124999331 |
| 170 | −6.725576504 | 0.00004620000 | 0.000751090 | 2.235840762 | 0.889155761 | −1.124662342 |
| 171 | −9.223976152 | 0.00000278000 | 0.000140257 | 5.139609489 | 0.889271424 | −1.124516063 |
| 172 | −5.086671011 | 0.00043842400 | 0.003367205 | −0.108066516 | 0.889486795 | −1.124243783 |
| 173 | −6.557217188 | 0.00005720000 | 0.000856101 | 2.012450668 | 0.890974834 | −1.122366157 |
| 174 | −5.606610708 | 0.00020624200 | 0.002008025 | 0.677010146 | 0.891656084 | −1.121508638 |
| 175 | −6.152539392 | 0.00009730000 | 0.001222803 | 1.459547106 | 0.891906129 | −1.121194224 |
| 176 | −9.029584345 | 0.00000338000 | 0.000154851 | 4.938642975 | 0.891927816 | −1.121166963 |
| 177 | −7.773176867 | 0.00001310000 | 0.000338569 | 3.542755797 | 0.892320463 | −1.120673616 |

TABLE 1.d3-continued

|  | t | P.Value | adj. P.Val | B | FC | FC_1 |
|---|---|---|---|---|---|---|
| 178 | −3.931754114 | 0.00268358500 | 0.012258029 | −1.983302218 | 0.892726646 | −1.120163719 |
| 179 | −6.094548905 | 0.00010519100 | 0.001290304 | 1.378439476 | 0.892817381 | −1.120049879 |
| 180 | −4.377302648 | 0.00130537400 | 0.007284682 | −1.240107008 | 0.89321256 | −1.119554343 |
| 181 | −7.4412892 | 0.00001930000 | 0.000434267 | 3.143716166 | 0.893623817 | −1.119039109 |
| 182 | −2.947668664 | 0.01423557000 | 0.042361163 | −3.677544832 | 0.894182836 | −1.118339516 |
| 183 | −7.690183808 | 0.00001440000 | 0.000361067 | 3.444226195 | 0.894253659 | −1.118250946 |
| 184 | −4.458017464 | 0.00114886400 | 0.006651262 | −1.10794705 | 0.894480593 | −1.11796724 |
| 185 | −7.035502311 | 0.00003140000 | 0.000581633 | 2.637144966 | 0.894576711 | −1.117847121 |
| 186 | −5.690028109 | 0.00018339000 | 0.001862995 | 0.799345244 | 0.89466234 | −1.11774013 |
| 187 | −6.204852631 | 0.00009070000 | 0.001165246 | 1.532307434 | 0.895255058 | −1.117000111 |
| 188 | −5.699454074 | 0.00018098300 | 0.001844393 | 0.813105827 | 0.895473607 | −1.116727498 |
| 189 | −8.406010145 | 0.00000650000 | 0.000223939 | 4.267601817 | 0.8955144 | −1.116676627 |
| 190 | −4.255312553 | 0.00158598400 | 0.008382570 | −1.441362142 | 0.896052109 | −1.116006524 |
| 191 | −5.410812733 | 0.00027274400 | 0.002422901 | 0.3859262 | 0.896220954 | −1.115796272 |
| 192 | −5.030639438 | 0.00047664400 | 0.003574555 | −0.194976515 | 0.896240392 | −1.115772073 |
| 193 | −7.050761716 | 0.00003080000 | 0.000573918 | 2.656576685 | 0.8967057 | −1.11519309 |
| 194 | −6.511242084 | 0.00006070000 | 0.000890100 | 1.950776985 | 0.896979973 | −1.114852093 |
| 195 | −6.247769863 | 0.00008570000 | 0.001121376 | 1.591712007 | 0.897325957 | −1.114422236 |
| 196 | −6.419907226 | 0.00006840000 | 0.000962212 | 1.827393464 | 0.8975737 | −1.11411464 |
| 197 | −8.514647533 | 0.00000578000 | 0.000210469 | 4.387493728 | 0.897838236 | −1.113786381 |
| 198 | −5.287869683 | 0.00032596900 | 0.002741288 | 0.20033182 | 0.898355228 | −1.113145412 |
| 199 | −3.020061123 | 0.01256025500 | 0.038539753 | −3.552262166 | 0.89857859 | −1.112868714 |

TABLE 1.d4

| | LS | Loop detected | Probe sequence 60 mer |
|---|---|---|---|
| 140 | −1 | PD-L1 responder | ATTTGACAACGCTGGCACGGAGGCAAGATCGACCTCCCTGTCCCTCCTGGGCCTCTCCGG (SEQ ID NO: 141) |
| 141 | −1 | PD-L1 responder | TCTTCTCTCCCTCACTCAGTATCCTCACTCGATGCGCGCCCGCCGGGGCCCGGTCGGAGC (SEQ ID NO: 142) |
| 142 | −1 | PD-L1 responder | GAGGATTAATAAAACCCAAACTGTATTTCGAGAAAATAGTGTTTTGCTATTTAGATAAG (SEQ ID NO: 143) |
| 143 | −1 | PD-L1 responder | GCGCCCTATTTCCACCTTGTGCCTTCTGTCGAGACATCTAAGAAGGTCCAGCCAGATGTT (SEQ ID NO: 144) |
| 144 | −1 | PD-L1 responder | TACAGACTTTTTTTCTCTTCTCAGAAAATCGATGTTTGGGGCGGAGGGCTTTGATGAGA (SEQ ID NO: 145) |
| 145 | −1 | PD-L1 responder | GTGACAATTAAGAGTGTGACATTGCTTCTCGAGGACTCACTGGGCCTGCAGGGGGCAGC (SEQ ID NO: 146) |
| 146 | −1 | PD-L1 responder | GTGGCAGGAGAAAAACGCGGCCCCACCCTCGAAAATACTAGAATTATGCCGCACAGTCAG (SEQ ID NO: 147) |
| 147 | −1 | PD-L1 responder | ACATCGCTACCAGGCCGATGTGCTGATATCGAGGTCCCCAACCCCCTGCCGCTCATCGTG (SEQ ID NO: 148) |
| 148 | −1 | PD-L1 responder | AAGTCTTTTGTTTGGTTATTGTGCTGTATCGAATCAAAGCTGTGTCACAAACTATGTAAC (SEQ ID NO: 149) |
| 149 | −1 | PD-L1 responder | GCGGGGCTTCCCTCAACTTCAGGGAGGTCGAGGCGCGGCGCGCAGGCCGCCATCGCCAC (SEQ ID NO: 150) |
| 150 | −1 | PD-L1 responder | CGTAGAACTAAGATGTATTCAAAGTCAGTCGAAATCACCTGTCCCGGCCTCTTTCCAAAC (SEQ ID NO: 151) |
| 151 | −1 | PD-L1 responder | GACCTAAGGATTAAGAAGATTAATGGAGTCGAGCATCCTCTACCTCTATCTCCAACCCCT (SEQ ID NO: 152) |
| 152 | −1 | PD-L1 responder | CTGGCGTTCCAGCCCTCGCACCTTGGCCTCGAACTTTACAGAGGGATCTAGAATGAGTGA (SEQ ID NO: 153) |
| 153 | −1 | PD-L1 responder | ACATGACCGTGATACCTCTGTCACTCTGTCGATGGGACCTGAACCGGGGCCGCACAAGC (SEQ ID NO: 154) |
| 154 | −1 | PD-L1 responder | TGGAAGCAGCTATACAGCTGTGACCACATCGACGCCCCTGTCACGGGCCCTGTTATTCAA (SEQ ID NO: 155) |
| 155 | −1 | PD-L1 responder | AGGCGACACTCTTGTCCCCGCCATCTTTTCGAAGGCCCCCGTCCTCCTGCGCCATGGAGA (SEQ ID NO: 156) |

TABLE 1.d4-continued

| | LS | Loop detected | Probe sequence 60 mer |
|---|---|---|---|
| 156 | -1 | PD-L1 responder | AATAAACATCTTTTTGCTCATACATTATTCGAATCCCCAGCCCTTCCCTCTGCCCACCCT (SEQ ID NO: 157) |
| 157 | -1 | PD-L1 responder | GGACCTTGTCATCCTGCCCCTTCTTGGCTCGAGCCCTGCCTGGCCAGCACACACTGCATC (SEQ ID NO: 158) |
| 158 | -1 | PD-L1 responder | CATCATAGCAACCCATTGTAACTAGACTTCGAATAGATACTTCAGGAAAGAAATGTATAT (SEQ ID NO: 159) |
| 159 | -1 | PD-L1 responder | ATCCCAACAAAAGAGAAGAACTTCTCCCTCGATGTTTGGGGGCGGAGGGCTTTGATGAGA (SEQ ID NO: 160) |
| 160 | -1 | PD-L1 responder | GCAGCCAGCCCGGTGGGGGTGGGGGGGTCGACGCTCGCCTCCGCTCACAGCCTCAGCAT (SEQ ID NO: 161) |
| 161 | -1 | PD-L1 responder | ACATGAGATGTCCTTCAAGTGAAACTGTTCGACCATGCCCGGGCAGGTGGCTGAGACCTC (SEQ ID NO: 162) |
| 162 | -1 | PD-L1 responder | TAAACCATAGTTAATTTTATGTAAATATTCGAATCTTTTCAGGATGGTAGCATCTTTAAA (SEQ ID NO: 163) |
| 163 | -1 | PD-L1 responder | ACATGACCGTGATACCTCTGTCACTCTGTCGATGGGGACCTGAACCGGGGCCGCACAAGC (SEQ ID NO: 164) |
| 164 | -1 | PD-L1 responder | TGACTGTATTTACAACATGTCTAGATTTTCGAGTGTAAAAGGGCTTTTACTGGTGCACAC (SEQ ID NO: 165) |
| 165 | -1 | PD-L1 responder | TAGGCCTGGGGGCCGAAAGGAAGAAGCTTCGACTGAGGCGGGTCCCAGCCCCTCCAGGGA (SEQ ID NO: 166) |
| 166 | -1 | PD-L1 responder | CTGACCCCTCCAGGGGAGGCCCGGCCCCTCGAGAACTCAGGGCCAGCCTTCCCAGCTTGG (SEQ ID NO: 167) |
| 167 | -1 | PD-L1 responder | GTAGTTCACTCTGTCCCTTTTCCTATGATCGATTTTGCTCCCCCCACCTTACCCCCAGAG (SEQ ID NO: 168) |
| 168 | -1 | PD-L1 responder | TGTTTTTTATTGTTTGATGTCCAATGTATCGATAAACAAATTATACAACAAAAGTCTAAG (SEQ ID NO: 169) |
| 169 | -1 | PD-L1 responder | AGGCGACACTCTTGTCCCCGCCATCTTTTCGAAGGCCCCCGTCCTCCTGCGCCATGGAGA (SEQ ID NO: 170) |
| 170 | -1 | PD-L1 responder | TCCATTGTCTTATTCCAGTCTAGGCTTGTCGAACTGGCGGCAACCGCTGCAGCGCCTGCT (SEQ ID NO: 171) |
| 171 | -1 | PD-L1 responder | TTAATGCTGATACAATTCTATTGGATAATCGACGTGCCTTGGGGCCTCCCCTTTCCCTAT (SEQ ID NO: 172) |
| 172 | -1 | PD-L1 responder | TTTTTTTCCTCTCTTATCTTGATGCCTCTCGAGCTTCCTGGCCACTTTGTTTACCTACTC (SEQ ID NO: 173) |
| 173 | -1 | PD-L1 responder | CGTGGATCCAGACTGGGAGCCCCCAGCCTCGAACCACGCCAGGCTTCCAGGCGTCAGTGC (SEQ ID NO: 174) |
| 174 | -1 | PD-L1 responder | ATAAAATGGGGAGGCCTTCCAGAAGCTCTCGACCTCCAGGTCCCCCGCCACTTCCACGGC (SEQ ID NO: 175) |
| 175 | -1 | PD-L1 responder | AAGTCTTTTGTTTGGTTATTGTGCTGTATCGAAGTCTTGACCTCAGGTGATCCACCCACC (SEQ ID NO: 176) |
| 176 | -1 | PD-L1 responder | GTGTCTCGGCCCCTGGGGCCCCACCCTTCGAGTGCATCCTGCAGCTGTTTGTCCAGAAG (SEQ ID NO: 177) |
| 177 | -1 | PD-L1 responder | CATCATCACAGTCTACGGCTGTTTCCTCTCGAAGGCCCCCGTCCTCCTGCGCCATGGAGA (SEQ ID NO: 178) |
| 178 | -1 | PD-L1 responder | CACTAATCTTTACTCTTTTTCCACTTATTCGAAGTTTCCAGAAAAGTCCTGAAGTTTTAA (SEQ ID NO: 179) |
| 179 | -1 | PD-L1 responder | CCGCCTCCGTCTGCGCCTGGGCAGGCCTCGACCTGCCTGTCAATATTTGCAATCACTGC (SEQ ID NO: 180) |
| 180 | -1 | PD-L1 responder | ACGCCCGCCTCCATGAGATTCAGAGCCCTCGACTCCTTTCCCAGACACATTCAGCACGTG (SEQ ID NO: 181) |

TABLE 1.d4-continued

| | LS | Loop detected | Probe sequence 60 mer |
|---|---|---|---|
| 181 | -1 | PD-L1 responder | TCCCACCCACTCTTAATCAACATTCCATTCGATTTAATCCTACATGCTCCTTTCTTATGT (SEQ ID NO: 182) |
| 182 | -1 | PD-L1 responder | ATTTTGACATCTGCATTTTACAGCAGCCTCGATGCGAGCTCGTGGTGGGTGCTCAAGACT (SEQ ID NO: 183) |
| 183 | -1 | PD-L1 responder | AAGTCTTTTGTTTGGTTATTGTGCTGTATCGATCCAGCTTTTTGACTCTAAAATGAGCTT (SEQ ID NO: 184) |
| 184 | -1 | PD-L1 responder | GGCAAATGCTACAAATCAGAGTTGTTTTTCGATCACACTGGGAGCTGCAGACCGGAGCTG (SEQ ID NO: 185) |
| 185 | -1 | PD-L1 responder | GCAGCCAGCCCGGTGGGGGTGGGGGGGTCGACGCTCGCCTCCGCTCACAGCCTCAGCAT (SEQ ID NO: 186) |
| 186 | -1 | PD-L1 responder | GTGTGCACCAGTAAAAGCCCTTTTACACTCGACCTGCTGATCCTTGGATCCTGAATCTGT (SEQ ID NO: 187) |
| 187 | -1 | PD-L1 responder | CGGGTGCCTCCCCCCCATTCGCCCTGCTCGAGGGAGGGAAATGATTGGATTACGGGGGT (SEQ ID NO: 188) |
| 188 | -1 | PD-L1 responder | CTCCATCTCCCTGCCCTCTGGATCCCCCTCGATTCTACAGTGGTTTTAACAGCAGGCCCC (SEQ ID NO: 189) |
| 189 | -1 | PD-L1 responder | GTGTGGGCCCCCCTGCTACCGCTGCGTATCGAGCACCTCTTCAGGGGAGGATTACTGCAA (SEQ ID NO: 190) |
| 190 | -1 | PD-L1 responder | CGTTGCAAATTGTACATCTTCTGCTATTTCGAGACCTCATATAACTCGGTGATTGACTGC (SEQ ID NO: 191) |
| 191 | -1 | PD-L1 responder | TAACAAGGAGTGGAGTATTCCTGGGATATCGACCCCACCCCCTAGATTAAGACATTCCTG (SEQ ID NO: 192) |
| 192 | -1 | PD-L1 responder | AACAAGGCAGGTAGTGTTCCTGCCCTCATCGATGTGGCAGCGGGCCCGGACGGGTCGGTG (SEQ ID NO: 193) |
| 193 | -1 | PD-L1 responder | TCTTCTCTCCCTCACTCAGTATCCTCACTCGATGCGCGCCCGCCGGGGCCCGGTCGGAGC (SEQ ID NO: 194) |
| 194 | -1 | PD-L1 responder | GTGACAATTAAGAGTGTGACATTGCTTCTCGAGGACTCACTGGGCCTGCAGGGGGCAGC (SEQ ID NO: 195) |
| 195 | -1 | PD-L1 responder | AGGTGGAGATCAGAAGACCCCCACGCCCTCGAGTCACAGCTGTAGTGGGGTGGGGGTGA (SEQ ID NO: 196) |
| 196 | -1 | PD-L1 responder | GCACTACCCCGGCCTGCCGGAGCCCCAGTCGAGTTGGTTTCTGGGTCCGCACCCCCTCCC (SEQ ID NO: 197) |
| 197 | -1 | PD-L1 responder | GAATGTTTACCTATTATAAAAATGAGGATCGAGCACAGCGCCGGCTGGGGTACCTGGCAC (SEQ ID NO: 198) |
| 198 | -1 | PD-L1 responder | GCGGGGCTTCCCTCAACTTCAGGGAGGTCGAGGCGCGGCGCGCAGGCCGCCATCGCCAC (SEQ ID NO: 199) |
| 199 | -1 | PD-L1 responder | TCAGATAAGTAACTTCCTGATAATTAACTCGAAAAAACATTAATTTCTTCAGGTGTAAAG (SEQ ID NO: 200) |

TABLE 1.d5

| | Probe Location | | | | 4 kb Sequence Location | |
|---|---|---|---|---|---|---|
| | Chr | Start1 | End1 | Start2 | End2 | Chr | Start1 |
| 140 | 1 | 116708743 | 116708772 | 116735760 | 116735789 | 1 | 116704773 |
| 141 | 11 | 119671083 | 119671112 | 119729290 | 119729319 | 11 | 119671083 |
| 142 | 4 | 86131385 | 86131414 | 86343454 | 86343483 | 4 | 86127415 |
| 143 | 20 | 1891491 | 1891520 | 1924635 | 1924664 | 20 | 1891491 |
| 144 | 5 | 157249290 | 157249319 | 157266727 | 157266756 | 5 | 157249290 |
| 145 | 11 | 2113134 | 2113163 | 2180330 | 2180359 | 11 | 2113134 |
| 146 | 15 | 67098634 | 67098663 | 67199586 | 67199615 | 15 | 67098634 |
| 147 | 16 | 31278028 | 31278057 | 31331190 | 31331219 | 16 | 31278028 |
| 148 | 8 | 140725050 | 140725079 | 140877457 | 140877486 | 8 | 140721080 |
| 149 | 5 | 140647396 | 140647425 | 140672697 | 140672726 | 5 | 140643426 |

TABLE 1.d5-continued

| | | Probe Location | | | | 4 kb Sequence Location | |
|---|---|---|---|---|---|---|---|
| | Chr | Start1 | End1 | Start2 | End2 | Chr | Start1 |
| 150 | 15 | 98737003 | 98737032 | 98790083 | 98790112 | 15 | 98733033 |
| 151 | 5 | 67182229 | 67182258 | 67233991 | 67234020 | 5 | 67178259 |
| 152 | 11 | 60922071 | 60922100 | 60977086 | 60977115 | 11 | 60922071 |
| 153 | 16 | 2500834 | 2500863 | 2548487 | 2548516 | 16 | 2500834 |
| 154 | 22 | 17735513 | 17735542 | 17806908 | 17806937 | 22 | 17731543 |
| 155 | 16 | 29613906 | 29613935 | 29632050 | 29632079 | 16 | 29613906 |
| 156 | 11 | 124746041 | 124746070 | 124787707 | 124787736 | 11 | 124746041 |
| 157 | 11 | 119677784 | 119677813 | 119705118 | 119705147 | 11 | 119673814 |
| 158 | 3 | 122014666 | 122014695 | 122100771 | 122100800 | 3 | 122014666 |
| 159 | 5 | 157181017 | 157181046 | 157266727 | 157266756 | 5 | 157177047 |
| 160 | 19 | 49654784 | 49654813 | 49691434 | 49691463 | 19 | 49654784 |
| 161 | 7 | 155794442 | 155794471 | 155842904 | 155842933 | 7 | 155794442 |
| 162 | 6 | 151873860 | 151873889 | 151997847 | 151997876 | 6 | 151869890 |
| 163 | 16 | 2500834 | 2500863 | 2548487 | 2548516 | 16 | 2500834 |
| 164 | 15 | 98784942 | 98784971 | 98893486 | 98893515 | 15 | 98780972 |
| 165 | 14 | 104760240 | 104760269 | 104843290 | 104843319 | 14 | 104760240 |
| 166 | 12 | 6934236 | 6934265 | 6965163 | 6965192 | 12 | 6934236 |
| 167 | 1 | 56943860 | 56943889 | 56962731 | 56962760 | 1 | 56939890 |
| 168 | 1 | 198595740 | 198595769 | 198749225 | 198749254 | 1 | 198591770 |
| 169 | 16 | 29613906 | 29613935 | 29632050 | 29632079 | 16 | 29613906 |
| 170 | 20 | 2816711 | 2816740 | 2967982 | 2968011 | 20 | 2816711 |
| 171 | 11 | 60983696 | 60983725 | 60996253 | 60996282 | 11 | 60979726 |
| 172 | 2 | 201267208 | 201267237 | 201291005 | 201291034 | 2 | 201263238 |
| 173 | 19 | 47240983 | 47241012 | 47256214 | 47256243 | 19 | 47237013 |
| 174 | 9 | 120893289 | 120893318 | 120913548 | 120913577 | 9 | 120889319 |
| 175 | 8 | 140725050 | 140725079 | 140783929 | 140783958 | 8 | 140721080 |
| 176 | 5 | 132477881 | 132477910 | 132536452 | 132536481 | 5 | 132473911 |
| 177 | 16 | 29613906 | 29613935 | 29687198 | 29687227 | 16 | 29613906 |
| 178 | 9 | 125608175 | 125608204 | 125635069 | 125635098 | 9 | 125608175 |
| 179 | 12 | 6773968 | 6773997 | 6796697 | 6796726 | 12 | 6769998 |
| 180 | 11 | 44564825 | 44564854 | 44629575 | 44629604 | 11 | 44560855 |
| 181 | 5 | 149378174 | 149378203 | 149421075 | 149421104 | 5 | 149378174 |
| 182 | 1 | 56962698 | 56962727 | 56998048 | 56998077 | 1 | 56958728 |
| 183 | 8 | 140725050 | 140725079 | 140771375 | 140771404 | 8 | 140721080 |
| 184 | 10 | 96186300 | 96186329 | 96286444 | 96286473 | 10 | 96186300 |
| 185 | 19 | 49654784 | 49654813 | 49691434 | 49691463 | 19 | 49654784 |
| 186 | 15 | 98893486 | 98893515 | 98957434 | 98957463 | 15 | 98893486 |
| 187 | 19 | 48955702 | 48955731 | 48973072 | 48973101 | 19 | 48955702 |
| 188 | 14 | 23324245 | 23324274 | 23359390 | 23359419 | 14 | 23324245 |
| 189 | 11 | 60933651 | 60933680 | 61017869 | 61017898 | 11 | 60929681 |
| 190 | 5 | 68213305 | 68213334 | 68277738 | 68277767 | 5 | 68209335 |
| 191 | 5 | 132053242 | 132053271 | 132074960 | 132074989 | 5 | 132049272 |
| 192 | 12 | 112418671 | 112418700 | 112482384 | 112482413 | 12 | 112418671 |
| 193 | 11 | 119671083 | 119671112 | 119729290 | 119729319 | 11 | 119671083 |
| 194 | 11 | 2113134 | 2113163 | 2180330 | 2180359 | 11 | 2113134 |
| 195 | 21 | 44243733 | 44243762 | 44267561 | 44267590 | 21 | 44243733 |
| 196 | 11 | 64269780 | 64269809 | 64296893 | 64296922 | 11 | 64265810 |
| 197 | 13 | 23627960 | 23627989 | 23678004 | 23678033 | 13 | 23627960 |
| 198 | 5 | 140647396 | 140647425 | 140672697 | 140672726 | 5 | 140643426 |
| 199 | 8 | 81018076 | 81018105 | 81077567 | 81077596 | 8 | 81014106 |

TABLE 1.d6

| | 4 kb Sequence Location | | |
|---|---|---|---|
| | End1 | Start2 | End2 |
| 140 | 116708772 | 116735760 | 116739759 |
| 141 | 119675082 | 119729290 | 119733289 |
| 142 | 86131414 | 86339484 | 86343483 |
| 143 | 1895490 | 1924635 | 1928634 |
| 144 | 157253289 | 157266727 | 157270726 |
| 145 | 2117133 | 2180330 | 2184329 |
| 146 | 67102633 | 67199586 | 67203585 |
| 147 | 31282027 | 31331190 | 31335189 |
| 148 | 140725079 | 140877457 | 140881456 |
| 149 | 140647425 | 140668727 | 140672726 |
| 150 | 98737032 | 98786113 | 98790112 |
| 151 | 67182258 | 67233991 | 67237990 |
| 152 | 60926070 | 60977086 | 60981085 |
| 153 | 2504833 | 2544517 | 2548516 |
| 154 | 17735542 | 17802938 | 17806937 |
| 155 | 29617905 | 29628080 | 29632079 |
| 156 | 124750040 | 124783737 | 124787736 |
| 157 | 119677813 | 119701148 | 119705147 |
| 158 | 122018665 | 122096801 | 122100800 |
| 159 | 157181046 | 157266727 | 157270726 |
| 160 | 49658783 | 49691434 | 49695433 |
| 161 | 155798441 | 155838934 | 155842933 |
| 162 | 151873889 | 151993877 | 151997876 |
| 163 | 2504833 | 2544517 | 2548516 |
| 164 | 98784971 | 98893486 | 98897485 |
| 165 | 104764239 | 104839320 | 104843319 |
| 166 | 6938235 | 6965163 | 6969162 |
| 167 | 56943889 | 56962731 | 56966730 |
| 168 | 198595769 | 198745255 | 198749254 |
| 169 | 29617905 | 29628080 | 29632079 |
| 170 | 2820710 | 2964012 | 2968011 |
| 171 | 60983725 | 60996253 | 61000252 |

TABLE 1.d6-continued 4 kb Sequence Location

| | End1 | Start2 | End2 |
|---|---|---|---|
| 172 | 201267237 | 201287035 | 201291034 |
| 173 | 47241012 | 47256214 | 47260213 |
| 174 | 120893318 | 120913548 | 120917547 |
| 175 | 140725079 | 140779959 | 140783958 |
| 176 | 132477910 | 132536452 | 132540451 |
| 177 | 29617905 | 29683228 | 29687227 |
| 178 | 125612174 | 125631099 | 125635098 |
| 179 | 6773997 | 6796697 | 6800696 |
| 180 | 44564854 | 44625605 | 44629604 |
| 181 | 149382173 | 149421075 | 149425074 |
| 182 | 56962727 | 56994078 | 56998077 |
| 183 | 140725079 | 140767405 | 140771404 |
| 184 | 96190299 | 96282474 | 96286473 |
| 185 | 49658783 | 49691434 | 49695433 |
| 186 | 98897485 | 98957434 | 98961433 |

TABLE 1.d6-continued 4 kb Sequence Location

| | End1 | Start2 | End2 |
|---|---|---|---|
| 187 | 48959701 | 48973072 | 48977071 |
| 188 | 23328244 | 23355420 | 23359419 |
| 189 | 60933680 | 61017869 | 61021868 |
| 190 | 68213334 | 68273768 | 68277767 |
| 191 | 132053271 | 132070990 | 132074989 |
| 192 | 112422670 | 112478414 | 112482413 |
| 193 | 119675082 | 119729290 | 119733289 |
| 194 | 2117133 | 2180330 | 2184329 |
| 195 | 44247732 | 44267561 | 44271560 |
| 196 | 64269809 | 64292923 | 64296922 |
| 197 | 23631959 | 23678004 | 23682003 |
| 198 | 140647425 | 140668727 | 140672726 |
| 199 | 81018105 | 81077567 | 81081566 |

TABLE 1.e1

| | probe | GeneLocus | Probe_Count_Total |
|---|---|---|---|
| 200 | IKBKB_8_42231188_42234849_42264241_42271203_RF | IKBKB | 46 |
| 201 | SPN_16_29613904_29616227_29686079_29687229_RF | SPN | 56 |
| 202 | PTK2_8_140763162_140771406_141001274_141004301_FR | PTK2 | 248 |
| 203 | ORF263_11_78304460_78312808_78374350_78382835_RF | GAB2 | 132 |
| 204 | PVRL1_11_119711187_119714047_119729288_119738834_FR | PVRL1 | 96 |
| 205 | CD6_11_60932387_60933682_60977084_60983727_FR | CD6 | 56 |
| 206 | ORF490_16_2500832_2504754_2601193_2603749_RF | PDPK1 | 60 |
| 207 | ORF456_11_119671081_119677815_119700077_119705149_FR | PVRL1 | 96 |
| 208 | ORF712_9_120888366_120893320_120913546_120919710_RR | TRAF1 | 42 |
| 209 | ORF104_17_36075902_36084513_36095759_36100192_RF | CCL18 | 42 |
| 210 | BOK_2_241535460_241542885_241559192_241566423_RR | BOK | 44 |
| 211 | IRF1_5_132472660_132477912_132517598_132521351_FF | IRF1 | 42 |
| 212 | ORF173_4_77534161_77541495_77571558_77583817_RF | CXCL13 | 108 |
| 213 | ORF58_19_47236830_47241014_47256212_47257706_FR | BBC3 | 56 |
| 214 | ORF55_11_64267793_64269811_64288581_64290103_FR | BAD | 70 |
| 215 | PTPN11_12_112418669_112423831_112478543_112482415_RF | PTPN11 | 56 |
| 216 | CD82_11_44515603_44522167_44561823_44564856_RF | CD82 | 50 |
| 217 | ORF104_17_36023309_36028028_36075902_36084513_RF | CCL18 | 42 |
| 218 | ORF122_19_51189093_51190958_51254261_51263712_FR | CD33 | 32 |
| 219 | ORF305_15_98652565_98657862_98874707_98883774_RR | IGF1R | 104 |
| 220 | ORF104_17_36051957_36057144_36075902_36084513_RF | CCL18 | 42 |
| 221 | ITK_5_157225228_157231430_157266725_157271762_FR | ITK | 26 |
| 222 | EGF_4_109875299_109879120_110005130_110011368_FF | EGF | 48 |
| 223 | ORF293_6_32626930_32634077_32662361_32664960_RF | HLA-DQA1 | 28 |
| 224 | ORF479_8_81053410_81059648_81095100_81099880_RR | PAG1 | 144 |
| 225 | ORF130_11_60977084_60983727_60996251_60998956_FR | CD6 | 56 |
| 226 | ORF108_6_167109295_167112439_167149742_167154610_FF | CCR6 | 46 |
| 227 | ORF538_8_140715391_140725081_140891408_140893244_FF | PTK2 | 248 |
| 228 | ORF55_11_64267793_64269811_64301867_64303120_FR | BAD | 70 |
| 229 | ORF544_1_198619087_198627361_198650099_198652874_FF | PTPRC | 214 |
| 230 | PDCD1_2_241872992_241878216_241891223_241897247_RR | PDCD1 | 36 |
| 231 | SHH_7_155807951_155810124_155829183_155832221_FR | SHH | 36 |
| 232 | ORF670_9_90767553_90774633_90856872_90861170_RR | SYK | 78 |
| 233 | ORF546_19_44596239_44600261_44664293_44665588_FR | PVR | 65 |
| 234 | ORF403_9_125518474_125526994_125631239_125635100_RF | MAPKAP1 | 52 |
| 235 | ORF544_1_198591683_198595771_198768850_198775826_FF | PTPRC | 214 |
| 236 | RPTOR_17_80636056_80643737_80661868_80664436_FR | RPTOR | 86 |
| 237 | ORF168_15_74772372_74779791_74801744_74804023_RF | CSK | 48 |
| 238 | NCK2_2_105715815_105716905_105886459_105893355_FR | NCK2 | 66 |
| 239 | CD4_12_6767426_6773999_6813425_6817229_FR | CD4 | 42 |
| 240 | ORF538_8_140763162_140771406_141001274_141004301_FR | PTK2 | 248 |
| 241 | ORF250_2_215361328_215366837_215435722_215439709_FR | FN1 | 42 |
| 242 | BAD_11_64267793_64269811_64292591_64296924_FF | BAD | 70 |
| 243 | ORF398_17_45280830_45283423_45297938_45303012_RR | MAP3K14 | 44 |
| 244 | RPTOR_17_80636056_80643737_80793263_80796075_FF | RPTOR | 86 |
| 245 | ORF163_12_93752886_93759416_93791200_93797905_FF | CRADD | 231 |
| 246 | ORF95_2_201224034_201225522_201286114_201291036_FF | CASP8 | 41 |
| 247 | ORF215_12_47728716_47732358_47745284_47751054_FR | ENDOU | 26 |
| 248 | ORF480_11_77430379_77437843_77514783_77519103_RF | PAK1 | 136 |
| 249 | ORF306_11_2113132_2119465_2170498_2173159_RR | IGF2 | 32 |
| 250 | CASP9_1_15520953_15524014_15542554_15547367_FR | CASP9 | 46 |
| 251 | STAT5A_17_42251917_42254441_42312276_42316438_FR | STAT5A | 99 |
| 252 | SMAD3_15_67098632_67101498_67199584_67204251_RR | SMAD3 | 34 |
| 253 | STAT3_17_42312276_42316438_42406596_42409990_RF | STAT3 | 100 |

TABLE 1.e1-continued

| | probe | GeneLocus | Probe_Count_Total |
|---|---|---|---|
| 254 | PIK3R2_19_18105164_18110364_18179077_18180271_FR | PIK3R2 | 116 |
| 255 | MCL1_1_150570652_150572543_150615513_150618018_RR | MCL1 | 77 |
| 256 | ORF701_13_23612221_23617919_23627958_23632852_FF | TNFRSF19 | 60 |
| 257 | ORF55_11_64267793_64269811_64317605_64318816_FR | BAD | 70 |
| 258 | ORF263_11_78204241_78207061_78304460_78312808_RR | GAB2 | 132 |
| 259 | BBC3_19_47214451_47217416_47236830_47241014_RF | BBC3 | 56 |

TABLE 1.e2

| | Probe_Count_Sig | HyperG_Stats | FDR_HyperG | Percent_Sig | logFC | AveExpr |
|---|---|---|---|---|---|---|
| 200 | 12 | 0.00018363 | 0.010627608 | 26.09 | −0.153734995 | −0.153734995 |
| 201 | 4 | 0.659150649 | 0.99999793 | 7.14 | −0.153139995 | −0.153139995 |
| 202 | 12 | 0.979779286 | 0.99999793 | 4.84 | −0.152326374 | −0.152326374 |
| 203 | 4 | 0.994374946 | 0.99999793 | 3.03 | −0.152150489 | −0.152150489 |
| 204 | 8 | 0.497039718 | 0.99999793 | 8.33 | −0.15064075 | −0.15064075 |
| 205 | 14 | 9.03E−05 | 0.005970563 | 25 | −0.149724624 | −0.149724624 |
| 206 | 6 | 0.340695433 | 0.99999793 | 10 | −0.149355476 | −0.149355476 |
| 207 | 8 | 0.497039718 | 0.99999793 | 8.33 | −0.149050171 | −0.149050171 |
| 208 | 6 | 0.112492545 | 0.789152247 | 14.29 | −0.148665785 | −0.148665785 |
| 209 | 8 | 0.016095432 | 0.256971894 | 19.05 | −0.147845095 | −0.147845095 |
| 210 | 10 | 0.001969408 | 0.075986326 | 22.73 | −0.147733184 | −0.147733184 |
| 211 | 8 | 0.016095432 | 0.256971894 | 19.05 | −0.147678268 | −0.147678268 |
| 212 | 14 | 0.046569042 | 0.598929617 | 12.96 | −0.147196733 | −0.147196733 |
| 213 | 8 | 0.073465475 | 0.710624303 | 14.29 | −0.147180745 | −0.147180745 |
| 214 | 8 | 0.18964104 | 0.954389149 | 11.43 | −0.146341453 | −0.146341453 |
| 215 | 6 | 0.283634013 | 0.99999793 | 10.71 | −0.146237304 | −0.146237304 |
| 216 | 6 | 0.203083688 | 0.988148592 | 12 | −0.145793053 | −0.145793053 |
| 217 | 8 | 0.016095432 | 0.256971894 | 19.05 | −0.145522289 | −0.145522289 |
| 218 | 4 | 0.246707931 | 0.99999793 | 12.5 | −0.145368223 | −0.145368223 |
| 219 | 16 | 0.007797893 | 0.171924974 | 15.38 | −0.14534477 | −0.14534477 |
| 220 | 8 | 0.016095432 | 0.256971894 | 19.05 | −0.145186047 | −0.145186047 |
| 221 | 10 | 1.57E−05 | 0.002607465 | 38.46 | −0.144955613 | −0.144955613 |
| 222 | 2 | 0.903229407 | 0.99999793 | 4.17 | −0.144822276 | −0.144822276 |
| 223 | 4 | 0.178427395 | 0.954389149 | 14.29 | −0.144695604 | −0.144695604 |
| 224 | 12 | 0.474481533 | 0.99999793 | 8.33 | −0.143993345 | −0.143993345 |
| 225 | 14 | 9.03E−05 | 0.005970563 | 25 | −0.143973167 | −0.143973167 |
| 226 | 4 | 0.501622356 | 0.99999793 | 8.7 | −0.14391148 | −0.14391148 |
| 227 | 12 | 0.979779286 | 0.99999793 | 4.84 | −0.14318365 | −0.14318365 |
| 228 | 8 | 0.18964104 | 0.954389149 | 11.43 | −0.142614975 | −0.142614975 |
| 229 | 10 | 0.978491243 | 0.99999793 | 4.67 | −0.142566804 | −0.142566804 |
| 230 | 2 | 0.791365183 | 0.99999793 | 5.56 | −0.141810476 | −0.141810476 |
| 231 | 6 | 0.062022042 | 0.70039526 | 16.67 | −0.140520637 | −0.140520637 |
| 232 | 6 | 0.592795697 | 0.99999793 | 7.69 | −0.140441943 | −0.140441943 |
| 233 | 2 | 0.969655536 | 0.99999793 | 3.08 | −0.140409158 | −0.140409158 |
| 234 | 6 | 0.229017635 | 0.99999793 | 11.54 | −0.140408889 | −0.140408889 |
| 235 | 10 | 0.978491243 | 0.99999793 | 4.67 | −0.14040288 | −0.14040288 |
| 236 | 6 | 0.687444338 | 0.99999793 | 6.98 | −0.140265969 | −0.140265969 |
| 237 | 6 | 0.178303905 | 0.954389149 | 12.5 | −0.14006922 | −0.14006922 |
| 238 | 4 | 0.779227696 | 0.99999793 | 6.06 | −0.14004291 | −0.14004291 |
| 239 | 6 | 0.112492545 | 0.789152247 | 14.29 | −0.139921516 | −0.139921516 |
| 240 | 12 | 0.979779286 | 0.99999793 | 4.84 | −0.13991747 | −0.13991747 |
| 241 | 4 | 0.430324418 | 0.99999793 | 9.52 | −0.139856487 | −0.139856487 |
| 242 | 8 | 0.18964104 | 0.954389149 | 11.43 | −0.139786492 | −0.139786492 |
| 243 | 2 | 0.874387211 | 0.99999793 | 4.55 | −0.139621418 | −0.139621418 |
| 244 | 6 | 0.687444338 | 0.99999793 | 6.98 | −0.139084539 | −0.139084539 |
| 245 | 4 | 0.999992975 | 0.99999793 | 1.73 | −0.138988579 | −0.138988579 |
| 246 | 4 | 0.412035429 | 0.99999793 | 9.76 | −0.138820075 | −0.138820075 |
| 247 | 2 | 0.622797749 | 0.99999793 | 7.69 | −0.138484187 | −0.138484187 |
| 248 | 6 | 0.963851563 | 0.99999793 | 4.41 | −0.138029302 | −0.138029302 |
| 249 | 6 | 0.037675475 | 0.528598335 | 18.75 | −0.137735512 | −0.137735512 |
| 250 | 2 | 0.889742685 | 0.99999793 | 4.35 | −0.137531489 | −0.137531489 |
| 251 | 3 | 0.987493488 | 0.99999793 | 3.03 | −0.137312489 | −0.137312489 |
| 252 | 2 | 0.764125503 | 0.99999793 | 5.88 | −0.13672288 | −0.13672288 |
| 253 | 3 | 0.988282647 | 0.99999793 | 3 | −0.136436646 | −0.136436646 |
| 254 | 8 | 0.71102088 | 0.99999793 | 6.9 | −0.136435703 | −0.136435703 |
| 255 | 2 | 0.987032863 | 0.99999793 | 2.6 | −0.136350796 | −0.136350796 |
| 256 | 8 | 0.100733588 | 0.781478358 | 13.33 | −0.136324733 | −0.136324733 |
| 257 | 8 | 0.18964104 | 0.954389149 | 11.43 | −0.135663101 | −0.135663101 |
| 258 | 4 | 0.994374946 | 0.99999793 | 3.03 | −0.13560486 | −0.13560486 |
| 259 | 8 | 0.073465475 | 0.710624303 | 14.29 | −0.135407703 | −0.135407703 |

TABLE 1.e3

|     | t | P.Value | adj.P.Val | B | FC | FC_1 |
|---|---|---|---|---|---|---|
| 200 | −7.304936683 | 0.00002260000 | 0.000477724 | 2.975832882 | 0.898920232 | −1.11244576 |
| 201 | −6.667140097 | 0.00004970000 | 0.000781417 | 2.158738806 | 0.899291043 | −1.111987056 |
| 202 | −7.625429518 | 0.00001550000 | 0.000380419 | 3.366772483 | 0.899798349 | −1.111360118 |
| 203 | −4.577281937 | 0.00095286200 | 0.005814117 | −0.914179847 | 0.899908054 | −1.111224636 |
| 204 | −6.783904683 | 0.00004290000 | 0.000712857 | 2.312341711 | 0.900850275 | −1.110062379 |
| 205 | −8.117825922 | 0.00000890000 | 0.000266511 | 3.943211829 | 0.901422506 | −1.109357702 |
| 206 | −7.836679042 | 0.00001220000 | 0.000321613 | 3.617589371 | 0.901653186 | −1.109073883 |
| 207 | −6.891048765 | 0.00003750000 | 0.000650749 | 2.451683607 | 0.901844015 | −1.108839204 |
| 208 | −4.410767412 | 0.00123791600 | 0.007019121 | −1.185214291 | 0.902084331 | −1.108543809 |
| 209 | −4.251334919 | 0.00159613900 | 0.008419218 | −1.447954133 | 0.902597636 | −1.107913382 |
| 210 | −6.666436335 | 0.00004980000 | 0.000781822 | 2.15706744 | 0.902667654 | −1.107827445 |
| 211 | −6.626064358 | 0.00005240000 | 0.000805791 | 2.104266413 | 0.902702014 | −1.107785276 |
| 212 | −5.836984087 | 0.00014946900 | 0.001619866 | 1.012428105 | 0.903003364 | −1.107415586 |
| 213 | −6.340071543 | 0.00007590000 | 0.001036334 | 1.718599523 | 0.903013371 | −1.107403314 |
| 214 | −5.009008006 | 0.00049233200 | 0.003660595 | −0.228627352 | 0.903538855 | −1.106759266 |
| 215 | −4.993800795 | 0.00050369000 | 0.003715147 | −0.252357852 | 0.903604084 | −1.106679372 |
| 216 | −5.45369143 | 0.00025643200 | 0.002326445 | 0.450144339 | 0.903882374 | −1.106338644 |
| 217 | −6.211155845 | 0.00009000000 | 0.001158865 | 1.541048326 | 0.904052031 | −1.106131026 |
| 218 | −5.088815906 | 0.00043703100 | 0.003357770 | −0.104768116 | 0.90414858 | −1.106012908 |
| 219 | −5.753969471 | 0.00016771300 | 0.001754983 | 0.892439998 | 0.904163278 | −1.105994929 |
| 220 | −7.577635502 | 0.00001640000 | 0.000394253 | 3.309278087 | 0.904262758 | −1.105873255 |
| 221 | −8.636856152 | 0.00000508000 | 0.000194036 | 4.520831371 | 0.904407203 | −1.105696634 |
| 222 | −7.422808069 | 0.00001970000 | 0.000439652 | 3.121097762 | 0.904483898 | −1.105602877 |
| 223 | −3.861408042 | 0.00301392500 | 0.013289266 | −2.102539121 | 0.904570214 | −1.105497379 |
| 224 | −4.923920109 | 0.00055958200 | 0.004010305 | −0.361729876 | 0.905010637 | −1.104959388 |
| 225 | −8.04914211 | 0.00000960000 | 0.000278481 | 3.864510034 | 0.905023296 | −1.104943933 |
| 226 | −7.030078326 | 0.00003160000 | 0.000584325 | 2.630230614 | 0.905061993 | −1.104896689 |
| 227 | −8.097864547 | 0.00000910000 | 0.000269771 | 3.920394803 | 0.905518706 | −1.104339417 |
| 228 | −6.189561727 | 0.00009260000 | 0.001182316 | 1.511079783 | 0.90587571 | −1.103904199 |
| 229 | −4.553892926 | 0.00098831100 | 0.005962042 | −0.952034894 | 0.905905957 | −1.103867341 |
| 230 | −5.565131269 | 0.00021872300 | 0.002087609 | 0.615826138 | 0.906381 | −1.103288794 |
| 231 | −6.954162178 | 0.00003470000 | 0.000620295 | 2.533051066 | 0.907191711 | −1.102302841 |
| 232 | −3.707755589 | 0.00389163500 | 0.016071261 | −2.3644857 | 0.907241196 | −1.102242716 |
| 233 | −7.239219785 | 0.00002450000 | 0.000501173 | 2.894081942 | 0.907261813 | −1.102217668 |
| 234 | −5.951614421 | 0.00012769200 | 0.001464818 | 1.176490654 | 0.907261983 | −1.102217462 |
| 235 | −5.186348648 | 0.00037827900 | 0.003044422 | 0.045441754 | 0.907265761 | −1.102212872 |
| 236 | −6.28050969 | 0.00008210000 | 0.001088928 | 1.636855792 | 0.907351864 | −1.102108277 |
| 237 | −6.053728742 | 0.00011114700 | 0.001336285 | 1.321061584 | 0.907475614 | −1.101957986 |
| 238 | −6.51116257 | 0.00006070000 | 0.000890100 | 1.95067007 | 0.907492164 | −1.10193789 |
| 239 | −5.076520451 | 0.00044510100 | 0.003404610 | −0.123778106 | 0.907568527 | −1.101845173 |
| 240 | −7.555319063 | 0.00001690000 | 0.000399575 | 3.282336571 | 0.907571072 | −1.101842083 |
| 241 | −5.882100302 | 0.00014045600 | 0.001559082 | 1.077224081 | 0.907609436 | −1.101795508 |
| 242 | −5.923845607 | 0.00013263500 | 0.001500230 | 1.136919402 | 0.907653471 | −1.101742055 |
| 243 | −6.354108322 | 0.00007450000 | 0.001022368 | 1.737754331 | 0.907757331 | −1.101616 |
| 244 | −6.11708923 | 0.00010205000 | 0.001261051 | 1.410021654 | 0.908095203 | −1.101206125 |
| 245 | −7.545550183 | 0.00001700000 | 0.000402097 | 3.270523863 | 0.908155607 | −1.101132881 |
| 246 | −3.749454698 | 0.00362988500 | 0.015257888 | −2.293205904 | 0.908261684 | −1.101004278 |
| 247 | −8.619846124 | 0.00000517000 | 0.000196113 | 4.502368589 | 0.90847317 | −1.100747973 |
| 248 | −5.075029024 | 0.00044609100 | 0.003407902 | −0.126087743 | 0.908759659 | −1.100400959 |
| 249 | −4.018012402 | 0.00232944900 | 0.011026268 | −1.837743779 | 0.908944737 | −1.100176896 |
| 250 | −6.968042831 | 0.00003410000 | 0.000615455 | 2.550875988 | 0.909073287 | −1.100021323 |
| 251 | −6.125083705 | 0.00010096000 | 0.001251488 | 1.421205788 | 0.909211294 | −1.099854353 |
| 252 | −5.70594319 | 0.00017934600 | 0.001836241 | 0.822571596 | 0.909582952 | −1.09940495 |
| 253 | −4.603251935 | 0.00091507100 | 0.005639667 | −0.87223129 | 0.909763434 | −1.099186847 |
| 254 | −5.56320903 | 0.00021932100 | 0.002091340 | 0.612963373 | 0.909764028 | −1.099186129 |
| 255 | −3.79495011 | 0.00336509800 | 0.014441992 | −2.215595065 | 0.909817572 | −1.09912144 |
| 256 | −5.224608881 | 0.00035758400 | 0.002919671 | 0.103988299 | 0.909834008 | −1.099101584 |
| 257 | −6.060210734 | 0.00011017700 | 0.001329805 | 1.330188615 | 0.910251362 | −1.098597642 |
| 258 | −5.625009378 | 0.00020095100 | 0.001974506 | 0.704078694 | 0.910288109 | −1.098553294 |
| 259 | −5.668113394 | 0.00018911800 | 0.001899617 | 0.767303424 | 0.910412516 | −1.098403177 |

TABLE 1.e4

|     | LS | Loop detected | Probe sequence 60 mer |
|---|---|---|---|
| 200 | −1 | PD-L1 responder | CCACCCCCGCCCCGGGGGAGTCGCCCGGTCGAGGTGGCTTGGGTCTTAGTCTTCCAGGCA (SEQ ID NO: 201) |
| 201 | −1 | PD-L1 responder | CATCATCACAGTCTACGGCTGTTTCCTCTCGAAGGCCCCCGTCCTCCTGCGCCATGGAGA (SEQ ID NO: 202) |
| 202 | −1 | PD-L1 responder | AAGCTCATTTTAGAGTCAAAAAGCTGGATCGAGGCCGTGCTGCGTCGGCGCGGGCCCGCG (SEQ ID NO: 203) |

TABLE 1.e4-continued

| | LS | Loop detected | Probe sequence 60 mer |
|---|---|---|---|
| 203 | -1 | PD-L1 responder | TATTTTATTTGTTACTAAAACAAGGAACTCGATTTCGCCAAGGGCCAGGCTCCCAAGGCA (SEQ ID NO: 204) |
| 204 | -1 | PD-L1 responder | GAGGCTTCTGAGTTGCTCTGAGGGTACATCGATGCGCGCCCGCCGGGGCCCGGTCGGAGC (SEQ ID NO: 205) |
| 205 | -1 | PD-L1 responder | GTGTGGGCCCCCTGCTACCGCTGCGTATCGAACTTTACAGAGGGATCTAGAATGAGTGA (SEQ ID NO: 206) |
| 206 | -1 | PD-L1 responder | CGGACAAGGTGAGGACCACGTGGGCCAGTCGATGGGGACCTGAACCGGGGCCGCACAAGC (SEQ ID NO: 207) |
| 207 | -1 | PD-L1 responder | GGACCTTGTCATCCTGCCCCTTCTTGGCTCGAGGCCCTGAAACAGGACTCTATGTCTCCT (SEQ ID NO: 208) |
| 208 | -1 | PD-L1 responder | AGTGCTGGGTTCCACACCTCTCAGCTCTTCGACCTCCAGGTCCCCCGCCACTTCCACGGC (SEQ ID NO: 209) |
| 209 | -1 | PD-L1 responder | TCAATGCCATCACTAGACATGGAACTCTTCGAGCCATCCTCCCAGTGACACTCCGCAAAG (SEQ ID NO: 210) |
| 210 | -1 | PD-L1 responder | GACCCCCGGGAATTGGCTCCAGCACATCTCGAGGGCGGGCCCGGCGGCCCCGGAGCAAAC (SEQ ID NO: 211) |
| 211 | -1 | PD-L1 responder | GTGTCTCGGCCCCCTGGGGCCCCACCCTTCGATACTATTACGAATGGAATCACTGTCTTA (SEQ ID NO: 212) |
| 212 | -1 | PD-L1 responder | GGCACCTGTTAGCAATGAAGGATAACCATCGACCATCTTGGTTCCACCTGGCAGTTTCTT (SEQ ID NO: 213) |
| 213 | -1 | PD-L1 responder | CGTGGATCCAGACTGGGAGCCCCCAGCCTCGAACCACGCCAGGCTTCCAGGCGTCAGTGC (SEQ ID NO: 214) |
| 214 | -1 | PD-L1 responder | GCACTACCCCGGCCTGCCGGAGCCCCAGTCGATGATGGCTTCCTCCCCCAGAGCACCAGC (SEQ ID NO: 215) |
| 215 | -1 | PD-L1 responder | AACAAGGCAGGTAGTGTTCCTGCCCTCATCGATGTGGCAGCGGGCCCGGACGGGTCGGTG (SEQ ID NO: 216) |
| 216 | -1 | PD-L1 responder | ACGCCCGCCTCCATGAGATTCAGAGCCCTCGAGAATGTGGACTCTCCTTTCCCCCAGCAC (SEQ ID NO: 217) |
| 217 | -1 | PD-L1 responder | TGAGCTAATAAACTATTTCTGGTTTTGCTCGAGCCATCCTCCCAGTGACACTCCGCAAAG (SEQ ID NO: 218) |
| 218 | -1 | PD-L1 responder | GTCACCAGGGCTCCCTCCTCCTGCGGAATCGAGGCTGTAGATAGCTGTGATTGTACCACT (SEQ ID NO: 219) |
| 219 | -1 | PD-L1 responder | TCTTAGAGTTGAACTTTTCTAATCTTTTTCGAAGACCCCTTCCATTGGGCATTCATCTAA (SEQ ID NO: 220) |
| 220 | -1 | PD-L1 responder | CCAGAAATTCTGTGGTTGATGAATTTGGTCGAGCCATCCTCCCAGTGACACTCCGCAAAG (SEQ ID NO: 221) |
| 221 | -1 | PD-L1 responder | TGAGATGAAGCCTATATTTTCCCAATCCTCGATGTTTGGGGCGGAGGGCTTTGATGAGA (SEQ ID NO: 222) |
| 222 | -1 | PD-L1 responder | CAGGCTATTGTAGTGCTCTTCCTGGCCCTCGACACCCCCTTCAAGGGTCTGTGTCCCATA (SEQ ID NO: 223) |
| 223 | -1 | PD-L1 responder | CACCGCGCGGTACACCCCCACGTCGCTGTCGACATTTTCTTACCAGCCTGGCTGATAAAC (SEQ ID NO: 224) |
| 224 | -1 | PD-L1 responder | GTAAGCCATGGAAATATGAATCCATTTCTCGATGCCAATCCACGTCATTAGATGAGGACC (SEQ ID NO: 225) |
| 225 | -1 | PD-L1 responder | TTAATGCTGATACAATTCTATTGGATAATCGACGTGCCTTGGGGCCTCCCCTTTCCCTAT (SEQ ID NO: 226) |
| 226 | -1 | PD-L1 responder | CCATCTGCAAGTCGCTTTTGACTAGCACTCGAGTTCTTTCTGACATCTCCTGGGTGGAGC (SEQ ID NO: 227) |
| 227 | -1 | PD-L1 responder | AAGTCTTTTGTTTGGTTATTGTGCTGTATCGACCTCCTGGACTCAAGCAATCCTCGGCCT (SEQ ID NO: 228) |
| 228 | -1 | PD-L1 responder | GCACTACCCCGGCCTGCCGGAGCCCCAGTCGACATGTTGCCCCAGCTGGTCTCAAACTCC (SEQ ID NO: 229) |

TABLE 1.e4-continued

| | LS | Loop detected | Probe sequence 60 mer |
|---|---|---|---|
| 229 | -1 | PD-L1 responder | AGGAAGTATGTTTGATTTAGAATGTTATTCGAGCCGCCCTTGACATAACACCATCTTTTA (SEQ ID NO: 230) |
| 230 | -1 | PD-L1 responder | GTGGCCACCGCCCTTGCGCTTTATGACATCGATTTTGGCTCTGTAGGGAAAGGCTCTTAT (SEQ ID NO: 231) |
| 231 | -1 | PD-L1 responder | CGCGCACTGAAACCCTAGCCGCGGGGGATCGAAATCATATCACCAGTCATTCCACTCCTG (SEQ ID NO: 232) |
| 232 | -1 | PD-L1 responder | TTTGCTAAATTACCCAAAATTTTGCTTTTCGATGCTGGGAACACTTTCCTCCAGAGTTGA (SEQ ID NO: 233) |
| 233 | -1 | PD-L1 responder | GTCCCTGAAAATGTTTGTAAATGTGGGGTCGACCTGCTGGGCTCGGGCTATCCTTCCATC (SEQ ID NO: 234) |
| 234 | -1 | PD-L1 responder | CACTAATCTTTACTCTTTTTCCACTTATTCGAGACCAGTGAAACCTCGTCGCTACAAAAA (SEQ ID NO: 235) |
| 235 | -1 | PD-L1 responder | TGTTTTTTATTGTTTGATGTCCAATGTATCGAGTCACATGATCAAGCGCTCATTTCTGTT (SEQ ID NO: 236) |
| 236 | -1 | PD-L1 responder | CTTTTCCATTGCTTCCTCAGATCCTCTGTCGAGATTCACTGCGCTGCACACCAGGGCCTC (SEQ ID NO: 237) |
| 237 | -1 | PD-L1 responder | AGGACCTGAAATCCAGGAAGATCTGACTTCGAGACGATCCCGGCCAACATGGTGAAACCC (SEQ ID NO: 238) |
| 238 | -1 | PD-L1 responder | TATTTGTATCCTTTCCTCATTTATTTACTCGAATCTCTGGGGTAGGGCTCTGCAACCTTG (SEQ ID NO: 239) |
| 239 | -1 | PD-L1 responder | CCGCCTCCGTCTGCGCCTGGGCCAGGCCTCGAGAATTATTCTTTTCATATACAAAGAATA (SEQ ID NO: 240) |
| 240 | -1 | PD-L1 responder | AAGCTCATTTTAGAGTCAAAAAGCTGGATCGAGGCCGTGCTGCGTCGGCGCGGGCCCGCG (SEQ ID NO: 241) |
| 241 | -1 | PD-L1 responder | GTAATAAACATACAAACTTAAACGTAGTTCGAGGCTCCCGTGGAGGGCACCGCTGTCCCC (SEQ ID NO: 242) |
| 242 | -1 | PD-L1 responder | GCACTACCCCGGCCTGCCGGAGCCCCAGTCGAGTTGGTTTCTGGGTCCGCACCCCCTCCC (SEQ ID NO: 243) |
| 243 | -1 | PD-L1 responder | AGCGGGCAGATCACTTGAGGTCAGGAGTTCGAACTCCTGACCTCAGGTGATCTGCCTGCC (SEQ ID NO: 244) |
| 244 | -1 | PD-L1 responder | CTTTTCCATTGCTTCCTCAGATCCTCTGTCGAGAGCACGGCCTCTCTGGCGCCTTGCCAT (SEQ ID NO: 245) |
| 245 | -1 | PD-L1 responder | AAACTTCCTTTCTTTGCTTAGAACTAGCTCGATCCTGGAAGCCCCCTAAAGGCAGGAACT (SEQ ID NO: 246) |
| 246 | -1 | PD-L1 responder | TTGCACTCTCGGTCTGTTTTACTAATCATCGAGCTTCCTGGCCACTTTGTTTACCTACTC (SEQ ID NO: 247) |
| 247 | -1 | PD-L1 responder | GCCATTAAATTCCCCTAATGCCATTGCCTCGACTTCAGTGGCGTCCATTGTCTGCTGGAG (SEQ ID NO: 248) |
| 248 | -1 | PD-L1 responder | TAACAAAAGTAACACCTCTTTGGTATCATCGAAGAGTCCTTGTTCCCATTTTGGCCCAGT (SEQ ID NO: 249) |
| 249 | -1 | PD-L1 responder | GTGACAATTAAGAGTGTGACATTGCTTCTCGATCCCAGAGCCGTCCCAGGCCTGGACAGA (SEQ ID NO: 250) |
| 250 | -1 | PD-L1 responder | GAAGGCTAGGCTCCCGCACAACGCCTCCTCGAGCAAGTTAGTTGAACCCAAGGAGGGTCA (SEQ ID NO: 251) |
| 251 | -1 | PD-L1 responder | TTCCATAGATTACTTTTCAAATCATCCTTCGAAGCTGGCGGCTGAGGGCCCGGCGCCAAG (SEQ ID NO: 252) |
| 252 | -1 | PD-L1 responder | GTGGCAGGAGAAAAACGCGGCCCCACCCTCGAAAATACTAGAATTATGCCGCACAGTCAG (SEQ ID NO: 253) |
| 253 | -1 | PD-L1 responder | TTGCCAAGCACACATAGCTCCTCAATCCTCGAAGCTGGCGGCTGAGGGCCCGGCGCCAAG (SEQ ID NO: 254) |

TABLE 1.e4-continued

| LS | Loop detected | Probe sequence 60 mer |
|---|---|---|
| 254 −1 | PD-L1 responder | GACAAGCTGCACATCCCGGCGCTGACCCTCGAGGAAGTGAGGCTTAATTCCACTCCCTAC (SEQ ID NO: 255) |
| 255 −1 | PD-L1 responder | AATTTATGGATTGTATGTTACTACTGTATCGAGATCTTCCTACCTCACCGTCCCAAGTAG (SEQ ID NO: 256) |
| 256 −1 | PD-L1 responder | GCACTACAGACAAAAGACTCTAACTGGATCGATTAGCTTCTCCTCTCTCTTCTAATCCTC (SEQ ID NO: 257) |
| 257 −1 | PD-L1 responder | GCACTACCCCGGCCTGCCGGAGCCCCAGTCGATGCTATTGGATAGCCAGGAGAACCGGAA (SEQ ID NO: 258) |
| 258 −1 | PD-L1 responder | CTCTCAAACTGGCTTGTACCAGGAGTGTTCGATTTCGCCAAGGGCCAGGCTCCCAAGGCA (SEQ ID NO: 259) |
| 259 −1 | PD-L1 responder | CGTGGATCCAGACTGGGAGCCCCCAGCCTCGAGCAGTTGCACTCCAGCCTAGGCAACAAG (SEQ ID NO: 260) |

TABLE 1.e5

| | Probe Location | | | | 4 kb Sequence Location | |
|---|---|---|---|---|---|---|
| | Chr | Start1 | End1 | Start2 | End2 | Chr | Start1 |
| 200 | 8 | 42231190 | 42231219 | 42271172 | 42271201 | 8 | 42231190 |
| 201 | 16 | 29613906 | 29613935 | 29687198 | 29687227 | 16 | 29613906 |
| 202 | 8 | 140771375 | 140771404 | 141001276 | 141001305 | 8 | 140767405 |
| 203 | 11 | 78304462 | 78304491 | 78382804 | 78382833 | 11 | 78304462 |
| 204 | 11 | 119714016 | 119714045 | 119729290 | 119729319 | 11 | 119710046 |
| 205 | 11 | 60933651 | 60933680 | 60977086 | 60977115 | 11 | 60929681 |
| 206 | 16 | 2500834 | 2500863 | 2603718 | 2603747 | 16 | 2500834 |
| 207 | 11 | 119677784 | 119677813 | 119700079 | 119700108 | 11 | 119673814 |
| 208 | 9 | 120888368 | 120888397 | 120913548 | 120913577 | 9 | 120888368 |
| 209 | 17 | 36075904 | 36075933 | 36100161 | 36100190 | 17 | 36075904 |
| 210 | 2 | 241535462 | 241535491 | 241559194 | 241559223 | 2 | 241535462 |
| 211 | 5 | 132477881 | 132477910 | 132521320 | 132521349 | 5 | 132473911 |
| 212 | 4 | 77534163 | 77534192 | 77583786 | 77583815 | 4 | 77534163 |
| 213 | 19 | 47240983 | 47241012 | 47256214 | 47256243 | 19 | 47237013 |
| 214 | 11 | 64269780 | 64269809 | 64288583 | 64288612 | 11 | 64265810 |
| 215 | 12 | 112418671 | 112418700 | 112482384 | 112482413 | 12 | 112418671 |
| 216 | 11 | 44515605 | 44515634 | 44564825 | 44564854 | 11 | 44515605 |
| 217 | 17 | 36027997 | 36028026 | 36075904 | 36075933 | 17 | 36024027 |
| 218 | 19 | 51190927 | 51190956 | 51254263 | 51254292 | 19 | 51186957 |
| 219 | 15 | 98652567 | 98652596 | 98874709 | 98874738 | 15 | 98652567 |
| 220 | 17 | 36057113 | 36057142 | 36075904 | 36075933 | 17 | 36053143 |
| 221 | 5 | 157231399 | 157231428 | 157266727 | 157266756 | 5 | 157227429 |
| 222 | 4 | 109879089 | 109879118 | 110011337 | 110011366 | 4 | 109875119 |
| 223 | 6 | 32626932 | 32626961 | 32664929 | 32664958 | 6 | 32626932 |
| 224 | 8 | 81053412 | 81053441 | 81095102 | 81095131 | 8 | 81053412 |
| 225 | 11 | 60983696 | 60983725 | 60996253 | 60996282 | 11 | 60979726 |
| 226 | 6 | 167112408 | 167112437 | 167154579 | 167154608 | 6 | 167108438 |
| 227 | 8 | 140725050 | 140725079 | 140893213 | 140893242 | 8 | 140721080 |
| 228 | 11 | 64269780 | 64269809 | 64301869 | 64301898 | 11 | 64265810 |
| 229 | 1 | 198627330 | 198627359 | 198652843 | 198652872 | 1 | 198623360 |
| 230 | 2 | 241872994 | 241873023 | 241891225 | 241891254 | 2 | 241872994 |
| 231 | 7 | 155810093 | 155810122 | 155829185 | 155829214 | 7 | 155806123 |
| 232 | 9 | 90767555 | 90767584 | 90856874 | 90856903 | 9 | 90767555 |
| 233 | 19 | 44600230 | 44600259 | 44664295 | 44664324 | 19 | 44596260 |
| 234 | 9 | 125518476 | 125518505 | 125635069 | 125635098 | 9 | 125518476 |
| 235 | 1 | 198595740 | 198595769 | 198775795 | 198775824 | 1 | 198591770 |
| 236 | 17 | 80643706 | 80643735 | 80661870 | 80661899 | 17 | 80639736 |
| 237 | 15 | 74772374 | 74772403 | 74803992 | 74804021 | 15 | 74772374 |
| 238 | 2 | 105716874 | 105716903 | 105886461 | 105886490 | 2 | 105712904 |
| 239 | 12 | 6773968 | 6773997 | 6813427 | 6813456 | 12 | 6769998 |
| 240 | 8 | 140771375 | 140771404 | 141001276 | 141001305 | 8 | 140767405 |
| 241 | 2 | 215366806 | 215366835 | 215435724 | 215435753 | 2 | 215362836 |
| 242 | 11 | 64269780 | 64269809 | 64296893 | 64296922 | 11 | 64265810 |
| 243 | 17 | 45280832 | 45280861 | 45297940 | 45297969 | 17 | 45280832 |
| 244 | 17 | 80643706 | 80643735 | 80796044 | 80796073 | 17 | 80639736 |
| 245 | 12 | 93759385 | 93759414 | 93797874 | 93797903 | 12 | 93755415 |
| 246 | 2 | 201225491 | 201225520 | 201291005 | 201291034 | 2 | 201221521 |
| 247 | 12 | 47732327 | 47732356 | 47745286 | 47745315 | 12 | 47728357 |
| 248 | 11 | 77430381 | 77430410 | 77519072 | 77519101 | 11 | 77430381 |

TABLE 1.e5-continued

| | Probe Location | | | | 4 kb Sequence Location | |
|---|---|---|---|---|---|---|
| | Chr | Start1 | End1 | Start2 | End2 | Chr | Start1 |
| 249 | 11 | 2113134 | 2113163 | 2170500 | 2170529 | 11 | 2113134 |
| 250 | 1 | 15523983 | 15524012 | 15542556 | 15542585 | 1 | 15520013 |
| 251 | 17 | 42254410 | 42254439 | 42312278 | 42312307 | 17 | 42250440 |
| 252 | 15 | 67098634 | 67098663 | 67199586 | 67199615 | 15 | 67098634 |
| 253 | 17 | 42312278 | 42312307 | 42409959 | 42409988 | 17 | 42312278 |
| 254 | 19 | 18110333 | 18110362 | 18179079 | 18179108 | 19 | 18106363 |
| 255 | 1 | 150570654 | 150570683 | 150615515 | 150615544 | 1 | 150570654 |
| 256 | 13 | 23617888 | 23617917 | 23632821 | 23632850 | 13 | 23613918 |
| 257 | 11 | 64269780 | 64269809 | 64317607 | 64317636 | 11 | 64265810 |
| 258 | 11 | 78204243 | 78204272 | 78304462 | 78304491 | 11 | 78204243 |
| 259 | 19 | 47214453 | 47214482 | 47240983 | 47241012 | 19 | 47214453 |

TABLE 1.e6

| | 4 kb Sequence Location | | |
|---|---|---|---|
| | End1 | Start2 | End2 |
| 200 | 42235189 | 42267202 | 42271201 |
| 201 | 29617905 | 29683228 | 29687227 |
| 202 | 140771404 | 141001276 | 141005275 |
| 203 | 78308461 | 78378834 | 78382833 |
| 204 | 119714045 | 119729290 | 119733289 |
| 205 | 60933680 | 60977086 | 60981085 |
| 206 | 2504833 | 2599748 | 2603747 |
| 207 | 119677813 | 119700079 | 119704078 |
| 208 | 120892367 | 120913548 | 120917547 |
| 209 | 36079903 | 36096191 | 36100190 |
| 210 | 241539461 | 241559194 | 241563193 |
| 211 | 132477910 | 132517350 | 132521349 |
| 212 | 77538162 | 77579816 | 77583815 |
| 213 | 47241012 | 47256214 | 47260213 |
| 214 | 64269809 | 64288583 | 64292582 |
| 215 | 112422670 | 112478414 | 112482413 |
| 216 | 44519604 | 44560855 | 44564854 |
| 217 | 36028026 | 36075904 | 36079903 |
| 218 | 51190956 | 51254263 | 51258262 |
| 219 | 98656566 | 98874709 | 98878708 |
| 220 | 36057142 | 36075904 | 36079903 |
| 221 | 157231428 | 157266727 | 157270726 |
| 222 | 109879118 | 110007367 | 110011366 |
| 223 | 32630931 | 32660959 | 32664958 |
| 224 | 81057411 | 81095102 | 81099101 |
| 225 | 60983725 | 60996253 | 61000252 |
| 226 | 167112437 | 167150609 | 167154608 |
| 227 | 140725079 | 140889243 | 140893242 |
| 228 | 64269809 | 64301869 | 64305868 |
| 229 | 198627359 | 198648873 | 198652872 |
| 230 | 241876993 | 241891225 | 241895224 |

TABLE 1.e6-continued

| | 4 kb Sequence Location | | |
|---|---|---|---|
| | End1 | Start2 | End2 |
| 231 | 155810122 | 155829185 | 155833184 |
| 232 | 90771554 | 90856874 | 90860873 |
| 233 | 44600259 | 44664295 | 44668294 |
| 234 | 125522475 | 125631099 | 125635098 |
| 235 | 198595769 | 198771825 | 198775824 |
| 236 | 80643735 | 80661870 | 80665869 |
| 237 | 74776373 | 74800022 | 74804021 |
| 238 | 105716903 | 105886461 | 105890460 |
| 239 | 6773997 | 6813427 | 6817426 |
| 240 | 140771404 | 141001276 | 141005275 |
| 241 | 215366835 | 215435724 | 215439723 |
| 242 | 64269809 | 64292923 | 64296922 |
| 243 | 45284831 | 45297940 | 45301939 |
| 244 | 80643735 | 80792074 | 80796073 |
| 245 | 93759414 | 93793904 | 93797903 |
| 246 | 201225520 | 201287035 | 201291034 |
| 247 | 47732356 | 47745286 | 47749285 |
| 248 | 77434380 | 77515102 | 77519101 |
| 249 | 2117133 | 2170500 | 2174499 |
| 250 | 15524012 | 15542556 | 15546555 |
| 251 | 42254439 | 42312278 | 42316277 |
| 252 | 67102633 | 67199586 | 67203585 |
| 253 | 42316277 | 42405989 | 42409988 |
| 254 | 18110362 | 18179079 | 18183078 |
| 255 | 150574653 | 150615515 | 150619514 |
| 256 | 23617917 | 23628851 | 23632850 |
| 257 | 64269809 | 64317607 | 64321606 |
| 258 | 78208242 | 78304462 | 78308461 |
| 259 | 47218452 | 47237013 | 47241012 |

TABLE 1.f1

| | probe | GeneLocus | Probe_Count_Total |
|---|---|---|---|
| 260 | ORF402_16_30112759_30117149_30162846_30165864_FF | MAPK3 | 44 |
| 261 | ORF224_6_151760868_151764563_151928859_151937822_RR | ESR1 | 198 |
| 262 | CDKN2A_9_21967881_21969374_22029989_22034039_RF | CDKN2A | 44 |
| 263 | CD6_11_60922069_60925026_60977084_60983727_RR | CD6 | 56 |
| 264 | ORF300_21_44209217_44216751_44251677_44254768_RR | ICOSLG | 40 |
| 265 | ORF708_1_3611941_3615812_3638742_3642185_FF | TP73 | 32 |
| 266 | ORF86_1_56902220_56908104_56927372_56932246_RF | C8A | 166 |
| 267 | ORF574_5_38976283_38980760_39037737_39046956_RF | RICTOR | 114 |
| 268 | LYN_8_55939615_55941582_55961822_55966587_RF | LYN | 48 |
| 269 | ORF456_11_119711187_119714047_119729288_119738834_FR | PVRL1 | 96 |
| 270 | SIRPA_20_1849966_1853129_1924633_1930962_RR | SIRPA | 56 |
| 271 | ORF173_4_77503292_77510413_77524478_77530204_RR | CXCL13 | 108 |
| 272 | MTOR_1_11153017_11157168_11226037_11228251_FF | MTOR | 60 |
| 273 | ORF318_12_68159448_68161660_68183648_68186563_RR | IL26 | 20 |
| 274 | CD33_19_51200116_51202883_51233917_51238043_RF | CD33 | 32 |
| 275 | PTPRA_20_2873115_2878192_2986126_2989451_RF | PTPRA | 82 |
| 276 | ITK_5_157249288_157254103_157266725_157271762_FR | ITK | 26 |
| 277 | ORF368_1_32254316_32257966_32281860_32285193_RR | LCK | 46 |

TABLE 1.f1-continued

| | probe | GeneLocus | Probe_Count_Total |
|---|---|---|---|
| 278 | ORF173_4_77571558_77583817_77593834_77598247_FF | CXCL13 | 108 |
| 279 | CD4_12_6813425_6817229_6829192_6834733_RR | CD4 | 42 |
| 280 | BLNK_10_96186298_96190208_96274838_96286475_RF | BLNK | 66 |
| 281 | ORF332_6_379279_387635_399013_400061_RF | IRF4 | 40 |
| 282 | CXCL13_4_77524478_77530204_77571558_77583817_RF | CXCL13 | 108 |
| 283 | ORF480_11_77430379_77437843_77488853_77494447_FF | PAK1 | 136 |
| 284 | ORF127_3_108038610_108048605_108107363_108112891_RF | CD47 | 46 |
| 285 | ARHGEF7_13_111147918_111152467_111170222_111182176_FF | ARHGEF7 | 122 |
| 286 | BBC3_19_47236830_47241014_47275384_47276951_FR | BBC3 | 56 |
| 287 | TP73_1_3605228_3610228_3716440_3718086_FF | TP73 | 32 |
| 288 | CD79A_19_41852821_41857717_41894637_41898341_RF | CD79A | 44 |
| 289 | ORF143_9_21967881_21969374_22029989_22034039_RF | CDKN2A | 44 |
| 290 | UBC_12_124897705_124900704_124946470_124947649_RF | UBC | 64 |
| 291 | ORF723_19_10361427_10365738_10416039_10417435_FR | TYK2 | 75 |
| 292 | ORF673_6_149229853_149231712_149361564_149369248_FF | TAB2 | 151 |
| 293 | ORF305_15_98652565_98657862_98957432_98962130_RR | IGF1R | 104 |
| 294 | ORF463_4_102522760_102539034_102577393_102582880_FR | NFKB1 | 64 |
| 295 | ORF73_10_96204016_96209130_96290525_96304713_FR | BLNK | 66 |
| 296 | ORF401_4_85995509_86001303_86120725_86131416_RF | MAPK10 | 186 |
| 297 | CD6_11_60922069_60925026_60977084_60983727_FF | CD6 | 56 |
| 298 | PDPK1_16_2543954_2548518_2569272_2571597_FR | PDPK1 | 60 |
| 299 | SHH_7_155800574_155803187_155834849_155837762_FF | SHH | 36 |
| 300 | ORF502_19_18105164_18110364_18179077_18180271_FR | PIK3R2 | 116 |
| 301 | ORF241_10_88957987_88964666_88985428_88990419_FF | FAS | 50 |
| 302 | ORF698_18_62296384_62304812_62350513_62353490_FF | TNFRSF11A | 58 |
| 303 | ORF524_10_70591312_70596315_70645615_70650323_RR | PRF1 | 28 |
| 304 | ORF168_15_74750296_74755004_74772372_74779791_FR | CSK | 48 |
| 305 | ORF311_5_149367706_149370779_149412565_149416567_RF | IL17B | 44 |
| 306 | ORF479_8_80976747_80979473_81007411_81018107_RF | PAG1 | 144 |
| 307 | HLA-DMB_6_32954633_32960310_32978237_32979648_RR | HLA-DMB | 26 |
| 308 | ORF70_22_17731946_17735544_17804446_17806939_FF | BID | 42 |
| 309 | ORF87_1_56920282_56923866_56991331_56998079_FR | C8B | 151 |
| 310 | CCR6_6_167100641_167107689_167149742_167154610_FR | CCR6 | 46 |
| 311 | ORF124_12_6767426_6773999_6813425_6817229_FR | CD4 | 42 |
| 312 | PRF1_10_70625039_70635552_70645615_70650323_FR | PRF1 | 28 |
| 313 | ORF703_1_6481328_6484248_6494588_6498048_FR | TNFRSF25 | 68 |
| 314 | ORF112_5_140643798_140647427_140673116_140675478_RR | CD14 | 62 |
| 315 | ORF98_11_119243827_119245328_119294588_119299643_RF | CBL | 55 |
| 316 | SYK_9_90761728_90767553_90799858_90802263_FF | SYK | 78 |
| 317 | ORF338_5_157249288_157254103_157266725_157271762_FR | ITK | 26 |
| 318 | ORF480_11_77352593_77360453_77413948_77425707_FR | PAK1 | 136 |
| 319 | ORF723_19_10345998_10347157_10361427_10365738_RF | TYK2 | 75 |

TABLE 1.f2

| | Probe_Count_Sig | HyperG_Stats | FDR_HyperG | Percent_Sig | logFC | AveExpr |
|---|---|---|---|---|---|---|
| 260 | 4 | 0.466402982 | 0.99999793 | 9.09 | −0.135367103 | −0.135367103 |
| 261 | 4 | 0.999928673 | 0.99999793 | 2.02 | −0.135314539 | −0.135314539 |
| 262 | 4 | 0.466402982 | 0.99999793 | 9.09 | −0.135272194 | −0.135272194 |
| 263 | 14 | 9.03E−05 | 0.005970563 | 25 | −0.134887567 | −0.134887567 |
| 264 | 8 | 0.012066038 | 0.223463015 | 20 | −0.134719018 | −0.134719018 |
| 265 | 4 | 0.246707931 | 0.99999793 | 12.5 | −0.134700098 | −0.134700098 |
| 266 | 8 | 0.957766442 | 0.99999793 | 4.82 | −0.134558534 | −0.134558534 |
| 267 | 2 | 0.99915023 | 0.99999793 | 1.75 | −0.134523968 | −0.134523968 |
| 268 | 2 | 0.903339407 | 0.99999793 | 4.17 | −0.133947883 | −0.133947883 |
| 269 | 8 | 0.497039718 | 0.99999793 | 8.33 | −0.133203879 | −0.133203879 |
| 270 | 4 | 0.659150649 | 0.99999793 | 7.14 | −0.133176015 | −0.133176015 |
| 271 | 14 | 0.046569042 | 0.598929617 | 12.96 | −0.13317108 | −0.13317108 |
| 272 | 4 | 0.711822793 | 0.99999793 | 6.67 | −0.133096756 | −0.133096756 |
| 273 | 2 | 0.479107134 | 0.99999793 | 10 | −0.133028046 | −0.133028046 |
| 274 | 4 | 0.246707931 | 0.99999793 | 12.5 | −0.132614212 | −0.132614212 |
| 275 | 8 | 0.325435728 | 0.99999793 | 9.76 | −0.13255617 | −0.13255617 |
| 276 | 10 | 1.57E−05 | 0.002607465 | 38.46 | −0.132455148 | −0.132455148 |
| 277 | 4 | 0.501622356 | 0.99999793 | 8.7 | −0.132015778 | −0.132015778 |
| 278 | 14 | 0.046569042 | 0.598929617 | 12.96 | −0.131874693 | −0.131874693 |
| 279 | 6 | 0.112492545 | 0.789152247 | 14.29 | −0.131485584 | −0.131485584 |
| 280 | 4 | 0.779227696 | 0.99999793 | 6.06 | −0.130818373 | −0.130818373 |
| 281 | 2 | 0.837619347 | 0.99999793 | 5 | −0.130756722 | −0.130756722 |
| 282 | 14 | 0.046569042 | 0.598929617 | 12.96 | −0.13064065 | −0.13064065 |
| 283 | 6 | 0.963851563 | 0.99999793 | 4.41 | −0.130320594 | −0.130320594 |
| 284 | 2 | 0.889742685 | 0.99999793 | 4.35 | −0.13011673 | −0.13011673 |
| 285 | 6 | 0.928958915 | 0.99999793 | 4.92 | −0.12916025 | −0.12916025 |
| 286 | 8 | 0.073465475 | 0.710624303 | 14.29 | −0.129003985 | −0.129003985 |

TABLE 1.f2-continued

| | Probe_Count_Sig | HyperG_Stats | FDR_HyperG | Percent_Sig | logFC | AveExpr |
|---|---|---|---|---|---|---|
| 287 | 4 | 0.246707931 | 0.99999793 | 12.5 | −0.128934989 | −0.128934989 |
| 288 | 2 | 0.874387211 | 0.99999793 | 4.55 | −0.128929587 | −0.128929587 |
| 289 | 4 | 0.466402982 | 0.99999793 | 9.09 | −0.128681113 | −0.128681113 |
| 290 | 2 | 0.967461559 | 0.99999793 | 3.12 | −0.128570744 | −0.128570744 |
| 291 | 4 | 0.856164977 | 0.99999793 | 5.33 | −0.128545894 | −0.128545894 |
| 292 | 4 | 0.998322979 | 0.99999793 | 2.65 | −0.12793801 | −0.12793801 |
| 293 | 16 | 0.007797893 | 0.171924974 | 15.38 | −0.127837192 | −0.127837192 |
| 294 | 6 | 0.398773743 | 0.99999793 | 9.38 | −0.127131862 | −0.127131862 |
| 295 | 4 | 0.779227696 | 0.99999793 | 6.06 | −0.126872989 | −0.126872989 |
| 296 | 10 | 0.931377207 | 0.99999793 | 5.38 | −0.126502065 | −0.126502065 |
| 297 | 14 | 9.03E−05 | 0.005970563 | 25 | −0.126459458 | −0.126459458 |
| 298 | 6 | 0.340695433 | 0.99999793 | 10 | −0.126355782 | −0.126355782 |
| 299 | 6 | 0.062022042 | 0.70039526 | 16.67 | −0.125630545 | −0.125630545 |
| 300 | 8 | 0.71102088 | 0.99999793 | 6.9 | −0.125584908 | −0.125584908 |
| 301 | 8 | 0.041957105 | 0.555032562 | 16 | −0.125541145 | −0.125541145 |
| 302 | 4 | 0.686266831 | 0.99999793 | 6.9 | −0.125497235 | −0.125497235 |
| 303 | 4 | 0.178427395 | 0.954389149 | 14.29 | −0.125470372 | −0.125470372 |
| 304 | 6 | 0.178303905 | 0.954389149 | 12.5 | −0.124886899 | −0.124886899 |
| 305 | 4 | 0.466402982 | 0.99999793 | 9.09 | −0.124824226 | −0.124824226 |
| 306 | 12 | 0.474481533 | 0.99999793 | 8.33 | −0.124687296 | −0.124687296 |
| 307 | 2 | 0.622797749 | 0.99999793 | 7.69 | −0.124537792 | −0.124537792 |
| 308 | 2 | 0.857080857 | 0.99999793 | 4.76 | −0.124385789 | −0.124385789 |
| 309 | 9 | 0.85591599 | 0.99999793 | 5.96 | −0.124075137 | −0.124075137 |
| 310 | 4 | 0.501622356 | 0.99999793 | 8.7 | −0.123511821 | −0.123511821 |
| 311 | 6 | 0.112492545 | 0.789152247 | 14.29 | −0.123094724 | −0.123094724 |
| 312 | 4 | 0.178427395 | 0.954389149 | 14.29 | −0.12298462 | −0.12298462 |
| 313 | 16 | 6.44E−05 | 0.004967399 | 23.53 | −0.122075997 | −0.122075997 |
| 314 | 6 | 0.369692981 | 0.99999793 | 9.68 | −0.122003303 | −0.122003303 |
| 315 | 2 | 0.939538153 | 0.99999793 | 3.64 | −0.121481932 | −0.121481932 |
| 316 | 6 | 0.592795697 | 0.99999793 | 7.69 | −0.121037593 | −0.121037593 |
| 317 | 10 | 1.57E−05 | 0.002607465 | 38.46 | −0.120710117 | −0.120710117 |
| 318 | 6 | 0.963851563 | 0.99999793 | 4.41 | −0.12002146 | −0.12002146 |
| 319 | 4 | 0.856164977 | 0.99999793 | 5.33 | −0.119396577 | −0.119396577 |

TABLE 1.f3

| | t | P.Value | adj.P.Val | B | FC | FC_1 |
|---|---|---|---|---|---|---|
| 260 | −3.149031853 | 0.01005514500 | 0.032628994 | −3.328767115 | 0.910438137 | −1.098372266 |
| 261 | −5.0414432 | 0.00046900800 | 0.003533752 | −0.178184397 | 0.910471309 | −1.098332248 |
| 262 | −5.610750575 | 0.00020503800 | 0.002000516 | 0.683105065 | 0.910498033 | −1.098300011 |
| 263 | −3.981542416 | 0.00247280800 | 0.011523827 | −1.899195685 | 0.910740807 | −1.09800724 |
| 264 | −4.354892024 | 0.00135270800 | 0.007473785 | −1.276944573 | 0.910847214 | −1.097878968 |
| 265 | −3.915446617 | 0.00275663900 | 0.012498582 | −2.010902308 | 0.91085916 | −1.09786457 |
| 266 | −6.002981158 | 0.00011906100 | 0.001397518 | 1.249399806 | 0.910948542 | −1.097756848 |
| 267 | −5.011745141 | 0.00049031700 | 0.003651403 | −0.22438317 | 0.910970368 | −1.097730547 |
| 268 | −7.272499177 | 0.00002350000 | 0.000488496 | 2.935549576 | 0.911334202 | −1.097292297 |
| 269 | −5.919580786 | 0.00013341200 | 0.001506976 | 1.130832175 | 0.911804302 | −1.096726565 |
| 270 | −5.32199774 | 0.00031016400 | 0.002644833 | 0.252069164 | 0.911821913 | −1.096705383 |
| 271 | −6.487267552 | 0.00006260000 | 0.000907643 | 1.918501156 | 0.911825031 | −1.096701632 |
| 272 | −4.700405212 | 0.00078717700 | 0.005039991 | −0.716093761 | 0.911872007 | −1.096645134 |
| 273 | −6.078653164 | 0.00010746800 | 0.001309762 | 1.356124071 | 0.911915438 | −1.096592906 |
| 274 | −6.29211388 | 0.00008080000 | 0.001077771 | 1.652820413 | 0.912177056 | −1.096278396 |
| 275 | −7.017751886 | 0.00003210000 | 0.000590507 | 2.61450293 | 0.912213756 | −1.096234291 |
| 276 | −6.269560727 | 0.00008330000 | 0.001098005 | 1.621775349 | 0.912277634 | −1.096157533 |
| 277 | −4.505737936 | 0.00106576100 | 0.006305461 | −1.03019695 | 0.912555508 | −1.095823751 |
| 278 | −3.592674384 | 0.00472075700 | 0.018547070 | −2.561861516 | 0.912644754 | −1.095716593 |
| 279 | −6.054125084 | 0.00011108700 | 0.001336285 | 1.32161983 | 0.912890936 | −1.095421107 |
| 280 | −3.959369224 | 0.00256445500 | 0.011843660 | −1.936622527 | 0.913313223 | −1.094914619 |
| 281 | −5.313027786 | 0.00031423700 | 0.002670279 | 0.238487116 | 0.913352254 | −1.09486783 |
| 282 | −5.318017005 | 0.00031196700 | 0.002656279 | 0.246061516 | 0.91342574 | −1.094779746 |
| 283 | −7.189479005 | 0.00002600000 | 0.000519646 | 2.831839416 | 0.913628402 | −1.094536901 |
| 284 | −7.294936947 | 0.00002290000 | 0.000481540 | 2.963428677 | 0.913757514 | −1.094382245 |
| 285 | −4.103081237 | 0.00202785500 | 0.009963814 | −1.694937692 | 0.914363519 | −1.09365693 |
| 286 | −5.508465599 | 0.00023709600 | 0.002203392 | 0.531562745 | 0.914462564 | −1.093538478 |
| 287 | −3.811259412 | 0.00327514400 | 0.014160524 | −2.187814845 | 0.914506298 | −1.093486181 |
| 288 | −5.352279339 | 0.00029682400 | 0.002574803 | 0.297835331 | 0.914509723 | −1.093482087 |
| 289 | −3.685689982 | 0.00403801000 | 0.016534854 | −2.402257893 | 0.914667241 | −1.093293774 |
| 290 | −6.22305225 | 0.00008860000 | 0.001147264 | 1.557509293 | 0.914737218 | −1.093210138 |
| 291 | −5.633416165 | 0.00019858300 | 0.001960017 | 0.716430725 | 0.914752974 | −1.093191308 |
| 292 | −3.056473063 | 0.01179465000 | 0.036808385 | −3.489189991 | 0.915138489 | −1.092730785 |
| 293 | −2.485374714 | 0.03172122800 | 0.077306468 | −4.4686147 | 0.915202443 | −1.092654426 |
| 294 | −2.581209623 | 0.02687197300 | 0.068079912 | −4.306547541 | 0.915649992 | −1.092120361 |
| 295 | −4.83847752 | 0.00063702100 | 0.004371365 | −0.496382047 | 0.915814309 | −1.091924412 |

TABLE 1.f3-continued

|     | t           | P.Value      | adj.P.Val   | B            | FC        | FC_1         |
|-----|-------------|--------------|-------------|--------------|-----------|--------------|
| 296 | −4.919218514 | 0.00056357200 | 0.004023477 | −0.369112955 | 0.9160498 | −1.091643708 |
| 297 | −4.254485223 | 0.00158809000 | 0.008387378 | −1.442733094 | 0.916076853 | −1.091611469 |
| 298 | −5.139970533 | 0.00040509200 | 0.003180979 | −0.02580694  | 0.916142688 | −1.091533026 |
| 299 | −4.39945421  | 0.00126030000 | 0.007108949 | −1.20375598  | 0.916603345 | −1.090984455 |
| 300 | −4.704109135 | 0.00078269300 | 0.005020534 | −0.710166036 | 0.91663234 | −1.090949944 |
| 301 | −5.122385245 | 0.00041578200 | 0.003234453 | −0.052902519 | 0.916660146 | −1.090916851 |
| 302 | −3.32132345  | 0.00748217300 | 0.026196088 | −3.030208996 | 0.916688046 | −1.090883648 |
| 303 | −5.658379001 | 0.00019172400 | 0.001913238 | 0.753048456  | 0.916705114 | −1.090863337 |
| 304 | −5.128181214 | 0.00041222600 | 0.003218804 | −0.043967178 | 0.917075935 | −1.090422245 |
| 305 | −4.051920293 | 0.00220395800 | 0.010583936 | −1.780751029 | 0.917115775 | −1.090374876 |
| 306 | −4.032457988 | 0.00227509500 | 0.010841231 | −1.813440415 | 0.917202825 | −1.090271391 |
| 307 | −5.626658694 | 0.00020048400 | 0.001971776 | 0.706502825  | 0.917297878 | −1.090158414 |
| 308 | −5.6137313  | 0.00020417700 | 0.001994223 | 0.68749191   | 0.91739453 | −1.09004356  |
| 309 | −3.320634296 | 0.00749099100 | 0.026219939 | −3.031402175 | 0.917592092 | −1.089808869 |
| 310 | −5.273154933 | 0.00033304700 | 0.002781909 | 0.177973048  | 0.917950446 | −1.089383424 |
| 311 | −5.618781302 | 0.00020272600 | 0.001985854 | 0.694921264  | 0.918215873 | −1.089068518 |
| 312 | −4.83756529 | 0.00063790700 | 0.004375282 | −0.497825111 | 0.918285952 | −1.088985406 |
| 313 | −3.56192511 | 0.00497193600 | 0.019283080 | −2.614747846 | 0.918864479 | −1.088299769 |
| 314 | −4.421253446 | 0.00121754200 | 0.006935681 | −1.168042507 | 0.91891078 | −1.088244933 |
| 315 | −3.162143862 | 0.00983080300 | 0.032085012 | −3.30603666  | 0.919242922 | −1.087851727 |
| 316 | −2.933230541 | 0.01459586800 | 0.043165204 | −3.70250958  | 0.919526085 | −1.087516728 |
| 317 | −5.631541557 | 0.00019910800 | 0.001961946 | 0.713677259  | 0.919734832 | −1.087269902 |
| 318 | −5.084264999 | 0.00044000000 | 0.003375661 | −0.111789333 | 0.920173963 | −1.086751027 |
| 319 | −5.397839603 | 0.00027789500 | 0.002452456 | 0.366444576  | 0.92057261 | −1.086280419 |

TABLE 1.f4

|     | LS | Loop detected | Probe sequence 60 mer |
|-----|----|---------------|------------------------|
| 260 | −1 | PD-L1 responder | GTTTATCCCACACCCACCCTCATGTCTCTCGAATATGCGACGACGCACCCTCCCCTTGTT (SEQ ID NO: 261) |
| 261 | −1 | PD-L1 responder | ATCTTTTAATAGATAAGTGAAACTTTAATCGATATTTTCCAGCTATCTTTCTGTTGATTT (SEQ ID NO: 262) |
| 262 | −1 | PD-L1 responder | TGCTTTTTAAAAAATCAAAGGTGTAACTTCGACAGCTTCCGGAGGCTGCGAGGCTCGCAA (SEQ ID NO: 263) |
| 263 | −1 | PD-L1 responder | CTGGCGTTCCAGCCCTCGCACCTTGGCCTCGAACTTTACAGAGGGATCTAGAATGAGTGA (SEQ ID NO: 264) |
| 264 | −1 | PD-L1 responder | TGCCCAGAATGACCCCAACTAGGAACAATCGAAGGGTCCCCACTCCTCCACCTGCAGGAC (SEQ ID NO: 265) |
| 265 | −1 | PD-L1 responder | GCTTCTCCCCTCTTTATCCCACCTGGCCTCGAGCTCCTAAACTCACGCAATCCTTCCTTC (SEQ ID NO: 266) |
| 266 | −1 | PD-L1 responder | ATAATTGCCTAGCTTAGACTTGAATACCTCGACCTTATGCTAAGCCTAAACTTGCCTTCC (SEQ ID NO: 267) |
| 267 | −1 | PD-L1 responder | TTACCCTTTAAGTCAATGCCTCAAAAGTTCGATTGTCCCTTTTTTCCTGTGCCACCTTTT (SEQ ID NO: 268) |
| 268 | −1 | PD-L1 responder | GGGTTTCACTGTTTTAGCCAGGCTGGTTTCGAGCGGCCCGGTGCGCTGTGGGTTGGCCGC (SEQ ID NO: 269) |
| 269 | −1 | PD-L1 responder | GAGGCTTCTGAGTTGCTCTGAGGGTACATCGATGCGCGCCCGCCGGGGCCCGGTCGGAGC (SEQ ID NO: 270) |
| 270 | −1 | PD-L1 responder | ACCCCCTCCCAGCCTCCTGGTCAGGAGTTCGAGACATCTAAGAAGGTCCAGCCAGATGTT (SEQ ID NO: 271) |
| 271 | −1 | PD-L1 responder | GTATTTTGATGATAAAAGCTGAACAACTTCGATCTCAGGCTGTTGCACTTTCTCCATGGG (SEQ ID NO: 272) |
| 272 | −1 | PD-L1 responder | CTAGGAAGCTCACCATTCCCCCAAGGCCTCGAGCCACCGTGCTTCAGCTTGGACGACAGA (SEQ ID NO: 273) |
| 273 | −1 | PD-L1 responder | CTTGTTTGTGGTTGAAAATGACTGAATATCGATCGCACGCCTGAACTCCAGTCTTGGCAA (SEQ ID NO: 274) |
| 274 | −1 | PD-L1 responder | ATGAGCAAAGATAGCTCACGGGCTCTGCTCGAGTGTGACCGACGCTGCCCCTCACTTTCA (SEQ ID NO: 275) |

TABLE 1.f4-continued

| | LS | Loop detected | Probe sequence 60 mer |
|---|---|---|---|
| 275 | -1 | PD-L1 responder | ACTCCATCTCAAAAAAACAAGAGCTTCCTCGAGTTGCAGGCCGCCCTGGTGGCTAGACAT (SEQ ID NO: 276) |
| 276 | -1 | PD-L1 responder | CCGCAATACACAGATTCTTTATTCCTATTCGATGTTTGGGGGCGGAGGGCTTTGATGAGA (SEQ ID NO: 277) |
| 277 | -1 | PD-L1 responder | GGGATTCACCATGATGGCCAGGCTGGTTTCGAGACCAGCCTGACCAACATGGTGAAACCC (SEQ ID NO: 278) |
| 278 | -1 | PD-L1 responder | GGCACCTGTTAGCAATGAAGGATAACCATCGATTCTGAACCAACGGCTTCCGCAAATCTT (SEQ ID NO: 279) |
| 279 | -1 | PD-L1 responder | TATTCTTTGTATATGAAAAGAATAATTCTCGAAGATGGAGGGACAGGGCCGCCTCTTCCT (SEQ ID NO: 280) |
| 280 | -1 | PD-L1 responder | GGCAAATGCTACAAATCAGAGTTGTTTTCGATCACACTGGGAGCTGCAGACCGGAGCTG (SEQ ID NO: 281) |
| 281 | -1 | PD-L1 responder | TGAAATGAAACCTGCCCCGAGAATCACCTCGAGGCTCCCTCCTCCTAGCATGTGGCTTAA (SEQ ID NO: 282) |
| 282 | -1 | PD-L1 responder | GGCACCTGTTAGCAATGAAGGATAACCATCGATCTCAGGCTGTTGCACTTTCTCCATGGG (SEQ ID NO: 283) |
| 283 | -1 | PD-L1 responder | AGACTTTATTAGATAGGTATAAATGTTTTCGATACCAGCCTGGGCAACAAGACTCTTTGT (SEQ ID NO: 284) |
| 284 | -1 | PD-L1 responder | GTCCTAGGCCACGCCTTTAGACAGATCTTCGAAGCTTCTGTGGCTGTCTTTCAAGGGCAA (SEQ ID NO: 285) |
| 285 | -1 | PD-L1 responder | TGCCATTCCACTGAAAAAATGTACAGTTTCGACACCGTGAAGATCAACGAGACTGCTGCG (SEQ ID NO: 286) |
| 286 | -1 | PD-L1 responder | CGTGGATCCAGACTGGGAGCCCCCAGCCTCGAGAGCTCTGTGCTCCACGCCGAGGATGCA (SEQ ID NO: 287) |
| 287 | -1 | PD-L1 responder | GAGCTTGGACCCCCTCCTCTTCACCAGCTCGACCTGGGCCAGTGGCGGAGGGAGGCCCAG (SEQ ID NO: 288) |
| 288 | -1 | PD-L1 responder | GTCTGCTGCACGGGCCACCCTGCGGGCATCGAAGGATCCATAAAAGGTTAAGAAACATTT (SEQ ID NO: 289) |
| 289 | -1 | PD-L1 responder | TGCTTTTTAAAAAATCAAGGTGTAACTTCGACAGCTTCCGGAGGCTGCGAGGCTCGCAA (SEQ ID NO: 290) |
| 290 | -1 | PD-L1 responder | CACGGGCGGCAGCACCCTTCATACGGGATCGAAAACCTGCTGCTAAGTGAGAGAAGTCAG (SEQ ID NO: 291) |
| 291 | -1 | PD-L1 responder | CTCTGTGCCGAAGCGGGGTGCCAGCCGCTCGAGTTCTAACAGGCTCCCACAGGGTCAGAT (SEQ ID NO: 292) |
| 292 | -1 | PD-L1 responder | AAAACACCTAAAATTAAGCAAAGTATTTTCGAAGTTGAAAACTACCCACCTTATTTTTAT (SEQ ID NO: 293) |
| 293 | -1 | PD-L1 responder | TCTTAGAGTTGAACTTTTCTAATCTTTTTCGACCTGCTGATCCTTGGATCCTGAATCTGT (SEQ ID NO: 294) |
| 294 | -1 | PD-L1 responder | GAGGCTAGCAGATCACAAGGTCAGGAGTTCGAAAACCAATGCAGAAATCAAGACTTTGTC (SEQ ID NO: 295) |
| 295 | -1 | PD-L1 responder | ATTCAATAAGAAAGAATGACTGTCACTTTCGAAACCCAGTGGATGATTCTAACTTCCCGG (SEQ ID NO: 296) |
| 296 | -1 | PD-L1 responder | GAGGATTTAATAAAACCCAAACTGTATTTCGAAGTAGTCGTGCCACCAGTAGCAGTGACA (SEQ ID NO: 297) |
| 297 | -1 | PD-L1 responder | TTCTGCGAGGGACCCCTCAGCCCGGGCATCGATTATCCAATAGAATTGTATCAGCATTAA (SEQ ID NO: 298) |
| 298 | -1 | PD-L1 responder | ACATGACCGTGATACCTCTGTCACTCTGTCGATCATTTGCGCCCAGGAGTTTGAGACCAG (SEQ ID NO: 299) |
| 299 | -1 | PD-L1 responder | GAAGGCCCGGTGCGCCCAGCTGTGCTCCTCGAGAACAGCCAGGCTAACACGGAGAAACCC (SEQ ID NO: 300) |
| 300 | -1 | PD-L1 responder | GACAAGCTGCACATCCCGGCGCTGACCCTCGAGGAAGTGAGGCTTAATTCCACTCCCTAC (SEQ ID NO: 301) |

TABLE 1.f4-continued

| | LS | Loop detected | Probe sequence 60 mer |
|---|---|---|---|
| 301 | -1 | PD-L1 responder | GGGCAGAGAGATTTTTTGTATCTACTTCTCGAGAGCCGGCCTCCTGCCCTTTCTAAAGGC (SEQ ID NO: 302) |
| 302 | -1 | PD-L1 responder | GTTGGTGAAAAAGAAAGAAGAAATGGACTCGATGCTCTGCCTTCTTGTTTCAGCTCACAG (SEQ ID NO: 303) |
| 303 | -1 | PD-L1 responder | CCACTGGCTGATGAGGTCCTTTCCAGCCTCGAAGTGACCTCCGACCCTTTTATGTTTGAA (SEQ ID NO: 304) |
| 304 | -1 | PD-L1 responder | GAGTTCAGCGTGCCGCCGGGCGTGAAAGTCGAGACGATCCCGGCCAACATGGTGAAACCC (SEQ ID NO: 305) |
| 305 | -1 | PD-L1 responder | ATAAGCTGTCCTCGTGTGGACCCCGGCATCGACCCAGCCTTTTTCTGTTGACCGATGAGG (SEQ ID NO: 306) |
| 306 | -1 | PD-L1 responder | TCAGATAAGTAACTTCCTGATAATTAACTCGAAGTCTTTAACAGTAGCATAGAGATCATT (SEQ ID NO: 307) |
| 307 | -1 | PD-L1 responder | TTGGGTGATCTTATTCATGGCCTCTGCTTCGAGGCCGAGCTGGGGCCGATGAAGATGACA (SEQ ID NO: 308) |
| 308 | -1 | PD-L1 responder | TGGAAGCAGCTATACAGCTGTGACCACATCGACGCCCCTGTCACGGGCCCTGTTATTCAA (SEQ ID NO: 309) |
| 309 | -1 | PD-L1 responder | TCACCTTAGTGAAGGGAAGTCCATCAAATCGACTCACCAGTGAAGATAGTGTGCTCCACT (SEQ ID NO: 310) |
| 310 | -1 | PD-L1 responder | AAGTAAATTATGGTGTTAAAAACCACCATCGAGAGCGGCACGACCTGTGGGGACTGATGG (SEQ ID NO: 311) |
| 311 | -1 | PD-L1 responder | CCGCCTCCGTCTGCGCCTGGGCCAGGCCTCGAGAATTATTCTTTTCATATACAAAGAATA (SEQ ID NO: 312) |
| 312 | -1 | PD-L1 responder | ACTCCTCGCCTCAAAGGATTCTCCTATCTCGAAGTGACCTCCGACCCTTTTATGTTTGAA (SEQ ID NO: 313) |
| 313 | -1 | PD-L1 responder | GCACCCCACCCTGGATCCCTTGAAAGCCTCGACAATGTTATTCTTTGTTTCTCTTACCAA (SEQ ID NO: 314) |
| 314 | -1 | PD-L1 responder | CTGCCTCAGTTAGCAGGTTGCTTAGACATCGACGGGCGGGTGGACGTGGAGCCACAGTT (SEQ ID NO: 315) |
| 315 | -1 | PD-L1 responder | ACCGCCTCACCTCAGCTCTCCAGTGAGATCGAGCAATTCTCTTGCCTTAGCCTCCTGAGT (SEQ ID NO: 316) |
| 316 | -1 | PD-L1 responder | AGGCTTTTAAAAGAAATAGAATATGAAATCGACTTCCTCGCGCTGTGCCTGATCCCAATC (SEQ ID NO: 317) |
| 317 | -1 | PD-L1 responder | CCGCAATACACAGATTCTTTATTCCTATTCGATGTTTGGGGCGGAGGGCTTTGATGAGA (SEQ ID NO: 318) |
| 318 | -1 | PD-L1 responder | AGGTCCTTTCCCTGTCAAAATATGTATTTCGACTTCCCACCCCATGCAGCATCCTCTTAT (SEQ ID NO: 319) |
| 319 | -1 | PD-L1 responder | CTCTGTGCCGAAGCGGGGTGCCAGCCGCTCGAGCAAATGCAATTGGGGACTTTGTTTGTA (SEQ ID NO: 320) |

TABLE 1.f5

| | Probe Location | | | | 4 kb Sequence Location | |
|---|---|---|---|---|---|---|
| | Chr | Start1 | End1 | Start2 | End2 | Chr | Start1 |
| 260 | 16 | 30117118 | 30117147 | 30165833 | 30165862 | 16 | 30113148 |
| 261 | 6 | 151760870 | 151760899 | 151928861 | 151928890 | 6 | 151760870 |
| 262 | 9 | 21967883 | 21967912 | 22034008 | 22034037 | 9 | 21967883 |
| 263 | 11 | 60922071 | 60922100 | 60977086 | 60977115 | 11 | 60922071 |
| 264 | 21 | 44209219 | 44209248 | 44251679 | 44251708 | 21 | 44209219 |
| 265 | 1 | 3615781 | 3615810 | 3642154 | 3642183 | 1 | 3611811 |
| 266 | 1 | 56902222 | 56902251 | 56932215 | 56932244 | 1 | 56902222 |
| 267 | 5 | 38976285 | 38976314 | 39046925 | 39046954 | 5 | 38976285 |
| 268 | 8 | 55939617 | 55939646 | 55966556 | 55966585 | 8 | 55939617 |
| 269 | 11 | 119714016 | 119714045 | 119729290 | 119729319 | 11 | 119710046 |

TABLE 1.f5-continued

| | | Probe Location | | | | 4 kb Sequence Location | |
|---|---|---|---|---|---|---|---|
| | Chr | Start1 | End1 | Start2 | End2 | Chr | Start1 |
| 270 | 20 | 1849968 | 1849997 | 1924635 | 1924664 | 20 | 1849968 |
| 271 | 4 | 77503294 | 77503323 | 77524480 | 77524509 | 4 | 77503294 |
| 272 | 1 | 11157137 | 11157166 | 11228220 | 11228249 | 1 | 11153167 |
| 273 | 12 | 68159450 | 68159479 | 68183650 | 68183679 | 12 | 68159450 |
| 274 | 19 | 51200118 | 51200147 | 51238012 | 51238041 | 19 | 51200118 |
| 275 | 20 | 2873117 | 2873146 | 2989420 | 2989449 | 20 | 2873117 |
| 276 | 5 | 157254072 | 157254101 | 157266727 | 157266756 | 5 | 157250102 |
| 277 | 1 | 32254318 | 32254347 | 32281862 | 32281891 | 1 | 32254318 |
| 278 | 4 | 77583786 | 77583815 | 77598216 | 77598245 | 4 | 77579816 |
| 279 | 12 | 6813427 | 6813456 | 6829194 | 6829223 | 12 | 6813427 |
| 280 | 10 | 96186300 | 96186329 | 96286444 | 96286473 | 10 | 96186300 |
| 281 | 6 | 379281 | 379310 | 400030 | 400059 | 6 | 379281 |
| 282 | 4 | 77524480 | 77524509 | 77583786 | 77583815 | 4 | 77524480 |
| 283 | 11 | 77437812 | 77437841 | 77494416 | 77494445 | 11 | 77433842 |
| 284 | 3 | 108038612 | 108038641 | 108112860 | 108112889 | 3 | 108038612 |
| 285 | 13 | 111152436 | 111152465 | 111182145 | 111182174 | 13 | 111148466 |
| 286 | 19 | 47240983 | 47241012 | 47275386 | 47275415 | 19 | 47237013 |
| 287 | 1 | 3610197 | 3610226 | 3718055 | 3718084 | 1 | 3606227 |
| 288 | 19 | 41852823 | 41852852 | 41898310 | 41898339 | 19 | 41852823 |
| 289 | 9 | 21967883 | 21967912 | 22034008 | 22034037 | 9 | 21967883 |
| 290 | 12 | 124897707 | 124897736 | 124947618 | 124947647 | 12 | 124897707 |
| 291 | 19 | 10365707 | 10365736 | 10416041 | 10416070 | 19 | 10361737 |
| 292 | 6 | 149231681 | 149231710 | 149369217 | 149369246 | 6 | 149227711 |
| 293 | 15 | 98652567 | 98652596 | 98957434 | 98957463 | 15 | 98652567 |
| 294 | 4 | 102539003 | 102539032 | 102577395 | 102577424 | 4 | 102535033 |
| 295 | 10 | 96209099 | 96209128 | 96290527 | 96290556 | 10 | 96205129 |
| 296 | 4 | 85995511 | 85995540 | 86131385 | 86131414 | 4 | 85995511 |
| 297 | 11 | 60924995 | 60925024 | 60983696 | 60983725 | 11 | 60921025 |
| 298 | 16 | 2548487 | 2548516 | 2569274 | 2569303 | 16 | 2544517 |
| 299 | 7 | 155803156 | 155803185 | 155837731 | 155837760 | 7 | 155799186 |
| 300 | 19 | 18110333 | 18110362 | 18179079 | 18179108 | 19 | 18106363 |
| 301 | 10 | 88964635 | 88964664 | 88990388 | 88990417 | 10 | 88960665 |
| 302 | 18 | 62304781 | 62304810 | 62353459 | 62353488 | 18 | 62300811 |
| 303 | 10 | 70591314 | 70591343 | 70645617 | 70645646 | 10 | 70591314 |
| 304 | 15 | 74754973 | 74755002 | 74772374 | 74772403 | 15 | 74751003 |
| 305 | 5 | 149367708 | 149367737 | 149416536 | 149416565 | 5 | 149367708 |
| 306 | 8 | 80976749 | 80976778 | 81018076 | 81018105 | 8 | 80976749 |
| 307 | 6 | 32954635 | 32954664 | 32978239 | 32978268 | 6 | 32954635 |
| 308 | 22 | 17735513 | 17735542 | 17806908 | 17806937 | 22 | 17731543 |
| 309 | 1 | 56923835 | 56923864 | 56991333 | 56991362 | 1 | 56919865 |
| 310 | 6 | 167107658 | 167107687 | 167149744 | 167149773 | 6 | 167103688 |
| 311 | 12 | 6773968 | 6773997 | 6813427 | 6813456 | 12 | 6769998 |
| 312 | 10 | 70635521 | 70635550 | 70645617 | 70645646 | 10 | 70631551 |
| 313 | 1 | 6484217 | 6484246 | 6494590 | 6494619 | 1 | 6480247 |
| 314 | 5 | 140643800 | 140643829 | 140673118 | 140673147 | 5 | 140643800 |
| 315 | 11 | 119243829 | 119243858 | 119299612 | 119299641 | 11 | 119243829 |
| 316 | 9 | 90767522 | 90767551 | 90802232 | 90802261 | 9 | 90763552 |
| 317 | 5 | 157254072 | 157254101 | 157266727 | 157266756 | 5 | 157250102 |
| 318 | 11 | 77360422 | 77360451 | 77413950 | 77413979 | 11 | 77356452 |
| 319 | 19 | 10346000 | 10346029 | 10365707 | 10365736 | 19 | 10346000 |

TABLE 1.f6

| | 4 kb Sequence Location | | |
|---|---|---|---|
| | End1 | Start2 | End2 |
| 260 | 30117147 | 30161863 | 30165862 |
| 261 | 151764869 | 151928861 | 151932860 |
| 262 | 21971882 | 22030038 | 22034037 |
| 263 | 60926070 | 60977086 | 60981085 |
| 264 | 44213218 | 44251679 | 44255678 |
| 265 | 3615810 | 3638184 | 3642183 |
| 266 | 56906221 | 56928245 | 56932244 |
| 267 | 38980284 | 39042955 | 39046954 |
| 268 | 55943616 | 55962586 | 55966585 |
| 269 | 119714045 | 119729290 | 119733289 |
| 270 | 1853967 | 1924635 | 1928634 |
| 271 | 77507293 | 77524480 | 77528479 |
| 272 | 11157166 | 11224250 | 11228249 |
| 273 | 68163449 | 68183650 | 68187649 |
| 274 | 51204117 | 51234042 | 51238041 |
| 275 | 2877116 | 2985450 | 2989449 |
| 276 | 157254101 | 157266727 | 157270726 |
| 277 | 32258317 | 32281862 | 32285861 |
| 278 | 77583815 | 77594246 | 77598245 |
| 279 | 6817426 | 6829194 | 6833193 |
| 280 | 96190299 | 96282474 | 96286473 |
| 281 | 383280 | 396060 | 400059 |
| 282 | 77528479 | 77579816 | 77583815 |
| 283 | 77437841 | 77490446 | 77494445 |
| 284 | 108042611 | 108108890 | 108112889 |
| 285 | 111152465 | 111178175 | 111182174 |
| 286 | 47241012 | 47275386 | 47279385 |
| 287 | 3610226 | 3714085 | 3718084 |
| 288 | 41856822 | 41894340 | 41898339 |
| 289 | 21971882 | 22030038 | 22034037 |
| 290 | 124901706 | 124943648 | 124947647 |
| 291 | 10365736 | 10416041 | 10420040 |

TABLE 1.f6-continued

4 kb Sequence Location

| | End1 | Start2 | End2 |
|---|---|---|---|
| 292 | 149231710 | 149365247 | 149369246 |
| 293 | 98656566 | 98957434 | 98961433 |
| 294 | 102539032 | 102577395 | 102581394 |
| 295 | 96209128 | 96290527 | 96294526 |
| 296 | 85999510 | 86127415 | 86131414 |
| 297 | 60925024 | 60979726 | 60983725 |
| 298 | 2548516 | 2569274 | 2573273 |
| 299 | 155803185 | 155833761 | 155837760 |
| 300 | 18110362 | 18179079 | 18183078 |
| 301 | 88964664 | 88986418 | 88990417 |
| 302 | 62304810 | 62349489 | 62353488 |
| 303 | 70595313 | 70645617 | 70649616 |
| 304 | 74755002 | 74772374 | 74776373 |
| 305 | 149371707 | 149412566 | 149416565 |
| 306 | 80980748 | 81014106 | 81018105 |

TABLE 1.f6-continued

4 kb Sequence Location

| | End1 | Start2 | End2 |
|---|---|---|---|
| 307 | 32958634 | 32978239 | 32982238 |
| 308 | 17735542 | 17802938 | 17806937 |
| 309 | 56923864 | 56991333 | 56995332 |
| 310 | 167107687 | 167149744 | 167153743 |
| 311 | 6773997 | 6813427 | 6817426 |
| 312 | 70635550 | 70645617 | 70649616 |
| 313 | 6484246 | 6494590 | 6498589 |
| 314 | 140647799 | 140673118 | 140677117 |
| 315 | 119247828 | 119295642 | 119299641 |
| 316 | 90767551 | 90798262 | 90802261 |
| 317 | 157254101 | 157266727 | 157270726 |
| 318 | 77360451 | 77413950 | 77417949 |
| 319 | 10349999 | 10361737 | 10365736 |

TABLE 1.g1

| | probe | GeneLocus | Probe_Count_Total |
|---|---|---|---|
| 320 | ORF501_5_68187850_68194388_68258878_68268897_FF | PIK3R1 | 148 |
| 321 | ORF250_2_215347261_215350354_215361328_215366837_RF | FN1 | 42 |
| 322 | TNFRSF19_13_23643081_23657941_23678002_23680230_RR | TNFRSF19 | 60 |
| 323 | TNFRSF19_13_23612221_23617919_23678002_23680230_RR | TNFRSF19 | 60 |
| 324 | ORF312_16_88606860_88608937_88633762_88637512_RR | IL17C | 40 |
| 325 | ORF366_16_28975508_28978445_28988508_28993162_RR | LAT | 58 |
| 326 | ORF73_10_96204016_96209130_96290525_96304713_FF | BLNK | 66 |
| 327 | ORF490_16_2543954_2548518_2569272_2571597_FR | PDPK1 | 60 |
| 328 | TYROBP_19_35889288_35891587_35942103_35947317_FF | TYROBP | 50 |
| 329 | CCL18_17_36023309_36028028_36075902_36084513_FR | CCL18 | 42 |
| 330 | ORF173_4_77571558_77583817_77605999_77607786_FF | CXCL13 | 108 |
| 331 | ORF543_20_2873115_2878192_2940645_2944261_RR | PTPRA | 82 |
| 332 | ORF463_4_102577393_102582880_102627099_102634363_FR | NFKB1 | 64 |
| 333 | ARHGEF7_13_111255999_111262146_111317973_111320769_RR | ARHGEF7 | 122 |
| 334 | BAD_11_64267793_64269811_64288581_64290103_FR | BAD | 70 |
| 335 | ORF112_5_140643798_140647427_140680993_140683629_FF | CD14 | 62 |
| 336 | ORF658_17_42251917_42254441_42312276_42316438_FR | STAT5A | 99 |
| 337 | ORF133_17_63937911_63939713_63953850_63955210_FR | CD79B | 20 |
| 338 | ORF701_13_23612221_23617919_23627958_23632852_FR | TNFRSF19 | 60 |
| 339 | ORF402_16_30100267_30104814_30117766_30120768_RR | MAPK3 | 44 |
| 340 | PTPRA_20_2816709_2821045_2986126_2989451_RF | PTPRA | 82 |
| 341 | ORF401_4_86050968_86053502_86086078_86098061_FF | MAPK10 | 186 |
| 342 | ORF168_15_74750296_74755004_74782868_74787702_FF | CSK | 48 |
| 343 | ORF705_9_114882931_114894596_114920994_114929419_RR | TNFSF8 | 50 |
| 344 | BAD_11_64267793_64269811_64301867_64303120_FR | BAD | 70 |
| 345 | ORF587_17_80636056_80643737_80939071_80942385_FF | RPTOR | 86 |
| 346 | ORF173_4_77571558_77583817_77602626_77605431_FR | CXCL13 | 108 |
| 347 | ORF542_12_6934234_6935639_6946597_6948368_RR | PTPN6 | 46 |
| 348 | ORF143_9_22005915_22007157_22029989_22034039_RR | CDKN2A | 44 |
| 349 | ORF113_5_67178844_67182260_67231162_67233989_FR | CD180 | 38 |
| 350 | IRF1_5_132472660_132477912_132527799_132529394_FR | IRF1 | 42 |
| 351 | ORF58_19_47205563_47207855_47236830_47241014_RF | BBC3 | 56 |
| 352 | ORF104_17_36075902_36084513_36106111_36108394_RF | CCL18 | 42 |
| 353 | AKT1_14_104800011_104801022_104839372_104843321_RF | AKT1 | 60 |
| 354 | ITK_5_157113872_157116385_157266725_157271762_FR | ITK | 26 |
| 355 | ORF531_22_44658236_44661757_44696835_44701888_RF | PRR5 | 64 |
| 356 | ORF305_15_98642083_98644969_98874707_98883774_FR | IGF1R | 104 |
| 357 | IGF2_11_2141386_2143749_2170498_2173159_FR | IGF2 | 32 |
| 358 | TNFRSF25_1_6461604_6466207_6514024_6515315_RR | TNFRSF25 | 68 |
| 359 | ORF401_4_86086215_86098061_86316594_86322797_FR | MAPK10 | 186 |
| 360 | ORF401_4_86098061_86104840_86327055_86336679_FF | MAPK10 | 186 |

TABLE 1.g2

| | Probe_Count_Sig | HyperG_Stats | FDR_HyperG | Percent_Sig | logFC | AveExpr |
|---|---|---|---|---|---|---|
| 320 | 12 | 0.513477047 | 0.99999793 | 8.11 | −0.11882825 | −0.11882825 |
| 321 | 4 | 0.430324418 | 0.99999793 | 9.52 | −0.118808326 | −0.118808326 |
| 322 | 8 | 0.100733588 | 0.781478358 | 13.33 | −0.118340655 | −0.118340655 |
| 323 | 8 | 0.100733588 | 0.781478358 | 13.33 | −0.118259243 | −0.118259243 |
| 324 | 2 | 0.837619347 | 0.99999793 | 5 | −0.117868499 | −0.117868499 |

TABLE 1.g2-continued

| | Probe_Count_Sig | HyperG_Stats | FDR_HyperG | Percent_Sig | logFC | AveExpr |
|---|---|---|---|---|---|---|
| 325 | 4 | 0.686266831 | 0.99999793 | 6.9 | −0.117762431 | −0.117762431 |
| 326 | 4 | 0.779227696 | 0.99999793 | 6.06 | −0.117391959 | −0.117391959 |
| 327 | 6 | 0.340695433 | 0.99999793 | 10 | −0.117182824 | −0.117182824 |
| 328 | 2 | 0.915356314 | 0.99999793 | 4 | −0.117179185 | −0.117179185 |
| 329 | 8 | 0.016095432 | 0.256971894 | 19.05 | −0.117094871 | −0.117094871 |
| 330 | 14 | 0.046569042 | 0.598929617 | 12.96 | −0.117077567 | −0.117077567 |
| 331 | 8 | 0.325435728 | 0.99999793 | 9.76 | −0.11662568 | −0.11662568 |
| 332 | 6 | 0.398773743 | 0.99999793 | 9.38 | −0.116513518 | −0.116513518 |
| 333 | 6 | 0.928958915 | 0.99999793 | 4.92 | −0.116248719 | −0.116248719 |
| 334 | 8 | 0.18964104 | 0.954389149 | 11.43 | −0.116128982 | −0.116128982 |
| 335 | 6 | 0.369692981 | 0.99999793 | 9.68 | −0.116023993 | −0.116023993 |
| 336 | 3 | 0.987493488 | 0.99999793 | 3.03 | −0.11591907 | −0.11591907 |
| 337 | 2 | 0.479107134 | 0.99999793 | 10 | −0.115917608 | −0.115917608 |
| 338 | 8 | 0.100733588 | 0.781478358 | 13.33 | −0.11572367 | −0.11572367 |
| 339 | 4 | 0.466402982 | 0.99999793 | 9.09 | −0.115670925 | −0.115670925 |
| 340 | 8 | 0.325435728 | 0.99999793 | 9.76 | −0.115508213 | −0.115508213 |
| 341 | 10 | 0.931377207 | 0.99999793 | 5.38 | −0.115273143 | −0.115273143 |
| 342 | 6 | 0.178303905 | 0.954389149 | 12.5 | −0.11493711 | −0.11493711 |
| 343 | 4 | 0.568728839 | 0.99999793 | 8 | −0.114816222 | −0.114816222 |
| 344 | 8 | 0.18964104 | 0.954389149 | 11.43 | −0.11476243 | −0.11476243 |
| 345 | 6 | 0.687444338 | 0.99999793 | 6.98 | −0.114623135 | −0.114623135 |
| 346 | 14 | 0.046569042 | 0.598929617 | 12.96 | −0.114256917 | −0.114256917 |
| 347 | 4 | 0.501622356 | 0.99999793 | 8.7 | −0.113829612 | −0.113829612 |
| 348 | 4 | 0.466402982 | 0.99999793 | 9.09 | −0.113818103 | −0.113818103 |
| 349 | 4 | 0.356577228 | 0.99999793 | 10.53 | −0.113814422 | −0.113814422 |
| 350 | 8 | 0.016095432 | 0.256971894 | 19.05 | −0.113325615 | −0.113325615 |
| 351 | 8 | 0.073465475 | 0.710624303 | 14.29 | −0.113310708 | −0.113310708 |
| 352 | 8 | 0.016095432 | 0.256971894 | 19.05 | −0.113014974 | −0.113014974 |
| 353 | 4 | 0.711822793 | 0.99999793 | 6.67 | −0.112838336 | −0.112838336 |
| 354 | 10 | 1.57E−05 | 0.002607465 | 38.46 | −0.112451827 | −0.112451827 |
| 355 | 4 | 0.7582782 | 0.99999793 | 6.25 | −0.112451732 | −0.112451732 |
| 356 | 16 | 0.007797893 | 0.171924974 | 15.38 | −0.11237057 | −0.11237057 |
| 357 | 6 | 0.037675475 | 0.528598335 | 18.75 | −0.111918978 | −0.111918978 |
| 358 | 16 | 6.44E−05 | 0.004967399 | 23.53 | −0.111885742 | −0.111885742 |
| 359 | 10 | 0.931377207 | 0.99999793 | 5.38 | −0.111716151 | −0.111716151 |
| 360 | 10 | 0.931377207 | 0.99999793 | 5.38 | −0.111190729 | −0.111190729 |

TABLE 1.g3

| | t | P.Value | adj.P.Val | B | FC | FC_1 |
|---|---|---|---|---|---|---|
| 320 | −3.28569851 | 0.00795229900 | 0.027348446 | −3.091904234 | 0.920935326 | −1.08585258 |
| 321 | −5.515807304 | 0.00023462500 | 0.002190731 | 0.542703708 | 0.920948045 | −1.085837584 |
| 322 | −5.826586351 | 0.00015163500 | 0.001635661 | 0.997453523 | 0.921246632 | −1.085485651 |
| 323 | −5.468019963 | 0.00025121700 | 0.002297775 | 0.471544728 | 0.92129862 | −1.085424398 |
| 324 | −4.149900419 | 0.00187961300 | 0.009459704 | −1.616672944 | 0.921548181 | −1.085130459 |
| 325 | −5.560189598 | 0.00022026300 | 0.002097026 | 0.608497575 | 0.921615937 | −1.085050681 |
| 326 | −2.849923133 | 0.01686220500 | 0.048027440 | −3.846341043 | 0.92185219 | −1.084772085 |
| 327 | −4.624546759 | 0.00088526700 | 0.005497061 | −0.837900587 | 0.921986273 | −1.084614847 |
| 328 | −4.850787441 | 0.00062519600 | 0.004318657 | −0.476920106 | 0.921988599 | −1.084612111 |
| 329 | −5.670796723 | 0.00018840600 | 0.001897248 | 0.771230471 | 0.922042483 | −1.084548726 |
| 330 | −4.321578858 | 0.00142644200 | 0.007770947 | −1.331816291 | 0.922053542 | −1.084535718 |
| 331 | −5.531878455 | 0.00022931200 | 0.002158503 | 0.566560299 | 0.922342397 | −1.084196068 |
| 332 | −3.011085086 | 0.01275662000 | 0.038978718 | −3.567805275 | 0.922414107 | −1.084111781 |
| 333 | −2.85057896 | 0.01684304500 | 0.047979425 | −3.845210285 | 0.922583427 | −1.083912816 |
| 334 | −4.025458886 | 0.00230126300 | 0.010935916 | −1.825213078 | 0.92266 | −1.08382286 |
| 335 | −3.603776786 | 0.00463332800 | 0.018277657 | −2.542780708 | 0.922727147 | −1.08374399 |
| 336 | −5.245214347 | 0.00034694100 | 0.002861465 | 0.135432481 | 0.922794256 | −1.083665176 |
| 337 | −3.614904266 | 0.00454738300 | 0.018046224 | −2.523664746 | 0.922795192 | −1.083664077 |
| 338 | −6.491621867 | 0.00006230000 | 0.000903821 | 1.924369043 | 0.922919249 | −1.083518413 |
| 339 | −4.570910561 | 0.00096243832 | 0.005851655 | −0.924484832 | 0.922952992 | −1.0834788 |
| 340 | −4.368296497 | 0.00132418300 | 0.007358200 | −1.254903515 | 0.923057091 | −1.083356609 |
| 341 | −2.392253605 | 0.03725465400 | 0.087236543 | −4.624664393 | 0.923207505 | −1.083180103 |
| 342 | −3.586023328 | 0.00477395000 | 0.018706685 | −2.57329588 | 0.923422564 | −1.082927837 |
| 343 | −4.50464524 | 0.00106759200 | 0.006313971 | −1.031974604 | 0.923499943 | −1.082837099 |
| 344 | −4.136140891 | 0.00192196100 | 0.009605427 | −1.639648926 | 0.923534378 | −1.082796725 |
| 345 | −3.091482075 | 0.01110326500 | 0.035177499 | −3.428523652 | 0.923623551 | −1.082692184 |
| 346 | −3.936906064 | 0.00266092900 | 0.012188053 | −1.974587934 | 0.923858036 | −1.082417386 |
| 347 | −5.350503047 | 0.00029759900 | 0.002579295 | 0.295154367 | 0.924131709 | −1.082096837 |
| 348 | −3.781820935 | 0.00343937900 | 0.014676164 | −2.237974722 | 0.924139082 | −1.082088205 |
| 349 | −6.848194152 | 0.00003960000 | 0.000673517 | 2.396134025 | 0.92414144 | −1.082085444 |
| 350 | −6.471854762 | 0.00006390000 | 0.000919240 | 1.897709884 | 0.924454606 | −1.081718879 |
| 351 | −5.120964583 | 0.00041665800 | 0.003238646 | −0.055093408 | 0.924464158 | −1.081707702 |
| 352 | −3.992024269 | 0.00243068300 | 0.011377126 | −1.881520038 | 0.924653681 | −1.081485988 |

TABLE 1.g3-continued

|     | t | P.Value | adj.P.Val | B | FC | FC_1 |
|-----|---|---------|-----------|---|----|----|
| 353 | −2.287328866 | 0.04462249800 | 0.099984429 | −4.798481305 | 0.924766899 | −1.081353584 |
| 354 | −4.745750173 | 0.00073410000 | 0.004795176 | −0.643651395 | 0.925014684 | −1.081063919 |
| 355 | −3.502877434 | 0.00549380500 | 0.020792455 | −2.716459446 | 0.925014745 | −1.081063848 |
| 356 | −5.696914179 | 0.00018162800 | 0.001849178 | 0.809399196 | 0.925066785 | −1.081003032 |
| 357 | −3.235990306 | 0.00865942800 | 0.029201748 | −3.178032026 | 0.925356395 | −1.08066471 |
| 358 | −5.236400527 | 0.00035145200 | 0.002884770 | 0.121989924 | 0.925377713 | −1.080639815 |
| 359 | −3.160153052 | 0.00986453300 | 0.032155286 | −3.309487854 | 0.925486499 | −1.080512791 |
| 360 | −2.563478976 | 0.02771024400 | 0.069657481 | −4.336632301 | 0.925823617 | −1.080119346 |

TABLE 1.g4

| | LS | Loop detected | Probe sequence 60 mer |
|---|---|---|---|
| 320 | −1 | PD-L1 responder | CTGAGTCTTCATTACCAAAAAAAAAAGTTCGACAGTCCTTGGGCACCAGCGGTGTGTGGG (SEQ ID NO: 321) |
| 321 | −1 | PD-L1 responder | GTAATAAACATACAAACTTAAACGTAGTTCGAGGTGCCTGCCACCACGTCATGCATGGTG (SEQ ID NO: 322) |
| 322 | −1 | PD-L1 responder | TTTGGTACTGACAGAACATTACTCTGGATCGAGCACAGCGCCGGCTGGGGTACCTGGCAC (SEQ ID NO: 323) |
| 323 | −1 | PD-L1 responder | AAAGAGGGAAAACAGCTGAAAGGGAAGCTCGAGCACAGCGCCGGCTGGGGTACCTGGCAC (SEQ ID NO: 324) |
| 324 | −1 | PD-L1 responder | CTCCAGCGATGGGTGGCTACGAACACCCTCGATGGGCGTCCACGCCCTCCAGGGACGTCC (SEQ ID NO: 325) |
| 325 | −1 | PD-L1 responder | GCTACTGTCCCCGATGTTGAAGAACTGCTCGAGACTGACCTGGCCAACATGGCGAAACCC (SEQ ID NO: 326) |
| 326 | −1 | PD-L1 responder | ATTCAATAAGAAAGAATGACTGTCACTTTCGATGCTGTCCTACCTGAGCTCATTTTCAAC (SEQ ID NO: 327) |
| 327 | −1 | PD-L1 responder | ACATGACCGTGATACCTCTGTCACTCTGTCGATCATTTGCGCCCAGGAGTTTGAGACCAG (SEQ ID NO: 328) |
| 328 | −1 | PD-L1 responder | ATACTGAGGTTTAAAAAGTTCTTTTTTTTCGAAACACTATGCCCCTGCTCCTAGGCCCCT (SEQ ID NO: 329) |
| 329 | −1 | PD-L1 responder | TGAGCTAATAAACTATTTCTGGTTTTGCTCGAGCCATCCTCCCAGTGACACTCCGCAAAG (SEQ ID NO: 330) |
| 330 | −1 | PD-L1 responder | GGCACCTGTTAGCAATGAAGGATAACCATCGATCAATGAAGCGTCTAGGGATAAAGACTG (SEQ ID NO: 331) |
| 331 | −1 | PD-L1 responder | ATGTCTAGCCACCAGGGCGGCCTGCAACTCGACCTCCCAGGCTCATGGGATCCTCCTGTC (SEQ ID NO: 332) |
| 332 | −1 | PD-L1 responder | TGTGATTGTTTGCAGATGACATCCAGATTCGATATTTTACATGGAATCTTTCCCTTTTTA (SEQ ID NO: 333) |
| 333 | −1 | PD-L1 responder | CTATTTTAGGAAAAAAATAATTAAAATATCGATTACATCGGCAAAGACCCTATTTCCAAA (SEQ ID NO: 334) |
| 334 | −1 | PD-L1 responder | GCACTACCCCGGCCTGCCGGAGCCCCAGTCGATGATGGCTTCCTCCCCCAGAGCACCAGC (SEQ ID NO: 335) |
| 335 | −1 | PD-L1 responder | GCGGGGGCTTCCCTCAACTTCAGGGAGGTCGAACCCCTGACCTCAGGCAATCCATCTGCC (SEQ ID NO: 336) |
| 336 | −1 | PD-L1 responder | TTCCATAGATTACTTTTCAAATCATCCTTCGAAGCTGGCGGCTGAGGGCCCGGCGCCAAG (SEQ ID NO: 337) |
| 337 | −1 | PD-L1 responder | TGGGCCTTCCCTGCTGCACGCCCCAGGGTCGAACCAGGATTCTAGTCATTGTATAACTTT (SEQ ID NO: 338) |
| 338 | −1 | PD-L1 responder | GCACTACAGACAAAAGACTCTAACTGGATCGATCCTCATTTTTATAATAGGTAAACATTC (SEQ ID NO: 339( |
| 339 | −1 | PD-L1 responder | TCCTGAAATGAACAGGTCATCTGCCTATTCGATGGACTTGGTATAGCCCTGGGGGAGAGG (SEQ ID NO: 340) |

TABLE 1.g4-continued

| | LS | Loop detected | Probe sequence 60 mer |
|---|---|---|---|
| 340 | -1 | PD-L1 responder | ACTCCATCTCAAAAAAACAAGAGCTTCCTCGAACTGGCGGCAACCGCTGCAGCGCCTGCT (SEQ ID NO: 341) |
| 341 | -1 | PD-L1 responder | TTCCCCAATTTTGTAGCCTCTACTTATCTCGACACTAAATCAAGTCTTTAACAGGTCAAT (SEQ ID NO: 342) |
| 342 | -1 | PD-L1 responder | GAGTTCAGCGTGCCGCCGGGCGTGAAAGTCGACTCTGGGCCCAGACCACAGAAGGAGGGG (SEQ ID NO: 343) |
| 343 | -1 | PD-L1 responder | GGGGCCTGGCCCAGGCCTAGCCCTGAGCTCGAGTAATACTGACACTCCTGGCCCACAGAA (SEQ ID NO:344) |
| 344 | -1 | PD-L1 responder | GCACTACCCCGGCCTGCCGGAGCCCCAGTCGACATGTTGCCCCAGCTGGTCTCAAACTCC (SEQ ID NO: 345) |
| 345 | -1 | PD-L1 responder | CTTTTCCATTGCTTCCTCAGATCCTCTGTCGAATGCCGGCTCTGTTTCGCACCCTGCTCA (SEQ ID NO: 346) |
| 346 | -1 | PD-L1 responder | GGCACCTGTTAGCAATGAAGGATAACCATCGATTCCAAAGTGAAGCAAAAAAAAAACTTC (SEQ ID NO: 347) |
| 347 | -1 | PD-L1 responder | CTGACCCCTCCAGGGGAGGCCCGGCCCCTCGAGGAGGAAGTGGCTGATTACTGAGCGGTT (SEQ ID NO: 348) |
| 348 | -1 | PD-L1 responder | CCCAATTTCCCACCCCCACCCACCTAATTCGATTTTAAGTCTATTTTGTTAGATCTAAAG (SEQ ID NO: 349) |
| 349 | -1 | PD-L1 responder | GACCTAAGGATTAAGAAGATTAATGGAGTCGAACTAATCTTGCATTCCTAGGATGATACC (SEQ ID NO: 350) |
| 350 | -1 | PD-L1 responder | GTGTCTCGGCCCCTGGGGCCCCACCCTTCGAACATTACAACCTAATCTGTGCCCACACA (SEQ ID NO: 351) |
| 351 | -1 | PD-L1 responder | CGTGGATCCAGACTGGGAGCCCCCAGCCTCGAGCAGGATTCTGAGGCTCCCTGTAGACAA (SEQ ID NO: 352) |
| 352 | -1 | PD-L1 responder | AGCAATTACAAACAGCAGAATGGAATCCTCGAGCCATCCTCCCAGTGACACTCCGCAAAG (SEQ ID NO: 353) |
| 353 | -1 | PD-L1 responder | TAGGCCTGGGGGCCGAAAGGAAGAAGCTTCGACATCCTGCTTGAATGTTTGGAAGAGGGT (SEQ ID NO: 354) |
| 354 | -1 | PD-L1 responder | TGCTCCTGCCTGAGTAACTAAATGTCTTTCGATGTTTGGGGCGGAGGGCTTTGATGAGA (SEQ ID NO: 355) |
| 355 | -1 | PD-L1 responder | CTGTGGAGGGAGACCTCCGGGGCCGGGGTCGATCATCCATGTAGAAGACGCTAAGGAATC (SEQ ID NO: 356) |
| 356 | -1 | PD-L1 responder | TGTCTTTTGATTTTTGTCTTAAATTGCATCGAAGACCCCTTCCATTGGGCATTCATCTAA (SEQ ID NO: 357) |
| 357 | -1 | PD-L1 responder | TAACGTCCAAGAAAATTATTGTGACCCGTCGATCCCAGAGCCGTCCCAGGCCTGGACAGA (SEQ ID NO: 358) |
| 358 | -1 | PD-L1 responder | CGCACGCTGGGGCTGCGCGAGGCAGAGATCGAGAAGCATAAAGCAGGGACAGGTATGGAG (SEQ ID NO: 359) |
| 359 | -1 | PD-L1 responder | ATTGACCTGTTAAAGACTTGATTTAGTGTCGAAATAAGACATAAAAGCAAAGCATTTTGC (SEQ ID NO: 360) |
| 360 | -1 | PD-L1 responder | ATGACCTTGTTTTATTACTTTTTACTCTTCGAGGAGAATGTTGAGCAGAAATATGGAATA (SEQ ID NO: 361) |

TABLE 1.g5

| | | Probe Location | | | | 4 kb Sequence Location | |
|---|---|---|---|---|---|---|---|
| | Chr | Start1 | End1 | Start2 | End2 | Chr | Start1 |
| 320 | 5 | 68194357 | 68194386 | 68268866 | 68268895 | 5 | 68190387 |
| 321 | 2 | 215347263 | 215347292 | 215366806 | 215366835 | 2 | 215347263 |
| 322 | 13 | 23643083 | 23643112 | 23678004 | 23678033 | 13 | 23643083 |
| 323 | 13 | 23612223 | 23612252 | 23678004 | 23678033 | 13 | 23612223 |

TABLE 1.g5-continued

| | | Probe Location | | | 4 kb Sequence Location | |
|---|---|---|---|---|---|---|
| | Chr | Start1 | End1 | Start2 | End2 | Chr | Start1 |
| 324 | 16 | 88606862 | 88606891 | 88633764 | 88633793 | 16 | 88606862 |
| 325 | 16 | 28975510 | 28975539 | 28988510 | 28988539 | 16 | 28975510 |
| 326 | 10 | 96209099 | 96209128 | 96304682 | 96304711 | 10 | 96205129 |
| 327 | 16 | 2548487 | 2548516 | 2569274 | 2569303 | 16 | 2544517 |
| 328 | 19 | 35891556 | 35891585 | 35947286 | 35947315 | 19 | 35887586 |
| 329 | 17 | 36027997 | 36028026 | 36075904 | 36075933 | 17 | 36024027 |
| 330 | 4 | 77583786 | 77583815 | 77607755 | 77607784 | 4 | 77579816 |
| 331 | 20 | 2873117 | 2873146 | 2940647 | 2940676 | 20 | 2873117 |
| 332 | 4 | 102582849 | 102582878 | 102627101 | 102627130 | 4 | 102578879 |
| 333 | 13 | 111256001 | 111256030 | 111317975 | 111318004 | 13 | 111256001 |
| 334 | 11 | 64269780 | 64269809 | 64288583 | 64288612 | 11 | 64265810 |
| 335 | 5 | 140647396 | 140647425 | 140683598 | 140683627 | 5 | 140643426 |
| 336 | 17 | 42254410 | 42254439 | 42312278 | 42312307 | 17 | 42250440 |
| 337 | 17 | 63939682 | 63939711 | 63953852 | 63953881 | 17 | 63935712 |
| 338 | 13 | 23617888 | 23617917 | 23627960 | 23627989 | 13 | 23613918 |
| 339 | 16 | 30100269 | 30100298 | 30117768 | 30117797 | 16 | 30100269 |
| 340 | 20 | 2816711 | 2816740 | 2989420 | 2989449 | 20 | 2816711 |
| 341 | 4 | 86053471 | 86053500 | 86098030 | 86098059 | 4 | 86049501 |
| 342 | 15 | 74754973 | 74755002 | 74787671 | 74787700 | 15 | 74751003 |
| 343 | 9 | 114882933 | 114882962 | 114920996 | 114921025 | 9 | 114882933 |
| 344 | 11 | 64269780 | 64269809 | 64301869 | 64301898 | 11 | 64265810 |
| 345 | 17 | 80643706 | 80643735 | 80942354 | 80942383 | 17 | 80639736 |
| 346 | 4 | 77583786 | 77583815 | 77602628 | 77602657 | 4 | 77579816 |
| 347 | 12 | 6934236 | 6934265 | 6946599 | 6946628 | 12 | 6934236 |
| 348 | 9 | 22005917 | 22005946 | 22029991 | 22030020 | 9 | 22005917 |
| 349 | 5 | 67182229 | 67182258 | 67231164 | 67231193 | 5 | 67178259 |
| 350 | 5 | 132477881 | 132477910 | 132527801 | 132527830 | 5 | 132473911 |
| 351 | 19 | 47205565 | 47205594 | 47240983 | 47241012 | 19 | 47205565 |
| 352 | 17 | 36075904 | 36075933 | 36108363 | 36108392 | 17 | 36075904 |
| 353 | 14 | 104800013 | 104800042 | 104843290 | 104843319 | 14 | 104800013 |
| 354 | 5 | 157116354 | 157116383 | 157266727 | 157266756 | 5 | 157112384 |
| 355 | 22 | 44658238 | 44658267 | 44701857 | 44701886 | 22 | 44658238 |
| 356 | 15 | 98644938 | 98644967 | 98874709 | 98874738 | 15 | 98640968 |
| 357 | 11 | 2143718 | 2143747 | 2170500 | 2170529 | 11 | 2139748 |
| 358 | 1 | 6461606 | 6461635 | 6514026 | 6514055 | 1 | 6461606 |
| 359 | 4 | 86098030 | 86098059 | 86316596 | 86316625 | 4 | 86094060 |
| 360 | 4 | 86104809 | 86104838 | 86336648 | 86336677 | 4 | 86100839 |

TABLE 1.g6

| | 4 kb Sequence Location | | |
|---|---|---|---|
| | End1 | Start2 | End2 |
| 320 | 68194386 | 68264896 | 68268895 |
| 321 | 215351262 | 215362836 | 215366835 |
| 322 | 23647082 | 23678004 | 23682003 |
| 323 | 23616222 | 23678004 | 23682003 |
| 324 | 88610861 | 88633764 | 88637763 |
| 325 | 28979509 | 28988510 | 28992509 |
| 326 | 96209128 | 96300712 | 96304711 |
| 327 | 2548516 | 2569274 | 2573273 |
| 328 | 35891585 | 35943305 | 35947315 |
| 329 | 36028026 | 36075904 | 36079903 |
| 330 | 77583815 | 77603785 | 77607784 |
| 331 | 2877116 | 2940647 | 2944646 |
| 332 | 102582878 | 102627101 | 102631100 |
| 333 | 111260000 | 111317975 | 111321974 |
| 334 | 64269809 | 64288583 | 64292582 |
| 335 | 140647425 | 140679628 | 140683627 |
| 336 | 42254439 | 42312278 | 42316277 |
| 337 | 63939711 | 63953852 | 63957851 |
| 338 | 23617917 | 23627960 | 23631959 |
| 339 | 30104268 | 30117768 | 30121767 |
| 340 | 2820710 | 2985450 | 2989449 |
| 341 | 86053500 | 86094060 | 86098059 |
| 342 | 74755002 | 74783701 | 74787700 |
| 343 | 114886932 | 114920996 | 114924995 |
| 344 | 64269809 | 64301869 | 64305868 |
| 345 | 80643735 | 80938384 | 80942383 |
| 346 | 77583815 | 77602628 | 77606627 |
| 347 | 6938235 | 6946599 | 6950598 |
| 348 | 22009916 | 22029991 | 22033990 |
| 349 | 67182258 | 67231164 | 67235163 |
| 350 | 132477910 | 132527801 | 132531800 |
| 351 | 47209564 | 47237013 | 47241012 |
| 352 | 36079903 | 36104393 | 36108392 |
| 353 | 104804012 | 104839320 | 104843319 |
| 354 | 157116383 | 157266727 | 157270726 |
| 355 | 44662237 | 44697887 | 44701886 |
| 356 | 98644967 | 98874709 | 98878708 |
| 357 | 2143747 | 2170500 | 2174499 |
| 358 | 6465605 | 6514026 | 6518025 |
| 359 | 86098059 | 86316596 | 86320595 |
| 360 | 86104838 | 86332678 | 86336677 |

TABLE 2.a

| | GeneLocus | Probe_Count_Total | Probe_Count_Sig | HyperG_Stats | FDR_HyperG | Percent_Sig |
|---|---|---|---|---|---|---|
| 1 | PLEKHG5 | 61 | 16 | 0.0000150989812546337 | 0.00260746509581861 | 26.23 |
| 2 | TNFRSF25 | 68 | 16 | 0.0000643723460057543 | 0.00496739936677737 | 23.53 |
| 3 | IGF1R | 104 | 16 | 0.0077978929721586500 | 0.17192497362426000 | 15.38 |
| 4 | CD6 | 56 | 14 | 0.0000902676865389941 | 0.00597056269536490 | 25 |
| 5 | CXCL13 | 108 | 14 | 0.0465690415089977000 | 0.59892961718516500 | 12.96 |
| 6 | ESPN | 74 | 13 | 0.0051548594302418800 | 0.12817437438629700 | 17.57 |
| 7 | IKBKB | 46 | 12 | 0.0001836303678197500 | 0.01062760753756800 | 26.09 |
| 8 | PAG1 | 144 | 12 | 0.4744815327484530000 | 0.99999793037206300 | 8.33 |
| 9 | PIK3R1 | 148 | 12 | 0.5134770470327030000 | 0.99999793037206300 | 8.11 |
| 10 | PTK2 | 248 | 12 | 0.9797792860301600000 | 0.99999793037206300 | 4.84 |
| 11 | SLC15A3 | 34 | 11 | 0.0000393466912660957 | 0.00364350361124046 | 32.35 |
| 12 | NOL9 | 41 | 11 | 0.0002590590457356080 | 0.01209080667757340 | 26.83 |
| 13 | ITK | 26 | 10 | 0.0000157274410598937 | 0.00260746509581861 | 38.46 |
| 14 | TMEM132A | 28 | 10 | 0.0000335363454334773 | 0.00364350361124046 | 35.71 |
| 15 | BOK | 44 | 10 | 0.0019694080241128800 | 0.07598632626368880 | 22.73 |
| 16 | MAPK10 | 186 | 10 | 0.9313772067444170000 | 0.99999793037206300 | 5.38 |
| 17 | PTPRC | 214 | 10 | 0.9784912428998600000 | 0.99999793037206300 | 4.67 |
| 18 | THAP4 | 38 | 9 | 0.0024177875111874500 | 0.08611043212921460 | 23.68 |

TABLE 2.b

| | GeneLocus | Probe_Count_Total | Probe_Count_Sig | HyperG_Stats | FDR_HyperG | Percent_Sig |
|---|---|---|---|---|---|---|
| 19 | C8B | 151 | 9 | 0.855915990410304000 | 0.9999979303720630 | 5.96 |
| 20 | TMEM239 | 24 | 8 | 0.000359183930018026 | 0.0151183781453042 | 33.33 |
| 21 | STAMBPL1 | 35 | 8 | 0.005252298370397750 | 0.1281743743862970 | 22.86 |
| 22 | CCDC9 | 37 | 8 | 0.007481143494126220 | 0.1719249736242600 | 21.62 |
| 23 | CYFIP2 | 40 | 8 | 0.012066037542322000 | 0.2234630152838030 | 20 |
| 24 | ICOSLG | 40 | 8 | 0.012066037542322000 | 0.2234630152838030 | 20 |
| 25 | ITGAX | 41 | 8 | 0.013975308160204600 | 0.2396506547472120 | 19.51 |
| 26 | CCL18 | 42 | 8 | 0.016095431795565600 | 0.2569718938395470 | 19.05 |
| 27 | IRF1 | 42 | 8 | 0.016095431795565600 | 0.2569718938395470 | 19.05 |
| 28 | ACTA2 | 48 | 8 | 0.033871482209146300 | 0.5058869762204760 | 16.67 |
| 29 | FAS | 50 | 8 | 0.041957105143561900 | 0.5550325623276900 | 16 |
| 30 | ITGAM | 50 | 8 | 0.041957105143561900 | 0.5550325623276900 | 16 |
| 31 | BBC3 | 56 | 8 | 0.073465474806733000 | 0.7106243027906220 | 14.29 |
| 32 | PRDX5 | 57 | 8 | 0.079810936814497600 | 0.7106243027906220 | 14.04 |
| 33 | TRMT112 | 57 | 8 | 0.079810936814497600 | 0.7106243027906220 | 14.04 |
| 34 | PLCB3 | 58 | 8 | 0.086471735887070700 | 0.7554040323719570 | 13.79 |
| 35 | TNFRSF19 | 60 | 8 | 0.100733588397967000 | 0.7814783579039930 | 13.33 |
| 36 | ESRRA | 64 | 8 | 0.132924777221067000 | 0.8316779980182970 | 12.5 |
| 37 | BAD | 70 | 8 | 0.189641040334946000 | 0.9543891486421730 | 11.43 |
| 38 | GPR137 | 70 | 8 | 0.189641040334946000 | 0.95438914864217300 | 11.43 |
| 39 | KCNK4 | 70 | 8 | 0.189641040334946000 | 0.95438914864217300 | 11.43 |
| 40 | TEX40 | 70 | 8 | 0.189641040334946000 | 0.95438914864217300 | 11.43 |
| 41 | C8A | 166 | 8 | 0.957766442168891000 | 0.99999793037206300 | 4.82 |
| 42 | PIK3R2 | 116 | 8 | 0.711020879711135000 | 0.99999793037206300 | 6.9 |
| 43 | PTPRA | 82 | 8 | 0.325435728472061000 | 0.99999793037206300 | 9.76 |
| 44 | PVRL1 | 96 | 8 | 0.497039718077448000 | 0.99999793037206300 | 8.33 |
| 45 | STK25 | 28 | 7 | 0.005259855536370700 | 0.1281743743862970 | 25 5 |
| 46 | CCL4 | 32 | 7 | 0.011323324912557700 | 0.22346301528380300 | 21.88 |
| 47 | CCL3 | 33 | 7 | 0.013410837025657200 | 0.23881605934151000 | 21.21 |
| 48 | SAE1 | 53 | 7 | 0.124484434023389000 | 0.83167799801829700 | 13.21 |
| 49 | PRPF19 | 9 | 6 | 0.000016895022219127 | 0.00260746509581861 | 66.67 |
| 50 | TMEM109 | 13 | 6 | 0.000261140532992945 | 0.01209080667757340 | 46.15 |
| 51 | C5AR1 | 20 | 6 | 0.003637021795314110 | 0.10524631820190200 | 30 |
| 52 | INAFM1 | 20 | 6 | 0.003637021795314110 | 0.10524631820190200 | 30 |
| 53 | TH | 20 | 6 | 0.003637021795314110 | 0.10524631820190200 | 30 |
| 54 | INS | 24 | 6 | 0.009607292033915510 | 0.20218982780467700 | 25 |
| 55 | IGF2 | 32 | 6 | 0.037675475247509100 | 0.52859833453323400 | 18.75 |
| 56 | INS-IGF2 | 32 | 6 | 0.037675475247509100 | 0.52859833453323400 | 18.75 |
| 57 | C5orf56 | 36 | 6 | 0.062022042427259000 | 0.70039525960538800 | 16.67 |
| 58 | HARS2 | 36 | 6 | 0.062022042427259000 | 0.70039525960538800 | 16.67 |
| 59 | SHH | 36 | 6 | 0.062022042427259000 | 0.70039525960538800 | 16.67 |
| 60 | CYP1A2 | 38 | 6 | 0.077003035039102400 | 0.71062430279062200 | 15.79 |
| 61 | GPR162 | 41 | 6 | 0.102947013034154000 | 0.78147835790399300 | 14.63 |
| 62 | CD4 | 42 | 6 | 0.112492544866268000 | 0.78915224656185100 | 14.29 |
| 63 | PHF19 | 42 | 6 | 0.1124925448662680 | 0.789152246561851 | 14.29 |
| 64 | TRAF1 | 42 | 6 | 0.1124925448662680 | 0.789152246561851 | 14.29 |
| 65 | DND1 | 43 | 6 | 0.1224692325513000 | 0.831677998018297 | 13.95 |

TABLE 2.c

| | GeneLocus | Probe_Count_Total | Probe_Count_Sig | HyperG_Stats | FDR_HyperG | Percent_Sig |
|---|---|---|---|---|---|---|
| 66 | FKBP2 | 44 | 6 | 0.1328638379525590 | 0.831677998018297 | 13.64 |
| 67 | HARS | 43 | 6 | 0.1224692325513000 | 0.831677998018297 | 13.95 |
| 68 | PPP1R14B | 44 | 6 | 0.1328638379525590 | 0.831677998018297 | 13.64 |
| 69 | CSK | 48 | 6 | 0.1783039053731780 | 0.954389148642173 | 12.5 |
| 70 | WDR55 | 47 | 6 | 0.1663997350749940 | 0.954389148642173 | 12.77 |
| 71 | CD82 | 50 | 6 | 0.2030836877588850 | 0.988148591681669 | 12 |
| 72 | ARHGEF7 | 122 | 6 | 0.9289589150111290 | 0.999997930372063 | 4.92 |
| 73 | CD14 | 62 | 6 | 0.3696929812329760 | 0.999997930372063 | 9.68 |
| 74 | IK | 54 | 6 | 0.2559285532533580 | 0.999997930372063 | 11.11 |
| 75 | MAPKAP1 | 52 | 6 | 0.2290176352787400 | 0.999997930372063 | 11.54 |
| 76 | NDUFA2 | 62 | 6 | 0.3696929812329760 | 0.999997930372063 | 9.68 |
| 77 | NFKB1 | 64 | 6 | 0.3987737426208590 | 0.999997930372063 | 9.38 |
| 78 | PAK1 | 136 | 6 | 0.9638515628459290 | 0.999997930372063 | 4.41 |
| 79 | PDPK1 | 60 | 6 | 0.3406954325448980 | 0.999997930372063 | 10 |
| 80 | PTPN11 | 56 | 6 | 0.2836340134590460 | 0.999997930372063 | 10.71 |
| 81 | RPTOR | 86 | 6 | 0.6874443375772050 | 0.999997930372063 | 6.98 |
| 82 | SYK | 78 | 6 | 0.5927956968440460 | 0.999997930372063 | 7.69 |
| 83 | TMCO6 | 62 | 6 | 0.3696929812329760 | 0.999997930372063 | 9.68 |
| 84 | LAG3 | 29 | 5 | 0.0755533118617940 | 0.710624302790622 | 17.24 |
| 85 | MLF2 | 29 | 5 | 0.0755533118617940 | 0.710624302790622 | 17.24 |
| 86 | PTMS | 29 | 5 | 0.0755533118617940 | 0.710624302790622 | 17.24 |
| 87 | VEGFB | 28 | 5 | 0.0666925244865456 | 0.710624302790622 | 17.86 |
| 88 | AMDHD2 | 47 | 5 | 0.3164628013515880 | 0.999997930372063 | 10.64 |
| 89 | ATP6V0C | 47 | 5 | 0.3164628013515880 | 0.999997930372063 | 10.64 |
| 90 | CEMP1 | 47 | 5 | 0.3164628013515880 | 0.999997930372063 | 10.64 |
| 91 | HES2 | 44 | 5 | 0.2689995823620770 | 0.999997930372063 | 11.36 |
| 92 | RP11-20123.1 | 47 | 5 | 0.3164628013515880 | 0.999997930372063 | 10.64 |
| 93 | RP11-20123.3 | 47 | 5 | 0.3164628013515880 | 0.999997930372063 | 10.64 |
| 94 | IL5 | 20 | 4 | 0.0689391987008704 | 0.710624302790622 | 20 |
| 95 | DNAJC4 | 23 | 4 | 0.1046472099137100 | 0.781478357903993 | 17.39 |
| 96 | FERMT3 | 23 | 4 | 0.1046472099137100 | 0.781478357903993 | 17.39 |
| 97 | HLA-DQB1 | 22 | 4 | 0.0919452518195525 | 0.781478357903993 | 18.18 |
| 98 | NUDT22 | 23 | 4 | 0.1046472099137100 | 0.781478357903993 | 17.39 |
| 99 | TRPT1 | 23 | 4 | 0.1046472099137100 | 0.781478357903993 | 17.39 |
| 100 | CDCA3 | 26 | 4 | 0.1470546899826340 | 0.876931603559146 | 15.38 |
| 101 | GNB3 | 26 | 4 | 0.1470546899826340 | 0.876931603559146 | 15.38 |
| 102 | CYP1A1 | 27 | 4 | 0.1624652709870240 | 0.952169879329012 | 14.81 |
| 103 | HLA-DQA1 | 28 | 4 | 0.1784273954037700 | 0.954389148642173 | 14.29 |
| 104 | ITGAD | 28 | 4 | 0.1784273954037700 | 0.954389148642173 | 14.29 |
| 105 | PCED1A | 28 | 4 | 0.1784273954037700 | 0.954389148642173 | 14.29 |
| 106 | PRF1 | 28 | 4 | 0.1784273954037700 | 0.954389148642173 | 14.29 |
| 107 | CPLX3 | 29 | 4 | 0.1948872487704860 | 0.970245120222958 | 13.79 |
| 108 | AARS2 | 30 | 4 | 0.2117903328050300 | 0.988148591681669 | 13.33 |
| 109 | P3H3 | 30 | 4 | 0.2117903328050300 | 0.988148591681669 | 13.33 |
| 110 | RBM33 | 30 | 4 | 0.2117903328050300 | 0.988148591681669 | 13.33 |
| 111 | AC009133.22 | 56 | 4 | 0.6591506486986940 | 0.999997930372063 | 7.14 |
| 112 | AKT1 | 60 | 4 | 0.7118227932872120 | 0.999997930372063 | 6.67 |
| 113 | ATN1 | 46 | 4 | 0.501622355732139 | 0.999997930372063 | 8.7 |

TABLE 2.d

| | GeneLocus | Probe_Count_Total | Probe_Count_Sig | HyperG_Stats | FDR_HyperG | Percent_Sig |
|---|---|---|---|---|---|---|
| 114 | BLNK | 66 | 4 | 0.779227696215700 | 0.999997930372063 | 6.06 |
| 115 | C12orf57 | 46 | 4 | 0.501622355732139 | 0.999997930372063 | 8.7 |
| 116 | C5 | 41 | 4 | 0.412035428682661 | 0.999997930372063 | 9.76 |
| 117 | CASP8 | 41 | 4 | 0.412035428682661 | 0.999997930372063 | 9.76 |
| 118 | CCR6 | 46 | 4 | 0.501622355732139 | 0.999997930372063 | 8.7 |
| 119 | CD180 | 38 | 4 | 0.356577228215362 | 0.999997930372063 | 10.53 |
| 120 | CD19 | 56 | 4 | 0.659150648698694 | 0.999997930372063 | 7.14 |
| 121 | CD33 | 32 | 4 | 0.246707930589528 | 0.999997930372063 | 12.5 |
| 122 | CDC37 | 43 | 4 | 0.448457218409109 | 0.999997930372063 | 9.3 |
| 123 | CDKN2A | 44 | 4 | 0.466402982013812 | 0.999997930372063 | 9.09 |
| 124 | CDKN2B | 32 | 4 | 0.246707930589528 | 0.999997930372063 | 12.5 |
| 125 | CRADD | 231 | 4 | 0.999992974704591 | 0.999997930372063 | 1.73 |
| 126 | DAB1 | 60 | 4 | 0.711822793287212 | 0.999997930372063 | 6.67 |
| 127 | DNMT3L | 32 | 4 | 0.246707930589528 | 0.999997930372063 | 12.5 |
| 128 | EMG1 | 40 | 4 | 0.393623595746639 | 0.999997930372063 | 10 |
| 129 | ENO2 | 40 | 4 | 0.393623595746639 | 0.999997930372063 | 10 |
| 130 | ESR1 | 198 | 4 | 0.999928673478001 | 0.999997930372063 | 2.02 |
| 131 | FAM167B | 33 | 4 | 0.264614551688586 | 0.999997930372063 | 12.12 |

TABLE 2.d-continued

| | GeneLocus | Probe_Count_Total | Probe_Count_Sig | HyperG_Stats | FDR_HyperG | Percent_Sig |
|---|---|---|---|---|---|---|
| 132 | FN1 | 42 | 4 | 0.430324417757699 | 0.999997930372063 | 9.52 |
| 133 | GAB2 | 132 | 4 | 0.994374946176707 | 0.999997930372063 | 3.03 |
| 134 | GDPD3 | 44 | 4 | 0.466402982013812 | 0.999997930372063 | 9.09 |
| 135 | GPR31 | 44 | 4 | 0.466402982013812 | 0.999997930372063 | 9.09 |
| 136 | HDAC1 | 33 | 4 | 0.264614551688586 | 0.999997930372063 | 12.12 |
| 137 | IL17B | 44 | 4 | 0.466402982013812 | 0.999997930372063 | 9.09 |
| 138 | KIAA1468 | 48 | 4 | 0.535784564968372 | 0.999997930372063 | 8.33 |
| 139 | LAT | 58 | 4 | 0.686266830720114 | 0.999997930372063 | 6.9 |
| 140 | LCK | 46 | 4 | 0.501622355732139 | 0.999997930372063 | 8.7 |
| 141 | LMAN1L | 33 | 4 | 0.264614551688586 | 0.999997930372063 | 12.12 |
| 142 | LPCAT3 | 37 | 4 | 0.338021739919006 | 0.999997930372063 | 10.81 |
| 143 | LRRC23 | 43 | 4 | 0.448457218409109 | 0.999997930372063 | 9.3 |
| 144 | MANBA | 33 | 4 | 0.264614551688586 | 0.999997930372063 | 12.12 |
| 145 | MAPK3 | 44 | 4 | 0.466402982013812 | 0.999997930372063 | 9.09 |
| 146 | MFRP | 84 | 4 | 0.909003420730453 | 0.999997930372063 | 4.76 |
| 147 | MTOR | 60 | 4 | 0.711822793287212 | 0.999997930372063 | 6.67 |
| 148 | MYC | 42 | 4 | 0.430324417757699 | 0.999997930372063 | 9.52 |
| 149 | NCK2 | 66 | 4 | 0.779227696215700 | 0.999997930372063 | 6.06 |
| 150 | NFATC2IP | 54 | 4 | 0.630491543675306 | 0.999997930372063 | 7.41 |
| 151 | NFKBIE | 44 | 4 | 0.466402982013812 | 0.999997930372063 | 9.09 |
| 152 | PHB2 | 40 | 4 | 0.393623595746639 | 0.999997930372063 | 10 |
| 153 | PRR5 | 64 | 4 | 0.758278200178880 | 0.999997930372063 | 6.25 |
| 154 | PRR5-ARHGAP8 | 62 | 4 | 0.735820497241091 | 0.999997930372063 | 6.45 |
| 155 | PTPN6 | 46 | 4 | 0.501622355732139 | 0.999997930372063 | 8.7 |
| 156 | RP11-145E5.5 | 44 | 4 | 0.466402982013812 | 0.999997930372063 | 9.09 |
| 157 | RP11-444E17.6 | 39 | 4 | 0.375124758475278 | 0.999997930372063 | 10.26 |
| 158 | RP3-461F17.3 | 40 | 4 | 0.393623595746639 | 0.999997930372063 | 10 |
| 159 | SIRPA | 56 | 4 | 0.659150648698694 | 0.999997930372063 | 7.14 |
| 160 | SLC35B2 | 44 | 4 | 0.466402982013812 | 0.999997930372063 | 9.09 |
| 161 | SPN | 56 | 4 | 0.659150648698694 | 0.999997930372063 | 7.14 |

TABLE 2.e

| | GeneLocus | Probe_Count_Total | Probe_Count_Sig | HyperG_Stats | FDR_HyperG | Percent_Sig |
|---|---|---|---|---|---|---|
| 162 | SPNS1 | 58 | 4 | 0.686266830720114 | 0.999997930372063 | 6.9 |
| 163 | TAB2 | 151 | 4 | 0.998322792214390 | 0.999997930372063 | 2.65 |
| 164 | TBC1D24 | 41 | 4 | 0.412035428682661 | 0.999997930372063 | 9.76 |
| 165 | TCP10L2 | 46 | 4 | 0.501622355732139 | 0.999997930372063 | 8.7 |
| 166 | TCTE1 | 39 | 4 | 0.375124758475278 | 0.999997930372063 | 10.26 |
| 167 | TMEM151B | 39 | 4 | 0.375124758475278 | 0.999997930372063 | 10.26 |
| 168 | TNFRSF11A | 58 | 4 | 0.686266830720114 | 0.999997930372063 | 6.9 |
| 169 | TNFSF8 | 50 | 4 | 0.568728838576346 | 0.999997930372063 | 8 |
| 170 | TP73 | 32 | 4 | 0.246707930589528 | 0.999997930372063 | 12.5 |
| 171 | TYK2 | 75 | 4 | 0.856164977014928 | 0.999997930372063 | 5.33 |
| 172 | VPS16 | 33 | 4 | 0.264614551688586 | 0.999997930372063 | 12.12 |
| 173 | ZBTB42 | 58 | 4 | 0.686266830720114 | 0.999997930372063 | 6.9 |
| 174 | ADAMTS14 | 11 | 3 | 0.0508678018832711 | 0.619784007156698 | 27.27 |
| 175 | TAS1R1 | 11 | 3 | 0.0508678018832711 | 0.619784007156698 | 27.27 |
| 176 | MIPEP | 12 | 3 | 0.0639334616325914 | 0.704790303235472 | 25 |
| 177 | PGPEP1L | 13 | 3 | 0.0783691103023943 | 0.710624302790622 | 23.08 |
| 178 | POLB | 15 | 3 | 0.1109490178464970 | 0.789152246561851 | 20 |
| 179 | FARP2 | 16 | 3 | 0.1288732831899840 | 0.831677998018297 | 18.75 |
| 180 | RAD50 | 16 | 3 | 0.1288732831899840 | 0.831677998018297 | 18.75 |
| 181 | AIRE | 17 | 3 | 0.1477336178782150 | 0.876931603559146 | 17.65 |
| 182 | ATIC | 17 | 3 | 0.1477336178782150 | 0.876931603559146 | 17.65 |
| 183 | MEGF6 | 20 | 3 | 0.2087722402131870 | 0.988148591681669 | 15 |
| 184 | TPRG1L | 20 | 3 | 0.2087722402131870 | 0.988148591681669 | 15 |
| 185 | AC105009.1 | 54 | 3 | 0.8132350734881700 | 0.999997930372063 | 5.56 |
| 186 | ALDOA | 26 | 3 | 0.3412775623453530 | 0.999997930372063 | 11.54 |
| 187 | ALS2CR12 | 21 | 3 | 0.2302291415790290 | 0.999997930372063 | 14.29 |
| 188 | ANGPTL7 | 38 | 3 | 0.5901926157849590 | 0.999997930372063 | 7.89 |
| 189 | CCDC88B | 42 | 3 | 0.6586694353499270 | 0.999997930372063 | 7.14 |
| 190 | CTD-2369P2.10 | 66 | 3 | 0.9040238254594840 | 0.999997930372063 | 4.55 |
| 191 | CTD-2369P2.12 | 60 | 3 | 0.8652252087613920 | 0.999997930372063 | 5 |
| 192 | FDX1L | 60 | 3 | 0.8652252087613920 | 0.999997930372063 | 5 |
| 193 | HECTD4 | 59 | 3 | 0.8575550879876830 | 0.999997930372063 | 5.08 |
| 194 | ICAM3 | 70 | 3 | 0.9239561433116700 | 0.999997930372063 | 4.29 |
| 195 | PCYOX1L | 39 | 3 | 0.6081149372274330 | 0.999997930372063 | 7.69 |
| 196 | PPP4C | 29 | 3 | 0.4078878479067430 | 0.999997930372063 | 10.34 |
| 197 | RABEP2 | 50 | 3 | 0.7698155828032130 | 0.999997930372063 | 6 |

TABLE 2.e-continued

| | GeneLocus | Probe_Count_Total | Probe_Count_Sig | HyperG_Stats | FDR_HyperG | Percent_Sig |
|---|---|---|---|---|---|---|
| 198 | RAVER1 | 61 | 3 | 0.8725291522297110 | 0.999997930372063 | 4.92 |
| 199 | RPL6 | 36 | 3 | 0.5527984128114050 | 0.999997930372063 | 8.33 |
| 200 | SIGLECL1 | 29 | 3 | 0.4078878479067430 | 0.999997930372063 | 10.34 |
| 201 | SPSB2 | 30 | 3 | 0.4296764606958220 | 0.999997930372063 | 10 |
| 202 | STAT3 | 100 | 3 | 0.9882826466279560 | 0.999997930372063 | 3 |
| 203 | STAT5A | 99 | 3 | 0.9874934884705020 | 0.999997930372063 | 3.03 |
| 204 | STAT5B | 106 | 3 | 0.9921011727563130 | 0.999997930372063 | 2.83 |
| 205 | TBX6 | 29 | 3 | 0.4078878479067430 | 0.999997930372063 | 10.34 |
| 206 | TPI1 | 25 | 3 | 0.3188672309188860 | 0.999997930372063 | 12 |
| 207 | USP5 | 31 | 3 | 0.4511687243316760 | 0.999997930372063 | 9.68 |
| 208 | WRAP73 | 25 | 3 | 0.3188672309188860 | 0.999997930372063 | 12 |
| 209 | YPEL3 | 29 | 3 | 0.4078878479067430 | 0.999997930372063 | 10.34 |

TABLE 2.f

| | GeneLocus | Probe_Count_Total | Probe_Count_Sig | HyperG_Stats | FDR_HyperG | Percent_Sig |
|---|---|---|---|---|---|---|
| 210 | ZMAT2 | 23 | 3 | 0.2741758744693630 | 0.999997930372063 | 13.04 |
| 211 | ZP1 | 3 | 2 | 0.0178992933709331 | 0.276245761024734 | 66.67 |
| 212 | SIGLEC7 | 7 | 2 | 0.1012229245865700 | 0.781478357903993 | 28.57 |
| 213 | UBIAD1 | 7 | 2 | 0.1012229245865700 | 0.781478357903993 | 28.57 |
| 214 | HAVCR2 | 10 | 2 | 0.1856137157633120 | 0.954389148642173 | 20 |
| 215 | IFNG | 10 | 2 | 0.1856137157633120 | 0.954389148642173 | 20 |
| 216 | MED7 | 10 | 2 | 0.1856137157633120 | 0.954389148642173 | 20 |
| 217 | ATG4B | 11 | 2 | 0.2155572521810980 | 0.988148591681669 | 18.18 |
| 218 | HLA-DOA | 11 | 2 | 0.2155572521810980 | 0.988148591681669 | 18.18 |
| 219 | ABCD3 | 31 | 2 | 0.7175015183076030 | 0.999997930372063 | 6.45 |
| 220 | ADM5 | 30 | 2 | 0.7003187574059310 | 0.999997930372063 | 6.67 |
| 221 | AFAP1L1 | 36 | 2 | 0.7913651829204500 | 0.999997930372063 | 5.56 |
| 222 | AGMAT | 18 | 2 | 0.4242550801595520 | 0.999997930372063 | 11.11 |
| 223 | AP000866.1 | 23 | 2 | 0.5550530577755810 | 0.999997930372063 | 8.7 |
| 224 | ARHGAP24 | 14 | 2 | 0.3067159393788740 | 0.999997930372063 | 14.29 |
| 225 | ARHGEF1 | 44 | 2 | 0.8743872112910340 | 0.999997930372063 | 4.55 |
| 226 | BAX | 52 | 2 | 0.9259587031948710 | 0.999997930372063 | 3.85 |
| 227 | BCL2L12 | 30 | 2 | 0.7003187574059310 | 0.999997930372063 | 6.67 |
| 228 | BCL2L2 | 86 | 2 | 0.9932337395965280 | 0.999997930372063 | 2.33 |
| 229 | BCL2L2-PABPN1 | 93 | 2 | 0.9959456131341410 | 0.999997930372063 | 2.15 |
| 230 | BID | 42 | 2 | 0.8570808572073380 | 0.999997930372063 | 4.76 |
| 231 | BRD2 | 15 | 2 | 0.3368339273069320 | 0.999997930372063 | 13.33 |
| 232 | C16orf59 | 17 | 2 | 0.3957171204687430 | 0.999997930372063 | 11.76 |
| 233 | C1orf137 | 16 | 2 | 0.366542590752210 | 0.999997930372063 | 12.5 |
| 234 | C1S | 29 | 2 | 0.682275937625257 | 0.999997930372063 | 6.9 |
| 235 | C20orf141 | 12 | 2 | 0.245882010290800 | 0.999997930372063 | 16.67 |
| 236 | C8G | 35 | 2 | 0.778111473469947 | 0.999997930372063 | 5.71 |
| 237 | CASP10 | 53 | 2 | 0.930777371745053 | 0.999997930372063 | 3.77 |
| 238 | CASP6 | 28 | 2 | 0.663352621092945 | 0.999997930372063 | 7.14 |
| 239 | CASP9 | 46 | 2 | 0.889742684761849 | 0.999997930372063 | 4.35 |
| 240 | CBL | 55 | 2 | 0.939538153185284 | 0.999997930372063 | 3.64 |
| 241 | CBLB | 182 | 2 | 0.999995464473068 | 0.999997930372063 | 1.1 |
| 242 | CCDC109B | 20 | 2 | 0.479107133771006 | 0.999997930372063 | 10 |
| 243 | CCDC28B | 22 | 2 | 0.530628954879388 | 0.999997930372063 | 9.09 |
| 244 | CCL15 | 12 | 2 | 0.245882010290800 | 0.999997930372063 | 16.67 |
| 245 | CCL23 | 16 | 2 | 0.366542590752210 | 0.999997930372063 | 12.5 |
| 246 | CCNF | 16 | 2 | 0.366542590752210 | 0.999997930372063 | 12.5 |
| 247 | CD2 | 34 | 2 | 0.764125503160783 | 0.999997930372063 | 5.88 |
| 248 | CD47 | 46 | 2 | 0.889742684761849 | 0.999997930372063 | 4.35 |
| 249 | CD79A | 44 | 2 | 0.874387211291034 | 0.999997930372063 | 4.55 |
| 250 | CD79B | 20 | 2 | 0.479107133771006 | 0.999997930372063 | 10 |
| 251 | CD86 | 46 | 2 | 0.889742684761849 | 0.999997930372063 | 4.35 |
| 252 | CEP170B | 24 | 2 | 0.578560340672839 | 0.999997930372063 | 8.33 |
| 253 | CFI | 16 | 2 | 0.366542590752210 | 0.999997930372063 | 12.5 |
| 254 | CLNS1A | 28 | 2 | 0.663352621092945 | 0.999997930372063 | 7.14 |
| 255 | CMTM5 | 74 | 2 | 0.983929844323545 | 0.999997930372063 | 2.7 |
| 256 | COPS7A | 16 | 2 | 0.366542590752210 | 0.999997930372063 | 12.5 |
| 257 | COX6A2 | 12 | 2 | 0.245882010290800 | 0.999997930372063 | 16.67 |

TABLE 2.g

| | GeneLocus | Probe_Count_Total | Probe_Count_Sig | HyperG_Stats | FDR_HyperG | Percent_Sig |
|---|---|---|---|---|---|---|
| 258 | CPT1C | 30 | 2 | 0.700318757405931 | 0.999997930372063 | 6.67 |
| 259 | CPXM1 | 12 | 2 | 0.245882010290800 | 0.999997930372063 | 16.67 |
| 260 | CSF2 | 36 | 2 | 0.791365182920450 | 0.999997930372063 | 5.56 |
| 261 | CSHL1 | 20 | 2 | 0.479107133771006 | 0.999997930372063 | 10 |
| 262 | CYBA | 40 | 2 | 0.837619347075832 | 0.999997930372063 | 5 |
| 263 | DCDC2B | 22 | 2 | 0.530628954879388 | 0.999997930372063 | 9.09 |
| 264 | DHDH | 48 | 2 | 0.903339406944514 | 0.999997930372063 | 4.17 |
| 265 | DHX37 | 24 | 2 | 0.578560340672839 | 0.999997930372063 | 8.33 |
| 266 | DMRTC2 | 39 | 2 | 0.827013686075902 | 0.999997930372063 | 5.13 |
| 267 | DNAJC16 | 31 | 2 | 0.717501518307603 | 0.999997930372063 | 6.45 |
| 268 | DNMT1 | 25 | 2 | 0.601142350216661 | 0.999997930372063 | 8 |
| 269 | DNTT | 32 | 2 | 0.733846963466398 | 0.999997930372063 | 6.25 |
| 270 | DUSP22 | 48 | 2 | 0.903339406944514 | 0.999997930372063 | 4.17 |
| 271 | EFS | 78 | 2 | 0.987931057370678 | 0.999997930372063 | 2.56 |
| 272 | EGF | 48 | 2 | 0.903339406944514 | 0.999997930372063 | 4.17 |
| 273 | EIF31 | 22 | 2 | 0.530628954879388 | 0.999997930372063 | 9.09 |
| 274 | ENDOU | 26 | 2 | 0.622797749205937 | 0.999997930372063 | 7.69 |
| 275 | ENSA | 88 | 2 | 0.994151783490876 | 0.999997930372063 | 2.27 |
| 276 | ESAM | 32 | 2 | 0.733846963466398 | 0.999997930372063 | 6.25 |
| 277 | F3 | 36 | 2 | 0.791365182920450 | 0.999997930372063 | 5.56 |
| 278 | FAM220A | 52 | 2 | 0.925958703194871 | 0.999997930372063 | 3.85 |
| 279 | FAM71B | 12 | 2 | 0.245882010290800 | 0.999997930372063 | 16.67 |
| 280 | FBXW5 | 35 | 2 | 0.778111473469947 | 0.999997930372063 | 5.71 |
| 281 | FTL | 52 | 2 | 0.925958703194871 | 0.999997930372063 | 3.85 |
| 282 | GH1 | 20 | 2 | 0.479107133771006 | 0.999997930372063 | 10 |
| 283 | GRPEL2 | 36 | 2 | 0.791365182920450 | 0.999997930372063 | 5.56 |
| 284 | GYS1 | 46 | 2 | 0.889742684761849 | 0.999997930372063 | 4.35 |
| 285 | HCST | 50 | 2 | 0.915356314014006 | 0.999997930372063 | 4 |
| 286 | HLA-DMA | 16 | 2 | 0.366542590752210 | 0.999997930372063 | 12.5 |
| 287 | HLA-DMB | 26 | 2 | 0.622797749205937 | 0.999997930372063 | 7.69 |
| 288 | HLA-DRB1 | 13 | 2 | 0.276338901197783 | 0.999997930372063 | 15.38 |
| 289 | HSP90AB1 | 36 | 2 | 0.791365182920450 | 0.999997930372063 | 5.56 |
| 290 | ICAM1 | 63 | 2 | 0.965115210029707 | 0.999997930372063 | 3.17 |
| 291 | ICAM5 | 57 | 2 | 0.947238725405958 | 0.999997930372063 | 3.51 |
| 292 | IGSF23 | 48 | 2 | 0.903339406944514 | 0.999997930372063 | 4.17 |
| 293 | IL17C | 40 | 2 | 0.837619347075832 | 0.999997930372063 | 5 |
| 294 | IL25 | 74 | 2 | 0.983929844323545 | 0.999997930372063 | 2.7 |
| 295 | IL26 | 20 | 2 | 0.479107133771006 | 0.999997930372063 | 10 |
| 296 | IL3 | 42 | 2 | 0.857080857207338 | 0.999997930372063 | 4.76 |
| 297 | IQCC | 22 | 2 | 0.530628954879388 | 0.999997930372063 | 9.09 |
| 298 | IRF2 | 38 | 2 | 0.815788109211877 | 0.999997930372063 | 5.26 |
| 299 | IRF3 | 30 | 2 | 0.700318757405931 | 0.999997930372063 | 6.67 |
| 300 | IRF4 | 40 | 2 | 0.837619347075832 | 0.999997930372063 | 5 |
| 301 | LCN12 | 35 | 2 | 0.778111473469947 | 0.999997930372063 | 5.71 |
| 302 | LRFN3 | 41 | 2 | 0.847632694261747 | 0.999997930372063 | 4.88 |
| 303 | LTBR | 33 | 2 | 0.749379646925559 | 0.999997930372063 | 6.06 |
| 304 | LYN | 48 | 2 | 0.903339406944514 | 0.999997930372063 | 4.17 |
| 305 | LYPD4 | 35 | 2 | 0.778111473469947 | 0.999997930372063 | 5.71 |

TABLE 2.h

| | GeneLocus | Probe_Count_Total | Probe_Count_Sig | HyperG_Stats | FDR_HyperG | Percent_Sig |
|---|---|---|---|---|---|---|
| 306 | MAP3K11 | 41 | 2 | 0.847632694261747 | 0.999997930372063 | 4.88 |
| 307 | MAP3K14 | 44 | 2 | 0.874387211291034 | 0.999997930372063 | 4.55 |
| 308 | MARCKSL1 | 24 | 2 | 0.578560340672839 | 0.999997930372063 | 8.33 |
| 309 | MAST3 | 62 | 2 | 0.962606551119358 | 0.999997930372063 | 3.23 |
| 310 | MAST4 | 25 | 2 | 0.601142350216661 | 0.999997930372063 | 8 |
| 311 | MCL1 | 77 | 2 | 0.987032863322398 | 0.999997930372063 | 2.6 |
| 312 | MRPL4 | 40 | 2 | 0.837619347075832 | 0.999997930372063 | 5 |
| 313 | MSANTD2 | 30 | 2 | 0.700318757405931 | 0.999997930372063 | 6.67 |
| 314 | MVD | 36 | 2 | 0.791365182920450 | 0.999997930372063 | 5.56 |
| 315 | NFKBID | 50 | 2 | 0.915356314014006 | 0.999997930372063 | 4 |
| 316 | NRGN | 30 | 2 | 0.700318757405931 | 0.999997930372063 | 6.67 |
| 317 | NTN3 | 17 | 2 | 0.395717120468743 | 0.999997930372063 | 11.76 |
| 318 | NUCB1 | 44 | 2 | 0.874387211291034 | 0.999997930372063 | 4.55 |
| 319 | PABPN1 | 90 | 2 | 0.994947395103974 | 0.999997930372063 | 2.22 |
| 320 | PCNXL3 | 48 | 2 | 0.903339406944514 | 0.999997930372063 | 4.17 |
| 321 | PDCD1 | 36 | 2 | 0.791365182920450 | 0.999997930372063 | 5.56 |
| 322 | PDYN | 32 | 2 | 0.733846963466398 | 0.999997930372063 | 6.25 |
| 323 | PFKL | 14 | 2 | 0.306715939378874 | 0.999997930372063 | 14.29 |
| 324 | PLA2G12A | 23 | 2 | 0.555053057775581 | 0.999997930372063 | 8.7 |
| 325 | PLAT | 14 | 2 | 0.306715939378874 | 0.999997930372063 | 14.29 |

TABLE 2.h-continued

| | GeneLocus | Probe_Count_Total | Probe_Count_Sig | HyperG_Stats | FDR_HyperG | Percent_Sig |
|---|---|---|---|---|---|---|
| 326 | PRKCQ | 106 | 2 | 0.998452565953663 | 0.999997930372063 | 1.89 |
| 327 | PRMT1 | 30 | 2 | 0.700318757405931 | 0.999997930372063 | 6.67 |
| 328 | PRR5L | 192 | 2 | 0.999997930372063 | 0.999997930372063 | 1.04 |
| 329 | PSMD5 | 14 | 2 | 0.306715939378874 | 0.999997930372063 | 14.29 |
| 330 | PVR | 65 | 2 | 0.969655535986940 | 0.999997930372063 | 3.08 |
| 331 | QPRT | 47 | 2 | 0.896749389307423 | 0.999997930372063 | 4.26 |
| 332 | RABL6 | 46 | 2 | 0.889742684761849 | 0.999997930372063 | 4.35 |
| 333 | RAC1 | 64 | 2 | 0.967461558699041 | 0.999997930372063 | 3.12 |
| 334 | RAG1 | 51 | 2 | 0.920824527564584 | 0.999997930372063 | 3.92 |
| 335 | RAPGEF3 | 25 | 2 | 0.601142350216661 | 0.999997930372063 | 8 |
| 336 | RELA | 56 | 2 | 0.943513219685347 | 0.999997930372063 | 3.57 |
| 337 | RICTOR | 114 | 2 | 0.999150230460213 | 0.999997930372063 | 1.75 |
| 338 | RPAP3 | 25 | 2 | 0.601142350216661 | 0.999997930372063 | 8 |
| 339 | RPS19 | 44 | 2 | 0.874387211291034 | 0.999997930372063 | 4.55 |
| 340 | RTP5 | 30 | 2 | 0.700318757405931 | 0.999997930372063 | 6.67 |
| 341 | RUVBL2 | 29 | 2 | 0.682275937625257 | 0.999997930372063 | 6.9 |
| 342 | S1PR2 | 25 | 2 | 0.601142350216661 | 0.999997930372063 | 8 |
| 343 | SCAF1 | 26 | 2 | 0.622797749205937 | 0.999997930372063 | 7.69 |
| 344 | SCN4A | 23 | 2 | 0.555053057775581 | 0.999997930372063 | 8.7 |
| 345 | SCNN1A | 39 | 2 | 0.827013686075902 | 0.999997930372063 | 5.13 |
| 346 | SIPA1 | 69 | 2 | 0.977087651131023 | 0.999997930372063 | 2.9 |
| 347 | SIVA1 | 36 | 2 | 0.791365182920450 | 0.999997930372063 | 5.56 |
| 348 | SLC22A17 | 87 | 2 | 0.993709149379117 | 0.999997930372063 | 2.3 |
| 349 | SLC29A1 | 29 | 2 | 0.682275937625257 | 0.999997930372063 | 6.9 |
| 350 | SLC48A1 | 18 | 2 | 0.424255080159552 | 0.999997930372063 | 11.11 |
| 351 | SMAD3 | 34 | 2 | 0.764125503160783 | 0.999997930372063 | 5.88 |
| 352 | SPATA32 | 24 | 2 | 0.578560340672839 | 0.999997930372063 | 8.33 |
| 353 | SPATS1 | 15 | 2 | 0.336833927306932 | 0.999997930372063 | 13.33 |

TABLE 2.i

| | GeneLocus | Probe_Count_Total | Probe_Count_Sig | HyperG_Stats | FDR_HyperG | Percent_Sig |
|---|---|---|---|---|---|---|
| 354 | STAT4 | 58 | 2 | 0.950729209348889 | 0.999997930372063 | 3.45 |
| 355 | SUMO4 | 87 | 2 | 0.993709149379117 | 0.999997930372063 | 2.3 |
| 356 | TEX29 | 29 | 2 | 0.682275937625257 | 0.999997930372063 | 6.9 |
| 357 | TMEM234 | 22 | 2 | 0.530628954879388 | 0.999997930372063 | 9.09 |
| 358 | TNFRSF1A | 46 | 2 | 0.889742684761849 | 0.999997930372063 | 4.35 |
| 359 | TRAF2 | 46 | 2 | 0.889742684761849 | 0.999997930372063 | 4.35 |
| 360 | TRAF6 | 60 | 2 | 0.957059623937612 | 0.999997930372063 | 3.33 |
| 361 | TRIM72 | 16 | 2 | 0.366542590752210 | 0.999997930372063 | 12.5 |
| 362 | TYROBP | 50 | 2 | 0.915356314014006 | 0.999997930372063 | 4 |
| 363 | UBC | 64 | 2 | 0.967461558699041 | 0.999997930372063 | 3.12 |
| 364 | ULK3 | 20 | 2 | 0.479107133771006 | 0.999997930372063 | 10 |
| 365 | VSIG2 | 30 | 2 | 0.700318757405931 | 0.999997930372063 | 6.67 |
| 366 | XXbac-BPG181M17.5 | 26 | 2 | 0.622797749205937 | 0.999997930372063 | 7.69 |
| 367 | ZC3H18 | 35 | 2 | 0.778111473469947 | 0.999997930372063 | 5.71 |
| 368 | ZNF518A | 34 | 2 | 0.764125503160783 | 0.999997930372063 | 5.88 |
| 369 | ZNF843 | 12 | 2 | 0.245882010290800 | 0.999997930372063 | 16.67 |
| 370 | AAGAB | 18 | 1 | 0.774551015160648 | 0.999997930372063 | 5.56 |
| 371 | AC138028.1 | 29 | 1 | 0.909346620735280 | 0.999997930372063 | 3.45 |
| 372 | ACSL6 | 22 | 1 | 0.838118527757470 | 0.999997930372063 | 4.55 |
| 373 | ADAMTSL4 | 48 | 1 | 0.981231994372307 | 0.999997930372063 | 2.08 |
| 374 | ADSSL1 | 21 | 1 | 0.824141728990284 | 0.999997930372063 | 4.76 |
| 375 | APLP1 | 42 | 1 | 0.969133876315432 | 0.999997930372063 | 2.38 |
| 376 | ATP6VOA1 | 17 | 1 | 0.755090129882809 | 0.999997930372063 | 5.88 |
| 377 | BCL2L13 | 30 | 1 | 0.916554478091464 | 0.999997930372063 | 3.33 |
| 378 | BOLA2B | 15 | 1 | 0.710987544197401 | 0.999997930372063 | 6.67 |
| 379 | BRI3BP | 13 | 1 | 0.658949110426667 | 0.999997930372063 | 7.69 |
| 380 | C1orf168 | 55 | 1 | 0.989498382048305 | 0.999997930372063 | 1.82 |
| 381 | C1QTNF5 | 35 | 1 | 0.944859652291972 | 0.999997930372063 | 2.86 |
| 382 | CCDC153 | 27 | 1 | 0.893010740890946 | 0.999997930372063 | 3.7 |
| 383 | CCDC27 | 10 | 1 | 0.562821502082175 | 0.999997930372063 | 10 |
| 384 | CCL14 | 9 | 1 | 0.525100723450289 | 0.999997930372063 | 11.11 |
| 385 | CCL15-CCL14 | 10 | 1 | 0.562821502082175 | 0.999997930372063 | 10 |
| 386 | CCL16 | 9 | 1 | 0.525100723450289 | 0.999997930372063 | 11.11 |
| 387 | CEACAM16 | 48 | 1 | 0.981231994372307 | 0.999997930372063 | 2.08 |
| 388 | CEACAM19 | 53 | 1 | 0.987603129345602 | 0.999997930372063 | 1.89 |
| 389 | CEACAM3 | 19 | 1 | 0.792466424646505 | 0.999997930372063 | 5.26 |
| 390 | CELA2A | 30 | 1 | 0.916554478091464 | 0.999997930372063 | 3.33 |
| 391 | CELA2B | 38 | 1 | 0.956998223828945 | 0.999997930372063 | 2.63 |
| 392 | CFLAR | 58 | 1 | 0.991812373295601 | 0.999997930372063 | 1.72 |
| 393 | CGB | 15 | 1 | 0.710987544197401 | 0.999997930372063 | 6.67 |
| 394 | CHMP6 | 7 | 1 | 0.439621833115841 | 0.999997930372063 | 14.29 |
| 395 | CORO1A | 17 | 1 | 0.755090129882809 | 0.999997930372063 | 5.88 |

TABLE 2.i-continued

| | GeneLocus | Probe_Count_Total | Probe_Count_Sig | HyperG_Stats | FDR_HyperG | Percent_Sig |
|---|---|---|---|---|---|---|
| 396 | CSH1 | 12 | 1 | 0.629517555870599 | 0.999997930372063 | 8.33 |
| 397 | CTB-60B18.6 | 15 | 1 | 0.710987544197401 | 0.999997930372063 | 6.67 |
| 398 | DAGLB | 74 | 1 | 0.997830586254369 | 0.999997930372063 | 1.35 |
| 399 | DKK4 | 7 | 1 | 0.439621833115841 | 0.999997930372063 | 14.29 |
| 400 | EDF1 | 21 | 1 | 0.824141728990284 | 0.999997930372063 | 4.76 |

TABLE 2.j

| | GeneLocus | Probe_Count_Total | Probe_Count_Sig | HyperG_Stats | FDR_HyperG | Percent_Sig |
|---|---|---|---|---|---|---|
| 401 | EHBP1L1 | 43 | 1 | 0.971589673511865 | 0.999997930372063 | 2.33 |
| 402 | ELOVL6 | 12 | 1 | 0.629517555870599 | 0.999997930372063 | 8.33 |
| 403 | FAM57B | 18 | 1 | 0.774551015160648 | 0.999997930372063 | 5.56 |
| 404 | FGFR1OP | 32 | 1 | 0.929297402985911 | 0.999997930372063 | 3.12 |
| 405 | FMNL1 | 14 | 1 | 0.686043969738036 | 0.999997930372063 | 7.14 |
| 406 | FUS | 6 | 1 | 0.391279131897374 | 0.999997930372063 | 16.67 |
| 407 | GOLPH3L | 53 | 1 | 0.987603129345602 | 0.999997930372063 | 1.89 |
| 408 | HDAC7 | 8 | 1 | 0.484127577317580 | 0.999997930372063 | 12.5 |
| 409 | HOMEZ | 74 | 1 | 0.997830586254369 | 0.999997930372063 | 1.35 |
| 410 | ICAM2 | 24 | 1 | 0.862829696523136 | 0.999997930372063 | 4.17 |
| 411 | ICAM4 | 53 | 1 | 0.987603129345602 | 0.999997930372063 | 1.89 |
| 412 | IFI30 | 40 | 1 | 0.963567575263993 | 0.999997930372063 | 2.5 |
| 413 | IFT57 | 16 | 1 | 0.733950541093747 | 0.999997930372063 | 6.25 |
| 414 | IGLON5 | 13 | 1 | 0.658949110426667 | 0.999997930372063 | 7.69 |
| 415 | IGSF3 | 54 | 1 | 0.988590014250795 | 0.999997930372063 | 1.85 |
| 416 | IL12RB1 | 51 | 1 | 0.985366094431372 | 0.999997930372063 | 1.96 |
| 417 | ILDR1 | 23 | 1 | 0.850985140029373 | 0.999997930372063 | 4.35 |
| 418 | INF2 | 21 | 1 | 0.824141728990284 | 0.999997930372063 | 4.76 |
| 419 | KCNK7 | 38 | 1 | 0.956998223828945 | 0.999997930372063 | 2.63 |
| 420 | KCTD21 | 19 | 1 | 0.792466424646505 | 0.999997930372063 | 5.26 |
| 421 | KDELR2 | 49 | 1 | 0.982725688322447 | 0.999997930372063 | 2.04 |
| 422 | KIRREL2 | 31 | 1 | 0.923189576750926 | 0.999997930372063 | 3.23 |
| 423 | LCNL1 | 21 | 1 | 0.824141728990284 | 0.999997930372063 | 4.76 |
| 424 | LHB | 18 | 1 | 0.774551015160648 | 0.999997930372063 | 5.56 |
| 425 | LRIT3 | 23 | 1 | 0.850985140029373 | 0.999997930372063 | 4.35 |
| 426 | MAMDC4 | 19 | 1 | 0.792466424646505 | 0.999997930372063 | 5.26 |
| 427 | MCAM | 33 | 1 | 0.934919832862797 | 0.999997930372063 | 3.03 |
| 428 | MICAL3 | 24 | 1 | 0.862829696523136 | 0.999997930372063 | 4.17 |
| 429 | MPV17L2 | 37 | 1 | 0.953282168181128 | 0.999997930372063 | 2.7 |
| 430 | MTAP | 26 | 1 | 0.883770759422438 | 0.999997930372063 | 3.85 |
| 431 | MYH6 | 59 | 1 | 0.992464337028886 | 0.999997930372063 | 1.69 |
| 432 | NPHS1 | 31 | 1 | 0.923189576750926 | 0.999997930372063 | 3.23 |
| 433 | OPALIN | 13 | 1 | 0.658949110426667 | 0.999997930372063 | 7.69 |
| 434 | OSMR | 53 | 1 | 0.987603129345602 | 0.999997930372063 | 1.89 |
| 435 | PALD1 | 17 | 1 | 0.755090129882809 | 0.999997930372063 | 5.88 |
| 436 | PDE4A | 22 | 1 | 0.838118527757470 | 0.999997930372063 | 4.55 |
| 437 | PDE4C | 37 | 1 | 0.953282168181128 | 0.999997930372063 | 2.7 |
| 438 | PLEKHG6 | 44 | 1 | 0.973850195889094 | 0.999997930372063 | 2.27 |
| 439 | PPP1R3E | 82 | 1 | 0.998883779596881 | 0.999997930372063 | 1.22 |
| 440 | PRR12 | 9 | 1 | 0.525100723450289 | 0.999997930372063 | 11.11 |
| 441 | PRR29 | 19 | 1 | 0.792466424646505 | 0.999997930372063 | 5.26 |
| 442 | PTGDS | 21 | 1 | 0.824141728990284 | 0.999997930372063 | 4.76 |
| 443 | PTRF | 46 | 1 | 0.977846256754934 | 0.999997930372063 | 2.17 |
| 444 | PYCARD | 6 | 1 | 0.391279131897374 | 0.999997930372063 | 16.67 |
| 445 | PYDC1 | 10 | 1 | 0.562821502082175 | 0.999997930372063 | 10 |
| 446 | RAB3A | 37 | 1 | 0.953282168181128 | 0.999997930372063 | 2.7 |
| 447 | RNF26 | 32 | 1 | 0.929297402985911 | 0.999997930372063 | 3.12 |
| 448 | RP11-347C12.3 | 13 | 1 | 0.658949110426667 | 0.999997930372063 | 7.69 |

TABLE 2.k

| | GeneLocus | Probe_Count_Total | Probe_Count_Sig | HyperG_Stats | FDR_HyperG | Percent_Sig |
|---|---|---|---|---|---|---|
| 449 | RPS6KA4 | 20 | 1 | 0.808959018903111 | 0.999997930372063 | 5 |
| 450 | RRAS | 13 | 1 | 0.658949110426667 | 0.999997930372063 | 7.69 |
| 451 | RRH | 10 | 1 | 0.562821502082175 | 0.999997930372063 | 10 |
| 452 | SCAMP2 | 17 | 1 | 0.755090129882809 | 0.999997930372063 | 5.88 |
| 453 | SCARB1 | 78 | 1 | 0.998443813773922 | 0.999997930372063 | 1.28 |
| 454 | SDHAF1 | 6 | 1 | 0.391279131897374 | 0.999997930372063 | 16.67 |
| 455 | SLX1A | 15 | 1 | 0.710987544197401 | 0.999997930372063 | 6.67 |
| 456 | SLX1A-SULT1A3 | 15 | 1 | 0.710987544197401 | 0.999997930372063 | 6.67 |
| 457 | SNAI3 | 29 | 1 | 0.909346620735280 | 0.999997930372063 | 3.45 |
| 458 | SPA17 | 17 | 1 | 0.755090129882809 | 0.999997930372063 | 5.88 |

TABLE 2.k-continued

| | GeneLocus | Probe_Count_Total | Probe_Count_Sig | HyperG_Stats | FDR_HyperG | Percent_Sig |
|---|---|---|---|---|---|---|
| 459 | SULT1A3 | 14 | 1 | 0.686043969738036 | 0.999997930372063 | 7.14 |
| 460 | TSKS | 17 | 1 | 0.755090129882809 | 0.999997930372063 | 5.88 |
| 461 | TSSK3 | 15 | 1 | 0.710987544197401 | 0.999997930372063 | 6.67 |
| 462 | USP35 | 31 | 1 | 0.923189576750926 | 0.999997930372063 | 3.23 |
| 463 | ZGLP1 | 57 | 1 | 0.991104042882726 | 0.999997930372063 | 1.75 |

TABLE 3.a

| | gene | Probe_Count_Total | Probe_Count_Sig | HyperG_Stats | FDR_HyperG | Percent_Sig |
|---|---|---|---|---|---|---|
| 1 | IGF1R | 104 | 16 | 0.007797893 | 0.171924974 | 15.38 |
| 2 | CD6 | 56 | 14 | 0.000090300 | 0.005970563 | 25 |
| 3 | CXCL13 | 108 | 14 | 0.046569042 | 0.598929617 | 12.96 |
| 4 | IKBKB | 46 | 12 | 0.000183630 | 0.010627608 | 26.09 |
| 5 | PIK3R1 | 148 | 12 | 0.513477047 | 0.99999793 | 8.11 |
| 6 | ITK | 26 | 10 | 0.000015700 | 0.002607465 | 38.46 |
| 7 | PTPRC | 214 | 10 | 0.978491243 | 0.99999793 | 4.67 |
| 8 | C8B | 151 | 9 | 0.855915990 | 0.99999793 | 5.96 |
| 9 | C8A | 166 | 8 | 0.957766442 | 0.99999793 | 4.82 |
| 10 | CCL18 | 42 | 8 | 0.016095432 | 0.256971894 | 19.05 |
| 11 | CYFIP2 | 40 | 8 | 0.012066038 | 0.223463015 | 20 |
| 12 | FAS | 50 | 8 | 0.041957105 | 0.555032562 | 16 |
| 13 | ICOSLG | 40 | 8 | 0.012066038 | 0.223463015 | 20 |
| 14 | IRF1 | 42 | 8 | 0.016095432 | 0.256971894 | 19.05 |
| 15 | ITGAM | 50 | 8 | 0.041957105 | 0.555032562 | 16 |
| 16 | ITGAX | 41 | 8 | 0.013975308 | 0.239650655 | 19.51 |
| 17 | CCL3 | 33 | 7 | 0.013410837 | 0.238816059 | 21.21 |
| 18 | CCL4 | 32 | 7 | 0.011323325 | 0.223463015 | 21.88 |
| 19 | CD14 | 62 | 6 | 0.369692981 | 0.99999793 | 9.68 |
| 20 | CD4 | 42 | 6 | 0.112492545 | 0.789152247 | 14.29 |
| 21 | NFKB1 | 64 | 6 | 0.398773743 | 0.99999793 | 9.38 |
| 22 | SYK | 78 | 6 | 0.592795697 | 0.99999793 | 7.69 |
| 23 | LAG3 | 29 | 5 | 0.075553312 | 0.710624303 | 17.24 |
| 24 | AKT1 | 60 | 4 | 0.711822793 | 0.99999793 | 6.67 |
| 25 | BLNK | 66 | 4 | 0.779227696 | 0.99999793 | 6.06 |
| 26 | C5 | 41 | 4 | 0.412035429 | 0.99999793 | 9.76 |
| 27 | CASP8 | 41 | 4 | 0.412035429 | 0.99999793 | 9.76 |
| 28 | CCR6 | 46 | 4 | 0.501622356 | 0.99999793 | 8.7 |
| 29 | CD180 | 38 | 4 | 0.356577228 | 0.99999793 | 10.53 |
| 30 | CD19 | 56 | 4 | 0.659150649 | 0.99999793 | 7.14 |

TABLE 3.b

| | gene | Probe_Count_Total | Probe_Count_Sig | HyperG_Stats | FDR_HyperG | Percent_Sig |
|---|---|---|---|---|---|---|
| 31 | CD33 | 32 | 4 | 0.246707931 | 0.99999793 | 12.5 |
| 32 | FN1 | 42 | 4 | 0.430324418 | 0.99999793 | 9.52 |
| 33 | HLA-DQA1 | 28 | 4 | 0.178427395 | 0.954389149 | 14.29 |
| 34 | HLA-DQB1 | 22 | 4 | 0.091945252 | 0.781478358 | 18.18 |
| 35 | IL17B | 44 | 4 | 0.466402982 | 0.99999793 | 9.09 |
| 36 | IL5 | 20 | 4 | 0.068939199 | 0.710624303 | 20 |
| 37 | LCK | 46 | 4 | 0.501622356 | 0.99999793 | 8.7 |
| 38 | MAPK3 | 44 | 4 | 0.466402982 | 0.99999793 | 9.09 |
| 39 | MTOR | 60 | 4 | 0.711822793 | 0.99999793 | 6.67 |
| 40 | PRF1 | 28 | 4 | 0.178427395 | 0.954389149 | 14.29 |
| 41 | SPN | 56 | 4 | 0.659150649 | 0.99999793 | 7.14 |
| 42 | TNFRSF11A | 58 | 4 | 0.686266831 | 0.99999793 | 6.9 |
| 43 | TNFSF8 | 50 | 4 | 0.568728839 | 0.99999793 | 8 |
| 44 | TYK2 | 75 | 4 | 0.856164977 | 0.99999793 | 5.33 |
| 45 | AIRE | 17 | 3 | 0.147733618 | 0.876931604 | 17.65 |
| 46 | ICAM3 | 70 | 3 | 0.923956143 | 0.99999793 | 4.29 |
| 47 | STAT3 | 100 | 3 | 0.988282647 | 0.99999793 | 3 |
| 48 | STAT5B | 106 | 3 | 0.992101173 | 0.99999793 | 2.83 |
| 49 | BAX | 52 | 2 | 0.925958703 | 0.99999793 | 3.85 |
| 50 | BID | 42 | 2 | 0.857080857 | 0.99999793 | 4.76 |
| 51 | C1S | 29 | 2 | 0.682275938 | 0.99999793 | 6.9 |
| 52 | C8G | 35 | 2 | 0.778111473 | 0.99999793 | 5.71 |
| 53 | CASP10 | 53 | 2 | 0.930777372 | 0.99999793 | 3.77 |
| 54 | CCL15 | 12 | 2 | 0.245882010 | 0.99999793 | 16.67 |
| 55 | CCL23 | 16 | 2 | 0.366542591 | 0.99999793 | 12.5 |
| 56 | CD2 | 34 | 2 | 0.764125503 | 0.99999793 | 5.88 |
| 57 | CD47 | 46 | 2 | 0.889742685 | 0.99999793 | 4.35 |
| 58 | CD79A | 44 | 2 | 0.874387211 | 0.99999793 | 4.55 |

TABLE 3.b-continued

|    | gene  | Probe_Count_Total | Probe_Count_Sig | HyperG_Stats | FDR_HyperG | Percent_Sig |
|----|-------|-------------------|-----------------|--------------|------------|-------------|
| 59 | CD79B | 20                | 2               | 0.479107134  | 0.99999793 | 10          |
| 60 | CD86  | 46                | 2               | 0.889742685  | 0.99999793 | 4.35        |
| 61 | CFI   | 16                | 2               | 0.366542591  | 0.99999793 | 12.5        |
| 62 | CSF2  | 36                | 2               | 0.791365183  | 0.99999793 | 5.56        |

TABLE 3.c

|    | gene     | Probe_Count_Total | Probe_Count_Sig | HyperG_Stats | FDR_HyperG  | Percent_Sig |
|----|----------|-------------------|-----------------|--------------|-------------|-------------|
| 63 | HAVCR2   | 10                | 2               | 0.185613716  | 0.954389149 | 20          |
| 64 | HLA-DMA  | 16                | 2               | 0.366542591  | 0.99999793  | 12.5        |
| 65 | HLA-DMB  | 26                | 2               | 0.622797749  | 0.99999793  | 7.69        |
| 66 | ICAM1    | 63                | 2               | 0.965115210  | 0.99999793  | 3.17        |
| 67 | IFNG     | 10                | 2               | 0.185613716  | 0.954389149 | 20          |
| 68 | IL25     | 74                | 2               | 0.983929844  | 0.99999793  | 2.7         |
| 69 | IL26     | 20                | 2               | 0.479107134  | 0.99999793  | 10          |
| 70 | IL3      | 42                | 2               | 0.857080857  | 0.99999793  | 4.76        |
| 71 | IRF2     | 38                | 2               | 0.815788109  | 0.99999793  | 5.26        |
| 72 | IRF3     | 30                | 2               | 0.700318757  | 0.99999793  | 6.67        |
| 73 | IRF4     | 40                | 2               | 0.837619347  | 0.99999793  | 5           |
| 74 | LTBR     | 33                | 2               | 0.749379647  | 0.99999793  | 6.06        |
| 75 | LYN      | 48                | 2               | 0.903339407  | 0.99999793  | 4.17        |
| 76 | PDCD1    | 36                | 2               | 0.791365183  | 0.99999793  | 5.56        |
| 77 | PVR      | 65                | 2               | 0.969655536  | 0.99999793  | 3.08        |
| 78 | RAC1     | 64                | 2               | 0.967461559  | 0.99999793  | 3.12        |
| 79 | RAG1     | 51                | 2               | 0.920824528  | 0.99999793  | 3.92        |
| 80 | RELA     | 56                | 2               | 0.943513220  | 0.99999793  | 3.57        |
| 81 | SMAD3    | 34                | 2               | 0.764125503  | 0.99999793  | 5.88        |
| 82 | STAT4    | 58                | 2               | 0.950729209  | 0.99999793  | 3.45        |
| 83 | TNFRSF1A | 46                | 2               | 0.889742685  | 0.99999793  | 4.35        |
| 84 | TRAF2    | 46                | 2               | 0.889742685  | 0.99999793  | 4.35        |
| 85 | TRAF6    | 60                | 2               | 0.957059624  | 0.99999793  | 3.33        |
| 86 | UBC      | 64                | 2               | 0.967461559  | 0.99999793  | 3.12        |
| 87 | CCL14    | 9                 | 1               | 0.525100723  | 0.99999793  | 11.11       |
| 88 | CCL16    | 9                 | 1               | 0.525100723  | 0.99999793  | 11.11       |
| 89 | ICAM2    | 24                | 1               | 0.862829697  | 0.99999793  | 4.17        |
| 90 | ICAM4    | 53                | 1               | 0.987603129  | 0.99999793  | 1.89        |
| 91 | IL12RB1  | 51                | 1               | 0.985366094  | 0.99999793  | 1.96        |
| 92 | MCAM     | 33                | 1               | 0.934919833  | 0.99999793  | 3.03        |
| 93 | PYCARD   | 6                 | 1               | 0.391279132  | 0.99999793  | 16.67       |
| 94 | SPA17    | 17                | 1               | 0.755090130  | 0.99999793  | 5.88        |

TABLE 4.a

| probe | GeneLocus | Probe_Count_Total |
|-------|-----------|-------------------|
| STAT5A_STAT5B_17_40403935_40406459_40464294_40468456_FR | STAT5A-STAT5B | 20 |
| IRF1_5_131808352_131813604_131831068_131832754_FF | IRF1 | 19 |
| ITK_5_156605330_156608059_156693735_156698772_FR | ITK | 63 |
| CD14_5_140023383_140027012_140050153_140052313_RF | CD14 | 22 |
| PDCD1LG2_9_5495992_5498009_5563479_5572986_RR | CD274-PDCD1LG2 | 8 |

TABLE 4.b

| HyperG_Stats | FDR_HyperG  | Percent_Sig | logFC               | AveExpr              |
|--------------|-------------|-------------|---------------------|----------------------|
| 0.001866853  | 0.066190912 | 60          | 0.847262651666667   | 0.847262651666666    |
| 0.000987668  | 0.046843683 | 63.16       | 0.575333619         | 0.575333619          |
| 0.653537516  | 1           | 25.4        | 0.929375192333334   | 0.929375192333333    |
| 0.218923992  | 0.865271017 | 36.36       | 0.720976047333333   | 0.720976047333333    |
| 0.918612302  | 1           | 12.5        | −0.351310575666667  | −0.351310575666667   |

TABLE 4.c

| t                 | P.Value              | adj.P.Val           | B                   |
|-------------------|----------------------|---------------------|---------------------|
| 7.35944594338825  | 0.000150927923435752 | 0.0102743339719173  | 1.64393419184962    |
| 5.64430691077999  | 0.000700956470870541 | 0.0155534374671815  | −0.0160747735782962 |
| 8.2961135309084   | 0.0000610123228131512| 0.00959185677856724 | 2.42787963605984    |

TABLE 4.c-continued

| t | P.Value | adj.P.Val | B |
|---|---|---|---|
| 7.76177819268656 | 0.0000944498918420986 | 0.0097813496834544 | 2.00179581849286 |
| −6.21225357321395 | 0.000390149640704813 | 0.0122622958225811 | 0.582455106574847 |

TABLE 4.d

| FC | FC_1 | LS | Loop detected |
|---|---|---|---|
| 1.79931599399832 | 1.79931599399832 | 1 | R |
| 1.49002198650363 | 1.49002198650363 | 1 | R |
| 1.90445103081467 | 1.90445103081467 | 1 | R |
| 1.64829680346345 | 1.64829680346345 | 1 | R |
| 0.783871688209362 | −1.27571899207682 | −1 | NR |

TABLE 4.e

| Probe sequence 60 mer | Probe Location Chr |
|---|---|
| TTCCATAGATTACTTTTCAAATCATCCTTCGAAGCTGGCGGCTGAGGGCCCGGCGCCAAG (SEQ ID NO: 362) | 17 |
| GTGTCTCGGCCCCCTGGGGCCCCACCCTTCGATTTCCCTGTTGCCGCCGCGTTTGCAAGA (SEQ ID NO: 363) | 5 |
| ATCCCAACAAAAGAGAAGAACTTCTCCCTCGATGTTTGGGGGCGGAGGGCTTTGATGAGA (SEQ ID NO: 364) | 5 |
| GTGGCGATGGCGGCCTGCGCGCCGCGCCTCGATGTCTAAGCAACCTGCTAACTGAGGCAG (SEQ ID NO: 365) | 5 |
| ACAGTTATTAGAAAAATAAAACATTTGGTCGAACAGCAAAGAGAAGATATTCAACTGCGA (SEQ ID NO: 366) | 9 |

TABLE 4.f

| Probe Location | | | | 4 kb Sequence Location | | | |
|---|---|---|---|---|---|---|---|
| Start1 | End1 | Start2 | End2 | Chr | Start1 | End1 | Start2 |
| 40406428 | 40406457 | 40464296 | 40464325 | 17 | 40402458 | 40406457 | 40464296 |
| 131813573 | 131813602 | 131832723 | 131832752 | 5 | 131809603 | 131813602 | 131828753 |
| 156608028 | 156608057 | 156693737 | 156693766 | 5 | 156604058 | 156608057 | 156693737 |
| 140023385 | 140023414 | 140052282 | 140052311 | 5 | 140023385 | 140027384 | 140048312 |
| 5495994 | 5496023 | 5563481 | 5563510 | 9 | 5495994 | 5499993 | 5563481 |

TABLE 4.g

| 4 kb Sequence Location End2 |
|---|
| 40468295 |
| 131832752 |
| 156697736 |
| 140052311 |
| 5567480 |

TABLE 4.h

| probe | Inner_primers PCR-Primer1_ID |
|---|---|
| STAT5A_STAT5B_17_40403935_40406459_40464294_40468456_FR | OBD117-009 |
| IRF1_5_131808352_131813604_131831068_131832754_FF | OBD117-045 |
| ITK_5_156605330_156608059_156693735_156698772_FR | OBD117-089 |
| CD14_5_140023383_140027012_140050153_140052313_RF | OBD117-105 |
| PDCD1LG2_9_5495992_5498009_5563479_5572986_RR | OBD117-029 |

TABLE 4.i

Inner_primers

| PCR_Primer1 | PCR-Primer2_ID | PCR_Primer2 | GLMNET |
|---|---|---|---|
| TCTACAGCCCAAGATCCTGCTTT (SEQ ID NO: 367) | OBD117-011 | CCCCGAGGGTTGAGAAGCAT (SEQ ID NO: 372) | 0.251515381 |
| GGACCCAACAGAGGGTCTGG (SEQ ID NO: 368) | OBD117-047 | ACTTGGGATAGACCTGCGGC (SEQ ID NO: 373) | 0 |
| TTGTGCTAAGAGGTGATGCCCA (SEQ ID NO: 369) | OBD117-090 | TGTGGTTTCGGCCTTTGACATC (SEQ ID NO: 374) | −0.332188811 |
| CAGCGGATGGTTGTGCAGC (SEQ ID NO: 370) | OBD117-107 | CCTGGGCAGATTATGGTGCG (SEQ ID NO: 375) | 0.070125046 |
| CTCACTGCCCAACAGGCTAGAA (SEQ ID NO: 371) | OBD117-031 | TCTTGACTCAGAGCCCACAACAA (SEQ ID NO: 376) | −0.1009401 |

TABLE 4.j

| Gene | Marker | GLMNET |
|---|---|---|
| STAT5A-STAT5B | OBD117-009/011 | 0.1947148 |
| IRF1 | OBD117-045/047 | 0.1946348 |
| ITK | OBD117-089/090 | 0.1938877 |
| CD14 | OBD117-105/107 | 0.193081 |
| CD274-PDCD1LG2 | OBD117-029/030 | −0.1922868 |

TABLE 5a

| Gene Locus | Probes | Chr | Start1 | End1 | Start2 |
|---|---|---|---|---|---|
| PVRL1 | AGAAAATATAGTATTGATTGCTTTCAAGTCGATGCGCCGCCCGGGCCCGGTCGGAGC (SEQ ID NO: 377) | 11 | 119577280 | 119577309 | 119599999 |
| HLA-DQB1 | TACTGTAGTAAGTTCTCTGAGGAGATATCGATTTTTATTGTATCCTATATTTTTCTA (SEQ ID NO: 378) | 6 | 32607973 | 32608002 | 32669133 |
| HLA-DQB1 | TACTGTAGTAAGTTCTCTGAGGAGATATCGAAGTCTTGATTAAGGTTCATTCAACAAA (SEQ ID NO: 379) | 6 | 32607973 | 32608002 | 32630139 |
| BOK | CACTTCCCCACATAAGCCTCGGTCTCTTCGAGGGCGGCCCGGCCCGGAGCAAAC (SEQ ID NO: 380) | 2 | 242498608 | 242498637 | 242532080 |
| CSK | GAGTTCAGCGTGCCCCGGCGTGAAAGTCGAGGCATATTTGAGTTTAGGGAGGTGTTGC (SEQ ID NO: 381) | 15 | 75047316 | 75047345 | 75083505 |
| CSK | GAGTTCAGCGTGCCCCGGGCGTGAAAGTCGACTCTGGGCCCAGACCACAGAAGGAGGGG (SEQ ID NO: 382) | 15 | 75047316 | 75047345 | 75080014 |
| CSK | GAGTTCAGCGTGCCCCGGGCGTGAAAGTCGATTTGTTTATGGTTTATCCCCAGTGCCT (SEQ ID NO: 383) | 15 | 75047316 | 75047345 | 75072258 |
| HLA-DQB1 | TTTGTTGAATGAACCTTAATCCAAGACTTCGATTTTTATTGTATCCTATATTTTTCTA (SEQ ID NO: 384) | 6 | 32630139 | 32630168 | 32669133 |
| STAT5B | TTCCATAGATTACTTTTCAAATCATCCTTCGAAGCTGGCGGCCCGGCCCAAG (SEQ ID NO: 385) | 17 | 40406430 | 40406459 | 40464295 |
| BOK | GTTTGCTCCCCGGGGCCGCCGGCCCCTCGATTTTAACACCACCATGGTTTGAATGAAT (SEQ ID NO: 386) | 2 | 242498608 | 242498637 | 242517412 |
| PTPRA | TCCATTGTCTTATTCCAGTCTAGGCTTGTCGAGTTGCAGGCCGCCCTGGTGGCTAGACAT (SEQ ID NO: 387) | 20 | 2853762 | 2853791 | 2948630 |
| FCGR2B | AAAAAACAATTATGTAATTGAAAAACCCATCGAGGGGCTTACTAATGCCTTTTAGCTCCCT (SEQ ID NO: 388) | 1 | 161569925 | 161569954 | 161615628 |
| BOK | GACCCCGGGAATTGGCTCCAGCACATCTCGAGGGCGGGCCCGGAGCAAAC (SEQ ID NO: 389) | 2 | 242454061 | 242454090 | 242498608 |
| FCGR2B | AAAAAACAATTATGTAATTGAAAACCATCGAAGCTCTTTGGTTCCACAGAGTGATTCTG (SEQ ID NO: 390) | 15 | 75047316 | 75047345 | 75075210 |
| HLA-DQB1 | AGGCATTCGTTCTTCAGCTCTTCTATAATCGATTTTTATTGTATCCTATATTTTTCTA (SEQ ID NO: 391) | 1 | 6526238 | 6526267 | 6554649 |
| PTPRA | GCTCTTATAAATTATGTATTCAAAGAAAATCGAGTTGCAGCCGCCCTGGTGGCTAGACAT (SEQ ID NO: 392) | 7 | 155595852 | 155595881 | 155630427 |

TABLE 5a-continued

| Gene Locus | Probes | Chr | Start1 | End1 | Start2 |
|---|---|---|---|---|---|
| AKT1 | CCCGCGGGCGGAGCTGCTACTGTTTACTTTCGAAGCTTCTTCCTTTCGGCCCCCAGGCCTA (SEQ ID NO: 393) | 20 | 2797356 | 2797385 | 2948630 |
| PTPRA | GCTCTTATAAATTATGTATTCAAAGAAATCGAACTGGCGCGCAACCGCTGCAGCGCCTGCT (SEQ ID NO: 394) | 1 | 6526238 | 6526267 | 6558079 |
| FCGR2B | AAAAACAATTATGTAATTGAAAACCCATCGAGGGGCTTACTATGCCTTTTAGCTCCCT (SEQ ID NO: 395) | 2 | 242454061 | 242454090 | 242498608 |
| BOK | TCTCCTGCCTACCACACTGTGAGAAAGCTCGAGGGCGGACCCCGGAGCAAAC (SEQ ID NO: 396) | 15 | 75047316 | 75047345 | 75075210 |
| CSK | GAGTTCAGCGTGCCGCCGGGCGTGAAAGTCGAATTCTCCAGGAGCCACTGTCAGAACCC (SEQ ID NO: 397) | 1 | 6526238 | 6526267 | 6554649 |
| TNFRSF25 | CCGCCCCGCAGGGCCCGCCCCGCCCGTCGACAATGTTATTCTTTGTTTCTCTTACCAA (SEQ ID NO: 398) | 7 | 155595852 | 155595881 | 155630427 |
| SHH | GAAGGCCCGTGCGCCACAGCTGTCTCCTCGAGAACAGCCAGGCTAACACGGAGAAACCC (SEQ ID NO: 399) | 20 | 2797356 | 2797385 | 2948630 |
| PTPRA | TCCATTGTCTTATTCCAGTCTAGGCTTGTCGAACTGGCGCGCAACCGCTGCAGCGCCTGCT (SEQ ID NO: 400) | 1 | 6526238 | 6526267 | 6558079 |
| TNFRSF25 | CCGCGCCCCGCAGGGCCCCGCCCCGCCCGTCGATGTGTTGGAAGTCAGGGCGGCGGTGCCC (SEQ ID NO: 401) | 2 | 242454061 | 242454090 | 242498608 |
| PIK3CA | | | | | |
| IL12B | | | | | |
| MYD88 | | | | | |
| PVRL1 | | | | | |
| PIK3R3 | | | | | |
| CD6 | | | | | |
| TREM1 | | | | | |
| IL12A | | | | | |
| | CCGCGCCCCGCAGGGCCCGCCCCGCCCGTCGAGGCTTTCAAGGGATCCAGGGTGGGGTGC (SEQ ID NO: 402) | 1 | 6526238 | 6526267 | 6544279 |
| | CCGCGCCCCGCAGGGCCCGCCCCGCCCGTCGACAATGTTATTCTTTGTTTCTCTTACCAA (SEQ ID NO: 403) | 1 | 6526238 | 6526267 | 6554649 |
| | CCGCGCCCCGCAGGGCCCGCCCCGCCCGTCGATGTGTTGGAAGTCAGGGCGGCGGTGCCC (SEQ ID NO: 404) | 1 | 6526238 | 6526267 | 6558079 |

TABLE 5a-continued

| Gene Locus | Probes | Chr | Start1 | End1 | Start2 |
|---|---|---|---|---|---|
| | CACTTCCCCAACACATAAGCCTCGGTCTCTTCGAGGGCGGGCCCGGCCCGGAGCAAAC (SEQ ID NO: 405) | 2 | 242498608 | 242498637 | 242532080 |
| | CCGCCCCGCAGGGCCCGCCCGCCGTCGAGAAGCAGGGACATAAAGCAGGTATGGAG (SEQ ID NO: 406) | 1 | 6526238 | 6526267 | 6574085 |
| | GACCCCGGGAATTGGCTCCAGCACATCTCGAGGGCGGGCCCGGCCCGGAGCAAAC (SEQ ID NO: 407) | 2 | 242474876 | 242474905 | 242498608 |
| | GTTTGCTCCGGGGCCCGCCGGGCCCGCCCCTCGATTTTAACACCACATGTTTGAATGAAT (SEQ ID NO: 408) | 2 | 242498608 | 242498637 | 242517412 |
| | GTGTCTCGGCCCCCCTGGGGCCCCACCCTTCGATTTCCCTGTTGCCGCCGTTTGCAAGA (SEQ ID NO: 409) | 5 | 131813575 | 131813604 | 131832725 |
| | TCTCCTGCCTACCACACTGTGAGAAAGCTCGAGGGCGGGCCCCGGAGCAAAC (SEQ ID NO: 410) | 2 | 242454061 | 242454090 | 242498608 |
| | GAGTTCAGCGTGCCGCCGGGGCGTGAAAGTCGAGCGCATATTTGAGTTAGGGAGGTGTTGC (SEQ ID NO: 411) | 15 | 75047316 | 75047345 | 75083505 |
| | GGGACACCGCCGCCCTGACTTCCAACACATCGATCTCTGCCTCCGCCAGCCCCAGCGTGCG (SEQ ID NO: 412) | 1 | 6521665 | 6521694 | 6558079 |
| | CCACCCCCGCCCGGGGAGTCGCCCGGTCGATTTCCAAAAGCTCACACATGGGTGCACA (SEQ ID NO: 413) | 8 | 42128692 | 42128721 | 42148498 |
| | GGGACACCGCCGCCCTGACTTCCAACACATCGAAGAATGGGTGGGCCTTGCACCTCATAC (SEQ ID NO: 414) | 1 | 6510664 | 6510693 | 6558079 |
| | CCACCCCCGCCCGGGGAGTCGCCCGGTCGACCCCCTGACATGGGCTGCCTGAGCAG (SEQ ID NO: 415) | 8 | 42128692 | 42128721 | 42188563 |
| | GGGACACCGCCGCCCTGACTTCCAACACATCGAGAAGCATAAAGCAGGGACAGGTATGGAG (SEQ ID NO: 416) | 1 | 6558079 | 6558108 | 6574085 |
| | GAGTTCAGCGTGCCGCCGGGCGTGAAAGTCGACTTCTGGGCCCAGACCACAGAAGGAGGGG (SEQ ID NO: 417) | 15 | 75047316 | 75047345 | 75080014 |
| | AATTCTGTTGGAAGAATAATTTAAAATATCGATGTGGCACGGCCTGTGGGGTCACGGA (SEQ ID NO: 418) | 13 | 111748013 | 111748042 | 111954400 |
| | TTCCATAGATTACTTTTCAAATCATCCTTCGAAGCTGGCGCTGAGGGCCCGGCGCCAAG (SEQ ID NO: 419) | 17 | 40406430 | 40406459 | 40464295 |
| | GAGTTCAGCGTGCCGCCGGGCGTGAAAGTCGATTTGTTTATGTTTTATCCCCAGTGCCT (SEQ ID NO: 420) | 15 | 75047316 | 75047345 | 75072258 |
| | CACCCTCCCCTTCTTCCTGGGCCCTCAGATCGACCCCCCACCCGGGCTGGCTGC (SEQ ID NO: 421) | 19 | 50158040 | 50158069 | 50185426 |

TABLE 5a-continued

| Gene Locus | Probes | Chr | Start1 | End1 | Start2 |
|---|---|---|---|---|---|
| | CCACCCCCGCCCCGGGGAGTCGCCGGTCGCCCGGTCGAGGGCCTGGCAAGAAGACAGAAGCCGACT (SEQ ID NO: 422) | 8 | 42128692 | 42128721 | 42138741 |
| | TATGAGTAATAATTACAATTCCCCCTTTCGACCTCCAGTCCCCGCCACTTCCACGGC (SEQ ID NO: 423) | 9 | 123675825 | 123675854 | 123702717 |
| | CAGAAACTGCTGGTTGGGCTCATACTTTTCGAGGGCCAGCTCCCCGCACCCCCACCAAGC (SEQ ID NO: 424) | 11 | 64023978 | 64024007 | 64060064 |
| | TTCCCCTGTAAGATTCATTTCCTGTGATTCGAGTCACAGCTGTAGTGGGGTGGGGGGTGA (SEQ ID NO: 425) | 21 | 45665442 | 45665471 | 45687443 |
| | TCTTTGTTACTGGAATATACGAATAAAATCGATGTGGCGACCGGCTGTGGGGGTCACGGA (SEQ ID NO: 426) | 13 | 111732623 | 111732652 | 111748013 |

TABLE 5b

| Gene Locus | End2 | Chr | Start1 | End1 | Start2 | End2 |
|---|---|---|---|---|---|---|
| PVRL1 | 119600028 | 11 | 119573310 | 119577309 | 119599999 | 119603998 |
| HLA-DQB1 | 32669162 | 6 | 32607973 | 32611972 | 32669133 | 32673132 |
| HLA-DQB1 | 32630168 | 6 | 32607973 | 32611972 | 32630139 | 32634138 |
| BOK | 242532109 | 2 | 242498608 | 242502607 | 242528110 | 242532109 |
| CSK | 75083534 | 15 | 75043346 | 75047345 | 75083505 | 75087504 |
| CSK | 75080043 | 15 | 75043346 | 75047345 | 75076044 | 75080043 |
| CSK | 75072287 | 15 | 75043346 | 75047345 | 75072258 | 75076257 |
| HLA-DQB1 | 32669162 | 6 | 32630139 | 32634138 | 32669133 | 32673132 |
| STAT5B | 40464324 | 17 | 40402460 | 40406459 | 40464295 | 40468294 |
| BOK | 242517441 | 2 | 242498608 | 242502607 | 242517412 | 242521411 |
| PTPRA | 2948659 | 20 | 2853762 | 2857761 | 2944660 | 2948659 |
| FCGR2B | 161615657 | 1 | 161565955 | 161569954 | 161615628 | 161619627 |
| BOK | 242498637 | 2 | 242454061 | 242458060 | 242498608 | 242502607 |
| FCGR2B | 75075239 | 15 | 75043346 | 75047345 | 75075210 | 75079209 |
| HLA-DQB1 | 6554678 | 1 | 6522268 | 6526267 | 6554649 | 6558648 |
| PTPRA | 155630456 | 7 | 155591882 | 155595881 | 155626457 | 155630456 |
| AKT1 | 2948659 | 20 | 2797356 | 2801355 | 2944660 | 2948659 |
| PTPRA | 6558108 | 1 | 6522268 | 6526267 | 6554109 | 6558108 |
| FCGR2B | 242498637 | 2 | 242454061 | 242458060 | 242498608 | 242502607 |
| BOK | 75075239 | 15 | 75043346 | 75047345 | 75075210 | 75079209 |
| CSK | 6554678 | 1 | 6522268 | 6526267 | 6554649 | 6558648 |
| TNFRSF25 | 155630456 | 7 | 155591882 | 155595881 | 155626457 | 155630456 |
| SHH | 2948659 | 20 | 2797356 | 2801355 | 2944660 | 2948659 |
| PTPRA | 6558108 | 1 | 6522268 | 6526267 | 6554109 | 6558108 |
| TNFRSF25 | 242498637 | 2 | 242454061 | 242458060 | 242498608 | 242502607 |
| | 6544308 | 1 | 6522268 | 6526267 | 6540309 | 6544308 |
| | 6554678 | 1 | 6522268 | 6526267 | 6554649 | 6558648 |
| | 6558108 | 1 | 6522268 | 6526267 | 6554109 | 6558108 |
| | 242532109 | 2 | 242498608 | 242502607 | 242528110 | 242532109 |
| | 6574114 | 1 | 6522268 | 6526267 | 6574085 | 6578084 |
| | 242498637 | 2 | 242474876 | 242478875 | 242498608 | 242502607 |
| | 242517441 | 2 | 242498608 | 242502607 | 242517412 | 242521411 |
| | 131832754 | 5 | 131809605 | 131813604 | 131828755 | 131832754 |
| | 242498637 | 2 | 242454061 | 242458060 | 242498608 | 242502607 |
| | 75083534 | 15 | 75043346 | 75047345 | 75083505 | 75087504 |
| | 6558108 | 1 | 6521665 | 6525664 | 6554109 | 6558108 |
| | 42148527 | 8 | 42124722 | 42128721 | 42148498 | 42152497 |
| | 6558108 | 1 | 6510664 | 6514663 | 6554109 | 6558108 |
| | 42188592 | 8 | 42124722 | 42128721 | 42188563 | 42192562 |
| | 6574114 | 1 | 6554109 | 6558108 | 6574085 | 6578084 |
| | 75080043 | 15 | 75043346 | 75047345 | 75076044 | 75080043 |
| | 111954429 | 13 | 111748013 | 111752012 | 111950430 | 111954429 |
| | 40464324 | 17 | 40402460 | 40406459 | 40464295 | 40468294 |
| | 75072287 | 15 | 75043346 | 75047345 | 75072258 | 75076257 |
| | 50185455 | 19 | 50158040 | 50162039 | 50181456 | 50185455 |
| | 42138770 | 8 | 42124722 | 42128721 | 42138741 | 42142740 |
| | 123702746 | 9 | 123675825 | 123679824 | 123698747 | 123702746 |
| | 64060093 | 11 | 64023978 | 64027977 | 64060064 | 64064063 |
| | 45687472 | 21 | 45661472 | 45665471 | 45687443 | 45691442 |
| | 111748042 | 13 | 111728653 | 111732652 | 111748013 | 111752012 |

TABLE 6a

| Gene Locus | Probe | Chr | Start1 | End1 | Start2 |
|---|---|---|---|---|---|
| BAX | AAGGCAGGCAGATCAGGAGCTCAAGGAGTCGAAAGAAAAAAAAAAGCATAAAAATCCA (SEQ ID NO: 427) | 19 | 49419941 | 49419970 | 49474800 |
| BAX | AAGGCAGGCAGATCAGGAGCTCAAGAGATCGAACCTAAGTGTAGTTTAACACCTACTAG (SEQ ID NO: 428) | 19 | 49419941 | 49419970 | 49438538 |
| CASP1 | ATAGTAAAATGTGAAAATGTTACAGTTATCGAAGTTCAGCGAGTATATTTTACTGATAC (SEQ ID NO: 429) | 11 | 104941452 | 104941481 | 104994206 |
| NCK2 | AAGCCCAAGAACCAGGAATCTAGTATTCGAAAAGCCCTAAAGTTGGCTTAATAAACTT (SEQ ID NO: 430) | 2 | 106375591 | 106375620 | 106457773 |
| JAM2 | GGTGGGCAGATCACTTAAGGCCAGGAATTCGAATCAAAACTCACTACCCACTGGTAAGA (SEQ ID NO: 431) | 21 | 26998354 | 26998383 | 27012523 |
| JAM2 | GGTGGGCAGATCACTTAAGGCCAGGAATTCGATTCTATCAACTCTAGAATTTTTTAAAT (SEQ ID NO: 432) | 21 | 26998354 | 26998383 | 27073929 |
| BAX | AAGGCAGGCAGATCAGGAGCTCAAGAGATCGAGGTAAATGTGGGGGTTCTAGAACCCAGT (SEQ ID NO: 433) | 19 | 49419941 | 49419970 | 49471564 |
| JAM2 | GGTGGGCAGATCACTTAAGGCCAGGAATTCGAAATTCTTTCCTAATGCCAAGTGTGTTAT (SEQ ID NO: 434) | 21 | 26998354 | 26998383 | 27076729 |
| CXCL2 | GGTCCCTGATTTCCATCCTAGTGCTTCTCGAAACATGTCTCTGGAGATAAAGCGCCAA (SEQ ID NO: 435) | 4 | 74949500 | 74949529 | 74968427 |
| JAM2 | GGTGGGCAGATCACTTAAGGCCAGGAATTCGATATTCAATAAAAGACCGATGTGCAAAG (SEQ ID NO: 436) | 21 | 26998354 | 26998383 | 27056448 |
| JAM2 | GGTGGGCAGATCACTTAAGGCCAGGAATTCGAGAAATGTTTATCCAATTCATCCAAAAT (SEQ ID NO: 437) | 21 | 26998354 | 26998383 | 27060381 |
| JAM2 | GGTGGGCAGATCACTTAAGGCCAGGAATTCGAGAGACTGTAAAGACATGTCTCTGCCTCT (SEQ ID NO: 438) | 21 | 26998354 | 26998383 | 27047036 |
| JAM2 | GGTGGGCAGATCACTTAAGGCCAGGAATTCGATCACTTCTTAAAGGCCCTACCTTCTAAT (SEQ ID NO: 439) | 21 | 26998354 | 26998383 | 27035796 |
| IL2 | GTTGGGTTGAAGATGAAATCATAGGAAGTCGAGCTGTACCTCTGCTTGTTATTCTCCCT (SEQ ID NO: 440) | 4 | 123404410 | 123404439 | 123422745 |
| JAM2 | GGTGGGCAGATCACTTAAGGCCAGGAATTCGAAACACCAGTCTCTTAAATCCTGTGCCT (SEQ ID NO: 441) | 21 | 26998354 | 26998383 | 27028108 |
| JAM2 | GGTGGGCAGATCACTTAAGGCCAGGAATTCGAGGAAAAACCTCGGGCAAAATAGGGAAAG (SEQ ID NO: 442) | 21 | 26998354 | 26998383 | 27050012 |

TABLE 6a-continued

| Gene Locus | Probe | Chr | Start1 | End1 | Start2 |
|---|---|---|---|---|---|
| BAX | TGAGAATGGAATAGATCAAAGGAGGGTTCGAGACAAGGTCTCACTTTATCACCCAACCT (SEQ ID NO: 443) | 19 | 49421752 | 49421781 | 49475137 |
| JAM2 | GGTGGGCAGATCACTTAAGGCCAGGAATTCGACTGTGTCGTGCCCATGAAGAAGATGGG (SEQ ID NO: 444) | 21 | 26998354 | 26998383 | 27070794 |
| IL4 | AGTGATAGAAGAGGGACAAGGTGGCAGTTCGATTTTAAAACACGCTCTCAATAAAAGA (SEQ ID NO: 445) | 5 | 131972293 | 131972322 | 131985853 |
| CBLB | AGCAGGGGATCACATAAGGCCAGGAGTTCGATAAATAAATTAGAAGAAGATATAATAA (SEQ ID NO: 446) | 3 | 105394496 | 105394525 | 105635546 |
| JAM2 | GGTGGGCAGATCACTTAAGGCCAGAATTCGATTCTGCTTCTCACAGCCCACATC (SEQ ID NO: 447) | 21 | 26998354 | 26998383 | 27083337 |
| NCK2 | TCTTTGCAGATGTGTAAGATAAGGATGTCGAAAAGCCCTAAAGTTGGCTTAATAAACTT (SEQ ID NO: 448) | 2 | 106358253 | 106358282 | 106457773 |
| CXCL2 | GGTCCCCTGATTTCCATCCTAGTGCTTCTCGATGATATAATACTCTGCTGACTACATTTT (SEQ ID NO: 449) | 4 | 74949500 | 74949529 | 74983629 |
| NCK2 | AAGGCCCAAGAACCAGGAATCTAGGTATTCGACCACCTTAAAAGAAAATCTCTTGGAAC (SEQ ID NO: 450) | 2 | 106375591 | 106375620 | 106435341 |
| CBLB | AGCAGGGGATCACATAAGGCCAGGAGTTCGATGAACGTTTACCCAATTATTCTAAACA (SEQ ID NO: 451) | 3 | 105394496 | 105394525 | 105606665 |
| MAP3K14 | GATGCGGACTGTTTCCCTGCTTTGATTTATCGACTTCTTATTTCTATTTGTGACTTAGGA (SEQ ID NO: 452) | | | | |
| MAP3K14 | GATGCGGACTGTTTCCCTGCTTTGATTTATCGACACAGTGTCTGAAGTTTGGGGTGTA (SEQ ID NO: 453) | | | | |
| MAP3K14 | GATGCGGACTGTTTCCCTGCTTTGATTTATCGATATCTCCCTCTTCGCTTCTTCCTTTC (SEQ ID NO: 454) | | | | |
| MAP3K14 | GATGCGGACTGTTTCCCTGCTTTGATTTATCGAGTCATTAAGAGACTCTCCGCCTGGTGG (SEQ ID NO: 455) | | | | |
| PRKCQ | TTCCACCTGTAATACTGTCCTGATTCTCGACTCTTCGCCCTCTTCTCCAGCTCTCT (SEQ ID NO: 456) | | | | |
| SIRPA | TAAAGTACTGTCCCACATATAAGGTACTCGACCAAGAAATTCATTCTTACCTCCTAAGA (SEQ ID NO: 457) | | | | |
| MAPK1 | ACCCCACCAATCTATAATAAGATTCGATTTCGACACAAGGGTTTGTAACAAAAACAAAAA (SEQ ID NO: 458) | | | | |
| SIRPA | AGCGCTTTATTTGTCAGGACGATAGACCTCGACAATGTCCTATTCTTCCAGAAACTCATT (SEQ ID NO: 459) | | | | |

TABLE 6a-continued

| Gene Locus | Probe | Chr | Start1 | End1 | Start2 |
|---|---|---|---|---|---|
| CBLB | TTATTACTTTATTCTGACTGAATATCATTCGAAAGAAACCAAAAACACAAGTATACATCA (SEQ ID NO: 460) | | | | |
| CBLB | TATCCTTTGTTTAGAAGTATTTCTTATTCGACAAAATTTAACATGTTATGCAGTTACA (SEQ ID NO: 461) | | | | |
| PRKCQ | TTCAGCTATTCACTGGTTTTTCTCAGATCGACTCCTGCTTCCCTCCCCTCATCTTTAAA (SEQ ID NO: 462) | | | | |
| CBLB | TCCAGTACAATAAACAATGACCAAAGATCGACAAAATTTAACATGTTATGCAGTTACA (SEQ ID NO: 463) | | | | |
| IGKC | TAAACTCTGACATGCCTATTAGCATTCTCGAATGCATGCTCACTGTAACCTCCAACTC (SEQ ID NO: 464) | | | | |
| CBLB | TATCCTTTGGTTTAGAAGTATTTCTTATTCGACAACTACTGGCTTAAAAAAGGCAAAACA (SEQ ID NO: 465) | | | | |
| PRKCQ | TACCTCCTTGGGAACATATTTGAGAGTTTCGACTCCTGCTTCCCTCCCCTCATCTTTAAA (SEQ ID NO: 466) | | | | |
| SIRPA | ACACTTGATTTTGCTTTCCAAGCTGACTCGAGACATCTAAGAAGGTCCAGCCAGATGTT (SEQ ID NO: 467) | | | | |
| SIRPA | GCGCCCTATTTCCACCTTGTGCCTTCTGTCGACACCAAGATGTCACGGAGGAGTCTGT (SEQ ID NO: 468) | | | | |
| NCK2 | CCAGCTGAAGTTTCGCAGGTCCCCTGCTTCGAGTAGGCCAATCCCATTTTTGGCGAAAAC (SEQ ID NO: 469) | | | | |
| PRKCQ | TACCTCCTTGGGAACATATTTGAGAGTTTCGACTCCTGCTTCCCTCCCCTCATCTTTAAA (SEQ ID NO: 470) | | | | |
| SIRPA | ACACTTGATTTTGCTTTCCAAGCTGACTCGAGACATCTAAGAAGGTCCAGCCAGATGTT (SEQ ID NO: 471) | | | | |
| SIRPA | GCGCCCTATTTCCACCTTGTGCCTTCTGTCGACACCACCAAGATGTCACGGAGGAGTCTGT (SEQ ID NO: 472) | | | | |
| NCK2 | CCAGCTGAAGTTTCGCAGGTCCCCTGCTTCGAGTAGGCCAATCCCATTTTTGGCGAAAAC (SEQ ID NO: 473) | | | | |
| PRKCQ | ACTTTGGCTCAAGAGTGAAGATATTCAGTCGACTCCTGCTTCCCTCCCCTCATCTTTAAA (SEQ ID NO: 474) | | | | |
| MAPK1 | TTCCTTAGGCAAGTCATCCAATTCCATGTCGACACAAGGTTTGTAACAAAAACAAAAA (SEQ ID NO: 475) | | | | |
| SIRPA | TCTTAGGAGGTAAGAATGAATTCTTGGTCGAACTCCTGACCAGAGAGGCTGGGAGGGGT (SEQ ID NO: 476) | | | | |

TABLE 6a-continued

| Gene Locus | Probe | Chr | Start1 | End1 | Start2 |
|---|---|---|---|---|---|
| CASP7 | CATCATTTTAATAGTGCAAGAGTTCCGTCGAACGCCCATACCTGTGGGAATCAAGCAAT (SEQ ID NO: 477) | | | | |
| NCK2 | AAAACAAAAAGCCAATTCTGTACCCCTCGAACCAGCCTGGCTCTGTCCCCAGACCTT (SEQ ID NO: 478) | | | | |
| SIRPA | GCGCCCTATTTCCACCTTGTGCCTTCTGTCGAGACATCTAAGAGAGGTCCAGCCAGATGTT (SEQ ID NO: 479) | | | | |
| PRKCQ | TTGATTATTTCAGGTTGACAGCTGTAAATCGACTCCTGCTTCCCTCCCCTCATCTTTAAA (SEQ ID NO: 480) | | | | |
| | | 10 | 6474856 | 6474885 | 6548385 |
| | | 3 | 105471109 | 105471138 | 105544694 |
| | | 2 | 89164038 | 89164067 | 89179765 |
| | | 3 | 105442256 | 105442285 | 105466913 |
| | | 10 | 6474856 | 6474885 | 6595633 |
| | | 20 | 1905280 | 1905309 | 1933305 |
| | | 20 | 1872136 | 1872165 | 1900305 |
| | | 2 | 106403394 | 106403423 | 106473848 |
| | | 10 | 6474856 | 6474885 | 6605104 |
| | | 22 | 22123553 | 22123582 | 22210842 |
| | | 20 | 1830613 | 1830642 | 1877967 |
| | | 10 | 115421381 | 115421410 | 115481392 |
| | | 2 | 106383184 | 106383213 | 106439122 |
| | | 20 | 1872136 | 1872165 | 1905280 |
| | | 10 | 6474856 | 6474885 | 6515326 |

TABLE 6b

| Gene Locus | End2 | Chr | Start1 | End1 | Start2 | End2 |
|---|---|---|---|---|---|---|
| BAX | 49474829 | 19 | 49415971 | 49419970 | 49470830 | 5E+07 |
| BAX | 49438567 | 19 | 49415971 | 49419970 | 49434568 | 5E+07 |
| CASP1 | 104994235 | 11 | 104941452 | 104945451 | 104994206 | 1E+08 |
| NCK2 | 106457802 | 2 | 106375591 | 106379590 | 106457773 | 1E+08 |
| JAM2 | 27012552 | 21 | 26994384 | 26998383 | 27012523 | 3E+07 |
| JAM2 | 27073958 | 21 | 26994384 | 26998383 | 27069959 | 3E+07 |
| BAX | 49471593 | 19 | 49415971 | 49419970 | 49471564 | 5E+07 |
| JAM2 | 27076758 | 21 | 26994384 | 26998383 | 27072759 | 3E+07 |
| CXCL2 | 74968456 | 4 | 74949500 | 74953499 | 74968427 | 7E+07 |
| JAM2 | 27056477 | 21 | 26994384 | 26998383 | 27056448 | 3E+07 |
| JAM2 | 27060410 | 21 | 26994384 | 26998383 | 27056411 | 3E+07 |
| JAM2 | 27047065 | 21 | 26994384 | 26998383 | 27047036 | 3E+07 |
| JAM2 | 27035825 | 21 | 26994384 | 26998383 | 27031826 | 3E+07 |
| IL2 | 123422774 | 4 | 123400440 | 123404439 | 123418775 | 1E+08 |
| JAM2 | 27028137 | 21 | 26994384 | 26998383 | 27028108 | 3E+07 |
| JAM2 | 27050041 | 21 | 26994384 | 26998383 | 27046042 | 3E+07 |
| BAX | 49475166 | 19 | 49421752 | 49425751 | 49475137 | 5E+07 |
| JAM2 | 27070823 | 21 | 26994384 | 26998383 | 27070794 | 3E+07 |
| IL4 | 131985882 | 5 | 131968323 | 131972322 | 131985853 | 1E+08 |
| CBLB | 105635575 | 3 | 105390526 | 105394525 | 105631576 | 1E+08 |
| JAM2 | 27083366 | 21 | 26994384 | 26998383 | 27079367 | 3E+07 |
| NCK2 | 106457802 | 2 | 106354283 | 106358282 | 106457773 | 1E+08 |
| CXCL2 | 74983658 | 4 | 74949500 | 74953499 | 74983629 | 7E+07 |
| NCK2 | 106435370 | 2 | 106375591 | 106379590 | 106435341 | 1E+08 |
| CBLB | 105606694 | 3 | 105390526 | 105394525 | 105606665 | 1E+08 |
| | 6548414 | 10 | 6474856 | 6478855 | 6544415 | 7E+06 |
| | 105544723 | 3 | 105471109 | 105475108 | 105540724 | 1E+08 |
| | 89179794 | 2 | 89160068 | 89164067 | 89175795 | 9E+07 |
| | 105466942 | 3 | 105442256 | 105446255 | 105466913 | 1E+08 |
| | 6595662 | 10 | 6474856 | 6478855 | 6591663 | 7E+06 |
| | 1933334 | 20 | 1905280 | 1909279 | 1929335 | 2E+06 |
| | 1900334 | 20 | 1872136 | 1876135 | 1900305 | 2E+06 |
| | 106473877 | 2 | 106403394 | 106407393 | 106473848 | 1E+08 |
| | 6605133 | 10 | 6474856 | 6478855 | 6601134 | 7E+06 |
| | 22210871 | 22 | 22119583 | 22123582 | 22210842 | 2E+07 |
| | 1877996 | 20 | 1830613 | 1834612 | 1873997 | 2E+06 |
| | 115481421 | 10 | 115417411 | 115421410 | 115477422 | 1E+08 |
| | 106439151 | 2 | 106383184 | 106387183 | 106435152 | 1E+08 |
| | 1905309 | 20 | 1872136 | 1876135 | 1905280 | 2E+06 |
| | 6515355 | 10 | 6474856 | 6478855 | 6511356 | 7E+06 |

TABLE 7a

| Gene Locus | PCR Primer 1 Sequence | PCR Primer 2 Sequence | Probe |
|---|---|---|---|
| IL15 | TGAGTAACACAAAGCATCTG (SEQ ID NO: 481) | AGTGACTGGCTATGTTCC (SEQ ID NO: 489) | |
| MYD88 | CTGGTGATTTGTGTGACTTTG (SEQ ID NO: 482) | AGGGAAGATGTGGAGGAG (SEQ ID NO: 490) | |
| HLA-DQB1 | GTACGACTCCAGCCAAATG (SEQ ID NO: 483) | GCTGTCTGTTACTAGATTGCAC (SEQ ID NO: 491) | |
| IL12B | ACCTTGCAAGAAGCACAG (SEQ ID NO: 484) | ATGATACTTCCCAACTGACAC (SEQ ID NO: 492) | |
| PVRL1 | AGGAGCATCCATATCAAGTG (SEQ ID NO: 485) | CTGCCATGTCTGACTATCC (SEQ ID NO: 493) | |
| PIK3R3 | CAGTGAAGAAGCCATCATCG (SEQ ID NO: 486) | CTTAGAGAAATACACCAGCAG (SEQ ID NO: 494) | |
| CD6 | ATGGGCAGCATTTCTCAC (SEQ ID NO: 487) | AGGGACGATTTATATGACTTGC (SEQ ID NO: 495) | |
| STAT5B | GTGCTGGTATGTACCTGTAATC (SEQ ID NO: 488) | GAGGGTTGAGAAGCATCTTG (SEQ ID NO: 496) | |
| IL15 | | | TGTAAACTGTAATATCAAAAATTCAAAATCGAAGAGTTGATTTACTTATTAACATTAGAA (SEQ ID NO: 497) |
| MYD88 | | | ACTTTTATAGTGAAAAGTGCCATTTGAGTCGACTGTGATTGAATGTAAAAGGTTTTAAAT (SEQ ID NO: 498) |
| HLA-DQB1 | | | TACTGTAGTAAGTTCTCTGAGGAGGATATCGAAGTCTTGGATTAAGGTTCATTCAACAAA (SEQ ID NO: 499) |
| IL12B | | | TCCATTTGAAGGATGAGAAAACTGAGGCTCGAGGCTTAGAAAGTTTCATTTGGTTGCTCA (SEQ ID NO: 500) |
| PVRL1 | | | TTTTAAACCCAGGTGCACACACAAGAGCTCGAAGCAGGAATCCTGGTTCTGTTCCCAGGC (SEQ ID NO: 501) |
| PIK3R3 | | | CCACTCCCCAGGCTTACCTGCGAGCCATCGAGGTGGGCCTGGGTTCTCGTGGAGGGAGA (SEQ ID NO: 502) |
| CD6 | | | TCACTCATTCTAGATCCCTCTGTAAAGTTCGAACTCTGGACCTTGTGATCCACCCACCTT (SEQ ID NO: 503) |
| STAT5B | | | TTCCATAGATTACTTTTCAAATCATCCTTCGAAGCTGGCGGCTGAGGGCCCGGCGCCAAG (SEQ ID NO: 504) |

TABLE 7b

| Gene Locus | Chr | Start1 | End1 | Start2 | End2 | Chr | Start1 | End1 | Start2 | End2 |
|---|---|---|---|---|---|---|---|---|---|---|
| IL15 | 4 | 142530357 | 142530386 | 142659035 | 142659066 | 4 | 142530357 | 142534356 | 142655067 | 142659066 |

TABLE 8

| Stimulatory checkpoint molecules | Inhibitory checkpoint molecules |
|---|---|
| CD27 | A2AR |
| CD28 | B7-H3 |
| CD40 | B7-H4 |
| CD122 | CTLA-4 |
| CD137 | IDO |
| OX40 | KIR |
| GITR | LAG3 |
| ICOS | PD-1 |
|  | TIM-3 |
|  | VISTA |

TABLE 9

| Drug | Targets | Preferred Cancer |
|---|---|---|
| Alemtuzumab (monoclonal antibody). | CD52 | Fludarabine-refractory Chronic lymphocytic leukemia<br>Cutaneous T-cell lymphoma<br>Peripheral T-cell lymphoma<br>T-cell prolymphocytic leukemia |
| Ofatumumab (Second generation human IgG1 antibody). | CD20 | Chronic lymphocytic leukemia Follicular lymphoma<br>Diffuse large B cell lymphoma |
| Pegylated liposomal doxorubicin (PLD) plus motolimod (VTX2337). |  |  |
| Sipuleucel-T (Approved Cancer Vaccine). |  | Prostate cancer |
| Rituximab (monoclonal antibody). | CD20 | B-cell malignancies<br>Aggressive and indolent lymphomas such as diffuse large B-cell lymphoma and follicular lymphoma and leukaemias such as B-cell chronic lymphocytic leukaemia |
| Interferon gamma |  |  |
| Combinatorial ablation and immunotherapy. |  | Curative metastatic cancer treatment |
| Polysaccharide-K |  | Stimulate the immune systems of patients undergoing chemotherapy. |
| Adoptive cell therapy |  |  |
| Anti-CD47 antibodies. | CD47 |  |
| Polypurine reverse Hoogsteen oligonucleotides (PPRHs). |  | Breast cancer |
| Anti-GD2 antibodies. | GD2 |  |
| BGB-A317 (monoclonal antibody). | PD-1 inhibitor |  |
| Affimer biotherapeutic. | PD-L1 inhibitor |  |
| Polysaccharides |  |  |
| Neoantigens |  |  |

TABLE 10

Combinations in cancer immunotherapy (biologics, immunocytokines (L19-IL2 and L19-TNF), cytotoxics (Paxlitaxel)

| Drug | targets | Preferred Disease |
|---|---|---|
| Ipilimumab & Nivolumab | PD-1 and CTLA-4 | metastatic melanoma |
| Paclitaxel, ipilimumab & carboplatin | CTLA4 | non-small-cell lung cancer |
| Ipilimumab & GVAX | CTLA-4 | pancreatic cancer |
| Pidilizumab & rituximab | PD-1 | hematologic malignancies |
| L19-IL2 & L19-TNF | STAT | melanoma |
| MEDI0680 & Durvalumab | PD1/PDL1 | Advanced solid malignancies |

TABLE 11

Other single molecules, immunocytokines and biologics for cancer therapy

| Drug | targets | Disease |
|---|---|---|
| CA-170 (small molecule) | PD1-PDL1 and VISTA | Advanced solid tumour and lymphoma |
| Ruxolitinib (small molecule) | JAK | myelofibrosis and multiple myeloma |
| Tofacitinib (small molecule) | JAK | autoimmune disease |
| Galiellelactone (small molecule) | STAT3 | prostate cancer |
| Ipilimumab (monoclonal antibody) | CTLA4 | melanoma, prostate |
| L19-IL2 (immunocytokine) | STAT | melanoma, pancreatic cancer, RCC |
| L19-TNF (immunocytokine) | STAT | melanoma |
| Tremelimumab (monoclonal antibody) | CTLA4 | mesothelioma |
| Nivolumab (ditto) | PD1 | melanoma, non-small-cell lung cancer, renal cell carcinoma, and other solid tumors |
| Pembrolizumab | PD1 | melanoma, non-small-cell lung cancer, renal cell carcinoma, and other solid tumors |
| Pidilizumab | PD1 | hematologic malignancies |
| BMS935559 | PD-L1 | variety of solid tumors |
| GVAXMPDL3280A | PD-L1 | bladder cancer, head and neck cancer, and GI malignancies |
| MEDI4736 | PD-L1 | bladder cancer, head and neck cancer, and GI malignancies |
| MSB0010718C | PD-L1 | bladder cancer, head and neck cancer, and GI malignancies |
| MDX-1105/BMS-936559 | PD-L1 | cancer |
| AMP-224 | PD1 | colorectal cancer |
| MEDI0680 | PD1 | advanced solid tumors |
| Durvalumab | PDL1 | non-small -cell lung cancer |
| Atezolizumab | PDL1 | advanced or metastatic urothelial carcinoma |
| Avelumab | PDL1 | metastatic Merkel cell carcinoma |

TABLE 12

| Gene | Name | Function |
|---|---|---|
| AAGAB | Alpha- And Gamma-Adaptin Binding Protein | Protein Coding gene, interacts with gamma and alpha-adaptin subunits of complexes associated with clathrin-coated vesicle trafficking, associated with Punctate Palmoplantar Keratoderma |
| AARS2 | Alanyl-TRNA Synthetase 2, Mitochondrial | Protein Coding gene, encodes a class-II aminoacyl-tRNA synthetase that aminoacylates alanyl-tRNA, associated with Combined Oxidative Phosphorylation Deficiency 8 and Leukoencephalopathy |
| ABCD3 | ATP Binding Cassette Subfamily D Member 3 | Protein Coding gene, member of ALD sub family of ATP-binding cassette (ABC) transporters, associated with Congenital Bile Acid Synthesis Defect 5 and Zellweger Syndrome |
| AC009133.22 | ENSG00000277669 | Protein Coding gene, associated with carboxylating and transferase activity |
| AC105009.1 | ENSG00000281855 | Predicted intracellular Protein Coding gene |
| AC138028.1 | ENSG00000280603 | Predicted intracellular Protein Coding gene, breast cancer |
| ACSL6 | Acyl-CoA Synthetase Long-Chain Family Member 6 | Protein Coding gene, catalyzes formation of acyl-CoA from fatty acids, associated with myelodysplastic syndromes and Chronic Intestinal Vascular Insufficiency |
| ACTA2 | Actin, Alpha 2, Smooth Muscle, Aorta | Protein Coding gene, alpha actin found in skeletal muscle, associated with type 6 familial thoracic aortic aneurysms, multisystemic smooth muscle dysfunction syndrome and moyamoya disease |
| ADAMTS14 | ADAM Metallopeptidase With Thrombospondin Type 1 Motif 14 | Protein Coding gene, preproprotein processed into enzyme that cleaves amino-terminal propeptides from type I procollagen, may be associated with osteoarthritis |
| ADAMTSL4 | ADAMTS Like 4 | Protein Coding gene, protein with 7 thrombospondin type 1 repeats, associated with Ectopia Lentis Et Pupillae and Autosomal Recessive Isolated Ectopia Lentis |
| ADM5 | Adrenomedullin 5 (Putative) | Protein Coding gene, associated with phlebotomus fever |
| ADSSL1 | Adenylosuccinate Synthase Like 1 | Protein Coding gene, functions in the purine nucleotide cycle during conversion of IMP to AMP, associated with adolescent distal myopathy, ADSS is an important paralog |
| AFAP1L1 | Actin Filament Associated Protein 1 Like 1 | Protein Coding gene, may have role in invadosome and podosome formation, AFAP1 is a paralog, associated with spindle cell sarcomas possibly prognostic |
| AGMAT | Agmatinase | Protein Coding gene, Involved in synthesising putrescine from agmatine, ARG2 is a paralog |
| AIRE | Autoimmune Regulator | Protein Coding gene, transcriptional regulator, regulates expression of autoantigens and role in the thymus selecting negatively against autoreactive T-Cells, associated with autoimmune polyendocrinopathy syndromes, APECED |
| ALDOA | Aldolase, Fructose-Bisphosphate A | Protein Coding gene, encodes Aldolase A, an enzyme that serves as a catalyst in conversion of fructose-1,6-bisphosphate to glyceraldehyde 3-phosphate and dihydroxyacetone phosphate (glycolysis and glucogenesis), associated with myopathy, hemolytic anaemia, potential oncogene in pancreatic cancer and marker in osteosarcoma |
| ALS2CR12 | Amyotrophic Lateral Sclerosis 2 Chromosome Region 12 | Protein coding gene, associated with ALS2 and lateral sclerosis, potential implication in breast cancer risk |
| AMDHD2 | Amidohydrolase Domain Containing 2 | Protein Coding gene, functions in Neu5Gc pathway by hydrolysing N-glycolyl group from N-glycolylglucosamine 6-phosphate (GlcNGc-6-P), ENSG00000259784 is a paralog |
| ANGPTL7 | Angiopoietin Like 7 | Protein Coding gene, a paralog is ANGPT4, may be associated with glaucoma |
| APLP1 | Amyloid Beta Precursor Like Protein 1 | Protein Coding gene, may act as transcriptional activator and function during maturation of synapses, associated with Alzheimer disease and Subendocardial Myocardial Infarction, APLP2 is a paralog |

TABLE 12-continued

| Gene | Name | Function |
|---|---|---|
| ARHGAP24 | Rho GTPase Activating Protein 24 | Protein coding gene, is an antagonist of Rac, regulating cell polarity, associated with Atypical Autism and Familial Idiopathic Steroid-Resistant Nephrotic Syndrome With Focal Segmental Hyalinosis |
| ARHGEF1 | Rho Guanine Nucleotide Exchange Factor 1 | Protein coding gene, may trigger signals dependent on Rho by forming complexes with G proteins, associated diseases are Skin Lipoma and Third Cranial Nerve Disease, ARHGEF2 is a paralog |
| ATG4B | Autophagy Related 4B Cysteine Peptidase | Protein Coding gene, needed for autophagy and Cvt, exposes glycine at C-terminus of ATG8 proteins this step is needed so ATG8 proteins can conjugate to phosphatidylethanolamine and insert in to membranes which is need for autophagy |
| ATIC | 5-Aminoimidazole-4-Carboxamide Ribonucleotide Formyltransferase/IMP Cyclohydrolase | Protein Coding gene, is a catalyst for the final 2 steps in the de novo purine biosynthetic pathway, associated with AICA-ribosiduria and Mental retardation epilepsy |
| ATN1 | Atrophin 1 | Protein coding gene, transcriptional corepressor, promotes VSMC migration, corepressor of MTG8, associated with Dentatorubral pallidoluysian atrophy and Spinocerebellar Ataxia |
| ATP6VOA1 | ATPase H+ Transporting VO Subunit A1 | Protein Coding gene, part of vacuolar ATPase, needed for sorting proteins, receptor-mediated endocytosis, synaptic vesicle proton gradient generation and zymogen activation, associated with Inferior Myocardial infarction and potentially CRC |
| ATP6VOC | ATPase H+ Transporting VO Subunit C | Protein Coding gene, part of vacuolar ATPase, needed for sorting proteins, receptor-mediated endocytosis, synaptic vesicle proton gradient generation and zymogen activation, associated with Dravet syndrome |
| BCL2L12 | BCL2 Like 12 | Protein Coding gene, encodes anti-apoptotic inhibitor of Caspases 3 and 7, interacts with p53 protein, over expressed in different cancers, associated with breast cancer and AML |
| BCL2L13 | BCL2 Like 13 | Protein Coding gene, may have role activating caspase-3 and influencing apoptosis, overexpression causes apoptosis, associated with cat-eye syndrome, ALL and glioblastoma |
| BCL2L2 | BCL2 Like 2 | Protein coding gene, cell survival promoter, stops apoptosis by dexamethasone, and inhibits BAX activity on Sertoli cells, associated with small intestinal adenocarcinoma, BCL2L1 is a paralog |
| BCL2L2-PABPN1 | BCL2L2-PABPN1 Readthrough | Protein Coding gene, fusion protein shares sequence from the two neighbouring genes, cell survival promoter, stops apoptosis by dexamethasone, inhibits BAX activity on Sertoli cells, PABPN1 is a paralog |
| BOLA2B | BolA Family Member 2B | Protein Coding Gene, may be associated with iron maturation, BOLA2 is a paralog |
| BRD2 | Bromodomain Containing 2 | Protein Coding gene, transcriptional regulator, potentially through chromatin remodelling through binding hyperacetylated chromatin, transcription regulator of CCND1, may have roles in folliculogenesis, spermatogenesis and, assembly of nucleosomes, associated with junior myoclonic epilepsy, BRD3 is a paralog. |
| BRI3BP | BRI3 Binding Protein | Protein Coding gene, has role in tumourigenesis, may stabilise p53/TP53, possible association to cervical cancer |
| C12orf57 | Chromosome 12 Open Reading Frame 57 | Protein Coding gene, functions in the development of corpus callosum, associated with Temtamy Syndrome and Colobomatous Microphthalmia |
| C16orf59 | Chromosome 16 Open Reading Frame 59 | Protein Coding gene, protein not characterised |
| C1orf137 | Chromosome 1 Open Reading Frame 137 | Protein Coding gene, protein not characterised |
| C1orf168 | Chromosome 1 Open Reading Frame 168 | Protein Coding gene, adapter protein that has function TCR activated signalling pathways, need for activating T-Cells and their response to TCR stimulaltion and integrin control adhesion |
| C1QTNF5 | C1q And TNF Related 5 | Protein Coding gene, may have function in cell adhesion, family member of proteins that have roles in basement membranes, associated with Retinal degradation and macular degeneration, C1QTNF9 is a paralog |
| C20orf141 | Chromosome 20 Open Reading Frame 141 | Protein Coding gene, protein not characterised, ENSG00000241690 is a paralog |
| C5AR1 | Complement C5a Receptor 1 | Protein Coding gene, receptor for C5a, activated can stimulate chemotaxis, granule enzyme release, superoxide anion production and role in the relase of intracellular calcium, associated with Listeria Meningitis and Malaria, C5AR2 is important paralog |
| C5orf56 | Chromosome 5 Open Reading Frame 56 | RNA gene associated to ncRNA family |
| NDUFA2 | NADH: Ubiquinone Oxidoreductase Subunit A2 | Protein coding gene, forms a subunit of the NADH: Ubiquinone oxidoreductase complex1, enzyme in electron transport chain |
| NFATC2IP | Nuclear Factor Of Activated T-Cells 2 Interacting Protein | Protein coding gene, promotes cytokine expression in T helper 2 cells through the magnitude regulation of NFAT- driven transcription |
| NFKB1 | Nuclear Factor Kappa B Subunit 1 | Protein coding gene, Rel ptorein-specific transcription inhibitor and as part of the DNA binding subunit of NF-kappa-B protein complex- transcritpion regulator controled by a large number of intra and extra cellular signals |
| NFKBID | NFKB Inhibitor Delta | Protein coding gene, regulates IL-2, IL-6 and others through its regualtion of NF-kappa-B activity |
| NFKBIE | NFKB Inhibitor Epsilon | Protein coding gene, binds to NF-kappa-B preventing cellular translocation from the cytoplasm to nucleus |
| NOL9 | Nucleolar Protein 9 | Protein coding gene, polynucleotide 5-kinase processes rRNA in the nucleos and cytosol, required for processing of 5.8s and 28S rRNA |
| NPHS1 | Nephrin | Immunoglobulin family of cell adhesion member involved in the filtration barrier of the kidneys, primarily expressed in renal tissue, mutations can cause Finnish-type congenital nephrosis 1 |
| NRGN | Neurogranin | Encodes a protein kinase substrate, exon 1 and 2 encode protein, exons 3+4 contain UTR, protein binds calmodulin in the absence of calcium |
| NTN3 | Netrin 3 | Protein encoding gene, involved in Axon guidence of central nervous system and peripheral motor neurons |
| NUCB1 | Nucleobindin 1 | Protein coding gene, involved in Golgi calcium homoestasis and calcium regulated signal transduction |
| NUDT22 | Nudix Hydrolase 22 | Protein coding gene, protein with hydrolyase activity |
| OPALIN | Oligodendrocytic Myelin Paranodal And Inner Loop Protein | Protein coding gene, expression mostly found in brain tissues |
| OSMR | Oncostatin M Receptor | Protein coding gene, type I cytokine receptor, heteodimerizes with IL-6 signal transducer to form type II oncostatin M receptor and also IL-31 receptor A to form IL 31 receptor, mutations assoocated with familial primary localized cutaneous amyloidosis |

TABLE 12-continued

| Gene | Name | Function |
|---|---|---|
| P3H3 | Prolyl 3-Hydroxylase 3 | Protein coding, proteoglycan of the leprecan family, reuqired for collagen biosynthesis, folding and assembly. Found in the endoplasmic reticulum.Associated with breast and other cancers through epigenetics inactivation. |
| PABPN1 | Poly(A) Binding Protein Nuclear 1 | Protein coding gene, binds to nacent poly(A) tails with high affinity, required to enlarge poly(A) tail to apporx. 250 nt., expansion of GCG trinucleotide repeat of the 5' coding region associated with OPMD - oculopharyngeal muscular dystrophy |
| PAG1 | Phosphoprotein Membrane Anchor With Glycosphingolipid Microdomains 1 | Protein coding, type III transmembrane adaptor protein, involved in the regualtion of T cell activation through the binding of csk protein |
| PAK1 | P21 (RAC1) Activated Kinase 1 | Protein coding, encodes a emember of the PAK proteins (serine/threonine p21-activating kinases), link RhoGTPase to cytoskeletal reorganization and nuclear signaling, regaultes cell motility and morphology |
| PALD1 | Phosphatase Domain Containing, Paladin 1 | Protein coding |
| PCED1A | PC-Esterase Domain Containing 1A | Protein coding, a member of the GDSL/SGNH superfamily, Hydrolytic enzyme wither esterase activity |
| PCNXL3 | Pecanex-like 3 (Drosophila) | Protein coding, paralog of PCNX1 |
| PCYOX1L | Prenylcysteine Oxidase 1 Like | Protein coding, paralog of PCYOX1, involved in Resposne to elevated platelet cytosolic Ca2+ |
| PDCD1 | Programmed Cell Death 1 | Protein coding, expressed in pro-B-cells and involved in their differentiaiton, important in T cell function and contribution to prevention of autoimmune disease |
| PDE4A | Phosphodiesterase 4A | Protein coding, cyclic nucleotide phoshodiesterase (PDE) family and PDE4 subfamily, hydrolyzes CAMP, through regulation of cAMP the protein can regulate a number of cellular responses to extracellular symbols |
| PDE4C | Phosphodiesterase 4C | Protein coding, cyclic nucleotide phoshodiesterase (PDE) family and PDE4 subfamily, hydrolyzes CAMP, through regulation of cAMP the protein can regulate a number of cellular responses to extracellular symbols |
| PDPK1 | 3-Phosphoinositide Dependent Protein Kinase 1 | Protein coding, master serine/threonine kinase, phosphorylates and activates subgroup of AGC protein family, regulates pathways including insulin signal transduction, TGF-beta signaling and a mulitiude of others |
| PDYN | Prodynorphin | Protein coding, a preproprotein, after proteolytic processing forms sectreted opiod peptides beta-neoendorphin, dynorphin, leuenkephalin, rimorphon and leumorphin, each is a ligan for kappa-type opioid receptor |
| PFKL | Phosphofructokinase, Liver Type | Protein coding, involved in te citrate cycle (TCA cycle) and innate immune system, forms a subunit of the enzyme theat catalyzes production of D-fructose 1,6-bisphosphate from D-fructose 6-phosphate |
| PGPEP1L | Pyroglutamyl-Peptidase I-Like | Protein coding, paralog of PGPEP1, cycteine-type peptidae activity |
| PHB2 | Prohibitin 2 | Protein coding, related to MAPK signalling Mitogen stimulation pathway and GPCR pathway, is an estrogen receptor selective coregulator and competes with NCOA1, modulating ER transcriptional activity |
| PHF19 | PHD Finger Protein 19 | Protein coding, specifically binds H3K36me3, recruiting PRC2 complex and changing active state loci in embryonic stem cells to a repressed state loci, paralog of MTF2 |
| PIK3R1 | Phosphoinositide-3-Kinase Regulatory Subunit 1 | Protein coding, the enzyme phosphorylates the inositol ring of phosphatidylinositol, the enzyme is importatnt in the metabolism of insulin, mutation of the gene is associated with insulin resistance |
| AKT1 | AKT Serine/Threonine Kinase 1 | Protein Coding gene, regulator of mediator of growth factor-induced neuronal survival, apoptosis suppressor, associated with Proteus syndrome |
| ARHGEF7 | Rho Guanine Nucleotide Exchange Factor 7 | Protein Coding gene, associated with Syndromic X-Linked Intellectual Disability and Non-Syndromic X-Linked Intellectual Disability |
| BAD | Protein Coding gene, BCL2 Associated Agonist Of Cell Death | Mediator of programmed cell death |
| BAX | BCL2 Associated X, Apoptosis Regulator | Protein Coding gene, anti or pro apoptotic mediator, regulated by tumor suppressor P53, associated with Colorectal Cancer and Leukemia |
| BBC3 | BCL2 Binding Component 3 | Initiates mitochondrial outer membrane permeabilization, apoptosis, mitochondrila dysfunction, caspase activation, potential drug target for cancer therapy |
| BID | BH3 Interacting Domain Death Agonist | Protein Coding gene, cell death and mitochondrial damage mediator |
| BLNK | B-Cell Linker | Involved in B-cell development, associated with pre-B acute lymphoblastic leukemia |
| BOK | BCL2 family apoptosis regulator | Protein coding gene, proapoptotic regulator involved in a wide variety of cellular processes |
| C8A | Complement C8 alpha chain | Encodes the alpha subunit of the C8 component of the complement system, which participates in formation of membrane attack complex |
| CASP6 | Caspase 6 | Encodes a caspase enzyme involved in the activation cascade responsible for the execution of cell apoptosis, associated with dystrophinopathies |
| CASP8 | Caspase 8 | Encodes a caspase enzyme involved in the activation cascade responsible for the execution of cell apoptosis, associated with hepatocellular carcinoma and autoimmune lymphopropiferative syndrome (ALPS). Also implicated in Huntington's disease/neurodegenertaive diseases. |
| CASP9 | Caspase 9 | Encodes a cysteine-aspartic acid protease thought to play a central role in apoptopsis through activation of the caspase cascade and to be a tumour supressor |
| CBL | cbl proto-oncogene | Proto-oncogene encoding a RING finger E3 ubiquitin ligase, required for targeting substrates for proteasome degradation, found to be mutated/translocated in many cancers, associated with a range of acute myeloid leukemias and Noonan-like disorders |
| CBLB | cbl proto-oncogene B | Protein coding gene, E3 ubiquitin-protein ligase generally promoting degradation by the proteasome, negatively regulates T-cell receptor and B-cell receptor signal transduction pathways |
| CCL18 | C-C motif chemokine receptor 18 | Antimicrobial gene- a Cys-Cys cytokine gene on the q arm of chromosome 17, displays chemotactic activity for naive T cells, CD4+ and CD8+ T cells and nonactivated lymphocytes, attracts naive T lymphocytes towards dendritiv cells and activated macrophages in lymph nodes |

TABLE 12-continued

| Gene | Name | Function |
|---|---|---|
| CCR6 | C-C motif chemokine receptor 6 | Encodes a member of the beta chemokine receptor family, the gene is preferentially expressed by immature dendritic cells and memory T-cells, the receptor is important in B-lineage maturation and antigen driven B-cell differentiation, It may also regulate migration and recruitment of dendritic and T-cells during inflammatory and immunlogical responses |
| CD14 | CD14 molecule | Protein coding gene, encodes a surface antigen that is preferentially expressed on monocytes/macrophages, it works with other proteins to mediate the innate immune response to bacterial lipopolysaccharide, acts via MyD88, TIRAP and TRAF6 to activate NF-kappaB, secrete cytokines and induce the inflamatory response |
| CD180 | CD180 molecule | Cell surface molecule consisting of extracellular leucine-rich repeats(LRR) and a short cytoplasmic tail, belongs to the TLR family of pathogen receptors, the LRR associates with a molecule called MD-1 to form a cell surface receptor complex, RP105/MD-1, which controls B-cell recognition and signalling of lipopolysaccharide via interaction with TLR4 |
| CD19 | CD19 molecule | Protein coding gene- encodes a cell surface molecule which assembles with the antigen receptor of B lymphocytes to decease the threshold for antigen receptor-dependent stimulation, associated with immunodeficiency |
| CD33 | CD33 molecule | Generally thought to be an adhesion molecule of myelomonocytic-derived cells that mediates sialic-acid dependent binding to cells, also seen to induce apoptosis in acute myeloid leukemoia in vitro |
| CD4 | CD4 molecule | Protein coding gene, encodes a membrane glycoprotein of T-lymphocytes, interacts with MHCII antigens and is a receptor for HIV, expressed in B cells, macrophages, granulocytes and specific regions of the brain, functions to initate or augment early phase T-cell activation |
| CD47 | CD47 molecule | Protein coding gene, encodes a membrane protein involved in increasing calcium concentration when cell binds to extracellular matrix, may also play a role in membrane transport and signal transduction, associated with neonatal meningitis |
| CD6 | CD6 molecule | Protein coding gene, endcodes a protein found on the outer membrane of T-lymphocytes and other immune cells, responsible for cell adhesion, mediating cell-cell contact and regulating T-cell responses via interactions with ALCAM/CD166, associated with bronchus cancer and lower lip cancer |
| CD79A | CD79a molecule | Encodes the Ig-alpha protein which non-convalently associates with Ig-beta and surface Ig to cause the expression and function of B-cell antigen receptors, associated with agammaglobulinemia |
| CD79B | CD79b molecule | Encodes the Ig-beta protein which non-convalently associates with Ig-alpha and surface Ig to cause the expression and function of B-cell antigen receptors, associated with agammaglobulinemia |
| CD82 | CD82 molecule | Metastasis suppressor gene encoding a membrane glycoprotein, gene expression shown to be down regulated in tumour progression of human cancers, expression is strongly correlated with p53 and loss of both proteins is associated with poor survival in prostate cancer, also associated with bladder cancer |
| CD86 | CD86 molecule | Encodes a type I membrane protein of the immunoglobulin superfamily, the protein is expressed by antigen-presenting cells and is the ligand for 2 cell surface proteins on T-cells, binding with CD28 antigen caused a costimulatory signal for T-cell activation, associated with gallbladder squamous cell carcinoma and myocarditis |
| CDKN2A | Cyclin dependent kinase inhibitor 2A | Encodes at least 3 alternatively spliced varients, each encoding distinct proteins, 2 of which function as CDK4 kinase inhobitors. Known to be an important tumour suppressor gene. Frequently mutated or deleted in a wide variey of tumours including pancreatic cancer, melanoma and neural system tumours. |
| CRADD | CASP2 and RIPK1 domain containing adaptor with death domain | Promotes apoptosis by recruting caspase2/ICH1 to the cell death signal transduction complex, mutations of this gene assoicated with cognitive/intellectual disability |
| CSF2 | Colony stimulating factor 2 | Controls the production, differentiation and function of granulocytes and macrophages, associated with deletions in acute myeloid leukemia |
| CSK | C-terminal Src kinase | Protein coding gene, roles in the regulation of cell growth, differentiation, migration and immune response, associated with colorectal cancer and breast cancer |
| CXCL13 | C-X-C motif chemokine ligand 13 | Protein coding gene, chemoattractant of B-lymphocytes, strongly expressed in the follicles of the spleen, lymph nodes and Peyer's patches, asssociated with T-cell lymphoma and Burkitt lymphoma |
| EGF | Epidermal growth factor | Protein coding gene, encodes a preproprotein that acts as an important mitogenic factor in the growth, proliferation and differentiation of numerous cell types Dysregulation of gene associated with growth and progression of certain cancers. |
| ENDOU | Endonuclease Poly (U) specific | Protein coding gene- protease activity and expressed in the placenta. Associated with non-gestational choriocarcinoma. |
| ESAM | Endothelial cell adhesion molecule | Protein coding gene, related to the blood-brain barrier transmigration signalling pathway, may also mediate aggregation |
| ESR1 | Estrogen receptor 1 | Protein coding gene, encodes an estrogen receptor which localizes to the nucleus and is important for hormone binding, DNA binding and activation of transcription Associated with breast cancer, endometrial cancer and osteoporosis. |
| F3 | Coagulation factor III, Tissue factor | Protein coding gene, encodes a cell surface glycoprotein which enables cells to initiate the blood coagulation cascade and is a receptor for coagulation factor VII Associated with carotid artery thrombosis and disseminated intravascular coagulation. |
| FAS | Fas cell surface death receptor | Protein coding gene, encodes a TNF-receptor containing a death domain, plays central roles in the regulation of programmed cell death, forms a death-inducing signalling complex with its ligand and has also been shown to activate NF-kappaB, associated with autoimmune lymphoproliferative syndrome |
| EN1 | Fibronectin 1 | Involved in cell adhesion and migration processes including embryogenesis, wound healing, blood coagulation, host defense, and metastasis |
| GAB2 | GRB2 Associated Binding Protein 2 | Activates phosphatidylinositol-3 kinase, involves in trasmitting various signals |
| HLA-DMB | Major Histocompatibility Complex, Class II, DM Beta | Protein Coding gene, involves in peptide loading |
| HLA-DQA1 | Major Histocompatibility Complex, Class II, DQ Alpha 1 | Protein Coding gene,involed in the immune system |
| ICAM1 | Intercellular Adhesion Molecule 1 | Encodes a cell surface glycoprotein, cell-cell adhesion, cell to extracellular binding, cell proliferation, differentiation, motility, apoptosis, trafiking tissue architecture, associated with Malaria and Leukostasis |

TABLE 12-continued

| Gene | Name | Function |
| --- | --- | --- |
| ICOSLG | Inducible T-Cell Costimulator Ligand | Associated with Inclusion Body Myositis and Diffuse Cutaneous Systemic Sclerosis, signaling for T-cell proliferation and cytokine secretion, involved in B-cell proliferation and differentiation to plasma cells |
| IGF1R | Insulin Like Growth Factor 1 Receptor | Involved in transformation events, cell growth, survival control, anti apoptosis, tumor transformation and malignant cell survival |
| IGF2 | Insulin Like Growth Factor 2 | Growth-promoting activity, fetal development |
| IKBKB | Inhibitor Of Nuclear Factor Kappa B Kinase Subunit Beta | Protein Coding gene, activation of NF-kappa-B |
| IL17B | Interleukin 17B | Protein Coding gene, associated with Leiomyoma, induces the secretion of TNF alpha and IL1 beta from a monocytic cell line |
| IL17C | Interleukin 17C | Protein Coding gene, induces the secretion of tumor necrosis factor alpha and interleukin 1 beta from a monocytic cell line |
| IL25 | Interleukin 25 | Stimulates NF-kappaB activation and interleukin 8 production |
| IL26 | Interleukin 26 | Protein Coding gene, initiates STAT1, STAT3 MPK1/3 (ERK1/2) and AKT, reduces proliferation of intestinal epithelial cells |
| IRF1 | Interferon Regulatory Factor 1 | Initiates the trascription of interferons alpha nad beta, regulates apoptosis and tumor suppression |
| IRF2 | Interferon Regulatory Factor 2 | Inhibits the transcription of interferons gamma and beta, activates the transcription of histone H4, associated with interferon gamma signaling |
| IRF3 | Interferon Regulatory Factor 3 | Initiates the transcription of interferons alpha, beta and other interferon-regulated genes |
| IRF4 | Interferon Regulatory Factor 4 | Mediates interferons in reponse to infection by virus, mediates interferon-induced genes, associated with multiple myeloma, mediates Toll-like-receptor signaling which activates immune system |
| ITGAM | Integrin Subunit Alpha M | Involved in the adhesion of neutrophils and monocytes to stimulated endothelium |
| ITGAX | Integrin Subunit Alpha X | Involved in the adhesion of neutrophils and monocytes to stimulated endothelium |
| ITK | IL2 Inducible T-Cell Kinase | T-cell proliferation and differentiation |
| LAT | Linker For Activation Of T-Cells | Protein Coding gene, associated with CTLA4 signaling |
| LCK | LCK Proto-Oncogene, Src Family Tyrosine Kinase | Involved in developing T-cell, mediates protein-protein interactions with phosphotyrosine-containing and protein-rich motifs |
| LYN | LYN Proto-Oncogene, Src Family Tyrosine Kinase | Regulates mast cell degranulation and erythroid differentiation, associated with Sacoma and Hantavirus Pulmonary Syndrome |
| MAP3K14 | Mitogen-Activated Protein Kinase Kinase Kinase 14 | Initiates the activity of NF-kappa B |
| MAPK10 | Mitogen-Activated Protein Kinase 10 | Involved in variouse cellular processes including proliferation, differentiation, trascription and development |
| MAPK3 | Mitogen-Activated Protein Kinase 3 | Involved in variety of cell processes including proliferation, differentiation and cell cycle progression |
| MAPKAP1 | Mitogen-Activated Protein Kinase Associated Protein 1 | Protein Coding gene, associated with Nephrogenic Systemic Fibrosis and Scleral Disease, related to Constitutive Signaling by AKT1 E17K in Cancer and Regulation of TP53 Activity pathways |
| MCL1 | MCL1, BCL2 Family Apoptosis Regulator | Protein Coding gene, associated with Myeloid Leukemia and leukemia, cell survival, apoptosis, death-inducing |
| MTOR | Mechanistic Target Of Rapamycin | Protein Coding gene, DNA damage, nutrient deprivation, target for cell cycle arrest and immunosuppressive effects |
| MYC | MYC Proto-Oncogene, BHLH Transcription Factor | Protein Coding gene, associated with Burkitt Lymphoma and Precursor T-Cell Acute Lymphoblastic Leukemia |
| NCK2 | NCK Adaptor Protein 2 | Protein Coding gene, cytoskeletal restructure |
| PIK3R2 | Phosphoinositide-3-Kinase Regulatory Subunit 2 | Encods regulatory component of PI3K, related to growth signaling pathway |
| PRKCQ | Protein Kinase C Theta | Involved in variety of cellular signaling pathways, activates transcriptional facrors NF-kappa B and AP-1 |
| PRR5 | Proline Rich 5 | Tumor suppressor gene, involved in breaset and colorectal tumorigenesis |
| PTK2 | Protein Tyrosine Kinase 2 | Involved in cell growth and intracellular signal transduction pathways |
| PTPN11 | Protein Tyrosine Phosphatase, Non-Receptor Type 11 | Regulates various cell processes such as ell growth, differentiation, mitotic cycle, and oncogenic transformation |
| PTPN6 | Protein Tyrosine Phosphatase, Non-Receptor Type 6 | Involved in variouse cell processes such as cell growth, differentiation, mitotic cycle, and oncogenic transformation |
| PTPRA | Protein Tyrosine Phosphatase, Receptor Type A | Involved in variouse cell processes such as cell growth, differentiation, mitotic cycle, oncogenic transformation, cell adhesion and proliferation |
| PVRL1 | HGNC symbole for (NECTIN1) Nectin Cell Adhesion Molecule 1 | adshesion of junctions and tight junctions in epithelial and endothelial cells |
| RELA | RELA Proto-Oncogene, NF-KB Subunit | Activates the transcription of specefic genes |
| RICTOR | RPTOR Independent Companion Of MTOR Complex 2 | Cell growth |
| RPTOR | Regulatory Associated Protein Of MTOR Complex 1 | Cell growth, negatively mediates the mTOR kinase, |
| SHH | Sonic Hedgehog | Induces patterning of the ventral neural tube, the anterior-posterior limb axis, and the ventral somites, associated with VACTERL syndrome |
| SIRPA | Signal Regulatory Protein Alpha | Negatively regulates receptor tyrosine kinase-coupled signaling processes, involved in transcuctional signals mediated by growth facror receptors |
| TAB2 | TGF-Beta Activated Kinase 1/MAP3K7 Binding Protein 2 | MAP3K7/TAK1 activator, involved in transduction signals, mediates the development and function of osteoclasts |
| TNFRSF19 | TNF Receptor Superfamily Member 19 | Activates JNK signaling pathway, initiates apoptosis, involved in embryonic development |

TABLE 12-continued

| Gene | Name | Function |
|---|---|---|
| TNFRSF25 | TNF Receptor Superfamily Member 25 | Regulates lymphocyte homeostasis and apoptosis, activates NF-kappa B function, regulates lymphocyte proliferation |
| TP73 | Tumor Protein P73 | Involved in cellular responses to stress and development, potential candidate gene for neuroblastoma |
| TRAF1 | TNF Receptor Associated Factor 1 | Mediates signal transduction from various receptors, mediates activation of MAPK8/JNK and NF-kappa B, regulates anti apoptotic signals, |
| TYROBP | TYRO Protein Tyrosine Kinase Binding Protein | Signal transduction activator, bone modeling, brain myelination and inflammation |
| C1S | Complement C1s | Protein Coding gene, lack of C1S, associated with Ehlers-Danlos Syndrome, Periodontal Type 2 and C1s Deficiency |
| C5 | Complement C5 | Inflammation, host homeostasis, host defense against pathogens, associated with Immunodeficiency disase |
| C8B | Complement C8 Beta Chain | Cell lysis, induces membrane penetration, associated with meningococcal infections |
| C8G | Complement C8 Gamma Chain | Membrane attack complex, associated with immunodeficiency and acute salpingo-Oophoritis, involved in Complement and Innate Immune System pathways |
| CASP10 | Caspase 10 | Apoptosis, associated with type IIA autoimmune lymphoproliferative syndrome, non-Hodgkin lymphoma and gastric cancer |
| CCL14 | C-C Motif Chemokine Ligand 14 | Protein Coding gene, related to PEDF Induced Signaling and TGF-Beta Pathway |
| CCL15 | C-C Motif Chemokine Ligand 15 | Protein Coding gene, related to PEDF Induced Signaling and TGF-Beta Pathway, associated with Hepatocellular Carcinoma and Spherocytosis |
| CCL16 | C.C Motif Chemokine Ligand 16 | Immunoregulatory process, inflammation, proliferation |
| CCL23 | C-C Motif Chemokine Ligand 23 | Protein Coding gene, immunoregulatory process, inflammation |
| CCL3 | C-C Motif Chemokine Ligand 3 | Protein Coding gene, inflammatory responses |
| CCL4 | C-C Motif Chemokine Ligand 4 | Chemokinetic and inflammatory processes |
| CCR6 | C-C Motif Chemokine Receptor 6 | B-lineage maturation, antigen-driven B-cell differentiation, migration and recruitment of dentritic and T cells during inflammatory and immunological responses, associated with Diffuse Cutaneous Systemic Sclerosis and Limited Scleroderma |
| CFI | Complement Factor I | Complement cascade regulator, associated with diseases including microangiopathic hemolytic anemia, thrombocytopenia and glomerulonephritis |
| CYFIP2 | Cytoplasmic FMR1 Interacting Protein 2 | Protein Coding gene, associated with Fragile X Syndrome and Amyotrophic Lateral Sclerosis 1, related to innate immune system and RET signaling pathways |
| FAS | Fas Cell Surface Death Receptor | Programmed cell death regulator, associated with malignant and immune diseases, |
| FN1 | Fibronectin 1 | Cell adhesion and migration processes such as embryogenesis, wound healing, blood coagulation, host defense, and metastasis |
| HAVCR2 | Hepatitis A Virus Cellular Receptor 2 | Protein Coding gene, innate and adaptive immune responses, |
| HLA-DMA | Major Histocompatibility Complex, Class II, DM Alpha | Membrane structure, associated with rheumatoid arthritis and systemic lupus erythematosus |
| HLA-DMB | Major Histocompatibility Complex, Class II, DM Beta | Protein Coding gene, peptide loading, related to CTLA4 signaling |
| HLA-DQA1 | Major Histocompatibility Complex, Class II, DQ Alpha 1 | Protein Coding gene, immune system, related to CRLA4 signaling |
| HLA-DQB1 | Major Histocompatibility Complex, Class II, DO Beta 1 | Protein Coding gene, immune system, related to CRLA4 signaling |
| ICAM1 | Intercellular Adhesion Molecule 1 | Protein Coding gene, Immune system, associated with malaria and leukostasis |
| ICAM2 | Intercellular Adhesion Molecule 2 | Cell adhesion, regulator of adhesive process for antigen-specific immune response, assocoated with colon carcinoma |
| ICAM3 | Intercellular Adhesion Molecule 3 | Protein Coding gene,cell adhesion, signaling pathways, associated with Marburg Hemorrhagic Fever and Trichosporonosis |
| ICAM4 | Intercellular Adhesion Molecule 4 | Protein Coding gene, related to innate and immune system pathways |
| ICOSLG | Inducible T-Cell Costimulator Ligand | Protein Coding gene, related to immune system and CD28-co-stimulation, associated with Inclusion Body Myositis and Diffuse Cutaneous Systemic Sclerosis |
| IFNG | Interferon Gamma | Protein Coding gene, released by cells of innate and adaptive immune system, related to autoimmune diseases |
| IGF1R | Insulin Like Growth Factor 1 Receptor | Protein Coding gene, transformation processes, apoptosis suppressor, cell survival inhancer |
| IKBKB | Inhibitor Of Nuclear Factor Kappa B Kinase Subunit Beta | Protein Coding gene, NF-kappa-B activation, related to ICos-ICosL pathway in T-helper cell and development IGF-1 receptor signaling |
| IL12RB1 | Interleukin 12 Receptor Subunit Beta 1 | Protein Coding gene, IL12 receptor complex formation, related to immune response IL-23 signaling pathway and innate immune system |
| IL17B | Interleukin 178 | Protein Coding gene, initiates the secretion of TNF alpha and IL1 beta, associated with Leiomyoma |
| IL25 | Interleukin 25 | Protein Coding gene, activates NF-kappaB, initiates interleukin 8 production, related to Th2 differentiation pathway and IL-17 family signaling pathways |
| IL26 | Interleukin 26 | T cell phenotype transformation, related to PEDF induced signaling and TGF-Beta pathways |
| IL3 | Interleukin 3 | Hematopoietic cell types proliferation, cell growth, differentiationa nd apoptosis, possesses neurotrophic activity, associated with neurologic disorders |
| IL5 | Interleukin 5 | Differentiation and growth for B cell and eosinophils, regulate eosinophil formation, maturation recruitmen and survival |

TABLE 12-continued

| Gene | Name | Function |
| --- | --- | --- |
| IRF1 | Interferon Regulatory Factor 1 | Activates interferons alpha and beta transcription, regulates apoptosis and tumor-suppressoion |
| IRF2 | Interferon Regulatory Factor 2 | Transcriptional inhibitor of interferons alpha and beta, transcriptional activator of histone H4, H4 and IL7 genes activator, regulates cell cycle |
| IRF3 | Interferon Regulatory Factor 3 | Transcriptional activator of interferons alpha and beta and other interferon mediated genes |
| IRF4 | Interferon Regulatory Factor 4 | Regulates interferons in response to infection, regulates interferon-innduced genes, negatively mediates Toll-like -receptor signaling, associated with myeloma |
| ITGAM | Integrin Subunit Alpha M | Adherence of neutrophils and monocytes to stimulated endothelium phagocytosis of complement coated particles |
| ITGAX | Integrin Subunit Alpha X | Adherence of neutrophils and monocytes to stimulated endothelium phagocytosis of complement coated particles |
| ITK | IL2 Inducible T-Cell Kinase | Protein Coding gene, T-cell proliferationa nd differentiation |
| LAG3 | Lymphocyte Activating 3 | Protein coding gene, related to innate immune system and NF-kappaB signaling pathways |
| LCK | LCK Proto-Oncogene, Src Family Tyrosine Kinase | Selection and maturation of developing T-cells, regulated protein-protein interactions |
| LTBR | Lymphotoxin Beta Receptor | Involved in signalling during the lymphoid and other organs development, lipid metabolism, immune response and programmed cell death |
| LYN | LYN Proto-Oncogene, Src Family Tyrosine Kinase | Regulates mast cell degranulation and erythroid differentiation, associated with Sarcoma and d Hantavirus Pulmonary Syndrome |
| MCAM | Melanoma Cell Adhesion Molecule | Cell adhesion, cohesion of the endothelial monolayer at intercellular junctions in vascular tissue, enhances hematogeneous tumor spread, adhesion agent in neural crest cells, associated with melanoma and skin melanoma |
| NFKB1 | Nuclear Factor Kappa B Subunit 1 | Induces the expression of genes involved in various biological processes, associated with inflammatory diseases |
| PRF1 | Perforin 1 | Generates transmembrane tubules, lyses non-specifically a variety of target cells, affects molecule for T-cell and natural killer-cell-regulated cytolysis, associated with lethal autosomal recessive disorder |
| PTPRC | Protein Tyrosine Phosphatase, Receptor Type C | Mediates a wide veriaty of cellular events such as cell growth, differentiation and mitosis and oncogenic transformation, inhibits JAK kinases and regulates cytokin receptor signaling |
| PVR | Poliovirus Receptor | Cell adhesion, poliovirus receptor |
| PYCARD | PYD And CARD Domain Containing | Inflammation, apoptosis |
| RAC1 | Ras-Related C3 Botulinum Toxin Substrate 1 | Regulates cell growth, cytoskeletal restructure and the activation of protein kinases |
| RELA | RELA Proto-Oncogene, NF-KB Subunit | Protein Coding gene, initiates the transcription of specific genes |
| SMAD3 | SMAD Family Member 3 | Regulated multiple signaling pathways, carsinogenesis regulator |
| SPA17 | Sperm Autoantigenic Protein 17 | Cell-cell adhesion, immune cell migration and metastasis |
| SPN | Sialophorin | Y-cell activation, negatively regulates adaptive immune responses |
| STAT3 | Signal Transducer And Activator Of Transcription 3 | Cell gwoth, apoptosis, mediates various genes in response to cell stimuli, associated with autoimmune diseases |
| STAT4 | Signal Transducer And Activator Of Transcription 4 | Transcriptional inducers, regulates T helper differentiation, regulates responses to IL12, associated with systemic lupus erythematosus and rheumatoid arthritis |
| STAT5B | Signal Transducer And Activator Of Transcription 5B | Transcriptional activator mediates the signal trasduction initiated by cell ligands and growth hormones, involved in TDR signaling, apoptosis, gland development |
| SYK | Spleen Associated Tyrosine Kinase | Proliferation, differentiation, phagocytosis, epithelial cell growth, tumor suppressor in breast carcinomas |
| TNFRSF11A | TNF Receptor Superfamily Member 11a | NF-kappa B and MAPK8/JNK activator,Tcell and dendritic cell interactions regulator, osteoclast and lymph node development |
| TNFRSF1A | TNF Receptor Superfamily Member 1Å | Cell survival, apoptosis and inflammation |
| TNFSF8 | TNF Superfamily Member 8 | Ig class switch inhibitor, enhance cell proliferation and cell death |
| TRAF2 | TNF Receptor Associated Factor 2 | Activates MAPK8/JNK and NF-kappa B, apoptosis |
| TRAF6 | TNF Receptor Associated Factor 6 | Signal transducer in the NF-kappaB pathway, Smad activation |
| TYK2 | Tyrosine Kinase 2 | Encodes component of type I and III interferon signaling pathways, associated with Immunodeficiency 35 and Primary Cutaneous Anaplastic Large Cell Lymphoma |
| UBC | Ubiquitin C | Protein degradation, DNA repair, cell cycel mediation, kinase modification endocytosis and other cell signaling pathway regulation |
| CD247 | CD247 Molecule | Involved in coupling recognition to multiple intracellular signal transduction pathways |
| PDCD1LG2 | Programmed Cell Death 1 Ligand 2 | Protein Coding gene, related to innate immune system and CD28 co-stimulation, associated with Cysticercosis and Mediastinal Malignant Lymphoma |
| STAT5A | Signal Transducer And Activator Of Transcription 5A | Transcription inducer, regulates the responses of many cell ligands, crusial for tumorogenesis |

TABLE 13.a1

| | Probe | GeneLocus | Probe_Count_Total | Probe_Count_Sig |
| --- | --- | --- | --- | --- |
| 1 | AKT1_14_104800011_104801022_104839372_104843321_FF | AKT1 | 60 | 4 |
| 2 | BAD_11_64267793_64269811_64292591_64296924_FF | BAD | 70 | 8 |
| 3 | BAX_19_48955700_48958764_48973070_48975293_RR | BAX | 52 | 2 |
| 4 | BBC3_19_47236830_47241014_47256212_47257706_FR | BBC3 | 56 | 8 |

TABLE 13.a1-continued

| | Probe | GeneLocus | Probe_Count_Total | Probe_Count_Sig |
|---|---|---|---|---|
| 5 | BID_22_17731946_17735544_17804446_17806939_FF | BID | 42 | 2 |
| 6 | BOK_2_241559192_241566423_241577996_241581000_RR | BOK | 44 | 10 |
| 7 | C8A_1_56824227_56829583_56902220_56908104_FR | C8A | 166 | 8 |
| 8 | C8A_1_56841210_56844685_56902220_56908104_RF | C8A | 4 | 1 |
| 9 | C8B_1_56959632_56962729_56991331_56998079_FF | C8B | 151 | 9 |
| 10 | CASP6_4_109703339_109705583_109735036_109741090_RF | CASP6 | 28 | 2 |
| 11 | CASP9_1_15520953_15524014_15542554_15547367_FR | CASP9 | 46 | 2 |
| 12 | CBLB_3_105723411_105731672_105883590_105884656_RF | CBLB | 5 | 2 |
| 13 | CD14_5_140643798_140647427_140670568_140672728_FF | CD14 | 62 | 6 |
| 14 | CD2_1_116707374_116708774_116735758_116740399_FR | CD2 | 34 | 2 |
| 15 | CD4_12_6767426_6773999_6813425_6817229_FR | CD4 | 42 | 6 |
| 16 | CD6_11_60922069_60925026_61017867_61025585_RR | CD6 | 56 | 14 |
| 17 | CD6_11_60932387_60933682_60977084_60983727_FR | CD6 | 56 | 14 |
| 18 | CD6_11_60932387_60933682_61017867_61025585_FR | CD6 | 56 | 14 |
| 19 | CD6_11_60938640_60941215_60977084_60983727_RF | CD6 | 56 | 14 |
| 20 | CD6_11_60938640_60941215_61017867_61025585_RF | CD6 | 56 | 14 |
| 21 | CD6_11_60977084_60983727_60996251_60998956_FR | CD6 | 56 | 14 |
| 22 | CD82_11_44515603_44522167_44561823_44564856_RF | CD82 | 50 | 6 |
| 23 | CD82_11_44526701_44529279_44592038_44600902_RF | CD82 | 50 | 6 |
| 24 | CD82_11_44561823_44564856_44624533_44629606_FF | CD82 | 50 | 6 |
| 25 | CFP_X_47636868_47644403_47672279_47679605_RR | CFP | 1 | 1 |
| 26 | CRADD_12_93830263_93837995_93848656_93851009_FR | CRADD | 231 | 4 |
| 27 | EGF_4_109875299_109879120_110005130_110011368_RF | EGF | 48 | 2 |
| 28 | ELK1_X_47636868_47644403_47672279_47679605_RR | ELK1 | 2 | 1 |
| 29 | FAS_10_88940885_88944343_88985428_88990419_FF | FAS | 50 | 8 |
| 30 | FAS_10_88953662_88956472_88985428_88990419_FF | FAS | 50 | 8 |
| 31 | FCGR2B_1_161620964_161624310_161645837_161653201_RR | FCGR2B | 1 | 1 |
| 32 | HLA-DQA1_6_32634077_32639503_32662361_32664960_FF | HLA-DQA1 | 28 | 4 |
| 33 | ICOSLG_21_44243731_44245588_44267559_44270033_RR | ICOSLG | 40 | 8 |
| 34 | IGF1R_15_98731539_98737034_98785670_98790114_FF | IGF1R | 104 | 16 |
| 35 | IGF2_11_2113132_2119465_2180328_2182624_RR | IGF2 | 32 | 6 |
| 36 | IKBKB_8_42241866_42245619_42264241_42271203_RF | IKBKB | 46 | 12 |
| 37 | IKBKB_8_42264241_42271203_42281222_42285075_FR | IKBKB | 46 | 12 |
| 38 | IKBKB_8_42264241_42271203_42290979_42292124_FF | IKBKB | 46 | 12 |
| 39 | IKBKB_8_42264241_42271203_42290979_42292124_FR | IKBKB | 46 | 12 |
| 40 | IKBKB_8_42264241_42271203_42302441_42304680_FF | IKBKB | 46 | 12 |
| 41 | IKBKB_8_42264241_42271203_42331044_42332799_FR | IKBKB | 46 | 12 |
| 42 | IL17D_13_20664875_20671757_20688261_20691044_FF | IL17D | 2 | 1 |
| 43 | IL17RA_22_17061373_17065953_17132107_17134862_RR | IL17RA | 3 | 1 |
| 44 | IRF1_5_132472660_132477912_132495376_132497062_FF | IRF1 | 42 | 8 |
| 45 | IRF1_5_132472660_132477912_132517598_132521351_FR | IRF1 | 42 | 8 |
| 46 | IRF1_5_132472660_132477912_132536450_132537922_FR | IRF1 | 42 | 8 |
| 47 | IRF2_4_184439815_184446749_184518370_184519514_RF | IRF2 | 38 | 2 |
| 48 | IRF3_19_49654782_49660360_49691432_49693107_RR | IRF3 | 30 | 2 |
| 49 | ITGAM_16_31214801_31216194_31318595_31324659_RF | ITGAM | 50 | 8 |
| 50 | ITGAM_16_31278026_31284381_31331188_31333058_RF | ITGAM | 50 | 8 |
| 51 | ITGAM_16_31331188_31333058_31344274_31352361_RF | ITGAM | 50 | 8 |
| 52 | ITGAX_16_31331188_31333058_31344274_31352361_RF | ITGAX | 41 | 8 |

TABLE 13.a2

| | HyperG_Stats | FDR_HyperG | Percent_Sig | logFC | AveExpr | t |
|---|---|---|---|---|---|---|
| 1 | 0.711822793 | 0.99999793 | 6.67 | −0.219972658 | −0.219972658 | −4.996552469 |
| 2 | 0.18964104 | 0.954389149 | 11.43 | −0.139786492 | −0.139786492 | −5.923845607 |
| 3 | 0.925958703 | 0.99999793 | 3.85 | −0.15962933 | −0.15962933 | −6.204852631 |
| 4 | 0.073465475 | 0.710624303 | 14.29 | −0.166543413 | −0.166543413 | −6.557217188 |
| 5 | 0.857080857 | 0.99999793 | 4.76 | −0.1760267 | −0.1760267 | −8.001384234 |
| 6 | 0.001969408 | 0.075986326 | 22.73 | −0.362483584 | −0.362483584 | −10.9324899 |
| 7 | 0.957766442 | 0.99999793 | 4.82 | −0.374033997 | −0.374033997 | −10.68867959 |
| 8 | 0.229343441 | 1 | 25 | 0.338570638 | 0.338570638 | 3.416892289 |
| 9 | 0.85591599 | 0.99999793 | 5.96 | −0.161358241 | −0.161358241 | −2.947668664 |
| 10 | 0.663352621 | 0.99999793 | 7.14 | −0.339412631 | −0.339412631 | −13.55417084 |
| 11 | 0.889742685 | 0.99999793 | 4.35 | −0.137531489 | −0.137531489 | −6.968042831 |
| 12 | 0.034964245 | 0.465381017 | 40 | 0.464289848 | 0.464289848 | 8.34149661 |
| 13 | 0.369692981 | 0.99999793 | 9.68 | −0.178209877 | −0.178209877 | −7.696109127 |
| 14 | 0.764125503 | 0.99999793 | 5.88 | −0.18498091 | −0.18498091 | −9.04469975 |
| 15 | 0.112492545 | 0.789152247 | 14.29 | −0.139921516 | −0.139921516 | −5.076520451 |
| 16 | 9.03E−05 | 0.005970563 | 25 | −0.21998431 | −0.21998431 | −6.891261434 |
| 17 | 9.03E−05 | 0.005970563 | 25 | −0.149724624 | −0.149724624 | −8.117825922 |
| 18 | 9.03E−05 | 0.005970563 | 25 | −0.159211463 | −0.159211463 | −8.406010145 |
| 19 | 9.03E−05 | 0.005970563 | 25 | −0.321565937 | −0.321565937 | −13.11065547 |
| 20 | 9.03E−05 | 0.005970563 | 25 | −0.207569599 | −0.207569599 | −8.105335573 |
| 21 | 9.03E−05 | 0.005970563 | 25 | −0.169304269 | −0.169304269 | −9.223976152 |
| 22 | 0.203083688 | 0.988148592 | 12 | −0.145793053 | −0.145793053 | −5.45369143 |

TABLE 13.a2-continued

|    | HyperG_Stats | FDR_HyperG  | Percent_Sig | logFC        | AveExpr      | t           |
|----|--------------|-------------|-------------|--------------|--------------|-------------|
| 23 | 0.203083688  | 0.988148592 | 12          | −0.348220668 | −0.348220668 | −12.64682486 |
| 24 | 0.203083688  | 0.988148592 | 12          | −0.162924558 | −0.162924558 | −4.377302648 |
| 25 | 0.06993762   | 0.594154735 | 100         | −0.191997367 | −0.191997367 | −3.324047424 |
| 26 | 0.999992975  | 0.99999793  | 1.73        | −0.249667458 | −0.249667458 | −9.588148198 |
| 27 | 0.903339407  | 0.99999793  | 4.17        | −0.144833276 | −0.144833276 | −7.422808069 |
| 28 | 0.13498553   | 0.877871412 | 50          | −0.18736422  | −0.18736422  | −3.275422717 |
| 29 | 0.041957105  | 0.555032562 | 16          | −0.193599779 | −0.193599779 | −5.573764843 |
| 30 | 0.041957105  | 0.555032562 | 16          | −0.194159165 | −0.194159165 | −8.590649368 |
| 31 | 0.066362764  | 0.687693257 | 100         | 0.187306985  | 0.187306985  | 3.719020117 |
| 32 | 0.178427395  | 0.954389149 | 14.29       | −0.211239457 | −0.211239457 | −3.939059704 |
| 33 | 0.012066038  | 0.223463015 | 20          | −0.156295949 | −0.156295949 | −6.247769863 |
| 34 | 0.007797893  | 0.171924974 | 15.38       | −0.178097117 | −0.178097117 | −7.086728608 |
| 35 | 0.037675475  | 0.528598335 | 18.75       | −0.180180699 | −0.180180699 | −8.22189382 |
| 36 | 0.00018363   | 0.010627608 | 26.09       | −0.304258892 | −0.304258892 | −11.89187759 |
| 37 | 0.00018363   | 0.010627608 | 26.09       | −0.265642352 | −0.265642352 | −11.56467535 |
| 38 | 0.00018363   | 0.010627608 | 26.09       | −0.325741973 | −0.325741973 | −15.03154881 |
| 39 | 0.00018363   | 0.010627608 | 26.09       | −0.307578042 | −0.307578042 | −13.22491838 |
| 40 | 0.00018363   | 0.010627608 | 26.09       | −0.393553534 | −0.393553534 | −17.46788221 |
| 41 | 0.00018363   | 0.010627608 | 26.09       | −0.363126662 | −0.363126662 | −16.40706083 |
| 42 | 0.122126697  | 0.904598768 | 50          | 0.19255788   | 0.19255788   | 6.703121045 |
| 43 | 0.195485486  | 0.98238612  | 33.33       | −0.261366196 | −0.261366196 | −5.18175145 |
| 44 | 0.016095432  | 0.256971894 | 19.05       | −0.25495765  | −0.25495765  | −13.36737718 |
| 45 | 0.016095432  | 0.256971894 | 19.05       | −0.147678268 | −0.147678268 | −6.626064358 |
| 46 | 0.016095432  | 0.256971894 | 19.05       | −0.165001138 | −0.165001138 | −9.029584345 |
| 47 | 0.815788109  | 0.99999793  | 5.26        | −0.204963087 | −0.204963087 | −3.763496869 |
| 48 | 0.700318757  | 0.99999793  | 6.67        | −0.175351435 | −0.175351435 | −7.320634642 |
| 49 | 0.041957105  | 0.555032562 | 16          | −0.266411523 | −0.266411523 | −9.608582862 |
| 50 | 0.041957105  | 0.555032562 | 16          | −0.179650611 | −0.179650611 | −8.796652754 |
| 51 | 0.041957105  | 0.555032562 | 16          | −0.215030115 | −0.215030115 | −9.152973735 |
| 52 | 0.013975308  | 0.239650655 | 19.51       | −0.212953478 | −0.212953478 | −9.692570589 |

TABLE 13.a3

|    | P.Value      | adj.P.Val   | B            | FC          | FC_1         | LS |
|----|--------------|-------------|--------------|-------------|--------------|----|
| 1  | 0.000501614  | 0.003704426 | −0.24806514  | 0.858581708 | −1.164711512 | −1 |
| 2  | 0.000132635  | 0.00150023  | 1.136919402  | 0.907653471 | −1.101742055 | −1 |
| 3  | 0.0000907    | 0.001165246 | 1.532307434  | 0.895255058 | −1.117000111 | 1  |
| 4  | 0.0000572    | 0.000856101 | 2.012450668  | 0.890974834 | −1.122366157 | −1 |
| 5  | 0.0000101    | 0.000288637 | 3.809465717  | 0.885137383 | −1.129768123 | −1 |
| 6  | 0.000000565  | 0.0000062   | 6.755470255  | 0.77782441  | −1.285637205 | −1 |
| 7  | 0.0000007    | 0.0000689   | 6.540229405  | 0.771621904 | −1.295971504 | −1 |
| 8  | 0.006357009  | 0.023175587 | −2.864888701 | 1.264503156 | 1.264503156  | 1  |
| 9  | 0.01423557   | 0.042361163 | −3.677544832 | 0.894182836 | −1.118339516 | −1 |
| 10 | 0.0000000712 | 0.0000221   | 8.801357166  | 0.790363029 | −1.265241367 | −1 |
| 11 | 0.0000341    | 0.000615455 | 2.550875988  | 0.909073287 | −1.100021323 | −1 |
| 12 | 0.00000696   | 0.000231622 | 4.19579057   | 1.379638073 | 1.379638073  | 1  |
| 13 | 0.0000143    | 0.000359185 | 3.451288223  | 0.883798951 | −1.131479053 | −1 |
| 14 | 0.00000333   | 0.00015367  | 4.954405786  | 0.879660716 | −1.13680193  | −1 |
| 15 | 0.000445101  | 0.00340461  | −0.123778016 | 0.907568527 | −1.101845173 | −1 |
| 16 | 0.0000375    | 0.000650749 | 2.451958669  | 0.858574774 | −1.164720919 | −1 |
| 17 | 0.0000089    | 0.000266511 | 3.943211829  | 0.901422506 | −1.109357702 | −1 |
| 18 | 0.0000065    | 0.000223939 | 4.267601817  | 0.8955144   | −1.116676627 | −1 |
| 19 | 0.0000000984 | 0.0000263   | 8.486465281  | 0.800200848 | −1.249686254 | −1 |
| 20 | 0.00000902   | 0.000268394 | 3.928939971  | 0.86599488  | −1.154741238 | −1 |
| 21 | 0.00000278   | 0.000140257 | 5.139609489  | 0.889271424 | −1.124516063 | −1 |
| 22 | 0.000256432  | 0.002326445 | 0.450144339  | 0.903882374 | −1.106338644 | −1 |
| 23 | 0.00000014   | 0.0000332   | 8.144494866  | 0.785552353 | −1.272989631 | −1 |
| 24 | 0.001305374  | 0.007284682 | −1.240107008 | 0.89321256  | −1.119554343 | −1 |
| 25 | 0.007447421  | 0.026094146 | −3.025492926 | 0.875392927 | −1.142344162 | −1 |
| 26 | 0.00000194   | 0.000115278 | 5.506120648  | 0.841090265 | −1.188933034 | −1 |
| 27 | 0.0000197    | 0.000439652 | 3.121097762  | 0.904483898 | −1.105602877 | −1 |
| 28 | 0.00809346   | 0.027703335 | −3.109705135 | 0.878208729 | −1.138681462 | −1 |
| 29 | 0.00021606   | 0.002072157 | 0.628565303  | 0.874421161 | −1.143613677 | −1 |
| 30 | 0.00000533   | 0.000200984 | 4.470605821  | 0.874082182 | −1.144057184 | −1 |
| 31 | 0.003819047  | 0.015841136 | −2.345217043 | 1.138636289 | 1.138636289  | 1  |
| 32 | 0.002651517  | 0.012158182 | −1.970945908 | 0.863794804 | −1.157682352 | −1 |
| 33 | 0.0000857    | 0.001121376 | 1.591712007  | 0.897325957 | −1.114422236 | −1 |
| 34 | 0.0000295    | 0.000560642 | 2.702258066  | 0.88386803  | −1.131390622 | −1 |
| 35 | 0.00000793   | 0.000252813 | 4.061431872  | 0.882592444 | −1.133025789 | −1 |
| 36 | 0.000000253  | 0.0000427   | 7.5583041    | 0.809858131 | −1.234784169 | −1 |
| 37 | 0.00000033   | 0.0000483   | 7.292110963  | 0.833828285 | −1.202171191 | −1 |
| 38 | 0.0000000258 | 0.0000141   | 9.772437866  | 0.79788793  | −1.253308845 | −1 |
| 39 | 0.0000000905 | 0.0000252   | 8.56869633   | 0.807997065 | −1.237628258 | −1 |
| 40 | 0.0000000059 | 0.0000101   | 11.15054812  | 0.761252236 | −1.313625041 | −1 |

TABLE 13.a3-continued

|    | P.Value | adj.P.Val | B | FC | FC_1 | LS |
|---|---|---|---|---|---|---|
| 41 | 0.0000000109 | 0.0000107 | 10.58128991 | 0.777477774 | −1.286210402 | −1 |
| 42 | 0.0000475 | 0.000761747 | 2.20626716 | 1.142788069 | 1.142788069 | 1 |
| 43 | 0.000380851 | 0.003058531 | 0.038392966 | 0.834297487 | −1.198613224 | −1 |
| 44 | 0.0000000815 | 0.000024 | 8.670136499 | 0.838011734 | −1.193300714 | −1 |
| 45 | 0.0000524 | 0.000805791 | 2.104266413 | 0.902702014 | −1.107785276 | −1 |
| 46 | 0.00000338 | 0.000154851 | 4.938642975 | 0.891927816 | −1.121166963 | −1 |
| 47 | 0.003545919 | 0.015017871 | −2.269233273 | 0.867560884 | −1.152656855 | −1 |
| 48 | 0.0000222 | 0.000473074 | 2.995279965 | 0.885551776 | −1.12923945 | −1 |
| 49 | 0.0000019 | 0.000114103 | 5.526310904 | 0.831384915 | −1.202812298 | −1 |
| 50 | 0.0000043 | 0.000176706 | 4.692775469 | 0.882916793 | −1.132609559 | −1 |
| 51 | 0.00000298 | 0.000144884 | 5.066643761 | 0.861528176 | −1.160728143 | −1 |
| 52 | 0.00000175 | 0.000109375 | 5.608883602 | 0.862769165 | −1.159058576 | −1 |

TABLE 13.a4

|    | Loop detected | Probe sequence 60 mer |
|---|---|---|
| 1 | PD-L1 responder | CCCGCGGCGGAGCTGCTACTGTTTACTTTCGAAGCTTCTTCCTTTCGGCCCCCAGGCCTA (SEQ ID NO: 505) |
| 2 | PD-L1 responder | GCACTACCCCGGCCTGCCGGAGCCCCAGTCGAGTTGGTTTCTGGGTCCGCACCCCCTCCC (SEQ ID NO: 506) |
| 3 | PD-L1 responder | CGGGTGCCTCCCCCCCCATTCGCCCTGCTCGAGGGAGGGAAATGATTGGATTACGGGGGT (SEQ ID NO: 507) |
| 4 | PD-L1 responder | CGTGGATCCAGACTGGGAGCCCCCAGCCTCGAACCACGCCAGGCTTCCAGGCGTCAGTGC (SEQ ID NO: 508) |
| 5 | PD-L1 responder | TGGAAGCAGCTATACAGCTGTGACCACATCGACGCCCCTGTCACGGGCCCTGTTATTCAA (SEQ ID NO: 509) |
| 6 | PD-L1 responder | GTTTGCTCCGGGGCCGCCGGGCCCGCCCTCGATTTTAACACCACCATGGTTTGAATGAAT (SEQ ID NO: 510) |
| 7 | PD-L1 responder | GGTGACTGCTCAGAAGAGCAGTACTCATTCGACCTTATGCTAAGCCTAAACTTGCCTTCC (SEQ ID NO: 511) |
| 8 | PD-L1 Non-responder | AGGTCATTAAAGTATAATCCTGTTGTTATCGAGAGATCAAGACCATCCTGGCCAACATGG (SEQ ID NO: 512) |
| 9 | PD-L1 responder | ATTTTGACATCTGCATTTTACAGCAGCCTCGATGCGAGCTCGTGGTGGGTGCTCAAGACT (SEQ ID NO: 513) |
| 10 | PD-L1 responder | GGGGCCTCCAGAGTCCCCTTTACAGGCATCGACGCCCCCTGCCTACCTGCCGGGTGCCCC (SEQ ID NO: 514) |
| 11 | PD-L1 responder | GAAGGCTAGGCTCCCGCACAACGCCTCCTCGAGCAAGTTAGTTGAACCCAAGGAGGGTCA (SEQ ID NO: 515) |
| 12 | PD-L1 Non-responder | CCTAATATTTCATTATGATAAGAAAGATTCGAATAAGAAATACTTCTAAACCAAAGGATA (SEQ ID NO: 516) |
| 13 | PD-L1 responder | GCGGGGCTTCCCTCAACTTCAGGGAGGTCGAGGCGCGGCGCGCAGGCCGCCATCGCCAC (SEQ ID NO: 517) |
| 14 | PD-L1 responder | ATTTGACAACGCTGGCACGGAGGCAAGATCGACCTCCCTGTCCCTCCTGGGCCTCTCCGG (SEQ ID NO: 518) |
| 15 | PD-L1 responder | CCGCCTCCGTCTGCGCCTGGGCCAGGCCTCGAGAATTATTCTTTTCATATACAAAGAATA (SEQ ID NO: 519) |
| 16 | PD-L1 responder | CTGGCGTTCCAGCCCTCGCACCTTGGCCTCGAGCACCTCTTCAGGGGAGGATTACTGCAA (SEQ ID NO: 520) |
| 17 | PD-L1 responder | GTGTGGGCCCCCCTGCTACCGCTGCGTATCGAACTTTACAGAGGGATCTAGAATGAGTGA (SEQ ID NO: 521) |
| 18 | PD-L1 responder | GTGTGGGCCCCCCTGCTACCGCTGCGTATCGAGCACCTCTTCAGGGGAGGATTACTGCAA (SEQ ID NO: 522) |
| 19 | PD-L1 responder | TTAATGCTGATACAATTCTATTGGATAATCGACACTTCGGCTCCCTGCACCTCCCATGCC (SEQ ID NO: 523) |

TABLE 13.a4-continued

| | Loop detected | Probe sequence 60 mer |
|---|---|---|
| 20 | PD-L1 responder | CAATATGACGGTGACATTAATGATAGCTTCGACACTTCGGCTCCCTGCACCTCCCATGCC (SEQ ID NO: 524) |
| 21 | PD-L1 responder | TTAATGCTGATACAATTCTATTGGATAATCGACGTGCCTTGGGGCCTCCCCTTTCCCTAT (SEQ ID NO: 525) |
| 22 | PD-L1 responder | ACGCCCGCCTCCATGAGATTCAGAGCCCTCGAGAATGTGGACTCTCCTTTCCCCCAGCAC (SEQ ID NO: 526) |
| 23 | PD-L1 responder | CACAGCTTCTAAATGGTAGGTGTGGGACTCGACCCGCTTTCCTCCCCGCCCCCTCATCCG (SEQ ID NO: 527) |
| 24 | PD-L1 responder | ACGCCCGCCTCCATGAGATTCAGAGCCCTCGACTCCTTTCCCAGACACATTCAGCACGTG (SEQ ID NO: 528) |
| 25 | PD-L1 responder | CATCCCTTCTATCAGCGTGGATGGCCTCTCGAGGCCCAAGGGCTTGTCAGTCAGCTTGTG (SEQ ID NO: 529) |
| 26 | PD-L1 responder | ACAGTTTTATTGTTGACCTTCCATGGACTCGAGATGCGCCACGCCCTGTTCCTCCTTCAT (SEQ ID NO: 530) |
| 27 | PD-L1 responder | CAGGCTATTGTAGTGCTCTTCCTGGCCCTCGACACCCCCTTCAAGGGTCTGTGTCCCATA (SEQ ID NO: 531) |
| 28 | PD-L1 responder | CATCCCTTCTATCAGCGTGGATGGCCTCTCGAGGCCCAAGGGCTTGTCAGTCAGCTTGTG (SEQ ID NO: 532) |
| 29 | PD-L1 responder | GTCTTTGTGTAAATAAATAAGGTAACCCTCGAGAGCCGGCCTCCTGCCCTTTCTAAAGGC (SEQ ID NO: 533) |
| 30 | PD-L1 responder | CGTGAATATATTGGGCTCTAATGGATAATCGAGAGCCGGCCTCCTGCCCTTTCTAAAGGC (SEQ ID NO: 534) |
| 31 | PD-L1 Non-responder | AGGACAGAGACCCCTAATTCCACCACCATCGAGGGGCTTACTAATGCCTTTTAGCTCCCT (SEQ ID NO: 535) |
| 32 | PD-L1 responder | CCCGTCTTCCCCAAAATCTATGTGGTCCTCGACAGCGACGTGGGGGTGTACCGCGCGGTG (SEQ ID NO: 536) |
| 33 | PD-L1 responder | AGGTGGAGATCAGAAGACCCCCACGCCCTCGAGTCACAGCTGTAGTGGGGTGGGGGGTGA (SEQ ID NO: 537) |
| 34 | PD-L1 responder | CGTAGAACTAAGATGTATTCAAAGTCAGTCGAAATCACCTGTCCCGGCCTCTTTCCAAAC (SEQ ID NO: 538) |
| 35 | PD-L1 responder | GTGACAATTAAGAGTGTGACATTGCTTCTCGAGGACTCACTGGGCCTGCAGGGGGCAGC (SEQ ID NO: 539) |
| 36 | PD-L1 responder | CCACCCCGCCCCGGGGGAGTCGCCCGGTCGAACTAATATTAGAGGAGAGAGGTCAGTTA (SEQ ID NO: 540) |
| 37 | PD-L1 responder | CCACCCCGCCCCGGGGGAGTCGCCCGGTCGAGGGCCTGGCAAGAAGACAGAAGCCGACT (SEQ ID NO: 541) |
| 38 | PD-L1 responder | CCACCCCGCCCCGGGGGAGTCGCCCGGTCGAAGTGCTGTTGAGTTCCCCCATCTCTCAT (SEQ ID NO: 542) |
| 39 | PD-L1 responder | CCACCCCGCCCCGGGGGAGTCGCCCGGTCGATTTCCAAAAGCTCACACATGGGTGCACA (SEQ ID NO: 543) |
| 40 | PD-L1 responder | CCACCCCGCCCCGGGGGAGTCGCCCGGTCGACAGTCCCAAGAGGTCAGAACTGGCTTCC (SEQ ID NO: 544) |
| 41 | PD-L1 responder | CCACCCCGCCCCGGGGGAGTCGCCCGGTCGACCCCCTGACATGGGGCTGCCTGGAGCAG (SEQ ID NO: 545) |
| 42 | PD-L1 Non-responder | TTAAAGAAGCTAATTTTAAAAATAAATGTCGAAGAGATTGTCACGTTAGAGTTATGTAAA (SEQ ID NO: 546) |
| 43 | PD-L1 responder | TATTATCCTGCACCCTGAAAAGGTGTTATCGATGCACTCAGTCTTTTTTTTTATTCACT (SEQ ID NO: 547) |
| 44 | PD-L1 responder | GTGTCTCGGCCCCCTGGGGCCCCACCCTTCGATTTCCCTGTTGCCGCCGCGTTTGCAAGA (SEQ ID NO 548) |
| 45 | PD-L1 responder | GTGTCTCGGCCCCCTGGGGCCCCACCCTTCGATACTATTACGAATGGAATCACTGTCTTA (SEQ ID NO: 549) |

TABLE 13.a4-continued

| | Loop detected | Probe sequence 60 mer |
|---|---|---|
| 46 | PD-L1 responder | GTGTCTCGGCCCCCTGGGGCCCCACCCTTCGAGTGCATCCTGCAGCTGTTTGTCCAGAAG (SEQ ID NO: 550) |
| 47 | PD-L1 responder | TTATGATATTGTAAATTATTTTTAATATTCGAGCAAACTGACTTGGGGCCCCTATGTGTG (SEQ ID NO: 551) |
| 48 | PD-L1 responder | GCAGCCAGCCCGGTGGGGGTGGGGGGGTCGACGCTCGCCTCCGCTCACAGCCTCAGCAT (SEQ ID NO: 552) |
| 49 | PD-L1 responder | CAAATCCCGGCTATCTCTTAGAATTGCATCGACGCGCCCGTGACAGCCGAGTGCGGCCAC (SEQ ID NO: 553) |
| 50 | PD-L1 responder | ACATCGCTACCAGGCCGATGTGCTGATATCGAGGTCCCCAACCCCCTGCCGCTCATCGTG (SEQ ID NO: 554) |
| 51 | PD-L1 responder | AGTGGTCTCACCATGGCTTTCTTCCAATTCGAGGTCCCCAACCCCCTGCCGCTCATCGTG (SEQ ID NO: 555) |
| 52 | PD-L1 responder | AGTGGTCTCACCATGGCTTTCTTCCAATTCGAGGTCCCCAACCCCCTGCCGCTCATCGTG (SEQ ID NO: 556) |

TABLE 13.a5

| | Probe Location | | | | 4 kb Sequence Location | | |
|---|---|---|---|---|---|---|---|
| | Chr | Start1 | End1 | Start2 | End2 | Chr | Start1 | End1 |
| 1 | 14 | 104800993 | 104801022 | 104843292 | 104843321 | 14 | 104797023 | 104801022 |
| 2 | 11 | 64269782 | 64269811 | 64296895 | 64296924 | 11 | 64265812 | 64269811 |
| 3 | 19 | 48955700 | 48955729 | 48973070 | 48973099 | 19 | 48955700 | 48959699 |
| 4 | 19 | 47240985 | 47241014 | 47256212 | 47256241 | 19 | 47237015 | 47241014 |
| 5 | 22 | 17735515 | 17735544 | 17806910 | 17806939 | 22 | 17731545 | 17735544 |
| 6 | 2 | 241559192 | 241559221 | 241577996 | 241578025 | 2 | 241559192 | 241563191 |
| 7 | 1 | 56829554 | 56829583 | 56902220 | 56902249 | 1 | 56825584 | 56829583 |
| 8 | 1 | 56841210 | 56841239 | 56908075 | 56908104 | 1 | 56841210 | 56845209 |
| 9 | 1 | 56962700 | 56962729 | 56998050 | 56998079 | 1 | 56958730 | 56962729 |
| 10 | 4 | 109703339 | 109703368 | 109741061 | 109741090 | 4 | 109703339 | 109707338 |
| 11 | 1 | 15523985 | 15524014 | 15542554 | 15542583 | 1 | 15520015 | 15524014 |
| 12 | 3 | 105723411 | 105723440 | 105884627 | 105884656 | 3 | 105723411 | 105727410 |
| 13 | 5 | 140647398 | 140647427 | 140672699 | 140672728 | 5 | 140643428 | 140647427 |
| 14 | 1 | 116708745 | 116708774 | 116735758 | 116735787 | 1 | 116704775 | 116708774 |
| 15 | 12 | 6773970 | 6773999 | 6813425 | 6813454 | 12 | 6770000 | 6773999 |
| 16 | 11 | 60922069 | 60922098 | 61017867 | 61017896 | 11 | 60922069 | 60926068 |
| 17 | 11 | 60933653 | 60933682 | 60977084 | 60977113 | 11 | 60929683 | 60933682 |
| 18 | 11 | 60933653 | 60933682 | 61017867 | 61017896 | 11 | 60929683 | 60933682 |
| 19 | 11 | 60938640 | 60938669 | 60983698 | 60983727 | 11 | 60938640 | 60942639 |
| 20 | 11 | 60938640 | 60938669 | 61025556 | 61025585 | 11 | 60938640 | 60942639 |
| 21 | 11 | 60983698 | 60983727 | 60996251 | 60996280 | 11 | 60979728 | 60983727 |
| 22 | 11 | 44515603 | 44515632 | 44564827 | 44564856 | 11 | 44515603 | 44519602 |
| 23 | 11 | 44526701 | 44526730 | 44600873 | 44600902 | 11 | 44526701 | 44530700 |
| 24 | 11 | 44564827 | 44564856 | 44629577 | 44629606 | 11 | 44560857 | 44564856 |
| 25 | X | 47636868 | 47636897 | 47672279 | 47672308 | X | 47636868 | 47640867 |
| 26 | 12 | 93837966 | 93837995 | 93848656 | 93848685 | 12 | 93833996 | 93837995 |
| 27 | 4 | 109879091 | 109879120 | 110011339 | 110011368 | 4 | 109875121 | 109879120 |
| 28 | X | 47636868 | 47636897 | 47672279 | 47672308 | X | 47636868 | 47640867 |
| 29 | 10 | 88944344 | 88944343 | 88990390 | 88990419 | 10 | 88940344 | 88944343 |
| 30 | 10 | 88956443 | 88956472 | 88990390 | 88990419 | 10 | 88952473 | 88956472 |
| 31 | 1 | 161620964 | 161620993 | 161645837 | 161645866 | 1 | 161620964 | 161624963 |
| 32 | 6 | 32639474 | 32639503 | 32664931 | 32664960 | 6 | 32635504 | 32639503 |
| 33 | 21 | 44243731 | 44243760 | 44267559 | 44267588 | 21 | 44243731 | 44247730 |
| 34 | 15 | 98737005 | 98737034 | 98790085 | 98790114 | 15 | 98733035 | 98737034 |
| 35 | 11 | 2113132 | 2113161 | 2180328 | 2180357 | 11 | 2113132 | 2117131 |
| 36 | 8 | 42241866 | 42241895 | 42271174 | 42271203 | 8 | 42241866 | 42245865 |
| 37 | 8 | 42271174 | 42271203 | 42281222 | 42281251 | 8 | 42267204 | 42271203 |
| 38 | 8 | 42271174 | 42271203 | 42292095 | 42292124 | 8 | 42267204 | 42271203 |
| 39 | 8 | 42271174 | 42271203 | 42290979 | 42291008 | 8 | 42267204 | 42271203 |
| 40 | 8 | 42271174 | 42271203 | 42304651 | 42304680 | 8 | 42267204 | 42271203 |
| 41 | 8 | 42271174 | 42271203 | 42331044 | 42331073 | 8 | 42267204 | 42271203 |
| 42 | 13 | 20671728 | 20671757 | 20691015 | 20691044 | 13 | 20667758 | 20671757 |
| 43 | 22 | 17061373 | 17061402 | 17132107 | 17132136 | 22 | 17061373 | 17065372 |
| 44 | 5 | 132477883 | 132477912 | 132497033 | 132497062 | 5 | 132473913 | 132477912 |
| 45 | 5 | 132477883 | 132477912 | 132521322 | 132521351 | 5 | 132473913 | 132477912 |
| 46 | 5 | 132477883 | 132477912 | 132536450 | 132536479 | 5 | 132473913 | 132477912 |

TABLE 13.a5-continued

|    | Probe Location | | | | 4 kb Sequence Location | | |
|----|-----|-----------|-----------|-----------|-----------|-----|-----------|-----------|
|    | Chr | Start1 | End1 | Start2 | End2 | Chr | Start1 | End1 |
| 47 | 4 | 184439815 | 184439844 | 184519485 | 184519514 | 4 | 184439815 | 184443814 |
| 48 | 19 | 49654782 | 49654811 | 49691432 | 49691461 | 19 | 49654782 | 49658781 |
| 49 | 16 | 31214801 | 31214830 | 31324630 | 31324659 | 16 | 31214801 | 31218800 |
| 50 | 16 | 31278026 | 31278055 | 31331188 | 31331217 | 16 | 31278026 | 31282025 |
| 51 | 16 | 31331188 | 31331217 | 31352332 | 31352361 | 16 | 31331188 | 31335187 |
| 52 | 16 | 31331188 | 31331217 | 31352332 | 31352361 | 16 | 31331188 | 31335187 |

TABLE 13.a6

|    | 4 kb Sequence Location | | Inner_primers | | |
|----|-----------|-----------|----------------|------------------------------------------|---------------|
|    | Start2 | End2 | PCR-Primer1_ID | PCR_Primer1 | PCR-Primer2_ID |
| 1  | 104839322 | 104843321 | OBD117.1.833 | GGGAGTGAAGTTCAGGAGCG (SEQ ID NO: 557) | OBD117.1.835 |
| 2  | 64292925 | 64296924 | OBD117.1.265 | TGTCGCTGGATGTCAGGCAGAGC (SEQ ID NO: 558) | OBD117.1.267 |
| 3  | 48973070 | 48977069 | OBD117.1.781 | ACACTCGCTCAGCTTCTTGG (SEQ ID NO: 559) | OBD117.1.783 |
| 4  | 47256212 | 47260211 | OBD117.1.405 | AGGAGGGAGTAGTGGAGAGGTTG (SEQ ID NO: 560) | OBD117.1.407 |
| 5  | 17802940 | 17806939 | OBD117.1.277 | GTGGAAATAAAGGCACCGTGTGTAGA (SEQ ID NO: 561) | OBD117.1.279 |
| 6  | 241577996 | 241581995 | OBD117.1.737 | GCGCCACCTTCTTTCAGAG (SEQ ID NO: 562) | OBD117.1.739 |
| 7  | 56902220 | 56906219 | OBD117.1.817 | GAAACATTACAGGGGCTTGG (SEQ ID NO: 563) | OBD117.1.819 |
| 8  | 56904105 | 56908104 | OBD117.1.1573 | CTTGGCACAGAACAGGAGCACCA (SEQ ID NO: 564) | OBD117.1.1575 |
| 9  | 56994080 | 56998079 | OBD117.1.321 | CCTGGGACTAACGAGGAGCCACA (SEQ ID NO: 565) | OBD117.1.323 |
| 10 | 109737091 | 109741090 | OBD117.1.821 | CAGACTAAGGGGCCTCCAGA (SEQ ID NO: 566) | OBD117.1.823 |
| 11 | 15542554 | 15546553 | OBD117.1.121 | GGATTCTTTGGCTCCGCTGAGGG (SEQ ID NO: 567) | OBD117.1.123 |
| 12 | 105880657 | 105884656 | OBD117.1.1453 | CCTATTGCCTGGAGCATAAAGGGAAA (SEQ ID NO: 568) | OBD117.1.1455 |
| 13 | 140668729 | 140672728 | OBD117.1.797 | GGAGCATTCGCGGATTAGGA (SEQ ID NO: 569) | OBD117.1.799 |
| 14 | 116735758 | 116739757 | OBD117.1.009 | GGCAGGAGCCAGCAGACACAAAG (SEQ ID NO: 570) | OBD117.1.011 |
| 15 | 6813425 | 6817424 | OBD117.1.769 | CGGGGACTTCTCGCTATGG (SEQ ID NO: 571) | OBD117.1.771 |
| 16 | 61017867 | 61021866 | OBD117.1.345 | GCTCTTTGGTATGACACTGGCGG (SEQ ID NO: 572) | OBD117.1.347 |
| 17 | 60977084 | 60981083 | OBD117.1.373 | TGTTCGTGGCTGGCAAGGAGAGC (SEQ ID NO: 573) | OBD117.1.375 |
| 18 | 61017867 | 61021866 | OBD117.1.337 | TGTTCGTGGCTGGCAAGGAGAGC (SEQ ID NO: 574) | OBD117.1.339 |
| 19 | 60979728 | 60983727 | OBD117.1.329 | TGTCCCTTTCTCCTAAATACCCCAAC (SEQ ID NO: 575) | OBD117.1.331 |
| 20 | 61021586 | 61025585 | OBD117.1.085 | CCAACACAGCAGCCTCCAGCCAT (SEQ ID NO: 576) | OBD117.1.087 |
| 21 | 60996251 | 61000250 | OBD117.1.293 | GTCCCTTTCTCCTAAATACCCCAACG (SEQ ID NO: 577) | OBD117.1.295 |
| 22 | 44560857 | 44564856 | OBD117.1.393 | TGGTTGTTCTGGGCTACTTCCCC (SEQ ID NO: 578) | OBD117.1.395 |
| 23 | 44596903 | 44600902 | OBD117.1.741 | GCTGATGAGGCACCTGCTAT (SEQ ID NO: 579) | OBD117.1.743 |
| 24 | 44625607 | 44629606 | OBD117.1.025 | TGGTTGTTCTGGGCTACTTCCCC (SEQ ID NO: 580) | OBD117.1.027 |
| 25 | 47672279 | 47676278 | OBD117.1.941 | CCAGTTTCCATCCAGTGGCAGCG (SEQ ID NO: 581) | OBD117.1.943 |
| 26 | 93848656 | 93852655 | OBD117.1.109 | GTGTCCACCCTACCACCCACCTT (SEQ ID NO: 582) | OBD117.1.111 |
| 27 | 110007369 | 110011368 | OBD117.1.117 | CCAGGAGACACCCTCTAAAGGAG (SEQ ID NO: 583) | OBD117.1.119 |
| 28 | 47672279 | 47676278 | OBD117.1.429 | CCAGTTTCCATCCAGTGGCAGCG (SEQ ID NO: 584) | OBD117.1.431 |
| 29 | 88986420 | 88990419 | OBD117.1.133 | GTGAGGCAGGATGGTATGGCAGT (SEQ ID NO: 585) | OBD117.1.135 |
| 30 | 88986420 | 88990419 | OBD117.1.409 | TAATCCTCCTGTCTCCCTCTTAGAAG (SEQ ID NO: 586) | OBD117.1.411 |

TABLE 13.a6-continued

| | 4 kb Sequence Location | | Inner_primers | | |
|---|---|---|---|---|---|
| | Start2 | End2 | PCR-Primer1_ID | PCR_Primer1 | PCR-Primer2_ID |
| 31 | 161645837 | 161649836 | OBD117.1.713 | ATTAGTCTTCAACCCACGCTGTTTTG (SEQ ID NO: 587) | OBD117.1.715 |
| 32 | 32660961 | 32664960 | OBD117.1.385 | TGGTTCTGCTACCTGTGTGCCTG (SEQ ID NO: 588) | OBD117.1.387 |
| 33 | 44267559 | 44271558 | OBD117.1.353 | TGTGCCAGACCCCAAAAGGACCC (SEQ ID NO: 589) | OBD117.1.355 |
| 34 | 98786115 | 98790114 | OBD117.1.777 | AATTCACCACACCCCAACAT (SEQ ID NO: 590) | OBD117.1.779 |
| 35 | 2180328 | 2184327 | OBD117.1.801 | AGGATTGTACACACAGCCCC (SEQ ID NO: 591) | OBD117.1.803 |
| 36 | 42267204 | 42271203 | OBD117.1.825 | GGTGTAACGGGGGTCATTTC (SEQ ID NO: 592) | OBD117.1.827 |
| 37 | 42281222 | 42285221 | OBD117.1.201 | GCACGGTCTGTCTACTTTCCCTC (SEQ ID NO: 593) | OBD117.1.203 |
| 38 | 42288125 | 42292124 | OBD117.1.417 | GCACGGTCTGTCTACTTTCCCTC (SEQ ID NO: 594) | OBD117.1.419 |
| 39 | 42290979 | 42294978 | OBD117.1.753 | GGTGTAACGGGGGTCATTTC (SEQ ID NO: 595) | OBD117.1.755 |
| 40 | 42300681 | 42304680 | OBD117.1.077 | GCACGGTCTGTCTACTTTCCCTC (SEQ ID NO: 596) | OBD117.1.079 |
| 41 | 42331044 | 42335043 | OBD117.1.261 | CGGTGAGCACGGTCTGTCTACTT (SEQ ID NO: 597) | OBD117.1.263 |
| 42 | 20687045 | 20691044 | OBD117.1.645 | TCTCTACTTCAGGCAGGCAGTGTAAG (SEQ ID NO: 598) | OBD117.1.647 |
| 43 | 17132107 | 17136106 | OBD117.1.537 | CACTCCAGTCCACCCACACTTTACTC (SEQ ID NO: 599) | OBD117.1.539 |
| 44 | 132493063 | 132497062 | OBD117.1.805 | CACTGAGGCCAAGTTACAAGC (SEQ ID NO: 600) | OBD117.1.807 |
| 45 | 132517352 | 132521351 | OBD117.1.785 | CTGAGTCTCACAGCCATCCA (SEQ ID NO: 601) | OBD117.1.787 |
| 46 | 132536450 | 132540449 | OBD117.1.837 | CATCTGTGCATGGTCCTGAG (SEQ ID NO: 602) | OBD117.1.839 |
| 47 | 184515515 | 184519514 | OBD117.1.1077 | GCTGGCATTTGGATTGAGA (SEQ ID NO: 603) | OBD117.1.1079 |
| 48 | 49691432 | 49695431 | OBD117.1.197 | GCTGCCCTCTCTCTTGTCAGACG (SEQ ID NO: 604) | OBD117.1.199 |
| 49 | 31320660 | 31324659 | OBD117.1.789 | TCTTCCAAGCATGGAGTGGG (SEQ ID NO: 605) | OBD117.1.791 |
| 50 | 31331188 | 31335187 | OBD117.1.309 | CTGGGTGCCCTTGACATTAGCGT (SEQ ID NO: 606) | OBD117.1.311 |
| 51 | 31348362 | 31352361 | OBD117.1.937 | CCTGTCTTCCTCTTTGCTGAG CC (SEQ ID NO: 607) | OBD117.1.939 |
| 52 | 31348362 | 31352361 | OBD117.1.369 | CCTGTCTTCCTCTTTGCTGAGCC (SEQ ID NO: 608) | OBD117.1.371 |

TABLE 13.a7

| | Inner_primers | |
|---|---|---|
| | PCR_Primer2 | GLMNET |
| 1 | TGGCAGATGAGGTACCAGGA (SEQ ID NO: 609) | 0.000126471 |
| 2 | TCTGCTGTAAGGGACTGCCTCCT (SEQ ID NO: 610) | 0 |
| 3 | GGTGCAGGAAAAACGAACAT (SEQ ID NO: 611) | -0.0000963 |
| 4 | TTTCCGCCTCCAGCCCCTCATTC (SEQ ID NO: 612) | -0.012797314 |
| 5 | GGCAAAACCCTAACGCCAATCTTCAG (SEQ ID NO: 613) | -0.001049357 |
| 6 | CCCTGAGAACCCATTAGTCC (SEQ ID NO: 614) | 0.000120571 |
| 7 | ATTTGTGTGGTTGCAAGGGC (SEQ ID NO: 615) | -0.003603391 |
| 8 | TCCTGCCTCAGCCTCCCAAGTAG (SEQ ID NO: 616) | 0 |
| 9 | GCCTGTCGTGATGCTGATGTCCA (SEQ ID NO: 617) | -0.002344366 |
| 10 | CGCAATCAGAACCAACTGGC (SEQ ID NO: 618) | -0.015124118 |
| 11 | CCAGAAGTCCCAGGTTGTGTCCT (SEQ ID NO: 619) | 0.003583466 |

TABLE 13.a7-continued

| | Inner_primers | |
|---|---|---|
| | PCR_Primer2 | GLMNET |
| 12 | GTGGAGAATGTAGTATTATGAAGGTT (SEQ ID NO: 620) | 0 |
| 13 | TCAACGCTCAGCTCACACTT (SEQ ID NO: 621) | 0.000119448 |
| 14 | CCAAAGGAGGAGACCAGCATTGC (SEQ ID NO: 622) | 0.007257883 |
| 15 | TGCAGCCGTAAGAGAGGAAT (SEQ ID NO: 623) | −0.007336559 |
| 16 | GCTTTATGCCTCCTCCAGCCAGG (SEQ ID NO: 624) | 0.013413486 |
| 17 | CCCCAGGGAGAAGTCTGATTCCT (SEQ ID NO: 625) | −0.020821569 |
| 18 | CTTACCTGAAAAGGCTGGCTGGG (SEQ ID NO: 626) | 0.017522073 |
| 19 | TAGGAGGAGCGGTCTTACAGGCAGA (SEQ ID NO: 627) | 0.000137163 |
| 20 | TAGGAGGAGCGGTCTTACAGGCA (SEQ ID NO: 628) | −0.009581325 |
| 21 | TGTGATGCTTCCCACTGCTCTGATAG (SEQ ID NO: 629) | −0.003930475 |
| 22 | GTGAGGCTCTGGGTGAAGGTGCT (SEQ ID NO: 630) | −0.013038403 |
| 23 | CTCCCCTTATTGCTCCCCAC (SEQ ID NO: 631) | −0.009743329 |
| 24 | CGGTGTCCTGAGTCCCTGGCAAT (SEQ ID NO: 632) | −0.015977346 |
| 25 | GAAGGAAGAGACTCAGGACTGGC (SEQ ID NO: 633) | 0 |
| 26 | TGTGCCCAGCAAAACCAGTGAGC (SEQ ID NO: 634) | −0.00783453 |
| 27 | GTCCCCAGGTAATGGAGCGAAGC (SEQ ID NO: 635) | 0.01716512 |
| 28 | GAAGGAAGAGACTCAGGACTGGC (SEQ ID NO: 636) | 0 |
| 29 | CAAGACCTCCCCAACTTCCCAGG (SEQ ID NO: 637) | −0.016360123 |
| 30 | CCCAGGTTGAACTACAGCAGAAGCCT (SEQ ID NO: 638) | −0.006985618 |
| 31 | GGTTCTAAGGAGAGTTGTAAAGAGAG (SEQ ID NO: 639) | −0.00011137 |
| 32 | CGCCACCTCGTAGTTGTGTCTGC (SEQ ID NO: 640) | 0.001576194 |
| 33 | CAGCGGCACTTTGTCTTCAGGAG (SEQ ID NO: 641) | −0.010502797 |
| 34 | CTCCGGAGGATTTCTGTGAA (SEQ ID NO: 642) | −0.008978891 |
| 35 | CAGGGGCTCTTCTTTCAGC (SEQ ID NO: 643) | 0.00011913 |
| 36 | CCAGGCCAGCTTCAAACTC (SEQ ID NO: 644) | 0.000123838 |
| 37 | TGGAGATGCTGCTCTGCCCACCT (SEQ ID NO: 645) | −0.003994085 |
| 38 | CACAGCCCTTGGCATCACCCACA (SEQ ID NO: 646) | −0.023515041 |
| 39 | TGTGGGAACCATACCTGTGC (SEQ ID NO: 647) | 0.01434467 |
| 40 | CGTTGCCTCCTCACAGCAGAAGC (SEQ ID NO: 648) | −0.001425541 |
| 41 | GTCCTGGGTCCTGGGTGAAAGTC (SEQ ID NO: 649) | 0.01710902 |
| 42 | GGGAGACCATTTCTGTTCACTCTGAG (SEQ ID NO: 650) | −0.0134076 |
| 43 | CTAAACCCTGGAACCAAAACTCATCC (SEQ ID NO: 651) | 0 |
| 44 | TGTAAATTGCCGCAGGGGAA (SEQ ID NO: 652) | 0.006327654 |
| 45 | GGCACTCACACACGAGAAAA (SEQ ID NO: 653) | 0.000121603 |
| 46 | ATCAGGATCAGGCTTCAAGG (SEQ ID NO: 654) | 0.000116599 |
| 47 | GGCTTGATCTCTGGACGAAG (SEQ ID NO: 655) | 0 |
| 48 | GTCCACCCCATTGCCGCTTTTCA (SEQ ID NO: 656) | 0.018616515 |
| 49 | CTGCAGGTTGGTGCTGAGT (SEQ ID NO: 657) | −0.01814247 |

TABLE 13.a7-continued

| | Inner primers | |
|---|---|---|
| | PCR_Primer2 | GLMNET |
| 50 | GCCACCCTCCCTAAGAGACTGAG (SEQ ID NO: 658) | -0.010425 |
| 51 | GCCACCCTCCCTAAGAGACTGAG (SEQ ID NO: 659) | 0 |
| 52 | GCCACCCTCCCTAAGAGACTGAG (SEQ ID NO: 660) | 0.00590703 |

TABLE 13.b1

| | Probe | GeneLocus | Probe_Count_Total | Probe_Count_Sig |
|---|---|---|---|---|
| 53 | ITK_5_157178319_157181048_157266725_157271762_FR | ITK | 26 | 10 |
| 54 | ITK_5_157178319_157181048_157266725_157271762_RR | ITK | 26 | 10 |
| 55 | ITK_5_157225228_157231430_157263646_157266576_FR | ITK | 26 | 10 |
| 56 | ITK_5_157225228_157231430_157266725_157271762_FR | ITK | 26 | 10 |
| 57 | ITK_5_157249288_157254103_157266725_157271762_RR | ITK | 26 | 10 |
| 58 | LYN_8_55939615_55941582_55961822_55966587_RR | LYN | 48 | 2 |
| 59 | MAPKAP1_9_125549822_125553339_125631239_125635100_RF | MAPKAP1 | 52 | 6 |
| 60 | MTOR_1_11162452_11169997_11281372_11283081_FR | MTOR | 60 | 4 |
| 61 | MYC_8_127691489_127694045_127732337_127733526_FF | MYC | 42 | 4 |
| 62 | MYC_8_127691489_127694045_127738939_127740424_FR | MYC | 42 | 4 |
| 63 | NCK2_2_105715815_105716905_105886459_105893355_FR | NCK2 | 66 | 4 |
| 64 | NFKBIE_6_44253666_44257911_44307667_44312139_RF | NFKBIE | 44 | 4 |
| 65 | NFKBIE_6_44270723_44274914_44307667_44312139_RF | NFKBIE | 44 | 4 |
| 66 | ORF102_17_34316073_34325822_34367538_34373948_RF | ORF102 | 11 | 1 |
| 67 | ORF104_17_36075902_36084513_36095759_36100192_FR | CCL18 | 42 | 8 |
| 68 | ORF107_6_41947755_41951350_42050648_42055406_RF | ORF107 | 6 | 1 |
| 69 | ORF108_6_167109295_167112439_167149742_167154610_FF | CCR6 | 46 | 4 |
| 70 | ORF110_3_46429853_46436496_46457806_46461162_RR | ORF110 | 23 | 0 |
| 71 | ORF113_5_67178844_67182260_67233989_67237362_FR | CD180 | 38 | 4 |
| 72 | ORF114_16_28959098_28963335_28975508_28978445_RF | CD19 | 56 | 4 |
| 73 | ORF116_3_112306429_112316088_112398394_112403968_RR | ORF116 | 58 | 3 |
| 74 | ORF117_19_35294083_35295665_35307063_35310549_FF | ORF117 | 27 | 1 |
| 75 | ORF118_18_69825656_69827597_69936161_69945341_RR | ORF118 | 86 | 5 |
| 76 | ORF120_9_5422951_5431331_5460319_5468105_RR | ORF120 | 29 | 2 |
| 77 | ORF120_9_5422951_5431331_5512277_5514690_FR | ORF120 | 29 | 2 |
| 78 | ORF128_11_61068642_61071684_61139962_61143879_RR | ORF128 | 27 | 1 |
| 79 | ORF130_11_60938640_60941215_60977084_60983727_RF | CD6 | 56 | 14 |
| 80 | ORF130_11_60938640_60941215_61017867_61025585_RF | CD6 | 56 | 14 |
| 81 | ORF130_11_60977084_60983727_60996251_60998956_FR | CD6 | 56 | 14 |
| 82 | ORF136_6_14070076_14075830_14126334_14131467_FF | ORF136 | 28 | 9 |
| 83 | ORF136_6_14083566_14087253_14136228_14137347_FR | ORF136 | 28 | 9 |
| 84 | ORF138_3_122014664_122021863_122097537_122100802_RF | CD86 | 46 | 2 |
| 85 | ORF139_5_131244508_131249689_131303538_131314316_FR | ORF139 | 69 | 2 |
| 86 | ORF140_7_90713266_90719769_90855907_90868783_FF | ORF140 | 174 | 48 |
| 87 | ORF140_7_90855907_90868783_90936378_90943000_FF | ORF140 | 174 | 48 |
| 88 | ORF140_7_90855907_90868783_90994572_90999177_FR | ORF140 | 174 | 48 |
| 89 | ORF140_7_90855907_90868783_91103050_91110422_FF | ORF140 | 174 | 48 |
| 90 | ORF140_7_90936378_90943000_91140859_91158297_RF | ORF140 | 174 | 48 |
| 91 | ORF142_6_36654202_36659227_36691067_36693657_RF | ORF142 | 31 | 3 |
| 92 | ORF142_6_36684519_36687230_36719341_36723631_RR | ORF142 | 31 | 3 |
| 93 | ORF142_6_36691067_36693657_36719341_36723631_FR | ORF142 | 31 | 3 |
| 94 | ORF145_6_4826110_4834568_4928803_4930806_RF | ORF145 | 38 | 4 |
| 95 | ORF146_10_11274452_11277542_11303118_11312162_RR | ORF146 | 188 | 11 |
| 96 | ORF147_2_168472568_168475902_168685690_168692951_RF | ORF147 | 182 | 25 |
| 97 | ORF149_X_47581313_47587657_47613512_47618008_FF | ORF149 | 23 | 15 |
| 98 | ORF149_X_47581313_47587657_47636868_47644403_FR | ORF149 | 23 | 15 |
| 99 | ORF149_X_47581313_47587657_47636868_47644403_RR | ORF149 | 23 | 15 |
| 100 | ORF149_X_47581313_47587657_47652990_47657846_FF | ORF149 | 23 | 15 |
| 101 | ORF149_X_47581313_47587657_47652990_47657846_FR | ORF149 | 23 | 15 |
| 102 | ORF149_X_47581313_47587657_47672279_47679605_FR | ORF149 | 23 | 15 |
| 103 | ORF149_X_47599663_47605051_47636868_47644403_FR | ORF149 | 23 | 0 |
| 104 | ORF149_X_47613512_47618008_47636868_47644403_FF | ORF149 | 23 | 15 |

TABLE 13.b2

| | HyperG_Stats | FDR_HyperG | Percent_Sig | logFC | AveExpr | t |
|---|---|---|---|---|---|---|
| 53 | 1.57E-05 | 0.002607465 | 38.46 | -0.17535973 | -0.17535973 | -7.936893754 |
| 54 | 1.57E-05 | 0.002607465 | 38.46 | -0.204619133 | -0.204619133 | -9.041273175 |
| 55 | 1.57E-05 | 0.002607465 | 38.46 | -0.226854713 | -0.226854713 | -7.188770374 |
| 56 | 1.57E-05 | 0.002607465 | 38.46 | -0.144955613 | -0.144955613 | -8.636856152 |

TABLE 13.b2-continued

| | HyperG_Stats | FDR_HyperG | Percent_Sig | logFC | AveExpr | t |
|---|---|---|---|---|---|---|
| 57 | 1.57E−05 | 0.002607465 | 38.46 | −0.191450511 | −0.191450511 | −6.961093779 |
| 58 | 0.903339407 | 0.99999793 | 4.17 | −0.237388831 | −0.237388831 | −9.072038739 |
| 59 | 0.229017635 | 0.99999793 | 11.54 | −0.208545117 | −0.208545117 | −7.711401904 |
| 60 | 0.711822793 | 0.99999793 | 6.67 | −0.206498971 | −0.206498971 | −2.697141397 |
| 61 | 0.430324418 | 0.99999793 | 9.52 | −0.204707302 | −0.204707302 | −8.414783357 |
| 62 | 0.430324418 | 0.99999793 | 9.52 | −0.186601169 | −0.186601169 | −8.01397424 |
| 63 | 0.779227696 | 0.99999793 | 6.06 | −0.14004291 | −0.14004291 | −6.51116257 |
| 64 | 0.466402982 | 0.99999793 | 9.09 | −0.195945166 | −0.195945166 | −9.511762166 |
| 65 | 0.466402982 | 0.99999793 | 9.09 | −0.293579626 | −0.293579626 | −14.68901883 |
| 66 | 0.511527165 | 1 | 9.09 | 0.2840641 | 0.2840641 | 6.643829188 |
| 67 | 0.016095432 | 0.256971894 | 19.05 | −0.291933406 | −0.291933406 | −10.89682004 |
| 68 | 0.352766908 | 1 | 16.67 | −0.242419598 | −0.242419598 | −10.57460987 |
| 69 | 0.501622356 | 0.99999793 | 8.7 | −0.14391148 | −0.14391148 | −7.030078326 |
| 70 | 1 | 1 | 0 | −0.362268923 | −0.362268923 | −16.68456661 |
| 71 | 0.356577228 | 0.99999793 | 10.53 | −0.176986579 | −0.176986579 | −9.75949409 |
| 72 | 0.659150649 | 0.99999793 | 7.14 | −0.295598703 | −0.295598703 | −10.15502575 |
| 73 | 0.716692043 | 1 | 5.17 | 0.602056594 | 0.602056594 | 15.84030024 |
| 74 | 0.858892218 | 1 | 3.7 | −0.186844857 | −0.186844857 | −7.153732488 |
| 75 | 0.637873022 | 1 | 5.81 | 0.289045633 | 0.289045633 | 7.422638917 |
| 76 | 0.582184628 | 1 | 6.9 | 0.184678337 | 0.184678337 | 10.5440004 |
| 77 | 0.582184628 | 1 | 6.9 | 0.167067809 | 0.167067809 | 6.795574962 |
| 78 | 0.843487021 | 1 | 3.7 | 0.147449655 | 0.147449655 | 5.62371066 |
| 79 | 9.03E−05 | 0.005970563 | 25 | −0.262767321 | −0.262767321 | −9.763551812 |
| 80 | 9.03E−05 | 0.005970563 | 25 | −0.24505568 | −0.24505568 | −9.532818868 |
| 81 | 9.03E−05 | 0.005970563 | 25 | −0.143973167 | −0.143973167 | −8.04914211 |
| 82 | 3.57E−05 | 0.00197047 | 32.14 | 0.304730566 | 0.304730566 | 7.972556939 |
| 83 | 3.57E−05 | 0.00197047 | 32.14 | 0.45046821 | 0.45046821 | 8.040999966 |
| 84 | 0.889742685 | 0.99999793 | 4.35 | −0.17550915 | −0.17550915 | −7.944299089 |
| 85 | 0.937060046 | 1 | 2.9 | 0.337466811 | 0.337466811 | 7.122034666 |
| 86 | 1.33E−18 | 6.25E−16 | 27.59 | 0.299560844 | 0.299560844 | 7.349855302 |
| 87 | 1.33E−18 | 6.25E−16 | 27.59 | 0.376066641 | 0.376066641 | 11.18729546 |
| 88 | 1.33E−18 | 6.25E−16 | 27.59 | 0.328115734 | 0.328115734 | 8.388709848 |
| 89 | 1.33E−18 | 6.25E−16 | 27.59 | 0.426278456 | 0.426278456 | 9.130196924 |
| 90 | 1.33E−18 | 6.25E−16 | 27.59 | 0.290736601 | 0.290736601 | 14.83391512 |
| 91 | 0.370280429 | 1 | 9.68 | −0.157021793 | −0.157021793 | −5.367709243 |
| 92 | 0.370280429 | 1 | 9.68 | −0.155240529 | −0.155240529 | −6.981397089 |
| 93 | 0.370280429 | 1 | 9.68 | −0.165320069 | −0.165320069 | −6.491602168 |
| 94 | 0.216095329 | 1 | 10.53 | 0.357099569 | 0.357099569 | 3.100523963 |
| 95 | 0.644185758 | 1 | 5.85 | 0.350492829 | 0.350492829 | 2.971293917 |
| 96 | 0.000206728 | 0.007220151 | 13.74 | 0.313589664 | 0.313589664 | 9.144161779 |
| 97 | 1.30E−12 | 6.11E−10 | 65.22 | −0.325788697 | −0.325788697 | −3.268992003 |
| 98 | 1.30E−12 | 6.11E−10 | 65.22 | −0.184978686 | −0.184978686 | −3.038398575 |
| 99 | 1.30E−12 | 6.11E−10 | 65.22 | −0.140733478 | −0.140733478 | −2.92069017 |
| 100 | 1.30E−12 | 6.11E−10 | 65.22 | −0.317936544 | −0.317936544 | −3.193281824 |
| 101 | 1.30E−12 | 6.11E−10 | 65.22 | −0.392260745 | −0.392260745 | −3.656585798 |
| 102 | 1.30E−12 | 6.11E−10 | 65.22 | −0.213145814 | −0.213145814 | −3.009155124 |
| 103 | 1 | 1 | 0 | −0.146041724 | −0.146041724 | −4.02292989 |
| 104 | 1.30E−12 | 6.11E−10 | 65.22 | −0.222139537 | −0.222139537 | −5.68201205 |

TABLE 13.b3

| | P. Value | adj. P. Val | B | FC | FC_1 | LS |
|---|---|---|---|---|---|---|
| 53 | 0.0000109 | 0.000300885 | 3.734715272 | 0.885546684 | −1.129245942 | −1 |
| 54 | 0.00000334 | 0.000153695 | 4.950834477 | 0.867767745 | −1.152382081 | −1 |
| 55 | 0.000026 | 0.000519842 | 2.830950394 | 0.854495789 | −1.170280782 | −1 |
| 56 | 0.00000508 | 0.000194036 | 4.520831371 | 0.904407203 | −1.105696634 | −1 |
| 57 | 0.0000344 | 0.000618186 | 2.541955486 | 0.87574481 | −1.141911236 | −1 |
| 58 | 0.00000324 | 0.000150461 | 4.982857006 | 0.848279245 | −1.178857087 | −1 |
| 59 | 0.0000141 | 0.000355136 | 3.469495184 | 0.865409512 | −1.155522312 | −1 |
| 60 | 0.02197855 | 0.058573399 | −4.108873892 | 0.866637776 | −1.153884619 | −1 |
| 61 | 0.00000643 | 0.000223311 | 4.277331934 | 0.867714714 | −1.15245251 | −1 |
| 62 | 0.00000998 | 0.000286168 | 3.824002229 | 0.878673343 | −1.138079365 | −1 |
| 63 | 0.0000607 | 0.0008901 | 1.95067007 | 0.907492164 | −1.10193789 | 1 |
| 64 | 0.00000209 | 0.000119285 | 5.430299258 | 0.873000772 | −1.14547436 | −1 |
| 65 | 0.0000000324 | 0.000158 | 9.557329978 | 0.815875189 | −1.225677668 | −1 |
| 66 | 0.0000512 | 0.000797045 | 2.127853229 | 1.217620117 | 1.217620117 | −1 |
| 67 | 0.000000583 | 0.0000632 | 6.724276277 | 0.816806693 | −1.224279879 | −1 |
| 68 | 0.000000774 | 0.0000716 | 6.437875016 | 0.845326394 | −1.18297501 | −1 |
| 69 | 0.0000316 | 0.000584325 | 2.630230616 | 0.905061993 | −1.104896689 | −1 |
| 70 | 0.0000000092 | 0.0000107 | 10.73453386 | 0.777940153 | −1.285445926 | −1 |
| 71 | 0.00000165 | 0.000106067 | 5.674210448 | 0.884548664 | −1.13052005 | −1 |
| 72 | 0.00000113 | 0.0000855 | 6.052012506 | 0.814734156 | −1.227394227 | −1 |
| 73 | 0.0000000154 | 0.0000115 | 10.25824114 | 1.517878795 | 1.517878795 | 1 |
| 74 | 0.0000272 | 0.00053455 | 2.786912756 | 0.878524937 | −1.138271616 | −1 |

TABLE 13.b3-continued

|  | P. Value | adj. P. Val | B | FC | FC_1 | LS |
|---|---|---|---|---|---|---|
| 75 | 0.0000197 | 0.000439652 | 3.120890546 | 1.221831748 | 1.221831748 | 1 |
| 76 | 0.000000796 | 0.0000726 | 6.410227046 | 1.136563537 | 1.136563537 | 1 |
| 77 | 0.0000423 | 0.00070501 | 2.327593259 | 1.122774193 | 1.122774193 | 1 |
| 78 | 0.00020132 | 0.001977662 | 0.70216959 | 1.107609748 | 1.107609748 | 1 |
| 79 | 0.00000164 | 0.000106067 | 5.678158075 | 0.833487622 | −1.199777866 | −1 |
| 80 | 0.00000205 | 0.000117891 | 5.451255469 | 0.84378323 | −1.18513851 | −1 |
| 81 | 0.0000096 | 0.000278481 | 3.864510034 | 0.905023296 | −1.104943933 | −1 |
| 82 | 0.0000105 | 0.000294144 | 3.776112142 | 1.235187935 | 1.235187935 | 1 |
| 83 | 0.00000969 | 0.000280237 | 3.855144299 | 1.366483661 | 1.366483661 | 1 |
| 84 | 0.0000108 | 0.000298984 | 3.743323414 | 0.885454973 | −1.129362905 | −1 |
| 85 | 0.0000282 | 0.00054663 | 2.746937043 | 1.263536036 | 1.263536036 | 1 |
| 86 | 0.0000215 | 0.000464107 | 3.031396559 | 1.230769711 | 1.230769711 | 1 |
| 87 | 0.000000454 | 0.0000563 | 6.975413589 | 1.297798713 | 1.297798713 | 1 |
| 88 | 0.00000662 | 0.000226164 | 4.248389692 | 1.255372694 | 1.255372694 | 1 |
| 89 | 0.00000305 | 0.000145428 | 5.043130801 | 1.343762761 | 1.343762761 | 1 |
| 90 | 0.0000000294 | 0.0000153 | 9.64902897 | 1.223264684 | 1.223264684 | 1 |
| 91 | 0.000290264 | 0.002534245 | 0.32110467 | 0.896874612 | −1.114983061 | −1 |
| 92 | 0.0000335 | 0.000609191 | 2.568001061 | 0.897982647 | −1.113607265 | −1 |
| 93 | 0.0000623 | 0.000903821 | 1.924342502 | 0.891730663 | −1.121414842 | −1 |
| 94 | 0.010931496 | 0.034736273 | −3.41285233 | 1.280848257 | 1.280848257 | 1 |
| 95 | 0.013665308 | 0.041030377 | −3.636678978 | 1.274996095 | 1.274996095 | 1 |
| 96 | 0.00000301 | 0.000144884 | 5.057553149 | 1.242796139 | 1.242796139 | 1 |
| 97 | 0.008183105 | 0.027939057 | −3.120846211 | 0.797862089 | −1.253349437 | −1 |
| 98 | 0.012168576 | 0.037672866 | −3.520502123 | 0.879662072 | −1.136800178 | −1 |
| 99 | 0.014916282 | 0.043846027 | −3.724182352 | 0.907057882 | −1.102465476 | −1 |
| 100 | 0.009318298 | 0.030820985 | −3.252058133 | 0.80221645 | −1.246546365 | −1 |
| 101 | 0.004239872 | 0.0171443 | −2.452133159 | 0.761934695 | −1.312448438 | −1 |
| 102 | 0.012799247 | 0.039057427 | −3.571146947 | 0.862654151 | −1.159213108 | −1 |
| 103 | 0.002310795 | 0.010964378 | −1.829468152 | 0.90372659 | −1.106529354 | −1 |
| 104 | 0.000185463 | 0.001878108 | 0.787632865 | 0.857293116 | −1.166462184 | −1 |

TABLE 13.b4

|  | Loop detected | Probe sequence 60 mer |
|---|---|---|
| 53 | PD-L1 responder | ATCCCAACAAAAGAGAAGAACTTCTCCCTCGATGTTTGGGGGCGGAGGGCTTTGATGAGA (SEQ ID NO: 661) |
| 54 | PD-L1 responder | CAAAATCAAACACAAATCTAATCAAACTTCGATGTTTGGGGGCGGAGGGCTTTGATGAGA (SEQ ID NO: 662) |
| 55 | PD-L1 responder | GGCCGCGAGCCCGGCAGCGGCGACATCCTCGAGAAATTCTCCCGCTTTAGCCTCCCAAAG (SEQ ID NO: 663) |
| 56 | PD-L1 responder | TGAGATGAAGCCTATATTTTCCCAATCCTCGATGTTTGGGGGCGGAGGGCTTTGATGAGA (SEQ ID NO: 664) |
| 57 | PD-L1 responder | TACAGACTTTTTTTCTCTTCTCAGAAAATCGATGTTTGGGGGCGGAGGGCTTTGATGAGA (SEQ ID NO: 665) |
| 58 | PD-L1 responder | GCGGCCAACCCACAGCGCACCGGGCCGCTCGACCTCTGAGAGGAAACTTGCTAGCCCCAG (SEQ ID NO: 666) |
| 59 | PD-L1 responder | CACTAATCTTTACTCTTTTTCCACTTATTCGACCCTCCCCTTCCAGCTGGGCACAGGTGG (SEQ ID NO: 667) |
| 60 | PD-L1 responder | ATTCCCAATGTTTCCTGAGTAGAACTGTTCGACTGCGAGCTCCCTCCCTGCAGTCAGGGA (SEQ ID NO: 668) |
| 61 | PD-L1 responder | AGGGAGAACAAAAGAAGTTCCATCCATCTCGATCCCCCCGGGCTCAAAGCAAACCTCCTA (SEQ ID NO: 669) |
| 62 | PD-L1 responder | AGGGAGAACAAAAGAAGTTCCATCCATCTCGACGGAGTCCTCCCCGCAGGGCAGCCCCGA (SEQ ID NO: 670) |
| 63 | PD-L1 responder | TATTTGTATCCTTTCCTCATTTATTTACTCGAATCTCTGGGGTAGGGCTCTGCAACCTTG (SEQ ID NO: 671) |
| 64 | PD-L1 responder | TTTCAAAGAAGGTATGATGGGAAAGGTCTCGAGTGCCCCTGTCCCACCTGGCTCCCCCTG (SEQ ID NO: 672) |
| 65 | PD-L1 responder | TTTCAAAGAAGGTATGATGGGAAAGGTCTCGACGCGCCCCCTCTACGCCATGTCCCCCCC (SEQ ID NO: 673) |

TABLE 13.b4-continued

| | Loop detected | Probe sequence 60 mer |
|---|---|---|
| 66 | PD-L1 Non-responder | ATATAAATCTACTTTATAAATAAGGAAATCGAAGTATAATTCAATATACTGTCCAGTAAA (SEQ ID NO: 674) |
| 67 | PD-L1 responder | TCCAGCCTTGCCTGGAGCTAGGGCCACCTCGATCTTGGCTCACCGCAACCTTGGCCTCCC (SEQ ID NO: 675) |
| 68 | PD-L1 responder | CTGTGAACATTGGTGTACTAGTAGCTTTTCGATTTCCACTTCTACCCCCCGGTCCGAGTT (SEQ ID NO: 676) |
| 69 | PD-L1 responder | CCATCTGCAAGTCGCTTTTGACTAGCACTCGAGTTCTTTCTGACATCTCCTGGGTGGAGC (SEQ ID NO: 677) |
| 70 | PD-L1 responder | GTGGATTACATCCTTCTATAGGTGTGGCTCGAGCGGAGTCACCCAGGCTGGAGTGCAGTG (SEQ ID NO: 678) |
| 71 | PD-L1 responder | GACCTAAGGATTAAGAAGATTAATGGAGTCGAGCATCCTCTACCTCTATCTCCAACCCCT (SEQ ID NO: 679) |
| 72 | PD-L1 responder | CCTGCACTTCCTCACGCCTGCTCACCCCTCGAGTGAGTGGGAGAGATGGCTCTCCACGCC (SEQ ID NO: 680) |
| 73 | PD-L1 Non-responder | TATATAATTTCCACTTTGTTTTTAATAATCGAAATTAAAAATTATTTTATCTCACATAGA (SEQ ID NO: 681) |
| 74 | PD-L1 responder | GCCTGGATGCCCTCGTCCATCTCGGCCTTCGATCTGAGGACAGAAAAGACCCAGGCGCCC (SEQ ID NO: 682) |
| 75 | PD-L1 Non-responder | TTAAATCTTGAATAGAAGTTATGATTGATCGATTATTGAATTCAATTGTGTATATAAATT (SEQ ID NO: 683) |
| 76 | PD-L1 Non-responder | TATTAAGAAAATAAGTCAGCCAGGTGTTTCGAGTACTACTACAATTAGCACTTGCTTATT (SEQ ID NO: 684) |
| 77 | PD-L1 Non-responder | GGCCAGTAGATCATTTGAGGCCAGGAGTTCGATAACCTTCAAATCAACTCACAGAATTCC (SEQ ID NO: 685) |
| 78 | PD-L1 Non-responder | TGGGAGGTGGCCAGAGTCTGACTACATCTCGAACTACTGGGCTCAAACAATTCTCCTGCC (SEQ ID NO: 686) |
| 79 | PD-L1 responder | TTAATGCTGATACAATTCTATTGGATAATCGACACTTCGGCTCCCTGCACCTCCCATGCC (SEQ ID NO: 687) |
| 80 | PD-L1 responder | CAATATGACGGTGACATTAATGATAGCTTCGACACTTCGGCTCCCTGCACCTCCCATGCC (SEQ ID NO: 688) |
| 81 | PD-L1 responder | TTAATGCTGATACAATTCTATTGGATAATCGACGTGCCTTGGGGCCTCCCCTTTCCCTAT (SEQ ID NO: 689) |
| 82 | PD-L1 Non-responder | AATAAAAATAGAAAACAATCCTTCAAAATCGACACCAATGTTTCCATTTTGTTTTCAGAA (SEQ ID NO: 690) |
| 83 | PD-L1 Non-responder | AATGATTAAATGTGTACCTTAATGAGTTTCGAAACTCCATTGAGTCATTATCCTTGCTAT (SEQ ID NO: 691) |
| 84 | PD-L1 responder | CATCATAGCAACCCATTGTAACTAGACTTCGAATAGATACTTCAGGAAAGAAATGTATAT (SEQ ID NO: 692) |
| 85 | PD-L1 Non-responder | AGACAATATTAAAATTGAGAACTTTTGTTCGATTTTATTTTTAACTTATAAGAAGATCTG (SEQ ID NO: 693) |
| 86 | PD-L1 Non-responder | TGTGATGATTTCTTCTTTTTATATGTTTTCGATAAAATACTTCATAAAAATAACATGCTA (SEQ ID NO: 694) |
| 87 | PD-L1 Non-responder | TAGCATGTTATTTTTATGAAGTATTTTATCGACAGTTTTTTTAAAAAAAAACCTTGACA (SEQ ID NO: 695) |
| 88 | PD-L1 Non-responder | TAGCATGTTATTTTTATGAAGTATTTTATCGAGCTGATAAACAGCTTTGTAGGGAAAAAC (SEQ ID NO: 696) |
| 89 | PD-L1 Non-responder | TAGCATGTTATTTTTATGAAGTATTTTATCGAAGAATTATAAACACTTATAGTTGTATCT (SEQ ID NO: 697) |
| 90 | PD-L1 Non-responder | AGTGGTGCAATCTTGACTCACTGCAGTCTCGAAATCTAGTAACATCATATTCTAACATGA (SEQ ID NO: 698) |
| 91 | PD-L1 responder | GGCCTCGGCACTCACCGTTCCCTCCCCCTCGATTTCCATGAGCCCCTCTGAATCCTTCCA (SEQ ID NO: 699) |

TABLE 13.b4-continued

| | Loop detected | Probe sequence 60 mer |
|---|---|---|
| 92 | PD-L1 responder | CACCTGTCATGCTGGTCTGCCGCCGTTTTCGAGGCAGGCCCCTCCTGCCAAGTGAAGAGA (SEQ ID NO: 700) |
| 93 | PD-L1 responder | GGCCTCGGCACTCACCGTTCCCTCCCCCTCGAGGCAGGCCCCTCCTGCCAAGTGAAGAGA (SEQ ID NO: 701) |
| 94 | PD-L1 Non-responder | GAGATACTAAAATAGGTTTCTTTCCTAGTCGACTAGGATCAGTTGTTTGTAGGATTATAA (SEQ ID NO: 702) |
| 95 | PD-L1 Non-responder | AACTCACAACTATCTGGTGCTATGTACATCGAACTAAAATCTGCCTCTGAACAGCTTCCA (SEQ ID NO: 703) |
| 96 | PD-L1 Non-responder | ATCTTTAGCATATATGTTAAATTGATAATCGAATTTAATAAAGAAATTACTGAAAAGGA (SEQ ID NO: 704) |
| 97 | PD-L1 responder | CCCCTCACCCAAACTAGGGTCTCTAGACTCGAGCTCCCATAGATCAACTTTCTGCACTCC (SEQ ID NO: 705) |
| 98 | PD-L1 responder | CCCCTCACCCAAACTAGGGTCTCTAGACTCGAGAGGCCATCCACGCTGATAGAAGGGATG (SEQ ID NO: 706) |
| 99 | PD-L1 responder | CCCTGGGGTTCTGATTAACATCCTTAATTCGAGAGGCCATCCACGCTGATAGAAGGGATG (SEQ ID NO: 707) |
| 100 | PD-L1 responder | CCCCTCACCCAAACTAGGGTCTCTAGACTCGAGACAAGGTATATGAGCAGCTGGCCAAAT SEQ ID NO: 708) |
| 101 | PD-L1 responder | CCCTGGGGTTCTGATTAACATCCTTAATTCGAAGAATGCCTAATGGTTAAGCAGTAGGAA (SEQ ID NO: 709) |
| 102 | PD-L1 responder | CCCCTCACCCAAACTAGGGTCTCTAGACTCGAGGCCCAAGGGCTTGTCAGTCAGCTTGTG (SEQ ID NO: 710) |
| 103 | PD-L1 responder | ATTCTTCTGTCCCCAGTTTCTTATGCAGTCGAGAGGCCATCCACGCTGATAGAAGGGATG (SEQ ID NO: 711) |
| 104 | PD-L1 responder | GGAGTGCAGAAAGTTGATCTATGGGAGCTCGACTGTATCCGCAGCACCTGGCCCACAGTA (SEQ ID NO: 712) |

TABLE 13.b5

| | Probe Location | | | | | 4 kb Sequence Location | | |
|---|---|---|---|---|---|---|---|---|
| | Chr | Start1 | End1 | Start2 | End2 | Chr | Start1 | End1 |
| 53 | 5 | 157181019 | 157181048 | 157266725 | 157266754 | 5 | 157177049 | 157181048 |
| 54 | 5 | 157178319 | 157178348 | 157266725 | 157266754 | 5 | 157178319 | 157182318 |
| 55 | 5 | 157225228 | 157225257 | 157266547 | 157266576 | 5 | 157225228 | 157229227 |
| 56 | 5 | 157231401 | 157231430 | 157266725 | 157266754 | 5 | 157227431 | 157231430 |
| 57 | 5 | 157249288 | 157249317 | 157266725 | 157266754 | 5 | 157249288 | 157253287 |
| 58 | 8 | 55939615 | 55939644 | 55961822 | 55961851 | 8 | 55939615 | 55943614 |
| 59 | 9 | 125549822 | 125549851 | 125635071 | 125635100 | 9 | 125549822 | 125553821 |
| 60 | 1 | 11169968 | 11169997 | 11281372 | 11281401 | 1 | 11165998 | 11169997 |
| 61 | 8 | 127694016 | 127694045 | 127733497 | 127733526 | 8 | 127690046 | 127694045 |
| 62 | 8 | 127694016 | 127694045 | 127738939 | 127738968 | 8 | 127690046 | 127694045 |
| 63 | 2 | 105716876 | 105716905 | 105886459 | 105886488 | 2 | 105712906 | 105716905 |
| 64 | 6 | 44253666 | 44253695 | 44312110 | 44312139 | 6 | 44253666 | 44257665 |
| 65 | 6 | 44270723 | 44270752 | 44312110 | 44312139 | 6 | 44270723 | 44274722 |
| 66 | 17 | 34316073 | 34316102 | 34373919 | 34373948 | 17 | 34316073 | 34320072 |
| 67 | 17 | 36084484 | 36084513 | 36095759 | 36095788 | 17 | 36080514 | 36084513 |
| 68 | 6 | 41947755 | 41947784 | 42055377 | 42055406 | 6 | 41947755 | 41951754 |
| 69 | 6 | 167112410 | 167112439 | 167154581 | 167154610 | 6 | 167108440 | 167112439 |
| 70 | 3 | 46429853 | 46429882 | 46457806 | 46457835 | 3 | 46429853 | 46433852 |
| 71 | 5 | 67182231 | 67182260 | 67233989 | 67234018 | 5 | 67178251 | 67182260 |
| 72 | 16 | 28959098 | 28959127 | 28978416 | 28978445 | 16 | 28959098 | 28963097 |
| 73 | 3 | 112306429 | 112306458 | 112398394 | 112398423 | 3 | 112306429 | 112310428 |
| 74 | 19 | 35295636 | 35295665 | 35310520 | 35310549 | 19 | 35291666 | 35295665 |
| 75 | 18 | 69825656 | 69825685 | 69936161 | 69936190 | 18 | 69825656 | 69829655 |
| 76 | 9 | 5422951 | 5422980 | 5460319 | 5460348 | 9 | 5422951 | 5426950 |
| 77 | 9 | 5431302 | 5431331 | 5512277 | 5512306 | 9 | 5427332 | 5431331 |
| 78 | 11 | 61068642 | 61068671 | 61139962 | 61139991 | 11 | 61068642 | 61072641 |
| 79 | 11 | 60938640 | 60938669 | 60983698 | 60983727 | 11 | 60938640 | 60942639 |
| 80 | 11 | 60938640 | 60938669 | 61025556 | 61025585 | 11 | 60938640 | 60942639 |

TABLE 13.b5-continued

|  | Probe Location | | | | 4 kb Sequence Location | | |
|---|---|---|---|---|---|---|---|
|  | Chr | Start1 | End1 | Start2 | End2 | Chr | Start1 | End1 |
| 81 | 11 | 60983698 | 60983727 | 60996251 | 60996280 | 11 | 60979728 | 60983727 |
| 82 | 6 | 14075801 | 14075830 | 14131438 | 14131467 | 6 | 14071831 | 14075830 |
| 83 | 6 | 14087224 | 14087253 | 14136228 | 14136257 | 6 | 14083254 | 14087253 |
| 84 | 3 | 122014664 | 122014693 | 122100773 | 122100802 | 3 | 122014664 | 122018663 |
| 85 | 5 | 131249660 | 131249689 | 131303538 | 131303567 | 5 | 131245690 | 131249689 |
| 86 | 7 | 90719740 | 90719769 | 90868754 | 90868783 | 7 | 90715770 | 90719769 |
| 87 | 7 | 90868754 | 90868783 | 90942971 | 90943000 | 7 | 90864784 | 90868783 |
| 88 | 7 | 90868754 | 90868783 | 90994572 | 90994601 | 7 | 90864784 | 90868783 |
| 89 | 7 | 90868754 | 90868783 | 91110393 | 91110422 | 7 | 90864784 | 90868783 |
| 90 | 7 | 90936378 | 90936407 | 91158268 | 91158297 | 7 | 90936378 | 90940377 |
| 91 | 6 | 36654202 | 36654231 | 36693628 | 36693657 | 6 | 36654202 | 36658201 |
| 92 | 6 | 36684519 | 36684548 | 36719341 | 36719370 | 6 | 36684519 | 36688518 |
| 93 | 6 | 36693628 | 36693657 | 36719341 | 36719370 | 6 | 36689658 | 36693657 |
| 94 | 6 | 4826110 | 4826139 | 4930777 | 4930806 | 6 | 4826110 | 4830109 |
| 95 | 10 | 11274452 | 11274481 | 11303118 | 11303147 | 10 | 11274452 | 11278451 |
| 96 | 2 | 168472568 | 168472597 | 168692922 | 168692951 | 2 | 168472568 | 168476567 |
| 97 | X | 47587628 | 47587657 | 47617979 | 47618008 | X | 47583658 | 47587657 |
| 98 | X | 47587628 | 47587657 | 47636868 | 47636897 | X | 47583658 | 47587657 |
| 99 | X | 47581313 | 47581342 | 47636868 | 47636897 | X | 47581313 | 47585312 |
| 100 | X | 47587628 | 47587657 | 47657817 | 47657846 | X | 47583658 | 47587657 |
| 101 | X | 47581313 | 47581342 | 47652990 | 47653019 | X | 47581313 | 47585312 |
| 102 | X | 47587628 | 47587657 | 47672279 | 47672308 | X | 47583658 | 47587657 |
| 103 | X | 47605022 | 47605051 | 47636868 | 47636897 | X | 47601052 | 47605051 |
| 104 | X | 47617979 | 47618008 | 47644374 | 47644403 | X | 47614009 | 47618008 |

TABLE 13.b6

|  | 4 kb Sequence Location | | Inner_primers | | |
|---|---|---|---|---|---|
|  | Start2 | End2 | PCR-Primer1 ID | PCR_Primer1 | PCR-Primer2_ID |
| 53 | 157266725 | 157270724 | OBD117.1.269 | CTAAGAGGTGATGCCCAAGGTGC (SEQ ID NO: 713) | OBD117.1.271 |
| 54 | 157266725 | 157270724 | OBD117.1.397 | GTCTCCTGAGGTGAAGCAAGAGG (SEQ ID NO: 714) | OBD117.1.399 |
| 55 | 157262577 | 157266576 | OBD117.1.773 | GGTGCTAATCTCAGGGACCG (SEQ ID NO: 715) | OBD117.1.775 |
| 56 | 157266725 | 157270724 | OBD117.1.001 | CTCTCTTGCTGGCATTCCCTTCCC (SEQ ID NO: 716) | OBD117.1.003 |
| 57 | 157266725 | 157270724 | OBD117.1.041 | GTAAATGAGCCACCTGGGCGGGT (SEQ ID NO: 717) | OBD117.1.043 |
| 58 | 55961822 | 55965821 | OBD117.1.809 | GGCAAATACGTTAATAGCAGCAC (SEQ ID NO: 718) | OBD117.1.811 |
| 59 | 125631101 | 125635100 | OBD117.1.257 | GTCATCTCCTCTCCAGTTAGTCAACA (SEQ ID NO: 719) | OBD117.1.259 |
| 60 | 11281372 | 11285371 | OBD117.1.793 | TTCAGAGGGTTCTTCGGGGA (SEQ ID NO: 720) | OBD117.1.795 |
| 61 | 127729527 | 127733526 | OBD117.1.377 | GCCCCTAAGCAACCACCTTGGAC (SEQ ID NO: 721) | OBD117.1.379 |
| 62 | 127738939 | 127742938 | OBD117.1.045 | CCCTAAGCAACCACCTTGGACTG (SEQ ID NO: 722) | OBD117.1.047 |
| 63 | 105886459 | 105890458 | OBD117.1.813 | AATGTTGGCATGGTGTTTTC (SEQ ID NO: 723) | OBD117.1.815 |
| 64 | 44308140 | 44312139 | OBD117.1.049 | CACTTTGCCTCCACATCTGGTATGAG (SEQ ID NO: 724) | OBD117.1.051 |
| 65 | 44308140 | 44312139 | OBD117.1.1069 | TAGCACTTTGCCTCCACATC (SEQ ID NO: 725) | OBD117.1.1071 |
| 66 | 34369949 | 34373948 | OBD117.1.893 | ACTTGTGGCTTCCTTAGCCC (SEQ ID NO: 726) | OBD117.1.895 |

TABLE 13.b6-continued

| | 4 kb Sequence Location | | Inner_primers | | |
|---|---|---|---|---|---|
| | Start2 | End2 | PCR-Primer1 ID | PCR_Primer1 | PCR-Primer2_ID |
| 67 | 36095759 | 36099758 | OBD117.1.389 | CAGAAAGAGAAGCAAAGAGGACTCAT (SEQ ID NO: 727) | OBD117.1.391 |
| 68 | 42051407 | 42055406 | OBD117.1.1045 | GGCTGCTGTGAATCATGCTG (SEQ ID NO: 728) | OBD117.1.1047 |
| 69 | 167150611 | 167154610 | OBD117.1.185 | GGCGGTAAAGTCACACAGCCAGA (SEQ ID NO: 729) | OBD117.1.187 |
| 70 | 46457806 | 46461805 | OBD117.1.953 | AGTGTCGCTGTACATGACCAG (SEQ ID NO: 730) | OBD117.1.955 |
| 71 | 67233989 | 67237988 | OBD117.1.313 | CTGCCTGGTTTCTGAACTGAGTGAGG (SEQ ID NO: 731) | OBD117.1.315 |
| 72 | 28974446 | 28978445 | OBD117.1.125 | GAGCGTGGTGCCAGTGTGGGTAA (SEQ ID NO: 732) | OBD117.1.127 |
| 73 | 112398394 | 112402393 | OBD117.1.1293 | GCACCTTACTCGGAGGAGGACCA (SEQ ID NO: 733) | OBD117.1.1295 |
| 74 | 35306550 | 35310549 | OBD117.1.433 | AGGTAACGGCTGACAGGTGCTGG (SEQ ID NO: 734) | OBD117.1.435 |
| 75 | 69936161 | 69940160 | OBD117.1.1221 | TCAAAAGAGCACAGCATAATCTGAAT (SEQ ID NO: 735) | OBD117.1.1223 |
| 76 | 5460319 | 5464318 | OBD117.1.577 | CTAAGTGCCAGCAGACTATGGAGCCA (SEQ ID NO: 736) | OBD117.1.579 |
| 77 | 5512277 | 5516276 | OBD117.1.625 | GTTTCCGTGCCTTTTCCAGCCTC (SEQ ID NO: 737) | OBD117.1.627 |
| 78 | 61139962 | 61143961 | OBD117.1.913 | CAGGGAGAACACCCGGAAGG (SEQ ID NO: 738) | OBD117.1.915 |
| 79 | 60979728 | 60983727 | OBD117.1.089 | TGTCCCTTTCTCCTAAATACCCCAAC (SEQ ID NO: 739) | OBD117.1.091 |
| 80 | 61021586 | 61025585 | OBD117.1.237 | CCAACACAGCAGCCTCCAGCCAT (SEQ ID NO: 740) | OBD117.1.239 |
| 81 | 60996251 | 61000250 | OBD117.1.153 | GTCCCTTTCTCCTAAATACCCCAACG (SEQ ID NO: 741) | OBD117.1.155 |
| 82 | 14127468 | 14131467 | OBD117.1.1865 | CTTTGGACTTATGTAAATGTTTT (SEQ ID NO: 742) | OBD117.1.1867 |
| 83 | 14136228 | 14140227 | OBD117.1.1501 | TAAATACCAGCCTTGGAATCAGGGC (SEQ ID NO: 743) | OBD117.1.1503 |
| 84 | 122096803 | 122100802 | OBD117.1.253 | CTGGATTCTTGAGCGACTTGTTCCTG (SEQ ID NO: 744) | OBD117.1.255 |
| 85 | 131303538 | 131307537 | OBD117.1.1305 | GAAGAAACTGGATTCCTACCTGGCAC (SEQ ID NO: 745) | OBD117.1.1307 |
| 86 | 90864784 | 90868783 | OBD117.1.1193 | GCTGTGCTCTTTCAAATCCACTGCTG (SEQ ID NO: 746) | OBD117.1.1195 |
| 87 | 90939001 | 90943000 | OBD117.1.1117 | TTATTTTATTAGATGCCACCCTCAGC (SEQ ID NO: 747) | OBD117.1.1119 |
| 88 | 90994572 | 90998571 | OBD117.1.1517 | TTATTTTATTAGATGCCACCCTCAGC (SEQ ID NO: 748) | OBD117.1.1519 |
| 89 | 91106423 | 91110422 | OBD117.1.1533 | TTATTTTATTAGATGCCACCCTCAGC (SEQ ID NO: 749) | OBD117.1.1535 |
| 90 | 91154298 | 91158297 | OBD117.1.1393 | GGGATGCCACTGTATTTCTCAAAGCC (SEQ ID NO: 750) | OBD117.1.1395 |
| 91 | 36689658 | 36693657 | OBD117.1.957 | CCATATGGTCTCCGGGTCCT (SEQ ID NO: 751) | OBD117.1.959 |

TABLE 13.b6-continued

| | 4 kb Sequence Location | | Inner_primers | | |
|---|---|---|---|---|---|
| | Start2 | End2 | PCR-Primer1 ID | PCR_Primer1 | PCR-Primer2_ID |
| 92 | 36719341 | 36723340 | OBD117.1.501 | TGGTCCCTTACAAAGTCCTTCCGTGC (SEQ ID NO: 752) | OBD117.1.503 |
| 93 | 36719341 | 36723340 | OBD117.1.473 | TTTCCTCTGTCTCCATCTCCGCCCAT (SEQ ID NO: 753) | OBD117.1.475 |
| 94 | 4926807 | 4930806 | OBD117.1.1597 | GGTGGGAAGAGGGTGTCACAAGTCAT (SEQ ID NO: 754) | OBD117.1.1599 |
| 95 | 11303118 | 11307117 | OBD117.1.1641 | GGTTCACTGACTCTGGTGCCAAC (SEQ ID NO: 755) | OBD117.1.1643 |
| 96 | 168688952 | 168692951 | OBD117.1.1633 | GCTGATTTCTTTGTGTGTGGGTGGG (SEQ ID NO: 756) | OBD117.1.1635 |
| 97 | 47614009 | 47618008 | OBD117.1.481 | ACACACCTCCCTCAACCCAACTGTC (SEQ ID NO: 757) | OBD117.1.483 |
| 98 | 47636868 | 47640867 | OBD117.1.453 | CACACCTCCCTCAACCCAACTGT (SEQ ID NO: 758) | OBD117.1.455 |
| 99 | 47636868 | 47640867 | OBD117.1.493 | AACTAATCCCCACCCCATCCTGC (SEQ ID NO: 759) | OBD117.1.495 |
| 100 | 47653847 | 47657846 | OBD117.1.509 | CCACACACCTCCCTCAACCCAAC (SEQ ID NO: 760) | OBD117.1.511 |
| 101 | 47652990 | 47656989 | OBD117.1.529 | ACTAATCCCCACCCCATCCTGCC (SEQ ID NO: 761) | OBD117.1.531 |
| 102 | 47672279 | 47676278 | OBD117.1.973 | CTCCCTCAACCCAACTGTCC (SEQ ID NO: 762) | OBD117.1.975 |
| 103 | 47636868 | 47640867 | OBD117.1.441 | CTCCTGCCCACTCTATTTTCCCC (SEQ ID NO: 763) | OBD117.1.443 |
| 104 | 47640404 | 47644403 | OBD117.1.469 | AGAAGACACTCCATAAATGCTCAGGG (SEQ ID NO: 764) | OBD117.1.471 |

TABLE 13.b7

| | Inner_primers | |
|---|---|---|
| | PCR_Primer2 | GLMNET |
| 53 | GACGCCACAACAGACAGGCAAGC (SEQ ID NO: 765) | 0.013514368 |
| 54 | AGTCAGCCCACTCATCCCCTTCC (SEQ ID NO: 766) | -0.009002897 |
| 55 | TTTGGCAAGCTTTGTGAGG (SEQ ID NO: 767) | 0.000108207 |
| 56 | GTAGACGCCACAACAGACAGGCA (SEQ ID NO: 768) | -0.006474726 |
| 57 | GGCAAGCATCTTCCTGGTTCTTCAG (SEQ ID NO: 769) | -0.021298663 |
| 58 | CAGGAAGGTCGGAATAGCTG (SEQ ID NO: 770) | -0.024082323 |
| 59 | GGTTGGAAGTAGCCCACGGTGTGTTT (SEQ ID NO: 771) | 0.017680421 |
| 60 | ATGACGGGGTGTGGGTTAT (SEQ ID NO:772) | 0.01727269 |
| 61 | CCAGCAGTTTCAGAGGCAAAGGC (SEQ ID NO: 773) | -0.006220015 |
| 62 | GCTTCGCTTACCAGAGTCGCTGC (SEQ ID NO: 774) | -0.010058174 |
| 63 | TCAAGTGCATACTCCACAACG (SEQ ID NO: 775) | 0.000127348 |
| 64 | GGCTTGACACCCTTAGTTTACTGCCT (SEQ ID NO: 776) | -0.009744914 |
| 65 | CCTAGACTCTCACCTCCTCTCG (SEQ ID NO: 777) | 0 |
| 66 | TCCTTTGCAGGTATGGACATC (SEQ ID NO: 778) | 0.008460581 |

TABLE 13.b7-continued

| | Inner_primers | |
|---|---|---|
| | PCR_Primer2 | GLMNET |
| 67 | GTTGGATGCTGTGTGGTGGGATAGAT (SEQ ID NO: 779) | −0.011403512 |
| 68 | TGAGACTAGACTGGAGGGCC (SEQ ID NO: 780) | 0 |
| 69 | ACACCTGTGAGCAGAGTGGAGGG (SEQ ID NO: 781) | 0.005137905 |
| 70 | GCCCGGCCTTGAGTTATTCT (SEQ ID NO: 782) | −0.007948899 |
| 71 | AGAAACTGATGGAAGAAGGAAACTCC (SEQ ID NO: 783) | 0.000116162 |
| 72 | GGGAGGGAAGTTGAACGATGGGT (SEQ ID NO: 784) | −0.011725271 |
| 73 | CAGCCTTCTCTCCAAAGCAGGGA (SEQ ID NO: 785) | 0 |
| 74 | TCACCACCACCCATAGCCCTAAG (SEQ ID NO: 786) | 0 |
| 75 | AATCAACCCTCAGGCTTTCAGGCAAA (SEQ ID NO: 787) | 0 |
| 76 | GACACACTCAGATTTCAGACACAACA (SEQ ID NO: 788) | 0.001022887 |
| 77 | GGGCAGTTCATCATAGGGAGCCG (SEQ ID NO: 789) | −0.005572532 |
| 78 | GCTATGGAGCTGGACATGG (SEQ ID NO: 790) | 0.000119295 |
| 79 | TAGGAGGAGCGGTCTTACAGGCAGA (SEQ ID NO: 791) | 0 |
| 80 | TAGGAGGAGCGGTCTTACAGGCA (SEQ ID NO: 792) | 0.00011596 |
| 81 | TGTGATGCTTCCCACTGCTCTGATAG (SEQ ID NO: 793) | −0.014829951 |
| 82 | ACAAACATAAGTTGAGGCTGGAT (SEQ ID NO: 794) | 0 |
| 83 | CACCCTCTCATCCCCAAAACACCATC (SEQ ID NO: 795) | 0 |
| 84 | GGGACTGTCACTGGCTATTTATGGGA (SEQ ID NO: 796) | −0.001718735 |
| 85 | GGAATGTCCTGCCTTAGGGTATCTGT (SEQ ID NO: 797) | 0 |
| 86 | TTATTTTATTAGATGCCACCCTCAGC (SEQ ID NO: 798) | 0 |
| 87 | CAGAACAGTGGGTAGGGACTTGCTTT (SEQ ID NO: 799) | 0 |
| 88 | TGCTAAGAAGTGTCACCACCTCCTCA (SEQ ID NO: 800) | 0 |
| 89 | GACAAAGGCTCTGATGTTGAAAATGC (SEQ ID NO: 801) | 0 |
| 90 | GGTAAAAGGAAGCAAAGGACTGATTC (SEQ ID NO: 802) | 0 |
| 91 | ACCCAGAGGTTCCTTTGTCA (SEQ ID NO: 803) | 0.009388509 |
| 92 | GGGTGAAGGAATAAATGATTGGAGGG (SEQ ID NO: 804) | 0 |
| 93 | GGGTGAAGGAATAAATGATTGGAGGG (SEQ ID NO: 805) | 0 |
| 94 | GGATACTAAACCACCTGCTCATAAGG (SEQ ID NO: 806) | 0 |
| 95 | GTCCCGAGAAGGGTGACCAGACA (SEQ ID NO: 807) | 0 |
| 96 | CATTCTGACATCCTCTTCCCATTCCT (SEQ ID NO: 808) | 0 |
| 97 | AGAAGACACTCCATAAATGCTCAGGG (SEQ ID NO: 809) | 0 |
| 98 | CCAGTTTCCATCCAGTGGCAGCG (SEQ ID NO: 810) | 0 |
| 99 | CCAGTTTCCATCCAGTGGCAGCG (SEQ ID NO: 811) | 0 |
| 100 | CCTCCCTTGCCCACACATACCAA (SEQ ID NO: 812) | 0 |
| 101 | GCCACTTTCCCTCCCCACTCAAT (SEQ ID NO: 813) | 0 |
| 102 | CTGGCAGCATTCACCACAAG (SEQ ID NO: 814) | 0 |

TABLE 13.b7-continued

| | Inner primers | |
|---|---|---|
| | PCR_Primer2 | GLMNET |
| 103 | CCAGTTTCCATCCAGTGGCAGCG (SEQ ID NO: 815) | -0.017184561 |
| 104 | CCCACTTGACCCCTCATAAGAGTTCT (SEQ ID NO: 816) | 0.001327318 |

TABLE 13.c1

| | Probe | GeneLocus | Probe_Count_Total | Probe_Count_Sig |
|---|---|---|---|---|
| 105 | ORF149_X_47613512_47618008_47636868_47644403_FR | ORF149 | 23 | 15 |
| 106 | ORF149_X_47613512_47618008_47636868_47644403_RR | ORF149 | 23 | 15 |
| 107 | ORF149_X_47613512_47618008_47672279_47679605_RR | ORF149 | 23 | 15 |
| 108 | ORF157_9_121063123_121064862_121152751_121162678_RF | ORF157 | 64 | 5 |
| 109 | ORF159_8_120045608_120049042_120170620_120179901_FR | ORF159 | 171 | 15 |
| 110 | ORF159_8_120058539_120067601_120170620_120179901_FR | ORF159 | 171 | 15 |
| 111 | ORF159_8_120324759_120327604_120388396_120396997_RR | ORF159 | 171 | 15 |
| 112 | ORF159_8_120368738_120373426_120388396_120396997_RR | ORF159 | 171 | 15 |
| 113 | ORF16_10_74576267_74586651_74616954_74620476_RF | ORF16 | 115 | 7 |
| 114 | ORF160_5_178219671_178228100_178451151_178455914_FR | ORF160 | 34 | 11 |
| 115 | ORF160_5_178219671_178228100_178475905_178480029_FF | ORF160 | 34 | 11 |
| 116 | ORF160_5_178254981_178259471_178436965_178443271_FR | ORF160 | 34 | 11 |
| 117 | ORF163_12_93752886_93759416_93791200_93797905_FF | CRADD | 231 | 4 |
| 118 | ORF167_5_132051982_132053273_132068115_132074991_FF | CSF2 | 36 | 2 |
| 119 | ORF171_1_112368886_112372835_112478496_112485740_FF | ORF171 | 37 | 7 |
| 120 | ORF171_1_112478496_112485740_112502466_112507019_FR | ORF171 | 37 | 7 |
| 121 | ORF175_4_74083782_74086942_74117911_74125141_RR | ORF175 | 38 | 1 |
| 122 | ORF179_2_157461901_157469311_157533412_157536043_RF | ORF179 | 33 | 1 |
| 123 | ORF185_12_122194669_122198199_122226656_122228976_RR | ORF185 | 20 | 1 |
| 124 | ORF188_1_231816751_231823980_231852208_231857319_FF | ORF188 | 173 | 14 |
| 125 | ORF189_13_50726484_50732327_50881905_50885725_RR | ORF189 | 107 | 10 |
| 126 | ORF190_18_4001462_4005154_4185416_4194441_RF | ORF190 | 182 | 15 |
| 127 | ORF190_18_4185416_4194441_4248756_4252697_FR | ORF190 | 182 | 15 |
| 128 | ORF190_18_4185416_4194441_4410806_4417824_FR | ORF190 | 182 | 15 |
| 129 | ORF193_2_224946941_224952242_224984447_224994669_RF | ORF193 | 190 | 29 |
| 130 | ORF195_7_111887117_111893545_112094382_112105308_FF | ORF195 | 158 | 7 |
| 131 | ORF195_7_112094382_112105308_112160919_112168008_FF | ORF195 | 158 | 7 |
| 132 | ORF197_8_26561792_26565691_26638318_26644530_FR | ORF197 | 31 | 9 |
| 133 | ORF197_8_26561792_26565691_26638318_26644530_RR | ORF197 | 31 | 9 |
| 134 | ORF20_5_281198_284937_355623_362397_FR | ORF20 | 33 | 6 |
| 135 | ORF20_5_281198_284937_467048_471770_FF | ORF20 | 33 | 6 |
| 136 | ORF202_8_29312029_29317185_29361816_29366925_FF | ORF202 | 22 | 1 |
| 137 | ORF205_3_5223126_5230817_5254657_5258841_FF | ORF205 | 30 | 5 |
| 138 | ORF206_12_92776962_92786640_92823177_92825247_RR | ORF206 | 46 | 7 |
| 139 | ORF209_4_109875299_109879120_110005130_110011368_FF | EGF | 48 | 2 |
| 140 | ORF211_11_34573815_34582810_34673477_34682282_RF | ORF211 | 99 | 7 |
| 141 | ORF211_11_34659116_34661654_34673477_34682282_RF | ORF211 | 99 | 7 |
| 142 | ORF212_X_47636868_47644403_47688049_47692767_RR | ORF212 | 2 | 1 |
| 143 | ORF213_7_36990112_36997961_37106040_37113398_RR | ORF213 | 171 | 10 |
| 144 | ORF214_2_42145559_42150768_42194745_42201093_FF | ORF214 | 114 | 14 |
| 145 | ORF214_2_42237154_42240281_42363233_42373092_FR | ORF214 | 114 | 14 |
| 146 | ORF215_17_47728716_47732358_47745284_47751054_FR | ENDOU | 26 | 2 |
| 147 | ORF224_6_151870936_151873891_151928859_151937822_FR | ORF224 | 158 | 22 |
| 148 | ORF226_1_94522204_94526809_94565070_94571537_RR | F3 | 36 | 2 |
| 149 | ORF229_8_58019132_58028120_58156560_58160085_FR | ORF229 | 173 | 12 |
| 150 | ORF229_8_58019132_58028120_58192936_58197384_FR | ORF229 | 173 | 12 |
| 151 | ORF229_8_58207979_58216653_58245172_58252090_FR | ORF229 | 173 | 12 |
| 152 | ORF233_12_61732349_61741819_61763501_61778266_RR | ORF233 | 196 | 4 |
| 153 | ORF240_12_29277865_29278935_29307954_29317490_FR | ORF240 | 136 | 11 |
| 154 | ORF241_10_88946200_88948398_88998943_89014190_FF | FAS | 50 | 8 |
| 155 | ORF243_1_161620964_161624310_161643724_161645551_RR | ORF243 | 17 | 6 |
| 156 | ORF243_1_161620964_161624310_161645837_161653201_RR | ORF243 | 17 | 6 |

TABLE 13.c2

| | HyperG_Stats | FDR_HyperG | Percent_Sig | logFC | AveExpr | t |
|---|---|---|---|---|---|---|
| 105 | 1.30E-12 | 6.11E-10 | 65.22 | -0.191402284 | -0.191402284 | -3.367194119 |
| 106 | 1.30E-12 | 6.11E-10 | 65.22 | -0.18368985 | -0.18368985 | -3.875425412 |
| 107 | 1.30E-12 | 6.11E-10 | 65.22 | -0.178892791 | -0.178892791 | -2.633426192 |
| 108 | 0.378198431 | 1 | 7.81 | 0.311603864 | 0.311603864 | 10.97706382 |
| 109 | 0.122880445 | 0.904598768 | 8.77 | 0.281827736 | 0.281827736 | 4.843986126 |

TABLE 13.c2-continued

|     | HyperG_Stats | FDR_HyperG  | Percent_Sig | logFC        | AveExpr      | t            |
|-----|--------------|-------------|-------------|--------------|--------------|--------------|
| 110 | 0.122880445  | 0.904598768 | 8.77        | 0.315358869  | 0.315358869  | 8.713690406  |
| 111 | 0.122880445  | 0.904598768 | 8.77        | 0.362400462  | 0.362400462  | 7.04193327   |
| 112 | 0.122880445  | 0.904598768 | 8.77        | 0.323044543  | 0.323044543  | 11.51888935  |
| 113 | 0.593052688  | 1           | 6.09        | 0.335907499  | 0.335907499  | 6.250465094  |
| 114 | 7.38E−06     | 0.000580328 | 32.35       | 0.236876295  | 0.236876295  | 4.314666444  |
| 115 | 4.52E−06     | 0.000387515 | 32.35       | 0.246788348  | 0.246788348  | 4.478260313  |
| 116 | 7.38E−06     | 0.000580328 | 32.35       | 0.140271069  | 0.140271069  | 6.960305101  |
| 117 | 0.999992975  | 0.99999793  | 1.73        | −0.138988579 | −0.138988579 | −7.545550183 |
| 118 | 0.791365183  | 0.99999793  | 5.56        | −0.158073637 | −0.158073637 | −5.410812733 |
| 119 | 0.00759753   | 0.152435545 | 18.92       | 0.293285512  | 0.293285512  | 16.18229062  |
| 120 | 0.00759753   | 0.152435545 | 18.92       | 0.352425494  | 0.352425494  | 11.00394191  |
| 121 | 0.926506445  | 1           | 2.63        | 0.141461092  | 0.141461092  | 3.611237851  |
| 122 | 0.883515927  | 1           | 3.03        | 0.298609963  | 0.298609963  | 7.099629688  |
| 123 | 0.746824008  | 1           | 5           | 0.154427751  | 0.154427751  | 9.022897646  |
| 124 | 0.203516369  | 1           | 8.09        | 0.280940922  | 0.280940922  | 5.410547977  |
| 125 | 0.137504735  | 0.956987014 | 9.35        | 0.281307391  | 0.281307391  | 3.125990032  |
| 126 | 0.175422864  | 1           | 8.24        | 0.379009191  | 0.379009191  | 8.972595592  |
| 127 | 0.175422864  | 1           | 8.24        | 0.306592709  | 0.306592709  | 5.979272377  |
| 128 | 0.175422864  | 1           | 8.24        | 0.5021624    | 0.5021624    | 7.058516782  |
| 129 | 9.14E−06     | 0.000663127 | 15.26       | 0.282386591  | 0.282386591  | 6.179848359  |
| 130 | 0.876059487  | 1           | 4.43        | 0.319388984  | 0.319388984  | 7.281636739  |
| 131 | 0.876059487  | 1           | 4.43        | 0.475565551  | 0.475565551  | 9.654875537  |
| 132 | 8.78E−05     | 0.003599994 | 29.03       | 0.283654606  | 0.283654606  | 8.975747403  |
| 133 | 8.78E−05     | 0.003599994 | 29.03       | 0.329174321  | 0.329174321  | 10.11190446  |
| 134 | 0.015893505  | 0.26293992  | 18.18       | 0.367007322  | 0.367007322  | 3.722842716  |
| 135 | 0.015893505  | 0.26293992  | 18.18       | 0.37888586   | 0.37888586   | 4.011231915  |
| 136 | 0.797192199  | 1           | 4.55        | −0.159809632 | −0.159809632 | −4.427546783 |
| 137 | 0.037848586  | 0.469621268 | 16.67       | 0.300529644  | 0.300529644  | 2.711336791  |
| 138 | 0.02419036   | 0.362087451 | 15.22       | 0.397149182  | 0.397149182  | 10.0125645   |
| 139 | 0.903339407  | 0.99999793  | 4.17        | −0.210308957 | −0.210308957 | −10.40736882 |
| 140 | 0.433763829  | 1           | 7.07        | 0.342396305  | 0.342396305  | 7.282974678  |
| 141 | 0.433763829  | 1           | 7.07        | 0.311736862  | 0.311736862  | 14.33468227  |
| 142 | 0.13498553   | 0.877871412 | 50          | −0.137915679 | −0.137915679 | −2.573853727 |
| 143 | 0.642310571  | 1           | 5.85        | 0.837580169  | 0.837580169  | 2.690859837  |
| 144 | 0.012609648  | 0.224347261 | 12.28       | 0.331373318  | 0.331373318  | 9.145897755  |
| 145 | 0.012609648  | 0.224347261 | 12.28       | 0.392170538  | 0.392170538  | 8.386917517  |
| 146 | 0.622797749  | 0.99999793  | 7.69        | −0.138484187 | −0.138484187 | −8.619846124 |
| 147 | 0.000398298  | 0.012833299 | 13.92       | 0.519014068  | 0.519014068  | 14.44253214  |
| 148 | 0.791365183  | 0.99999793  | 5.56        | −0.436454288 | −0.436454288 | −6.068793285 |
| 149 | 0.409269399  | 1           | 6.94        | 0.281775997  | 0.281775997  | 9.229228715  |
| 150 | 0.409269399  | 1           | 6.94        | 0.304197038  | 0.304197038  | 6.706923479  |
| 151 | 0.409269399  | 1           | 6.94        | 0.442742286  | 0.442742286  | 8.01968993   |
| 152 | 0.998659439  | 1           | 2.04        | 0.337166653  | 0.337166653  | 7.064012738  |
| 153 | 0.239371673  | 1           | 8.09        | 0.359322711  | 0.359322711  | 5.631130929  |
| 154 | 0.041957105  | 0.555032562 | 16          | −0.625760222 | −0.625760222 | −6.24344027  |
| 155 | 0.000555352  | 0.016365522 | 35.29       | 0.151463789  | 0.151463789  | 3.447879011  |
| 156 | 0.000421879  | 0.012833299 | 35.29       | 0.152480082  | 0.152480082  | 3.157950885  |

TABLE 13.c3

|     | P. Value    | adj. P. Val | B            | FC          | FC_1         | LS |
|-----|-------------|-------------|--------------|-------------|--------------|----|
| 105 | 0.006918565 | 0.024672545 | −2.950820981 | 0.875754084 | −1.141873065 | −1 |
| 106 | 0.002944867 | 0.013082931 | −2.078743148 | 0.880448272 | −1.135785068 | −1 |
| 107 | 0.024546577 | 0.063658901 | −4.217709989 | 0.883380694 | −1.132014777 | −1 |
| 108 | 0.000000543 | 0.0000607   | 6.79431013   | 1.241086666 | 1.241086666  | 1  |
| 109 | 0.0006317   | 0.004343505 | −0.487670379 | 1.21573411  | 1.21573411   | 1  |
| 110 | 0.00000468  | 0.000184004 | 4.603843587  | 1.244321138 | 1.244321138  | 1  |
| 111 | 0.0000311   | 0.000577835 | 2.645338013  | 1.285563133 | 1.285563133  | 1  |
| 112 | 0.000000343 | 0.0000498   | 7.254248938  | 1.250967703 | 1.250967703  | 1  |
| 113 | 0.0000854   | 0.001117726 | 1.595434033  | 1.262171103 | 1.262171103  | 1  |
| 114 | 0.001442265 | 0.007834621 | −1.343218857 | 1.178438357 | 1.178438357  | 1  |
| 115 | 0.001112805 | 0.006508715 | −1.074930345 | 1.186562709 | 1.186562709  | 1  |
| 116 | 0.0000344   | 0.000618386 | 2.54094266   | 1.102112173 | 1.102112173  | 1  |
| 117 | 0.000017    | 0.000402097 | 3.270523863  | 0.908155607 | −1.101132881 | −1 |
| 118 | 0.000272744 | 0.002422901 | 0.3859262    | 0.896220954 | −1.115796272 | −1 |
| 119 | 0.0000000125| 0.0000107   | 10.45481919  | 1.225427822 | 1.225427822  | 1  |
| 120 | 0.000000531 | 0.0000601   | 6.817655292  | 1.276705252 | 1.276705252  | 1  |
| 121 | 0.004575517 | 0.018119918 | −2.529962413 | 1.103021638 | 1.103021638  | 1  |
| 122 | 0.000029    | 0.00055581  | 2.718602774  | 1.229958777 | 1.229958777  | 1  |
| 123 | 0.0000034   | 0.000155397 | 4.931662488  | 1.112980064 | 1.112980064  | 1  |
| 124 | 0.000272848 | 0.00242331  | 0.385528861  | 1.214987037 | 1.214987037  | 1  |
| 125 | 0.010462121 | 0.033595661 | −3.368710433 | 1.215295704 | 1.215295704  | 1  |
| 126 | 0.00000358  | 0.000160081 | 4.879004534  | 1.300448431 | 1.300448431  | 1  |
| 127 | 0.000122964 | 0.001428447 | 1.215794625  | 1.23678327  | 1.23678327   | 1  |

TABLE 13.c3-continued

|     | P. Value    | adj. P. Val | B            | FC          | FC_1         | LS |
|-----|-------------|-------------|--------------|-------------|--------------|----|
| 128 | 0.0000305   | 0.000571478 | 2.66644057   | 1.416334861 | 1.416334861  | 1  |
| 129 | 0.0000938   | 0.001195013 | 1.497578085  | 1.216205139 | 1.216205139  | 1  |
| 130 | 0.0000233   | 0.000485595 | 2.946910771  | 1.247801963 | 1.247801963  | 1  |
| 131 | 0.00000182  | 0.000112168 | 5.571905072  | 1.390463188 | 1.390463188  | 1  |
| 132 | 0.00000357  | 0.000159919 | 4.882311538  | 1.217274557 | 1.217274557  | 1  |
| 133 | 0.00000118  | 0.0000874   | 6.011500362  | 1.25629417  | 1.25629417   | 1  |
| 134 | 0.003794736 | 0.015760102 | −2.338680459 | 1.289674796 | 1.289674796  | 1  |
| 135 | 0.002355428 | 0.011122308 | −1.849158701 | 1.300337265 | 1.300337265  | 1  |
| 136 | 0.001205485 | 0.006894159 | −1.157743215 | 0.89514318  | −1.117139718 | −1 |
| 137 | 0.02144394  | 0.057515838 | −4.084567148 | 1.231596475 | 1.231596475  | 1  |
| 138 | 0.00000129  | 0.0000932   | 5.917548476  | 1.316903089 | 1.316903089  | 1  |
| 139 | 0.0000009   | 0.000077    | 6.285863051  | 0.864352108 | −1.156935918 | −1 |
| 140 | 0.0000233   | 0.000485546 | 2.948573409  | 1.267860752 | 1.267860752  | 1  |
| 141 | 0.0000000412| 0.0000172   | 9.328618853  | 1.241201084 | 1.241201084  | 1  |
| 142 | 0.027216654 | 0.068727574 | −4.319033972 | 0.908831233 | −1.100314297 | −1 |
| 143 | 0.022219346 | 0.059045237 | −4.119623299 | 1.787050209 | 1.787050209  | 1  |
| 144 | 0.000003    | 0.000144884 | 5.059344635  | 1.258210509 | 1.258210509  | 1  |
| 145 | 0.00000663  | 0.000226164 | 4.246397404  | 1.312366378 | 1.312366378  | 1  |
| 146 | 0.00000517  | 0.000196113 | 4.502368539  | 0.90847317  | −1.100747973 | −1 |
| 147 | 0.0000000383| 0.000017    | 9.398912888  | 1.432975624 | 1.432975624  | 1  |
| 148 | 0.000108908 | 0.001320738 | 1.342264192  | 0.738948493 | −1.353274294 | −1 |
| 149 | 0.00000276  | 0.000139969 | 5.144987441  | 1.215690512 | 1.215690512  | 1  |
| 150 | 0.0000473   | 0.000761013 | 2.211279703  | 1.23473123  | 1.23473123   | 1  |
| 151 | 0.00000992  | 0.000285195 | 3.830595539  | 1.359185424 | 1.359185424  | 1  |
| 152 | 0.0000303   | 0.00056988  | 2.673426296  | 1.263273181 | 1.263273181  | 1  |
| 153 | 0.000199224 | 0.001962619 | 0.713074052  | 1.282823521 | 1.282823521  | 1  |
| 154 | 0.0000862   | 0.001125209 | 1.58573085   | 0.648078185 | −1.543023701 | −1 |
| 155 | 0.006030852 | 0.022309044 | −2.811359709 | 1.110695836 | 1.110695836  | 1  |
| 156 | 0.009901982 | 0.032241793 | −3.313305449 | 1.111478531 | 1.111478531  | 1  |

TABLE 13.c4

|     | Loop detected       | Probe sequence 60 mer |
|-----|---------------------|------------------------|
| 105 | PD-L1 responder     | GGAGTGCAGAAAGTTGATCTATGGGAGCTCGAGAGGCCATCCACGCTGATAGAAGGGATG (SEQ ID NO: 817) |
| 106 | PD-L1 responder     | ACTCAAATATGGAATATTCCAGTCAAAATCGAGAGGCCATCCACGCTGATAGAAGGGATG (SEQ ID NO: 818) |
| 107 | PD-L1 responder     | ACTCAAATATGGAATATTCCAGTCAAAATCGAGGCCCAAGGGCTTGTCAGTCAGCTTGTG (SEQ ID NO: 819) |
| 108 | PD-L1 Non-responder | CTGGTTCTAAAATTATATGAACCTAGAATCGATGGTATACCAAAGGTCTGTCTTTATGTA (SEQ ID NO: 820) |
| 109 | PD-L1 Non-responder | TGGACTTAATATCATGTTTAAGTTTACATCGATGGTATTAGTCCATTTCTATTTGTAACT (SEQ ID NO: 821) |
| 110 | PD-L1 Non-responder | ATTAAATGCACATTGTTGAATATATTTTTCGATGGTATTAGTCCATTTCTATTTGTAACT (SEQ ID NO: 822) |
| 111 | PD-L1 Non-responder | ATTATACTATTCTTCATTCATATCTTCTTCGATCTTTTGAAATAGTTTCAGTAGGATTGG (SEQ ID NO: 823) |
| 112 | PD-L1 Non-responder | TGGAGGGGACCAATGACAAGTTTGACATTCGATCTTTTGAAATAGTTTCAGTAGGATTGG (SEQ ID NO: 824) |
| 113 | PD-L1 Non-responder | TTCATTCTTCTTTATAGATAAGTAGTATTCGATGAAGTCTCATTTTTCATGTATTAAATT (SEQ ID NO: 825) |
| 114 | PD-L1 Non-responder | GTCAGATGTCACAGGGGCAGTTAGAACCTCGAACAATTATTTACATTTTAAGAACTGGTA (SEQ ID NO: 826) |
| 115 | Non-Responder       | GTCAGATGTCACAGGGGCAGTTAGAACCTCGATACACACATACCTACCGTTTTATCTCAG (SEQ ID NO: 827) |
| 116 | PD-L1 Non-responder | CCCTGAAGTGGGCAGGAATTTCATGTGTTCGAATTGCTTGTTTCCTGGTGATCCCCCTCC (SEQ ID NO: 828) |
| 117 | PD-L1 responder     | AAACTTCCTTTCTTTGCTTAGAACTAGCTCGATCCTGGAAGCCCCCTAAAGGCAGGAACT (SEQ ID NO: 829) |

TABLE 13.c4-continued

| | Loop detected | Probe sequence 60 mer |
|---|---|---|
| 118 | PD-L1 responder | TAACAAGGAGTGGAGTATTCCTGGGATATCGACCCCACCCCCTAGATTAAGACATTCCTG (SEQ ID NO: 830) |
| 119 | PD-L1 Non-responder | AGGTGGGAGGATCATCTGAACCCGGAGGTCGAAAATATATCTTCAGTTAATTTTTGTATA (SEQ ID NO: 831) |
| 120 | PD-L1 Non-responder | TATACAAAAATTAACTGAAGATATATTTTCGAAAATAAGGTAATGATTTGGCAGAGGGAA (SEQ ID NO: 832) |
| 121 | PD-L1 Non-responder | GGTCCCCTGATTTCCATCCTAGTGCTTCTCGATGATATAATACTCTGCTGACTACATTTT (SEQ ID NO: 833) |
| 122 | PD-L1 Non-responder | TCAGAAATAAATAAATAAAGTAGAAAACTCGACAGGACAAATTTTCTAAAGACTGAATGA (SEQ ID NO: 834) |
| 123 | PD-L1 Non-responder | CAGGAGTTCAAGACCAACCTGGTCAACATCGAAACAGCAAACGAAGGCCAGGAAGCCCAC (SEQ ID NO: 835) |
| 124 | PD-L1 Non-responder | TTTTAAGAAACATTAAGATATTAAACTGTCGAAATGTGTGAAAAAGTAAGAGTAGTACTT (SEQ ID NO: 836) |
| 125 | PD-L1 Non-responder | TACCCTTAATTTAAACCCTTGTGTATTTTCGATGATTTCATTACTGTAATTACCTCATAT (SEQ ID NO: 837) |
| 126 | PD-L1 Non-responder | TTAGCTTTATTACAGATAAAATATTATATCGATGGCCATTTTTTTCTTTATTAATGTTTA (SEQ ID NO: 838) |
| 127 | PD-L1 Non-responder | TTAGCTTTATTACAGATAAAATATTATATCGAATCACGTTACTCCTTTCTTAAAAACCTA (SEQ ID NO: 839) |
| 128 | PD-L1 Non-responder | TTAGCTTTATTACAGATAAAATATTATATCGATGGATCTCACAATTATAACCAACAAAAG (SEQ ID NO: 840) |
| 129 | PD-L1 Non-responder | GAAAGAGGTCACTGGTACACATCCAGTGTCGAAAACTCATCGTATTGCTATAATTTGAGT (SEQ ID NO: 841) |
| 130 | PD-L1 Non-responder | ACATTTATATGAAGTACCATTTATGTTTTCGATTTTTAAATTTCTTTCCCTAAACATATT (SEQ ID NO: 842) |
| 131 | PD-L1 Non-responder | AATATGTTTAGGGAAAGAAATTTAAAAATCGATACAGTTTCAAATTTTAATTTAGATGTA (SEQ ID NO: 843) |
| 132 | PD-L1 Non-responder | ATAAATAGACTCCACTATGTATAATGACTCGAAATTTTGCTATAAATGTGAGCTTTGAAA (SEQ ID NO: 844) |
| 133 | PD-L1 Non-responder | CAGCCAGCCAGTAGATCTTCATAGGAGCTCGAAATTTTGCTATAAATGTGAGCTTTGAAA (SEQ ID NO: 845) |
| 134 | PD-L1 Non-responder | GCTGGAGACCCGGGGAGGAATATCAAACTCGATTCTGGTGTTTCCAGCAAGTTTGGACAC (SEQ ID NO: 846) |
| 135 | PD-L1 Non-responder | GCTGGAGACCCGGGGAGGAATATCAAACTCGACCCTAACTGCAGTCACTGTTACTTGGAT (SEQ ID NO: 847) |
| 136 | PD-L1 responder | CTATCTAGTCCTTATCAGAAGGGAACCTTCGAAGTCTCTCTTGAGATGGGTTCTTACTTT (SEQ ID NO: 848) |
| 137 | PD-L1 Non-responder | AATAAAGTGCACTATAGATGTTATGTGCTCGAAATTTCTTTTGAGCTCTGCATTGTTTGA (SEQ ID NO: 849) |
| 138 | PD-L1 Non-responder | TCTTTAAAATGTTGAATACTATAATATATCGACAAGAATATTCTATTTAAAAAGCAAATC (SEQ ID NO: 850) |
| 139 | PD-L1 responder | CAGGCTATTGTAGTGCTCTTCCTGGCCCTCGACACCCCCTTCAAGGGTCTGTGTCCCATA (SEQ ID NO: 851) |
| 140 | PD-L1 Non-responder | AAAAAATAAATATAAAATAGAAAAATATCGATATTTTCATTTGTCTTTCCTAGGAACTC (SEQ ID NO: 852) |
| 141 | PD-L1 Non-responder | AAAAAAATAAATATAAAATAGAAAAATATCGAAGTATGTCCTATATGGGAAAAAACGTA (SEQ ID NO: 853) |
| 142 | PD-L1 responder | CATCCCTTCTATCAGCGTGGATGGCCTCTCGATGTTAACCTTGATCCTTTGGTTAAAGTA (SEQ ID NO: 854) |

TABLE 13.c4-continued

| | Loop detected | Probe sequence 60 mer |
|---|---|---|
| 143 | PD-L1 Non-responder | CCCATGCAAAAATTCTTTGGAAGTTTCCTCGATTAACAAAAAAGAGTTAATACATATTAG (SEQ ID NO: 855) |
| 144 | PD-L1 Non-responder | CAAATAATGTTACTAAAATCAATTCAAGTCGACTTGATTGATGGAAATTAGAATACAGGT (SEQ ID NO: 856) |
| 145 | PD-L1 Non-responder | AAATTAATACACATTTTTATTGTGAAATTCGACTACCTCAAAAGAAAATGATCCATTGAC (SEQ ID NO: 857) |
| 146 | PD-L1 responder | GCCATTAAATTCCCCTAATGCCATTGCCTCGACTTCAGTGGCGTCCATTGTCTGCTGGAG (SEQ ID NO: 858) |
| 147 | PD-L1 Non-responder | TAAACCATAGTTAATTTTATGTAAATATTCGATATTTTCCAGCTATCTTTCTGTTGATTT (SEQ ID NO: 859) |
| 148 | PD-L1 responder | TTAGCATCACTTGAAAGCTAGTTAAAAATCGATTGCAAATGATATGACAGAATTGCTTTG (SEQ ID NO: 860) |
| 149 | PD-L1 Non-responder | ATCCTTATAAACACTTTATATTTTCTTTTCGAGGATTTCTAGGCATACATAATCTTTTCC (SEQ ID NO: 861) |
| 150 | PD-L1 Non-responder | ATCCTTATAAACACTTTATATTTTCTTTTCGAAATAACTATAGAAGCTAGGAGCTGATAA (SEQ ID NO: 862) |
| 151 | PD-L1 Non-responder | TGAAAAGAAAAAAAGAAATCTACTTTTTCGAATATAAGCTTTCTTCAATATTATCAAAT (SEQ ID NO: 863) |
| 152 | PD-L1 Non-responder | TTCATTGAATAATTCATTGAGTTATTCATCGATGTTAAGAAAGGTGTATCTAAAGGAATA (SEQ ID NO: 864) |
| 153 | PD-L1 Non-responder | ATTTTTATTTTTGGATTTAAGATACTATCGAATATGAACCCATTATACTAGGGCAAAAT (SEQ ID NO: 865) |
| 154 | PD-L1 responder | GTAATATTATGTAAAATTGCATTTGGTATCGAACAAAGCCTTTAACTTGACTTAGTGTCA (SEQ ID NO: 866) |
| 155 | PD-L1 Non-responder | AGGACAGAGACCCCTAATTCCACCACCATCGAACAACTGCAAACTCCACTCAACATCTTT (SEQ ID NO: 867) |
| 156 | Non-Responder | AGGACAGAGACCCCTAATTCCACCACCATCGAGGGGCTTACTAATGCCTTTTAGCTCCCT (SEQ ID NO: 868) |

TABLE 13.c5

| | Probe Location | | | | 4 kb Sequence Location | | |
|---|---|---|---|---|---|---|---|
| | Chr | Start1 | End1 | Start2 | End2 | Chr | Start1 | End1 |
| 105 | X | 47617979 | 47618008 | 47636868 | 47636897 | X | 47614009 | 47618008 |
| 106 | X | 47613512 | 47613541 | 47636868 | 47636897 | X | 47613512 | 47617511 |
| 107 | X | 47613512 | 47613541 | 47672279 | 47672308 | X | 47613512 | 47617511 |
| 108 | 9 | 121063123 | 121063152 | 121162649 | 121162678 | 9 | 121063123 | 121067122 |
| 109 | 8 | 120049013 | 120049042 | 120170620 | 120170649 | 8 | 120045043 | 120049042 |
| 110 | 8 | 120067572 | 120067601 | 120170620 | 120170649 | 8 | 120063602 | 120067601 |
| 111 | 8 | 120324759 | 120324788 | 120388396 | 120388425 | 8 | 120324759 | 120328758 |
| 112 | 8 | 120368738 | 120368767 | 120388396 | 120388425 | 8 | 120368738 | 120372737 |
| 113 | 10 | 74576267 | 74576296 | 74620447 | 74620476 | 10 | 74576267 | 74580266 |
| 114 | 5 | 178228071 | 178228100 | 178451151 | 178451180 | 5 | 178224101 | 178228100 |
| 115 | 5 | 178228071 | 178228100 | 178480000 | 178480029 | 5 | 178224101 | 178228100 |
| 116 | 5 | 178259442 | 178259471 | 178436965 | 178436994 | 5 | 178255472 | 178259471 |
| 117 | 12 | 93759387 | 93759416 | 93797876 | 93797905 | 12 | 93755417 | 93759416 |
| 118 | 5 | 132053244 | 132053273 | 132074962 | 132074991 | 5 | 132049274 | 132053273 |
| 119 | 1 | 112372806 | 112372835 | 112485711 | 112485740 | 1 | 112368836 | 112372835 |
| 120 | 1 | 112485711 | 112485740 | 112502466 | 112502495 | 1 | 112481741 | 112485740 |
| 121 | 4 | 74083782 | 74083811 | 74117911 | 74117940 | 4 | 74083782 | 74087781 |
| 122 | 2 | 157461901 | 157461930 | 157536014 | 157536043 | 2 | 157461901 | 157465900 |
| 123 | 12 | 122194669 | 122194698 | 122226656 | 122226685 | 12 | 122194669 | 122198668 |
| 124 | 1 | 231823951 | 231823980 | 231857290 | 231857319 | 1 | 231819981 | 231823980 |
| 125 | 13 | 50726484 | 50726513 | 50881905 | 50881934 | 13 | 50726484 | 50730483 |
| 126 | 18 | 4001462 | 4001491 | 4194412 | 4194441 | 18 | 4001462 | 4005461 |
| 127 | 18 | 4194412 | 4194441 | 4248756 | 4248785 | 18 | 4190442 | 4194441 |
| 128 | 18 | 4194412 | 4194441 | 4410806 | 4410835 | 18 | 4190442 | 4194441 |
| 129 | 2 | 224946941 | 224946970 | 224994640 | 224994669 | 2 | 224946941 | 224950940 |

TABLE 13.c5-continued

| | | Probe Location | | | | 4 kb Sequence Location | | |
|---|---|---|---|---|---|---|---|---|
| | Chr | Start1 | End1 | Start2 | End2 | Chr | Start1 | End1 |
| 130 | 7 | 111893516 | 111893545 | 112105279 | 112105308 | 7 | 111889546 | 111893545 |
| 131 | 7 | 112105279 | 112105308 | 112167979 | 112168008 | 7 | 112101309 | 112105308 |
| 132 | 8 | 26565662 | 26565691 | 26638318 | 26638347 | 8 | 26561692 | 26565691 |
| 133 | 8 | 26561792 | 26561821 | 26638318 | 26638347 | 8 | 26561792 | 26565791 |
| 134 | 5 | 284908 | 284937 | 355623 | 355652 | 5 | 280938 | 284937 |
| 135 | 5 | 284908 | 284937 | 471741 | 471770 | 5 | 280938 | 284937 |
| 136 | 8 | 29317156 | 29317185 | 29366896 | 29366925 | 8 | 29313186 | 29317185 |
| 137 | 3 | 5230788 | 5230817 | 5258812 | 5258841 | 3 | 5226818 | 5230817 |
| 138 | 12 | 92776962 | 92776991 | 92823177 | 92823206 | 12 | 92776962 | 92780961 |
| 139 | 4 | 109879091 | 109879120 | 110011339 | 110011368 | 4 | 109875121 | 109879120 |
| 140 | 11 | 34573815 | 34573844 | 34682253 | 34682282 | 11 | 34573815 | 34577814 |
| 141 | 11 | 34659116 | 34659145 | 34682253 | 34682282 | 11 | 34659116 | 34663115 |
| 142 | X | 47636868 | 47636897 | 47688049 | 47688078 | X | 47636868 | 47640867 |
| 143 | 7 | 36990112 | 36990141 | 37106040 | 37106069 | 7 | 36990112 | 36994111 |
| 144 | 2 | 42150739 | 42150768 | 42201064 | 42201093 | 2 | 42146769 | 42150768 |
| 145 | 2 | 42240252 | 42240281 | 42363233 | 42363262 | 2 | 42236282 | 42240281 |
| 146 | 12 | 47732329 | 47732358 | 47745284 | 47745313 | 12 | 47728359 | 47732358 |
| 147 | 6 | 151873862 | 151873891 | 151928859 | 151928888 | 6 | 151869892 | 151873891 |
| 148 | 1 | 94522204 | 94522233 | 94565070 | 94565099 | 1 | 94522204 | 94526203 |
| 149 | 8 | 58028091 | 58028120 | 58156560 | 58156589 | 8 | 58024121 | 58028120 |
| 150 | 8 | 58028091 | 58028120 | 58192936 | 58192965 | 8 | 58024121 | 58028120 |
| 151 | 8 | 58216624 | 58216653 | 58245172 | 58245201 | 8 | 58212654 | 58216653 |
| 152 | 12 | 61732349 | 61732378 | 61763501 | 61763530 | 12 | 61732349 | 61736348 |
| 153 | 12 | 29278906 | 29278935 | 29307954 | 29307983 | 12 | 29274936 | 29278935 |
| 154 | 10 | 88948369 | 88948398 | 89014161 | 89014190 | 10 | 88944399 | 88948398 |
| 155 | 1 | 161620964 | 161620993 | 161643724 | 161643753 | 1 | 161620964 | 161624963 |
| 156 | 1 | 161620964 | 161620993 | 161645837 | 161645866 | 1 | 161620964 | 161624963 |

TABLE 13.c6

| | 4 kb Sequence Location | | Inner_primers | | |
|---|---|---|---|---|---|
| | Start2 | End2 | PCR-Primer1_ID | PCR_Primer1 | PCR-Primer2_ID |
| 105 | 47636868 | 47640867 | OBD117.1.437 | AGAAGACACTCCATAAATGCTCAGGG (SEQ ID NO: 869) | OBD117.1.439 |
| 106 | 47636868 | 47640867 | OBD117.1.513 | CGGGTGGCGTGGTGTGTAATACC (SEQ ID NO: 870) | OBD117.1.515 |
| 107 | 47672279 | 47676278 | OBD117.1.489 | CGGGTGGCGTGGTGTGTAATACC (SEQ ID NO: 871) | OBD117.1.491 |
| 108 | 121158679 | 121162678 | OBD117.1.1521 | AAATCTCAATAGCCTTTCCTTGTGGA (SEQ ID NO: 872) | OBD117.1.1523 |
| 109 | 120170620 | 120174619 | OBD117.1.1549 | CCTCATCTTTTCCACAGTGACAGAGC (SEQ ID NO: 873) | OBD117.1.1551 |
| 110 | 120170620 | 120174619 | OBD117.1.1169 | ATGACTATGAAGAGTGGAAATGTCC (SEQ ID NO: 874) | OBD117.1.1171 |
| 111 | 120388396 | 120392395 | OBD117.1.1253 | CTGTAGCCAGCGGAAATACTGCTTAG (SEQ ID NO: 875) | OBD117.1.1255 |
| 112 | 120388396 | 120392395 | OBD117.1.1329 | CAACCTCATCAACAGTTAGAATAGCC (SEQ ID NO: 876) | OBD117.1.1331 |
| 113 | 74616477 | 74620476 | OBD117.1.1309 | TTCTTACCCTTCCCAGCCTCTAATA (SEQI D NO: 877) | OBD117.1.1311 |
| 114 | 178451151 | 178455150 | OBD117.1.1025 | GGTGAGTGGGGATAGCCTTC (SEQ ID NO: 878) | OBD117.1.1027 |
| 115 | 178476030 | 178480029 | OBD117.1.609 | CTTGGGCAGGTGAGGGAGAACAG (SEQ ID NO: 879) | OBD117.1.611 |
| 116 | 178436965 | 178440964 | OBD117.1.701 | GGGCTGGTCAAACAAACTCTGGC (SEQ ID NO: 880) | OBD117.1.703 |
| 117 | 93793906 | 93797905 | OBD117.1.213 | TGCCTTGGAGGTAGCGATGGGTG (SEQ ID NO: 881) | OBD117.1.215 |

TABLE 13.c6-continued

| | 4 kb Sequence Location | | Inner_primers | | |
|---|---|---|---|---|---|
| | Start2 | End2 | PCR-Primer1_ID | PCR_Primer1 | PCR-Primer2_ID |
| 118 | 132070992 | 132074991 | OBD117.1.225 | CCCCAAGATGAAAACTGAGCGGC (SEQ ID NO: 882) | OBD117.1.227 |
| 119 | 112481741 | 112485740 | OBD117.1.1209 | GCCTGGACAAGATGGTGAAACCCTGT (SEQ ID NO: 883) | OBD117.1.1211 |
| 120 | 112502466 | 112506465 | OBD117.1.1121 | GCCTGGGCGACAAAGTGAGACTC (SEQ ID NO: 884) | OBD117.1.1123 |
| 121 | 74117911 | 74121910 | OBD117.1.605 | GGCTCTGGGCAATAGTTGTAGTGTGG (SEQ ID NO: 885) | OBD117.1.607 |
| 122 | 157532044 | 157536043 | OBD117.1.1673 | TATCCCTATGGACTGAGCCAGGC (SEQ ID NO: 886) | OBD117.1.1675 |
| 123 | 122226656 | 122230655 | OBD117.1.909 | GTGCCCCACATCTGTAATTG (SEQ ID NO: 887) | OBD117.1.911 |
| 124 | 231853320 | 231857319 | OBD117.1.1241 | CTTCAAAGCAGGAGGGACTGTGC (SEQ ID NO: 888) | OBD117.1.1243 |
| 125 | 50881905 | 50885904 | OBD117.1.1409 | CCAGTGGGCTCTTAGAACGATGACAC (SEQ ID NO: 889) | OBD117.1.1411 |
| 126 | 4190442 | 4194441 | OBD117.1.1805 | TAAGATACACATTTATTGTCCAA (SEQ ID NO: 890) | OBD117.1.1807 |
| 127 | 4248756 | 4252755 | OBD117.1.1781 | TAAGATACACATTTATTGTCCAA (SEQ ID NO: 891) | OBD117.1.1783 |
| 128 | 4410806 | 4414805 | OBD117.1.1769 | TAAGATACACATTTATTGTCCAA (SEQ ID NO: 892) | OBD117.1.1771 |
| 129 | 224990670 | 224994669 | OBD117.1.1413 | CTCTACTTCTGCTTTCTCTCACAGGC (SEQ ID NO: 893) | OBD117.1.1415 |
| 130 | 112101309 | 112105308 | OBD117.1.1817 | TTATCTCAGCCTTATCTTTTCTG (SEQ ID NO: 894) | OBD117.1.1819 |
| 131 | 112164009 | 112168008 | OBD117.1.1097 | CTGCCTTTATTTTCCATCTTTCTCTT (SEQ ID NO: 895) | OBD117.1.1099 |
| 132 | 26638318 | 26642317 | OBD117.1.661 | GATGCTGCTGGTGAGAGTAGTCC (SEQ ID NO: 896) | OBD117.1.663 |
| 133 | 26638318 | 26642317 | OBD117.1.613 | GCAAGTGAGCCAGCATTACCGCC (SEQ ID NO: 897) | OBD117.1.615 |
| 134 | 355623 | 359622 | OBD117.1.1593 | TGATGTTCCAGTCTGAGGGTCTTGC (SEQ ID NO: 898) | OBD117.1.1595 |
| 135 | 467771 | 471770 | OBD117.1.1265 | GCTGATGTTCCAGTCTGAGGGTC (SEQ ID NO: 899) | OBD117.1.1267 |
| 136 | 29362926 | 29366925 | OBD117.1.497 | CTCTGTGCCTGTCATCACCCTCT (SEQ ID NO: 900) | OBD117.1.499 |
| 137 | 5254842 | 5258841 | OBD117.1.1373 | TCTGTCACTGTCTCCCACCACCC (SEQ ID NO: 901) | OBD117.1.1375 |
| 138 | 92823177 | 92827176 | OBD117.1.1561 | CTCTGGCAGCAAGTTAGAAATAATCT (SEQ ID NO: 902) | OBD117.1.1563 |
| 139 | 110007369 | 110011368 | OBD117.1.149 | CCAGGAGACACCCTCTAAAGGAG (SEQ ID NO: 903) | OBD117.1.151 |
| 140 | 34678283 | 34682282 | OBD117.1.1425 | GGGCTGGAATGAGAAGTGGTAGG (SEQ ID NO: 904) | OBD117.1.1427 |
| 141 | 34678283 | 34682282 | OBD117.1.1433 | GGCTGGAATGAGAAGTGGTAGGATGG (SEQ ID NO: 905) | OBD117.1.1435 |
| 142 | 47688049 | 47692048 | OBD117.1.521 | TTCCCCGTTTTGGACAGGGTGAGAGA (SEQ ID NO: 906) | OBD117.1.523 |

TABLE 13.c6-continued

| | 4 kb Sequence Location | | Inner_primers | | |
|---|---|---|---|---|---|
| | Start2 | End2 | PCR-Primer1_ID | PCR_Primer1 | PCR-Primer2_ID |
| 143 | 37106040 | 37110039 | OBD117.1.1669 | CCATAACAAAACCGCTGGACAAGAT (SEQ ID NO: 907) | OBD117.1.1671 |
| 144 | 42197094 | 42201093 | OBD117.1.1145 | GGAATCGGGAAAGTCTAAACCAGAAG (SEQ ID NO: 908) | OBD117.1.1147 |
| 145 | 42363233 | 42367232 | OBD117.1.1105 | GGAACACTGTAACTGGAGGAAACTTG (SEQ ID NO: 909) | OBD117.1.1107 |
| 146 | 47745284 | 47749283 | OBD117.1.325 | CCCCTGTAACATTCTCCCACCCT (SEQ ID NO: 910) | OBD117.1.327 |
| 147 | 151928859 | 151932858 | OBD117.1.1261 | GTTCCTGGATGCTTCAAAATGTGATA (SEQ ID NO: 911) | OBD117.1.1263 |
| 148 | 94565070 | 94569069 | OBD117.1.113 | CTGCTACTTCAACTGTGGTCTGGGAC (SEQ ID NO: 912) | OBD117.1.115 |
| 149 | 58156560 | 58160559 | OBD117.1.1553 | TAAGGCTGCTGTGAACATTCTTGTGC (SEQ ID NO: 913) | OBD117.1.1555 |
| 150 | 58192936 | 58196935 | OBD117.1.1365 | TAAGGCTGCTGTGAACATTCTTGTGC (SEQ ID NO: 914) | OBD117.1.1367 |
| 151 | 58245172 | 58249171 | OBD117.1.1629 | GAAGAGAAGGAGTGGAGCAAGGGTTG (SEQ ID NO: 915) | OBD117.1.1631 |
| 152 | 61763501 | 61767500 | OBD117.1.1321 | GTCTGCTTTTGCCTACGGTTTAGCCT (SEQ ID NO: 916) | OBD117.1.1323 |
| 153 | 29307954 | 29311953 | OBD117.1.1557 | GGGTAGATGAGACTGATTGCTTACAG (SEQ ID NO: 917) | OBD117.1.1559 |
| 154 | 89010191 | 89014190 | OBD117.1.305 | GGCATAAACATCAATCAGATAGCCTC (SEQ ID NO: 918) | OBD117.1.307 |
| 155 | 161643724 | 161647723 | OBD117.1.649 | ATTAGTCTTCAACCCACGCTGTTTTG (SEQ ID NO: 919) | OBD117.1.651 |
| 156 | 161645837 | 161649836 | OBD117.1.717 | ATTAGTCTTCAACCCACGCTGTTTTG (SEQ ID NO: 920) | OBD117.1.719 |

TABLE 13.c7

| | Inner_primers | |
|---|---|---|
| | PCR_Primer2 | GLMNET |
| 105 | CCCCATCTGTGACCTCTCCCTCTTTT (SEQ ID NO: 921) | 0 |
| 106 | CCCATCTGTGACCTCTCCCTCTT (SEQ ID NO: 922) | 0 |
| 107 | GAAGGAAGAGACTCAGGACTGGC (SEQ ID NO: 923) | 0 |
| 108 | TTGAGATTATCCAGTCTGAGGAGCAG (SEQ ID NO: 924) | 0 |
| 109 | CTTGAACTTGAGACACAAAGAGAGTG (SEQ ID NO: 925) | 0 |
| 110 | AGATAAAATAGTCCTTGAGGTGAATA (SEQ ID NO: 926) | 0 |
| 111 | CCCAAACAGCCCAATAACAAGCAGAG (SEQ ID NO: 927) | 0 |
| 112 | CCCAAACAGCCCAATAACAAGCAGAG (SEQ ID NO: 928) | 0 |
| 113 | CTCCTATTACTTTTCATTTGTGGTT (SEQ ID NO: 929) | 0 |
| 114 | TTCTAGAGATCAGAGTGTTTGGG (SEQ ID NO: 930) | 0 |
| 115 | CCACTGCTCCTGGCTACAAACCT (SEQ ID NO: 931) | 0.011827837 |
| 116 | CACTGAGGTGGAGGGCAGGGTAT (SEQ ID NO: 932) | 0.00010841 |

TABLE 13.c7-continued

| | Inner_primers | |
|---|---|---|
| | PCR_Primer2 | GLMNET |
| 117 | GGCAAGTATGGCGTAGAAAGGGC (SEQ ID NO: 933) | 0.012057101 |
| 118 | GCCAGCCACTACAAGCAGCACTG (SEQ ID NO: 934) | 0.002120736 |
| 119 | AGAATGAAGAGTCCAGAAACAGTCTC (SEQ ID NO: 935) | 0 |
| 120 | CCAGCCCTTCTCTGAGGTTTCCT (SEQ ID NO: 936) | 0 |
| 121 | CAAGCACGGTTGTAGGAGTTGTAAGT (SEQ ID NO: 937) | -0.005375017 |
| 122 | CCCCATCCCACACAACTAAGCACC (SEQ ID NO: 938) | 0 |
| 123 | ACGAGGGCAGTTTGGGTTGA (SEQ ID NO: 939) | 0.019526388 |
| 124 | GACCCTCCAGAACTACAGGCTCC (SEQ ID NO: 940) | 0 |
| 125 | GACCAGTCACAAAAGGGCAAATACTA (SEQ ID NO: 941) | 0 |
| 126 | TACAAGAAAACTCATCTCACTTA (SEQ ID NO: 942) | 0 |
| 127 | ACAAAGGAAGCCATTCGGTAGGT (SEQ ID NO: 943) | 0 |
| 128 | GCTGGGAAAACGATTACCTCAGG (SEQ ID NO: 944) | 0 |
| 129 | TTGTTCAGCCTGGTGACGCTTCAGAA (SEQ ID NO: 945) | 0 |
| 130 | CTTTATTTTCCATCTTTCTCTTA (SEQ ID NO: 946) | 0 |
| 131 | TTTTCTTCATACCTCTAAATAACAAT (SEQ ID NO: 947) | 0 |
| 132 | CATTACTACTCCTCCCAGGGCAGG (SEQ ID NO: 948) | 0.027392782 |
| 133 | ATTACTACTCCTCCCAGGGCAGG (SEQ ID NO: 949) | 0.0000923 |
| 134 | GGGCAGGCAGCAGGATGGGAAGC (SEQ ID NO: 950) | 0 |
| 135 | TCACTGACTGGGCAGGGCTTGCT (SEQ ID NO: 951) | 0 |
| 136 | CTGCCCCAGTTGCCCTTTTCCTG (SEQ ID NO: 952) | 0 |
| 137 | GTGAGTTCCAGGCAGCAGAGGTA (SEQ ID NO: 953) | 0 |
| 138 | GGTGGTAGTGAGAAGTTTACTCCAGA (SEQ ID NO: 954) | 0 |
| 139 | GTCCCCAGGTAATGGAGCGAAGC (SEQ ID NO: 955) | -0.013629912 |
| 140 | CACAGTGGAGGGCACACCAGCAA (SEQ ID NO: 956) | 0 |
| 141 | GCACAAGGCTACAAATCCTGTTACTC (SEQ ID NO: 957) | 0 |
| 142 | GGTGGAGAAACTGGCAGACATTACTT (SEQ ID NO: 958) | 0 |
| 143 | CCTGCTTCAATGGCTTGTGAGGACC (SEQ ID NO: 959) | 0 |
| 144 | TGGGCTGCCTGCTGTATTCTCCTAAG (SEQ ID NO: 960) | 0 |
| 145 | GAAGTCAGTGGGATGGAGACAGTAGC (SEQ ID NO: 961) | 0 |
| 146 | AGAGTAGGACCCCAGAGCAGGCA (SEQ ID NO: 962) | 0 |
| 147 | GCACCAAGATAGACCACATTCTGGGT (SEQ ID NO: 963) | 0 |
| 148 | TTCTGACAAACCTCATTGCCAGGATG (SEQ ID NO: 964) | 0.006221331 |
| 149 | CTCACCTGGCTGCTGTTCTCCATCTA (SEQ ID NO: 965) | 0 |
| 150 | CTGTCGTGGTATTGGTGGGTGTGTGA (SEQ ID NO: 966) | 0 |
| 151 | GCTCTTTGTGGTCTTATGCCCTATCA (SEQ ID NO: 967) | 0 |
| 152 | GGTTACCTGACTCCTGATACCAGACA (SEQ ID NO: 968) | 0 |
| 153 | GTCAAGATAACTGCCAGAGGAGCCAC (SEQ ID NO: 969) | 0 |
| 154 | CTCTTCATAGACCTTTAGGACTTAGC (SEQ ID NO: 970) | 0.011677917 |

TABLE 13.c7-continued

| | Inner primers | |
|---|---|---|
| | PCR_Primer2 | GLMNET |
| 155 | CCATTTCTTCCTTTCCACACACCCTC (SEQ ID NO: 971) | −0.003930014 |
| 156 | GGTTCTAAGGAGAGTTGTAAAGAGAG (SEQ ID NO: 972) | −0.023642297 |

TABLE 13.d1

| | Probe | GeneLocus | Probe_Count_Total | Probe_Count_Sig |
|---|---|---|---|---|
| 157 | ORF243_1_161620964_161624310_161718261_161721039_RF | ORF243 | 17 | 6 |
| 158 | ORF243_1_161633494_161637462_161657362_161661864_RF | ORF243 | 17 | 6 |
| 159 | ORF243_1_161643724_161645551_161657362_161661864_RF | ORF243 | 17 | 6 |
| 160 | ORF243_1_161657362_161661864_161718261_161721039_FF | ORF243 | 17 | 6 |
| 161 | ORF249_2_152472124_152479172_152576166_152584355_RR | ORF249 | 179 | 14 |
| 162 | ORF249_2_152472124_152479172_152664286_152673031_RR | ORF249 | 179 | 14 |
| 163 | ORF25_11_10273331_10278409_10371170_10376885_RR | ORF25 | 130 | 14 |
| 164 | ORF25_11_10376885_10382511_10426676_10435291_FR | ORF25 | 130 | 14 |
| 165 | ORF252_14_65046195_65050388_65076556_65085228_FF | ORF252 | 22 | 3 |
| 166 | ORF257_10_13924860_13932958_14052225_14057587_RF | ORF257 | 118 | 11 |
| 167 | ORF263_11_78304460_78312808_78374350_78382835_RF | GAB2 | 132 | 4 |
| 168 | ORF263_11_78351934_78362957_78374350_78382835_FR | ORF263 | 87 | 13 |
| 169 | ORF264_11_11305555_11318540_11360474_11364977_RR | ORF264 | 188 | 18 |
| 170 | ORF264_11_11305555_11318540_11366643_11369350_RR | ORF264 | 188 | 18 |
| 171 | ORF264_11_11305555_11318540_11464315_11471329_RR | ORF264 | 188 | 18 |
| 172 | ORF264_11_11305555_11318540_11473385_11479393_RR | ORF264 | 188 | 18 |
| 173 | ORF264_11_11305555_11318540_11483465_11487603_RR | ORF264 | 188 | 18 |
| 174 | ORF264_11_11305555_11318540_11547650_11553187_RR | ORF264 | 188 | 18 |
| 175 | ORF264_11_11305555_11318540_11553187_11562871_RR | ORF264 | 188 | 18 |
| 176 | ORF264_11_11438569_11448713_11547650_11553187_RF | ORF264 | 188 | 18 |
| 177 | ORF272_9_3998831_4010284_4158439_4161041_RR | ORF272 | 181 | 4 |
| 178 | ORF276_X_133488174_133495210_133692164_133694868_FF | ORF276 | 144 | 74 |
| 179 | ORF285_14_24595596_24607974_24651000_24656891_FR | ORF285 | 38 | 1 |
| 180 | ORF290_6_11980949_11988889_12009862_12015635_RR | ORF290 | 58 | 8 |
| 181 | ORF290_6_11980949_11988889_12060031_12070485_RR | ORF290 | 58 | 8 |
| 182 | ORF293_6_32626930_32634077_32662361_32664960_RF | HLA-DQA1 | 28 | 4 |
| 183 | ORF293_6_32626930_32634077_32662361_32664960_RR | HLA-DQA1 | 28 | 4 |
| 184 | ORF293_6_32634077_32639503_32662361_32664960_FF | HLA-DQA1 | 28 | 4 |
| 185 | ORF293_6_32634077_32639503_32662361_32664960_FR | HLA-DQA1 | 28 | 4 |
| 186 | ORF30_3_15678757_15686176_15802964_15806181_RF | ORF30 | 123 | 8 |
| 187 | ORF305_15_98779700_98784973_98893484_98899517_FR | IGF1R | 104 | 16 |
| 188 | ORF305_15_98886232_98891127_98957432_98962130_FR | IGF1R | 104 | 16 |
| 189 | ORF305_15_98893484_98899517_98957432_98962130_RR | IGF1R | 104 | 16 |
| 190 | ORF307_8_42241866_42245619_42264241_42271203_RF | IKBKB | 46 | 12 |
| 191 | ORF307_8_42264241_42271203_42281222_42285075_FR | IKBKB | 46 | 12 |
| 192 | ORF307_8_42264241_42271203_42302441_42304680_FF | IKBKB | 46 | 12 |
| 193 | ORF307_8_42264241_42271203_42331044_42332799_FF | IKBKB | 46 | 12 |
| 194 | ORF313_13_20664875_20671757_20688261_20691044_FF | ORF313 | 33 | 4 |
| 195 | ORF313_13_20664875_20671757_20695143_20698635_FF | ORF313 | 33 | 4 |
| 196 | ORF313_13_20664875_20671757_20728864_20730586_FR | ORF313 | 33 | 4 |
| 197 | ORF313_13_20664875_20671757_20737979_20744490_FR | ORF313 | 33 | 4 |
| 198 | ORF316_2_102199956_102206419_102218862_102223625_FF | ORF316 | 31 | 2 |
| 199 | ORF316_2_102206419_102213233_102261221_102268036_RF | ORF316 | 31 | 2 |
| 200 | ORF317_14_23324243_23329232_23356396_23359421_RF | IL25 | 74 | 2 |
| 201 | ORF319_10_6057923_6061396_6103786_6110024_FF | ORF319 | 15 | 1 |
| 202 | ORF325_5_76475531_76481400_76658102_76664388_FR | ORF325 | 148 | 12 |
| 203 | ORF325_5_76540898_76542545_76717099_76725306_RF | ORF325 | 148 | 12 |
| 204 | ORF325_5_76654480_76657126_76717099_76725306_RF | ORF325 | 148 | 13 |
| 205 | ORF329_5_132472660_132477912_132495376_132497062_FF | IRF1 | 42 | 8 |
| 206 | ORF331_19_49654782_49660360_49691432_49693107_RR | IRF3 | 30 | 2 |
| 207 | ORF336_16_31318595_31324659_31385398_31389135_FF | ITGAX | 41 | 8 |
| 208 | ORF336_16_31344274_31352361_31385398_31389135_FF | ITGAX | 41 | 8 |

TABLE 13.d2

| | HyperG_Stats | FDR_HyperG | Percent_Sig | logFC | AveExpr | t |
|---|---|---|---|---|---|---|
| 157 | 0.000555352 | 0.016365522 | 35.29 | 0.190429167 | 0.190429167 | 2.868181541 |
| 158 | 0.000421879 | 0.012833299 | 35.29 | 0.218107645 | 0.218107645 | 8.463198869 |
| 159 | 0.000555352 | 0.016365522 | 35.29 | 0.272288899 | 0.272288899 | 13.97024262 |
| 160 | 0.000555352 | 0.016365522 | 35.29 | 0.240440097 | 0.240440097 | 10.87424514 |
| 161 | 0.23994375 | 1 | 7.82 | 0.329346898 | 0.329346898 | 5.487827099 |
| 162 | 0.23994375 | 1 | 7.82 | 0.440433009 | 0.440433009 | 7.855500481 |

TABLE 13.d2-continued

| | HyperG_Stats | FDR_HyperG | Percent_Sig | logFC | AveExpr | t |
|---|---|---|---|---|---|---|
| 163 | 0.035039292 | 0.465381017 | 10.77 | 0.35621009 | 0.35621009 | 4.725121222 |
| 164 | 0.035039292 | 0.465381017 | 10.77 | 0.318598485 | 0.318598485 | 10.52304142 |
| 165 | 0.158363507 | 1 | 13.64 | 0.296111136 | 0.296111136 | 6.243845297 |
| 166 | 0.125273656 | 0.904598768 | 9.32 | 0.28667877 | 0.28667877 | 16.14644629 |
| 167 | 0.994374946 | 0.99999793 | 3.03 | −0.152150489 | −0.152150489 | −4.577281937 |
| 168 | 0.003092682 | 0.074779463 | 14.94 | 0.329695975 | 0.329695975 | 9.796649349 |
| 169 | 0.051180377 | 0.595840686 | 9.57 | 0.32375356 | 0.32375356 | 8.313452807 |
| 170 | 0.051180377 | 0.595840686 | 9.57 | 0.296855026 | 0.296855026 | 7.019357248 |
| 171 | 0.051180377 | 0.595840686 | 9.57 | 0.297470188 | 0.297470188 | 7.154103826 |
| 172 | 0.051180377 | 0.595840686 | 9.57 | 0.296912063 | 0.296912063 | 6.910476496 |
| 173 | 0.051180377 | 0.595840686 | 9.57 | 0.315806978 | 0.315806978 | 7.244128466 |
| 174 | 0.051180377 | 0.595840686 | 9.57 | 0.334773184 | 0.334773184 | 4.919067102 |
| 175 | 0.051180377 | 0.595840686 | 9.57 | 0.288731756 | 0.288731756 | 6.132980113 |
| 176 | 0.051180377 | 0.595840686 | 9.57 | 0.286221172 | 0.286221172 | 4.735145343 |
| 177 | 0.997131949 | 1 | 2.21 | 0.285774765 | 0.285774765 | 11.23232236 |
| 178 | 1.43E−46 | 1.35E−43 | 51.39 | −0.694724463 | −0.694724463 | −7.136811388 |
| 179 | 0.926506445 | 1 | 2.63 | 0.159055003 | 0.159055003 | 6.118067037 |
| 180 | 0.028416181 | 0.407301886 | 13.79 | 0.310955216 | 0.310955216 | 6.317177296 |
| 181 | 0.028416181 | 0.407301886 | 13.79 | 0.423599949 | 0.423599949 | 10.84857261 |
| 182 | 0.178427395 | 0.954389149 | 14.29 | −0.144695604 | −0.144695604 | −3.861408042 |
| 183 | 0.178427395 | 0.954389149 | 14.29 | −0.491099473 | −0.491099473 | −3.580221478 |
| 184 | 0.178427395 | 0.954389149 | 14.29 | −0.188169485 | −0.188169485 | −3.287365783 |
| 185 | 0.178427395 | 0.954389149 | 14.29 | −0.64455528 | −0.64455528 | −2.980618242 |
| 186 | 0.516062575 | 1 | 6.5 | 0.30577162 | 0.30577162 | 8.841735547 |
| 187 | 0.007797893 | 0.171924974 | 15.38 | −0.171537182 | −0.171537182 | −4.993189956 |
| 188 | 0.007797893 | 0.171924974 | 15.38 | −0.193623643 | −0.193623643 | −4.845372443 |
| 189 | 0.007797893 | 0.171924974 | 15.38 | −0.160584806 | −0.160584806 | −5.690028109 |
| 190 | 0.00018363 | 0.010627608 | 26.09 | −0.291244548 | −0.291244548 | −11.89788921 |
| 191 | 0.00018363 | 0.010627608 | 26.09 | −0.291439389 | −0.291439389 | −11.64817138 |
| 192 | 0.00018363 | 0.010627608 | 26.09 | −0.346675126 | −0.346675126 | −16.03607714 |
| 193 | 0.00018363 | 0.010627608 | 26.09 | −0.348439424 | −0.348439424 | −16.6498587 |
| 194 | 0.151869322 | 0.98090939 | 12.12 | 0.162592643 | 0.162592643 | 5.607585861 |
| 195 | 0.151869322 | 0.98090939 | 12.12 | 0.213925835 | 0.213925835 | 5.878475438 |
| 196 | 0.172978396 | 1 | 12.12 | 0.225971443 | 0.225971443 | 5.816491381 |
| 197 | 0.151869322 | 0.98090939 | 12.12 | 0.261432751 | 0.261432751 | 5.250369871 |
| 198 | 0.648170238 | 1 | 6.45 | −0.143835834 | −0.143835834 | −5.364884245 |
| 199 | 0.648170238 | 1 | 6.45 | −0.218690375 | −0.218690375 | −9.469982161 |
| 200 | 0.983929844 | 0.99999793 | 2.7 | −0.159277184 | −0.159277184 | −5.699454074 |
| 201 | 0.643060444 | 1 | 6.67 | 0.158451923 | 0.158451923 | 6.957742989 |
| 202 | 0.224208567 | 1 | 8.11 | 0.302741837 | 0.302741837 | 4.645263853 |
| 203 | 0.224208567 | 1 | 8.11 | 0.362966909 | 0.362966909 | 15.17483554 |
| 204 | 0.184544386 | 1 | 8.78 | 0.196151577 | 0.196151577 | 3.614499961 |
| 205 | 0.016095432 | 0.256971894 | 19.05 | −0.279967907 | −0.279967907 | −13.66679402 |
| 206 | 0.700318757 | 0.99999793 | 6.67 | −0.160722895 | −0.160722895 | −7.035502311 |
| 207 | 0.013975308 | 0.239650655 | 19.51 | −0.187127305 | −0.187127305 | −10.29247019 |
| 208 | 0.013975308 | 0.239650655 | 19.51 | −0.204949768 | −0.204949768 | −11.39755162 |

TABLE 13.d3

| | P. Value | adj. P. Val | B | FC | FC_1 | LS |
|---|---|---|---|---|---|---|
| 157 | 0.016336892 | 0.046928877 | −3.814850432 | 1.141103116 | 1.141103116 | 1 |
| 158 | 0.00000611 | 0.000216321 | 4.330876071 | 1.16320683 | 1.16320683 | 1 |
| 159 | 0.000000053 | 0.0000198 | 9.086555803 | 1.207722413 | 1.207722413 | 1 |
| 160 | 0.000000594 | 0.0000638 | 6.704482072 | 1.181352981 | 1.181352981 | 1 |
| 161 | 0.000244192 | 0.002250317 | 0.501078985 | 1.256444458 | 1.256444458 | 1 |
| 162 | 0.0000119 | 0.000317452 | 3.639677292 | 1.357011558 | 1.357011558 | 1 |
| 163 | 0.00075776 | 0.004908191 | −0.676573444 | 1.280058807 | 1.280058807 | 1 |
| 164 | 0.000000811 | 0.0000728 | 6.391251092 | 1.247118439 | 1.247118439 | 1 |
| 165 | 0.0000862 | 0.001125109 | 1.58629049 | 1.227830265 | 1.227830265 | 1 |
| 166 | 0.0000000128 | 0.0000107 | 10.43445283 | 1.219828873 | 1.219828873 | 1 |
| 167 | 0.000952862 | 0.005814117 | −0.914179847 | 0.899908054 | −1.111224636 | −1 |
| 168 | 0.00000159 | 0.000104892 | 5.710301134 | 1.256748507 | 1.256748507 | 1 |
| 169 | 0.00000718 | 0.000235815 | 4.164430478 | 1.251582646 | 1.251582646 | 1 |
| 170 | 0.000032 | 0.000589865 | 2.616552385 | 1.228463528 | 1.228463528 | 1 |
| 171 | 0.0000272 | 0.00053455 | 2.787380302 | 1.228987454 | 1.228987454 | 1 |
| 172 | 0.0000366 | 0.000640507 | 2.476786347 | 1.228512097 | 1.228512097 | 1 |
| 173 | 0.0000244 | 0.000499696 | 2.900207241 | 1.244707692 | 1.244707692 | 1 |
| 174 | 0.000563701 | 0.004023477 | −0.369350773 | 1.261179114 | 1.261179114 | 1 |
| 175 | 0.0000999 | 0.001241731 | 1.432243865 | 1.221565952 | 1.221565952 | 1 |
| 176 | 0.000746164 | 0.004854957 | −0.660568608 | 1.219442026 | 1.219442026 | 1 |
| 177 | 0.000000437 | 0.0000553 | 7.013760547 | 1.219064757 | 1.219064757 | 1 |
| 178 | 0.0000277 | 0.000540415 | 2.765588821 | 0.617827304 | −1.618575276 | −1 |
| 179 | 0.000101916 | 0.001260517 | 1.411390075 | 1.11655553 | 1.11655553 | 1 |
| 180 | 0.0000782 | 0.001056594 | 1.687237591 | 1.240528789 | 1.240528789 | 1 |

TABLE 13.d3-continued

|  | P. Value | adj. P. Val | B | FC | FC_1 | LS |
|---|---|---|---|---|---|---|
| 181 | 0.000000608 | 0.0000645 | 6.681922607 | 1.341270247 | 1.341270247 | 1 |
| 182 | 0.003013925 | 0.013289266 | −2.102539121 | 0.904570214 | −1.105497379 | −1 |
| 183 | 0.004820858 | 0.01883207 | −2.583272553 | 0.711482673 | −1.405515606 | −1 |
| 184 | 0.007929635 | 0.027297251 | −3.089016199 | 0.877718679 | −1.139317214 | −1 |
| 185 | 0.013446654 | 0.040517443 | −3.620544416 | 0.639689949 | −1.563257327 | −1 |
| 186 | 0.0000041 | 0.000173496 | 4.74079963 | 1.236079573 | 1.236079573 | 1 |
| 187 | 0.000504152 | 0.003717896 | −0.253310928 | 0.88789613 | −1.126257866 | −1 |
| 188 | 0.000630368 | 0.004341248 | −0.485478626 | 0.874406698 | −1.143632594 | −1 |
| 189 | 0.00018339 | 0.001862995 | 0.799345244 | 0.89466234 | −1.11774013 | −1 |
| 190 | 0.000000252 | 0.0000426 | 7.56312403 | 0.817196796 | −1.223695449 | −1 |
| 191 | 0.000000308 | 0.0000464 | 7.360765169 | 0.817086438 | −1.223860725 | −1 |
| 192 | 0.0000000137 | 0.0000109 | 10.37139589 | 0.786394357 | −1.271626622 | −1 |
| 193 | 0.00000000942 | 0.0000107 | 10.71553998 | 0.785433249 | −1.273182669 | −1 |
| 194 | 0.000205957 | 0.002007604 | 0.678446037 | 1.119296801 | 1.119296801 | 1 |
| 195 | 0.000141158 | 0.001563544 | 1.07202881 | 1.159840029 | 1.159840029 | 1 |
| 196 | 0.000153765 | 0.001651404 | 0.982900151 | 1.169564513 | 1.169564513 | 1 |
| 197 | 0.000344332 | 0.002847073 | 0.143290367 | 1.19866852 | 1.19866852 | 1 |
| 198 | 0.000291453 | 0.002541967 | 0.316846942 | 0.90510945 | −1.104838757 | −1 |
| 199 | 0.00000218 | 0.000122482 | 5.388593691 | 0.859345164 | −1.163676764 | −1 |
| 200 | 0.000180983 | 0.001844393 | 0.813105827 | 0.895473607 | −1.116727498 | −1 |
| 201 | 0.0000345 | 0.000618944 | 2.537651809 | 1.116088881 | 1.116088881 | 1 |
| 202 | 0.000857256 | 0.0053651 | −0.804558824 | 1.233486424 | 1.233486424 | 1 |
| 203 | 0.0000000235 | 0.0000135 | 9.86073016 | 1.286067985 | 1.286067985 | 1 |
| 204 | 0.004550477 | 0.018055062 | −2.524359163 | 1.145638258 | 1.145638258 | 1 |
| 205 | 0.0000000657 | 0.0000214 | 8.879509786 | 0.823609338 | −1.214167875 | −1 |
| 206 | 0.0000314 | 0.000581633 | 2.637144966 | 0.894576711 | −1.117847121 | −1 |
| 207 | 0.000000999 | 0.0000814 | 6.180062011 | 0.878352958 | −1.138494487 | −1 |
| 208 | 0.00000038 | 0.0000516 | 7.153167186 | 0.867568894 | −1.152646213 | −1 |

TABLE 13.d4

|  | Loop detected | Probe sequence 60 mer |
|---|---|---|
| 157 | PD-L1 Non-responder | GTTTTGGTGTACTAAGGTTTCTTCTGAATCGATGGTGGTGGAATTAGGGGTCTCTGTCCT (SEQ ID NO: 973) |
| 158 | Non-Responder | AAAGCACGCGTCAGAGTGGGTGGGGCTGTCGATTGTCATCCTCTAGGACTTACAGTTTCT (SEQ ID NO: 974) |
| 159 | PD-L1 Non-responder | AAAGCACGCGTCAGAGTGGGTGGGGCTGTCGAACAACTGCAAACTCCACTCAACATCTTT (SEQ ID NO: 975) |
| 160 | PD-L1 Non-responder | AAAGCACGCGTCAGAGTGGGTGGGGCTGTCGATTCAGAAGAAACCTTAGTACACCAAAAC (SEQ ID NO: 976) |
| 161 | PD-L1 Non-responder | CTATTATAATGTAGAAAGACTATATTAATCGAGGGTTGGTGTTAGAGTTCAAACCAACAC (SEQ ID NO: 977) |
| 162 | PD-L1 Non-responder | CTATTATAATGTAGAAAGACTATATTAATCGAGTACATGAGAAATAAGCGTCTAACATGA (SEQ ID NO: 978) |
| 163 | PD-L1 Non-responder | TTGAAGCAATTTTTTAAAAAACAGTAATTCGATGTACCATCCACAGTTCTTTAGGATACT (SEQ ID NO: 979) |
| 164 | PD-L1 Non-responder | AGGGGCTGGTAGATTTGACTACATAAACTCGAGTATGTCAGCTTGATGATGAAAGAGACT (SEQ ID NO: 980) |
| 165 | PD-L1 Non-responder | GCCGAGTTGGGCAGATCATTTTAGGAGTTCGAGTAGAACCAATTAAAAAGTTAAACAGGT (SEQ ID NO: 981) |
| 166 | PD-L1 Non-responder | GGCGGGTGGATCACCTGAGCTGAGGATTTCGAAAAAAAAAAAAAGATTATAAATTCACAC (SEQ ID NO: 982) |
| 167 | PD-L1 responder | TATTTATTTGTTACTAAAACAAGGAACTCGATTTCGCCAAGGGCCAGGCTCCCAAGGCA (SEQ ID NO: 983) |
| 168 | PD-L1 Non-responder | AAAAGTATGTGTACCTAGTAATATGGCCTCGAGCCATTTCTGAACTCATTATAAAACTAT (SEQ ID NO: 984) |
| 169 | PD-L1 Non-responder | TCGTGGGTAGTGGGGGCAGAGACTTGAGTCGATTTTCTATAGACCAAATTAAAATATTTC (SEQ ID NO: 985) |
| 170 | PD-L1 Non-responder | TCGTGGGTAGTGGGGGCAGAGACTTGAGTCGAAAATATAGATGAAAGGTACTGCCATTGT (SEQ ID NO: 986) |

TABLE 13.d4-continued

| | Loop detected | Probe sequence 60 mer |
|---|---|---|
| 171 | PD-L1 Non-responder | TCGTGGGTAGTGGGGGCAGAGACTTGAGTCGAGGTCTCCTAGGCTCAGATCTAAGGAGGA (SEQ ID NO: 987) |
| 172 | PD-L1 Non-responder | TCGTGGGTAGTGGGGGCAGAGACTTGAGTCGAAATGAAAGATTTGCCTTTCAATGGAGAA (SEQ ID NO: 988) |
| 173 | PD-L1 Non-responder | TCGTGGGTAGTGGGGGCAGAGACTTGAGTCGAAGAGGAAAGGATGTCCACTGGACATTAT (SEQ ID NO: 989) |
| 174 | PD-L1 Non-responder | TCGTGGGTAGTGGGGGCAGAGACTTGAGTCGAGACCCTGCTACCATGAATCTTAGGGTTC (SEQ ID NO: 990) |
| 175 | PD-L1 Non-responder | TCGTGGGTAGTGGGGGCAGAGACTTGAGTCGAGAACCACTCTGAAGTTTGGCCTAGTTTT (SEQ ID NO: 991) |
| 176 | PD-L1 Non-responder | TCCAGGTGACTCCGACCTACTCTCAAGTTCGAGATGGTAAGTTATCTTCCAGGGTTTAAA (SEQ ID NO: 992) |
| 177 | PD-L1 Non-responder | TGATTGGAGAATACCTACTTAAATAGTTTCGAGATTAAGAAAGAAGAGCTTCATTTACCT (SEQ ID NO: 993) |
| 178 | PD-L1 responder | AATCAGTCAATCCCTAATTTGAGTATTTTCGAACCTCATCTTGATCTTCTTCAAATTGTC (SEQ ID NO: 994) |
| 179 | PD-L1 Non-responder | TTGCCTTCAGGAAATATCATGAAATTGCTCGAAAAGATATGTCATCCCAGGGATGTAGGG (SEQ ID NO: 995) |
| 180 | PD-L1 Non-responder | AATATTCCTTCAACATTTCATATATACATCGAAATTGCATGTATGTTTTGTTAGAAAGTT (SEQ ID NO: 996) |
| 181 | PD-L1 Non-responder | AATATTCCTTCAACATTTCATATATACATCGAATACATGTTTTGGAGAATATTAAACCCA (SEQ ID NO: 997) |
| 182 | PD-L1 responder | CACCGCGCGGTACACCCCCACGTCGCTGTCGACATTTTCTTACCAGCCTGGCTGATAAAC (SEQ ID NO: 998) |
| 183 | PD-L1 responder | GTTTATCAGCCAGGCTGGTAAGAAAATGTCGAAGTCTTGGATTAAGGTTCATTCAACAAA (SEQ ID NO: 999) |
| 184 | PD-L1 responder | CCCGTCTTCCCCAAAATCTATGTGGTCCTCGACAGCGACGTGGGGGTGTACCGCGCGGTG (SEQ ID NO: 1000) |
| 185 | PD-L1 responder | CCCGTCTTCCCCAAAATCTATGTGGTCCTCGAAGTCTTGGATTAAGGTTCATTCAACAAA (SEQ ID NO: 1001) |
| 186 | PD-L1 Non-responder | TTTCTTTTATACATAAATTTTCACGCCTTCGAAAGAGAGGGAAAAATATTTACATGTTAA (SEQ ID NO: 1002) |
| 187 | PD-L1 responder | TGACTGTATTTACAACATGTCTAGATTTTCGAGTGTAAAAGGGCTTTTACTGGTGCACAC (SEQ ID NO: 1003) |
| 188 | PD-L1 responder | TCCTAGGAGAGACTGAACTTTAAAGATATCGACCTGCTGATCCTTGGATCCTGAATCTGT (SEQ ID NO: 1004) |
| 189 | PD-L1 responder | GTGTGCACCAGTAAAAGCCCTTTTACACTCGACCTGCTGATCCTTGGATCCTGAATCTGT (SEQ ID NO: 1005) |
| 190 | PD-L1 responder | CCACCCCCGCCCCGGGGAGTCGCCCGGTCGAACTAATATTAGAGGAGAGAGGTCAGTTA (SEQ ID NO: 1006) |
| 191 | PD-L1 responder | CCACCCCCGCCCCGGGGAGTCGCCCGGTCGAGGGCCTGGCAAGAAGACAGAAGCCGACT (SEQ ID NO: 1007) |
| 192 | PD-L1 responder | CCACCCCCGCCCCGGGGAGTCGCCCGGTCGACAGTCCCAAGAGGTCAGAACTGGCTTCC (SEQ ID NO: 1008) |
| 193 | PD-L1 responder | CCACCCCCGCCCCGGGGAGTCGCCCGGTCGACCCCCTGACATGGGCTGCCTGGAGCAG (SEQ ID NO: 1009) |
| 194 | Non-Responder | TTAAAGAAGCTAATTTTAAAAATAAATGTCGAAGAGATTGTCACGTTAGAGTTATGTAAA (SEQ ID NO: 1010) |
| 195 | Non-Responder | TTAAAGAAGCTAATTTTAAAAATAAATGTCGAGGAGCATCTGGATTTAATGATAGTTCAA (SEQ ID NO: 1011) |

TABLE 13.d4-continued

| | Loop detected | Probe sequence 60 mer |
|---|---|---|
| 196 | PD-L1 Non-responder | TTAAAGAAGCTAATTTTAAAAATAAATGTCGAATTCCATGGATTCAGGTTGGCAGAAGAC (SEQ ID NO: 1012) |
| 197 | Non-Responder | TTAAAGAAGCTAATTTTAAAAATAAATGTCGAAATTACTTTAAATTAATACAAGCCCCTA (SEQ ID NO: 1013) |
| 198 | PD-L1 responder | GGAAGGCCTTCCAAAGGATTTGAGTGTTTCGAGAGTACTGATGCCCTCTGCTCTGTAAAC (SEQ ID NO: 1014) |
| 199 | PD-L1 responder | CCACTCCACTTGACATTCACTCTGCTTGTCGATCAAAGCTGTATCTGCTTTAGGGGGCAC (SEQ ID NO: 1015) |
| 200 | PD-L1 responder | CTCCATCTCCCTGCCCTCTGGATCCCCCTCGATTCTACAGTGGTTTTAACAGCAGGCCCC (SEQ ID NO: 1016) |
| 201 | PD-L1 Non-responder | CAGAGACAGTGTCAAAAAAAAAAAATCTTCGAGGTCTTGAGTCCTCTTCATAAGGAAAAT (SEQ ID NO: 1017) |
| 202 | PD-L1 Non-responder | CAATGTACAAAAAAAGTTTTTTTTTTTTCGAGGTAACTTATGTTAACTTTCTTTCCCAG (SEQ ID NO: 1018) |
| 203 | PD-L1 Non-responder | ATTTAAACTATTTAATAATTTGCTGTATTCGAATGAGTGATAGTGCTTATTCCTGTATTG (SEQ ID NO: 1019) |
| 204 | PD-L1 Non-responder | ATTTAAACTATTTAATAATTTGCTGTATTCGATAGAAAATGGGTGAGGGGAAAACTGTGG (SEQ ID NO: 1020) |
| 205 | PD-L1 responder | GTGTCTCGGCCCCTGGGGCCCCACCCTTCGATTTCCCTGTTGCCGCCGCGTTTGCAAGA (SEQ ID NO: 1021) |
| 206 | PD-L1 responder | GCAGCCAGCCCGGTGGGGGTGGGGGGGGTCGACGCTCGCCTCCGCTCACAGCCTCAGCAT (SEQ ID NO: 1022) |
| 207 | PD-L1 responder | CAAATCCCGGCTATCTCTTAGAATTGCATCGATTCACCCTCCTCAGCCTCCCAAAGTGCT (SEQ ID NO: 1023) |
| 208 | PD-L1 responder | AGTGGTCTCACCATGGCTTTCTTCCAATTCGATTCACCCTCCTCAGCCTCCCAAAGTGCT (SEQ ID NO: 1024) |

TABLE 13.d5

| | Probe Location | | | | | 4 kb Sequence Location | | |
|---|---|---|---|---|---|---|---|---|
| | Chr | Start1 | End1 | Start2 | End2 | Chr | Start1 | End1 |
| 157 | 1 | 161620964 | 161620993 | 161721010 | 161721039 | 1 | 161620964 | 161624963 |
| 158 | 1 | 161633494 | 161633523 | 161661835 | 161661864 | 1 | 161633494 | 161637493 |
| 159 | 1 | 161643724 | 161643753 | 161661835 | 161661864 | 1 | 161643724 | 161647723 |
| 160 | 1 | 161661835 | 161661864 | 161721010 | 161721039 | 1 | 161657865 | 161661864 |
| 161 | 2 | 152472124 | 152472153 | 152576166 | 152576195 | 2 | 152472124 | 152476123 |
| 162 | 2 | 152472124 | 152472153 | 152664286 | 152664315 | 2 | 152472124 | 152476123 |
| 163 | 11 | 10273331 | 10273360 | 10371170 | 10371199 | 11 | 10273331 | 10277330 |
| 164 | 11 | 10382482 | 10382511 | 10426676 | 10426705 | 11 | 10378512 | 10382511 |
| 165 | 14 | 65050359 | 65050388 | 65085199 | 65085228 | 14 | 65046389 | 65050388 |
| 166 | 10 | 13932929 | 13932958 | 14057558 | 14057587 | 10 | 13928959 | 13932958 |
| 167 | 11 | 78304460 | 78304489 | 78382806 | 78382835 | 11 | 78304460 | 78308459 |
| 168 | 11 | 78362928 | 78362957 | 78374350 | 78374379 | 11 | 78358958 | 78362957 |
| 169 | 11 | 11305555 | 11305584 | 11360474 | 11360503 | 11 | 11305555 | 11309554 |
| 170 | 11 | 11305555 | 11305584 | 11366643 | 11366672 | 11 | 11305555 | 11309554 |
| 171 | 11 | 11305555 | 11305584 | 11464315 | 11464344 | 11 | 11305555 | 11309554 |
| 172 | 11 | 11305555 | 11305584 | 11473385 | 11473414 | 11 | 11305555 | 11309554 |
| 173 | 11 | 11305555 | 11305584 | 11483465 | 11483494 | 11 | 11305555 | 11309554 |
| 174 | 11 | 11305555 | 11305584 | 11547650 | 11547679 | 11 | 11305555 | 11309554 |
| 175 | 11 | 11305555 | 11305584 | 11553187 | 11553216 | 11 | 11305555 | 11309554 |
| 176 | 11 | 11438569 | 11438598 | 11553158 | 11553187 | 11 | 11438569 | 11442568 |
| 177 | 9 | 3998831 | 3998860 | 4158439 | 4158468 | 9 | 3998831 | 4002830 |
| 178 | X | 133495181 | 133495210 | 133694839 | 133694868 | X | 133491211 | 133495210 |
| 179 | 14 | 24607945 | 24607974 | 24651000 | 24651029 | 14 | 24603975 | 24607974 |
| 180 | 6 | 11980949 | 11980978 | 12009862 | 12009891 | 6 | 11980949 | 11984948 |
| 181 | 6 | 11980949 | 11980978 | 12060031 | 12060060 | 6 | 11980949 | 11984948 |
| 182 | 6 | 32626930 | 32626959 | 32664931 | 32664960 | 6 | 32626930 | 32630929 |
| 183 | 6 | 32626930 | 32626959 | 32662361 | 32662390 | 6 | 32626930 | 32630929 |
| 184 | 6 | 32639474 | 32639503 | 32664931 | 32664960 | 6 | 32635504 | 32639503 |

TABLE 13.d5-continued

| | Probe Location | | | | 4 kb Sequence Location | | |
|---|---|---|---|---|---|---|---|
| | Chr | Start1 | End1 | Start2 | End2 | Chr | Start1 | End1 |
| 185 | 6 | 32639474 | 32639503 | 32662361 | 32662390 | 6 | 32635504 | 32639503 |
| 186 | 3 | 15678757 | 15678786 | 15806152 | 15806181 | 3 | 15678757 | 15682756 |
| 187 | 15 | 98784944 | 98784973 | 98893484 | 98893513 | 15 | 98780974 | 98784973 |
| 188 | 15 | 98891098 | 98891127 | 98957432 | 98957461 | 15 | 98887128 | 98891127 |
| 189 | 15 | 98893484 | 98893513 | 98957432 | 98957461 | 15 | 98893484 | 98897483 |
| 190 | 8 | 42241866 | 42241895 | 42271174 | 42271203 | 8 | 42241866 | 42245865 |
| 191 | 8 | 42271174 | 42271203 | 42281222 | 42281251 | 8 | 42267204 | 42271203 |
| 192 | 8 | 42271174 | 42271203 | 42304651 | 42304680 | 8 | 42267204 | 42271203 |
| 193 | 8 | 42271174 | 42271203 | 42331044 | 42331073 | 8 | 42267204 | 42271203 |
| 194 | 13 | 20671728 | 20671757 | 20691015 | 20691044 | 13 | 20667758 | 20671757 |
| 195 | 13 | 20671728 | 20671757 | 20698606 | 20698635 | 13 | 20667758 | 20671757 |
| 196 | 13 | 20671728 | 20671757 | 20728864 | 20728893 | 13 | 20667758 | 20671757 |
| 197 | 13 | 20671728 | 20671757 | 20737979 | 20738008 | 13 | 20667758 | 20671757 |
| 198 | 2 | 102206390 | 102206419 | 102223596 | 102223625 | 2 | 102202420 | 102206419 |
| 199 | 2 | 102206419 | 102206448 | 102268007 | 102268036 | 2 | 102206419 | 102210418 |
| 200 | 14 | 23324243 | 23324272 | 23359392 | 23359421 | 14 | 23324243 | 23328242 |
| 201 | 10 | 6061367 | 6061396 | 6109995 | 6110024 | 10 | 6057397 | 6061396 |
| 202 | 5 | 76481371 | 76481400 | 76658102 | 76658131 | 5 | 76477401 | 76481400 |
| 203 | 5 | 76540898 | 76540927 | 76725277 | 76725306 | 5 | 76540898 | 76544897 |
| 204 | 5 | 76654480 | 76654509 | 76725277 | 76725306 | 5 | 76654480 | 76658479 |
| 205 | 5 | 132477883 | 132477912 | 132497033 | 132497062 | 5 | 132473913 | 132477912 |
| 206 | 19 | 49654782 | 49654811 | 49691432 | 49691461 | 19 | 49654782 | 49658781 |
| 207 | 16 | 31324630 | 31324659 | 31389106 | 31389135 | 16 | 31320660 | 31324659 |
| 208 | 16 | 31352332 | 31352361 | 31389106 | 31389135 | 16 | 31348362 | 31352361 |

TABLE 13.d6

| | 4 kb Sequence Location | | Inner_primers | | |
|---|---|---|---|---|---|
| | Start2 | End2 | PCR-Primer1_ID | PCR_Primer1 | PCR-Primer2_ID |
| 157 | 161717040 | 161721039 | OBD117.1.901 | TGGATGGTTCCAGAGGTTTC (SEQ ID NO: 1025) | OBD117.1.903 |
| 158 | 161657865 | 161661864 | OBD117.1.905 | GCTGGAGATGGATCTGGGGG (SEQ ID NO: 1026) | OBD117.1.907 |
| 159 | 161657865 | 161661864 | OBD117.1.573 | GCCACCTGTCTCAGATACCCTTGGTT (SEQ ID NO: 1027) | OBD117.1.575 |
| 160 | 161717040 | 161721039 | OBD117.1.897 | GGGTAGAACGGGGGCAGTAG (SEQ ID NO: 1028) | OBD117.1.899 |
| 161 | 152576166 | 152580165 | OBD117.1.1317 | CCTTCAGGACACTGCTGGGAGGT (SEQ ID NO: 1029) | OBD117.1.1319 |
| 162 | 152664286 | 152668285 | OBD117.1.1529 | CTTCAGGACACTGCTGGGAGGTTTCT (SEQ ID NO: 1030) | OBD117.1.1531 |
| 163 | 10371170 | 10375169 | OBD117.1.1445 | CAGCAGTGTGGGAAGGGACATCT (SEQ ID NO: 1031) | OBD117.1.1447 |
| 164 | 10426676 | 10430675 | OBD117.1.1165 | GAGTGGGAAAGACCATTCTGAGATTC (SEQ ID NO: 1032) | OBD117.1.1167 |
| 165 | 65081229 | 65085228 | OBD117.1.1201 | GTGGTGGCTCACGCCTGTAATCCTA (SEQ ID NO: 1033) | OBD117.1.1203 |
| 166 | 14053588 | 14057587 | OBD117.1.1401 | TCTGAAAGGCTGGGTGCGGTAGC (SEQ ID NO: 1034) | OBD117.1.1403 |
| 167 | 78378836 | 78382835 | OBD117.1.141 | AGTCCCTGTAGATTTGAGAGCAGAAA (SEQ ID NO: 1035) | OBD117.1.143 |
| 168 | 78374350 | 78378349 | OBD117.1.1325 | CAAAGAGGGTCAGGCACTTCACAAAG (SEQ ID NO: 1036) | OBD117.1.1327 |
| 169 | 11360474 | 11364473 | OBD117.1.1333 | GGATGAATGGCTGTGTAAACTGTCTC (SEQ ID NO: 1037) | OBD117.1.1335 |
| 170 | 11366643 | 11370642 | OBD117.1.1833 | AATGGCTGTGTAAACTGTCTCTA (SEQ ID NO: 1038) | OBD117.1.1835 |

TABLE 13.d6-continued

| | 4 kb Sequence Location | | Inner_primers | | |
|---|---|---|---|---|---|
| | Start2 | End2 | PCR-Primer1_ID | PCR_Primer1 | PCR-Primer2_ID |
| 171 | 11464315 | 11468314 | OBD117.1.1785 | AATGGCTGTGTAAACTGTCTCTA (SEQ ID NO: 1039) | OBD117.1.1787 |
| 172 | 11473385 | 11477384 | OBD117.1.1377 | GGATGAATGGCTGTGTAAACTGTCTC (SEQ ID NO: 1040) | OBD117.1.1379 |
| 173 | 11483465 | 11487464 | OBD117.1.1741 | AATGGCTGTGTAAACTGTCTCTA (SEQ ID NO: 1041) | OBD117.1.1743 |
| 174 | 11547650 | 11551649 | OBD117.1.1141 | GGATGAATGGCTGTGTAAACTGTCTC (SEQ ID NO: 1042) | OBD117.1.1143 |
| 175 | 11553187 | 11557186 | OBD117.1.1841 | AATGGCTGTGTAAACTGTCTCTA (SEQ ID NO: 1043) | OBD117.1.1843 |
| 176 | 11549188 | 11553187 | OBD117.1.1845 | ATACCCACTGAAGCAGAAACTCT (SEQ ID NO: 1044) | OBD117.1.1847 |
| 177 | 4158439 | 4162438 | OBD117.1.1225 | CAGGATAGATAAGCCAGAAGGTAATA (SEQ ID NO: 1045) | OBD117.1.1227 |
| 178 | 133690869 | 133694868 | OBD117.1.1061 | TCTTCCTCCCCCTACCCTCT (SEQ ID NO: 1046) | OBD117.1.1063 |
| 179 | 24651000 | 24654999 | OBD117.1.923 | TTCCGGTTCAATATGAGATGG (SEQ ID NO: 1047) | OBD117.1.921 |
| 180 | 12009862 | 12013861 | OBD117.1.1777 | AAATAAAATCACCAACCCAGACG (SEQ ID NO: 1048) | OBD117.1.1779 |
| 181 | 12060031 | 12064030 | OBD117.1.1101 | CCTAAATAAAATCACCAACCCAGACG (SEQ ID NO: 1049) | OBD117.1.1103 |
| 182 | 32660961 | 32664960 | OBD117.1.401 | CGCCACCTCGTAGTTGTGTCTGC (SEQ ID NO: 1050) | OBD117.1.403 |
| 183 | 32662361 | 32666360 | OBD117.1.721 | AGTCAGCCACAAATCCTGGG (SEQ ID NO: 1051) | OBD117.1.723 |
| 184 | 32660961 | 32664960 | OBD117.1.413 | TGGTTCTGCTACCTGTGTGCCTG (SEQ ID NO: 1052) | OBD117.1.415 |
| 185 | 32662361 | 32666360 | OBD117.1.425 | TGGTTCTGCTACCTGTGTGCCTGC (SEQ ID NO: 1053) | OBD117.1.427 |
| 186 | 15802182 | 15806181 | OBD117.1.1749 | TGTAATGTGTCTCAGGTGTGGAG (SEQ ID NO: 1054) | OBD117.1.1751 |
| 187 | 98893484 | 98897483 | OBD117.1.209 | GATTTGTATCCGTGGGAGTCCTGG (SEQ ID NO: 1055) | OBD117.1.211 |
| 188 | 98957432 | 98961431 | OBD117.1.317 | TTCCTGTAGGGCTTCCACTGGCT (SEQ ID NO: 1056) | OBD117.1.319 |
| 189 | 98957432 | 98961431 | OBD117.1.101 | CCCACTTTGCCACAACTCTGGTG (SEQ ID NO: 1057) | OBD117.1.103 |
| 190 | 42267204 | 42271203 | OBD117.1.757 | GGTGTAACGGGGGTCATTTC (SEQ ID NO: 1058) | OBD117.1.759 |
| 191 | 42281222 | 42285221 | OBD117.1.281 | GCACGGTCTGTCTACTTTCCCTC (SEQ ID NO: 1059) | OBD117.1.283 |
| 192 | 42300681 | 42304680 | OBD117.1.037 | GCACGGTCTGTCTACTTTCCCTC (SEQ ID NO: 1060) | OBD117.1.039 |
| 193 | 42331044 | 42335043 | OBD117.1.073 | CGGTGAGCACGGTCTGTCTACTT (SEQ ID NO: 1061) | OBD117.1.075 |
| 194 | 20687045 | 20691044 | OBD117.1.693 | TCTCTACTTCAGGCAGGCAGTGTAAG (SEQ ID NO: 1062) | OBD117.1.695 |
| 195 | 20694636 | 20698635 | OBD117.1.929 | AGTTTTCCACCCCTTCTTCC (SEQ ID NO: 1063) | OBD117.1.931 |

TABLE 13.d6-continued

| | 4 kb Sequence Location | | Inner_primers | | |
|---|---|---|---|---|---|
| | Start2 | End2 | PCR-Primer1_ID | PCR_Primer1 | PCR-Primer2_ID |
| 196 | 20728864 | 20732863 | OBD117.1.665 | TCTCTACTTCAGGCAGGCAGTGTAAG (SEQ ID NO: 1064) | OBD117.1.667 |
| 197 | 20737979 | 20741978 | OBD117.1.581 | TCTCTACTTCAGGCAGGCAGTGTAAG (SEQ ID NO: 1065) | OBD117.1.583 |
| 198 | 102219626 | 102223625 | OBD117.1.1041 | GAATTTCTTTGCGTTTCCTCAAC (SEQ ID NO: 1066) | OBD117.1.1043 |
| 199 | 102264037 | 102268036 | OBD117.1.485 | GCCTGGCATTGCTCCTCTTCAGC (SEQ ID NO: 1067) | OBD117.1.487 |
| 200 | 23355422 | 23359421 | OBD117.1.289 | TTGTGGTGTCCTGCTGGGTCATC (SEQ ID NO: 1068) | OBD117.1.291 |
| 201 | 6106025 | 6110024 | OBD117.1.1017 | TGGTTTGAGGTAGAAGTTGGTGGT (SEQ ID NO: 1069) | OBD117.1.1019 |
| 202 | 76658102 | 76662101 | OBD117.1.1861 | TTTAACCTAGTATATCCCAAAC (SEQ ID NO: 1070) | OBD117.1.1863 |
| 203 | 76721307 | 76725306 | OBD117.1.1129 | GAAGGGCAGAACTGTGAGTCAAAACC (SEQ ID NO: 1071) | OBD117.1.1131 |
| 204 | 76721307 | 76725306 | OBD117.1.653 | CCCGAAGGGCAGAACTGTGAGTCAAA (SEQ ID NO: 1072) | OBD117.1.655 |
| 205 | 132493063 | 132497062 | OBD117.1.765 | GCATGGTCCTGAGTCTCACA (SEQ ID NO: 1073) | OBD117.1.767 |
| 206 | 49691432 | 49695431 | OBD117.1.285 | GCTGCCCTCTCTCTTGTCAGACG (SEQ ID NO: 1074) | OBD117.1.287 |
| 207 | 31385136 | 31389135 | OBD117.1.177 | AAGAACAGCACACGCAGACAGACACA (SEQ ID NO: 1075) | OBD117.1.179 |
| 208 | 31385136 | 31389135 | OBD117.1.173 | CCTCTTTGCTGAGCCTGAGTTGTCTG (SEQ ID NO: 1076) | OBD117.1.175 |

TABLE 13.d7

| | Inner_primers | |
|---|---|---|
| | PCR_Primer2 | GLMNET |
| 157 | GTCTGAGGACAGAGACCCCT (SEQ ID NO: 1077) | 0.007197773 |
| 158 | TGTCACAGTCCCTCTAGCACT (SEQ ID NO: 1078) | −0.014372166 |
| 159 | CTTCCTTTCCACACACCCTCAAATAC (SEQ ID NO: 1079) | −0.000142339 |
| 160 | TCCAGAGGTTTCTAGGGACGAC (SEQ ID NO: 1080) | 0.009781389 |
| 161 | GTCTCCCCTCCCTGGAAAGTAAG (SEQ ID NO: 1081) | 0 |
| 162 | GGTTTGGGATAACATTGGTAGAAGAG (SEQ ID NO: 1082) | 0 |
| 163 | GTAGGCTCTCTCCCTGTGTGTCAC (SEQ ID NO: 1083) | 0 |
| 164 | TGGAGAGATGTGAGGCTTGTGGTCCT (SEQ ID NO: 1084) | 0 |
| 165 | GAGGCAGGTTCTTTTCACATCCACT (SEQ ID NO: 1085) | 0 |
| 166 | GCCTCCCTTCCTATCTACTGTGTG (SEQ ID NO: 1086) | 0 |
| 167 | GGGACTACAGTTTCTCTGAGGGCTAA (SEQ ID NO: 1087) | −0.007419107 |
| 168 | CCCCAAGTCTTTCCTTTGTTGTAGGG (SEQ ID NO: 1088) | 0 |
| 169 | CAGGAAAACTAAACTTGGTGGAAATC (SEQ ID NO: 1089) | 0 |
| 170 | CTGGCTTTGTCTGCTGCTTCTAT (SEQ ID NO: 1090) | 0 |

TABLE 13.d7-continued

| | Inner_primers | |
|---|---|---|
| | PCR_Primer2 | GLMNET |
| 171 | TGGAGGAGGAACTTCAGGGCTGC (SEQ ID NO: 1091) | 0 |
| 172 | CCCAAAACGAGCCTTCTGGAATCCTC (SEQ ID NO: 1092) | 0 |
| 173 | TGACCTTTCCTGAACCCTCCTCA (SEQ ID NO: 1093) | 0 |
| 174 | CAGCGTAGAGGATGGGATAGAAGGGA (SEQ ID NO: 1094) | 0 |
| 175 | CGGTGGGATAAAGAAAGGAAAAC (SEQ ID NO: 1095) | 0 |
| 176 | GGAATCAAATGAGCCCAGGTTTA (SEQ ID NO: 1096) | 0 |
| 177 | GGAAAATGAGGAAAAGTCTGACAACT (SEQ ID NO: 1097) | 0 |
| 178 | CCCTACCTCCAAACCCCCTC (SEQ ID NO: 1098) | 0 |
| 179 | GGGGATGGGTCTTTTCACAG (SEQ ID NO: 1099) | 0.000121346 |
| 180 | GGATTCAGCATTACTACGAACTT (SEQ ID NO: 1100) | 0 |
| 181 | GGAACAAGATACTACTGGTGAACAAT (SEQ ID NO: 1101) | 0 |
| 182 | CCTTCCCTCCTTATTCCCACCCA (SEQ ID NO: 1102) | 0.009992562 |
| 183 | GCTGTCTGTTACTAGATTGCAC (SEQ ID NO: 1103) | 0.00011425 |
| 184 | CGCCACCTCGTAGTTGTGTCTGC (SEQ ID NO: 1104) | 0.002234049 |
| 185 | GGATGAGATGTGTAAAAGAGGCGGG (SEQ ID NO: 1105) | 0.0000993 |
| 186 | ACTACTGGCTGGTGTGAGAGAAT (SEQ ID NO: 1106) | 0 |
| 187 | ATTCCCACTTTGCCACAACTCTGGTG (SEQ ID NO: 1107) | 0.012827643 |
| 188 | GGGCAGCAAGGGCAGTTCTGAAG (SEQ ID NO: 1108) | -0.010330599 |
| 189 | GGGCAGCAAGGGCAGTTCTGAAG (SEQ ID NO: 1109) | 0.0000979 |
| 190 | TGCAACCTCTGCCTTCTG (SEQ ID NO: 1110) | 0.00012094 |
| 191 | TGGAGATGCTGCTCTGCCCACCT (SEQ ID NO: 1111) | -0.00399849 |
| 192 | CGTTGCCTCCTCACAGCAGAAGC (SEQ ID NO: 1112) | 0.002891486 |
| 193 | GTCCTGGGTCCTGGGTGAAAGTC (SEQ ID NO: 1113) | 0.017565968 |
| 194 | GGGAGACCATTTCTGTTCACTCTGAG (SEQ ID NO: 1114) | -0.022219432 |
| 195 | GGGCTGTGTCCTGATAAACC (SEQ ID NO: 1115) | -0.015662127 |
| 196 | TTATTGTTTCCTTAGGGAGGGCGTCC (SEQ ID NO: 1116) | 0.000119444 |
| 197 | GGTAATAGCCGTTGATACTCAGTGCC (SEQ ID NO: 1117) | -0.027382095 |
| 198 | TACATCAACAGTGGGCTCCC (SEQ ID NO: 1118) | 0 |
| 199 | TGCCTGTGTCACTCCACCATCAG (SEQ ID NO: 1119) | 0 |
| 200 | GGAGCAGCCCATCTATCCTGACC (SEQ ID NO: 1120) | 0.007589853 |
| 201 | TCCAATAGTACCCCGAGATTTTCCT (SEQ ID NO: 1121) | 0 |
| 202 | GAGAGAGAGCTGATAAAAGGGATA (SEQ ID NO: 1122) | 0.000113252 |
| 203 | GGTAGGTGTCTGTCAAAAGGAGTGCT (SEQ ID NO: 1123) | 0 |
| 204 | TATTCAGGAAGAAATCCCTCCCAGG (SEQ ID NO: 1124) | 0.003005705 |
| 205 | CTGGGTTTCGGTTTCTTGC (SEQ ID NO: 1125) | -0.010031296 |
| 206 | GTCCACCCCATTGCCGCTTTTCA (SEQ ID NO: 1126) | -0.025409945 |

TABLE 13.d7-continued

| | Inner primers | |
|---|---|---|
| | PCR_Primer2 | GLMNET |
| 207 | CCCTCTGGACAAAGGTATTATCCCTG (SEQ ID NO: 1127) | 0.006986068 |
| 208 | CCTCTGGACAAAGGTATTATCCCTGA (SEQ ID NO: 1128) | 0.004807037 |

TABLE 13.e1

| | Probe | GeneLocus | Probe_Count_Total | Probe_Count_Sig |
|---|---|---|---|---|
| 209 | ORF338_5_157249288_157254103_157266725_157271762_RR | ITK | 26 | 10 |
| 210 | ORF344_11_134020188_134023093_134179549_134189517_FR | ORF344 | 34 | 2 |
| 211 | ORF344_11_134159769_134169350_134179549_134189517_FF | ORF344 | 34 | 2 |
| 212 | ORF346_7_27813244_27816991_28040393_28050768_RR | ORF346 | 183 | 7 |
| 213 | ORF346_7_28023391_28029625_28087716_28092793_FR | ORF346 | 183 | 7 |
| 214 | ORF348_9_554821_562273_667141_671048_RR | ORF348 | 106 | 14 |
| 215 | ORF348_9_554821_562273_787920_792102_RR | ORF348 | 106 | 14 |
| 216 | ORF362_6_112077312_112085830_112110080_112119298_RR | ORF362 | 167 | 8 |
| 217 | ORF362_6_112212817_112219150_112260826_112263612_FF | ORF362 | 167 | 8 |
| 218 | ORF368_1_32214585_32217213_32237144_32241139_RF | ORF368 | 29 | 2 |
| 219 | ORF369_13_46087370_46090583_46186579_46193039_RF | ORF369 | 31 | 1 |
| 220 | ORF375_8_29646848_29651360_29765923_29776926_RF | ORF375 | 94 | 12 |
| 221 | ORF38_13_111078224_111080305_111255999_111262146_RF | ORF38 | 86 | 4 |
| 222 | ORF38_13_111170222_111182176_111317973_111320769_FF | ARHGEF7 | 122 | 6 |
| 223 | ORF38_13_111255999_111262146_111299563_111302082_RF | ORF38 | 86 | 4 |
| 224 | ORF38_13_111255999_111262146_111317973_111320769_FF | ARHGEF7 | 122 | 6 |
| 225 | ORF380_4_150333761_150340859_150518099_150527260_RF | ORF380 | 167 | 15 |
| 226 | ORF380_4_150518099_150527260_150647820_150652813_FR | ORF380 | 167 | 15 |
| 227 | ORF382_1_89794704_89801882_89881274_89886132_RR | ORF382 | 44 | 2 |
| 228 | ORF385_6_31567353_31572622_31588788_31590397_FR | ORF385 | 16 | 2 |
| 229 | ORF385_6_31567353_31572622_31621846_31623705_FF | ORF385 | 16 | 2 |
| 230 | ORF39_6_156816268_156822259_157042082_157049787_RF | ORF39 | 156 | 10 |
| 231 | ORF39_6_156830748_156835572_157042082_157049787_RF | ORF39 | 156 | 10 |
| 232 | ORF390_6_6365985_6370040_6413040_6420698_RR | ORF390 | 136 | 6 |
| 233 | ORF393_1_235718481_235723036_235759465_235763923_RR | ORF393 | 32 | 5 |
| 234 | ORF396_20_34509223_34513477_34530923_34534728_FR | ORF396 | 30 | 2 |
| 235 | ORF396_20_34530923_34534728_34578621_34584178_RF | ORF396 | 30 | 2 |
| 236 | ORF400_6_136518089_136523843_136551414_136554889_FR | ORF400 | 170 | 13 |
| 237 | ORF401_4_86120725_86131416_86336679_86343485_FF | MAPK10 | 186 | 10 |
| 238 | ORF403_9_125608173_125614421_125631239_125635100_RF | MAPKAP1 | 52 | 6 |
| 239 | ORF404_3_192770374_192778803_192893705_192896438_FF | ORF404 | 95 | 5 |
| 240 | ORF404_3_192893705_192896438_192941417_192949607_FF | ORF404 | 95 | 5 |
| 241 | ORF408_11_86466088_86493462_86595548_86597707_RF | ORF408 | 141 | 26 |
| 242 | ORF41_3_5096550_5098368_5223126_5230817_FR | ORF41 | 16 | 2 |
| 243 | ORF41_3_5096550_5098368_5223126_5230817_RR | ORF41 | 16 | 2 |
| 244 | ORF415_11_123335039_123337301_123352543_123361037_FR | ORF415 | 27 | 2 |
| 245 | ORF415_11_123335039_123337301_123381608_123388566_FR | ORF415 | 27 | 2 |
| 246 | ORF420_17_62595182_62602105_62650420_62653849_FR | ORF420 | 30 | 5 |
| 247 | ORF430_17_32545190_32546373_32729890_32740232_FR | ORF430 | 168 | 28 |
| 248 | ORF430_17_32585527_32592720_32673793_32677732_FR | ORF430 | 168 | 28 |
| 249 | ORF430_17_32585527_32592720_32729890_32740232_FF | ORF430 | 168 | 28 |
| 250 | ORF430_17_32585527_32592720_32729890_32740232_FR | ORF430 | 168 | 28 |
| 251 | ORF430_17_32585527_32592720_32761107_32765317_FF | ORF430 | 168 | 28 |
| 252 | ORF430_17_32585527_32592720_32797503_32800497_FR | ORF430 | 168 | 28 |
| 253 | ORF430_17_32585527_32592720_32833313_32837843_FR | ORF430 | 168 | 28 |
| 254 | ORF430_17_32585527_32592720_32856904_32867594_FR | ORF430 | 168 | 28 |
| 255 | ORF430_17_32585527_32592720_32890505_32898320_FF | ORF430 | 168 | 28 |
| 256 | ORF433_17_78250119_78253853_78298158_78301405_RF | ORF433 | 6 | 1 |
| 257 | ORF439_4_153659613_153661830_153693586_153700349_RF | ORF439 | 31 | 4 |
| 258 | ORF440_5_142382167_142389103_142659891_142662908_RF | ORF440 | 107 | 11 |
| 259 | ORF440_5_142457784_142464671_142659891_142662908_RF | ORF440 | 107 | 11 |
| 260 | ORF441_5_68187850_68194388_68215410_68221074_FR | PIK3R1 | 148 | 12 |

TABLE 13.e2

| | HyperG_Stats | FDR_HyperG | Percent_Sig | logFC | AveExpr | t |
|---|---|---|---|---|---|---|
| 209 | 1.57E−05 | 0.002607465 | 38.46 | −0.180610127 | −0.180610127 | −7.561434137 |
| 210 | 0.669241433 | 1 | 5.88 | 0.357950707 | 0.357950707 | 2.340298734 |
| 211 | 0.669241433 | 1 | 5.88 | 0.152342312 | 0.152342312 | 3.053183376 |
| 212 | 0.946917297 | 1 | 3.83 | 0.283333374 | 0.283333374 | 12.94789466 |
| 213 | 0.946917297 | 1 | 3.83 | 0.298409308 | 0.298409308 | 7.840334822 |

TABLE 13.e2-continued

|     | HyperG_Stats | FDR_HyperG | Percent_Sig | logFC | AveExpr | t |
|---|---|---|---|---|---|---|
| 214 | 0.006786743 | 0.142219973 | 13.21 | 0.387341996 | 0.387341996 | 5.392692894 |
| 215 | 0.006786743 | 0.142219973 | 13.21 | 0.428239329 | 0.428239329 | 3.25451194 |
| 216 | 0.832957146 | 1 | 4.79 | 0.330158237 | 0.330158237 | 7.62185597 |
| 217 | 0.832957146 | 1 | 4.79 | 0.328841609 | 0.328841609 | 6.21961495 |
| 218 | 0.553587753 | 1 | 6.9 | 0.320236904 | 0.320236904 | 6.484888245 |
| 219 | 0.867297772 | 1 | 3.23 | 0.148960904 | 0.148960904 | 5.342674119 |
| 220 | 0.015049943 | 0.258038105 | 12.77 | 0.287047599 | 0.287047599 | 7.276689361 |
| 221 | 0.79882882 | 1 | 4.65 | 0.380176873 | 0.380176873 | 5.637761714 |
| 222 | 0.928958915 | 0.99999793 | 4.92 | −0.390398405 | −0.390398405 | −17.0031469 |
| 223 | 0.79882882 | 1 | 4.65 | 0.376927136 | 0.376927136 | 11.41950058 |
| 224 | 0.928958915 | 0.99999793 | 4.92 | −0.47329526 | −0.47329526 | −22.94378205 |
| 225 | 0.106360783 | 0.853264106 | 8.98 | 0.329280423 | 0.329280423 | 7.536413978 |
| 226 | 0.106360783 | 0.853264106 | 8.98 | 0.30661866 | 0.30661866 | 8.522452372 |
| 227 | 0.774574169 | 1 | 4.55 | 0.280706816 | 0.280706816 | 6.330999822 |
| 228 | 0.309387385 | 1 | 12.5 | −0.206647528 | −0.206647528 | −10.52550054 |
| 229 | 0.309387385 | 1 | 12.5 | −0.139665252 | −0.139665252 | −6.665441939 |
| 230 | 0.525030009 | 1 | 6.41 | 0.475425436 | 0.475425436 | 10.95020836 |
| 231 | 0.525030009 | 1 | 6.41 | 0.311742802 | 0.311742802 | 7.907001501 |
| 232 | 0.86474997 | 1 | 4.41 | 0.337386785 | 0.337386785 | 5.875969399 |
| 233 | 0.048263623 | 0.576108821 | 15.62 | 0.284781992 | 0.284781992 | 11.20881501 |
| 234 | 0.630241863 | 1 | 6.67 | −0.161515168 | −0.161515168 | −9.011068418 |
| 235 | 0.630241863 | 1 | 6.67 | −0.153338244 | −0.153338244 | −7.520061763 |
| 236 | 0.276096504 | 1 | 7.65 | 0.310767638 | 0.310767638 | 3.855741234 |
| 237 | 0.931377207 | 0.99999793 | 5.38 | −0.18453906 | −0.18453906 | −3.956476668 |
| 238 | 0.229017635 | 0.99999793 | 11.54 | −0.163709607 | −0.163709607 | −3.931754114 |
| 239 | 0.72257664 | 1 | 5.26 | 0.345706098 | 0.345706098 | 4.276857582 |
| 240 | 0.72257664 | 1 | 5.26 | 0.579695032 | 0.579695032 | 2.972500329 |
| 241 | 7.32E−07 | 0.000126288 | 18.44 | 0.292429157 | 0.292429157 | 8.470996679 |
| 242 | 0.267454675 | 1 | 12.5 | 0.310792224 | 0.310792224 | 9.411865337 |
| 243 | 0.267454675 | 1 | 12.5 | 0.304505394 | 0.304505394 | 7.908184476 |
| 244 | 0.514651704 | 1 | 7.41 | 0.285130311 | 0.285130311 | 10.6103307 |
| 245 | 0.514651704 | 1 | 7.41 | 0.292704671 | 0.292704671 | 6.331170439 |
| 246 | 0.037848586 | 0.469621268 | 16.67 | 0.333271938 | 0.333271938 | 10.68233567 |
| 247 | 2.30E−06 | 0.000217011 | 16.67 | 0.313678475 | 0.313678475 | 6.668777731 |
| 248 | 2.30E−06 | 0.000217011 | 16.67 | 0.718337876 | 0.718337876 | 3.390385035 |
| 249 | 2.30E−06 | 0.000217011 | 16.67 | 0.67380724 | 0.67380724 | 3.364859567 |
| 250 | 2.30E−06 | 0.000217011 | 16.67 | 0.922461761 | 0.922461761 | 3.446514196 |
| 251 | 2.30E−06 | 0.000217011 | 16.67 | 0.914009139 | 0.914009139 | 3.641671967 |
| 252 | 2.30E−06 | 0.000217011 | 16.67 | 0.942537109 | 0.942537109 | 3.821121196 |
| 253 | 2.30E−06 | 0.000217011 | 16.67 | 0.722069612 | 0.722069612 | 3.216502836 |
| 254 | 2.30E−06 | 0.000217011 | 16.67 | 0.476534879 | 0.476534879 | 3.333055657 |
| 255 | 2.30E−06 | 0.000217011 | 16.67 | 0.419624416 | 0.419624416 | 3.646251648 |
| 256 | 0.352766908 | 1 | 16.67 | −0.195782617 | −0.195782617 | −5.226124183 |
| 257 | 0.128543197 | 0.904598768 | 12.9 | 0.29139179 | 0.29139179 | 8.633276617 |
| 258 | 0.074555092 | 0.72879893 | 10.28 | 0.330476001 | 0.330476001 | 11.06260353 |
| 259 | 0.074555092 | 0.72879893 | 10.28 | 0.364678783 | 0.364678783 | 12.7287492 |
| 260 | 0.513477047 | 0.99999793 | 8.11 | −0.396269087 | −0.396269087 | −16.24057806 |

TABLE 13.e3

|     | P. Value | adj. P. Val | B | FC | FC_1 | LS |
|---|---|---|---|---|---|---|
| 209 | 0.0000167 | 0.000397765 | 3.289725067 | 0.882329773 | −1.133363092 | −1 |
| 210 | 0.040741366 | 0.093212255 | −4.711020953 | 1.281604134 | 1.281604134 | 1 |
| 211 | 0.011861827 | 0.036959918 | −3.494889529 | 1.111372396 | 1.111372396 | 1 |
| 212 | 0.000000111 | 0.0000279 | 8.36797508 | 1.217003548 | 1.217003548 | 1 |
| 213 | 0.0000121 | 0.000321152 | 3.621882899 | 1.229787722 | 1.229787722 | 1 |
| 214 | 0.000279967 | 0.002466566 | 0.358709102 | 1.307981373 | 1.307981373 | 1 |
| 215 | 0.008388704 | 0.028471537 | −3.14593534 | 1.34559041 | 1.34559041 | 1 |
| 216 | 0.0000156 | 0.000381287 | 3.362483276 | 1.257151253 | 1.257151253 | 1 |
| 217 | 0.000089 | 0.001151446 | 1.5527701 | 1.256004479 | 1.256004479 | 1 |
| 218 | 0.0000628 | 0.000908877 | 1.915293694 | 1.248535553 | 1.248535553 | 1 |
| 219 | 0.000300988 | 0.002596993 | 0.283332726 | 1.108770596 | 1.108770596 | 1 |
| 220 | 0.0000234 | 0.000487262 | 2.940760759 | 1.220140766 | 1.220140766 | 1 |
| 221 | 0.00019737 | 0.001952202 | 0.722811617 | 1.301501408 | 1.301501408 | 1 |
| 222 | 0.00000000765 | 0.0000107 | 10.90661915 | 0.762918893 | −1.310755324 | −1 |
| 223 | 0.000000373 | 0.0000513 | 7.171532484 | 1.298573016 | 1.298573016 | 1 |
| 224 | 0.000000000382 | 0.00000159 | 13.50068753 | 0.72031744 | −1.388276813 | −1 |
| 225 | 0.0000172 | 0.000404351 | 3.259465584 | 1.256386566 | 1.256386566 | 1 |
| 226 | 0.00000573 | 0.000209476 | 4.396057544 | 1.236805517 | 1.236805517 | 1 |
| 227 | 0.0000768 | 0.001043977 | 1.70618126 | 1.214789898 | 1.214789898 | 1 |
| 228 | 0.000000809 | 0.0000728 | 6.393479433 | 0.866548541 | −1.154003443 | −1 |
| 229 | 0.0000498 | 0.000782222 | 2.156491332 | 0.907729751 | −1.101649471 | −1 |
| 230 | 0.000000556 | 0.0000617 | 6.770928087 | 1.390328153 | 1.390328153 | 1 |
| 231 | 0.0000113 | 0.000306728 | 3.699902454 | 1.241206194 | 1.241206194 | 1 |

TABLE 13.e3-continued

|  | P. Value | adj. P. Val | B | FC | FC_1 | LS |
|---|---|---|---|---|---|---|
| 232 | 0.000141646 | 0.001566448 | 1.068435975 | 1.26346595 | 1.26346595 | 1 |
| 233 | 0.000000445 | 0.0000562 | 6.993759854 | 1.218226162 | 1.218226162 | 1 |
| 234 | 0.00000345 | 0.000156596 | 4.919302407 | 0.894085578 | −1.118461168 | −1 |
| 235 | 0.0000176 | 0.000409391 | 3.239647539 | 0.899167475 | −1.112139872 | −1 |
| 236 | 0.003042322 | 0.013373385 | −2.112164163 | 1.240367507 | 1.240367507 | 1 |
| 237 | 0.00257667 | 0.0118777 | −1.941508536 | 0.879930168 | −1.136453819 | −1 |
| 238 | 0.002683585 | 0.012258029 | −1.983302218 | 0.892726646 | −1.120163719 | −1 |
| 239 | 0.001532146 | 0.008180014 | −1.405688605 | 1.270772784 | 1.270772784 | 1 |
| 240 | 0.013636816 | 0.040961218 | −3.634591611 | 1.494533289 | 1.494533289 | 1 |
| 241 | 0.00000606 | 0.000215806 | 4.339475884 | 1.224700649 | 1.224700649 | 1 |
| 242 | 0.00000231 | 0.0001274 | 5.329296753 | 1.240388645 | 1.240388645 | 1 |
| 243 | 0.0000112 | 0.000306728 | 3.701282153 | 1.234995165 | 1.234995165 | 1 |
| 244 | 0.00000075 | 0.0000707 | 6.470042002 | 1.218520321 | 1.218520321 | 1 |
| 245 | 0.0000768 | 0.001043977 | 1.706414923 | 1.224934555 | 1.224934555 | 1 |
| 246 | 0.000000704 | 0.0000689 | 6.534564973 | 1.259867433 | 1.259867433 | 1 |
| 247 | 0.0000496 | 0.000780674 | 2.160905808 | 1.242872647 | 1.242872647 | 1 |
| 248 | 0.006650427 | 0.023946067 | −2.910710578 | 1.645285415 | 1.645285415 | 1 |
| 249 | 0.006946167 | 0.024741342 | −2.95485979 | 1.595277318 | 1.595277318 | 1 |
| 250 | 0.006044847 | 0.022344385 | −2.813716523 | 1.895346684 | 1.895346684 | 1 |
| 251 | 0.004347344 | 0.017453856 | −2.477713882 | 1.884274484 | 1.884274484 | 1 |
| 252 | 0.003221971 | 0.013975957 | −2.171027926 | 1.921905112 | 1.921905112 | 1 |
| 253 | 0.008953939 | 0.029904578 | −3.211807256 | 1.649546688 | 1.649546688 | 1 |
| 254 | 0.007333674 | 0.025784467 | −3.009898236 | 1.391397737 | 1.391397737 | 1 |
| 255 | 0.004314044 | 0.017363236 | −2.469857016 | 1.337579291 | 1.337579291 | 1 |
| 256 | 0.00035679 | 0.002914808 | 0.106302737 | 0.873099138 | −1.145345306 | −1 |
| 257 | 0.0000051 | 0.000194414 | 4.516948685 | 1.223820347 | 1.223820347 | 1 |
| 258 | 0.000000505 | 0.0000588 | 6.868410636 | 1.257428181 | 1.257428181 | 1 |
| 259 | 0.000000131 | 0.000032 | 8.205867689 | 1.287594914 | 1.287594914 | 1 |
| 260 | 0.000000012 | 0.0000107 | 10.48782055 | 0.759820695 | −1.316099977 | −1 |

TABLE 13.e4

|  | Loop detected | Probe sequence 60 mer |
|---|---|---|
| 209 | PD-L1 responder | TACAGACTTTTTTTCTCTTCTCAGAAAATCGATGTTTGGGGGCGGAGGGCTTTGATGAGA (SEQ ID NO: 1129) |
| 210 | PD-L1 Non-responder | TGCCCATTTGCATTTCATATCCATCATCTCGATTAGCTCTGGTGAACACCTGTGTATCCT (SEQ ID NO: 1130) |
| 211 | PD-L1 Non-responder | CCAGCTGCAGTTCAAGTGGGGAAAGTAATCGAAGGTCAAAGACCAGTGAATTGGAAGATT (SEQ ID NO: 1131) |
| 212 | PD-L1 Non-responder | GGCAGGAGGATCACTTCAGCCCAAGAGGTCGAAGAGAGATGAGTACTATAAAGAAAATTA (SEQ ID NO: 1132) |
| 213 | PD-L1 Non-responder | TCTATAGAATTCTTAGGAAATAATGTTTTCGACATAAGGTTTTTCAAAATTCCTAATCAG (SEQ ID NO: 1133) |
| 214 | PD-L1 Non-responder | TTTTAAATTTTCACATCGTTCTAGTATATCGAGGTTTTCTCTTTCTTCGTGGTTCAATTT (SEQ ID NO: 1134) |
| 215 | PD-L1 Non-responder | TTTTAAATTTTCACATCGTTCTAGTATATCGAAGAAAGATGAAAAGGATTGAGAAAATCT (SEQ ID NO: 1135) |
| 216 | PD-L1 Non-responder | ATCAGAAAGTTATCTTTAATGAGATTCCTCGAATAAACTAAGATTCAATTTTTCTGAGCT (SEQ ID NO: 1136) |
| 217 | PD-L1 Non-responder | TATTTTTACTGAATCTTTCTTTGAAATTTCGATTATTAAATACTCAAGGAATAAGGGATG (SEQ ID NO: 1137) |
| 218 | PD-L1 Non-responder | AAGGGCTCGGGAGCTCCCTCGGCACACCTCGAGGAGTGCCAGGCATCTACTGCTCTGTCC (SEQ ID NO: 1138) |
| 219 | Non-Responder | AGGAGGGAGAAAAGTGATGAAGGCCATTTCGAGATGGGTGCCTGGGTGAGAATTTTAATA (SEQ ID NO: 1139) |
| 220 | PD-L1 Non-responder | GTGAATTCTGCAGGATATGATGGCCAATTCGAGATAATTTTAATTTGTCTACTGATGAGC (SEQ ID NO: 1140) |
| 221 | PD-L1 Non-responder | GTAAATGAATTTGAAATATTACAAAAGATCGATTACAGGCATTTTATAGCCACAAACTCA (SEQ ID NO: 1141) |

TABLE 13.e4-continued

| | Loop detected | Probe sequence 60 mer |
|---|---|---|
| 222 | PD-L1 responder | CGCAGCAGTCTCGTTGATCTTCACGGTGTCGACTCACCTGCGCCTCACATCCCAGGCGGG (SEQ ID NO: 1142) |
| 223 | PD-L1 Non-responder | AATTCTGTTGGAAGAATAATTTAAAATATCGATATTTTAATTATTTTTTTCCTAAAATAG (SEQ ID NO: 1143) |
| 224 | PD-L1 responder | GTAAATGAATTTGAAATATTACAAAAGATCGACTCACCTGCGCCTCACATCCCAGGCGGG (SEQ ID NO: 1144) |
| 225 | PD-L1 Non-responder | ATACTTTTCTTTCTAGATTATTTAAACATCGATATCAGTTAAGTTTAAAAACATATTAAT (SEQ ID NO: 1145) |
| 226 | PD-L1 Non-responder | ATACTTTTCTTTCTAGATTATTTAAACATCGAGATATTTATCTACATCTATTATTGTGGT (SEQ ID NO: 1146) |
| 227 | PD-L1 Non-responder | CCCCCAAAATAGGGTCTGATTTGGGGGTTCGATTGCATATTCTTTGGAAAATACAAAGTG (SEQ ID NO: 1147) |
| 228 | PD-L1 responder | CTCTGACTGCATCTTGTCCCCTTCTCTGTCGAGCCTCCGTTCAAATTGATCATCATCAAA (SEQ ID NO: 1148) |
| 229 | PD-L1 responder | CTCTGACTGCATCTTGTCCCCTTCTCTGTCGAAAATGCCTCATGTGGGAGATCTGATGGC (SEQ ID NO: 1149) |
| 230 | PD-L1 Non-responder | TATTCTAAAATTAATTTCAAACAAATTTTCGATTTTCATAATTTTATTACTTATACTTGA (SEQ ID NO: 1150) |
| 231 | PD-L1 Non-responder | TATTCTAAAATTAATTTCAAACAAATTTTCGAGACCCTAAAAAAAAAAGAAATAAAATAA (SEQ ID NO: 1151) |
| 232 | PD-L1 Non-responder | CTAATTAAATATAATCTAAATTTCCATCTCGACGTACATACGAGGAGAATGAGTAGGAAC (SEQ ID NO: 1152) |
| 233 | PD-L1 Non-responder | GGCAGGCAGATCACCTGACGTCAGGAGTTCGATACTACAACCCAAACTTCCAGTCAGTTT (SEQ ID NO: 1153) |
| 234 | PD-L1 responder | GTACTGCTACTTACCACAACACTGGGAGTCGAGCCATCTGCCACTGCCTTTTGACATCTC (SEQ ID NO: 1154) |
| 235 | PD-L1 responder | TGGGAAAATCATCCCACCTCTCTGAGCATCGAGCCATCTGCCACTGCCTTTTGACATCTC (SEQ ID NO: 1155) |
| 236 | PD-L1 Non-responder | CAAAAATTGCCAAAAATAAGTAGGTTTTTCGAGAACAGTATTGGATTTATTGTTAGGGTT (SEQ ID NO: 1156) |
| 237 | PD-L1 responder | GAGGATTTAATAAAACCCAAACTGTATTTCGAGAAAATAGTGTTTTGCTATTTAGATAAG (SEQ ID NO: 1157) |
| 238 | PD-L1 responder | CACTAATCTTTACTCTTTTTCCACTTATTCGAAGTTTCCAGAAAAGTCCTGAAGTTTTAA (SEQ ID NO: 1158) |
| 239 | PD-L1 Non-responder | TGTCCCCAGATGGATTGTAGACATAAATTCGAAGTTGCAGTGTACTATGACTGCACAACA (SEQ ID NO: 1159) |
| 240 | PD-L1 Non-responder | TGTTGTGCAGTCATAGTACACTGCAACTTCGAACTGACTTCTTCCACTCAGTATAATGTC (SEQ ID NO: 1160) |
| 241 | PD-L1 Non-responder | TTCTTTAAAATATTTGAAGAGATTTATTTCGAGTTTTGTAACCTATTTTTCCTTTTAACA (SEQ ID NO: 1161) |
| 242 | PD-L1 Non-responder | TTAGGGTGCACCCTAACCCAATAGGATGTCGAAGAAAATGACCTGATCATTTGAAAAGCT (SEQ ID NO: 1162) |
| 243 | PD-L1 Non-responder | CCTCCCTTACTGGGTATCATTATTAAGCTCGAAGAAAATGACCTGATCATTTGAAAAGCT (SEQ ID NO: 1163) |
| 244 | PD-L1 Non-responder | TAAATGTAAAACATAAAACTACAAAACTTCGATTATCACATTATATACTTATCGTGTGGC (SEQ ID NO: 1164) |
| 245 | PD-L1 Non-responder | TAAATGTAAAACATAAAACTACAAAACTTCGAGGTTCTAATATATAGGTTGAAGGTTCCT (SEQ ID NO: 1165) |
| 246 | PD-L1 Non-responder | AGAGATAAAAATTACAGATTTTGGTCTTTCGACTGGAAATCTACATTTTTATGTGTAATC (SEQ ID NO: 1166) |

TABLE 13.e4-continued

| | Loop detected | Probe sequence 60 mer |
|---|---|---|
| 247 | PD-L1 Non-responder | CCTCTGCGAGGAGCTCTGTCTGTCTTTGTCGAACTGATATAAACTTTCAGTTGTTCTATT (SEQ ID NO: 1167) |
| 248 | PD-L1 Non-responder | GAGAAAACAATCTAGCTGTTACAAATGTTCGATAGTTCTTAATTGTTTTGGGGTAACTGG (SEQ ID NO: 1168) |
| 249 | PD-L1 Non-responder | GAGAAAACAATCTAGCTGTTACAAATGTTCGAAATTTTCAAAGTACACAAAGTGCAATTT (SEQ ID NO: 1169) |
| 250 | PD-L1 Non-responder | GAGAAAACAATCTAGCTGTTACAAATGTTCGAACTGATATAAACTTTCAGTTGTTCTATT (SEQ ID NO: 1170) |
| 251 | PD-L1 Non-responder | GAGAAAACAATCTAGCTGTTACAAATGTTCGATTACATAAAAATGTAAAACTTTTATCTA (SEQ ID NO: 1171) |
| 252 | PD-L1 Non-responder | GAGAAAACAATCTAGCTGTTACAAATGTTCGAGAGAAACATCACATTCATATAACTTTTA (SEQ ID NO: 1172) |
| 253 | PD-L1 Non-responder | GAGAAAACAATCTAGCTGTTACAAATGTTCGAGAATCCATCTATCTTCAAAGTATAAACA (SEQ ID NO: 1173) |
| 254 | PD-L1 Non-responder | GAGAAAACAATCTAGCTGTTACAAATGTTCGATATTCTACACATACAGTCATCCCCTCCC (SEQ ID NO: 1174) |
| 255 | PD-L1 Non-responder | GAGAAAACAATCTAGCTGTTACAAATGTTCGACTCAAGTTGTCTCACCTTTCCAGACTGA (SEQ ID NO: 1175) |
| 256 | PD-L1 responder | GGATTCACCTTGATGCTATCTAAGTCCCTCGAGGGAGACGCCGCTGCTCCCATTTCACAG (SEQ ID NO: 1176) |
| 257 | PD-L1 Non-responder | TAAAACTATTTTAAATGTTTTTAAAGTATCGATGTGTACTTTGACATCTGTGATGATGAT (SEQ ID NO: 1177) |
| 258 | PD-L1 Non-responder | AGTGGCACAATCTCAGCTCATTATAGCCTCGAATCAGAATGTTTGGGGGTGAGCTTGGAA (SEQ ID NO: 1178) |
| 259 | PD-L1 Non-responder | AGTGGCACAATCTCAGCTCATTATAGCCTCGAATTGTAACTACCAGTGTTGGAGGAGGGG (SEQ ID NO: 1179) |
| 260 | PD-L1 responder | CTGAGTCTTCATTACCAAAAAAAAAAGTTCGACCTCCCCGAACCCCTCCGCCTCTGCGCT (SEQ ID NO: 1180) |

TABLE 13.e5

| | Probe Location | | | | 4 kb Sequence Location | | |
|---|---|---|---|---|---|---|---|
| | Chr | Start1 | End1 | Start2 | End2 | Chr | Start1 | End1 |
| 209 | 5 | 157249288 | 157249317 | 157266725 | 157266754 | 5 | 157249288 | 157253287 |
| 210 | 11 | 134023064 | 134023093 | 134179549 | 134179578 | 11 | 134019094 | 134023093 |
| 211 | 11 | 134169321 | 134169350 | 134189488 | 134189517 | 11 | 134165351 | 134169350 |
| 212 | 7 | 27813244 | 27813273 | 28040393 | 28040422 | 7 | 27813244 | 27817243 |
| 213 | 7 | 28029596 | 28029625 | 28087716 | 28087745 | 7 | 28025626 | 28029625 |
| 214 | 9 | 554821 | 554850 | 667141 | 667170 | 9 | 554821 | 558820 |
| 215 | 9 | 554821 | 554850 | 787920 | 787949 | 9 | 554821 | 558820 |
| 216 | 6 | 112077312 | 112077341 | 112110080 | 112110109 | 6 | 112077312 | 112081311 |
| 217 | 6 | 112219121 | 112219150 | 112263583 | 112263612 | 6 | 112215151 | 112219150 |
| 218 | 1 | 32214585 | 32214614 | 32241110 | 32241139 | 1 | 32214585 | 32218584 |
| 219 | 13 | 46087370 | 46087399 | 46193010 | 46193039 | 13 | 46087370 | 46091369 |
| 220 | 8 | 29646848 | 29646877 | 29776897 | 29776926 | 8 | 29646848 | 29650847 |
| 221 | 13 | 111078224 | 111078253 | 111262117 | 111262146 | 13 | 111078224 | 111082223 |
| 222 | 13 | 111182147 | 111182176 | 111320740 | 111320769 | 13 | 111178177 | 111182176 |
| 223 | 13 | 111255999 | 111256028 | 111302053 | 111302082 | 13 | 111255999 | 111259998 |
| 224 | 13 | 111262117 | 111262146 | 111320740 | 111320769 | 13 | 111258147 | 111262146 |
| 225 | 4 | 150333761 | 150333790 | 150527231 | 150527260 | 4 | 150333761 | 150337760 |
| 226 | 4 | 150527231 | 150527260 | 150647820 | 150647849 | 4 | 150523261 | 150527260 |
| 227 | 1 | 89794704 | 89794733 | 89881274 | 89881303 | 1 | 89794704 | 89798703 |
| 228 | 6 | 31572593 | 31572622 | 31588788 | 31588817 | 6 | 31568623 | 31572622 |
| 229 | 6 | 31572593 | 31572622 | 31623676 | 31623705 | 6 | 31568623 | 31572622 |
| 230 | 6 | 156816268 | 156816297 | 157049758 | 157049787 | 6 | 156816268 | 156820267 |
| 231 | 6 | 156830748 | 156830777 | 157049758 | 157049787 | 6 | 156830748 | 156834747 |
| 232 | 6 | 6365985 | 6366014 | 6413040 | 6413069 | 6 | 6365985 | 6369984 |
| 233 | 1 | 235718481 | 235718510 | 235759465 | 235759494 | 1 | 235718481 | 235722480 |

TABLE 13.e5-continued

| | Probe Location | | | | 4 kb Sequence Location | | |
|---|---|---|---|---|---|---|---|
| | Chr | Start1 | End1 | Start2 | End2 | Chr | Start1 | End1 |
| 234 | 20 | 34513448 | 34513477 | 34530923 | 34530952 | 20 | 34509478 | 34513477 |
| 235 | 20 | 34530923 | 34530952 | 34584149 | 34584178 | 20 | 34530923 | 34534922 |
| 236 | 6 | 136523814 | 136523843 | 136551414 | 136551443 | 6 | 136519844 | 136523843 |
| 237 | 4 | 86131387 | 86131416 | 86343456 | 86343485 | 4 | 86127417 | 86131416 |
| 238 | 9 | 125608173 | 125608202 | 125635071 | 125635100 | 9 | 125608173 | 125612172 |
| 239 | 3 | 192778774 | 192778803 | 192896409 | 192896438 | 3 | 192774804 | 192778803 |
| 240 | 3 | 192896409 | 192896438 | 192949578 | 192949607 | 3 | 192892439 | 192896438 |
| 241 | 11 | 86466088 | 86466117 | 86597678 | 86597707 | 11 | 86466088 | 86470087 |
| 242 | 3 | 5098339 | 5098368 | 5223126 | 5223155 | 3 | 5094369 | 5098368 |
| 243 | 3 | 5096550 | 5096579 | 5223126 | 5223155 | 3 | 5096550 | 5100549 |
| 244 | 11 | 123337272 | 123337301 | 123352543 | 123352572 | 11 | 123333302 | 123337301 |
| 245 | 11 | 123337272 | 123337301 | 123381608 | 123381637 | 11 | 123333302 | 123337301 |
| 246 | 17 | 62602076 | 62602105 | 62650420 | 62650449 | 17 | 62598106 | 62602105 |
| 247 | 17 | 32546344 | 32546373 | 32729890 | 32729919 | 17 | 32542374 | 32546373 |
| 248 | 17 | 32592691 | 32592720 | 32673793 | 32673822 | 17 | 32588721 | 32592720 |
| 249 | 17 | 32592691 | 32592720 | 32740203 | 32740232 | 17 | 32588721 | 32592720 |
| 250 | 17 | 32592691 | 32592720 | 32729890 | 32729919 | 17 | 32588721 | 32592720 |
| 251 | 17 | 32592691 | 32592720 | 32765288 | 32765317 | 17 | 32588721 | 32592720 |
| 252 | 17 | 32592691 | 32592720 | 32797503 | 32797532 | 17 | 32588721 | 32592720 |
| 253 | 17 | 32592691 | 32592720 | 32833313 | 32833342 | 17 | 32588721 | 32592720 |
| 254 | 17 | 32592691 | 32592720 | 32856904 | 32856933 | 17 | 32588721 | 32592720 |
| 255 | 17 | 32592691 | 32592720 | 32898291 | 32898320 | 17 | 32588721 | 32592720 |
| 256 | 17 | 78250119 | 78250148 | 78301376 | 78301405 | 17 | 78250119 | 78254118 |
| 257 | 4 | 153659613 | 153659642 | 153700320 | 153700349 | 4 | 153659613 | 153663612 |
| 258 | 5 | 142382167 | 142382196 | 142662879 | 142662908 | 5 | 142382167 | 142386166 |
| 259 | 5 | 142457784 | 142457813 | 142662879 | 142662908 | 5 | 142457784 | 142461783 |
| 260 | 5 | 68194359 | 68194388 | 68215410 | 68215439 | 5 | 68190389 | 68194388 |

TABLE 13.e6

| | 4 kb Sequence Location | | Inner_primers | | |
|---|---|---|---|---|---|
| | Start2 | End2 | PCR-Primer1_ID | PCR_Primer1 | PCR-Primer2_ID |
| 209 | 157266725 | 157270724 | OBD117.1.165 | GTAAATGAGCCACCTGGGCGGGT (SEQ ID NO: 1181) | OBD117.1.167 |
| 210 | 134179549 | 134183548 | OBD117.1.585 | GAACACGAGAATGGAGAGGGAGCATC (SEQ ID NO: 1182) | OBD117.1.587 |
| 211 | 134185518 | 134189517 | OBD117.1.593 | GCTATTTGGTCTGTCCTTGCTCCACA (SEQ ID NO: 1183) | OBD117.1.595 |
| 212 | 28040393 | 28044392 | OBD117.1.1717 | AGCCTGGGTGACAGAGTAAGACC (SEQ ID NO: 1184) | OBD117.1.1719 |
| 213 | 28087716 | 28091715 | OBD117.1.1617 | CAAGCACAGGCAACAGAACAGACCAT (SEQ ID NO: 1185) | OBD117.1.1619 |
| 214 | 667141 | 671140 | OBD117.1.1289 | CTGTTTGCCCTGAGAATACTTGCCCA (SEQ ID NO: 1186) | OBD117.1.1291 |
| 215 | 787920 | 791919 | OBD117.1.1605 | GCCAACTTGACTGGGCAAACGGA (SEQ ID NO: 1187) | OBD117.1.1607 |
| 216 | 112110080 | 112114079 | OBD117.1.1513 | CATCGGATTAGAGGATTCCAGTTTTA (SEQ ID NO: 1188) | OBD117.1.1515 |
| 217 | 112259613 | 112263612 | OBD117.1.1469 | CGTCTGGTGTTGTGGAACTTTGGAGG (SEQ ID NO: 1189) | OBD117.1.1471 |
| 218 | 32237140 | 32241139 | OBD117.1.1337 | GCGGAGCCTCTTTGAACAGAAGC (SEQ ID NO: 1190) | OBD117.1.1339 |
| 219 | 46189040 | 46193039 | OBD117.1.925 | TGATGTATAGCTGGGCCTTG (SEQ ID NO: 1191) | OBD117.1.927 |
| 220 | 29772927 | 29776926 | OBD117.1.1397 | CTAAGAAGCAGATGCCACAGGCTGGT (SEQ ID NO: 1192) | OBD117.1.1399 |
| 221 | 111258147 | 111262146 | OBD117.1.1113 | GTGCTCCTGAATGACCAGTGGGT (SEQ ID NO: 1193) | OBD117.1.1115 |

TABLE 13.e6-continued

| | 4 kb Sequence Location | | Inner_primers | | |
|---|---|---|---|---|---|
| | Start2 | End2 | PCR-Primer1_ID | PCR_Primer1 | PCR-Primer2_ID |
| 222 | 111316770 | 111320769 | OBD117.1.157 | TGGGAGGGTTTTATTCACAAGAGTGG (SEQ ID NO: 1194) | OBD117.1.159 |
| 223 | 111298083 | 111302082 | OBD117.1.1457 | TGAGCCACAGAGCAAGACTCCGTC (SEQ ID NO: 1195) | OBD117.1.1459 |
| 224 | 111316770 | 111320769 | OBD117.1.725 | AAGTGATCGTGGAAACACAGC (SEQ ID NO: 1196) | OBD117.1.727 |
| 225 | 150523261 | 150527260 | OBD117.1.1849 | TTTCCAAGAACGGTTTTGCTTTC (SEQ ID NO: 1197) | OBD117.1.1851 |
| 226 | 150647820 | 150651819 | OBD117.1.1829 | TTTCCAAGAACGGTTTTGCTTTC (SEQ ID NO: 1198) | OBD117.1.1831 |
| 227 | 89881274 | 89885273 | OBD117.1.1421 | CAGCCTGGCAACAGAGTGAGACT (SEQ ID NO: 1199) | OBD117.1.1423 |
| 228 | 31588788 | 31592787 | OBD117.1.977 | CCGTGCTTCGTGCTTTGGAC (SEQ ID NO: 1200) | OBD117.1.979 |
| 229 | 31619706 | 31623705 | OBD117.1.965 | TTCGTGCTTTGGACTACCGC (SEQ ID NO: 1201) | OBD117.1.967 |
| 230 | 157045788 | 157049787 | OBD117.1.1821 | TATCACGGTAAAATCAATAAAAT (SEQ ID NO: 1202) | OBD117.1.1823 |
| 231 | 157045788 | 157049787 | OBD117.1.1857 | TATCACGGTAAAATCAATAAAAT (SEQ ID NO: 1203) | OBD117.1.1859 |
| 232 | 6413040 | 6417039 | OBD117.1.1301 | GGTGTGTCTGGGAGATTAGTAGATGG (SEQ ID NO: 1204) | OBD117.1.1303 |
| 233 | 235759465 | 235763464 | OBD117.1.1229 | GTGGCTCAAGTCTGTAATCCCAGCAC (SEQ ID NO: 1205) | OBD117.1.1231 |
| 234 | 34530923 | 34534922 | OBD117.1.477 | TCCAGGATGGTTTGACTCTAAAGCAT (SEQ ID NO: 1206) | OBD117.1.479 |
| 235 | 34580179 | 34584178 | OBD117.1.553 | CTCTTTCAGGTTCCCCAGACCATC (SEQ ID NO: 1207) | OBD117.1.555 |
| 236 | 136551414 | 136555413 | OBD117.1.1177 | AATACCTACCCTTGCCCTTCCCACCA (SEQ ID NO: 1208) | OBD117.1.1179 |
| 237 | 86339486 | 86343485 | OBD117.1.221 | TGGCAGATTGTAGGTGGTTGGAGAAT (SEQ ID NO: 1209) | OBD117.1.223 |
| 238 | 125631101 | 125635100 | OBD117.1.033 | GTCATCTCCTCTCCAGTTAGTCAACA (SEQ ID NO: 1210) | OBD117.1.035 |
| 239 | 192892439 | 192896438 | OBD117.1.1133 | GTGATACAACACTTTAGATACCTGGA (SEQ ID NO: 1211) | OBD117.1.1135 |
| 240 | 192945608 | 192949607 | OBD117.1.1285 | ACACAACCCAGCGTCCTTCGCCTTTT (SEQ ID NO: 1212) | OBD117.1.1287 |
| 241 | 86593708 | 86597707 | OBD117.1.1693 | CCACCTCTGTGAAGTATGCTCTCTGG (SEQ ID NO: 1213) | OBD117.1.1695 |
| 242 | 5223126 | 5227125 | OBD117.1.1581 | GAGTCCAAGCAAACGACAAGGAAGTC (SEQ ID NO: 1214) | OBD117.1.1583 |
| 243 | 5223126 | 5227125 | OBD117.1.1637 | TTGAGATGACAGGCTGGCACCCC (SEQ ID NO: 1215) | OBD117.1.1639 |
| 244 | 123352543 | 123356542 | OBD117.1.1713 | GCAGAAACTCAAAATGGATGGTAGGC (SEQ ID NO: 1216) | OBD117.1.1715 |
| 245 | 123381608 | 123385607 | OBD117.1.1205 | GCAGAAACTCAAAATGGATGGTAGGC (SEQ ID NO: 1217) | OBD117.1.1207 |
| 246 | 62650420 | 62654419 | OBD117.1.1729 | TATCTGCTATTACTTTGGGTTTT (SEQ ID NO: 1218) | OBD117.1.1731 |

TABLE 13.e6-continued

| | 4 kb Sequence Location | | Inner_primers | | |
|---|---|---|---|---|---|
| | Start2 | End2 | PCR-Primer1_ID | PCR_Primer1 | PCR-Primer2_ID |
| 247 | 32729890 | 32733889 | OBD117.1.1429 | GCCACTTTGAGGGCTGAACAGTAGC (SEQ ID NO: 1219) | OBD117.1.1431 |
| 248 | 32673793 | 32677792 | OBD117.1.1089 | GGATGCCAGAATAAGATGGAACTGTG (SEQ ID NO: 1220) | OBD117.1.1091 |
| 249 | 32736233 | 32740232 | OBD117.1.1589 | GGATGCCAGAATAAGATGGAACTGTG (SEQ ID NO: 1221) | OBD117.1.1591 |
| 250 | 32729890 | 32733889 | OBD117.1.1493 | GGATGCCAGAATAAGATGGAACTGTG (SEQ ID NO: 1222) | OBD117.1.1495 |
| 251 | 32761318 | 32765317 | OBD117.1.1661 | GGATGCCAGAATAAGATGGAACTGTG (SEQ ID NO: 1223) | OBD117.1.1663 |
| 252 | 32797503 | 32801502 | OBD117.1.1081 | GGATGCCAGAATAAGATGGAACTGTG (SEQ ID NO: 1224) | OBD117.1.1083 |
| 253 | 32833313 | 32837312 | OBD117.1.1085 | GGATGCCAGAATAAGATGGAACTGTG (SEQ ID NO: 1225) | OBD117.1.1087 |
| 254 | 32856904 | 32860903 | OBD117.1.1509 | GGATGCCAGAATAAGATGGAACTGTG (SEQ ID NO: 1226) | OBD117.1.1511 |
| 255 | 32894321 | 32898320 | OBD117.1.1489 | GGATGCCAGAATAAGATGGAACTGTG (SEQ ID NO: 1227) | OBD117.1.1491 |
| 256 | 78297406 | 78301405 | OBD117.1.1053 | TCACCCAGCTGCTGTATATGACT (SEQ ID NO: 1228) | OBD117.1.1055 |
| 257 | 153696350 | 153700349 | OBD117.1.1697 | AACGCTTTCCACCAGGTCCTACC (SEQ ID NO: 1229) | OBD117.1.1699 |
| 258 | 142658909 | 142662908 | OBD117.1.1149 | CATCTCACTCCCTCACCAGGCTG (SEQ ID NO: 1230) | OBD117.1.1151 |
| 259 | 142658909 | 142662908 | OBD117.1.1505 | CATCTCACTCCCTCACCAGGCTG (SEQ ID NO: 1231) | OBD117.1.1507 |
| 260 | 68215410 | 68219409 | OBD117.1.829 | GGGGAATGACTCAGGTTCAC (SEQ ID NO: 1232) | OBD117.1.831 |

TABLE 13.e7

| | Inner_primers | |
|---|---|---|
| | PCR_Primer2 | GLMNET |
| 209 | GGCAAGCATCTTCCTGGTTCTTCAG (SEQ ID NO: 1233) | −0.004038003 |
| 210 | CTGAGGAAAGAGAGCAGTATCTAAGG (SEQ ID NO: 1234) | 0.000108113 |
| 211 | GCTCATCAGTTTTCAGTCCTTTTCCT (SEQ ID NO: 1235) | −0.012488304 |
| 212 | GGCACCGTGTATCCCTCTCTCTG (SEQ ID NO: 1236) | 0 |
| 213 | ATAGACAAATGACCTCCTCCTTGC (SEQ ID NO: 1237) | 0 |
| 214 | GAAGACAAAGATACATTCCTGGACAT (SEQ ID NO: 1238) | 0 |
| 215 | CCCCTTTCTGTCCTGCTCTCTGC (SEQ ID NO: 1239) | 0 |
| 216 | GTGCCCACACAAAGACTAAGCGAGTT (SEQ ID NO: 1240) | 0 |
| 217 | GCCAAGCATAGACTCAGACTTTTAGG (SEQ ID NO: 1241) | 0 |
| 218 | GCCTCTTCCCACCAGCCTGACTT (SEQ ID NO: 1242) | 0 |
| 219 | ACCAAGGATGCACCAGAAAG (SEQ ID NO: 1243) | 0.015771071 |
| 220 | TCTGAGGGTGACCTTATTTTGTCCAC (SEQ ID NO: 1244) | 0 |

TABLE 13.e7-continued

| | Inner_primers | |
|---|---|---|
| | PCR_Primer2 | GLMNET |
| 221 | CAGCCTGGGCGACAGAAACCTTG (SEQ ID NO: 1245) | 0 |
| 222 | ACAGTCCATAGTGAGCGGCAGACAGA (SEQ ID NO: 1246) | −0.008898153 |
| 223 | GCTACAGCCTACTAATCAAGGAACTG (SEQ ID NO: 1247) | 0 |
| 224 | CCACAGTCCATAGTGAGCGG (SEQ ID NO: 1248) | 0.00011344 |
| 225 | ATTTACTTGCTATGGGTCCTTTT (SEQ ID NO: 1249) | 0 |
| 226 | ATTTACTTGCTATGGGTCCTTTT (SEQ ID NO: 1250) | 0 |
| 227 | GAAATCTCCTCCCCACCCTCAGC (SEQ ID NO: 1251) | 0 |
| 228 | GGTGGAAGGGTGAGCCATGT (SEQ ID NO: 1252) | 0 |
| 229 | CCCAGGATAGGAGGCCATCAGA (SEQ ID NO: 1253) | −0.006509693 |
| 230 | AAGCCATCCTTTTCTAAACAATA (SEQ ID NO: 1254) | 0 |
| 231 | AGAGGAAAGACAACATTTTATTT (SEQ ID NO: 1255) | 0 |
| 232 | CCGTAGAGGATAAAAGGAAAGAAAGC (SEQ ID NO: 1256) | 0 |
| 233 | CCAGCATTCCCTACTTCTTCACTACT (SEQ ID NO: 1257) | 0 |
| 234 | TGTGGGTAGCAGCAGAGGATGGCA (SEQ ID NO: 1258) | 0.011140328 |
| 235 | TGGGTAGCAGCAGAGGATGGCAG (SEQ ID NO: 1259) | 0 |
| 236 | TCATCACAGACCACAGCAGAAGTGTT (SEQ ID NO: 1260) | 0 |
| 237 | GTCTGGCAGCCTTCCTCATTTATGGT (SEQ ID NO: 1261) | −0.009554407 |
| 238 | CCCTTGCTATGATGGCTTGTTCACTG (SEQ ID NO: 1262) | −0.010767501 |
| 239 | TTCTTCCCACTACACCACACAACCCA (SEQ ID NO: 1263) | 0 |
| 240 | CAGCAGCAAGAATGGAGTTCAAAGAC (SEQ ID NO: 1264) | 0 |
| 241 | CCAGCATCAAAGAGCAAGAATGGAGT (SEQ ID NO: 1265) | 0 |
| 242 | CGATGGCAACTGGCTCTTGTTCCTTT (SEQ ID NO: 1266) | 0 |
| 243 | CGATGGCAACTGGCTCTTGTTCC (SEQ ID NO: 1267) | 0 |
| 244 | CTATGTGGGTGTGTGGATGTGTATGG (SEQ ID NO: 1268) | 0 |
| 245 | TTTGTTCCCCAGGCAGCATTCAGTGC (SEQ ID NO: 1269) | 0 |
| 246 | TTCAGGATGTGTGAGAGAGATTA (SEQ ID NO: 1270) | 0 |
| 247 | AAAACAAAGAATCCTCCCTGCCCC (SEQ ID NO: 1271) | 0 |
| 248 | GAAACAGCCTCACTTTGGAGTTCAGG (SEQ ID NO: 1272) | 0 |
| 249 | CATCACCAGCAAGCAGTGCCAACTAC (SEQ ID NO: 1273) | 0 |
| 250 | AAAACAAAGAATCCTCCCTGCCCC (SEQ ID NO: 1274) | 0 |
| 251 | CCATTCTCAATAAGAGGCGTGTCACC (SEQ ID NO: 1275) | 0 |
| 252 | CTGTGAGGGATACACTCCAAGACATC (SEQ ID NO: 1276) | 0 |
| 253 | GCAGAGGTGGTGAGAAGTAGTCAGAC (SEQ ID NO: 1277) | 0 |
| 254 | GTGCTTGACATTTCTGCTACCCCTGC (SEQ ID NO: 1278) | 0 |
| 255 | TCCGTGACACAGTCTCAGGAGGTTCT (SEQ ID NO: 1279) | 0 |
| 256 | ACAAGCTCGTGTGAGTGCCC (SEQ ID NO: 1280) | 0 |
| 257 | GGAAAGTGGGCACCAGCCGCATT (SEQ ID NO: 1281) | 0 |
| 258 | GGCAGGAGAAGGGCTACTGAAAG (SEQ ID NO: 1282) | 0 |

TABLE 13.e7-continued

| | Inner primers | |
|---|---|---|
| | PCR_Primer2 | GLMNET |
| 259 | CAAACCACCTCCCATCAAACCCC (SEQ ID NO: 1283) | 0 |
| 260 | GCGGAGTGCTCTGGCTCTAC (SEQ ID NO: 1284) | 0.000114527 |

TABLE 13.f1

| | Probe | GeneLocus | Probe_Count_Total | Probe_Count_Sig |
|---|---|---|---|---|
| 261 | ORF442_7_142753523_142755244_142766140_142771360_FR | ORF442 | 30 | 8 |
| 262 | ORF442_7_142753523_142755244_142812001_142818261_FF | ORF442 | 30 | 8 |
| 263 | ORF447_13_32504086_32509501_32577917_32582372_FF | ORF447 | 29 | 3 |
| 264 | ORF447_13_32540613_32545777_32577917_32582372_FF | ORF447 | 29 | 3 |
| 265 | ORF454_2_105728227_105741825_105841316_105844511_FF | NCK2 | 66 | 4 |
| 266 | ORF456_11_119671081_119677815_119700077_119705149_FR | PVRL1 | 96 | 8 |
| 267 | ORF457_1_198199892_198201903_198244755_198253085_FF | ORF457 | 130 | 22 |
| 268 | ORF457_1_198199892_198201903_198346795_198354552_FR | ORF457 | 130 | 22 |
| 269 | ORF457_1_198279876_198287932_198346795_198354552_RR | ORF457 | 130 | 22 |
| 270 | ORF458_17_31150085_31156746_31224131_31234469_FR | ORF458 | 136 | 9 |
| 271 | ORF458_17_31332261_31339438_31382125_31387511_FR | ORF458 | 136 | 9 |
| 272 | ORF460_20_51355850_51362174_51482831_51487722_FR | ORF460 | 65 | 2 |
| 273 | ORF462_1_60869920_60875614_60989414_60996659_RR | ORF462 | 165 | 19 |
| 274 | ORF464_6_44253666_44257911_44307667_44312139_RF | NFKBIE | 44 | 4 |
| 275 | ORF464_6_44270723_44274914_44307667_44312139_RF | NFKBIE | 44 | 4 |
| 276 | ORF465_3_101806474_101809017_101822519_101827725_RR | ORF465 | 26 | 6 |
| 277 | ORF472_16_27189621_27195287_27236516_27245702_FF | ORF472 | 16 | 1 |
| 278 | ORF479_8_80968986_80975857_81095100_81099880_RR | PAG1 | 144 | 12 |
| 279 | ORF479_8_81007411_81018107_81053410_81059648_FR | PAG1 | 144 | 12 |
| 280 | ORF479_8_81007411_81018107_81077565_81079322_FR | PAG1 | 144 | 12 |
| 281 | ORF479_8_81007411_81018107_81095100_81099880_FR | PAG1 | 144 | 12 |
| 282 | ORF479_8_81053410_81059648_81095100_81099880_RR | PAG1 | 144 | 12 |
| 283 | ORF48_1_212523302_212528520_212585744_212588822_RF | ORF48 | 30 | 11 |
| 284 | ORF48_1_212572997_212579940_212643074_212645915_RF | ORF48 | 30 | 11 |
| 285 | ORF480_11_77430379_77437843_77514783_77519103_RF | PAK1 | 136 | 6 |
| 286 | ORF481_4_168689667_168697449_168861254_168870461_FF | ORF481 | 125 | 18 |
| 287 | ORF482_5_168579937_168582137_168614429_168620163_RR | ORF482 | 25 | 5 |
| 288 | ORF489_10_95194975_95203396_95282952_95289853_RR | ORF489 | 35 | 10 |
| 289 | ORF494_3_170115709_170117792_170195523_170206472_FR | ORF494 | 23 | 1 |
| 290 | ORF500_7_106905450_106908201_106938904_106944761_FF | ORF500 | 31 | 3 |
| 291 | ORF501_5_68203536_68213336_68272048_68277769_FF | PIK3R1 | 148 | 12 |
| 292 | ORF501_5_68215410_68221074_68272048_68277769_RF | PIK3R1 | 148 | 12 |
| 293 | ORF505_17_67329565_67337138_67493397_67497612_FR | ORF505 | 61 | 8 |
| 294 | ORF510_12_19116277_19126697_19175194_19181683_RR | ORF510 | 105 | 20 |
| 295 | ORF510_12_19116277_19126697_19247123_19249380_RR | ORF510 | 105 | 20 |
| 296 | ORF510_12_19116277_19126697_19321592_19322644_RF | ORF510 | 105 | 20 |
| 297 | ORF510_12_19116277_19126697_19330800_19333489_RR | ORF510 | 105 | 20 |
| 298 | ORF514_16_57264324_57265825_57311821_57315910_RF | ORF514 | 13 | 4 |
| 299 | ORF518_12_62612835_62616434_62635972_62643837_FR | ORF518 | 98 | 7 |
| 300 | ORF52_6_16559432_16569316_16745336_16747298_RR | ORF52 | 170 | 12 |
| 301 | ORF520_4_100984121_100992210_101215421_101227213_RR | ORF520 | 151 | 14 |
| 302 | ORF520_4_100993481_100996110_101215421_101227213_FR | ORF520 | 151 | 14 |
| 303 | ORF527_16_23918616_23926918_24180817_24184913_FF | ORF527 | 167 | 6 |
| 304 | ORF529_10_6432893_6439235_6460245_6464187_RF | PRKCQ | 106 | 2 |
| 305 | ORF531_22_44662780_44666500_44696835_44701888_FF | PRR5 | 64 | 4 |
| 306 | ORF532_11_36295021_36302583_36442359_36447012_FF | ORF532 | 154 | 18 |
| 307 | ORF532_11_36295021_36302583_36486258_36488847_FF | ORF532 | 154 | 18 |
| 308 | ORF534_2_113175431_113181015_113215780_113218742_RR | ORF534 | 28 | 1 |
| 309 | ORF538_8_140715391_140725081_140763162_140771406_FF | PTK2 | 248 | 12 |
| 310 | ORF538_8_140715391_140725081_140877455_140883144_FR | PTK2 | 248 | 12 |
| 311 | ORF538_8_140725196_140731179_140877455_140883144_RF | PTK2 | 248 | 12 |
| 312 | ORF540_12_112418669_112423831_112478543_112482415_RR | PTPN11 | 56 | 6 |

TABLE 13.f2

| | HyperG_Stats | FDR_HyperG | Percent_Sig | logFC | AveExpr | t |
|---|---|---|---|---|---|---|
| 261 | 0.000412702 | 0.012833299 | 26.67 | 0.282182665 | 0.282182665 | 8.633617733 |
| 262 | 0.000412702 | 0.012833299 | 26.67 | 0.296850132 | 0.296850132 | 10.04415773 |
| 263 | 0.302066279 | 1 | 10.34 | 0.254568442 | 0.254568442 | 5.844514895 |
| 264 | 0.275359272 | 1 | 10.34 | 0.257220838 | 0.257220838 | 4.875635995 |
| 265 | 0.779227696 | 0.99999793 | 6.06 | −0.308568317 | −0.308568317 | −13.88505293 |
| 266 | 0.497039718 | 0.99999793 | 8.33 | −0.149050171 | −0.149050171 | −6.891048765 |

TABLE 13.f2-continued

|  | HyperG_Stats | FDR_HyperG | Percent_Sig | logFC | AveExpr | t |
|---|---|---|---|---|---|---|
| 267 | 2.09E−05 | 0.00123352 | 16.92 | 0.326119857 | 0.326119857 | 14.46240036 |
| 268 | 2.09E−05 | 0.00123352 | 16.92 | 0.364744284 | 0.364744284 | 4.767804449 |
| 269 | 2.09E−05 | 0.00123352 | 16.92 | 0.407405048 | 0.407405048 | 4.303224495 |
| 270 | 0.489837398 | 1 | 6.62 | 0.356227721 | 0.356227721 | 5.408044247 |
| 271 | 0.489837398 | 1 | 6.62 | 0.306778753 | 0.306778753 | 8.548684381 |
| 272 | 0.922199982 | 1 | 3.08 | 0.315145804 | 0.315145804 | 4.450181318 |
| 273 | 0.008195505 | 0.161007518 | 11.52 | 0.522735303 | 0.522735303 | 8.344744415 |
| 274 | 0.466402982 | 0.99999793 | 9.09 | −0.239598775 | −0.239598775 | −11.49610245 |
| 275 | 0.466402982 | 0.99999793 | 9.09 | −0.361055592 | −0.361055592 | −19.65763701 |
| 276 | 0.004811744 | 0.105522664 | 23.08 | 0.39419325 | 0.39419325 | 7.788511223 |
| 277 | 0.666756467 | 1 | 6.25 | 0.240506289 | 0.240506289 | 6.459645292 |
| 278 | 0.474481533 | 0.99999793 | 8.33 | −0.226025291 | −0.226025291 | −8.99633921 |
| 279 | 0.474481533 | 0.99999793 | 8.33 | −0.229747184 | −0.229747184 | −5.910931698 |
| 280 | 0.474481533 | 0.99999793 | 8.33 | −0.154283407 | −0.154283407 | −3.020061123 |
| 281 | 0.474481533 | 0.99999793 | 8.33 | −0.219792116 | −0.219792116 | −8.380946819 |
| 282 | 0.474481533 | 0.99999793 | 8.33 | −0.143993345 | −0.143993345 | −4.923920109 |
| 283 | 1.09E−06 | 0.000147069 | 36.67 | 0.347208645 | 0.347208645 | 10.26020662 |
| 284 | 1.81E−06 | 0.000223432 | 36.67 | 0.247499169 | 0.247499169 | 10.06614725 |
| 285 | 0.963851563 | 0.99999793 | 4.41 | −0.138029302 | −0.138029302 | −5.075029024 |
| 286 | 0.000866538 | 0.022698472 | 14.4 | 0.282685362 | 0.282685362 | 6.001930767 |
| 287 | 0.018277026 | 0.292122629 | 20 | 0.139860217 | 0.139860217 | 2.682542914 |
| 288 | 4.16E−05 | 0.002051839 | 28.57 | 0.345918136 | 0.345918136 | 5.148443654 |
| 289 | 0.776490089 | 1 | 4.35 | 0.349135569 | 0.349135569 | 13.52580262 |
| 290 | 0.310510231 | 1 | 9.68 | 0.305010185 | 0.305010185 | 6.196106538 |
| 291 | 0.513477047 | 0.99999793 | 8.11 | −0.158345461 | −0.158345461 | −4.255312553 |
| 292 | 0.513477047 | 0.99999793 | 8.11 | −0.384094729 | −0.384094729 | −16.16361934 |
| 293 | 0.047733938 | 0.555717324 | 13.11 | 0.145028051 | 0.145028051 | 5.238896186 |
| 294 | 8.08E−06 | 0.000635046 | 19.05 | 0.376644852 | 0.376644852 | 11.02917154 |
| 295 | 8.08E−06 | 0.000635046 | 19.05 | 0.326634321 | 0.326634321 | 7.908617509 |
| 296 | 8.08E−06 | 0.000635046 | 19.05 | 0.296253745 | 0.296253745 | 4.138933763 |
| 297 | 8.08E−06 | 0.000635046 | 19.05 | 0.351520286 | 0.351520286 | 15.21067568 |
| 298 | 0.008516834 | 0.15747793 | 30.77 | 0.227494853 | 0.227494853 | 8.573818628 |
| 299 | 0.423328583 | 1 | 7.14 | 0.299633874 | 0.299633874 | 7.710688541 |
| 300 | 0.385937569 | 1 | 7.06 | 0.333292833 | 0.333292833 | 6.455577776 |
| 301 | 0.095696301 | 0.807051655 | 9.27 | 0.37381143 | 0.37381143 | 15.1958863 |
| 302 | 0.095696301 | 0.807051655 | 9.27 | 0.327001567 | 0.327001567 | 6.995430928 |
| 303 | 0.955788004 | 1 | 3.59 | 0.315269518 | 0.315269518 | 8.479485602 |
| 304 | 0.998452566 | 0.99999793 | 1.89 | −0.301937872 | −0.301937872 | −16.13705896 |
| 305 | 0.7582782 | 0.99999793 | 6.25 | −0.38593493 | −0.38593493 | −15.39183699 |
| 306 | 0.008522642 | 0.164017369 | 11.69 | 0.327277188 | 0.327277188 | 15.01502481 |
| 307 | 0.008522642 | 0.164017369 | 11.69 | 0.285606598 | 0.285606598 | 13.61645345 |
| 308 | 0.853880387 | 1 | 3.57 | 0.146480654 | 0.146480654 | 4.980868538 |
| 309 | 0.979779286 | 0.99999793 | 4.84 | −0.161243979 | −0.161243979 | −7.690183808 |
| 310 | 0.979779286 | 0.99999793 | 4.84 | −0.179032383 | −0.179032383 | −4.998863428 |
| 311 | 0.979779286 | 0.99999793 | 4.84 | −0.205518478 | −0.205518478 | −7.923787367 |
| 312 | 0.283634013 | 0.99999793 | 10.71 | −0.281116435 | −0.281116435 | −10.51176015 |

TABLE 13.f3

|  | P. Value | adj. P. Val | B | FC | FC_1 | LS |
|---|---|---|---|---|---|---|
| 261 | 0.0000051 | 0.000194414 | 4.517318749 | 1.21603324 | 1.21603324 | 1 |
| 262 | 0.00000126 | 0.0000913 | 5.947522775 | 1.228459361 | 1.228459361 | 1 |
| 263 | 0.000147922 | 0.001608124 | 1.023264128 | 1.19297883 | 1.19297883 | 1 |
| 264 | 0.00060203 | 0.004200216 | −0.437698362 | 1.19517414 | 1.19517414 | 1 |
| 265 | 0.0000000563 | 0.0000204 | 9.028942709 | 0.807442641 | −1.238478065 | −1 |
| 266 | 0.0000375 | 0.000650749 | 2.451683607 | 0.901844015 | −1.108839204 | −1 |
| 267 | 0.0000000378 | 0.000017 | 9.411796984 | 1.253637166 | 1.253637166 | 1 |
| 268 | 0.000709669 | 0.004690158 | −0.608518471 | 1.287653374 | 1.287653374 | 1 |
| 269 | 0.001468864 | 0.007933618 | −1.362105846 | 1.326298076 | 1.326298076 | 1 |
| 270 | 0.000273835 | 0.002430708 | 0.381770825 | 1.280074451 | 1.280074451 | 1 |
| 271 | 0.00000558 | 0.000205624 | 4.42479206 | 1.236942771 | 1.236942771 | 1 |
| 272 | 0.001163152 | 0.006712076 | −1.120741967 | 1.244137384 | 1.244137384 | 1 |
| 273 | 0.00000694 | 0.000231622 | 4.199416787 | 1.43667656 | 1.43667656 | 1 |
| 274 | 0.00000035 | 0.0000501 | 7.235348626 | 0.846980832 | −1.180664264 | −1 |
| 275 | 0.00000000180 | 0.00000577 | 12.19684795 | 0.778594689 | −1.284365299 | −1 |
| 276 | 0.0000129 | 0.00033477 | 3.560870429 | 1.314207654 | 1.314207654 | 1 |
| 277 | 0.0000649 | 0.000929428 | 1.881216554 | 1.181407184 | 1.181407184 | 1 |
| 278 | 0.0000035 | 0.00015845 | 4.90389231 | 0.854987189 | −1.169608168 | −1 |
| 279 | 0.000135003 | 0.001520418 | 1.118479259 | 0.85278432 | −1.172629441 | −1 |
| 280 | 0.012560255 | 0.038539753 | −3.552262166 | 0.89857859 | −1.112868714 | −1 |
| 281 | 0.00000667 | 0.000227068 | 4.239758043 | 0.85868916 | −1.164565767 | −1 |
| 282 | 0.000559582 | 0.004010305 | −0.361729876 | 0.905010637 | −1.104959388 | −1 |
| 283 | 0.00000103 | 0.0000822 | 6.150150312 | 1.272096966 | 1.272096966 | 1 |
| 284 | 0.00000123 | 0.0000904 | 5.968333273 | 1.187147477 | 1.187147477 | 1 |

TABLE 13.f3-continued

|     | P. Value | adj. P. Val | B | FC | FC_1 | LS |
| --- | --- | --- | --- | --- | --- | --- |
| 285 | 0.000446091 | 0.003407902 | −0.126087743 | 0.908759659 | −1.100400959 | −1 |
| 286 | 0.000119231 | 0.001398727 | 1.247912659 | 1.216457032 | 1.216457032 | 1 |
| 287 | 0.022542218 | 0.05969012 | −4.133849469 | 1.101798357 | 1.101798357 | 1 |
| 288 | 0.000400046 | 0.003156349 | −0.012767176 | 1.270959568 | 1.270959568 | 1 |
| 289 | 0.0000000727 | 0.0000221 | 8.78155797 | 1.273797167 | 1.273797167 | 1 |
| 290 | 0.0000918 | 0.001174535 | 1.520169664 | 1.235427359 | 1.235427359 | 1 |
| 291 | 0.001585984 | 0.00838257 | −1.441362142 | 0.896052109 | −1.116006524 | −1 |
| 292 | 0.0000000126 | 0.0000107 | 10.44421723 | 0.766259665 | −1.305040636 | −1 |
| 293 | 0.000350168 | 0.002877636 | 0.125797352 | 1.105752153 | 1.105752153 | 1 |
| 294 | 0.000000519 | 0.0000596 | 6.839517342 | 1.298318956 | 1.298318956 | 1 |
| 295 | 0.0000112 | 0.000306728 | 3.701787155 | 1.254084292 | 1.254084292 | 1 |
| 296 | 0.001913285 | 0.009573546 | −1.634983629 | 1.22795164 | 1.22795164 | 1 |
| 297 | 0.000000023 | 0.0000135 | 9.882661566 | 1.275904444 | 1.275904444 | 1 |
| 298 | 0.00000543 | 0.000202914 | 4.452254274 | 1.170800164 | 1.170800164 | 1 |
| 299 | 0.0000141 | 0.000355212 | 3.468646509 | 1.230832014 | 1.230832014 | 1 |
| 300 | 0.0000653 | 0.000933916 | 1.875717331 | 1.259885681 | 1.259885681 | 1 |
| 301 | 0.0000000232 | 0.0000135 | 9.873618979 | 1.295771588 | 1.295771588 | 1 |
| 302 | 0.000033 | 0.000601894 | 2.585972415 | 1.254403567 | 1.254403567 | 1 |
| 303 | 0.000006 | 0.000215141 | 4.348830339 | 1.244244076 | 1.244244076 | 1 |
| 304 | 0.0000000128 | 0.0000107 | 10.432910997 | 0.811162087 | −1.232799235 | −1 |
| 305 | 0.0000000205 | 0.0000131 | 9.992593359 | 0.765282901 | −1.306706316 | −1 |
| 306 | 0.0000000261 | 0.0000141 | 9.762192491 | 1.254643239 | 1.254643239 | 1 |
| 307 | 0.0000000681 | 0.0000215 | 8.844665717 | 1.218922666 | 1.218922666 | 1 |
| 308 | 0.000513568 | 0.003768664 | −0.272546891 | 1.10686606 | 1.10686606 | 1 |
| 309 | 0.0000144 | 0.000361067 | 3.444226195 | 0.894253659 | −1.118250946 | −1 |
| 310 | 0.000499878 | 0.003693568 | −0.24446078 | 0.883295225 | −1.132124314 | −1 |
| 311 | 0.000011 | 0.000303945 | 3.719464345 | 0.867226966 | −1.153100675 | −1 |
| 312 | 0.000000819 | 0.0000729 | 6.381022079 | 0.822953925 | −1.215134857 | −1 |

TABLE 13.f4

|     | Loop detected | Probe sequence 60 mer |
| --- | --- | --- |
| 261 | PD-L1 Non-responder | TGAAAGTCTGCAGGGTGTGTGCTCAGGATCGAGGCTGGTACTGTTCACCTGTGGGTCCAG (SEQ ID NO: 1285) |
| 262 | PD-L1 Non-responder | TGAAAGTCTGCAGGGTGTGTGCTCAGGATCGACCAAGATCTAGTAATTATTCATACTGTA (SEQ ID NO: 1286) |
| 263 | PD-L1 Non-responder | TGTTTTAGGGAGAAGACTGTGCCTAATATCGAGTGGAGTGGAAGAATACCAAAATCATCT (SEQ ID NO: 1287) |
| 264 | Non-Responder | AAGACTGAGATAAAAATTCTCAAGATCATCGAGTGGAGTGGAAGAATACCAAAATCATCT (SEQ ID NO: 1288) |
| 265 | PD-L1 responder | TCTTTGCAGATGTTGTAAGATAAGGATGTCGACTTCATAATCCGCCCGCCTCAGCCTCCC (SEQ ID NO: 1289) |
| 266 | PD-L1 responder | GGACCTTGTCATCCTGCCCCTTCTTGGCTCGAGGCCCTGAAACAGGACTCTATGTCTCCT (SEQ ID NO: 1290) |
| 267 | PD-L1 Non-responder | CAAGCTTTATTTAAAAATATAGCATATATCGAAAGTTGGCTAATGTATTATAGCCCATAT (SEQ ID NO: 1291) |
| 268 | PD-L1 Non-responder | CAAGCTTTATTTAAAAATATAGCATATATCGAACAACCAGGGGAAATAACAATGGTTACA (SEQ ID NO: 1292) |
| 269 | PD-L1 Non-responder | AGGTACTGTTTTAGAAATATAGAAAAATTCGAACAACCAGGGGAAATAACAATGGTTACA (SEQ ID NO: 1293) |
| 270 | PD-L1 Non-responder | ATTTCTTTCTTCTTCCCATTTTCTAAAATCGATTCCTCCAATAAGGGTTTCACCTCTTGA (SEQ ID NO: 1294) |
| 271 | PD-L1 Non-responder | GTTTTTGTATTAATAAAATGAAAAAGATTCGAAAACTTCCTTATTAGGTAGTAAAACAAA (SEQ ID NO: 1295) |
| 272 | PD-L1 Non-responder | GTGGCTAAAACAAGATTCAATCTCAATCTCGAGTTTATGTACTGTCTCCATTGACTAAGA (SEQ ID NO: 1296) |
| 273 | PD-L1 Non-responder | TTAATATACTTACATATATTTATAATGGTCGATCTCACTATTGATAGCTCCATTTTACAG (SEQ ID NO: 1297) |
| 274 | PD-L1 responder | TTTCAAAGAAGGTATGATGGGAAAGGTCTCGAGTGCCCCTGTCCCACCTGGCTCCCCCTG (SEQ ID NO: 1298) |

TABLE 13.f4-continued

| | Loop detected | Probe sequence 60 mer |
|---|---|---|
| 275 | PD-L1 responder | TTTCAAAGAAGGTATGATGGGAAAGGTCTCGACGCGCCCCCTCTACGCCATGTCCCCCCC (SEQ ID NO: 1299) |
| 276 | PD-L1 Non-responder | AAATAAAATAAAATAAAACATATACTACTCGAGTTTTTTAGTGAATATTTACAATTTCCT (SEQ ID NO: 1300) |
| 277 | PD-L1 Non-responder | GCTGCCTATGGGGCAGTGTGCAGGGGTGTCGATGAATTTCTCAACATACAGAATTGACAG (SEQ ID NO: 1301) |
| 278 | PD-L1 responder | CTTTTTAAAAATTATCTTTTTATTTGCTTCGATGCCAATCCACGTCATTAGATGAGGACC (SEQ ID NO: 1302) |
| 279 | PD-L1 responder | TCAGATAAGTAACTTCCTGATAATTAACTCGAGAAATGGATTCATATTTCCATGGCTTAC (SEQ ID NO: 1303) |
| 280 | PD-L1 responder | TCAGATAAGTAACTTCCTGATAATTAACTCGAAAAAACATTAATTTCTTCAGGTGTAAAG (SEQ ID NO: 1304) |
| 281 | PD-L1 responder | TCAGATAAGTAACTTCCTGATAATTAACTCGATGCCAATCCACGTCATTAGATGAGGACC (SEQ ID NO: 1305) |
| 282 | PD-L1 responder | GTAAGCCATGGAAATATGAATCCATTTCTCGATGCCAATCCACGTCATTAGATGAGGACC (SEQ ID NO: 1306) |
| 283 | PD-L1 Non-responder | TATCTATTTCTTTCTTATTTTGGACATTTCGAGGGTGATAATGCTAAGGGGTCTGGATTG (SEQ ID NO: 1307) |
| 284 | PD-L1 Non-responder | GAGAGGAGAGTAAGGTTGGGGTGTAAGGTCGATTCTAATAATTCTTAGTTGAATTGTTCT (SEQ ID NO: 1308) |
| 285 | PD-L1 responder | TAACAAAAGTAACACCTCTTTGGTATCATCGAAGAGTCCTTGTTCCCATTTTGGCCCAGT (SEQ ID NO: 1309) |
| 286 | PD-L1 Non-responder | GGGCAAGTTCAGATTGAAGCCTCGTGTCTCGAGAGGCAGATAAAAACAATTCCATGGTAA (SEQ ID NO: 1310) |
| 287 | Non-Responder | GAATGGCCGAACAGCCATGACAGTCCTCTCGAGGCTACTGGAGTCATTGAAAAGAGGAAT (SEQ ID NO: 1311) |
| 288 | PD-L1 Non-responder | TTTTTATTGATTGTCTCATTTAATCTTCTCGAGTTCCTCAAAAGTTTCCAAACAAGCTCC (SEQ ID NO: 1312) |
| 289 | PD-L1 Non-responder | CAAGGTGGGTGGATCACCTGAGGAGAATTCGAATCCAACAGCACATCAAAAAAATACACC (SEQ ID NO: 1313) |
| 290 | PD-L1 Non-responder | TCCCATCATTCAAAAATTATTAAGAAATTCGAGGTATTAAAGTATGCTTTTATTGTGTAA (SEQ ID NO: 1314) |
| 291 | PD-L1 responder | CGTTGCAAATTGTACATCTTCTGCTATTTCGAGACCTCATATAACTCGGTGATTGACTGC (SEQ ID NO: 1315) |
| 292 | PD-L1 responder | GCAGTCAATCACCGAGTTATATGAGGTCTCGACCTCCCCGAACCCCTCCGCCTCTGCGCT (SEQ ID NO: 1316) |
| 293 | PD-L1 Non-responder | AGGAGGGGCAAAGTCCGTCAGCTGGCTTTCGAGACTCAGAAATAAATTTGCAGTCTTTTA (SEQ ID NO: 1317) |
| 294 | PD-L1 Non-responder | TTTTTTCTCTATAGTTCATTACTTATTTTCGAGTGTAAACTGTGAAAATAGTCAAATATA (SEQ ID NO: 1318) |
| 295 | PD-L1 Non-responder | TTTTTTCTCTATAGTTCATTACTTATTTTCGACTCTACGAAAAGTATCTTCCTTTAATTA (SEQ ID NO: 1319) |
| 296 | PD-L1 Non-responder | ATTTACAAAATGGACTGCTTAGTACGTGTCGAAAATAAGTAATGAACTATAGAGAAAAAA (SEQ ID NO: 1320) |
| 297 | PD-L1 Non-responder | TTTTTTCTCTATAGTTCATTACTTATTTTCGAAATATACCAGTAAAATTAATTTAAATAT (SEQ ID NO: 1321) |
| 298 | PD-L1 Non-responder | GATGGGCAGATTACTTGAAGTCAAGAGTTCGAGCTTGGAAGTCAAAAGCTGTGTGGCTGT (SEQ ID NO: 1322) |
| 299 | PD-L1 Non-responder | TTGGTTTTAATTTTTTTTTTTAAATAAATCGACTACATATAAGCTTTAGATTTGAAATAT (SEQ ID NO: 1323) |

TABLE 13.f4-continued

| | Loop detected | Probe sequence 60 mer |
|---|---|---|
| 300 | PD-L1 Non-responder | TTATTCTTTTTTAGTATCTAAATAGTATTCGAATGTCCAAAAATGATAGGAAACTTAAAA (SEQ ID NO: 1324) |
| 301 | PD-L1 Non-responder | TTTGTTGAATTTTTAATATTGAATTTATTCGATTTCTTCCCAATTCCTCATTTCTAATAT (SEQ ID NO: 1325) |
| 302 | PD-L1 Non-responder | ATTATCTAGATCTTGTAAGATGGAAAAATCGATTTCTTCCCAATTCCTCATTTCTAATAT (SEQ ID NO: 1326) |
| 303 | PD-L1 Non-responder | TTTTTAAAAGCAAGTTTTCTCAAAAGCTTCGAAGCACTAAGTAAGGTGTATTGTTATTAT (SEQ ID NO: 1327) |
| 304 | PD-L1 responder | TCACAACCTGGGAAAACTGTCGCCTTGCTCGACTCCTGCTTCCCTCCCCTCATCTTTAAA (SEQ ID NO: 1328) |
| 305 | PD-L1 responder | CCAAACTGGCAATCAACCCAGATAGTCTTCGACCCCGGCCCCGGAGGTCTCCCTCCACAG (SEQ ID NO: 1329) |
| 306 | PD-L1 Non-responder | GGCAGGCAGATCACCTGAGCTCAGGAGTTCGATCAGGTACAAACCAAACACAGAACATAA (SEQ ID NO: 1330) |
| 307 | PD-L1 Non-responder | GGCAGGCAGATCACCTGAGCTCAGGAGTTCGATTAAAAAGAACAAAATTGATTTCCTAAA (SEQ ID NO: 1331) |
| 308 | PD-L1 Non-responder | GGGTCTGAAGCACCGTGAGAGAAATGACTCGAATTGTCTTTCTTTCGCCCGATACATAAA (SEQ ID NO: 1332) |
| 309 | PD-L1 responder | AAGTCTTTTGTTTGGTTATTGTGCTGTATCGATCCAGCTTTTTGACTCTAAAATGAGCTT (SEQ ID NO: 1333) |
| 310 | PD-L1 responder | AAGTCTTTTGTTTGGTTATTGTGCTGTATCGAATCAAAGCTGTGTCACAAACTATGTAAC (SEQ ID NO: 1334) |
| 311 | PD-L1 responder | CTTTCAAACAAATGACCTTCACCACTGTTCGATCACGGCTCACTGCAGCCTTGGCCTCCT (SEQ ID NO: 1335) |
| 312 | PD-L1 responder | CACCGACCCGTCCGGGCCCGCTGCCACATCGAATAGCTTCTTTTGCTATGTCTCCAAGTT (SEQ ID NO: 1336) |

TABLE 13.f5

| | Probe Location | | | | | 4 kb Sequence Location | | |
|---|---|---|---|---|---|---|---|---|
| | Chr | Start1 | End1 | Start2 | End2 | Chr | Start1 | End1 |
| 261 | 7 | 142755215 | 142755244 | 142766140 | 142766169 | 7 | 142751245 | 142755244 |
| 262 | 7 | 142755215 | 142755244 | 142818232 | 142818261 | 7 | 142751245 | 142755244 |
| 263 | 13 | 32509472 | 32509501 | 32582343 | 32582372 | 13 | 32505502 | 32509501 |
| 264 | 13 | 32545748 | 32545777 | 32582343 | 32582372 | 13 | 32541778 | 32545777 |
| 265 | 2 | 105741796 | 105741825 | 105844482 | 105844511 | 2 | 105737826 | 105741825 |
| 266 | 11 | 119677786 | 119677815 | 119700077 | 119700106 | 11 | 119673816 | 119677815 |
| 267 | 1 | 198201874 | 198201903 | 198253056 | 198253085 | 1 | 198197904 | 198201903 |
| 268 | 1 | 198201874 | 198201903 | 198346795 | 198346824 | 1 | 198197904 | 198201903 |
| 269 | 1 | 198279876 | 198279905 | 198346795 | 198346824 | 1 | 198279876 | 198283875 |
| 270 | 17 | 31156717 | 31156746 | 31224131 | 31224160 | 17 | 31152747 | 31156746 |
| 271 | 17 | 31339409 | 31339438 | 31382125 | 31382154 | 17 | 31335439 | 31339438 |
| 272 | 20 | 51362145 | 51362174 | 51482831 | 51482860 | 20 | 51358175 | 51362174 |
| 273 | 1 | 60869920 | 60869949 | 60989414 | 60989443 | 1 | 60869920 | 60873919 |
| 274 | 6 | 44253666 | 44253695 | 44312110 | 44312139 | 6 | 44253666 | 44257665 |
| 275 | 6 | 44270723 | 44270752 | 44312110 | 44312139 | 6 | 44270723 | 44274722 |
| 276 | 3 | 101806474 | 101806503 | 101822519 | 101822548 | 3 | 101806474 | 101810473 |
| 277 | 16 | 27195258 | 27195287 | 27245673 | 27245702 | 16 | 27191288 | 27195287 |
| 278 | 8 | 80968986 | 80969015 | 81095100 | 81095129 | 8 | 80968986 | 80972985 |
| 279 | 8 | 81018078 | 81018107 | 81053410 | 81053439 | 8 | 81014108 | 81018107 |
| 280 | 8 | 81018078 | 81018107 | 81077565 | 81077594 | 8 | 81014108 | 81018107 |
| 281 | 8 | 81018078 | 81018107 | 81095100 | 81095129 | 8 | 81014108 | 81018107 |
| 282 | 8 | 81053410 | 81053439 | 81095100 | 81095129 | 8 | 81053410 | 81057409 |
| 283 | 1 | 212523302 | 212523331 | 212588793 | 212588822 | 1 | 212523302 | 212527301 |
| 284 | 1 | 212572997 | 212573026 | 212645886 | 212645915 | 1 | 212572997 | 212576996 |
| 285 | 11 | 77430379 | 77430408 | 77519074 | 77519103 | 11 | 77430379 | 77434378 |
| 286 | 4 | 168697420 | 168697449 | 168870432 | 168870461 | 4 | 168693450 | 168697449 |
| 287 | 5 | 168579937 | 168579966 | 168614429 | 168614458 | 5 | 168579937 | 168583936 |
| 288 | 10 | 95194975 | 95195004 | 95282952 | 95282981 | 10 | 95194975 | 95198974 |

TABLE 13.f5-continued

| | | Probe Location | | | | 4 kb Sequence Location | | |
|---|---|---|---|---|---|---|---|---|
| | Chr | Start1 | End1 | Start2 | End2 | Chr | Start1 | End1 |
| 289 | 3 | 170117763 | 170117792 | 170195523 | 170195552 | 3 | 170113793 | 170117792 |
| 290 | 7 | 106908172 | 106908201 | 106944732 | 106944761 | 7 | 106904202 | 106908201 |
| 291 | 5 | 68213307 | 68213336 | 68277740 | 68277769 | 5 | 68209337 | 68213336 |
| 292 | 5 | 68215410 | 68215439 | 68277740 | 68277769 | 5 | 68215410 | 68219409 |
| 293 | 17 | 67337109 | 67337138 | 67493397 | 67493426 | 17 | 67333139 | 67337138 |
| 294 | 12 | 19116277 | 19116306 | 19175194 | 19175223 | 12 | 19116277 | 19120276 |
| 295 | 12 | 19116277 | 19116306 | 19247123 | 19247152 | 12 | 19116277 | 19120276 |
| 296 | 12 | 19116277 | 19116306 | 19322615 | 19322644 | 12 | 19116277 | 19120276 |
| 297 | 12 | 19116277 | 19116306 | 19330800 | 19330829 | 12 | 19116277 | 19120276 |
| 298 | 16 | 57264324 | 57264353 | 57315881 | 57315910 | 16 | 57264324 | 57268323 |
| 299 | 12 | 62616405 | 62616434 | 62635972 | 62636001 | 12 | 62612435 | 62616434 |
| 300 | 6 | 16559432 | 16559461 | 16745336 | 16745365 | 6 | 16559432 | 16563431 |
| 301 | 4 | 100984121 | 100984150 | 101215421 | 101215450 | 4 | 100984121 | 100988120 |
| 302 | 4 | 100996081 | 100996110 | 101215421 | 101215450 | 4 | 100992111 | 100996110 |
| 303 | 16 | 23926889 | 23926918 | 24184884 | 24184913 | 16 | 23922919 | 23926918 |
| 304 | 10 | 6432893 | 6432922 | 6464158 | 6464187 | 10 | 6432893 | 6436892 |
| 305 | 22 | 44666471 | 44666500 | 44701859 | 44701888 | 22 | 44662501 | 44666500 |
| 306 | 11 | 36302554 | 36302583 | 36446983 | 36447012 | 11 | 36298584 | 36302583 |
| 307 | 11 | 36302554 | 36302583 | 36488818 | 36488847 | 11 | 36298584 | 36302583 |
| 308 | 2 | 113175431 | 113175460 | 113215780 | 113215809 | 2 | 113175431 | 113179430 |
| 309 | 8 | 140725052 | 140725081 | 140771377 | 140771406 | 8 | 140721082 | 140725081 |
| 310 | 8 | 140725052 | 140725081 | 140877455 | 140877484 | 8 | 140721082 | 140725081 |
| 311 | 8 | 140725196 | 140725225 | 140883115 | 140883144 | 8 | 140725196 | 140729195 |
| 312 | 12 | 112418669 | 112418698 | 112478543 | 112478572 | 12 | 112418669 | 112422668 |

TABLE 13.f6

| | 4 kb Seequence Location | | Inner_primers | | |
|---|---|---|---|---|---|
| | Start2 | End2 | PCR-Primer1_ID | PCR_Primer1 | PCR-Primer2_ID |
| 261 | 142766140 | 142770139 | OBD117.1.1417 | AGGGTTGCCAGAAGAAACAGGGC (SEQ ID NO: 1337) | OBD117.1.1419 |
| 262 | 142814262 | 142818261 | OBD117.1.1677 | CCCCAGTGAGAAGGGTTGCCAGA (SEQ ID NO: 1338) | OBD117.1.1679 |
| 263 | 32578373 | 32582372 | OBD117.1.1021 | ACTGCCCTGTAACGTTGCTC (SEQ ID NO: 1339) | OBD117.1.1023 |
| 264 | 32578373 | 32582372 | OBD117.1.885 | TGTTGGGGATTTGTCTGGAT (SEQ ID NO: 1340) | OBD117.1.887 |
| 265 | 105840512 | 105844511 | OBD117.1.751 | ATCCTGGGTGGGATCTTG (SEQ ID NO: 1341) | OBD117.1.749 |
| 266 | 119700077 | 119704076 | OBD117.1.057 | GGATACCACACTGGGAGGCTTCC (SEQ ID NO: 1342) | OBD117.1.059 |
| 267 | 198249086 | 198253085 | OBD117.1.1161 | GGAGCCTCACCCTGTTGATAGTC (SEQ ID NO: 1343) | OBD117.1.1163 |
| 268 | 198346795 | 198350794 | OBD117.1.1281 | CGGAGCCTCACCCTGTTGATAGTC (SEQ ID NO: 1344) | OBD117.1.1283 |
| 269 | 198346795 | 198350794 | OBD117.1.1665 | GTGCTGGGCAAACTTATCCATTTCTT (SEQ ID NO: 1345) | OBD117.1.1667 |
| 270 | 31224131 | 31228130 | OBD117.1.1657 | CGGTTGTCCCAGCCCTAAGTAGATGA (SEQ ID NO: 1346) | OBD117.1.1659 |
| 271 | 31382125 | 31386124 | OBD117.1.1809 | CCACTGTTTTAGGATGGTCTGAC (SEQ ID NO: 1347) | OBD117.1.1811 |
| 272 | 51482831 | 51486830 | OBD117.1.1341 | AGCCTGGGTGACAGAGTGAGACT (SEQ ID NO: 1348) | OBD117.1.1343 |
| 273 | 60989414 | 60993413 | OBD117.1.1269 | ACCTATCCCATTCAGATTTTGCTTGC (SEQ ID NO: 1349) | OBD117.1.1271 |
| 274 | 44308140 | 44312139 | OBD117.1.065 | CACTTTGCCTCCACATCTGGTATGAG (SEQ ID NO: 1350) | OBD117.1.067 |

TABLE 13.f6-continued

|  | 4 kb Seequence Location | | Inner_primers | | |
|---|---|---|---|---|---|
|  | Start2 | End2 | PCR-Primer1_ID | PCR_Primer1 | PCR-Primer2_ID |
| 275 | 44308140 | 44312139 | OBD117.1.1065 | CCGGCTCAACTAGCACTTTG (SEQ ID NO: 1351) | OBD117.1.1067 |
| 276 | 101822519 | 101826518 | OBD117.1.1249 | CCAGGACTCTTTAGTGTCTGTTCCCC (SEQ ID NO: 1352) | OBD117.1.1251 |
| 277 | 27241703 | 27245702 | OBD117.1.641 | AAGCACTGGGACAAGCCTGGAGG (SEQ ID NO: 1353) | OBD117.1.643 |
| 278 | 81095100 | 81099099 | OBD117.1.081 | CCTATGTGCCACTACCCGCCCAT (SEQ ID NO: 1354) | OBD117.1.083 |
| 279 | 81053410 | 81057409 | OBD117.1.145 | AAAACCCAGCACTGAAATACTACAGC (SEQ ID NO: 1355) | OBD117.1.147 |
| 280 | 81077565 | 81081564 | OBD117.1.129 | AAAACCCAGCACTGAAATACTACAGC (SEQ ID NO: 1356) | OBD117.1.131 |
| 281 | 81095100 | 81099099 | OBD117.1.105 | GGACAGCCACTACTCAACCTTTTCCT (SEQ ID NO: 1357) | OBD117.1.107 |
| 282 | 81095100 | 81099099 | OBD117.1.217 | GCCTGATGTCTTCAAAAGGGCTGTTC (SEQ ID NO: 1358) | OBD117.1.219 |
| 283 | 212584823 | 212588822 | OBD117.1.709 | CCTGATTCCCACTCCCTGAAGGCAAT (SEQ ID NO: 1359) | OBD117.1.711 |
| 284 | 212641916 | 212645915 | OBD117.1.705 | GGGAAGAAGCCTGTTGTCTGGTAGG (SEQ ID NO: 1360) | OBD117.1.707 |
| 285 | 77515104 | 77519103 | OBD117.1.297 | CATAACCACACTGCTACCAACACACC (SEQ ID NO: 1361) | OBD117.1.299 |
| 286 | 168866462 | 168870461 | OBD117.1.1545 | AAGCAAGAGGCAAAGGGCATCCC (SEQ ID NO: 1362) | OBD117.1.1547 |
| 287 | 168614429 | 168618428 | OBD117.1.669 | CCGACCCTAACATTCAAGGTGTCTCT (SEQ ID NO: 1363) | OBD117.1.671 |
| 288 | 95282952 | 95286951 | OBD117.1.1645 | TGAGTGTTTTCAGGGTGTTGAGTCCT (SEQ ID NO: 1364) | OBD117.1.1647 |
| 289 | 170195523 | 170199522 | OBD117.1.1277 | CTGTAATGCCAGCACTTTGGGAGGTC (SEQ ID NO: 1365) | OBD117.1.1279 |
| 290 | 106940762 | 106944761 | OBD117.1.1361 | CATCCTGCTACTGGGAACTACCC (SEQ ID NO: 1366) | OBD117.1.1363 |
| 291 | 68273770 | 68277769 | OBD117.1.069 | TGACACCCTGTATCACCCCTTTCGT (SEQ ID NO: 1367) | OBD117.1.071 |
| 292 | 68273770 | 68277769 | OBD117.1.735 | CTCTGGCTCTACACGTCCC (SEQ ID NO: 1368) | OBD117.1.733 |
| 293 | 67493397 | 67497396 | OBD117.1.569 | CCACCAACCCCAAATCGGGAGTT (SEQ ID NO: 1369) | OBD117.1.571 |
| 294 | 19175194 | 19179193 | OBD117.1.1461 | GAGTAGAGAAGAAGGATAGGTAATCT (SEQ ID NO: 1370) | OBD117.1.1463 |
| 295 | 19247123 | 19251122 | OBD117.1.1525 | CGGTAGGCTGAGGCAGGGAGAAT (SEQ ID NO: 1371) | OBD117.1.1527 |
| 296 | 19318645 | 19322644 | OBD117.1.1381 | CCCAGCAGCCATTCAGACAGTGG (SEQ ID NO: 1372) | OBD117.1.1383 |
| 297 | 19330800 | 19334799 | OBD117.1.1137 | TGGGTGACAAGAGCAAGACTCCGTC (SEQ ID NO: 1373) | OBD117.1.1139 |
| 298 | 57311911 | 57315910 | OBD117.1.561 | CCCCTAACTTCCTCTTCTCACCC (SEQ ID NO: 1374) | OBD117.1.563 |
| 299 | 62635972 | 62639971 | OBD117.1.1853 | AAGTAGTAAGCCTTCATTTCTTT (SEQ ID NO: 1375) | OBD117.1.1855 |

TABLE 13.f6-continued

| | 4 kb Seequence Location | | Inner_primers | | |
|---|---|---|---|---|---|
| | Start2 | End2 | PCR-Primer1_ID | PCR_Primer1 | PCR-Primer2_ID |
| 300 | 16745336 | 16749335 | OBD117.1.1313 | CACCTAACAGTGTGTCCTGGAAAACC (SEQ ID NO: 1376) | OBD117.1.1315 |
| 301 | 101215421 | 101219420 | OBD117.1.1473 | AAGTTTGCCCCTCACTGGTGCTAAT (SEQ ID NO: 1377) | OBD117.1.1475 |
| 302 | 101215421 | 101219420 | OBD117.1.1157 | AGGAATCGCATTGGGAACAGAGACTT (SEQ ID NO: 1378) | OBD117.1.1159 |
| 303 | 24180914 | 24184913 | OBD117.1.1345 | CTTTATCCAGTCATCCATTGATTGAT (SEQ ID NO: 1379) | OBD117.1.1347 |
| 304 | 6460188 | 6464187 | OBD117.1.365 | GCCTGATGAATCGGGATGGTTCCTTA (SEQ ID NO: 1380) | OBD117.1.367 |
| 305 | 44697889 | 44701888 | OBD117.1.005 | TTACACTCCTGGGCACTCTTCCC (SEQ ID NO: 1381) | OBD117.1.007 |
| 306 | 36443013 | 36447012 | OBD117.1.1565 | GGGCTCACACCTGTTATCCCAGC (SEQ ID NO: 1382) | OBD117.1.1567 |
| 307 | 36484848 | 36488847 | OBD117.1.1217 | GGCTCACACCTGTTATCCCAGCACTT (SEQ ID NO: 1383) | OBD117.1.1219 |
| 308 | 113215780 | 113219779 | OBD117.1.673 | CGCTCCCTCCTTTTACCCTGGAA (SEQ ID NO: 1384) | OBD117.1.675 |
| 309 | 140767407 | 140771406 | OBD117.1.229 | TAGGGATGGCATACCTGGAAGTAGC (SEQ ID NO: 1385) | OBD117.1.231 |
| 310 | 140877455 | 140881454 | OBD117.1.233 | GGGATGGCATACCTGGAAGTAGC (SEQ ID NO: 1386) | OBD117.1.235 |
| 311 | 140879145 | 140883144 | OBD117.1.357 | GCTTGGTTCCATTTAGCCACTTACCT (SEQ ID NO: 1387) | OBD117.1.359 |
| 312 | 112478543 | 112482542 | OBD117.1.761 | ACTTCCTGCTTCCCGTCAG (SEQ ID NO: 1388) | OBD117.1.763 |

TABLE 13.f7

| | Inner_primers | |
|---|---|---|
| | PCR_Primer2 | GLMNET |
| 261 | GCCGTGGCGGTGGACAGAGTTAT (SEQ ID NO: 1389) | 0 |
| 262 | CCATTGGGTGAAACTCCACAGGG (SEQ ID NO: 1390) | 0 |
| 263 | TCAAAGCAGCAGTCTAAATTCTCC (SEQ ID NO: 1391) | 0 |
| 264 | TGGATGATAATGCAAGCTACG (SEQ ID NO: 1392) | 0.019910002 |
| 265 | CCCATGTTAAGCCTTGCAGT (SEQ ID NO: 1393) | 0.011140328 |
| 266 | TGACCACAAGGGCAGATTCTCCC (SEQ ID NO: 1394) | 0.002451894 |
| 267 | CAGTGTGTAGGACAGTGCCTGGC (SEQ ID NO: 1395) | 0 |
| 268 | GGAGCCCAAAATGTCCAGGTGAC (SEQ ID NO: 1396) | 0 |
| 269 | TAAGGAGCCCAAAATGTCCAGGTGAC (SEQ ID NO: 1397) | 0 |
| 270 | CTTCTCTATCTTCCACAACCTCACCA (SEQ ID NO: 1398) | 0 |
| 271 | CAAAGCATAATCTGGACCTTCTA (SEQ ID NO: 1399) | 0 |
| 272 | GTCCGAACCCTGGGATGTGCCAT (SEQ ID NO: 1400) | 0 |
| 273 | GAGCATTGTCTGGGAATCAGGTGTTT (SEQ ID NO: 1401) | 0 |
| 274 | GGCTTGACACCCTTAGTTTACTGCCT (SEQ ID NO: 1402) | 0.006729048 |

TABLE 13.f7-continued

| | Inner_primers | |
|---|---|---|
| | PCR_Primer2 | GLMNET |
| 275 | CCCTAGACTCTCACCTCCTCTC (SEQ ID NO: 1403) | 0 |
| 276 | CCCCTTCCAGTTCCAAAAGTAGTTAT (SEQ ID NO: 1404) | 0 |
| 277 | GCCAGCAAGAGCCAGAGACACAA (SEQ ID NO: 1405) | 0.000955334 |
| 278 | CAGATTGGACCTCACAGCCCCAT (SEQ ID NO: 1406) | 0.0196745 |
| 279 | TATGCCCAAGGTGTATCTCCCCT (SEQ ID NO: 1407) | 0.012784814 |
| 280 | GGTCAGTCTGTCCTTGTCTCTAACCA (SEQ ID NO: 1408) | 0.000107394 |
| 281 | AAATGCTGGGCTCCTCTTTTGTCCTC (SEQ ID NO: 1409) | 0.011672595 |
| 282 | AATGCTGGGCTCCTCTTTTGTCCTCT (SEQ ID NO: 1410) | 0.006914365 |
| 283 | TCTCGTCTTAGTTGAAATCCACCCAG (SEQ ID NO: 1411) | 0.000126022 |
| 284 | CACAAACACTGGAAGGGAGAAAATAG (SEQ ID NO: 1412) | −0.002734128 |
| 285 | GGTTATTCGGACACTCATAGGACTGG (SEQ ID NO: 1413) | −0.020410863 |
| 286 | ATAGCAGAACCACATCCAACTCTA (SEQ ID NO: 1414) | 0 |
| 287 | CCACTTCATTTCATCCCTACTGCCAC (SEQ ID NO: 1415) | 0.022244309 |
| 288 | TTAGGCTTTGGGTTATGGGTGGTAGC (SEQ ID NO: 1416) | 0 |
| 289 | GTGGTGAAAGTAGGCATCCTTGTCTT (SEQ ID NO: 1417) | 0 |
| 290 | GCACCACTCCCTCTTCCCACAGT (SEQ ID NO: 1418) | 0 |
| 291 | GGATACTACCTTCTCCCACTCATTTA (SEQ ID NO: 1419) | −0.007209703 |
| 292 | CCTAGTGGGCAAGTTTGG (SEQ ID NO: 1420) | 0.000117929 |
| 293 | TCCAAGGTCAAAGCCACCCTCCC (SEQ ID NO: 1421) | 0.000114434 |
| 294 | TGCTATTTTGTATGTGTTGGGTGTAT (SEQ ID NO: 1422) | 0 |
| 295 | CTGTTGTTTGCCTCCCTTTCCAGG (SEQ ID NO: 1423) | 0 |
| 296 | GGTGACAAGAGCAAGACTCCGTC (SEQ ID NO: 1424) | 0 |
| 297 | GAGGGAGAGGCAATAGATGTAGTGTA (SEQ ID NO: 1425) | 0 |
| 298 | CGGGCACTGTTGGGCACTGAAGA (SEQ ID NO: 1426) | 0.010030034 |
| 299 | GCCAAGTAGCACCAAAGCCAATA (SEQ ID NO: 1427) | 0 |
| 300 | CCCTTTGATTCCACCATTCCAGTCCA (SEQ ID NO: 1428) | 0 |
| 301 | GAACTTTCTTTCCCCTTCATTTAGT (SEQ ID NO: 1429) | 0 |
| 302 | GTTAGAAGGGACATTAGGATTAGAAT (SEQ ID NO: 1430) | 0 |
| 303 | TACAGAGGAGTAAAGACAGTTTT (SEQ ID NO: 1431) | 0 |
| 304 | GCTGAGCCCTGAAAGATAAGGCAGAA (SEQ ID NO: 1432) | 0.007672168 |
| 305 | AGCAAATCCTCCAGGCAGCCAGG (SEQ ID NO: 1433) | 0.016924425 |
| 306 | GGCAGATGGACTTCAGGAGGGAT (SEQ ID NO: 1434) | 0 |
| 307 | GTTAGGCTACAGCAACATACTCAAGC (SEQ ID NO: 1435) | 0 |
| 308 | GGGTCCCCTTTTCGGGCTCAGAA (SEQ ID NO: 1436) | 0.006586768 |
| 309 | GCATTACGGATTCATTTGCTCACTCA (SEQ ID NO: 1437) | −0.017032217 |
| 310 | GGGACTCTGCCATCTGTATGCTGC (SEQ ID NO: 1438) | 0.000119638 |

TABLE 13.f7-continued

| | Inner primers | |
|---|---|---|
| | PCR_Primer2 | GLMNET |
| 311 | AATCTGGCTGCCTATGGTTGCTCTCC (SEQ ID NO: 1439) | −0.01499141 |
| 312 | AGAGCGGATGACATATTGCAG (SEQ ID NO: 1440) | 0.00011938 |

TABLE 13.g1

| | Probe | GeneLocus | Probe_Count_Total | Probe_Count_Sig |
|---|---|---|---|---|
| 313 | ORF541_7_77589308_77593066_77652906_77658625_RF | ORF541 | 23 | 4 |
| 314 | ORF541_7_77628734_77632614_77645983_77651804_FF | ORF541 | 23 | 4 |
| 315 | ORF544_1_198591683_198595771_198768850_198775826_FF | PTPRC | 214 | 10 |
| 316 | ORF544_1_198659753_198666156_198697386_198704777_FR | ORF544 | 187 | 30 |
| 317 | ORF544_1_198659753_198666156_198735456_198749256_FF | ORF544 | 187 | 30 |
| 318 | ORF544_1_198735456_198749256_198779053_198786841_RF | ORF544 | 187 | 30 |
| 319 | ORF547_11_82936602_82938148_83048972_83059269_RR | ORF547 | 99 | 7 |
| 320 | ORF547_11_82938763_82948488_82974616_82981008_FR | ORF547 | 99 | 7 |
| 321 | ORF55_11_64267793_64269811_64288581_64290103_FR | BAD | 70 | 8 |
| 322 | ORF55_11_64267793_64269811_64292591_64296924_FF | BAD | 70 | 8 |
| 323 | ORF552_1_174835362_174838725_175007460_175017921_RF | ORF552 | 93 | 6 |
| 324 | ORF553_7_6325447_6327369_6392091_6396545_RR | RAC1 | 64 | 2 |
| 325 | ORF554_20_20425025_20439432_20458256_20459854_RF | ORF554 | 117 | 8 |
| 326 | ORF556_13_97440604_97443754_97479189_97487608_FF | ORF556 | 66 | 5 |
| 327 | ORF558_2_33390711_33398991_33442363_33444238_FR | ORF558 | 34 | 5 |
| 328 | ORF56_14_75477136_75478350_75491596_75496634_FR | ORF56 | 18 | 2 |
| 329 | ORF56_14_75491596_75496634_75573735_75577816_RF | ORF56 | 18 | 2 |
| 330 | ORF560_21_14176916_14181369_14267912_14269012_RF | ORF560 | 37 | 3 |
| 331 | ORF560_21_14210379_14215717_14236469_14248873_RR | ORF560 | 37 | 3 |
| 332 | ORF564_21_34500925_34506011_34574861_34579728_FR | ORF564 | 67 | 7 |
| 333 | ORF567_11_65634932_65641044_65653258_65654626_RF | RELA | 56 | 2 |
| 334 | ORF568_12_18259444_18261081_18350532_18364514_FF | ORF568 | 34 | 5 |
| 335 | ORF569_3_16448043_16456162_16496760_16499694_FF | ORF569 | 139 | 10 |
| 336 | ORF57_19_48914276_48916713_48932242_48935310_FF | ORF57 | 30 | 6 |
| 337 | ORF57_19_48914276_48916713_48968306_48971572_FF | ORF57 | 30 | 6 |
| 338 | ORF576_6_3027907_3030237_3146778_3149848_FR | ORF576 | 25 | 8 |
| 339 | ORF576_6_3045545_3051391_3146778_3149848_FR | ORF576 | 25 | 8 |
| 340 | ORF576_6_3114019_3116008_3146778_3149848_RR | ORF576 | 25 | 8 |
| 341 | ORF586_6_166614982_166618999_166826698_166835940_RR | ORF586 | 176 | 12 |
| 342 | ORF586_6_166614982_166618999_166877620_166884513_RR | ORF586 | 176 | 12 |
| 343 | ORF589_21_35511164_35517830_35766255_35775694_FF | ORF589 | 197 | 5 |
| 344 | ORF59_20_50749321_50753502_50888426_50893318_FR | ORF59 | 17 | 4 |
| 345 | ORF596_1_243286011_243289794_243392615_243398557_RF | ORF596 | 151 | 9 |
| 346 | ORF596_1_243386248_243390518_243516824_243527512_RF | ORF596 | 151 | 9 |
| 347 | ORF603_18_44885635_44895879_44997556_45002564_FR | ORF603 | 156 | 11 |
| 348 | ORF603_18_44885635_44895879_45014599_45017752_FR | ORF603 | 156 | 11 |
| 349 | ORF605_1_66506442_66514114_66751280_66753550_RF | ORF605 | 163 | 8 |
| 350 | ORF605_1_66578981_66592963_66761002_66762820_RF | ORF605 | 163 | 7 |
| 351 | ORF611_20_1857555_1861228_1955166_1964657_FR | ORF611 | 59 | 7 |
| 352 | ORF611_20_1891489_1897350_1924633_1930962_RR | SIRPA | 56 | 4 |
| 353 | ORF613_1_160707882_160714935_160743813_160744937_RF | ORF613 | 27 | 1 |
| 354 | ORF618_6_3272293_3273348_3492046_3503752_FF | ORF618 | 158 | 8 |
| 355 | ORF624_2_27626184_27635183_27719544_27726504_RF | ORF624 | 24 | 2 |
| 356 | ORF626_5_150149497_150151091_150181302_150194775_FR | ORF626 | 34 | 5 |
| 357 | ORF626_5_150162904_150166548_150181302_150194775_FR | ORF626 | 34 | 5 |
| 358 | ORF626_5_150162904_150166548_150194890_150198993_FR | ORF626 | 34 | 0 |
| 359 | ORF626_5_150181302_150194775_150230115_150237336_RF | ORF626 | 34 | 5 |
| 360 | ORF626_5_150181302_150194775_150237336_150238718_RF | ORF626 | 34 | 5 |
| 361 | ORF630_17_35287155_35289074_35307929_35312497_FF | ORF630 | 18 | 3 |
| 362 | ORF631_15_67098632_67101498_67199584_67204251_RR | SMAD3 | 34 | 2 |
| 363 | ORF642_16_29613904_29616227_29630194_29632081_RF | SPN | 56 | 4 |
| 364 | ORF642_16_29613904_29616227_29686079_29687229_RF | SPN | 56 | 4 |

TABLE 13.g2

| | HyperG_Stats | FDR_HyperG | Percent_Sig | logFC | AveExpr | t |
|---|---|---|---|---|---|---|
| 313 | 0.053424912 | 0.606428812 | 17.39 | 0.356643448 | 0.356643448 | 3.960789133 |
| 314 | 0.053424912 | 0.606428812 | 17.39 | 0.285214138 | 0.285214138 | 4.609256093 |
| 315 | 0.978491243 | 0.99999793 | 4.67 | −0.14040288 | −0.14040288 | −5.186348648 |
| 316 | 2.30E−06 | 0.000217011 | 16.04 | 0.283822723 | 0.283822723 | 11.36017484 |
| 317 | 2.30E−06 | 0.000217011 | 16.04 | 0.28622671 | 0.28622671 | 10.23998629 |

TABLE 13.g2-continued

| | HyperG_Stats | FDR_HyperG | Percent_Sig | logFC | AveExpr | t |
|---|---|---|---|---|---|---|
| 318 | 2.30E−06 | 0.000217011 | 16.04 | 0.312760316 | 0.312760316 | 7.112432884 |
| 319 | 0.433763829 | 1 | 7.07 | 0.377286081 | 0.377286081 | 4.904828931 |
| 320 | 0.433763829 | 1 | 7.07 | 0.319635014 | 0.319635014 | 4.836776666 |
| 321 | 0.18964104 | 0.954389149 | 11.43 | −0.146341453 | −0.146341453 | −5.009008006 |
| 322 | 0.18964104 | 0.954389149 | 11.43 | −0.155897691 | −0.155897691 | −6.419907226 |
| 323 | 0.587989675 | 1 | 6.45 | 0.162077594 | 0.162077594 | 6.758085183 |
| 324 | 0.967461559 | 0.99999793 | 3.12 | −0.432758998 | −0.432758998 | −5.571884831 |
| 325 | 0.459116235 | 1 | 6.84 | 0.446838664 | 0.446838664 | 12.24134889 |
| 326 | 0.403635377 | 1 | 7.58 | 0.423159851 | 0.423159851 | 10.02547665 |
| 327 | 0.06020741 | 0.646636236 | 14.71 | 0.297744446 | 0.297744446 | 8.756884365 |
| 328 | 0.337741302 | 1 | 11.11 | 0.196386472 | 0.196386472 | 6.01640946 |
| 329 | 0.337741302 | 1 | 11.11 | 0.168913942 | 0.168913942 | 6.493464138 |
| 330 | 0.415513464 | 1 | 8.11 | 0.309983092 | 0.309983092 | 11.42911374 |
| 331 | 0.415513464 | 1 | 8.11 | 0.355272886 | 0.355272886 | 9.89272102 |
| 332 | 0.12838934 | 0.904598768 | 10.45 | 0.289530526 | 0.289530526 | 10.39257872 |
| 333 | 0.94351322 | 0.99999793 | 3.57 | −0.335793252 | −0.335793252 | −14.59846809 |
| 334 | 0.06020741 | 0.646636236 | 14.71 | 0.301770409 | 0.301770409 | 9.8018573 |
| 335 | 0.380387396 | 1 | 7.19 | 0.306584347 | 0.306584347 | 2.955558359 |
| 336 | 0.01000538 | 0.181608098 | 20 | 0.319528065 | 0.319528065 | 12.82607629 |
| 337 | 0.01000538 | 0.181608098 | 20 | 0.294074256 | 0.294074256 | 15.40919841 |
| 338 | 0.000101223 | 0.003977202 | 32 | 0.342315512 | 0.342315512 | 4.823515277 |
| 339 | 0.000101223 | 0.003977202 | 32 | 0.381150282 | 0.381150282 | 7.660425289 |
| 340 | 0.000101223 | 0.003977202 | 32 | 0.471818762 | 0.471818762 | 6.947243306 |
| 341 | 0.432643309 | 1 | 6.82 | 0.334089996 | 0.334089996 | 5.008617015 |
| 342 | 0.432643309 | 1 | 6.82 | 0.378448027 | 0.378448027 | 6.858042974 |
| 343 | 0.995427013 | 1 | 2.54 | 0.309719719 | 0.309719719 | 3.570772465 |
| 344 | 0.019351438 | 0.304140094 | 23.53 | 0.310572354 | 0.310572354 | 7.361954056 |
| 345 | 0.617155598 | 1 | 5.96 | 0.388082401 | 0.388082401 | 11.1208405 |
| 346 | 0.617155598 | 1 | 5.96 | 0.295082217 | 0.295082217 | 6.643633956 |
| 347 | 0.395653632 | 1 | 7.05 | 0.2983925 | 0.2983925 | 6.884745917 |
| 348 | 0.395653632 | 1 | 7.05 | 0.286095812 | 0.286095812 | 5.99074538 |
| 349 | 0.854051613 | 1 | 4.91 | 0.249385621 | 0.249385621 | 2.70486202 |
| 350 | 0.894561341 | 1 | 4.29 | 0.302395192 | 0.302395192 | 6.269378105 |
| 351 | 0.076789008 | 0.731434696 | 11.86 | 0.347062258 | 0.347062258 | 6.676297968 |
| 352 | 0.659150649 | 0.99999793 | 7.14 | −0.183746617 | −0.183746617 | −7.539838325 |
| 353 | 0.858892218 | 1 | 3.7 | −0.306060504 | −0.306060504 | −4.552793946 |
| 354 | 0.785606032 | 1 | 5.06 | 0.307291844 | 0.307291844 | 7.043291289 |
| 355 | 0.479347944 | 1 | 8.33 | 0.148041193 | 0.148041193 | 4.147781826 |
| 356 | 0.085664563 | 0.667617217 | 14.71 | −0.191241299 | −0.191241299 | −9.324329472 |
| 357 | 0.085664563 | 0.667617217 | 14.71 | −0.213609391 | −0.213609391 | −10.1665293 |
| 358 | 1 | 1 | 0 | −0.157170259 | −0.157170259 | −6.502829914 |
| 359 | 0.085664563 | 0.667617217 | 14.71 | −0.193972875 | −0.193972875 | −11.86119945 |
| 360 | 0.085664563 | 0.667617217 | 14.71 | −0.152338864 | −0.152338864 | −9.193910673 |
| 361 | 0.100654026 | 0.825363011 | 16.67 | 0.309628617 | 0.309628617 | 5.989078991 |
| 362 | 0.764125503 | 0.99999793 | 5.88 | −0.180175335 | −0.180175335 | −8.471609217 |
| 363 | 0.659150649 | 0.99999793 | 7.14 | −0.175972335 | −0.175972335 | −7.054965999 |
| 364 | 0.659150649 | 0.99999793 | 7.14 | −0.16436617 | −0.16436617 | −7.773176867 |

TABLE 13.g3

| | P.Value | adj.P.Val | B | FC | FC 1 | LS |
|---|---|---|---|---|---|---|
| 313 | 0.002558481 | 0.011825242 | −1.934224365 | 1.280443369 | 1.280443369 | 1 |
| 314 | 0.000906562 | 0.005597155 | −0.862545562 | 1.218591124 | 1.218591124 | 1 |
| 315 | 0.000378279 | 0.003044422 | 0.045441754 | 0.907265761 | −1.102212872 | −1 |
| 316 | 0.000000392 | 0.0000522 | 7.121810671 | 1.217416415 | 1.217416415 | 1 |
| 317 | 0.00000105 | 0.0000827 | 6.131358316 | 1.219446707 | 1.219446707 | 1 |
| 318 | 0.0000286 | 0.000550434 | 2.734802175 | 1.24208191 | 1.24208191 | 1 |
| 319 | 0.000575972 | 0.004077688 | −0.391728534 | 1.298896144 | 1.298896144 | 1 |
| 320 | 0.000638673 | 0.004378379 | −0.499072732 | 1.248014775 | 1.248014775 | 1 |
| 321 | 0.000492332 | 0.003660595 | −0.228647352 | 0.903538855 | −1.106759266 | −1 |
| 322 | 0.0000684 | 0.000962212 | 1.827393464 | 0.8975737 | −1.11411464 | −1 |
| 323 | 0.0000443 | 0.000727991 | 2.278534173 | 1.118897278 | 1.118897278 | 1 |
| 324 | 0.000216637 | 0.00207522 | 0.625787741 | 0.740843647 | −1.34981248 | −1 |
| 325 | 0.000000191 | 0.0000378 | 7.834376391 | 1.363050169 | 1.363050169 | 1 |
| 326 | 0.00000128 | 0.0000923 | 5.92980967 | 1.340861152 | 1.340861152 | 1 |
| 327 | 0.00000448 | 0.000179825 | 4.650235925 | 1.229221108 | 1.229221108 | 1 |
| 328 | 0.00011691 | 0.00138082 | 1.268397808 | 1.145824803 | 1.145824803 | 1 |
| 329 | 0.0000621 | 0.000902589 | 1.926850909 | 1.124211861 | 1.124211861 | 1 |
| 330 | 0.00000037 | 0.000051 | 7.179564842 | 1.239693171 | 1.239693171 | 1 |
| 331 | 0.00000145 | 0.0000986 | 5.803035818 | 1.279227525 | 1.279227525 | 1 |
| 332 | 0.000000912 | 0.0000775 | 6.272306869 | 1.222242477 | 1.222242477 | 1 |
| 333 | 0.0000000344 | 0.0000161 | 9.499491123 | 0.792348352 | −1.262071156 | −1 |
| 334 | 0.00000158 | 0.000104705 | 5.715349753 | 1.232656145 | 1.232656145 | 1 |
| 335 | 0.0140425 | 0.041914834 | −3.663900054 | 1.236776102 | 1.236776102 | 1 |

TABLE 13.g3-continued

|     | P.Value | adj.P.Val | B | FC | FC 1 | LS |
|-----|---------|-----------|---|-----|------|-----|
| 336 | 0.000000122 | 0.0000302 | 8.278231076 | 1.247922262 | 1.247922262 | 1 |
| 337 | 0.0000000202 | 0.0000131 | 10.00304815 | 1.226097966 | 1.226097966 | 1 |
| 338 | 0.000651715 | 0.004434959 | −0.520065389 | 1.267789753 | 1.267789753 | 1 |
| 339 | 0.0000149 | 0.000370113 | 3.408694648 | 1.302379848 | 1.302379848 | 1 |
| 340 | 0.000035 | 0.000623193 | 2.524156698 | 1.386856735 | 1.386856735 | 1 |
| 341 | 0.000492621 | 0.003661363 | −0.229256562 | 1.260582024 | 1.260582024 | 1 |
| 342 | 0.0000391 | 0.000668286 | 2.408921964 | 1.299942695 | 1.299942695 | 1 |
| 343 | 0.004898278 | 0.019080854 | −2.599525191 | 1.239466878 | 1.239466878 | 1 |
| 344 | 0.0000212 | 0.000459585 | 3.046319093 | 1.240199621 | 1.240199621 | 1 |
| 345 | 0.00000048 | 0.0000579 | 6.918534793 | 1.308652814 | 1.308652814 | 1 |
| 346 | 0.0000512 | 0.000797045 | 2.127594248 | 1.226954898 | 1.226954898 | 1 |
| 347 | 0.0000378 | 0.000653933 | 2.443528915 | 1.229773394 | 1.229773394 | 1 |
| 348 | 0.000121059 | 0.001415354 | 1.232066621 | 1.21933607 | 1.21933607 | 1 |
| 349 | 0.021686156 | 0.057998117 | −4.095656378 | 1.188700793 | 1.188700793 | 1 |
| 350 | 0.0000833 | 0.001098005 | 1.621523674 | 1.233190082 | 1.233190082 | 1 |
| 351 | 0.0000491 | 0.000776177 | 2.170852318 | 1.271967896 | 1.271967896 | 1 |
| 352 | 0.0000172 | 0.000403646 | 3.263611548 | 0.880413629 | −1.135829759 | −1 |
| 353 | 0.000990011 | 0.005969135 | −0.953815343 | 0.808847426 | −1.236327109 | −1 |
| 354 | 0.0000311 | 0.000577254 | 2.64706744 | 1.237382765 | 1.237382765 | 1 |
| 355 | 0.001886069 | 0.00947947 | −1.620209255 | 1.108063986 | 1.108063986 | 1 |
| 356 | 0.00000251 | 0.000133818 | 5.24188899 | 0.875851812 | −1.141745655 | −1 |
| 357 | 0.00000112 | 0.0000854 | 6.062792551 | 0.862377002 | −1.159585655 | −1 |
| 358 | 0.0000614 | 0.000895467 | 1.939461051 | 0.89678232 | −1.115097808 | −1 |
| 359 | 0.000000259 | 0.0000428 | 7.533668036 | 0.874195057 | −1.143909466 | −1 |
| 360 | 0.00000286 | 0.000142904 | 5.10877376 | 0.89979056 | −1.111369739 | −1 |
| 361 | 0.000121333 | 0.001416487 | 1.229704368 | 1.239388612 | 1.239388612 | 1 |
| 362 | 0.00000605 | 0.000215806 | 4.34015114 | 0.882595726 | −1.133021576 | −1 |
| 363 | 0.0000306 | 0.000572312 | 2.661925201 | 0.885170738 | −1.129725551 | −1 |
| 364 | 0.0000131 | 0.000338569 | 3.542755797 | 0.892320463 | −1.120673616 | −1 |

TABLE 13.g4

|     | Loop detected | Probe sequence 60 mer |
|-----|---------------|------------------------|
| 313 | PD-L1 Non-responder | CTCATTTTTCCAAAAACGTGAAGAAATCTCGAAGTAAAATTTATTTCAAAGCTATTCTGG (SEQ ID NO: 1441) |
| 314 | PD-L1 Non-responder | TTTAAATTATATTTTTTACTTGCTAAGATCGAGTGACTTTTCTAAATTTTTTGACCCATA (SEQ ID NO: 1442) |
| 315 | PD-L1 responder | TGTTTTTTATTGTTTGATGTCCAATGTATCGAGTCACATGATCAAGCGCTCATTTCTGTT (SEQ ID NO: 1443) |
| 316 | PD-L1 Non-responder | AGAGGCTGAGGTGAAAAGATTGTTTGAGTCGACAACCCAATTTTGTTATTTGAGTTTCTT (SEQ ID NO: 1444) |
| 317 | PD-L1 Non-responder | AGAGGCTGAGGTGAAAAGATTGTTTGAGTCGATAAACAAATTATACAACAAAGTCTAAG (SEQ ID NO: 1445) |
| 318 | PD-L1 Non-responder | TTTAGTCAAATAATTACAAAGTATAAAATCGAAAGAATTATACTGTATTAATTAATTATC (SEQ ID NO: 1446) |
| 319 | PD-L1 Non-responder | AAAAAGGAAAAATAAAGTATATTTAACATCGAAAAAGAACCACATGGTTAAAAAGAAACT (SEQ ID NO: 1447) |
| 320 | PD-L1 Non-responder | TTTTTTCAATCTTTCTATATCTTTGTCTTCGAGTTCATAAAACTCAGTGATTAACCTGTT (SEQ ID NO: 1448) |
| 321 | PD-L1 responder | GCACTACCCCGGCCTGCCGGAGCCCCAGTCGATGATGGCTTCCTCCCCAGAGCACCAGC (SEQ ID NO: 1449) |
| 322 | PD-L1 responder | GCACTACCCCGGCCTGCCGGAGCCCCAGTCGAGTTGGTTTCTGGGTCCGCACCCCCTCCC (SEQ ID NO: 1450) |
| 323 | PD-L1 Non-responder | CAGATGGGTGGATCACAAGATCAGGAGTTCGAACAAGTCAGGATGTAATGATAATGAAAA (SEQ ID NO: 1451) |
| 324 | PD-L1 responder | GGATGTATATATATATACTATTTTTATATCGAGCGCTTAATTAGTGCATGTTACCTATGG (SEQ ID NO: 1452) |
| 325 | PD-L1 Non-responder | AGCAGCAGCTAGAAATAATCTTTTCCCTTCGACCATTCTATTTTGAAGGCAAAAGCGACT (SEQ ID NO: 1453) |

TABLE 13.g4-continued

| | Loop detected | Probe sequence 60 mer |
|---|---|---|
| 326 | PD-L1 Non-responder | ATTATGAATACTGTATGTATTATAATTCTCGATCATATTTTCTTTTGCATAGGATTTTTA (SEQ ID NO: 1454) |
| 327 | PD-L1 Non-responder | TTTTTAAAAATCTCAAATGAAAAAGTCTTCGAAAAAAAATTTCTGGTTGGTGGGATAATG (SEQ ID NO: 1455) |
| 328 | PD-L1 Non-responder | GTCAGAGACTCAGCAACGCAAGGTTCTCTCGATGGATGATGTCTGGGATAATGACTGAGG (SEQ ID NO: 1456) |
| 329 | PD-L1 Non-responder | CGCCAAGGACAGAGGTCAGTGCAACGAGTCGATGGATGATGTCTGGGATAATGACTGAGG (SEQ ID NO: 1457) |
| 330 | PD-L1 Non-responder | AAGGTGGGTGGATCATGATGTCAAAAGATCGAAATGTTTGAGAATATTTTTAAGGCTCAG (SEQ ID NO: 1458) |
| 331 | PD-L1 Non-responder | TGAAGAAAATTCTTACTTGGATAAATTATCGAATTTAGAAGAATTAGTGGTATTTTGAAA (SEQ ID NO: 1459) |
| 332 | PD-L1 Non-responder | TAAAATAGAACATTATTTTGAAATTACTTCGAAGAACATTTTTATAGCTGTATTAGCATA (SEQ ID NO: 1460) |
| 333 | PD-L1 responder | GTTCAGCAGCTGCTGAAACTCGGAGTTGTCGACACCCCTCTCTCCCCTCCCTGTTTTTCC (SEQ ID NO: 1461) |
| 334 | PD-L1 Non-responder | TAAATTCTAATTAAATAAAGAAAATACCTCGACTAAATAAAATTAAAAAAAAAATCTTTG (SEQ ID NO: 1462) |
| 335 | PD-L1 Non-responder | AATCCAAGAACAGCTAATTCTTAAGACCTCGAGCAGACTTGGTATATAAGTTGCTTATGG (SEQ ID NO: 1463) |
| 336 | PD-L1 Non-responder | AAGGCAGGCAGATCAGGAGCTCAAGAGATCGAACGCTAAGTGTAGTTTAACACCTACTAG (SEQ ID NO: 1464) |
| 337 | PD-L1 Non-responder | AAGGCAGGCAGATCAGGAGCTCAAGAGATCGAAAGAAAAAAAAAAAAGCATAAAAATCCA (SEQ ID NO: 1465) |
| 338 | PD-L1 Non-responder | AAACTTGGTATGTGTCTAATAAACAGCTTCGAGTGCTGGTTTGGGTCGGAGTGCTGGTTC (SEQ ID NO: 1466) |
| 339 | PD-L1 Non-responder | TGATCACTCCAAACACCCAAAGGTGACTTCGAGTGCTGGTTTGGGTCGGAGTGCTGGTTC (SEQ ID NO: 1467) |
| 340 | PD-L1 Non-responder | AATATAAATTCAATTCATTAAAAAAATAATCGAGTGCTGGTTTGGGTCGGAGTGCTGGTTC (SEQ ID NO: 1468) |
| 341 | PD-L1 Non-responder | TGGGTGTGGAAGGCTGGATAATGTCTCCTCGATTTTGCCATTATACTCTCTGTTTACATT (SEQ ID NO: 1469) |
| 342 | PD-L1 Non-responder | TGGGTGTGGAAGGCTGGATAATGTCTCCTCGATCAACCTACATTGGTTTGGTCTGGAAAG (SEQ ID NO: 1470) |
| 343 | PD-L1 Non-responder | GAATATGTGGGAGTGGGTATAAGAAAGATCGAGGTCACATGAAAACCCTCTGTTTAATCT (SEQ ID NO: 1471) |
| 344 | PD-L1 Non-responder | TATCTTAAGTAAATTTATGATAATGTTCTCGAGGACTCAGTACTAGTAGTCTGAGGTCTA (SEQ ID NO: 1472) |
| 345 | PD-L1 Non-responder | TCTTATTAATCTAAAATTTTATATAAAATCGATTCCTTGGAGAAAAGGAAATTGTCAGAA (SEQ ID NO: 1473) |
| 346 | PD-L1 Non-responder | TGTTTTATAATCATTATAATTTTTCTTTCGAAGCAGGTTTTGAACCCCAGTAAGTTGCC (SEQ ID NO: 1474) |
| 347 | PD-L1 Non-responder | TTTTTGCATTATGAGCTATTTATTAACATCGAGGTTTTTAGACTAATGATTTGATCTCCA (SEQ ID NO: 1475) |
| 348 | PD-L1 Non-responder | TTTTTGCATTATGAGCTATTTATTAACATCGAGGGAACTCAATGTCTGATTCTTGACAGG (SEQ ID NO: 1476) |
| 349 | PD-L1 Non-responder | TGCTCTTTACAAACTATGTAAATGTTGCTCGAAGAGGCTGATTTGAGTAATAATAAACTC (SEQ ID NO: 1477) |
| 350 | PD-L1 Non-responder | TATAGTTAGCAATAATTTATTATATATTTCGAGAGAATTAGGGGGTATATCTACAAGTCA (SEQ ID NO: 1478) |

TABLE 13.g4-continued

| | Loop detected | Probe sequence 60 mer |
|---|---|---|
| 351 | PD-L1 Non-responder | TAAAGTACTGTGTCCCACATATAAGTACTCGAGAAAAGATGCAATAGTGTTGTATTCAGG (SEQ ID NO: 1479) |
| 352 | PD-L1 responder | GCGCCCTATTTCCACCTTGTGCCTTCTGTCGAGACATCTAAGAAGGTCCAGCCAGATGTT (SEQ ID NO: 1480) |
| 353 | PD-L1 responder | CACTCCTAAAGATGAACAAAGAGAGCAGTCGAATAACTATGCAGTAAGCAGTTACTATGT (SEQ ID NO: 1481) |
| 354 | PD-L1 Non-responder | CAGGAAGTAGCCTTTCTGGTTGTGCAGCTCGACAACTTATTTTTTAAAATCATCAAAGAA (SEQ ID NO: 1482) |
| 355 | PD-L1 Non-responder | TTCTGGGCAGACAAAACAATAAGTCTTCTCGATGGCACTTAAAAAAAAGTTGTCCAAAT (SEQ ID NO: 1483) |
| 356 | PD-L1 responder | GCAGGTTAAAGTTTTCCATTAGTGGTCATCGATCACCCAGGCTAGAATGCAGTGGTGTAA (SEQ ID NO: 1484) |
| 357 | PD-L1 responder | GCAAGCGATTCCCACTCGCAGCGCGGCCTCGATCACCCAGGCTAGAATGCAGTGGTGTAA (SEQ ID NO: 1485) |
| 358 | PD-L1 responder | GCAAGCGATTCCCACTCGCAGCGCGGCCTCGAGCGTACACCAATGGAGGAGGTATGGGCC (SEQ ID NO: 1486) |
| 359 | PD-L1 responder | ATATCTAAACTGGTACTGCTGAGTTCCCTCGATCACCCAGGCTAGAATGCAGTGGTGTAA (SEQ ID NO: 1487) |
| 360 | PD-L1 responder | CCCCTCCCTACCTTTGGTGTCTTCATCCTCGATCACCCAGGCTAGAATGCAGTGGTGTAA (SEQ ID NO: 1488) |
| 361 | PD-L1 Non-responder | ATTGTTTAAGCCAGCCAGCCTATGGTATTCGACGCAAGGAAACTACTAAAGCAATCCAGA (SEQ ID NO: 1489) |
| 362 | PD-L1 responder | GTGGCAGGAGAAAAACGCGGCCCCACCCTCGAAAATACTAGAATTATGCCGCACAGTCAG (SEQ ID NO: 1490) |
| 363 | PD-L1 responder | AGGCGACACTCTTGTCCCCGCCATCTTTTCGAAGGCCCCCGTCCTCCTGCGCCATGGAGA (SEQ ID NO: 1491) |
| 364 | PD-L1 responder | CATCATCACAGTCTACGGCTGTTTCCTCTCGAAGGCCCCCGTCCTCCTGCGCCATGGAGA (SEQ ID NO: 1492) |

TABLE 13.g5

| | Probe Location | | | | 4 kb Sequence Location | | |
|---|---|---|---|---|---|---|---|
| | Chr | Start1 | End1 | Start2 | End2 | Chr | Start1 | End1 |
| 313 | 7 | 77589308 | 77589337 | 77658596 | 77658625 | 7 | 77589308 | 77593307 |
| 314 | 7 | 77632585 | 77632614 | 77651775 | 77651804 | 7 | 77628615 | 77632614 |
| 315 | 1 | 198595742 | 198595771 | 198775797 | 198775826 | 1 | 198591772 | 198595771 |
| 316 | 1 | 198666127 | 198666156 | 198697386 | 198697415 | 1 | 198662157 | 198666156 |
| 317 | 1 | 198666127 | 198666156 | 198749227 | 198749256 | 1 | 198662157 | 198666156 |
| 318 | 1 | 198735456 | 198735485 | 198786812 | 198786841 | 1 | 198735456 | 198739455 |
| 319 | 11 | 82936602 | 82936631 | 83048972 | 83049001 | 11 | 82936602 | 82940601 |
| 320 | 11 | 82948459 | 82948488 | 82974616 | 82974645 | 11 | 82944489 | 82948488 |
| 321 | 11 | 64269782 | 64269811 | 64288581 | 64288610 | 11 | 64265812 | 64269811 |
| 322 | 11 | 64269782 | 64269811 | 64296895 | 64296924 | 11 | 64265812 | 64269811 |
| 323 | 1 | 174835362 | 174835391 | 175017892 | 175017921 | 1 | 174835362 | 174839361 |
| 324 | 7 | 6325447 | 6325476 | 6392091 | 6392120 | 7 | 6325447 | 6329446 |
| 325 | 20 | 20425025 | 20425054 | 20459825 | 20459854 | 20 | 20425025 | 20429024 |
| 326 | 13 | 97443725 | 97443754 | 97487579 | 97487608 | 13 | 97439755 | 97443754 |
| 327 | 2 | 33398962 | 33398991 | 33442363 | 33442392 | 2 | 33394992 | 33398991 |
| 328 | 14 | 75478321 | 75478350 | 75491596 | 75491625 | 14 | 75474351 | 75478350 |
| 329 | 14 | 75491596 | 75491625 | 75577787 | 75577816 | 14 | 75491596 | 75495595 |
| 330 | 21 | 14176916 | 14176945 | 14268983 | 14269012 | 21 | 14176916 | 14180915 |
| 331 | 21 | 14210379 | 14210408 | 14236469 | 14236498 | 21 | 14210379 | 14214378 |
| 332 | 21 | 34505982 | 34506011 | 34574861 | 34574890 | 21 | 34502012 | 34506011 |
| 333 | 11 | 65634932 | 65634961 | 65654597 | 65654626 | 11 | 65634932 | 65638931 |
| 334 | 12 | 18261052 | 18261081 | 18364485 | 18364514 | 12 | 18257082 | 18261081 |
| 335 | 3 | 16456133 | 16456162 | 16499665 | 16499694 | 3 | 16452163 | 16456162 |
| 336 | 19 | 48916684 | 48916713 | 48935281 | 48935310 | 19 | 48912714 | 48916713 |
| 337 | 19 | 48916684 | 48916713 | 48971543 | 48971572 | 19 | 48912714 | 48916713 |

TABLE 13.g5-continued

|  | Probe Location | | | | 4 kb Sequence Location | | |
| --- | --- | --- | --- | --- | --- | --- | --- |
|  | Chr | Start1 | End1 | Start2 | End2 | Chr | Start1 | End1 |
| 338 | 6 | 3030208 | 3030237 | 3146778 | 3146807 | 6 | 3026238 | 3030237 |
| 339 | 6 | 3051362 | 3051391 | 3146778 | 3146807 | 6 | 3047392 | 3051391 |
| 340 | 6 | 3114019 | 3114048 | 3146778 | 3146807 | 6 | 3114019 | 3118018 |
| 341 | 6 | 166614982 | 166615011 | 166826698 | 166826727 | 6 | 166614982 | 166618981 |
| 342 | 6 | 166614982 | 166615011 | 166877620 | 166877649 | 6 | 166614982 | 166618981 |
| 343 | 21 | 35517801 | 35517830 | 35775665 | 35775694 | 21 | 35513831 | 35517830 |
| 344 | 20 | 50753473 | 50753502 | 50888426 | 50888455 | 20 | 50749503 | 50753502 |
| 345 | 1 | 243286011 | 243286040 | 243398528 | 243398557 | 1 | 243286011 | 243290010 |
| 346 | 1 | 243386248 | 243386277 | 243527483 | 243527512 | 1 | 243386248 | 243390247 |
| 347 | 18 | 44895850 | 44895879 | 44997556 | 44997585 | 18 | 44891880 | 44895879 |
| 348 | 18 | 44895850 | 44895879 | 45014599 | 45014628 | 18 | 44891880 | 44895879 |
| 349 | 1 | 66506442 | 66506471 | 66753521 | 66753550 | 1 | 66506442 | 66510441 |
| 350 | 1 | 66578981 | 66579010 | 66762791 | 66762820 | 1 | 66578981 | 66582980 |
| 351 | 20 | 1861199 | 1861228 | 1955166 | 1955195 | 20 | 1857229 | 1861228 |
| 352 | 20 | 1891489 | 1891518 | 1924633 | 1924662 | 20 | 1891489 | 1895488 |
| 353 | 1 | 160707882 | 160707911 | 160744908 | 160744937 | 1 | 160707882 | 160711881 |
| 354 | 6 | 3273319 | 3273348 | 3503723 | 3503752 | 6 | 3269349 | 3273348 |
| 355 | 2 | 27626184 | 27626213 | 27726475 | 27726504 | 2 | 27626184 | 27630183 |
| 356 | 5 | 150151062 | 150151091 | 150181302 | 150181331 | 5 | 150147092 | 150151091 |
| 357 | 5 | 150166519 | 150166548 | 150181302 | 150181331 | 5 | 150162549 | 150166548 |
| 358 | 5 | 150166519 | 150166548 | 150194890 | 150194919 | 5 | 150162549 | 150166548 |
| 359 | 5 | 150181302 | 150181331 | 150237307 | 150237336 | 5 | 150181302 | 150185301 |
| 360 | 5 | 150181302 | 150181331 | 150238689 | 150238718 | 5 | 150181302 | 150185301 |
| 361 | 17 | 35289045 | 35289074 | 35312468 | 35312497 | 17 | 35285075 | 35289074 |
| 362 | 15 | 67098632 | 67098661 | 67199584 | 67199613 | 15 | 67098632 | 67102631 |
| 363 | 16 | 29613904 | 29613933 | 29632052 | 29632081 | 16 | 29613904 | 29617903 |
| 364 | 16 | 29613904 | 29613933 | 29687200 | 29687229 | 16 | 29613904 | 29617903 |

TABLE 13.g6

|  | 4 kb Sequence Location | | Inner_primers | | |
| --- | --- | --- | --- | --- | --- |
|  | Start2 | End2 | PCR-Primer1_ID | PCR_Primer1 | PCR-Primer2_ID |
| 313 | 77654626 | 77658625 | OBD117.1.1757 | AAGGAAAACAATCTAAAATGTAA (SEQ ID NO: 1493) | OBD117.1.1759 |
| 314 | 77647805 | 77651804 | OBD117.1.1721 | CCTCCCCTACCTGAAAGAACTCC (SEQ ID NO: 1494) | OBD117.1.1723 |
| 315 | 198771827 | 198775826 | OBD117.1.189 | CTTCCCTGTTCTGAGGTCTGGATTAT (SEQ ID NO: 1495) | OBD117.1.191 |
| 316 | 198697386 | 198701385 | OBD117.1.1237 | GGAGAATCACTTGAGCCTAAGAGTTC (SEQ ID NO: 1496) | OBD117.1.1239 |
| 317 | 198745257 | 198749256 | OBD117.1.1801 | GAAGAGATAACTAATGAGAGGTA (SEQ ID NO: 1497) | OBD117.1.1803 |
| 318 | 198782842 | 198786841 | OBD117.1.1173 | GCCAGTCAGTCAATCATTTAGTCAGC (SEQ ID NO: 1498) | OBD117.1.1175 |
| 319 | 83048972 | 83052971 | OBD117.1.1541 | ACTCAAGCAAGCCTCCTGCCTCG (SEQ ID NO: 1499) | OBD117.1.1543 |
| 320 | 82974616 | 82978615 | OBD117.1.1737 | ACCACCACTGACTCTTTACTCTT (SEQ ID NO: 1500) | OBD117.1.1739 |
| 321 | 64288581 | 64292580 | OBD117.1.341 | AGTTTCCCTCGTAAGACAGCGGC (SEQ ID NO: 1501) | OBD117.1.343 |
| 322 | 64292925 | 64296924 | OBD117.1.245 | TGTCGCTGGATGTCAGGCAGAGC (SEQ ID NO: 1502) | OBD117.1.247 |
| 323 | 175013922 | 175017921 | OBD117.1.689 | TTGGGATGCGGCTGGACACAGTG (SEQ ID NO: 1503) | OBD117.1.691 |
| 324 | 6392091 | 6396090 | OBD117.1.729 | GTTCCAGGTGGCCTGTTGT (SEQ ID NO: 1504) | OBD117.1.731 |
| 325 | 20455855 | 20459854 | OBD117.1.1761 | GAAGAGATAACTAATGAGAGGTA (SEQ ID NO: 1505) | OBD117.1.1763 |

TABLE 13.g6-continued

| | 4 kb Sequence Location | | Inner_primers | | |
|---|---|---|---|---|---|
| | Start2 | End2 | PCR-Primer1_ID | PCR_Primer1 | PCR-Primer2_ID |
| 326 | 97483609 | 97487608 | OBD117.1.1869 | AGCCACTGCCCCTGGTCCTAAAT (SEQ ID NO: 1506) | OBD117.1.1871 |
| 327 | 33442363 | 33446362 | OBD117.1.1837 | GTTGTATTATTATGTTGTTTTGT (SEQ ID NO: 1507) | OBD117.1.1839 |
| 328 | 75491596 | 75495595 | OBD117.1.617 | AAGAAGAGGAGGCAGCAGCCCCT (SEQ ID NO: 1508) | OBD117.1.619 |
| 329 | 75573817 | 75577816 | OBD117.1.685 | CCTTGGTCTACAGTGGCACCTCA (SEQ ID NO: 1509) | OBD117.1.687 |
| 330 | 14265013 | 14269012 | OBD117.1.1357 | CTGTAATCCCAGCACTTTGGTAGGC (SEQ ID NO: 1510) | OBD117.1.1359 |
| 331 | 14236469 | 14240468 | OBD117.1.1577 | GAGAATAAATAGAAATACTCAAGAGA (SEQ ID NO: 1511) | OBD117.1.1579 |
| 332 | 34574861 | 34578860 | OBD117.1.1709 | CCACCTCCCAGGACAAGCAAAGG (SEQ ID NO: 1512) | OBD117.1.1711 |
| 333 | 65650627 | 65654626 | OBD117.1.017 | GCTTTTGGAGGGCTTCAATCCCC (SEQ ID NO: 1513) | OBD117.1.019 |
| 334 | 18360515 | 18364514 | OBD117.1.1185 | GTCTCAGAGTCTCCACACATTGTTCA (SEQ ID NO: 1514) | OBD117.1.1187 |
| 335 | 16495695 | 16499694 | OBD117.1.1613 | CAGCAAATGAAAATCAAGTTCTCTGC (SEQ ID NO: 1515) | OBD117.1.1615 |
| 336 | 48931311 | 48935310 | OBD117.1.1653 | GTAGTCCCAGCACTTTCGGAGGC (SEQ ID NO: 1516) | OBD117.1.1655 |
| 337 | 48967573 | 48971572 | OBD117.1.1681 | GTAGTCCCAGCACTTTCGGAGGC (SEQ ID NO: 1517) | OBD117.1.1683 |
| 338 | 3146778 | 3150777 | OBD117.1.1813 | TTTTGTTGTAGTCACGGTTAGTA (SEQ ID NO: 1518) | OBD117.1.1815 |
| 339 | 3146778 | 3150777 | OBD117.1.1765 | GGCACTGTCACTCCCCAAGAGGA (SEQ ID NO: 1519) | OBD117.1.1767 |
| 340 | 3146778 | 3150777 | OBD117.1.1825 | TTTTGTTGTAGTCACGGTTAGTA (SEQ ID NO: 1520) | OBD117.1.1827 |
| 341 | 166826698 | 166830697 | OBD117.1.1153 | CAGGTGCTCAGGTGTAGACCCCT (SEQ ID NO: 1521) | OBD117.1.1155 |
| 342 | 166877620 | 166881619 | OBD117.1.1585 | GTGTAGACCCCTGGTGTTCTTGG (SEQ ID NO: 1522) | OBD117.1.1587 |
| 343 | 35771695 | 35775694 | OBD117.1.1349 | AAAGTGCTGGGATTACAGGTGTGAG (SEQ ID NO: 1523) | OBD117.1.1351 |
| 344 | 50888426 | 50892425 | OBD117.1.1609 | ACTAAATGTCAAGCCTAACTGTGAAT (SEQ ID NO: 1524) | OBD117.1.1611 |
| 345 | 243394558 | 243398557 | OBD117.1.1109 | GAAGATGTTGATTTACTCCTGTGCTG (SEQ ID NO: 1525) | OBD117.1.1111 |
| 346 | 243523513 | 243527512 | OBD117.1.1789 | ATCTTTTCTAAGTTGTGCTTTAT (SEQ ID NO: 1526) | OBD117.1.1791 |
| 347 | 44997556 | 45001555 | OBD117.1.1197 | TATCTTTTCTTCCCACTGGACAGGTG (SEQ ID NO: 1527) | OBD117.1.1199 |
| 348 | 45014599 | 45018598 | OBD117.1.1705 | GGGAAGGTGGCAATGGTGTTAGGATG (SEQ ID NO: 1528) | OBD117.1.1707 |
| 349 | 66749551 | 66753550 | OBD117.1.601 | GTTCTGGGAAGTCCATTGCTACTACC (SEQ ID NO: 1529) | OBD117.1.603 |
| 350 | 66758821 | 66762820 | OBD117.1.889 | ATGGGGTGAAAAGAAGTTGG (SEQ ID NO: 1530) | OBD117.1.891 |

TABLE 13.g6-continued

| | 4 kb Sequence Location | | Inner_primers | | |
|---|---|---|---|---|---|
| | Start2 | End2 | PCR-Primer1_ID | PCR_Primer1 | PCR-Primer2_ID |
| 351 | 1955166 | 1959165 | OBD117.1.1441 | CAGCCAAGTCCTGTTCTCACGGG (SEQ ID NO: 1531) | OBD117.1.1443 |
| 352 | 1924633 | 1928632 | OBD117.1.161 | AGAGGGCACAATCTGTCAGCAAATCC (SEQ ID NO: 1532) | OBD117.1.163 |
| 353 | 160740938 | 160744937 | OBD117.1.557 | TTCCTGGCACTATTTGGACTTGACAC (SEQ ID NO: 1533) | OBD117.1.559 |
| 354 | 3499753 | 3503752 | OBD117.1.1181 | TTCTCAGGCAGGTTCTGGTCCCT (SEQ ID NO: 1534) | OBD117.1.1183 |
| 355 | 27722505 | 27726504 | OBD117.1.589 | CACTCATTCCTGTGAACACTGGAGCA (SEQ ID NO: 1535) | OBD117.1.591 |
| 356 | 150181302 | 150185301 | OBD117.1.961 | AACTGAGCACGTTAAGGGGC (SEQ ID NO: 1536) | OBD117.1.963 |
| 357 | 150181302 | 150185301 | OBD117.1.449 | TCTGCGTTGCCCCTCACCTCAAG (SEQ ID NO: 1537) | OBD117.1.451 |
| 358 | 150194890 | 150198889 | OBD117.1.445 | TTGAAGTCTGCGTTGCCCCTCAC (SEQ ID NO: 1538) | OBD117.1.447 |
| 359 | 150233337 | 150237336 | OBD117.1.1033 | ATGTGGTGCGTCAAAACTGC (SEQ ID NO: 1539) | OBD117.1.1035 |
| 360 | 150234719 | 150238718 | OBD117.1.969 | CCAGAAGTCTAAGGGGTCCC (SEQ ID NO: 1540) | OBD117.1.971 |
| 361 | 35308498 | 35312497 | OBD117.1.1497 | GACTTCTTGCCTCCCTAACTGTGAGA (SEQ ID NO: 1541) | OBD117.1.1499 |
| 362 | 67199584 | 67203583 | OBD117.1.061 | ACCAAAGCAAGCCTCCCCAAGTG (SEQ ID NO: 1542) | OBD117.1.063 |
| 363 | 29628082 | 29632081 | OBD117.1.945 | TGGAGCTCTCCTCGTTGTTT (SEQ ID NO: 1543) | OBD117.1.947 |
| 364 | 29683230 | 29687229 | OBD117.1.985 | ATGCTGTTGCAGGACTGTGC (SEQ ID NO: 1544) | OBD117.1.987 |

TABLE 13.g7

| | Inner_primers | |
|---|---|---|
| | PCR_Primer2 | GLMNET |
| 313 | TGTAAGTTTGATTTGTATGCCAT (SEQ ID NO: 1545) | 0 |
| 314 | CCACCAGAAGAGGGCAGCAAAGC (SEQ ID NO: 1546) | 0 |
| 315 | TTGGCAGGAACTGGTGCTGGAATAGG (SEQ ID NO: 1547) | −0.020382337 |
| 316 | GTATTCTAAGGAGCATAGTGCCCCTC (SEQ ID NO: 1548) | 0 |
| 317 | CATTTACTTGTTATCTATCGTAT (SEQ ID NO: 1549) | 0 |
| 318 | GTAGGAACTCACTGACAATGAAGACA (SEQ ID NO: 1550) | 0 |
| 319 | GAGCCACCACACCCAGCATCTTT (SEQ ID NO: 1551) | 0 |
| 320 | TATCTTATTGTAGAGGCAGTCTG (SEQ ID NO: 1552) | 0 |
| 321 | CTGCCCATTGAGGATGTGGCTGG (SEQ ID NO: 1553) | 0.007677493 |
| 322 | TCTGCTGTAAGGGACTGCCTCCT (SEQ ID NO: 1554) | 0.017957539 |
| 323 | GCCACAGCGTCTCTCTCCGAATA (SEQ ID NO: 1555) | 0 |
| 324 | AGCTGGTAACGCTCAAAACAC (SEQ ID NO: 1556) | −0.01057369 |

TABLE 13.g7-continued

| | Inner_primers | |
|---|---|---|
| | PCR_Primer2 | GLMNET |
| 325 | CATTTACTTGTTATCTATCGTAT (SEQ ID NO: 1557) | 0 |
| 326 | AGTTGGCTTGTTTCACTAAAATA (SEQ ID NO: 1558) | 0 |
| 327 | GTAGAAAATCAAAATCACCATTA (SEQ ID NO: 1559) | 0 |
| 328 | AATCGCAACCACTTCCTCTGCCC (SEQ ID NO: 1560) | 0 |
| 329 | ATCGCAACCACTTCCTCTGCCCC (SEQ ID NO: 1561) | −0.005472121 |
| 330 | ATAGAACATTACACCTGAGAACTGC (SEQ ID NO: 1562) | 0 |
| 331 | ATAGTCTTCTCACTCTGGATGTTTCA (SEQ ID NO: 1563) | 0 |
| 332 | TCTTGATTCCCATCTGCCCGTGC (SEQ ID NO: 1564) | 0 |
| 333 | GAAGGGCTCCAGGCTAAGTGGGA (SEQ ID NO: 1565) | 0.005732814 |
| 334 | CTTCCCTTGCTTGGTCTAACCTGTAA (SEQ ID NO: 1566) | 0 |
| 335 | TGTTTCACCAAGCCCTGCCAAAGC (SEQ ID NO: 1567) | 0 |
| 336 | CTTGGTCTGGGACTGGCTGTCTA (SEQ ID NO: 1568) | 0 |
| 337 | GCGGGAAAGTCCATAGTTGGGAG (SEQ ID NO: 1569) | 0 |
| 338 | GAACCAGCACTCCAACCCGAACC (SEQ ID NO: 1570) | 0 |
| 339 | GAACCAGCACTCCAACCCGAACC (SEQ ID NO: 1571) | 0 |
| 340 | GAACCAGCACTCCAACCCGAACC (SEQ ID NO: 1572) | 0 |
| 341 | CCACCTCCCTACCCTTACTAACC (SEQ ID NO: 1573) | 0 |
| 342 | CCCCTGCTTCAAGTTGTCCCAGC (SEQ ID NO: 1574) | 0 |
| 343 | GCTAAACCAAATACTAAATACTGCCA (SEQ ID NO: 1575) | 0 |
| 344 | CCAATGCCTACTCCTTTGTAACATCC (SEQ ID NO: 1576) | 0 |
| 345 | TAGATAACAAAGAGAAGGCTGGG (SEQ ID NO: 1577) | 0 |
| 346 | ACTGATTTTCTAAGTTGTCTTTT (SEQ ID NO: 1578) | 0 |
| 347 | TACAATGGTATGGCTTAGAAGATGCC (SEQ ID NO: 1579) | 0 |
| 348 | ATGCCATACGGTCCTTGTTTCTTGAC (SEQ ID NO: 1580) | 0 |
| 349 | GCCAGCCAAGTGGTAGAATAGGAGTT (SEQ ID NO: 1581) | −0.010880594 |
| 350 | ATGTAGCTTCGGGAAACAGC (SEQ ID NO: 1582) | −0.013055638 |
| 351 | GCAGGGCAAGGTCAGAAAGAGAC (SEQ ID NO: 1583) | 0 |
| 352 | ACCCACCACTGCTTTTCACCACTAAG (SEQ ID NO: 1584) | −0.014311214 |
| 353 | GGGAAGGAGCCACATCTATCTATTGC (SEQ ID NO: 1585) | 0 |
| 354 | TTGGGAAGGTGGAGGAGGAGGGA (SEQ ID NO: 1586) | 0 |
| 355 | GCTAAGCCCCTACAAGTTTGAGAAGG (SEQ ID NO: 1587) | −0.005626404 |
| 356 | AAGAGTCATGTAGGGCCAGG (SEQ ID NO: 1588) | −0.013176922 |
| 357 | GCTGAGGCGGAAAACAGGAGAA (SEQ ID NO: 1589) | −0.000113816 |
| 358 | AGACACCCTCCGACAGGACCTCA (SEQ ID NO: 1590) | −0.026223064 |
| 359 | ACTTTATGGGAGGCTGAGGG (SEQ ID NO: 1591) | 0 |
| 360 | AAGAGTCATGTAGGGCCAGG (SEQ ID NO: 1592) | 0 |
| 361 | TGCTTATCTCTTCCTTCATTTTCTGG (SEQ ID NO: 1593) | 0 |
| 362 | CTCTTCACTCTCTGCTGCCCCTGT (SEQ ID NO: 1594) | 0 |

TABLE 13.g7-continued

Inner primers

| | PCR_Primer2 | GLMNET |
|---|---|---|
| 363 | GACGAAGCCTCTTTGGTTTC (SEQ ID NO: 1595) | −0.016440702 |
| 364 | CTCCCAGGCTTGACGAGAGG (SEQ ID NO: 1596) | 0 |

TABLE 13.h1

| | Probe | GeneLocus | Probe_Count_Total | Probe_Count_Sig |
|---|---|---|---|---|
| 365 | ORF642_16_29613904_29616227_29699675_29702049_RF | ORF642 | 17 | 4 |
| 366 | ORF642_16_29686079_29687229_29699675_29702049_FF | ORF642 | 17 | 4 |
| 367 | ORF657_2_191108390_191117485_191168431_191171042_FF | ORF657 | 51 | 3 |
| 368 | ORF657_2_191108390_191117485_191182179_191184623_FR | ORF657 | 51 | 3 |
| 369 | ORF657_2_191108390_191117485_191184623_191189153_FF | ORF657 | 51 | 3 |
| 370 | ORF667_20_47635013_47638590_47797013_47801718_FF | ORF667 | 30 | 3 |
| 371 | ORF670_9_90816328_90822228_90852643_90856872_FR | ORF670 | 44 | 3 |
| 372 | ORF671_1_114103465_114105233_114168595_114177937_FR | ORF671 | 92 | 9 |
| 373 | ORF684_8_132829420_132832263_132988146_132998009_RR | ORF684 | 192 | 18 |
| 374 | ORF685_2_70401554_70403744_70565683_70581054_FR | ORF685 | 79 | 5 |
| 375 | ORF690_9_72618535_72623611_72793872_72807440_RR | ORF690 | 122 | 6 |
| 376 | ORF695_6_137822043_137829972_137904022_137905775_FR | ORF695 | 28 | 1 |
| 377 | ORF696_5_119229308_119233411_119299768_119309624_RF | ORF696 | 24 | 21 |
| 378 | ORF696_5_119283840_119286417_119299768_119309624_RF | ORF696 | 24 | 21 |
| 379 | ORF696_5_119299768_119309624_119358022_119362710_FF | ORF696 | 24 | 21 |
| 380 | ORF697_8_22979979_22981340_23078156_23085865_FF | ORF697 | 13 | 2 |
| 381 | ORF697_8_23078156_23085865_23111436_23115456_FF | ORF697 | 13 | 2 |
| 382 | ORF698_18_62280369_62283590_62356961_62362521_RR | ORF698 | 32 | 4 |
| 383 | ORF698_18_62280369_62283590_62420808_62426226_RR | ORF698 | 32 | 4 |
| 384 | ORF698_18_62296384_62304812_62385139_62386748_FF | ORF698 | 32 | 2 |
| 385 | ORF698_18_62296384_62304812_62391728_62393598_FF | ORF698 | 32 | 2 |
| 386 | ORF698_18_62328039_62332469_62356961_62362521_FR | TNFRSF11A | 58 | 4 |
| 387 | ORF698_18_62356961_62362521_62391728_62393598_RF | ORF698 | 32 | 2 |
| 388 | ORF699_8_118882360_118886789_118946661_118952757_RR | ORF699 | 33 | 3 |
| 389 | ORF699_8_118901885_118906751_118946661_118952757_RR | ORF699 | 33 | 2 |
| 390 | ORF70_22_17690372_17692909_17820737_17823770_FR | ORF70 | 28 | 1 |
| 391 | ORF700_22_41905695_41906846_41942147_41943520_RF | ORF700 | 17 | 1 |
| 392 | ORF700_22_41905695_41906846_41946565_41950791_RF | ORF700 | 17 | 2 |
| 393 | ORF703_1_6450603_6452273_6494588_6498048_RF | TNFRSF25 | 68 | 16 |
| 394 | ORF703_1_6461604_6466207_6481328_6484248_FF | TNFRSF25 | 68 | 16 |
| 395 | ORF703_1_6461604_6466207_6494588_6498048_FF | TNFRSF25 | 68 | 16 |
| 396 | ORF703_1_6461604_6466207_6494588_6498048_FR | TNFRSF25 | 68 | 16 |
| 397 | ORF703_1_6461604_6466207_6514024_6515315_FR | TNFRSF25 | 68 | 16 |
| 398 | ORF705_9_114855753_114859111_114882931_114894596_FF | ORF705 | 33 | 0 |
| 399 | ORF705_9_114855753_114859111_114882931_114894596_RF | ORF705 | 33 | 4 |
| 400 | ORF705_9_114855753_114859111_114920994_114929419_FR | ORF705 | 33 | 0 |
| 401 | ORF705_9_114882931_114894596_114957908_114962933_FR | TNFSF8 | 50 | 4 |
| 402 | ORF706_5_150983477_150991968_151047772_151050718_RF | ORF706 | 52 | 6 |
| 403 | ORF708_1_3611941_3615812_3638742_3642185_FR | TP73 | 32 | 4 |
| 404 | ORF71_11_102291091_102294492_102307526_102311117_RR | ORF71 | 13 | 2 |
| 405 | ORF71_11_102291091_102294492_102337635_102346660_RR | ORF71 | 13 | 2 |
| 406 | ORF712_9_120888366_120893320_120913546_120919710_FR | TRAF1 | 42 | 6 |
| 407 | ORF712_9_120888366_120893320_120913546_120919710_RR | TRAF1 | 42 | 6 |
| 408 | ORF712_9_120888366_120893320_120919710_120922922_FR | TRAF1 | 42 | 6 |
| 409 | ORF712_9_120913546_120919710_120936524_120940468_RF | TRAF1 | 42 | 6 |
| 410 | ORF718_19_6698236_6701303_6781841_6783687_FR | ORF718 | 13 | 1 |
| 411 | ORF722_9_110209817_110214913_110296637_110303915_FF | ORF722 | 14 | 2 |
| 412 | ORF730_3_23901404_23907629_23923438_23926768_FF | ORF730 | 18 | 3 |
| 413 | ORF741_11_75790711_75798287_75817276_75823568_FR | ORF741 | 159 | 6 |
| 414 | ORF76_2_241559192_241566423_241577996_241581000_RR | BOK | 44 | 10 |
| 415 | ORF762_8_104964347_104973135_105209447_105218050_FR | ORF762 | 184 | 14 |
| 416 | ORF83_6_31852623_31856339_31978950_31986111_RR | ORF83 | 29 | 7 |

TABLE 13.h2

| | HyperG_Stats | FDR_HyperG | Percent_Sig | logFC | AveExpr | t |
|---|---|---|---|---|---|---|
| 365 | 0.027232137 | 0.337893495 | 23.53 | −0.202471668 | −0.202471668 | −6.315923973 |
| 366 | 0.027232137 | 0.337893495 | 23.53 | −0.154927207 | −0.154927207 | −5.674884507 |
| 367 | 0.63170859 | 1 | 5.88 | 0.519129457 | 0.519129457 | 2.977884092 |
| 368 | 0.63170859 | 1 | 5.88 | 0.617640584 | 0.617640584 | 2.79135711 |
| 369 | 0.63170859 | 1 | 5.88 | 0.284908892 | 0.284908892 | 6.270152298 |
| 370 | 0.292900518 | 1 | 10 | 0.290479186 | 0.290479186 | 8.351795594 |

TABLE 13.h2-continued

|   | HyperG_Stats | FDR_HyperG | Percent_Sig | logFC | AveExpr | t |
|---|---|---|---|---|---|---|
| 371 | 0.530531532 | 1 | 6.82 | 0.307304294 | 0.307304294 | 7.829405666 |
| 372 | 0.125670239 | 0.904598768 | 9.78 | 0.329823616 | 0.329823616 | 3.977368273 |
| 373 | 0.060363548 | 0.646636236 | 9.38 | 0.300112568 | 0.300112568 | 4.039709924 |
| 374 | 0.561965233 | 1 | 6.33 | 0.293122718 | 0.293122718 | 7.224786679 |
| 375 | 0.788253399 | 1 | 4.92 | 0.290541179 | 0.290541179 | 5.494475001 |
| 376 | 0.868767357 | 1 | 3.57 | −0.152941022 | −0.152941022 | −6.293551206 |
| 377 | 2.83E−22 | 2.66E−19 | 87.5 | 0.229344865 | 0.229344865 | 11.43247953 |
| 378 | 2.83E−22 | 2.66E−19 | 87.5 | 0.24275565 | 0.24275565 | 12.45525285 |
| 379 | 2.83E−22 | 2.66E−19 | 87.5 | 0.177823165 | 0.177823165 | 10.17772231 |
| 380 | 0.229466748 | 1 | 15.38 | −0.179387458 | −0.179387458 | −9.712191434 |
| 381 | 0.229466748 | 1 | 15.38 | −0.218037237 | −0.218037237 | −12.57980453 |
| 382 | 0.182398388 | 0.960903242 | 12.5 | −0.243101878 | −0.243101878 | −4.208949606 |
| 383 | 0.182398388 | 0.960903242 | 12.5 | −0.232725718 | −0.232725718 | −4.760235812 |
| 384 | 0.607730303 | 1 | 6.25 | −0.157966119 | −0.157966119 | −7.417609124 |
| 385 | 0.607730303 | 1 | 6.25 | 0.712949305 | 0.712949305 | 4.461764999 |
| 386 | 0.686266831 | 0.99999793 | 6.9 | −0.351747423 | −0.351747423 | −2.587519517 |
| 387 | 0.607730303 | 1 | 6.25 | 0.307835206 | 0.307835206 | 8.640900231 |
| 388 | 0.345775878 | 1 | 9.09 | −0.235758677 | −0.235758677 | −10.84175415 |
| 389 | 0.681942534 | 1 | 6.06 | −0.194826505 | −0.194826505 | −6.703691813 |
| 390 | 0.838642022 | 1 | 3.57 | 0.330305388 | 0.330305388 | 6.588172922 |
| 391 | 0.66956866 | 1 | 5.88 | −0.184624561 | −0.184624561 | −5.89087632 |
| 392 | 0.335769804 | 1 | 11.76 | −0.161300759 | −0.161300759 | −7.221684584 |
| 393 | 6.44E−05 | 0.004967399 | 23.53 | −0.316909254 | −0.316909254 | −18.81843594 |
| 394 | 6.44E−05 | 0.004967399 | 23.53 | −0.391557328 | −0.391557328 | −9.736436082 |
| 395 | 6.44E−05 | 0.004967399 | 23.53 | −0.347052896 | −0.347052896 | −12.44559121 |
| 396 | 6.44E−05 | 0.004967399 | 23.53 | −0.316023276 | −0.316023276 | −9.967999414 |
| 397 | 6.44E−05 | 0.004967399 | 23.53 | −0.324809038 | −0.324809038 | −10.99489816 |
| 398 | 1 | 1 | 0 | −0.193263231 | −0.193263231 | −5.150192691 |
| 399 | 0.196893931 | 0.98238612 | 12.12 | −0.152757686 | −0.152757686 | −4.644039162 |
| 400 | 1 | 1 | 0 | −0.211999593 | −0.211999593 | −11.86064828 |
| 401 | 0.568728839 | 0.99999793 | 8 | −0.415876997 | −0.415876997 | −6.927544857 |
| 402 | 0.107675958 | 0.853264106 | 11.54 | 0.293172978 | 0.293172978 | 9.456672576 |
| 403 | 0.246707931 | 0.99999793 | 12.5 | −0.248090073 | −0.248090073 | −8.279478026 |
| 404 | 0.211981801 | 1 | 15.38 | 0.163726198 | 0.163726198 | 4.523059159 |
| 405 | 0.195961879 | 1 | 15.38 | 0.201110561 | 0.201110561 | 6.744214044 |
| 406 | 0.112492545 | 0.789152247 | 14.29 | −0.196616458 | −0.196616458 | −6.590704313 |
| 407 | 0.112492545 | 0.789152247 | 14.29 | −0.148665785 | −0.148665785 | −4.410767412 |
| 408 | 0.112492545 | 0.789152247 | 14.29 | −0.199273043 | −0.199273043 | −6.213719238 |
| 409 | 0.112492545 | 0.789152247 | 14.29 | −0.255423865 | −0.255423865 | −10.52329131 |
| 410 | 0.571197975 | 1 | 7.69 | −0.191042683 | −0.191042683 | −10.87727058 |
| 411 | 0.219619008 | 1 | 14.29 | 0.597573234 | 0.597573234 | 13.70784629 |
| 412 | 0.100654026 | 0.825363011 | 16.67 | 0.290493679 | 0.290493679 | 4.193084229 |
| 413 | 0.940134463 | 1 | 3.77 | 0.282876057 | 0.282876057 | 12.42727971 |
| 414 | 0.001969408 | 0.075986326 | 22.73 | −0.367707426 | −0.367707426 | −11.11416276 |
| 415 | 0.272101156 | 1 | 7.61 | 0.365971074 | 0.365971074 | 10.70453823 |
| 416 | 0.001789508 | 0.045608266 | 24.14 | 0.361761092 | 0.361761092 | 4.073141197 |

TABLE 13.h3

|   | P. Value | adj. P. Val | B | FC | FC_1 | LS |
|---|---|---|---|---|---|---|
| 365 | 0.0000783 | 0.001057554 | 1.685518605 | 0.869060387 | −1.150668026 | −1 |
| 366 | 0.000187328 | 0.001890561 | 0.777210943 | 0.898177691 | −1.11336544 | −1 |
| 367 | 0.0135104 | 0.040653116 | −3.625275836 | 1.43309024 | 1.43309024 | 1 |
| 368 | 0.018664657 | 0.051850278 | −3.94720067 | 1.534363795 | 1.534363795 | 1 |
| 369 | 0.0000832 | 0.001097922 | 1.622590571 | 1.218333322 | 1.218333322 | 1 |
| 370 | 0.00000689 | 0.000230944 | 4.20728549 | 1.223046441 | 1.223046441 | 1 |
| 371 | 0.0000123 | 0.000322648 | 3.609042444 | 1.237393443 | 1.237393443 | 1 |
| 372 | 0.002489795 | 0.011583149 | −1.906237636 | 1.256859701 | 1.256859701 | 1 |
| 373 | 0.002248311 | 0.010748006 | −1.801247822 | 1.231240479 | 1.231240479 | 1 |
| 374 | 0.0000249 | 0.000505697 | 2.876053795 | 1.225289553 | 1.225289553 | 1 |
| 375 | 0.000241882 | 0.002233638 | 0.510978947 | 1.223098996 | 1.223098996 | 1 |
| 376 | 0.0000807 | 0.001076073 | 1.654796525 | 0.89941508 | −1.111833704 | −1 |
| 377 | 0.000000369 | 0.000051 | 7.182375543 | 1.17230248 | 1.17230248 | 1 |
| 378 | 0.000000162 | 0.0000357 | 7.999309139 | 1.183250597 | 1.183250597 | 1 |
| 379 | 0.00000111 | 0.0000849 | 6.073270515 | 1.131175803 | 1.131175803 | 1 |
| 380 | 0.00000172 | 0.000108368 | 5.628079247 | 0.883077855 | −1.132402986 | −1 |
| 381 | 0.000000147 | 0.0000335 | 8.09397041 | 0.859734296 | −1.163150063 | −1 |
| 382 | 0.0017087 | 0.008848343 | −1.518311904 | 0.844926717 | −1.183534596 | −1 |
| 383 | 0.000717954 | 0.004728245 | −0.62056802 | 0.851025509 | −1.175052908 | −1 |
| 384 | 0.0000198 | 0.000441092 | 3.114727283 | 0.896287748 | −1.11571312 | −1 |
| 385 | 0.001142097 | 0.006622538 | −1.101830789 | 1.639151616 | 1.639151616 | 1 |
| 386 | 0.026579755 | 0.067536623 | −4.295830899 | 0.783634368 | −1.276105338 | −1 |
| 387 | 0.00000506 | 0.000193388 | 4.525216296 | 1.237848888 | 1.237848888 | 1 |
| 388 | 0.000000611 | 0.0000645 | 6.675922138 | 0.849238289 | −1.177525805 | −1 |

TABLE 13.h3-continued

|     | P. Value     | adj. P. Val | B            | FC          | FC_1         | LS |
|-----|--------------|-------------|--------------|-------------|--------------|----|
| 389 | 0.0000475    | 0.000761747 | 2.207019697  | 0.873677956 | −1.144586507 | −1 |
| 390 | 0.000055     | 0.000832022 | 2.053813675  | 1.257279485 | 1.257279485  | 1  |
| 391 | 0.000138772  | 0.001546149 | 1.089794369  | 0.879878021 | −1.136521172 | −1 |
| 392 | 0.000025     | 0.000506888 | 2.872175551  | 0.894218465 | −1.118294958 | −1 |
| 393 | 0.00000000279| 0.00000683  | 11.81480874  | 0.802787883 | −1.245659061 | −1 |
| 394 | 0.00000168   | 0.000107198 | 5.651749271  | 0.762306283 | −1.311808681 | −1 |
| 395 | 0.000000163  | 0.0000357   | 7.991924175  | 0.786188466 | −1.271959642 | −1 |
| 396 | 0.00000135   | 0.0000949   | 5.875116011  | 0.803281037 | −1.24489432  | −1 |
| 397 | 0.000000535  | 0.0000603   | 6.809806578  | 0.79840406  | −1.252498641 | −1 |
| 398 | 0.000399013  | 0.003153947 | −0.010076757 | 0.874625168 | −1.143346929 | −1 |
| 399 | 0.000858885  | 0.005371224 | −0.806528239 | 0.899529384 | −1.111692423 | −1 |
| 400 | 0.000000259  | 0.0000428   | 7.533224813  | 0.863339802 | −1.158292479 | −1 |
| 401 | 0.0000359    | 0.000632929 | 2.498799383  | 0.749563705 | −1.33410942  | −1 |
| 402 | 0.00000221   | 0.000123757 | 5.375272803  | 1.225332239 | 1.225332239  | 1  |
| 403 | 0.00000745   | 0.000241272 | 4.126320504  | 0.842010382 | −1.187633812 | −1 |
| 404 | 0.001037188  | 0.006177722 | −1.00204781  | 1.120176602 | 1.120176602  | 1  |
| 405 | 0.0000451    | 0.000738802 | 2.260334671  | 1.149582943 | 1.149582943  | 1  |
| 406 | 0.0000548    | 0.000830816 | 2.057190334  | 0.872594655 | −1.146007478 | −1 |
| 407 | 0.001237916  | 0.007019121 | −1.185214291 | 0.902084331 | −1.108543809 | −1 |
| 408 | 0.0000897    | 0.001156677 | 1.544601478  | 0.870989334 | −1.148119685 | −1 |
| 409 | 0.000000811  | 0.0000728   | 6.391477553  | 0.837740969 | −1.193686398 | −1 |
| 410 | 0.000000593  | 0.0000638   | 6.707137194  | 0.875972399 | −1.141588481 | −1 |
| 411 | 0.0000000638 | 0.0000214   | 8.907819219  | 1.513169114 | 1.513169114  | 1  |
| 412 | 0.001752953  | 0.009007702 | −1.544700881 | 1.223058727 | 1.223058727  | 1  |
| 413 | 0.000000165  | 0.0000357   | 7.977910939  | 1.216617834 | 1.216617834  | 1  |
| 414 | 0.000000483  | 0.0000579   | 6.912800589  | 0.775013085 | −1.290300795 | −1 |
| 415 | 0.00000069   | 0.0000687   | 6.554375143  | 1.288748791 | 1.288748791  | 1  |
| 416 | 0.002129042  | 0.010339113 | −1.745111267 | 1.284993527 | 1.284993527  | 1  |

TABLE 13.h4

|     | Loop detected       | Probe sequence 60 mer |
|-----|---------------------|------------------------|
| 365 | PD-L1 responder     | CCACTGCACTCCACCCCGGGGAACAAGATCGAAGGCCCCCGTCCTCCTGCGCCATGGAGA (SEQ ID NO: 1597) |
| 366 | PD-L1 responder     | CATCATCACAGTCTACGGCTGTTTCCTCTCGATCTTGTTCCCCGGGGTGGAGTGCAGTGG (SEQ ID NO: 1598) |
| 367 | PD-L1 Non-responder | CATTAGACTCTATCTTTATTACTGTAAGTCGAATATAACTCCTTGATTTAGTAAAACCAT (SEQ ID NO: 1599) |
| 368 | PD-L1 Non-responder | CATTAGACTCTATCTTTATTACTGTAAGTCGAGTGATATAACTGCATAGTCTCCTACTGA (SEQ ID NO: 1600) |
| 369 | PD-L1 Non-responder | CATTAGACTCTATCTTTATTACTGTAAGTCGAAGGTGGTAATTGTAGTCTCGGGTGCAAT (SEQ ID NO: 1601) |
| 370 | PD-L1 Non-responder | AGAAGGGGATTTTACATTTTATTTCTTTTCGATGTAAGTATTTGTTAAATAAAAATATAG (SEQ ID NO: 1602) |
| 371 | PD-L1 Non-responder | TTTTACTGTTTTTGTAAGAGATATGTTTTCGATTAATGTTAAAAATAAAAGGTAGTATTT (SEQ ID NO: 1603) |
| 372 | PD-L1 Non-responder | AGATAATGACTTCTGGGAGAGAAGAGTCGAACTGATACATAGAAACAATCACATTCAG (SEQ ID NO: 1604) |
| 373 | PD-L1 Non-responder | GTACTTTACAATGATTACTTTATTTAATTCGAAAGTCCATCTGCACAGTGGAACTGTTCC (SEQ ID NO: 1605) |
| 374 | PD-L1 Non-responder | GCAGCCATAATCCTCCTAGGGACACAACTCGAAATACTCCTTTCCTTTCAGATGCTCATT (SEQ ID NO: 1606) |
| 375 | PD-L1 Non-responder | TTTATTTATATTTACCTTTATTTCTATCTCGATCAAGTAGCAGCTCTGTAACTCCCTGGA (SEQ ID NO: 1607) |
| 376 | PD-L1 responder     | GAGGTTACTGTTTTCCTAACCATTGTATTCGATATTTTCACCATGTAGCCCAGGCTGGTC (SEQ ID NO: 1608) |
| 377 | PD-L1 Non-responder | AGAGCAGGGTGGGTAGTTCTGCACGTGATCGATTTTGTGGTCAGATTGCTTAAAAGGTAA (SEQ ID NO: 1609) |
| 378 | PD-L1 Non-responder | AGAGCAGGGTGGGTAGTTCTGCACGTGATCGAGACAAATAAGGACTTGGGTTAAAAAAAC (SEQ ID NO: 1610) |

TABLE 13.h4-continued

| | Loop detected | Probe sequence 60 mer |
|---|---|---|
| 379 | PD-L1 Non-responder | AGAGCAGGGTGGGTAGTTCTGCACGTGATCGAATGATCTTCCTGATTTTCCCAAGTAGCT (SEQ ID NO: 1611) |
| 380 | PD-L1 responder | ATCATTTTTAAACCTAGGCTGAATTTTATCGAATTCCGGGCCCTCTCTGTCTCTAAGGAA (SEQ ID NO: 1612) |
| 381 | PD-L1 responder | TTCCTTAGAGACAGAGAGGGCCCGGAATTCGATCTTCCTTACCACCCACCCCCTCCCACT (SEQ ID NO: 1613) |
| 382 | PD-L1 responder | GCTTGTCAACTAACGCTTCACTCATGCCTCGATTTTGAGGGCTTCTCACAACTCTAGATT (SEQ ID NO: 1614) |
| 383 | PD-L1 responder | GCTTGTCAACTAACGCTTCACTCATGCCTCGAAGTTCTGTCTGCTCTATCTCACGCACTC (SEQ ID NO: 1615) |
| 384 | PD-L1 responder | GTTGGTGAAAAGAAAGAAGAAATGGACTCGACCGCTACCACCCCAGCATTTCCAGCAGG (SEQ ID NO: 1616) |
| 385 | PD-L1 Non-responder | GTTGGTGAAAAGAAAGAAGAAATGGACTCGACTGGAGTTTTATATTTTCAAGAGTACCT (SEQ ID NO: 1617) |
| 386 | PD-L1 responder | GAGAATCAATTCCATTTTTAAAGCTTAGTCGATTTTGAGGGCTTCTCACAACTCTAGATT (SEQ ID NO: 1618) |
| 387 | PD-L1 Non-responder | AGGTACTCTTGAAAATATAAAACTCCAGTCGATTTTGAGGGCTTCTCACAACTCTAGATT (SEQ ID NO: 1619) |
| 388 | PD-L1 responder | ATAAAGCAACTTGTTTTTCCTTGTATTGTCGATATCAGAATTGTGCTCTGGGGGCGGCTT (SEQ ID NO: 1620) |
| 389 | PD-L1 responder | TATCAAGAAATTACAAACCGGTTCCTAATCGATATCAGAATTGTGCTCTGGGGGCGGCTT (SEQ ID NO: 1621) |
| 390 | PD-L1 Non-responder | TTCAACATGTATTCAGTACAAAAAATTATCGATATTATTGCTTTAATTTAAACAAATTTA (SEQ ID NO: 1622) |
| 391 | PD-L1 responder | GAGCTGCCTCGCTCGGATACTAAGTCCTTCGATTTCTCTCTCTCCCCCTCAGCATCTTCC (SEQ ID NO: 1623) |
| 392 | PD-L1 responder | GTGGGCACTAGGAATGAGGTCCCCTGCCTCGACCCACTCCCGGGGGGATCGGGACACCGC (SEQ ID NO: 1624) |
| 393 | PD-L1 responder | GGGCACCGCCGCCCTGACTTCCAACACATCGAAGAATGGGTGGGGCCTTGCACCTCATAC (SEQ ID NO: 1625) |
| 394 | PD-L1 responder | CCGCGCCCGCAGGGCCCGCCCCGCGCCGTCGAGGCTTTCAAGGGATCCAGGGTGGGGTGC (SEQ ID NO: 1626) |
| 395 | PD-L1 responder | CCGCGCCCGCAGGGCCCGCCCCGCGCCGTCGATGTGTTGGAAGTCAGGGCGGCGGTGCCC (SEQ ID NO: 1627) |
| 396 | PD-L1 responder | CCGCGCCCGCAGGGCCCGCCCCGCGCCGTCGACAATGTTATTCTTTGTTTCTCTTACCAA (SEQ ID NO: 1628) |
| 397 | PD-L1 responder | CCGCGCCCGCAGGGCCCGCCCCGCGCCGTCGAGAAGCATAAAGCAGGGACAGGTATGGAG (SEQ ID NO: 1629) |
| 398 | PD-L1 responder | TTCACTGTTGCCTTTTGTTGTCATTATATCGAAGAAATGCTTAAGTATGTCTAAGTTTCA (SEQ ID NO: 1630) |
| 399 | PD-L1 responder | TGAAACTTAGACATACTTAAGCATTTCTTCGATTTGTCTGTCTGCCAAGACCATTTCTGA (SEQ ID NO: 1631) |
| 400 | PD-L1 responder | TTCACTGTTGCCTTTTGTTGTCATTATATCGAGTAATACTGACACTCCTGGCCCACAGAA (SEQ ID NO: 1632) |
| 401 | PD-L1 responder | TGAAACTTAGACATACTTAAGCATTTCTTCGAAAGCTAATGAGGTATGAGGGGAGAATAC (SEQ ID NO: 1633) |
| 402 | PD-L1 Non-responder | AGTGGCCCAATCTCGGCTCACCACAGCCTCGATATTATACAGTCTTAGAACAGAAAGAAA (SEQ ID NO: 1634) |
| 403 | PD-L1 responder | GCTTCTCCCCTCTTTATCCCACCTGGCCTCGACTCACCCTGCAGACAAGCTTTCGGGTAT (SEQ ID NO: 1635) |

TABLE 13.h4-continued

| | Loop detected | Probe sequence 60 mer |
|---|---|---|
| 404 | PD-L1 Non-responder | GCCAGCTTCCAGAGAGTGGGAACATGTGTCGAGAGTCAATTCACAGCAAACAGTGAGAAG (SEQ ID NO: 1636) |
| 405 | Non-Responder | GCCAGCTTCCAGAGAGTGGGAACATGTGTCGAAGGTGTGCATATATGTTGAATGACATTT (SEQ ID NO: 1637) |
| 406 | PD-L1 responder | ATAAAATGGGGAGGCCTTCCAGAAGCTCTCGACCTCCAGGTCCCCCGCCACTTCCACGGC (SEQ ID NO: 1638) |
| 407 | PD-L1 responder | AGTGCTGGGTTCCACACCTCTCAGCTCTTCGACCTCCAGGTCCCCCGCCACTTCCACGGC (SEQ ID NO: 1639) |
| 408 | PD-L1 responder | ATAAAATGGGGAGGCCTTCCAGAAGCTCTCGACCGCCACCTCCTCCAGGAAGCCCTGCCT (SEQ ID NO: 1640) |
| 409 | PD-L1 responder | TATGAGTAATAATTACAATTTCCCCCTTTCGACCTCCAGGTCCCCCGCCACTTCCACGGC (SEQ ID NO: 1641) |
| 410 | PD-L1 responder | TAAAAAACACACCTCTGGGTGGAGATTTTCGAGTGATCCACCCGTCTTGGCCTCCCAAAG (SEQ ID NO: 1642) |
| 411 | PD-L1 Non-responder | TTTGTAAGATAAAAGATTTAAATGGATATCGATACCAATGTATAAGAGCTCTGAGAAGTT (SEQ ID NO: 1643) |
| 412 | PD-L1 Non-responder | GGTAAAACTGCCGGTACCTTAGTGCAAATCGACCAAAACCTTTTTTCTTAGAAAAGGTGT (SEQ ID NO: 1644) |
| 413 | PD-L1 Non-responder | GAGAATGAAGTGTACAAGCAGGTGATCTTCGAGAGTGTGTGGGATTAGGAAAGAGAAAGC (SEQ ID NO: 1645) |
| 414 | PD-L1 responder | GTTTGCTCCGGGGCCGCCGGGCCCGCCCTCGATTTTAACACCACCATGGTTTGAATGAAT (SEQ ID NO: 1646) |
| 415 | PD-L1 Non-responder | TATATTTAAAAATACATACTGGTATACATCGAATATGCCAATTAGATCAAGTTGGTTAAT (SEQ ID NO: 1647) |
| 416 | PD-L1 Non-responder | GTCCTCACTAGATTAGCTAGATACAGTGTCGACTTGGATGCCCATGGAATTATCTTCACT (SEQ ID NO: 1648) |

TABLE 13.h5

| | Probe Location | | | | | 4 kb Sequence Location | | |
|---|---|---|---|---|---|---|---|---|
| | Chr | Start1 | End1 | Start2 | End2 | Chr | Start1 | End1 |
| 365 | 16 | 29613904 | 29613933 | 29702020 | 29702049 | 16 | 29613904 | 29617903 |
| 366 | 16 | 29687200 | 29687229 | 29702020 | 29702049 | 16 | 29683230 | 29687229 |
| 367 | 2 | 191117456 | 191117485 | 191171013 | 191171042 | 2 | 191113486 | 191117485 |
| 368 | 2 | 191117456 | 191117485 | 191182179 | 191182208 | 2 | 191113486 | 191117485 |
| 369 | 2 | 191117456 | 191117485 | 191189124 | 191189153 | 2 | 191113486 | 191117485 |
| 370 | 20 | 47638561 | 47638590 | 47801689 | 47801718 | 20 | 47634591 | 47638590 |
| 371 | 9 | 90822199 | 90822228 | 90852643 | 90852672 | 9 | 90818229 | 90822228 |
| 372 | 1 | 114105204 | 114105233 | 114168595 | 114168624 | 1 | 114101234 | 114105233 |
| 373 | 8 | 132829420 | 132829449 | 132988146 | 132988175 | 8 | 132829420 | 132833419 |
| 374 | 2 | 70403715 | 70403744 | 70565683 | 70565712 | 2 | 70399745 | 70403744 |
| 375 | 9 | 72618535 | 72618564 | 72793872 | 72793901 | 9 | 72618535 | 72622534 |
| 376 | 6 | 137829943 | 137829972 | 137904022 | 137904051 | 6 | 137825973 | 137829972 |
| 377 | 5 | 119229308 | 119229337 | 119309595 | 119309624 | 5 | 119229308 | 119233307 |
| 378 | 5 | 119283840 | 119283869 | 119309595 | 119309624 | 5 | 119283840 | 119287839 |
| 379 | 5 | 119309595 | 119309624 | 119362681 | 119362710 | 5 | 119305625 | 119309624 |
| 380 | 8 | 22981311 | 22981340 | 23085836 | 23085865 | 8 | 22977341 | 22981340 |
| 381 | 8 | 23085836 | 23085865 | 23115427 | 23115456 | 8 | 23081866 | 23085865 |
| 382 | 18 | 62280369 | 62280398 | 62356961 | 62356990 | 18 | 62280369 | 62284368 |
| 383 | 18 | 62280369 | 62280398 | 62420808 | 62420837 | 18 | 62280369 | 62284368 |
| 384 | 18 | 62304783 | 62304812 | 62386719 | 62386748 | 18 | 62300813 | 62304812 |
| 385 | 18 | 62304783 | 62304812 | 62393569 | 62393598 | 18 | 62300813 | 62304812 |
| 386 | 18 | 62332440 | 62332469 | 62356961 | 62356990 | 18 | 62328470 | 62332469 |
| 387 | 18 | 62356961 | 62356990 | 62393569 | 62393598 | 18 | 62356961 | 62360960 |
| 388 | 8 | 118882360 | 118882389 | 118946661 | 118946690 | 8 | 118882360 | 118886359 |
| 389 | 8 | 118901885 | 118901914 | 118946661 | 118946690 | 8 | 118901885 | 118905884 |
| 390 | 22 | 17692880 | 17692909 | 17820737 | 17820766 | 22 | 17688910 | 17692909 |
| 391 | 22 | 41905695 | 41905724 | 41943491 | 41943520 | 22 | 41905695 | 41909694 |
| 392 | 22 | 41906817 | 41906846 | 41946565 | 41946594 | 22 | 41902847 | 41906846 |

TABLE 13.h5-continued

| | Probe Location | | | | 4 kb Sequence Location | | |
|---|---|---|---|---|---|---|---|
| | Chr | Start1 | End1 | Start2 | End2 | Chr | Start1 | End1 |
| 393 | 1 | 6450603 | 6450632 | 6498019 | 6498048 | 1 | 6450603 | 6454602 |
| 394 | 1 | 6466178 | 6466207 | 6484219 | 6484248 | 1 | 6462208 | 6466207 |
| 395 | 1 | 6466178 | 6466207 | 6498019 | 6498048 | 1 | 6462208 | 6466207 |
| 396 | 1 | 6466178 | 6466207 | 6494588 | 6494617 | 1 | 6462208 | 6466207 |
| 397 | 1 | 6466178 | 6466207 | 6514024 | 6514053 | 1 | 6462208 | 6466207 |
| 398 | 9 | 114859082 | 114859111 | 114894567 | 114894596 | 9 | 114855112 | 114859111 |
| 399 | 9 | 114855753 | 114855782 | 114894567 | 114894596 | 9 | 114855753 | 114859752 |
| 400 | 9 | 114859082 | 114859111 | 114920994 | 114921023 | 9 | 114855112 | 114859111 |
| 401 | 9 | 114894567 | 114894596 | 114957908 | 114957937 | 9 | 114890597 | 114894596 |
| 402 | 5 | 150983477 | 150983506 | 151050689 | 151050718 | 5 | 150983477 | 150987476 |
| 403 | 1 | 3615783 | 3615812 | 3638742 | 3638771 | 1 | 3611813 | 3615812 |
| 404 | 11 | 102291091 | 102291120 | 102307526 | 102307555 | 11 | 102291091 | 102295090 |
| 405 | 11 | 102291091 | 102291120 | 102337635 | 102337664 | 11 | 102291091 | 102295090 |
| 406 | 9 | 120893291 | 120893320 | 120913546 | 120913575 | 9 | 120889321 | 120893320 |
| 407 | 9 | 120888366 | 120888395 | 120913546 | 120913575 | 9 | 120888366 | 120892365 |
| 408 | 9 | 120893291 | 120893320 | 120919710 | 120919739 | 9 | 120889321 | 120893320 |
| 409 | 9 | 120913546 | 120913575 | 120940439 | 120940468 | 9 | 120913546 | 120917545 |
| 410 | 19 | 6701274 | 6701303 | 6781841 | 6781870 | 19 | 6697304 | 6701303 |
| 411 | 9 | 110214884 | 110214913 | 110303886 | 110303915 | 9 | 110210914 | 110214913 |
| 412 | 3 | 23907600 | 23907629 | 23926739 | 23926768 | 3 | 23903630 | 23907629 |
| 413 | 11 | 75798258 | 75798287 | 75817276 | 75817305 | 11 | 75794288 | 75798287 |
| 414 | 2 | 241559192 | 241559221 | 241577996 | 241578025 | 2 | 241559192 | 241563191 |
| 415 | 8 | 104973106 | 104973135 | 105209447 | 105209476 | 8 | 104969136 | 104973135 |
| 416 | 6 | 31852623 | 31852652 | 31978950 | 31978979 | 6 | 31852623 | 31856622 |

TABLE 13.h6

| | 4 kb Sequence Location | | Inner primers | | |
|---|---|---|---|---|---|
| | Start2 | End2 | PCR-Primer1_ID | PCR_Primer1 | PCR-Primer2_ID |
| 365 | 29698050 | 29702049 | OBD117.1.989 | TGAGGCCGTGAAAGGTAAAAGC (SEQ ID NO: 1649) | OBD117.1.991 |
| 366 | 29698050 | 29702049 | OBD117.1.1037 | TCCTCATCCCCAATCTCCCC (SEQ ID NO: 1650) | OBD117.1.1039 |
| 367 | 191167043 | 191171042 | OBD117.1.1093 | CATCCTCGGGCATTTCTTCTTGTCCT (SEQ ID NO: 1651) | OBD117.1.1095 |
| 368 | 191182179 | 191186178 | OBD117.1.1481 | CATCCTCGGGCATTTCTTCTTGTCCT (SEQ ID NO: 1652) | OBD117.1.1483 |
| 369 | 191185154 | 191189153 | OBD117.1.1725 | CATCCTCGGGCATTTCTTCTTGTCC (SEQ ID NO: 1653) | OBD117.1.1727 |
| 370 | 47797719 | 47801718 | OBD117.1.1701 | CAGCCTGGGTGACAGAGTGAGAC (SEQ ID NO: 1654) | OBD117.1.1703 |
| 371 | 90852643 | 90856642 | OBD117.1.1449 | CCCCTGAGAAGCGATGGGCTACT (SEQ ID NO: 1655) | OBD117.1.1451 |
| 372 | 114168595 | 114172594 | OBD117.1.1485 | GACCAGCAGGAGGCTACAGTTGTTGA (SEQ ID NO: 1656) | OBD117.1.1487 |
| 373 | 132988146 | 132992145 | OBD117.1.1189 | GCAGTCTTTGGGCAGCACTACGC (SEQ ID NO: 1657) | OBD117.1.1191 |
| 374 | 70565683 | 70569682 | OBD117.1.1389 | CCCTGCTTGTCCACTGTCTGAAAACA (SEQ ID NO: 1658) | OBD117.1.1391 |
| 375 | 72793872 | 72797871 | OBD117.1.1797 | GAAATCTTGGTCCCTAATGGCAT (SEQ ID NO: 1659) | OBD117.1.1799 |
| 376 | 137904022 | 137908021 | OBD117.1.549 | CTGAAACACTCACCAGCCAATGACAA (SEQ ID NO: 1660) | OBD117.1.551 |
| 377 | 119305625 | 119309624 | OBD117.1.1029 | GAAGATGGCTCTCAAGACTATAATG (SEQ ID NO: 1661) | OBD117.1.1031 |
| 378 | 119305625 | 119309624 | OBD117.1.681 | GGCTCGCTCCAGCACATTCTCCA (SEQ ID NO: 1662) | OBD117.1.683 |

TABLE 13.h6-continued

| | 4 kb Sequence Location | | Inner_primers | | |
|---|---|---|---|---|---|
| | Start2 | End2 | PCR-Primer1_ID | PCR_Primer1 | PCR-Primer2_ID |
| 379 | 119358711 | 119362710 | OBD117.1.677 | GGCTCGCTCCAGCACATTCTCCA (SEQ ID NO: 1663) | OBD117.1.679 |
| 380 | 23081866 | 23085865 | OBD117.1.461 | GCACACCTGCCAGAACTCATTCAAGA (SEQ ID NO: 1664) | OBD117.1.463 |
| 381 | 23111457 | 23115456 | OBD117.1.541 | GTTTGCCTGACACAGTTCCCTGC (SEQ ID NO: 1665) | OBD117.1.543 |
| 382 | 62356961 | 62360960 | OBD117.1.457 | ATCACTGGACAAGGTAACAAGGGC (SEQ ID NO: 1666) | OBD117.1.459 |
| 383 | 62420808 | 62424807 | OBD117.1.981 | GAGCAACCCGCTTGTCAAC (SEQ ID NO: 1667) | OBD117.1.983 |
| 384 | 62382749 | 62386748 | OBD117.1.505 | TGTGTTTATTCCCTACAGAGCAGGTT (SEQ ID NO: 1668) | OBD117.1.507 |
| 385 | 62389599 | 62393598 | OBD117.1.1625 | TGTGTTTATTCCCTACAGAGCAGGTT (SEQ ID NO: 1669) | OBD117.1.1627 |
| 386 | 62356961 | 62360960 | OBD117.1.053 | AATCCTACTGGCACCACTGTGTTGGC (SEQ ID NO: 1670) | OBD117.1.055 |
| 387 | 62389599 | 62393598 | OBD117.1.1745 | CCCGAACCAGCCTTCCCAAGAGC (SEQ ID NO: 1671) | OBD117.1.1747 |
| 388 | 118946661 | 118950660 | OBD117.1.465 | CCACAACCCACACCTGCCACTGT (SEQ ID NO: 1672) | OBD117.1.467 |
| 389 | 118946661 | 118950660 | OBD117.1.533 | GCCTAACTGATGTGGCTGTCTTTGTG (SEQ ID NO: 1673) | OBD117.1.535 |
| 390 | 17820737 | 17824736 | OBD117.1.1773 | TGTGTCATCAGGATTCTTTTCTG (SEQ ID NO: 1674) | OBD117.1.1775 |
| 391 | 41939521 | 41943520 | OBD117.1.525 | ATCCTGTGTCTCCCTCCCCTTCA (SEQ ID NO: 1675) | OBD117.1.527 |
| 392 | 41946565 | 41950564 | OBD117.1.993 | CAGAGGGTTGCCTATGGTGG (SEQ ID NO: 1676) | OBD117.1.995 |
| 393 | 6494049 | 6498048 | OBD117.1.381 | AATAACCTGTGCCCAGACCGAGC (SEQ ID NO: 1677) | OBD117.1.383 |
| 394 | 6480249 | 6484248 | OBD117.1.193 | AGCCTCCTGCGTCTCAACTCACC (SEQ ID NO: 1678 | OBD117.1.195 |
| 395 | 6494049 | 6498048 | OBD117.1.181 | AGCCTCCTGCGTCTCAACTCACC (SEQ ID NO: 1679) | OBD117.1.183 |
| 396 | 6494588 | 6498587 | OBD117.1.137 | AGCCTCCTGCGTCTCAACTCACC (SEQ ID NO: 1680) | OBD117.1.139 |
| 397 | 6514024 | 6518023 | OBD117.1.745 | CTAGCCTCCTGCGTCTCAAC (SEQ ID NO: 1681) | OBD117.1.747 |
| 398 | 114890597 | 114894596 | OBD117.1.545 | GTTGCTCAGGCTGCCCTCTTGCT (SEQ ID NO: 1682) | OBD117.1.547 |
| 399 | 114890597 | 114894596 | OBD117.1.1049 | TCAGGGTAGTGCAGTGTAGTGT (SEQ ID NO: 1683) | OBD117.1.1051 |
| 400 | 114920994 | 114924993 | OBD117.1.517 | TGTTGCTCAGGCTGCCCTCTTGCTAT (SEQ ID NO: 1684) | OBD117.1.519 |
| 401 | 114957908 | 114961907 | OBD117.1.273 | GCACCAGGTCAAGTAGCCTCAGG (SEQ ID NO: 1685) | OBD117.1.275 |
| 402 | 151046719 | 151050718 | OBD117.1.1385 | GTCTCGTTCTGTCACCCAGGCTG (SEQ ID NO: 1686) | OBD117.1.1387 |
| 403 | 3638742 | 3642741 | OBD117.1.349 | CCAAATGTAGATGCCCGCACCCG (SEQ ID NO: 1687) | OBD117.1.351 |

TABLE 13.h6-continued

| | 4 kb Sequence Location | | Inner primers | | |
|---|---|---|---|---|---|
| | Start2 | End2 | PCR-Primer1_ID | PCR_Primer1 | PCR-Primer2_ID |
| 404 | 102307526 | 102311525 | OBD117.1.697 | TGCCTTGAACAGATTGCCAGCCTCCT (SEQ ID NO: 1688) | OBD117.1.699 |
| 405 | 102337635 | 102341634 | OBD117.1.597 | TGCCTTGAACAGATTGCCAGCCTCCT (SEQ ID NO: 1689) | OBD117.1.599 |
| 406 | 120913546 | 120917545 | OBD117.1.021 | GACGCTCTCCCTTTGCTCAAGCC (SEQ ID NO: 1690) | OBD117.1.023 |
| 407 | 120913546 | 120917545 | OBD117.1.301 | CCCAGTIGTCCAGGTTGCTGCCT (SEQ ID NO: 1691) | OBD117.1.303 |
| 408 | 120919710 | 120923709 | OBD117.1.013 | GACGCTCTCCCTTTGCTCAAGCC (SEQ ID NO: 1692) | OBD117.1.015 |
| 409 | 120936469 | 120940468 | OBD117.1.169 | GCTGTGTATCTCAGGGCACTCAG (SEQ ID NO: 1693) | OBD117.1.171 |
| 410 | 6781841 | 6785840 | OBD117.1.949 | GGCCCTGAAGGGGACTTATC (SEQ ID NO: 1694) | OBD117.1.951 |
| 411 | 110299916 | 110303915 | OBD117.1.933 | CTGATTGCTCAACCCAAAGC (SEQ ID NO: 1695) | OBD117.1.935 |
| 412 | 23922769 | 23926768 | OBD117.1.1873 | TCATACTACTACCAAAGCCATTT (SEQ ID NO: 1696) | OBD117.1.1875 |
| 413 | 75817276 | 75821275 | OBD117.1.1233 | GACCTGGTTCCCATCTACTCCTTTGG (SEQ ID NO: 1697) | OBD117.1.1235 |
| 414 | 241577996 | 241581995 | OBD117.1.841 | AGCGCCACCTTCTTTCAGAG (SEQ ID NO: 1698) | OBD117.1.843 |
| 415 | 105209447 | 105213446 | OBD117.1.1649 | AGGCATTACTGAAGTTGCTGGTATTC (SEQ ID NO: 1699) | OBD117.1.1651 |
| 416 | 31978950 | 31982949 | OBD117.1.1013 | CCAGAGCGGGATGTCACTAC (SEQ ID NO: 1700) | OBD117.1.1015 |

TABLE 13.h7

| | Inner primers | |
|---|---|---|
| | PCR_Primer2 | GLMNET |
| 365 | GCTCCCAGGCTTGACGAGA (SEQ ID NO: 1701) | 0 |
| 366 | CTGGGGCACTCAATCTAGAGGT (SEQ ID NO: 1702) | 0 |
| 367 | CCGTGACTCATCAGAGGAAAACTACG (SEQ ID NO: 1703) | 0 |
| 368 | GGAAAGAGTAGGAACCTGAAACCTGC (SEQ ID NO: 1704) | 0 |
| 369 | CCTCTTCCTGGCTCACAGACAGC (SEQ ID NO: 1705) | 0 |
| 370 | CTCACGCTCTGGTCCTTGTCACT (SEQ ID NO: 1706) | 0 |
| 371 | GGGCAGGGACTAAGGTCTGACTT (SEQ ID NO: 1707) | 0 |
| 372 | CTCCCATCTTGAGGCTGTAAACAAAC (SEQ ID NO: 1708) | 0 |
| 373 | CACACTCCTCCTCCAAGTCACAG (SEQ ID NO: 1709) | 0 |
| 374 | CCACACAGTTTCCACCTTACCACCAT (SEQ ID NO: 1710) | 0 |
| 375 | GTAGTGGCAGAGGAACTTTCAGT (SEQ ID NO: 1711) | 0 |

TABLE 13.h7-continued

| | Inner_primers | |
|---|---|---|
| | PCR_Primer2 | GLMNET |
| 376 | AACAGGCAGGGTGAACTCTTCCAGAC (SEQ ID NO: 1712) | 0.009721306 |
| 377 | CCAAGCTGGCTAATATGTGTG (SEQ ID NO: 1713) | 0 |
| 378 | GGGCTAACCAGAGGCAAAAGGCA (SEQ ID NO: 1714) | 0.007305849 |
| 379 | GGTTGAAGGAGGTGGGTCAGTTG (SEQ ID NO: 1715) | 0.001120789 |
| 380 | GGCTTAGTGGTTTTGGAGTCCTGGTA (SEQ ID NO: 1716) | −0.017294821 |
| 381 | ATGAGCCCTGAGTGTGCTGGTGC (SEQ ID NO: 1717) | 0.000113082 |
| 382 | ATCATAATCAGGCAACTGGCTGGTGC (SEQ ID NO: 1718) | 0.000110518 |
| 383 | TGTAGCCAGCCATCCAAAGACA (SEQ ID NO: 1719) | 0 |
| 384 | TGAGCACTGGTTCCCCGCAAATACTG (SEQ ID NO: 1720) | 0.027764821 |
| 385 | AACCTTACCCGAACCAGCCTTCCCAA (SEQ ID NO: 1721) | 0 |
| 386 | GAAGAGCCCAGTTGACATCTAATAAC (SEQ ID NO: 1722) | 0.008919637 |
| 387 | GTTGACATCTAATAACTCACATT (SEQ ID NO: 1723) | 0 |
| 388 | GCCAAGAGAGAAGAGTGTGAAGCC (SEQ ID NO: 1724) | −0.009297019 |
| 389 | AAGCCAAGAGAGAAGAGTGTGAAGCC (SEQ ID NO: 1725) | 0 |
| 390 | AGGTCCACATACCACACACCATA (SEQ ID NO: 1726) | 0 |
| 391 | AGGCTCTTCCCCACCACTCTCAG (SEQ ID NO: 1727) | −0.016217397 |
| 392 | GTAGTAGAGAGTGCGGTGCC (SEQ ID NO: 1728) | 0 |
| 393 | GGGAAAATCGGTGTGGCTGGCTC (SEQ ID NO: 1729) | 0.000134142 |
| 394 | ATACGGACTGAGCCCTATGACGC (SEQ ID NO: 1730) | 0 |
| 395 | AATAACCTGTGCCCAGACCGAGC (SEQ ID NO: 1731) | −0.007419688 |
| 396 | AGAACAGAGGCAAGGGCAGTCCA (SEQ ID NO: 1732) | −0.005042919 |
| 397 | CCTCCATACCTGTCCCTGCT (SEQ ID NO: 1733) | 0.020530456 |
| 398 | GTCAAGTAGCCTCAGGGTAGTGC (SEQ ID NO: 1734) | 0.013121857 |
| 399 | TGCCATGTAACCTTGTGTTCAGA (SEQ ID NO: 1735) | 0 |
| 400 | CCTGTTTGAGATGCTCTGCTTTTGAC (SEQ ID NO: 1736) | 0.012738078 |
| 401 | AGCCCTCGCTAAAGCCAAATGGG (SEQ ID NO: 1737) | 0.010145959 |
| 402 | GGCAGTGGTTTGTCCTGTGACCT (SEQ ID NO: 1738) | 0 |
| 403 | GGATAACCGTCTGGTCCTTGTGC (SEQ ID NO: 1739) | −0.021145842 |
| 404 | CCTGGCTTGCTTTTGAATCCTGACTT (SEQ ID NO: 1740) | 0.006301587 |
| 405 | AAGGTATGGAAAGAGTCTGGGAGTGA (SEQ ID NO: 1741) | 0.01482896 |
| 406 | TGGAGCAGAACCTGTCAGACCTG (SEQ ID NO: 1742) | −0.016381908 |
| 407 | TGGAGCAGAACCTGTCAGACCTG (SEQ ID NO: 1743) | 0.024168377 |

TABLE 13.h7-continued

| | Inner primers | |
|---|---|---|
| | PCR_Primer2 | GLMNET |
| 408 | GGAGTCCACCAAGTGCTATGGGA (SEQ ID NO: 1744) | −0.003508085 |
| 409 | CCTGGAGCAGAACCTGTCAGACC (SEQ ID NO: 1745) | −0.01000752 |
| 410 | TCAGGGATCCAATAGGTTAAGTAAT (SEQ ID NO: 1746) | −0.018046798 |
| 411 | GCTGCGAAAATGTTGAGGCT (SEQ ID NO: 1747) | 0.008860872 |
| 412 | GAAGAATGAACTGCTACAACACC (SEQ ID NO: 1748) | 0 |
| 413 | GAACTGTTATCAGAGAATAGGCTCCA (SEQ ID NO: 1749) | 0 |
| 414 | GGGCATTATGTGAGGGTCTC (SEQ ID NO: 1750) | 0.000117272 |
| 415 | AAGAGCAATAAGGATGTCAAAGTTTT (SEQ ID NO: 1751) | 0 |
| 416 | CCTGTCTCCCCCAACCTGTG (SEQ ID NO: 1752) | 0 |

TABLE 13.i1

| | Probe | GeneLocus | Probe_Count_Total | Probe_Count_Sig |
|---|---|---|---|---|
| 417 | ORF83_6_31878016_31881028_31925606_31928820_RF | ORF83 | 29 | 7 |
| 418 | ORF83_6_31899557_31901172_31978950_31986111_FR | ORF83 | 29 | 7 |
| 419 | ORF83_6_31918302_31923229_31940368_31942384_FR | ORF83 | 29 | 7 |
| 420 | ORF83_6_31918302_31923229_31942384_31947035_FF | ORF83 | 29 | 7 |
| 421 | ORF83_6_31925606_31928820_31942384_31947035_FF | ORF83 | 29 | 7 |
| 422 | ORF83_6_31925606_31928820_31978950_31986111_FR | ORF83 | 29 | 7 |
| 423 | ORF86_1_56841210_56844685_56902220_56908104_RF | ORF86 | 113 | 2 |
| 424 | ORF99_3_105671315_105675681_105723411_105731672_FR | ORF99 | 169 | 24 |
| 425 | ORF99_3_105671315_105675681_105803937_105818229_RF | ORF99 | 169 | 24 |
| 426 | ORF99_3_105671315_105675681_105828793_105836033_FR | ORF99 | 169 | 24 |
| 427 | ORF99_3_105723411_105731672_105748068_105752264_RF | ORF99 | 169 | 24 |
| 428 | ORF99_3_105723411_105731672_105795346_105800869_RR | ORF99 | 169 | 24 |
| 429 | ORF99_3_105723411_105731672_105803937_105818229_RF | ORF99 | 169 | 24 |
| 430 | ORF99_3_105748068_105752264_105803937_105818229_FF | ORF99 | 169 | 24 |
| 431 | ORF99_3_105803937_105818229_105883590_105884656_RF | CBLB | 182 | 2 |
| 432 | ORF99_3_105887817_105896306_105908853_105916728_RF | ORF99 | 169 | 24 |
| 433 | PIK3R1_5_68187850_68194388_68215410_68221074_FR | PIK3R1 | 148 | 12 |
| 434 | PIK3R1_5_68195469_68198352_68215410_68221074_RR | PIK3R1 | 148 | 12 |
| 435 | PIK3R1_5_68215410_68221074_68272048_68277769_RF | PIK3R1 | 148 | 12 |
| 436 | PRR5_22_44662780_44666500_44696835_44701888_FF | PRR5 | 64 | 4 |
| 437 | PTPRC_1_198646662_198649713_198659753_198666156_FR | PTPRC | 32 | 11 |
| 438 | PTPRC_1_198659753_198666156_198768850_198775826_FF | PTPRC | 32 | 11 |
| 439 | RPTOR_17_80636056_80643737_80661868_80664436_FR | RPTOR | 86 | 6 |
| 440 | RPTOR_17_80636056_80643737_80661868_80664436_RR | RPTOR | 86 | 6 |
| 441 | RPTOR_17_80636056_80643737_80793263_80796075_FF | RPTOR | 86 | 6 |
| 442 | SHH_7_155794440_155798922_155840981_155842935_RF | SHH | 36 | 6 |
| 443 | SHH_7_155807951_155810124_155829183_155832221_FR | SHH | 36 | 6 |
| 444 | SPN_16_29613904_29616227_29630194_29632081_RF | SPN | 56 | 4 |
| 445 | SPN_16_29613904_29616227_29686079_29687229_RF | SPN | 56 | 4 |
| 446 | STAT5B_17_40403935_40406459_40464294_40468456_FR | STAT5B | 20 | 12 |
| 447 | SYK_9_90816328_90822228_90852643_90856872_FR | SYK | 6 | 2 |
| 448 | SYK_9_90816328_90822228_90872966_90875740_FR | SYK | 6 | 2 |
| 449 | TNFRSF11A_18_62317997_62323752_62391728_62393598_RF | TNFRSF11A | 7 | 1 |
| 450 | TNFRSF13C_22_41905695_41906846_41946565_41950791_FR | TNFRSF13C | 4 | 1 |
| 451 | TNFRSF1A_12_6358656_6362143_6379726_6384063_FF | TNFRSF1A | 46 | 2 |
| 452 | TNFRSF25_1_6450603_6452273_6494588_6498048_RF | TNFRSF25 | 68 | 16 |
| 453 | TNFRSF25_1_6461604_6466207_6481328_6484248_FF | TNFRSF25 | 68 | 16 |
| 454 | TNFRSF25_1_6461604_6466207_6494588_6498048_FF | TNFRSF25 | 68 | 16 |
| 455 | TNFRSF25_1_6461604_6466207_6514024_6515315_FR | TNFRSF25 | 68 | 16 |
| 456 | TNFRSF25_1_6494588_6498048_6514024_6515315_FR | TNFRSF25 | 68 | 16 |
| 457 | TNFSF8_9_114957908_114962933_114975258_114977746_RF | TNFSF8 | 3 | 1 |
| 458 | TRAF1_9_120888366_120893320_120913546_120919710_FR | TRAF1 | 42 | 6 |
| 459 | TRAF1_9_120913546_120919710_120936524_120940468_RF | TRAF1 | 42 | 6 |
| 460 | TRAF2_9_136904007_136906211_136939587_136941363_RF | TRAF2 | 46 | 2 |

TABLE 13.i2

|     | HyperG_Stats | FDR_HyperG | Percent_Sig | logFC | AveExpr | t |
| --- | --- | --- | --- | --- | --- | --- |
| 417 | 0.001789508 | 0.045608266 | 24.14 | 0.168923652 | 0.168923652 | 4.273129747 |
| 418 | 0.002398244 | 0.056538599 | 24.14 | 0.144207368 | 0.144207368 | 6.014120556 |
| 419 | 0.002398244 | 0.056538599 | 24.14 | 0.199604737 | 0.199604737 | 8.688296791 |
| 420 | 0.002398244 | 0.056538599 | 24.14 | 0.1824608 | 0.1824608 | 7.192394868 |
| 421 | 0.002398244 | 0.056538599 | 24.14 | 0.172829165 | 0.172829165 | 5.388588036 |
| 422 | 0.002398244 | 0.056538599 | 24.14 | 0.173973685 | 0.173973685 | 6.172747925 |
| 423 | 0.994563707 | 1 | 1.77 | 0.295771685 | 0.295771685 | 3.019840274 |
| 424 | 0.000164355 | 0.005961019 | 14.2 | 0.340118684 | 0.340118684 | 13.02892826 |
| 425 | 0.000164355 | 0.005961019 | 14.2 | 0.313675221 | 0.313675221 | 5.453800736 |
| 426 | 0.000164355 | 0.005961019 | 14.2 | 0.308984949 | 0.308984949 | 13.67253532 |
| 427 | 0.000164355 | 0.005961019 | 14.2 | 0.370970871 | 0.370970871 | 8.877555847 |
| 428 | 0.000164355 | 0.005961019 | 14.2 | 0.293427802 | 0.293427802 | 8.432951342 |
| 429 | 0.000164355 | 0.005961019 | 14.2 | 0.30374268 | 0.30374268 | 7.655073619 |
| 430 | 0.000164355 | 0.005961019 | 14.2 | 0.355774756 | 0.355774756 | 5.513101893 |
| 431 | 0.999995464 | 0.99997746 | 1.1 | −0.197007746 | −0.197007746 | −4.723247929 |
| 432 | 0.000164355 | 0.005961019 | 14.2 | 0.30240493 | 0.30240493 | 7.643472828 |
| 433 | 0.513477047 | 0.99999793 | 8.11 | −0.331665721 | −0.331665721 | −11.91788456 |
| 434 | 0.513477047 | 0.99999793 | 8.11 | 0.356573442 | −0.356573442 | −14.85687535 |
| 435 | 0.513477047 | 0.99999793 | 8.11 | −0.31812964 | −0.31812964 | −14.30149147 |
| 436 | 0.7582782 | 0.99999793 | 6.25 | −0.385982839 | −0.385982839 | −17.18527923 |
| 437 | 2.29E−06 | 0.000217011 | 34.38 | 0.321601025 | 0.321601025 | 10.73971674 |
| 438 | 2.29E−06 | 0.000217011 | 34.38 | 0.284709632 | 0.284709632 | 9.679151953 |
| 439 | 0.687444338 | 0.99999793 | 6.98 | −0.140265969 | −0.140265969 | −6.28050969 |
| 440 | 0.687444338 | 0.99999793 | 6.98 | −0.187583846 | −0.187583846 | −5.431560127 |
| 441 | 0.687444338 | 0.99999793 | 6.98 | −0.139084539 | −0.139084539 | −6.11708923 |
| 442 | 0.062022042 | 0.70039526 | 16.67 | −0.174771304 | −0.174771304 | −4.501723442 |
| 443 | 0.062022042 | 0.70039526 | 16.67 | −0.140520637 | −0.140520637 | −6.954162178 |
| 444 | 0.659150649 | 0.99999793 | 7.14 | −0.169924144 | 0.169924144 | −7.327193408 |
| 445 | 0.659150649 | 0.99999793 | 7.14 | −0.153139995 | 0.153139995 | −6.667140097 |
| 446 | 0.001866853 | 0.066190912 | 60 | 0.870424687 | 0.870424687 | 6.817040924 |
| 447 | 0.050279839 | 0.592673603 | 33.33 | 0.289411908 | 0.289411908 | 8.185158835 |
| 448 | 0.050279839 | 0.592673603 | 33.33 | 0.421540272 | 0.421540272 | 12.7959067 |
| 449 | 0.366131493 | 1 | 14.29 | 0.295150757 | 0.295150757 | 5.356815514 |
| 450 | 0.251755367 | 1 | 25 | −0.152450898 | −0.152450898 | −7.330250938 |
| 451 | 0.889742685 | 0.99999793 | 4.35 | −0.200276865 | −0.200276865 | −7.487088438 |
| 452 | 6.44E−05 | 0.004967399 | 23.53 | −0.330748028 | −0.330748028 | −18.17630665 |
| 453 | 6.44E−05 | 0.004967399 | 23.53 | −0.375198131 | −0.375198131 | −11.77686613 |
| 454 | 6.44E−05 | 0.004967399 | 23.53 | −0.342250575 | −0.342250575 | −12.06306132 |
| 455 | 6.44E−05 | 0.004967399 | 23.53 | −0.358891419 | −0.358891419 | −10.66682351 |
| 456 | 6.44E−05 | 0.004967399 | 23.53 | −0.282267049 | −0.282267049 | −15.53979703 |
| 457 | 0.177479538 | 1 | 33.33 | 0.138918287 | 0.138918287 | 7.319723967 |
| 458 | 0.112492545 | 0.789152247 | 14.29 | −0.165440732 | −0.165440732 | −5.606610708 |
| 459 | 0.112492545 | 0.789152247 | 14.29 | −0.22976066 | −0.22976066 | −9.762488772 |
| 460 | 0.889742685 | 0.99999793 | 4.35 | −0.18670662 | −0.18670662 | −5.163579985 |

TABLE 13.i3

|     | P. Value | adj. P. Val | B | FC | FC_1 | LS |
| --- | --- | --- | --- | --- | --- | --- |
| 417 | 0.001541322 | 0.008215323 | −1.41185712 | 1.124219428 | 1.124219428 | 1 |
| 418 | 0.000117273 | 0.001382765 | 1.265161339 | 1.10512332 | 1.10512332 | 1 |
| 419 | 0.00000481 | 0.000187071 | 4.576477583 | 1.148383683 | 1.148383683 | 1 |
| 420 | 0.0000259 | 0.000518564 | 2.835496877 | 1.134817891 | 1.134817891 | 1 |
| 421 | 0.000281632 | 0.002477042 | 0.352536792 | 1.127266921 | 1.127266921 | 1 |
| 422 | 0.0000947 | 0.001202019 | 1.487699995 | 1.128161559 | 1.128161559 | 1 |
| 423 | 0.01256505 | 0.038542086 | −3.55264462 | 1.227541403 | 1.227541403 | 1 |
| 424 | 0.000000105 | 0.0000268 | 8.427168566 | 1.265860726 | 1.265860726 | 1 |
| 425 | 0.000256392 | 0.002326445 | 0.450307706 | 1.242869843 | 1.242869843 | 1 |
| 426 | 0.0000000654 | 0.0000214 | 8.883474649 | 1.238835774 | 1.238835774 | 1 |
| 427 | 0.00000395 | 0.00016934 | 4.778806192 | 1.293222821 | 1.293222821 | 1 |
| 428 | 0.00000631 | 0.000221388 | 4.297454598 | 1.225548689 | 1.225548689 | 1 |
| 429 | 0.000015 | 0.000371302 | 3.4022934 | 1.234342429 | 1.234342429 | 1 |
| 430 | 0.000235533 | 0.00219625 | 0.538683933 | 1.279672607 | 1.279672607 | 1 |
| 431 | 0.000759949 | 0.004919307 | −0.679565911 | 0.872358022 | −1.14631834 | −1 |
| 432 | 0.0000152 | 0.000374316 | 3.388405516 | 1.233198406 | 1.233198406 | 1 |
| 433 | 0.000000248 | 0.0000426 | 7.579137577 | 0.794618496 | −1.258465547 | −1 |
| 434 | 0.000000029 | 0.0000153 | 9.663464141 | 0.78101738 | −1.280381239 | −1 |
| 435 | 0.0000000421 | 0.0000172 | 9.306864203 | 0.802109086 | −1.246713219 | −1 |
| 436 | 0.00000000688 | 0.0000106 | 11.00320387 | 0.765257487 | −1.30674971 | −1 |
| 437 | 0.000000669 | 0.0000679 | 6.585681171 | 1.249716647 | 1.249716647 | 1 |
| 438 | 0.00000178 | 0.000110226 | 5.595735187 | 1.218165062 | 1.218165062 | 1 |
| 439 | 0.0000821 | 0.001088928 | 1.636855792 | 0.907351864 | −1.102108277 | −1 |
| 440 | 0.000264717 | 0.002374878 | 0.417032009 | 0.878075047 | −1.138854821 | −1 |
| 441 | 0.00010205 | 0.001261051 | 1.410021654 | 0.908095203 | −1.101206125 | −1 |
| 442 | 0.001072501 | 0.006331857 | −1.036726499 | 0.885907942 | −1.128785456 | −1 |

TABLE 13.i3-continued

|  | P. Value | adj. P. Val | B | FC | FC_1 | LS |
|---|---|---|---|---|---|---|
| 443 | 0.0000347 | 0.000620295 | 2.533051066 | 0.907191711 | −1.102302841 | −1 |
| 444 | 0.0000221 | 0.000471182 | 3.003395936 | 0.888889417 | −1.124999331 | −1 |
| 445 | 0.0000497 | 0.000781417 | 2.158738806 | 0.899291043 | −1.111987056 | −1 |
| 446 | 0.000217825 | NA | 1.17150928 | 1.82820099 | 1.82820099 | 1 |
| 447 | 0.00000826 | 0.000257888 | 4.019841765 | 1.222141989 | 1.222141989 | 1 |
| 448 | 0.000000125 | 0.0000307 | 8.255863058 | 1.339356736 | 1.339356736 | 1 |
| 449 | 0.000294879 | 0.00256113 | 0.304679742 | 1.22701319 | 1.22701319 | 1 |
| 450 | 0.000022 | 0.000469868 | 3.00717754 | 0.899720688 | −1.111456047 | −1 |
| 451 | 0.0000183 | 0.000418541 | 3.199585235 | 0.870383513 | −1.148918821 | −1 |
| 452 | 0.00000000394 | 0.00000864 | 11.50694716 | 0.79512411 | −1.257665297 | −1 |
| 453 | 0.000000277 | 0.0000445 | 7.465604014 | 0.770999521 | −1.297017667 | −1 |
| 454 | 0.00000022 | 0.0000394 | 7.6945755 | 0.788809824 | −1.26773269 | −1 |
| 455 | 0.000000713 | 0.0000695 | 6.520700487 | 0.779763527 | −1.282440079 | −1 |
| 456 | 0.0000000186 | 0.0000129 | 10.08124721 | 0.822297844 | −1.216104368 | −1 |
| 457 | 0.0000223 | 0.000473074 | 2.994152645 | 1.101079232 | 1.101079232 | 1 |
| 458 | 0.000206242 | 0.002008025 | 0.677010146 | 0.891656084 | −1.121508638 | −1 |
| 459 | 0.00000164 | 0.000106067 | 5.677124024 | 0.852776354 | −1.172640394 | −1 |
| 460 | 0.000391198 | 0.003113294 | 0.010501538 | 0.87860912 | −1.138162554 | −1 |

TABLE 13.i4

|  | Loop detected | Probe sequence 60 mer |
|---|---|---|
| 417 | Non-Responder | TCCTATCCCGTGGGTGGCAATGTGAGCTTCGAGAAGGTCCCTCATAGGGGTTCCTTCCCC (SEQ ID NO: 1753) |
| 418 | PD-L1 Non-responder | AGCAGGCGGCCAAGATGACCTTGTGGCCTCGACTTGGATGCCCATGGAATTATCTTCACT (SEQ ID NO: 1754) |
| 419 | PD-L1 Non-responder | CACAGGTCAGGTCATGGTCCTTCCACATTCGATTCCCTCTGGGGAATGTCCCTGGTGGTT (SEQ ID NO: 1755) |
| 420 | PD-L1 Non-responder | CACAGGTCAGGTCATGGTCCTTCCACATTCGAAGTCGTGTGGTCTTGGACAGTGGATTGC (SEQ ID NO: 1756) |
| 421 | PD-L1 Non-responder | TCCTATCCCGTGGGTGGCAATGTGAGCTTCGAAGTCGTGTGGTCTTGGACAGTGGATTGC (SEQ ID NO: 1757) |
| 422 | PD-L1 Non-responder | TCCTATCCCGTGGGTGGCAATGTGAGCTTCGACTTGGATGCCCATGGAATTATCTTCACT (SEQ ID NO: 1758) |
| 423 | PD-L1 Non-responder | AGGTCATTAAAGTATAATCCTGTTGTTATCGAGAGATCAAGACCATCCTGGCCAACATGG (SEQ ID NO: 1759) |
| 424 | PD-L1 Non-responder | AGCAGGGGGATCACATAAGGCCAGGAGTTCGAATAAGAAATACTTCTAAACCAAAGGATA (SEQ ID NO: 1760) |
| 425 | PD-L1 Non-responder | ATGTATTTATAGGTCTAATCATGTAAAATCGATATCTCTGAAAGTACCGTCAATTCTTCT (SEQ ID NO: 1761) |
| 426 | PD-L1 Non-responder | AGCAGGGGGATCACATAAGGCCAGGAGTTCGATTTTAACAAGAAACTGTAGGTCTAAGGA (SEQ ID NO: 1762) |
| 427 | PD-L1 Non-responder | TTATTACTTTATTCTGACTGAATATCATTCGAATAAGAAATACTTCTAAACCAAAGGATA (SEQ ID NO: 1763) |
| 428 | PD-L1 Non-responder | TATCCTTTGGTTTAGAAGTATTTCTTATTCGAAAGAAACCAAAAACACAAGTATACATCA (SEQ ID NO: 1764) |
| 429 | PD-L1 Non-responder | ATGTATTTATAGGTCTAATCATGTAAAATCGAATAAGAAATACTTCTAAACCAAAGGATA (SEQ ID NO: 1765) |
| 430 | PD-L1 Non-responder | TTATTACTTTATTCTGACTGAATATCATTCGATTTTACATGATTAGACCTATAAATACAT (SEQ ID NO: 1766) |
| 431 | PD-L1 responder | CCTAATATTTCATTATGATAAGAAAGATTCGAGAGTAAGTTTCTTCTGTTCACTCAGGAG (SEQ ID NO: 1767) |
| 432 | PD-L1 Non-responder | TTATTTATATCTTCTCTAATTTATTTTATCGATGAACGTTTACCCAATTATTTCTAAACA (SEQ ID NO: 1768) |
| 433 | PD-L1 responder | CTGAGTCTTCATTACCAAAAAAAAAAGTTCGACCTCCCCGAACCCCTCCGCCTCTGCGCT (SEQ ID NO: 1769) |

TABLE 13.i4-continued

| | Loop detected | Probe sequence 60 mer |
|---|---|---|
| 434 | PD-L1 responder | AAATCATAATTGTGCAGATGATTTGCCTTCGACCTCCCCGAACCCCTCCGCCTCTGCGCT (SEQ ID NO: 1770) |
| 435 | PD-L1 responder | GCAGTCAATCACCGAGTTATATGAGGTCTCGACCTCCCCGAACCCCTCCGCCTCTGCGCT (SEQ ID NO: 1771) |
| 436 | PD-L1 responder | CCAAACTGGCAATCAACCCAGATAGTCTTCGACCCCGGCCCCGGAGGTCTCCCTCCACAG (SEQ ID NO: 1772) |
| 437 | PD-L1 Non-responder | AGAGGCTGAGGTGAAAAGATTGTTTGAGTCGATTATTTCTTATCTAGCCAATAGAAACTT (SEQ ID NO: 1773) |
| 438 | PD-L1 Non-responder | AGAGGCTGAGGTGAAAAGATTGTTTGAGTCGAGTCACATGATCAAGCGCTCATTTCTGTT (SEQ ID NO: 1774) |
| 439 | PD-L1 responder | CTTTTCCATTGCTTCCTCAGATCCTCTGTCGAGATTCACTGCGCTGCACACCAGGGCCTC (SEQ ID NO: 1775) |
| 440 | PD-L1 responder | AGCTGGAGTCTTGATTAACACAAAAATCTCGAGATTCACTGCGCTGCACACCAGGGCCTC (SEQ ID NO: 1776) |
| 441 | PD-L1 responder | CTTTTCCATTGCTTCCTCAGATCCTCTGTCGAGAGCACGGCCTCTCTGGCGCCTTGCCAT (SEQ ID NO: 1777) |
| 442 | PD-L1 responder | ACATGAGATGTCCTTCAAGTGAAACTGTTCGACCATGCCCGGGCAGGTGGCTGAGACCTC (SEQ ID NO: 1778) |
| 443 | PD-L1 responder | CGCGCACTGAAACCCTAGCCGCGGGGGATCGAAATCATATCACCAGTCATTCCACTCCTG (SEQ ID NO: 1779) |
| 444 | PD-L1 responder | AGGCGACACTCTTGTCCCCGCCATCTTTTCGAAGGCCCCCGTCCTCCTGCGCCATGGAGA (SEQ ID NO: 1780) |
| 445 | PD-L1 responder | CATCATACAGTCTACGGCTGTTTCCTCTCGAAGGCCCCCGTCCTCCTGCGCCATGGAGA (SEQ ID NO: 1781) |
| 446 | PD-L1 Non-responder | TTCCATAGATTACTTTTCAAATCATCCTTCGAAGCTGGCGGCTGAGGGCCCGGCGCCAAG (SEQ ID NO: 1782) |
| 447 | PD-L1 Non-responder | TTTTACTGTTTTTGTAAGAGATATGTTTTCGATTAATGTTAAAAATAAAAGGTAGTATTT (SEQ ID NO: 1783) |
| 448 | PD-L1 Non-responder | TTTTACTGTTTTTGTAAGAGATATGTTTTCGACATCATTTTTACAAATAAGACCAGATGT (SEQ ID NO: 1784) |
| 449 | PD-L1 Non-responder | AGGTACTCTTGAAAATATAAAACTCCAGTCGACATTATACAAAGAATTCCCACAAATCCA (SEQ ID NO: 1785) |
| 450 | PD-L1 responder | GTGGGCACTAGGAATGAGGTCCCCTGCCTCGACCCACTCCCGGGGGGATCGGGACACCGC (SEQ ID NO: 1786) |
| 451 | PD-L1 responder | TCCAGGGATGGCAGAGTCTCTGGCAGCCTCGATGCGGGCGGGAGGGGCGGCCGGGAAAG (SEQ ID NO: 1787) |
| 452 | PD-L1 responder | GGGCACCGCCGCCCTGACTTCCAACACATCGAAGAATGGGTGGGGCCTTGCACCTCATAC (SEQ ID NO: 1788) |
| 453 | PD-L1 responder | CCGCGCCCGCAGGGCCCGCCCCGCGCCGTCGAGGCTTTCAAGGGATCCAGGGTGGGGTGC (SEQ ID NO: 1789) |
| 454 | PD-L1 responder | CCGCGCCCGCAGGGCCCGCCCCGCGCCGTCGATGTGTTGGAAGTCAGGGCGGCGGTGCCC (SEQ ID NO: 1790) |
| 455 | PD-L1 responder | CCGCGCCCGCAGGGCCCGCCCCGCGCCGTCGAGAAGCATAAAGCAGGGACAGGTATGGAG (SEQ ID NO: 1791) |
| 456 | PD-L1 responder | GGGCACCGCCGCCCTGACTTCCAACACATCGAGAAGCATAAAGCAGGGACAGGTATGGAG (SEQ ID NO: 1792) |
| 457 | Non-Responder | AGTAGTGCAATCATAGCTCACTGAAACCTCGAAAGCTAATGAGGTATGAGGGGAGAATAC (SEQ ID NO: 1793) |
| 458 | PD-L1 responder | ATAAAATGGGGAGGCCTTCCAGAAGCTCTCGACCTCCAGGTCCCCCGCCACTTCCACGGC (SEQ ID NO: 1794) |

TABLE 13.i4-continued

| | Loop detected | Probe sequence 60 mer |
|---|---|---|
| 459 | PD-L1 responder | TATGAGTAATAATTACAATTTCCCCCTTTCGACCTCCAGGTCCCCCGCCACTTCCACGGC (SEQ ID NO: 1795) |
| 460 | PD-L1 responder | CCGCCTCACCTCCCGCATGGTCTTGAGGTCGAGCATGCAGCGCATCTGAGCAGTGAGGCT (SEQ ID NO: 1796) |

TABLE 13.i5

| | Probe Location | | | | 4 kb Sequence Location | | |
|---|---|---|---|---|---|---|---|
| | Chr | Start1 | End1 | Start2 | End2 | Chr | Start1 | End1 |
| 417 | 6 | 31878016 | 31878045 | 31928791 | 31928820 | 6 | 31878016 | 31882015 |
| 418 | 6 | 31901143 | 31901172 | 31978950 | 31978979 | 6 | 31897173 | 31901172 |
| 419 | 6 | 31923200 | 31923229 | 31940368 | 31940397 | 6 | 31919230 | 31923229 |
| 420 | 6 | 31923200 | 31923229 | 31947006 | 31947035 | 6 | 31919230 | 31923229 |
| 421 | 6 | 31928791 | 31928820 | 31947006 | 31947035 | 6 | 31924821 | 31928820 |
| 422 | 6 | 31928791 | 31928820 | 31978950 | 31978979 | 6 | 31924821 | 31928820 |
| 423 | 1 | 56841210 | 56841239 | 56908075 | 56908104 | 1 | 56841210 | 56845209 |
| 424 | 3 | 105675652 | 105675681 | 105723411 | 105723440 | 3 | 105671682 | 105675681 |
| 425 | 3 | 105671315 | 105671344 | 105818200 | 105818229 | 3 | 105671315 | 105675314 |
| 426 | 3 | 105675652 | 105675681 | 105828793 | 105828822 | 3 | 105671682 | 105675681 |
| 427 | 3 | 105723411 | 105723440 | 105752235 | 105752264 | 3 | 105723411 | 105727410 |
| 428 | 3 | 105723411 | 105723440 | 105795346 | 105795375 | 3 | 105723411 | 105727410 |
| 429 | 3 | 105723411 | 105723440 | 105818200 | 105818229 | 3 | 105723411 | 105727410 |
| 430 | 3 | 105752235 | 105752264 | 105818200 | 105818229 | 3 | 105748265 | 105752264 |
| 431 | 3 | 105803937 | 105803966 | 105884627 | 105884656 | 3 | 105803937 | 105807936 |
| 432 | 3 | 105887817 | 105887846 | 105916699 | 105916728 | 3 | 105887817 | 105891816 |
| 433 | 5 | 68194359 | 68194388 | 68215410 | 68215439 | 5 | 68190389 | 68194388 |
| 434 | 5 | 68195469 | 68195498 | 68215410 | 68215439 | 5 | 68195469 | 68199468 |
| 435 | 5 | 68215410 | 68215439 | 68277740 | 68277769 | 5 | 68215410 | 68219409 |
| 436 | 22 | 44666471 | 44666500 | 44701859 | 44701888 | 22 | 44662501 | 44666500 |
| 437 | 1 | 198646662 | 198646691 | 198666127 | 198666156 | 1 | 198646662 | 198650661 |
| 438 | 1 | 198666127 | 198666156 | 198775797 | 198775826 | 1 | 198662157 | 198666156 |
| 439 | 17 | 80643708 | 80643737 | 80661868 | 80661897 | 17 | 80639738 | 80643737 |
| 440 | 17 | 80636056 | 80636085 | 80661868 | 80661897 | 17 | 80636056 | 80640055 |
| 441 | 17 | 80643708 | 80643737 | 80796046 | 80796075 | 17 | 80639738 | 80643737 |
| 442 | 7 | 155794440 | 155794469 | 155842906 | 155842935 | 7 | 155794440 | 155798439 |
| 443 | 7 | 155810095 | 155810124 | 155829183 | 155829212 | 7 | 155806125 | 155810124 |
| 444 | 16 | 29613904 | 29613933 | 29632052 | 29632081 | 16 | 29613904 | 29617903 |
| 445 | 16 | 29613904 | 29613933 | 29687200 | 29687229 | 16 | 29613904 | 29617903 |
| 446 | 17 | 40406430 | 40406459 | 40464294 | 40464323 | 17 | 40402460 | 40406459 |
| 447 | 9 | 90822199 | 90822228 | 90852643 | 90852672 | 9 | 90818229 | 90822228 |
| 448 | 9 | 90822199 | 90822228 | 90872966 | 90872995 | 9 | 90818229 | 90822228 |
| 449 | 18 | 62317997 | 62318026 | 62393569 | 62393598 | 18 | 62317997 | 62321996 |
| 450 | 22 | 41906817 | 41906846 | 41946565 | 41946594 | 22 | 41902847 | 41906846 |
| 451 | 12 | 6362114 | 6362143 | 6384034 | 6384063 | 12 | 6358144 | 6362143 |
| 452 | 1 | 6450603 | 6450632 | 6498019 | 6498048 | 1 | 6450603 | 6454602 |
| 453 | 1 | 6466178 | 6466207 | 6484219 | 6484248 | 1 | 6462208 | 6466207 |
| 454 | 1 | 6466178 | 6466207 | 6498019 | 6498048 | 1 | 6462208 | 6466207 |
| 455 | 1 | 6466178 | 6466207 | 6514024 | 6514053 | 1 | 6462208 | 6466207 |
| 456 | 1 | 6498019 | 6498048 | 6514024 | 6514053 | 1 | 6494049 | 6498048 |
| 457 | 9 | 114957908 | 114957937 | 114977717 | 114977746 | 9 | 114957908 | 114961907 |
| 458 | 9 | 120893291 | 120893320 | 120913546 | 120913575 | 9 | 120889321 | 120893320 |
| 459 | 9 | 120913546 | 120913575 | 120940439 | 120940468 | 9 | 120913546 | 120917545 |
| 460 | 9 | 136904007 | 136904036 | 136941334 | 136941363 | 9 | 136904007 | 136908006 |

TABLE 13.i6

| | 4 kb Sequence Location | | Inner_primers | | |
|---|---|---|---|---|---|
| | Start2 | End2 | PCR-Primer1_ID | PCR_Primer1 | PCR-Primer2_ID |
| 417 | 31924821 | 31928820 | OBD117.1.877 | CCCAGGTGTTATCCATCCAG (SEQ ID NO: 1797) | OBD117.1.879 |
| 418 | 31978950 | 31982949 | OBD117.1.637 | AGCAGGAACTGGTCCCGCAGGAA (SEQ ID NO: 1798) | OBD117.1.639 |
| 419 | 31940368 | 31944367 | OBD117.1.657 | AGCCAAGGTCGCCCTCATCTGGT (SEQ ID NO: 1799) | OBD117.1.659 |

TABLE 13.i6-continued

| | 4 kb Sequence Location | | Inner_primers | | |
|---|---|---|---|---|---|
| | Start2 | End2 | PCR-Primer1_ID | PCR_Primer1 | PCR-Primer2_ID |
| 420 | 31943036 | 31947035 | OBD117.1.565 | AGCCAAGGTCGCCCTCATCTGGT (SEQ ID NO: 1800) | OBD117.1.567 |
| 421 | 31943036 | 31947035 | OBD117.1.629 | TGTCCAGCCCCTGTCTCCTTTGA (SEQ ID NO: 1801) | OBD117.1.631 |
| 422 | 31978950 | 31982949 | OBD117.1.633 | GTCCAGCCCCTGTCTCCTTTGAG (SEQ ID NO: 1802) | OBD117.1.635 |
| 423 | 56904105 | 56908104 | OBD117.1.1685 | CTTGGCACAGAACAGGAGCACCA (SEQ ID NO: 1803) | OBD117.1.1687 |
| 424 | 105723411 | 105727410 | OBD117.1.1297 | GCAAAACAATACTCAAATGCTCAT (SEQ ID NO: 1804) | OBD117.1.1299 |
| 425 | 105814230 | 105818229 | OBD117.1.1537 | ATGATGATGAAACTTGCTTCCTGGA (SEQ ID NO: 1805) | OBD117.1.1539 |
| 426 | 105828793 | 105832792 | OBD117.1.1353 | GCAAAACAATACTCAAATGCTCAT (SEQ ID NO: 1806) | OBD117.1.1355 |
| 427 | 105748265 | 105752264 | OBD117.1.1477 | TTCTGCCACAACCCTGATGTTTTCTG (SEQ ID NO: 1807) | OBD117.1.1479 |
| 428 | 105795346 | 105799345 | OBD117.1.1689 | TAATGGTTGAAATGTGAGTCTGAAT (SEQ ID NO: 1808) | OBD117.1.1691 |
| 429 | 105814230 | 105818229 | OBD117.1.1601 | ATGAAAACTTATCCCAAAGAAACTTC (SEQ ID NO: 1809) | OBD117.1.1603 |
| 430 | 105814230 | 105818229 | OBD117.1.1125 | TTTCTGCCACAACCCTGATGTTTTCT (SEQ ID NO: 1810) | OBD117.1.1127 |
| 431 | 105880657 | 105884656 | OBD117.1.205 | CACCTATTGCCTGGAGCATAAAGGGA (SEQ ID NO: 1811) | OBD117.1.207 |
| 432 | 105912729 | 105916728 | OBD117.1.1369 | ATCACTTTGGGTAGTATGACCTTTT (SEQ ID NO: 1812) | OBD117.1.1371 |
| 433 | 68215410 | 68219409 | OBD117.1.853 | CACCATTGTATGGGGAATGAC (SEQ ID NO: 1813) | OBD117.1.855 |
| 434 | 68215410 | 68219409 | OBD117.1.849 | AAGCCAAACTTGCTAGCATCC (SEQ ID NO: 1814) | OBD117.1.851 |
| 435 | 68273770 | 68277769 | OBD117.1.857 | GAACGTCGGCCTACCTAGTG (SEQ ID NO: 1815) | OBD117.1.859 |
| 436 | 44697889 | 44701888 | OBD117.1.249 | TTACACTCCTGGGCACTCTTCCC (SEQ ID NO: 1816) | OBD117.1.251 |
| 437 | 198662157 | 198666156 | OBD117.1.1437 | GGAGAATCACTTGAGCCTAAGAGTTC (SEQ ID NO: 1817) | OBD117.1.1439 |
| 438 | 198771827 | 198775826 | OBD117.1.1245 | CCAGCAAAGGGCAGGTCATCATC (SEQ ID NO: 1818) | OBD117.1.1247 |
| 439 | 80661868 | 80665867 | OBD117.1.097 | ATAAGGAGAAACTGTGGAAGAGAGGC (SEQ ID NO: 1819) | OBD117.1.099 |
| 440 | 80661868 | 80665867 | OBD117.1.865 | CATGAGGTACACGGCATCAC (SEQ ID NO: 1820) | OBD117.1.867 |
| 441 | 80792076 | 80796075 | OBD117.1.093 | ATAAGGAGAAACTGTGGAAGAGAGGC (SEQ ID NO: 1821) | OBD117.1.095 |
| 442 | 155838936 | 155842935 | OBD117.1.873 | ACTTCATGGAAGGGTGGTCA (SEQ ID NO: 1822) | OBD117.1.875 |
| 443 | 155829183 | 155833182 | OBD117.1.1073 | GCGCTGCTGTTAGCTCCTG (SEQ ID NO: 1823) | OBD117.1.1075 |
| 444 | 29628082 | 29632081 | OBD117.1.1001 | CCTCATCCGTCCGCACATCT (SEQ ID NO: 1824) | OBD117.1.1003 |

TABLE 13.i6-continued

| | 4 kb Sequence Location | | Inner_primers | | |
|---|---|---|---|---|---|
| | Start2 | End2 | PCR-Primer1_ID | PCR_Primer1 | PCR-Primer2_ID |
| 445 | 29683230 | 29687229 | OBD117.1.1009 | ATGCTGTTGCAGGACTGTGC (SEQ ID NO: 1825) | OBD117.1.1011 |
| 446 | 40464294 | 40468293 | OBD117.009 | TCTACAGCCCAAGATCCTGCTTT (SEQ. ID NO: 1826) | OBD117.011 |
| 447 | 90852643 | 90856642 | OBD117.1.1213 | CCCCTGAGAAGCGATGGGCTACT (SEQ ID NO: 1827) | OBD117.1.1215 |
| 448 | 90872966 | 90876965 | OBD117.1.1273 | CCCCTGAGAAGCGATGGGCTACT (SEQ ID NO: 1828) | OBD117.1.1275 |
| 449 | 62389599 | 62393598 | OBD117.1.1793 | CCCGAACCAGCCTTCCCAAGAGC (SEQ ID NO: 1829) | OBD117.1.1795 |
| 450 | 41946565 | 41950564 | OBD117.1.997 | CAGAGGGTTGCCTATGGTGG (SEQ ID NO: 1830) | OBD117.1.999 |
| 451 | 6380064 | 6384063 | OBD117.1.1005 | AGGAGACCTGGTTGAAGCGG (SEQ ID NO: 1831) | OBD117.1.1007 |
| 452 | 6494049 | 6498048 | OBD117.1.421 | AATAACCTGTGCCCAGACCGAGC (SEQ ID NO: 1832) | OBD117.1.423 |
| 453 | 6480249 | 6484248 | OBD117.1.241 | AGCCTCCTGCGTCTCAACTCACC (SEQ ID NO: 1833) | OBD117.1.243 |
| 454 | 6494049 | 6498048 | OBD117.1.029 | AGCCTCCTGCGTCTCAACTCACC (SEQ ID NO: 1834) | OBD117.1.031 |
| 455 | 6514024 | 6518023 | OBD117.1.845 | CTAGCCTCCTGCGTCTCAAC (SEQ ID NO: 1835) | OBD117.1.847 |
| 456 | 6514024 | 6518023 | OBD117.1.861 | GCTCTTGCTGCATGTCCTCT (SEQ ID NO: 1836) | OBD117.1.863 |
| 457 | 114973747 | 114977746 | OBD117.1.917 | TTGCTTGTGAGTTTGATGCAG (SEQ ID NO: 1837) | OBD117.1.919 |
| 458 | 120913546 | 120917545 | OBD117.1.361 | GACGCTCTCCCTTTGCTCAAGCC (SEQ ID NO: 1838) | OBD117.1.363 |
| 459 | 120936469 | 120940468 | OBD117.1.333 | GCTGTGTATCTCAGGGCACTCAG (SEQ ID NO: 1839) | OBD117.1.335 |
| 460 | 136937364 | 136941363 | OBD117.1.869 | TGAAGAAGCACTCGTCGTTG (SEQ ID NO: 1840) | OBD117.1.871 |

TABLE 13.i7

| | Inner_primers | |
|---|---|---|
| | PCR_Primer2 | GLMNET |
| 417 | GTTCCTGTGAAGGGTGAAGC (SEQ ID NO: 1841) | 0.015890823 |
| 418 | CTCTGGTCCTGTAGTCCTCAGTG (SEQ ID NO: 1842) | 0.000171766 |
| 419 | CTCCCTGTCTGAGCATCTCTCTC (SEQ ID NO: 1843) | −0.007266336 |
| 420 | AGGAGGGATACACCTAAGGCAGC (SEQ ID NO: 1844) | 0.013024 |
| 421 | GGAGGGATACACCTAAGGCAGCC (SEQ ID NO: 1845) | −0.000108617 |
| 422 | CTCTGGTCCTGTAGTCCTCAGTG (SEQ ID NO: 1846) | 0 |

TABLE 13.i7-continued

Inner_primers

| | PCR_Primer2 | GLMNET |
|---|---|---|
| 423 | TCCTGCCTCAGCCTCCCAAGTAG (SEQ ID NO: 1847) | 0 |
| 424 | TAATGGTTGAAATGTGAGTCTGAAT (SEQ ID NO: 1848) | 0 |
| 425 | GGTGCTATGTTTGATTTAGGAGGTAT (SEQ ID NO: 1849) | 0 |
| 426 | TCCTTTGACCTTTCTGGACTCAG (SEQ ID NO: 1850) | 0 |
| 427 | GTGGAGAATGTAGTATTATGAAGGTT (SEQ ID NO: 1851) | 0 |
| 428 | AGTTTTGACAGAAAGTAGAGGTTCCT (SEQ ID NO: 1852) | 0 |
| 429 | GTGGAGAATGTAGTATTATGAAGGTT (SEQ ID NO: 1853) | 0 |
| 430 | ATGAAAACTTATCCCAAAGAAACTTC (SEQ ID NO: 1854) | 0 |
| 431 | GCCTAAGAGAAAAGCACACAGACTCC (SEQ ID NO: 1855) | 0.00674446 |
| 432 | GGACAGGAATCCATAGGGAAGAAGT (SEQ ID NO: 1856) | 0 |
| 433 | GAGTGCTCTGGCTCTACACG (SEQ ID NO: 1857) | 0.0001037 |
| 434 | TGCTCTGGCTCTACACGTC (SEQ ID NO: 1858) | 0.000117852 |
| 435 | AGTGCTCTGGCTCTACACGTC (SEQ ID NO: 1859) | 0.000136129 |
| 436 | AGCAAATCCTCCAGGCAGCCAGG (SEQ ID NO: 1860) | −0.013597927 |
| 437 | GATGATTTGACACTTTCCCCACACAC (SEQ ID NO: 1861) | 0 |
| 438 | GCAGGAACTGGTGCTGGAATAGGC (SEQ ID NO: 1862) | 0 |
| 439 | GCAGGAGGATACAACTGTCAAAACTC (SEQ ID NO: 1863) | 0.004679577 |
| 440 | GCATCTAAAAATCGCCTGGA (SEQ ID NO: 1864) | −0.006781145 |
| 441 | CTGTAGTTCTGTAAGCGTCTCCCACG (SEQ ID NO: 1865) | −0.013087312 |
| 442 | ATCCCATCCAAGGCATCATA (SEQ ID NO: 1866) | −0.010277817 |
| 443 | CCATTGTGCACATACACTGC (SEQ ID NO: 1867) | 0 |
| 444 | CTCCCAGGCTTGACGAGAGG (SEQ ID NO: 1868) | −0.000111539 |
| 445 | CTCCCAGGCTTGACGAGAGG (SEQ ID NO: 1869) | 0.021717076 |
| 446 | CCCCGAGGGTTGAGAAGCAT (SEQ ID NO: 1870) | 0.000094 |
| 447 | GGGCAGGGACTAAGGTCTGACTT (SEQ ID NO: 1871) | 0 |

TABLE 13.i7-continued

| | Inner_primers | |
|---|---|---|
| | PCR_Primer2 | GLMNET |
| 448 | CCGCCACTCAGCCATTGTTTCCA (SEQ ID NO: 1872) | 0 |
| 449 | GGGTTCTTGTCCTCCTTATGGAT (SEQ ID NO: 1873) | 0 |
| 450 | GTAGTAGAGAGTGCGGTGCC (SEQ ID NO: 1874) | 0 |
| 451 | ATCGGGCTTCCGAAGAAGGG (SEQ ID NO: 1875) | 0.000108061 |
| 452 | GGGAAAATCGGTGTGGCTGGCTC (SEQ ID NO: 1876) | −0.009810191 |
| 453 | ATACGGACTGAGCCCTATGACGC (SEQ ID NO: 1877) | −0.020246781 |
| 454 | AATAACCTGTGCCCAGACCGAGC (SEQ ID NO: 1878) | 0.016525715 |
| 455 | GCTGAGACTGTAGACGTGAACC (SEQ ID NO: 1879) | 0.005356938 |
| 456 | AGACGTGAACCTCCATACCTG (SEQ ID NO: 1880) | 0.000119941 |
| 457 | AAGCCAAATGGGCCTAGCCA (SEQ ID NO: 1881) | 0.012278549 |
| 458 | TGGAGCAGAACCTGTCAGACCTG (SEQ ID NO: 1882) | 0.011703991 |
| 459 | CCTGGAGCAGAACCTGTCAGACC (SEQ ID NO: 1883) | −0.01117453 |
| 460 | AGCGGCACACCTCTACTCTC (SEQ ID NO: 1884) | −0.018227673 |

TABLE 14.A

| Gene | Marker | GLMNET |
|---|---|---|
| AKT1 | OBD117.1.833.835 | 0.000126471 |
| BAD | OBD117.1.265.267 | 0 |
| BAX | OBD117.1.781.783 | −0.0000963 |
| BBC3 | OBD117.1.405.407 | −0.012797314 |
| BID | OBD117.1.277.279 | −0.001049357 |
| BOK | OBD117.1.737.739 | 0.000120571 |
| C8A | OBD117.1.817.819 | −0.003603391 |
| C8A | OBD117.1.1573.1575 | 0 |
| C8B | OBD117.1.321.323 | −0.002344366 |
| CASP6 | OBD117.1.821.823 | −0.015124118 |
| CASP9 | OBD117.1.121.123 | 0.003583466 |
| CBLB | OBD117.1.1453.1455 | 0 |
| CD14 | OBD117.1.797.799 | 0.000119448 |
| CD2 | OBD117.1.009.011 | 0.007257883 |
| CD4 | OBD117.1.769.771 | −0.007336559 |
| CD6 | OBD117.1.345.347 | 0.013413486 |
| CD6 | OBD117.1.373.375 | −0.020821569 |
| CD6 | OBD117.1.337.339 | 0.017522073 |
| CD6 | OBD117.1.329.331 | 0.000137163 |
| CD6 | OBD117.1.085.087 | −0.009581325 |
| CD6 | OBD117.1.293.295 | −0.003930475 |
| CD82 | OBD117.1.393.395 | −0.013038403 |
| CD82 | OBD117.1.741.743 | −0.009743329 |
| CD82 | OBD117.1.025.027 | −0.015977346 |
| CFP | OBD117.1.941.943 | 0 |
| CRADD | OBD117.1.109.111 | −0.00783453 |
| EGF | OBD117.1.117.119 | 0.01716512 |
| ELK1 | OBD117.1.429.431 | 0 |
| FAS | OBD117.1.133.135 | −0.016360123 |
| FAS | OBD117.1.409.411 | −0.006985618 |
| FCGR2B | OBD117.1.713.715 | −0.00011137 |
| HLA-DQA1 | OBD117.1.385.387 | 0.001576194 |
| ICOSLG | OBD117.1.353.355 | −0.010502797 |
| IGF1R | OBD117.1.777.779 | −0.008978891 |
| IGF2 | OBD117.1.801.803 | 0.00011913 |
| IKBKB | OBD117.1.825.827 | 0.000123838 |
| IKBKB | OBD117.1.201.203 | −0.003994085 |
| IKBKB | OBD117.1.417.419 | −0.023515041 |
| IKBKB | OBD117.1.753.755 | 0.01434467 |
| IKBKB | OBD117.1.077.079 | −0.001425541 |
| IKBKB | OBD117.1.261.263 | 0.01710902 |
| IL17D | OBD117.1.645.647 | −0.0134076 |
| IL17RA | OBD117.1.537.539 | 0 |
| IRF1 | OBD117.1.805.807 | 0.006327654 |
| IRF1 | OBD117.1.785.787 | 0.000121603 |
| IRF1 | OBD117.1.837.839 | 0.000116599 |
| IRF2 | OBD117.1.1077.1079 | 0 |

TABLE 14.B

| Gene | Marker | GLMNET |
|---|---|---|
| IRF3 | OBD117.1.197.199 | 0.018616515 |
| ITGAM | OBD117.1.789.791 | −0.01814247 |
| ITGAM | OBD117.1.309.311 | −0.010425 |
| ITGAM | OBD117.1.937.939 | 0 |
| ITGAX | OBD117.1.369.371 | 0.00590703 |
| ITK | OBD117.1.269.271 | 0.013514368 |

TABLE 14.B-continued

| Gene | Marker | GLMNET |
|---|---|---|
| ITK | OBD117.1.397.399 | −0.009002897 |
| ITK | OBD117.1.773.775 | 0.000108207 |
| ITK | OBD117.1.001.003 | −0.006474726 |
| ITK | OBD117.1.041.043 | −0.021298663 |
| LYN | OBD117.1.809.811 | −0.024082323 |
| MAPKAP1 | OBD117.1.257.529 | 0.017680421 |
| MTOR | OBD117.1.793.795 | 0.01727269 |
| MYC | OBD117.1.377.379 | −0.006220015 |
| MYC | OBD117.1.045.047 | −0.010058174 |
| NCK2 | OBD117.1.813.815 | 0.000127348 |
| NFKBIE | OBD117.1.049.051 | −0.009744914 |
| NFKBIE | OBD117.1.1069.1071 | 0 |
| ORF102 | OBD117.1.893.895 | 0.008460581 |
| CCL18 | OBD117.1.389.391 | −0.011403512 |
| ORF107 | OBD117.1.1045.1047 | 0 |
| CCR6 | OBD117.1.185.187 | 0.005137905 |
| ORF110 | OBD117.1.953.955 | −0.007948899 |
| CD180 | OBD117.1.313.315 | 0.000116162 |
| CD19 | OBD117.1.125.127 | −0.011725271 |
| ORF116 | OBD117.1.1293.1295 | 0 |
| ORF117 | OBD117.1.433.435 | 0 |
| ORF118 | OBD117.1.1221.1223 | 0 |
| ORF120 | OBD117.1.577.579 | 0.001022887 |
| ORF120 | OBD117.1.625.627 | −0.005572532 |
| ORF128 | OBD117.1.913.915 | 0.000119295 |
| CD6 | OBD117.1.089.091 | 0 |
| CD6 | OBD117.1.237.139 | 0.00011596 |
| CD6 | OBD117.1.153.155 | −0.014829951 |
| ORF136 | OBD117.1.1865.1867 | 0 |
| ORF136 | OBD117.1.1501.1503 | 0 |
| CD86 | OBD117.1.253.255 | −0.001718735 |
| ORF139 | OBD117.1.1305.1307 | 0 |
| ORF140 | OBD117.1.1193.1195 | 0 |
| ORF140 | OBD117.1.1117.1119 | 0 |
| ORF140 | OBD117.1.1517.1519 | 0 |
| ORF140 | OBD117.1.1533.1535 | 0 |
| ORF140 | OBD117.1.1393.1395 | 0 |
| ORF142 | OBD117.1.957.959 | 0.009388509 |
| ORF142 | OBD117.1.501.503 | 0 |
| ORF142 | OBD117.1.473.475 | 0 |
| ORF145 | OBD117.1.1597.1599 | 0 |
| ORF146 | OBD117.1.1641.1643 | 0 |
| ORF147 | OBD117.1.1633.1635 | 0 |
| ORF149 | OBD117.1.481.483 | 0 |
| ORF149 | OBD117.1.453.455 | 0 |
| ORF149 | OBD117.1.493.495 | 0 |
| ORF149 | OBD117.1.509.511 | 0 |
| ORF149 | OBD117.1.529.531 | 0 |

TABLE 14.C

| Gene | Marker | GLMNET |
|---|---|---|
| ORF149 | OBD117.1.973.975 | 0 |
| ORF149 | OBD117.1.441.443 | −0.017184561 |
| ORF149 | OBD117.1.469.471 | 0.001327318 |
| ORF149 | OBD117.1.437.439 | 0 |
| ORF149 | OBD117.1.513.515 | 0 |
| ORF149 | OBD117.1.489.491 | 0 |
| ORF157 | OBD117.1.1521.1523 | 0 |
| ORF159 | OBD117.1.1549.1551 | 0 |
| ORF159 | OBD117.1.1169.1171 | 0 |
| ORF159 | OBD117.1.1253.1255 | 0 |
| ORF159 | OBD117.1.1329.1331 | 0 |
| ORF16 | OBD117.1.1309.1311 | 0 |
| ORF160 | OBD117.1.1025.1027 | 0 |
| ORF160 | OBD117.1.609.611 | 0.011827837 |
| ORF160 | OBD117.1.701.703 | 0.00010841 |
| CRADD | OBD117.1.213.215 | 0.012057101 |
| CSF2 | OBD117.1.225.227 | 0.002120736 |
| ORF171 | OBD117.1.1209.1211 | 0 |
| ORF171 | OBD117.1.1121.1221 | 0 |
| ORF175 | OBD117.1.605.607 | −0.005375017 |
| ORF179 | OBD117.1.1673.1675 | 0 |
| ORF185 | OBD117.1.909.911 | 0.019526388 |

TABLE 14.C-continued

| Gene | Marker | GLMNET |
|---|---|---|
| ORF188 | OBD117.1.1241.1243 | 0 |
| ORF189 | OBD117.1.1409.1411 | 0 |
| ORF190 | OBD117.1.1805.807 | 0 |
| ORF190 | OBD117.1.1781.1783 | 0 |
| ORF190 | OBD117.1.1769.1771 | 0 |
| ORF193 | OBD117.1.1413.1415 | 0 |
| ORF195 | OBD117.1.1817.1819 | 0 |
| ORF195 | OBD117.1.1097.1099 | 0 |
| ORF197 | OBD117.1.661.663 | 0.027392782 |
| ORF197 | OBD117.1.613.615 | 0.0000923 |
| ORF20 | OBD117.1.1593.1595 | 0 |
| ORF20 | OBD117.1.1265.1267 | 0 |
| ORF202 | OBD117.1.497.499 | 0 |
| ORF205 | OBD117.1.1373.1375 | 0 |
| ORF206 | OBD117.1.1561.1563 | 0 |
| EGF | OBD117.1.149.151 | −0.013629912 |
| ORF211 | OBD117.1.1425.1427 | 0 |
| ORF211 | OBD117.1.1433.1435 | 0 |
| ORF212 | OBD117.1.521.523 | 0 |
| ORF213 | OBD117.1.1669.1671 | 0 |
| ORF214 | OBD117.1.1145.1147 | 0 |
| ORF214 | OBD117.1.1105.1107 | 0 |
| ENDOU | OBD117.1.325.327 | 0 |
| ORF224 | OBD117.1.1261.1263 | 0 |
| F3 | OBD117.1.113.115 | 0.006221331 |
| ORF229 | OBD117.1.1553.1555 | 0 |
| ORF229 | OBD117.1.1365.1367 | 0 |
| ORF229 | OBD117.1.1629.1631 | 0 |
| ORF233 | OBD117.1.1321.1323 | 0 |
| ORF240 | OBD117.1.1557.1559 | 0 |
| FAS | OBD117.1.305.307 | 0.011677917 |
| ORF243 | OBD117.1.649.651 | −0.003930014 |

TABLE 14.D

| Gene | Marker | GLMNET |
|---|---|---|
| ORF243 | OBD117.1.717.719 | −0.023642297 |
| ORF243 | OBD117.1.901.903 | 0.007197773 |
| ORF243 | OBD117.1.905.907 | −0.014372166 |
| ORF243 | OBD117.1.573.575 | −0.000142339 |
| ORF243 | OBD117.1.897.899 | 0.009781389 |
| ORF249 | OBD117.1.1317.1319 | 0 |
| ORF249 | OBD117.1.1529.1531 | 0 |
| ORF25 | OBD117.1.1445.1447 | 0 |
| ORF25 | OBD117.1.1165.1167 | 0 |
| ORF252 | OBD117.1.1201.1203 | 0 |
| ORF257 | OBD117.1.1401.1403 | 0 |
| GAB2 | OBD117.1.141.143 | −0.007419107 |
| ORF263 | OBD117.1.1325.1327 | 0 |
| ORF264 | OBD117.1.1333.1335 | 0 |
| ORF264 | OBD117.1.1833.1835 | 0 |
| ORF264 | OBD117.1.1785.1787 | 0 |
| ORF264 | OBD117.1.1377.1379 | 0 |
| ORF264 | OBD117.1.1741.1743 | 0 |
| ORF264 | OBD117.1.1141.1143 | 0 |
| ORF264 | OBD117.1.1841.1843 | 0 |
| ORF264 | OBD117.1.1845.1847 | 0 |
| ORF272 | OBD117.1.1225.1227 | 0 |
| ORF276 | OBD117.1.1061.1063 | 0 |
| ORF285 | OBD117.1.923.925 | 0.000121346 |
| ORF290 | OBD117.1.1777.1779 | 0 |
| ORF290 | OBD117.1.1101.1103 | 0 |
| HLA-DQA1 | OBD117.1.401.403 | 0.009992562 |
| HLA-DQA1 | OBD117.1.721.723 | 0.00011425 |
| HLA-DQA1 | OBD117.1.413.415 | 0.002234049 |
| HLA-DQA1 | OBD117.1.425.427 | 0.0000993 |
| ORF30 | OBD117.1.1749.1751 | 0 |
| IGF1R | OBD117.1.209.211 | 0.012827643 |
| IGF1R | OBD117.1.317.319 | −0.010330599 |
| IGF1R | OBD117.1.101.103 | 0.0000979 |
| IKBKB | OBD117.1.757.759 | 0.00012094 |
| IKBKB | OBD117.1.281.283 | −0.00399849 |
| IKBKB | OBD117.1.037.039 | 0.002891486 |
| IKBKB | OBD117.1.073.075 | 0.017565968 |

TABLE 14.D-continued

| Gene | Marker | GLMNET |
|---|---|---|
| ORF313 | OBD117.1.693.695 | −0.022219432 |
| ORF313 | OBD117.1.929.931 | −0.015662127 |
| ORF313 | OBD117.1.665.667 | 0.000119444 |
| ORF313 | OBD117.1.581.583 | −0.027382095 |
| ORF316 | OBD117.1.1041.1043 | 0 |
| ORF316 | OBD117.1.485.487 | 0 |
| IL25 | OBD117.1.289.291 | 0.007589853 |
| ORF319 | OBD117.1.1017.1019 | 0 |
| ORF325 | OBD117.1.881.883 | 0.000113252 |
| ORF325 | OBD117.1.1129.1131 | 0 |
| ORF325 | OBD117.1.653.655 | 0.003005705 |
| IRF1 | OBD117.1.765.767 | −0.010031296 |
| IRF3 | OBD117.1.285.287 | −0.025409945 |
| ITGAX | OBD117.1.177.179 | 0.006986068 |
| ITGAX | OBD117.1.173.175 | 0.004807037 |
| ITK | OBD117.1.165.167 | −0.004038003 |

TABLE 14.E

| Gene | Marker | GLMNET |
|---|---|---|
| ORF344 | OBD117.1.585.587 | 0.000108113 |
| ORF344 | OBD117.1.593.595 | −0.012488304 |
| ORF346 | OBD117.1.1717.1719 | 0 |
| ORF346 | OBD117.1.1617.1919 | 0 |
| ORF348 | OBD117.1.1289.1291 | 0 |
| ORF348 | OBD117.1.1605.1607 | 0 |
| ORF362 | OBD117.1.1513.1515 | 0 |
| ORF362 | OBD117.1.1469.1471 | 0 |
| ORF368 | OBD117.1.1337.1339 | 0 |
| ORF369 | OBD117.1.925.927 | 0.015771071 |
| ORF375 | OBD117.1.1397.1399 | 0 |
| ORF38 | OBD117.1.1113.1115 | 0 |
| ARHGEF7 | OBD117.1.157.159 | −0.008898153 |
| ORF38 | OBD117.1.1457.1459 | 0 |
| ARHGEF7 | OBD117.1.725.727 | 0.00011344 |
| ORF380 | OBD117.1.1849.1851 | 0 |
| ORF380 | OBD117.1.1829.1831 | 0 |
| ORF382 | OBD117.1.1421.1423 | 0 |
| ORF385 | OBD117.1.977.979 | 0 |
| ORF385 | OBD117.1.965.967 | −0.006509693 |
| ORF39 | OBD117.1.1821.1823 | 0 |
| ORF39 | OBD117.1.1857.1859 | 0 |
| ORF390 | OBD117.1.1301.1303 | 0 |
| ORF393 | OBD117.1.1229.1231 | 0 |
| ORF396 | OBD117.1.477.479 | 0.011140328 |
| ORF396 | OBD117.1.553.555 | 0 |
| ORF400 | OBD117.1.1177.1179 | 0 |
| MAPK10 | OBD117.1.221.223 | −0.009554407 |
| MAPKAP1 | OBD117.1.033.035 | −0.010767501 |
| ORF404 | OBD117.1.1133.1135 | 0 |
| ORF404 | OBD117.1.1285.1287 | 0 |
| ORF408 | OBD117.1.1693.1695 | 0 |
| ORF41 | OBD117.1.1581.1583 | 0 |
| ORF41 | OBD117.1.1637.1639 | 0 |
| ORF415 | OBD117.1.1713.1715 | 0 |
| ORF415 | OBD117.1.1205.1207 | 0 |
| ORF420 | OBD117.1.1729.1731 | 0 |
| ORF430 | OBD117.1.1429.1431 | 0 |
| ORF430 | OBD117.1.1089.1091 | 0 |
| ORF430 | OBD117.1.1589.1591 | 0 |
| ORF430 | OBD117.1.1493.1495 | 0 |
| ORF430 | OBD117.1.1661.1663 | 0 |
| ORF430 | OBD117.1.1081.1083 | 0 |
| ORF430 | OBD117.1.1085.1087 | 0 |
| ORF430 | OBD117.1.1509.1511 | 0 |
| ORF430 | OBD117.1.1489.1491 | 0 |
| ORF433 | OBD117.1.1053.1055 | 0 |
| ORF439 | OBD117.1.1697.1699 | 0 |
| ORF440 | OBD117.1.1149.1151 | 0 |
| ORF440 | OBD117.1.1505.1507 | 0 |
| PIK3R1 | OBD117.1.829.831 | 0.000114527 |
| ORF442 | OBD117.1.1417.1419 | 0 |

TABLE 14.E-continued

| Gene | Marker | GLMNET |
|---|---|---|
| ORF442 | OBD117.1.1677.1679 | 0 |
| ORF447 | OBD117.1.1021.1023 | 0 |

TABLE 14.F

| Gene | Marker | GLMNET |
|---|---|---|
| ORF447 | OBD117.1.885.887 | 0.019910002 |
| NCK2 | OBD117.1.749.751 | 0.011140328 |
| PVRL1 | OBD117.1.057.059 | 0.002451894 |
| ORF457 | OBD117.1.1161.1163 | 0 |
| ORF457 | OBD117.1.1281.1283 | 0 |
| ORF457 | OBD117.1.1665.1667 | 0 |
| ORF458 | OBD117.1.1657.1659 | 0 |
| ORF458 | OBD117.1.1809.1811 | 0 |
| ORF460 | OBD117.1.1341.1343 | 0 |
| ORF462 | OBD117.1.1269.1271 | 0 |
| NFKBIE | OBD117.1.065.067 | 0.006729048 |
| NFKBIE | OBD117.1.1065.1067 | 0 |
| ORF465 | OBD117.1.1249.1251 | 0 |
| ORF472 | OBD117.1.641.643 | 0.000955334 |
| PAG1 | OBD117.1.081.083 | 0.0196745 |
| PAG1 | OBD117.1.145.147 | 0.012784814 |
| PAG1 | OBD117.1.129.131 | 0.000107394 |
| PAG1 | OBD117.1.105.107 | 0.011672595 |
| PAG1 | OBD117.1.217.219 | 0.006914365 |
| ORF48 | OBD117.1.709.711 | 0.000126022 |
| ORF48 | OBD117.1.705.707 | −0.002734128 |
| PAK1 | OBD117.1.297.299 | −0.020410863 |
| ORF481 | OBD117.1.1545.1547 | 0 |
| ORF482 | OBD117.1.669.671 | 0.022244309 |
| ORF489 | OBD117.1.1645.1647 | 0 |
| ORF494 | OBD117.1.1277.1279 | 0 |
| ORF500 | OBD117.1.1361.1363 | 0 |
| PIK3R1 | OBD117.1.069.071 | −0.007209703 |
| PIK3R1 | OBD117.1.735.737 | 0.000117929 |
| ORF505 | OBD117.1.569.571 | 0.000114434 |
| ORF510 | OBD117.1.1461.1463 | 0 |
| ORF510 | OBD117.1.1525.1527 | 0 |
| ORF510 | OBD117.1.1381.1383 | 0 |
| ORF510 | OBD117.1.1137.1139 | 0 |
| ORF514 | OBD117.1.561.563 | 0.010030034 |
| ORF518 | OBD117.1.1853.1855 | 0 |
| ORF52 | OBD117.1.1313.1315 | 0 |
| ORF520 | OBD117.1.1473.1475 | 0 |
| ORF520 | OBD117.1.1157.1159 | 0 |
| ORF527 | OBD117.1.1345.1347 | 0 |
| PRKCQ | OBD117.1.365.367 | 0.007672168 |
| PRR5 | OBD117.1.005.007 | 0.016924425 |
| ORF532 | OBD117.1.1565.1567 | 0 |
| ORF532 | OBD117.1.1217.1219 | 0 |
| ORF534 | OBD117.1.673.675 | 0.006586768 |
| PTK2 | OBD117.1.229.231 | −0.017032217 |
| PTK2 | OBD117.1.233.235 | 0.000119638 |
| PTK2 | OBD117.1.357.359 | −0.01499141 |
| PTPN11 | OBD117.1.761.763 | 0.00011938 |
| ORF541 | OBD117.1.1757.1759 | 0 |
| ORF541 | OBD117.1.1721.1723 | 0 |
| PTPRC | OBD117.1.189.191 | −0.020382337 |
| ORF544 | OBD117.1.1237.1239 | 0 |
| ORF544 | OBD117.1.1801.1803 | 0 |

TABLE 14.G

| Gene | Marker | GLMNET |
|---|---|---|
| ORF544 | OBD117.1.1173.1175 | 0 |
| ORF547 | OBD117.1.1541.1543 | 0 |
| ORF547 | OBD117.1.1737.1739 | 0 |
| BAD | OBD117.1.341.343 | 0.007677493 |
| BAD | OBD117.1.245.247 | 0.017957539 |
| ORF552 | OBD117.1.689.691 | 0 |
| RAC1 | OBD117.1.729.731 | −0.01057369 |

TABLE 14.G-continued

| Gene | Marker | GLMNET |
|---|---|---|
| ORF554 | OBD117.1.1761.1763 | 0 |
| ORF556 | OBD117.1.1869.1871 | 0 |
| ORF558 | OBD117.1.1837.1839 | 0 |
| ORF56 | OBD117.1.617.619 | 0 |
| ORF56 | OBD117.1.685.687 | −0.005472121 |
| ORF560 | OBD117.1.1357.1359 | 0 |
| ORF560 | OBD117.1.1577.1579 | 0 |
| ORF564 | OBD117.1.1709.1711 | 0 |
| RELA | OBD117.1.017.019 | 0.005732814 |
| ORF568 | OBD117.1.1185.1187 | 0 |
| ORF569 | OBD117.1.1613.1615 | 0 |
| ORF57 | OBD117.1.1653.1655 | 0 |
| ORF57 | OBD117.1.1681.1683 | 0 |
| ORF576 | OBD117.1.1813.1815 | 0 |
| ORF576 | OBD117.1.1765.1767 | 0 |
| ORF576 | OBD117.1.1825.1827 | 0 |
| ORF586 | OBD117.1.1153.1155 | 0 |
| ORF586 | OBD117.1.1585.1587 | 0 |
| ORF589 | OBD117.1.1349.1351 | 0 |
| ORF59 | OBD117.1.1609.1611 | 0 |
| ORF596 | OBD117.1.1109.1111 | 0 |
| ORF596 | OBD117.1.1789.1791 | 0 |
| ORF603 | OBD117.1.1197.1199 | 0 |
| ORF603 | OBD117.1.1705.1707 | 0 |
| ORF605 | OBD117.1.601.603 | −0.010880594 |
| ORF605 | OBD117.1.889.891 | −0.013055638 |
| ORF611 | OBD117.1.1441.1443 | 0 |
| SIRPA | OBD117.1.161.163 | −0.014311214 |
| ORF613 | OBD117.1.557.559 | 0 |
| ORF618 | OBD117.1.1181.1183 | 0 |
| ORF624 | OBD117.1.589.591 | −0.005626404 |
| ORF626 | OBD117.1.961.963 | −0.013176922 |
| ORF626 | OBD117.1.449.451 | −0.000113816 |
| ORF626 | OBD117.1.445.447 | −0.026223064 |
| ORF626 | OBD117.1.1033.1035 | 0 |
| ORF626 | OBD117.1.969.971 | 0 |
| ORF630 | OBD117.1.1497.1499 | 0 |
| SMAD3 | OBD117.1.061.063 | 0 |
| SPN | OBD117.1.945.947 | −0.016440702 |
| SPN | OBD117.1.985.987 | 0 |
| ORF642 | OBD117.1.989.991 | 0 |
| ORF642 | OBD117.1.1037.1039 | 0 |
| ORF657 | OBD117.1.1093.1095 | 0 |
| ORF657 | OBD117.1.1481.1483 | 0 |
| ORF657 | OBD117.1.1725.1727 | 0 |
| ORF667 | OBD117.1.1701.1703 | 0 |
| ORF670 | OBD117.1.1449.1451 | 0 |

TABLE 14.H

| Gene | Marker | GLMNET |
|---|---|---|
| ORF671 | OBD117.1.1485.1487 | 0 |
| ORF684 | OBD117.1.1189.1191 | 0 |
| ORF685 | OBD117.1.1389.1391 | 0 |
| ORF690 | OBD117.1.1797.1799 | 0 |
| ORF695 | OBD117.1.549.551 | 0.009721306 |
| ORF696 | OBD117.1.1029.1031 | 0 |
| ORF696 | OBD117.1.681.683 | 0.007305849 |
| ORF696 | OBD117.1.677.679 | 0.001120789 |
| ORF697 | OBD117.1.461.463 | −0.017294821 |
| ORF697 | OBD117.1.541.543 | 0.000113082 |
| ORF698 | OBD117.1.457.459 | 0.000110518 |
| ORF698 | OBD117.1.981.983 | 0 |
| ORF698 | OBD117.1.505.507 | 0.027764821 |
| ORF698 | OBD117.1.1625.1627 | 0 |
| TNFRSF11A | OBD117.1.053.055 | 0.008919637 |
| ORF698 | OBD117.1.1745.1747 | 0 |
| ORF699 | OBD117.1.465.467 | −0.009297019 |
| ORF699 | OBD117.1.533.535 | 0 |
| ORF70 | OBD117.1.1773.1775 | 0 |
| ORF700 | OBD117.1.525.527 | −0.016217397 |
| ORF700 | OBD117.1.993.995 | 0 |
| TNFRSF25 | OBD117.1.381.383 | 0.000134142 |
| TNFRSF25 | OBD117.1.193.195 | 0 |

TABLE 14.H-continued

| Gene | Marker | GLMNET |
|---|---|---|
| TNFRSF25 | OBD117.1.181.183 | −0.007419688 |
| TNFRSF25 | OBD117.1.137.139 | −0.005042919 |
| TNFRSF25 | OBD117.1.745.747 | 0.020530456 |
| ORF705 | OBD117.1.545.547 | 0.013121857 |
| ORF705 | OBD117.1.1049.1051 | 0 |
| ORF705 | OBD117.1.517.519 | 0.012738078 |
| TNFSF8 | OBD117.1.273.275 | 0.010145959 |
| ORF706 | OBD117.1.1385.1387 | 0 |
| TP73 | OBD117.1.349.351 | −0.021145842 |
| ORF71 | OBD117.1.697.699 | 0.006301587 |
| ORF71 | OBD117.1.597.599 | 0.01482896 |
| TRAF1 | OBD117.1.021.023 | −0.016381908 |
| TRAF1 | OBD117.1.301.303 | 0.024168377 |
| TRAF1 | OBD117.1.013.015 | −0.003508085 |
| TRAF1 | OBD117.1.169.171 | −0.01000752 |
| ORF718 | OBD117.1.949.951 | −0.018046798 |
| ORF722 | OBD117.1.933.935 | 0.008860872 |
| ORF730 | OBD117.1.1873.1875 | 0 |
| ORF741 | OBD117.1.1233.1235 | 0 |
| BOK | OBD117.1.841.843 | 0.000117272 |
| ORF762 | OBD117.1.1649.1651 | 0 |
| ORF83 | OBD117.1.1013.1015 | 0 |
| ORF83 | OBD117.1.877.879 | 0.015890823 |
| ORF83 | OBD117.1.637.639 | 0.000171766 |
| ORF83 | OBD117.1.657.659 | −0.007266336 |
| ORF83 | OBD117.1.565.567 | 0.013024 |
| ORF83 | OBD117.1.629.631 | −0.000108617 |
| ORF83 | OBD117.1.633.635 | 0 |
| ORF86 | OBD117.1.1685.1687 | 0 |
| ORF99 | OBD117.1.1297.1299 | 0 |
| ORF99 | OBD117.1.1537.1539 | 0 |

TABLE 14.I

| Gene | Marker | GLMNET |
|---|---|---|
| ORF99 | OBD117.1.1353.1355 | 0 |
| ORF99 | OBD117.1.1477.1479 | 0 |
| ORF99 | OBD117.1.1689.1691 | 0 |
| ORF99 | OBD117.1.1601.1603 | 0 |
| ORF99 | OBD117.1.1125.1127 | 0 |
| CBLB | OBD117.1.205.207 | 0.00674446 |
| ORF99 | OBD117.1.1369.1371 | 0 |
| PIK3R1 | OBD117.1.853.855 | 0.0001037 |
| PIK3R1 | OBD117.1.849.851 | 0.000117852 |
| PIK3R1 | OBD117.1.857.859 | 0.000136129 |
| PRR5 | OBD117.1.249.251 | −0.013597927 |
| PTPRC | OBD117.1.1437.1439 | 0 |
| PTPRC | OBD117.1.1245.1247 | 0 |
| RPTOR | OBD117.1.097.099 | 0.004679577 |
| RPTOR | OBD117.1.865.867 | −0.006781145 |
| RPTOR | OBD117.1.093.095 | −0.013087312 |
| SHH | OBD117.1.873.875 | −0.010277817 |
| SHH | OBD117.1.1073.1075 | 0 |
| SPN | OBD117.1.1001.1003 | −0.000111539 |
| SPN | OBD117.1.1009.1011 | 0.021717076 |
| STAT5B | OBD117.009.011 | 0.000094 |
| SYK | OBD117.1.1213.1215 | 0 |
| SYK | OBD117.1.1273.1275 | 0 |
| TNFRSF11A | OBD117.1.1793.1795 | 0 |
| TNFRSF13C | OBD117.1.997.999 | 0 |
| TNFRSF1A | OBD117.1.1005.1007 | 0.000108061 |
| TNFRSF25 | OBD117.1.421.423 | −0.009810191 |
| TNFRSF25 | OBD117.1.241.243 | −0.020246781 |
| TNFRSF25 | OBD117.1.029.031 | 0.016525715 |
| TNFRSF25 | OBD117.1.845.847 | 0.005356938 |
| TNFRSF25 | OBD117.1.861.863 | 0.000119941 |
| TNFSF8 | OBD117.1.917.919 | 0.012278549 |
| TRAF1 | OBD117.1.361.363 | 0.011703991 |
| TRAF1 | OBD117.1.333.335 | −0.01117453 |
| TRAF2 | OBD117.1.869.871 | −0.018227673 |

TABLE 15

| | | |
|---|---|---|
| CD2 | CD2 Molecule | Protein coding gene, associated with penis squamous cell carcinoma and immune defect due to absence of thymus, related to Akt signaling and hematopoietic stem cell differentiation pathways and lineage-specific markers |
| CFP | Complement Factor Properdin | Protein coding gene, associated with properdin deficiency, X-linked and properdin deficiency, related to Immune response Lectin induced complement pathway and O-linked glycosylation |
| ELK1 | ELK1 ETS Transcription Factor | Protein coding gene, associated with Hypervitaminosis A, related to p38 MAPK signaling pathway (WikiPathways) and focal ddhesion. |
| FCGR2B | Fc Fragment Of IgG Receptor IIb | Protein coding gene, associated with systemic lupus erythematosus and malaria, related to Immune response Fc epsilon RI pathway and Fc-gammaR pathway |
| IL17D | Interleukin 17D | Protein coding gene, associated with psoriasis, related pathways are IL-17 family signaling pathways and C-type lectin receptor signaling pathway |
| IL17RA | Interleukin 17 Receptor A | Protein coding gene, associated with immunodeficiency 51 and chronic mucocutaneous candidiasis, related to Akt and ERK signaling |
| TNFRSF13C | TNF Receptor Superfamily Member 13C | Protein coding gene, associated with immunodeficiency, common variable, 4 and common variable immunodeficiency, related to Akt signaling and NF-kappa B signaling pathway |

TABLE 16.A

| | Probe | GeneLocus | Probe_Count_Total | Probe_Count_Sig |
|---|---|---|---|---|
| 1 | IL17RA_22_17555467_17556730_17583829_17589696_RF | IL17RA | 23 | 14 |
| 2 | TP53_17_7568905_7571771_7590321_7591415_FF | TP53 | 8 | 5 |
| 3 | IL4_5_131966700_131972322_132015552_132017427_FF | IL4 | 17 | 10 |
| 4 | EFNB1_X_68004262_68015195_68068238_68069630_RR | EFNB1 | 24 | 12 |
| 5 | IFNA2_9_21392770_21395335_21414238_21418494_FF | IFNA2 | 30 | 8 |
| 6 | BBC3_19_47759469_47760963_47778641_47780208_FR | BBC3 | 12 | 7 |
| 7 | KLRK1_12_10544349_10549161_10570098_10578163_RF | KLRK1 | 30 | 11 |
| 8 | IFNA1_9_21392770_21395335_21437177_21443318_RR | IFNA1 | 8 | 3 |
| 9 | PIK3CA_3_178832360_178841413_178871576_178873671_FF | PIK3CA | 25 | 13 |
| 10 | BIRC2_11_102178257_102181848_102266251_102268479_FF | BIRC2 | 13 | 4 |
| 11 | PDCD1_2_242777613_242779346_242826000_242827096_FF | PDCD1 | 12 | 6 |
| 12 | XIAP_X_123017153_123019333_123035293_123038006_FR | XIAP | 13 | 3 |
| 13 | AKT1_14_105266348_105267359_105305709_105309658_RF | AKT1 | 18 | 11 |
| 14 | ARHGEF7_13_111822569_111834523_111970320_111973116_FF | ARHGEF7 | 175 | 56 |
| 15 | ARHGEF7_13_111908346_111914493_111970320_111973116_FF | ARHGEF7 | 175 | 56 |
| 16 | BCL2_18_60884271_60893545_60998913_61003098_FR | BCL2 | 193 | 30 |
| 17 | C8B_1_57385955_57389539_57428402_57432779_FR | C8B | 121 | 33 |
| 18 | CBLB_3_105390159_105394525_105442255_105450516_FR | CBLB | 168 | 42 |
| 19 | CBLB_3_105390159_105394525_105547637_105554877_FR | CBLB | 168 | 42 |
| 20 | CCL16_17_34304462_34314203_34339929_34346837_RR | CCL16 | 32 | 9 |
| 21 | CCL7_17_32553749_32557219_32574048_32580497_FR | CCL7 | 17 | 3 |
| 22 | CD3E_11_118135384_118142619_118163915_118173402_RR | CD3E | 13 | 2 |
| 23 | CD3E_11_118144515_118145854_118163915_118173402_FR | CD3E | 13 | 2 |
| 24 | CD4_12_6876592_6883165_6912128_6913978_FR | CD4 | 14 | 7 |
| 25 | CD40_20_44718691_44720694_44762355_44767158_RF | CD40 | 24 | 12 |
| 26 | CD6_11_60689541_60692498_60785339_60793057_RF | CD6 | 62 | 33 |
| 27 | CD6_11_60699859_60701154_60744556_60751199_FR | CD6 | 62 | 33 |
| 28 | CDKN2A_9_21978375_21981767_22029988_22034038_FF | CDKN2A | 14 | 10 |
| 29 | FAS_10_90717744_90724423_90745185_90750176_FF | FAS | 59 | 25 |
| 30 | FCGR2B_1_161519223_161525894_161627152_161631654_RR | FCGR2B | 72 | 28 |
| 31 | FCGR2B_1_161562782_161569954_161627152_161631654_FR | FCGR2B | 72 | 28 |
| 32 | IKBKB_8_42099384_42103137_42121759_42128721_RF | IKBKB | 24 | 12 |
| 33 | IKBKB_8_42121759_42128721_42148497_42149642_FF | IKBKB | 24 | 12 |
| 34 | IKBKB_8_42121759_42128721_42159959_42162198_FF | IKBKB | 24 | 12 |
| 35 | IKBKB_8_42121759_42128721_42159959_42162198_FR | IKBKB | 24 | 12 |
| 36 | MAPK1_22_22117703_22122470_22210841_22217782_RR | MAPK1 | 48 | 10 |
| 37 | MAPKAP1_9_128280753_128289273_128393518_128397379_RF | MAPKAP1 | 100 | 22 |
| 38 | MTOR_1_11245934_11254334_11280008_11283155_FF | MTOR | 149 | 42 |
| 39 | NCK2_2_106375590_106379449_106403393_106408079_RR | NCK2 | 164 | 36 |
| 40 | NCK2_2_106403393_106408079_106439151_106441507_FR | NCK2 | 164 | 36 |
| 41 | PAK1_11_77141424_77148888_77185846_77188900_FR | PAK1 | 155 | 38 |
| 42 | PTK2_8_141745642_141749152_141773261_141781505_FF | PTK2 | 152 | 48 |
| 43 | PTPRA_20_2797355_2801691_3004582_3011246_RF | PTPRA | 137 | 57 |
| 44 | PTPRA_20_2853761_2858838_2966772_2970097_RF | PTPRA | 137 | 57 |
| 45 | PTPRA_20_2853761_2858838_3004582_3011246_RF | PTPRA | 137 | 57 |
| 46 | PTPRA_20_2943750_2948659_2966772_2970097_RF | PTPRA | 137 | 57 |
| 47 | PVR_19_45099561_45103576_45113698_45116399_FF | PVR | 25 | 13 |
| 48 | PVR_19_45099561_45103576_45167560_45168855_FR | PVR | 25 | 1 |
| 49 | PVRL1_11_119551289_119555164_119570787_119575859_FF | PVRL1 | 95 | 44 |
| 50 | PVRL1_11_119581897_119584757_119599998_119609544_FR | PVRL1 | 95 | 44 |
| 51 | PVRL1_11_119599998_119609544_119620830_119624585_RF | PVRL1 | 95 | 44 |
| 52 | SHH_7_155593268_155595881_155627543_155630456_RR | SHH | 25 | 12 |
| 53 | SIRPA_20_1830612_1833775_1864775_1869190_RR | SIRPA | 56 | 12 |

TABLE 16.A-continued

| | Probe | GeneLocus | Probe_Count_Total | Probe_Count_Sig |
|---|---|---|---|---|
| 54 | SIRPA_20_1830612_1833775_1905279_1911608_RF | SIRPA | 56 | 12 |
| 55 | SRC_20_35981178_35984981_36049517_36053821_RF | SRC | 25 | 0 |
| 56 | SYK_9_93529835_93536915_93555880_93559839_RR | SYK | 141 | 48 |
| 57 | TNFRSF11B_8_119933591_119936942_119958900_119964996_FR | TNFRSF11B | 24 | 12 |
| 58 | TNFRSF11B_8_119958900_119964996_119985773_119986987_RR | TNFRSF11B | 24 | 12 |
| 59 | TNFRSF25_1_6521664_6526267_6541388_6544308_RF | TNFRSF25 | 23 | 16 |
| 60 | TP63_3_189395557_189406042_189416264_189422493_FR | TP63 | 131 | 44 |
| 61 | TRBV12-3_HG7_PATCH_142268038_142272453_142299803_142302443_FF | TRBV12-3 | 21 | 7 |
| 62 | TYROBP_19_36380190_36382489_36405491_36408643_FR | TYROBP | 8 | 3 |
| 63 | YES1_18_703962_705806_820113_825053_RF | YES1 | 12 | 2 |

TABLE 16.b

| | HyperG_Stats | FDR_HyperG | Percent_Sig | logFC | AveExpr | t |
|---|---|---|---|---|---|---|
| 1 | 0.000115042 | 0.007430257 | 60.87 | −0.013772346 | −0.013772346 | −0.240285183 |
| 2 | 0.019609346 | 0.224493201 | 62.5 | 0.147930594 | 0.147930594 | 1.54773245 |
| 3 | 0.001648192 | 0.054719962 | 58.82 | −0.09302015 | −0.09302015 | −0.9155182 |
| 4 | 0.003650795 | 0.086576007 | 50 | 0.22695709 | 0.22695709 | 3.4316055 |
| 5 | 0.581066149 | 1 | 26.67 | −0.42260763 | −0.42260763 | −7.3816234 |
| 6 | 0.021403774 | 0.222064153 | 58.33 | 0.52026112 | 0.52026112 | 8.1265262 |
| 7 | 0.158099772 | 0.672937493 | 36.67 | −0.45326382 | −0.45326382 | −5.2822758 |
| 8 | 0.369467375 | 1 | 37.5 | −0.39902611 | −0.39902611 | −6.1923548 |
| 9 | 0.006619293 | 0.146507027 | 52 | −0.44521152 | −0.44521152 | −7.5310764 |
| 10 | 0.479547592 | 1 | 30.77 | −0.46394556 | −0.46394556 | −7.8281466 |
| 11 | 0.07482778 | 0.443952662 | 50 | −0.33213477 | −0.33213477 | −5.1973943 |
| 12 | 0.722168484 | 1 | 23.08 | −0.63653446 | −0.63653446 | −4.1311757 |
| 13 | 0.002366254 | 0.071417842 | 61.11 | 0.471980659 | 0.471980659 | 7.433543962 |
| 14 | 0.075877919 | 0.443952662 | 32 | 0.102617139 | 0.102617139 | 1.288701188 |
| 15 | 0.075877919 | 0.443952662 | 32 | 0.050243809 | 0.050243809 | 0.810857617 |
| 16 | 0.99994673 | 1 | 15.54 | 0.030761848 | 0.030761848 | 0.459625443 |
| 17 | 0.49856502 | 1 | 27.27 | 0.087796109 | 0.087796109 | 0.831720025 |
| 18 | 0.739516406 | 1 | 25 | −0.01141347 | −0.01141347 | −0.203551326 |
| 19 | 0.739516406 | 1 | 25 | −0.017865418 | −0.017865418 | −0.321765089 |
| 20 | 0.505143193 | 1 | 28.12 | 0.084236571 | 0.084236571 | 1.302140629 |
| 21 | 0.875581427 | 1 | 17.65 | −0.045569025 | −0.045569025 | −0.753475926 |
| 22 | 0.901807168 | 1 | 15.38 | 0.081062908 | 0.081062908 | 0.685184811 |
| 23 | 0.901807168 | 1 | 15.38 | 0.060479289 | 0.060479289 | 0.503342984 |
| 24 | 0.055268149 | 0.407756121 | 50 | −0.01956492 | −0.01956492 | −0.202506703 |
| 25 | 0.01320722 | 0.182699883 | 50 | 0.453964947 | 0.453964947 | 4.645992114 |
| 26 | 9.60E−06 | 0.001593482 | 53.23 | 0.465039657 | 0.465039657 | 7.987834809 |
| 27 | 9.60E−06 | 0.001593482 | 53.23 | 0.449010255 | 0.449010255 | 7.086525198 |
| 28 | 0.000646498 | 0.035772897 | 71.43 | 0.463949032 | 0.463949032 | 6.463178912 |
| 29 | 0.007195307 | 0.149302618 | 42.37 | 0.498577819 | 0.498577819 | 7.028755206 |
| 30 | 0.017535464 | 0.207920508 | 38.89 | −0.030766524 | −0.030766524 | −0.553783792 |
| 31 | 0.017535464 | 0.207920508 | 38.89 | 0.115781119 | 0.115781119 | 1.99167408 |
| 32 | 0.01320722 | 0.182699883 | 50 | 0.416374779 | 0.416374779 | 4.865919407 |
| 33 | 0.01320722 | 0.182699883 | 50 | 0.418275622 | 0.418275622 | 4.359821333 |
| 34 | 0.01320722 | 0.182699883 | 50 | 0.381661827 | 0.381661827 | 4.157210523 |
| 35 | 0.01320722 | 0.182699883 | 50 | 0.377780658 | 0.377780658 | 5.221207867 |
| 36 | 0.869089583 | 1 | 20.83 | 0.05911233 | 0.05911233 | 0.930447108 |
| 37 | 0.891633842 | 1 | 22 | 0.126849618 | 0.126849618 | 1.741819751 |
| 38 | 0.391767947 | 1 | 28.19 | −0.118120085 | −0.118120085 | −1.681387975 |
| 39 | 0.939603617 | 1 | 21.95 | −0.03216772 | −0.03216772 | −0.494246209 |
| 40 | 0.939603617 | 1 | 21.95 | −0.137021654 | −0.137021654 | −1.988270617 |
| 41 | 0.776895392 | 1 | 24.52 | 0.032810973 | 0.032810973 | 0.504074254 |
| 42 | 0.113105973 | 0.536445473 | 31.58 | 0.12642549 | 0.12642549 | 1.328126332 |
| 43 | 0.000126919 | 0.00842741 | 41.61 | 0.59038148 | 0.59038148 | 4.747669645 |
| 44 | 0.000126919 | 0.00842741 | 41.61 | 0.662663936 | 0.662663936 | 7.095181111 |
| 45 | 0.000126919 | 0.00842741 | 41.61 | 0.62773389 | 0.62773389 | 7.960830244 |
| 46 | 0.000126919 | 0.00842741 | 41.61 | −0.034569831 | −0.034569831 | −0.540303228 |
| 47 | 0.006619293 | 0.146507027 | 52 | 0.510054367 | 0.510054367 | 7.019512745 |
| 48 | 0.006619293 | 0.146507027 | 52 | 0.46085773 | 0.46085773 | 5.690775832 |
| 49 | 3.65E−05 | 0.003027108 | 46.32 | 0.079697088 | 0.079697088 | 1.242102392 |
| 50 | 3.65E−05 | 0.003027108 | 46.32 | 0.568094527 | 0.568094527 | 6.294476998 |
| 51 | 3.65E−05 | 0.003027108 | 46.32 | 0.62095435 | 0.62095435 | 6.968998342 |
| 52 | 0.019288384 | 0.22081874 | 48 | −0.109701651 | −0.109701651 | −1.612003006 |
| 53 | 0.860606844 | 1 | 21.43 | 0.128697259 | 0.128697259 | 2.281706671 |
| 54 | 0.860606844 | 1 | 21.43 | 0.028610792 | 0.028610792 | 0.429215356 |
| 55 | 1 | 1 | 0 | 0.091685254 | 0.091685254 | 1.589549618 |
| 56 | 0.036032885 | 0.332806348 | 34.04 | 0.022347263 | 0.022347263 | 0.277666921 |
| 57 | 0.01320722 | 0.182699883 | 50 | 0.525181749 | 0.525181749 | 4.601541756 |
| 58 | 0.01320722 | 0.182699883 | 50 | 0.527381914 | 0.527381914 | 9.698751213 |
| 59 | 2.37E−05 | 0.002619074 | 69.57 | 0.108337346 | 0.108337346 | 1.637060864 |

TABLE 16.b-continued

|    | HyperG_Stats | FDR_HyperG  | Percent_Sig | logFC        | AveExpr      | t            |
|----|--------------|-------------|-------------|--------------|--------------|--------------|
| 60 | 0.053257016  | 0.407756121 | 33.59       | 0.027917618  | 0.027917618  | 0.428723434  |
| 61 | 0.326841379  | 1           | 33.33       | 0.313249511  | 0.313249511  | 3.70351688   |
| 62 | 0.369467375  | 1           | 37.5        | 0.079273829  | 0.079273829  | 0.887069778  |
| 63 | 0.874170448  | 1           | 16.67       | −0.02812739  | −0.02812739  | −0.494526106 |

TABLE 16.c

|    | P. Value     | adj. P. Val  | B            | FC          | FC_1         | LS | Loop Detected   |
|----|--------------|--------------|--------------|-------------|--------------|----|-----------------|
| 1  | 0.816795568  | 0.8914063    | −6.653954243 | 0.990499158 | −1.009591973 | 0  | Non-Responder   |
| 2  | 0.164353966  | 0.314486691  | −5.52937568  | 1.107979043 | 1.107979043  | 1  | Responder       |
| 3  | 0.389499204  | 0.558346665  | −6.2420323   | 0.937558    | −1.066601    | 0  | Non-Responder   |
| 4  | 0.010464785  | 0.05875152   | −2.8122673   | 1.1703638   | 1.170364     | 1  | Responder       |
| 5  | 0.000130857  | 0.00978135   | 1.6800907    | 0.7460749   | −1.340348    | −1 | Non-Responder   |
| 6  | 0.0000699    | 0.009591857  | 2.2958233    | 1.4342148   | 1.434215     | 1  | Responder       |
| 7  | 0.001040222  | 0.017977033  | −0.4221012   | 0.7303886   | −1.369134    | −1 | Non-Responder   |
| 8  | 0.000397981  | 0.012391118  | 0.562249     | 0.75837     | −1.318617    | −1 | Non-Responder   |
| 9  | 0.000114934  | 0.00978135   | 1.8084821    | 0.7344766   | −1.361514    | −1 | Non-Responder   |
| 10 | 0.0000893    | 0.00978135   | 2.0563379    | 0.7250008   | −1.379309    | −1 | Non-Responder   |
| 11 | 0.001143977  | 0.018798179  | −0.5201626   | 0.7943602   | −1.258875    | −1 | Non-Responder   |
| 12 | 0.004120455  | 0.035897704  | −1.8475599   | 0.6432563   | −1.55459     | −1 | Non-Responder   |
| 13 | 0.00012506   | 0.00978135   | 1.724980841  | 1.387012375 | 1.387012375  | 1  | Responder       |
| 14 | 0.237291965  | 0.4030718    | −5.849682939 | 1.073719491 | 1.073719491  | 0  | Responder       |
| 15 | 0.443374677  | 0.604581249  | −6.333671754 | 1.035439894 | 1.035439894  | 0  | Responder       |
| 16 | 0.65931764   | 0.779777623  | −6.569484186 | 1.021551437 | 1.021551437  | 0  | Non-Responder   |
| 17 | 0.432235131  | 0.596473312  | −6.31612829  | 1.06274547  | 1.06274547   | 0  | Non-Responder   |
| 18 | 0.84432778   | 0.909374308  | −6.663031225 | 0.992119997 | −1.007942591 | 0  | Non-Responder   |
| 19 | 0.756754959  | 0.850026261  | −6.628568047 | 0.987692994 | −1.012460356 | 0  | Non-Responder   |
| 20 | 0.232903788  | 0.397959585  | −5.833902583 | 1.060126607 | 1.060126607  | 0  | Non-Responder   |
| 21 | 0.475034273  | 0.631532497  | −6.379996896 | 0.968907587 | −1.032090174 | 0  | Non-Responder   |
| 22 | 0.514636091  | 0.666439232  | −6.431327032 | 1.057797087 | 1.057797087  | 0  | Non-Responder   |
| 23 | 0.629727466  | 0.757957974  | −6.546630196 | 1.042812144 | 1.042812144  | 0  | Non-Responder   |
| 24 | 0.84511434   | 0.910037934  | −6.663267658 | 0.986530172 | −1.013653742 | 0  | Non-Responder   |
| 25 | 0.002174068  | 0.025916536  | −1.184382177 | 1.369799698 | 1.369799698  | 1  | Responder       |
| 26 | 0.0000783    | 0.009721979  | 2.18565792   | 1.380355296 | 1.380355296  | 1  | Responder       |
| 27 | 0.000170122  | 0.009942962  | 1.419020174  | 1.365103422 | 1.365103422  | 1  | Responder       |
| 28 | 0.000304847  | 0.011606249  | 0.83266885   | 1.379312192 | 1.379312192  | 1  | Responder       |
| 29 | 0.000179269  | 0.009942962  | 1.366705698  | 1.412820144 | 1.412820144  | 1  | Responder       |
| 30 | 0.596468127  | 0.731758241  | −6.517870372 | 0.978900056 | −1.021554748 | 0  | Non-Responder   |
| 31 | 0.08546631   | 0.204154819  | −4.920965082 | 1.08356156  | 1.08356156   | 0  | Non-Responder   |
| 32 | 0.001674193  | 0.022692964  | −0.913760678 | 1.334569815 | 1.334569815  | 1  | Responder       |
| 33 | 0.003086815  | 0.030845315  | −1.547910416 | 1.336329355 | 1.336329355  | 1  | Responder       |
| 34 | 0.003985576  | 0.035412035  | −1.81303301  | 1.302841722 | 1.302841722  | 1  | Responder       |
| 35 | 0.001113756  | 0.018506461  | −0.492540142 | 1.2993415   | 1.2993415    | 1  | Responder       |
| 36 | 0.382223612  | 0.551023134  | −6.228239304 | 1.041824544 | 1.041824544  | 0  | Non-Responder   |
| 37 | 0.123810276  | 0.260011317  | −5.270706943 | 1.091906723 | 1.091906723  | 0  | Non-Responder   |
| 38 | 0.135302587  | 0.276375393  | −5.352673235 | 0.92138749  | −1.085319706 | 0  | Non-Responder   |
| 39 | 0.635827663  | 0.762978908  | −6.551545554 | 0.977949776 | −1.0225474   | 0  | Non-Responder   |

TABLE 16.c-continued

|    | P. Value | adj. P. Val | B | FC | FC_1 | LS | Loop Detected |
|----|----------|-------------|-----|-----|------|----|----|
| 40 | 0.085901221 | 0.204801549 | −4.925826912 | 0.909394602 | −1.099632654 | 0 | Non-Responder |
| 41 | 0.62923841 | 0.757540065 | −6.546231435 | 1.023003423 | 1.023003423 | 0 | Non-Responder |
| 42 | 0.224617635 | 0.388210511 | −5.803108233 | 1.091585768 | 1.091585768 | 0 | Non-Responder |
| 43 | 0.001925031 | 0.024132924 | −1.0583223 | 1.50564482 | 1.50564482 | 1 | Responder |
| 44 | 0.000168797 | 0.009942962 | 1.426824141 | 1.583002941 | 1.583002941 | 1 | Responder |
| 45 | 0.00008 | 0.00978135 | 2.163976731 | 1.545136068 | 1.545136068 | 1 | Responder |
| 46 | 0.605261259 | 0.738428481 | −6.525804538 | 0.976322828 | −1.024251376 | 0 | Non-Responder |
| 47 | 0.000180782 | 0.009942962 | 1.358298716 | 1.424103861 | 1.424103861 | 1 | Responder |
| 48 | 0.000667147 | 0.015161131 | 0.034631546 | 1.376359866 | 1.376359866 | 1 | Responder |
| 49 | 0.253060559 | 0.421018665 | −5.903603004 | 1.056796129 | 1.056796129 | 0 | Non-Responder |
| 50 | 0.000359565 | 0.012119064 | 0.665377174 | 1.482564146 | 1.482564146 | 1 | Responder |
| 51 | 0.000189314 | 0.010133451 | 1.312167529 | 1.537892169 | 1.537892169 | 1 | Responder |
| 52 | 0.149729695 | 0.295448526 | −5.445243195 | 0.9267797 | −1.079005075 | 0 | Non-Responder |
| 53 | 0.055409796 | 0.154727941 | −4.499882988 | 1.09330601 | 1.09330601 | 0 | Non-Responder |
| 54 | 0.680295532 | 0.796125405 | −6.58422725 | 1.02002944 | 1.02002944 | 0 | Non-Responder |
| 55 | 0.154696532 | 0.302455365 | −5.474819603 | 1.06561423 | 1.06561423 | 0 | Non-Responder |
| 56 | 0.789058348 | 0.871284215 | −6.643201491 | 1.015610533 | 1.015610533 | 0 | Non-Responder |
| 57 | 0.00229391 | 0.026232608 | −1.24000317 | 1.439114867 | 1.439114867 | 1 | Responder |
| 58 | 0.0000215 | 0.008847609 | 3.417854093 | 1.441311246 | 1.441311246 | 1 | Responder |
| 59 | 0.144361583 | 0.288372184 | −5.412012178 | 1.077985182 | 1.077985182 | 0 | Non-Responder |
| 60 | 0.680637436 | 0.796222402 | −6.58445788 | 1.019539463 | 1.019539463 | 0 | Non-Responder |
| 61 | 0.007222384 | 0.047648108 | −2.429187546 | 1.242503151 | 1.242503151 | 1 | Responder |
| 62 | 0.403646431 | 0.571190716 | −6.267826761 | 1.056486132 | 1.056486132 | 0 | Non-Responder |
| 63 | 0.635639513 | 0.762924558 | −6.551395561 | 0.980692405 | −1.019687717 | 0 | Non-Responder |

TABLE 16.d

|    | Probe sequence 60 mer | Probe Location Chr | Start1 |
|----|-----------------------|--------------------|--------|
| 1 | GCGCCGCGGTACCCGCTCATGGACAGGTTCGAACTCCTGAGCTCAGGCACCTTGGCCTCC (SEQ ID NO: 1885) | 22 | 17555467 |
| 2 | CAGCAAAGTTTTATTGTAAAATAAGAGATCGAGCTCTTACTTGCTACCCAGCACTGATAT (SEQ ID NO: 1886) | 17 | 7571740 |
| 3 | AGTGATAGAAGAGGGACAAGGTGGCAGTTCGATATTAGATAACATCCACTCTGGGCTACA (SEQ ID NO: 1887) | 5 | 131972291 |
| 4 | CTCTGCCCATTCCATGTCCACGGCCCCCTCGACTTGAATGGGCTTGGCTGGGCTGGGACA (SEQ ID NO: 1888) | X | 68004262 |
| 5 | AAGGATATCTAGGGCATAAAAATAAAAATCGATCTCCTGATCTCATGATCCACCTGCCTC (SEQ ID NO: 1889) | 9 | 21395304 |
| 6 | GAATCCTTTCGGGGGAGGCGGGAGGCTGTCGAGAGCTCTGTGCTCCACGCCGAGGATGCA (SEQ ID NO: 1890) | 19 | 47760932 |
| 7 | CGTGACTGTATATCATGTCCTTTGTTAATCGATTGAATAGAGATTGTCTCTTAAATACAG (SEQ ID NO: 1891) | 12 | 10544349 |
| 8 | TATAGTGGGCACACACTTTTACACAATATCGAAGAAAAAAGTCTTGACAATATTTAGGTG (SEQ ID NO: 1892) | 9 | 21392770 |
| 9 | ACCAAAATAGCAAGTAGATAATCACACTTCGAATTTTTTTCACCACAGCACACAGCCTC (SEQ ID NO: 1893) | 3 | 178841382 |
| 10 | CACCTCACAAAATATGATATCTAAAGTGTCGATATTACTCAGATTTGGGGAAATGACATT (SEQ ID NO: 1894) | 11 | 102181817 |

TABLE 16.d-continued

| | Probe sequence 60 mer | Probe Location Chr | Start1 |
|---|---|---|---|
| 11 | GCCCTGTGTCTCATGAAAGCCGTTCACTTCGAACTCCTAAGTTCAAGCAATCCTCCTGCC (SEQ ID NO: 1895) | 2 | 242779315 |
| 12 | ACTTTATGACTTGAATGATGTGGTAATGTCGAAGGTTAAAGAAGAAGTTTCAAACTGAGT (SEQ ID NO: 1896) | X | 123019302 |
| 13 | TAGGCCTGGGGGCCGAAAGGAAGAAGCTTCGACATCCTGCTTGAATGTTTGGAAGAGGGT (SEQ ID NO: 1897) | 14 | 105266348 |
| 14 | CGCAGCAGTCTCGTTGATCTTCACGGTGTCGACTCACCTGCGCCTCACATCCCAGGCGGG (SEQ ID NO: 1898) | 13 | 111834492 |
| 15 | GTAAATGAATTTGAAATATTACAAAAGATCGACTCACCTGCGCCTCACATCCCAGGCGGG (SEQ ID NO: 1899) | 13 | 111914462 |
| 16 | CCATGGGTGGTTTTGGAAAAGGCAACATTCGAAAACAATACATAAGTGTCTATAGGCCAA (SEQ ID NO: 1900) | 18 | 60893514 |
| 17 | TCACCTTAGTGAAGGGAAGTCCATCAAATCGATTTTGCTCCCCCCACCTTACCCCCAGAG (SEQ ID NO: 1901) | 1 | 57389508 |
| 18 | AGCAGGGGATCACATAAGGCCAGGAGTTCGATTTTAACAAGAAACTGTAGGTCTAAGGA (SEQ ID NO: 1902) | 3 | 105394494 |
| 19 | AGCAGGGGATCACATAAGGCCAGGAGTTCGAATAAGAAATACTTCTAAACCAAAGGATA (SEQ ID NO: 1903) | 3 | 105394494 |
| 20 | ACAATGATCAAAATAAAGGAGAAGTATTTCGAGCTTCCCCACCTTGTATGTCTCTTTTCT (SEQ ID NO: 1904) | 17 | 34304462 |
| 21 | AGGAGGGTAGATCACCTGAAGTCAGGATTCGAAGGCTTCATTTCTCTGTCTATAAAACAA (SEQ ID NO: 1905) | 17 | 32557188 |
| 22 | GAATTCCGACTCCCGTTTTGAAATTGTATCGACCGCGTCACTCTACTCCAGCCTGGGCGA (SEQ ID NO: 1906) | 11 | 118135381 |
| 23 | TTCTCAGCATCTCTCCTGAAAGAAAAAGTCGACCGCGTCACTCTACTCCAGCCTGGGCGA (SEQ ID NO: 1907) | 11 | 118145823 |
| 24 | CCGCCTCCGTCTGCGCCTGGGCCAGGCCTCGACTTCGTGATCAGCCCGGCTTGGCCTCCC (SEQ ID NO: 1908) | 12 | 6883134 |
| 25 | TTATTGTGAAATAAATCCATACAGATGATCGATCTCCTTGGCAATGAGGGCCCGGGAAGT (SEQ ID NO: 1909) | 20 | 44718691 |
| 26 | CAATATGACGGTGACATTAATGATAGCTTCGAGGCCAAGGTGCGAGGGCTGGAACGCCAG (SEQ ID NO: 1910) | 11 | 60689541 |
| 27 | GTGTGGGCCCCCCTGCTACCGCTGCGTATCGAACTTTACAGAGGGATCTAGAATGAGTGA (SEQ ID NO: 1911) | 11 | 60701123 |
| 28 | AAGCTGCCCCGGATAAAAATTCTGATAATCGAAGTTACACCTTTGATTTTTAAAAAGCA (SEQ ID NO: 1912) | 9 | 21981736 |
| 29 | GGGCAGAGAGATTTTTGTATCTACTTCTCGAGAGCCGGCCTCCTGCCCTTTCTAAAGGC (SEQ ID NO: 1913) | 10 | 90724392 |
| 30 | CAGAATCACTCTGTGGAACCAAAGAGCTTCGACCCTTCTGCTTTCTCTCCAGGGGATGGC (SEQ ID NO: 1914) | 1 | 161519223 |
| 31 | AAAAAACAATTATGTAATTGAAAACCCATCGACCCTTCTGCTTTCTCTCCAGGGGATGGC (SEQ ID NO: 1915) | 1 | 161569923 |
| 32 | CCACCCCCGCCCCGGGGGAGTCGCCCGGTCGAACTAATATTAGAGGAGAGAGGTCAGTTA (SEQ ID NO: 1916) | 8 | 42099384 |
| 33 | CCACCCCCGCCCCGGGGGAGTCGCCCGGTCGAAGTGCTGTTGAGTTCCCCCATCTCTCAT (SEQ ID NO: 1917) | 8 | 42128690 |
| 34 | CCACCCCCGCCCCGGGGGAGTCGCCCGGTCGACAGTCCCAAGAGGTCAGAACTGGCTTCC (SEQ ID NO: 1918) | 8 | 42128690 |
| 35 | CCACCCCCGCCCCGGGGGAGTCGCCCGGTCGAAGGCTGGACTTAAAAGAGCAGATGCAAG (SEQ ID NO: 1919) | 8 | 42128690 |

TABLE 16.d-continued

| | Probe sequence 60 mer | Probe Location Chr | Start1 |
|---|---|---|---|
| 36 | AAAAAAAGATTTAAAGTGGCAGCTTCACTCGACACAAGGGTTTGTAACAAAAAACAAAAA (SEQ ID NO: 1920) | 22 | 22117703 |
| 37 | CACTAATCTTTACTCTTTTTCCACTTATTCGAGACCAGTGAAACCTCGTCGCTACAAAAA (SEQ ID NO: 1921) | 9 | 128280753 |
| 38 | AGGCCATATGGTGAATCAGGAAAGAAGTTCGAAGTGTCTTAATTTCCTATAAACTAGTTA (SEQ ID NO: 1922) | 1 | 11254303 |
| 39 | AAGGCCCAAGAACCAGGAATCTAGGTATTCGAAGCAGGGGACCTGCGAAACTTCAGCTGG (SEQ ID NO: 1923) | 2 | 106375590 |
| 40 | TTTAAACTTCTCTAGAGCAAAGAGCATTTCGACCTTCTTTTCCTTAGATAGAAACTGAAT (SEQ ID NO: 1924) | 2 | 106408048 |
| 41 | AGACTTTATTAGATAGGTATAAATGTTTTCGACCCAAAGCTTTCTTTCTCCTGAGCTCAG (SEQ ID NO: 1925) | 11 | 77148857 |
| 42 | TCCATACGTCACTAGCTGAGGTAAAACGTCGATCCAGCTTTTTGACTCTAAAATGAGCTT (SEQ ID NO: 1926) | 8 | 141749121 |
| 43 | ACAATATTAAGTTCCCAGAGAAAAAAATTCGAACTGGCGGCAACCGCTGCAGCGCCTGCT (SEQ ID NO: 1927) | 20 | 2797355 |
| 44 | ACTCCATCTCAAAAAAACAAGAGCTTCCTCGAGTTGCAGGCCGCCCTGGTGGCTAGACAT (SEQ ID NO: 1928) | 20 | 2853761 |
| 45 | ACAATATTAAGTTCCCAGAGAAAAAAATTCGAGTTGCAGGCCGCCCTGGTGGCTAGACAT (SEQ ID NO: 1929) | 20 | 2853761 |
| 46 | ACTCCATCTCAAAAAAACAAGAGCTTCCTCGAGGTGGAATAAAGGTTGAGAACAGCTATA (SEQ ID NO: 1930) | 20 | 2943750 |
| 47 | GTCCCTGAAAATGTTTGTAAATGTGGGGTCGAGGGGTAGATATGAGCATCCCCATTTTCT (SEQ ID NO: 1931) | 19 | 45103545 |
| 48 | GTCCCTGAAAATGTTTGTAAATGTGGGGTCGACCTGCTGGGCTCGGGCTATCCTTCCATC (SEQ ID NO: 1932) | 19 | 45103545 |
| 49 | GGGCTCCGCCATAAGGGCCTCTGTGAAATCGAGCCCTGCCTGGCCAGCACACACTGCATC (SEQ ID NO: 1933) | 11 | 119555133 |
| 50 | GAGGCTTCTGAGTTGCTCTGAGGGTACATCGATGCGCGCCCGCCGGGGCCCGGTCGGAGC (SEQ ID NO: 1934) | 11 | 119584726 |
| 51 | TGATCATGGGACCCTGAAATGTCAGCGCTCGATGCGCGCCCGCCGGGGCCCGGTCGGAGC (SEQ ID NO: 1935) | 11 | 119599998 |
| 52 | TTGACAGTTCAGTCTGATTTCAAGTCAGTCGACTGGAATCTGCATTCGCTTCGCAGGAGC (SEQ ID NO: 1936) | 7 | 155593268 |
| 53 | ACCCCCTCCCAGCCTCCTGGTCAGGAGTTCGACCAGGCTGCAGCGAATCACCTCAGCTCC (SEQ ID NO: 1937) | 20 | 1830612 |
| 54 | AATGAGTTTCTGGAAGAATAGGACATTGTCGAACTCCTGACCAGGAGGCTGGGAGGGGGT (SEQ ID NO: 1938) | 20 | 1830612 |
| 55 | CTCCACCTGGCTAACTTCTATGCATCCTTCGAGCCGTAGCTATCTTCCTGCCTGACCGGG (SEQ ID NO: 1939) | 20 | 35981178 |
| 56 | TTTGCTAAATTACCCAAAATTTTGCTTTTCGATAAATTGAACTTCATCAAAATTAAAAAC (SEQ ID NO: 1940) | 9 | 93529835 |
| 57 | TAAGCTTTCCATCAAGCTACGAAGCTGCTCGATATCAGAATTGTGCTCTGGGGGCGGCTT (SEQ ID NO: 1941) | 8 | 119936911 |
| 58 | AAGCCGCCCCCAGAGCACAATTCTGATATCGAAGTACACAAGTCAAAAAGACAAAAGAAT (SEQ ID NO: 1942) | 8 | 119958900 |
| 59 | GCACCCCACCCTGGATCCCTTGAAAGCCTCGATCTCTGCCTCGCGCAGCCCCAGCGTGCG (SEQ ID NO: 1943) | 1 | 6521664 |
| 60 | GTCTTCCTCCATTTTAGAAATGAATAACTCGAAGGGGGAATAGAGAATGTAATGATACCT (SEQ ID NO: 1944) | 3 | 189406011 |

TABLE 16.d-continued

| | Probe sequence 60 mer | Probe Location Chr | Start1 |
|---|---|---|---|
| 61 | TTTCCACTTTTCATACTTAGACTCACAATCGATCCTCGGGCATCCCTGAATCATCTATCG (SEQ ID NO: 1945) | 7 | 142272422 |
| 62 | ATACTGAGGTTTAAAAAGTTCTTTTTTTTCGATCTCGGCTCATTGCAGCCTCCCCGTCCC (SEQ ID NO: 1946) | 19 | 36382458 |
| 63 | CACATACAAGCTTTCTGTTCGTTTATTTTCGACATAGGACGTGCCTGCTCCCCCTTCACC (SEQ ID NO: 1947) | 18 | 703962 |

TABLE 16.e

| | Probe Location | | | 4 kb Sequence Location | | | | |
|---|---|---|---|---|---|---|---|---|
| | End1 | Start2 | End2 | Chr | Start1 | End1 | Start2 | End2 |
| 1 | 17555498 | 17589665 | 17589696 | 22 | 17555467 | 17559468 | 17585695 | 17589696 |
| 2 | 7571771 | 7591384 | 7591415 | 17 | 7567770 | 7571771 | 7587414 | 7591415 |
| 3 | 131972322 | 132017396 | 132017427 | 5 | 131968321 | 131972322 | 132013426 | 132017427 |
| 4 | 68004293 | 68068238 | 68068269 | X | 68004262 | 68008263 | 68068238 | 68072239 |
| 5 | 21395335 | 21418463 | 21418494 | 9 | 21391334 | 21395335 | 21414493 | 21418494 |
| 6 | 47760963 | 47778641 | 47778672 | 19 | 47756962 | 47760963 | 47778641 | 47782642 |
| 7 | 10544380 | 10578132 | 10578163 | 12 | 10544349 | 10548350 | 10574162 | 10578163 |
| 8 | 21392801 | 21437777 | 21437808 | 9 | 21392770 | 21396771 | 21437777 | 21441778 |
| 9 | 178841413 | 178873640 | 178873671 | 3 | 178837412 | 178841413 | 178869670 | 178873671 |
| 10 | 102181848 | 102268448 | 102268479 | 11 | 102177847 | 102181848 | 102264478 | 102268479 |
| 11 | 242779346 | 242827065 | 242827096 | 2 | 242775345 | 242779346 | 242823095 | 242827096 |
| 12 | 123019333 | 123035293 | 123035324 | X | 123015332 | 123019333 | 123035293 | 123039294 |
| 13 | 105266379 | 105309627 | 105309658 | 14 | 105266348 | 105270349 | 105305657 | 105309658 |
| 14 | 111834523 | 111973085 | 111973116 | 13 | 111830522 | 111834523 | 111969115 | 111973116 |
| 15 | 111914493 | 111973085 | 111973116 | 13 | 111910492 | 111914493 | 111969115 | 111973116 |
| 16 | 60893545 | 60998913 | 60998944 | 18 | 60889544 | 60893545 | 60998913 | 61002914 |
| 17 | 57389539 | 57428402 | 57428433 | 1 | 57385538 | 57389539 | 57428402 | 57432403 |
| 18 | 105394525 | 105547637 | 105547668 | 3 | 105390524 | 105394525 | 105547637 | 105551638 |
| 19 | 105394525 | 105442255 | 105442286 | 3 | 105390524 | 105394525 | 105442255 | 105446256 |
| 20 | 34304463 | 34339929 | 34339960 | 17 | 34304462 | 34308463 | 34339929 | 34343930 |
| 21 | 32557219 | 32574048 | 32574079 | 17 | 32553218 | 32557219 | 32574048 | 32578049 |
| 22 | 118135415 | 118163915 | 118163946 | 11 | 118135384 | 118139385 | 118163915 | 118167916 |
| 23 | 118145854 | 118163915 | 118163946 | 11 | 118141853 | 118145854 | 118163915 | 118167916 |
| 24 | 6883165 | 6912128 | 6912159 | 12 | 6879164 | 6883165 | 6912128 | 6916129 |
| 25 | 44718722 | 44767127 | 44767158 | 20 | 44718691 | 44722692 | 44763157 | 44767158 |
| 26 | 60689572 | 60793026 | 60793057 | 11 | 60689541 | 60693542 | 60789056 | 60793057 |
| 27 | 60701154 | 60744556 | 60744587 | 11 | 60697153 | 60701154 | 60744556 | 60748557 |
| 28 | 21981767 | 22034007 | 22034038 | 11 | 21977766 | 21981767 | 22030037 | 22034038 |
| 29 | 90724423 | 90750145 | 90750176 | 10 | 90720422 | 90724423 | 90746175 | 90750176 |
| 30 | 161519254 | 161627152 | 161627183 | 1 | 161519223 | 161523224 | 161627152 | 161631153 |
| 31 | 161569954 | 161627152 | 161627183 | 1 | 161565953 | 161569954 | 161627152 | 161631153 |
| 32 | 42099415 | 42128690 | 42128721 | 8 | 42099384 | 42103385 | 42124720 | 42128721 |
| 33 | 42128721 | 42149611 | 42149642 | 8 | 42124720 | 42128721 | 42145641 | 42149642 |
| 34 | 42128721 | 42162167 | 42162198 | 8 | 42124720 | 42128721 | 42158197 | 42162198 |
| 35 | 42128721 | 42159959 | 42159990 | 8 | 42124720 | 42128721 | 42159959 | 42163960 |
| 36 | 22117734 | 22210841 | 22210872 | 22 | 22117703 | 22121704 | 22210841 | 22214842 |
| 37 | 128280784 | 128397348 | 128397379 | 9 | 128280753 | 128284754 | 128393378 | 128397379 |
| 38 | 11254334 | 11283124 | 11283155 | 1 | 11250333 | 11254334 | 11279154 | 11283155 |
| 39 | 106375621 | 106403393 | 106403424 | 2 | 106375590 | 106379591 | 106403393 | 106407394 |
| 40 | 106408079 | 106439151 | 106439182 | 2 | 106404078 | 106408079 | 106439151 | 106443152 |
| 41 | 77148888 | 77185846 | 77185877 | 11 | 77144887 | 77148888 | 77185846 | 77189847 |
| 42 | 141749152 | 141781474 | 141781505 | 8 | 141745151 | 141749152 | 141777504 | 141781505 |
| 43 | 2797386 | 3011215 | 3011246 | 20 | 2797355 | 2801356 | 3007245 | 3011246 |
| 44 | 2853792 | 2970066 | 2970097 | 20 | 2853761 | 2857762 | 2966096 | 2970097 |
| 45 | 2853792 | 3011215 | 3011246 | 20 | 2853761 | 2857762 | 3007245 | 3011246 |
| 46 | 2943781 | 2970066 | 2970097 | 20 | 2943750 | 2947751 | 2966096 | 2970097 |
| 47 | 45103576 | 45116368 | 45116399 | 19 | 45099575 | 45103576 | 45112398 | 45116399 |
| 48 | 45103576 | 45167560 | 45167591 | 19 | 45099575 | 45103576 | 45167560 | 45171561 |
| 49 | 119555164 | 119575828 | 119575859 | 11 | 119551163 | 119555164 | 119571858 | 119575859 |
| 50 | 119584757 | 119599998 | 119600029 | 11 | 119580756 | 119584757 | 119599998 | 119603999 |
| 51 | 119600029 | 119624554 | 119624585 | 11 | 119599998 | 119603999 | 119620584 | 119624585 |
| 52 | 155593299 | 155627543 | 155627574 | 7 | 155593268 | 155597269 | 155627543 | 155631544 |
| 53 | 1830643 | 1864775 | 1864806 | 20 | 1830612 | 1834613 | 1864775 | 1868776 |
| 54 | 1830643 | 1911577 | 1911608 | 20 | 1830612 | 1834613 | 1907607 | 1911608 |
| 55 | 35981209 | 36053790 | 36053821 | 20 | 35981178 | 35985179 | 36049820 | 36053821 |
| 56 | 93529866 | 93555880 | 93555911 | 9 | 93529835 | 93533836 | 93555880 | 93559881 |
| 57 | 119936942 | 119958900 | 119958931 | 8 | 119932941 | 119936942 | 119958900 | 119962901 |
| 58 | 119958931 | 119985773 | 119985804 | 8 | 119958900 | 119962901 | 119985773 | 119989774 |

TABLE 16.e-continued

|    | Probe Location | | | 4 kb Sequence Location | | | | |
|----|------|---------|---------|-----|-----------|-----------|-----------|-----------|
|    | End1 | Start2  | End2    | Chr | Start1    | End1      | Start2    | End2      |
| 59 | 6521695 | 6544277 | 6544308 | 1 | 6521664 | 6525665 | 6540307 | 6544308 |
| 60 | 189406042 | 189416264 | 189416295 | 3 | 189402041 | 189406042 | 189416264 | 189420265 |
| 61 | 142272453 | 142302412 | 142302443 | 7 | 142268452 | 142272453 | 142298442 | 142302443 |
| 62 | 36382489 | 36405491 | 36405522 | 19 | 36378488 | 36382489 | 36405491 | 36409492 |
| 63 | 703993 | 825022 | 825053 | 18 | 703962 | 707963 | 821052 | 825053 |

TABLE 17.A

| | Probe | Inner_primers PCR-Primer1_ID |
|---|---|---|
| 1 | IL17RA_22_17555467_17556730_17583829_17589696_RF | OBD115-385 |
| 2 | TP53_17_7568905_7571771_7590321_7591415_FF | OBD115-397 |
| 3 | IL4_5_131966700_131972322_132015552_132017427_FF | OBD115-425 |
| 4 | EFNB1_X_68004262_68015195_68068238_68069630_RR | OBD115-477 |
| 5 | IFNA2_9_21392770_21395335_21414238_21418494_FF | OBD117-109 |
| 6 | BBC3_19_47759469_47760963_47778641_47780208_FR | OBD117-085 |
| 7 | KLRK1_12_10544349_10549161_10570098_10578163_RF | OBD117-053 |
| 8 | IFNA1_9_21392770_21395335_21437777_21443318_RR | OBD117-033 |
| 9 | PIK3CA_3_178832360_178841413_178871576_178873671_FF | OBD117-117 |
| 10 | BIRC2_11_102178257_102181848_102266251_102268479_FF | OBD117-101 |
| 11 | PDCD1_2_242777613_242779346_242826000_242827096_FF | OBD117-057 |
| 12 | XIAP_X_123017153_123019333_123035293_123038006_FR | OBD117-073 |
| 13 | AKT1_14_105266348_105267359_105305709_105309658_RF | n/a |
| 14 | ARHGEF7_13_111822569_111834523_111970320_111973116_FF | n/a |
| 15 | ARHGEF7_13_111908346_111914493_111970320_111973116_FF | n/a |
| 16 | BCL2_18_60884271_60893545_60998913_61003098_FR | OBD115-429 |
| 17 | C8B_1_57385955_57389539_57428402_57432779_FR | n/a |
| 18 | CBLB_3_105390159_105394525_105547637_105554877_FR | n/a |
| 19 | CBLB_3_105390159_105394525_105442255_105450516_FR | n/a |
| 20 | CCL16_17_34304462_34314203_34339929_34346837_RR | n/a |
| 21 | CCL7_17_32553749_32557219_32574048_32580497_FR | n/a |
| 22 | CD3E_11_118135384_118142619_118163915_118173402_RR | n/a |
| 23 | CD3E_11_118144515_118145854_118163915_118173402_FR | n/a |
| 24 | CD4_12_6876592_6883165_6912128_6913978_FR | n/a |
| 25 | CD40_20_44718691_44720694_44762355_44767158_RF | n/a |
| 26 | CD6_11_60689541_60692498_60785339_60793057_RF | OBD115-281 |
| 27 | CD6_11_60699859_60701154_60744556_60751199_FR | n/a |
| 28 | CDKN2A_9_21978375_21981767_22029988_22034038_FF | OBD115-277 |
| 29 | FAS_10_90717744_90724423_90745185_90750176_FF | OBD115-293 |
| 30 | FCGR2B_1_161519223_161525894_161627152_161631654_RR | n/a |
| 31 | FCGR2B_1_161562782_161569954_161627152_161631654_FR | n/a |
| 32 | IKBKB_8_42099384_42103137_42117759_42128721_RF | n/a |
| 33 | IKBKB_8_42121759_42128721_42148497_42149642_FF | n/a |
| 34 | IKBKB_8_42121759_42128721_42159959_42162198_FF | n/a |
| 35 | IKBKB_8_42121759_42128721_42159959_42162198_FR | n/a |
| 36 | MAPK1_22_22117703_22122470_22210841_22217782_RR | n/a |
| 37 | MAPKAP1_9_128280753_128289273_128393518_128397379_RF | n/a |
| 38 | MTOR_1_11245934_11254334_11280008_11283155_FF | n/a |
| 39 | NCK2_2_106375590_106379449_106403393_106408079_RR | n/a |
| 40 | NCK2_2_106403393_106408079_106439151_106441507_FR | n/a |
| 41 | PAK1_11_77141424_77148888_77185846_77189900_FR | n/a |
| 42 | PTK2_8_141745642_141749152_141773261_141781505_FF | n/a |
| 43 | PTPRA_20_2797355_2801691_3004582_3011246_RF | n/a |
| 44 | PTPRA_20_2853761_2858838_2966772_2970097_RF | OBD115-165 |
| 45 | PTPRA_20_2853761_2858838_3004582_3011246_RF | n/a |
| 46 | PTPRA_20_2943750_2948659_2966772_2970097_RF | n/a |
| 47 | PVR_19_45099561_45103576_45113698_45116399_FF | n/a |
| 48 | PVR_19_45099561_45103576_45167560_45168855_FR | n/a |
| 49 | PVRL1_11_119551289_119555164_119570787_119575859_FF | n/a |
| 50 | PVRL1_11_119581897_119584757_119599998_119609544_FR | n/a |
| 51 | PVRL1_11_119599998_119609544_119620830_119624585_RF | n/a |
| 52 | SHH_7_155593268_155595881_155627543_155630456_RR | n/a |
| 53 | SIRPA_20_1830612_1833775_1864775_1869190_RR | n/a |
| 54 | SIRPA_20_1830612_1833775_1905279_1911608_RF | n/a |
| 55 | SRC_20_35981178_35984981_36049517_36053821_RF | n/a |
| 56 | SYK_9_93529835_93536915_93555880_93559839_RR | n/a |
| 57 | TNFRSF11B_8_119933591_119936942_119958900_119964996_FR | n/a |
| 58 | TNFRSF11B_8_119958900_119964996_119985773_119986987_RR | n/a |
| 59 | TNFRSF25_1_6521664_6526267_6541388_6544308_RF | n/a |
| 60 | TP63_3_189395557_189406042_189416264_189422493_FR | n/a |
| 61 | TRBV12-3_HG7_PATCH_142268038_142272453_142299803_142302443_FF | n/a |

TABLE 17.A-continued

| | Probe | Inner_primers PCR-Primer1_ID |
|---|---|---|
| 62 | TYROBP_19_36380190_36382489_36405491_36408643_FR | |
| 63 | YES1_18_703962_705806_820113_825053_RF | n/a |

TABLE 17.b

| | Inner_primers | | |
|---|---|---|---|
| | PCR_Primer1 | PCR-Primer2_ID | PCR_Primer2 |
| 1 | CTAAGATCATCGTCCTGTGC (SEQ ID NO: 1948) | OBD115-387 | AGTCAGCAATCTGTGAACC (SEQ ID NO: 1965) |
| 2 | CAGTCTCCAGCCTTTGTTC (SEQ ID NO: 1949) | OBD115-399 | CTCCTTCACAACCCTTATCAC (SEQ ID NO: 1966) |
| 3 | AACCAACATAAGAAGCTGAC (SEQ ID NO: 1950) | OBD115-427 | AGGGTGGTTATGGAGTGAG (SEQ ID NO: 1967) |
| 4 | TGCCACGAGAATCAAATCC (SEQ ID NO: 1951) | OBD115-479 | AGATGTTGACTCTCCAGATTG (SEQ ID NO: 1968) |
| 5 | TGTCACATTTGTGCCTTACTCAGC (SEQ ID NO: 1952) | OBD117-111 | AAGCAAGATACACCTTACCCAGTA (SEQ ID NO: 1969) |
| 6 | GGAAGCCTCGCCAGTGAGTT (SEQ ID NO: 1953) | OBD117-087 | CCGGACCAATCCAGAGACGG (SEQ ID NO: 1970) |
| 7 | TATTCCACTGGCAGCAAGGT (SEQ ID NO: 1954) | OBD117-055 | ACTCTCCCTGGTGCTTAGCTTT (SEQ ID NO: 1971) |
| 8 | GGGGCTCCACTAGGGTGACT (SEQ ID NO: 1955) | OBD117-035 | TGTGACACGCTGACTCCCTT (SEQ ID NO: 1972) |
| 9 | CAGATAAATGACAAACTGGGAAACA (SEQ ID NO: 1956) | OBD117-119 | AGACATTTTGGCAAAGATTGTTAGG (SEQ ID NO: 1973) |
| 10 | CAATGACAGGACTCAACCCAGG (SEQ ID NO: 1957) | OBD117-103 | TTCAGCATGGAGTAAGAGGAGGG (SEQ ID NO: 1974) |
| 11 | ACAGGAAAAGGAAGCTCACAGGT (SEQ ID NO: 1958) | OBD117-059 | TAGGAGGCAGAGGCAGGAGG (SEQ ID NO: 1975) |
| 12 | TCTGCCTGCTTAAATATTACTTTCC (SEQ ID NO: 1959) | OBD117-075 | TTTGGAGGGAGGATGGTCAA (SEQ ID NO: 1976) |
| 13 | n/a | n/a | n/a |
| 14 | n/a | n/a | n/a |
| 15 | n/a | n/a | n/a |
| 16 | GCCAAACTCCTGTCTGAAG (SEQ ID NO: 1960) | OBD115-431 | AATAGTCTTGTACCGTTGGATG (SEQ ID NO: 1977) |
| 17 | n/a | n/a | n/a |
| 18 | n/a | n/a | n/a |
| 19 | n/a | n/a | n/a |
| 20 | n/a | n/a | n/a |
| 21 | n/a | n/a | n/a |
| 22 | n/a | n/a | n/a |
| 23 | n/a | n/a | n/a |
| 24 | n/a | n/a | n/a |
| 25 | n/a | n/a | n/a |
| 26 | CGGATGCTCTAGAAAGGTTG (SEQ ID NO: 1961) | OBD115-283 | GCTCTTTGGTATGACACTGG (SEQ ID NO: 1978) |

TABLE 17.b-continued

| | Inner_primers | | |
|---|---|---|---|
| | PCR_Primer1 | PCR-Primer2_ID | PCR_Primer2 |
| 27 | n/a | n/a | n/a |
| 28 | GAGTTCTAGAATAGGATGTTGGG (SEQ ID NO: 1962) | OBD115-279 | GCTTTGTTGGCACTGAATG (SEQ ID NO: 1979) |
| 29 | TTCTTGGTAGAGAGGGAAGG (SEQ ID NO: 1963) | OBD115-295 | GGACAGCCCAGTCAAATG (SEQ ID NO: 1980) |
| 30 | n/a | n/a | n/a |
| 31 | n/a | n/a | n/a |
| 32 | n/a | n/a | n/a |
| 33 | n/a | n/a | n/a |
| 34 | n/a | n/a | n/a |
| 35 | n/a | n/a | n/a |
| 36 | n/a | n/a | n/a |
| 37 | n/a | n/a | n/a |
| 38 | n/a | n/a | n/a |
| 39 | n/a | n/a | n/a |
| 40 | n/a | n/a | n/a |
| 41 | n/a | n/a | n/a |
| 42 | n/a | n/a | n/a |
| 43 | n/a | n/a | n/a |
| 44 | TGGCTGACTTGGTGAAAC (SEQ ID NO: 1964) | OBD115-103 | CATGACTTGGGCCTTCTTC (SEQ ID NO: 1981) |
| 45 | n/a | n/a | n/a |
| 46 | n/a | n/a | n/a |
| 47 | n/a | n/a | n/a |
| 48 | n/a | n/a | n/a |
| 49 | n/a | n/a | n/a |
| 50 | n/a | n/a | n/a |
| 51 | n/a | n/a | n/a |
| 52 | n/a | n/a | n/a |
| 53 | n/a | n/a | n/a |
| 54 | n/a | n/a | n/a |
| 55 | n/a | n/a | n/a |
| 56 | n/a | n/a | n/a |
| 57 | n/a | n/a | n/a |
| 58 | n/a | n/a | n/a |
| 59 | n/a | n/a | n/a |
| 60 | n/a | n/a | n/a |
| 61 | n/a | n/a | n/a |

TABLE 17.b-continued

| | Inner_primers | | |
|---|---|---|---|
| | PCR_Primer1 | PCR-Primer2_ID | PCR_Primer2 |
| 62 | n/a | n/a | n/a |
| 63 | n/a | n/a | n/a |

TABLE 18

| Gene | Marker | GLMNET |
|---|---|---|
| IL17RA | OBD115-385.387 | −0.099598169 |
| TP53 | OBD115-397.399 | −0.089892616 |
| IL4 | OBD115-425.427 | −0.095230215 |
| EFNB1 | OBD115-477.479 | 0.091808032 |
| IFNA2 | OBD117-109.111 | −0.130270706 |
| BBC3 | OBD117-085.087 | −0.076629581 |
| KLRK1 | OBD117-053.055 | −0.088944337 |
| IFNA1 | OBD117-033.035 | 0.111911072 |
| PIK3CA | OBD117-117.119 | −0.039841311 |
| BIRC2 | OBD117-101.103 | −0.116970742 |
| PDCD1 | OBD117-057.059 | 0.13271562 |
| XIAP | OBD117-073.075 | 0.036539075 |
| BCL2 | OBD115-429.431 | 0 |
| CD6 | OBD115-281.283 | 0.031298493 |
| CDKN2A | OBD115-277.279 | 0 |
| FAS | OBD115-293.295 | 0.035034651 |
| PTPRA | OBD115-165.103 | −0.042684846 |

The invention claimed is:

1. A process for selecting a human subject who is responsive to an immunotherapy for melanoma or lung cancer and treating the selected human subject, the process comprising selecting the human subject by detecting the presence or absence of a first, second, third, fourth and fifth chromosome interaction,
wherein selecting the human subject as responsive to an immunotherapy for melanoma or lung cancer is based on detection of:
presence of the first chromosome interaction,
presence of the second chromosome interaction,
presence of the third chromosome interaction,
presence of the fourth chromosome interaction, and
absence of the fifth chromosome interaction,
wherein said detecting is carried out by
(a) cross-linking of chromosome regions of the subject which have come together in a chromosome interaction;
(b) subjecting said cross-linked regions to cleavage;
(c) ligating said cross-linked cleaved DNA ends to form ligated nucleic acids; and
(d) detecting the presence or absence of the ligated nucleic acids to thereby detect whether regions have been brought together in a chromosome interaction; and wherein:
the ligated nucleic acid corresponding to the first chromosome interaction is detected by the probe sequence:
TTCCATAGATTACTTTTCAAAT-CATCCTTCGAAGCTGGCGGCTGAGGGC CCGGCGCCAAG (SEQ ID NO: 362);
the ligated nucleic acid corresponding to the second chromosome interaction is detected by the probe sequence:
GTGTCTCGGCCCCCTGGGGCCCCACCCTTC-GATTTCCCTGTTGCCGCCG CGTTTGCAAGA (SEQ ID NO: 363);
the ligated nucleic acid corresponding to the third chromosome interaction is detected by the probe sequence:
ATCCCAACAAAAGAGAAGAACTTCTCCCTC-GATGTTTGGGGGCGGAGG GCTTTGATGAGA (SEQ ID NO: 364);
the ligated nucleic acid corresponding to the fourth chromosome interaction is detected by the probe sequence:
GTGGCGATGGCGGCCTGCGCGCCGCGCCTC-GATGTCTAAGCAACCTGC TAACTGAGGCAG (SEQ ID NO: 365); and
the ligated nucleic acid corresponding to the fifth chromosome interaction is detected by the probe sequence:
ACAGTTATTAGAAAAATAAAACAT-TTGGTCGAACAGCAAAGAGAAGAT ATTCAACTGCGA (SEQ ID NO: 366);
and said treating comprises administering said immunotherapy to the subject, wherein the said immunotherapy comprises a PD-1 inhibitor or a PD-L1 inhibitor and wherein the subject is in need of said immunotherapy for melanoma or lung cancer.

2. The process according to claim 1, wherein the process is carried out to determine responsiveness to immunotherapy at one or more defined time points, wherein optionally at least one of the time points is during the course of therapy.

3. The process according to claim 1, wherein the detecting comprises specific detection of the ligated product by quantitative PCR (qPCR) which uses primers capable of amplifying the ligated product and the said probe comprises:
a fluorophore covalently attached to the 5' end of the probe, and/or
a quencher covalently attached to the 3' end of the probe, and
optionally
said fluorophore is selected from HEX, Texas Red and FAM.

4. The process according to claim 1 wherein the immunotherapy comprises an antibody specific for PD-1 or PD-L1.

* * * * *

SEQUENCE LISTING

<160> NUMBER OF SEQ ID NOS: 1981

<210> SEQ ID NO 1
<211> LENGTH: 14
<212> TYPE: DNA
<213> ORGANISM: Homo sapiens
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t

<400> SEQUENCE: 1
ccgcgnggng gcag				14

<210> SEQ ID NO 2
<211> LENGTH: 60
<212> TYPE: DNA
<213> ORGANISM: Homo sapiens

<400> SEQUENCE: 2
cccgtcttcc ccaaaatcta tgtggtcctc gaagtcttgg attaaggttc attcaacaaa		60

<210> SEQ ID NO 3
<211> LENGTH: 60
<212> TYPE: DNA
<213> ORGANISM: Homo sapiens

<400> SEQUENCE: 3
gtaatattat gtaaaattgc atttggtatc gaacaaagcc tttaacttga cttagtgtca		60

<210> SEQ ID NO 4
<211> LENGTH: 60
<212> TYPE: DNA
<213> ORGANISM: Homo sapiens

<400> SEQUENCE: 4
gtttatcagc caggctggta agaaaatgtc gaagtcttgg attaaggttc attcaacaaa		60

```
<210> SEQ ID NO 5
<211> LENGTH: 60
<212> TYPE: DNA
<213> ORGANISM: Homo sapiens

<400> SEQUENCE: 5
gtaaatgaat tgaaatatt acaaaagatc gactcacctg cgcctcacat cccaggcggg      60

<210> SEQ ID NO 6
<211> LENGTH: 60
<212> TYPE: DNA
<213> ORGANISM: Homo sapiens

<400> SEQUENCE: 6
ttagcatcac ttgaaagcta gttaaaaatc gattgcaaat gatatgacag aattgctttg      60

<210> SEQ ID NO 7
<211> LENGTH: 60
<212> TYPE: DNA
<213> ORGANISM: Homo sapiens

<400> SEQUENCE: 7
ggatgtatat atatatacta tttttatatc gagcgcttaa ttagtgcatg ttacctatgg      60

<210> SEQ ID NO 8
<211> LENGTH: 60
<212> TYPE: DNA
<213> ORGANISM: Homo sapiens

<400> SEQUENCE: 8
tgaaacttag acatacttaa gcatttcttc gaaagctaat gaggtatgag gggagaatac      60

<210> SEQ ID NO 9
<211> LENGTH: 60
<212> TYPE: DNA
<213> ORGANISM: Homo sapiens

<400> SEQUENCE: 9
ctgagtcttc attaccaaaa aaaaaagttc gacctccccg aacccctccg cctctgcgct      60

<210> SEQ ID NO 10
<211> LENGTH: 60
<212> TYPE: DNA
<213> ORGANISM: Homo sapiens

<400> SEQUENCE: 10
ccacccccgc cccgggggag tcgcccggtc gacagtccca agaggtcaga actggcttcc      60

<210> SEQ ID NO 11
<211> LENGTH: 60
<212> TYPE: DNA
<213> ORGANISM: Homo sapiens

<400> SEQUENCE: 11
ccgcgcccgc agggcccgcc ccgcgccgtc gaggctttca agggatccag ggtggggtgc      60

<210> SEQ ID NO 12
<211> LENGTH: 60
<212> TYPE: DNA
<213> ORGANISM: Homo sapiens

<400> SEQUENCE: 12
cgcagcagtc tcgttgatct tcacggtgtc gactcacctg cgcctcacat cccaggcggg      60
```

<210> SEQ ID NO 13
<211> LENGTH: 60
<212> TYPE: DNA
<213> ORGANISM: Homo sapiens

<400> SEQUENCE: 13
ccaaactggc aatcaaccca gatagtcttc gaccccggcc ccggaggtct ccctccacag    60

<210> SEQ ID NO 14
<211> LENGTH: 60
<212> TYPE: DNA
<213> ORGANISM: Homo sapiens

<400> SEQUENCE: 14
ccaaactggc aatcaaccca gatagtcttc gaccccggcc ccggaggtct ccctccacag    60

<210> SEQ ID NO 15
<211> LENGTH: 60
<212> TYPE: DNA
<213> ORGANISM: Homo sapiens

<400> SEQUENCE: 15
gcagtcaatc accgagttat atgaggtctc gacctccccg aacccctccg cctctgcgct    60

<210> SEQ ID NO 16
<211> LENGTH: 60
<212> TYPE: DNA
<213> ORGANISM: Homo sapiens

<400> SEQUENCE: 16
ccgcgcccgc agggcccgcc ccgcgccgtc gaggctttca agggatccag ggtggggtgc    60

<210> SEQ ID NO 17
<211> LENGTH: 60
<212> TYPE: DNA
<213> ORGANISM: Homo sapiens

<400> SEQUENCE: 17
ggtgactgct cagaagagca gtactcattc gaccttatgc taagcctaaa cttgccttcc    60

<210> SEQ ID NO 18
<211> LENGTH: 60
<212> TYPE: DNA
<213> ORGANISM: Homo sapiens

<400> SEQUENCE: 18
gtttgctccg gggccgccgg gcccgccctc gattttaaca ccaccatggt ttgaatgaat    60

<210> SEQ ID NO 19
<211> LENGTH: 60
<212> TYPE: DNA
<213> ORGANISM: Homo sapiens

<400> SEQUENCE: 19 ccaccccgc cccgggggag tcgcccggtc gaccccctga catggggctg cctggagcag    60

<210> SEQ ID NO 20
<211> LENGTH: 60
<212> TYPE: DNA
<213> ORGANISM: Homo sapiens

<400> SEQUENCE: 20

```
gtttgctccg gggccgccgg gcccgccctc gattttaaca ccaccatggt ttgaatgaat    60

<210> SEQ ID NO 21
<211> LENGTH: 60
<212> TYPE: DNA
<213> ORGANISM: Homo sapiens

<400> SEQUENCE: 21
tttcaaagaa ggtatgatgg gaaaggtctc gacgcgcccc ctctacgcca tgtccccccc    60

<210> SEQ ID NO 22
<211> LENGTH: 60
<212> TYPE: DNA
<213> ORGANISM: Homo sapiens

<400> SEQUENCE: 22
ccgcgcccgc agggcccgcc ccgcgccgtc gagaagcata aagcagggac aggtatggag    60

<210> SEQ ID NO 23
<211> LENGTH: 60
<212> TYPE: DNA
<213> ORGANISM: Homo sapiens

<400> SEQUENCE: 23
aaatcataat tgtgcagatg atttgccttc gacctccccg aaccccctccg cctctgcgct    60

<210> SEQ ID NO 24
<211> LENGTH: 60
<212> TYPE: DNA
<213> ORGANISM: Homo sapiens

<400> SEQUENCE: 24
gagaatcaat tccattttta aagcttagtc gattttgagg gcttctcaca actctagatt    60

<210> SEQ ID NO 25
<211> LENGTH: 60
<212> TYPE: DNA
<213> ORGANISM: Homo sapiens

<400> SEQUENCE: 25
ccacccccgc cccgggggag tcgcccggtc gaccccctga catggggctg cctggagcag    60

<210> SEQ ID NO 26
<211> LENGTH: 60
<212> TYPE: DNA
<213> ORGANISM: Homo sapiens

<400> SEQUENCE: 26
cacagcttct aaatggtagg tgtgggactc gacccgcttt cctccccgcc ccctcatccg    60

<210> SEQ ID NO 27
<211> LENGTH: 60
<212> TYPE: DNA
<213> ORGANISM: Homo sapiens

<400> SEQUENCE: 27
ccgcgcccgc agggcccgcc ccgcgccgtc gatgtgttgg aagtcagggc ggcggtgccc    60

<210> SEQ ID NO 28
<211> LENGTH: 60
<212> TYPE: DNA
<213> ORGANISM: Homo sapiens

<400> SEQUENCE: 28
```

```
ccaccccgc ccggggggag tcgcccggtc gacagtccca agaggtcaga actggcttcc    60
```

<210> SEQ ID NO 29
<211> LENGTH: 60
<212> TYPE: DNA
<213> ORGANISM: Homo sapiens

<400> SEQUENCE: 29

```
ccgcgcccgc agggcccgcc ccgcgccgtc gatgtgttgg aagtcagggc ggcggtgccc    60
```

<210> SEQ ID NO 30
<211> LENGTH: 60
<212> TYPE: DNA
<213> ORGANISM: Homo sapiens

<400> SEQUENCE: 30

```
ggggcctcca gagtcccctt tacaggcatc gacgccccct gcctacctgc cgggtgcccc    60
```

<210> SEQ ID NO 31
<211> LENGTH: 60
<212> TYPE: DNA
<213> ORGANISM: Homo sapiens

<400> SEQUENCE: 31

```
gttcagcagc tgctgaaact cggagttgtc gacacccctc tctccctcc ctgttttcc     60
```

<210> SEQ ID NO 32
<211> LENGTH: 60
<212> TYPE: DNA
<213> ORGANISM: Homo sapiens

<400> SEQUENCE: 32

```
ctgagtcttc attaccaaaa aaaaagttc gacctccccg aacccctccg cctctgcgct    60
```

<210> SEQ ID NO 33
<211> LENGTH: 60
<212> TYPE: DNA
<213> ORGANISM: Homo sapiens

<400> SEQUENCE: 33

```
gggcaccgcc gccctgactt ccaacacatc gaagaatggg tggggccttg cacctcatac    60
```

<210> SEQ ID NO 34
<211> LENGTH: 60
<212> TYPE: DNA
<213> ORGANISM: Homo sapiens

<400> SEQUENCE: 34

```
ccaccccgc ccggggggag tcgcccggtc gaagtgctgt tgagttcccc catctctcat    60
```

<210> SEQ ID NO 35
<211> LENGTH: 60
<212> TYPE: DNA
<213> ORGANISM: Homo sapiens

<400> SEQUENCE: 35

```
ccgcgcccgc agggcccgcc ccgcgccgtc gagaagcata aagcagggac aggtatggag    60
```

<210> SEQ ID NO 36
<211> LENGTH: 60
<212> TYPE: DNA
<213> ORGANISM: Homo sapiens

<400> SEQUENCE: 36
ttaatgctga tacaattcta ttggataatc gacacttcgg ctccctgcac ctcccatgcc    60

<210> SEQ ID NO 37
<211> LENGTH: 60
<212> TYPE: DNA
<213> ORGANISM: Homo sapiens

<400> SEQUENCE: 37
gcagtcaatc accgagttat atgaggtctc gacctccccg aacccctccg cctctgcgct    60

<210> SEQ ID NO 38
<211> LENGTH: 60
<212> TYPE: DNA
<213> ORGANISM: Homo sapiens

<400> SEQUENCE: 38
gggcaccgcc gccctgactt ccaacacatc gaagaatggg tggggccttg cacctcatac    60

<210> SEQ ID NO 39
<211> LENGTH: 60
<212> TYPE: DNA
<213> ORGANISM: Homo sapiens

<400> SEQUENCE: 39
ccgcgcccgc agggcccgcc ccgcgccgtc gacaatgtta ttctttgttt ctcttaccaa    60

<210> SEQ ID NO 40
<211> LENGTH: 60
<212> TYPE: DNA
<213> ORGANISM: Homo sapiens

<400> SEQUENCE: 40
tctttgcaga tgttgtaaga taaggatgtc gacttcataa tccgcccgcc tcagcctccc    60

<210> SEQ ID NO 41
<211> LENGTH: 60
<212> TYPE: DNA
<213> ORGANISM: Homo sapiens

<400> SEQUENCE: 41 ccaccccgc cccgggggag tcgcccggtc gatttccaaa agctcacaca tgggtgcaca    60

<210> SEQ ID NO 42
<211> LENGTH: 60
<212> TYPE: DNA
<213> ORGANISM: Homo sapiens

<400> SEQUENCE: 42 ccaccccgc cccgggggag tcgcccggtc gaactaatat tagaggagag aggtcagtta    60

<210> SEQ ID NO 43
<211> LENGTH: 60
<212> TYPE: DNA
<213> ORGANISM: Homo sapiens

<400> SEQUENCE: 43
tcacaacctg ggaaaactgt cgccttgctc gactcctgct tccctcccct catctttaaa    60

<210> SEQ ID NO 44
<211> LENGTH: 60
<212> TYPE: DNA
<213> ORGANISM: Homo sapiens -continued

<400> SEQUENCE: 44
cctgcacttc ctcacgcctg ctcacccctc gagtgagtgg gagagatggc tctccacgcc    60

<210> SEQ ID NO 45
<211> LENGTH: 60
<212> TYPE: DNA
<213> ORGANISM: Homo sapiens

<400> SEQUENCE: 45
tttcaaagaa ggtatgatgg gaaaggtctc gacgcgcccc ctctacgcca tgtccccccc    60

<210> SEQ ID NO 46
<211> LENGTH: 60
<212> TYPE: DNA
<213> ORGANISM: Homo sapiens

<400> SEQUENCE: 46
tccagccttg cctggagcta gggccacctc gatcttggct caccgcaacc ttggcctccc    60

<210> SEQ ID NO 47
<211> LENGTH: 60
<212> TYPE: DNA
<213> ORGANISM: Homo sapiens

<400> SEQUENCE: 47
ccacccccgc ccgggggag tcgcccggtc gagggcctgg caagaagaca gaagccgact    60

<210> SEQ ID NO 48
<211> LENGTH: 60
<212> TYPE: DNA
<213> ORGANISM: Homo sapiens

<400> SEQUENCE: 48
ccacccccgc ccgggggag tcgcccggtc gaactaatat tagaggagag aggtcagtta    60

<210> SEQ ID NO 49
<211> LENGTH: 60
<212> TYPE: DNA
<213> ORGANISM: Homo sapiens

<400> SEQUENCE: 49
gggcaccgcc gccctgactt ccaacacatc gagaagcata aagcagggac aggtatggag    60

<210> SEQ ID NO 50
<211> LENGTH: 60
<212> TYPE: DNA
<213> ORGANISM: Homo sapiens

<400> SEQUENCE: 50
caccgacccg tccgggcccg ctgccacatc gaatagcttc ttttgctatg tctccaagtt    60

<210> SEQ ID NO 51
<211> LENGTH: 60
<212> TYPE: DNA
<213> ORGANISM: Homo sapiens

<400> SEQUENCE: 51
gtgtctcggc ccctgggc ccacccttc gatttccctg ttgccgccgc gtttgcaaga    60

<210> SEQ ID NO 52
<211> LENGTH: 60
<212> TYPE: DNA

<213> ORGANISM: Homo sapiens

<400> SEQUENCE: 52
cccgcggcgg agctgctact gtttactttc gaagcttctt cctttcggcc cccaggccta    60

<210> SEQ ID NO 53
<211> LENGTH: 60
<212> TYPE: DNA
<213> ORGANISM: Homo sapiens

<400> SEQUENCE: 53
tctcctgcct accacactgt gagaaagctc gagggcgggc ccggcggccc cggagcaaac    60

<210> SEQ ID NO 54
<211> LENGTH: 60
<212> TYPE: DNA
<213> ORGANISM: Homo sapiens

<400> SEQUENCE: 54
gggcaccgcc gccctgactt ccaacacatc gatctctgcc tcgcgcagcc ccagcgtgcg    60

<210> SEQ ID NO 55
<211> LENGTH: 60
<212> TYPE: DNA
<213> ORGANISM: Homo sapiens

<400> SEQUENCE: 55 ccaccccgc cccggggag tcgcccggtc gatttccaaa agctcacaca tgggtgcaca    60

<210> SEQ ID NO 56
<211> LENGTH: 60
<212> TYPE: DNA
<213> ORGANISM: Homo sapiens

<400> SEQUENCE: 56
gggcaccgcc gccctgactt ccaacacatc gagaagcata aagcagggac aggtatggag    60

<210> SEQ ID NO 57
<211> LENGTH: 60
<212> TYPE: DNA
<213> ORGANISM: Homo sapiens

<400> SEQUENCE: 57
caccgacccg tccgggcccg ctgccacatc gaatagcttc ttttgctatg tctccaagtt    60

<210> SEQ ID NO 58
<211> LENGTH: 60
<212> TYPE: DNA
<213> ORGANISM: Homo sapiens

<400> SEQUENCE: 58
caaatcccgg ctatctctta gaattgcatc gacgcgcccg tgacagccga gtgcggccac    60

<210> SEQ ID NO 59
<211> LENGTH: 60
<212> TYPE: DNA
<213> ORGANISM: Homo sapiens

<400> SEQUENCE: 59 ccaccccgc cccggggag tcgcccggtc gagggcctgg caagaagaca gaagccgact    60

<210> SEQ ID NO 60
<211> LENGTH: 60

<212> TYPE: DNA
<213> ORGANISM: Homo sapiens

<400> SEQUENCE: 60
ttaatgctga tacaattcta ttggataatc gacacttcgg ctccctgcac ctcccatgcc    60

<210> SEQ ID NO 61
<211> LENGTH: 60
<212> TYPE: DNA
<213> ORGANISM: Homo sapiens

<400> SEQUENCE: 61 gcacccacc ctggatccct tgaaagcctc gatctctgcc tcgcgcagcc ccagcgtgcg    60

<210> SEQ ID NO 62
<211> LENGTH: 60
<212> TYPE: DNA
<213> ORGANISM: Homo sapiens

<400> SEQUENCE: 62 ccaccccgc cccggggag tcgcccggtc gaaggctgga cttaaaagag cagatgcaag    60

<210> SEQ ID NO 63
<211> LENGTH: 60
<212> TYPE: DNA
<213> ORGANISM: Homo sapiens

<400> SEQUENCE: 63
taatgctttt ttttttgttc tctctgtgtc gacctcagat gatcgcctgc ctcggcctcc    60

<210> SEQ ID NO 64
<211> LENGTH: 60
<212> TYPE: DNA
<213> ORGANISM: Homo sapiens

<400> SEQUENCE: 64
tatgagtaat aattacaatt tccccctttc gacctccagg tccccgcca cttccacggc    60

<210> SEQ ID NO 65
<211> LENGTH: 60
<212> TYPE: DNA
<213> ORGANISM: Homo sapiens

<400> SEQUENCE: 65
gtgtctcggc ccctgggc cccacccttc gatttccctg ttgccgccgc gtttgcaaga    60

<210> SEQ ID NO 66
<211> LENGTH: 60
<212> TYPE: DNA
<213> ORGANISM: Homo sapiens

<400> SEQUENCE: 66 ccaccccgc cccggggag tcgcccggtc gaaggctgga cttaaaagag cagatgcaag    60

<210> SEQ ID NO 67
<211> LENGTH: 60
<212> TYPE: DNA
<213> ORGANISM: Homo sapiens

<400> SEQUENCE: 67
ataaaaataa ggtgggtagt tttcaacttc gaacctaatc tatttcatgt acctgctaga    60

<210> SEQ ID NO 68

<211> LENGTH: 60
<212> TYPE: DNA
<213> ORGANISM: Homo sapiens

<400> SEQUENCE: 68 gcacccacc ctggatccct tgaaagcctc gatgtgttgg aagtcagggc ggcggtgccc    60

<210> SEQ ID NO 69
<211> LENGTH: 60
<212> TYPE: DNA
<213> ORGANISM: Homo sapiens

<400> SEQUENCE: 69
acagttttat tgttgacctt ccatggactc gagatgcgcc acgccctgtt cctccttcat    60

<210> SEQ ID NO 70
<211> LENGTH: 60
<212> TYPE: DNA
<213> ORGANISM: Homo sapiens

<400> SEQUENCE: 70
gcttctcccc tctttatccc acctggcctc gactcaccct gcagacaagc tttcgggtat    60

<210> SEQ ID NO 71
<211> LENGTH: 60
<212> TYPE: DNA
<213> ORGANISM: Homo sapiens

<400> SEQUENCE: 71
caatatgacg gtgacattaa tgatagcttc gacacttcgg ctccctgcac ctcccatgcc    60

<210> SEQ ID NO 72
<211> LENGTH: 60
<212> TYPE: DNA
<213> ORGANISM: Homo sapiens

<400> SEQUENCE: 72 ccaccccgc cccgggggag tcgcccggtc gaagtgctgt tgagttcccc catctctcat    60

<210> SEQ ID NO 73
<211> LENGTH: 60
<212> TYPE: DNA
<213> ORGANISM: Homo sapiens

<400> SEQUENCE: 73
agtgttggtg agatattgtc tctcagtttc gactcactgc aaccccgcc tctgggttct    60

<210> SEQ ID NO 74
<211> LENGTH: 60
<212> TYPE: DNA
<213> ORGANISM: Homo sapiens

<400> SEQUENCE: 74
gggcaccgcc gccctgactt ccaacacatc gatctctgcc tcgcgcagcc ccagcgtgcg    60

<210> SEQ ID NO 75
<211> LENGTH: 60
<212> TYPE: DNA
<213> ORGANISM: Homo sapiens

<400> SEQUENCE: 75
cccacacacc gctggtgccc aaggactgtc gacctccccg aacccctccg cctctgcgct    60

```
<210> SEQ ID NO 76
<211> LENGTH: 60
<212> TYPE: DNA
<213> ORGANISM: Homo sapiens

<400> SEQUENCE: 76
tttcaaagaa ggtatgatgg gaaaggtctc gagtgcccct gtcccacctg gctcccctg    60

<210> SEQ ID NO 77
<211> LENGTH: 60
<212> TYPE: DNA
<213> ORGANISM: Homo sapiens

<400> SEQUENCE: 77
tcatctttaa tgaacaagac tgtcactatc gaatttccac aagtgggtgc caaccacggt    60

<210> SEQ ID NO 78
<211> LENGTH: 60
<212> TYPE: DNA
<213> ORGANISM: Homo sapiens

<400> SEQUENCE: 78
gcggccaacc cacagcgcac cgggccgctc gacctctgag aggaaacttg ctagccccag    60

<210> SEQ ID NO 79
<211> LENGTH: 60
<212> TYPE: DNA
<213> ORGANISM: Homo sapiens

<400> SEQUENCE: 79
gaccccgggg aattggctcc agcacatctc gagggcgggc ccggcggccc cggagcaaac    60

<210> SEQ ID NO 80
<211> LENGTH: 60
<212> TYPE: DNA
<213> ORGANISM: Homo sapiens

<400> SEQUENCE: 80
tctcctgcct accacactgt gagaaagctc gagggcgggc ccggcggccc cggagcaaac    60

<210> SEQ ID NO 81
<211> LENGTH: 60
<212> TYPE: DNA
<213> ORGANISM: Homo sapiens

<400> SEQUENCE: 81
gcgcagcctc tggcgccccc tgccggcctc gagaagcata aagcagggac aggtatggag    60

<210> SEQ ID NO 82
<211> LENGTH: 60
<212> TYPE: DNA
<213> ORGANISM: Homo sapiens

<400> SEQUENCE: 82
aggaagtatg tttgatttag aatgttattc gaagatcatt gtctcatttt tttacttgtt    60

<210> SEQ ID NO 83
<211> LENGTH: 60
<212> TYPE: DNA
<213> ORGANISM: Homo sapiens

<400> SEQUENCE: 83
tatgagtaat aattacaatt tccccctttc gacctccagg tccccgcca cttccacggc    60
```

<210> SEQ ID NO 84
<211> LENGTH: 60
<212> TYPE: DNA
<213> ORGANISM: Homo sapiens

<400> SEQUENCE: 84
tcagataagt aacttcctga taattaactc gagaaatgga ttcatatttc catggcttac    60

<210> SEQ ID NO 85
<211> LENGTH: 60
<212> TYPE: DNA
<213> ORGANISM: Homo sapiens

<400> SEQUENCE: 85
gaattagcaa tagtgtgtta cttctttctc gatattttac atggaatctt tcccttttta    60

<210> SEQ ID NO 86
<211> LENGTH: 60
<212> TYPE: DNA
<213> ORGANISM: Homo sapiens

<400> SEQUENCE: 86
ggccgcgagc ccggcagcgg cgacatcctc gagaaattct cccgctttag cctcccaaag    60

<210> SEQ ID NO 87
<211> LENGTH: 60
<212> TYPE: DNA
<213> ORGANISM: Homo sapiens

<400> SEQUENCE: 87 cttttaaaa attatctttt tatttgcttc gatgccaatc cacgtcatta gatgaggacc     60

<210> SEQ ID NO 88
<211> LENGTH: 60
<212> TYPE: DNA
<213> ORGANISM: Homo sapiens

<400> SEQUENCE: 88
agtggtctca ccatggcttt cttccaattc gaggtcccca accccctgcc gctcatcgtg    60

<210> SEQ ID NO 89
<211> LENGTH: 60
<212> TYPE: DNA
<213> ORGANISM: Homo sapiens

<400> SEQUENCE: 89
cgggtgcctc cccccccatt cgccctgctc gagggaggga aatgattgga ttacggggt     60

<210> SEQ ID NO 90
<211> LENGTH: 60
<212> TYPE: DNA
<213> ORGANISM: Homo sapiens

<400> SEQUENCE: 90
cacttcccca acataagcct cggtctcttc gagggcgggc ccggcggccc cggagcaaac    60

<210> SEQ ID NO 91
<211> LENGTH: 60
<212> TYPE: DNA
<213> ORGANISM: Homo sapiens

<400> SEQUENCE: 91
tattccatat ttctgctcaa cattctcctc gagtaattta aatcaacaaa gccatagaca    60

<210> SEQ ID NO 92
<211> LENGTH: 60
<212> TYPE: DNA
<213> ORGANISM: Homo sapiens

<400> SEQUENCE: 92
tcttagagtt gaacttttct aatctttttc gagtgtaaaa gggcttttac tggtgcacac    60

<210> SEQ ID NO 93
<211> LENGTH: 60
<212> TYPE: DNA
<213> ORGANISM: Homo sapiens

<400> SEQUENCE: 93
ctggcgttcc agccctcgca ccttggcctc gagcacctct tcagggagg attactgcaa     60

<210> SEQ ID NO 94
<211> LENGTH: 60
<212> TYPE: DNA
<213> ORGANISM: Homo sapiens

<400> SEQUENCE: 94
cccgcggcgg agctgctact gtttactttc gaagcttctt cctttcggcc cccaggccta    60

<210> SEQ ID NO 95
<211> LENGTH: 60
<212> TYPE: DNA
<213> ORGANISM: Homo sapiens

<400> SEQUENCE: 95
tcagataagt aacttcctga taattaactc gatgccaatc cacgtcatta gatgaggacc    60

<210> SEQ ID NO 96
<211> LENGTH: 60
<212> TYPE: DNA
<213> ORGANISM: Homo sapiens

<400> SEQUENCE: 96
agaaaatata gtattgattg ctttcaagtc gatgcgcgcc cgccggggcc cggtcggagc    60

<210> SEQ ID NO 97
<211> LENGTH: 60
<212> TYPE: DNA
<213> ORGANISM: Homo sapiens

<400> SEQUENCE: 97
agtggtctca ccatggcttt cttccaattc gaggtcccca accccctgcc gctcatcgtg    60

<210> SEQ ID NO 98
<211> LENGTH: 60
<212> TYPE: DNA
<213> ORGANISM: Homo sapiens

<400> SEQUENCE: 98
agtggtctca ccatggcttt cttccaattc gaggtcccca accccctgcc gctcatcgtg    60

<210> SEQ ID NO 99
<211> LENGTH: 60
<212> TYPE: DNA
<213> ORGANISM: Homo sapiens

<400> SEQUENCE: 99

```
cgtggatcca gactgggagc ccccagcctc gagcagttgc actccagcct aggcaacaag    60
```

<210> SEQ ID NO 100
<211> LENGTH: 60
<212> TYPE: DNA
<213> ORGANISM: Homo sapiens

<400> SEQUENCE: 100

```
cccgtcttcc ccaaaatcta tgtggtcctc gacagcgacg tgggggtgta ccgcgcggtg    60
```

<210> SEQ ID NO 101
<211> LENGTH: 60
<212> TYPE: DNA
<213> ORGANISM: Homo sapiens

<400> SEQUENCE: 101

```
gcaccccacc ctggatccct tgaaagcctc gatgtgttgg aagtcagggc ggcggtgccc    60
```

<210> SEQ ID NO 102
<211> LENGTH: 60
<212> TYPE: DNA
<213> ORGANISM: Homo sapiens

<400> SEQUENCE: 102

```
caggctattg tagtgctctt cctggccctc gacaccccct tcaagggtct gtgtcccata    60
```

<210> SEQ ID NO 103
<211> LENGTH: 60
<212> TYPE: DNA
<213> ORGANISM: Homo sapiens

<400> SEQUENCE: 103

```
ccaccccgc cccggggag tcgcccggtc gaggtggctt gggtcttagt cttccaggca     60
```

<210> SEQ ID NO 104
<211> LENGTH: 60
<212> TYPE: DNA
<213> ORGANISM: Homo sapiens

<400> SEQUENCE: 104

```
cacttcccca acataagcct cggtctcttc gagggcgggc ccggcggccc cggagcaaac    60
```

<210> SEQ ID NO 105
<211> LENGTH: 60
<212> TYPE: DNA
<213> ORGANISM: Homo sapiens

<400> SEQUENCE: 105

```
cactaatctt tactcttttt ccacttattc gaccctcccc ttccagctgg gcacaggtgg    60
```

<210> SEQ ID NO 106
<211> LENGTH: 60
<212> TYPE: DNA
<213> ORGANISM: Homo sapiens

<400> SEQUENCE: 106

```
caccgacccg tccgggcccg ctgccacatc gaggtgaagt tttaaaaaaa aagttgtgga    60
```

<210> SEQ ID NO 107
<211> LENGTH: 60
<212> TYPE: DNA
<213> ORGANISM: Homo sapiens

<400> SEQUENCE: 107
caatatgacg gtgacattaa tgatagcttc gacacttcgg ctccctgcac ctcccatgcc    60

<210> SEQ ID NO 108
<211> LENGTH: 60
<212> TYPE: DNA
<213> ORGANISM: Homo sapiens

<400> SEQUENCE: 108
attcccaatg tttcctgagt agaactgttc gactgcgagc tccctccctg cagtcaggga    60

<210> SEQ ID NO 109
<211> LENGTH: 60
<212> TYPE: DNA
<213> ORGANISM: Homo sapiens

<400> SEQUENCE: 109
ctttcaaaca aatgaccttc accactgttc gatcacggct cactgcagcc ttggcctcct    60

<210> SEQ ID NO 110
<211> LENGTH: 60
<212> TYPE: DNA
<213> ORGANISM: Homo sapiens

<400> SEQUENCE: 110
cccacacacc gctggtgccc aaggactgtc gacctccccg aaccccctccg cctctgcgct    60

<210> SEQ ID NO 111
<211> LENGTH: 60
<212> TYPE: DNA
<213> ORGANISM: Homo sapiens

<400> SEQUENCE: 111
ttatgatatt gtaaattatt tttaatattc gagcaaactg acttggggcc cctatgtgtg    60

<210> SEQ ID NO 112
<211> LENGTH: 60
<212> TYPE: DNA
<213> ORGANISM: Homo sapiens

<400> SEQUENCE: 112
agtggtctca ccatggcttt cttccaattc gattcaccct cctcagcctc ccaaagtgct    60

<210> SEQ ID NO 113
<211> LENGTH: 60
<212> TYPE: DNA
<213> ORGANISM: Homo sapiens

<400> SEQUENCE: 113
agggagaaca aagaagttc catccatctc gatcccccg ggctcaaagc aaacctccta    60

<210> SEQ ID NO 114
<211> LENGTH: 60
<212> TYPE: DNA
<213> ORGANISM: Homo sapiens

<400> SEQUENCE: 114
caaaatcaaa cacaaatcta atcaaacttc gatgtttggg ggcggagggc tttgatgaga    60

<210> SEQ ID NO 115
<211> LENGTH: 60
<212> TYPE: DNA
<213> ORGANISM: Homo sapiens

```
<400> SEQUENCE: 115
gcgcagcctc tggcgccccc tgccggcctc gagaagcata aagcagggac aggtatggag      60

<210> SEQ ID NO 116
<211> LENGTH: 60
<212> TYPE: DNA
<213> ORGANISM: Homo sapiens

<400> SEQUENCE: 116
aatttatgga ttgtatgtta ctactgtatc gagatcttcc tacctcaccg tcccaagtag      60

<210> SEQ ID NO 117
<211> LENGTH: 60
<212> TYPE: DNA
<213> ORGANISM: Homo sapiens

<400> SEQUENCE: 117
tccagggatg gcagagtctc tggcagcctc gatgcggggc gggaggggcg gccgggaaag      60

<210> SEQ ID NO 118
<211> LENGTH: 60
<212> TYPE: DNA
<213> ORGANISM: Homo sapiens

<400> SEQUENCE: 118
gggtttcacc ctgttggcca ggctggtctc gagaccggcc tggccaacat ggtgaaaccc      60

<210> SEQ ID NO 119
<211> LENGTH: 60
<212> TYPE: DNA
<213> ORGANISM: Homo sapiens

<400> SEQUENCE: 119
ataaaatggg gaggccttcc agaagctctc gaccgccacc tcctccagga agccctgcct      60

<210> SEQ ID NO 120
<211> LENGTH: 60
<212> TYPE: DNA
<213> ORGANISM: Homo sapiens

<400> SEQUENCE: 120
ctgacccctc caggggaggc ccggcccctc gaggaggaag tggctgatta ctgagcggtt      60

<210> SEQ ID NO 121
<211> LENGTH: 60
<212> TYPE: DNA
<213> ORGANISM: Homo sapiens

<400> SEQUENCE: 121
cctaatattt cattatgata agaaagattc gagagtaagt ttcttctgtt cactcaggag      60

<210> SEQ ID NO 122
<211> LENGTH: 60
<212> TYPE: DNA
<213> ORGANISM: Homo sapiens

<400> SEQUENCE: 122
ataaaatggg gaggccttcc agaagctctc gacctccagg tcccccgcca cttccacggc      60

<210> SEQ ID NO 123
<211> LENGTH: 60
<212> TYPE: DNA
<213> ORGANISM: Homo sapiens
```

```
<400> SEQUENCE: 123
tttcaaagaa ggtatgatgg gaaaggtctc gagtgcccct gtcccacctg gctcccctg      60

<210> SEQ ID NO 124
<211> LENGTH: 60
<212> TYPE: DNA
<213> ORGANISM: Homo sapiens

<400> SEQUENCE: 124
cgcacgctgg ggctgcgcga ggcagagatc gatccccgcc cagccctggg ggtgcccact      60

<210> SEQ ID NO 125
<211> LENGTH: 60
<212> TYPE: DNA
<213> ORGANISM: Homo sapiens

<400> SEQUENCE: 125 ctgaccctc caggggaggc ccggcccctc gagaactcag ggccagcctt cccagcttgg      60

<210> SEQ ID NO 126
<211> LENGTH: 60
<212> TYPE: DNA
<213> ORGANISM: Homo sapiens

<400> SEQUENCE: 126
cgtgaatata ttgggctcta atggataatc gagagccggc ctcctgccct ttctaaaggc      60

<210> SEQ ID NO 127
<211> LENGTH: 60
<212> TYPE: DNA
<213> ORGANISM: Homo sapiens

<400> SEQUENCE: 127
attgacctgt taaagacttg atttagtgtc gaaggaattc agctttcaaa atgcacctaa      60

<210> SEQ ID NO 128
<211> LENGTH: 60
<212> TYPE: DNA
<213> ORGANISM: Homo sapiens

<400> SEQUENCE: 128
tcctaggaga gactgaactt taaagatatc gacctgctga tccttggatc ctgaatctgt      60

<210> SEQ ID NO 129
<211> LENGTH: 60
<212> TYPE: DNA
<213> ORGANISM: Homo sapiens

<400> SEQUENCE: 129
gtctttgtgt aaataaataa ggtaaccctc gagagccggc ctcctgccct ttctaaaggc      60

<210> SEQ ID NO 130
<211> LENGTH: 60
<212> TYPE: DNA
<213> ORGANISM: Homo sapiens

<400> SEQUENCE: 130
tacagacttt ttttctcttc tcagaaaatc gatgtttggg ggcggagggc tttgatgaga      60

<210> SEQ ID NO 131
<211> LENGTH: 60
<212> TYPE: DNA
```

<213> ORGANISM: Homo sapiens

<400> SEQUENCE: 131
gttcatggat tactttgaag tcaggagttc gatgtggcag cgggcccgga cgggtcggtg    60

<210> SEQ ID NO 132
<211> LENGTH: 60
<212> TYPE: DNA
<213> ORGANISM: Homo sapiens

<400> SEQUENCE: 132
cccgtcttcc ccaaaatcta tgtggtcctc gacagcgacg tgggggtgta ccgcgcggtg    60

<210> SEQ ID NO 133
<211> LENGTH: 60
<212> TYPE: DNA
<213> ORGANISM: Homo sapiens

<400> SEQUENCE: 133
tgcggaaatg atggacacta caccttcatc gagatcttgg ttcactgcaa cctctgtctc    60

<210> SEQ ID NO 134
<211> LENGTH: 60
<212> TYPE: DNA
<213> ORGANISM: Homo sapiens

<400> SEQUENCE: 134
agctggagtc ttgattaaca caaaaatctc gagattcact gcgctgcaca ccagggcctc    60

<210> SEQ ID NO 135
<211> LENGTH: 60
<212> TYPE: DNA
<213> ORGANISM: Homo sapiens

<400> SEQUENCE: 135
caaatcccgg ctatctctta gaattgcatc gattcaccct cctcagcctc ccaaagtgct    60

<210> SEQ ID NO 136
<211> LENGTH: 60
<212> TYPE: DNA
<213> ORGANISM: Homo sapiens

<400> SEQUENCE: 136
ccgcctcacc tcccgcatgg tcttgaggtc gagcatgcag cgcatctgag cagtgaggct    60

<210> SEQ ID NO 137
<211> LENGTH: 60
<212> TYPE: DNA
<213> ORGANISM: Homo sapiens

<400> SEQUENCE: 137
agggagaaca aaagaagttc catccatctc gacggagtcc tccccgcagg gcagccccga    60

<210> SEQ ID NO 138
<211> LENGTH: 60
<212> TYPE: DNA
<213> ORGANISM: Homo sapiens

<400> SEQUENCE: 138
ttttactgtt tttgtaagag atatgttttc gaaactctct ccaatgaaac aattctttga    60

<210> SEQ ID NO 139
<211> LENGTH: 60

<212> TYPE: DNA
<213> ORGANISM: Homo sapiens

<400> SEQUENCE: 139 gtatttgat gataaaagct gaacaacttc gattccaaag tgaagcaaaa aaaaaacttc    60

<210> SEQ ID NO 140
<211> LENGTH: 60
<212> TYPE: DNA
<213> ORGANISM: Homo sapiens

<400> SEQUENCE: 140
tgttttttat tgtttgatgt ccaatgtatc gagtttcagt gtatttgaca tgttattcca    60

<210> SEQ ID NO 141
<211> LENGTH: 60
<212> TYPE: DNA
<213> ORGANISM: Homo sapiens

<400> SEQUENCE: 141
atttgacaac gctggcacgg aggcaagatc gacctccctg tccctcctgg gcctctccgg    60

<210> SEQ ID NO 142
<211> LENGTH: 60
<212> TYPE: DNA
<213> ORGANISM: Homo sapiens

<400> SEQUENCE: 142
tcttctctcc ctcactcagt atcctcactc gatgcgcgcc cgccggggcc cggtcggagc    60

<210> SEQ ID NO 143
<211> LENGTH: 60
<212> TYPE: DNA
<213> ORGANISM: Homo sapiens

<400> SEQUENCE: 143
gaggatttaa taaaacccaa actgtatttc gagaaaatag tgttttgcta tttagataag    60

<210> SEQ ID NO 144
<211> LENGTH: 60
<212> TYPE: DNA
<213> ORGANISM: Homo sapiens

<400> SEQUENCE: 144
gcgccctatt tccaccttgt gccttctgtc gagacatcta agaaggtcca gccagatgtt    60

<210> SEQ ID NO 145
<211> LENGTH: 60
<212> TYPE: DNA
<213> ORGANISM: Homo sapiens

<400> SEQUENCE: 145
tacagacttt ttttctcttc tcagaaaatc gatgtttggg ggcggagggc tttgatgaga    60

<210> SEQ ID NO 146
<211> LENGTH: 60
<212> TYPE: DNA
<213> ORGANISM: Homo sapiens

<400> SEQUENCE: 146
gtgacaatta agagtgtgac attgcttctc gaggactcac tgggcctgca gggggggcagc    60

<210> SEQ ID NO 147

```
<211> LENGTH: 60
<212> TYPE: DNA
<213> ORGANISM: Homo sapiens

<400> SEQUENCE: 147
gtggcaggag aaaaacgcgg ccccaccctc gaaaatacta gaattatgcc gcacagtcag      60

<210> SEQ ID NO 148
<211> LENGTH: 60
<212> TYPE: DNA
<213> ORGANISM: Homo sapiens

<400> SEQUENCE: 148
acatcgctac caggccgatg tgctgatatc gaggtcccca accccctgcc gctcatcgtg      60

<210> SEQ ID NO 149
<211> LENGTH: 60
<212> TYPE: DNA
<213> ORGANISM: Homo sapiens

<400> SEQUENCE: 149
aagtcttttg tttggttatt gtgctgtatc gaatcaaagc tgtgtcacaa actatgtaac      60

<210> SEQ ID NO 150
<211> LENGTH: 60
<212> TYPE: DNA
<213> ORGANISM: Homo sapiens

<400> SEQUENCE: 150
gcggggcttt ccctcaactt cagggaggtc gaggcgcggc gcgcaggccg ccatcgccac      60

<210> SEQ ID NO 151
<211> LENGTH: 60
<212> TYPE: DNA
<213> ORGANISM: Homo sapiens

<400> SEQUENCE: 151
cgtagaacta agatgtattc aaagtcagtc gaaatcacct gtcccggcct ctttccaaac      60

<210> SEQ ID NO 152
<211> LENGTH: 60
<212> TYPE: DNA
<213> ORGANISM: Homo sapiens

<400> SEQUENCE: 152
gacctaagga ttaagaagat taatggagtc gagcatcctc tacctctatc tccaacccct      60

<210> SEQ ID NO 153
<211> LENGTH: 60
<212> TYPE: DNA
<213> ORGANISM: Homo sapiens

<400> SEQUENCE: 153
ctggcgttcc agccctcgca ccttggcctc gaactttaca gagggatcta gaatgagtga      60

<210> SEQ ID NO 154
<211> LENGTH: 60
<212> TYPE: DNA
<213> ORGANISM: Homo sapiens

<400> SEQUENCE: 154
acatgaccgt gatacctctg tcactctgtc gatggggacc tgaaccgggg ccgcacaagc      60
```

```
<210> SEQ ID NO 155
<211> LENGTH: 60
<212> TYPE: DNA
<213> ORGANISM: Homo sapiens

<400> SEQUENCE: 155
tggaagcagc tatacagctg tgaccacatc gacgccctg tcacgggccc tgttattcaa      60

<210> SEQ ID NO 156
<211> LENGTH: 60
<212> TYPE: DNA
<213> ORGANISM: Homo sapiens

<400> SEQUENCE: 156
aggcgacact cttgtccccg ccatcttttc gaaggcccc gtcctcctgc gccatggaga      60

<210> SEQ ID NO 157
<211> LENGTH: 60
<212> TYPE: DNA
<213> ORGANISM: Homo sapiens

<400> SEQUENCE: 157
aataaacatc ttttgctca tacattattc gaatccccag cccttccctc tgcccaccct      60

<210> SEQ ID NO 158
<211> LENGTH: 60
<212> TYPE: DNA
<213> ORGANISM: Homo sapiens

<400> SEQUENCE: 158
ggaccttgtc atcctgcccc ttcttggctc gagccctgcc tggccagcac acactgcatc      60

<210> SEQ ID NO 159
<211> LENGTH: 60
<212> TYPE: DNA
<213> ORGANISM: Homo sapiens

<400> SEQUENCE: 159
catcatagca acccattgta actagacttc gaatagatac ttcaggaaag aaatgtatat      60

<210> SEQ ID NO 160
<211> LENGTH: 60
<212> TYPE: DNA
<213> ORGANISM: Homo sapiens

<400> SEQUENCE: 160
atcccaacaa aagagaagaa cttctccctc gatgtttggg ggcggagggc tttgatgaga      60

<210> SEQ ID NO 161
<211> LENGTH: 60
<212> TYPE: DNA
<213> ORGANISM: Homo sapiens

<400> SEQUENCE: 161
gcagccagcc cggtgggggt gggggggtc gacgctcgcc tccgctcaca gcctcagcat      60

<210> SEQ ID NO 162
<211> LENGTH: 60
<212> TYPE: DNA
<213> ORGANISM: Homo sapiens

<400> SEQUENCE: 162
acatgagatg tccttcaagt gaaactgttc gaccatgccc gggcaggtgg ctgagacctc      60
```

<210> SEQ ID NO 163
<211> LENGTH: 60
<212> TYPE: DNA
<213> ORGANISM: Homo sapiens

<400> SEQUENCE: 163
taaaccatag ttaattttat gtaaatattc gaatcttttc aggatggtag catctttaaa    60

<210> SEQ ID NO 164
<211> LENGTH: 60
<212> TYPE: DNA
<213> ORGANISM: Homo sapiens

<400> SEQUENCE: 164
acatgaccgt gatacctctg tcactctgtc gatggggacc tgaaccgggg ccgcacaagc    60

<210> SEQ ID NO 165
<211> LENGTH: 60
<212> TYPE: DNA
<213> ORGANISM: Homo sapiens

<400> SEQUENCE: 165
tgactgtatt tacaacatgt ctagattttc gagtgtaaaa gggcttttac tggtgcacac    60

<210> SEQ ID NO 166
<211> LENGTH: 60
<212> TYPE: DNA
<213> ORGANISM: Homo sapiens

<400> SEQUENCE: 166
taggcctggg ggccgaaagg aagaagcttc gactgaggcg ggtcccagcc cctccaggga    60

<210> SEQ ID NO 167
<211> LENGTH: 60
<212> TYPE: DNA
<213> ORGANISM: Homo sapiens

<400> SEQUENCE: 167
ctgacccctc caggggaggc ccggcccctc gagaactcag ggccagcctt cccagcttgg    60

<210> SEQ ID NO 168
<211> LENGTH: 60
<212> TYPE: DNA
<213> ORGANISM: Homo sapiens

<400> SEQUENCE: 168
gtagttcact ctgtcccttt tcctatgatc gattttgctc cccccacctt accccccagag    60

<210> SEQ ID NO 169
<211> LENGTH: 60
<212> TYPE: DNA
<213> ORGANISM: Homo sapiens

<400> SEQUENCE: 169 tgtttttat tgtttgatgt ccaatgtatc gataaacaaa ttatacaaca aaagtctaag    60

<210> SEQ ID NO 170
<211> LENGTH: 60
<212> TYPE: DNA
<213> ORGANISM: Homo sapiens

<400> SEQUENCE: 170
aggcgacact cttgtccccg ccatcttttc gaaggccccc gtcctcctgc gccatggaga    60

<210> SEQ ID NO 171
<211> LENGTH: 60
<212> TYPE: DNA
<213> ORGANISM: Homo sapiens

<400> SEQUENCE: 171
tccattgtct tattccagtc taggcttgtc gaactggcgg caaccgctgc agcgcctgct    60

<210> SEQ ID NO 172
<211> LENGTH: 60
<212> TYPE: DNA
<213> ORGANISM: Homo sapiens

<400> SEQUENCE: 172
ttaatgctga tacaattcta ttggataatc gacgtgcctt ggggcctccc ctttccctat    60

<210> SEQ ID NO 173
<211> LENGTH: 60
<212> TYPE: DNA
<213> ORGANISM: Homo sapiens

<400> SEQUENCE: 173
tttttttcct ctcttatctt gatgcctctc gagcttcctg gccactttgt ttacctactc    60

<210> SEQ ID NO 174
<211> LENGTH: 60
<212> TYPE: DNA
<213> ORGANISM: Homo sapiens

<400> SEQUENCE: 174
cgtggatcca gactgggagc ccccagcctc gaaccacgcc aggcttccag gcgtcagtgc    60

<210> SEQ ID NO 175
<211> LENGTH: 60
<212> TYPE: DNA
<213> ORGANISM: Homo sapiens

<400> SEQUENCE: 175
ataaaatggg gaggccttcc agaagctctc gacctccagg tcccccgcca cttccacggc    60

<210> SEQ ID NO 176
<211> LENGTH: 60
<212> TYPE: DNA
<213> ORGANISM: Homo sapiens

<400> SEQUENCE: 176
aagtcttttg tttggttatt gtgctgtatc gaagtcttga cctcaggtga tccacccacc    60

<210> SEQ ID NO 177
<211> LENGTH: 60
<212> TYPE: DNA
<213> ORGANISM: Homo sapiens

<400> SEQUENCE: 177
gtgtctcggc ccctggggc cccacccttc gagtgcatcc tgcagctgtt tgtccagaag    60

<210> SEQ ID NO 178
<211> LENGTH: 60
<212> TYPE: DNA
<213> ORGANISM: Homo sapiens

<400> SEQUENCE: 178

```
catcatcaca gtctacggct gtttcctctc gaaggccccc gtcctcctgc gccatggaga    60
```

<210> SEQ ID NO 179
<211> LENGTH: 60
<212> TYPE: DNA
<213> ORGANISM: Homo sapiens

<400> SEQUENCE: 179

```
cactaatctt tactctttt ccacttattc gaagtttcca gaaaagtcct gaagttttaa    60
```

<210> SEQ ID NO 180
<211> LENGTH: 60
<212> TYPE: DNA
<213> ORGANISM: Homo sapiens

<400> SEQUENCE: 180

```
ccgcctccgt ctgcgcctgg gccaggcctc gacctgcctg tcaatatttg caatcactgc    60
```

<210> SEQ ID NO 181
<211> LENGTH: 60
<212> TYPE: DNA
<213> ORGANISM: Homo sapiens

<400> SEQUENCE: 181

```
acgcccgcct ccatgagatt cagagccctc gactcctttc ccagacacat tcagcacgtg    60
```

<210> SEQ ID NO 182
<211> LENGTH: 60
<212> TYPE: DNA
<213> ORGANISM: Homo sapiens

<400> SEQUENCE: 182

```
tcccacccac tcttaatcaa cattccattc gatttaatcc tacatgctcc tttcttatgt    60
```

<210> SEQ ID NO 183
<211> LENGTH: 60
<212> TYPE: DNA
<213> ORGANISM: Homo sapiens

<400> SEQUENCE: 183

```
attttgacat ctgcattta cagcagcctc gatgcgagct cgtggtgggt gctcaagact    60
```

<210> SEQ ID NO 184
<211> LENGTH: 60
<212> TYPE: DNA
<213> ORGANISM: Homo sapiens

<400> SEQUENCE: 184

```
aagtcttttg tttggttatt gtgctgtatc gatccagctt tttgactcta aaatgagctt    60
```

<210> SEQ ID NO 185
<211> LENGTH: 60
<212> TYPE: DNA
<213> ORGANISM: Homo sapiens

<400> SEQUENCE: 185

```
ggcaaatgct acaaatcaga gttgtttttc gatcacactg ggagctgcag accggagctg    60
```

<210> SEQ ID NO 186
<211> LENGTH: 60
<212> TYPE: DNA
<213> ORGANISM: Homo sapiens

<400> SEQUENCE: 186

```
gcagccagcc cggtgggggt ggggggggtc gacgctcgcc tccgctcaca gcctcagcat    60
```

<210> SEQ ID NO 187
<211> LENGTH: 60
<212> TYPE: DNA
<213> ORGANISM: Homo sapiens

<400> SEQUENCE: 187

```
gtgtgcacca gtaaaagccc ttttacactc gacctgctga tccttggatc ctgaatctgt    60
```

<210> SEQ ID NO 188
<211> LENGTH: 60
<212> TYPE: DNA
<213> ORGANISM: Homo sapiens

<400> SEQUENCE: 188

```
cgggtgcctc cccccccatt cgccctgctc gagggaggga aatgattgga ttacggggt    60
```

<210> SEQ ID NO 189
<211> LENGTH: 60
<212> TYPE: DNA
<213> ORGANISM: Homo sapiens

<400> SEQUENCE: 189

```
ctccatctcc ctgccctctg atcccccctc gattctacag tggttttaac agcaggcccc    60
```

<210> SEQ ID NO 190
<211> LENGTH: 60
<212> TYPE: DNA
<213> ORGANISM: Homo sapiens

<400> SEQUENCE: 190

```
gtgtgggccc ccctgctacc gctgcgtatc gagcacctct tcaggggagg attactgcaa    60
```

<210> SEQ ID NO 191
<211> LENGTH: 60
<212> TYPE: DNA
<213> ORGANISM: Homo sapiens

<400> SEQUENCE: 191

```
cgttgcaaat tgtacatctt ctgctatttc gagacctcat ataactcggt gattgactgc    60
```

<210> SEQ ID NO 192
<211> LENGTH: 60
<212> TYPE: DNA
<213> ORGANISM: Homo sapiens

<400> SEQUENCE: 192

```
taacaaggag tggagtattc ctgggatatc gaccccaccc cctagattaa gacattcctg    60
```

<210> SEQ ID NO 193
<211> LENGTH: 60
<212> TYPE: DNA
<213> ORGANISM: Homo sapiens

<400> SEQUENCE: 193

```
aacaaggcag gtagtgttcc tgccctcatc gatgtggcag cgggcccgga cgggtcggtg    60
```

<210> SEQ ID NO 194
<211> LENGTH: 60
<212> TYPE: DNA
<213> ORGANISM: Homo sapiens -continued

<400> SEQUENCE: 194
tcttctctcc ctcactcagt atcctcactc gatgcgcgcc cgccggggcc cggtcggagc    60

<210> SEQ ID NO 195
<211> LENGTH: 60
<212> TYPE: DNA
<213> ORGANISM: Homo sapiens

<400> SEQUENCE: 195
gtgacaatta agagtgtgac attgcttctc gaggactcac tgggcctgca gggggggcagc   60

<210> SEQ ID NO 196
<211> LENGTH: 60
<212> TYPE: DNA
<213> ORGANISM: Homo sapiens

<400> SEQUENCE: 196
aggtggagat cagaagaccc ccacgccctc gagtcacagc tgtagtgggg tgggggtga    60

<210> SEQ ID NO 197
<211> LENGTH: 60
<212> TYPE: DNA
<213> ORGANISM: Homo sapiens

<400> SEQUENCE: 197
gcactacccc ggcctgccgg agcccagtc gagttggttt ctgggtccgc accccctccc    60

<210> SEQ ID NO 198
<211> LENGTH: 60
<212> TYPE: DNA
<213> ORGANISM: Homo sapiens

<400> SEQUENCE: 198
gaatgtttac ctattataaa aatgaggatc gagcacagcg ccggctgggg tacctggcac    60

<210> SEQ ID NO 199
<211> LENGTH: 60
<212> TYPE: DNA
<213> ORGANISM: Homo sapiens

<400> SEQUENCE: 199 gcggggctt ccctcaactt cagggaggtc gaggcgcggc gcgcaggccg ccatcgccac     60

<210> SEQ ID NO 200
<211> LENGTH: 60
<212> TYPE: DNA
<213> ORGANISM: Homo sapiens

<400> SEQUENCE: 200
tcagataagt aacttcctga taattaactc gaaaaaacat taatttcttc aggtgtaaag    60

<210> SEQ ID NO 201
<211> LENGTH: 60
<212> TYPE: DNA
<213> ORGANISM: Homo sapiens

<400> SEQUENCE: 201
ccacccccgc cccgggggag tcgcccggtc gaggtggctt gggtcttagt cttccaggca    60

<210> SEQ ID NO 202
<211> LENGTH: 60
<212> TYPE: DNA
<213> ORGANISM: Homo sapiens

<400> SEQUENCE: 202
catcatcaca gtctacggct gtttcctctc gaaggccccc gtcctcctgc gccatggaga    60

<210> SEQ ID NO 203
<211> LENGTH: 60
<212> TYPE: DNA
<213> ORGANISM: Homo sapiens

<400> SEQUENCE: 203
aagctcattt tagagtcaaa aagctggatc gaggccgtgc tgcgtcggcg cgggcccgcg    60

<210> SEQ ID NO 204
<211> LENGTH: 60
<212> TYPE: DNA
<213> ORGANISM: Homo sapiens

<400> SEQUENCE: 204
tattttattt gttactaaaa caaggaactc gatttcgcca agggccaggc tcccaaggca    60

<210> SEQ ID NO 205
<211> LENGTH: 60
<212> TYPE: DNA
<213> ORGANISM: Homo sapiens

<400> SEQUENCE: 205
gaggcttctg agttgctctg agggtacatc gatgcgcgcc cgccggggcc cggtcggagc    60

<210> SEQ ID NO 206
<211> LENGTH: 60
<212> TYPE: DNA
<213> ORGANISM: Homo sapiens

<400> SEQUENCE: 206
gtgtgggccc ccctgctacc gctgcgtatc gaactttaca gagggatcta gaatgagtga    60

<210> SEQ ID NO 207
<211> LENGTH: 60
<212> TYPE: DNA
<213> ORGANISM: Homo sapiens

<400> SEQUENCE: 207
cggacaaggt gaggaccacg tgggccagtc gatggggacc tgaaccgggg ccgcacaagc    60

<210> SEQ ID NO 208
<211> LENGTH: 60
<212> TYPE: DNA
<213> ORGANISM: Homo sapiens

<400> SEQUENCE: 208
ggaccttgtc atcctgcccc ttcttggctc gaggccctga acaggactc tatgtctcct    60

<210> SEQ ID NO 209
<211> LENGTH: 60
<212> TYPE: DNA
<213> ORGANISM: Homo sapiens

<400> SEQUENCE: 209
agtgctgggt tccacacctc tcagctcttc gacctccagg tcccccgcca cttccacggc    60

<210> SEQ ID NO 210
<211> LENGTH: 60
<212> TYPE: DNA

<213> ORGANISM: Homo sapiens

<400> SEQUENCE: 210
tcaatgccat cactagacat ggaactcttc gagccatcct cccagtgaca ctccgcaaag    60

<210> SEQ ID NO 211
<211> LENGTH: 60
<212> TYPE: DNA
<213> ORGANISM: Homo sapiens

<400> SEQUENCE: 211
gacccccggg aattggctcc agcacatctc gagggcgggc ccggcggccc cggagcaaac    60

<210> SEQ ID NO 212
<211> LENGTH: 60
<212> TYPE: DNA
<213> ORGANISM: Homo sapiens

<400> SEQUENCE: 212
gtgtctcggc ccctggggc cccacccttc gatactatta cgaatggaat cactgtctta    60

<210> SEQ ID NO 213
<211> LENGTH: 60
<212> TYPE: DNA
<213> ORGANISM: Homo sapiens

<400> SEQUENCE: 213
ggcacctgtt agcaatgaag gataaccatc gaccatcttg gttccacctg gcagtttctt    60

<210> SEQ ID NO 214
<211> LENGTH: 60
<212> TYPE: DNA
<213> ORGANISM: Homo sapiens

<400> SEQUENCE: 214
cgtggatcca gactgggagc ccccagcctc gaaccacgcc aggcttccag gcgtcagtgc    60

<210> SEQ ID NO 215
<211> LENGTH: 60
<212> TYPE: DNA
<213> ORGANISM: Homo sapiens

<400> SEQUENCE: 215
gcactacccc ggcctgccgg agcccagtc gatgatggct tcctccccca gagcaccagc    60

<210> SEQ ID NO 216
<211> LENGTH: 60
<212> TYPE: DNA
<213> ORGANISM: Homo sapiens

<400> SEQUENCE: 216
aacaaggcag gtagtgttcc tgccctcatc gatgtggcag cgggcccgga cgggtcggtg    60

<210> SEQ ID NO 217
<211> LENGTH: 60
<212> TYPE: DNA
<213> ORGANISM: Homo sapiens

<400> SEQUENCE: 217
acgcccgcct ccatgagatt cagagccctc gagaatgtgg actctccttt cccccagcac    60

<210> SEQ ID NO 218
<211> LENGTH: 60

-continued

<212> TYPE: DNA
<213> ORGANISM: Homo sapiens

<400> SEQUENCE: 218
tgagctaata aactatttct ggttttgctc gagccatcct cccagtgaca ctccgcaaag    60

<210> SEQ ID NO 219
<211> LENGTH: 60
<212> TYPE: DNA
<213> ORGANISM: Homo sapiens

<400> SEQUENCE: 219
gtcaccaggg ctccctcctc ctgcggaatc gaggctgtag atagctgtga ttgtaccact    60

<210> SEQ ID NO 220
<211> LENGTH: 60
<212> TYPE: DNA
<213> ORGANISM: Homo sapiens

<400> SEQUENCE: 220
tcttagagtt gaacttttct aatcttttc gaagacccct tccattgggc attcatctaa    60

<210> SEQ ID NO 221
<211> LENGTH: 60
<212> TYPE: DNA
<213> ORGANISM: Homo sapiens

<400> SEQUENCE: 221
ccagaaattc tgtggttgat gaatttggtc gagccatcct cccagtgaca ctccgcaaag    60

<210> SEQ ID NO 222
<211> LENGTH: 60
<212> TYPE: DNA
<213> ORGANISM: Homo sapiens

<400> SEQUENCE: 222
tgagatgaag cctatatttt cccaatcctc gatgtttggg ggcggagggc tttgatgaga    60

<210> SEQ ID NO 223
<211> LENGTH: 60
<212> TYPE: DNA
<213> ORGANISM: Homo sapiens

<400> SEQUENCE: 223
caggctattg tagtgctctt cctggccctc gacacccct tcaagggtct gtgtcccata    60

<210> SEQ ID NO 224
<211> LENGTH: 60
<212> TYPE: DNA
<213> ORGANISM: Homo sapiens

<400> SEQUENCE: 224
caccgcgcgg tacacccca cgtcgctgtc gacattttct taccagcctg gctgataaac    60

<210> SEQ ID NO 225
<211> LENGTH: 60
<212> TYPE: DNA
<213> ORGANISM: Homo sapiens

<400> SEQUENCE: 225
gtaagccatg gaaatatgaa tccatttctc gatgccaatc cacgtcatta gatgaggacc    60

<210> SEQ ID NO 226

```
<211> LENGTH: 60
<212> TYPE: DNA
<213> ORGANISM: Homo sapiens

<400> SEQUENCE: 226
ttaatgctga tacaattcta ttggataatc gacgtgcctt ggggcctccc ctttccctat    60

<210> SEQ ID NO 227
<211> LENGTH: 60
<212> TYPE: DNA
<213> ORGANISM: Homo sapiens

<400> SEQUENCE: 227
ccatctgcaa gtcgcttttg actagcactc gagttctttc tgacatctcc tgggtggagc    60

<210> SEQ ID NO 228
<211> LENGTH: 60
<212> TYPE: DNA
<213> ORGANISM: Homo sapiens

<400> SEQUENCE: 228
aagtcttttg tttggttatt gtgctgtatc gacctcctgg actcaagcaa tcctcggcct    60

<210> SEQ ID NO 229
<211> LENGTH: 60
<212> TYPE: DNA
<213> ORGANISM: Homo sapiens

<400> SEQUENCE: 229
gcactacccc ggcctgccgg agccccagtc gacatgttgc cccagctggt ctcaaactcc    60

<210> SEQ ID NO 230
<211> LENGTH: 60
<212> TYPE: DNA
<213> ORGANISM: Homo sapiens

<400> SEQUENCE: 230
aggaagtatg tttgatttag aatgttattc gagccgccct tgacataaca ccatctttta    60

<210> SEQ ID NO 231
<211> LENGTH: 60
<212> TYPE: DNA
<213> ORGANISM: Homo sapiens

<400> SEQUENCE: 231
gtggccaccg cccttgcgct ttatgacatc gattttggct ctgtagggaa aggctcttat    60

<210> SEQ ID NO 232
<211> LENGTH: 60
<212> TYPE: DNA
<213> ORGANISM: Homo sapiens

<400> SEQUENCE: 232
cgcgcactga aaccctagcc gcgggggatc gaaatcatat caccagtcat tccactcctg    60

<210> SEQ ID NO 233
<211> LENGTH: 60
<212> TYPE: DNA
<213> ORGANISM: Homo sapiens

<400> SEQUENCE: 233
tttgctaaat tacccaaaat tttgcttttc gatgctggga acactttcct ccagagttga    60
```

```
<210> SEQ ID NO 234
<211> LENGTH: 60
<212> TYPE: DNA
<213> ORGANISM: Homo sapiens

<400> SEQUENCE: 234
gtccctgaaa atgtttgtaa atgtggggtc gacctgctgg gctcgggcta tccttccatc    60

<210> SEQ ID NO 235
<211> LENGTH: 60
<212> TYPE: DNA
<213> ORGANISM: Homo sapiens

<400> SEQUENCE: 235
cactaatctt tactcttttt ccacttattc gagaccagtg aaacctcgtc gctacaaaaa    60

<210> SEQ ID NO 236
<211> LENGTH: 60
<212> TYPE: DNA
<213> ORGANISM: Homo sapiens

<400> SEQUENCE: 236
tgttttttat tgtttgatgt ccaatgtatc gagtcacatg atcaagcgct catttctgtt    60

<210> SEQ ID NO 237
<211> LENGTH: 60
<212> TYPE: DNA
<213> ORGANISM: Homo sapiens

<400> SEQUENCE: 237
cttttccatt gcttcctcag atcctctgtc gagattcact gcgctgcaca ccagggcctc    60

<210> SEQ ID NO 238
<211> LENGTH: 60
<212> TYPE: DNA
<213> ORGANISM: Homo sapiens

<400> SEQUENCE: 238
aggacctgaa atccaggaag atctgacttc gagacgatcc cggccaacat ggtgaaaccc    60

<210> SEQ ID NO 239
<211> LENGTH: 60
<212> TYPE: DNA
<213> ORGANISM: Homo sapiens

<400> SEQUENCE: 239
tatttgtatc ctttcctcat ttatttactc gaatctctgg ggtagggctc tgcaaccttg    60

<210> SEQ ID NO 240
<211> LENGTH: 60
<212> TYPE: DNA
<213> ORGANISM: Homo sapiens

<400> SEQUENCE: 240
ccgcctccgt ctgcgcctgg gccaggcctc gagaattatt cttttcatat acaaagaata    60

<210> SEQ ID NO 241
<211> LENGTH: 60
<212> TYPE: DNA
<213> ORGANISM: Homo sapiens

<400> SEQUENCE: 241
aagctcattt tagagtcaaa aagctggatc gaggccgtgc tgcgtcggcg cgggcccgcg    60
```

<210> SEQ ID NO 242
<211> LENGTH: 60
<212> TYPE: DNA
<213> ORGANISM: Homo sapiens

<400> SEQUENCE: 242
gtaataaaca tacaaactta aacgtagttc gaggctcccg tggagggcac cgctgtcccc    60

<210> SEQ ID NO 243
<211> LENGTH: 60
<212> TYPE: DNA
<213> ORGANISM: Homo sapiens

<400> SEQUENCE: 243
gcactacccc ggcctgccgg agccccagtc gagttggttt ctgggtccgc accccctccc    60

<210> SEQ ID NO 244
<211> LENGTH: 60
<212> TYPE: DNA
<213> ORGANISM: Homo sapiens

<400> SEQUENCE: 244
agcgggcaga tcacttgagg tcaggagttc gaactcctga cctcaggtga tctgcctgcc    60

<210> SEQ ID NO 245
<211> LENGTH: 60
<212> TYPE: DNA
<213> ORGANISM: Homo sapiens

<400> SEQUENCE: 245
cttttccatt gcttcctcag atcctctgtc gagagcacgg cctctctggc gccttgccat    60

<210> SEQ ID NO 246
<211> LENGTH: 60
<212> TYPE: DNA
<213> ORGANISM: Homo sapiens

<400> SEQUENCE: 246
aaacttcctt tctttgctta gaactagctc gatcctggaa gcccctaaa ggcaggaact    60

<210> SEQ ID NO 247
<211> LENGTH: 60
<212> TYPE: DNA
<213> ORGANISM: Homo sapiens

<400> SEQUENCE: 247
ttgcactctc ggtctgtttt actaatcatc gagcttcctg gccactttgt ttacctactc    60

<210> SEQ ID NO 248
<211> LENGTH: 60
<212> TYPE: DNA
<213> ORGANISM: Homo sapiens

<400> SEQUENCE: 248
gccattaaat tccctaatg ccattgcctc gacttcagtg gcgtccattg tctgctggag    60

<210> SEQ ID NO 249
<211> LENGTH: 60
<212> TYPE: DNA
<213> ORGANISM: Homo sapiens

<400> SEQUENCE: 249
taacaaaagt aacacctctt tggtatcatc gaagagtcct tgttcccatt ttggcccagt    60

```
<210> SEQ ID NO 250
<211> LENGTH: 60
<212> TYPE: DNA
<213> ORGANISM: Homo sapiens

<400> SEQUENCE: 250
gtgacaatta agagtgtgac attgcttctc gatcccagag ccgtcccagg cctggacaga    60

<210> SEQ ID NO 251
<211> LENGTH: 60
<212> TYPE: DNA
<213> ORGANISM: Homo sapiens

<400> SEQUENCE: 251
gaaggctagg ctcccgcaca acgcctcctc gagcaagtta gttgaaccca aggagggtca    60

<210> SEQ ID NO 252
<211> LENGTH: 60
<212> TYPE: DNA
<213> ORGANISM: Homo sapiens

<400> SEQUENCE: 252
ttccatagat tacttttcaa atcatccttc gaagctggcg gctgagggcc cggcgccaag    60

<210> SEQ ID NO 253
<211> LENGTH: 60
<212> TYPE: DNA
<213> ORGANISM: Homo sapiens

<400> SEQUENCE: 253
gtggcaggag aaaaacgcgg ccccaccctc gaaaatacta gaattatgcc gcacagtcag    60

<210> SEQ ID NO 254
<211> LENGTH: 60
<212> TYPE: DNA
<213> ORGANISM: Homo sapiens

<400> SEQUENCE: 254
ttgccaagca cacatagctc ctcaatcctc gaagctggcg gctgagggcc cggcgccaag    60

<210> SEQ ID NO 255
<211> LENGTH: 60
<212> TYPE: DNA
<213> ORGANISM: Homo sapiens

<400> SEQUENCE: 255
gacaagctgc acatcccggc gctgaccctc gaggaagtga ggcttaattc cactccctac    60

<210> SEQ ID NO 256
<211> LENGTH: 60
<212> TYPE: DNA
<213> ORGANISM: Homo sapiens

<400> SEQUENCE: 256
aatttatgga ttgtatgtta ctactgtatc gagatcttcc tacctcaccg tcccaagtag    60

<210> SEQ ID NO 257
<211> LENGTH: 60
<212> TYPE: DNA
<213> ORGANISM: Homo sapiens

<400> SEQUENCE: 257
```

```
gcactacaga caaaagactc taactggatc gattagcttc tcctctctct tctaatcctc    60

<210> SEQ ID NO 258
<211> LENGTH: 60
<212> TYPE: DNA
<213> ORGANISM: Homo sapiens

<400> SEQUENCE: 258
gcactacccc ggcctgccgg agccccagtc gatgctattg gatagccagg agaaccggaa    60

<210> SEQ ID NO 259
<211> LENGTH: 60
<212> TYPE: DNA
<213> ORGANISM: Homo sapiens

<400> SEQUENCE: 259
ctctcaaact ggcttgtacc aggagtgttc gatttcgcca agggccaggc tcccaaggca    60

<210> SEQ ID NO 260
<211> LENGTH: 60
<212> TYPE: DNA
<213> ORGANISM: Homo sapiens

<400> SEQUENCE: 260
cgtggatcca gactgggagc ccccagcctc gagcagttgc actccagcct aggcaacaag    60

<210> SEQ ID NO 261
<211> LENGTH: 60
<212> TYPE: DNA
<213> ORGANISM: Homo sapiens

<400> SEQUENCE: 261
gtttatccca cacccaccct catgtctctc gaatatgcga cgacgcaccc tccccttgtt    60

<210> SEQ ID NO 262
<211> LENGTH: 60
<212> TYPE: DNA
<213> ORGANISM: Homo sapiens

<400> SEQUENCE: 262 atctttaat agataagtga aactttaatc gatattttcc agctatcttt ctgttgattt    60

<210> SEQ ID NO 263
<211> LENGTH: 60
<212> TYPE: DNA
<213> ORGANISM: Homo sapiens

<400> SEQUENCE: 263 tgcttttaa aaaatcaaag gtgtaacttc gacagcttcc ggaggctgcg aggctcgcaa    60

<210> SEQ ID NO 264
<211> LENGTH: 60
<212> TYPE: DNA
<213> ORGANISM: Homo sapiens

<400> SEQUENCE: 264
ctggcgttcc agccctcgca ccttggcctc gaactttaca gagggatcta gaatgagtga    60

<210> SEQ ID NO 265
<211> LENGTH: 60
<212> TYPE: DNA
<213> ORGANISM: Homo sapiens

<400> SEQUENCE: 265
```

-continued tgcccagaat gaccccaact aggaacaatc gaagggtccc cactcctcca cctgcaggac    60

<210> SEQ ID NO 266
<211> LENGTH: 60
<212> TYPE: DNA
<213> ORGANISM: Homo sapiens

<400> SEQUENCE: 266
gcttctcccc tctttatccc acctggcctc gagctcctaa actcacgcaa tccttccttc    60

<210> SEQ ID NO 267
<211> LENGTH: 60
<212> TYPE: DNA
<213> ORGANISM: Homo sapiens

<400> SEQUENCE: 267
ataattgcct agcttagact tgaatacctc gaccttatgc taagcctaaa cttgccttcc    60

<210> SEQ ID NO 268
<211> LENGTH: 60
<212> TYPE: DNA
<213> ORGANISM: Homo sapiens

<400> SEQUENCE: 268
ttacccttta agtcaatgcc tcaaaagttc gattgtccct tttttcctgt gccaccttt    60

<210> SEQ ID NO 269
<211> LENGTH: 60
<212> TYPE: DNA
<213> ORGANISM: Homo sapiens

<400> SEQUENCE: 269
gggtttcact gttttagcca ggctggtttc gagcggcccg gtgcgctgtg ggttggccgc    60

<210> SEQ ID NO 270
<211> LENGTH: 60
<212> TYPE: DNA
<213> ORGANISM: Homo sapiens

<400> SEQUENCE: 270
gaggcttctg agttgctctg agggtacatc gatgcgcgcc cgccggggcc cggtcggagc    60

<210> SEQ ID NO 271
<211> LENGTH: 60
<212> TYPE: DNA
<213> ORGANISM: Homo sapiens

<400> SEQUENCE: 271
accccctccc agcctcctgg tcaggagttc gagacatcta agaaggtcca gccagatgtt    60

<210> SEQ ID NO 272
<211> LENGTH: 60
<212> TYPE: DNA
<213> ORGANISM: Homo sapiens

<400> SEQUENCE: 272
gtattttgat gataaaagct gaacaacttc gatctcaggc tgttgcactt tctccatggg    60

<210> SEQ ID NO 273
<211> LENGTH: 60
<212> TYPE: DNA
<213> ORGANISM: Homo sapiens

```
<400> SEQUENCE: 273
ctaggaagct caccattccc ccaaggcctc gagccaccgt gcttcagctt ggacgacaga     60

<210> SEQ ID NO 274
<211> LENGTH: 60
<212> TYPE: DNA
<213> ORGANISM: Homo sapiens

<400> SEQUENCE: 274
cttgtttgtg gttgaaaatg actgaatatc gatcgcacgc ctgaactcca gtcttggcaa     60

<210> SEQ ID NO 275
<211> LENGTH: 60
<212> TYPE: DNA
<213> ORGANISM: Homo sapiens

<400> SEQUENCE: 275
atgagcaaag atagctcacg ggctctgctc gagtgtgacc gacgctgccc ctcactttca     60

<210> SEQ ID NO 276
<211> LENGTH: 60
<212> TYPE: DNA
<213> ORGANISM: Homo sapiens

<400> SEQUENCE: 276
actccatctc aaaaaaacaa gagcttcctc gagttgcagg ccgccctggt ggctagacat     60

<210> SEQ ID NO 277
<211> LENGTH: 60
<212> TYPE: DNA
<213> ORGANISM: Homo sapiens

<400> SEQUENCE: 277
ccgcaataca cagattcttt attcctattc gatgtttggg ggcggagggc tttgatgaga     60

<210> SEQ ID NO 278
<211> LENGTH: 60
<212> TYPE: DNA
<213> ORGANISM: Homo sapiens

<400> SEQUENCE: 278
gggattcacc atgatggcca ggctggtttc gagaccagcc tgaccaacat ggtgaaaccc     60

<210> SEQ ID NO 279
<211> LENGTH: 60
<212> TYPE: DNA
<213> ORGANISM: Homo sapiens

<400> SEQUENCE: 279
ggcacctgtt agcaatgaag gataaccatc gattctgaac caacggcttc cgcaaatctt     60

<210> SEQ ID NO 280
<211> LENGTH: 60
<212> TYPE: DNA
<213> ORGANISM: Homo sapiens

<400> SEQUENCE: 280
tattctttgt atatgaaaag aataattctc gaagatggag ggacagggcc gcctcttcct     60

<210> SEQ ID NO 281
<211> LENGTH: 60
<212> TYPE: DNA
<213> ORGANISM: Homo sapiens
```

```
<400> SEQUENCE: 281
ggcaaatgct acaaatcaga gttgtttttc gatcacactg ggagctgcag accggagctg    60

<210> SEQ ID NO 282
<211> LENGTH: 60
<212> TYPE: DNA
<213> ORGANISM: Homo sapiens

<400> SEQUENCE: 282
tgaaatgaaa cctgccccga gaatcacctc gaggctccct cctcctagca tgtggcttaa    60

<210> SEQ ID NO 283
<211> LENGTH: 60
<212> TYPE: DNA
<213> ORGANISM: Homo sapiens

<400> SEQUENCE: 283
ggcacctgtt agcaatgaag dataaccatc gatctcaggc tgttgcactt tctccatggg    60

<210> SEQ ID NO 284
<211> LENGTH: 60
<212> TYPE: DNA
<213> ORGANISM: Homo sapiens

<400> SEQUENCE: 284
agactttatt agataggtat aaatgttttc gataccagcc tgggcaacaa gactctttgt    60

<210> SEQ ID NO 285
<211> LENGTH: 60
<212> TYPE: DNA
<213> ORGANISM: Homo sapiens

<400> SEQUENCE: 285
gtcctaggcc acgcctttag acagatcttc gaagcttctg tggctgtctt tcaagggcaa    60

<210> SEQ ID NO 286
<211> LENGTH: 60
<212> TYPE: DNA
<213> ORGANISM: Homo sapiens

<400> SEQUENCE: 286
tgccattcca ctgaaaaaat gtacagtttc gacaccgtga agatcaacga gactgctgcg    60

<210> SEQ ID NO 287
<211> LENGTH: 60
<212> TYPE: DNA
<213> ORGANISM: Homo sapiens

<400> SEQUENCE: 287
cgtggatcca gactgggagc ccccagcctc gagagctctg tgctccacgc cgaggatgca    60

<210> SEQ ID NO 288
<211> LENGTH: 60
<212> TYPE: DNA
<213> ORGANISM: Homo sapiens

<400> SEQUENCE: 288
gagcttggac cccctcctct tcaccagctc gacctgggcc agtggcggag ggaggcccag    60

<210> SEQ ID NO 289
<211> LENGTH: 60
<212> TYPE: DNA
```

<213> ORGANISM: Homo sapiens

<400> SEQUENCE: 289
gtctgctgca cgggccaccc tgcgggcatc gaaggatcca taaaaggtta agaaacattt    60

<210> SEQ ID NO 290
<211> LENGTH: 60
<212> TYPE: DNA
<213> ORGANISM: Homo sapiens

<400> SEQUENCE: 290 tgcttttta aaaatcaaag gtgtaacttc gacagcttcc ggaggctgcg aggctcgcaa    60

<210> SEQ ID NO 291
<211> LENGTH: 60
<212> TYPE: DNA
<213> ORGANISM: Homo sapiens

<400> SEQUENCE: 291
cacgggcggc agcacccttc atacgggatc gaaaacctgc tgctaagtga gagaagtcag    60

<210> SEQ ID NO 292
<211> LENGTH: 60
<212> TYPE: DNA
<213> ORGANISM: Homo sapiens

<400> SEQUENCE: 292
ctctgtgccg aagcggggtg ccagccgctc gagttctaac aggctcccac agggtcagat    60

<210> SEQ ID NO 293
<211> LENGTH: 60
<212> TYPE: DNA
<213> ORGANISM: Homo sapiens

<400> SEQUENCE: 293
aaaacaccta aaattaagca aagtattttc gaagttgaaa actacccacc ttatttttat    60

<210> SEQ ID NO 294
<211> LENGTH: 60
<212> TYPE: DNA
<213> ORGANISM: Homo sapiens

<400> SEQUENCE: 294
tcttagagtt gaacttttct aatcttttc gacctgctga tccttggatc ctgaatctgt    60

<210> SEQ ID NO 295
<211> LENGTH: 60
<212> TYPE: DNA
<213> ORGANISM: Homo sapiens

<400> SEQUENCE: 295
gaggctagca gatcacaagg tcaggagttc gaaaaccaat gcagaaatca agactttgtc    60

<210> SEQ ID NO 296
<211> LENGTH: 60
<212> TYPE: DNA
<213> ORGANISM: Homo sapiens

<400> SEQUENCE: 296
attcaataag aaagaatgac tgtcactttc gaaacccagt ggatgattct aacttcccgg    60

<210> SEQ ID NO 297
<211> LENGTH: 60

```
<212> TYPE: DNA
<213> ORGANISM: Homo sapiens

<400> SEQUENCE: 297
gaggatttaa taaaacccaa actgtatttc gaagtagtcg tgccaccagt agcagtgaca    60

<210> SEQ ID NO 298
<211> LENGTH: 60
<212> TYPE: DNA
<213> ORGANISM: Homo sapiens

<400> SEQUENCE: 298
ttctgcgagg gaccccctcag cccgggcatc gattatccaa tagaattgta tcagcattaa    60

<210> SEQ ID NO 299
<211> LENGTH: 60
<212> TYPE: DNA
<213> ORGANISM: Homo sapiens

<400> SEQUENCE: 299
acatgaccgt gatacctctg tcactctgtc gatcatttgc gcccaggagt ttgagaccag    60

<210> SEQ ID NO 300
<211> LENGTH: 60
<212> TYPE: DNA
<213> ORGANISM: Homo sapiens

<400> SEQUENCE: 300
gaaggcccgg tgcgcccagc tgtgctcctc gagaacagcc aggctaacac ggagaaaccc    60

<210> SEQ ID NO 301
<211> LENGTH: 60
<212> TYPE: DNA
<213> ORGANISM: Homo sapiens

<400> SEQUENCE: 301
gacaagctgc acatcccggc gctgaccctc gaggaagtga ggcttaattc cactccctac    60

<210> SEQ ID NO 302
<211> LENGTH: 60
<212> TYPE: DNA
<213> ORGANISM: Homo sapiens

<400> SEQUENCE: 302
gggcagagag attttttgta tctacttctc gagagccggc tcctgcccct ttctaaaggc    60

<210> SEQ ID NO 303
<211> LENGTH: 60
<212> TYPE: DNA
<213> ORGANISM: Homo sapiens

<400> SEQUENCE: 303
gttggtgaaa agaaagaag aaatggactc gatgctctgc cttcttgttt cagctcacag    60

<210> SEQ ID NO 304
<211> LENGTH: 60
<212> TYPE: DNA
<213> ORGANISM: Homo sapiens

<400> SEQUENCE: 304
ccactggctg atgaggtcct ttccagcctc gaagtgacct ccgaccctt tatgtttgaa    60

<210> SEQ ID NO 305
```

-continued

```
<211> LENGTH: 60
<212> TYPE: DNA
<213> ORGANISM: Homo sapiens

<400> SEQUENCE: 305
gagttcagcg tgccgccggg cgtgaaagtc gagacgatcc cggccaacat ggtgaaaccc    60

<210> SEQ ID NO 306
<211> LENGTH: 60
<212> TYPE: DNA
<213> ORGANISM: Homo sapiens

<400> SEQUENCE: 306
ataagctgtc ctcgtgtgga ccccggcatc gacccagcct ttttctgttg accgatgagg    60

<210> SEQ ID NO 307
<211> LENGTH: 60
<212> TYPE: DNA
<213> ORGANISM: Homo sapiens

<400> SEQUENCE: 307
tcagataagt aacttcctga taattaactc gaagtcttta acagtagcat agagatcatt    60

<210> SEQ ID NO 308
<211> LENGTH: 60
<212> TYPE: DNA
<213> ORGANISM: Homo sapiens

<400> SEQUENCE: 308
ttgggtgatc ttattcatgg cctctgcttc gaggccgagc tggggccgat gaagatgaca    60

<210> SEQ ID NO 309
<211> LENGTH: 60
<212> TYPE: DNA
<213> ORGANISM: Homo sapiens

<400> SEQUENCE: 309
tggaagcagc tatacagctg tgaccacatc gacgccctg tcacgggccc tgttattcaa     60

<210> SEQ ID NO 310
<211> LENGTH: 60
<212> TYPE: DNA
<213> ORGANISM: Homo sapiens

<400> SEQUENCE: 310
tcaccttagt gaagggaagt ccatcaaatc gactcaccag tgaagatagt gtgctccact    60

<210> SEQ ID NO 311
<211> LENGTH: 60
<212> TYPE: DNA
<213> ORGANISM: Homo sapiens

<400> SEQUENCE: 311
aagtaaatta tggtgttaaa aaccaccatc gagagcggca cgacctgtgg ggactgatgg    60

<210> SEQ ID NO 312
<211> LENGTH: 60
<212> TYPE: DNA
<213> ORGANISM: Homo sapiens

<400> SEQUENCE: 312
ccgcctccgt ctgcgcctgg gccaggcctc gagaattatt cttttcatat acaaagaata    60
```

```
<210> SEQ ID NO 313
<211> LENGTH: 60
<212> TYPE: DNA
<213> ORGANISM: Homo sapiens

<400> SEQUENCE: 313
actcctcgcc tcaaaggatt ctcctatctc gaagtgacct ccgaccettt tatgtttgaa    60

<210> SEQ ID NO 314
<211> LENGTH: 60
<212> TYPE: DNA
<213> ORGANISM: Homo sapiens

<400> SEQUENCE: 314
gcaccccacc ctggatccct tgaaagcctc gacaatgtta ttctttgttt ctcttaccaa    60

<210> SEQ ID NO 315
<211> LENGTH: 60
<212> TYPE: DNA
<213> ORGANISM: Homo sapiens

<400> SEQUENCE: 315
ctgcctcagt tagcaggttg cttagacatc gacggggcgg gtggacgtgg agccacagtt    60

<210> SEQ ID NO 316
<211> LENGTH: 60
<212> TYPE: DNA
<213> ORGANISM: Homo sapiens

<400> SEQUENCE: 316
accgcctcac ctcagctctc cagtgagatc gagcaattct cttgccttag cctcctgagt    60

<210> SEQ ID NO 317
<211> LENGTH: 60
<212> TYPE: DNA
<213> ORGANISM: Homo sapiens

<400> SEQUENCE: 317
aggcttttaa aagaaataga atatgaaatc gacttcctcg cgctgtgcct gatcccaatc    60

<210> SEQ ID NO 318
<211> LENGTH: 60
<212> TYPE: DNA
<213> ORGANISM: Homo sapiens

<400> SEQUENCE: 318
ccgcaataca cagattcttt attcctattc gatgtttggg ggcggagggc tttgatgaga    60

<210> SEQ ID NO 319
<211> LENGTH: 60
<212> TYPE: DNA
<213> ORGANISM: Homo sapiens

<400> SEQUENCE: 319
aggtcctttc cctgtcaaaa tatgtatttc gacttcccac cccatgcagc atcctcttat    60

<210> SEQ ID NO 320
<211> LENGTH: 60
<212> TYPE: DNA
<213> ORGANISM: Homo sapiens

<400> SEQUENCE: 320
ctctgtgccg aagcggggtg ccagccgctc gagcaaatgc aattggggac tttgtttgta    60
```

<210> SEQ ID NO 321
<211> LENGTH: 60
<212> TYPE: DNA
<213> ORGANISM: Homo sapiens

<400> SEQUENCE: 321
ctgagtcttc attaccaaaa aaaaaagttc gacagtcctt gggcaccagc ggtgtgtggg    60

<210> SEQ ID NO 322
<211> LENGTH: 60
<212> TYPE: DNA
<213> ORGANISM: Homo sapiens

<400> SEQUENCE: 322
gtaataaaca tacaaactta aacgtagttc gaggtgcctg ccaccacgtc atgcatggtg    60

<210> SEQ ID NO 323
<211> LENGTH: 60
<212> TYPE: DNA
<213> ORGANISM: Homo sapiens

<400> SEQUENCE: 323
tttggtactg acagaacatt actctggatc gagcacagcg ccggctgggg tacctggcac    60

<210> SEQ ID NO 324
<211> LENGTH: 60
<212> TYPE: DNA
<213> ORGANISM: Homo sapiens

<400> SEQUENCE: 324
aaagagggaa aacagctgaa agggaagctc gagcacagcg ccggctgggg tacctggcac    60

<210> SEQ ID NO 325
<211> LENGTH: 60
<212> TYPE: DNA
<213> ORGANISM: Homo sapiens

<400> SEQUENCE: 325
ctccagcgat gggtggctac gaacaccctc gatgggcgtc cacgccctcc agggacgtcc    60

<210> SEQ ID NO 326
<211> LENGTH: 60
<212> TYPE: DNA
<213> ORGANISM: Homo sapiens

<400> SEQUENCE: 326
gctactgtcc ccgatgttga agaactgctc gagactgacc tggccaacat ggcgaaaccc    60

<210> SEQ ID NO 327
<211> LENGTH: 60
<212> TYPE: DNA
<213> ORGANISM: Homo sapiens

<400> SEQUENCE: 327
attcaataag aaagaatgac tgtcactttc gatgctgtcc tacctgagct cattttcaac    60

<210> SEQ ID NO 328
<211> LENGTH: 60
<212> TYPE: DNA
<213> ORGANISM: Homo sapiens

<400> SEQUENCE: 328
acatgaccgt gatacctctg tcactctgtc gatcatttgc gcccaggagt ttgagaccag    60

<210> SEQ ID NO 329
<211> LENGTH: 60
<212> TYPE: DNA
<213> ORGANISM: Homo sapiens

<400> SEQUENCE: 329
atactgaggt ttaaaaagtt cttttttttc gaaacactat gccctgctc ctaggcccct    60

<210> SEQ ID NO 330
<211> LENGTH: 60
<212> TYPE: DNA
<213> ORGANISM: Homo sapiens

<400> SEQUENCE: 330
tgagctaata aactatttct ggttttgctc gagccatcct cccagtgaca ctccgcaaag    60

<210> SEQ ID NO 331
<211> LENGTH: 60
<212> TYPE: DNA
<213> ORGANISM: Homo sapiens

<400> SEQUENCE: 331
ggcacctgtt agcaatgaag gataaccatc gatcaatgaa gcgtctaggg ataaagactg    60

<210> SEQ ID NO 332
<211> LENGTH: 60
<212> TYPE: DNA
<213> ORGANISM: Homo sapiens

<400> SEQUENCE: 332
atgtctagcc accagggcgg cctgcaactc gacctcccag gctcatggga tcctcctgtc    60

<210> SEQ ID NO 333
<211> LENGTH: 60
<212> TYPE: DNA
<213> ORGANISM: Homo sapiens

<400> SEQUENCE: 333
tgtgattgtt tgcagatgac atccagattc gatattttac atggaatctt tcccttttta    60

<210> SEQ ID NO 334
<211> LENGTH: 60
<212> TYPE: DNA
<213> ORGANISM: Homo sapiens

<400> SEQUENCE: 334
ctattttagg aaaaaaataa ttaaaatatc gattacatcg gcaaagaccc tatttccaaa    60

<210> SEQ ID NO 335
<211> LENGTH: 60
<212> TYPE: DNA
<213> ORGANISM: Homo sapiens

<400> SEQUENCE: 335
gcactacccc ggcctgccgg agcccagtc gatgatggct tcctccccca gagcaccagc    60

<210> SEQ ID NO 336
<211> LENGTH: 60
<212> TYPE: DNA
<213> ORGANISM: Homo sapiens

<400> SEQUENCE: 336

```
gcggggggctt ccctcaactt cagggaggtc gaaccccctga cctcaggcaa tccatctgcc    60
```

<210> SEQ ID NO 337
<211> LENGTH: 60
<212> TYPE: DNA
<213> ORGANISM: Homo sapiens

<400> SEQUENCE: 337

```
ttccatagat tactttttcaa atcatccttc gaagctggcg gctgagggcc cggcgccaag    60
```

<210> SEQ ID NO 338
<211> LENGTH: 60
<212> TYPE: DNA
<213> ORGANISM: Homo sapiens

<400> SEQUENCE: 338

```
tgggccttcc ctgctgcacg ccccagggtc gaaccaggat tctagtcatt gtataacttt    60
```

<210> SEQ ID NO 339
<211> LENGTH: 60
<212> TYPE: DNA
<213> ORGANISM: Homo sapiens

<400> SEQUENCE: 339

```
gcactacaga caaaagactc taactggatc gatcctcatt tttataatag gtaaacattc    60
```

<210> SEQ ID NO 340
<211> LENGTH: 60
<212> TYPE: DNA
<213> ORGANISM: Homo sapiens

<400> SEQUENCE: 340

```
tcctgaaatg aacaggtcat ctgcctattc gatggacttg gtatagccct gggggagagg    60
```

<210> SEQ ID NO 341
<211> LENGTH: 60
<212> TYPE: DNA
<213> ORGANISM: Homo sapiens

<400> SEQUENCE: 341

```
actccatctc aaaaaaacaa gagcttcctc gaactggcgg caaccgctgc agcgcctgct    60
```

<210> SEQ ID NO 342
<211> LENGTH: 60
<212> TYPE: DNA
<213> ORGANISM: Homo sapiens

<400> SEQUENCE: 342

```
ttccccaatt ttgtagcctc tacttatctc gacactaaat caagtctttta acaggtcaat    60
```

<210> SEQ ID NO 343
<211> LENGTH: 60
<212> TYPE: DNA
<213> ORGANISM: Homo sapiens

<400> SEQUENCE: 343

```
gagttcagcg tgccgccggg cgtgaaagtc gactctgggc ccagaccaca gaaggagggg    60
```

<210> SEQ ID NO 344
<211> LENGTH: 60
<212> TYPE: DNA
<213> ORGANISM: Homo sapiens

<400> SEQUENCE: 344

```
ggggcctggc ccaggcctag ccctgagctc gagtaatact gacactcctg gcccacagaa    60
```

<210> SEQ ID NO 345
<211> LENGTH: 60
<212> TYPE: DNA
<213> ORGANISM: Homo sapiens

<400> SEQUENCE: 345

```
gcactacccc ggcctgccgg agccccagtc gacatgttgc cccagctggt ctcaaactcc    60
```

<210> SEQ ID NO 346
<211> LENGTH: 60
<212> TYPE: DNA
<213> ORGANISM: Homo sapiens

<400> SEQUENCE: 346

```
cttttccatt gcttcctcag atcctctgtc gaatgccggc tctgtttcgc accctgctca    60
```

<210> SEQ ID NO 347
<211> LENGTH: 60
<212> TYPE: DNA
<213> ORGANISM: Homo sapiens

<400> SEQUENCE: 347

```
ggcacctgtt agcaatgaag gataaccatc gattccaaag tgaagcaaaa aaaaaacttc    60
```

<210> SEQ ID NO 348
<211> LENGTH: 60
<212> TYPE: DNA
<213> ORGANISM: Homo sapiens

<400> SEQUENCE: 348

```
ctgacccctc caggggaggc ccggcccctc gaggaggaag tggctgatta ctgagcggtt    60
```

<210> SEQ ID NO 349
<211> LENGTH: 60
<212> TYPE: DNA
<213> ORGANISM: Homo sapiens

<400> SEQUENCE: 349

```
cccaatttcc caccccacc cacctaattc gatttttaagt ctattttgtt agatctaaag    60
```

<210> SEQ ID NO 350
<211> LENGTH: 60
<212> TYPE: DNA
<213> ORGANISM: Homo sapiens

<400> SEQUENCE: 350

```
gacctaagga ttaagaagat taatggagtc gaactaatct tgcattccta ggatgatacc    60
```

<210> SEQ ID NO 351
<211> LENGTH: 60
<212> TYPE: DNA
<213> ORGANISM: Homo sapiens

<400> SEQUENCE: 351

```
gtgtctcggc ccctggggc ccaccccttc gaacattaca acctaatctg tgcccacaca    60
```

<210> SEQ ID NO 352
<211> LENGTH: 60
<212> TYPE: DNA
<213> ORGANISM: Homo sapiens

```
<400> SEQUENCE: 352
cgtggatcca gactgggagc ccccagcctc gagcaggatt ctgaggctcc ctgtagacaa    60

<210> SEQ ID NO 353
<211> LENGTH: 60
<212> TYPE: DNA
<213> ORGANISM: Homo sapiens

<400> SEQUENCE: 353
agcaattaca aacagcagaa tggaatcctc gagccatcct cccagtgaca ctccgcaaag    60

<210> SEQ ID NO 354
<211> LENGTH: 60
<212> TYPE: DNA
<213> ORGANISM: Homo sapiens

<400> SEQUENCE: 354
taggcctggg ggccgaaagg aagaagcttc gacatcctgc ttgaatgttt ggaagagggt    60

<210> SEQ ID NO 355
<211> LENGTH: 60
<212> TYPE: DNA
<213> ORGANISM: Homo sapiens

<400> SEQUENCE: 355
tgctcctgcc tgagtaacta aatgtctttc gatgtttggg ggcggagggc tttgatgaga    60

<210> SEQ ID NO 356
<211> LENGTH: 60
<212> TYPE: DNA
<213> ORGANISM: Homo sapiens

<400> SEQUENCE: 356
ctgtggaggg agacctccgg ggccggggtc gatcatccat gtagaagacg ctaaggaatc    60

<210> SEQ ID NO 357
<211> LENGTH: 60
<212> TYPE: DNA
<213> ORGANISM: Homo sapiens

<400> SEQUENCE: 357
tgtcttttga tttttgtctt aaattgcatc gaagacccct tccattgggc attcatctaa    60

<210> SEQ ID NO 358
<211> LENGTH: 60
<212> TYPE: DNA
<213> ORGANISM: Homo sapiens

<400> SEQUENCE: 358
taacgtccaa gaaaattatt gtgacccgtc gatcccagag ccgtcccagg cctggacaga    60

<210> SEQ ID NO 359
<211> LENGTH: 60
<212> TYPE: DNA
<213> ORGANISM: Homo sapiens

<400> SEQUENCE: 359
cgcacgctgg ggctgcgcga ggcagagatc gagaagcata aagcagggac aggtatggag    60

<210> SEQ ID NO 360
<211> LENGTH: 60
<212> TYPE: DNA
<213> ORGANISM: Homo sapiens
```

-continued

```
<400> SEQUENCE: 360
attgacctgt taaagacttg atttagtgtc gaaataagac ataaaagcaa agcattttgc      60

<210> SEQ ID NO 361
<211> LENGTH: 60
<212> TYPE: DNA
<213> ORGANISM: Homo sapiens

<400> SEQUENCE: 361
atgaccttgt tttattactt tttactcttc gaggagaatg ttgagcagaa atatggaata      60

<210> SEQ ID NO 362
<211> LENGTH: 60
<212> TYPE: DNA
<213> ORGANISM: Homo sapiens

<400> SEQUENCE: 362
ttccatagat tacttttcaa atcatccttc gaagctggcg gctgagggcc cggcgccaag      60

<210> SEQ ID NO 363
<211> LENGTH: 60
<212> TYPE: DNA
<213> ORGANISM: Homo sapiens

<400> SEQUENCE: 363
gtgtctcggc cccctggggc cccaccttc gatttccctg ttgccgccgc gtttgcaaga      60

<210> SEQ ID NO 364
<211> LENGTH: 60
<212> TYPE: DNA
<213> ORGANISM: Homo sapiens

<400> SEQUENCE: 364
atcccaacaa aagagaagaa cttctccctc gatgtttggg ggcggagggc tttgatgaga      60

<210> SEQ ID NO 365
<211> LENGTH: 60
<212> TYPE: DNA
<213> ORGANISM: Homo sapiens

<400> SEQUENCE: 365
gtggcgatgg cggcctgcgc gccgcgcctc gatgtctaag caacctgcta actgaggcag      60

<210> SEQ ID NO 366
<211> LENGTH: 60
<212> TYPE: DNA
<213> ORGANISM: Homo sapiens

<400> SEQUENCE: 366
acagttatta gaaaaataaa acatttggtc gaacagcaaa gagaagatat tcaactgcga      60

<210> SEQ ID NO 367
<211> LENGTH: 23
<212> TYPE: DNA
<213> ORGANISM: Homo sapiens

<400> SEQUENCE: 367
tctacagccc aagatcctgc ttt                                             23

<210> SEQ ID NO 368
<211> LENGTH: 20
<212> TYPE: DNA
```

<213> ORGANISM: Homo sapiens

<400> SEQUENCE: 368
ggacccaaca gagggtctgg                                                    20

<210> SEQ ID NO 369
<211> LENGTH: 22
<212> TYPE: DNA
<213> ORGANISM: Homo sapiens

<400> SEQUENCE: 369
ttgtgctaag aggtgatgcc ca                                                 22

<210> SEQ ID NO 370
<211> LENGTH: 19
<212> TYPE: DNA
<213> ORGANISM: Homo sapiens

<400> SEQUENCE: 370
cagcggatgg ttgtgcagc                                                     19

<210> SEQ ID NO 371
<211> LENGTH: 22
<212> TYPE: DNA
<213> ORGANISM: Homo sapiens

<400> SEQUENCE: 371
ctcactgccc aacaggctag aa                                                 22

<210> SEQ ID NO 372
<211> LENGTH: 20
<212> TYPE: DNA
<213> ORGANISM: Homo sapiens

<400> SEQUENCE: 372
ccccgagggt tgagaagcat                                                    20

<210> SEQ ID NO 373
<211> LENGTH: 20
<212> TYPE: DNA
<213> ORGANISM: Homo sapiens

<400> SEQUENCE: 373
acttgggata gacctgcggc                                                    20

<210> SEQ ID NO 374
<211> LENGTH: 22
<212> TYPE: DNA
<213> ORGANISM: Homo sapiens

<400> SEQUENCE: 374
tgtggtttcg gcctttgaca tc                                                 22

<210> SEQ ID NO 375
<211> LENGTH: 20
<212> TYPE: DNA
<213> ORGANISM: Homo sapiens

<400> SEQUENCE: 375
cctgggcaga ttatggtgcg                                                    20

<210> SEQ ID NO 376
<211> LENGTH: 23

```
<212> TYPE: DNA
<213> ORGANISM: Homo sapiens

<400> SEQUENCE: 376
tcttgactca gagcccacaa caa                                    23

<210> SEQ ID NO 377
<211> LENGTH: 60
<212> TYPE: DNA
<213> ORGANISM: Homo sapiens

<400> SEQUENCE: 377
agaaaatata gtattgattg ctttcaagtc gatgcgcgcc cgccggggcc cggtcggagc    60

<210> SEQ ID NO 378
<211> LENGTH: 60
<212> TYPE: DNA
<213> ORGANISM: Homo sapiens

<400> SEQUENCE: 378
tactgtagta agttctctga ggaggatatc gattttttat tgtatcctat attttttcta    60

<210> SEQ ID NO 379
<211> LENGTH: 60
<212> TYPE: DNA
<213> ORGANISM: Homo sapiens

<400> SEQUENCE: 379
tactgtagta agttctctga ggaggatatc gaagtcttgg attaaggttc attcaacaaa    60

<210> SEQ ID NO 380
<211> LENGTH: 60
<212> TYPE: DNA
<213> ORGANISM: Homo sapiens

<400> SEQUENCE: 380
cacttcccca acataagcct cggtctcttc gagggcgggc ccggcggccc cggagcaaac    60

<210> SEQ ID NO 381
<211> LENGTH: 60
<212> TYPE: DNA
<213> ORGANISM: Homo sapiens

<400> SEQUENCE: 381
gagttcagcg tgccgccggg cgtgaaagtc gaggcatatt tgagtttagg gaggtgttgc    60

<210> SEQ ID NO 382
<211> LENGTH: 60
<212> TYPE: DNA
<213> ORGANISM: Homo sapiens

<400> SEQUENCE: 382
gagttcagcg tgccgccggg cgtgaaagtc gactctgggc ccagaccaca gaaggagggg    60

<210> SEQ ID NO 383
<211> LENGTH: 60
<212> TYPE: DNA
<213> ORGANISM: Homo sapiens

<400> SEQUENCE: 383
gagttcagcg tgccgccggg cgtgaaagtc gatttgttta tggttttatc cccagtgcct    60

<210> SEQ ID NO 384
```

```
<211> LENGTH: 60
<212> TYPE: DNA
<213> ORGANISM: Homo sapiens

<400> SEQUENCE: 384
tttgttgaat gaaccttaat ccaagacttc gatttttat tgtatcctat atttttcta      60

<210> SEQ ID NO 385
<211> LENGTH: 60
<212> TYPE: DNA
<213> ORGANISM: Homo sapiens

<400> SEQUENCE: 385
ttccatagat tacttttcaa atcatccttc gaagctggcg gctgagggcc cggcgccaag     60

<210> SEQ ID NO 386
<211> LENGTH: 60
<212> TYPE: DNA
<213> ORGANISM: Homo sapiens

<400> SEQUENCE: 386
gtttgctccg gggccgccgg gcccgccctc gattttaaca ccaccatggt ttgaatgaat     60

<210> SEQ ID NO 387
<211> LENGTH: 60
<212> TYPE: DNA
<213> ORGANISM: Homo sapiens

<400> SEQUENCE: 387
tccattgtct tattccagtc taggcttgtc gagttgcagg ccgccctggt ggctagacat     60

<210> SEQ ID NO 388
<211> LENGTH: 60
<212> TYPE: DNA
<213> ORGANISM: Homo sapiens

<400> SEQUENCE: 388
aaaaaacaat tatgtaattg aaaacccatc gaggggctta ctaatgcctt ttagctccct     60

<210> SEQ ID NO 389
<211> LENGTH: 60
<212> TYPE: DNA
<213> ORGANISM: Homo sapiens

<400> SEQUENCE: 389
gaccccgggg aattggctcc agcacatctc gagggcgggc ccggcggccc cggagcaaac    60

<210> SEQ ID NO 390
<211> LENGTH: 60
<212> TYPE: DNA
<213> ORGANISM: Homo sapiens

<400> SEQUENCE: 390
aaaaaacaat tatgtaattg aaaacccatc gaagctcttt ggttccacag agtgattctg     60

<210> SEQ ID NO 391
<211> LENGTH: 60
<212> TYPE: DNA
<213> ORGANISM: Homo sapiens

<400> SEQUENCE: 391
aggcattcgt tcttcagctc ttctataatc gatttttat tgtatcctat atttttcta      60
```

```
<210> SEQ ID NO 392
<211> LENGTH: 60
<212> TYPE: DNA
<213> ORGANISM: Homo sapiens

<400> SEQUENCE: 392
gctcttataa attatgtatt caaagaaatc gagttgcagg ccgccctggt ggctagacat     60

<210> SEQ ID NO 393
<211> LENGTH: 60
<212> TYPE: DNA
<213> ORGANISM: Homo sapiens

<400> SEQUENCE: 393
cccgcggcgg agctgctact gtttactttc gaagcttctt cctttcggcc cccaggccta     60

<210> SEQ ID NO 394
<211> LENGTH: 60
<212> TYPE: DNA
<213> ORGANISM: Homo sapiens

<400> SEQUENCE: 394
gctcttataa attatgtatt caaagaaatc gaactggcgg caaccgctgc agcgcctgct     60

<210> SEQ ID NO 395
<211> LENGTH: 60
<212> TYPE: DNA
<213> ORGANISM: Homo sapiens

<400> SEQUENCE: 395
aaaaaacaat tatgtaattg aaacccatc gaggggctta ctaatgcctt ttagctccct      60

<210> SEQ ID NO 396
<211> LENGTH: 60
<212> TYPE: DNA
<213> ORGANISM: Homo sapiens

<400> SEQUENCE: 396
tctcctgcct accacactgt gagaaagctc gagggcgggc ccggcggccc cggagcaaac     60

<210> SEQ ID NO 397
<211> LENGTH: 60
<212> TYPE: DNA
<213> ORGANISM: Homo sapiens

<400> SEQUENCE: 397
gagttcagcg tgccgccggg cgtgaaagtc gaattctccc aggagccact gtcagaaccc     60

<210> SEQ ID NO 398
<211> LENGTH: 60
<212> TYPE: DNA
<213> ORGANISM: Homo sapiens

<400> SEQUENCE: 398
ccgcgcccgc agggcccgcc ccgcgccgtc gacaatgtta ttctttgttt ctcttaccaa     60

<210> SEQ ID NO 399
<211> LENGTH: 60
<212> TYPE: DNA
<213> ORGANISM: Homo sapiens

<400> SEQUENCE: 399
gaaggcccgg tgcgcccagc tgtgctcctc gagaacagcc aggctaacac ggagaaaccc     60
```

<210> SEQ ID NO 400
<211> LENGTH: 60
<212> TYPE: DNA
<213> ORGANISM: Homo sapiens

<400> SEQUENCE: 400
tccattgtct tattccagtc taggcttgtc gaactggcgg caaccgctgc agcgcctgct    60

<210> SEQ ID NO 401
<211> LENGTH: 60
<212> TYPE: DNA
<213> ORGANISM: Homo sapiens

<400> SEQUENCE: 401
ccgcgcccgc agggcccgcc ccgcgccgtc gatgtgttgg aagtcagggc ggcggtgccc    60

<210> SEQ ID NO 402
<211> LENGTH: 60
<212> TYPE: DNA
<213> ORGANISM: Homo sapiens

<400> SEQUENCE: 402
ccgcgcccgc agggcccgcc ccgcgccgtc gaggctttca agggatccag ggtggggtgc    60

<210> SEQ ID NO 403
<211> LENGTH: 60
<212> TYPE: DNA
<213> ORGANISM: Homo sapiens

<400> SEQUENCE: 403
ccgcgcccgc agggcccgcc ccgcgccgtc gacaatgtta ttctttgttt ctcttaccaa    60

<210> SEQ ID NO 404
<211> LENGTH: 60
<212> TYPE: DNA
<213> ORGANISM: Homo sapiens

<400> SEQUENCE: 404
ccgcgcccgc agggcccgcc ccgcgccgtc gatgtgttgg aagtcagggc ggcggtgccc    60

<210> SEQ ID NO 405
<211> LENGTH: 60
<212> TYPE: DNA
<213> ORGANISM: Homo sapiens

<400> SEQUENCE: 405
cacttcccca acataagcct cggtctcttc gagggcgggc ccggcggccc cggagcaaac    60

<210> SEQ ID NO 406
<211> LENGTH: 60
<212> TYPE: DNA
<213> ORGANISM: Homo sapiens

<400> SEQUENCE: 406
ccgcgcccgc agggcccgcc ccgcgccgtc gagaagcata aagcagggac aggtatggag    60

<210> SEQ ID NO 407
<211> LENGTH: 60
<212> TYPE: DNA
<213> ORGANISM: Homo sapiens

<400> SEQUENCE: 407
gaccccgggg aattggctcc agcacatctc gagggcgggc ccggcggccc cggagcaaac    60

<210> SEQ ID NO 408
<211> LENGTH: 60
<212> TYPE: DNA
<213> ORGANISM: Homo sapiens

<400> SEQUENCE: 408
gtttgctccg gggccgccgg gcccgccctc gattttaaca ccaccatggt ttgaatgaat    60

<210> SEQ ID NO 409
<211> LENGTH: 60
<212> TYPE: DNA
<213> ORGANISM: Homo sapiens

<400> SEQUENCE: 409
gtgtctcggc ccctggggc cccaccttc gatttccctg ttgccgccgc gtttgcaaga     60

<210> SEQ ID NO 410
<211> LENGTH: 60
<212> TYPE: DNA
<213> ORGANISM: Homo sapiens

<400> SEQUENCE: 410
tctcctgcct accacactgt gagaaagctc gagggcgggc ccggcggccc cggagcaaac    60

<210> SEQ ID NO 411
<211> LENGTH: 60
<212> TYPE: DNA
<213> ORGANISM: Homo sapiens

<400> SEQUENCE: 411
gagttcagcg tgccgccggg cgtgaaagtc gaggcatatt tgagtttagg gaggtgttgc    60

<210> SEQ ID NO 412
<211> LENGTH: 60
<212> TYPE: DNA
<213> ORGANISM: Homo sapiens

<400> SEQUENCE: 412
gggcaccgcc gccctgactt ccaacacatc gatctctgcc tcgcgcagcc ccagcgtgcg    60

<210> SEQ ID NO 413
<211> LENGTH: 60
<212> TYPE: DNA
<213> ORGANISM: Homo sapiens

<400> SEQUENCE: 413 ccaccccgc cccgggggag tcgcccggtc gatttccaaa agctcacaca tgggtgcaca    60

<210> SEQ ID NO 414
<211> LENGTH: 60
<212> TYPE: DNA
<213> ORGANISM: Homo sapiens

<400> SEQUENCE: 414
gggcaccgcc gccctgactt ccaacacatc gaagaatggg tggggccttg cacctcatac    60

<210> SEQ ID NO 415
<211> LENGTH: 60
<212> TYPE: DNA
<213> ORGANISM: Homo sapiens

<400> SEQUENCE: 415 ccaccccgc cccggggag tcgcccggtc gaccccctga catgggctg cctggagcag    60

<210> SEQ ID NO 416
<211> LENGTH: 60
<212> TYPE: DNA
<213> ORGANISM: Homo sapiens

<400> SEQUENCE: 416
gggcaccgcc gccctgactt ccaacacatc gagaagcata aagcagggac aggtatggag    60

<210> SEQ ID NO 417
<211> LENGTH: 60
<212> TYPE: DNA
<213> ORGANISM: Homo sapiens

<400> SEQUENCE: 417
gagttcagcg tgccgccggg cgtgaaagtc gactctgggc ccagaccaca gaaggagggg    60

<210> SEQ ID NO 418
<211> LENGTH: 60
<212> TYPE: DNA
<213> ORGANISM: Homo sapiens

<400> SEQUENCE: 418
aattctgttg gaagaataat ttaaaatatc gatgtggcga ccggctgtgg gggtcacgga    60

<210> SEQ ID NO 419
<211> LENGTH: 60
<212> TYPE: DNA
<213> ORGANISM: Homo sapiens

<400> SEQUENCE: 419
ttccatagat tactttttcaa atcatccttc gaagctggcg gctgagggcc cggcgccaag    60

<210> SEQ ID NO 420
<211> LENGTH: 60
<212> TYPE: DNA
<213> ORGANISM: Homo sapiens

<400> SEQUENCE: 420
gagttcagcg tgccgccggg cgtgaaagtc gatttgttta tggttttatc cccagtgcct    60

<210> SEQ ID NO 421
<211> LENGTH: 60
<212> TYPE: DNA
<213> ORGANISM: Homo sapiens

<400> SEQUENCE: 421
caccctccct tcttcctggg ccctcagatc gacccccccc accccaccg ggctggctgc    60

<210> SEQ ID NO 422
<211> LENGTH: 60
<212> TYPE: DNA
<213> ORGANISM: Homo sapiens

<400> SEQUENCE: 422 ccaccccgc cccggggag tcgcccggtc gagggcctgg caagaagaca gaagccgact    60

<210> SEQ ID NO 423
<211> LENGTH: 60
<212> TYPE: DNA
<213> ORGANISM: Homo sapiens

<400> SEQUENCE: 423
tatgagtaat aattacaatt tccccctttc gacctccagg tccccgcca cttccacggc    60

<210> SEQ ID NO 424
<211> LENGTH: 60
<212> TYPE: DNA
<213> ORGANISM: Homo sapiens

<400> SEQUENCE: 424
cagaaactgc tggttgggct catactttc gagggccagc tccccgcacc cccaccaagc    60

<210> SEQ ID NO 425
<211> LENGTH: 60
<212> TYPE: DNA
<213> ORGANISM: Homo sapiens

<400> SEQUENCE: 425
ttcccctgta agattcattt cctgtgattc gagtcacagc tgtagtgggg tgggggtga    60

<210> SEQ ID NO 426
<211> LENGTH: 60
<212> TYPE: DNA
<213> ORGANISM: Homo sapiens

<400> SEQUENCE: 426
tctttgttac tggaatatac gaataaaatc gatgtggcga ccggctgtgg gggtcacgga    60

<210> SEQ ID NO 427
<211> LENGTH: 60
<212> TYPE: DNA
<213> ORGANISM: Homo sapiens

<400> SEQUENCE: 427
aaggcaggca gatcaggagc tcaagagatc gaaagaaaaa aaaaaagca taaaatcca     60

<210> SEQ ID NO 428
<211> LENGTH: 60
<212> TYPE: DNA
<213> ORGANISM: Homo sapiens

<400> SEQUENCE: 428
aaggcaggca gatcaggagc tcaagagatc gaacgctaag tgtagtttaa cacctactag    60

<210> SEQ ID NO 429
<211> LENGTH: 60
<212> TYPE: DNA
<213> ORGANISM: Homo sapiens

<400> SEQUENCE: 429
atagtaaaat gtgaaaatgt tacagttatc gaagttcagc gagtatattt ttactgatac    60

<210> SEQ ID NO 430
<211> LENGTH: 60
<212> TYPE: DNA
<213> ORGANISM: Homo sapiens

<400> SEQUENCE: 430
aaggcccaag aaccaggaat ctaggtattc gaaaagccct aaagttggct taataaactt    60

<210> SEQ ID NO 431
<211> LENGTH: 60
<212> TYPE: DNA
<213> ORGANISM: Homo sapiens

```
<400> SEQUENCE: 431
ggtgggcaga tcacttaagg ccaggaattc gaatgcaaaa ctcactaccc actggtaaga      60

<210> SEQ ID NO 432
<211> LENGTH: 60
<212> TYPE: DNA
<213> ORGANISM: Homo sapiens

<400> SEQUENCE: 432
ggtgggcaga tcacttaagg ccaggaattc gattctatca actctagaat ttttttaaat      60

<210> SEQ ID NO 433
<211> LENGTH: 60
<212> TYPE: DNA
<213> ORGANISM: Homo sapiens

<400> SEQUENCE: 433
aaggcaggca gatcaggagc tcaagagatc gaggtaaatg tgggggttct agaacccagt      60

<210> SEQ ID NO 434
<211> LENGTH: 60
<212> TYPE: DNA
<213> ORGANISM: Homo sapiens

<400> SEQUENCE: 434
ggtgggcaga tcacttaagg ccaggaattc gaaattcttt cctaatgcca agtgtgttat      60

<210> SEQ ID NO 435
<211> LENGTH: 60
<212> TYPE: DNA
<213> ORGANISM: Homo sapiens

<400> SEQUENCE: 435
ggtcccctga tttccatcct agtgcttctc gaaacatgtg ctctggagat aaagcgccaa      60

<210> SEQ ID NO 436
<211> LENGTH: 60
<212> TYPE: DNA
<213> ORGANISM: Homo sapiens

<400> SEQUENCE: 436
ggtgggcaga tcacttaagg ccaggaattc gatattcaat aaaagaccgg atgtgcaaag      60

<210> SEQ ID NO 437
<211> LENGTH: 60
<212> TYPE: DNA
<213> ORGANISM: Homo sapiens

<400> SEQUENCE: 437
ggtgggcaga tcacttaagg ccaggaattc gagaaatggt ttatccaatt catccaaaat      60

<210> SEQ ID NO 438
<211> LENGTH: 60
<212> TYPE: DNA
<213> ORGANISM: Homo sapiens

<400> SEQUENCE: 438
ggtgggcaga tcacttaagg ccaggaattc gagagactgt aaagacatgt gtctgcctct      60

<210> SEQ ID NO 439
<211> LENGTH: 60
<212> TYPE: DNA
<213> ORGANISM: Homo sapiens
```

-continued

<400> SEQUENCE: 439
ggtgggcaga tcacttaagg ccaggaattc gatcacttct taaaggccct acctcttaat    60

<210> SEQ ID NO 440
<211> LENGTH: 60
<212> TYPE: DNA
<213> ORGANISM: Homo sapiens

<400> SEQUENCE: 440
gttgggttga agatgaaatc ataggaagtc gagctgtaac ctctgcttgg tattctccct    60

<210> SEQ ID NO 441
<211> LENGTH: 60
<212> TYPE: DNA
<213> ORGANISM: Homo sapiens

<400> SEQUENCE: 441
ggtgggcaga tcacttaagg ccaggaattc gaaacaccag ctctcttaaa tcctgtgcct    60

<210> SEQ ID NO 442
<211> LENGTH: 60
<212> TYPE: DNA
<213> ORGANISM: Homo sapiens

<400> SEQUENCE: 442
ggtgggcaga tcacttaagg ccaggaattc gaggaaaacc tcggggcaaa atagggaaag    60

<210> SEQ ID NO 443
<211> LENGTH: 60
<212> TYPE: DNA
<213> ORGANISM: Homo sapiens

<400> SEQUENCE: 443
tgagaatgga atagatcaaa gggagggttc gagacaaggt ctcactttat cacccaacct    60

<210> SEQ ID NO 444
<211> LENGTH: 60
<212> TYPE: DNA
<213> ORGANISM: Homo sapiens

<400> SEQUENCE: 444
ggtgggcaga tcacttaagg ccaggaattc gactgtgtgc ccatgaagaa agaagatggg    60

<210> SEQ ID NO 445
<211> LENGTH: 60
<212> TYPE: DNA
<213> ORGANISM: Homo sapiens

<400> SEQUENCE: 445
agtgatagaa gagggacaag gtggcagttc gattttaaaa cacgctcttc aataaaaaga    60

<210> SEQ ID NO 446
<211> LENGTH: 60
<212> TYPE: DNA
<213> ORGANISM: Homo sapiens

<400> SEQUENCE: 446
agcaggggga tcacataagg ccaggagttc gataaaataa attagagaag atataaataa    60

<210> SEQ ID NO 447
<211> LENGTH: 60
<212> TYPE: DNA

<213> ORGANISM: Homo sapiens

<400> SEQUENCE: 447
ggtgggcaga tcacttaagg ccaggaattc gatttctctg cttctctcac agcccacatc    60

<210> SEQ ID NO 448
<211> LENGTH: 60
<212> TYPE: DNA
<213> ORGANISM: Homo sapiens

<400> SEQUENCE: 448
tctttgcaga tgttgtaaga taaggatgtc gaaaagccct aaagttggct taataaactt    60

<210> SEQ ID NO 449
<211> LENGTH: 60
<212> TYPE: DNA
<213> ORGANISM: Homo sapiens

<400> SEQUENCE: 449
ggtcccctga tttccatcct agtgcttctc gatgatataa tactctgctg actacatttt    60

<210> SEQ ID NO 450
<211> LENGTH: 60
<212> TYPE: DNA
<213> ORGANISM: Homo sapiens

<400> SEQUENCE: 450
aaggcccaag aaccaggaat ctaggtattc gaccacctta aaagaaaaat ctcttggaac    60

<210> SEQ ID NO 451
<211> LENGTH: 60
<212> TYPE: DNA
<213> ORGANISM: Homo sapiens

<400> SEQUENCE: 451
agcaggggga tcacataagg ccaggagttc gatgaacgtt tacccaatta tttctaaaca    60

<210> SEQ ID NO 452
<211> LENGTH: 60
<212> TYPE: DNA
<213> ORGANISM: Homo sapiens

<400> SEQUENCE: 452
gatgcggact gtttcctgct ttgatttatc gacttcttat ttctattttg tgacttagga    60

<210> SEQ ID NO 453
<211> LENGTH: 60
<212> TYPE: DNA
<213> ORGANISM: Homo sapiens

<400> SEQUENCE: 453
gatgcggact gtttcctgct ttgatttatc gacacagtgt gtctgaagtt tggggtggta    60

<210> SEQ ID NO 454
<211> LENGTH: 60
<212> TYPE: DNA
<213> ORGANISM: Homo sapiens

<400> SEQUENCE: 454
gatgcggact gtttcctgct ttgatttatc gatatctccc tcctttcgct tcttcctttc    60

<210> SEQ ID NO 455
<211> LENGTH: 60

```
<212> TYPE: DNA
<213> ORGANISM: Homo sapiens

<400> SEQUENCE: 455
gatgcggact gtttcctgct ttgatttatc gagtcattaa gagactctcc gcctgggtgg    60

<210> SEQ ID NO 456
<211> LENGTH: 60
<212> TYPE: DNA
<213> ORGANISM: Homo sapiens

<400> SEQUENCE: 456
ttccacctgt aatactgtgc ctgtattctc gactcttctc gccctcttct ccagctctct    60

<210> SEQ ID NO 457
<211> LENGTH: 60
<212> TYPE: DNA
<213> ORGANISM: Homo sapiens

<400> SEQUENCE: 457
taaagtactg tgtcccacat ataagtactc gaccaagaaa ttcattctta cctcctaaga    60

<210> SEQ ID NO 458
<211> LENGTH: 60
<212> TYPE: DNA
<213> ORGANISM: Homo sapiens

<400> SEQUENCE: 458
accccaccaa tctataataa gattgatttc gacacaaggg tttgtaacaa aaacaaaaa     60

<210> SEQ ID NO 459
<211> LENGTH: 60
<212> TYPE: DNA
<213> ORGANISM: Homo sapiens

<400> SEQUENCE: 459
agcgctttat ttgtcaggac gatagacctc gacaatgtcc tattcttcca gaaactcatt    60

<210> SEQ ID NO 460
<211> LENGTH: 60
<212> TYPE: DNA
<213> ORGANISM: Homo sapiens

<400> SEQUENCE: 460
ttattacttt attctgactg aatatcattc gaaagaaacc aaaaacacaa gtatacatca    60

<210> SEQ ID NO 461
<211> LENGTH: 60
<212> TYPE: DNA
<213> ORGANISM: Homo sapiens

<400> SEQUENCE: 461
tatcctttgg tttagaagta tttcttattc gacaaaattt taacatgtta tgcagttaca    60

<210> SEQ ID NO 462
<211> LENGTH: 60
<212> TYPE: DNA
<213> ORGANISM: Homo sapiens

<400> SEQUENCE: 462
ttcagctatt cactggtttt tcttcagatc gactcctgct tccctcccct catctttaaa    60

<210> SEQ ID NO 463
```

```
<211> LENGTH: 60
<212> TYPE: DNA
<213> ORGANISM: Homo sapiens

<400> SEQUENCE: 463
tccagtacaa taaacaatgt accaaagatc gacaaaattt taacatgtta tgcagttaca        60

<210> SEQ ID NO 464
<211> LENGTH: 60
<212> TYPE: DNA
<213> ORGANISM: Homo sapiens

<400> SEQUENCE: 464
taaactctga cattgcctat tagcattctc gaatgcatgg ctcactgtaa cctccaactc        60

<210> SEQ ID NO 465
<211> LENGTH: 60
<212> TYPE: DNA
<213> ORGANISM: Homo sapiens

<400> SEQUENCE: 465
tatcctttgg tttagaagta tttcttattc gacaactact ggcttaaaaa aggcaaaaca        60

<210> SEQ ID NO 466
<211> LENGTH: 60
<212> TYPE: DNA
<213> ORGANISM: Homo sapiens

<400> SEQUENCE: 466
tacctccttg ggaacatatt tgagagtttc gactcctgct tccctcccct catctttaaa       60

<210> SEQ ID NO 467
<211> LENGTH: 60
<212> TYPE: DNA
<213> ORGANISM: Homo sapiens

<400> SEQUENCE: 467
acacttgatt tttgctttcc aagctgactc gagacatcta agaaggtcca gccagatgtt       60

<210> SEQ ID NO 468
<211> LENGTH: 60
<212> TYPE: DNA
<213> ORGANISM: Homo sapiens

<400> SEQUENCE: 468
gcgccctatt tccaccttgt gccttctgtc gacacaccaa gatgtcacgg aggagtctgt       60

<210> SEQ ID NO 469
<211> LENGTH: 60
<212> TYPE: DNA
<213> ORGANISM: Homo sapiens

<400> SEQUENCE: 469
ccagctgaag tttcgcaggt ccctgcttc gagtaggcca atcccatttt tggcgaaaac        60

<210> SEQ ID NO 470
<211> LENGTH: 60
<212> TYPE: DNA
<213> ORGANISM: Homo sapiens

<400> SEQUENCE: 470
tacctccttg ggaacatatt tgagagtttc gactcctgct tccctcccct catctttaaa       60
```

```
<210> SEQ ID NO 471
<211> LENGTH: 60
<212> TYPE: DNA
<213> ORGANISM: Homo sapiens

<400> SEQUENCE: 471
acacttgatt tttgctttcc aagctgactc gagacatcta agaaggtcca gccagatgtt      60

<210> SEQ ID NO 472
<211> LENGTH: 60
<212> TYPE: DNA
<213> ORGANISM: Homo sapiens

<400> SEQUENCE: 472
gcgccctatt tccaccttgt gccttctgtc gacacaccaa gatgtcacgg aggagtctgt      60

<210> SEQ ID NO 473
<211> LENGTH: 60
<212> TYPE: DNA
<213> ORGANISM: Homo sapiens

<400> SEQUENCE: 473
ccagctgaag tttcgcaggt cccctgcttc gagtaggcca atcccatttt tggcgaaaac      60

<210> SEQ ID NO 474
<211> LENGTH: 60
<212> TYPE: DNA
<213> ORGANISM: Homo sapiens

<400> SEQUENCE: 474
actttggctc aagagtgaag atattcagtc gactcctgct tccctcccct catctttaaa      60

<210> SEQ ID NO 475
<211> LENGTH: 60
<212> TYPE: DNA
<213> ORGANISM: Homo sapiens

<400> SEQUENCE: 475
ttccttaggc aagtcatcca attccatgtc gacacaaggg tttgtaacaa aaaacaaaaa      60

<210> SEQ ID NO 476
<211> LENGTH: 60
<212> TYPE: DNA
<213> ORGANISM: Homo sapiens

<400> SEQUENCE: 476
tcttaggagg taagaatgaa tttcttggtc gaactcctga ccaggaggct gggaggggggt    60

<210> SEQ ID NO 477
<211> LENGTH: 60
<212> TYPE: DNA
<213> ORGANISM: Homo sapiens

<400> SEQUENCE: 477
catcatttta ataggtgcaa gagttccgtc gaacgcccat acctgtggga atcaagcaat      60

<210> SEQ ID NO 478
<211> LENGTH: 60
<212> TYPE: DNA
<213> ORGANISM: Homo sapiens

<400> SEQUENCE: 478
aaaaacaaaa aagccaattc tgtacccctc gaaccagccc tggctctgtc cccagacctt      60
```

<210> SEQ ID NO 479
<211> LENGTH: 60
<212> TYPE: DNA
<213> ORGANISM: Homo sapiens

<400> SEQUENCE: 479
gcgccctatt tccaccttgt gccttctgtc gagacatcta agaaggtcca gccagatgtt    60

<210> SEQ ID NO 480
<211> LENGTH: 60
<212> TYPE: DNA
<213> ORGANISM: Homo sapiens

<400> SEQUENCE: 480
ttgattattt caggttgaca gctgtaaatc gactcctgct tccctcccct catctttaaa    60

<210> SEQ ID NO 481
<211> LENGTH: 20
<212> TYPE: DNA
<213> ORGANISM: Homo sapiens

<400> SEQUENCE: 481
tgagtaacac aaagcatctg                                                20

<210> SEQ ID NO 482
<211> LENGTH: 21
<212> TYPE: DNA
<213> ORGANISM: Homo sapiens

<400> SEQUENCE: 482
ctggtgattt gtgtgacttt g                                              21

<210> SEQ ID NO 483
<211> LENGTH: 19
<212> TYPE: DNA
<213> ORGANISM: Homo sapiens

<400> SEQUENCE: 483
gtacgactcc agccaaatg                                                 19

<210> SEQ ID NO 484
<211> LENGTH: 18
<212> TYPE: DNA
<213> ORGANISM: Homo sapiens

<400> SEQUENCE: 484
accttgcaag aagcacag                                                  18

<210> SEQ ID NO 485
<211> LENGTH: 20
<212> TYPE: DNA
<213> ORGANISM: Homo sapiens

<400> SEQUENCE: 485
aggagcatcc atatcaagtg                                                20

<210> SEQ ID NO 486
<211> LENGTH: 20
<212> TYPE: DNA
<213> ORGANISM: Homo sapiens

<400> SEQUENCE: 486
cagtgaagaa gccatcatcg                                                20

```
<210> SEQ ID NO 487
<211> LENGTH: 18
<212> TYPE: DNA
<213> ORGANISM: Homo sapiens

<400> SEQUENCE: 487
atgggcagca tttctcac                                                 18

<210> SEQ ID NO 488
<211> LENGTH: 22
<212> TYPE: DNA
<213> ORGANISM: Homo sapiens

<400> SEQUENCE: 488
gtgctggtat gtacctgtaa tc                                            22

<210> SEQ ID NO 489
<211> LENGTH: 18
<212> TYPE: DNA
<213> ORGANISM: Homo sapiens

<400> SEQUENCE: 489
agtgactggc tatgttcc                                                 18

<210> SEQ ID NO 490
<211> LENGTH: 18
<212> TYPE: DNA
<213> ORGANISM: Homo sapiens

<400> SEQUENCE: 490
agggaagatg tggaggag                                                 18

<210> SEQ ID NO 491
<211> LENGTH: 22
<212> TYPE: DNA
<213> ORGANISM: Homo sapiens

<400> SEQUENCE: 491
gctgtctgtt actagattgc ac                                            22

<210> SEQ ID NO 492
<211> LENGTH: 21
<212> TYPE: DNA
<213> ORGANISM: Homo sapiens

<400> SEQUENCE: 492
atgatacttc ccaactgaca c                                             21

<210> SEQ ID NO 493
<211> LENGTH: 19
<212> TYPE: DNA
<213> ORGANISM: Homo sapiens

<400> SEQUENCE: 493
ctgccatgtc tgactatcc                                                19

<210> SEQ ID NO 494
<211> LENGTH: 21
<212> TYPE: DNA
<213> ORGANISM: Homo sapiens

<400> SEQUENCE: 494
```

-continued

```
cttagagaaa tacaccagca g                                      21

<210> SEQ ID NO 495
<211> LENGTH: 22
<212> TYPE: DNA
<213> ORGANISM: Homo sapiens

<400> SEQUENCE: 495
agggacgatt tatatgactt gc                                     22

<210> SEQ ID NO 496
<211> LENGTH: 20
<212> TYPE: DNA
<213> ORGANISM: Homo sapiens

<400> SEQUENCE: 496
gagggttgag aagcatcttg                                        20

<210> SEQ ID NO 497
<211> LENGTH: 60
<212> TYPE: DNA
<213> ORGANISM: Homo sapiens

<400> SEQUENCE: 497
tgtaaactgt aatatcaaaa attcaaaatc gaagagttga tttacttatt aacattagaa   60

<210> SEQ ID NO 498
<211> LENGTH: 60
<212> TYPE: DNA
<213> ORGANISM: Homo sapiens

<400> SEQUENCE: 498
acttttatag tgaaaagtgc catttgagtc gactgtgatt gaatgtaaaa ggttttaaat   60

<210> SEQ ID NO 499
<211> LENGTH: 60
<212> TYPE: DNA
<213> ORGANISM: Homo sapiens

<400> SEQUENCE: 499
tactgtagta agttctctga ggaggatatc gaagtcttgg attaaggttc attcaacaaa   60

<210> SEQ ID NO 500
<211> LENGTH: 60
<212> TYPE: DNA
<213> ORGANISM: Homo sapiens

<400> SEQUENCE: 500
tccatttgaa ggatgagaaa actgaggctc gaggcttaga aagtttcatt tggttgctca   60

<210> SEQ ID NO 501
<211> LENGTH: 60
<212> TYPE: DNA
<213> ORGANISM: Homo sapiens

<400> SEQUENCE: 501
ttttaaaccc aggtgcacac acaagagctc gaagcaggaa tcctggttct gttcccaggc   60

<210> SEQ ID NO 502
<211> LENGTH: 60
<212> TYPE: DNA
<213> ORGANISM: Homo sapiens

<400> SEQUENCE: 502
```
ccactccccc aggcttacct gcgagccatc gaggtgggcc tgggttctcg tggagggaga    60

<210> SEQ ID NO 503
<211> LENGTH: 60
<212> TYPE: DNA
<213> ORGANISM: Homo sapiens

<400> SEQUENCE: 503
tcactcattc tagatccctc tgtaaagttc gaactctgga ccttgtgatc cacccacctt    60

<210> SEQ ID NO 504
<211> LENGTH: 60
<212> TYPE: DNA
<213> ORGANISM: Homo sapiens

<400> SEQUENCE: 504
ttccatagat tacttttcaa atcatccttc gaagctggcg gctgagggcc cggcgccaag    60

<210> SEQ ID NO 505
<211> LENGTH: 60
<212> TYPE: DNA
<213> ORGANISM: Homo sapiens

<400> SEQUENCE: 505
cccgcggcgg agctgctact gtttactttc gaagcttctt cctttcggcc cccaggccta    60

<210> SEQ ID NO 506
<211> LENGTH: 60
<212> TYPE: DNA
<213> ORGANISM: Homo sapiens

<400> SEQUENCE: 506
gcactacccc ggcctgccgg agcccagtc gagttggttt ctgggtccgc accccctccc    60

<210> SEQ ID NO 507
<211> LENGTH: 60
<212> TYPE: DNA
<213> ORGANISM: Homo sapiens

<400> SEQUENCE: 507
cgggtgcctc ccccccatt cgccctgctc gagggaggga aatgattgga ttacgggggt    60

<210> SEQ ID NO 508
<211> LENGTH: 60
<212> TYPE: DNA
<213> ORGANISM: Homo sapiens

<400> SEQUENCE: 508
cgtggatcca gactgggagc ccccagcctc gaaccacgcc aggcttccag gcgtcagtgc    60

<210> SEQ ID NO 509
<211> LENGTH: 60
<212> TYPE: DNA
<213> ORGANISM: Homo sapiens

<400> SEQUENCE: 509
tggaagcagc tatacagctg tgaccacatc gacgcccctg tcacgggccc tgttattcaa    60

<210> SEQ ID NO 510
<211> LENGTH: 60
<212> TYPE: DNA
<213> ORGANISM: Homo sapiens

<400> SEQUENCE: 510
gtttgctccg gggccgccgg gcccgccctc gattttaaca ccaccatggt ttgaatgaat      60

<210> SEQ ID NO 511
<211> LENGTH: 60
<212> TYPE: DNA
<213> ORGANISM: Homo sapiens

<400> SEQUENCE: 511
ggtgactgct cagaagagca gtactcattc gaccttatgc taagcctaaa cttgccttcc      60

<210> SEQ ID NO 512
<211> LENGTH: 60
<212> TYPE: DNA
<213> ORGANISM: Homo sapiens

<400> SEQUENCE: 512
aggtcattaa agtataatcc tgttgttatc gagagatcaa gaccatcctg gccaacatgg      60

<210> SEQ ID NO 513
<211> LENGTH: 60
<212> TYPE: DNA
<213> ORGANISM: Homo sapiens

<400> SEQUENCE: 513
attttgacat ctgcatttta cagcagcctc gatgcgagct cgtggtgggt gctcaagact      60

<210> SEQ ID NO 514
<211> LENGTH: 60
<212> TYPE: DNA
<213> ORGANISM: Homo sapiens

<400> SEQUENCE: 514
ggggcctcca gagtcccctt tacaggcatc gacgcccccct gcctacctgc cgggtgcccc     60

<210> SEQ ID NO 515
<211> LENGTH: 60
<212> TYPE: DNA
<213> ORGANISM: Homo sapiens

<400> SEQUENCE: 515
gaaggctagg ctcccgcaca acgcctcctc gagcaagtta gttgaaccca aggagggtca     60

<210> SEQ ID NO 516
<211> LENGTH: 60
<212> TYPE: DNA
<213> ORGANISM: Homo sapiens

<400> SEQUENCE: 516
cctaatattt cattatgata agaaagattc gaataagaaa tacttctaaa ccaaaggata     60

<210> SEQ ID NO 517
<211> LENGTH: 60
<212> TYPE: DNA
<213> ORGANISM: Homo sapiens

<400> SEQUENCE: 517
gcgggggctt ccctcaactt cagggaggtc gaggcgcggc gcgcaggccg ccatcgccac     60

<210> SEQ ID NO 518
<211> LENGTH: 60
<212> TYPE: DNA
<213> ORGANISM: Homo sapiens -continued

<400> SEQUENCE: 518
atttgacaac gctggcacgg aggcaagatc gacctccctg tccctcctgg gcctctccgg    60

<210> SEQ ID NO 519
<211> LENGTH: 60
<212> TYPE: DNA
<213> ORGANISM: Homo sapiens

<400> SEQUENCE: 519
ccgcctccgt ctgcgcctgg gccaggcctc gagaattatt cttttcatat acaaagaata    60

<210> SEQ ID NO 520
<211> LENGTH: 60
<212> TYPE: DNA
<213> ORGANISM: Homo sapiens

<400> SEQUENCE: 520
ctggcgttcc agccctcgca ccttggcctc gagcacctct tcagggagg attactgcaa    60

<210> SEQ ID NO 521
<211> LENGTH: 60
<212> TYPE: DNA
<213> ORGANISM: Homo sapiens

<400> SEQUENCE: 521
gtgtgggccc ccctgctacc gctgcgtatc gaactttaca gagggatcta gaatgagtga    60

<210> SEQ ID NO 522
<211> LENGTH: 60
<212> TYPE: DNA
<213> ORGANISM: Homo sapiens

<400> SEQUENCE: 522
gtgtgggccc ccctgctacc gctgcgtatc gagcacctct tcagggagg attactgcaa    60

<210> SEQ ID NO 523
<211> LENGTH: 60
<212> TYPE: DNA
<213> ORGANISM: Homo sapiens

<400> SEQUENCE: 523
ttaatgctga tacaattcta ttggataatc gacacttcgg ctccctgcac ctcccatgcc    60

<210> SEQ ID NO 524
<211> LENGTH: 60
<212> TYPE: DNA
<213> ORGANISM: Homo sapiens

<400> SEQUENCE: 524
caatatgacg gtgacattaa tgatagcttc gacacttcgg ctccctgcac ctcccatgcc    60

<210> SEQ ID NO 525
<211> LENGTH: 60
<212> TYPE: DNA
<213> ORGANISM: Homo sapiens

<400> SEQUENCE: 525
ttaatgctga tacaattcta ttggataatc gacgtgcctt ggggcctccc ctttccctat    60

<210> SEQ ID NO 526
<211> LENGTH: 60
<212> TYPE: DNA

<213> ORGANISM: Homo sapiens

<400> SEQUENCE: 526
acgcccgcct ccatgagatt cagagccctc gagaatgtgg actctccttt cccccagcac     60

<210> SEQ ID NO 527
<211> LENGTH: 60
<212> TYPE: DNA
<213> ORGANISM: Homo sapiens

<400> SEQUENCE: 527
cacagcttct aaatggtagg tgtgggactc gacccgcttt cctccccgcc ccctcatccg     60

<210> SEQ ID NO 528
<211> LENGTH: 60
<212> TYPE: DNA
<213> ORGANISM: Homo sapiens

<400> SEQUENCE: 528
acgcccgcct ccatgagatt cagagccctc gactcctttc ccagacacat tcagcacgtg     60

<210> SEQ ID NO 529
<211> LENGTH: 60
<212> TYPE: DNA
<213> ORGANISM: Homo sapiens

<400> SEQUENCE: 529
catcccttct atcagcgtgg atggcctctc gaggcccaag ggcttgtcag tcagcttgtg     60

<210> SEQ ID NO 530
<211> LENGTH: 60
<212> TYPE: DNA
<213> ORGANISM: Homo sapiens

<400> SEQUENCE: 530
acagttttat tgttgacctt ccatggactc gagatgcgcc acgccctgtt cctccttcat     60

<210> SEQ ID NO 531
<211> LENGTH: 60
<212> TYPE: DNA
<213> ORGANISM: Homo sapiens

<400> SEQUENCE: 531
caggctattg tagtgctctt cctggccctc gacaccccct tcaagggtct gtgtcccata     60

<210> SEQ ID NO 532
<211> LENGTH: 60
<212> TYPE: DNA
<213> ORGANISM: Homo sapiens

<400> SEQUENCE: 532
catcccttct atcagcgtgg atggcctctc gaggcccaag ggcttgtcag tcagcttgtg     60

<210> SEQ ID NO 533
<211> LENGTH: 60
<212> TYPE: DNA
<213> ORGANISM: Homo sapiens

<400> SEQUENCE: 533
gtctttgtgt aaataaataa ggtaaccctc gagagccggc ctcctgccct ttctaaaggc     60

<210> SEQ ID NO 534
<211> LENGTH: 60

```
<212> TYPE: DNA
<213> ORGANISM: Homo sapiens

<400> SEQUENCE: 534
cgtgaatata ttgggctcta atggataatc gagagccggc ctcctgccct ttctaaaggc    60

<210> SEQ ID NO 535
<211> LENGTH: 60
<212> TYPE: DNA
<213> ORGANISM: Homo sapiens

<400> SEQUENCE: 535
aggacagaga cccctaattc caccaccatc gagggcctta ctaatgcctt ttagctccct    60

<210> SEQ ID NO 536
<211> LENGTH: 60
<212> TYPE: DNA
<213> ORGANISM: Homo sapiens

<400> SEQUENCE: 536
cccgtcttcc ccaaaatcta tgtggtcctc gacagcgacg tgggggtgta ccgcgcggtg    60

<210> SEQ ID NO 537
<211> LENGTH: 60
<212> TYPE: DNA
<213> ORGANISM: Homo sapiens

<400> SEQUENCE: 537
aggtggagat cagaagaccc ccacgccctc gagtcacagc tgtagtgggg tgggggtga    60

<210> SEQ ID NO 538
<211> LENGTH: 60
<212> TYPE: DNA
<213> ORGANISM: Homo sapiens

<400> SEQUENCE: 538
cgtagaacta agatgtattc aaagtcagtc gaaatcacct gtcccggcct ctttccaaac    60

<210> SEQ ID NO 539
<211> LENGTH: 60
<212> TYPE: DNA
<213> ORGANISM: Homo sapiens

<400> SEQUENCE: 539
gtgacaatta agagtgtgac attgcttctc gaggactcac tgggcctgca gggggcagc    60

<210> SEQ ID NO 540
<211> LENGTH: 60
<212> TYPE: DNA
<213> ORGANISM: Homo sapiens

<400> SEQUENCE: 540 ccaccccgc cccggggag tcgcccggtc gaactaatat tagaggagag aggtcagtta    60

<210> SEQ ID NO 541
<211> LENGTH: 60
<212> TYPE: DNA
<213> ORGANISM: Homo sapiens

<400> SEQUENCE: 541 ccaccccgc cccggggag tcgcccggtc gagggcctgg caagaagaca gaagccgact    60

<210> SEQ ID NO 542
```

```
-continued

<211> LENGTH: 60
<212> TYPE: DNA
<213> ORGANISM: Homo sapiens

<400> SEQUENCE: 542 ccaccccgc cccggggag tcgcccggtc gaagtgctgt tgagttcccc catctctcat      60

<210> SEQ ID NO 543
<211> LENGTH: 60
<212> TYPE: DNA
<213> ORGANISM: Homo sapiens

<400> SEQUENCE: 543 ccaccccgc cccggggag tcgcccggtc gatttccaaa agctcacaca tgggtgcaca      60

<210> SEQ ID NO 544
<211> LENGTH: 60
<212> TYPE: DNA
<213> ORGANISM: Homo sapiens

<400> SEQUENCE: 544 ccaccccgc cccggggag tcgcccggtc gacagtccca agaggtcaga actggcttcc      60

<210> SEQ ID NO 545
<211> LENGTH: 60
<212> TYPE: DNA
<213> ORGANISM: Homo sapiens

<400> SEQUENCE: 545 ccaccccgc cccggggag tcgcccggtc gaccccctga catggggctg cctggagcag      60

<210> SEQ ID NO 546
<211> LENGTH: 60
<212> TYPE: DNA
<213> ORGANISM: Homo sapiens

<400> SEQUENCE: 546
ttaaagaagc taattttaaa aataaatgtc gaagagattg tcacgttaga gttatgtaaa    60

<210> SEQ ID NO 547
<211> LENGTH: 60
<212> TYPE: DNA
<213> ORGANISM: Homo sapiens

<400> SEQUENCE: 547
tattatcctg caccctgaaa aggtgttatc gatgcactca gtctttttt tttattcact     60

<210> SEQ ID NO 548
<211> LENGTH: 60
<212> TYPE: DNA
<213> ORGANISM: Homo sapiens

<400> SEQUENCE: 548
gtgtctcggc ccctggggc cccacccttc gatttccctg ttgccgccgc gtttgcaaga    60

<210> SEQ ID NO 549
<211> LENGTH: 60
<212> TYPE: DNA
<213> ORGANISM: Homo sapiens

<400> SEQUENCE: 549
gtgtctcggc ccctggggc cccacccttc gatactatta cgaatggaat cactgtctta   60
```

```
<210> SEQ ID NO 550
<211> LENGTH: 60
<212> TYPE: DNA
<213> ORGANISM: Homo sapiens

<400> SEQUENCE: 550
gtgtctcggc ccctggggc cccacccttc gagtgcatcc tgcagctgtt tgtccagaag      60

<210> SEQ ID NO 551
<211> LENGTH: 60
<212> TYPE: DNA
<213> ORGANISM: Homo sapiens

<400> SEQUENCE: 551
ttatgatatt gtaaattatt tttaatattc gagcaaactg acttggggcc cctatgtgtg      60

<210> SEQ ID NO 552
<211> LENGTH: 60
<212> TYPE: DNA
<213> ORGANISM: Homo sapiens

<400> SEQUENCE: 552
gcagccagcc cggtgggggt ggggggggtc gacgctcgcc tccgctcaca gcctcagcat      60

<210> SEQ ID NO 553
<211> LENGTH: 60
<212> TYPE: DNA
<213> ORGANISM: Homo sapiens

<400> SEQUENCE: 553
caaatcccgg ctatctctta gaattgcatc gacgcgcccg tgacagccga gtgcggccac      60

<210> SEQ ID NO 554
<211> LENGTH: 60
<212> TYPE: DNA
<213> ORGANISM: Homo sapiens

<400> SEQUENCE: 554
acatcgctac caggccgatg tgctgatatc gaggtcccca accccctgcc gctcatcgtg      60

<210> SEQ ID NO 555
<211> LENGTH: 60
<212> TYPE: DNA
<213> ORGANISM: Homo sapiens

<400> SEQUENCE: 555
agtggtctca ccatggcttt cttccaattc gaggtcccca accccctgcc gctcatcgtg      60

<210> SEQ ID NO 556
<211> LENGTH: 60
<212> TYPE: DNA
<213> ORGANISM: Homo sapiens

<400> SEQUENCE: 556
agtggtctca ccatggcttt cttccaattc gaggtcccca accccctgcc gctcatcgtg      60

<210> SEQ ID NO 557
<211> LENGTH: 20
<212> TYPE: DNA
<213> ORGANISM: Homo sapiens

<400> SEQUENCE: 557
gggagtgaag ttcaggagcg                                                 20
```

<210> SEQ ID NO 558
<211> LENGTH: 23
<212> TYPE: DNA
<213> ORGANISM: Homo sapiens

<400> SEQUENCE: 558
tgtcgctgga tgtcaggcag agc                                              23

<210> SEQ ID NO 559
<211> LENGTH: 20
<212> TYPE: DNA
<213> ORGANISM: Homo sapiens

<400> SEQUENCE: 559
acactcgctc agcttcttgg                                                  20

<210> SEQ ID NO 560
<211> LENGTH: 23
<212> TYPE: DNA
<213> ORGANISM: Homo sapiens

<400> SEQUENCE: 560
aggagggagt agtggagagg ttg                                              23

<210> SEQ ID NO 561
<211> LENGTH: 26
<212> TYPE: DNA
<213> ORGANISM: Homo sapiens

<400> SEQUENCE: 561
gtggaaataa aggcaccgtg tgtaga                                           26

<210> SEQ ID NO 562
<211> LENGTH: 19
<212> TYPE: DNA
<213> ORGANISM: Homo sapiens

<400> SEQUENCE: 562
gcgccacctt ctttcagag                                                   19

<210> SEQ ID NO 563
<211> LENGTH: 20
<212> TYPE: DNA
<213> ORGANISM: Homo sapiens

<400> SEQUENCE: 563
gaaacattac aggggcttgg                                                  20

<210> SEQ ID NO 564
<211> LENGTH: 23
<212> TYPE: DNA
<213> ORGANISM: Homo sapiens

<400> SEQUENCE: 564
cttggcacag aacaggagca cca                                              23

<210> SEQ ID NO 565
<211> LENGTH: 23
<212> TYPE: DNA
<213> ORGANISM: Homo sapiens

<400> SEQUENCE: 565
cctgggacta acgaggagcc aca                                              23

<210> SEQ ID NO 566
<211> LENGTH: 20
<212> TYPE: DNA
<213> ORGANISM: Homo sapiens

<400> SEQUENCE: 566
cagactaagg ggcctccaga                                              20

<210> SEQ ID NO 567
<211> LENGTH: 23
<212> TYPE: DNA
<213> ORGANISM: Homo sapiens

<400> SEQUENCE: 567
ggattctttg gctccgctga ggg                                          23

<210> SEQ ID NO 568
<211> LENGTH: 26
<212> TYPE: DNA
<213> ORGANISM: Homo sapiens

<400> SEQUENCE: 568
cctattgcct ggagcataaa gggaaa                                       26

<210> SEQ ID NO 569
<211> LENGTH: 20
<212> TYPE: DNA
<213> ORGANISM: Homo sapiens

<400> SEQUENCE: 569
ggagcattcg cggattagga                                              20

<210> SEQ ID NO 570
<211> LENGTH: 23
<212> TYPE: DNA
<213> ORGANISM: Homo sapiens

<400> SEQUENCE: 570
ggcaggagcc agcagacaca aag                                          23

<210> SEQ ID NO 571
<211> LENGTH: 19
<212> TYPE: DNA
<213> ORGANISM: Homo sapiens

<400> SEQUENCE: 571
cggggacttc tcgctatgg                                               19

<210> SEQ ID NO 572
<211> LENGTH: 23
<212> TYPE: DNA
<213> ORGANISM: Homo sapiens

<400> SEQUENCE: 572
gctctttggt atgacactgg cgg                                          23

<210> SEQ ID NO 573
<211> LENGTH: 23
<212> TYPE: DNA
<213> ORGANISM: Homo sapiens

<400> SEQUENCE: 573
tgttcgtggc tggcaaggag agc                                          23

<210> SEQ ID NO 574
<211> LENGTH: 23
<212> TYPE: DNA
<213> ORGANISM: Homo sapiens

<400> SEQUENCE: 574
tgttcgtggc tggcaaggag agc                                          23

<210> SEQ ID NO 575
<211> LENGTH: 26
<212> TYPE: DNA
<213> ORGANISM: Homo sapiens

<400> SEQUENCE: 575
tgtccctttc tcctaaatac cccaac                                       26

<210> SEQ ID NO 576
<211> LENGTH: 23
<212> TYPE: DNA
<213> ORGANISM: Homo sapiens

<400> SEQUENCE: 576
ccaacacagc agcctccagc cat                                          23

<210> SEQ ID NO 577
<211> LENGTH: 26
<212> TYPE: DNA
<213> ORGANISM: Homo sapiens

<400> SEQUENCE: 577
gtccctttct cctaaatacc ccaacg                                       26

<210> SEQ ID NO 578
<211> LENGTH: 23
<212> TYPE: DNA
<213> ORGANISM: Homo sapiens

<400> SEQUENCE: 578
tggttgttct gggctacttc ccc                                          23

<210> SEQ ID NO 579
<211> LENGTH: 20
<212> TYPE: DNA
<213> ORGANISM: Homo sapiens

<400> SEQUENCE: 579
gctgatgagg cacctgctat                                              20

<210> SEQ ID NO 580
<211> LENGTH: 23
<212> TYPE: DNA
<213> ORGANISM: Homo sapiens

<400> SEQUENCE: 580
tggttgttct gggctacttc ccc                                          23

<210> SEQ ID NO 581
<211> LENGTH: 23
<212> TYPE: DNA
<213> ORGANISM: Homo sapiens

<400> SEQUENCE: 581

```
ccagtttcca tccagtggca gcg                                            23

<210> SEQ ID NO 582
<211> LENGTH: 23
<212> TYPE: DNA
<213> ORGANISM: Homo sapiens

<400> SEQUENCE: 582
gtgtccaccc taccacccac ctt                                            23

<210> SEQ ID NO 583
<211> LENGTH: 23
<212> TYPE: DNA
<213> ORGANISM: Homo sapiens

<400> SEQUENCE: 583
ccaggagaca ccctctaaag gag                                            23

<210> SEQ ID NO 584
<211> LENGTH: 23
<212> TYPE: DNA
<213> ORGANISM: Homo sapiens

<400> SEQUENCE: 584
ccagtttcca tccagtggca gcg                                            23

<210> SEQ ID NO 585
<211> LENGTH: 23
<212> TYPE: DNA
<213> ORGANISM: Homo sapiens

<400> SEQUENCE: 585
gtgaggcagg atggtatggc agt                                            23

<210> SEQ ID NO 586
<211> LENGTH: 26
<212> TYPE: DNA
<213> ORGANISM: Homo sapiens

<400> SEQUENCE: 586
taatcctcct gtctccctct tagaag                                         26

<210> SEQ ID NO 587
<211> LENGTH: 26
<212> TYPE: DNA
<213> ORGANISM: Homo sapiens

<400> SEQUENCE: 587
attagtcttc aacccacgct gttttg                                         26

<210> SEQ ID NO 588
<211> LENGTH: 23
<212> TYPE: DNA
<213> ORGANISM: Homo sapiens

<400> SEQUENCE: 588
tggttctgct acctgtgtgc ctg                                            23

<210> SEQ ID NO 589
<211> LENGTH: 23
<212> TYPE: DNA
<213> ORGANISM: Homo sapiens
```

```
<400> SEQUENCE: 589
tgtgccagac cccaaaagga ccc                                             23

<210> SEQ ID NO 590
<211> LENGTH: 20
<212> TYPE: DNA
<213> ORGANISM: Homo sapiens

<400> SEQUENCE: 590
aattcaccac accccaacat                                                 20

<210> SEQ ID NO 591
<211> LENGTH: 20
<212> TYPE: DNA
<213> ORGANISM: Homo sapiens

<400> SEQUENCE: 591
aggattgtac acacagcccc                                                 20

<210> SEQ ID NO 592
<211> LENGTH: 20
<212> TYPE: DNA
<213> ORGANISM: Homo sapiens

<400> SEQUENCE: 592
ggtgtaacgg gggtcatttc                                                 20

<210> SEQ ID NO 593
<211> LENGTH: 23
<212> TYPE: DNA
<213> ORGANISM: Homo sapiens

<400> SEQUENCE: 593
gcacggtctg tctactttcc ctc                                             23

<210> SEQ ID NO 594
<211> LENGTH: 23
<212> TYPE: DNA
<213> ORGANISM: Homo sapiens

<400> SEQUENCE: 594
gcacggtctg tctactttcc ctc                                             23

<210> SEQ ID NO 595
<211> LENGTH: 20
<212> TYPE: DNA
<213> ORGANISM: Homo sapiens

<400> SEQUENCE: 595
ggtgtaacgg gggtcatttc                                                 20

<210> SEQ ID NO 596
<211> LENGTH: 23
<212> TYPE: DNA
<213> ORGANISM: Homo sapiens

<400> SEQUENCE: 596
gcacggtctg tctactttcc ctc                                             23

<210> SEQ ID NO 597
<211> LENGTH: 23
<212> TYPE: DNA
<213> ORGANISM: Homo sapiens
```

<400> SEQUENCE: 597
cggtgagcac ggtctgtcta ctt                                    23

<210> SEQ ID NO 598
<211> LENGTH: 26
<212> TYPE: DNA
<213> ORGANISM: Homo sapiens

<400> SEQUENCE: 598
tctctacttc aggcaggcag tgtaag                                 26

<210> SEQ ID NO 599
<211> LENGTH: 26
<212> TYPE: DNA
<213> ORGANISM: Homo sapiens

<400> SEQUENCE: 599
cactccagtc cacccacact ttactc                                 26

<210> SEQ ID NO 600
<211> LENGTH: 21
<212> TYPE: DNA
<213> ORGANISM: Homo sapiens

<400> SEQUENCE: 600
cactgaggcc aagttacaag c                                      21

<210> SEQ ID NO 601
<211> LENGTH: 20
<212> TYPE: DNA
<213> ORGANISM: Homo sapiens

<400> SEQUENCE: 601
ctgagtctca cagccatcca                                        20

<210> SEQ ID NO 602
<211> LENGTH: 20
<212> TYPE: DNA
<213> ORGANISM: Homo sapiens

<400> SEQUENCE: 602
catctgtgca tggtcctgag                                        20

<210> SEQ ID NO 603
<211> LENGTH: 19
<212> TYPE: DNA
<213> ORGANISM: Homo sapiens

<400> SEQUENCE: 603
gctggcattt ggattgaga                                         19

<210> SEQ ID NO 604
<211> LENGTH: 23
<212> TYPE: DNA
<213> ORGANISM: Homo sapiens

<400> SEQUENCE: 604
gctgccctct ctcttgtcag acg                                    23

<210> SEQ ID NO 605
<211> LENGTH: 20
<212> TYPE: DNA

-continued

```
<213> ORGANISM: Homo sapiens

<400> SEQUENCE: 605
tcttccaagc atggagtggg                                              20

<210> SEQ ID NO 606
<211> LENGTH: 23
<212> TYPE: DNA
<213> ORGANISM: Homo sapiens

<400> SEQUENCE: 606
ctgggtgccc ttgacattag cgt                                          23

<210> SEQ ID NO 607
<211> LENGTH: 23
<212> TYPE: DNA
<213> ORGANISM: Homo sapiens

<400> SEQUENCE: 607
cctgtcttcc tctttgctga gcc                                          23

<210> SEQ ID NO 608
<211> LENGTH: 23
<212> TYPE: DNA
<213> ORGANISM: Homo sapiens

<400> SEQUENCE: 608
cctgtcttcc tctttgctga gcc                                          23

<210> SEQ ID NO 609
<211> LENGTH: 20
<212> TYPE: DNA
<213> ORGANISM: Homo sapiens

<400> SEQUENCE: 609
tggcagatga ggtaccagga                                              20

<210> SEQ ID NO 610
<211> LENGTH: 23
<212> TYPE: DNA
<213> ORGANISM: Homo sapiens

<400> SEQUENCE: 610
tctgctgtaa gggactgcct cct                                          23

<210> SEQ ID NO 611
<211> LENGTH: 20
<212> TYPE: DNA
<213> ORGANISM: Homo sapiens

<400> SEQUENCE: 611
ggtgcaggaa aaacgaacat                                              20

<210> SEQ ID NO 612
<211> LENGTH: 23
<212> TYPE: DNA
<213> ORGANISM: Homo sapiens

<400> SEQUENCE: 612
tttccgcctc cagcccctca ttc                                          23

<210> SEQ ID NO 613
<211> LENGTH: 26
```

<212> TYPE: DNA
<213> ORGANISM: Homo sapiens

<400> SEQUENCE: 613
ggcaaaaccc taacgccaat cttcag                                              26

<210> SEQ ID NO 614
<211> LENGTH: 20
<212> TYPE: DNA
<213> ORGANISM: Homo sapiens

<400> SEQUENCE: 614
ccctgagaac ccattagtcc                                                     20

<210> SEQ ID NO 615
<211> LENGTH: 20
<212> TYPE: DNA
<213> ORGANISM: Homo sapiens

<400> SEQUENCE: 615
atttgtgtgg ttgcaagggc                                                     20

<210> SEQ ID NO 616
<211> LENGTH: 23
<212> TYPE: DNA
<213> ORGANISM: Homo sapiens

<400> SEQUENCE: 616
tcctgcctca gcctcccaag tag                                                 23

<210> SEQ ID NO 617
<211> LENGTH: 23
<212> TYPE: DNA
<213> ORGANISM: Homo sapiens

<400> SEQUENCE: 617
gcctgtcgtg atgctgatgt cca                                                 23

<210> SEQ ID NO 618
<211> LENGTH: 20
<212> TYPE: DNA
<213> ORGANISM: Homo sapiens

<400> SEQUENCE: 618
cgcaatcaga accaactggc                                                     20

<210> SEQ ID NO 619
<211> LENGTH: 23
<212> TYPE: DNA
<213> ORGANISM: Homo sapiens

<400> SEQUENCE: 619
ccagaagtcc caggttgtgt cct                                                 23

<210> SEQ ID NO 620
<211> LENGTH: 26
<212> TYPE: DNA
<213> ORGANISM: Homo sapiens

<400> SEQUENCE: 620
gtggagaatg tagtattatg aaggtt                                              26

<210> SEQ ID NO 621

```
<211> LENGTH: 20
<212> TYPE: DNA
<213> ORGANISM: Homo sapiens

<400> SEQUENCE: 621
tcaacgctca gctcacactt                                                    20

<210> SEQ ID NO 622
<211> LENGTH: 23
<212> TYPE: DNA
<213> ORGANISM: Homo sapiens

<400> SEQUENCE: 622
ccaaaggagg agaccagcat tgc                                                23

<210> SEQ ID NO 623
<211> LENGTH: 20
<212> TYPE: DNA
<213> ORGANISM: Homo sapiens

<400> SEQUENCE: 623
tgcagccgta agagaggaat                                                    20

<210> SEQ ID NO 624
<211> LENGTH: 23
<212> TYPE: DNA
<213> ORGANISM: Homo sapiens

<400> SEQUENCE: 624
gctttatgcc tcctccagcc agg                                                23

<210> SEQ ID NO 625
<211> LENGTH: 23
<212> TYPE: DNA
<213> ORGANISM: Homo sapiens

<400> SEQUENCE: 625
ccccagggag aagtctgatt cct                                                23

<210> SEQ ID NO 626
<211> LENGTH: 23
<212> TYPE: DNA
<213> ORGANISM: Homo sapiens

<400> SEQUENCE: 626
cttacctgaa aaggctggct ggg                                                23

<210> SEQ ID NO 627
<211> LENGTH: 25
<212> TYPE: DNA
<213> ORGANISM: Homo sapiens

<400> SEQUENCE: 627
taggaggagc ggtcttacag gcaga                                              25

<210> SEQ ID NO 628
<211> LENGTH: 23
<212> TYPE: DNA
<213> ORGANISM: Homo sapiens

<400> SEQUENCE: 628
taggaggagc ggtcttacag gca                                                23
```

```
<210> SEQ ID NO 629
<211> LENGTH: 26
<212> TYPE: DNA
<213> ORGANISM: Homo sapiens

<400> SEQUENCE: 629
tgtgatgctt cccactgctc tgatag                                          26

<210> SEQ ID NO 630
<211> LENGTH: 23
<212> TYPE: DNA
<213> ORGANISM: Homo sapiens

<400> SEQUENCE: 630
gtgaggctct gggtgaaggt gct                                             23

<210> SEQ ID NO 631
<211> LENGTH: 20
<212> TYPE: DNA
<213> ORGANISM: Homo sapiens

<400> SEQUENCE: 631
ctccccttat tgctccccac                                                 20

<210> SEQ ID NO 632
<211> LENGTH: 23
<212> TYPE: DNA
<213> ORGANISM: Homo sapiens

<400> SEQUENCE: 632
cggtgtcctg agtccctggc aat                                             23

<210> SEQ ID NO 633
<211> LENGTH: 23
<212> TYPE: DNA
<213> ORGANISM: Homo sapiens

<400> SEQUENCE: 633
gaaggaagag actcaggact ggc                                             23

<210> SEQ ID NO 634
<211> LENGTH: 23
<212> TYPE: DNA
<213> ORGANISM: Homo sapiens

<400> SEQUENCE: 634
tgtgcccagc aaaaccagtg agc                                             23

<210> SEQ ID NO 635
<211> LENGTH: 23
<212> TYPE: DNA
<213> ORGANISM: Homo sapiens

<400> SEQUENCE: 635
gtccccaggt aatggagcga agc                                             23

<210> SEQ ID NO 636
<211> LENGTH: 23
<212> TYPE: DNA
<213> ORGANISM: Homo sapiens

<400> SEQUENCE: 636
gaaggaagag actcaggact ggc                                             23
```

<210> SEQ ID NO 637
<211> LENGTH: 23
<212> TYPE: DNA
<213> ORGANISM: Homo sapiens

<400> SEQUENCE: 637
caagacctcc ccaacttccc agg                                            23

<210> SEQ ID NO 638
<211> LENGTH: 26
<212> TYPE: DNA
<213> ORGANISM: Homo sapiens

<400> SEQUENCE: 638
cccaggttga actacagcag aagcct                                         26

<210> SEQ ID NO 639
<211> LENGTH: 26
<212> TYPE: DNA
<213> ORGANISM: Homo sapiens

<400> SEQUENCE: 639
ggttctaagg agagttgtaa agagag                                         26

<210> SEQ ID NO 640
<211> LENGTH: 23
<212> TYPE: DNA
<213> ORGANISM: Homo sapiens

<400> SEQUENCE: 640
cgccacctcg tagttgtgtc tgc                                            23

<210> SEQ ID NO 641
<211> LENGTH: 23
<212> TYPE: DNA
<213> ORGANISM: Homo sapiens

<400> SEQUENCE: 641
cagcggcact tgtcttcag gag                                             23

<210> SEQ ID NO 642
<211> LENGTH: 20
<212> TYPE: DNA
<213> ORGANISM: Homo sapiens

<400> SEQUENCE: 642
ctccggagga tttctgtgaa                                                20

<210> SEQ ID NO 643
<211> LENGTH: 19
<212> TYPE: DNA
<213> ORGANISM: Homo sapiens

<400> SEQUENCE: 643 cagggctct tctttcagc                                                  19

<210> SEQ ID NO 644
<211> LENGTH: 19
<212> TYPE: DNA
<213> ORGANISM: Homo sapiens

<400> SEQUENCE: 644
ccaggccagc ttcaaactc                                                 19

```
<210> SEQ ID NO 645
<211> LENGTH: 23
<212> TYPE: DNA
<213> ORGANISM: Homo sapiens

<400> SEQUENCE: 645
tggagatgct gctctgccca cct                                          23

<210> SEQ ID NO 646
<211> LENGTH: 23
<212> TYPE: DNA
<213> ORGANISM: Homo sapiens

<400> SEQUENCE: 646
cacagccctt ggcatcaccc aca                                          23

<210> SEQ ID NO 647
<211> LENGTH: 20
<212> TYPE: DNA
<213> ORGANISM: Homo sapiens

<400> SEQUENCE: 647
tgtgggaacc atacctgtgc                                              20

<210> SEQ ID NO 648
<211> LENGTH: 23
<212> TYPE: DNA
<213> ORGANISM: Homo sapiens

<400> SEQUENCE: 648
cgttgcctcc tcacagcaga agc                                          23

<210> SEQ ID NO 649
<211> LENGTH: 23
<212> TYPE: DNA
<213> ORGANISM: Homo sapiens

<400> SEQUENCE: 649
gtcctgggtc ctgggtgaaa gtc                                          23

<210> SEQ ID NO 650
<211> LENGTH: 26
<212> TYPE: DNA
<213> ORGANISM: Homo sapiens

<400> SEQUENCE: 650
gggagaccat ttctgttcac tctgag                                       26

<210> SEQ ID NO 651
<211> LENGTH: 26
<212> TYPE: DNA
<213> ORGANISM: Homo sapiens

<400> SEQUENCE: 651
ctaaaccctg gaaccaaaac tcatcc                                       26

<210> SEQ ID NO 652
<211> LENGTH: 20
<212> TYPE: DNA
<213> ORGANISM: Homo sapiens

<400> SEQUENCE: 652
```

```
tgtaaattgc cgcaggggaa                                              20

<210> SEQ ID NO 653
<211> LENGTH: 20
<212> TYPE: DNA
<213> ORGANISM: Homo sapiens

<400> SEQUENCE: 653
ggcactcaca cacgagaaaa                                              20

<210> SEQ ID NO 654
<211> LENGTH: 20
<212> TYPE: DNA
<213> ORGANISM: Homo sapiens

<400> SEQUENCE: 654
atcaggatca ggcttcaagg                                              20

<210> SEQ ID NO 655
<211> LENGTH: 20
<212> TYPE: DNA
<213> ORGANISM: Homo sapiens

<400> SEQUENCE: 655
ggcttgatct ctggacgaag                                              20

<210> SEQ ID NO 656
<211> LENGTH: 23
<212> TYPE: DNA
<213> ORGANISM: Homo sapiens

<400> SEQUENCE: 656
gtccacccca ttgccgcttt tca                                          23

<210> SEQ ID NO 657
<211> LENGTH: 19
<212> TYPE: DNA
<213> ORGANISM: Homo sapiens

<400> SEQUENCE: 657
ctgcaggttg gtgctgagt                                               19

<210> SEQ ID NO 658
<211> LENGTH: 23
<212> TYPE: DNA
<213> ORGANISM: Homo sapiens

<400> SEQUENCE: 658
gccaccctcc ctaagagact gag                                          23

<210> SEQ ID NO 659
<211> LENGTH: 23
<212> TYPE: DNA
<213> ORGANISM: Homo sapiens

<400> SEQUENCE: 659
gccaccctcc ctaagagact gag                                          23

<210> SEQ ID NO 660
<211> LENGTH: 23
<212> TYPE: DNA
<213> ORGANISM: Homo sapiens

<400> SEQUENCE: 660
```

-continued gccaccctcc ctaagagact gag                                            23

<210> SEQ ID NO 661
<211> LENGTH: 60
<212> TYPE: DNA
<213> ORGANISM: Homo sapiens

<400> SEQUENCE: 661
atcccaacaa aagagaagaa cttctccctc gatgtttggg ggcggagggc tttgatgaga    60

<210> SEQ ID NO 662
<211> LENGTH: 60
<212> TYPE: DNA
<213> ORGANISM: Homo sapiens

<400> SEQUENCE: 662
caaaatcaaa cacaaatcta atcaaacttc gatgtttggg ggcggagggc tttgatgaga    60

<210> SEQ ID NO 663
<211> LENGTH: 60
<212> TYPE: DNA
<213> ORGANISM: Homo sapiens

<400> SEQUENCE: 663
ggccgcgagc ccggcagcgg cgacatcctc gagaaattct cccgctttag cctcccaaag   60

<210> SEQ ID NO 664
<211> LENGTH: 60
<212> TYPE: DNA
<213> ORGANISM: Homo sapiens

<400> SEQUENCE: 664
tgagatgaag cctatatttt cccaatcctc gatgtttggg ggcggagggc tttgatgaga    60

<210> SEQ ID NO 665
<211> LENGTH: 60
<212> TYPE: DNA
<213> ORGANISM: Homo sapiens

<400> SEQUENCE: 665
tacagacttt ttttctcttc tcagaaaatc gatgtttggg ggcggagggc tttgatgaga    60

<210> SEQ ID NO 666
<211> LENGTH: 60
<212> TYPE: DNA
<213> ORGANISM: Homo sapiens

<400> SEQUENCE: 666
gcggccaacc cacagcgcac cgggccgctc gacctctgag aggaaacttg ctagcccag    60

<210> SEQ ID NO 667
<211> LENGTH: 60
<212> TYPE: DNA
<213> ORGANISM: Homo sapiens

<400> SEQUENCE: 667
cactaatctt tactcttttt ccacttattc gaccctcccc ttccagctgg gcacaggtgg    60

<210> SEQ ID NO 668
<211> LENGTH: 60
<212> TYPE: DNA
<213> ORGANISM: Homo sapiens

<400> SEQUENCE: 668
attcccaatg tttcctgagt agaactgttc gactgcgagc tccctccctg cagtcaggga    60

<210> SEQ ID NO 669
<211> LENGTH: 60
<212> TYPE: DNA
<213> ORGANISM: Homo sapiens

<400> SEQUENCE: 669
agggagaaca aagaagttc catccatctc gatcccccg ggctcaaagc aaacctccta    60

<210> SEQ ID NO 670
<211> LENGTH: 60
<212> TYPE: DNA
<213> ORGANISM: Homo sapiens

<400> SEQUENCE: 670
agggagaaca aagaagttc catccatctc gacggagtcc tccccgcagg gcagccccga    60

<210> SEQ ID NO 671
<211> LENGTH: 60
<212> TYPE: DNA
<213> ORGANISM: Homo sapiens

<400> SEQUENCE: 671
tatttgtatc ctttcctcat ttatttactc gaatctctgg ggtagggctc tgcaaccttg    60

<210> SEQ ID NO 672
<211> LENGTH: 60
<212> TYPE: DNA
<213> ORGANISM: Homo sapiens

<400> SEQUENCE: 672
tttcaaagaa ggtatgatgg gaaaggtctc gagtgcccct gtcccacctg gctccccctg    60

<210> SEQ ID NO 673
<211> LENGTH: 60
<212> TYPE: DNA
<213> ORGANISM: Homo sapiens

<400> SEQUENCE: 673
tttcaaagaa ggtatgatgg gaaaggtctc gacgcgcccc ctctacgcca tgtcccccc    60

<210> SEQ ID NO 674
<211> LENGTH: 60
<212> TYPE: DNA
<213> ORGANISM: Homo sapiens

<400> SEQUENCE: 674
atataaatct actttataaa taaggaaatc gaagtataat tcaatatact gtccagtaaa    60

<210> SEQ ID NO 675
<211> LENGTH: 60
<212> TYPE: DNA
<213> ORGANISM: Homo sapiens

<400> SEQUENCE: 675
tccagccttg cctggagcta gggccacctc gatcttggct caccgcaacc ttggcctccc    60

<210> SEQ ID NO 676
<211> LENGTH: 60
<212> TYPE: DNA
<213> ORGANISM: Homo sapiens -continued

<400> SEQUENCE: 676
ctgtgaacat tggtgtacta gtagcttttc gatttccact tctacccccc ggtccgagtt      60

<210> SEQ ID NO 677
<211> LENGTH: 60
<212> TYPE: DNA
<213> ORGANISM: Homo sapiens

<400> SEQUENCE: 677
ccatctgcaa gtcgcttttg actagcactc gagttctttc tgacatctcc tgggtggagc      60

<210> SEQ ID NO 678
<211> LENGTH: 60
<212> TYPE: DNA
<213> ORGANISM: Homo sapiens

<400> SEQUENCE: 678
gtggattaca tccttctata ggtgtggctc gagcggagtc acccaggctg gagtgcagtg      60

<210> SEQ ID NO 679
<211> LENGTH: 60
<212> TYPE: DNA
<213> ORGANISM: Homo sapiens

<400> SEQUENCE: 679
gacctaagga ttaagaagat taatggagtc gagcatcctc tacctctatc tccaacccct      60

<210> SEQ ID NO 680
<211> LENGTH: 60
<212> TYPE: DNA
<213> ORGANISM: Homo sapiens

<400> SEQUENCE: 680
cctgcacttc ctcacgcctg ctcacccctc gagtgagtgg gagagatggc tctccacgcc      60

<210> SEQ ID NO 681
<211> LENGTH: 60
<212> TYPE: DNA
<213> ORGANISM: Homo sapiens

<400> SEQUENCE: 681
tatataattt ccactttgtt tttaataatc gaaattaaaa attattttat ctcacataga      60

<210> SEQ ID NO 682
<211> LENGTH: 60
<212> TYPE: DNA
<213> ORGANISM: Homo sapiens

<400> SEQUENCE: 682
gcctggatgc cctcgtccat ctcggccttc gatctgagga cagaaaagac ccaggcgccc      60

<210> SEQ ID NO 683
<211> LENGTH: 60
<212> TYPE: DNA
<213> ORGANISM: Homo sapiens

<400> SEQUENCE: 683
ttaaatcttg aatagaagtt atgattgatc gattattgaa ttcaattgtg tatataaatt      60

<210> SEQ ID NO 684
<211> LENGTH: 60
<212> TYPE: DNA

-continued

<213> ORGANISM: Homo sapiens

<400> SEQUENCE: 684
tattaagaaa ataagtcagc caggtgtttc gagtactact acaattagca cttgcttatt    60

<210> SEQ ID NO 685
<211> LENGTH: 60
<212> TYPE: DNA
<213> ORGANISM: Homo sapiens

<400> SEQUENCE: 685
ggccagtaga tcatttgagg ccaggagttc gataaccttc aaatcaactc acagaattcc    60

<210> SEQ ID NO 686
<211> LENGTH: 60
<212> TYPE: DNA
<213> ORGANISM: Homo sapiens

<400> SEQUENCE: 686
tgggaggtgg ccagagtctg actacatctc gaactactgg gctcaaacaa ttctcctgcc    60

<210> SEQ ID NO 687
<211> LENGTH: 60
<212> TYPE: DNA
<213> ORGANISM: Homo sapiens

<400> SEQUENCE: 687
ttaatgctga tacaattcta ttggataatc gacacttcgg ctccctgcac ctcccatgcc    60

<210> SEQ ID NO 688
<211> LENGTH: 60
<212> TYPE: DNA
<213> ORGANISM: Homo sapiens

<400> SEQUENCE: 688
caatatgacg gtgacattaa tgatagcttc gacacttcgg ctccctgcac ctcccatgcc    60

<210> SEQ ID NO 689
<211> LENGTH: 60
<212> TYPE: DNA
<213> ORGANISM: Homo sapiens

<400> SEQUENCE: 689
ttaatgctga tacaattcta ttggataatc gacgtgcctt ggggcctccc ctttccctat    60

<210> SEQ ID NO 690
<211> LENGTH: 60
<212> TYPE: DNA
<213> ORGANISM: Homo sapiens

<400> SEQUENCE: 690
aataaaaata gaaacaatc cttcaaaatc gacaccaatg tttccatttt gttttcagaa    60

<210> SEQ ID NO 691
<211> LENGTH: 60
<212> TYPE: DNA
<213> ORGANISM: Homo sapiens

<400> SEQUENCE: 691
aatgattaaa tgtgtacctt aatgagtttc gaaactccat tgagtcatta tccttgctat    60

<210> SEQ ID NO 692
<211> LENGTH: 60

```
<212> TYPE: DNA
<213> ORGANISM: Homo sapiens

<400> SEQUENCE: 692
catcatagca acccattgta actagacttc gaatagatac ttcaggaaag aaatgtatat    60

<210> SEQ ID NO 693
<211> LENGTH: 60
<212> TYPE: DNA
<213> ORGANISM: Homo sapiens

<400> SEQUENCE: 693
agacaatatt aaaattgaga acttttgttc gattttattt ttaacttata agaagatctg    60

<210> SEQ ID NO 694
<211> LENGTH: 60
<212> TYPE: DNA
<213> ORGANISM: Homo sapiens

<400> SEQUENCE: 694
tgtgatgatt tcttcttttt atatgttttc gataaaatac ttcataaaaa taacatgcta    60

<210> SEQ ID NO 695
<211> LENGTH: 60
<212> TYPE: DNA
<213> ORGANISM: Homo sapiens

<400> SEQUENCE: 695
tagcatgtta tttttatgaa gtattttatc gacagttttt tttaaaaaaa aaccttgaca    60

<210> SEQ ID NO 696
<211> LENGTH: 60
<212> TYPE: DNA
<213> ORGANISM: Homo sapiens

<400> SEQUENCE: 696
tagcatgtta tttttatgaa gtattttatc gagctgataa acagctttgt agggaaaaac    60

<210> SEQ ID NO 697
<211> LENGTH: 60
<212> TYPE: DNA
<213> ORGANISM: Homo sapiens

<400> SEQUENCE: 697
tagcatgtta tttttatgaa gtattttatc gaagaattat aaacacttat agttgtatct    60

<210> SEQ ID NO 698
<211> LENGTH: 60
<212> TYPE: DNA
<213> ORGANISM: Homo sapiens

<400> SEQUENCE: 698
agtggtgcaa tcttgactca ctgcagtctc gaaatctagt aacatcatat tctaacatga    60

<210> SEQ ID NO 699
<211> LENGTH: 60
<212> TYPE: DNA
<213> ORGANISM: Homo sapiens

<400> SEQUENCE: 699
ggcctcggca ctcaccgttc cctccccctc gatttccatg agcccctctg aatccttcca    60

<210> SEQ ID NO 700
```

```
<211> LENGTH: 60
<212> TYPE: DNA
<213> ORGANISM: Homo sapiens

<400> SEQUENCE: 700
cacctgtcat gctggtctgc cgccgttttc gaggcaggcc cctcctgcca agtgaagaga      60

<210> SEQ ID NO 701
<211> LENGTH: 60
<212> TYPE: DNA
<213> ORGANISM: Homo sapiens

<400> SEQUENCE: 701
ggcctcggca ctcaccgttc cctcccctc gaggcaggcc cctcctgcca agtgaagaga       60

<210> SEQ ID NO 702
<211> LENGTH: 60
<212> TYPE: DNA
<213> ORGANISM: Homo sapiens

<400> SEQUENCE: 702
gagatactaa aataggtttc tttcctagtc gactaggatc agttgtttgt aggattataa      60

<210> SEQ ID NO 703
<211> LENGTH: 60
<212> TYPE: DNA
<213> ORGANISM: Homo sapiens

<400> SEQUENCE: 703
aactcacaac tatctggtgc tatgtacatc gaactaaaat ctgcctctga acagcttcca      60

<210> SEQ ID NO 704
<211> LENGTH: 60
<212> TYPE: DNA
<213> ORGANISM: Homo sapiens

<400> SEQUENCE: 704
atctttagca tatatgttaa attgataatc gaatttaata aagaaattac tgaaaaagga      60

<210> SEQ ID NO 705
<211> LENGTH: 60
<212> TYPE: DNA
<213> ORGANISM: Homo sapiens

<400> SEQUENCE: 705
cccctcaccc aaactagggt ctctagactc gagctcccat agatcaactt tctgcactcc     60

<210> SEQ ID NO 706
<211> LENGTH: 60
<212> TYPE: DNA
<213> ORGANISM: Homo sapiens

<400> SEQUENCE: 706
cccctcaccc aaactagggt ctctagactc gagaggccat ccacgctgat agaagggatg     60

<210> SEQ ID NO 707
<211> LENGTH: 60
<212> TYPE: DNA
<213> ORGANISM: Homo sapiens

<400> SEQUENCE: 707
ccctggggtt ctgattaaca tccttaattc gagaggccat ccacgctgat agaagggatg     60
```

```
<210> SEQ ID NO 708
<211> LENGTH: 60
<212> TYPE: DNA
<213> ORGANISM: Homo sapiens

<400> SEQUENCE: 708
cccctcaccc aaactagggt ctctagactc gagacaaggt atatgagcag ctggccaaat    60

<210> SEQ ID NO 709
<211> LENGTH: 60
<212> TYPE: DNA
<213> ORGANISM: Homo sapiens

<400> SEQUENCE: 709
ccctggggtt ctgattaaca tccttaattc gaagaatgcc taatggttaa gcagtaggaa    60

<210> SEQ ID NO 710
<211> LENGTH: 60
<212> TYPE: DNA
<213> ORGANISM: Homo sapiens

<400> SEQUENCE: 710
cccctcaccc aaactagggt ctctagactc gaggcccaag ggcttgtcag tcagcttgtg    60

<210> SEQ ID NO 711
<211> LENGTH: 60
<212> TYPE: DNA
<213> ORGANISM: Homo sapiens

<400> SEQUENCE: 711
attcttctgt ccccagtttc ttatgcagtc gagaggccat ccacgctgat agaagggatg    60

<210> SEQ ID NO 712
<211> LENGTH: 60
<212> TYPE: DNA
<213> ORGANISM: Homo sapiens

<400> SEQUENCE: 712
ggagtgcaga aagttgatct atgggagctc gactgtatcc gcagcacctg gcccacagta    60

<210> SEQ ID NO 713
<211> LENGTH: 23
<212> TYPE: DNA
<213> ORGANISM: Homo sapiens

<400> SEQUENCE: 713
ctaagaggtg atgcccaagg tgc                                            23

<210> SEQ ID NO 714
<211> LENGTH: 23
<212> TYPE: DNA
<213> ORGANISM: Homo sapiens

<400> SEQUENCE: 714
gtctcctgag gtgaagcaag agg                                            23

<210> SEQ ID NO 715
<211> LENGTH: 20
<212> TYPE: DNA
<213> ORGANISM: Homo sapiens

<400> SEQUENCE: 715
ggtgctaatc tcagggaccg                                                20
```

<210> SEQ ID NO 716
<211> LENGTH: 24
<212> TYPE: DNA
<213> ORGANISM: Homo sapiens

<400> SEQUENCE: 716
ctctcttgct ggcattccct tccc                                              24

<210> SEQ ID NO 717
<211> LENGTH: 23
<212> TYPE: DNA
<213> ORGANISM: Homo sapiens

<400> SEQUENCE: 717
gtaaatgagc cacctgggcg ggt                                               23

<210> SEQ ID NO 718
<211> LENGTH: 23
<212> TYPE: DNA
<213> ORGANISM: Homo sapiens

<400> SEQUENCE: 718
ggcaaatacg ttaatagcag cac                                               23

<210> SEQ ID NO 719
<211> LENGTH: 26
<212> TYPE: DNA
<213> ORGANISM: Homo sapiens

<400> SEQUENCE: 719
gtcatctcct ctccagttag tcaaca                                            26

<210> SEQ ID NO 720
<211> LENGTH: 20
<212> TYPE: DNA
<213> ORGANISM: Homo sapiens

<400> SEQUENCE: 720
ttcagagggt tcttcgggga                                                   20

<210> SEQ ID NO 721
<211> LENGTH: 23
<212> TYPE: DNA
<213> ORGANISM: Homo sapiens

<400> SEQUENCE: 721 gccccctaagc aaccaccttg gac                                              23

<210> SEQ ID NO 722
<211> LENGTH: 23
<212> TYPE: DNA
<213> ORGANISM: Homo sapiens

<400> SEQUENCE: 722
ccctaagcaa ccaccttgga ctg                                               23

<210> SEQ ID NO 723
<211> LENGTH: 20
<212> TYPE: DNA
<213> ORGANISM: Homo sapiens

<400> SEQUENCE: 723
aatgttggca tggtgttttc                                                   20

<210> SEQ ID NO 724
<211> LENGTH: 26
<212> TYPE: DNA
<213> ORGANISM: Homo sapiens

<400> SEQUENCE: 724
cactttgcct ccacatctgg tatgag                                   26

<210> SEQ ID NO 725
<211> LENGTH: 20
<212> TYPE: DNA
<213> ORGANISM: Homo sapiens

<400> SEQUENCE: 725
tagcactttg cctccacatc                                          20

<210> SEQ ID NO 726
<211> LENGTH: 20
<212> TYPE: DNA
<213> ORGANISM: Homo sapiens

<400> SEQUENCE: 726
acttgtggct tccttagccc                                          20

<210> SEQ ID NO 727
<211> LENGTH: 26
<212> TYPE: DNA
<213> ORGANISM: Homo sapiens

<400> SEQUENCE: 727
cagaaagaga agcaaagagg actcat                                   26

<210> SEQ ID NO 728
<211> LENGTH: 20
<212> TYPE: DNA
<213> ORGANISM: Homo sapiens

<400> SEQUENCE: 728
ggctgctgtg aatcatgctg                                          20

<210> SEQ ID NO 729
<211> LENGTH: 23
<212> TYPE: DNA
<213> ORGANISM: Homo sapiens

<400> SEQUENCE: 729
ggcggtaaag tcacacagcc aga                                      23

<210> SEQ ID NO 730
<211> LENGTH: 21
<212> TYPE: DNA
<213> ORGANISM: Homo sapiens

<400> SEQUENCE: 730
agtgtcgctg tacatgacca g                                        21

<210> SEQ ID NO 731
<211> LENGTH: 26
<212> TYPE: DNA
<213> ORGANISM: Homo sapiens

<400> SEQUENCE: 731

```
ctgcctggtt tctgaactga gtgagg                                              26

<210> SEQ ID NO 732
<211> LENGTH: 23
<212> TYPE: DNA
<213> ORGANISM: Homo sapiens

<400> SEQUENCE: 732
gagcgtggtg ccagtgtggg taa                                                 23

<210> SEQ ID NO 733
<211> LENGTH: 23
<212> TYPE: DNA
<213> ORGANISM: Homo sapiens

<400> SEQUENCE: 733
gcaccttact cggaggagga cca                                                 23

<210> SEQ ID NO 734
<211> LENGTH: 23
<212> TYPE: DNA
<213> ORGANISM: Homo sapiens

<400> SEQUENCE: 734
aggtaacggc tgacaggtgc tgg                                                 23

<210> SEQ ID NO 735
<211> LENGTH: 26
<212> TYPE: DNA
<213> ORGANISM: Homo sapiens

<400> SEQUENCE: 735
tcaaaagagc acagcataat ctgaat                                              26

<210> SEQ ID NO 736
<211> LENGTH: 26
<212> TYPE: DNA
<213> ORGANISM: Homo sapiens

<400> SEQUENCE: 736
ctaagtgcca gcagactatg gagcca                                              26

<210> SEQ ID NO 737
<211> LENGTH: 23
<212> TYPE: DNA
<213> ORGANISM: Homo sapiens

<400> SEQUENCE: 737
gtttccgtgc cttttccagc ctc                                                 23

<210> SEQ ID NO 738
<211> LENGTH: 20
<212> TYPE: DNA
<213> ORGANISM: Homo sapiens

<400> SEQUENCE: 738
cagggagaac acccggaagg                                                     20

<210> SEQ ID NO 739
<211> LENGTH: 26
<212> TYPE: DNA
<213> ORGANISM: Homo sapiens

<400> SEQUENCE: 739
```
tgtccctttc tcctaaatac cccaac 26

<210> SEQ ID NO 740
<211> LENGTH: 23
<212> TYPE: DNA
<213> ORGANISM: Homo sapiens

<400> SEQUENCE: 740
ccaacacagc agcctccagc cat 23

<210> SEQ ID NO 741
<211> LENGTH: 26
<212> TYPE: DNA
<213> ORGANISM: Homo sapiens

<400> SEQUENCE: 741
gtccctttct cctaaatacc ccaacg 26

<210> SEQ ID NO 742
<211> LENGTH: 23
<212> TYPE: DNA
<213> ORGANISM: Homo sapiens

<400> SEQUENCE: 742
ctttggactt atgtaaatgt ttt 23

<210> SEQ ID NO 743
<211> LENGTH: 25
<212> TYPE: DNA
<213> ORGANISM: Homo sapiens

<400> SEQUENCE: 743
taaataccag ccttggaatc agggc 25

<210> SEQ ID NO 744
<211> LENGTH: 26
<212> TYPE: DNA
<213> ORGANISM: Homo sapiens

<400> SEQUENCE: 744
ctggattctt gagcgacttg ttcctg 26

<210> SEQ ID NO 745
<211> LENGTH: 26
<212> TYPE: DNA
<213> ORGANISM: Homo sapiens

<400> SEQUENCE: 745
gaagaaactg gattcctacc tggcac 26

<210> SEQ ID NO 746
<211> LENGTH: 26
<212> TYPE: DNA
<213> ORGANISM: Homo sapiens

<400> SEQUENCE: 746
gctgtgctct ttcaaatcca ctgctg 26

<210> SEQ ID NO 747
<211> LENGTH: 26
<212> TYPE: DNA
<213> ORGANISM: Homo sapiens

```
<400> SEQUENCE: 747
ttattttatt agatgccacc ctcagc                                              26

<210> SEQ ID NO 748
<211> LENGTH: 26
<212> TYPE: DNA
<213> ORGANISM: Homo sapiens

<400> SEQUENCE: 748
ttattttatt agatgccacc ctcagc                                              26

<210> SEQ ID NO 749
<211> LENGTH: 26
<212> TYPE: DNA
<213> ORGANISM: Homo sapiens

<400> SEQUENCE: 749
ttattttatt agatgccacc ctcagc                                              26

<210> SEQ ID NO 750
<211> LENGTH: 26
<212> TYPE: DNA
<213> ORGANISM: Homo sapiens

<400> SEQUENCE: 750
gggatgccac tgtatttctc aaagcc                                              26

<210> SEQ ID NO 751
<211> LENGTH: 20
<212> TYPE: DNA
<213> ORGANISM: Homo sapiens

<400> SEQUENCE: 751
ccatatggtc tccgggtcct                                                     20

<210> SEQ ID NO 752
<211> LENGTH: 26
<212> TYPE: DNA
<213> ORGANISM: Homo sapiens

<400> SEQUENCE: 752 tggtcccta caaagtcctt ccgtgc                                               26

<210> SEQ ID NO 753
<211> LENGTH: 26
<212> TYPE: DNA
<213> ORGANISM: Homo sapiens

<400> SEQUENCE: 753
tttcctctgt ctccatctcc gcccat                                              26

<210> SEQ ID NO 754
<211> LENGTH: 26
<212> TYPE: DNA
<213> ORGANISM: Homo sapiens

<400> SEQUENCE: 754
ggtgggaaga gggtgtcaca agtcat                                              26

<210> SEQ ID NO 755
<211> LENGTH: 23
<212> TYPE: DNA
<213> ORGANISM: Homo sapiens
```

<400> SEQUENCE: 755
ggttcactga ctctggtgcc aac                                         23

<210> SEQ ID NO 756
<211> LENGTH: 25
<212> TYPE: DNA
<213> ORGANISM: Homo sapiens

<400> SEQUENCE: 756
gctgatttct ttgtgtgtgg gtggg                                       25

<210> SEQ ID NO 757
<211> LENGTH: 25
<212> TYPE: DNA
<213> ORGANISM: Homo sapiens

<400> SEQUENCE: 757
acacacctcc ctcaacccaa ctgtc                                       25

<210> SEQ ID NO 758
<211> LENGTH: 23
<212> TYPE: DNA
<213> ORGANISM: Homo sapiens

<400> SEQUENCE: 758
cacacctccc tcaacccaac tgt                                         23

<210> SEQ ID NO 759
<211> LENGTH: 23
<212> TYPE: DNA
<213> ORGANISM: Homo sapiens

<400> SEQUENCE: 759
aactaatccc caccccatcc tgc                                         23

<210> SEQ ID NO 760
<211> LENGTH: 23
<212> TYPE: DNA
<213> ORGANISM: Homo sapiens

<400> SEQUENCE: 760
ccacacacct ccctcaaccc aac                                         23

<210> SEQ ID NO 761
<211> LENGTH: 23
<212> TYPE: DNA
<213> ORGANISM: Homo sapiens

<400> SEQUENCE: 761
actaatcccc accccatcct gcc                                         23

<210> SEQ ID NO 762
<211> LENGTH: 20
<212> TYPE: DNA
<213> ORGANISM: Homo sapiens

<400> SEQUENCE: 762
ctccctcaac ccaactgtcc                                             20

<210> SEQ ID NO 763
<211> LENGTH: 23
<212> TYPE: DNA

```
<213> ORGANISM: Homo sapiens

<400> SEQUENCE: 763
ctcctgccca ctctattttc ccc                                        23

<210> SEQ ID NO 764
<211> LENGTH: 26
<212> TYPE: DNA
<213> ORGANISM: Homo sapiens

<400> SEQUENCE: 764
agaagacact ccataaatgc tcaggg                                     26

<210> SEQ ID NO 765
<211> LENGTH: 23
<212> TYPE: DNA
<213> ORGANISM: Homo sapiens

<400> SEQUENCE: 765
gacgccacaa cagacaggca agc                                        23

<210> SEQ ID NO 766
<211> LENGTH: 23
<212> TYPE: DNA
<213> ORGANISM: Homo sapiens

<400> SEQUENCE: 766
agtcagccca ctcatcccct tcc                                        23

<210> SEQ ID NO 767
<211> LENGTH: 19
<212> TYPE: DNA
<213> ORGANISM: Homo sapiens

<400> SEQUENCE: 767
tttggcaagc tttgtgagg                                             19

<210> SEQ ID NO 768
<211> LENGTH: 23
<212> TYPE: DNA
<213> ORGANISM: Homo sapiens

<400> SEQUENCE: 768
gtagacgcca caacagacag gca                                        23

<210> SEQ ID NO 769
<211> LENGTH: 25
<212> TYPE: DNA
<213> ORGANISM: Homo sapiens

<400> SEQUENCE: 769
ggcaagcatc ttcctggttc ttcag                                      25

<210> SEQ ID NO 770
<211> LENGTH: 20
<212> TYPE: DNA
<213> ORGANISM: Homo sapiens

<400> SEQUENCE: 770
caggaaggtc ggaatagctg                                            20

<210> SEQ ID NO 771
<211> LENGTH: 26
```

```
<212> TYPE: DNA
<213> ORGANISM: Homo sapiens

<400> SEQUENCE: 771
ggttggaagt agcccacggt gtgttt                                           26

<210> SEQ ID NO 772
<211> LENGTH: 19
<212> TYPE: DNA
<213> ORGANISM: Homo sapiens

<400> SEQUENCE: 772
atgacggggt gtgggttat                                                   19

<210> SEQ ID NO 773
<211> LENGTH: 23
<212> TYPE: DNA
<213> ORGANISM: Homo sapiens

<400> SEQUENCE: 773
ccagcagttt cagaggcaaa ggc                                              23

<210> SEQ ID NO 774
<211> LENGTH: 23
<212> TYPE: DNA
<213> ORGANISM: Homo sapiens

<400> SEQUENCE: 774
gcttcgctta ccagagtcgc tgc                                              23

<210> SEQ ID NO 775
<211> LENGTH: 21
<212> TYPE: DNA
<213> ORGANISM: Homo sapiens

<400> SEQUENCE: 775
tcaagtgcat actccacaac g                                                21

<210> SEQ ID NO 776
<211> LENGTH: 26
<212> TYPE: DNA
<213> ORGANISM: Homo sapiens

<400> SEQUENCE: 776
ggcttgacac ccttagttta ctgcct                                           26

<210> SEQ ID NO 777
<211> LENGTH: 22
<212> TYPE: DNA
<213> ORGANISM: Homo sapiens

<400> SEQUENCE: 777
cctagactct cacctcctct cg                                               22

<210> SEQ ID NO 778
<211> LENGTH: 21
<212> TYPE: DNA
<213> ORGANISM: Homo sapiens

<400> SEQUENCE: 778
tcctttgcag gtatggacat c                                                21

<210> SEQ ID NO 779
```

```
<211> LENGTH: 26
<212> TYPE: DNA
<213> ORGANISM: Homo sapiens

<400> SEQUENCE: 779
gttggatgct gtgtggtggg atagat                                              26

<210> SEQ ID NO 780
<211> LENGTH: 20
<212> TYPE: DNA
<213> ORGANISM: Homo sapiens

<400> SEQUENCE: 780
tgagactaga ctggagggcc                                                     20

<210> SEQ ID NO 781
<211> LENGTH: 23
<212> TYPE: DNA
<213> ORGANISM: Homo sapiens

<400> SEQUENCE: 781
acacctgtga gcagagtgga ggg                                                 23

<210> SEQ ID NO 782
<211> LENGTH: 20
<212> TYPE: DNA
<213> ORGANISM: Homo sapiens

<400> SEQUENCE: 782
gcccggcctt gagttattct                                                     20

<210> SEQ ID NO 783
<211> LENGTH: 26
<212> TYPE: DNA
<213> ORGANISM: Homo sapiens

<400> SEQUENCE: 783
agaaactgat ggaagaagga aactcc                                              26

<210> SEQ ID NO 784
<211> LENGTH: 23
<212> TYPE: DNA
<213> ORGANISM: Homo sapiens

<400> SEQUENCE: 784
gggagggaag ttgaacgatg ggt                                                 23

<210> SEQ ID NO 785
<211> LENGTH: 23
<212> TYPE: DNA
<213> ORGANISM: Homo sapiens

<400> SEQUENCE: 785
cagccttctc tccaaagcag gga                                                 23

<210> SEQ ID NO 786
<211> LENGTH: 23
<212> TYPE: DNA
<213> ORGANISM: Homo sapiens

<400> SEQUENCE: 786
tcaccaccac ccatagccct aag                                                 23
```

```
<210> SEQ ID NO 787
<211> LENGTH: 26
<212> TYPE: DNA
<213> ORGANISM: Homo sapiens

<400> SEQUENCE: 787
aatcaaccct caggctttca ggcaaa                                         26

<210> SEQ ID NO 788
<211> LENGTH: 26
<212> TYPE: DNA
<213> ORGANISM: Homo sapiens

<400> SEQUENCE: 788
gacacactca gatttcagac acaaca                                         26

<210> SEQ ID NO 789
<211> LENGTH: 23
<212> TYPE: DNA
<213> ORGANISM: Homo sapiens

<400> SEQUENCE: 789
gggcagttca tcatagggag ccg                                            23

<210> SEQ ID NO 790
<211> LENGTH: 19
<212> TYPE: DNA
<213> ORGANISM: Homo sapiens

<400> SEQUENCE: 790
gctatggagc tggacatgg                                                 19

<210> SEQ ID NO 791
<211> LENGTH: 25
<212> TYPE: DNA
<213> ORGANISM: Homo sapiens

<400> SEQUENCE: 791
taggaggagc ggtcttacag gcaga                                          25

<210> SEQ ID NO 792
<211> LENGTH: 23
<212> TYPE: DNA
<213> ORGANISM: Homo sapiens

<400> SEQUENCE: 792
taggaggagc ggtcttacag gca                                            23

<210> SEQ ID NO 793
<211> LENGTH: 26
<212> TYPE: DNA
<213> ORGANISM: Homo sapiens

<400> SEQUENCE: 793
tgtgatgctt cccactgctc tgatag                                         26

<210> SEQ ID NO 794
<211> LENGTH: 23
<212> TYPE: DNA
<213> ORGANISM: Homo sapiens

<400> SEQUENCE: 794
acaaacataa gttgaggctg gat                                            23
```

```
<210> SEQ ID NO 795
<211> LENGTH: 26
<212> TYPE: DNA
<213> ORGANISM: Homo sapiens

<400> SEQUENCE: 795
caccctctca tccccaaaac accatc                                              26

<210> SEQ ID NO 796
<211> LENGTH: 26
<212> TYPE: DNA
<213> ORGANISM: Homo sapiens

<400> SEQUENCE: 796
gggactgtca ctggctattt atggga                                              26

<210> SEQ ID NO 797
<211> LENGTH: 26
<212> TYPE: DNA
<213> ORGANISM: Homo sapiens

<400> SEQUENCE: 797
ggaatgtcct gccttagggt atctgt                                              26

<210> SEQ ID NO 798
<211> LENGTH: 26
<212> TYPE: DNA
<213> ORGANISM: Homo sapiens

<400> SEQUENCE: 798
ttattttatt agatgccacc ctcagc                                              26

<210> SEQ ID NO 799
<211> LENGTH: 26
<212> TYPE: DNA
<213> ORGANISM: Homo sapiens

<400> SEQUENCE: 799
cagaacagtg ggtagggact tgcttt                                              26

<210> SEQ ID NO 800
<211> LENGTH: 26
<212> TYPE: DNA
<213> ORGANISM: Homo sapiens

<400> SEQUENCE: 800
tgctaagaag tgtcaccacc tcctca                                              26

<210> SEQ ID NO 801
<211> LENGTH: 26
<212> TYPE: DNA
<213> ORGANISM: Homo sapiens

<400> SEQUENCE: 801
gacaaaggct ctgatgttga aaatgc                                              26

<210> SEQ ID NO 802
<211> LENGTH: 26
<212> TYPE: DNA
<213> ORGANISM: Homo sapiens

<400> SEQUENCE: 802
ggtaaaagga agcaaaggac tgattc                                              26
```

<210> SEQ ID NO 803
<211> LENGTH: 20
<212> TYPE: DNA
<213> ORGANISM: Homo sapiens

<400> SEQUENCE: 803
acccagaggt tcctttgtca                                                   20

<210> SEQ ID NO 804
<211> LENGTH: 26
<212> TYPE: DNA
<213> ORGANISM: Homo sapiens

<400> SEQUENCE: 804
gggtgaagga ataaatgatt ggaggg                                            26

<210> SEQ ID NO 805
<211> LENGTH: 26
<212> TYPE: DNA
<213> ORGANISM: Homo sapiens

<400> SEQUENCE: 805
gggtgaagga ataaatgatt ggaggg                                            26

<210> SEQ ID NO 806
<211> LENGTH: 26
<212> TYPE: DNA
<213> ORGANISM: Homo sapiens

<400> SEQUENCE: 806
ggatactaaa ccacctgctc ataagg                                            26

<210> SEQ ID NO 807
<211> LENGTH: 23
<212> TYPE: DNA
<213> ORGANISM: Homo sapiens

<400> SEQUENCE: 807
gtcccgagaa gggtgaccag aca                                               23

<210> SEQ ID NO 808
<211> LENGTH: 26
<212> TYPE: DNA
<213> ORGANISM: Homo sapiens

<400> SEQUENCE: 808
cattctgaca tcctcttccc attcct                                            26

<210> SEQ ID NO 809
<211> LENGTH: 26
<212> TYPE: DNA
<213> ORGANISM: Homo sapiens

<400> SEQUENCE: 809
agaagacact ccataaatgc tcaggg                                            26

<210> SEQ ID NO 810
<211> LENGTH: 23
<212> TYPE: DNA
<213> ORGANISM: Homo sapiens

<400> SEQUENCE: 810

```
ccagtttcca tccagtggca gcg                                              23

<210> SEQ ID NO 811
<211> LENGTH: 23
<212> TYPE: DNA
<213> ORGANISM: Homo sapiens

<400> SEQUENCE: 811
ccagtttcca tccagtggca gcg                                              23

<210> SEQ ID NO 812
<211> LENGTH: 23
<212> TYPE: DNA
<213> ORGANISM: Homo sapiens

<400> SEQUENCE: 812
cctcccttgc ccacacatac caa                                              23

<210> SEQ ID NO 813
<211> LENGTH: 23
<212> TYPE: DNA
<213> ORGANISM: Homo sapiens

<400> SEQUENCE: 813
gccactttcc ctccccactc aat                                              23

<210> SEQ ID NO 814
<211> LENGTH: 20
<212> TYPE: DNA
<213> ORGANISM: Homo sapiens

<400> SEQUENCE: 814
ctggcagcat tcaccacaag                                                  20

<210> SEQ ID NO 815
<211> LENGTH: 23
<212> TYPE: DNA
<213> ORGANISM: Homo sapiens

<400> SEQUENCE: 815
ccagtttcca tccagtggca gcg                                              23

<210> SEQ ID NO 816
<211> LENGTH: 26
<212> TYPE: DNA
<213> ORGANISM: Homo sapiens

<400> SEQUENCE: 816
cccacttgac ccctcataag agttct                                           26

<210> SEQ ID NO 817
<211> LENGTH: 60
<212> TYPE: DNA
<213> ORGANISM: Homo sapiens

<400> SEQUENCE: 817
ggagtgcaga aagttgatct atgggagctc gagaggccat ccacgctgat agaagggatg     60

<210> SEQ ID NO 818
<211> LENGTH: 60
<212> TYPE: DNA
<213> ORGANISM: Homo sapiens

<400> SEQUENCE: 818
```

```
actcaaatat ggaatattcc agtcaaaatc gagaggccat ccacgctgat agaagggatg    60
```

<210> SEQ ID NO 819
<211> LENGTH: 60
<212> TYPE: DNA
<213> ORGANISM: Homo sapiens

<400> SEQUENCE: 819

```
actcaaatat ggaatattcc agtcaaaatc gaggcccaag ggcttgtcag tcagcttgtg    60
```

<210> SEQ ID NO 820
<211> LENGTH: 60
<212> TYPE: DNA
<213> ORGANISM: Homo sapiens

<400> SEQUENCE: 820

```
ctggttctaa aattatatga acctagaatc gatggtatac caaaggtctg tctttatgta    60
```

<210> SEQ ID NO 821
<211> LENGTH: 60
<212> TYPE: DNA
<213> ORGANISM: Homo sapiens

<400> SEQUENCE: 821

```
tggacttaat atcatgttta agtttacatc gatggtatta gtccatttct atttgtaact    60
```

<210> SEQ ID NO 822
<211> LENGTH: 60
<212> TYPE: DNA
<213> ORGANISM: Homo sapiens

<400> SEQUENCE: 822

```
attaaatgca cattgttgaa tatattttc gatggtatta gtccatttct atttgtaact    60
```

<210> SEQ ID NO 823
<211> LENGTH: 60
<212> TYPE: DNA
<213> ORGANISM: Homo sapiens

<400> SEQUENCE: 823

```
attatactat tcttcattca tatcttcttc gatcttttga aatagtttca gtaggattgg    60
```

<210> SEQ ID NO 824
<211> LENGTH: 60
<212> TYPE: DNA
<213> ORGANISM: Homo sapiens

<400> SEQUENCE: 824

```
tggaggggac caatgacaag tttgacattc gatcttttga aatagtttca gtaggattgg    60
```

<210> SEQ ID NO 825
<211> LENGTH: 60
<212> TYPE: DNA
<213> ORGANISM: Homo sapiens

<400> SEQUENCE: 825

```
ttcattcttc tttatagata agtagtattc gatgaagtct cattttcat gtattaaatt    60
```

<210> SEQ ID NO 826
<211> LENGTH: 60
<212> TYPE: DNA
<213> ORGANISM: Homo sapiens

<400> SEQUENCE: 826
gtcagatgtc acaggggcag ttagaacctc gaacaattat ttacatttta agaactggta    60

<210> SEQ ID NO 827
<211> LENGTH: 60
<212> TYPE: DNA
<213> ORGANISM: Homo sapiens

<400> SEQUENCE: 827
gtcagatgtc acaggggcag ttagaacctc gatacacaca tacctaccgt tttatctcag    60

<210> SEQ ID NO 828
<211> LENGTH: 60
<212> TYPE: DNA
<213> ORGANISM: Homo sapiens

<400> SEQUENCE: 828
ccctgaagtg ggcaggaatt tcatgtgttc gaattgcttg tttcctggtg atcccctcc    60

<210> SEQ ID NO 829
<211> LENGTH: 60
<212> TYPE: DNA
<213> ORGANISM: Homo sapiens

<400> SEQUENCE: 829
aaacttcctt tctttgctta gaactagctc gatcctggaa gcccctaaa ggcaggaact    60

<210> SEQ ID NO 830
<211> LENGTH: 60
<212> TYPE: DNA
<213> ORGANISM: Homo sapiens

<400> SEQUENCE: 830
taacaaggag tggagtattc ctgggatatc gaccccaccc cctagattaa gacattcctg    60

<210> SEQ ID NO 831
<211> LENGTH: 60
<212> TYPE: DNA
<213> ORGANISM: Homo sapiens

<400> SEQUENCE: 831
aggtgggagg atcatctgaa cccggaggtc gaaaatatat cttcagttaa tttttgtata    60

<210> SEQ ID NO 832
<211> LENGTH: 60
<212> TYPE: DNA
<213> ORGANISM: Homo sapiens

<400> SEQUENCE: 832
tatacaaaaa ttaactgaag atatattttc gaaaataagg taatgatttg gcagagggaa    60

<210> SEQ ID NO 833
<211> LENGTH: 60
<212> TYPE: DNA
<213> ORGANISM: Homo sapiens

<400> SEQUENCE: 833
ggtcccctga tttccatcct agtgcttctc gatgatataa tactctgctg actacatttt    60

<210> SEQ ID NO 834
<211> LENGTH: 60
<212> TYPE: DNA
<213> ORGANISM: Homo sapiens -continued

<400> SEQUENCE: 834
tcagaaataa ataaataaag tagaaaactc gacaggacaa attttctaaa gactgaatga    60

<210> SEQ ID NO 835
<211> LENGTH: 60
<212> TYPE: DNA
<213> ORGANISM: Homo sapiens

<400> SEQUENCE: 835
caggagttca agaccaacct ggtcaacatc gaaacagcaa acgaaggcca ggaagcccac    60

<210> SEQ ID NO 836
<211> LENGTH: 60
<212> TYPE: DNA
<213> ORGANISM: Homo sapiens

<400> SEQUENCE: 836
ttttaagaaa cattaagata ttaaactgtc gaaatgtgtg aaaaagtaag agtagtactt    60

<210> SEQ ID NO 837
<211> LENGTH: 60
<212> TYPE: DNA
<213> ORGANISM: Homo sapiens

<400> SEQUENCE: 837 taccettaat ttaaaccctt gtgtattttc gatgatttca ttactgtaat tacctcatat    60

<210> SEQ ID NO 838
<211> LENGTH: 60
<212> TYPE: DNA
<213> ORGANISM: Homo sapiens

<400> SEQUENCE: 838
ttagctttat tacagataaa atattatatc gatggccatt tttttcttta ttaatgttta    60

<210> SEQ ID NO 839
<211> LENGTH: 60
<212> TYPE: DNA
<213> ORGANISM: Homo sapiens

<400> SEQUENCE: 839
ttagctttat tacagataaa atattatatc gaatcacgtt actcctttct taaaaaccta    60

<210> SEQ ID NO 840
<211> LENGTH: 60
<212> TYPE: DNA
<213> ORGANISM: Homo sapiens

<400> SEQUENCE: 840
ttagctttat tacagataaa atattatatc gatggatctc acaattataa ccaacaaaag    60

<210> SEQ ID NO 841
<211> LENGTH: 60
<212> TYPE: DNA
<213> ORGANISM: Homo sapiens

<400> SEQUENCE: 841
gaaagaggtc actggtacac atccagtgtc gaaaactcat cgtattgcta taatttgagt    60

<210> SEQ ID NO 842
<211> LENGTH: 60
<212> TYPE: DNA

<213> ORGANISM: Homo sapiens

<400> SEQUENCE: 842
acatttatat gaagtaccat ttatgttttc gattttaaa tttctttccc taaacatatt    60

<210> SEQ ID NO 843
<211> LENGTH: 60
<212> TYPE: DNA
<213> ORGANISM: Homo sapiens

<400> SEQUENCE: 843
aatatgttta gggaaagaaa tttaaaaatc gatacagttt caaattttaa tttagatgta    60

<210> SEQ ID NO 844
<211> LENGTH: 60
<212> TYPE: DNA
<213> ORGANISM: Homo sapiens

<400> SEQUENCE: 844
ataaatagac tccactatgt ataatgactc gaaattttgc tataaatgtg agctttgaaa    60

<210> SEQ ID NO 845
<211> LENGTH: 60
<212> TYPE: DNA
<213> ORGANISM: Homo sapiens

<400> SEQUENCE: 845
cagccagcca gtagatcttc ataggagctc gaaattttgc tataaatgtg agctttgaaa    60

<210> SEQ ID NO 846
<211> LENGTH: 60
<212> TYPE: DNA
<213> ORGANISM: Homo sapiens

<400> SEQUENCE: 846
gctggagacc cggggaggaa tatcaaactc gattctggtg tttccagcaa gtttggacac    60

<210> SEQ ID NO 847
<211> LENGTH: 60
<212> TYPE: DNA
<213> ORGANISM: Homo sapiens

<400> SEQUENCE: 847
gctggagacc cggggaggaa tatcaaactc gaccctaact gcagtcactg ttacttggat    60

<210> SEQ ID NO 848
<211> LENGTH: 60
<212> TYPE: DNA
<213> ORGANISM: Homo sapiens

<400> SEQUENCE: 848
ctatctagtc cttatcagaa gggaaccttc gaagtctctc ttgagatggg ttcttacttt    60

<210> SEQ ID NO 849
<211> LENGTH: 60
<212> TYPE: DNA
<213> ORGANISM: Homo sapiens

<400> SEQUENCE: 849
aataaagtgc actatagatg ttatgtgctc gaaatttctt ttgagctctg cattgtttga    60

<210> SEQ ID NO 850
<211> LENGTH: 60

```
<212> TYPE: DNA
<213> ORGANISM: Homo sapiens

<400> SEQUENCE: 850
tctttaaaat gttgaatact ataatatatc gacaagaata ttctatttaa aaagcaaatc    60

<210> SEQ ID NO 851
<211> LENGTH: 60
<212> TYPE: DNA
<213> ORGANISM: Homo sapiens

<400> SEQUENCE: 851
caggctattg tagtgctctt cctggccctc gacacccct tcaagggtct gtgtcccata     60

<210> SEQ ID NO 852
<211> LENGTH: 60
<212> TYPE: DNA
<213> ORGANISM: Homo sapiens

<400> SEQUENCE: 852
aaaaaaataa atataaaata gaaaaatatc gatattttca tttgtctttc ctaggaactc    60

<210> SEQ ID NO 853
<211> LENGTH: 60
<212> TYPE: DNA
<213> ORGANISM: Homo sapiens

<400> SEQUENCE: 853
aaaaaaataa atataaaata gaaaaatatc gaagtatgtc ctatatgggg aaaaaacgta    60

<210> SEQ ID NO 854
<211> LENGTH: 60
<212> TYPE: DNA
<213> ORGANISM: Homo sapiens

<400> SEQUENCE: 854
catcccttct atcagcgtgg atggcctctc gatgttaacc ttgatccttt ggttaaagta    60

<210> SEQ ID NO 855
<211> LENGTH: 60
<212> TYPE: DNA
<213> ORGANISM: Homo sapiens

<400> SEQUENCE: 855
cccatgcaaa aattctttgg aagtttcctc gattaacaaa aaagagttaa tacatattag    60

<210> SEQ ID NO 856
<211> LENGTH: 60
<212> TYPE: DNA
<213> ORGANISM: Homo sapiens

<400> SEQUENCE: 856
caaataatgt tactaaaatc aattcaagtc gacttgattg atggaaatta gaatacaggt    60

<210> SEQ ID NO 857
<211> LENGTH: 60
<212> TYPE: DNA
<213> ORGANISM: Homo sapiens

<400> SEQUENCE: 857
aaattaatac acattttat tgtgaaattc gactacctca aaagaaaatg atccattgac     60

<210> SEQ ID NO 858
```

-continued

<211> LENGTH: 60
<212> TYPE: DNA
<213> ORGANISM: Homo sapiens

<400> SEQUENCE: 858
gccattaaat tccctaatg ccattgcctc gacttcagtg gcgtccattg tctgctggag        60

<210> SEQ ID NO 859
<211> LENGTH: 60
<212> TYPE: DNA
<213> ORGANISM: Homo sapiens

<400> SEQUENCE: 859
taaaccatag ttaattttat gtaaatattc gatattttcc agctatcttt ctgttgattt        60

<210> SEQ ID NO 860
<211> LENGTH: 60
<212> TYPE: DNA
<213> ORGANISM: Homo sapiens

<400> SEQUENCE: 860
ttagcatcac ttgaaagcta gttaaaaatc gattgcaaat gatatgacag aattgctttg        60

<210> SEQ ID NO 861
<211> LENGTH: 60
<212> TYPE: DNA
<213> ORGANISM: Homo sapiens

<400> SEQUENCE: 861
atccttataa acactttata ttttcttttc gaggatttct aggcatacat aatcttttcc        60

<210> SEQ ID NO 862
<211> LENGTH: 60
<212> TYPE: DNA
<213> ORGANISM: Homo sapiens

<400> SEQUENCE: 862
atccttataa acactttata ttttcttttc gaaataacta tagaagctag gagctgataa        60

<210> SEQ ID NO 863
<211> LENGTH: 60
<212> TYPE: DNA
<213> ORGANISM: Homo sapiens

<400> SEQUENCE: 863 tgaaaagaa aaaagaaat ctactttttc gaatataagc tttcttcaat attatcaaat        60

<210> SEQ ID NO 864
<211> LENGTH: 60
<212> TYPE: DNA
<213> ORGANISM: Homo sapiens

<400> SEQUENCE: 864
ttcattgaat aattcattga gttattcatc gatgttaaga aaggtgtatc taaaggaata        60

<210> SEQ ID NO 865
<211> LENGTH: 60
<212> TYPE: DNA
<213> ORGANISM: Homo sapiens

<400> SEQUENCE: 865 attttattt ttggattta agatactatc gaatatgaac ccattatact agggcaaaat        60

```
<210> SEQ ID NO 866
<211> LENGTH: 60
<212> TYPE: DNA
<213> ORGANISM: Homo sapiens

<400> SEQUENCE: 866
gtaatattat gtaaaattgc atttggtatc gaacaaagcc tttaacttga cttagtgtca    60

<210> SEQ ID NO 867
<211> LENGTH: 60
<212> TYPE: DNA
<213> ORGANISM: Homo sapiens

<400> SEQUENCE: 867
aggacagaga ccctaattc caccaccatc gaacaactgc aaactccact caacatcttt    60

<210> SEQ ID NO 868
<211> LENGTH: 60
<212> TYPE: DNA
<213> ORGANISM: Homo sapiens

<400> SEQUENCE: 868
aggacagaga ccctaattc caccaccatc gagggcttac taatgcctt ttagctccct     60

<210> SEQ ID NO 869
<211> LENGTH: 26
<212> TYPE: DNA
<213> ORGANISM: Homo sapiens

<400> SEQUENCE: 869
agaagacact ccataaatgc tcaggg                                         26

<210> SEQ ID NO 870
<211> LENGTH: 23
<212> TYPE: DNA
<213> ORGANISM: Homo sapiens

<400> SEQUENCE: 870
cgggtggcgt ggtgtgtaat acc                                            23

<210> SEQ ID NO 871
<211> LENGTH: 23
<212> TYPE: DNA
<213> ORGANISM: Homo sapiens

<400> SEQUENCE: 871
cgggtggcgt ggtgtgtaat acc                                            23

<210> SEQ ID NO 872
<211> LENGTH: 26
<212> TYPE: DNA
<213> ORGANISM: Homo sapiens

<400> SEQUENCE: 872
aaatctcaat agcctttcct tgtgga                                         26

<210> SEQ ID NO 873
<211> LENGTH: 26
<212> TYPE: DNA
<213> ORGANISM: Homo sapiens

<400> SEQUENCE: 873
cctcatcttt tccacagtga cagagc                                         26
```

```
<210> SEQ ID NO 874
<211> LENGTH: 25
<212> TYPE: DNA
<213> ORGANISM: Homo sapiens

<400> SEQUENCE: 874
atgactatga agagtggaaa tgtcc                                   25

<210> SEQ ID NO 875
<211> LENGTH: 26
<212> TYPE: DNA
<213> ORGANISM: Homo sapiens

<400> SEQUENCE: 875
ctgtagccag cggaaatact gcttag                                  26

<210> SEQ ID NO 876
<211> LENGTH: 26
<212> TYPE: DNA
<213> ORGANISM: Homo sapiens

<400> SEQUENCE: 876
caacctcatc aacagttaga atagcc                                  26

<210> SEQ ID NO 877
<211> LENGTH: 25
<212> TYPE: DNA
<213> ORGANISM: Homo sapiens

<400> SEQUENCE: 877
ttcttaccct tcccagcctc taata                                   25

<210> SEQ ID NO 878
<211> LENGTH: 20
<212> TYPE: DNA
<213> ORGANISM: Homo sapiens

<400> SEQUENCE: 878
ggtgagtggg gatagccttc                                         20

<210> SEQ ID NO 879
<211> LENGTH: 23
<212> TYPE: DNA
<213> ORGANISM: Homo sapiens

<400> SEQUENCE: 879
cttgggcagg tgagggagaa cag                                     23

<210> SEQ ID NO 880
<211> LENGTH: 23
<212> TYPE: DNA
<213> ORGANISM: Homo sapiens

<400> SEQUENCE: 880
gggctggtca aacaaactct ggc                                     23

<210> SEQ ID NO 881
<211> LENGTH: 23
<212> TYPE: DNA
<213> ORGANISM: Homo sapiens

<400> SEQUENCE: 881
tgccttggag gtagcgatgg gtg                                     23
```

<210> SEQ ID NO 882
<211> LENGTH: 23
<212> TYPE: DNA
<213> ORGANISM: Homo sapiens

<400> SEQUENCE: 882
ccccaagatg aaaactgagc ggc                                          23

<210> SEQ ID NO 883
<211> LENGTH: 26
<212> TYPE: DNA
<213> ORGANISM: Homo sapiens

<400> SEQUENCE: 883
gcctggacaa gatggtgaaa ccctgt                                       26

<210> SEQ ID NO 884
<211> LENGTH: 23
<212> TYPE: DNA
<213> ORGANISM: Homo sapiens

<400> SEQUENCE: 884
gcctgggcga caaagtgaga ctc                                          23

<210> SEQ ID NO 885
<211> LENGTH: 26
<212> TYPE: DNA
<213> ORGANISM: Homo sapiens

<400> SEQUENCE: 885
ggctctgggc aatagttgta gtgtgg                                       26

<210> SEQ ID NO 886
<211> LENGTH: 23
<212> TYPE: DNA
<213> ORGANISM: Homo sapiens

<400> SEQUENCE: 886
tatccctatg gactgagcca ggc                                          23

<210> SEQ ID NO 887
<211> LENGTH: 20
<212> TYPE: DNA
<213> ORGANISM: Homo sapiens

<400> SEQUENCE: 887
gtgccccaca tctgtaattg                                              20

<210> SEQ ID NO 888
<211> LENGTH: 23
<212> TYPE: DNA
<213> ORGANISM: Homo sapiens

<400> SEQUENCE: 888
cttcaaagca ggagggactg tgc                                          23

<210> SEQ ID NO 889
<211> LENGTH: 26
<212> TYPE: DNA
<213> ORGANISM: Homo sapiens

<400> SEQUENCE: 889
ccagtgggct cttagaacga tgacac                                           26

<210> SEQ ID NO 890
<211> LENGTH: 23
<212> TYPE: DNA
<213> ORGANISM: Homo sapiens

<400> SEQUENCE: 890
taagatacac atttattgtc caa                                              23

<210> SEQ ID NO 891
<211> LENGTH: 23
<212> TYPE: DNA
<213> ORGANISM: Homo sapiens

<400> SEQUENCE: 891
taagatacac atttattgtc caa                                              23

<210> SEQ ID NO 892
<211> LENGTH: 23
<212> TYPE: DNA
<213> ORGANISM: Homo sapiens

<400> SEQUENCE: 892
taagatacac atttattgtc caa                                              23

<210> SEQ ID NO 893
<211> LENGTH: 26
<212> TYPE: DNA
<213> ORGANISM: Homo sapiens

<400> SEQUENCE: 893
ctctacttct gctttctctc acaggc                                           26

<210> SEQ ID NO 894
<211> LENGTH: 23
<212> TYPE: DNA
<213> ORGANISM: Homo sapiens

<400> SEQUENCE: 894
ttatctcagc cttatctttt ctg                                              23

<210> SEQ ID NO 895
<211> LENGTH: 26
<212> TYPE: DNA
<213> ORGANISM: Homo sapiens

<400> SEQUENCE: 895
ctgcctttat tttccatctt tctctt                                           26

<210> SEQ ID NO 896
<211> LENGTH: 23
<212> TYPE: DNA
<213> ORGANISM: Homo sapiens

<400> SEQUENCE: 896
gatgctgctg gtgagagtag tcc                                              23

<210> SEQ ID NO 897
<211> LENGTH: 23
<212> TYPE: DNA
<213> ORGANISM: Homo sapiens

<400> SEQUENCE: 897

```
gcaagtgagc cagcattacc gcc                                        23

<210> SEQ ID NO 898
<211> LENGTH: 25
<212> TYPE: DNA
<213> ORGANISM: Homo sapiens

<400> SEQUENCE: 898
tgatgttcca gtctgagggt cttgc                                      25

<210> SEQ ID NO 899
<211> LENGTH: 23
<212> TYPE: DNA
<213> ORGANISM: Homo sapiens

<400> SEQUENCE: 899
gctgatgttc cagtctgagg gtc                                        23

<210> SEQ ID NO 900
<211> LENGTH: 23
<212> TYPE: DNA
<213> ORGANISM: Homo sapiens

<400> SEQUENCE: 900
ctctgtgcct gtcatcaccc tct                                        23

<210> SEQ ID NO 901
<211> LENGTH: 23
<212> TYPE: DNA
<213> ORGANISM: Homo sapiens

<400> SEQUENCE: 901
tctgtcactg tctcccacca ccc                                        23

<210> SEQ ID NO 902
<211> LENGTH: 26
<212> TYPE: DNA
<213> ORGANISM: Homo sapiens

<400> SEQUENCE: 902
ctctggcagc aagttagaaa taatct                                     26

<210> SEQ ID NO 903
<211> LENGTH: 23
<212> TYPE: DNA
<213> ORGANISM: Homo sapiens

<400> SEQUENCE: 903
ccaggagaca ccctctaaag gag                                        23

<210> SEQ ID NO 904
<211> LENGTH: 23
<212> TYPE: DNA
<213> ORGANISM: Homo sapiens

<400> SEQUENCE: 904
gggctggaat gagaagtggt agg                                        23

<210> SEQ ID NO 905
<211> LENGTH: 26
<212> TYPE: DNA
<213> ORGANISM: Homo sapiens
```

```
<400> SEQUENCE: 905
ggctggaatg agaagtggta ggatgg                                    26

<210> SEQ ID NO 906
<211> LENGTH: 26
<212> TYPE: DNA
<213> ORGANISM: Homo sapiens

<400> SEQUENCE: 906
ttccccgttt tggacagggt gagaga                                    26

<210> SEQ ID NO 907
<211> LENGTH: 25
<212> TYPE: DNA
<213> ORGANISM: Homo sapiens

<400> SEQUENCE: 907
ccataacaaa accgctggac aagat                                     25

<210> SEQ ID NO 908
<211> LENGTH: 26
<212> TYPE: DNA
<213> ORGANISM: Homo sapiens

<400> SEQUENCE: 908
ggaatcggga aagtctaaac cagaag                                    26

<210> SEQ ID NO 909
<211> LENGTH: 26
<212> TYPE: DNA
<213> ORGANISM: Homo sapiens

<400> SEQUENCE: 909
ggaacactgt aactggagga aacttg                                    26

<210> SEQ ID NO 910
<211> LENGTH: 23
<212> TYPE: DNA
<213> ORGANISM: Homo sapiens

<400> SEQUENCE: 910
cccctgtaac attctcccac cct                                       23

<210> SEQ ID NO 911
<211> LENGTH: 26
<212> TYPE: DNA
<213> ORGANISM: Homo sapiens

<400> SEQUENCE: 911
gttcctggat gcttcaaaat gtgata                                    26

<210> SEQ ID NO 912
<211> LENGTH: 26
<212> TYPE: DNA
<213> ORGANISM: Homo sapiens

<400> SEQUENCE: 912
ctgctacttc aactgtggtc tgggac                                    26

<210> SEQ ID NO 913
<211> LENGTH: 26
<212> TYPE: DNA
<213> ORGANISM: Homo sapiens
```

```
<400> SEQUENCE: 913
taaggctgct gtgaacattc ttgtgc                                            26

<210> SEQ ID NO 914
<211> LENGTH: 26
<212> TYPE: DNA
<213> ORGANISM: Homo sapiens

<400> SEQUENCE: 914
taaggctgct gtgaacattc ttgtgc                                            26

<210> SEQ ID NO 915
<211> LENGTH: 26
<212> TYPE: DNA
<213> ORGANISM: Homo sapiens

<400> SEQUENCE: 915
gaagagaagg agtggagcaa gggttg                                            26

<210> SEQ ID NO 916
<211> LENGTH: 26
<212> TYPE: DNA
<213> ORGANISM: Homo sapiens

<400> SEQUENCE: 916
gtctgctttt gcctacggtt tagcct                                            26

<210> SEQ ID NO 917
<211> LENGTH: 26
<212> TYPE: DNA
<213> ORGANISM: Homo sapiens

<400> SEQUENCE: 917
gggtagatga gactgattgc ttacag                                            26

<210> SEQ ID NO 918
<211> LENGTH: 26
<212> TYPE: DNA
<213> ORGANISM: Homo sapiens

<400> SEQUENCE: 918
ggcataaaca tcaatcagat agcctc                                            26

<210> SEQ ID NO 919
<211> LENGTH: 26
<212> TYPE: DNA
<213> ORGANISM: Homo sapiens

<400> SEQUENCE: 919
attagtcttc aacccacgct gttttg                                            26

<210> SEQ ID NO 920
<211> LENGTH: 26
<212> TYPE: DNA
<213> ORGANISM: Homo sapiens

<400> SEQUENCE: 920
attagtcttc aacccacgct gttttg                                            26

<210> SEQ ID NO 921
<211> LENGTH: 26
<212> TYPE: DNA
```

<213> ORGANISM: Homo sapiens

<400> SEQUENCE: 921
ccccatctgt gacctctccc tctttt                                          26

<210> SEQ ID NO 922
<211> LENGTH: 23
<212> TYPE: DNA
<213> ORGANISM: Homo sapiens

<400> SEQUENCE: 922
cccatctgtg acctctccct ctt                                             23

<210> SEQ ID NO 923
<211> LENGTH: 23
<212> TYPE: DNA
<213> ORGANISM: Homo sapiens

<400> SEQUENCE: 923
gaaggaagag actcaggact ggc                                             23

<210> SEQ ID NO 924
<211> LENGTH: 26
<212> TYPE: DNA
<213> ORGANISM: Homo sapiens

<400> SEQUENCE: 924
ttgagattat ccagtctgag gagcag                                          26

<210> SEQ ID NO 925
<211> LENGTH: 26
<212> TYPE: DNA
<213> ORGANISM: Homo sapiens

<400> SEQUENCE: 925
cttgaacttg agacacaaag agagtg                                          26

<210> SEQ ID NO 926
<211> LENGTH: 26
<212> TYPE: DNA
<213> ORGANISM: Homo sapiens

<400> SEQUENCE: 926
agataaaata gtccttgagg tgaata                                          26

<210> SEQ ID NO 927
<211> LENGTH: 26
<212> TYPE: DNA
<213> ORGANISM: Homo sapiens

<400> SEQUENCE: 927
cccaaacagc ccaataacaa gcagag                                          26

<210> SEQ ID NO 928
<211> LENGTH: 26
<212> TYPE: DNA
<213> ORGANISM: Homo sapiens

<400> SEQUENCE: 928
cccaaacagc ccaataacaa gcagag                                          26

<210> SEQ ID NO 929
<211> LENGTH: 26

```
<212> TYPE: DNA
<213> ORGANISM: Homo sapiens

<400> SEQUENCE: 929
ctcctattac ttttcatttt gtggtt                                              26

<210> SEQ ID NO 930
<211> LENGTH: 23
<212> TYPE: DNA
<213> ORGANISM: Homo sapiens

<400> SEQUENCE: 930
ttctagagat cagagtgttt ggg                                                 23

<210> SEQ ID NO 931
<211> LENGTH: 23
<212> TYPE: DNA
<213> ORGANISM: Homo sapiens

<400> SEQUENCE: 931
ccactgctcc tggctacaaa cct                                                 23

<210> SEQ ID NO 932
<211> LENGTH: 23
<212> TYPE: DNA
<213> ORGANISM: Homo sapiens

<400> SEQUENCE: 932
cactgaggtg gagggcaggg tat                                                 23

<210> SEQ ID NO 933
<211> LENGTH: 23
<212> TYPE: DNA
<213> ORGANISM: Homo sapiens

<400> SEQUENCE: 933
ggcaagtatg gcgtagaaag ggc                                                 23

<210> SEQ ID NO 934
<211> LENGTH: 23
<212> TYPE: DNA
<213> ORGANISM: Homo sapiens

<400> SEQUENCE: 934
gccagccact acaagcagca ctg                                                 23

<210> SEQ ID NO 935
<211> LENGTH: 26
<212> TYPE: DNA
<213> ORGANISM: Homo sapiens

<400> SEQUENCE: 935
agaatgaaga gtccagaaac agtctc                                              26

<210> SEQ ID NO 936
<211> LENGTH: 23
<212> TYPE: DNA
<213> ORGANISM: Homo sapiens

<400> SEQUENCE: 936
ccagcccttc tctgaggttt cct                                                 23

<210> SEQ ID NO 937
```

```
<211> LENGTH: 26
<212> TYPE: DNA
<213> ORGANISM: Homo sapiens

<400> SEQUENCE: 937
caagcacggt tgtaggagtt gtaagt                                        26

<210> SEQ ID NO 938
<211> LENGTH: 24
<212> TYPE: DNA
<213> ORGANISM: Homo sapiens

<400> SEQUENCE: 938
ccccatccca cacaactaag cacc                                          24

<210> SEQ ID NO 939
<211> LENGTH: 20
<212> TYPE: DNA
<213> ORGANISM: Homo sapiens

<400> SEQUENCE: 939
acgagggcag tttgggttga                                               20

<210> SEQ ID NO 940
<211> LENGTH: 23
<212> TYPE: DNA
<213> ORGANISM: Homo sapiens

<400> SEQUENCE: 940
gaccctccag aactacaggc tcc                                           23

<210> SEQ ID NO 941
<211> LENGTH: 26
<212> TYPE: DNA
<213> ORGANISM: Homo sapiens

<400> SEQUENCE: 941
gaccagtcac aaaagggcaa atacta                                        26

<210> SEQ ID NO 942
<211> LENGTH: 23
<212> TYPE: DNA
<213> ORGANISM: Homo sapiens

<400> SEQUENCE: 942
tacaagaaaa ctcatctcac tta                                           23

<210> SEQ ID NO 943
<211> LENGTH: 23
<212> TYPE: DNA
<213> ORGANISM: Homo sapiens

<400> SEQUENCE: 943
acaaaggaag ccattcggta ggt                                           23

<210> SEQ ID NO 944
<211> LENGTH: 23
<212> TYPE: DNA
<213> ORGANISM: Homo sapiens

<400> SEQUENCE: 944
gctgggaaaa cgattacctc agg                                           23
```

```
<210> SEQ ID NO 945
<211> LENGTH: 26
<212> TYPE: DNA
<213> ORGANISM: Homo sapiens

<400> SEQUENCE: 945
ttgttcagcc tggtgacgct tcagaa                                          26

<210> SEQ ID NO 946
<211> LENGTH: 23
<212> TYPE: DNA
<213> ORGANISM: Homo sapiens

<400> SEQUENCE: 946 ctttatttc catctttctc tta                                              23

<210> SEQ ID NO 947
<211> LENGTH: 26
<212> TYPE: DNA
<213> ORGANISM: Homo sapiens

<400> SEQUENCE: 947
ttttcttcat acctctaaat aacaat                                          26

<210> SEQ ID NO 948
<211> LENGTH: 24
<212> TYPE: DNA
<213> ORGANISM: Homo sapiens

<400> SEQUENCE: 948
cattactact cctcccaggg cagg                                            24

<210> SEQ ID NO 949
<211> LENGTH: 23
<212> TYPE: DNA
<213> ORGANISM: Homo sapiens

<400> SEQUENCE: 949
attactactc ctcccagggc agg                                             23

<210> SEQ ID NO 950
<211> LENGTH: 23
<212> TYPE: DNA
<213> ORGANISM: Homo sapiens

<400> SEQUENCE: 950
gggcaggcag caggatggga agc                                             23

<210> SEQ ID NO 951
<211> LENGTH: 23
<212> TYPE: DNA
<213> ORGANISM: Homo sapiens

<400> SEQUENCE: 951
tcactgactg ggcagggctt gct                                             23

<210> SEQ ID NO 952
<211> LENGTH: 23
<212> TYPE: DNA
<213> ORGANISM: Homo sapiens

<400> SEQUENCE: 952
ctgccccagt tgccctttc ctg                                              23
```

```
<210> SEQ ID NO 953
<211> LENGTH: 23
<212> TYPE: DNA
<213> ORGANISM: Homo sapiens

<400> SEQUENCE: 953
gtgagttcca ggcagcagag gta                                          23

<210> SEQ ID NO 954
<211> LENGTH: 26
<212> TYPE: DNA
<213> ORGANISM: Homo sapiens

<400> SEQUENCE: 954
ggtggtagtg agaagtttac tccaga                                       26

<210> SEQ ID NO 955
<211> LENGTH: 23
<212> TYPE: DNA
<213> ORGANISM: Homo sapiens

<400> SEQUENCE: 955
gtccccaggt aatggagcga agc                                          23

<210> SEQ ID NO 956
<211> LENGTH: 23
<212> TYPE: DNA
<213> ORGANISM: Homo sapiens

<400> SEQUENCE: 956
cacagtggag ggcacaccag caa                                          23

<210> SEQ ID NO 957
<211> LENGTH: 26
<212> TYPE: DNA
<213> ORGANISM: Homo sapiens

<400> SEQUENCE: 957
gcacaaggct acaaatcctg ttactc                                       26

<210> SEQ ID NO 958
<211> LENGTH: 26
<212> TYPE: DNA
<213> ORGANISM: Homo sapiens

<400> SEQUENCE: 958
ggtggagaaa ctggcagaca ttactt                                       26

<210> SEQ ID NO 959
<211> LENGTH: 25
<212> TYPE: DNA
<213> ORGANISM: Homo sapiens

<400> SEQUENCE: 959
cctgcttcaa tggcttgtga ggacc                                        25

<210> SEQ ID NO 960
<211> LENGTH: 26
<212> TYPE: DNA
<213> ORGANISM: Homo sapiens

<400> SEQUENCE: 960
tgggctgcct gctgtattct cctaag                                       26
```

<210> SEQ ID NO 961
<211> LENGTH: 26
<212> TYPE: DNA
<213> ORGANISM: Homo sapiens

<400> SEQUENCE: 961
gaagtcagtg ggatggagac agtagc                                          26

<210> SEQ ID NO 962
<211> LENGTH: 23
<212> TYPE: DNA
<213> ORGANISM: Homo sapiens

<400> SEQUENCE: 962
agagtaggac cccagagcag gca                                             23

<210> SEQ ID NO 963
<211> LENGTH: 26
<212> TYPE: DNA
<213> ORGANISM: Homo sapiens

<400> SEQUENCE: 963
gcaccaagat agaccacatt ctgggt                                          26

<210> SEQ ID NO 964
<211> LENGTH: 26
<212> TYPE: DNA
<213> ORGANISM: Homo sapiens

<400> SEQUENCE: 964
ttctgacaaa cctcattgcc aggatg                                          26

<210> SEQ ID NO 965
<211> LENGTH: 26
<212> TYPE: DNA
<213> ORGANISM: Homo sapiens

<400> SEQUENCE: 965
ctcacctggc tgctgttctc catcta                                          26

<210> SEQ ID NO 966
<211> LENGTH: 26
<212> TYPE: DNA
<213> ORGANISM: Homo sapiens

<400> SEQUENCE: 966
ctgtcgtggt attggtgggt gtgtga                                          26

<210> SEQ ID NO 967
<211> LENGTH: 26
<212> TYPE: DNA
<213> ORGANISM: Homo sapiens

<400> SEQUENCE: 967
gctctttgtg gtcttatgcc ctatca                                          26

<210> SEQ ID NO 968
<211> LENGTH: 26
<212> TYPE: DNA
<213> ORGANISM: Homo sapiens

<400> SEQUENCE: 968

```
ggttacctga ctcctgatac cagaca                                        26

<210> SEQ ID NO 969
<211> LENGTH: 26
<212> TYPE: DNA
<213> ORGANISM: Homo sapiens

<400> SEQUENCE: 969
gtcaagataa ctgccagagg agccac                                        26

<210> SEQ ID NO 970
<211> LENGTH: 26
<212> TYPE: DNA
<213> ORGANISM: Homo sapiens

<400> SEQUENCE: 970
ctcttcatag acctttagga cttagc                                        26

<210> SEQ ID NO 971
<211> LENGTH: 26
<212> TYPE: DNA
<213> ORGANISM: Homo sapiens

<400> SEQUENCE: 971
ccatttcttc ctttccacac accctc                                        26

<210> SEQ ID NO 972
<211> LENGTH: 26
<212> TYPE: DNA
<213> ORGANISM: Homo sapiens

<400> SEQUENCE: 972
ggttctaagg agagttgtaa agagag                                        26

<210> SEQ ID NO 973
<211> LENGTH: 60
<212> TYPE: DNA
<213> ORGANISM: Homo sapiens

<400> SEQUENCE: 973
gttttggtgt actaaggttt cttctgaatc gatggtggtg gaattagggg tctctgtcct   60

<210> SEQ ID NO 974
<211> LENGTH: 60
<212> TYPE: DNA
<213> ORGANISM: Homo sapiens

<400> SEQUENCE: 974
aaagcacgcg tcagagtggg tggggctgtc gattgtcatc ctctaggact tacagtttct   60

<210> SEQ ID NO 975
<211> LENGTH: 60
<212> TYPE: DNA
<213> ORGANISM: Homo sapiens

<400> SEQUENCE: 975
aaagcacgcg tcagagtggg tggggctgtc gaacaactgc aaactccact caacatcttt   60

<210> SEQ ID NO 976
<211> LENGTH: 60
<212> TYPE: DNA
<213> ORGANISM: Homo sapiens

<400> SEQUENCE: 976
```
aaagcacgcg tcagagtggg tggggctgtc gattcagaag aaaccttagt acaccaaaac       60

<210> SEQ ID NO 977
<211> LENGTH: 60
<212> TYPE: DNA
<213> ORGANISM: Homo sapiens

<400> SEQUENCE: 977
ctattataat gtagaaagac tatattaatc gagggttggt gttagagttc aaaccaacac       60

<210> SEQ ID NO 978
<211> LENGTH: 60
<212> TYPE: DNA
<213> ORGANISM: Homo sapiens

<400> SEQUENCE: 978
ctattataat gtagaaagac tatattaatc gagtacatga gaaataagcg tctaacatga       60

<210> SEQ ID NO 979
<211> LENGTH: 60
<212> TYPE: DNA
<213> ORGANISM: Homo sapiens

<400> SEQUENCE: 979
ttgaagcaat tttttaaaaa acagtaattc gatgtaccat ccacagttct ttaggatact       60

<210> SEQ ID NO 980
<211> LENGTH: 60
<212> TYPE: DNA
<213> ORGANISM: Homo sapiens

<400> SEQUENCE: 980
aggggctggt agatttgact acataaactc gagtatgtca gcttgatgat gaaagagact       60

<210> SEQ ID NO 981
<211> LENGTH: 60
<212> TYPE: DNA
<213> ORGANISM: Homo sapiens

<400> SEQUENCE: 981
gccgagttgg gcagatcatt ttaggagttc gagtagaacc aattaaaaag ttaaacaggt       60

<210> SEQ ID NO 982
<211> LENGTH: 60
<212> TYPE: DNA
<213> ORGANISM: Homo sapiens

<400> SEQUENCE: 982
ggcgggtgga tcacctgagc tgaggatttc gaaaaaaaaa aaaagattat aaattcacac       60

<210> SEQ ID NO 983
<211> LENGTH: 60
<212> TYPE: DNA
<213> ORGANISM: Homo sapiens

<400> SEQUENCE: 983
tattttattt gttactaaaa caaggaactc gatttcgcca agggccaggc tcccaaggca       60

<210> SEQ ID NO 984
<211> LENGTH: 60
<212> TYPE: DNA
<213> ORGANISM: Homo sapiens

<400> SEQUENCE: 984
aaaagtatgt gtacctagta atatggcctc gagccatttc tgaactcatt ataaaactat    60

<210> SEQ ID NO 985
<211> LENGTH: 60
<212> TYPE: DNA
<213> ORGANISM: Homo sapiens

<400> SEQUENCE: 985
tcgtgggtag tgggggcaga gacttgagtc gattttctat agaccaaatt aaaatatttc    60

<210> SEQ ID NO 986
<211> LENGTH: 60
<212> TYPE: DNA
<213> ORGANISM: Homo sapiens

<400> SEQUENCE: 986
tcgtgggtag tgggggcaga gacttgagtc gaaaatatag atgaaaggta ctgccattgt    60

<210> SEQ ID NO 987
<211> LENGTH: 60
<212> TYPE: DNA
<213> ORGANISM: Homo sapiens

<400> SEQUENCE: 987
tcgtgggtag tgggggcaga gacttgagtc gaggtctcct aggctcagat ctaaggagga    60

<210> SEQ ID NO 988
<211> LENGTH: 60
<212> TYPE: DNA
<213> ORGANISM: Homo sapiens

<400> SEQUENCE: 988
tcgtgggtag tgggggcaga gacttgagtc gaaatgaaag atttgccttt caatggagaa    60

<210> SEQ ID NO 989
<211> LENGTH: 60
<212> TYPE: DNA
<213> ORGANISM: Homo sapiens

<400> SEQUENCE: 989
tcgtgggtag tgggggcaga gacttgagtc gaagaggaaa ggatgtccac tggacattat    60

<210> SEQ ID NO 990
<211> LENGTH: 60
<212> TYPE: DNA
<213> ORGANISM: Homo sapiens

<400> SEQUENCE: 990
tcgtgggtag tgggggcaga gacttgagtc gagaccctgc taccatgaat cttagggttc    60

<210> SEQ ID NO 991
<211> LENGTH: 60
<212> TYPE: DNA
<213> ORGANISM: Homo sapiens

<400> SEQUENCE: 991
tcgtgggtag tgggggcaga gacttgagtc gagaaccact ctgaagtttg gcctagtttt    60

<210> SEQ ID NO 992
<211> LENGTH: 60
<212> TYPE: DNA
<213> ORGANISM: Homo sapiens -continued

<400> SEQUENCE: 992
tccaggtgac tccgacctac tctcaagttc gagatggtaa gttatcttcc agggtttaaa     60

<210> SEQ ID NO 993
<211> LENGTH: 60
<212> TYPE: DNA
<213> ORGANISM: Homo sapiens

<400> SEQUENCE: 993
tgattggaga atacctactt aaatagtttc gagattaaga aagaagagct tcatttacct     60

<210> SEQ ID NO 994
<211> LENGTH: 60
<212> TYPE: DNA
<213> ORGANISM: Homo sapiens

<400> SEQUENCE: 994
aatcagtcaa tccctaattt gagtattttc gaacctcatc ttgatcttct tcaaattgtc     60

<210> SEQ ID NO 995
<211> LENGTH: 60
<212> TYPE: DNA
<213> ORGANISM: Homo sapiens

<400> SEQUENCE: 995
ttgccttcag gaaatatcat gaaattgctc gaaaagatat gtcatcccag ggatgtaggg     60

<210> SEQ ID NO 996
<211> LENGTH: 60
<212> TYPE: DNA
<213> ORGANISM: Homo sapiens

<400> SEQUENCE: 996
aatattcctt caacatttca tatatacatc gaaattgcat gtatgttttg ttagaaagtt     60

<210> SEQ ID NO 997
<211> LENGTH: 60
<212> TYPE: DNA
<213> ORGANISM: Homo sapiens

<400> SEQUENCE: 997
aatattcctt caacatttca tatatacatc gaatacatgt tttggagaat attaaaccca     60

<210> SEQ ID NO 998
<211> LENGTH: 60
<212> TYPE: DNA
<213> ORGANISM: Homo sapiens

<400> SEQUENCE: 998
caccgcgcgg tacacccca cgtcgctgtc gacattttct taccagcctg gctgataaac     60

<210> SEQ ID NO 999
<211> LENGTH: 60
<212> TYPE: DNA
<213> ORGANISM: Homo sapiens

<400> SEQUENCE: 999
gtttatcagc caggctggta agaaaatgtc gaagtcttgg attaaggttc attcaacaaa     60

<210> SEQ ID NO 1000
<211> LENGTH: 60
<212> TYPE: DNA

<213> ORGANISM: Homo sapiens

<400> SEQUENCE: 1000
cccgtcttcc ccaaaatcta tgtggtcctc gacagcgacg tgggggtgta ccgcgcggtg    60

<210> SEQ ID NO 1001
<211> LENGTH: 60
<212> TYPE: DNA
<213> ORGANISM: Homo sapiens

<400> SEQUENCE: 1001
cccgtcttcc ccaaaatcta tgtggtcctc gaagtcttgg attaaggttc attcaacaaa    60

<210> SEQ ID NO 1002
<211> LENGTH: 60
<212> TYPE: DNA
<213> ORGANISM: Homo sapiens

<400> SEQUENCE: 1002
tttcttttat acataaattt tcacgccttc gaaagagagg gaaaaatatt tacatgttaa    60

<210> SEQ ID NO 1003
<211> LENGTH: 60
<212> TYPE: DNA
<213> ORGANISM: Homo sapiens

<400> SEQUENCE: 1003
tgactgtatt tacaacatgt ctagattttc gagtgtaaaa gggcttttac tggtgcacac    60

<210> SEQ ID NO 1004
<211> LENGTH: 60
<212> TYPE: DNA
<213> ORGANISM: Homo sapiens

<400> SEQUENCE: 1004
tcctaggaga gactgaactt taaagatatc gacctgctga tccttggatc ctgaatctgt    60

<210> SEQ ID NO 1005
<211> LENGTH: 60
<212> TYPE: DNA
<213> ORGANISM: Homo sapiens

<400> SEQUENCE: 1005
gtgtgcacca gtaaaagccc ttttacactc gacctgctga tccttggatc ctgaatctgt    60

<210> SEQ ID NO 1006
<211> LENGTH: 60
<212> TYPE: DNA
<213> ORGANISM: Homo sapiens

<400> SEQUENCE: 1006 ccaccccgc cccgggggag tcgcccggtc gaactaatat tagaggagag aggtcagtta    60

<210> SEQ ID NO 1007
<211> LENGTH: 60
<212> TYPE: DNA
<213> ORGANISM: Homo sapiens

<400> SEQUENCE: 1007 ccaccccgc cccgggggag tcgcccggtc gagggcctgg caagaagaca gaagccgact    60

<210> SEQ ID NO 1008
<211> LENGTH: 60

```
<212> TYPE: DNA
<213> ORGANISM: Homo sapiens

<400> SEQUENCE: 1008 ccaccccgc cccggggag tcgcccggtc gacagtccca agaggtcaga actggcttcc    60

<210> SEQ ID NO 1009
<211> LENGTH: 60
<212> TYPE: DNA
<213> ORGANISM: Homo sapiens

<400> SEQUENCE: 1009 ccaccccgc cccggggag tcgcccggtc gaccccctga catggggctg cctggagcag    60

<210> SEQ ID NO 1010
<211> LENGTH: 60
<212> TYPE: DNA
<213> ORGANISM: Homo sapiens

<400> SEQUENCE: 1010
ttaaagaagc taattttaaa aataaatgtc gaagagattg tcacgttaga gttatgtaaa    60

<210> SEQ ID NO 1011
<211> LENGTH: 60
<212> TYPE: DNA
<213> ORGANISM: Homo sapiens

<400> SEQUENCE: 1011
ttaaagaagc taattttaaa aataaatgtc gaggagcatc tggatttaat gatagttcaa    60

<210> SEQ ID NO 1012
<211> LENGTH: 60
<212> TYPE: DNA
<213> ORGANISM: Homo sapiens

<400> SEQUENCE: 1012
ttaaagaagc taattttaaa aataaatgtc gaattccatg gattcaggtt ggcagaagac    60

<210> SEQ ID NO 1013
<211> LENGTH: 60
<212> TYPE: DNA
<213> ORGANISM: Homo sapiens

<400> SEQUENCE: 1013
ttaaagaagc taattttaaa aataaatgtc gaaattactt taaattaata caagcccta    60

<210> SEQ ID NO 1014
<211> LENGTH: 60
<212> TYPE: DNA
<213> ORGANISM: Homo sapiens

<400> SEQUENCE: 1014
ggaaggcctt ccaaaggatt tgagtgtttc gagagtactg atgccctctg ctctgtaaac    60

<210> SEQ ID NO 1015
<211> LENGTH: 60
<212> TYPE: DNA
<213> ORGANISM: Homo sapiens

<400> SEQUENCE: 1015
ccactccact tgacattcac tctgcttgtc gatcaaagct gtatctgctt taggggcac     60

<210> SEQ ID NO 1016
```

```
<211> LENGTH: 60
<212> TYPE: DNA
<213> ORGANISM: Homo sapiens

<400> SEQUENCE: 1016
ctccatctcc ctgccctctg atcccctc gattctacag tggttttaac agcaggcccc        60

<210> SEQ ID NO 1017
<211> LENGTH: 60
<212> TYPE: DNA
<213> ORGANISM: Homo sapiens

<400> SEQUENCE: 1017
cagagacagt gtcaaaaaaa aaaatcttc gaggtcttga gtcctcttca taaggaaaat        60

<210> SEQ ID NO 1018
<211> LENGTH: 60
<212> TYPE: DNA
<213> ORGANISM: Homo sapiens

<400> SEQUENCE: 1018
caatgtacaa aaaagttttt ttttttttc gaggtaactt atgttaactt tctttcccag        60

<210> SEQ ID NO 1019
<211> LENGTH: 60
<212> TYPE: DNA
<213> ORGANISM: Homo sapiens

<400> SEQUENCE: 1019
atttaaacta tttaataatt tgctgtattc gaatgagtga tagtgcttat tcctgtattg        60

<210> SEQ ID NO 1020
<211> LENGTH: 60
<212> TYPE: DNA
<213> ORGANISM: Homo sapiens

<400> SEQUENCE: 1020
atttaaacta tttaataatt tgctgtattc gatagaaaat gggtgagggg aaaactgtgg        60

<210> SEQ ID NO 1021
<211> LENGTH: 60
<212> TYPE: DNA
<213> ORGANISM: Homo sapiens

<400> SEQUENCE: 1021
gtgtctcggc ccctggggc ccacccttc gatttccctg ttgccgccgc gtttgcaaga         60

<210> SEQ ID NO 1022
<211> LENGTH: 60
<212> TYPE: DNA
<213> ORGANISM: Homo sapiens

<400> SEQUENCE: 1022
gcagccagcc cggtgggggt ggggggggtc gacgctcgcc tccgctcaca gcctcagcat       60

<210> SEQ ID NO 1023
<211> LENGTH: 60
<212> TYPE: DNA
<213> ORGANISM: Homo sapiens

<400> SEQUENCE: 1023
caaatcccgg ctatctctta gaattgcatc gattcaccct cctcagcctc ccaaagtgct       60
```

```
<210> SEQ ID NO 1024
<211> LENGTH: 60
<212> TYPE: DNA
<213> ORGANISM: Homo sapiens

<400> SEQUENCE: 1024
agtggtctca ccatggcttt cttccaattc gattcaccct cctcagcctc ccaaagtgct    60

<210> SEQ ID NO 1025
<211> LENGTH: 20
<212> TYPE: DNA
<213> ORGANISM: Homo sapiens

<400> SEQUENCE: 1025
tggatggttc cagaggtttc                                                20

<210> SEQ ID NO 1026
<211> LENGTH: 20
<212> TYPE: DNA
<213> ORGANISM: Homo sapiens

<400> SEQUENCE: 1026
gctggagatg gatctggggg                                                20

<210> SEQ ID NO 1027
<211> LENGTH: 26
<212> TYPE: DNA
<213> ORGANISM: Homo sapiens

<400> SEQUENCE: 1027
gccacctgtc tcagataccc ttggtt                                         26

<210> SEQ ID NO 1028
<211> LENGTH: 20
<212> TYPE: DNA
<213> ORGANISM: Homo sapiens

<400> SEQUENCE: 1028
gggtagaacg ggggcagtag                                                20

<210> SEQ ID NO 1029
<211> LENGTH: 23
<212> TYPE: DNA
<213> ORGANISM: Homo sapiens

<400> SEQUENCE: 1029
ccttcaggac actgctggga ggt                                            23

<210> SEQ ID NO 1030
<211> LENGTH: 26
<212> TYPE: DNA
<213> ORGANISM: Homo sapiens

<400> SEQUENCE: 1030
cttcaggaca ctgctgggag gtttct                                         26

<210> SEQ ID NO 1031
<211> LENGTH: 23
<212> TYPE: DNA
<213> ORGANISM: Homo sapiens

<400> SEQUENCE: 1031
cagcagtgtg ggaagggaca tct                                            23
```

<210> SEQ ID NO 1032
<211> LENGTH: 26
<212> TYPE: DNA
<213> ORGANISM: Homo sapiens

<400> SEQUENCE: 1032
gagtgggaaa gaccattctg agattc        26

<210> SEQ ID NO 1033
<211> LENGTH: 25
<212> TYPE: DNA
<213> ORGANISM: Homo sapiens

<400> SEQUENCE: 1033
gtggtggctc acgcctgtaa tccta         25

<210> SEQ ID NO 1034
<211> LENGTH: 23
<212> TYPE: DNA
<213> ORGANISM: Homo sapiens

<400> SEQUENCE: 1034
tctgaaaggc tgggtgcggt agc           23

<210> SEQ ID NO 1035
<211> LENGTH: 26
<212> TYPE: DNA
<213> ORGANISM: Homo sapiens

<400> SEQUENCE: 1035
agtccctgta gatttgagag cagaaa        26

<210> SEQ ID NO 1036
<211> LENGTH: 26
<212> TYPE: DNA
<213> ORGANISM: Homo sapiens

<400> SEQUENCE: 1036
caaagagggt caggcacttc acaaag        26

<210> SEQ ID NO 1037
<211> LENGTH: 26
<212> TYPE: DNA
<213> ORGANISM: Homo sapiens

<400> SEQUENCE: 1037
ggatgaatgg ctgtgtaaac tgtctc        26

<210> SEQ ID NO 1038
<211> LENGTH: 23
<212> TYPE: DNA
<213> ORGANISM: Homo sapiens

<400> SEQUENCE: 1038
aatggctgtg taaactgtct cta           23

<210> SEQ ID NO 1039
<211> LENGTH: 23
<212> TYPE: DNA
<213> ORGANISM: Homo sapiens

<400> SEQUENCE: 1039
aatggctgtg taaactgtct cta           23

<210> SEQ ID NO 1040
<211> LENGTH: 26
<212> TYPE: DNA
<213> ORGANISM: Homo sapiens

<400> SEQUENCE: 1040
ggatgaatgg ctgtgtaaac tgtctc                                          26

<210> SEQ ID NO 1041
<211> LENGTH: 23
<212> TYPE: DNA
<213> ORGANISM: Homo sapiens

<400> SEQUENCE: 1041
aatggctgtg taaactgtct cta                                             23

<210> SEQ ID NO 1042
<211> LENGTH: 26
<212> TYPE: DNA
<213> ORGANISM: Homo sapiens

<400> SEQUENCE: 1042
ggatgaatgg ctgtgtaaac tgtctc                                          26

<210> SEQ ID NO 1043
<211> LENGTH: 23
<212> TYPE: DNA
<213> ORGANISM: Homo sapiens

<400> SEQUENCE: 1043
aatggctgtg taaactgtct cta                                             23

<210> SEQ ID NO 1044
<211> LENGTH: 23
<212> TYPE: DNA
<213> ORGANISM: Homo sapiens

<400> SEQUENCE: 1044
atacccactg aagcagaaac tct                                             23

<210> SEQ ID NO 1045
<211> LENGTH: 26
<212> TYPE: DNA
<213> ORGANISM: Homo sapiens

<400> SEQUENCE: 1045
caggatagat aagccagaag gtaata                                          26

<210> SEQ ID NO 1046
<211> LENGTH: 20
<212> TYPE: DNA
<213> ORGANISM: Homo sapiens

<400> SEQUENCE: 1046
tcttcctccc cctaccctct                                                 20

<210> SEQ ID NO 1047
<211> LENGTH: 21
<212> TYPE: DNA
<213> ORGANISM: Homo sapiens

<400> SEQUENCE: 1047

```
ttccggttca atatgagatg g                                              21

<210> SEQ ID NO 1048
<211> LENGTH: 23
<212> TYPE: DNA
<213> ORGANISM: Homo sapiens

<400> SEQUENCE: 1048
aaataaaatc accaacccag acg                                            23

<210> SEQ ID NO 1049
<211> LENGTH: 26
<212> TYPE: DNA
<213> ORGANISM: Homo sapiens

<400> SEQUENCE: 1049
cctaaataaa atcaccaacc cagacg                                         26

<210> SEQ ID NO 1050
<211> LENGTH: 23
<212> TYPE: DNA
<213> ORGANISM: Homo sapiens

<400> SEQUENCE: 1050
cgccacctcg tagttgtgtc tgc                                            23

<210> SEQ ID NO 1051
<211> LENGTH: 20
<212> TYPE: DNA
<213> ORGANISM: Homo sapiens

<400> SEQUENCE: 1051
agtcagccac aaatcctggg                                                20

<210> SEQ ID NO 1052
<211> LENGTH: 23
<212> TYPE: DNA
<213> ORGANISM: Homo sapiens

<400> SEQUENCE: 1052
tggttctgct acctgtgtgc ctg                                            23

<210> SEQ ID NO 1053
<211> LENGTH: 24
<212> TYPE: DNA
<213> ORGANISM: Homo sapiens

<400> SEQUENCE: 1053
tggttctgct acctgtgtgc ctgc                                           24

<210> SEQ ID NO 1054
<211> LENGTH: 23
<212> TYPE: DNA
<213> ORGANISM: Homo sapiens

<400> SEQUENCE: 1054
tgtaatgtgt ctcaggtgtg gag                                            23

<210> SEQ ID NO 1055
<211> LENGTH: 25
<212> TYPE: DNA
<213> ORGANISM: Homo sapiens

<400> SEQUENCE: 1055
```
gattttgtat ccgtgggagt cctgg                                         25

<210> SEQ ID NO 1056
<211> LENGTH: 23
<212> TYPE: DNA
<213> ORGANISM: Homo sapiens

<400> SEQUENCE: 1056
ttcctgtagg gcttccactg gct                                           23

<210> SEQ ID NO 1057
<211> LENGTH: 23
<212> TYPE: DNA
<213> ORGANISM: Homo sapiens

<400> SEQUENCE: 1057
cccactttgc cacaactctg gtg                                           23

<210> SEQ ID NO 1058
<211> LENGTH: 20
<212> TYPE: DNA
<213> ORGANISM: Homo sapiens

<400> SEQUENCE: 1058
ggtgtaacgg gggtcatttc                                               20

<210> SEQ ID NO 1059
<211> LENGTH: 23
<212> TYPE: DNA
<213> ORGANISM: Homo sapiens

<400> SEQUENCE: 1059
gcacggtctg tctactttcc ctc                                           23

<210> SEQ ID NO 1060
<211> LENGTH: 23
<212> TYPE: DNA
<213> ORGANISM: Homo sapiens

<400> SEQUENCE: 1060
gcacggtctg tctactttcc ctc                                           23

<210> SEQ ID NO 1061
<211> LENGTH: 23
<212> TYPE: DNA
<213> ORGANISM: Homo sapiens

<400> SEQUENCE: 1061
cggtgagcac ggtctgtcta ctt                                           23

<210> SEQ ID NO 1062
<211> LENGTH: 26
<212> TYPE: DNA
<213> ORGANISM: Homo sapiens

<400> SEQUENCE: 1062
tctctacttc aggcaggcag tgtaag                                        26

<210> SEQ ID NO 1063
<211> LENGTH: 20
<212> TYPE: DNA
<213> ORGANISM: Homo sapiens

```
<400> SEQUENCE: 1063
agttttccac cccttcttcc                                              20

<210> SEQ ID NO 1064
<211> LENGTH: 26
<212> TYPE: DNA
<213> ORGANISM: Homo sapiens

<400> SEQUENCE: 1064
tctctacttc aggcaggcag tgtaag                                       26

<210> SEQ ID NO 1065
<211> LENGTH: 26
<212> TYPE: DNA
<213> ORGANISM: Homo sapiens

<400> SEQUENCE: 1065
tctctacttc aggcaggcag tgtaag                                       26

<210> SEQ ID NO 1066
<211> LENGTH: 23
<212> TYPE: DNA
<213> ORGANISM: Homo sapiens

<400> SEQUENCE: 1066
gaatttcttt gcgtttcctc aac                                          23

<210> SEQ ID NO 1067
<211> LENGTH: 23
<212> TYPE: DNA
<213> ORGANISM: Homo sapiens

<400> SEQUENCE: 1067
gcctggcatt gctcctcttc agc                                          23

<210> SEQ ID NO 1068
<211> LENGTH: 23
<212> TYPE: DNA
<213> ORGANISM: Homo sapiens

<400> SEQUENCE: 1068
ttgtggtgtc ctgctgggtc atc                                          23

<210> SEQ ID NO 1069
<211> LENGTH: 24
<212> TYPE: DNA
<213> ORGANISM: Homo sapiens

<400> SEQUENCE: 1069
tggtttgagg tagaagttgg tggt                                         24

<210> SEQ ID NO 1070
<211> LENGTH: 22
<212> TYPE: DNA
<213> ORGANISM: Homo sapiens

<400> SEQUENCE: 1070
tttaacctag tatatcccaa ac                                           22

<210> SEQ ID NO 1071
<211> LENGTH: 26
<212> TYPE: DNA
<213> ORGANISM: Homo sapiens
```

```
<400> SEQUENCE: 1071
gaagggcaga actgtgagtc aaaacc                                        26

<210> SEQ ID NO 1072
<211> LENGTH: 26
<212> TYPE: DNA
<213> ORGANISM: Homo sapiens

<400> SEQUENCE: 1072
cccgaagggc agaactgtga gtcaaa                                        26

<210> SEQ ID NO 1073
<211> LENGTH: 20
<212> TYPE: DNA
<213> ORGANISM: Homo sapiens

<400> SEQUENCE: 1073
gcatggtcct gagtctcaca                                               20

<210> SEQ ID NO 1074
<211> LENGTH: 23
<212> TYPE: DNA
<213> ORGANISM: Homo sapiens

<400> SEQUENCE: 1074
gctgccctct ctcttgtcag acg                                           23

<210> SEQ ID NO 1075
<211> LENGTH: 26
<212> TYPE: DNA
<213> ORGANISM: Homo sapiens

<400> SEQUENCE: 1075
aagaacagca cacgcagaca gacaca                                        26

<210> SEQ ID NO 1076
<211> LENGTH: 26
<212> TYPE: DNA
<213> ORGANISM: Homo sapiens

<400> SEQUENCE: 1076
cctctttgct gagcctgagt tgtctg                                        26

<210> SEQ ID NO 1077
<211> LENGTH: 20
<212> TYPE: DNA
<213> ORGANISM: Homo sapiens

<400> SEQUENCE: 1077
gtctgaggac agagacccct                                               20

<210> SEQ ID NO 1078
<211> LENGTH: 21
<212> TYPE: DNA
<213> ORGANISM: Homo sapiens

<400> SEQUENCE: 1078
tgtcacagtc cctctagcac t                                             21

<210> SEQ ID NO 1079
<211> LENGTH: 26
<212> TYPE: DNA
```

```
<213> ORGANISM: Homo sapiens

<400> SEQUENCE: 1079
cttcctttcc acacccctc aaatac                                          26

<210> SEQ ID NO 1080
<211> LENGTH: 22
<212> TYPE: DNA
<213> ORGANISM: Homo sapiens

<400> SEQUENCE: 1080
tccagaggtt tctagggacg ac                                             22

<210> SEQ ID NO 1081
<211> LENGTH: 23
<212> TYPE: DNA
<213> ORGANISM: Homo sapiens

<400> SEQUENCE: 1081
gtctcccctc cctggaaagt aag                                            23

<210> SEQ ID NO 1082
<211> LENGTH: 26
<212> TYPE: DNA
<213> ORGANISM: Homo sapiens

<400> SEQUENCE: 1082
ggtttgggat aacattggta gaagag                                         26

<210> SEQ ID NO 1083
<211> LENGTH: 24
<212> TYPE: DNA
<213> ORGANISM: Homo sapiens

<400> SEQUENCE: 1083
gtaggctctc tccctgtgtg tcac                                           24

<210> SEQ ID NO 1084
<211> LENGTH: 26
<212> TYPE: DNA
<213> ORGANISM: Homo sapiens

<400> SEQUENCE: 1084
tggagagatg tgaggcttgt ggtcct                                         26

<210> SEQ ID NO 1085
<211> LENGTH: 26
<212> TYPE: DNA
<213> ORGANISM: Homo sapiens

<400> SEQUENCE: 1085
gaggcaggtt tcttttcaca tccact                                         26

<210> SEQ ID NO 1086
<211> LENGTH: 24
<212> TYPE: DNA
<213> ORGANISM: Homo sapiens

<400> SEQUENCE: 1086
gcctcccttc ctatctactg tgtg                                           24

<210> SEQ ID NO 1087
<211> LENGTH: 26
```

```
<212> TYPE: DNA
<213> ORGANISM: Homo sapiens

<400> SEQUENCE: 1087
gggactacag tttctctgag ggctaa                                              26

<210> SEQ ID NO 1088
<211> LENGTH: 26
<212> TYPE: DNA
<213> ORGANISM: Homo sapiens

<400> SEQUENCE: 1088
ccccaagtct ttcctttgtt gtaggg                                              26

<210> SEQ ID NO 1089
<211> LENGTH: 26
<212> TYPE: DNA
<213> ORGANISM: Homo sapiens

<400> SEQUENCE: 1089
caggaaaact aaacttggtg gaaatc                                              26

<210> SEQ ID NO 1090
<211> LENGTH: 23
<212> TYPE: DNA
<213> ORGANISM: Homo sapiens

<400> SEQUENCE: 1090
ctggctttgt ctgctgcttc tat                                                 23

<210> SEQ ID NO 1091
<211> LENGTH: 23
<212> TYPE: DNA
<213> ORGANISM: Homo sapiens

<400> SEQUENCE: 1091
tggaggagga acttcagggc tgc                                                 23

<210> SEQ ID NO 1092
<211> LENGTH: 26
<212> TYPE: DNA
<213> ORGANISM: Homo sapiens

<400> SEQUENCE: 1092
cccaaaacga gccttctgga atcctc                                              26

<210> SEQ ID NO 1093
<211> LENGTH: 23
<212> TYPE: DNA
<213> ORGANISM: Homo sapiens

<400> SEQUENCE: 1093
tgacctttcc tgaaccctcc tca                                                 23

<210> SEQ ID NO 1094
<211> LENGTH: 26
<212> TYPE: DNA
<213> ORGANISM: Homo sapiens

<400> SEQUENCE: 1094
cagcgtagag gatgggatag aaggga                                              26

<210> SEQ ID NO 1095
```

```
<211> LENGTH: 23
<212> TYPE: DNA
<213> ORGANISM: Homo sapiens

<400> SEQUENCE: 1095
cggtgggata aagaaaggaa aac                                          23

<210> SEQ ID NO 1096
<211> LENGTH: 23
<212> TYPE: DNA
<213> ORGANISM: Homo sapiens

<400> SEQUENCE: 1096
ggaatcaaat gagcccaggt tta                                          23

<210> SEQ ID NO 1097
<211> LENGTH: 26
<212> TYPE: DNA
<213> ORGANISM: Homo sapiens

<400> SEQUENCE: 1097
ggaaaatgag gaaaagtctg acaact                                       26

<210> SEQ ID NO 1098
<211> LENGTH: 20
<212> TYPE: DNA
<213> ORGANISM: Homo sapiens

<400> SEQUENCE: 1098
ccctacctcc aaaccccctc                                              20

<210> SEQ ID NO 1099
<211> LENGTH: 20
<212> TYPE: DNA
<213> ORGANISM: Homo sapiens

<400> SEQUENCE: 1099
ggggatgggt cttttcacag                                              20

<210> SEQ ID NO 1100
<211> LENGTH: 23
<212> TYPE: DNA
<213> ORGANISM: Homo sapiens

<400> SEQUENCE: 1100
ggattcagca ttactacgaa ctt                                          23

<210> SEQ ID NO 1101
<211> LENGTH: 26
<212> TYPE: DNA
<213> ORGANISM: Homo sapiens

<400> SEQUENCE: 1101
ggaacaagat actactggtg aacaat                                       26

<210> SEQ ID NO 1102
<211> LENGTH: 23
<212> TYPE: DNA
<213> ORGANISM: Homo sapiens

<400> SEQUENCE: 1102
ccttccctcc ttattcccac cca                                          23
```

```
<210> SEQ ID NO 1103
<211> LENGTH: 22
<212> TYPE: DNA
<213> ORGANISM: Homo sapiens

<400> SEQUENCE: 1103
gctgtctgtt actagattgc ac                                              22

<210> SEQ ID NO 1104
<211> LENGTH: 23
<212> TYPE: DNA
<213> ORGANISM: Homo sapiens

<400> SEQUENCE: 1104
cgccacctcg tagttgtgtc tgc                                             23

<210> SEQ ID NO 1105
<211> LENGTH: 25
<212> TYPE: DNA
<213> ORGANISM: Homo sapiens

<400> SEQUENCE: 1105
ggatgagatg tgtaaaagag gcggg                                           25

<210> SEQ ID NO 1106
<211> LENGTH: 23
<212> TYPE: DNA
<213> ORGANISM: Homo sapiens

<400> SEQUENCE: 1106
actactggct ggtgtgagag aat                                             23

<210> SEQ ID NO 1107
<211> LENGTH: 26
<212> TYPE: DNA
<213> ORGANISM: Homo sapiens

<400> SEQUENCE: 1107
attcccactt tgccacaact ctggtg                                          26

<210> SEQ ID NO 1108
<211> LENGTH: 23
<212> TYPE: DNA
<213> ORGANISM: Homo sapiens

<400> SEQUENCE: 1108
gggcagcaag ggcagttctg aag                                             23

<210> SEQ ID NO 1109
<211> LENGTH: 23
<212> TYPE: DNA
<213> ORGANISM: Homo sapiens

<400> SEQUENCE: 1109
gggcagcaag ggcagttctg aag                                             23

<210> SEQ ID NO 1110
<211> LENGTH: 18
<212> TYPE: DNA
<213> ORGANISM: Homo sapiens

<400> SEQUENCE: 1110
tgcaacctct gccttctg                                                   18
```

<210> SEQ ID NO 1111
<211> LENGTH: 23
<212> TYPE: DNA
<213> ORGANISM: Homo sapiens

<400> SEQUENCE: 1111
tggagatgct gctctgccca cct                                           23

<210> SEQ ID NO 1112
<211> LENGTH: 23
<212> TYPE: DNA
<213> ORGANISM: Homo sapiens

<400> SEQUENCE: 1112
cgttgcctcc tcacagcaga agc                                           23

<210> SEQ ID NO 1113
<211> LENGTH: 23
<212> TYPE: DNA
<213> ORGANISM: Homo sapiens

<400> SEQUENCE: 1113
gtcctgggtc ctgggtgaaa gtc                                           23

<210> SEQ ID NO 1114
<211> LENGTH: 26
<212> TYPE: DNA
<213> ORGANISM: Homo sapiens

<400> SEQUENCE: 1114
gggagaccat ttctgttcac tctgag                                        26

<210> SEQ ID NO 1115
<211> LENGTH: 20
<212> TYPE: DNA
<213> ORGANISM: Homo sapiens

<400> SEQUENCE: 1115
gggctgtgtc ctgataaacc                                               20

<210> SEQ ID NO 1116
<211> LENGTH: 26
<212> TYPE: DNA
<213> ORGANISM: Homo sapiens

<400> SEQUENCE: 1116
ttattgtttc cttagggagg gcgtcc                                        26

<210> SEQ ID NO 1117
<211> LENGTH: 26
<212> TYPE: DNA
<213> ORGANISM: Homo sapiens

<400> SEQUENCE: 1117
ggtaatagcc gttgatactc agtgcc                                        26

<210> SEQ ID NO 1118
<211> LENGTH: 20
<212> TYPE: DNA
<213> ORGANISM: Homo sapiens

<400> SEQUENCE: 1118
tacatcaaca gtgggctccc                                               20

<210> SEQ ID NO 1119
<211> LENGTH: 23
<212> TYPE: DNA
<213> ORGANISM: Homo sapiens

<400> SEQUENCE: 1119
tgcctgtgtc actccaccat cag                                           23

<210> SEQ ID NO 1120
<211> LENGTH: 23
<212> TYPE: DNA
<213> ORGANISM: Homo sapiens

<400> SEQUENCE: 1120
ggagcagccc atctatcctg acc                                           23

<210> SEQ ID NO 1121
<211> LENGTH: 25
<212> TYPE: DNA
<213> ORGANISM: Homo sapiens

<400> SEQUENCE: 1121
tccaatagta ccccgagatt ttcct                                         25

<210> SEQ ID NO 1122
<211> LENGTH: 24
<212> TYPE: DNA
<213> ORGANISM: Homo sapiens

<400> SEQUENCE: 1122
gagagagagc tgataaaagg gata                                          24

<210> SEQ ID NO 1123
<211> LENGTH: 26
<212> TYPE: DNA
<213> ORGANISM: Homo sapiens

<400> SEQUENCE: 1123
ggtaggtgtc tgtcaaaagg agtgct                                        26

<210> SEQ ID NO 1124
<211> LENGTH: 25
<212> TYPE: DNA
<213> ORGANISM: Homo sapiens

<400> SEQUENCE: 1124
tattcaggaa gaaatccctc ccagg                                         25

<210> SEQ ID NO 1125
<211> LENGTH: 19
<212> TYPE: DNA
<213> ORGANISM: Homo sapiens

<400> SEQUENCE: 1125
ctgggtttcg gtttcttgc                                                19

<210> SEQ ID NO 1126
<211> LENGTH: 23
<212> TYPE: DNA
<213> ORGANISM: Homo sapiens

<400> SEQUENCE: 1126

```
gtccacccca ttgccgcttt tca                                     23

<210> SEQ ID NO 1127
<211> LENGTH: 26
<212> TYPE: DNA
<213> ORGANISM: Homo sapiens

<400> SEQUENCE: 1127
ccctctggac aaaggtatta tccctg                                  26

<210> SEQ ID NO 1128
<211> LENGTH: 26
<212> TYPE: DNA
<213> ORGANISM: Homo sapiens

<400> SEQUENCE: 1128
cctctggaca aaggtattat ccctga                                  26

<210> SEQ ID NO 1129
<211> LENGTH: 60
<212> TYPE: DNA
<213> ORGANISM: Homo sapiens

<400> SEQUENCE: 1129
tacagacttt ttttctcttc tcagaaaatc gatgtttggg ggcggagggc tttgatgaga    60

<210> SEQ ID NO 1130
<211> LENGTH: 60
<212> TYPE: DNA
<213> ORGANISM: Homo sapiens

<400> SEQUENCE: 1130
tgcccatttg catttcatat ccatcatctc gattagctct ggtgaacacc tgtgtatcct    60

<210> SEQ ID NO 1131
<211> LENGTH: 60
<212> TYPE: DNA
<213> ORGANISM: Homo sapiens

<400> SEQUENCE: 1131
ccagctgcag ttcaagtggg gaaagtaatc gaaggtcaaa gaccagtgaa ttggaagatt    60

<210> SEQ ID NO 1132
<211> LENGTH: 60
<212> TYPE: DNA
<213> ORGANISM: Homo sapiens

<400> SEQUENCE: 1132
ggcaggagga tcacttcagc ccaagaggtc gaagagagat gagtactata aagaaaatta    60

<210> SEQ ID NO 1133
<211> LENGTH: 60
<212> TYPE: DNA
<213> ORGANISM: Homo sapiens

<400> SEQUENCE: 1133
tctatagaat tcttaggaaa taatgttttc gacataaggt ttttcaaaat tcctaatcag    60

<210> SEQ ID NO 1134
<211> LENGTH: 60
<212> TYPE: DNA
<213> ORGANISM: Homo sapiens

<400> SEQUENCE: 1134
```

```
ttttaaattt tcacatcgtt ctagtatatc gaggttttct ctttcttcgt ggttcaattt    60
```

<210> SEQ ID NO 1135
<211> LENGTH: 60
<212> TYPE: DNA
<213> ORGANISM: Homo sapiens

<400> SEQUENCE: 1135

```
ttttaaattt tcacatcgtt ctagtatatc gaagaaagat gaaaaggatt gagaaaatct    60
```

<210> SEQ ID NO 1136
<211> LENGTH: 60
<212> TYPE: DNA
<213> ORGANISM: Homo sapiens

<400> SEQUENCE: 1136

```
atcagaaagt tatctttaat gagattcctc gaataaacta agattcaatt tttctgagct    60
```

<210> SEQ ID NO 1137
<211> LENGTH: 60
<212> TYPE: DNA
<213> ORGANISM: Homo sapiens

<400> SEQUENCE: 1137

```
tatttttact gaatctttct ttgaaatttc gattattaaa tactcaagga ataagggatg    60
```

<210> SEQ ID NO 1138
<211> LENGTH: 60
<212> TYPE: DNA
<213> ORGANISM: Homo sapiens

<400> SEQUENCE: 1138

```
aagggctcgg gagctccctc ggcacacctc gaggagtgcc aggcatctac tgctctgtcc    60
```

<210> SEQ ID NO 1139
<211> LENGTH: 60
<212> TYPE: DNA
<213> ORGANISM: Homo sapiens

<400> SEQUENCE: 1139

```
aggagggaga aaagtgatga aggccatttc gagatgggtg cctgggtgag aattttaata    60
```

<210> SEQ ID NO 1140
<211> LENGTH: 60
<212> TYPE: DNA
<213> ORGANISM: Homo sapiens

<400> SEQUENCE: 1140

```
gtgaattctg caggatatga tggccaattc gagataattt taatttgtct actgatgagc    60
```

<210> SEQ ID NO 1141
<211> LENGTH: 60
<212> TYPE: DNA
<213> ORGANISM: Homo sapiens

<400> SEQUENCE: 1141

```
gtaaatgaat ttgaaatatt acaaaagatc gattacaggc attttatagc cacaaactca    60
```

<210> SEQ ID NO 1142
<211> LENGTH: 60
<212> TYPE: DNA
<213> ORGANISM: Homo sapiens

```
<400> SEQUENCE: 1142
cgcagcagtc tcgttgatct tcacggtgtc gactcacctg cgcctcacat cccaggcggg    60

<210> SEQ ID NO 1143
<211> LENGTH: 60
<212> TYPE: DNA
<213> ORGANISM: Homo sapiens

<400> SEQUENCE: 1143
aattctgttg gaagaataat ttaaaatatc gatattttaa ttatttttt cctaaaatag    60

<210> SEQ ID NO 1144
<211> LENGTH: 60
<212> TYPE: DNA
<213> ORGANISM: Homo sapiens

<400> SEQUENCE: 1144
gtaaatgaat ttgaaatatt acaaaagatc gactcacctg cgcctcacat cccaggcggg    60

<210> SEQ ID NO 1145
<211> LENGTH: 60
<212> TYPE: DNA
<213> ORGANISM: Homo sapiens

<400> SEQUENCE: 1145 atactttct ttctagatta tttaaacatc gatatcagtt aagtttaaaa acatattaat    60

<210> SEQ ID NO 1146
<211> LENGTH: 60
<212> TYPE: DNA
<213> ORGANISM: Homo sapiens

<400> SEQUENCE: 1146 atactttct ttctagatta tttaaacatc gagatattta tctacatcta ttattgtggt    60

<210> SEQ ID NO 1147
<211> LENGTH: 60
<212> TYPE: DNA
<213> ORGANISM: Homo sapiens

<400> SEQUENCE: 1147
cccccaaaat agggtctgat ttggggttc gattgcatat tctttggaaa atacaaagtg    60

<210> SEQ ID NO 1148
<211> LENGTH: 60
<212> TYPE: DNA
<213> ORGANISM: Homo sapiens

<400> SEQUENCE: 1148
ctctgactgc atcttgtccc cttctctgtc gagcctccgt tcaaattgat catcatcaaa    60

<210> SEQ ID NO 1149
<211> LENGTH: 60
<212> TYPE: DNA
<213> ORGANISM: Homo sapiens

<400> SEQUENCE: 1149
ctctgactgc atcttgtccc cttctctgtc gaaaatgcct catgtgggag atctgatggc    60

<210> SEQ ID NO 1150
<211> LENGTH: 60
<212> TYPE: DNA
<213> ORGANISM: Homo sapiens
```

```
<400> SEQUENCE: 1150
tattctaaaa ttaatttcaa acaaattttc gattttcata attttattac ttatacttga    60

<210> SEQ ID NO 1151
<211> LENGTH: 60
<212> TYPE: DNA
<213> ORGANISM: Homo sapiens

<400> SEQUENCE: 1151
tattctaaaa ttaatttcaa acaaattttc gagaccctaa aaaaaaaga aataaaataa    60

<210> SEQ ID NO 1152
<211> LENGTH: 60
<212> TYPE: DNA
<213> ORGANISM: Homo sapiens

<400> SEQUENCE: 1152
ctaattaaat ataatctaaa tttccatctc gacgtacata cgaggagaat gagtaggaac    60

<210> SEQ ID NO 1153
<211> LENGTH: 60
<212> TYPE: DNA
<213> ORGANISM: Homo sapiens

<400> SEQUENCE: 1153
ggcaggcaga tcacctgacg tcaggagttc gatactacaa cccaaacttc cagtcagttt    60

<210> SEQ ID NO 1154
<211> LENGTH: 60
<212> TYPE: DNA
<213> ORGANISM: Homo sapiens

<400> SEQUENCE: 1154
gtactgctac ttaccacaac actgggagtc gagccatctg ccactgcctt ttgacatctc    60

<210> SEQ ID NO 1155
<211> LENGTH: 60
<212> TYPE: DNA
<213> ORGANISM: Homo sapiens

<400> SEQUENCE: 1155
tgggaaaatc atcccacctc tctgagcatc gagccatctg ccactgcctt ttgacatctc    60

<210> SEQ ID NO 1156
<211> LENGTH: 60
<212> TYPE: DNA
<213> ORGANISM: Homo sapiens

<400> SEQUENCE: 1156
caaaaattgc caaaaataag taggtttttc gagaacagta ttggatttat tgttagggtt    60

<210> SEQ ID NO 1157
<211> LENGTH: 60
<212> TYPE: DNA
<213> ORGANISM: Homo sapiens

<400> SEQUENCE: 1157
gaggatttaa taaaacccaa actgtatttc gagaaaatag tgttttgcta tttagataag    60

<210> SEQ ID NO 1158
<211> LENGTH: 60
<212> TYPE: DNA
```

```
<213> ORGANISM: Homo sapiens

<400> SEQUENCE: 1158
cactaatctt tactctttttt ccacttattc gaagtttcca gaaaagtcct gaagttttaa    60

<210> SEQ ID NO 1159
<211> LENGTH: 60
<212> TYPE: DNA
<213> ORGANISM: Homo sapiens

<400> SEQUENCE: 1159
tgtccccaga tggattgtag acataaattc gaagttgcag tgtactatga ctgcacaaca    60

<210> SEQ ID NO 1160
<211> LENGTH: 60
<212> TYPE: DNA
<213> ORGANISM: Homo sapiens

<400> SEQUENCE: 1160
tgttgtgcag tcatagtaca ctgcaacttc gaactgactt cttccactca gtataatgtc    60

<210> SEQ ID NO 1161
<211> LENGTH: 60
<212> TYPE: DNA
<213> ORGANISM: Homo sapiens

<400> SEQUENCE: 1161
ttctttaaaa tatttgaaga gatttatttc gagttttgta acctatttttt ccttttaaca    60

<210> SEQ ID NO 1162
<211> LENGTH: 60
<212> TYPE: DNA
<213> ORGANISM: Homo sapiens

<400> SEQUENCE: 1162
ttagggtgca ccctaaccca ataggatgtc gaagaaaatg acctgatcat ttgaaaagct    60

<210> SEQ ID NO 1163
<211> LENGTH: 60
<212> TYPE: DNA
<213> ORGANISM: Homo sapiens

<400> SEQUENCE: 1163
cctcccttac tgggtatcat tattaagctc gaagaaaatg acctgatcat ttgaaaagct    60

<210> SEQ ID NO 1164
<211> LENGTH: 60
<212> TYPE: DNA
<213> ORGANISM: Homo sapiens

<400> SEQUENCE: 1164
taaatgtaaa acataaaact acaaaacttc gattatcaca ttatatactt atcgtgtggc    60

<210> SEQ ID NO 1165
<211> LENGTH: 60
<212> TYPE: DNA
<213> ORGANISM: Homo sapiens

<400> SEQUENCE: 1165
taaatgtaaa acataaaact acaaaacttc gaggttctaa tatataggtt gaaggttcct    60

<210> SEQ ID NO 1166
<211> LENGTH: 60
```

<212> TYPE: DNA
<213> ORGANISM: Homo sapiens

<400> SEQUENCE: 1166
agagataaaa attacagatt ttggtctttc gactggaaat ctacattttt atgtgtaatc    60

<210> SEQ ID NO 1167
<211> LENGTH: 60
<212> TYPE: DNA
<213> ORGANISM: Homo sapiens

<400> SEQUENCE: 1167
cctctgcgag gagctctgtc tgtctttgtc gaactgatat aaactttcag ttgttctatt    60

<210> SEQ ID NO 1168
<211> LENGTH: 60
<212> TYPE: DNA
<213> ORGANISM: Homo sapiens

<400> SEQUENCE: 1168
gagaaaacaa tctagctgtt acaaatgttc gatagttctt aattgttttg gggtaactgg    60

<210> SEQ ID NO 1169
<211> LENGTH: 60
<212> TYPE: DNA
<213> ORGANISM: Homo sapiens

<400> SEQUENCE: 1169
gagaaaacaa tctagctgtt acaaatgttc gaaattttca agtacacaa agtgcaattt    60

<210> SEQ ID NO 1170
<211> LENGTH: 60
<212> TYPE: DNA
<213> ORGANISM: Homo sapiens

<400> SEQUENCE: 1170
gagaaaacaa tctagctgtt acaaatgttc gaactgatat aaactttcag ttgttctatt    60

<210> SEQ ID NO 1171
<211> LENGTH: 60
<212> TYPE: DNA
<213> ORGANISM: Homo sapiens

<400> SEQUENCE: 1171
gagaaaacaa tctagctgtt acaaatgttc gattacataa aaatgtaaaa cttttatcta    60

<210> SEQ ID NO 1172
<211> LENGTH: 60
<212> TYPE: DNA
<213> ORGANISM: Homo sapiens

<400> SEQUENCE: 1172
gagaaaacaa tctagctgtt acaaatgttc gagagaaaca tcacattcat ataactttta    60

<210> SEQ ID NO 1173
<211> LENGTH: 60
<212> TYPE: DNA
<213> ORGANISM: Homo sapiens

<400> SEQUENCE: 1173
gagaaaacaa tctagctgtt acaaatgttc gagaatccat ctatcttcaa agtataaaca    60

<210> SEQ ID NO 1174

```
<211> LENGTH: 60
<212> TYPE: DNA
<213> ORGANISM: Homo sapiens

<400> SEQUENCE: 1174
gagaaaacaa tctagctgtt acaaatgttc gatattctac acatacagtc atccctccc      60

<210> SEQ ID NO 1175
<211> LENGTH: 60
<212> TYPE: DNA
<213> ORGANISM: Homo sapiens

<400> SEQUENCE: 1175
gagaaaacaa tctagctgtt acaaatgttc gactcaagtt gtctcacctt tccagactga      60

<210> SEQ ID NO 1176
<211> LENGTH: 60
<212> TYPE: DNA
<213> ORGANISM: Homo sapiens

<400> SEQUENCE: 1176
ggattcacct tgatgctatc taagtccctc gagggagacg ccgctgctcc catttcacag      60

<210> SEQ ID NO 1177
<211> LENGTH: 60
<212> TYPE: DNA
<213> ORGANISM: Homo sapiens

<400> SEQUENCE: 1177
taaaactatt ttaaatgttt ttaaagtatc gatgtgtact ttgacatctg tgatgatgat      60

<210> SEQ ID NO 1178
<211> LENGTH: 60
<212> TYPE: DNA
<213> ORGANISM: Homo sapiens

<400> SEQUENCE: 1178
agtggcacaa tctcagctca ttatagcctc gaatcagaat gtttgggggt gagcttggaa      60

<210> SEQ ID NO 1179
<211> LENGTH: 60
<212> TYPE: DNA
<213> ORGANISM: Homo sapiens

<400> SEQUENCE: 1179
agtggcacaa tctcagctca ttatagcctc gaattgtaac taccagtgtt ggaggagggg      60

<210> SEQ ID NO 1180
<211> LENGTH: 60
<212> TYPE: DNA
<213> ORGANISM: Homo sapiens

<400> SEQUENCE: 1180
ctgagtcttc attaccaaaa aaaaaagttc gacctccccg aaccctccg cctctgcgct      60

<210> SEQ ID NO 1181
<211> LENGTH: 23
<212> TYPE: DNA
<213> ORGANISM: Homo sapiens

<400> SEQUENCE: 1181
gtaaatgagc cacctgggcg ggt                                             23
```

```
<210> SEQ ID NO 1182
<211> LENGTH: 26
<212> TYPE: DNA
<213> ORGANISM: Homo sapiens

<400> SEQUENCE: 1182
gaacacgaga atggagaggg agcatc                                              26

<210> SEQ ID NO 1183
<211> LENGTH: 26
<212> TYPE: DNA
<213> ORGANISM: Homo sapiens

<400> SEQUENCE: 1183
gctatttggt ctgtccttgc tccaca                                              26

<210> SEQ ID NO 1184
<211> LENGTH: 23
<212> TYPE: DNA
<213> ORGANISM: Homo sapiens

<400> SEQUENCE: 1184
agcctgggtg acagagtaag acc                                                 23

<210> SEQ ID NO 1185
<211> LENGTH: 26
<212> TYPE: DNA
<213> ORGANISM: Homo sapiens

<400> SEQUENCE: 1185
caagcacagg caacagaaca gaccat                                              26

<210> SEQ ID NO 1186
<211> LENGTH: 26
<212> TYPE: DNA
<213> ORGANISM: Homo sapiens

<400> SEQUENCE: 1186
ctgtttgccc tgagaatact tgccca                                              26

<210> SEQ ID NO 1187
<211> LENGTH: 23
<212> TYPE: DNA
<213> ORGANISM: Homo sapiens

<400> SEQUENCE: 1187
gccaacttga ctgggcaaac gga                                                 23

<210> SEQ ID NO 1188
<211> LENGTH: 26
<212> TYPE: DNA
<213> ORGANISM: Homo sapiens

<400> SEQUENCE: 1188
catcggatta gaggattcca gtttta                                              26

<210> SEQ ID NO 1189
<211> LENGTH: 26
<212> TYPE: DNA
<213> ORGANISM: Homo sapiens

<400> SEQUENCE: 1189
cgtctggtgt tgtggaactt tggagg                                              26
```

```
<210> SEQ ID NO 1190
<211> LENGTH: 23
<212> TYPE: DNA
<213> ORGANISM: Homo sapiens

<400> SEQUENCE: 1190
gcggagcctc tttgaacaga agc                                              23

<210> SEQ ID NO 1191
<211> LENGTH: 20
<212> TYPE: DNA
<213> ORGANISM: Homo sapiens

<400> SEQUENCE: 1191
tgatgtatag ctgggccttg                                                  20

<210> SEQ ID NO 1192
<211> LENGTH: 26
<212> TYPE: DNA
<213> ORGANISM: Homo sapiens

<400> SEQUENCE: 1192
ctaagaagca gatgccacag gctggt                                           26

<210> SEQ ID NO 1193
<211> LENGTH: 23
<212> TYPE: DNA
<213> ORGANISM: Homo sapiens

<400> SEQUENCE: 1193
gtgctcctga atgaccagtg ggt                                              23

<210> SEQ ID NO 1194
<211> LENGTH: 26
<212> TYPE: DNA
<213> ORGANISM: Homo sapiens

<400> SEQUENCE: 1194
tgggagggtt ttattcacaa gagtgg                                           26

<210> SEQ ID NO 1195
<211> LENGTH: 24
<212> TYPE: DNA
<213> ORGANISM: Homo sapiens

<400> SEQUENCE: 1195
tgagccacag agcaagactc cgtc                                             24

<210> SEQ ID NO 1196
<211> LENGTH: 21
<212> TYPE: DNA
<213> ORGANISM: Homo sapiens

<400> SEQUENCE: 1196
aagtgatcgt ggaaacacag c                                                21

<210> SEQ ID NO 1197
<211> LENGTH: 23
<212> TYPE: DNA
<213> ORGANISM: Homo sapiens

<400> SEQUENCE: 1197
tttccaagaa cggttttgct ttc                                              23
```

<210> SEQ ID NO 1198
<211> LENGTH: 23
<212> TYPE: DNA
<213> ORGANISM: Homo sapiens

<400> SEQUENCE: 1198
tttccaagaa cggttttgct ttc                                               23

<210> SEQ ID NO 1199
<211> LENGTH: 23
<212> TYPE: DNA
<213> ORGANISM: Homo sapiens

<400> SEQUENCE: 1199
cagcctggca acagagtgag act                                               23

<210> SEQ ID NO 1200
<211> LENGTH: 20
<212> TYPE: DNA
<213> ORGANISM: Homo sapiens

<400> SEQUENCE: 1200
ccgtgcttcg tgctttggac                                                   20

<210> SEQ ID NO 1201
<211> LENGTH: 20
<212> TYPE: DNA
<213> ORGANISM: Homo sapiens

<400> SEQUENCE: 1201
ttcgtgcttt ggactaccgc                                                   20

<210> SEQ ID NO 1202
<211> LENGTH: 23
<212> TYPE: DNA
<213> ORGANISM: Homo sapiens

<400> SEQUENCE: 1202
tatcacggta aaatcaataa aat                                               23

<210> SEQ ID NO 1203
<211> LENGTH: 23
<212> TYPE: DNA
<213> ORGANISM: Homo sapiens

<400> SEQUENCE: 1203
tatcacggta aaatcaataa aat                                               23

<210> SEQ ID NO 1204
<211> LENGTH: 26
<212> TYPE: DNA
<213> ORGANISM: Homo sapiens

<400> SEQUENCE: 1204
ggtgtgtctg ggagattagt agatgg                                            26

<210> SEQ ID NO 1205
<211> LENGTH: 26
<212> TYPE: DNA
<213> ORGANISM: Homo sapiens

<400> SEQUENCE: 1205

```
gtggctcaag tctgtaatcc cagcac                                          26

<210> SEQ ID NO 1206
<211> LENGTH: 26
<212> TYPE: DNA
<213> ORGANISM: Homo sapiens

<400> SEQUENCE: 1206
tccaggatgg tttgactcta aagcat                                          26

<210> SEQ ID NO 1207
<211> LENGTH: 24
<212> TYPE: DNA
<213> ORGANISM: Homo sapiens

<400> SEQUENCE: 1207
ctctttcagg ttccccagac catc                                            24

<210> SEQ ID NO 1208
<211> LENGTH: 26
<212> TYPE: DNA
<213> ORGANISM: Homo sapiens

<400> SEQUENCE: 1208
aatacctacc cttgcccttc ccacca                                          26

<210> SEQ ID NO 1209
<211> LENGTH: 26
<212> TYPE: DNA
<213> ORGANISM: Homo sapiens

<400> SEQUENCE: 1209
tggcagattg taggtggttg gagaat                                          26

<210> SEQ ID NO 1210
<211> LENGTH: 26
<212> TYPE: DNA
<213> ORGANISM: Homo sapiens

<400> SEQUENCE: 1210
gtcatctcct ctccagttag tcaaca                                          26

<210> SEQ ID NO 1211
<211> LENGTH: 26
<212> TYPE: DNA
<213> ORGANISM: Homo sapiens

<400> SEQUENCE: 1211
gtgatacaac actttagata cctgga                                          26

<210> SEQ ID NO 1212
<211> LENGTH: 26
<212> TYPE: DNA
<213> ORGANISM: Homo sapiens

<400> SEQUENCE: 1212
acacaaccca gcgtccttcg cctttt                                          26

<210> SEQ ID NO 1213
<211> LENGTH: 26
<212> TYPE: DNA
<213> ORGANISM: Homo sapiens

<400> SEQUENCE: 1213
```

```
ccacctctgt gaagtatgct ctctgg                                          26

<210> SEQ ID NO 1214
<211> LENGTH: 26
<212> TYPE: DNA
<213> ORGANISM: Homo sapiens

<400> SEQUENCE: 1214
gagtccaagc aaacgacaag gaagtc                                          26

<210> SEQ ID NO 1215
<211> LENGTH: 23
<212> TYPE: DNA
<213> ORGANISM: Homo sapiens

<400> SEQUENCE: 1215
ttgagatgac aggctggcac ccc                                             23

<210> SEQ ID NO 1216
<211> LENGTH: 26
<212> TYPE: DNA
<213> ORGANISM: Homo sapiens

<400> SEQUENCE: 1216
gcagaaactc aaaatggatg gtaggc                                          26

<210> SEQ ID NO 1217
<211> LENGTH: 26
<212> TYPE: DNA
<213> ORGANISM: Homo sapiens

<400> SEQUENCE: 1217
gcagaaactc aaaatggatg gtaggc                                          26

<210> SEQ ID NO 1218
<211> LENGTH: 23
<212> TYPE: DNA
<213> ORGANISM: Homo sapiens

<400> SEQUENCE: 1218
tatctgctat tactttgggt ttt                                             23

<210> SEQ ID NO 1219
<211> LENGTH: 25
<212> TYPE: DNA
<213> ORGANISM: Homo sapiens

<400> SEQUENCE: 1219
gccactttga gggctgaaca gtagc                                           25

<210> SEQ ID NO 1220
<211> LENGTH: 26
<212> TYPE: DNA
<213> ORGANISM: Homo sapiens

<400> SEQUENCE: 1220
ggatgccaga ataagatgga actgtg                                          26

<210> SEQ ID NO 1221
<211> LENGTH: 26
<212> TYPE: DNA
<213> ORGANISM: Homo sapiens
```

<400> SEQUENCE: 1221
ggatgccaga ataagatgga actgtg                                        26

<210> SEQ ID NO 1222
<211> LENGTH: 26
<212> TYPE: DNA
<213> ORGANISM: Homo sapiens

<400> SEQUENCE: 1222
ggatgccaga ataagatgga actgtg                                        26

<210> SEQ ID NO 1223
<211> LENGTH: 26
<212> TYPE: DNA
<213> ORGANISM: Homo sapiens

<400> SEQUENCE: 1223
ggatgccaga ataagatgga actgtg                                        26

<210> SEQ ID NO 1224
<211> LENGTH: 26
<212> TYPE: DNA
<213> ORGANISM: Homo sapiens

<400> SEQUENCE: 1224
ggatgccaga ataagatgga actgtg                                        26

<210> SEQ ID NO 1225
<211> LENGTH: 26
<212> TYPE: DNA
<213> ORGANISM: Homo sapiens

<400> SEQUENCE: 1225
ggatgccaga ataagatgga actgtg                                        26

<210> SEQ ID NO 1226
<211> LENGTH: 26
<212> TYPE: DNA
<213> ORGANISM: Homo sapiens

<400> SEQUENCE: 1226
ggatgccaga ataagatgga actgtg                                        26

<210> SEQ ID NO 1227
<211> LENGTH: 26
<212> TYPE: DNA
<213> ORGANISM: Homo sapiens

<400> SEQUENCE: 1227
ggatgccaga ataagatgga actgtg                                        26

<210> SEQ ID NO 1228
<211> LENGTH: 23
<212> TYPE: DNA
<213> ORGANISM: Homo sapiens

<400> SEQUENCE: 1228
tcacccagct gctgtatatg act                                           23

<210> SEQ ID NO 1229
<211> LENGTH: 23
<212> TYPE: DNA
<213> ORGANISM: Homo sapiens -continued

<400> SEQUENCE: 1229
aacgctttcc accaggtcct acc          23

<210> SEQ ID NO 1230
<211> LENGTH: 23
<212> TYPE: DNA
<213> ORGANISM: Homo sapiens

<400> SEQUENCE: 1230
catctcactc cctcaccagg ctg          23

<210> SEQ ID NO 1231
<211> LENGTH: 23
<212> TYPE: DNA
<213> ORGANISM: Homo sapiens

<400> SEQUENCE: 1231
catctcactc cctcaccagg ctg          23

<210> SEQ ID NO 1232
<211> LENGTH: 20
<212> TYPE: DNA
<213> ORGANISM: Homo sapiens

<400> SEQUENCE: 1232
ggggaatgac tcaggttcac              20

<210> SEQ ID NO 1233
<211> LENGTH: 25
<212> TYPE: DNA
<213> ORGANISM: Homo sapiens

<400> SEQUENCE: 1233
ggcaagcatc ttcctggttc ttcag        25

<210> SEQ ID NO 1234
<211> LENGTH: 26
<212> TYPE: DNA
<213> ORGANISM: Homo sapiens

<400> SEQUENCE: 1234
ctgaggaaag agagcagtat ctaagg       26

<210> SEQ ID NO 1235
<211> LENGTH: 26
<212> TYPE: DNA
<213> ORGANISM: Homo sapiens

<400> SEQUENCE: 1235
gctcatcagt tttcagtcct tttcct       26

<210> SEQ ID NO 1236
<211> LENGTH: 23
<212> TYPE: DNA
<213> ORGANISM: Homo sapiens

<400> SEQUENCE: 1236
ggcaccgtgt atccctctct ctg          23

<210> SEQ ID NO 1237
<211> LENGTH: 24
<212> TYPE: DNA

<213> ORGANISM: Homo sapiens

<400> SEQUENCE: 1237
atagacaaat gacctcctcc ttgc                                          24

<210> SEQ ID NO 1238
<211> LENGTH: 26
<212> TYPE: DNA
<213> ORGANISM: Homo sapiens

<400> SEQUENCE: 1238
gaagacaaag atacattcct ggacat                                        26

<210> SEQ ID NO 1239
<211> LENGTH: 23
<212> TYPE: DNA
<213> ORGANISM: Homo sapiens

<400> SEQUENCE: 1239
cccctttctg tcctgctctc tgc                                           23

<210> SEQ ID NO 1240
<211> LENGTH: 26
<212> TYPE: DNA
<213> ORGANISM: Homo sapiens

<400> SEQUENCE: 1240
gtgcccacac aaagactaag cgagtt                                        26

<210> SEQ ID NO 1241
<211> LENGTH: 26
<212> TYPE: DNA
<213> ORGANISM: Homo sapiens

<400> SEQUENCE: 1241
gccaagcata gactcagact tttagg                                        26

<210> SEQ ID NO 1242
<211> LENGTH: 23
<212> TYPE: DNA
<213> ORGANISM: Homo sapiens

<400> SEQUENCE: 1242
gcctcttccc accagcctga ctt                                           23

<210> SEQ ID NO 1243
<211> LENGTH: 20
<212> TYPE: DNA
<213> ORGANISM: Homo sapiens

<400> SEQUENCE: 1243
accaaggatg caccagaaag                                               20

<210> SEQ ID NO 1244
<211> LENGTH: 26
<212> TYPE: DNA
<213> ORGANISM: Homo sapiens

<400> SEQUENCE: 1244
tctgagggtg accttatttt gtccac                                        26

<210> SEQ ID NO 1245
<211> LENGTH: 23

-continued

<212> TYPE: DNA
<213> ORGANISM: Homo sapiens

<400> SEQUENCE: 1245
cagcctgggc gacagaaacc ttg                                          23

<210> SEQ ID NO 1246
<211> LENGTH: 26
<212> TYPE: DNA
<213> ORGANISM: Homo sapiens

<400> SEQUENCE: 1246
acagtccata gtgagcggca gacaga                                       26

<210> SEQ ID NO 1247
<211> LENGTH: 26
<212> TYPE: DNA
<213> ORGANISM: Homo sapiens

<400> SEQUENCE: 1247
gctacagcct actaatcaag gaactg                                       26

<210> SEQ ID NO 1248
<211> LENGTH: 20
<212> TYPE: DNA
<213> ORGANISM: Homo sapiens

<400> SEQUENCE: 1248
ccacagtcca tagtgagcgg                                              20

<210> SEQ ID NO 1249
<211> LENGTH: 23
<212> TYPE: DNA
<213> ORGANISM: Homo sapiens

<400> SEQUENCE: 1249
atttacttgc tatgggtcct ttt                                          23

<210> SEQ ID NO 1250
<211> LENGTH: 23
<212> TYPE: DNA
<213> ORGANISM: Homo sapiens

<400> SEQUENCE: 1250
atttacttgc tatgggtcct ttt                                          23

<210> SEQ ID NO 1251
<211> LENGTH: 23
<212> TYPE: DNA
<213> ORGANISM: Homo sapiens

<400> SEQUENCE: 1251
gaaatctcct ccccaccctc agc                                          23

<210> SEQ ID NO 1252
<211> LENGTH: 20
<212> TYPE: DNA
<213> ORGANISM: Homo sapiens

<400> SEQUENCE: 1252
ggtggaaggg tgagccatgt                                              20

<210> SEQ ID NO 1253

```
<211> LENGTH: 22
<212> TYPE: DNA
<213> ORGANISM: Homo sapiens

<400> SEQUENCE: 1253
cccaggatag gaggccatca ga                                              22

<210> SEQ ID NO 1254
<211> LENGTH: 23
<212> TYPE: DNA
<213> ORGANISM: Homo sapiens

<400> SEQUENCE: 1254
aagccatcct tttctaaaca ata                                             23

<210> SEQ ID NO 1255
<211> LENGTH: 23
<212> TYPE: DNA
<213> ORGANISM: Homo sapiens

<400> SEQUENCE: 1255
agaggaaaga caacatttta ttt                                             23

<210> SEQ ID NO 1256
<211> LENGTH: 26
<212> TYPE: DNA
<213> ORGANISM: Homo sapiens

<400> SEQUENCE: 1256
ccgtagagga taaaggaaa gaaagc                                           26

<210> SEQ ID NO 1257
<211> LENGTH: 26
<212> TYPE: DNA
<213> ORGANISM: Homo sapiens

<400> SEQUENCE: 1257
ccagcattcc ctacttcttc actact                                          26

<210> SEQ ID NO 1258
<211> LENGTH: 24
<212> TYPE: DNA
<213> ORGANISM: Homo sapiens

<400> SEQUENCE: 1258
tgtgggtagc agcagaggat ggca                                            24

<210> SEQ ID NO 1259
<211> LENGTH: 23
<212> TYPE: DNA
<213> ORGANISM: Homo sapiens

<400> SEQUENCE: 1259
tgggtagcag cagaggatgg cag                                             23

<210> SEQ ID NO 1260
<211> LENGTH: 26
<212> TYPE: DNA
<213> ORGANISM: Homo sapiens

<400> SEQUENCE: 1260
tcatcacaga ccacagcaga agtgtt                                          26
```

```
<210> SEQ ID NO 1261
<211> LENGTH: 26
<212> TYPE: DNA
<213> ORGANISM: Homo sapiens

<400> SEQUENCE: 1261
gtctggcagc cttcctcatt tatggt                                          26

<210> SEQ ID NO 1262
<211> LENGTH: 26
<212> TYPE: DNA
<213> ORGANISM: Homo sapiens

<400> SEQUENCE: 1262
cccttgctat gatggcttgt tcactg                                          26

<210> SEQ ID NO 1263
<211> LENGTH: 26
<212> TYPE: DNA
<213> ORGANISM: Homo sapiens

<400> SEQUENCE: 1263
ttcttcccac tacaccacac aaccca                                          26

<210> SEQ ID NO 1264
<211> LENGTH: 26
<212> TYPE: DNA
<213> ORGANISM: Homo sapiens

<400> SEQUENCE: 1264
cagcagcaag aatggagttc aaagac                                          26

<210> SEQ ID NO 1265
<211> LENGTH: 26
<212> TYPE: DNA
<213> ORGANISM: Homo sapiens

<400> SEQUENCE: 1265
ccagcatcaa agagcaagaa tggagt                                          26

<210> SEQ ID NO 1266
<211> LENGTH: 26
<212> TYPE: DNA
<213> ORGANISM: Homo sapiens

<400> SEQUENCE: 1266
cgatggcaac tggctcttgt tccttt                                          26

<210> SEQ ID NO 1267
<211> LENGTH: 23
<212> TYPE: DNA
<213> ORGANISM: Homo sapiens

<400> SEQUENCE: 1267
cgatggcaac tggctcttgt tcc                                             23

<210> SEQ ID NO 1268
<211> LENGTH: 26
<212> TYPE: DNA
<213> ORGANISM: Homo sapiens

<400> SEQUENCE: 1268
ctatgtgggt gtgtggatgt gtatgg                                          26
```

<210> SEQ ID NO 1269
<211> LENGTH: 26
<212> TYPE: DNA
<213> ORGANISM: Homo sapiens

<400> SEQUENCE: 1269
tttgttcccc aggcagcatt cagtgc                                      26

<210> SEQ ID NO 1270
<211> LENGTH: 23
<212> TYPE: DNA
<213> ORGANISM: Homo sapiens

<400> SEQUENCE: 1270
ttcaggatgt gtgagagaga tta                                         23

<210> SEQ ID NO 1271
<211> LENGTH: 24
<212> TYPE: DNA
<213> ORGANISM: Homo sapiens

<400> SEQUENCE: 1271
aaaacaaaga atcctccctg cccc                                        24

<210> SEQ ID NO 1272
<211> LENGTH: 26
<212> TYPE: DNA
<213> ORGANISM: Homo sapiens

<400> SEQUENCE: 1272
gaaacagcct cactttggag ttcagg                                      26

<210> SEQ ID NO 1273
<211> LENGTH: 26
<212> TYPE: DNA
<213> ORGANISM: Homo sapiens

<400> SEQUENCE: 1273
catcaccagc aagcagtgcc aactac                                      26

<210> SEQ ID NO 1274
<211> LENGTH: 24
<212> TYPE: DNA
<213> ORGANISM: Homo sapiens

<400> SEQUENCE: 1274
aaaacaaaga atcctccctg cccc                                        24

<210> SEQ ID NO 1275
<211> LENGTH: 26
<212> TYPE: DNA
<213> ORGANISM: Homo sapiens

<400> SEQUENCE: 1275
ccattctcaa taagaggcgt gtcacc                                      26

<210> SEQ ID NO 1276
<211> LENGTH: 26
<212> TYPE: DNA
<213> ORGANISM: Homo sapiens

<400> SEQUENCE: 1276
ctgtgaggga tacactccaa gacatc                                      26

```
<210> SEQ ID NO 1277
<211> LENGTH: 26
<212> TYPE: DNA
<213> ORGANISM: Homo sapiens

<400> SEQUENCE: 1277
gcagaggtgg tgagaagtag tcagac                                          26

<210> SEQ ID NO 1278
<211> LENGTH: 26
<212> TYPE: DNA
<213> ORGANISM: Homo sapiens

<400> SEQUENCE: 1278
gtgcttgaca tttctgctac ccctgc                                          26

<210> SEQ ID NO 1279
<211> LENGTH: 26
<212> TYPE: DNA
<213> ORGANISM: Homo sapiens

<400> SEQUENCE: 1279
tccgtgacac agtctcagga ggttct                                          26

<210> SEQ ID NO 1280
<211> LENGTH: 20
<212> TYPE: DNA
<213> ORGANISM: Homo sapiens

<400> SEQUENCE: 1280
acaagctcgt gtgagtgccc                                                 20

<210> SEQ ID NO 1281
<211> LENGTH: 23
<212> TYPE: DNA
<213> ORGANISM: Homo sapiens

<400> SEQUENCE: 1281
ggaaagtggg caccagccgc att                                             23

<210> SEQ ID NO 1282
<211> LENGTH: 23
<212> TYPE: DNA
<213> ORGANISM: Homo sapiens

<400> SEQUENCE: 1282
ggcaggagaa gggctactga aag                                             23

<210> SEQ ID NO 1283
<211> LENGTH: 23
<212> TYPE: DNA
<213> ORGANISM: Homo sapiens

<400> SEQUENCE: 1283
caaaccacct cccatcaaac ccc                                             23

<210> SEQ ID NO 1284
<211> LENGTH: 20
<212> TYPE: DNA
<213> ORGANISM: Homo sapiens

<400> SEQUENCE: 1284
```
gcggagtgct ctggctctac                                          20

<210> SEQ ID NO 1285
<211> LENGTH: 60
<212> TYPE: DNA
<213> ORGANISM: Homo sapiens

<400> SEQUENCE: 1285
tgaaagtctg cagggtgtgt gctcaggatc gaggctggta ctgttcacct gtgggtccag    60

<210> SEQ ID NO 1286
<211> LENGTH: 60
<212> TYPE: DNA
<213> ORGANISM: Homo sapiens

<400> SEQUENCE: 1286
tgaaagtctg cagggtgtgt gctcaggatc gaccaagatc tagtaattat tcatactgta    60

<210> SEQ ID NO 1287
<211> LENGTH: 60
<212> TYPE: DNA
<213> ORGANISM: Homo sapiens

<400> SEQUENCE: 1287
tgttttaggg agaagactgt gcctaatatc gagtggagtg gaagaatacc aaaatcatct    60

<210> SEQ ID NO 1288
<211> LENGTH: 60
<212> TYPE: DNA
<213> ORGANISM: Homo sapiens

<400> SEQUENCE: 1288
aagactgaga taaaaattct caagatcatc gagtggagtg gaagaatacc aaaatcatct    60

<210> SEQ ID NO 1289
<211> LENGTH: 60
<212> TYPE: DNA
<213> ORGANISM: Homo sapiens

<400> SEQUENCE: 1289
tctttgcaga tgttgtaaga taaggatgtc gacttcataa tccgcccgcc tcagcctccc    60

<210> SEQ ID NO 1290
<211> LENGTH: 60
<212> TYPE: DNA
<213> ORGANISM: Homo sapiens

<400> SEQUENCE: 1290
ggaccttgtc atcctgcccc ttcttggctc gaggccctga acaggactc tatgtctcct     60

<210> SEQ ID NO 1291
<211> LENGTH: 60
<212> TYPE: DNA
<213> ORGANISM: Homo sapiens

<400> SEQUENCE: 1291
caagctttat ttaaaaatat agcatatatc gaaagttggc taatgtatta tagcccatat    60

<210> SEQ ID NO 1292
<211> LENGTH: 60
<212> TYPE: DNA
<213> ORGANISM: Homo sapiens

<400> SEQUENCE: 1292

```
caagctttat ttaaaaatat agcatatatc gaacaaccag gggaaataac aatggttaca    60

<210> SEQ ID NO 1293
<211> LENGTH: 60
<212> TYPE: DNA
<213> ORGANISM: Homo sapiens

<400> SEQUENCE: 1293
aggtactgtt ttagaaatat agaaaaattc gaacaaccag gggaaataac aatggttaca    60

<210> SEQ ID NO 1294
<211> LENGTH: 60
<212> TYPE: DNA
<213> ORGANISM: Homo sapiens

<400> SEQUENCE: 1294
atttctttct tcttcccatt ttctaaaatc gattcctcca ataagggttt cacctcttga    60

<210> SEQ ID NO 1295
<211> LENGTH: 60
<212> TYPE: DNA
<213> ORGANISM: Homo sapiens

<400> SEQUENCE: 1295
gtttttgtat taataaaatg aaaaagattc gaaaacttcc ttattaggta gtaaaacaaa    60

<210> SEQ ID NO 1296
<211> LENGTH: 60
<212> TYPE: DNA
<213> ORGANISM: Homo sapiens

<400> SEQUENCE: 1296
gtggctaaaa caagattcaa tctcaatctc gagtttatgt actgtctcca ttgactaaga    60

<210> SEQ ID NO 1297
<211> LENGTH: 60
<212> TYPE: DNA
<213> ORGANISM: Homo sapiens

<400> SEQUENCE: 1297
ttaatatact tacatatatt tataatggtc gatctcacta ttgatagctc cattttacag    60

<210> SEQ ID NO 1298
<211> LENGTH: 60
<212> TYPE: DNA
<213> ORGANISM: Homo sapiens

<400> SEQUENCE: 1298
tttcaaagaa ggtatgatgg gaaaggtctc gagtgcccct gtcccacctg gctcccctg    60

<210> SEQ ID NO 1299
<211> LENGTH: 60
<212> TYPE: DNA
<213> ORGANISM: Homo sapiens

<400> SEQUENCE: 1299
tttcaaagaa ggtatgatgg gaaaggtctc gacgcgcccc ctctacgcca tgtcccccc    60

<210> SEQ ID NO 1300
<211> LENGTH: 60
<212> TYPE: DNA
<213> ORGANISM: Homo sapiens
```

```
<400> SEQUENCE: 1300
aaataaaata aaataaaaca tatactactc gagttttta gtgaatattt acaatttcct        60

<210> SEQ ID NO 1301
<211> LENGTH: 60
<212> TYPE: DNA
<213> ORGANISM: Homo sapiens

<400> SEQUENCE: 1301
gctgcctatg gggcagtgtg cagggtgtc gatgaatttc tcaacataca gaattgacag        60

<210> SEQ ID NO 1302
<211> LENGTH: 60
<212> TYPE: DNA
<213> ORGANISM: Homo sapiens

<400> SEQUENCE: 1302
ctttttaaaa attatctttt tatttgcttc gatgccaatc cacgtcatta gatgaggacc       60

<210> SEQ ID NO 1303
<211> LENGTH: 60
<212> TYPE: DNA
<213> ORGANISM: Homo sapiens

<400> SEQUENCE: 1303
tcagataagt aacttcctga taattaactc gagaaatgga ttcatatttc catggcttac       60

<210> SEQ ID NO 1304
<211> LENGTH: 60
<212> TYPE: DNA
<213> ORGANISM: Homo sapiens

<400> SEQUENCE: 1304
tcagataagt aacttcctga taattaactc gaaaaaacat taatttcttc aggtgtaaag      60

<210> SEQ ID NO 1305
<211> LENGTH: 60
<212> TYPE: DNA
<213> ORGANISM: Homo sapiens

<400> SEQUENCE: 1305
tcagataagt aacttcctga taattaactc gatgccaatc cacgtcatta gatgaggacc       60

<210> SEQ ID NO 1306
<211> LENGTH: 60
<212> TYPE: DNA
<213> ORGANISM: Homo sapiens

<400> SEQUENCE: 1306
gtaagccatg gaaatatgaa tccatttctc gatgccaatc cacgtcatta gatgaggacc       60

<210> SEQ ID NO 1307
<211> LENGTH: 60
<212> TYPE: DNA
<213> ORGANISM: Homo sapiens

<400> SEQUENCE: 1307
tatctatttc tttcttattt tggacatttc gagggtgata atgctaaggg gtctggattg       60

<210> SEQ ID NO 1308
<211> LENGTH: 60
<212> TYPE: DNA
<213> ORGANISM: Homo sapiens
```

-continued

<400> SEQUENCE: 1308
gagaggagag taaggttggg gtgtaaggtc gattctaata attcttagtt gaattgttct    60

<210> SEQ ID NO 1309
<211> LENGTH: 60
<212> TYPE: DNA
<213> ORGANISM: Homo sapiens

<400> SEQUENCE: 1309
taacaaaagt aacacctctt tggtatcatc gaagagtcct tgttcccatt ttgcccagt     60

<210> SEQ ID NO 1310
<211> LENGTH: 60
<212> TYPE: DNA
<213> ORGANISM: Homo sapiens

<400> SEQUENCE: 1310
gggcaagttc agattgaagc ctcgtgtctc gagaggcaga taaaaacaat tccatggtaa    60

<210> SEQ ID NO 1311
<211> LENGTH: 60
<212> TYPE: DNA
<213> ORGANISM: Homo sapiens

<400> SEQUENCE: 1311
gaatggccga acagccatga cagtcctctc gaggctactg gagtcattga aagaggaat    60

<210> SEQ ID NO 1312
<211> LENGTH: 60
<212> TYPE: DNA
<213> ORGANISM: Homo sapiens

<400> SEQUENCE: 1312
tttttattga ttgtctcatt taatcttctc gagttcctca aaagtttcca aacaagctcc    60

<210> SEQ ID NO 1313
<211> LENGTH: 60
<212> TYPE: DNA
<213> ORGANISM: Homo sapiens

<400> SEQUENCE: 1313
caaggtgggt ggatcacctg aggagaattc gaatccaaca gcacatcaaa aaatacacc     60

<210> SEQ ID NO 1314
<211> LENGTH: 60
<212> TYPE: DNA
<213> ORGANISM: Homo sapiens

<400> SEQUENCE: 1314
tcccatcatt caaaaattat taagaaattc gaggtattaa agtatgcttt tattgtgtaa    60

<210> SEQ ID NO 1315
<211> LENGTH: 60
<212> TYPE: DNA
<213> ORGANISM: Homo sapiens

<400> SEQUENCE: 1315
cgttgcaaat tgtacatctt ctgctatttc gagacctcat ataactcggt gattgactgc    60

<210> SEQ ID NO 1316
<211> LENGTH: 60
<212> TYPE: DNA

<213> ORGANISM: Homo sapiens

<400> SEQUENCE: 1316
gcagtcaatc accgagttat atgaggtctc gacctcccg aacccctccg cctctgcgct    60

<210> SEQ ID NO 1317
<211> LENGTH: 60
<212> TYPE: DNA
<213> ORGANISM: Homo sapiens

<400> SEQUENCE: 1317
aggaggggca agtccgtca gctggctttc gagactcaga aataaatttg cagtcttta    60

<210> SEQ ID NO 1318
<211> LENGTH: 60
<212> TYPE: DNA
<213> ORGANISM: Homo sapiens

<400> SEQUENCE: 1318 tttttctct atagttcatt acttatttc gagtgtaaac tgtgaaaata gtcaaatata    60

<210> SEQ ID NO 1319
<211> LENGTH: 60
<212> TYPE: DNA
<213> ORGANISM: Homo sapiens

<400> SEQUENCE: 1319 tttttctct atagttcatt acttatttc gactctacga aaagtatctt cctttaatta    60

<210> SEQ ID NO 1320
<211> LENGTH: 60
<212> TYPE: DNA
<213> ORGANISM: Homo sapiens

<400> SEQUENCE: 1320
atttacaaaa tggactgctt agtacgtgtc gaaataagt aatgaactat agagaaaaaa    60

<210> SEQ ID NO 1321
<211> LENGTH: 60
<212> TYPE: DNA
<213> ORGANISM: Homo sapiens

<400> SEQUENCE: 1321 tttttctct atagttcatt acttatttc gaaatatacc agtaaaatta atttaaatat    60

<210> SEQ ID NO 1322
<211> LENGTH: 60
<212> TYPE: DNA
<213> ORGANISM: Homo sapiens

<400> SEQUENCE: 1322
gatgggcaga ttacttgaag tcaagagttc gagcttggaa gtcaaaagct gtgtggctgt    60

<210> SEQ ID NO 1323
<211> LENGTH: 60
<212> TYPE: DNA
<213> ORGANISM: Homo sapiens

<400> SEQUENCE: 1323
ttggttttaa tttttttttt taaataaatc gactacatat aagctttaga tttgaaatat    60

<210> SEQ ID NO 1324
<211> LENGTH: 60

```
<212> TYPE: DNA
<213> ORGANISM: Homo sapiens

<400> SEQUENCE: 1324
ttattctttt ttagtatcta aatagtattc gaatgtccaa aaatgatagg aaacttaaaa        60

<210> SEQ ID NO 1325
<211> LENGTH: 60
<212> TYPE: DNA
<213> ORGANISM: Homo sapiens

<400> SEQUENCE: 1325
tttgttgaat ttttaatatt gaatttattc gatttcttcc caattcctca tttctaatat        60

<210> SEQ ID NO 1326
<211> LENGTH: 60
<212> TYPE: DNA
<213> ORGANISM: Homo sapiens

<400> SEQUENCE: 1326
attatctaga tcttgtaaga tggaaaaatc gatttcttcc caattcctca tttctaatat        60

<210> SEQ ID NO 1327
<211> LENGTH: 60
<212> TYPE: DNA
<213> ORGANISM: Homo sapiens

<400> SEQUENCE: 1327
tttttaaaag caagttttct caaaagcttc gaagcactaa gtaaggtgta ttgttattat        60

<210> SEQ ID NO 1328
<211> LENGTH: 60
<212> TYPE: DNA
<213> ORGANISM: Homo sapiens

<400> SEQUENCE: 1328
tcacaacctg ggaaaactgt cgccttgctc gactcctgct tccctcccct catctttaaa       60

<210> SEQ ID NO 1329
<211> LENGTH: 60
<212> TYPE: DNA
<213> ORGANISM: Homo sapiens

<400> SEQUENCE: 1329
ccaaactggc aatcaaccca gatagtcttc gaccccggcc ccggaggtct ccctccacag       60

<210> SEQ ID NO 1330
<211> LENGTH: 60
<212> TYPE: DNA
<213> ORGANISM: Homo sapiens

<400> SEQUENCE: 1330
ggcaggcaga tcacctgagc tcaggagttc gatcaggtac aaaccaaaca cagaacataa       60

<210> SEQ ID NO 1331
<211> LENGTH: 60
<212> TYPE: DNA
<213> ORGANISM: Homo sapiens

<400> SEQUENCE: 1331
ggcaggcaga tcacctgagc tcaggagttc gattaaaaag aacaaaattg atttcctaaa       60

<210> SEQ ID NO 1332
```

```
<211> LENGTH: 60
<212> TYPE: DNA
<213> ORGANISM: Homo sapiens

<400> SEQUENCE: 1332
gggtctgaag caccgtgaga gaaatgactc gaattgtctt tctttcgccc gatacataaa    60

<210> SEQ ID NO 1333
<211> LENGTH: 60
<212> TYPE: DNA
<213> ORGANISM: Homo sapiens

<400> SEQUENCE: 1333
aagtcttttg tttggttatt gtgctgtatc gatccagctt tttgactcta aaatgagctt    60

<210> SEQ ID NO 1334
<211> LENGTH: 60
<212> TYPE: DNA
<213> ORGANISM: Homo sapiens

<400> SEQUENCE: 1334
aagtcttttg tttggttatt gtgctgtatc gaatcaaagc tgtgtcacaa actatgtaac    60

<210> SEQ ID NO 1335
<211> LENGTH: 60
<212> TYPE: DNA
<213> ORGANISM: Homo sapiens

<400> SEQUENCE: 1335
ctttcaaaca aatgaccttc accactgttc gatcacggct cactgcagcc ttggcctcct    60

<210> SEQ ID NO 1336
<211> LENGTH: 60
<212> TYPE: DNA
<213> ORGANISM: Homo sapiens

<400> SEQUENCE: 1336
caccgacccg tccgggcccg ctgccacatc gaatagcttc ttttgctatg tctccaagtt    60

<210> SEQ ID NO 1337
<211> LENGTH: 23
<212> TYPE: DNA
<213> ORGANISM: Homo sapiens

<400> SEQUENCE: 1337
agggttgcca gaagaaacag ggc    23

<210> SEQ ID NO 1338
<211> LENGTH: 23
<212> TYPE: DNA
<213> ORGANISM: Homo sapiens

<400> SEQUENCE: 1338
ccccagtgag aagggttgcc aga    23

<210> SEQ ID NO 1339
<211> LENGTH: 20
<212> TYPE: DNA
<213> ORGANISM: Homo sapiens

<400> SEQUENCE: 1339
actgccctgt aacgttgctc    20
```

```
<210> SEQ ID NO 1340
<211> LENGTH: 20
<212> TYPE: DNA
<213> ORGANISM: Homo sapiens

<400> SEQUENCE: 1340
tgttggggat ttgtctggat                                               20

<210> SEQ ID NO 1341
<211> LENGTH: 18
<212> TYPE: DNA
<213> ORGANISM: Homo sapiens

<400> SEQUENCE: 1341
atcctgggtg ggatcttg                                                 18

<210> SEQ ID NO 1342
<211> LENGTH: 23
<212> TYPE: DNA
<213> ORGANISM: Homo sapiens

<400> SEQUENCE: 1342
ggataccaca ctgggaggct tcc                                           23

<210> SEQ ID NO 1343
<211> LENGTH: 23
<212> TYPE: DNA
<213> ORGANISM: Homo sapiens

<400> SEQUENCE: 1343
ggagcctcac cctgttgata gtc                                           23

<210> SEQ ID NO 1344
<211> LENGTH: 24
<212> TYPE: DNA
<213> ORGANISM: Homo sapiens

<400> SEQUENCE: 1344
cggagcctca ccctgttgat agtc                                          24

<210> SEQ ID NO 1345
<211> LENGTH: 26
<212> TYPE: DNA
<213> ORGANISM: Homo sapiens

<400> SEQUENCE: 1345
gtgctgggca aacttatcca tttctt                                        26

<210> SEQ ID NO 1346
<211> LENGTH: 26
<212> TYPE: DNA
<213> ORGANISM: Homo sapiens

<400> SEQUENCE: 1346
cggttgtccc agccctaagt agatga                                        26

<210> SEQ ID NO 1347
<211> LENGTH: 23
<212> TYPE: DNA
<213> ORGANISM: Homo sapiens

<400> SEQUENCE: 1347
ccactgtttt aggatggtct gac                                           23
```

```
<210> SEQ ID NO 1348
<211> LENGTH: 23
<212> TYPE: DNA
<213> ORGANISM: Homo sapiens

<400> SEQUENCE: 1348
agcctgggtg acagagtgag act                                          23

<210> SEQ ID NO 1349
<211> LENGTH: 26
<212> TYPE: DNA
<213> ORGANISM: Homo sapiens

<400> SEQUENCE: 1349
acctatccca ttcagatttt gcttgc                                       26

<210> SEQ ID NO 1350
<211> LENGTH: 26
<212> TYPE: DNA
<213> ORGANISM: Homo sapiens

<400> SEQUENCE: 1350
cactttgcct ccacatctgg tatgag                                       26

<210> SEQ ID NO 1351
<211> LENGTH: 20
<212> TYPE: DNA
<213> ORGANISM: Homo sapiens

<400> SEQUENCE: 1351
ccggctcaac tagcactttg                                              20

<210> SEQ ID NO 1352
<211> LENGTH: 26
<212> TYPE: DNA
<213> ORGANISM: Homo sapiens

<400> SEQUENCE: 1352
ccaggactct ttagtgtctg ttcccc                                       26

<210> SEQ ID NO 1353
<211> LENGTH: 23
<212> TYPE: DNA
<213> ORGANISM: Homo sapiens

<400> SEQUENCE: 1353
aagcactggg acaagcctgg agg                                          23

<210> SEQ ID NO 1354
<211> LENGTH: 23
<212> TYPE: DNA
<213> ORGANISM: Homo sapiens

<400> SEQUENCE: 1354
cctatgtgcc actacccgcc cat                                          23

<210> SEQ ID NO 1355
<211> LENGTH: 26
<212> TYPE: DNA
<213> ORGANISM: Homo sapiens

<400> SEQUENCE: 1355
aaaacccagc actgaaatac tacagc                                       26
```

```
<210> SEQ ID NO 1356
<211> LENGTH: 26
<212> TYPE: DNA
<213> ORGANISM: Homo sapiens

<400> SEQUENCE: 1356
aaaacccagc actgaaatac tacagc                                              26

<210> SEQ ID NO 1357
<211> LENGTH: 26
<212> TYPE: DNA
<213> ORGANISM: Homo sapiens

<400> SEQUENCE: 1357
ggacagccac tactcaacct tttcct                                              26

<210> SEQ ID NO 1358
<211> LENGTH: 26
<212> TYPE: DNA
<213> ORGANISM: Homo sapiens

<400> SEQUENCE: 1358
gcctgatgtc ttcaaaaggg ctgttc                                              26

<210> SEQ ID NO 1359
<211> LENGTH: 26
<212> TYPE: DNA
<213> ORGANISM: Homo sapiens

<400> SEQUENCE: 1359
cctgattccc actccctgaa ggcaat                                              26

<210> SEQ ID NO 1360
<211> LENGTH: 25
<212> TYPE: DNA
<213> ORGANISM: Homo sapiens

<400> SEQUENCE: 1360
gggaagaagc ctgttgtctg gtagg                                               25

<210> SEQ ID NO 1361
<211> LENGTH: 26
<212> TYPE: DNA
<213> ORGANISM: Homo sapiens

<400> SEQUENCE: 1361
cataaccaca ctgctaccaa cacacc                                              26

<210> SEQ ID NO 1362
<211> LENGTH: 23
<212> TYPE: DNA
<213> ORGANISM: Homo sapiens

<400> SEQUENCE: 1362
aagcaagagg caaagggcat ccc                                                 23

<210> SEQ ID NO 1363
<211> LENGTH: 26
<212> TYPE: DNA
<213> ORGANISM: Homo sapiens

<400> SEQUENCE: 1363
```

-continued ccgaccctaa cattcaaggt gtctct                                      26

<210> SEQ ID NO 1364
<211> LENGTH: 26
<212> TYPE: DNA
<213> ORGANISM: Homo sapiens

<400> SEQUENCE: 1364
tgagtgtttt cagggtgttg agtcct                                      26

<210> SEQ ID NO 1365
<211> LENGTH: 26
<212> TYPE: DNA
<213> ORGANISM: Homo sapiens

<400> SEQUENCE: 1365
ctgtaatgcc agcactttgg gaggtc                                      26

<210> SEQ ID NO 1366
<211> LENGTH: 23
<212> TYPE: DNA
<213> ORGANISM: Homo sapiens

<400> SEQUENCE: 1366
catcctgcta ctgggaacta ccc                                         23

<210> SEQ ID NO 1367
<211> LENGTH: 26
<212> TYPE: DNA
<213> ORGANISM: Homo sapiens

<400> SEQUENCE: 1367
tgacacccct gtatcacccc tttcgt                                      26

<210> SEQ ID NO 1368
<211> LENGTH: 19
<212> TYPE: DNA
<213> ORGANISM: Homo sapiens

<400> SEQUENCE: 1368
ctctggctct acacgtccc                                              19

<210> SEQ ID NO 1369
<211> LENGTH: 23
<212> TYPE: DNA
<213> ORGANISM: Homo sapiens

<400> SEQUENCE: 1369
ccaccaaccc caaatcggga gtt                                         23

<210> SEQ ID NO 1370
<211> LENGTH: 26
<212> TYPE: DNA
<213> ORGANISM: Homo sapiens

<400> SEQUENCE: 1370
gagtagagaa gaaggatagg taatct                                      26

<210> SEQ ID NO 1371
<211> LENGTH: 23
<212> TYPE: DNA
<213> ORGANISM: Homo sapiens

<400> SEQUENCE: 1371

```
cggtaggctg aggcagggag aat                                          23

<210> SEQ ID NO 1372
<211> LENGTH: 23
<212> TYPE: DNA
<213> ORGANISM: Homo sapiens

<400> SEQUENCE: 1372
cccagcagcc attcagacag tgg                                          23

<210> SEQ ID NO 1373
<211> LENGTH: 25
<212> TYPE: DNA
<213> ORGANISM: Homo sapiens

<400> SEQUENCE: 1373
tgggtgacaa gagcaagact ccgtc                                        25

<210> SEQ ID NO 1374
<211> LENGTH: 23
<212> TYPE: DNA
<213> ORGANISM: Homo sapiens

<400> SEQUENCE: 1374
cccctaactt cctcttctca ccc                                          23

<210> SEQ ID NO 1375
<211> LENGTH: 23
<212> TYPE: DNA
<213> ORGANISM: Homo sapiens

<400> SEQUENCE: 1375
aagtagtaag ccttcatttc ttt                                          23

<210> SEQ ID NO 1376
<211> LENGTH: 26
<212> TYPE: DNA
<213> ORGANISM: Homo sapiens

<400> SEQUENCE: 1376
cacctaacag tgtgtcctgg aaaacc                                       26

<210> SEQ ID NO 1377
<211> LENGTH: 25
<212> TYPE: DNA
<213> ORGANISM: Homo sapiens

<400> SEQUENCE: 1377
aagtttgccc ctcactggtg ctaat                                        25

<210> SEQ ID NO 1378
<211> LENGTH: 26
<212> TYPE: DNA
<213> ORGANISM: Homo sapiens

<400> SEQUENCE: 1378
aggaatcgca ttgggaacag agactt                                       26

<210> SEQ ID NO 1379
<211> LENGTH: 26
<212> TYPE: DNA
<213> ORGANISM: Homo sapiens
```

```
<400> SEQUENCE: 1379
ctttatccag tcatccattg attgat                                          26

<210> SEQ ID NO 1380
<211> LENGTH: 26
<212> TYPE: DNA
<213> ORGANISM: Homo sapiens

<400> SEQUENCE: 1380
gcctgatgaa tcgggatggt tcctta                                          26

<210> SEQ ID NO 1381
<211> LENGTH: 23
<212> TYPE: DNA
<213> ORGANISM: Homo sapiens

<400> SEQUENCE: 1381
ttacactcct gggcactctt ccc                                             23

<210> SEQ ID NO 1382
<211> LENGTH: 23
<212> TYPE: DNA
<213> ORGANISM: Homo sapiens

<400> SEQUENCE: 1382
gggctcacac ctgttatccc agc                                             23

<210> SEQ ID NO 1383
<211> LENGTH: 26
<212> TYPE: DNA
<213> ORGANISM: Homo sapiens

<400> SEQUENCE: 1383
ggctcacacc tgttatccca gcactt                                          26

<210> SEQ ID NO 1384
<211> LENGTH: 23
<212> TYPE: DNA
<213> ORGANISM: Homo sapiens

<400> SEQUENCE: 1384
cgctccctcc ttttaccctg gaa                                             23

<210> SEQ ID NO 1385
<211> LENGTH: 25
<212> TYPE: DNA
<213> ORGANISM: Homo sapiens

<400> SEQUENCE: 1385
tagggatggc atacctggaa gtagc                                           25

<210> SEQ ID NO 1386
<211> LENGTH: 23
<212> TYPE: DNA
<213> ORGANISM: Homo sapiens

<400> SEQUENCE: 1386
gggatggcat acctggaagt agc                                             23

<210> SEQ ID NO 1387
<211> LENGTH: 26
<212> TYPE: DNA
<213> ORGANISM: Homo sapiens
```

<400> SEQUENCE: 1387
gcttggttcc atttagccac ttacct                                        26

<210> SEQ ID NO 1388
<211> LENGTH: 19
<212> TYPE: DNA
<213> ORGANISM: Homo sapiens

<400> SEQUENCE: 1388
acttcctgct tcccgtcag                                                19

<210> SEQ ID NO 1389
<211> LENGTH: 23
<212> TYPE: DNA
<213> ORGANISM: Homo sapiens

<400> SEQUENCE: 1389
gccgtggcgg tggacagagt tat                                           23

<210> SEQ ID NO 1390
<211> LENGTH: 23
<212> TYPE: DNA
<213> ORGANISM: Homo sapiens

<400> SEQUENCE: 1390
ccattgggtg aaactccaca ggg                                           23

<210> SEQ ID NO 1391
<211> LENGTH: 24
<212> TYPE: DNA
<213> ORGANISM: Homo sapiens

<400> SEQUENCE: 1391
tcaaagcagc agtctaaatt ctcc                                          24

<210> SEQ ID NO 1392
<211> LENGTH: 21
<212> TYPE: DNA
<213> ORGANISM: Homo sapiens

<400> SEQUENCE: 1392
tggatgataa tgcaagctac g                                             21

<210> SEQ ID NO 1393
<211> LENGTH: 20
<212> TYPE: DNA
<213> ORGANISM: Homo sapiens

<400> SEQUENCE: 1393
cccatgttaa gccttgcagt                                               20

<210> SEQ ID NO 1394
<211> LENGTH: 23
<212> TYPE: DNA
<213> ORGANISM: Homo sapiens

<400> SEQUENCE: 1394
tgaccacaag ggcagattct ccc                                           23

<210> SEQ ID NO 1395
<211> LENGTH: 23
<212> TYPE: DNA

<213> ORGANISM: Homo sapiens

<400> SEQUENCE: 1395
cagtgtgtag gacagtgcct ggc                                    23

<210> SEQ ID NO 1396
<211> LENGTH: 23
<212> TYPE: DNA
<213> ORGANISM: Homo sapiens

<400> SEQUENCE: 1396
ggagcccaaa atgtccaggt gac                                    23

<210> SEQ ID NO 1397
<211> LENGTH: 26
<212> TYPE: DNA
<213> ORGANISM: Homo sapiens

<400> SEQUENCE: 1397
taaggagccc aaaatgtcca ggtgac                                 26

<210> SEQ ID NO 1398
<211> LENGTH: 26
<212> TYPE: DNA
<213> ORGANISM: Homo sapiens

<400> SEQUENCE: 1398
cttctctatc ttccacaacc tcacca                                 26

<210> SEQ ID NO 1399
<211> LENGTH: 23
<212> TYPE: DNA
<213> ORGANISM: Homo sapiens

<400> SEQUENCE: 1399
caaagcataa tctggacctt cta                                    23

<210> SEQ ID NO 1400
<211> LENGTH: 23
<212> TYPE: DNA
<213> ORGANISM: Homo sapiens

<400> SEQUENCE: 1400
gtccgaaccc tgggatgtgc cat                                    23

<210> SEQ ID NO 1401
<211> LENGTH: 26
<212> TYPE: DNA
<213> ORGANISM: Homo sapiens

<400> SEQUENCE: 1401
gagcattgtc tgggaatcag gtgttt                                 26

<210> SEQ ID NO 1402
<211> LENGTH: 26
<212> TYPE: DNA
<213> ORGANISM: Homo sapiens

<400> SEQUENCE: 1402
ggcttgacac ccttagttta ctgcct                                 26

<210> SEQ ID NO 1403
<211> LENGTH: 22

<212> TYPE: DNA
<213> ORGANISM: Homo sapiens

<400> SEQUENCE: 1403
ccctagactc tcacctcctc tc 22

<210> SEQ ID NO 1404
<211> LENGTH: 26
<212> TYPE: DNA
<213> ORGANISM: Homo sapiens
<400> SEQUENCE: 1404
ccccttccag ttccaaaagt agttat 26

<210> SEQ ID NO 1405
<211> LENGTH: 23
<212> TYPE: DNA
<213> ORGANISM: Homo sapiens

<400> SEQUENCE: 1405
gccagcaaga gccagagaca caa 23

<210> SEQ ID NO 1406
<211> LENGTH: 23
<212> TYPE: DNA
<213> ORGANISM: Homo sapiens

<400> SEQUENCE: 1406
cagattggac ctcacagccc cat 23

<210> SEQ ID NO 1407
<211> LENGTH: 23
<212> TYPE: DNA
<213> ORGANISM: Homo sapiens

<400> SEQUENCE: 1407
tatgcccaag gtgtatctcc cct 23

<210> SEQ ID NO 1408
<211> LENGTH: 26
<212> TYPE: DNA
<213> ORGANISM: Homo sapiens

<400> SEQUENCE: 1408
ggtcagtctg tccttgtctc taacca 26

<210> SEQ ID NO 1409
<211> LENGTH: 26
<212> TYPE: DNA
<213> ORGANISM: Homo sapiens

<400> SEQUENCE: 1409
aaatgctggg ctcctctttt gtcctc 26

<210> SEQ ID NO 1410
<211> LENGTH: 26
<212> TYPE: DNA
<213> ORGANISM: Homo sapiens

<400> SEQUENCE: 1410
aatgctgggc tcctcttttg tcctct 26

<210> SEQ ID NO 1411
```
<211> LENGTH: 26
<212> TYPE: DNA
<213> ORGANISM: Homo sapiens

<400> SEQUENCE: 1411
tctcgtctta gttgaaatcc acccag                                              26

<210> SEQ ID NO 1412
<211> LENGTH: 26
<212> TYPE: DNA
<213> ORGANISM: Homo sapiens

<400> SEQUENCE: 1412
cacaaacact ggaagggaga aaatag                                              26

<210> SEQ ID NO 1413
<211> LENGTH: 26
<212> TYPE: DNA
<213> ORGANISM: Homo sapiens

<400> SEQUENCE: 1413
ggttattcgg acactcatag gactgg                                              26

<210> SEQ ID NO 1414
<211> LENGTH: 24
<212> TYPE: DNA
<213> ORGANISM: Homo sapiens

<400> SEQUENCE: 1414
atagcagaac cacatccaac tcta                                                24

<210> SEQ ID NO 1415
<211> LENGTH: 26
<212> TYPE: DNA
<213> ORGANISM: Homo sapiens

<400> SEQUENCE: 1415
ccacttcatt tcatccctac tgccac                                              26

<210> SEQ ID NO 1416
<211> LENGTH: 26
<212> TYPE: DNA
<213> ORGANISM: Homo sapiens

<400> SEQUENCE: 1416
ttaggctttg ggttatgggt ggtagc                                              26

<210> SEQ ID NO 1417
<211> LENGTH: 26
<212> TYPE: DNA
<213> ORGANISM: Homo sapiens

<400> SEQUENCE: 1417
gtggtgaaag taggcatcct tgtctt                                              26

<210> SEQ ID NO 1418
<211> LENGTH: 23
<212> TYPE: DNA
<213> ORGANISM: Homo sapiens

<400> SEQUENCE: 1418
gcaccactcc ctcttcccac agt                                                 23
```

```
<210> SEQ ID NO 1419
<211> LENGTH: 26
<212> TYPE: DNA
<213> ORGANISM: Homo sapiens

<400> SEQUENCE: 1419
ggatactacc ttctcccact cattta                                    26

<210> SEQ ID NO 1420
<211> LENGTH: 19
<212> TYPE: DNA
<213> ORGANISM: Homo sapiens

<400> SEQUENCE: 1420
cctagtgggg caagtttgg                                            19

<210> SEQ ID NO 1421
<211> LENGTH: 23
<212> TYPE: DNA
<213> ORGANISM: Homo sapiens

<400> SEQUENCE: 1421
tccaaggtca agccaccct ccc                                        23

<210> SEQ ID NO 1422
<211> LENGTH: 26
<212> TYPE: DNA
<213> ORGANISM: Homo sapiens

<400> SEQUENCE: 1422
tgctattttg tatgtgttgg gtgtat                                    26

<210> SEQ ID NO 1423
<211> LENGTH: 24
<212> TYPE: DNA
<213> ORGANISM: Homo sapiens

<400> SEQUENCE: 1423
ctgttgtttg cctcccttc cagg                                       24

<210> SEQ ID NO 1424
<211> LENGTH: 23
<212> TYPE: DNA
<213> ORGANISM: Homo sapiens

<400> SEQUENCE: 1424
ggtgacaaga gcaagactcc gtc                                       23

<210> SEQ ID NO 1425
<211> LENGTH: 26
<212> TYPE: DNA
<213> ORGANISM: Homo sapiens

<400> SEQUENCE: 1425
gagggagagg caatagatgt agtgta                                    26

<210> SEQ ID NO 1426
<211> LENGTH: 23
<212> TYPE: DNA
<213> ORGANISM: Homo sapiens

<400> SEQUENCE: 1426
cgggcactgt tgggcactga aga                                       23
```

```
<210> SEQ ID NO 1427
<211> LENGTH: 23
<212> TYPE: DNA
<213> ORGANISM: Homo sapiens

<400> SEQUENCE: 1427
gccaagtagc accaaagcca ata                                           23

<210> SEQ ID NO 1428
<211> LENGTH: 26
<212> TYPE: DNA
<213> ORGANISM: Homo sapiens

<400> SEQUENCE: 1428
ccctttgatt ccaccattcc agtcca                                        26

<210> SEQ ID NO 1429
<211> LENGTH: 25
<212> TYPE: DNA
<213> ORGANISM: Homo sapiens

<400> SEQUENCE: 1429
gaactttctt tccccttcat ttagt                                         25

<210> SEQ ID NO 1430
<211> LENGTH: 26
<212> TYPE: DNA
<213> ORGANISM: Homo sapiens

<400> SEQUENCE: 1430
gttagaaggg acattaggat tagaat                                        26

<210> SEQ ID NO 1431
<211> LENGTH: 23
<212> TYPE: DNA
<213> ORGANISM: Homo sapiens

<400> SEQUENCE: 1431
tacagaggag taaagacagt ttt                                           23

<210> SEQ ID NO 1432
<211> LENGTH: 26
<212> TYPE: DNA
<213> ORGANISM: Homo sapiens

<400> SEQUENCE: 1432
gctgagccct gaaagataag gcagaa                                        26

<210> SEQ ID NO 1433
<211> LENGTH: 23
<212> TYPE: DNA
<213> ORGANISM: Homo sapiens

<400> SEQUENCE: 1433
agcaaatcct ccaggcagcc agg                                           23

<210> SEQ ID NO 1434
<211> LENGTH: 23
<212> TYPE: DNA
<213> ORGANISM: Homo sapiens

<400> SEQUENCE: 1434
ggcagatgga cttcaggagg gat                                           23
```

<210> SEQ ID NO 1435
<211> LENGTH: 26
<212> TYPE: DNA
<213> ORGANISM: Homo sapiens

<400> SEQUENCE: 1435
gttaggctac agcaacatac tcaagc                                26

<210> SEQ ID NO 1436
<211> LENGTH: 23
<212> TYPE: DNA
<213> ORGANISM: Homo sapiens

<400> SEQUENCE: 1436
gggtcccctt ttcgggctca gaa                                   23

<210> SEQ ID NO 1437
<211> LENGTH: 26
<212> TYPE: DNA
<213> ORGANISM: Homo sapiens

<400> SEQUENCE: 1437
gcattacgga ttcatttgct cactca                                26

<210> SEQ ID NO 1438
<211> LENGTH: 24
<212> TYPE: DNA
<213> ORGANISM: Homo sapiens

<400> SEQUENCE: 1438
gggactctgc catctgtatg ctgc                                  24

<210> SEQ ID NO 1439
<211> LENGTH: 26
<212> TYPE: DNA
<213> ORGANISM: Homo sapiens

<400> SEQUENCE: 1439
aatctggctg cctatggttg ctctcc                                26

<210> SEQ ID NO 1440
<211> LENGTH: 21
<212> TYPE: DNA
<213> ORGANISM: Homo sapiens

<400> SEQUENCE: 1440
agagcggatg acatattgca g                                     21

<210> SEQ ID NO 1441
<211> LENGTH: 60
<212> TYPE: DNA
<213> ORGANISM: Homo sapiens

<400> SEQUENCE: 1441 ctcattttc caaaaacgtg aagaaatctc gaagtaaaat ttatttcaaa gctattctgg   60

<210> SEQ ID NO 1442
<211> LENGTH: 60
<212> TYPE: DNA
<213> ORGANISM: Homo sapiens

<400> SEQUENCE: 1442

```
tttaaattat attttttact tgctaagatc gagtgacttt tctaaatttt ttgacccata      60
```

<210> SEQ ID NO 1443
<211> LENGTH: 60
<212> TYPE: DNA
<213> ORGANISM: Homo sapiens

<400> SEQUENCE: 1443

```
tgtttttat tgtttgatgt ccaatgtatc gagtcacatg atcaagcgct catttctgtt       60
```

<210> SEQ ID NO 1444
<211> LENGTH: 60
<212> TYPE: DNA
<213> ORGANISM: Homo sapiens

<400> SEQUENCE: 1444

```
agaggctgag gtgaaaagat tgtttgagtc gacaacccaa ttttgttatt tgagtttctt     60
```

<210> SEQ ID NO 1445
<211> LENGTH: 60
<212> TYPE: DNA
<213> ORGANISM: Homo sapiens

<400> SEQUENCE: 1445

```
agaggctgag gtgaaaagat tgtttgagtc gataaacaaa ttatacaaca aaagtctaag     60
```

<210> SEQ ID NO 1446
<211> LENGTH: 60
<212> TYPE: DNA
<213> ORGANISM: Homo sapiens

<400> SEQUENCE: 1446

```
tttagtcaaa taattacaaa gtataaaatc gaaagaatta tactgtatta attaattatc     60
```

<210> SEQ ID NO 1447
<211> LENGTH: 60
<212> TYPE: DNA
<213> ORGANISM: Homo sapiens

<400> SEQUENCE: 1447

```
aaaaaggaaa aataaagtat atttaacatc gaaaaagaac cacatggtta aaaagaaact     60
```

<210> SEQ ID NO 1448
<211> LENGTH: 60
<212> TYPE: DNA
<213> ORGANISM: Homo sapiens

<400> SEQUENCE: 1448

```
tttttttcaat ctttctatat ctttgtcttc gagttcataa aactcagtga ttaacctgtt    60
```

<210> SEQ ID NO 1449
<211> LENGTH: 60
<212> TYPE: DNA
<213> ORGANISM: Homo sapiens

<400> SEQUENCE: 1449

```
gcactacccc ggcctgccgg agcccagtc gatgatggct tcctccccca gagcaccagc      60
```

<210> SEQ ID NO 1450
<211> LENGTH: 60
<212> TYPE: DNA
<213> ORGANISM: Homo sapiens

<400> SEQUENCE: 1450
gcactacccc ggcctgccgg agccccagtc gagttggttt ctgggtccgc accccctccc    60

<210> SEQ ID NO 1451
<211> LENGTH: 60
<212> TYPE: DNA
<213> ORGANISM: Homo sapiens

<400> SEQUENCE: 1451
cagatgggtg gatcacaaga tcaggagttc gaacaagtca ggatgtaatg ataatgaaaa    60

<210> SEQ ID NO 1452
<211> LENGTH: 60
<212> TYPE: DNA
<213> ORGANISM: Homo sapiens

<400> SEQUENCE: 1452
ggatgtatat atatatacta tttttatatc gagcgcttaa ttagtgcatg ttacctatgg    60

<210> SEQ ID NO 1453
<211> LENGTH: 60
<212> TYPE: DNA
<213> ORGANISM: Homo sapiens

<400> SEQUENCE: 1453
agcagcagct agaaataatc ttttcccttc gaccattcta ttttgaaggc aaaagcgact    60

<210> SEQ ID NO 1454
<211> LENGTH: 60
<212> TYPE: DNA
<213> ORGANISM: Homo sapiens

<400> SEQUENCE: 1454
attatgaata ctgtatgtat tataattctc gatcatattt tcttttgcat aggattttta    60

<210> SEQ ID NO 1455
<211> LENGTH: 60
<212> TYPE: DNA
<213> ORGANISM: Homo sapiens

<400> SEQUENCE: 1455
tttttaaaaa tctcaaatga aaaagtcttc gaaaaaaaat ttctggttgg tgggataatg    60

<210> SEQ ID NO 1456
<211> LENGTH: 60
<212> TYPE: DNA
<213> ORGANISM: Homo sapiens

<400> SEQUENCE: 1456
gtcagagact cagcaacgca aggttctctc gatggatgat gtctgggata atgactgagg    60

<210> SEQ ID NO 1457
<211> LENGTH: 60
<212> TYPE: DNA
<213> ORGANISM: Homo sapiens

<400> SEQUENCE: 1457
cgccaaggac agaggtcagt gcaacgagtc gatggatgat gtctgggata atgactgagg    60

<210> SEQ ID NO 1458
<211> LENGTH: 60
<212> TYPE: DNA
<213> ORGANISM: Homo sapiens

```
<400> SEQUENCE: 1458
aaggtgggtg gatcatgatg tcaaaagatc gaaatgtttg agaatatttt taaggctcag    60

<210> SEQ ID NO 1459
<211> LENGTH: 60
<212> TYPE: DNA
<213> ORGANISM: Homo sapiens

<400> SEQUENCE: 1459
tgaagaaaat tcttacttgg ataaattatc gaatttagaa gaattagtgg tattttgaaa    60

<210> SEQ ID NO 1460
<211> LENGTH: 60
<212> TYPE: DNA
<213> ORGANISM: Homo sapiens

<400> SEQUENCE: 1460
taaaatagaa cattattttg aaattacttc gaagaacatt tttatagctg tattagcata    60

<210> SEQ ID NO 1461
<211> LENGTH: 60
<212> TYPE: DNA
<213> ORGANISM: Homo sapiens

<400> SEQUENCE: 1461
gttcagcagc tgctgaaact cggagttgtc gacacccctc tctccctcc ctgttttcc     60

<210> SEQ ID NO 1462
<211> LENGTH: 60
<212> TYPE: DNA
<213> ORGANISM: Homo sapiens

<400> SEQUENCE: 1462
taaattctaa ttaaataaag aaaatacctc gactaaataa aattaaaaaa aaaatctttg    60

<210> SEQ ID NO 1463
<211> LENGTH: 60
<212> TYPE: DNA
<213> ORGANISM: Homo sapiens

<400> SEQUENCE: 1463
aatccaagaa cagctaattc ttaagacctc gagcagactt ggtatataag ttgcttatgg    60

<210> SEQ ID NO 1464
<211> LENGTH: 60
<212> TYPE: DNA
<213> ORGANISM: Homo sapiens

<400> SEQUENCE: 1464
aaggcaggca gatcaggagc tcaagagatc gaacgctaag tgtagtttaa cacctactag    60

<210> SEQ ID NO 1465
<211> LENGTH: 60
<212> TYPE: DNA
<213> ORGANISM: Homo sapiens

<400> SEQUENCE: 1465
aaggcaggca gatcaggagc tcaagagatc gaaagaaaaa aaaaaaagca taaaaatcca    60

<210> SEQ ID NO 1466
<211> LENGTH: 60
<212> TYPE: DNA
<213> ORGANISM: Homo sapiens
```

<400> SEQUENCE: 1466
aaacttggta tgtgtctaat aaacagcttc gagtgctggt ttgggtcgga gtgctggttc      60

<210> SEQ ID NO 1467
<211> LENGTH: 60
<212> TYPE: DNA
<213> ORGANISM: Homo sapiens

<400> SEQUENCE: 1467
tgatcactcc aaacacccaa aggtgacttc gagtgctggt ttgggtcgga gtgctggttc      60

<210> SEQ ID NO 1468
<211> LENGTH: 60
<212> TYPE: DNA
<213> ORGANISM: Homo sapiens

<400> SEQUENCE: 1468
aatataaatt caattcatta aaaaataatc gagtgctggt ttgggtcgga gtgctggttc      60

<210> SEQ ID NO 1469
<211> LENGTH: 60
<212> TYPE: DNA
<213> ORGANISM: Homo sapiens

<400> SEQUENCE: 1469
tgggtgtgga aggctggata atgtctcctc gattttgcca ttatactctc tgtttacatt      60

<210> SEQ ID NO 1470
<211> LENGTH: 60
<212> TYPE: DNA
<213> ORGANISM: Homo sapiens

<400> SEQUENCE: 1470
tgggtgtgga aggctggata atgtctcctc gatcaaccta cattggtttg gtctggaaag      60

<210> SEQ ID NO 1471
<211> LENGTH: 60
<212> TYPE: DNA
<213> ORGANISM: Homo sapiens

<400> SEQUENCE: 1471
gaatatgtgg gagtgggtat aagaaagatc gaggtcacat gaaaaccctc tgtttaatct      60

<210> SEQ ID NO 1472
<211> LENGTH: 60
<212> TYPE: DNA
<213> ORGANISM: Homo sapiens

<400> SEQUENCE: 1472
tatcttaagt aaatttatga taatgttctc gaggactcag tactagtagt ctgaggtcta      60

<210> SEQ ID NO 1473
<211> LENGTH: 60
<212> TYPE: DNA
<213> ORGANISM: Homo sapiens

<400> SEQUENCE: 1473
tcttattaat ctaaaatttt atataaaatc gattccttgg agaaaaggaa attgtcagaa      60

<210> SEQ ID NO 1474
<211> LENGTH: 60
<212> TYPE: DNA

<213> ORGANISM: Homo sapiens

<400> SEQUENCE: 1474
tgttttataa tcattataat tttttctttc gaagcaggtt ttgaacccca gtaagttgcc    60

<210> SEQ ID NO 1475
<211> LENGTH: 60
<212> TYPE: DNA
<213> ORGANISM: Homo sapiens

<400> SEQUENCE: 1475
tttttgcatt atgagctatt tattaacatc gaggttttta gactaatgat ttgatctcca    60

<210> SEQ ID NO 1476
<211> LENGTH: 60
<212> TYPE: DNA
<213> ORGANISM: Homo sapiens

<400> SEQUENCE: 1476
tttttgcatt atgagctatt tattaacatc gagggaactc aatgtctgat tcttgacagg    60

<210> SEQ ID NO 1477
<211> LENGTH: 60
<212> TYPE: DNA
<213> ORGANISM: Homo sapiens

<400> SEQUENCE: 1477
tgctctttac aaactatgta aatgttgctc gaagaggctg atttgagtaa taataaactc    60

<210> SEQ ID NO 1478
<211> LENGTH: 60
<212> TYPE: DNA
<213> ORGANISM: Homo sapiens

<400> SEQUENCE: 1478
tatagttagc aataatttat tatatatttc gagagaatta gggggtatat ctacaagtca    60

<210> SEQ ID NO 1479
<211> LENGTH: 60
<212> TYPE: DNA
<213> ORGANISM: Homo sapiens

<400> SEQUENCE: 1479
taaagtactg tgtcccacat ataagtactc gagaaaagat gcaatagtgt tgtattcagg    60

<210> SEQ ID NO 1480
<211> LENGTH: 60
<212> TYPE: DNA
<213> ORGANISM: Homo sapiens

<400> SEQUENCE: 1480
gcgccctatt tccaccttgt gccttctgtc gagacatcta agaaggtcca gccagatgtt    60

<210> SEQ ID NO 1481
<211> LENGTH: 60
<212> TYPE: DNA
<213> ORGANISM: Homo sapiens

<400> SEQUENCE: 1481
cactcctaaa gatgaacaaa gagagcagtc gaataactat gcagtaagca gttactatgt    60

<210> SEQ ID NO 1482
<211> LENGTH: 60

```
<212> TYPE: DNA
<213> ORGANISM: Homo sapiens

<400> SEQUENCE: 1482
caggaagtag cctttctggt tgtgcagctc gacaacttat tttttaaaat catcaaagaa      60

<210> SEQ ID NO 1483
<211> LENGTH: 60
<212> TYPE: DNA
<213> ORGANISM: Homo sapiens

<400> SEQUENCE: 1483
ttctgggcag acaaaacaat aagtcttctc gatggcactt aaaaaaaaag ttgtccaaat      60

<210> SEQ ID NO 1484
<211> LENGTH: 60
<212> TYPE: DNA
<213> ORGANISM: Homo sapiens

<400> SEQUENCE: 1484
gcaggttaaa gttttccatt agtggtcatc gatcacccag gctagaatgc agtggtgtaa      60

<210> SEQ ID NO 1485
<211> LENGTH: 60
<212> TYPE: DNA
<213> ORGANISM: Homo sapiens

<400> SEQUENCE: 1485
gcaagcgatt cccactcgca gcgcggcctc gatcacccag gctagaatgc agtggtgtaa      60

<210> SEQ ID NO 1486
<211> LENGTH: 60
<212> TYPE: DNA
<213> ORGANISM: Homo sapiens

<400> SEQUENCE: 1486
gcaagcgatt cccactcgca gcgcggcctc gagcgtacac caatggagga ggtatgggcc      60

<210> SEQ ID NO 1487
<211> LENGTH: 60
<212> TYPE: DNA
<213> ORGANISM: Homo sapiens

<400> SEQUENCE: 1487
atatctaaac tggtactgct gagttccctc gatcacccag gctagaatgc agtggtgtaa      60

<210> SEQ ID NO 1488
<211> LENGTH: 60
<212> TYPE: DNA
<213> ORGANISM: Homo sapiens

<400> SEQUENCE: 1488
cccctcccta cctttggtgt cttcatcctc gatcacccag gctagaatgc agtggtgtaa      60

<210> SEQ ID NO 1489
<211> LENGTH: 60
<212> TYPE: DNA
<213> ORGANISM: Homo sapiens

<400> SEQUENCE: 1489
attgtttaag ccagccagcc tatggtattc gacgcaagga aactactaaa gcaatccaga      60

<210> SEQ ID NO 1490
```

```
<211> LENGTH: 60
<212> TYPE: DNA
<213> ORGANISM: Homo sapiens

<400> SEQUENCE: 1490
gtggcaggag aaaaacgcgg ccccaccctc gaaaatacta gaattatgcc gcacagtcag    60

<210> SEQ ID NO 1491
<211> LENGTH: 60
<212> TYPE: DNA
<213> ORGANISM: Homo sapiens

<400> SEQUENCE: 1491
aggcgacact cttgtccccg ccatcttttc gaaggccccc gtcctcctgc gccatggaga    60

<210> SEQ ID NO 1492
<211> LENGTH: 60
<212> TYPE: DNA
<213> ORGANISM: Homo sapiens

<400> SEQUENCE: 1492
catcatcaca gtctacggct gtttcctctc gaaggccccc gtcctcctgc gccatggaga    60

<210> SEQ ID NO 1493
<211> LENGTH: 23
<212> TYPE: DNA
<213> ORGANISM: Homo sapiens

<400> SEQUENCE: 1493
aaggaaaaca atctaaaatg taa                                            23

<210> SEQ ID NO 1494
<211> LENGTH: 23
<212> TYPE: DNA
<213> ORGANISM: Homo sapiens

<400> SEQUENCE: 1494
cctcccctac ctgaaagaac tcc                                            23

<210> SEQ ID NO 1495
<211> LENGTH: 26
<212> TYPE: DNA
<213> ORGANISM: Homo sapiens

<400> SEQUENCE: 1495
cttccctgtt ctgaggtctg gattat                                         26

<210> SEQ ID NO 1496
<211> LENGTH: 26
<212> TYPE: DNA
<213> ORGANISM: Homo sapiens

<400> SEQUENCE: 1496
ggagaatcac ttgagcctaa gagttc                                         26

<210> SEQ ID NO 1497
<211> LENGTH: 23
<212> TYPE: DNA
<213> ORGANISM: Homo sapiens

<400> SEQUENCE: 1497
gaagagataa ctaatgagag gta                                            23
```

```
<210> SEQ ID NO 1498
<211> LENGTH: 26
<212> TYPE: DNA
<213> ORGANISM: Homo sapiens

<400> SEQUENCE: 1498
gccagtcagt caatcattta gtcagc                                          26

<210> SEQ ID NO 1499
<211> LENGTH: 23
<212> TYPE: DNA
<213> ORGANISM: Homo sapiens

<400> SEQUENCE: 1499
actcaagcaa gcctcctgcc tcg                                             23

<210> SEQ ID NO 1500
<211> LENGTH: 23
<212> TYPE: DNA
<213> ORGANISM: Homo sapiens

<400> SEQUENCE: 1500
accaccactg actctttact ctt                                             23

<210> SEQ ID NO 1501
<211> LENGTH: 23
<212> TYPE: DNA
<213> ORGANISM: Homo sapiens

<400> SEQUENCE: 1501
agtttccctc gtaagacagc ggc                                             23

<210> SEQ ID NO 1502
<211> LENGTH: 23
<212> TYPE: DNA
<213> ORGANISM: Homo sapiens

<400> SEQUENCE: 1502
tgtcgctgga tgtcaggcag agc                                             23

<210> SEQ ID NO 1503
<211> LENGTH: 23
<212> TYPE: DNA
<213> ORGANISM: Homo sapiens

<400> SEQUENCE: 1503
ttgggatgcg gctggacaca gtg                                             23

<210> SEQ ID NO 1504
<211> LENGTH: 19
<212> TYPE: DNA
<213> ORGANISM: Homo sapiens

<400> SEQUENCE: 1504
gttccaggtg gcctgttgt                                                  19

<210> SEQ ID NO 1505
<211> LENGTH: 23
<212> TYPE: DNA
<213> ORGANISM: Homo sapiens

<400> SEQUENCE: 1505
gaagagataa ctaatgagag gta                                             23
```

<210> SEQ ID NO 1506
<211> LENGTH: 23
<212> TYPE: DNA
<213> ORGANISM: Homo sapiens

<400> SEQUENCE: 1506
agccactgcc cctggtccta aat                                              23

<210> SEQ ID NO 1507
<211> LENGTH: 23
<212> TYPE: DNA
<213> ORGANISM: Homo sapiens

<400> SEQUENCE: 1507
gttgtattat tatgttgttt tgt                                              23

<210> SEQ ID NO 1508
<211> LENGTH: 23
<212> TYPE: DNA
<213> ORGANISM: Homo sapiens

<400> SEQUENCE: 1508
aagaagagga ggcagcagcc cct                                              23

<210> SEQ ID NO 1509
<211> LENGTH: 23
<212> TYPE: DNA
<213> ORGANISM: Homo sapiens

<400> SEQUENCE: 1509
ccttggtcta cagtggcacc tca                                              23

<210> SEQ ID NO 1510
<211> LENGTH: 25
<212> TYPE: DNA
<213> ORGANISM: Homo sapiens

<400> SEQUENCE: 1510
ctgtaatccc agcactttgg taggc                                            25

<210> SEQ ID NO 1511
<211> LENGTH: 26
<212> TYPE: DNA
<213> ORGANISM: Homo sapiens

<400> SEQUENCE: 1511
gagaataaat agaaatactc aagaga                                           26

<210> SEQ ID NO 1512
<211> LENGTH: 23
<212> TYPE: DNA
<213> ORGANISM: Homo sapiens

<400> SEQUENCE: 1512
ccacctccca ggacaagcaa agg                                              23

<210> SEQ ID NO 1513
<211> LENGTH: 23
<212> TYPE: DNA
<213> ORGANISM: Homo sapiens

<400> SEQUENCE: 1513
gcttttggag ggcttcaatc ccc                                              23

<210> SEQ ID NO 1514
<211> LENGTH: 26
<212> TYPE: DNA
<213> ORGANISM: Homo sapiens

<400> SEQUENCE: 1514
gtctcagagt ctccacacat tgttca                                              26

<210> SEQ ID NO 1515
<211> LENGTH: 26
<212> TYPE: DNA
<213> ORGANISM: Homo sapiens

<400> SEQUENCE: 1515
cagcaaatga aaatcaagtt ctctgc                                              26

<210> SEQ ID NO 1516
<211> LENGTH: 23
<212> TYPE: DNA
<213> ORGANISM: Homo sapiens

<400> SEQUENCE: 1516
gtagtcccag cactttcgga ggc                                                 23

<210> SEQ ID NO 1517
<211> LENGTH: 23
<212> TYPE: DNA
<213> ORGANISM: Homo sapiens

<400> SEQUENCE: 1517
gtagtcccag cactttcgga ggc                                                 23

<210> SEQ ID NO 1518
<211> LENGTH: 23
<212> TYPE: DNA
<213> ORGANISM: Homo sapiens

<400> SEQUENCE: 1518
ttttgttgta gtcacggtta gta                                                 23

<210> SEQ ID NO 1519
<211> LENGTH: 23
<212> TYPE: DNA
<213> ORGANISM: Homo sapiens

<400> SEQUENCE: 1519
ggcactgtca ctccccaaga gga                                                 23

<210> SEQ ID NO 1520
<211> LENGTH: 23
<212> TYPE: DNA
<213> ORGANISM: Homo sapiens

<400> SEQUENCE: 1520
ttttgttgta gtcacggtta gta                                                 23

<210> SEQ ID NO 1521
<211> LENGTH: 23
<212> TYPE: DNA
<213> ORGANISM: Homo sapiens

<400> SEQUENCE: 1521
caggtgctca ggtgtagacc cct                                    23

<210> SEQ ID NO 1522
<211> LENGTH: 23
<212> TYPE: DNA
<213> ORGANISM: Homo sapiens

<400> SEQUENCE: 1522
gtgtagaccc ctggtgttct tgg                                    23

<210> SEQ ID NO 1523
<211> LENGTH: 25
<212> TYPE: DNA
<213> ORGANISM: Homo sapiens

<400> SEQUENCE: 1523
aaagtgctgg gattacaggt gtgag                                  25

<210> SEQ ID NO 1524
<211> LENGTH: 26
<212> TYPE: DNA
<213> ORGANISM: Homo sapiens

<400> SEQUENCE: 1524
actaaatgtc aagcctaact gtgaat                                 26

<210> SEQ ID NO 1525
<211> LENGTH: 26
<212> TYPE: DNA
<213> ORGANISM: Homo sapiens

<400> SEQUENCE: 1525
gaagatgttg atttactcct gtgctg                                 26

<210> SEQ ID NO 1526
<211> LENGTH: 23
<212> TYPE: DNA
<213> ORGANISM: Homo sapiens

<400> SEQUENCE: 1526
atcttttcta agttgtgctt tat                                    23

<210> SEQ ID NO 1527
<211> LENGTH: 26
<212> TYPE: DNA
<213> ORGANISM: Homo sapiens

<400> SEQUENCE: 1527
tatcttttct tcccactgga caggtg                                 26

<210> SEQ ID NO 1528
<211> LENGTH: 26
<212> TYPE: DNA
<213> ORGANISM: Homo sapiens

<400> SEQUENCE: 1528
gggaaggtgg caatggtgtt aggatg                                 26

<210> SEQ ID NO 1529
<211> LENGTH: 26
<212> TYPE: DNA
<213> ORGANISM: Homo sapiens

<400> SEQUENCE: 1529
gttctgggaa gtccattgct actacc                                            26

<210> SEQ ID NO 1530
<211> LENGTH: 20
<212> TYPE: DNA
<213> ORGANISM: Homo sapiens

<400> SEQUENCE: 1530
atggggtgaa agaagttgg                                                    20

<210> SEQ ID NO 1531
<211> LENGTH: 23
<212> TYPE: DNA
<213> ORGANISM: Homo sapiens

<400> SEQUENCE: 1531
cagccaagtc ctgttctcac ggg                                               23

<210> SEQ ID NO 1532
<211> LENGTH: 26
<212> TYPE: DNA
<213> ORGANISM: Homo sapiens

<400> SEQUENCE: 1532
agagggcaca atctgtcagc aaatcc                                            26

<210> SEQ ID NO 1533
<211> LENGTH: 26
<212> TYPE: DNA
<213> ORGANISM: Homo sapiens

<400> SEQUENCE: 1533
ttcctggcac tatttggact tgacac                                            26

<210> SEQ ID NO 1534
<211> LENGTH: 23
<212> TYPE: DNA
<213> ORGANISM: Homo sapiens

<400> SEQUENCE: 1534
ttctcaggca ggttctggtc cct                                               23

<210> SEQ ID NO 1535
<211> LENGTH: 26
<212> TYPE: DNA
<213> ORGANISM: Homo sapiens

<400> SEQUENCE: 1535
cactcattcc tgtgaacact ggagca                                            26

<210> SEQ ID NO 1536
<211> LENGTH: 20
<212> TYPE: DNA
<213> ORGANISM: Homo sapiens

<400> SEQUENCE: 1536
aactgagcac gttaaggggc                                                   20

<210> SEQ ID NO 1537
<211> LENGTH: 23
<212> TYPE: DNA
<213> ORGANISM: Homo sapiens

<400> SEQUENCE: 1537
tctgcgttgc ccctcacctc aag                                    23

<210> SEQ ID NO 1538
<211> LENGTH: 23
<212> TYPE: DNA
<213> ORGANISM: Homo sapiens

<400> SEQUENCE: 1538
ttgaagtctg cgttgcccct cac                                    23

<210> SEQ ID NO 1539
<211> LENGTH: 20
<212> TYPE: DNA
<213> ORGANISM: Homo sapiens

<400> SEQUENCE: 1539
atgtggtgcg tcaaaactgc                                        20

<210> SEQ ID NO 1540
<211> LENGTH: 20
<212> TYPE: DNA
<213> ORGANISM: Homo sapiens

<400> SEQUENCE: 1540
ccagaagtct aagggtccc                                         20

<210> SEQ ID NO 1541
<211> LENGTH: 26
<212> TYPE: DNA
<213> ORGANISM: Homo sapiens

<400> SEQUENCE: 1541
gacttcttgc ctccctaact gtgaga                                 26

<210> SEQ ID NO 1542
<211> LENGTH: 23
<212> TYPE: DNA
<213> ORGANISM: Homo sapiens

<400> SEQUENCE: 1542
accaaagcaa gcctccccaa gtg                                    23

<210> SEQ ID NO 1543
<211> LENGTH: 20
<212> TYPE: DNA
<213> ORGANISM: Homo sapiens

<400> SEQUENCE: 1543
tggagctctc ctcgttgttt                                        20

<210> SEQ ID NO 1544
<211> LENGTH: 20
<212> TYPE: DNA
<213> ORGANISM: Homo sapiens

<400> SEQUENCE: 1544
atgctgttgc aggactgtgc                                        20

<210> SEQ ID NO 1545
<211> LENGTH: 23
<212> TYPE: DNA
<213> ORGANISM: Homo sapiens

```
<400> SEQUENCE: 1545
tgtaagtttg atttgtatgc cat                                             23

<210> SEQ ID NO 1546
<211> LENGTH: 23
<212> TYPE: DNA
<213> ORGANISM: Homo sapiens

<400> SEQUENCE: 1546
ccaccagaag agggcagcaa agc                                             23

<210> SEQ ID NO 1547
<211> LENGTH: 26
<212> TYPE: DNA
<213> ORGANISM: Homo sapiens

<400> SEQUENCE: 1547
ttggcaggaa ctggtgctgg aatagg                                          26

<210> SEQ ID NO 1548
<211> LENGTH: 26
<212> TYPE: DNA
<213> ORGANISM: Homo sapiens

<400> SEQUENCE: 1548
gtattctaag gagcatagtg cccctc                                          26

<210> SEQ ID NO 1549
<211> LENGTH: 23
<212> TYPE: DNA
<213> ORGANISM: Homo sapiens

<400> SEQUENCE: 1549
catttacttg ttatctatcg tat                                             23

<210> SEQ ID NO 1550
<211> LENGTH: 26
<212> TYPE: DNA
<213> ORGANISM: Homo sapiens

<400> SEQUENCE: 1550
gtaggaactc actgacaatg aagaca                                          26

<210> SEQ ID NO 1551
<211> LENGTH: 23
<212> TYPE: DNA
<213> ORGANISM: Homo sapiens

<400> SEQUENCE: 1551
gagccaccac acccagcatc ttt                                             23

<210> SEQ ID NO 1552
<211> LENGTH: 23
<212> TYPE: DNA
<213> ORGANISM: Homo sapiens

<400> SEQUENCE: 1552
tatcttattg tagaggcagt ctg                                             23

<210> SEQ ID NO 1553
<211> LENGTH: 23
<212> TYPE: DNA
```

```
<213> ORGANISM: Homo sapiens

<400> SEQUENCE: 1553
ctgcccattg aggatgtggc tgg                                              23

<210> SEQ ID NO 1554
<211> LENGTH: 23
<212> TYPE: DNA
<213> ORGANISM: Homo sapiens

<400> SEQUENCE: 1554
tctgctgtaa gggactgcct cct                                              23

<210> SEQ ID NO 1555
<211> LENGTH: 23
<212> TYPE: DNA
<213> ORGANISM: Homo sapiens

<400> SEQUENCE: 1555
gccacagcgt ctctctccga ata                                              23

<210> SEQ ID NO 1556
<211> LENGTH: 21
<212> TYPE: DNA
<213> ORGANISM: Homo sapiens

<400> SEQUENCE: 1556
agctggtaac gctcaaaaca c                                                21

<210> SEQ ID NO 1557
<211> LENGTH: 23
<212> TYPE: DNA
<213> ORGANISM: Homo sapiens

<400> SEQUENCE: 1557
catttacttg ttatctatcg tat                                              23

<210> SEQ ID NO 1558
<211> LENGTH: 23
<212> TYPE: DNA
<213> ORGANISM: Homo sapiens

<400> SEQUENCE: 1558
agttggcttg tttcactaaa ata                                              23

<210> SEQ ID NO 1559
<211> LENGTH: 23
<212> TYPE: DNA
<213> ORGANISM: Homo sapiens

<400> SEQUENCE: 1559
gtagaaaatc aaaatcacca tta                                              23

<210> SEQ ID NO 1560
<211> LENGTH: 23
<212> TYPE: DNA
<213> ORGANISM: Homo sapiens

<400> SEQUENCE: 1560
aatcgcaacc acttcctctg ccc                                              23

<210> SEQ ID NO 1561
<211> LENGTH: 23
```

```
<212> TYPE: DNA
<213> ORGANISM: Homo sapiens

<400> SEQUENCE: 1561
atcgcaacca cttcctctgc ccc                                    23

<210> SEQ ID NO 1562
<211> LENGTH: 25
<212> TYPE: DNA
<213> ORGANISM: Homo sapiens

<400> SEQUENCE: 1562
atagaacatt acacctgaga actgc                                  25

<210> SEQ ID NO 1563
<211> LENGTH: 26
<212> TYPE: DNA
<213> ORGANISM: Homo sapiens

<400> SEQUENCE: 1563
atagtcttct cactctggat gtttca                                 26

<210> SEQ ID NO 1564
<211> LENGTH: 23
<212> TYPE: DNA
<213> ORGANISM: Homo sapiens

<400> SEQUENCE: 1564
tcttgattcc catctgcccg tgc                                    23

<210> SEQ ID NO 1565
<211> LENGTH: 23
<212> TYPE: DNA
<213> ORGANISM: Homo sapiens

<400> SEQUENCE: 1565
gaagggctcc aggctaagtg gga                                    23

<210> SEQ ID NO 1566
<211> LENGTH: 26
<212> TYPE: DNA
<213> ORGANISM: Homo sapiens

<400> SEQUENCE: 1566
cttcccttgc ttggtctaac ctgtaa                                 26

<210> SEQ ID NO 1567
<211> LENGTH: 24
<212> TYPE: DNA
<213> ORGANISM: Homo sapiens

<400> SEQUENCE: 1567
tgtttcacca agccctgcca aagc                                   24

<210> SEQ ID NO 1568
<211> LENGTH: 23
<212> TYPE: DNA
<213> ORGANISM: Homo sapiens

<400> SEQUENCE: 1568
cttggtctgg gactggctgt cta                                    23

<210> SEQ ID NO 1569
```

```
<211> LENGTH: 23
<212> TYPE: DNA
<213> ORGANISM: Homo sapiens

<400> SEQUENCE: 1569
gcgggaaagt ccatagttgg gag                                          23

<210> SEQ ID NO 1570
<211> LENGTH: 23
<212> TYPE: DNA
<213> ORGANISM: Homo sapiens

<400> SEQUENCE: 1570
gaaccagcac tccaacccga acc                                          23

<210> SEQ ID NO 1571
<211> LENGTH: 23
<212> TYPE: DNA
<213> ORGANISM: Homo sapiens

<400> SEQUENCE: 1571
gaaccagcac tccaacccga acc                                          23

<210> SEQ ID NO 1572
<211> LENGTH: 23
<212> TYPE: DNA
<213> ORGANISM: Homo sapiens

<400> SEQUENCE: 1572
gaaccagcac tccaacccga acc                                          23

<210> SEQ ID NO 1573
<211> LENGTH: 23
<212> TYPE: DNA
<213> ORGANISM: Homo sapiens

<400> SEQUENCE: 1573
ccacctccct acccttacta acc                                          23

<210> SEQ ID NO 1574
<211> LENGTH: 23
<212> TYPE: DNA
<213> ORGANISM: Homo sapiens

<400> SEQUENCE: 1574
cccctgcttc aagttgtccc agc                                          23

<210> SEQ ID NO 1575
<211> LENGTH: 26
<212> TYPE: DNA
<213> ORGANISM: Homo sapiens

<400> SEQUENCE: 1575
gctaaaccaa atactaaata ctgcca                                       26

<210> SEQ ID NO 1576
<211> LENGTH: 26
<212> TYPE: DNA
<213> ORGANISM: Homo sapiens

<400> SEQUENCE: 1576
ccaatgccta ctcctttgta acatcc                                       26
```

```
<210> SEQ ID NO 1577
<211> LENGTH: 23
<212> TYPE: DNA
<213> ORGANISM: Homo sapiens

<400> SEQUENCE: 1577
tagataacaa agagaaggct ggg                                              23

<210> SEQ ID NO 1578
<211> LENGTH: 23
<212> TYPE: DNA
<213> ORGANISM: Homo sapiens

<400> SEQUENCE: 1578
actgattttc taagttgtct ttt                                              23

<210> SEQ ID NO 1579
<211> LENGTH: 26
<212> TYPE: DNA
<213> ORGANISM: Homo sapiens

<400> SEQUENCE: 1579
tacaatggta tggcttagaa gatgcc                                           26

<210> SEQ ID NO 1580
<211> LENGTH: 26
<212> TYPE: DNA
<213> ORGANISM: Homo sapiens

<400> SEQUENCE: 1580
atgccatacg gtccttgttt cttgac                                           26

<210> SEQ ID NO 1581
<211> LENGTH: 26
<212> TYPE: DNA
<213> ORGANISM: Homo sapiens

<400> SEQUENCE: 1581
gccagccaag tggtagaata ggagtt                                           26

<210> SEQ ID NO 1582
<211> LENGTH: 20
<212> TYPE: DNA
<213> ORGANISM: Homo sapiens

<400> SEQUENCE: 1582
atgtagcttc gggaaacagc                                                  20

<210> SEQ ID NO 1583
<211> LENGTH: 23
<212> TYPE: DNA
<213> ORGANISM: Homo sapiens

<400> SEQUENCE: 1583
gcagggcaag gtcagaaaga gac                                              23

<210> SEQ ID NO 1584
<211> LENGTH: 26
<212> TYPE: DNA
<213> ORGANISM: Homo sapiens

<400> SEQUENCE: 1584
acccaccact gcttttcacc actaag                                           26
```

<210> SEQ ID NO 1585
<211> LENGTH: 26
<212> TYPE: DNA
<213> ORGANISM: Homo sapiens

<400> SEQUENCE: 1585
gggaaggagc cacatctatc tattgc                                    26

<210> SEQ ID NO 1586
<211> LENGTH: 23
<212> TYPE: DNA
<213> ORGANISM: Homo sapiens

<400> SEQUENCE: 1586
ttgggaaggt ggaggaggag gga                                       23

<210> SEQ ID NO 1587
<211> LENGTH: 26
<212> TYPE: DNA
<213> ORGANISM: Homo sapiens

<400> SEQUENCE: 1587
gctaagcccc tacaagtttg agaagg                                    26

<210> SEQ ID NO 1588
<211> LENGTH: 20
<212> TYPE: DNA
<213> ORGANISM: Homo sapiens

<400> SEQUENCE: 1588
aagagtcatg tagggccagg                                           20

<210> SEQ ID NO 1589
<211> LENGTH: 23
<212> TYPE: DNA
<213> ORGANISM: Homo sapiens

<400> SEQUENCE: 1589
gctgaggcgg gaaaacagga gaa                                       23

<210> SEQ ID NO 1590
<211> LENGTH: 23
<212> TYPE: DNA
<213> ORGANISM: Homo sapiens

<400> SEQUENCE: 1590
agacaccctc cgacaggacc tca                                       23

<210> SEQ ID NO 1591
<211> LENGTH: 20
<212> TYPE: DNA
<213> ORGANISM: Homo sapiens

<400> SEQUENCE: 1591
actttatggg aggctgaggg                                           20

<210> SEQ ID NO 1592
<211> LENGTH: 20
<212> TYPE: DNA
<213> ORGANISM: Homo sapiens

<400> SEQUENCE: 1592
aagagtcatg tagggccagg                                           20

<210> SEQ ID NO 1593
<211> LENGTH: 26
<212> TYPE: DNA
<213> ORGANISM: Homo sapiens

<400> SEQUENCE: 1593
tgcttatctc ttccttcatt ttctgg                                  26

<210> SEQ ID NO 1594
<211> LENGTH: 24
<212> TYPE: DNA
<213> ORGANISM: Homo sapiens

<400> SEQUENCE: 1594
ctcttcactc tctgctgccc ctgt                                    24

<210> SEQ ID NO 1595
<211> LENGTH: 20
<212> TYPE: DNA
<213> ORGANISM: Homo sapiens

<400> SEQUENCE: 1595
gacgaagcct ctttggtttc                                         20

<210> SEQ ID NO 1596
<211> LENGTH: 20
<212> TYPE: DNA
<213> ORGANISM: Homo sapiens

<400> SEQUENCE: 1596
ctcccaggct tgacgagagg                                         20

<210> SEQ ID NO 1597
<211> LENGTH: 60
<212> TYPE: DNA
<213> ORGANISM: Homo sapiens

<400> SEQUENCE: 1597
ccactgcact ccaccccggg gaacaagatc gaaggccccc gtcctcctgc gccatggaga     60

<210> SEQ ID NO 1598
<211> LENGTH: 60
<212> TYPE: DNA
<213> ORGANISM: Homo sapiens

<400> SEQUENCE: 1598
catcatcaca gtctacggct gtttcctctc gatcttgttc cccggggtgg agtgcagtgg     60

<210> SEQ ID NO 1599
<211> LENGTH: 60
<212> TYPE: DNA
<213> ORGANISM: Homo sapiens

<400> SEQUENCE: 1599
cattagactc tatctttatt actgtaagtc gaatataact ccttgattta gtaaaaccat     60

<210> SEQ ID NO 1600
<211> LENGTH: 60
<212> TYPE: DNA
<213> ORGANISM: Homo sapiens

<400> SEQUENCE: 1600
cattagactc tatctttatt actgtaagtc gagtgatata actgcatagt ctcctactga        60

<210> SEQ ID NO 1601
<211> LENGTH: 60
<212> TYPE: DNA
<213> ORGANISM: Homo sapiens

<400> SEQUENCE: 1601
cattagactc tatctttatt actgtaagtc gaaggtggta attgtagtct cgggtgcaat        60

<210> SEQ ID NO 1602
<211> LENGTH: 60
<212> TYPE: DNA
<213> ORGANISM: Homo sapiens

<400> SEQUENCE: 1602
agaaggggat tttacatttt atttcttttc gatgtaagta tttgttaaat aaaaatatag        60

<210> SEQ ID NO 1603
<211> LENGTH: 60
<212> TYPE: DNA
<213> ORGANISM: Homo sapiens

<400> SEQUENCE: 1603
ttttactgtt tttgtaagag atatgttttc gattaatgtt aaaaataaaa ggtagtattt        60

<210> SEQ ID NO 1604
<211> LENGTH: 60
<212> TYPE: DNA
<213> ORGANISM: Homo sapiens

<400> SEQUENCE: 1604
agataatgac ttctgggaga gagaagagtc gaactgatac atagaaacaa tcacattcag        60

<210> SEQ ID NO 1605
<211> LENGTH: 60
<212> TYPE: DNA
<213> ORGANISM: Homo sapiens

<400> SEQUENCE: 1605
gtactttaca atgattactt tatttaattc gaaagtccat ctgcacagtg gaactgttcc        60

<210> SEQ ID NO 1606
<211> LENGTH: 60
<212> TYPE: DNA
<213> ORGANISM: Homo sapiens

<400> SEQUENCE: 1606
gcagccataa tcctcctagg gacacaactc gaaatactcc tttcctttca gatgctcatt        60

<210> SEQ ID NO 1607
<211> LENGTH: 60
<212> TYPE: DNA
<213> ORGANISM: Homo sapiens

<400> SEQUENCE: 1607
tttatttata tttaccttta tttctatctc gatcaagtag cagctctgta actccctgga        60

<210> SEQ ID NO 1608
<211> LENGTH: 60
<212> TYPE: DNA
<213> ORGANISM: Homo sapiens

<400> SEQUENCE: 1608
gaggttactg ttttcctaac cattgtattc gatattttca ccatgtagcc caggctggtc    60

<210> SEQ ID NO 1609
<211> LENGTH: 60
<212> TYPE: DNA
<213> ORGANISM: Homo sapiens

<400> SEQUENCE: 1609
agagcagggt gggtagttct gcacgtgatc gattttgtgg tcagattgct taaaaggtaa    60

<210> SEQ ID NO 1610
<211> LENGTH: 60
<212> TYPE: DNA
<213> ORGANISM: Homo sapiens

<400> SEQUENCE: 1610
agagcagggt gggtagttct gcacgtgatc gagacaaata aggacttggg ttaaaaaaac    60

<210> SEQ ID NO 1611
<211> LENGTH: 60
<212> TYPE: DNA
<213> ORGANISM: Homo sapiens

<400> SEQUENCE: 1611
agagcagggt gggtagttct gcacgtgatc gaatgatctt cctgattttc ccaagtagct    60

<210> SEQ ID NO 1612
<211> LENGTH: 60
<212> TYPE: DNA
<213> ORGANISM: Homo sapiens

<400> SEQUENCE: 1612
atcattttta aacctaggct gaattttatc gaattccggg ccctctctgt ctctaaggaa    60

<210> SEQ ID NO 1613
<211> LENGTH: 60
<212> TYPE: DNA
<213> ORGANISM: Homo sapiens

<400> SEQUENCE: 1613
ttccttagag acagagaggg cccggaattc gatcttcctt accacccacc ccctcccact    60

<210> SEQ ID NO 1614
<211> LENGTH: 60
<212> TYPE: DNA
<213> ORGANISM: Homo sapiens

<400> SEQUENCE: 1614
gcttgtcaac taacgcttca ctcatgcctc gattttgagg gcttctcaca actctagatt    60

<210> SEQ ID NO 1615
<211> LENGTH: 60
<212> TYPE: DNA
<213> ORGANISM: Homo sapiens

<400> SEQUENCE: 1615
gcttgtcaac taacgcttca ctcatgcctc gaagttctgt ctgctctatc tcacgcactc    60

<210> SEQ ID NO 1616
<211> LENGTH: 60
<212> TYPE: DNA
<213> ORGANISM: Homo sapiens -continued

<400> SEQUENCE: 1616
gttggtgaaa agaaagaag aaatggactc gaccgctacc accccagcat ttccagcagg    60

<210> SEQ ID NO 1617
<211> LENGTH: 60
<212> TYPE: DNA
<213> ORGANISM: Homo sapiens

<400> SEQUENCE: 1617
gttggtgaaa agaaagaag aaatggactc gactggagtt ttatatttc aagagtacct    60

<210> SEQ ID NO 1618
<211> LENGTH: 60
<212> TYPE: DNA
<213> ORGANISM: Homo sapiens

<400> SEQUENCE: 1618
gagaatcaat tccattttta aagcttagtc gattttgagg gcttctcaca actctagatt    60

<210> SEQ ID NO 1619
<211> LENGTH: 60
<212> TYPE: DNA
<213> ORGANISM: Homo sapiens

<400> SEQUENCE: 1619
aggtactctt gaaaatataa aactccagtc gattttgagg gcttctcaca actctagatt    60

<210> SEQ ID NO 1620
<211> LENGTH: 60
<212> TYPE: DNA
<213> ORGANISM: Homo sapiens

<400> SEQUENCE: 1620
ataaagcaac ttgttttttcc ttgtattgtc gatatcagaa ttgtgctctg ggggcggctt    60

<210> SEQ ID NO 1621
<211> LENGTH: 60
<212> TYPE: DNA
<213> ORGANISM: Homo sapiens

<400> SEQUENCE: 1621
tatcaagaaa ttacaaaccg gttcctaatc gatatcagaa ttgtgctctg ggggcggctt    60

<210> SEQ ID NO 1622
<211> LENGTH: 60
<212> TYPE: DNA
<213> ORGANISM: Homo sapiens

<400> SEQUENCE: 1622
ttcaacatgt attcagtaca aaaattatc gatattattg ctttaattta aacaaattta    60

<210> SEQ ID NO 1623
<211> LENGTH: 60
<212> TYPE: DNA
<213> ORGANISM: Homo sapiens

<400> SEQUENCE: 1623
gagctgcctc gctcggatac taagtccttc gatttctctc tctccccctc agcatcttcc    60

<210> SEQ ID NO 1624
<211> LENGTH: 60
<212> TYPE: DNA
<213> ORGANISM: Homo sapiens -continued

<400> SEQUENCE: 1624
gtgggcacta ggaatgaggt ccectgcctc gacccactcc cgggggggatc gggacaccgc    60

<210> SEQ ID NO 1625
<211> LENGTH: 60
<212> TYPE: DNA
<213> ORGANISM: Homo sapiens

<400> SEQUENCE: 1625
gggcaccgcc gccctgactt ccaacacatc gaagaatggg tggggccttg cacctcatac    60

<210> SEQ ID NO 1626
<211> LENGTH: 60
<212> TYPE: DNA
<213> ORGANISM: Homo sapiens

<400> SEQUENCE: 1626
ccgcgcccgc agggcccgcc ccgcgccgtc gaggctttca agggatccag ggtggggtgc    60

<210> SEQ ID NO 1627
<211> LENGTH: 60
<212> TYPE: DNA
<213> ORGANISM: Homo sapiens

<400> SEQUENCE: 1627
ccgcgcccgc agggcccgcc ccgcgccgtc gatgtgttgg aagtcagggc ggcggtgccc    60

<210> SEQ ID NO 1628
<211> LENGTH: 60
<212> TYPE: DNA
<213> ORGANISM: Homo sapiens

<400> SEQUENCE: 1628
ccgcgcccgc agggcccgcc ccgcgccgtc gacaatgtta ttctttgttt ctcttaccaa    60

<210> SEQ ID NO 1629
<211> LENGTH: 60
<212> TYPE: DNA
<213> ORGANISM: Homo sapiens

<400> SEQUENCE: 1629
ccgcgcccgc agggcccgcc ccgcgccgtc gagaagcata aagcagggac aggtatggag    60

<210> SEQ ID NO 1630
<211> LENGTH: 60
<212> TYPE: DNA
<213> ORGANISM: Homo sapiens

<400> SEQUENCE: 1630
ttcactgttg cctttttgttg tcattatatc gaagaaatgc ttaagtatgt ctaagtttca    60

<210> SEQ ID NO 1631
<211> LENGTH: 60
<212> TYPE: DNA
<213> ORGANISM: Homo sapiens

<400> SEQUENCE: 1631
tgaaacttag acatacttaa gcatttcttc gatttgtctg tctgccaaga ccatttctga    60

<210> SEQ ID NO 1632
<211> LENGTH: 60
<212> TYPE: DNA

```
<213> ORGANISM: Homo sapiens

<400> SEQUENCE: 1632
ttcactgttg cctttgttg tcattatatc gagtaatact gacactcctg gcccacagaa      60

<210> SEQ ID NO 1633
<211> LENGTH: 60
<212> TYPE: DNA
<213> ORGANISM: Homo sapiens

<400> SEQUENCE: 1633
tgaaacttag acatacttaa gcatttcttc gaaagctaat gaggtatgag gggagaatac      60

<210> SEQ ID NO 1634
<211> LENGTH: 60
<212> TYPE: DNA
<213> ORGANISM: Homo sapiens

<400> SEQUENCE: 1634
agtggcccaa tctcggctca ccacagcctc gatattatac agtcttagaa cagaaagaaa      60

<210> SEQ ID NO 1635
<211> LENGTH: 60
<212> TYPE: DNA
<213> ORGANISM: Homo sapiens

<400> SEQUENCE: 1635
gcttctcccc tctttatccc acctggcctc gactcaccct gcagacaagc tttcgggtat      60

<210> SEQ ID NO 1636
<211> LENGTH: 60
<212> TYPE: DNA
<213> ORGANISM: Homo sapiens

<400> SEQUENCE: 1636
gccagcttcc agagagtggg aacatgtgtc gagagtcaat tcacagcaaa cagtgagaag      60

<210> SEQ ID NO 1637
<211> LENGTH: 60
<212> TYPE: DNA
<213> ORGANISM: Homo sapiens

<400> SEQUENCE: 1637
gccagcttcc agagagtggg aacatgtgtc gaaggtgtgc atatatgttg aatgacattt      60

<210> SEQ ID NO 1638
<211> LENGTH: 60
<212> TYPE: DNA
<213> ORGANISM: Homo sapiens

<400> SEQUENCE: 1638
ataaaatggg gaggccttcc agaagctctc gacctccagg tcccccgcca cttccacggc      60

<210> SEQ ID NO 1639
<211> LENGTH: 60
<212> TYPE: DNA
<213> ORGANISM: Homo sapiens

<400> SEQUENCE: 1639
agtgctgggt tccacacctc tcagctcttc gacctccagg tcccccgcca cttccacggc      60

<210> SEQ ID NO 1640
<211> LENGTH: 60
```

```
<212> TYPE: DNA
<213> ORGANISM: Homo sapiens

<400> SEQUENCE: 1640
ataaaatggg gaggccttcc agaagctctc gaccgccacc tcctccagga agccctgcct    60

<210> SEQ ID NO 1641
<211> LENGTH: 60
<212> TYPE: DNA
<213> ORGANISM: Homo sapiens

<400> SEQUENCE: 1641
tatgagtaat aattacaatt tccccctttc gacctccagg tcccccgcca cttccacggc    60

<210> SEQ ID NO 1642
<211> LENGTH: 60
<212> TYPE: DNA
<213> ORGANISM: Homo sapiens

<400> SEQUENCE: 1642
taaaaaacac acctctgggt ggagattttc gagtgatcca cccgtcttgg cctcccaaag    60

<210> SEQ ID NO 1643
<211> LENGTH: 60
<212> TYPE: DNA
<213> ORGANISM: Homo sapiens

<400> SEQUENCE: 1643
tttgtaagat aaagattta aatggatatc gataccaatg tataagagct ctgagaagtt     60

<210> SEQ ID NO 1644
<211> LENGTH: 60
<212> TYPE: DNA
<213> ORGANISM: Homo sapiens

<400> SEQUENCE: 1644
ggtaaaactg ccggtacctt agtgcaaatc gaccaaaacc tttttctta gaaaggtgt      60

<210> SEQ ID NO 1645
<211> LENGTH: 60
<212> TYPE: DNA
<213> ORGANISM: Homo sapiens

<400> SEQUENCE: 1645
gagaatgaag tgtacaagca ggtgatcttc gagagtgtgt gggattagga aagagaaagc    60

<210> SEQ ID NO 1646
<211> LENGTH: 60
<212> TYPE: DNA
<213> ORGANISM: Homo sapiens

<400> SEQUENCE: 1646
gtttgctccg gggccgccgg gcccgccctc gattttaaca ccaccatggt ttgaatgaat    60

<210> SEQ ID NO 1647
<211> LENGTH: 60
<212> TYPE: DNA
<213> ORGANISM: Homo sapiens

<400> SEQUENCE: 1647
tatatttaaa aatacatact ggtatacatc gaatatgcca attagatcaa gttggttaat    60

<210> SEQ ID NO 1648
```

```
<211> LENGTH: 60
<212> TYPE: DNA
<213> ORGANISM: Homo sapiens

<400> SEQUENCE: 1648
gtcctcacta gattagctag atacagtgtc gacttggatg cccatggaat tatcttcact     60

<210> SEQ ID NO 1649
<211> LENGTH: 22
<212> TYPE: DNA
<213> ORGANISM: Homo sapiens

<400> SEQUENCE: 1649
tgaggccgtg aaaggtaaaa gc                                               22

<210> SEQ ID NO 1650
<211> LENGTH: 20
<212> TYPE: DNA
<213> ORGANISM: Homo sapiens

<400> SEQUENCE: 1650
tcctcatccc caatctcccc                                                  20

<210> SEQ ID NO 1651
<211> LENGTH: 26
<212> TYPE: DNA
<213> ORGANISM: Homo sapiens

<400> SEQUENCE: 1651
catcctcggg catttcttct tgtcct                                           26

<210> SEQ ID NO 1652
<211> LENGTH: 26
<212> TYPE: DNA
<213> ORGANISM: Homo sapiens

<400> SEQUENCE: 1652
catcctcggg catttcttct tgtcct                                           26

<210> SEQ ID NO 1653
<211> LENGTH: 25
<212> TYPE: DNA
<213> ORGANISM: Homo sapiens

<400> SEQUENCE: 1653
catcctcggg catttcttct tgtcc                                            25

<210> SEQ ID NO 1654
<211> LENGTH: 23
<212> TYPE: DNA
<213> ORGANISM: Homo sapiens

<400> SEQUENCE: 1654
cagcctgggt gacagagtga gac                                              23

<210> SEQ ID NO 1655
<211> LENGTH: 23
<212> TYPE: DNA
<213> ORGANISM: Homo sapiens

<400> SEQUENCE: 1655
cccctgagaa gcgatgggct act                                              23
```

```
<210> SEQ ID NO 1656
<211> LENGTH: 26
<212> TYPE: DNA
<213> ORGANISM: Homo sapiens

<400> SEQUENCE: 1656
gaccagcagg aggctacagt tgttga                                      26

<210> SEQ ID NO 1657
<211> LENGTH: 23
<212> TYPE: DNA
<213> ORGANISM: Homo sapiens

<400> SEQUENCE: 1657
gcagtctttg ggcagcacta cgc                                         23

<210> SEQ ID NO 1658
<211> LENGTH: 26
<212> TYPE: DNA
<213> ORGANISM: Homo sapiens

<400> SEQUENCE: 1658
ccctgcttgt ccactgtctg aaaaca                                      26

<210> SEQ ID NO 1659
<211> LENGTH: 23
<212> TYPE: DNA
<213> ORGANISM: Homo sapiens

<400> SEQUENCE: 1659
gaaatcttgg tccctaatgg cat                                         23

<210> SEQ ID NO 1660
<211> LENGTH: 26
<212> TYPE: DNA
<213> ORGANISM: Homo sapiens

<400> SEQUENCE: 1660
ctgaaacact caccagccaa tgacaa                                      26

<210> SEQ ID NO 1661
<211> LENGTH: 25
<212> TYPE: DNA
<213> ORGANISM: Homo sapiens

<400> SEQUENCE: 1661
gaagatggct ctcaagacta taatg                                       25

<210> SEQ ID NO 1662
<211> LENGTH: 23
<212> TYPE: DNA
<213> ORGANISM: Homo sapiens

<400> SEQUENCE: 1662
ggctcgctcc agcacattct cca                                         23

<210> SEQ ID NO 1663
<211> LENGTH: 23
<212> TYPE: DNA
<213> ORGANISM: Homo sapiens

<400> SEQUENCE: 1663
ggctcgctcc agcacattct cca                                         23
```

<210> SEQ ID NO 1664
<211> LENGTH: 26
<212> TYPE: DNA
<213> ORGANISM: Homo sapiens

<400> SEQUENCE: 1664
gcacacctgc cagaactcat tcaaga                                    26

<210> SEQ ID NO 1665
<211> LENGTH: 23
<212> TYPE: DNA
<213> ORGANISM: Homo sapiens

<400> SEQUENCE: 1665
gtttgcctga cacagttccc tgc                                       23

<210> SEQ ID NO 1666
<211> LENGTH: 24
<212> TYPE: DNA
<213> ORGANISM: Homo sapiens

<400> SEQUENCE: 1666
atcactggac aaggtaacaa gggc                                      24

<210> SEQ ID NO 1667
<211> LENGTH: 19
<212> TYPE: DNA
<213> ORGANISM: Homo sapiens

<400> SEQUENCE: 1667
gagcaacccg cttgtcaac                                            19

<210> SEQ ID NO 1668
<211> LENGTH: 26
<212> TYPE: DNA
<213> ORGANISM: Homo sapiens

<400> SEQUENCE: 1668
tgtgtttatt ccctacagag caggtt                                    26

<210> SEQ ID NO 1669
<211> LENGTH: 26
<212> TYPE: DNA
<213> ORGANISM: Homo sapiens

<400> SEQUENCE: 1669
tgtgtttatt ccctacagag caggtt                                    26

<210> SEQ ID NO 1670
<211> LENGTH: 26
<212> TYPE: DNA
<213> ORGANISM: Homo sapiens

<400> SEQUENCE: 1670
aatcctactg gcaccactgt gttggc                                    26

<210> SEQ ID NO 1671
<211> LENGTH: 23
<212> TYPE: DNA
<213> ORGANISM: Homo sapiens

<400> SEQUENCE: 1671
cccgaaccag ccttcccaag agc                                       23

-continued

<210> SEQ ID NO 1672
<211> LENGTH: 23
<212> TYPE: DNA
<213> ORGANISM: Homo sapiens

<400> SEQUENCE: 1672
ccacaaccca cacctgccac tgt                                              23

<210> SEQ ID NO 1673
<211> LENGTH: 26
<212> TYPE: DNA
<213> ORGANISM: Homo sapiens

<400> SEQUENCE: 1673
gcctaactga tgtggctgtc tttgtg                                           26

<210> SEQ ID NO 1674
<211> LENGTH: 23
<212> TYPE: DNA
<213> ORGANISM: Homo sapiens

<400> SEQUENCE: 1674
tgtgtcatca ggattctttt ctg                                              23

<210> SEQ ID NO 1675
<211> LENGTH: 23
<212> TYPE: DNA
<213> ORGANISM: Homo sapiens

<400> SEQUENCE: 1675
atcctgtgtc tccctcccct tca                                              23

<210> SEQ ID NO 1676
<211> LENGTH: 20
<212> TYPE: DNA
<213> ORGANISM: Homo sapiens

<400> SEQUENCE: 1676
cagagggttg cctatggtgg                                                  20

<210> SEQ ID NO 1677
<211> LENGTH: 23
<212> TYPE: DNA
<213> ORGANISM: Homo sapiens

<400> SEQUENCE: 1677
aataacctgt gcccagaccg agc                                              23

<210> SEQ ID NO 1678
<211> LENGTH: 23
<212> TYPE: DNA
<213> ORGANISM: Homo sapiens

<400> SEQUENCE: 1678
agcctcctgc gtctcaactc acc                                              23

<210> SEQ ID NO 1679
<211> LENGTH: 23
<212> TYPE: DNA
<213> ORGANISM: Homo sapiens

<400> SEQUENCE: 1679
agcctcctgc gtctcaactc acc                                               23

<210> SEQ ID NO 1680
<211> LENGTH: 23
<212> TYPE: DNA
<213> ORGANISM: Homo sapiens

<400> SEQUENCE: 1680
agcctcctgc gtctcaactc acc                                               23

<210> SEQ ID NO 1681
<211> LENGTH: 20
<212> TYPE: DNA
<213> ORGANISM: Homo sapiens

<400> SEQUENCE: 1681
ctagcctcct gcgtctcaac                                                   20

<210> SEQ ID NO 1682
<211> LENGTH: 23
<212> TYPE: DNA
<213> ORGANISM: Homo sapiens

<400> SEQUENCE: 1682
gttgctcagg ctgccctctt gct                                               23

<210> SEQ ID NO 1683
<211> LENGTH: 22
<212> TYPE: DNA
<213> ORGANISM: Homo sapiens

<400> SEQUENCE: 1683
tcagggtagt gcagtgtagt gt                                                22

<210> SEQ ID NO 1684
<211> LENGTH: 26
<212> TYPE: DNA
<213> ORGANISM: Homo sapiens

<400> SEQUENCE: 1684
tgttgctcag gctgccctct tgctat                                            26

<210> SEQ ID NO 1685
<211> LENGTH: 23
<212> TYPE: DNA
<213> ORGANISM: Homo sapiens

<400> SEQUENCE: 1685
gcaccaggtc aagtagcctc agg                                               23

<210> SEQ ID NO 1686
<211> LENGTH: 23
<212> TYPE: DNA
<213> ORGANISM: Homo sapiens

<400> SEQUENCE: 1686
gtctcgttct gtcacccagg ctg                                               23

<210> SEQ ID NO 1687
<211> LENGTH: 23
<212> TYPE: DNA
<213> ORGANISM: Homo sapiens

<400> SEQUENCE: 1687
ccaaatgtag atgcccgcac ccg                                      23

<210> SEQ ID NO 1688
<211> LENGTH: 26
<212> TYPE: DNA
<213> ORGANISM: Homo sapiens

<400> SEQUENCE: 1688
tgccttgaac agattgccag cctcct                                   26

<210> SEQ ID NO 1689
<211> LENGTH: 26
<212> TYPE: DNA
<213> ORGANISM: Homo sapiens

<400> SEQUENCE: 1689
tgccttgaac agattgccag cctcct                                   26

<210> SEQ ID NO 1690
<211> LENGTH: 23
<212> TYPE: DNA
<213> ORGANISM: Homo sapiens

<400> SEQUENCE: 1690
gacgctctcc ctttgctcaa gcc                                      23

<210> SEQ ID NO 1691
<211> LENGTH: 23
<212> TYPE: DNA
<213> ORGANISM: Homo sapiens

<400> SEQUENCE: 1691
cccagttgtc caggttgctg cct                                      23

<210> SEQ ID NO 1692
<211> LENGTH: 23
<212> TYPE: DNA
<213> ORGANISM: Homo sapiens

<400> SEQUENCE: 1692
gacgctctcc ctttgctcaa gcc                                      23

<210> SEQ ID NO 1693
<211> LENGTH: 23
<212> TYPE: DNA
<213> ORGANISM: Homo sapiens

<400> SEQUENCE: 1693
gctgtgtatc tcagggcact cag                                      23

<210> SEQ ID NO 1694
<211> LENGTH: 20
<212> TYPE: DNA
<213> ORGANISM: Homo sapiens

<400> SEQUENCE: 1694
ggccctgaag gggacttatc                                          20

<210> SEQ ID NO 1695
<211> LENGTH: 20
<212> TYPE: DNA
<213> ORGANISM: Homo sapiens

```
<400> SEQUENCE: 1695
ctgattgctc aacccaaagc                                              20

<210> SEQ ID NO 1696
<211> LENGTH: 23
<212> TYPE: DNA
<213> ORGANISM: Homo sapiens

<400> SEQUENCE: 1696
tcatactact accaaagcca ttt                                          23

<210> SEQ ID NO 1697
<211> LENGTH: 26
<212> TYPE: DNA
<213> ORGANISM: Homo sapiens

<400> SEQUENCE: 1697
gacctggttc ccatctactc ctttgg                                       26

<210> SEQ ID NO 1698
<211> LENGTH: 20
<212> TYPE: DNA
<213> ORGANISM: Homo sapiens

<400> SEQUENCE: 1698
agcgccacct tctttcagag                                              20

<210> SEQ ID NO 1699
<211> LENGTH: 26
<212> TYPE: DNA
<213> ORGANISM: Homo sapiens

<400> SEQUENCE: 1699
aggcattact gaagttgctg gtattc                                       26

<210> SEQ ID NO 1700
<211> LENGTH: 20
<212> TYPE: DNA
<213> ORGANISM: Homo sapiens

<400> SEQUENCE: 1700
ccagagcggg atgtcactac                                              20

<210> SEQ ID NO 1701
<211> LENGTH: 19
<212> TYPE: DNA
<213> ORGANISM: Homo sapiens

<400> SEQUENCE: 1701
gctcccaggc ttgacgaga                                               19

<210> SEQ ID NO 1702
<211> LENGTH: 22
<212> TYPE: DNA
<213> ORGANISM: Homo sapiens

<400> SEQUENCE: 1702
ctggggcact caatctagag gt                                           22

<210> SEQ ID NO 1703
<211> LENGTH: 26
<212> TYPE: DNA
<213> ORGANISM: Homo sapiens
```

```
<400> SEQUENCE: 1703
ccgtgactca tcagaggaaa actacg                                          26

<210> SEQ ID NO 1704
<211> LENGTH: 26
<212> TYPE: DNA
<213> ORGANISM: Homo sapiens

<400> SEQUENCE: 1704
ggaaagagta ggaacctgaa acctgc                                          26

<210> SEQ ID NO 1705
<211> LENGTH: 23
<212> TYPE: DNA
<213> ORGANISM: Homo sapiens

<400> SEQUENCE: 1705
cctcttcctg gctcacagac agc                                             23

<210> SEQ ID NO 1706
<211> LENGTH: 23
<212> TYPE: DNA
<213> ORGANISM: Homo sapiens

<400> SEQUENCE: 1706
ctcacgctct ggtccttgtc act                                             23

<210> SEQ ID NO 1707
<211> LENGTH: 23
<212> TYPE: DNA
<213> ORGANISM: Homo sapiens

<400> SEQUENCE: 1707
gggcagggac taaggtctga ctt                                             23

<210> SEQ ID NO 1708
<211> LENGTH: 26
<212> TYPE: DNA
<213> ORGANISM: Homo sapiens

<400> SEQUENCE: 1708
ctcccatctt gaggctgtaa acaaac                                          26

<210> SEQ ID NO 1709
<211> LENGTH: 23
<212> TYPE: DNA
<213> ORGANISM: Homo sapiens

<400> SEQUENCE: 1709
cacactcctc ctccaagtca cag                                             23

<210> SEQ ID NO 1710
<211> LENGTH: 26
<212> TYPE: DNA
<213> ORGANISM: Homo sapiens

<400> SEQUENCE: 1710
ccacacagtt tccaccttac caccat                                          26

<210> SEQ ID NO 1711
<211> LENGTH: 23
<212> TYPE: DNA
```

<213> ORGANISM: Homo sapiens

<400> SEQUENCE: 1711
gtagtggcag aggaactttc agt          23

<210> SEQ ID NO 1712
<211> LENGTH: 26
<212> TYPE: DNA
<213> ORGANISM: Homo sapiens

<400> SEQUENCE: 1712
aacaggcagg gtgaactctt ccagac          26

<210> SEQ ID NO 1713
<211> LENGTH: 21
<212> TYPE: DNA
<213> ORGANISM: Homo sapiens

<400> SEQUENCE: 1713
ccaagctggc taatatgtgt g          21

<210> SEQ ID NO 1714
<211> LENGTH: 23
<212> TYPE: DNA
<213> ORGANISM: Homo sapiens

<400> SEQUENCE: 1714
gggctaacca gaggcaaaag gca          23

<210> SEQ ID NO 1715
<211> LENGTH: 23
<212> TYPE: DNA
<213> ORGANISM: Homo sapiens

<400> SEQUENCE: 1715
ggttgaagga ggtgggtcag ttg          23

<210> SEQ ID NO 1716
<211> LENGTH: 26
<212> TYPE: DNA
<213> ORGANISM: Homo sapiens

<400> SEQUENCE: 1716
ggcttagtgg ttttggagtc ctggta          26

<210> SEQ ID NO 1717
<211> LENGTH: 23
<212> TYPE: DNA
<213> ORGANISM: Homo sapiens

<400> SEQUENCE: 1717
atgagccctg agtgtgctgg tgc          23

<210> SEQ ID NO 1718
<211> LENGTH: 26
<212> TYPE: DNA
<213> ORGANISM: Homo sapiens

<400> SEQUENCE: 1718
atcataatca ggcaactggc tggtgc          26

<210> SEQ ID NO 1719
<211> LENGTH: 22

<212> TYPE: DNA
<213> ORGANISM: Homo sapiens

<400> SEQUENCE: 1719
tgtagccagc catccaaaga ca                                     22

<210> SEQ ID NO 1720
<211> LENGTH: 26
<212> TYPE: DNA
<213> ORGANISM: Homo sapiens

<400> SEQUENCE: 1720
tgagcactgg ttccccgcaa atactg                                 26

<210> SEQ ID NO 1721
<211> LENGTH: 26
<212> TYPE: DNA
<213> ORGANISM: Homo sapiens

<400> SEQUENCE: 1721
aaccttaccc gaaccagcct tcccaa                                 26

<210> SEQ ID NO 1722
<211> LENGTH: 26
<212> TYPE: DNA
<213> ORGANISM: Homo sapiens

<400> SEQUENCE: 1722
gaagagccca gttgacatct aataac                                 26

<210> SEQ ID NO 1723
<211> LENGTH: 23
<212> TYPE: DNA
<213> ORGANISM: Homo sapiens

<400> SEQUENCE: 1723
gttgacatct aataactcac att                                    23

<210> SEQ ID NO 1724
<211> LENGTH: 24
<212> TYPE: DNA
<213> ORGANISM: Homo sapiens

<400> SEQUENCE: 1724
gccaagagag aagagtgtga agcc                                   24

<210> SEQ ID NO 1725
<211> LENGTH: 26
<212> TYPE: DNA
<213> ORGANISM: Homo sapiens

<400> SEQUENCE: 1725
aagccaagag agaagagtgt gaagcc                                 26

<210> SEQ ID NO 1726
<211> LENGTH: 23
<212> TYPE: DNA
<213> ORGANISM: Homo sapiens

<400> SEQUENCE: 1726
aggtccacat accacacacc ata                                    23

<210> SEQ ID NO 1727

```
<211> LENGTH: 23
<212> TYPE: DNA
<213> ORGANISM: Homo sapiens

<400> SEQUENCE: 1727
aggctcttcc ccaccactct cag                                             23

<210> SEQ ID NO 1728
<211> LENGTH: 20
<212> TYPE: DNA
<213> ORGANISM: Homo sapiens

<400> SEQUENCE: 1728
gtagtagaga gtgcggtgcc                                                 20

<210> SEQ ID NO 1729
<211> LENGTH: 23
<212> TYPE: DNA
<213> ORGANISM: Homo sapiens

<400> SEQUENCE: 1729
gggaaaatcg gtgtggctgg ctc                                             23

<210> SEQ ID NO 1730
<211> LENGTH: 23
<212> TYPE: DNA
<213> ORGANISM: Homo sapiens

<400> SEQUENCE: 1730
atacggactg agccctatga cgc                                             23

<210> SEQ ID NO 1731
<211> LENGTH: 23
<212> TYPE: DNA
<213> ORGANISM: Homo sapiens

<400> SEQUENCE: 1731
aataacctgt gcccagaccg agc                                             23

<210> SEQ ID NO 1732
<211> LENGTH: 23
<212> TYPE: DNA
<213> ORGANISM: Homo sapiens

<400> SEQUENCE: 1732
agaacagagg caagggcagt cca                                             23

<210> SEQ ID NO 1733
<211> LENGTH: 20
<212> TYPE: DNA
<213> ORGANISM: Homo sapiens

<400> SEQUENCE: 1733
cctccatacc tgtccctgct                                                 20

<210> SEQ ID NO 1734
<211> LENGTH: 23
<212> TYPE: DNA
<213> ORGANISM: Homo sapiens

<400> SEQUENCE: 1734
gtcaagtagc ctcagggtag tgc                                             23
```

```
<210> SEQ ID NO 1735
<211> LENGTH: 23
<212> TYPE: DNA
<213> ORGANISM: Homo sapiens

<400> SEQUENCE: 1735
tgccatgtaa ccttgtgttc aga                                          23

<210> SEQ ID NO 1736
<211> LENGTH: 26
<212> TYPE: DNA
<213> ORGANISM: Homo sapiens

<400> SEQUENCE: 1736
cctgtttgag atgctctgct tttgac                                       26

<210> SEQ ID NO 1737
<211> LENGTH: 23
<212> TYPE: DNA
<213> ORGANISM: Homo sapiens

<400> SEQUENCE: 1737
agccctcgct aaagccaaat ggg                                          23

<210> SEQ ID NO 1738
<211> LENGTH: 23
<212> TYPE: DNA
<213> ORGANISM: Homo sapiens

<400> SEQUENCE: 1738
ggcagtggtt tgtcctgtga cct                                          23

<210> SEQ ID NO 1739
<211> LENGTH: 23
<212> TYPE: DNA
<213> ORGANISM: Homo sapiens

<400> SEQUENCE: 1739
ggataaccgt ctggtccttg tgc                                          23

<210> SEQ ID NO 1740
<211> LENGTH: 26
<212> TYPE: DNA
<213> ORGANISM: Homo sapiens

<400> SEQUENCE: 1740
cctggcttgc ttttgaatcc tgactt                                       26

<210> SEQ ID NO 1741
<211> LENGTH: 26
<212> TYPE: DNA
<213> ORGANISM: Homo sapiens

<400> SEQUENCE: 1741
aaggtatgga aagagtctgg gagtga                                       26

<210> SEQ ID NO 1742
<211> LENGTH: 23
<212> TYPE: DNA
<213> ORGANISM: Homo sapiens

<400> SEQUENCE: 1742
tggagcagaa cctgtcagac ctg                                          23
```

<210> SEQ ID NO 1743
<211> LENGTH: 23
<212> TYPE: DNA
<213> ORGANISM: Homo sapiens

<400> SEQUENCE: 1743
tggagcagaa cctgtcagac ctg                                          23

<210> SEQ ID NO 1744
<211> LENGTH: 23
<212> TYPE: DNA
<213> ORGANISM: Homo sapiens

<400> SEQUENCE: 1744
ggagtccacc aagtgctatg gga                                          23

<210> SEQ ID NO 1745
<211> LENGTH: 23
<212> TYPE: DNA
<213> ORGANISM: Homo sapiens

<400> SEQUENCE: 1745
cctggagcag aacctgtcag acc                                          23

<210> SEQ ID NO 1746
<211> LENGTH: 25
<212> TYPE: DNA
<213> ORGANISM: Homo sapiens

<400> SEQUENCE: 1746
tcagggatcc aataggttaa gtaat                                        25

<210> SEQ ID NO 1747
<211> LENGTH: 20
<212> TYPE: DNA
<213> ORGANISM: Homo sapiens

<400> SEQUENCE: 1747
gctgcgaaaa tgttgaggct                                              20

<210> SEQ ID NO 1748
<211> LENGTH: 23
<212> TYPE: DNA
<213> ORGANISM: Homo sapiens

<400> SEQUENCE: 1748
gaagaatgaa ctgctacaac acc                                          23

<210> SEQ ID NO 1749
<211> LENGTH: 26
<212> TYPE: DNA
<213> ORGANISM: Homo sapiens

<400> SEQUENCE: 1749
gaactgttat cagagaatag gctcca                                       26

<210> SEQ ID NO 1750
<211> LENGTH: 20
<212> TYPE: DNA
<213> ORGANISM: Homo sapiens

<400> SEQUENCE: 1750
gggcattatg tgagggtctc                                              20

<210> SEQ ID NO 1751
<211> LENGTH: 26
<212> TYPE: DNA
<213> ORGANISM: Homo sapiens

<400> SEQUENCE: 1751
aagagcaata aggatgtcaa agtttt                                  26

<210> SEQ ID NO 1752
<211> LENGTH: 20
<212> TYPE: DNA
<213> ORGANISM: Homo sapiens

<400> SEQUENCE: 1752
cctgtctccc ccaacctgtg                                         20

<210> SEQ ID NO 1753
<211> LENGTH: 60
<212> TYPE: DNA
<213> ORGANISM: Homo sapiens

<400> SEQUENCE: 1753
tcctatcccg tgggtggcaa tgtgagcttc gagaaggtcc ctcatagggg ttccttcccc   60

<210> SEQ ID NO 1754
<211> LENGTH: 60
<212> TYPE: DNA
<213> ORGANISM: Homo sapiens

<400> SEQUENCE: 1754
agcaggcggc caagatgacc ttgtggcctc gacttggatg cccatggaat tatcttcact   60

<210> SEQ ID NO 1755
<211> LENGTH: 60
<212> TYPE: DNA
<213> ORGANISM: Homo sapiens

<400> SEQUENCE: 1755
cacaggtcag gtcatggtcc ttccacattc gattccctct ggggaatgtc cctggtggtt   60

<210> SEQ ID NO 1756
<211> LENGTH: 60
<212> TYPE: DNA
<213> ORGANISM: Homo sapiens

<400> SEQUENCE: 1756
cacaggtcag gtcatggtcc ttccacattc gaagtcgtgt ggtcttggac agtggattgc   60

<210> SEQ ID NO 1757
<211> LENGTH: 60
<212> TYPE: DNA
<213> ORGANISM: Homo sapiens

<400> SEQUENCE: 1757
tcctatcccg tgggtggcaa tgtgagcttc gaagtcgtgt ggtcttggac agtggattgc   60

<210> SEQ ID NO 1758
<211> LENGTH: 60
<212> TYPE: DNA
<213> ORGANISM: Homo sapiens

<400> SEQUENCE: 1758

```
tcctatcccg tgggtggcaa tgtgagcttc gacttggatg cccatggaat tatcttcact        60
```

<210> SEQ ID NO 1759
<211> LENGTH: 60
<212> TYPE: DNA
<213> ORGANISM: Homo sapiens

<400> SEQUENCE: 1759

```
aggtcattaa agtataatcc tgttgttatc gagagatcaa gaccatcctg gccaacatgg        60
```

<210> SEQ ID NO 1760
<211> LENGTH: 60
<212> TYPE: DNA
<213> ORGANISM: Homo sapiens

<400> SEQUENCE: 1760

```
agcaggggga tcacataagg ccaggagttc gaataagaaa tacttctaaa ccaaaggata        60
```

<210> SEQ ID NO 1761
<211> LENGTH: 60
<212> TYPE: DNA
<213> ORGANISM: Homo sapiens

<400> SEQUENCE: 1761

```
atgtatttat aggtctaatc atgtaaaatc gatatctctg aaagtaccgt caattcttct        60
```

<210> SEQ ID NO 1762
<211> LENGTH: 60
<212> TYPE: DNA
<213> ORGANISM: Homo sapiens

<400> SEQUENCE: 1762

```
agcaggggga tcacataagg ccaggagttc gattttaaca agaaactgta ggtctaagga        60
```

<210> SEQ ID NO 1763
<211> LENGTH: 60
<212> TYPE: DNA
<213> ORGANISM: Homo sapiens

<400> SEQUENCE: 1763

```
ttattacttt attctgactg aatatcattc gaataagaaa tacttctaaa ccaaaggata        60
```

<210> SEQ ID NO 1764
<211> LENGTH: 60
<212> TYPE: DNA
<213> ORGANISM: Homo sapiens

<400> SEQUENCE: 1764

```
tatcctttgg tttagaagta tttcttattc gaaagaaacc aaaaacacaa gtatacatca        60
```

<210> SEQ ID NO 1765
<211> LENGTH: 60
<212> TYPE: DNA
<213> ORGANISM: Homo sapiens

<400> SEQUENCE: 1765

```
atgtatttat aggtctaatc atgtaaaatc gaataagaaa tacttctaaa ccaaaggata        60
```

<210> SEQ ID NO 1766
<211> LENGTH: 60
<212> TYPE: DNA
<213> ORGANISM: Homo sapiens

<400> SEQUENCE: 1766

-continued

```
ttattacttt attctgactg aatatcattc gattttacat gattagacct ataaatacat    60

<210> SEQ ID NO 1767
<211> LENGTH: 60
<212> TYPE: DNA
<213> ORGANISM: Homo sapiens

<400> SEQUENCE: 1767
cctaatattt cattatgata agaaagattc gagagtaagt ttcttctgtt cactcaggag    60

<210> SEQ ID NO 1768
<211> LENGTH: 60
<212> TYPE: DNA
<213> ORGANISM: Homo sapiens

<400> SEQUENCE: 1768
ttatttatat cttctctaat ttattttatc gatgaacgtt tacccaatta tttctaaaca    60

<210> SEQ ID NO 1769
<211> LENGTH: 60
<212> TYPE: DNA
<213> ORGANISM: Homo sapiens

<400> SEQUENCE: 1769
ctgagtcttc attaccaaaa aaaaaagttc gacctccccg aacccctccg cctctgcgct    60

<210> SEQ ID NO 1770
<211> LENGTH: 60
<212> TYPE: DNA
<213> ORGANISM: Homo sapiens

<400> SEQUENCE: 1770
aaatcataat tgtgcagatg atttgccttc gacctccccg aacccctccg cctctgcgct    60

<210> SEQ ID NO 1771
<211> LENGTH: 60
<212> TYPE: DNA
<213> ORGANISM: Homo sapiens

<400> SEQUENCE: 1771
gcagtcaatc accgagttat atgaggtctc gacctccccg aacccctccg cctctgcgct    60

<210> SEQ ID NO 1772
<211> LENGTH: 60
<212> TYPE: DNA
<213> ORGANISM: Homo sapiens

<400> SEQUENCE: 1772
ccaaactggc aatcaaccca gatagtcttc gaccccggcc ccggaggtct ccctccacag    60

<210> SEQ ID NO 1773
<211> LENGTH: 60
<212> TYPE: DNA
<213> ORGANISM: Homo sapiens

<400> SEQUENCE: 1773
agaggctgag gtgaaaagat tgtttgagtc gattatttct tatctagcca atagaaactt    60

<210> SEQ ID NO 1774
<211> LENGTH: 60
<212> TYPE: DNA
<213> ORGANISM: Homo sapiens
```

<400> SEQUENCE: 1774
agaggctgag gtgaaaagat tgtttgagtc gagtcacatg atcaagcgct catttctgtt    60

<210> SEQ ID NO 1775
<211> LENGTH: 60
<212> TYPE: DNA
<213> ORGANISM: Homo sapiens

<400> SEQUENCE: 1775
cttttccatt gcttcctcag atcctctgtc gagattcact gcgctgcaca ccagggcctc    60

<210> SEQ ID NO 1776
<211> LENGTH: 60
<212> TYPE: DNA
<213> ORGANISM: Homo sapiens

<400> SEQUENCE: 1776
agctggagtc ttgattaaca caaaaatctc gagattcact gcgctgcaca ccagggcctc    60

<210> SEQ ID NO 1777
<211> LENGTH: 60
<212> TYPE: DNA
<213> ORGANISM: Homo sapiens

<400> SEQUENCE: 1777
cttttccatt gcttcctcag atcctctgtc gagagcacgg cctctctggc gccttgccat    60

<210> SEQ ID NO 1778
<211> LENGTH: 60
<212> TYPE: DNA
<213> ORGANISM: Homo sapiens

<400> SEQUENCE: 1778
acatgagatg tccttcaagt gaaactgttc gaccatgccc gggcaggtgg ctgagacctc    60

<210> SEQ ID NO 1779
<211> LENGTH: 60
<212> TYPE: DNA
<213> ORGANISM: Homo sapiens

<400> SEQUENCE: 1779
cgcgcactga aaccctagcc gcggggatc gaaatcatat caccagtcat tccactcctg    60

<210> SEQ ID NO 1780
<211> LENGTH: 60
<212> TYPE: DNA
<213> ORGANISM: Homo sapiens

<400> SEQUENCE: 1780
aggcgacact cttgtccccg ccatctttc gaaggccccc gtcctcctgc gccatggaga    60

<210> SEQ ID NO 1781
<211> LENGTH: 60
<212> TYPE: DNA
<213> ORGANISM: Homo sapiens

<400> SEQUENCE: 1781
catcatcaca gtctacggct gtttcctctc gaaggccccc gtcctcctgc gccatggaga    60

<210> SEQ ID NO 1782
<211> LENGTH: 60
<212> TYPE: DNA
<213> ORGANISM: Homo sapiens

<400> SEQUENCE: 1782
ttccatagat tacttttcaa atcatccttc gaagctggcg gctgagggcc cggcgccaag    60

<210> SEQ ID NO 1783
<211> LENGTH: 60
<212> TYPE: DNA
<213> ORGANISM: Homo sapiens

<400> SEQUENCE: 1783
ttttactgtt tttgtaagag atatgttttc gattaatgtt aaaataaaa ggtagtattt    60

<210> SEQ ID NO 1784
<211> LENGTH: 60
<212> TYPE: DNA
<213> ORGANISM: Homo sapiens

<400> SEQUENCE: 1784
ttttactgtt tttgtaagag atatgttttc gacatcattt ttacaaataa gaccagatgt    60

<210> SEQ ID NO 1785
<211> LENGTH: 60
<212> TYPE: DNA
<213> ORGANISM: Homo sapiens

<400> SEQUENCE: 1785
aggtactctt gaaaatataa aactccagtc gacattatac aaagaattcc cacaaatcca    60

<210> SEQ ID NO 1786
<211> LENGTH: 60
<212> TYPE: DNA
<213> ORGANISM: Homo sapiens

<400> SEQUENCE: 1786
gtgggcacta ggaatgaggt ccctgcctc gacccactcc cggggggatc gggacaccgc    60

<210> SEQ ID NO 1787
<211> LENGTH: 60
<212> TYPE: DNA
<213> ORGANISM: Homo sapiens

<400> SEQUENCE: 1787
tccagggatg gcagagtctc tggcagcctc gatgcggggc gggaggggcg gccgggaaag    60

<210> SEQ ID NO 1788
<211> LENGTH: 60
<212> TYPE: DNA
<213> ORGANISM: Homo sapiens

<400> SEQUENCE: 1788
gggcaccgcc gccctgactt ccaacacatc gaagaatggg tggggccttg cacctcatac    60

<210> SEQ ID NO 1789
<211> LENGTH: 60
<212> TYPE: DNA
<213> ORGANISM: Homo sapiens

<400> SEQUENCE: 1789
ccgcgcccgc agggcccgcc ccgcgccgtc gaggctttca agggatccag ggtgggtgc    60

<210> SEQ ID NO 1790
<211> LENGTH: 60
<212> TYPE: DNA

<213> ORGANISM: Homo sapiens

<400> SEQUENCE: 1790
ccgcgcccgc agggcccgcc ccgcgccgtc gatgtgttgg aagtcagggc ggcggtgccc    60

<210> SEQ ID NO 1791
<211> LENGTH: 60
<212> TYPE: DNA
<213> ORGANISM: Homo sapiens

<400> SEQUENCE: 1791
ccgcgcccgc agggcccgcc ccgcgccgtc gagaagcata aagcagggac aggtatggag    60

<210> SEQ ID NO 1792
<211> LENGTH: 60
<212> TYPE: DNA
<213> ORGANISM: Homo sapiens

<400> SEQUENCE: 1792
gggcaccgcc gccctgactt ccaacacatc gagaagcata aagcagggac aggtatggag    60

<210> SEQ ID NO 1793
<211> LENGTH: 60
<212> TYPE: DNA
<213> ORGANISM: Homo sapiens

<400> SEQUENCE: 1793
agtagtgcaa tcatagctca ctgaaacctc gaaagctaat gaggtatgag gggagaatac    60

<210> SEQ ID NO 1794
<211> LENGTH: 60
<212> TYPE: DNA
<213> ORGANISM: Homo sapiens

<400> SEQUENCE: 1794
ataaaatggg gaggccttcc agaagctctc gacctccagg tcccccgcca cttccacggc    60

<210> SEQ ID NO 1795
<211> LENGTH: 60
<212> TYPE: DNA
<213> ORGANISM: Homo sapiens

<400> SEQUENCE: 1795
tatgagtaat aattacaatt tccccctttc gacctccagg tcccccgcca cttccacggc    60

<210> SEQ ID NO 1796
<211> LENGTH: 60
<212> TYPE: DNA
<213> ORGANISM: Homo sapiens

<400> SEQUENCE: 1796
ccgcctcacc tcccgcatgg tcttgaggtc gagcatgcag cgcatctgag cagtgaggct    60

<210> SEQ ID NO 1797
<211> LENGTH: 20
<212> TYPE: DNA
<213> ORGANISM: Homo sapiens

<400> SEQUENCE: 1797
cccaggtgtt atccatccag                                                20

<210> SEQ ID NO 1798
<211> LENGTH: 23

<212> TYPE: DNA
<213> ORGANISM: Homo sapiens

<400> SEQUENCE: 1798
agcaggaact ggtcccgcag gaa                                          23

<210> SEQ ID NO 1799
<211> LENGTH: 23
<212> TYPE: DNA
<213> ORGANISM: Homo sapiens

<400> SEQUENCE: 1799
agccaaggtc gccctcatct ggt                                          23

<210> SEQ ID NO 1800
<211> LENGTH: 23
<212> TYPE: DNA
<213> ORGANISM: Homo sapiens

<400> SEQUENCE: 1800
agccaaggtc gccctcatct ggt                                          23

<210> SEQ ID NO 1801
<211> LENGTH: 23
<212> TYPE: DNA
<213> ORGANISM: Homo sapiens

<400> SEQUENCE: 1801
tgtccagccc ctgtctcctt tga                                          23

<210> SEQ ID NO 1802
<211> LENGTH: 23
<212> TYPE: DNA
<213> ORGANISM: Homo sapiens

<400> SEQUENCE: 1802
gtccagcccc tgtctccttt gag                                          23

<210> SEQ ID NO 1803
<211> LENGTH: 23
<212> TYPE: DNA
<213> ORGANISM: Homo sapiens

<400> SEQUENCE: 1803
cttggcacag aacaggagca cca                                          23

<210> SEQ ID NO 1804
<211> LENGTH: 24
<212> TYPE: DNA
<213> ORGANISM: Homo sapiens

<400> SEQUENCE: 1804
gcaaaacaat actcaaatgc tcat                                         24

<210> SEQ ID NO 1805
<211> LENGTH: 25
<212> TYPE: DNA
<213> ORGANISM: Homo sapiens

<400> SEQUENCE: 1805
atgatgatga aacttgcttc ctgga                                        25

<210> SEQ ID NO 1806

```
<211> LENGTH: 24
<212> TYPE: DNA
<213> ORGANISM: Homo sapiens

<400> SEQUENCE: 1806
gcaaaacaat actcaaatgc tcat                                          24

<210> SEQ ID NO 1807
<211> LENGTH: 26
<212> TYPE: DNA
<213> ORGANISM: Homo sapiens

<400> SEQUENCE: 1807
ttctgccaca accctgatgt tttctg                                        26

<210> SEQ ID NO 1808
<211> LENGTH: 25
<212> TYPE: DNA
<213> ORGANISM: Homo sapiens

<400> SEQUENCE: 1808
taatggttga aatgtgagtc tgaat                                         25

<210> SEQ ID NO 1809
<211> LENGTH: 26
<212> TYPE: DNA
<213> ORGANISM: Homo sapiens

<400> SEQUENCE: 1809
atgaaaactt atcccaaaga aacttc                                        26

<210> SEQ ID NO 1810
<211> LENGTH: 26
<212> TYPE: DNA
<213> ORGANISM: Homo sapiens

<400> SEQUENCE: 1810
tttctgccac aaccctgatg ttttct                                        26

<210> SEQ ID NO 1811
<211> LENGTH: 26
<212> TYPE: DNA
<213> ORGANISM: Homo sapiens

<400> SEQUENCE: 1811
cacctattgc ctggagcata aaggga                                        26

<210> SEQ ID NO 1812
<211> LENGTH: 25
<212> TYPE: DNA
<213> ORGANISM: Homo sapiens

<400> SEQUENCE: 1812
atcactttgg gtagtatgac cttt                                          25

<210> SEQ ID NO 1813
<211> LENGTH: 21
<212> TYPE: DNA
<213> ORGANISM: Homo sapiens

<400> SEQUENCE: 1813
caccattgta tggggaatga c                                             21
```

```
<210> SEQ ID NO 1814
<211> LENGTH: 21
<212> TYPE: DNA
<213> ORGANISM: Homo sapiens

<400> SEQUENCE: 1814
aagccaaact tgctagcatc c                                              21

<210> SEQ ID NO 1815
<211> LENGTH: 20
<212> TYPE: DNA
<213> ORGANISM: Homo sapiens

<400> SEQUENCE: 1815
gaacgtcggc ctacctagtg                                                20

<210> SEQ ID NO 1816
<211> LENGTH: 23
<212> TYPE: DNA
<213> ORGANISM: Homo sapiens

<400> SEQUENCE: 1816
ttacactcct gggcactctt ccc                                            23

<210> SEQ ID NO 1817
<211> LENGTH: 26
<212> TYPE: DNA
<213> ORGANISM: Homo sapiens

<400> SEQUENCE: 1817
ggagaatcac ttgagcctaa gagttc                                         26

<210> SEQ ID NO 1818
<211> LENGTH: 23
<212> TYPE: DNA
<213> ORGANISM: Homo sapiens

<400> SEQUENCE: 1818
ccagcaaagg gcaggtcatc atc                                            23

<210> SEQ ID NO 1819
<211> LENGTH: 26
<212> TYPE: DNA
<213> ORGANISM: Homo sapiens

<400> SEQUENCE: 1819
ataaggagaa actgtggaag agaggc                                         26

<210> SEQ ID NO 1820
<211> LENGTH: 20
<212> TYPE: DNA
<213> ORGANISM: Homo sapiens

<400> SEQUENCE: 1820
catgaggtac acggcatcac                                                20

<210> SEQ ID NO 1821
<211> LENGTH: 26
<212> TYPE: DNA
<213> ORGANISM: Homo sapiens

<400> SEQUENCE: 1821
ataaggagaa actgtggaag agaggc                                         26
```

<210> SEQ ID NO 1822
<211> LENGTH: 20
<212> TYPE: DNA
<213> ORGANISM: Homo sapiens

<400> SEQUENCE: 1822
acttcatgga agggtggtca                                              20

<210> SEQ ID NO 1823
<211> LENGTH: 19
<212> TYPE: DNA
<213> ORGANISM: Homo sapiens

<400> SEQUENCE: 1823
gcgctgctgt tagctcctg                                               19

<210> SEQ ID NO 1824
<211> LENGTH: 20
<212> TYPE: DNA
<213> ORGANISM: Homo sapiens

<400> SEQUENCE: 1824
cctcatccgt ccgcacatct                                              20

<210> SEQ ID NO 1825
<211> LENGTH: 20
<212> TYPE: DNA
<213> ORGANISM: Homo sapiens

<400> SEQUENCE: 1825
atgctgttgc aggactgtgc                                              20

<210> SEQ ID NO 1826
<211> LENGTH: 23
<212> TYPE: DNA
<213> ORGANISM: Homo sapiens

<400> SEQUENCE: 1826
tctacagccc aagatcctgc ttt                                          23

<210> SEQ ID NO 1827
<211> LENGTH: 23
<212> TYPE: DNA
<213> ORGANISM: Homo sapiens

<400> SEQUENCE: 1827
cccctgagaa gcgatgggct act                                          23

<210> SEQ ID NO 1828
<211> LENGTH: 23
<212> TYPE: DNA
<213> ORGANISM: Homo sapiens

<400> SEQUENCE: 1828
cccctgagaa gcgatgggct act                                          23

<210> SEQ ID NO 1829
<211> LENGTH: 23
<212> TYPE: DNA
<213> ORGANISM: Homo sapiens

<400> SEQUENCE: 1829
cccgaaccag ccttcccaag agc                                          23

<210> SEQ ID NO 1830
<211> LENGTH: 20
<212> TYPE: DNA
<213> ORGANISM: Homo sapiens

<400> SEQUENCE: 1830
cagagggttg cctatggtgg                                              20

<210> SEQ ID NO 1831
<211> LENGTH: 20
<212> TYPE: DNA
<213> ORGANISM: Homo sapiens

<400> SEQUENCE: 1831
aggagacctg gttgaagcgg                                              20

<210> SEQ ID NO 1832
<211> LENGTH: 23
<212> TYPE: DNA
<213> ORGANISM: Homo sapiens

<400> SEQUENCE: 1832
aataacctgt gcccagaccg agc                                          23

<210> SEQ ID NO 1833
<211> LENGTH: 23
<212> TYPE: DNA
<213> ORGANISM: Homo sapiens

<400> SEQUENCE: 1833
agcctcctgc gtctcaactc acc                                          23

<210> SEQ ID NO 1834
<211> LENGTH: 23
<212> TYPE: DNA
<213> ORGANISM: Homo sapiens

<400> SEQUENCE: 1834
agcctcctgc gtctcaactc acc                                          23

<210> SEQ ID NO 1835
<211> LENGTH: 20
<212> TYPE: DNA
<213> ORGANISM: Homo sapiens

<400> SEQUENCE: 1835
ctagcctcct gcgtctcaac                                              20

<210> SEQ ID NO 1836
<211> LENGTH: 20
<212> TYPE: DNA
<213> ORGANISM: Homo sapiens

<400> SEQUENCE: 1836
gctcttgctg catgtcctct                                              20

<210> SEQ ID NO 1837
<211> LENGTH: 21
<212> TYPE: DNA
<213> ORGANISM: Homo sapiens

<400> SEQUENCE: 1837
ttgcttgtga gtttgatgca g                                              21

<210> SEQ ID NO 1838
<211> LENGTH: 23
<212> TYPE: DNA
<213> ORGANISM: Homo sapiens

<400> SEQUENCE: 1838
gacgctctcc ctttgctcaa gcc                                            23

<210> SEQ ID NO 1839
<211> LENGTH: 23
<212> TYPE: DNA
<213> ORGANISM: Homo sapiens

<400> SEQUENCE: 1839
gctgtgtatc tcagggcact cag                                            23

<210> SEQ ID NO 1840
<211> LENGTH: 20
<212> TYPE: DNA
<213> ORGANISM: Homo sapiens

<400> SEQUENCE: 1840
tgaagaagca ctcgtcgttg                                                20

<210> SEQ ID NO 1841
<211> LENGTH: 20
<212> TYPE: DNA
<213> ORGANISM: Homo sapiens

<400> SEQUENCE: 1841
gttcctgtga agggtgaagc                                                20

<210> SEQ ID NO 1842
<211> LENGTH: 23
<212> TYPE: DNA
<213> ORGANISM: Homo sapiens

<400> SEQUENCE: 1842
ctctggtcct gtagtcctca gtg                                            23

<210> SEQ ID NO 1843
<211> LENGTH: 23
<212> TYPE: DNA
<213> ORGANISM: Homo sapiens

<400> SEQUENCE: 1843
ctccctgtct gagcatctct ctc                                            23

<210> SEQ ID NO 1844
<211> LENGTH: 23
<212> TYPE: DNA
<213> ORGANISM: Homo sapiens

<400> SEQUENCE: 1844
aggagggata cacctaaggc agc                                            23

<210> SEQ ID NO 1845
<211> LENGTH: 23
<212> TYPE: DNA
<213> ORGANISM: Homo sapiens

<400> SEQUENCE: 1845
ggagggatac acctaaggca gcc					23

<210> SEQ ID NO 1846
<211> LENGTH: 23
<212> TYPE: DNA
<213> ORGANISM: Homo sapiens

<400> SEQUENCE: 1846
ctctggtcct gtagtcctca gtg					23

<210> SEQ ID NO 1847
<211> LENGTH: 23
<212> TYPE: DNA
<213> ORGANISM: Homo sapiens

<400> SEQUENCE: 1847
tcctgcctca gcctcccaag tag					23

<210> SEQ ID NO 1848
<211> LENGTH: 25
<212> TYPE: DNA
<213> ORGANISM: Homo sapiens

<400> SEQUENCE: 1848
taatggttga aatgtgagtc tgaat					25

<210> SEQ ID NO 1849
<211> LENGTH: 26
<212> TYPE: DNA
<213> ORGANISM: Homo sapiens

<400> SEQUENCE: 1849
ggtgctatgt ttgatttagg aggtat					26

<210> SEQ ID NO 1850
<211> LENGTH: 23
<212> TYPE: DNA
<213> ORGANISM: Homo sapiens

<400> SEQUENCE: 1850
tcctttgacc tttctggact cag					23

<210> SEQ ID NO 1851
<211> LENGTH: 26
<212> TYPE: DNA
<213> ORGANISM: Homo sapiens

<400> SEQUENCE: 1851
gtggagaatg tagtattatg aaggtt					26

<210> SEQ ID NO 1852
<211> LENGTH: 26
<212> TYPE: DNA
<213> ORGANISM: Homo sapiens

<400> SEQUENCE: 1852
agttttgaca gaaagtagag gttcct					26

<210> SEQ ID NO 1853
<211> LENGTH: 26
<212> TYPE: DNA
<213> ORGANISM: Homo sapiens

```
<400> SEQUENCE: 1853
gtggagaatg tagtattatg aaggtt                                          26

<210> SEQ ID NO 1854
<211> LENGTH: 26
<212> TYPE: DNA
<213> ORGANISM: Homo sapiens

<400> SEQUENCE: 1854
atgaaaactt atcccaaaga aacttc                                          26

<210> SEQ ID NO 1855
<211> LENGTH: 26
<212> TYPE: DNA
<213> ORGANISM: Homo sapiens

<400> SEQUENCE: 1855
gcctaagaga aaagcacaca gactcc                                          26

<210> SEQ ID NO 1856
<211> LENGTH: 25
<212> TYPE: DNA
<213> ORGANISM: Homo sapiens

<400> SEQUENCE: 1856
ggacaggaat ccatagggaa gaagt                                           25

<210> SEQ ID NO 1857
<211> LENGTH: 20
<212> TYPE: DNA
<213> ORGANISM: Homo sapiens

<400> SEQUENCE: 1857
gagtgctctg gctctacacg                                                 20

<210> SEQ ID NO 1858
<211> LENGTH: 19
<212> TYPE: DNA
<213> ORGANISM: Homo sapiens

<400> SEQUENCE: 1858
tgctctggct ctacacgtc                                                  19

<210> SEQ ID NO 1859
<211> LENGTH: 21
<212> TYPE: DNA
<213> ORGANISM: Homo sapiens

<400> SEQUENCE: 1859
agtgctctgg ctctacacgt c                                               21

<210> SEQ ID NO 1860
<211> LENGTH: 23
<212> TYPE: DNA
<213> ORGANISM: Homo sapiens

<400> SEQUENCE: 1860
agcaaatcct ccaggcagcc agg                                             23

<210> SEQ ID NO 1861
<211> LENGTH: 26
<212> TYPE: DNA
<213> ORGANISM: Homo sapiens
```

```
<400> SEQUENCE: 1861
gatgatttga cactttcccc acacac                                         26

<210> SEQ ID NO 1862
<211> LENGTH: 24
<212> TYPE: DNA
<213> ORGANISM: Homo sapiens

<400> SEQUENCE: 1862
gcaggaactg gtgctggaat aggc                                           24

<210> SEQ ID NO 1863
<211> LENGTH: 26
<212> TYPE: DNA
<213> ORGANISM: Homo sapiens

<400> SEQUENCE: 1863
gcaggaggat acaactgtca aaactc                                         26

<210> SEQ ID NO 1864
<211> LENGTH: 20
<212> TYPE: DNA
<213> ORGANISM: Homo sapiens

<400> SEQUENCE: 1864
gcatctaaaa atcgcctgga                                                20

<210> SEQ ID NO 1865
<211> LENGTH: 26
<212> TYPE: DNA
<213> ORGANISM: Homo sapiens

<400> SEQUENCE: 1865
ctgtagttct gtaagcgtct cccacg                                         26

<210> SEQ ID NO 1866
<211> LENGTH: 20
<212> TYPE: DNA
<213> ORGANISM: Homo sapiens

<400> SEQUENCE: 1866
atcccatcca aggcatcata                                                20

<210> SEQ ID NO 1867
<211> LENGTH: 20
<212> TYPE: DNA
<213> ORGANISM: Homo sapiens

<400> SEQUENCE: 1867
ccattgtgca catacactgc                                                20

<210> SEQ ID NO 1868
<211> LENGTH: 20
<212> TYPE: DNA
<213> ORGANISM: Homo sapiens

<400> SEQUENCE: 1868
ctcccaggct tgacgagagg                                                20

<210> SEQ ID NO 1869
<211> LENGTH: 20
<212> TYPE: DNA
```

<213> ORGANISM: Homo sapiens

<400> SEQUENCE: 1869
ctcccaggct tgacgagagg                                          20

<210> SEQ ID NO 1870
<211> LENGTH: 20
<212> TYPE: DNA
<213> ORGANISM: Homo sapiens

<400> SEQUENCE: 1870
ccccgagggt tgagaagcat                                          20

<210> SEQ ID NO 1871
<211> LENGTH: 23
<212> TYPE: DNA
<213> ORGANISM: Homo sapiens

<400> SEQUENCE: 1871
gggcagggac taaggtctga ctt                                      23

<210> SEQ ID NO 1872
<211> LENGTH: 23
<212> TYPE: DNA
<213> ORGANISM: Homo sapiens

<400> SEQUENCE: 1872
ccgccactca gccattgttt cca                                      23

<210> SEQ ID NO 1873
<211> LENGTH: 23
<212> TYPE: DNA
<213> ORGANISM: Homo sapiens

<400> SEQUENCE: 1873
gggttcttgt cctccttatg gat                                      23

<210> SEQ ID NO 1874
<211> LENGTH: 20
<212> TYPE: DNA
<213> ORGANISM: Homo sapiens

<400> SEQUENCE: 1874
gtagtagaga gtgcggtgcc                                          20

<210> SEQ ID NO 1875
<211> LENGTH: 20
<212> TYPE: DNA
<213> ORGANISM: Homo sapiens

<400> SEQUENCE: 1875
atcgggcttc cgaagaaggg                                          20

<210> SEQ ID NO 1876
<211> LENGTH: 23
<212> TYPE: DNA
<213> ORGANISM: Homo sapiens

<400> SEQUENCE: 1876
gggaaaatcg gtgtggctgg ctc                                      23

<210> SEQ ID NO 1877
<211> LENGTH: 23

```
<212> TYPE: DNA
<213> ORGANISM: Homo sapiens

<400> SEQUENCE: 1877
atacggactg agccctatga cgc                                      23

<210> SEQ ID NO 1878
<211> LENGTH: 23
<212> TYPE: DNA
<213> ORGANISM: Homo sapiens

<400> SEQUENCE: 1878
aataacctgt gcccagaccg agc                                      23

<210> SEQ ID NO 1879
<211> LENGTH: 22
<212> TYPE: DNA
<213> ORGANISM: Homo sapiens

<400> SEQUENCE: 1879
gctgagactg tagacgtgaa cc                                       22

<210> SEQ ID NO 1880
<211> LENGTH: 21
<212> TYPE: DNA
<213> ORGANISM: Homo sapiens

<400> SEQUENCE: 1880
agacgtgaac ctccatacct g                                        21

<210> SEQ ID NO 1881
<211> LENGTH: 20
<212> TYPE: DNA
<213> ORGANISM: Homo sapiens

<400> SEQUENCE: 1881
aagccaaatg ggcctagcca                                          20

<210> SEQ ID NO 1882
<211> LENGTH: 23
<212> TYPE: DNA
<213> ORGANISM: Homo sapiens

<400> SEQUENCE: 1882
tggagcagaa cctgtcagac ctg                                      23

<210> SEQ ID NO 1883
<211> LENGTH: 23
<212> TYPE: DNA
<213> ORGANISM: Homo sapiens

<400> SEQUENCE: 1883
cctggagcag aacctgtcag acc                                      23

<210> SEQ ID NO 1884
<211> LENGTH: 20
<212> TYPE: DNA
<213> ORGANISM: Homo sapiens

<400> SEQUENCE: 1884
agcggcacac ctctactctc                                          20

<210> SEQ ID NO 1885
```

```
<211> LENGTH: 60
<212> TYPE: DNA
<213> ORGANISM: Homo sapiens

<400> SEQUENCE: 1885
gcgccgcggt acccgctcat ggacaggttc gaactcctga gctcaggcac cttggcctcc    60

<210> SEQ ID NO 1886
<211> LENGTH: 60
<212> TYPE: DNA
<213> ORGANISM: Homo sapiens

<400> SEQUENCE: 1886
cagcaaagtt ttattgtaaa ataagagatc gagctcttac ttgctaccca gcactgatat    60

<210> SEQ ID NO 1887
<211> LENGTH: 60
<212> TYPE: DNA
<213> ORGANISM: Homo sapiens

<400> SEQUENCE: 1887
agtgatagaa gagggacaag gtggcagttc gatattagat aacatccact ctgggctaca    60

<210> SEQ ID NO 1888
<211> LENGTH: 60
<212> TYPE: DNA
<213> ORGANISM: Homo sapiens

<400> SEQUENCE: 1888
ctctgcccat tccatgtcca cggcccctc gacttgaatg ggcttggctg ggctgggaca    60

<210> SEQ ID NO 1889
<211> LENGTH: 60
<212> TYPE: DNA
<213> ORGANISM: Homo sapiens

<400> SEQUENCE: 1889
aaggatatct agggcataaa aataaaaatc gatctcctga tctcatgatc cacctgcctc    60

<210> SEQ ID NO 1890
<211> LENGTH: 60
<212> TYPE: DNA
<213> ORGANISM: Homo sapiens

<400> SEQUENCE: 1890
gaatcctttc gggggaggcg ggaggctgtc gagagctctg tgctccacgc cgaggatgca    60

<210> SEQ ID NO 1891
<211> LENGTH: 60
<212> TYPE: DNA
<213> ORGANISM: Homo sapiens

<400> SEQUENCE: 1891
cgtgactgta tatcatgtcc tttgttaatc gattgaatag agattgtctc ttaaatacag    60

<210> SEQ ID NO 1892
<211> LENGTH: 60
<212> TYPE: DNA
<213> ORGANISM: Homo sapiens

<400> SEQUENCE: 1892
tatagtgggc acacactttt acacaatatc gaagaaaaaa gtcttgacaa tatttaggtg    60
```

<210> SEQ ID NO 1893
<211> LENGTH: 60
<212> TYPE: DNA
<213> ORGANISM: Homo sapiens

<400> SEQUENCE: 1893
accaaaatag caagtagata atcacacttc gaattttttt tcaccacagc acacagcctc    60

<210> SEQ ID NO 1894
<211> LENGTH: 60
<212> TYPE: DNA
<213> ORGANISM: Homo sapiens

<400> SEQUENCE: 1894
cacctcacaa aatatgatat ctaaagtgtc gatattactc agatttgggg aaatgacatt    60

<210> SEQ ID NO 1895
<211> LENGTH: 60
<212> TYPE: DNA
<213> ORGANISM: Homo sapiens

<400> SEQUENCE: 1895
gccctgtgtc tcatgaaagc cgttcacttc gaactcctaa gttcaagcaa tcctcctgcc    60

<210> SEQ ID NO 1896
<211> LENGTH: 60
<212> TYPE: DNA
<213> ORGANISM: Homo sapiens

<400> SEQUENCE: 1896
actttatgac ttgaatgatg tggtaatgtc gaaggttaaa gaagaagttt caaactgagt    60

<210> SEQ ID NO 1897
<211> LENGTH: 60
<212> TYPE: DNA
<213> ORGANISM: Homo sapiens

<400> SEQUENCE: 1897
taggcctggg ggccgaaagg aagaagcttc gacatcctgc ttgaatgttt ggaagagggt    60

<210> SEQ ID NO 1898
<211> LENGTH: 60
<212> TYPE: DNA
<213> ORGANISM: Homo sapiens

<400> SEQUENCE: 1898
cgcagcagtc tcgttgatct tcacggtgtc gactcacctg cgcctcacat cccaggcggg    60

<210> SEQ ID NO 1899
<211> LENGTH: 60
<212> TYPE: DNA
<213> ORGANISM: Homo sapiens

<400> SEQUENCE: 1899
gtaaatgaat ttgaaatatt acaaaagatc gactcacctg cgcctcacat cccaggcggg    60

<210> SEQ ID NO 1900
<211> LENGTH: 60
<212> TYPE: DNA
<213> ORGANISM: Homo sapiens

<400> SEQUENCE: 1900
ccatgggtgg ttttggaaaa ggcaacattc gaaaacaata cataagtgtc tataggccaa    60

```
<210> SEQ ID NO 1901
<211> LENGTH: 60
<212> TYPE: DNA
<213> ORGANISM: Homo sapiens

<400> SEQUENCE: 1901
tcaccttagt gaagggaagt ccatcaaatc gattttgctc ccccaccctt accccccagag    60

<210> SEQ ID NO 1902
<211> LENGTH: 60
<212> TYPE: DNA
<213> ORGANISM: Homo sapiens

<400> SEQUENCE: 1902
agcaggggga tcacataagg ccaggagttc gattttaaca agaaactgta ggtctaagga    60

<210> SEQ ID NO 1903
<211> LENGTH: 60
<212> TYPE: DNA
<213> ORGANISM: Homo sapiens

<400> SEQUENCE: 1903
agcaggggga tcacataagg ccaggagttc gaataagaaa tacttctaaa ccaaaggata    60

<210> SEQ ID NO 1904
<211> LENGTH: 60
<212> TYPE: DNA
<213> ORGANISM: Homo sapiens

<400> SEQUENCE: 1904
acaatgatca aaataaagga gaagtatttc gagcttcccc accttgtatg tctcttttct    60

<210> SEQ ID NO 1905
<211> LENGTH: 60
<212> TYPE: DNA
<213> ORGANISM: Homo sapiens

<400> SEQUENCE: 1905
aggagggtag atcacctgaa gtcaggattc gaaggcttca tttctctgtc tataaaacaa    60

<210> SEQ ID NO 1906
<211> LENGTH: 60
<212> TYPE: DNA
<213> ORGANISM: Homo sapiens

<400> SEQUENCE: 1906
gaattccgac tcccgttttg aaattgtatc gaccgcgtca ctctactcca gcctgggcga    60

<210> SEQ ID NO 1907
<211> LENGTH: 60
<212> TYPE: DNA
<213> ORGANISM: Homo sapiens

<400> SEQUENCE: 1907
ttctcagcat ctctcctgaa agaaaaagtc gaccgcgtca ctctactcca gcctgggcga    60

<210> SEQ ID NO 1908
<211> LENGTH: 60
<212> TYPE: DNA
<213> ORGANISM: Homo sapiens

<400> SEQUENCE: 1908
ccgcctccgt ctgcgcctgg gccaggcctc gacttcgtga tcagcccggc ttggcctccc    60
```

<210> SEQ ID NO 1909
<211> LENGTH: 60
<212> TYPE: DNA
<213> ORGANISM: Homo sapiens

<400> SEQUENCE: 1909
ttattgtgaa ataaatccat acagatgatc gatctccttg gcaatgaggg cccgggaagt    60

<210> SEQ ID NO 1910
<211> LENGTH: 60
<212> TYPE: DNA
<213> ORGANISM: Homo sapiens

<400> SEQUENCE: 1910
caatatgacg gtgacattaa tgatagcttc gaggccaagg tgcgagggct ggaacgccag    60

<210> SEQ ID NO 1911
<211> LENGTH: 60
<212> TYPE: DNA
<213> ORGANISM: Homo sapiens

<400> SEQUENCE: 1911
gtgtgggccc ccctgctacc gctgcgtatc gaactttaca gagggatcta gaatgagtga    60

<210> SEQ ID NO 1912
<211> LENGTH: 60
<212> TYPE: DNA
<213> ORGANISM: Homo sapiens

<400> SEQUENCE: 1912
aagctgcccc ggataaaaat tctgataatc gaagttacac ctttgatttt ttaaaaagca    60

<210> SEQ ID NO 1913
<211> LENGTH: 60
<212> TYPE: DNA
<213> ORGANISM: Homo sapiens

<400> SEQUENCE: 1913
gggcagagag attttttgta tctacttctc gagagccggc ctcctgccct ttctaaaggc    60

<210> SEQ ID NO 1914
<211> LENGTH: 60
<212> TYPE: DNA
<213> ORGANISM: Homo sapiens

<400> SEQUENCE: 1914
cagaatcact ctgtggaacc aaagagcttc gacccttctg ctttctctcc agggatggc    60

<210> SEQ ID NO 1915
<211> LENGTH: 60
<212> TYPE: DNA
<213> ORGANISM: Homo sapiens

<400> SEQUENCE: 1915
aaaaaacaat tatgtaattg aaaacccatc gacccttctg ctttctctcc agggatggc    60

<210> SEQ ID NO 1916
<211> LENGTH: 60
<212> TYPE: DNA
<213> ORGANISM: Homo sapiens

<400> SEQUENCE: 1916 ccaccccgc cccggggag tcgcccggtc gaactaatat tagaggagag aggtcagtta    60

<210> SEQ ID NO 1917
<211> LENGTH: 60
<212> TYPE: DNA
<213> ORGANISM: Homo sapiens

<400> SEQUENCE: 1917 ccaccccgc cccggggag tcgcccggtc gaagtgctgt tgagttcccc catctctcat    60

<210> SEQ ID NO 1918
<211> LENGTH: 60
<212> TYPE: DNA
<213> ORGANISM: Homo sapiens

<400> SEQUENCE: 1918 ccaccccgc cccggggag tcgcccggtc gacagtccca agaggtcaga actggcttcc    60

<210> SEQ ID NO 1919
<211> LENGTH: 60
<212> TYPE: DNA
<213> ORGANISM: Homo sapiens

<400> SEQUENCE: 1919 ccaccccgc cccggggag tcgcccggtc gaaggctgga cttaaaagag cagatgcaag    60

<210> SEQ ID NO 1920
<211> LENGTH: 60
<212> TYPE: DNA
<213> ORGANISM: Homo sapiens

<400> SEQUENCE: 1920 aaaaaagat ttaaagtggc agcttcactc gacacaaggg tttgtaacaa aaacaaaaa    60

<210> SEQ ID NO 1921
<211> LENGTH: 60
<212> TYPE: DNA
<213> ORGANISM: Homo sapiens

<400> SEQUENCE: 1921
cactaatctt tactctttt ccacttattc gagaccagtg aaacctcgtc gctacaaaaa    60

<210> SEQ ID NO 1922
<211> LENGTH: 60
<212> TYPE: DNA
<213> ORGANISM: Homo sapiens

<400> SEQUENCE: 1922
aggccatatg gtgaatcagg aaagaagttc gaagtgtctt aatttcctat aaactagtta    60

<210> SEQ ID NO 1923
<211> LENGTH: 60
<212> TYPE: DNA
<213> ORGANISM: Homo sapiens

<400> SEQUENCE: 1923
aaggcccaag aaccaggaat ctaggtattc gaagcagggg acctgcgaaa cttcagctgg    60

<210> SEQ ID NO 1924
<211> LENGTH: 60
<212> TYPE: DNA
<213> ORGANISM: Homo sapiens

<400> SEQUENCE: 1924

```
tttaaacttc tctagagcaa agagcatttc gaccttcttt tccttagata gaaactgaat    60
```

<210> SEQ ID NO 1925
<211> LENGTH: 60
<212> TYPE: DNA
<213> ORGANISM: Homo sapiens

<400> SEQUENCE: 1925

```
agactttatt agataggtat aaatgttttc gacccaaagc tttctttctc ctgagctcag    60
```

<210> SEQ ID NO 1926
<211> LENGTH: 60
<212> TYPE: DNA
<213> ORGANISM: Homo sapiens

<400> SEQUENCE: 1926

```
tccatacgtc actagctgag gtaaaacgtc gatccagctt tttgactcta aaatgagctt    60
```

<210> SEQ ID NO 1927
<211> LENGTH: 60
<212> TYPE: DNA
<213> ORGANISM: Homo sapiens

<400> SEQUENCE: 1927

```
acaatattaa gttcccagag aaaaaaattc gaactggcgg caaccgctgc agcgcctgct    60
```

<210> SEQ ID NO 1928
<211> LENGTH: 60
<212> TYPE: DNA
<213> ORGANISM: Homo sapiens

<400> SEQUENCE: 1928

```
actccatctc aaaaaaacaa gagcttcctc gagttgcagg ccgccctggt ggctagacat    60
```

<210> SEQ ID NO 1929
<211> LENGTH: 60
<212> TYPE: DNA
<213> ORGANISM: Homo sapiens

<400> SEQUENCE: 1929

```
acaatattaa gttcccagag aaaaaaattc gagttgcagg ccgccctggt ggctagacat    60
```

<210> SEQ ID NO 1930
<211> LENGTH: 60
<212> TYPE: DNA
<213> ORGANISM: Homo sapiens

<400> SEQUENCE: 1930

```
actccatctc aaaaaaacaa gagcttcctc gaggtggaat aaaggttgag aacagctata    60
```

<210> SEQ ID NO 1931
<211> LENGTH: 60
<212> TYPE: DNA
<213> ORGANISM: Homo sapiens

<400> SEQUENCE: 1931

```
gtccctgaaa atgtttgtaa atgtggggtc gaggggtaga tatgagcatc cccatttcct    60
```

<210> SEQ ID NO 1932
<211> LENGTH: 60
<212> TYPE: DNA
<213> ORGANISM: Homo sapiens

```
<400> SEQUENCE: 1932
gtccctgaaa atgtttgtaa atgtggggtc gacctgctgg gctcgggcta tccttccatc    60

<210> SEQ ID NO 1933
<211> LENGTH: 60
<212> TYPE: DNA
<213> ORGANISM: Homo sapiens

<400> SEQUENCE: 1933
gggctccgcc ataagggcct ctgtgaaatc gagccctgcc tggccagcac acactgcatc    60

<210> SEQ ID NO 1934
<211> LENGTH: 60
<212> TYPE: DNA
<213> ORGANISM: Homo sapiens

<400> SEQUENCE: 1934
gaggcttctg agttgctctg agggtacatc gatgcgcgcc cgccggggcc cggtcggagc    60

<210> SEQ ID NO 1935
<211> LENGTH: 60
<212> TYPE: DNA
<213> ORGANISM: Homo sapiens

<400> SEQUENCE: 1935
tgatcatggg accctgaaat gtcagcgctc gatgcgcgcc cgccggggcc cggtcggagc    60

<210> SEQ ID NO 1936
<211> LENGTH: 60
<212> TYPE: DNA
<213> ORGANISM: Homo sapiens

<400> SEQUENCE: 1936
ttgacagttc agtctgattt caagtcagtc gactggaatc tgcattcgct tcgcaggagc    60

<210> SEQ ID NO 1937
<211> LENGTH: 60
<212> TYPE: DNA
<213> ORGANISM: Homo sapiens

<400> SEQUENCE: 1937 acccccctccc agcctcctgg tcaggagttc gaccaggctg cagcgaatca cctcagctcc    60

<210> SEQ ID NO 1938
<211> LENGTH: 60
<212> TYPE: DNA
<213> ORGANISM: Homo sapiens

<400> SEQUENCE: 1938
aatgagtttc tggaagaata ggacattgtc gaactcctga ccaggaggct gggaggggt    60

<210> SEQ ID NO 1939
<211> LENGTH: 60
<212> TYPE: DNA
<213> ORGANISM: Homo sapiens

<400> SEQUENCE: 1939
ctccacctgg ctaacttcta tgcatccttc gagccgtagc tatcttcctg cctgaccggg    60

<210> SEQ ID NO 1940
<211> LENGTH: 60
<212> TYPE: DNA
<213> ORGANISM: Homo sapiens
```

<400> SEQUENCE: 1940
tttgctaaat tacccaaaat tttgcttttc gataaattga acttcatcaa aattaaaaac    60

<210> SEQ ID NO 1941
<211> LENGTH: 60
<212> TYPE: DNA
<213> ORGANISM: Homo sapiens

<400> SEQUENCE: 1941
taagctttcc atcaagctac gaagctgctc gatatcagaa ttgtgctctg ggggcggctt    60

<210> SEQ ID NO 1942
<211> LENGTH: 60
<212> TYPE: DNA
<213> ORGANISM: Homo sapiens

<400> SEQUENCE: 1942
aagccgcccc cagagcacaa ttctgatatc gaagtacaca agtcaaaaag acaaagaat     60

<210> SEQ ID NO 1943
<211> LENGTH: 60
<212> TYPE: DNA
<213> ORGANISM: Homo sapiens

<400> SEQUENCE: 1943
gcaccccacc ctggatccct tgaaagcctc gatctctgcc tcgcgcagcc ccagcgtgcg    60

<210> SEQ ID NO 1944
<211> LENGTH: 60
<212> TYPE: DNA
<213> ORGANISM: Homo sapiens

<400> SEQUENCE: 1944
gtcttcctcc attttagaaa tgaataactc gaaggggaa tagagaatgt aatgataacct    60

<210> SEQ ID NO 1945
<211> LENGTH: 60
<212> TYPE: DNA
<213> ORGANISM: Homo sapiens

<400> SEQUENCE: 1945
tttccacttt tcatacttag actcacaatc gatcctcggg catccctgaa tcatctatcg    60

<210> SEQ ID NO 1946
<211> LENGTH: 60
<212> TYPE: DNA
<213> ORGANISM: Homo sapiens

<400> SEQUENCE: 1946
atactgaggt ttaaaaagtt cttttttttc gatctcggct cattgcagcc tccccgtccc    60

<210> SEQ ID NO 1947
<211> LENGTH: 60
<212> TYPE: DNA
<213> ORGANISM: Homo sapiens

<400> SEQUENCE: 1947
cacatacaag ctttctgttc gtttattttc gacataggac gtgcctgctc ccccttcacc    60

<210> SEQ ID NO 1948
<211> LENGTH: 20
<212> TYPE: DNA

```
<213> ORGANISM: Homo sapiens

<400> SEQUENCE: 1948
ctaagatcat cgtcctgtgc                                              20

<210> SEQ ID NO 1949
<211> LENGTH: 19
<212> TYPE: DNA
<213> ORGANISM: Homo sapiens

<400> SEQUENCE: 1949
cagtctccag cctttgttc                                               19

<210> SEQ ID NO 1950
<211> LENGTH: 20
<212> TYPE: DNA
<213> ORGANISM: Homo sapiens

<400> SEQUENCE: 1950
aaccaacata agaagctgac                                              20

<210> SEQ ID NO 1951
<211> LENGTH: 19
<212> TYPE: DNA
<213> ORGANISM: Homo sapiens

<400> SEQUENCE: 1951
tgccacgaga atcaaatcc                                               19

<210> SEQ ID NO 1952
<211> LENGTH: 24
<212> TYPE: DNA
<213> ORGANISM: Homo sapiens

<400> SEQUENCE: 1952
tgtcacattt gtgccttact cagc                                         24

<210> SEQ ID NO 1953
<211> LENGTH: 20
<212> TYPE: DNA
<213> ORGANISM: Homo sapiens

<400> SEQUENCE: 1953
ggaagcctcg ccagtgagtt                                              20

<210> SEQ ID NO 1954
<211> LENGTH: 20
<212> TYPE: DNA
<213> ORGANISM: Homo sapiens

<400> SEQUENCE: 1954
tattccactg gcagcaaggt                                              20

<210> SEQ ID NO 1955
<211> LENGTH: 20
<212> TYPE: DNA
<213> ORGANISM: Homo sapiens

<400> SEQUENCE: 1955
ggggctccac tagggtgact                                              20

<210> SEQ ID NO 1956
<211> LENGTH: 25
```

<212> TYPE: DNA
<213> ORGANISM: Homo sapiens

<400> SEQUENCE: 1956
cagataaatg acaaactggg aaaca                                        25

<210> SEQ ID NO 1957
<211> LENGTH: 22
<212> TYPE: DNA
<213> ORGANISM: Homo sapiens

<400> SEQUENCE: 1957
caatgacagg actcaaccca gg                                           22

<210> SEQ ID NO 1958
<211> LENGTH: 23
<212> TYPE: DNA
<213> ORGANISM: Homo sapiens

<400> SEQUENCE: 1958
acaggaaaag gaagctcaca ggt                                          23

<210> SEQ ID NO 1959
<211> LENGTH: 25
<212> TYPE: DNA
<213> ORGANISM: Homo sapiens

<400> SEQUENCE: 1959
tctgcctgct taaatattac tttcc                                        25

<210> SEQ ID NO 1960
<211> LENGTH: 19
<212> TYPE: DNA
<213> ORGANISM: Homo sapiens

<400> SEQUENCE: 1960
gccaaactcc tgtctgaag                                               19

<210> SEQ ID NO 1961
<211> LENGTH: 20
<212> TYPE: DNA
<213> ORGANISM: Homo sapiens

<400> SEQUENCE: 1961
cggatgctct agaaaggttg                                              20

<210> SEQ ID NO 1962
<211> LENGTH: 23
<212> TYPE: DNA
<213> ORGANISM: Homo sapiens

<400> SEQUENCE: 1962
gagttctaga ataggatgtt ggg                                          23

<210> SEQ ID NO 1963
<211> LENGTH: 20
<212> TYPE: DNA
<213> ORGANISM: Homo sapiens

<400> SEQUENCE: 1963
ttcttggtag agagggaagg                                              20

<210> SEQ ID NO 1964

```
<210> SEQ ID NO 1964
<211> LENGTH: 18
<212> TYPE: DNA
<213> ORGANISM: Homo sapiens

<400> SEQUENCE: 1964
tggctgactt ggtgaaac                                                   18

<210> SEQ ID NO 1965
<211> LENGTH: 19
<212> TYPE: DNA
<213> ORGANISM: Homo sapiens

<400> SEQUENCE: 1965
agtcagcaat ctgtgaacc                                                  19

<210> SEQ ID NO 1966
<211> LENGTH: 21
<212> TYPE: DNA
<213> ORGANISM: Homo sapiens

<400> SEQUENCE: 1966
ctccttcaca acccttatca c                                               21

<210> SEQ ID NO 1967
<211> LENGTH: 19
<212> TYPE: DNA
<213> ORGANISM: Homo sapiens

<400> SEQUENCE: 1967
agggtggtta tggagtgag                                                  19

<210> SEQ ID NO 1968
<211> LENGTH: 21
<212> TYPE: DNA
<213> ORGANISM: Homo sapiens

<400> SEQUENCE: 1968
agatgttgac tctccagatt g                                               21

<210> SEQ ID NO 1969
<211> LENGTH: 24
<212> TYPE: DNA
<213> ORGANISM: Homo sapiens

<400> SEQUENCE: 1969
aagcaagata caccttaccc agta                                            24

<210> SEQ ID NO 1970
<211> LENGTH: 20
<212> TYPE: DNA
<213> ORGANISM: Homo sapiens

<400> SEQUENCE: 1970
ccggaccaat ccagagacgg                                                 20

<210> SEQ ID NO 1971
<211> LENGTH: 22
<212> TYPE: DNA
<213> ORGANISM: Homo sapiens

<400> SEQUENCE: 1971
actctccctg gtgcttagct tt                                              22
```

```
<210> SEQ ID NO 1972
<211> LENGTH: 20
<212> TYPE: DNA
<213> ORGANISM: Homo sapiens

<400> SEQUENCE: 1972
tgtgacacgc tgactccctt                                              20

<210> SEQ ID NO 1973
<211> LENGTH: 25
<212> TYPE: DNA
<213> ORGANISM: Homo sapiens

<400> SEQUENCE: 1973
agacattttg gcaaagattg ttagg                                        25

<210> SEQ ID NO 1974
<211> LENGTH: 23
<212> TYPE: DNA
<213> ORGANISM: Homo sapiens

<400> SEQUENCE: 1974
ttcagcatgg agtaagagga ggg                                          23

<210> SEQ ID NO 1975
<211> LENGTH: 20
<212> TYPE: DNA
<213> ORGANISM: Homo sapiens

<400> SEQUENCE: 1975
taggaggcag aggcaggagg                                              20

<210> SEQ ID NO 1976
<211> LENGTH: 20
<212> TYPE: DNA
<213> ORGANISM: Homo sapiens

<400> SEQUENCE: 1976
tttggaggga ggatggtcaa                                              20

<210> SEQ ID NO 1977
<211> LENGTH: 22
<212> TYPE: DNA
<213> ORGANISM: Homo sapiens

<400> SEQUENCE: 1977
aatagtcttg taccgttgga tg                                           22

<210> SEQ ID NO 1978
<211> LENGTH: 20
<212> TYPE: DNA
<213> ORGANISM: Homo sapiens

<400> SEQUENCE: 1978
gctctttggt atgacactgg                                              20

<210> SEQ ID NO 1979
<211> LENGTH: 19
<212> TYPE: DNA
<213> ORGANISM: Homo sapiens

<400> SEQUENCE: 1979
gctttgttgg cactgaatg                                               19
```

<210> SEQ ID NO 1980
<211> LENGTH: 18
<212> TYPE: DNA
<213> ORGANISM: Homo sapiens

<400> SEQUENCE: 1980
ggacagccca gtcaaatg                                    18

<210> SEQ ID NO 1981
<211> LENGTH: 19
<212> TYPE: DNA
<213> ORGANISM: Homo sapiens

<400> SEQUENCE: 1981
catgacttgg gccttcttc                                   19